US007067540B2

(12) United States Patent
Devadas et al.

(10) Patent No.: US 7,067,540 B2
(45) Date of Patent: Jun. 27, 2006

(54) SUBSTITUTED PYRIDINONES

(75) Inventors: Balekudru Devadas, Chesterfield, MO (US); John Walker, Maryland Heights, MO (US); Shaun R. Selness, Chesterfield, MO (US); Terri L. Boehm, Ballwin, MO (US); Richard C. Durley, Chesterfield, MO (US); Rajesh Devraj, Chesterfield, MO (US); Brian S. Hickory, Wildwood, MO (US); Paul V. Rucker, University City, MO (US); Kevin D. Jerome, Maryland Heights, MO (US); Heather M. Madsen, University City, MO (US); Edgardo Alvira, Chesterfield, MO (US); Michele A. Promo, Maryland Heights, MO (US); Radhika M. Blevis-Bal, St. Louis, MO (US); Laura D. Marruto, Ellisville, MO (US); Jeff Hitchcock, Saint Peters, MO (US); Thomas Owen, Chesterfield, MO (US); Win Naing, Chesterfield, MO (US); Li Xing, Chesterfield, MO (US); Huey S. Shieh, St. Louis, MO (US); Aruna Sambandam, Guilderland, NY (US); Shuang Liu, Schenectady, NY (US); Ian L. Scott, Woodinville, WA (US); Kevin F. McGee, Guilderland, NY (US)

(73) Assignee: Pharmacia Corporation, St. Louis, MO (US)

( * ) Notice: Subject to any disclaimer, the term of this patent is extended or adjusted under 35 U.S.C. 154(b) by 314 days.

(21) Appl. No.: 10/367,987

(22) Filed: Feb. 14, 2003

(65) Prior Publication Data

US 2004/0058964 A1 Mar. 25, 2004

Related U.S. Application Data

(60) Provisional application No. 60/357,029, filed on Feb. 14, 2002, and provisional application No. 60/436,915, filed on Dec. 30, 2002.

(51) Int. Cl.
*A61K 31/44* (2006.01)
*C07D 213/02* (2006.01)
*C07D 401/02* (2006.01)

(52) U.S. Cl. ............ 514/348; 514/256; 514/336; 546/283.4; 546/296; 544/333

(58) Field of Classification Search .......... 514/348, 514/256, 336, 345; 546/283.4, 296, 290, 546/297; 544/333
See application file for complete search history.

(56) References Cited

U.S. PATENT DOCUMENTS 3,644,626 A  2/1972  Witzel

| 3,654,291 A | 4/1972 | Graham et al. |
| 3,715,358 A | 2/1973 | Dorn et al. |
| 5,032,602 A | 7/1991 | Fey et al. |
| 5,164,506 A | 11/1992 | Fey et al. |
| 5,242,928 A | 9/1993 | Mederski et al. |
| 5,254,543 A | 10/1993 | Hanko et al. |
| 5,308,854 A | 5/1994 | Hoffman, Jr. et al. |
| 5,356,911 A | 10/1994 | Müller-Gliemann et al. |
| 5,378,720 A | 1/1995 | Hlasta et al. |
| 5,407,948 A | 4/1995 | Fey et al. |
| 5,414,003 A | 5/1995 | Fey et al. |
| 5,466,701 A | 11/1995 | Hlasta et al. |
| 5,532,276 A | 7/1996 | Mederski et al. |
| 5,599,823 A | 2/1997 | Müller-Gliemann et al. |
| 5,744,605 A | 4/1998 | Curran et al. |
| 6,255,330 B1 * | 7/2001 | Goldmann et al. ......... 514/369 |
| 6,265,350 B1 | 7/2001 | Schnatterer et al. |

FOREIGN PATENT DOCUMENTS

| DE | 267 045 | 5/1989 |
| EP | 0 336 369 | 10/1989 |
| EP | 0 500 297 | 8/1992 |
| EP | 0 547 708 | 6/1993 |
| EP | 0 626 378 | 11/1994 |
| EP | 0 733 629 | 3/1996 |

(Continued)

OTHER PUBLICATIONS

Bantick et al., *Bioorganic & Medicinal Chemistry Letters* (1994) 4(1):121–126.

(Continued)

*Primary Examiner*—Zinna Northington Davis
(74) *Attorney, Agent, or Firm*—Julie M. Lappin; Charles Ashbrook

(57) ABSTRACT

Disclosed are compounds Formula I

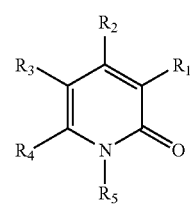

and pharmaceutically acceptable salts thereof, wherein $R_1$, $R_2$, $R_3$, $R_4$, and $R_5$ are defined herein. These compounds are useful for treating diseases and conditions caused or exacerbated by unregulated p38 MAP Kinase and/or TNF activity. Pharmaceutical compositions containing the compounds, methods of preparing the compounds and methods of treatment using the compounds are also disclosed.

45 Claims, No Drawings

FOREIGN PATENT DOCUMENTS

| | | |
|---|---|---|
| GB | 1 289 187 | 9/1972 |
| JP | 9-315008 | 12/1997 |
| JP | 2000128878 | 5/2000 |
| WO | WO 86/01815 | 3/1986 |
| WO | WO 94/22835 | 10/1994 |
| WO | WO 96/22021 | 7/1996 |
| WO | WO 96/41639 | 12/1996 |
| WO | WO 97/10712 | 3/1997 |
| WO | WO 97/30708 | 8/1997 |
| WO | WO 97/40024 | 10/1997 |
| WO | WO 98/14169 A1 * | 4/1998 |
| WO | WO 98/31670 | 7/1998 |
| WO | WO 98/42698 | 10/1998 |
| WO | WO 99/52893 | 10/1999 |
| WO | WO 00/24719 | 5/2000 |
| WO | WO 00/31063 | 6/2000 |
| WO | WO 00/39102 | 7/2000 |

OTHER PUBLICATIONS

Bartroli, et al., *Revista Icidca*, (1988) 12(3):44–49.
Castillo, et al., *Bulletin De La Societe Chimique De France* (1982) 7(8):257–261.
Edstrom, et al., *Tetrahedron Letters* (1994) 35(38):6985–6988.
Frutos, et al., *J. Comb. Chem.* (2000) 2:639–6.
Heber, et al., *Synlett* (1999) 11:1747–1748.
Ivanov et al., *Liebiegs Ann Recueil*, (1997) 8:1777–1781.
Ivanov, et al., *Chemical Abrstracts* (1998) Heterocyclic Compounds (One Hetero Atom) 128(20):243931.
Katagiri, et al., *J. of Chem. Soc.* (1986) 7:1289–1296.
Kiang, et al., *J. of Chem. Soc.* (1971) 15:2721–2726.
Peseke, et al., *Wiss Z Willheim–Univ Rostock Naturwiss Reihel*, (1988) 37(8):46–53.
Database Accession No. 5069110 (BRN)—XP002243098.
Database Accession No. 5587856 (BRN)—XP002243099.
Database Accession No. 63470000 (BRN)—XP002243100.
Database Accession No. 255148 (BRN)—XP00243101.
International Search Report for PCT/US03/04634.

* cited by examiner

SUBSTITUTED PYRIDINONES

CROSS REFERENCE TO RELATED APPLICATIONS

This application claims priority from U.S. Provisional Application Ser. No. 60/357,029, filed Feb. 14, 2002, and U.S. Provisional Application Ser. No. 60/436,915, filed Dec. 30, 2002, the disclosure of each of which is incorporated herein by reference in its entirety.

BACKGROUND OF THE INVENTION

1. Field of the Invention

The instant invention relates to substituted pyridinones that are useful for treating diseases and conditions caused or exacerbated by unregulated p38 MAP kinase activity. Pharmaceutical compositions containing the pyridinone compounds, methods of preparing the pyridone compounds and methods of treatment using the compounds are also disclosed.

2. Description of the Related Art

Numerous cell surface receptors use one or more of the mitogen-activated protein kinase (MAP kinase) cascades during signal transduction. MAP kinases are a family of protein-directed serine/threonine kinases that are activated by dual phosphorylation. One subgroup of the MAP kinases is p38 MAP kinase, which is activated by a variety of signals including proinflammatory cytokines such as tumor necrosis factor (TNF) and interleukin-1 (IL-1), as well as bacterial lipopolysaccharides and environmental stress such as osmotic shock and ultraviolet radiation (Ono, K. and J. Han, Cell Signal. 12: 1, 2000). Within the p38 kinase family, there are four distinct isozymes: p38 alpha, p38 beta, p38 gamma, and p38 delta. The p38 kinase family function downstream of an activating stimulus by phosphorylating and activating transcription factors (e.g. ATF2, CHOP and MEF2C) as well as other kinases (e.g. MAPKAP-2 and MAPKAP-3) (Trends in Cell biology 7, 353–361, 1997; Mol Cell Biology 19, 21–30, 1999; EMBO J 20, 466–479, 2001). Upon activation, the p38 kinase cascade leads to the induction of gene expression of several factors involved in inflammation and immunity including TNF, interleukin-6, granulocyte-macrophage colony stimulating factor (GM-CSF), and HIV long terminal repeat (Paul et al., Cell Signal. 9: 403–410, 1997). The products of the p38 phosphorylation stimulate the production of inflammatory cytokines and other proteins, including TNF and IL-1, and cyclooxygenase-2, and also possibly modulate the effects of these cytokines on their target cells, and thus stimulate inflammation processes (Lee, J. C. et al, Nature, 372: 376, 1994).

P38 MAP kinases have also been shown to promote apoptosis during ischemia in cardiac myocytes, which suggests that p38 MAP kinase inhibitors can be used to treat ischemic heart disease (J. Biol. Chem. 274, 6272, 1999). They are also required for T-cell HIV-1 replication and may be useful targets for AIDS therapy. P38 pathway inhibitors have been used to increase cancer cell sensitivity to cancer therapy also find use in the treatment of asthma (JPET 293, 281, 2000).

TNF is a cytokine and a potent proinflammatory mediator implicated in inflammatory conditions such as arthritis, asthma, septic shock, non-insulin dependent diabetes mellitus, multiple sclerosis, asthma, and inflammatory bowel disease. Thus inhibitors of p38 MAP kinases (required for TNF production) may be useful for the treatment of inflammatory conditions resulting from excessive cytokine production such as arthritis. (Boehm, J. C. and J. L. Adams, Exp. Opin. Ther. Patents 10: 25, 2000, and references cited therein). TNF has also been implicated in viral infections, such as HIV, influenza virus, and herpes virus including herpes simplex virus type-1 (HSV-1), herpes simplex virus type-2 (HSV-2), cytomegalovirus (CMV), varicella-zoster virus (VZV), Epstein-Barr virus, human herpesvirus-6 (HHV-6), human herpesvirus-7 (HHV-7), human herpesvirus-8 (HHV-8), pseudorabies and rhinotracheitis, among others.

Excessive or unregulated TNF production has also been shown to produce elevated levels of IL-1. Inhibition of TNF, therefore, should reduce levels of IL-1 (European Cytokine Netw 6, 225, 1995) and ameliorate disease states caused by unregulated IL-1 synthesis. Such disease states include rheumatoid arthritis, rheumatoid spondylitis, osteoarthritis, gouty arthritis, sepsis, septic shock, endotoxic shock, gram negative sepsis, toxic shock syndrome, adult respiratory distress syndrome, cerebral malaria, chronic pulmonary inflammatory disease, silicosis, pulmonary sarcosis, bone resorption diseases, reperfusion injury, graft versus host reaction, alallograft rejections, fever and myalgias due to infection, cachexia secondary to infection or malignancy, cachexia secondary to acquired immune deficiency syndrome (AIDS), AIDS related complex (ARC), keloid formation, scar tissue formation, Crohn's disease, ulcerative colitis, and pyresis.

IL-1 has also been shown to mediate a variety of biological activities such as the activation of T-helper cells, induction of fever, stimulation of prostaglandin or collagenase production, neutrophil chemotaxis, and the suppression of plasma iron levels (*Rev. Infect. Disease,* 6, 51 (1984)). Elevated levels of IL-1 have also been implicated in mediating or exacerbating a number of disease states including rheumatoid arthritis, osteoarthritis, rheumatoid spondylitis, gouty arthritis, inflammatory bowel disease, adult respiratory distress syndrome (ARDS), psoriasis, Crohn's disease, ulcerative colitis, anaphylaxis, muscle degeneration, cachexia, Reiter's syndrome, type I and type II diabetes, bone resorption diseases, ischemia reperfusion injury, arteriosclerosis, brain trauma, multiple sclerosis, sepsis, septic shock, and toxic shock syndrome. Viruses sensitive to TNF inhibition, such as HIV-1, HIV-2, HIV-3, are also affected by IL-1 production. In rheumatoid arthritis, both IL-1 and TNF induce collagenase synthesis and ultimately lead to tissue destruction within arthritic joints (*Lymphokine Cytokine Res.* (11): 253–256, (1992) and *Clin. Exp. Immunol.* 989:244–250, (1992)).

IL-6 is another pro-inflammatory cytokine, which is associated with many conditions including inflammation. Consequently, TNF, IL-1 and IL-6 affect a wide variety of cells and tissues and are important inflammatory mediators of a wide variety of disease states and conditions. The inhibition of these cytokines by inhibition or modulation of p38 kinase is of benefit in controlling, reducing and alleviating many of these disease states and conditions. Therefore, the present invention concerns finding small molecule inhibitors or modulators of p38 kinase and the p38 kinase pathway.

SUMMARY OF THE INVENTION

In a broad aspect, the invention provides compounds of Formula I (Embodiment I):

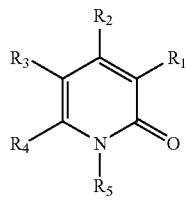

(I)

and pharmaceutically acceptable salts thereof, wherein
$R_1$ is H, halogen, $NO_2$, alkyl, carboxaldehyde, hydroxyalkyl, dihydroxyalkyl, arylalkoxy, arylalkyl, alkenyl, alkynyl, arylalkynyl, —CN, aryl, alkanoyl, alkoxy, alkoxyalkyl, haloalkyl, haloalkoxy, carboxyl, or arylalkanoyl,
  wherein the aryl portion of arylalkoxy, arylalkyl, and arylalkanoyl is unsubstituted or substituted with 1, 2, 3, 4, or 5 groups that are independently halogen, $C_1$–$C_4$ alkyl, $C_1$–$C_4$ alkoxy, nitro, CN, haloalkyl, haloalkoxy or $CO_2R$;
  wherein the alkyl portion of the alkyl, hydroxyalkyl, dihydroxyalkyl, arylalkoxy, arylalkyl, alkanoyl, alkoxy, alkoxyalkyl and arylalkanoyl groups is unsubstituted or substituted with 1, 2, or 3 groups that are independently halogen, $C_1$–$C_4$ alkoxy, $C_1$–$C_4$ alkoxycarbonyl, or $C_3$–$C_7$ cycloalkyl;
$R_2$ is H, OH, halogen, —$OSO_2$—($C_1$–$C_6$)alkyl, —$OSO_2$-aryl, arylalkoxy, aryloxy, arylthio, arylthioalkoxy, arylalkynyl, alkoxy, aryloxy($C_1$–$C_6$)alkyl, alkyl, alkynyl, —OC(O)NH($CH_2$)$_n$aryl, —OC(O)N(alkyl)($CH_2$)$_n$aryl, alkoxyalkoxy, dialkylamino, alkyl, alkoxy, aryl, arylalkyl, heteroaryl, heteroarylalkyl, arylalkenyl, heterocycloalkyl, heterocycloalkylalkyl, alkoxyalkoxy, $NR_8R_9$, dialkylamino, or $CO_2R$, wherein
  n is 0, 1, 2, 3, 4, 5 or 6;
  each of which groups is unsubstituted or substituted with 1, 2, 3, 4, or 5 groups that are independently halogen, —($C_1$–$C_6$)alkyl-N(R)—$CO_2R_{30}$, haloalkyl, heteroaryl, heteroarylalkyl, —$NR_6R_7$, $R_6R_7N$—($C_1$–$C_6$ alkyl)-, —C(O)$NR_6R_7$, —($C_1$–$C_4$)alkyl-C(O)$NR_6R_7$, —($C_1$–$C_4$ alkyl)-NRC(O)$NR_{16}R_{17}$, haloalkoxy, alkyl, CN, hydroxyalkyl, dihydroxyalkyl, alkoxy, alkoxycarbonyl, phenyl, —$SO_2$-phenyl wherein the phenyl and —$SO_2$-phenyl groups are optionally substituted with 1, 2, or 3 groups that are independently halogen or $NO_2$, or —OC(O)$NR_6R_7$, wherein
  $R_{16}$ and $R_{17}$ are independently H or $C_1$–$C_6$ alkyl; or
  $R_{16}$, $R_{17}$ and the nitrogen to which they are attached form a morpholinyl ring;
  $R_6$ and $R_7$ are independently at each occurrence H, alkyl, hydroxyalkyl, dihydroxyalkyl, alkoxy, alkanoyl, arylalkyl, arylalkoxy, alkoxycarbonyl, —$SO_2$-alkyl, OH, alkoxy, alkoxyalkyl, arylalkoxycarbonyl, —($C_1$–$C_4$)alkyl-$CO_2$-alkyl, heteroarylalkyl, or arylalkanoyl, wherein each is unsubstituted or substituted with 1, 2, or 3 groups that are independently, halogen, OH, SH, heterocycloalkyl, heterocycloalkylalkyl, $C_3$–$C_7$ cycloalkyl, alkoxy, $NH_2$, NH(alkyl), N(alkyl)(alkyl), —O-alkanoyl, alkyl, haloalkyl, carboxaldehyde, or haloalkoxy; or
  $R_6$, $R_7$, and the nitrogen to which they are attached form a morpholinyl, pyrrolidinyl, thiomorpholinyl, thiomorpholinyl S-oxide, thiomorpholinyl S,S-dioxide, piperidinyl, pyrrolidinyl, or piperazinyl ring which is optionally substituted with 1 or 2 groups that are independently $C_1$–$C_4$ alkyl, alkoxycarbonyl, $C_1$–$C_4$ alkoxy, hydroxyl, hydroxyalkyl, dihydroxyalkyl, or halogen;
  R at each occurrence is independently hydrogen or $C_1$–$C_6$ alkyl optionally substituted with 1 or 2 groups that are independently OH, SH, halogen, amino, monoalkylamino, dialkylamino or $C_3$–$C_6$ cycloalkyl;
  $R_{30}$ is $C_1$–$C_6$ alkyl optionally substituted with 1 or 2 groups that are independently OH, SH, halogen, amino, monoalkylamino, dialkylamino or $C_3$–$C_6$ cycloalkyl;
  each $R_8$ is independently hydrogen, alkyl, alkanoyl, arylalkyl and arylalkanoyl, wherein each of the above is optionally substituted with 1, 2, 3, 4, or 5 groups that are independently alkyl, alkoxy, alkoxycarbonyl, halogen, or haloalkyl;
  each $R_9$ is hydrogen, alkyl, alkanoyl, arylalkyl, cycloalkyl, cycloalkylalkyl, alkenyl, heteroaryl, aminoalkyl, monoalkylaminoalkyl, dialkylaminoalkyl, arylalkanoyl, —$SO_2$-phenyl, and aryl wherein each of the above is optionally substituted with 1, 2, 3, 4, or 5 groups that are independently alkyl, alkoxy, alkoxycarbonyl, halogen, or haloalkyl;
$R_3$ is H, halogen, alkoxycarbonyl, arylalkoxycarbonyl, aryloxycarbonyl, arylalkyl, —OC(O)NH($CH_2$)$_n$aryl, arylalkoxy, —OC(O)N(alkyl)($CH_2$)$_n$aryl, aryloxy, arylthio, thioalkoxy, arylthioalkoxy, alkenyl, —$NR_6R_7$, $NR_6R_7$—($C_1$–$C_6$)alkyl, or alkyl, wherein
  the aryl portion of arylalkoxycarbonyl, aryloxycarbonyl, arylalkyl, —OC(O)NH($CH_2$)$_n$aryl, arylalkoxy, —OC(O)N(alkyl)($CH_2$)$_n$aryl, and arylthioalkoxy, is unsubstituted or substituted with 1, 2, 3, 4, or 5 groups that are independently, halogen, alkoxy, alkyl, haloalkyl, or haloalkoxy,
  wherein n is 0, 1, 2, 3, 4, 5, or 6; or
$R_4$ is hydrogen or $R_4$ is alkyl unsubstituted or substituted with one or two groups that are independently $CO_2R$, —$CO_2$—($C_1$–$C_6$)alkyl, —C(O)$NR_6R_7$, —C(O)$R_6$, —N($R_{30}$)C(O)$NR_{16}R_{17}$, —N($R_{30}$)C(O)—($C_1$–$C_6$) alkoxy, or —$NR_6R_7$, arylalkoxy, arylalkyl, heteroaryl, heteroarylalkyl, hydroxyalkyl, dihydroxyalkyl, haloalkyl, $R_6R_7N$—($C_1$–$C_6$ alkyl)-, —$NR_6R_7$, alkoxy, carboxaldehyde, —C(O)$NR_6R_7$, $CO_2R$, alkoxyalkyl, or alkoxyalkoxy, wherein the heteroaryl or aryl portions of is the above are unsubstituted or substituted with 1, 2, 3, 4, or 5 groups that are independently halogen, hydroxy, alkoxy, alkyl, —$CO_2$—($C_1$–$C_6$)alkyl, —$CONR_6R_7$, —$NR_6R_7$, $R_6R_7N$—($C_1$–$C_6$)alkyl-, nitro, haloalkyl, or haloalkoxy; and
$R_5$ is H, aryl, arylalkyl, arylthioalkyl, alkyl optionally substituted with 1, 2, or 3 groups that are independently arylalkoxycarbonyl, —$NR_8R_9$, halogen, —C(O)$NR_8R_9$, alkoxycarbonyl, $C_3$–$C_7$ cycloalkyl, or alkanoyl, alkoxy, alkoxyalkyl optionally substituted with one trimethylsilyl group, amino, alkoxycarbonyl, hydroxyalkyl, dihydroxyalkyl, alkynyl, —$SO_2$-alkyl, alkoxy optionally substituted with one trimethylsilyl group, heterocycloalkylalkyl, cycloalkyl, cycloalkylalkyl, -alkyl-S-aryl, -alkyl-$SO_2$-aryl, heteroarylalkyl, heterocycloalkyl, heteroaryl, or alkenyl optionally substituted with alkoxycarbonyl, wherein
each of the above is unsubstituted or substituted with 1, 2, 3, 4, or 5 groups that are independently alkyl, halogen, alkoxy, hydroxyalkyl, dihydroxyalkyl, arylalkoxy, thioalkoxy, alkoxycarbonyl, arylalkoxycarbonyl, $CO_2R$, CN, OH, hydroxyalkyl, dihydroxyalkyl, amidinooxime, $-NR_6R_7$, $-NR_8R_9$, $R_6R_7N-(C_1-C_6\ alkyl)$-, carboxaldehyde, $SO_2$ alkyl, $-SO_2H$, $-SO_2NR_6R_7$, alkanoyl wherein the alkyl portion is optionally substituted with OH, halogen or alkoxy, $-C(O)NR_6R_7$, $-(C_1-C_4\ alkyl)$-$C(O)NR_6R_7$, amidino, haloalkyl, $-(C_1-C_4\ alkyl)$-$NR_{15}C(O)NR_{16}R_{17}$, $-(C_1-C_4\ alkyl)$-$NR_{15}C(O)R_{18}$, $-O-CH_2-O$, $-O-CH_2CH_2-O-$, or haloalkoxy; wherein
  $R_{15}$ is H or $C_1-C_6$ alkyl; and
  $R_{18}$ is $C_1-C_6$ alkyl optionally substituted with $-O-$ ($C_2-C_6$ alkanoyl, $C_1-C_6$ hydroxyalkyl, $C_1-C_6$ dihydroxyalkyl, $C_1-C_6$ alkoxy, $C_1-C_6$ alkoxy $C_1-C_6$ alkyl; amino $C_1-C_6$ alkyl, mono or dialkylamino $C_1-C_6$ alkyl.

The invention also includes the intermediates that are useful in making the compounds of the invention.

These compounds bind and/or interact with p38 kinase and/or TNF. Preferably, they inhibit the activity of p38 kinase and/or TNF. They are therefore used in treating p38 map kinase or TNF mediated disorders. Preferably they are used in treating p38 alpha or TNF mediated disorders.

The instant invention also includes pharmaceutical compositions comprising at least one compound of formula I and at least one pharmaceutically acceptable carrier, solvent, adjuvant or excipient.

The instant invention also includes methods of treating a TNF mediated disorder, a p38 kinase mediated disorder, inflammation and/or arthritis in a subject, the method comprising treating a subject having or susceptible to such disorder or condition with a therapeutically-effective amount of a compound of Formula I.

DETAILED DESCRIPTION OF THE INVENTION

In a preferred aspect, the invention provides compounds of formula I wherein:
when $R_2$ is benzyloxy, $R_3$ is H, $R_4$ is H, and $R_5$ is benzyl or methyl, $R_1$ is not hydrogen;
no more than two of $R_1$, $R_2$, $R_4$, and $R_5$ are simultaneously hydrogen;
$R_6$ and $R_7$ are not simultaneously OH;
when $R_2$ is OH, $R_4$ is methyl and $R_5$ is phenyl, $R_1$ is not acetyl; and
$R_4$ and $R_5$ are not simultaneously hydrogen.

Embodiment 2. Compounds of the formula:

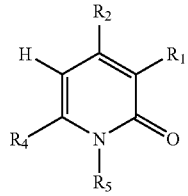

and the pharmaceutically acceptable salts thereof, wherein $R_1$ is H, halogen, alkyl, carboxaldehyde, hydroxyalkyl, dihydroxyalkyl, arylalkoxy, arylalkyl, alkenyl, alkynyl, arylalkynyl, CN, alkanoyl, alkoxy, alkoxyalkyl, haloalkyl, carboxyl, or arylalkanoyl,
  wherein the aryl portion of arylalkoxy, arylalkyl, and arylalkanoyl is unsubstituted or substituted with 1, 2, 3, 4, or 5 groups that are independently halogen, $C_1-C_4$ alkyl, $C_1-C_4$ alkoxy, nitro, CN, haloalkyl, haloalkoxy or $CO_2R$;

wherein the alkyl portion of the alkyl, hydroxyalkyl, dihydroxyalkyl, arylalkoxy, arylalkyl, alkanoyl, alkoxy, alkoxyalkyl and arylalkanoyl groups is unsubstituted or substituted with 1, 2, or 3 groups that are independently halogen, $C_1-C_4$ alkyl, $C_1-C_4$ alkoxycarbonyl, or cyclopropyl;

$R_2$ is H, OH, halogen, $-OSO_2-(C_1-C_6)$alkyl, $-OSO_2$-aryl, arylalkoxy, aryloxy, arylthioalkoxy, arylalkynyl, alkoxy, phenyloxy($C_1-C_6$)alkyl, $-OC(O)NH(CH_2)$aryl, $-OC(O)N(alkyl)(CH_2)_n$aryl, alkyl, alkynyl, alkoxyalkoxy, dialkylamino, heteroaryl, heterocycloalkyl, aryloxyalkyl, or $CO_2R$, wherein
  each of the above is unsubstituted or substituted with 1, 2, 3, 4, or 5 groups that are independently halogen, $-NR_6R_7$, haloalkyl, haloalkoxy, alkyl, heteroaryl, heteroarylalkyl, $-(C_1-C_4)$alkyl-$C(O)NR_6R_7$, $R_6R_7N-(C_1-C_6\ alkyl)$-, $-C(O)NR_6R_7$, $-(C_1-C_4\ alkyl)$-$NRC(O)NR_{16}R_{17}$, CN, hydroxyalkyl, dihydroxyalkyl, $-OC(O)NR_6R_7$, or $-(C_1-C_6)$alkyl-$N(R)-CO_2R_{30}$, wherein
    $R_{16}$ and $R_{17}$ are independently H or $C_1-C_6$ alkyl; or
    $R_{16}$, $R_{17}$ and the nitrogen to which they are attached form a morpholinyl ring;
  $R_6$ and $R_7$ are independently at each occurrence H, alkyl, hydroxyalkyl, dihydroxyalkyl, alkoxy, alkoxyalkyl, alkanoyl, arylalkyl, arylalkoxy, arylalkoxycarbonyl, or arylalkanoyl, wherein each of the above is unsubstituted or substituted with 1, 2, or 3 groups that are independently, halogen, alkoxy, alkyl, OH, SH, carboxaldehyde, haloalkyl, or haloalkoxy; or
  $R_6$, $R_7$, and the nitrogen to which they are attached form a morpholinyl, thiomorpholinyl, thiomorpholinyl S-oxide, thiomorpholinyl S,S-dioxide, piperidinyl, pyrrolidinyl, or piperazinyl ring which is optionally substituted with 1 or 2 groups that are independently $C_1-C_4$ alkyl, alkoxycarbonyl, hydroxyl, hydroxyalkyl, dihydroxyalkyl, or halogen;
n is 0, 1, 2, 3, 4, 5 or 6;
R at each occurrence is independently H or $C_1-C_6$ alkyl optionally substituted with 1 or 2 groups that are independently OH, SH, halogen, amino, monoalkylamino, dialkylamino or $C_3-C_6$ cycloalkyl;
$R_{30}$ is $C_1-C_6$ alkyl optionally substituted with 1 or 2 groups that are independently OH, SH, halogen, amino, monoalkylamino, dialkylamino or $C_3-C_6$ cycloalkyl;
$R_4$ is H, alkyl optionally substituted with one or two groups that are independently $CO_2R$, $-CO_2$alkyl, $-C(O)NR_6R_7$, $-C(O)R_6$, $-N(R_{30})C(O)NR_{16}R_{17}$, $-N(R_{30})C(O)-(C_1-C_6)$alkyl, or $-NR_6R_7$, arylalkoxy, heteroaryl, arylalkyl, hydroxyalkyl, dihydroxyalkyl, haloalkyl, $-NR_6R_7$, $-C(O)NR_6R_7$, alkoxy, alkoxyalkyl, or alkoxyalkoxy, wherein
  the heteroaryl or aryl portions of the above are unsubstituted or substituted with 1, 2, 3, 4, or 5 groups that are independently halogen, hydroxy, alkoxy, alkyl, $-CO_2-(C_1-C_6)$alkyl, $-CONR_6R_7$, $-NR_6R_7$, $R_6R_7N-(C_1-C_6)$alkyl-, nitro, haloalkyl, or haloalkoxy; and
$R_5$ is H, arylalkyl, alkyl optionally substituted with 1, 2, or 3 groups that are independently arylalkoxycarbonyl, $-NR_8R_9$, halogen, $-C(O)NR_8R_9$, alkoxycarbonyl, or alkanoyl, alkoxyalkyl optionally substituted with one trimethylsilyl group, alkoxycarbonyl, amino, hydroxyalkyl, dihydroxyalkyl, alkenyl optionally substituted with alkoxycarbonyl, alkynyl, $-SO_2$-alkyl, aryl, alkoxy optionally substituted with one trimethylsilyl group, heterocycloalkylalkyl, heteroarylalkyl, heterocycloalkyl, or heteroaryl, wherein each of the above is unsubstituted or substituted with 1, 2, 3, 4, or 5 groups that are independently alkyl, halogen, alkoxy, arylalkoxy, hydroxyalkyl, dihydroxyalkyl, thioalkoxy, —$SO_2$alkyl, alkoxycarbonyl, arylalkoxycarbonyl, $CO_2R$, CN, OH, amidinooxime, $NR_8R_9$, $R_6R_7N$—($C_1$–$C_6$ alkyl)-, —C(O)$NR_6R_7$, amidino, hydroxyalkyl, dihydroxyalkyl, carboxaldehyde, —$NR_6R_7$, haloalkyl, —($C_1$–$C_4$ alkyl)-C(O)$NR_6R_7$, —($C_1$–$C_4$ alkyl)-$CO_2R$, —($C_1$–$C_4$ alkyl)-$C_1$–$C_6$ alkoxycarbonyl, —($C_1$–$C_4$ alkyl)-CN, —($C_1$–$C_4$ alkyl)-$NR_{15}$C(O)$R_{18}$, —O—$CH_2$—O—, —O—$CH_2CH_2$—O—, phenyl or haloalkoxy;

$R_8$ is hydrogen, alkyl, alkanoyl, arylalkyl and arylalkanoyl;

$R_9$ is alkyl, alkanoyl, arylalkyl, heteroaryl, aminoalkyl, monoalkylaminoalkyl, dialkylaminoalkyl, and arylalkanoyl.

Embodiment 3. Compounds according to embodiment 2 wherein $R_1$ is H, halogen, alkyl optionally substituted with $C_1$–$C_4$ alkoxycarbonyl, carboxaldehyde, hydroxyalkyl, dihydroxyalkyl, phenyl($C_1$–$C_6$)alkoxy, phenyl($C_1$–$C_6$) alkyl, CN, alkanoyl, alkoxy, $C_2$–$C_4$ alkynyl, $C_2$–$C_6$ alkenyl optionally substituted with $C_1$–$C_4$ alkoxycarbonyl, alkoxyalkyl, haloalkyl, or phenyl($C_1$–$C_6$)alkanoyl, wherein the phenyl groups are unsubstituted or substituted with 1, 2, 3, 4, or 5 groups that are independently halogen, $C_1$–$C_4$ alkyl, $C_1$–$C_4$ alkoxy, nitro, CN, $CF_3$, $OCF_3$ or $CO_2R$;

wherein the alkyl groups are unsubstituted or substituted with 1, 2, or 3 groups that are independently halogen, methoxy, or ethoxy;

$R_2$ is OH, phenyl($C_1$–$C_6$)alkoxy, phenyloxy, phenyloxy ($C_1$–$C_6$)alkyl, phenyl($C_1$–$C_4$)thioalkoxy, $C_1$–$C_8$ alkoxy, alkoxyalkyl, —O—$SO_2$phenyl, alkynyl, phenyl($C_2$–$C_4$) alkynyl, alkyl, —OC(O)NH($CH_2$)phenyl, —OC(O)N (alkyl)($CH_2$)$_n$phenyl, dialkylamino, pyridyl, pyrimidyl, pyridazyl, pyrazolyl, imidazolyl, pyrrolyl, tetrahydroquinolinyl, tetrahydroisoquinolinyl, tetrazolyl, pyrazinyl, benzimidazolyl, triazinyl, tetrahydrofuryl, piperidinyl, hexahydropyrimidinyl, thiazolyl, thienyl, or $CO_2R$, wherein n is 0, 1, 2, 3, 4, 5 or 6;

each of the above is unsubstituted or substituted with 1, 2, 3, 4, or 5 groups that are independently halogen, $NR_6R_7$, haloalkyl, haloalkoxy, hydroxyalkyl, dihydroxyalkyl, alkyl, phenyl, pyridyl, piperidinyl, piperazinyl, —($C_1$–$C_6$)alkyl-N(R)—$CO_2R_{30}$, $R_6R_7N$—($C_1$–$C_6$ alkyl)-, —C(O)$NR_6R_7$, —($C_1$–$C_4$) alkyl-C(O)$NR_6R_7$, —($C_1$–$C_4$ alkyl)-NRC(O)$NR_{16}R_{17}$, or —OC(O)$NR_6R_7$, wherein $R_6$ and $R_7$ are independently at each occurrence H, alkyl, ($C_1$–$C_4$)hydroxyalkyl, ($C_1$–$C_4$) dihydroxyalkyl,($C_1$–$C_4$)alkoxy, ($C_1$–$C_4$)alkoxy ($C_1$–$C_4$)alkyl, ($C_1$–$C_4$)alkanoyl, phenyl($C_1$–$C_4$) alkyl, phenyl($C_1$–$C_4$)alkoxy, phenyl($C_1$–$C_4$) alkoxycarbonyl, or phenyl($C_1$–$C_4$)alkanoyl, wherein each of the above is unsubstituted or substituted with 1, 2, or 3 groups that are independently, halogen, OH, SH, $C_3$–$C_6$ cycloalkyl, ($C_1$–$C_4$)alkoxy, ($C_1$–$C_4$) alkyl, $CF_3$, carboxaldehyde, $NH_2$, NH($C_1$–$C_6$)alkyl, N($C_1$–$C_6$)alkyl($C_1$–$C_6$)alkyl, $OCF_3$; or $R_6$, $R_7$, and the nitrogen to which they are attached form a morpholinyl, thiomorpholinyl, piperidinyl, pyrrolidinyl, or piperazinyl ring which is optionally substituted with 1 or 2 groups that are independently $C_1$–$C_4$ alkyl, hydroxy, hydroxy $C_1$–$C_4$ alkyl, $C_1$–$C_4$ dihydroxyalkyl, $C_1$–$C_4$ alkoxycarbonyl, or halogen; and $R_4$ is H, alkyl optionally substituted with one or two groups that are independently $CO_2R$, —$CO_2$ alkyl, —C(O) $NR_6R_7$, —C(O)$R_6$, —N($R_{30}$)C(O)$NR_{16}R_{17}$, —N($R_{30}$)C (O)—($C_1$–$C_6$)alkoxy, or —$NR_6R_7$, —C(O)$NR_6R_7$, phenyl($C_1$–$C_6$)alkoxy, phenyl($C_1$–$C_6$)alkyl, hydroxyalkyl, dihydroxyalkyl, haloalkyl, alkoxy, alkoxyalkyl, or alkoxyalkoxy, wherein the phenyl groups are unsubstituted or substituted with 1, 2, 3, 4, or 5 groups that are independently halogen, hydroxy, alkoxy, alkyl, nitro, $CF_3$, $OCF_3$;

$R_5$ is phenyl($C_1$–$C_6$)alkyl, ($C_1$–$C_6$)alkyl optionally substituted with 1, 2, 3, 4, or 5 groups that are independently phenyl $C_1$–$C_4$ alkoxycarbonyl, —$NR_8R_9$, halogen, —C(O)$NR_8R_9$, alkoxycarbonyl, or alkanoyl, phenyl, alkoxy, $C_2$–$C_6$ alkynyl, $C_2$–$C_6$ alkenyl optionally substituted with alkoxycarbonyl, indolyl, quinolinyl, isoquinolinyl, isoindolyl, dihydroindolyl, pyrazolyl, imidazolyl, dihydroisoindolyl, indolon-2-yl, indazolyl, benzimidazolyl, pyridyl, imidazolidine dione, pyrazolyl ($C_1$–$C_6$ alkyl), imidazolyl($C_1$–$C_6$ alkyl), piperidinyl ($C_1$–$C_6$)alkyl, pyrrolidinyl($C_1$–$C_6$)alkyl, imidazolidinyl ($C_1$–$C_6$)alkyl, tetrahydroisoquinolinyl($C_1$–$C_6$)alkyl, 1H-indazolyl($C_1$–$C_6$)alkyl, dihydroindolon-2-yl($C_1$–$C_6$ alkyl), indolinyl($C_1$–$C_6$ alkyl), dihydrobenzimidazolyl ($C_1$–$C_6$ alkyl), or dihydrobenzoimidazolonyl($C_1$–$C_6$ alkyl), pyridyl($C_1$–$C_6$)alkyl, pyridazinyl($C_1$–$C_6$)alkyl, pyrimidinyl($C_1$–$C_6$)alkyl, pyrazinyl($C_1$–$C_6$)alkyl, tetrahydrofuryl($C_1$–$C_6$)alkyl, naphthyl($C_1$–$C_6$)alkyl, morpholinyl($C_1$–$C_6$)alkyl, tetrahydrofuryl($C_1$–$C_6$)alkyl, thienyl($C_1$–$C_6$)alkyl, piperazinyl($C_1$–$C_6$)alkyl, indolyl ($C_1$–$C_6$)alkyl, quinolinyl($C_1$–$C_6$)alkyl, isoquinolinyl ($C_1$–$C_6$)alkyl, isoindolyl($C_1$–$C_6$)alkyl, dihydroindolyl ($C_1$–$C_6$)alkyl, pyrazolyl($C_1$–$C_4$)alkyl, imidazolyl($C_1$–$C_4$) alkyl, dihydroisoindolyl($C_1$–$C_6$)alkyl, indoon-2-yl ($C_1$–$C_6$)alkyl, indolon-2-yl($C_1$–$C_6$)alkyl, or morpholinyl $C_1$–$C_6$ alkyl, wherein each of the above is unsubstituted or substituted with 1, 2, 3, 4, or 5 groups that are independently $C_1$–$C_6$ alkyl, halogen, $C_1$–$C_6$ alkoxy, phenyl $C_1$–$C_6$ alkoxy, $C_1$–$C_6$ thioalkoxy, $C_1$–$C_6$ alkoxycarbonyl, $CO_2R$, CN, —$SO_2$ ($C_1$–$C_6$)alkyl, amidinooxime, $NR_8R_9$, —$NR_6R_7$, $NR_6R_7C_1$–$C_6$ alkyl, —C(O)$NR_6R_7$, —($C_1$–$C_4$)alkyl-C (O)$NR_6R_7$, amidino, $C_1$–$C_4$ haloalkyl, hydroxy $C_1$–$C_6$ alkyl, $C_1$–$C_6$ dihydroxyalkyl, or $C_1$–$C_4$ haloalkoxy; wherein $R_8$ is hydrogen, $C_1$–$C_6$ alkyl, $C_1$–$C_6$ alkanoyl, phenyl $C_1$–$C_6$ alkyl and phenyl $C_1$–$C_6$ alkanoyl; and $R_9$ is aminoalkyl, mono $C_1$–$C_6$ alkylamino $C_1$–$C_6$ alkyl, di $C_1$–$C_6$ alkylamino $C_1$–$C_6$ alkyl, $C_1$–$C_6$ alkyl, $C_1$–$C_6$ alkanoyl, phenyl $C_1$–$C_6$ alkyl, indazolyl, and phenyl $C_1$–$C_6$ alkanoyl.

Embodiment 4. Compounds according to embodiment 3, wherein $R_1$ is H, halogen, $C_1$–$C_4$ alkyl optionally substituted with $C_1$–$C_4$ alkoxycarbonyl, $C_2$–$C_4$ alkenyl optionally substituted with $C_1$–$C_4$ alkoxycarbonyl, $C_2$–$C_4$ alkynyl, or carboxaldehyde;

$R_2$ is benzyloxy, OH, phenyloxy, phenyloxy($C_1$–$C_6$)alkyl, phenyl($C_1$–$C_4$)thioalkoxy, or pyridyl; wherein each of the above is optionally substituted with 1, 2, 3, 4, or 5 groups that are independently halogen, —($C_1$–$C_6$)alkyl-N(R)—

$CO_2R_{30}$, $NR_6R_7$, —($C_1$–$C_4$)alkyl-C(O)$NR_6R_7$, ($C_1$–$C_4$) haloalkyl, —C(O)$NR_6R_7$, —($C_1$–$C_4$ alkyl)-NRC(O) $NR_{16}R_{17}$, ($C_1$–$C_4$)haloalkoxy, hydroxyalkyl, $C_1$–$C_6$ dihydroxyalkyl, ($C_1$–$C_6$)alkyl, pyridyl, or $R_6R_7N$—($C_1$–$C_6$ alkyl)-.

Embodiment 4a. Compounds according to embodiment 4, wherein $R_1$ is H.

Embodiment 4b. Compounds according to embodiment 4, wherein $R_1$ is halogen.

Embodiment 4c. Compounds according to embodiment 4, wherein $R_1$ is $C_1$–$C_4$ alkyl optionally substituted with $C_1$–$C_4$ alkoxycarbonyl.

Embodiment 5. Compounds according to embodiment 4, wherein $R_5$ is indolyl, pyridyl, pyridazinyl, pyrimidinyl, indazolyl, tetrahydroquinolyl, tetrahydroisoquinolyl, pyrazolyl, imidazolyl, furanyl, quinolinyl, isoquinolinyl, isoindolyl, dihydroindolyl, dihydroisoindolyl, indolon-2-yl, or pyrazinyl, each of which is unsubstituted or substituted with 1, 2, 3, 4 or 5 groups that are independently $C_1$–$C_4$ alkyl, halogen, $CF_3$, $OCF_3$, —$CO_2CH_3$, $C_1$–$C_4$ hydroxyalkyl, dihydroxyalkyl, $C_1$–$C_4$ alkoxy, —$CO_2$($C_1$–$C_5$ alkyl), benzyloxy, —$NR_6R_7$, —($C_1$–$C_4$)alkyl-C(O)$NR_6R_7$, —$NR_8R_9$, $NR_6R_7$—($C_1$–$C_4$ alkyl), —C(O)$NR_6R_7$, or amidinooxime; wherein $R_6$ and $R_7$ are independently at each occurrence H, $C_1$–$C_4$ alkyl, $C_1$–$C_4$ hydroxyalkyl, $C_1$–$C_4$ dihydroxyalkyl, $C_1$–$C_4$ alkoxy, $C_1$–$C_4$ alkoxy $C_1$–$C_4$ alkyl, $C_1$–$C_4$ alkanoyl, phenyl $C_1$–$C_4$ alkyl, phenyl $C_1$–$C_4$ alkoxy, or phenyl $C_1$–$C_4$ alkanoyl, wherein each is unsubstituted or substituted with 1, 2, or 3 groups that are independently, halogen, OH, SH, $C_3$–$C_6$ cycloalkyl, aryl, $C_1$–$C_4$ alkoxy, $C_1$–$C_4$ alkyl, OH, $CF_3$, or $OCF_3$; or $R_6$, $R_7$, and the nitrogen to which they are attached form a morpholinyl, thiomorpholinyl, pyrrolidinyl, or piperazinyl ring which is optionally substituted with 1 or 2 groups that are independently $C_1$–$C_4$ alkyl, hydroxy, hydroxy $C_1$–$C_4$ alkyl, $C_1$–$C_4$ dihydroxyalkyl, or halogen.

Embodiment 6. Compounds according to embodiment 5, wherein $R_5$ is indolyl, pyridyl, pyrimidinyl, pyrazolyl, furanyl, indazolyl, dihydroindolyl, dihydroisoindolyl, indolon-2-yl, or pyrazinyl, each of which is unsubstituted or substituted with 1, 2, 3, or 4 groups that are independently $C_1$–$C_4$ alkyl, halogen, $CF_3$, $OCF_3$, —$CO_2CH_3$, $C_1$–$C_4$ hydroxyalkyl, $C_1$–$C_4$ dihydroxyalkyl, $C_1$–$C_4$ alkoxy, —$CO_2$($C_1$–$C_5$ alkyl), benzyloxy, —C(O)$NR_6R_7$, —$NR_8R_9$, —($C_1$–$C_4$)alkyl-C(O)$NR_6R_7$, —$NR_6R_7$, $NR_6R_7$—($C_1$–$C_4$ alkyl)-, and amidinooxime.

Embodiment 7. Compounds according to embodiment 6, wherein $R_5$ is indolyl, pyridyl, pyrimidinyl, dihydroindolyl, dihydroisoindolyl, pyrazolyl, or pyrazinyl, each of which is unsubstituted or substituted with 1, 2, 3, or 4 groups that are independently $C_1$–$C_4$ alkyl, halogen, $CF_3$, $OCF_3$, —$CO_2CH_3$, $C_1$–$C_4$ hydroxyalkyl, $C_1$–$C_4$ dihydroxyalkyl, $C_1$–$C_4$ alkoxy, —$CO_2$($C_1$–$C_5$ alkyl), benzyloxy, —C(O) $NR_6R_7$, $NR_8R_9$, —($C_1$–$C_4$)alkyl-C(O)$NR_6R_7$, —$NR_6R_7$, $NR_6R_7$—($C_1$–$C_4$ alkyl)-, or amidinooxime; wherein $R_6$ and $R_7$ are independently at each occurrence H, $C_1$–$C_4$ alkyl, $C_1$–$C_4$ hydroxyalkyl, $C_1$–$C_4$ dihydroxyalkyl, $C_1$–$C_4$ alkoxy, $C_1$–$C_4$ alkanoyl, $C_1$–$C_4$ alkoxy $C_1$–$C_4$ alkyl, each of which is optionally substituted with 1, 2, or 3 groups that are independently halogen, OH, SH, $C_3$–$C_6$ cycloalkyl, $C_1$–$C_4$ alkoxy, $C_1$–$C_4$ alkyl, OH, $CF_3$, or $OCF_3$.

Embodiment 8. Compounds according to embodiment 7, wherein $R_5$ is indolyl, pyridyl, pyrimidinyl, dihydroindolyl, dihydroisoindolyl, pyrazolyl, or pyrazinyl, each of which is unsubstituted or substituted with 1, 2, or 3 groups that are independently $C_1$–$C_4$ alkyl, halogen, $CF_3$, $OCF_3$, $C_1$–$C_4$ hydroxyalkyl, $C_1$–$C_4$ dihydroxyalkyl, $C_1$–$C_4$ alkoxy, —C(O)$NR_6R_7$, —($C_1$–$C_4$)alkyl-C(O)$NR_6R_7$, $NR_8R_9$, —$NR_6R_7$, or $NR_6R_7$—($C_1$–$C_4$ alkyl)-; wherein $R_6$ and $R_7$ are independently at each occurrence H, $C_1$–$C_4$ alkyl, $C_1$–$C_4$ hydroxyalkyl, $C_1$–$C_4$ dihydroxyalkyl, $C_1$–$C_4$ alkanoyl, or $C_1$–$C_4$ alkoxy, each of which is optionally substituted with 1, 2, or 3 groups that are independently halogen, OH, SH, $C_3$–$C_6$ cycloalkyl, $C_1$–$C_4$ alkoxy, $C_1$–$C_4$ alkyl, OH, $CF_3$, or $OCF_3$.

Embodiment 9. Compounds according to embodiment 4, wherein $R_5$ is phenyl, phenyl($C_1$–$C_6$)alkyl, or ($C_1$–$C_6$)alkyl, wherein each of the above is unsubstituted or substituted with 1, 2, 3, 4, or 5 groups that are independently alkyl, halogen, alkoxy, benzyloxy, hydroxyalkyl, dihydroxyalkyl, thioalkoxy, —$CO_2$($C_1$–$C_5$ alkyl), $CO_2R$, CN, amidinooxime, —$NR_8R_9$, —$NR_6R_7$, —$R_6R_7N$—($C_1$–$C_6$ alkyl)-, —C(O)$NR_6R_7$, —($C_1$–$C_4$)alkyl-C(O)$NR_6R_7$, amidino, $CF_3$, or $OCF_3$;

$R_8$ is hydrogen, $C_1$–$C_6$ alkyl, $C_1$–$C_6$ alkanoyl, phenyl $C_1$–$C_6$ alkyl and phenyl $C_1$–$C_6$ alkanoyl; and $R_9$ is aminoalkyl, mono $C_1$–$C_6$ alkylamino $C_1$–$C_6$ alkyl, di $C_1$–$C_6$ alkylamino $C_1$–$C_6$ alkyl, $C_1$–$C_6$ alkyl, $C_1$–$C_6$ alkanoyl, phenyl $C_1$–$C_4$ alkyl, indazolyl, and phenyl $C_1$–$C_4$ alkanoyl.

Embodiment 10. Compounds according to embodiment 4, wherein $R_5$ is phenyl, phenyl($C_1$–$C_6$)alkyl, which is unsubstituted or substituted with 1, 2, 3, 4, or 5 groups that are independently alkyl, halogen, alkoxy, benzyloxy, thioalkoxy, —$CO_2$($C_1$–$C_6$ alkyl), $CO_2R$, CN, amidinooxime, —$NR_8R_9$, —$NR_6R_7$, $R_6R_7N$—($C_1$–$C_6$ alkyl)-, $R_6R_7NC$(O)—($C_1$–$C_4$ alkyl)-, $R_6R_7NC$(O)—($C_5$–$C_6$ alkyl)-, —C(O)$NR_6R_7$, amidino, $CF_3$, or $OCF_3$; wherein $R_6$ and $R_7$ are independently at each occurrence H, $C_1$–$C_4$ alkyl, $C_1$–$C_4$ hydroxyalkyl, $C_1$–$C_4$ dihydroxyalkyl, $C_1$–$C_4$ alkoxy, $C_1$–$C_4$ alkoxy $C_1$–$C_4$ alkyl, $C_1$–$C_4$ alkanoyl, phenyl $C_1$–$C_4$ alkyl, phenyl $C_1$–$C_4$ alkoxy, or phenyl $C_1$–$C_4$ alkanoyl, wherein each is unsubstituted or substituted with 1, 2, or 3 groups that are independently, halogen, OH, SH, $C_3$–$C_6$ cycloalkyl, $C_1$–$C_4$ alkoxy, $C_1$–$C_4$ alkyl, $CF_3$, or $OCF_3$; or $R_6$, $R_7$, and the nitrogen to which they are attached form a morpholinyl, thiomorpholinyl, or piperazinyl ring which is optionally substituted with 1 or 2 groups that are independently $C_1$–$C_4$ alkyl, hydroxy, hydroxy $C_1$–$C_4$ alkyl, $C_1$–$C_4$ dihydroxyalkyl, or halogen;

$R_8$ is hydrogen, $C_1$–$C_6$ alkyl, $C_1$–$C_6$ alkanoyl, phenyl $C_1$–$C_6$ alkyl and phenyl $C_1$–$C_6$ alkanoyl; and $R_9$ is aminoalkyl, mono $C_1$–$C_6$ alkylamino $C_1$–$C_6$ alkyl, di $C_1$–$C_6$ alkylamino $C_1$–$C_6$ alkyl, $C_1$–$C_6$ alkyl, $C_1$–$C_6$ alkanoyl, phenyl $C_1$–$C_4$ alkyl, indazolyl, and phenyl $C_1$–$C_4$ alkanoyl.

Embodiment 11. Compounds according to embodiment 10, wherein $R_5$ is phenyl, benzyl or phenethyl, wherein each is optionally substituted with 1, 2, 3, 4, or 5 groups that are independently $C_1$–$C_6$ alkyl, —$NR_6R_7$, —C(O)$NR_6R_7$, —($C_1$–$C_4$ alkyl)-C(O)NR$_6$R$_7$, —NR$_8$R$_9$, halogen, C$_1$–C$_6$ alkoxy, CO$_2$R, —(C$_1$–C$_4$ alkyl)-CO$_2$R, C$_1$–C$_6$ thioalkoxy, amidinooxime, C$_1$–C$_6$ alkoxycarbonyl, —(C$_1$–C$_4$ alkyl)-C$_1$–C$_6$ alkoxycarbonyl, C$_1$–C$_6$ hydroxyalkyl, C$_1$–C$_6$ dihydroxyalkyl, —(C$_1$–C$_4$ alkyl)-CN, CN, phenyl C$_1$–C$_6$ alkoxy, OH, C$_1$–C$_4$ haloalkyl, C$_1$–C$_4$ haloalkoxy, R$_6$R$_7$N—(C$_1$–C$_6$ alkyl)-, —(C$_1$–C$_4$ alkyl)-NR$_{15}$C(O)R$_{18}$, amidinooxime, —SO$_2$(C$_1$–C$_6$ alkyl), —O—CH$_2$—O—, —O—CH$_2$CH$_2$—O—, phenyl C$_1$–C$_4$ alkoxy, or phenyl; wherein R$_6$ and R$_7$ are independently at each occurrence H, C$_1$–C$_4$ alkyl, C$_1$–C$_4$ hydroxyalkyl, C$_1$–C$_4$ dihydroxyalkyl, C$_1$–C$_4$ alkanoyl, or C$_1$–C$_4$ alkoxy, each of which is optionally substituted with 1, 2, or 3 groups that are independently halogen, OH, SH, C$_3$–C$_6$ cycloalkyl, C$_1$–C$_4$ alkoxy, C$_1$–C$_4$ alkyl, OH, CF$_3$, or OCF$_3$.

Embodiment 12. Compounds according to embodiment 11,
wherein
R$_5$ is phenyl, benzyl or phenethyl, each of which is unsubstituted or substituted with 1, 2, 3, 4, or 5 groups that are independently CN, halogen, C$_1$–C$_4$ alkoxy, CF$_3$, OCF$_3$, C$_1$–C$_4$ alkyl, —NR$_8$R$_9$, —NR$_6$R$_7$, R$_6$R$_7$N—(C$_1$–C$_6$ alkyl)-, or —C(O)NR$_6$R$_7$, wherein R$_6$ and R$_7$ are independently at each occurrence H, C$_1$–C$_4$ alkyl, C$_1$–C$_4$ hydroxyalkyl, C$_1$–C$_4$ dihydroxyalkyl, C$_1$–C$_4$ alkanoyl, or C$_1$–C$_4$ alkoxy, each of which is optionally substituted with 1, 2, or 3 groups that are independently halogen, OH, SH, C$_3$–C$_6$ cycloalkyl, C$_1$–C$_4$ alkoxy, C$_1$–C$_4$ alkyl, OH, CF$_3$, or OCF$_3$.

Embodiment 13. Compounds according to embodiment 4,
wherein
the R$_5$ group is of the formula:

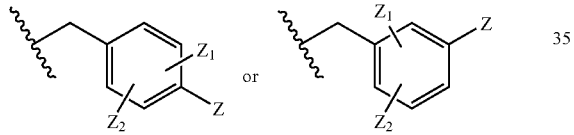

wherein
Z$_1$ and Z$_2$ are independently H, halogen, C$_1$–C$_4$ alkyl, or CO$_2$R; and
Z is —C(O)NR$_6$R$_7$, —(C$_1$–C$_4$)alkyl-C(O)NR$_6$R$_7$, —(C$_1$–C$_4$ alkyl)-NR$_{15}$C(O)R$_{18}$, —NR$_6$R$_7$, R$_6$R$_7$N—(C$_1$–C$_6$ alkyl)-, —NR$_8$R$_9$, C$_1$–C$_6$ hydroxyalkyl, C$_1$–C$_6$ dihydroxyalkyl, C$_1$–C$_6$ alkyl, CO$_2$R, or halogen; wherein R$_6$ and R$_7$ at each occurrence are independently H, OH, C$_1$–C$_6$ alkyl, amino C$_1$–C$_4$ alkyl, NH(C$_1$–C$_6$ alkyl) alkyl, N(C$_1$–C$_6$ alkyl)(C$_1$–C$_6$ alkyl)C$_1$–C$_6$ alkyl, C$_1$–C$_6$ hydroxyalkyl, C$_1$–C$_6$ dihydroxyalkyl, C$_1$–C$_6$ alkoxy C$_1$–C$_6$ alkyl, or —SO$_2$(C$_1$–C$_6$ alkyl) each of which is optionally substituted with 1, 2, or 3 groups that are independently halogen, OH, SH, C$_3$–C$_6$ cycloalkyl, C$_1$–C$_4$ alkoxy, C$_1$–C$_4$ alkyl, OH, CF$_3$, or OCF$_3$; or
R$_6$, R$_7$, and the nitrogen to which they are attached form a piperidinyl, pyrrolidinyl, piperazinyl, or a morpholinyl, thiomorpholinyl, ring optionally substituted with 1 or 2 groups that are independently alkyl, hydroxy, hydroxy C$_1$–C$_4$ alkyl, C$_1$–C$_4$ dihydroxyalkyl, or halogen; and
R$_{18}$ is C$_1$–C$_6$ alkyl optionally substituted with —O—(C$_2$–C$_6$ alkanoyl, C$_1$–C$_6$ hydroxyalkyl, C$_1$–C$_4$ dihydroxyalkyl, C$_1$–C$_6$ alkoxy, C$_1$–C$_6$ alkoxy C$_1$–C$_6$ alkyl; amino C$_1$–C$_6$ alkyl, mono or dialkylamino C$_1$–C$_6$ alkyl.

Embodiment 14. Compounds according to embodiment 4,
wherein
R$_5$ is pyrazolyl(C$_1$–C$_6$ alkyl), imidazolyl(C$_1$–C$_6$ alkyl), thienyl(C$_1$–C$_6$ alkyl), furanyl(C$_1$–C$_6$ alkyl), piperidinyl (C$_1$–C$_6$)alkyl, pyrrolidinyl(C$_1$–C$_6$)alkyl, imidazolidinyl (C$_1$–C$_6$)alkyl, piperazinyl(C$_1$–C$_6$)alkyl, pyridyl(C$_1$–C$_6$) alkyl, pyrimidyl(C$_1$–C$_6$)alkyl, pyridazyl(C$_1$–C$_6$)alkyl, pyrazinyl(C$_1$–C$_6$)alkyl, isoquinolinyl(C$_1$–C$_6$)alkyl, tetrahydroisoquinolinyl(C$_1$–C$_6$)alkyl, indolyl(C$_1$–C$_6$) alkyl, 1H-indazolyl(C$_1$–C$_6$)alkyl, dihydroindolyl(C$_1$–C$_6$ alkyl), dihydroindolon-2-yl(C$_1$–C$_6$ alkyl), indolinyl (C$_1$–C$_6$ alkyl), dihydroisoindolyl(C$_1$–C$_6$ alkyl), dihydrobenzimdazolyl(C$_1$–C$_6$ alkyl), or dihydrobenzoimidazolonyl(C$_1$–C$_6$ alkyl), wherein
each of the above is unsubstituted or substituted with 1, 2, 3, 4, or 5 groups that are independently (C$_1$–C$_6$)alkyl, halogen, (C$_1$–C$_6$)alkoxy, (C$_1$–C$_6$)hydroxyalkyl, C$_1$–C$_6$ dihydroxyalkyl, phenyl(C$_1$–C$_6$)alkoxy, (C$_1$–C$_6$) thioalkoxy, (C$_1$–C$_6$)alkoxycarbonyl, phenyl(C$_1$–C$_6$) alkoxycarbonyl, OH, CO$_2$R, CN, amidinooxime, —NR$_8$R$_9$, —NR$_6$R$_7$, R$_6$R$_7$N—(C$_1$–C$_6$ alkyl)-, —C(O) NR$_6$R$_7$, —(C$_1$–C$_4$ alkyl)-C(O)NR$_6$R$_7$, amidino, piperazinyl, morpholinyl, —SO$_2$ (C$_1$–C$_6$)alkyl, —SO$_2$NH$_2$, —SO$_2$NH(C$_1$–C$_6$)alkyl, —SO$_2$N(C$_1$–C$_6$) alkyl(C$_1$–C$_6$)alkyl, (C$_1$–C$_4$,)haloalkyl, —(C$_1$–C$_4$ alkyl)-NR$_{15}$C(O)NR$_{16}$R$_{17}$, —(C$_1$–C$_4$ alkyl)-NR$_{15}$C(O) R$_{18}$, —O—CH$_2$—O, —O—CH$_2$CH$_2$—O—, or (C$_1$–C$_4$)haloalkoxy; wherein R$_6$ and R$_7$ are independently at each occurrence H, (C$_1$–C$_6$)alkyl, (C$_1$–C$_6$)alkoxy, (C$_1$–C$_6$)alkoxy (C$_1$–C$_6$)alkyl, (C$_1$–C$_6$)alkoxycarbonyl, (C$_1$–C$_6$) hydroxyalkyl, C$_1$–C$_6$ dihydroxyalkyl, —(C$_1$–C$_4$) alkyl-CO$_2$—(C$_1$–C$_6$)alkyl, (C$_1$–C$_6$)alkanoyl, phenyl (C$_1$–C$_6$)alkyl, phenyl(C$_1$–C$_6$)alkoxy, or phenyl (C$_1$–C$_6$)alkanoyl, wherein each of the above is unsubstituted or substituted with 1, 2, or 3 groups that are independently, halogen, (C$_1$–C$_4$)alkoxy, OH, SH, C$_3$–C$_6$ cycloalkyl, NH$_2$, NH(C$_1$–C$_6$ alkyl), N(C$_1$–C$_6$ alkyl)(C$_1$–C$_6$ alkyl), (C$_1$–C$_4$)alkyl, CF$_3$ or OCF$_3$; or R$_6$, R$_7$, and the nitrogen to which they are attached form a morpholinyl, thiomorpholinyl, piperidinyl, pyrrolidinyl, or piperazinyl ring which is optionally substituted with 1 or 2 groups that are independently C$_1$–C$_4$ alkyl, hydroxy, hydroxy C$_1$–C$_4$ alkyl, C$_1$–C$_4$ dihydroxyalkyl, or halogen; and R$_{18}$ is C$_1$–C$_6$ alkyl optionally substituted with —O—(C$_2$–C$_6$ alkanoyl, C$_1$–C$_6$ hydroxyalkyl, C$_1$–C$_6$ dihydroxyalkyl, C$_1$–C$_6$ alkoxy, C$_1$–C$_6$ alkoxy C$_1$–C$_6$ alkyl; amino C$_1$–C$_6$ alkyl, mono or dialkylamino C$_1$–C$_6$ alkyl.

In this embodiment, it is preferred that R$_6$ and R$_7$ are not simultaneously OH; and
R$_6$ and R$_7$ are not simultaneously —SO$_2$(C$_1$–C$_6$ alkyl)

Embodiment 15. Compounds according to embodiment 14,
wherein
R$_5$ is pyrazolyl(C$_1$–C$_6$ alkyl), imidazolyl(C$_1$–C$_6$ alkyl), benzimidazolyl(C$_1$–C$_6$ alkyl), thienyl(C$_1$–C$_6$ alkyl), pyrimidyl(C$_1$–C$_6$)alkyl, indolyl(C$_1$–C$_6$ alkyl), dihydroindolyl(C$_1$–C$_6$ alkyl), dihydroisoindolyl(C$_1$–C$_6$ alkyl), dihydroindolon-2-yl(C$_1$–C$_6$ alkyl), pyridinyl (C$_1$–C$_6$ alkyl), piperazinyl(C$_1$–C$_6$ alkyl), or pyrazinyl (C$_1$–C$_6$ alkyl) each of which is optionally substituted with 1, 2, or 3 groups that are independently C$_1$–C$_4$ alkyl, C$_1$–C$_4$ hydroxyalkyl, C$_1$–C$_4$ dihydroxyalkyl, halogen, —C(O)NR$_6$R$_7$, -(C$_1$–C$_4$ alkyl)-C(O)NR$_6$R$_7$, C$_1$–C$_6$ alkoxycarbonyl, —NR$_6$R$_7$, R$_6$R$_7$N—(C$_1$–C$_6$ alkyl)-, haloalkyl, C$_1$–C$_6$ alkanoyl, R$_6$ and R$_7$ at each occurrence are independently H, C$_1$–C$_6$ alkyl optionally substituted with 1, 2, or 3 groups that are independently C$_1$–C$_4$ alkoxycarbonyl, halogen, C$_3$–C$_6$ cycloalkyl, OH, SH, or C$_1$–C$_4$ alkoxy;

or

R$_6$, R$_7$, and the nitrogen to which they are attached form a piperidinyl, pyrrolidinyl, piperazinyl, or a morpholinyl ring optionally substituted with 1 or 2 groups that are independently alkyl, hydroxy, hydroxy C$_1$–C$_4$ alkyl, C$_1$–C$_4$ dihydroxyalkyl, or halogen.

Embodiment 16. Compounds according to embodiment 15,
wherein
R$_5$ is of the formula:

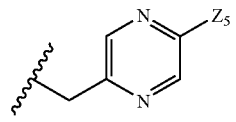

wherein
Z$_5$ is C$_1$–C$_4$ alkyl, C$_1$–C$_4$ hydroxyalkyl, C$_1$–C$_4$ dihydroxyalkyl, halogen, —C(O)NR$_6$R$_7$, —(C$_1$–C$_4$ alkyl)-C(O)NR$_6$R$_7$, C$_1$–C$_6$ alkoxycarbonyl, R$_6$R$_7$N—(C$_1$–C$_6$ alkyl)-, —NR$_6$R$_7$, CF$_3$, or C$_1$–C$_6$ alkanoyl, wherein R$_6$ and R$_7$ at each occurrence are independently H, C$_1$–C$_6$ alkyl optionally substituted with 1, 2, or 3 groups that are independently C$_1$–C$_4$ alkoxycarbonyl, halogen, C$_3$–C$_6$ cycloalkyl, OH, SH, or C$_1$–C$_4$ alkoxy;

or

R$_6$, R$_7$, and the nitrogen to which they are attached form a piperidinyl, pyrrolidinyl, piperazinyl, or a morpholinyl ring optionally substituted with 1 or 2 groups that are independently alkyl, hydroxy, hydroxy C$_1$–C$_4$ alkyl, C$_1$–C$_4$ dihydroxyalkyl, or halogen.

Embodiment 17. Compounds according to embodiment 15,
wherein
R$_5$ is of the formula:

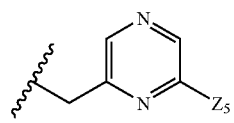

wherein
Z$_5$ is C$_1$–C$_4$ alkyl, C$_1$–C$_4$ hydroxyalkyl, C$_1$–C$_4$ dihydroxyalkyl, halogen, —C(O)NR$_6$R$_7$, —(C$_1$–C$_4$ alkyl)-C(O)NR$_6$R$_7$, C$_1$–C$_6$ alkoxycarbonyl, R$_6$R$_7$N—(C$_1$–C$_6$ alkyl)-, —NR$_6$R$_7$, CF$_3$, or C$_1$–C$_6$ alkanoyl, wherein R$_6$ and R$_7$ at each occurrence are independently H, C$_1$–C$_6$ alkyl optionally substituted with 1, 2, or 3 groups that are independently C$_1$–C$_4$ alkoxycarbonyl, halogen, C$_3$–C$_6$ cycloalkyl, OH, SH, or C$_1$–C$_4$ alkoxy;

or

R$_6$, R$_7$, and the nitrogen to which they are attached form a piperidinyl, pyrrolidinyl, piperazinyl, or a morpholinyl ring optionally substituted with 1 or 2 groups that are independently alkyl, hydroxy, hydroxy C$_1$–C$_4$ alkyl, C$_1$–C$_4$ dihydroxyalkyl, or halogen.

Embodiment 18. Compounds according to either embodiment 16 or 17, wherein
Z$_5$ is C$_1$–C$_4$ alkyl, C$_1$–C$_4$ hydroxyalkyl, C$_1$–C$_4$ dihydroxyalkyl, halogen, C$_1$–C$_6$ alkoxycarbonyl, CF$_3$, or C$_1$–C$_6$ alkanoyl.

Embodiment 19. Compounds according to either embodiment 16 or 17, wherein
Z$_5$ is C$_1$–C$_4$ alkyl, —C(O)NR$_6$R$_7$, —(C$_1$–C$_4$ alkyl)-C(O)NR$_6$R$_7$, R$_6$R$_7$N—(C$_1$–C$_6$ alkyl)-, or —NR$_6$R$_7$, CF$_3$, or C$_1$–C$_4$ alkanoyl, wherein R$_6$ and R$_7$ at each occurrence are independently H, C$_1$–C$_6$ alkyl optionally substituted with 1, 2, or 3 groups that are independently C$_1$–C$_4$ alkoxycarbonyl, halogen, C$_3$–C$_6$ cycloalkyl, OH, SH, or C$_1$–C$_4$ alkoxy;

or

R$_6$, R$_7$, and the nitrogen to which they are attached form a piperidinyl, pyrrolidinyl, piperazinyl, or a morpholinyl ring optionally substituted with 1 or 2 groups that are independently alkyl, hydroxy, hydroxy C$_1$–C$_4$ alkyl, C$_1$–C$_4$ dihydroxyalkyl, or halogen.

Embodiment 20. Compounds according to embodiment 19,
wherein
Z$_5$ is —C(O)NR$_6$R$_7$, —(C$_1$–C$_4$ alkyl)-C(O)NR$_6$R$_7$, R$_6$R$_7$N—(C$_1$–C$_6$ alkyl)-, or —NR$_6$R$_7$, wherein R$_6$ and R$_7$ at each occurrence are independently H, C$_1$–C$_6$ alkyl optionally substituted with 1, 2, or 3 groups that are independently C$_1$–C$_4$ alkoxycarbonyl, halogen, cyclopropyl, OH, SH, or C$_1$–C$_4$ alkoxy.

Embodiment 21. Compounds according to embodiment 15,
wherein
R$_5$ is of the formula:

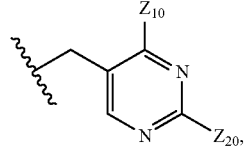

wherein
Z$_{10}$ is H or methyl; and
Z$_{20}$ is hydroxy(C$_1$–C$_4$)alkyl, C$_1$–C$_4$ dihydroxyalkyl, OH, halogen, haloalkyl, (C$_1$–C$_4$)alkyl, OCF$_3$, —NR$_6$R$_7$, R$_6$R$_7$N—(C$_1$–C$_6$ alkyl)-, —(C$_1$–C$_4$ alkyl)-C(O)NR$_6$R$_7$, or —C(O)NR$_6$R$_7$,
wherein
R$_6$ and R$_7$ at each occurrence are independently H, C$_1$–C$_6$ alkyl optionally substituted with 1, 2, or 3 groups that are independently C$_1$–C$_4$ alkoxycarbonyl, halogen, C$_3$–C$_6$ cycloalkyl, OH, SH, or C$_1$–C$_4$ alkoxy.

Embodiment 22. Compounds according to embodiment 15,
wherein
R$_5$ is of the formula:

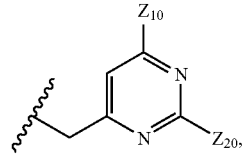

wherein $Z_{10}$ is H or methyl; and $Z_{20}$ is hydroxy($C_1$–$C_4$)alkyl, $C_1$–$C_4$ dihydroxyalkyl, OH, halogen, $CF_3$, ($C_1$–$C_4$)alkyl, $OCF_3$, —$NR_6R_7$, $R_6R_7N$—($C_1$–$C_6$ alkyl)-, —($C_1$–$C_4$ alkyl)-C(O)$NR_6R_7$, or —C(O)$NR_6R_7$, wherein $R_6$ and $R_7$ at each occurrence are independently H, $C_1$–$C_6$ alkyl optionally substituted with 1, 2, or 3 groups that are independently $C_1$–$C_4$ alkoxycarbonyl, halogen, $C_3$–$C_6$ cycloalkyl, OH, SH, or $C_1$–$C_4$ alkoxy.

Embodiment 23. Compounds according to embodiment 15, wherein $R_5$ is of the formula:

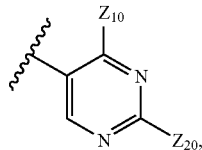

wherein $Z_{10}$ is H or methyl; and $Z_{20}$ is hydroxy($C_1$–$C_4$)alkyl, $C_1$–$C_4$ dihydroxyalkyl, OH, halogen, haloalkyl, ($C_1$–$C_4$)alkyl, $OCF_3$, —$NR_6R_7$, $R_6R_7N$—($C_1$–$C_6$ alkyl)-, —($C_1$–$C_4$ alkyl)-C(O)$NR_6R_7$, or —C(O)$NR_6R_7$, wherein $R_6$ and $R_7$ at each occurrence are independently H, $C_1$–$C_6$ alkyl optionally substituted with 1, 2, or 3 groups that are independently $C_1$–$C_4$ alkoxycarbonyl, halogen, $C_3$–$C_6$ cycloalkyl, OH, SH, or $C_1$–$C_4$ alkoxy.

Embodiment 24. Compounds according to embodiment 15, wherein $R_5$ is of the formula:

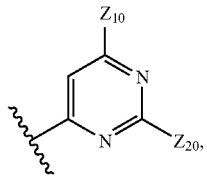

wherein $Z_{10}$ is H or methyl; and $Z_{20}$ is hydroxy($C_1$–$C_4$)alkyl, $C_1$–$C_4$ dihydroxyalkyl, OH, halogen, $CF_3$, ($C_1$–$C_4$)alkyl, $OCF_3$, —$NR_6R_7$, $R_6R_7N$—($C_1$–$C_6$ alkyl)-, —($C_1$–$C_4$ alkyl)-C(O)$NR_6R_7$, or —C(O)$NR_6R_7$ wherein $R_6$ and $R_7$ at each occurrence are independently H, $C_1$–$C_6$ alkyl optionally substituted with 1, 2, or 3 groups that are independently $C_1$–$C_4$ alkoxycarbonyl, halogen, $C_3$–$C_6$ cycloalkyl, OH, SH, or $C_1$–$C_4$ alkoxy.

Embodiment 25. Compounds according to embodiment 15, wherein $R_5$ is of the formula:

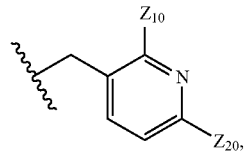

wherein $Z_{10}$ H or methyl; and $Z_{20}$ is hydroxy($C_1$–$C_4$)alkyl, $C_1$–$C_4$ dihydroxyalkyl, OH, halogen, haloalkyl, ($C_1$–$C_4$)alkyl, $OCF_3$, —$NR_6R_7$, $R_6R_7N$—($C_1$–$C_6$ alkyl)-, —($C_1$–$C_4$ alkyl)-C(O)$NR_6R_7$, or —C(O)$NR_6R_7$, wherein $R_6$ and $R_7$ at each occurrence are independently H, $C_1$–$C_6$ alkyl optionally substituted with 1, 2, or 3 groups that are independently $C_1$–$C_4$ alkoxycarbonyl, halogen, $C_3$–$C_6$ cycloalkyl, OH, SH, or $C_1$–$C_4$ alkoxy.

Embodiment 26. Compounds according to embodiment 15, wherein $R_5$ is of the formula:

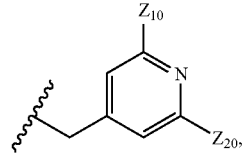

wherein $Z_{10}$ H or methyl; and $Z_{20}$ is hydroxy($C_1$–$C_4$)alkyl, $C_1$–$C_4$ dihydroxyalkyl, OH, halogen, $CF_3$, ($C_1$–$C_4$)alkyl, $OCF_3$, —$NR_6R_7$, $R_6R_7N$—($C_1$–$C_6$ alkyl)-, —($C_1$–$C_4$ alkyl)-C(O)$NR_6R_7$, or —C(O)$NR_6R_7$, wherein $R_6$ and $R_7$ at each occurrence are independently H, $C_1$–$C_6$ alkyl optionally substituted with 1, 2, or 3 groups that are independently $C_1$–$C_4$ alkoxycarbonyl, halogen, $C_3$–$C_6$ cycloalkyl, OH, SH, or $C_1$–$C_4$ alkoxy.

Embodiment 27. Compounds according to embodiment 15, wherein $R_5$ is of the formula:

wherein $Z_{10}$ H or methyl; and $Z_{20}$ is hydroxy($C_1$–$C_4$)alkyl, $C_1$–$C_4$ dihydroxyalkyl, OH, halogen, haloalkyl, ($C_1$–$C_4$)alkyl, $OCF_3$, —$NR_6R_7$, $R_6R_7N$—($C_1$–$C_6$ alkyl)-, —($C_1$–$C_4$ alkyl)-C(O)$NR_6R_7$, or —C(O)$NR_6R_7$, wherein $R_6$ and $R_7$ at each occurrence are independently H, $C_1$–$C_6$ alkyl optionally substituted with 1, 2, or 3 groups that are independently $C_1$–$C_4$ alkoxycarbonyl, halogen, $C_3$–$C_6$ cycloalkyl, OH, SH, or $C_1$–$C_4$ alkoxy.

Embodiment 28. Compounds according to embodiment 15, wherein
$R_5$ is of the formula:

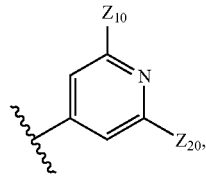

wherein
$Z_{10}$ H or methyl; and
$Z_{20}$ is hydroxy($C_1$–$C_4$)alkyl, $C_1$–$C_4$ dihydroxyalkyl, OH, halogen, $CF_3$, ($C_1$–$C_4$)alkyl, $OCF_3$, —$NR_6R_7$, $R_6R_7N$—($C_1$–$C_6$ alkyl)-, —($C_1$–$C_4$ alkyl)-C(O)$NR_6R_7$, or —C(O)$NR_6R_7$, wherein
$R_6$ and $R_7$ at each occurrence are independently H, $C_1$–$C_6$ alkyl optionally substituted with 1, 2, or 3 groups that are independently $C_1$–$C_4$ alkoxycarbonyl, halogen, $C_3$–$C_6$ cycloalkyl, OH, SH, or $C_1$–$C_4$ alkoxy.

Embodiment 29. Compounds according to embodiment 4, wherein
$R_5$ is phenyl, which is optionally substituted with 1, 2, 3, 4, or 5 groups that are independently $C_1$–$C_4$ alkyl, —C(O)$NR_6R_7$, —($C_1$–$C_4$ alkyl)-C(O)$NR_6R_7$, —$NR_6R_7$, $NR_6R_7$($C_1$–$C_6$ alkyl), $C_1$–$C_6$ hydroxyalkyl, dihydroxyalkyl, halogen, $C_1$–$C_4$ alkoxy, $CO_2R$, OH, $C_1$–$C_6$ alkoxycarbonyl, $CF_3$, —($C_1$–$C_4$ alkyl)-$NR_{15}$C(O)$NR_{16}R_{17}$, —($C_1$–$C_4$ alkyl)-$NR_{15}$C(O)$R_{18}$; wherein
$R_{15}$ is H or $C_1$–$C_6$ alkyl;
$R_{16}$ and $R_{17}$ are independently H or $C_1$–$C_6$ alkyl; or
$R_{16}$, $R_{17}$, and the nitrogen to which they are attached form a morpholinyl ring; and
$R_{18}$ is $C_1$–$C_6$ alkyl optionally substituted with —O—($C_2$–$C_6$ alkanoyl, $C_1$–$C_6$ hydroxyalkyl, $C_1$–$C_6$ dihydroxyalkyl, $C_1$–$C_6$ alkoxy, $C_1$–$C_6$ alkoxy $C_1$–$C_6$ alkyl; amino $C_1$–$C_6$ alkyl, mono or dialkylamino $C_1$–$C_6$ alkyl.

Embodiment 30. Compounds according to embodiment 29, wherein
$R_5$ is of the formula:

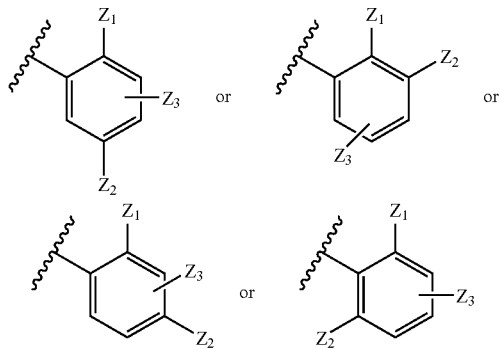

$Z_1$ is H, halogen, $C_1$–$C_4$ alkyl, $C_1$–$C_4$ haloalkyl, $C_1$–$C_4$ hydroxyalkyl, $C_1$–$C_4$ dihydroxyalkyl, or $C_1$–$C_4$ alkoxy; and
$Z_2$ is $C_1$–$C_4$ alkyl, —C(O)$NR_6R_7$, —($C_1$–$C_4$ alkyl)-C(O)$NR_6R_7$, —$NR_6R_7$, $NR_6R_7$($C_1$–$C_6$ alkyl), $C_1$–$C_6$ hydroxyalkyl, $C_1$–$C_6$ dihydroxyalkyl, halogen, $C_1$–$C_4$ alkoxy, $CO_2R$, OH, $C_1$–$C_6$ alkoxycarbonyl, or $C_1$–$C_4$ haloalkyl;

$Z_3$ is H, $C_1$–$C_4$ alkyl, —C(O)$NR_6R_7$, —($C_1$–$C_4$ alkyl)-C(O)$NR_6R_7$, —$NR_6R_7$, $NR_6R_7$($C_1$–$C_6$ alkyl), $C_1$–$C_6$ hydroxyalkyl, $C_1$–$C_6$ dihydroxyalkyl, halogen, $C_1$–$C_4$ alkoxy, $CO_2R$, OH, $C_1$–$C_6$ alkoxycarbonyl, or $C_1$–$C_4$ haloalkyl;
and wherein
$R_6$ and $R_7$ at each occurrence are independently H, OH, $C_1$–$C_6$ alkyl, amino $C_1$–$C_4$ alkyl, NH($C_1$–$C_6$ alkyl)alkyl, N($C_1$–$C_6$ alkyl)($C_1$–$C_6$ alkyl)$C_1$–$C_6$ alkyl, $C_1$–$C_6$ hydroxyalkyl, $C_1$–$C_6$ dihydroxyalkyl, $C_1$–$C_6$ alkoxy $C_1$–$C_6$ alkyl, —$SO_2$($C_1$–$C_6$ alkyl), —$SO_2NH_2$, —$SO_2NH$($C_1$–$C_6$ alkyl), —$SO_2N$($C_1$–$C_6$ alkyl)($C_1$–$C_6$ alkyl), or $C_1$–$C_6$ alkanoyl, each of which is optionally substituted with 1, 2, or 3 groups that are independently halogen, OH, SH, $C_3$–$C_6$ cycloalkyl, $C_1$–$C_4$ alkoxy, $C_1$–$C_4$ alkyl, OH, $CF_3$, or $OCF_3$.

In this embodiment, it is preferred that at least one of $Z_1$, $Z_2$, and $Z_3$ is not hydrogen.

Embodiment 31. Compounds according to embodiment 30, wherein $R_5$ is of the formula:

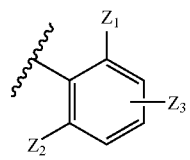

wherein $Z_1$ is H, halogen, $C_1$–$C_4$ alkyl, $C_1$–$C_4$ haloalkyl, $C_1$–$C_4$ hydroxyalkyl, $C_1$–$C_4$ dihydroxyalkyl, or $C_1$–$C_4$ alkoxy; and
$Z_2$ is $C_1$–$C_4$ alkyl, —C(O)$NR_6R_7$, —($C_1$–$C_4$ alkyl)-C(O)$NR_6R_7$, —$NR_6R_7$, $NR_6R_7$($C_1$–$C_6$ alkyl), $C_1$–$C_6$ hydroxyalkyl, $C_1$–$C_6$ dihydroxyalkyl, halogen, $C_1$–$C_4$ alkoxy, $CO_2R$, OH, $C_1$–$C_6$ alkoxycarbonyl, or $C_1$–$C_4$ haloalkyl;
$Z_3$ is H, $C_1$–$C_4$ alkyl, —C(O)$NR_6R_7$, —($C_1$–$C_4$ alkyl)-C(O)$NR_6R_7$, —$NR_6R_7$, $NR_6R_7$($C_1$–$C_6$ alkyl), $C_1$–$C_6$ hydroxyalkyl, $C_1$–$C_6$ dihydroxyalkyl, halogen, $C_1$–$C_4$ alkoxy, $CO_2R$, OH, $C_1$–$C_6$ alkoxycarbonyl, or $C_1$–$C_4$ haloalkyl, and wherein
$R_6$ and $R_7$ at each occurrence are independently H, OH, $C_1$–$C_6$ alkyl, amino $C_1$–$C_4$ alkyl, NH($C_1$–$C_6$ alkyl)alkyl, N($C_1$–$C_6$ alkyl)($C_1$–$C_6$ alkyl)$C_1$–$C_6$ alkyl, $C_1$–$C_6$ hydroxyalkyl, $C_1$–$C_6$ dihydroxyalkyl, $C_1$–$C_6$ alkoxy $C_1$–$C_6$ alkyl, —$SO_2$($C_1$–$C_6$ alkyl), —$SO_2NH_2$, —$SO_2NH$($C_1$–$C_6$ alkyl), —$SO_2N$($C_1$–$C_6$ alkyl)($C_1$–$C_6$ alkyl), or $C_1$–$C_6$ alkanoyl, each of which is optionally substituted with 1, 2, or 3 groups that are independently halogen, OH, SH, $C_3$–$C_6$ cycloalkyl, $C_1$–$C_4$ alkoxy, $C_1$–$C_4$ alkyl, OH, $CF_3$, or $OCF_3$.

In this embodiment, it is preferred that at least one of $Z_1$, $Z_2$, and $Z_3$ is not hydrogen.

Embodiment 32. Compounds according to embodiment 30,
wherein
$R_5$ is of the formula:

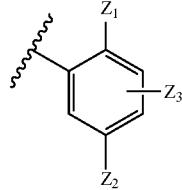

wherein
$Z_1$ is H, halogen, $C_1$–$C_4$ alkyl, $C_1$–$C_4$ haloalkyl, $C_1$–$C_4$ hydroxyalkyl, $C_1$–$C_4$ dihydroxyalkyl, or $C_1$–$C_4$ alkoxy; and $Z_2$ is $C_1$–$C_4$ alkyl, —C(O)$NR_6R_7$, —($C_1$–$C_4$ alkyl)-C(O)$NR_6R_7$, —$NR_6R_7$, $NR_6R_7$($C_1$–$C_6$ alkyl), $C_1$–$C_6$ hydroxyalkyl, $C_1$–$C_6$ dihydroxyalkyl, halogen, $C_1$–$C_4$ alkoxy, $CO_2R$, OH, $C_1$–$C_6$ alkoxycarbonyl, or $C_1$–$C_4$ haloalkyl;

$Z_3$ is H, $C_1$–$C_4$ alkyl, —C(O)$NR_6R_7$, —($C_1$–$C_4$ alkyl)-C(O)$NR_6R_7$, —$NR_6R_7$, $NR_6R_7$($C_1$–$C_6$ alkyl), $C_1$–$C_6$ hydroxyalkyl, $C_1$–$C_6$ dihydroxyalkyl, halogen, $C_1$–$C_4$ alkoxy, $CO_2R$, OH, $C_1$–$C_6$ alkoxycarbonyl, or $C_1$–$C_4$ haloalkyl, and wherein $R_6$ and $R_7$ at each occurrence are independently H, OH, $C_1$–$C_6$ alkyl, amino $C_1$–$C_4$ alkyl, NH($C_1$–$C_6$ alkyl) alkyl, N($C_1$–$C_6$ alkyl)($C_1$–$C_6$ alkyl)$C_1$–$C_6$ alkyl, $C_1$–$C_6$ hydroxyalkyl, $C_1$–$C_6$ dihydroxyalkyl, $C_1$–$C_6$ alkoxy $C_1$–$C_6$ alkyl, —$SO_2$($C_1$–$C_6$ alkyl), —$SO_2NH_2$, —$SO_2NH$($C_1$–$C_6$ alkyl), —$SO_2N$($C_1$–$C_6$ alkyl)($C_1$–$C_6$ alkyl), or $C_1$–$C_6$ alkanoyl, each of which is optionally substituted with 1, 2, or 3 groups that are independently halogen, OH, SH, $C_3$–$C_6$ cycloalkyl, $C_1$–$C_4$ alkoxy, $C_1$–$C_4$ alkyl, OH, $CF_3$, or $OCF_3$.

In this embodiment, it is preferred that at least one of $Z_1$, $Z_2$, and $Z_3$ is not hydrogen.

Embodiment 33. Compounds according to embodiment 29,
wherein
$R_5$ is either

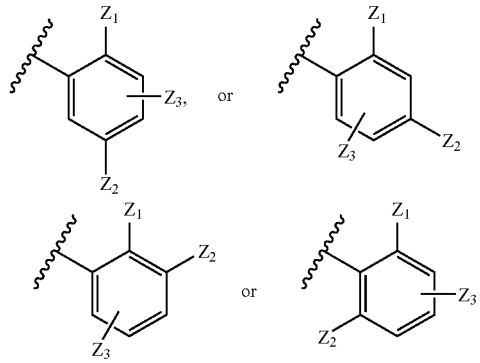

wherein
$Z_1$ is H, halogen, $C_1$–$C_4$ alkyl, $C_1$–$C_4$ haloalkyl, $C_1$–$C_4$ hydroxyalkyl, $C_1$–$C_4$ dihydroxyalkyl, or $C_1$–$C_4$ alkoxy; and $Z_2$ is $C_1$–$C_4$ alkyl, —C(O)$NR_6R_7$, —($C_1$–$C_4$ alkyl)-C(O)$NR_6R_7$, —$NR_6R_7$, $NR_6R_7$($C_1$–$C_6$ alkyl), $C_1$–$C_6$ hydroxyalkyl, $C_1$–$C_6$ dihydroxyalkyl, halogen, $C_1$–$C_4$ alkoxy, $CO_2R$, $C_1$–$C_6$ alkoxycarbonyl, —($C_1$–$C_4$ alkyl)-$NR_{15}C(O)NR_{16}R_{17}$, or —($C_1$–$C_4$ alkyl)-$NR_{15}C(O)R_{18}$;

$Z_3$ is H, $C_1$–$C_4$ alkyl, —C(O)$NR_6R_7$, —($C_1$–$C_4$ alkyl)-C(O)$NR_6R_7$, —$NR_6R_7$, $NR_6R_7$($C_1$–$C_6$ alkyl), $C_1$–$C_6$ hydroxyalkyl, $C_1$–$C_6$ dihydroxyalkyl, halogen, $C_1$–$C_4$ alkoxy, $CO_2R$, $C_1$–$C_6$ alkoxycarbonyl, —($C_1$–$C_4$ alkyl)-$NR_{15}C(O)NR_{16}R_{17}$, or —($C_1$–$C_4$ alkyl)-$NR_{15}C(O)R_{18}$;

$R_6$, $R_7$, and the nitrogen to which they are attached form a piperidinyl, pyrrolidinyl, piperazinyl, or a morpholinyl ring optionally substituted with 1 or 2 groups that are independently alkyl, hydroxy, hydroxy $C_1$–$C_4$ alkyl, $C_1$–$C_4$ dihydroxyalkyl, or halogen;

$R_{15}$ is H or $C_1$–$C_6$ alkyl;

$R_{16}$ and $R_{17}$ are independently H or $C_1$–$C_6$ alkyl; or $R_{16}$, $R_{17}$, and the nitrogen to which they are attached form a morpholinyl ring; and $R_{18}$ is $C_1$–$C_6$ alkyl optionally substituted with —O—($C_2$–$C_6$ alkanoyl, $C_1$–$C_6$ hydroxyalkyl, $C_1$–$C_6$ dihydroxyalkyl, $C_1$–$C_6$ alkoxy, $C_1$–$C_6$ alkoxy $C_1$–$C_6$ alkyl; amino $C_1$–$C_6$ alkyl, mono or dialkylamino $C_1$–$C_6$ alkyl.

In this embodiment, it is preferred that at least one of $Z_1$, $Z_2$, and $Z_3$ is not hydrogen.

Embodiment 34. Compounds according to embodiment 33,
wherein
$R_5$ is of the formula:

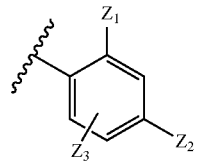

$Z_1$ is H, halogen, $C_1$–$C_4$ alkyl, $C_1$–$C_4$ haloalkyl, $C_1$–$C_4$ hydroxyalkyl, $C_1$–$C_4$ dihydroxyalkyl, or $C_1$–$C_4$ alkoxy; and $Z_2$ is $C_1$–$C_4$ alkyl, —C(O)$NR_6R_7$, —($C_1$–$C_4$ alkyl)-C(O)$NR_6R_7$, —$NR_6R_7$, $NR_6R_7$($C_1$–$C_6$ alkyl), $C_1$–$C_6$ hydroxyalkyl, $C_1$–$C_6$ dihydroxyalkyl, halogen, $C_1$–$C_4$ alkoxy, $CO_2R$, $C_1$–$C_6$ alkoxycarbonyl, —($C_1$–$C_4$ alkyl)-$NR_{15}C(O)NR_{16}R_{17}$, or —($C_1$–$C_4$ alkyl)-$NR_{15}C(O)R_{18}$;

$Z_3$ is H, $C_1$–$C_4$ alkyl, —C(O)$NR_6R_7$, —($C_1$–$C_4$ alkyl)-C(O)$NR_6R_7$, —$NR_6R_7$, $NR_6R_7$($C_1$–$C_6$ alkyl), $C_1$–$C_6$ hydroxyalkyl, $C_1$–$C_6$ dihydroxyalkyl, halogen, $C_1$–$C_4$ alkoxy, $CO_2R$, $C_1$–$C_6$ alkoxycarbonyl, —($C_1$–$C_4$ alkyl)-$NR_{15}C(O)NR_{16}R_{17}$, or —($C_1$–$C_4$ alkyl)-$NR_{15}C(O)R_{18}$;

$R_6$, $R_7$, and the nitrogen to which they are attached form a piperidinyl, pyrrolidinyl, piperazinyl, or a morpholinyl ring optionally substituted with 1 or 2 groups that are independently alkyl, hydroxy, hydroxy $C_1$–$C_4$ alkyl, $C_1$–$C_4$ dihydroxyalkyl, or halogen;

$R_{15}$ is H or $C_1$–$C_6$ alkyl;

$R_{16}$ and $R_{17}$ are independently H or $C_1$–$C_6$ alkyl; or $R_{16}$, $R_{17}$, and the nitrogen to which they are attached form a morpholinyl ring; and $R_{18}$ is $C_1$–$C_6$ alkyl optionally substituted with —O—($C_2$–$C_6$ alkanoyl, $C_1$–$C_6$ hydroxyalkyl, $C_1$–$C_6$ dihydroxyalkyl, $C_1$–$C_6$ alkoxy, $C_1$–$C_6$ alkoxy $C_1$–$C_6$ alkyl; amino $C_1$–$C_6$ alkyl, mono or dialkylamino $C_1$–$C_6$ alkyl.

In this embodiment, it is preferred that at least one of $Z_1$, $Z_2$, and $Z_3$ is not hydrogen.

Embodiment 35. Compounds according to embodiment 33, wherein $R_5$ is of the formula:

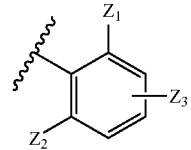

wherein $Z_1$ is H, halogen, $C_1$–$C_4$ alkyl $C_1$–$C_4$ haloalkyl, $C_1$–$C_4$ hydroxyalkyl, $C_1$–$C_4$ dihydroxyalkyl, or $C_1$–$C_4$ alkoxy; and $Z_2$ is $C_1$–$C_4$ alkyl, —C(O)$NR_6R_7$, —($C_1$–$C_4$ alkyl)-C(O)$NR_6R_7$, —$NR_6R_7$, $NR_6R_7$($C_1$–$C_6$ alkyl), $C_1$–$C_6$ hydroxyalkyl, $C_1$–$C_6$ dihydroxyalkyl, halogen, $C_1$–$C_4$ alkoxy, $CO_2R$, $C_1$–$C_6$ alkoxycarbonyl, —($C_1$–$C_4$ alkyl)-$NR_{15}C(O)NR_{16}R_{17}$, or —($C_1$–$C_4$ alkyl)-$NR_{15}C(O)R_{18}$;

$Z_3$ is H, $C_1$–$C_4$ alkyl, —C(O)$NR_6R_7$, —($C_1$–$C_4$ alkyl)-C(O)$NR_6R_7$, —$NR_6R_7$, $NR_6R_7$($C_1$–$C_6$ alkyl), $C_1$–$C_6$ hydroxyalkyl, $C_1$–$C_6$ dihydroxyalkyl, halogen, $C_1$–$C_4$ alkoxy, $CO_2R$, $C_1$–$C_6$ alkoxycarbonyl, —($C_1$–$C_4$ alkyl)-$NR_{15}C(O)NR_{16}R_{17}$, or —($C_1$–$C_4$ alkyl)-$NR_{15}C(O)R_{18}$;

$R_6$, $R_7$, and the nitrogen to which they are attached form a piperidinyl, pyrrolidinyl, piperazinyl, or a morpholinyl ring, each of which is optionally substituted with 1 or 2 groups that are independently alkyl, hydroxy, hydroxy $C_1$–$C_4$ alkyl, $C_1$–$C_4$ dihydroxyalkyl, or halogen;

$R_{15}$ is H or $C_1$–$C_6$ alkyl;

$R_{16}$ and $R_{17}$ are independently H or $C_1$–$C_6$ alkyl; or $R_{16}$, $R_{17}$, and the nitrogen to which they are attached form a morpholinyl ring; and $R_{18}$ is $C_1$–$C_6$ alkyl optionally substituted with —O—($C_2$–$C_6$ alkanoyl, $C_1$–$C_6$ hydroxyalkyl, $C_1$–$C_6$ dihydroxyalkyl, $C_1$–$C_6$ alkoxy, $C_1$–$C_6$ alkoxy $C_1$–$C_6$ alkyl; amino $C_1$–$C_6$ alkyl, mono or dialkylamino $C_1$–$C_6$ alkyl.

In this embodiment, it is preferred that at least one of $Z_1$, $Z_2$, and $Z_3$ is not hydrogen.

Embodiment 36. A compound of the formula

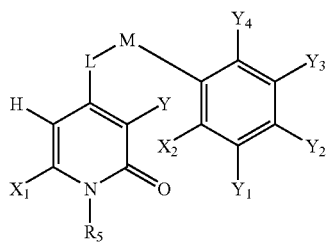

or a pharmaceutically acceptable salt thereof, wherein

L and M are indepedently selected from —O—, —$CH_2$—, —S—, —NR—, —N(R)—N(R)—, C(=O)—, —$SO_2$—;

$R_5$ is

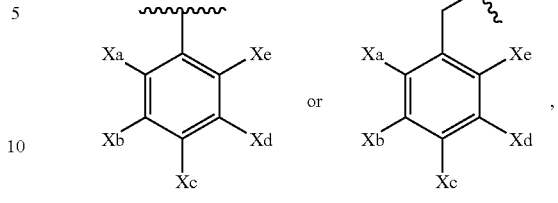

wherein $X_1$, $X_2$, $X_a$, $X_b$, $X_c$, $X_d$, and $X_e$ at are independently selected from —C(O)$NR_6R_7$, —($C_1$–$C_4$ alkyl)-C(O)$NR_6R_7$, —$NR_6R_7$, hydroxy($C_1$–$C_4$)alkyl, $C_1$–$C_4$ dihydroxyalkyl, H, OH, halogen, haloalkyl, alkyl, haloalkoxy, heteroaryl, heterocycloalkyl, $C_3$–$C_7$ cycloalkyl, $R_6R_7N$—($C_1$–$C_6$ alkyl)-, —$CO_2$—($C_1$–$C_6$)alkyl, —N(R)C(O)$NR_6R_7$, —N(R)C(O)—($C_1$–$C_6$)alkoxy, $CO_2R$—($C_1$–$C_6$ alkyl)-, or —$SO_2NR_6R_7$; wherein the heteroaryl and heterocycloalkyl groups are optionally substituted with —$NR_6R_7$, —C(O)$NR_6R_7$, $R_6R_7N$—($C_1$–$C_6$ alkyl)-, $C_1$–$C_6$ alkyl, $C_1$–$C_6$ alkoxy, or halogen; or $R_5$ is heteroaryl or heteroarylalkyl, wherein the heteroaryl and heteroaryl groups are optionally substituted with 1,2, 3, or 4 groups that are independently —C(O)$NR_6R_7$, —($C_1$–$C_4$ alkyl)-C(O)$NR_6R_7$, —$NR_6R_7$, hydroxy($C_1$–$C_4$)alkyl, $C_1$–$C_4$ dihydroxyalkyl, H, OH, halogen, haloalkyl, alkyl, haloalkoxy, $R_6R_7N$—($C_1$–$C_6$ alkyl)-, —$CO_2$—($C_1$–$C_6$)alkyl, —N(R)C(O)$NR_6R_7$, or —N(R)C(O)—($C_1$–$C_6$)alkoxy; wherein $R_6$ and $R_7$ are independently at each occurrence H, $C_1$–$C_6$ alkyl, $C_1$–$C_6$ alkoxy, $C_1$–$C_6$ alkoxy $C_1$–$C_6$ alkyl, $C_1$–$C_6$ alkoxycarbonyl, OH, $C_1$–$C_6$ hydroxyalkyl, $C_1$–$C_4$ dihydroxyalkyl, $C_1$–$C_6$ thiohydroxyalkyl, —($C_1$–$C_4$) alkyl-$CO_2$-alkyl, pyridyl $C_1$–$C_6$ alkyl, $C_1$–$C_6$ alkanoyl, benzyl, phenyl $C_1$–$C_6$ alkoxy, or phenyl $C_1$–$C_6$ alkanoyl, wherein each of the above is unsubstituted or substituted with 1, 2, or 3 groups that are independently, halogen, $C_3$–$C_6$ cycloalkyl, $C_1$–$C_6$ alkoxy, piperidinyl $C_1$–$C_6$ alkyl, morpholinyl $C_1$–$C_6$ alkyl, piperazinyl $C_1$–$C_6$ alkyl, OH, SH, $NH_2$, NH(alkyl), N(alkyl)(alkyl), —O—$C_1$–$C_4$ alkanoyl, $C_1$–$C_4$ alkyl, $CF_3$, or $OCF_3$; or $R_6$, $R_7$, and the nitrogen to which they are attached form a morpholinyl, thiomorpholinyl, piperidinyl, pyrrolidinyl, or piperazinyl ring which is optionally substituted with 1 or 2 groups that are independently $C_1$–$C_4$ alkyl, $C_1$–$C_4$ alkoxy, hydroxy, hydroxy $C_1$–$C_4$ alkyl, $C_1$–$C_4$ dihydroxyalkyl, or halogen;

R at each occurrence is independently H or $C_1$–$C_6$ alkyl; and

Y, $Y_1$, $Y_2$, Y3, and $Y_4$ are independently selected from H, halogen, alkyl, carboxaldehyde, hydroxyalkyl, dihydroxyalkyl, alkenyl, alkynyl, CN, alkanoyl, alkoxy, alkoxyalkyl, haloalkyl, and carboxyl.

Embodiment 37. Compounds according to embodiment 36 of the formula

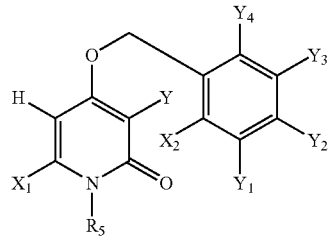

or a pharmaceutically acceptable salt thereof.

Embodiment 38. Compounds according to embodiment 37,
wherein
$R_5$ is

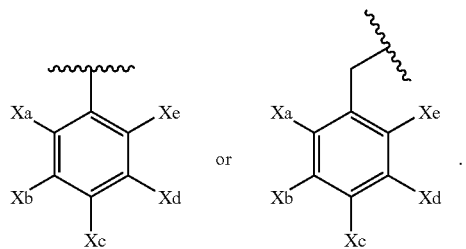

Embodiment 39. Compounds according to embodiment 31, wherein
$Y_2$, $Y_4$, and Y are independently halogen; and
$Y_1$ and $Y_3$ are both hydrogen.

Embodiment 40. Compounds according to embodiment 39,
wherein
$R_5$ is

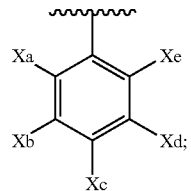

$X_1$ and $X_2$ are independently H, methyl, $NR_6R_7$, —($C_1$–$C_4$ alkyl)-C(O)$NR_6R_7$, $R_6R_7N$—($C_1$–$C_6$ alkyl)-, —C(O) $NR_6R_7$, $C_1$–$C_6$ hydroxyalkyl, $C_1$–$C_6$ dihydroxyalkyl, or —($C_1$–$C_4$ alkyl)-morpholinyl; and
$X_a$ and $X_e$ are independently halogen, $NH_2$, NH($C_1$–$C_6$ alkyl), N($C_1$–$C_6$ alkyl)($C_1$–$C_6$ alkyl), methyl, or hydrogen.

In this embodiment, it is preferred that one of $X_a$ and $X_e$ is not hydrogen.

Embodiment 41. Compounds according to embodiment 40,
wherein
one of $X_b$ and $X_c$ is hydrogen and the other is —$NR_6R_7$, $R_6R_7N$—($C_1$–$C_6$ alkyl)-, —C(O)$NR_6R_7$, —$SO_2NR_6R_7$, or halogen; where
$R_6$ and $R_7$ are independently at each occurrence H, $C_1$–$C_6$ alkyl, $C_1$–$C_6$ alkoxy, $C_1$–$C_6$ alkoxy $C_1$–$C_6$ alkyl, $C_1$–$C_6$ alkoxycarbonyl, OH, $C_1$–$C_6$ hydroxyalkyl, $C_1$–$C_6$ dihydroxyalkyl, —($C_1$–$C_4$)alkyl-$CO_2$-alkyl, pyridyl $C_1$–$C_6$ alkyl, $C_1$–$C_6$ alkanoyl, benzyl, phenyl $C_1$–$C_6$ alkoxy, or phenyl $C_1$–$C_6$ alkanoyl, wherein each of the above is unsubstituted or substituted with 1, 2, or 3 groups that are independently, halogen, $C_3$–$C_6$ cycloalkyl, $C_1$–$C_6$ alkoxy, piperidinyl $C_1$–$C_6$ alkyl, morpholinyl $C_1$–$C_6$ alkyl, piperazinyl $C_1$–$C_6$ alkyl, OH, SH, $NH_2$, NH(alkyl), N(alkyl)(alkyl), —O—$C_1$–$C_4$ alkanoyl, $C_1$–$C_4$ alkyl, $CF_3$, or $OCF_3$; or
$R_6$, $R_7$, and the nitrogen to which they are attached form a morpholinyl, thiomorpholinyl, piperidinyl, pyrrolidinyl, or piperazinyl ring which is optionally substituted with 1 or 2 groups that are independently $C_1$–$C_4$ alkyl, $C_1$–$C_4$ alkoxy, hydroxy, hydroxy $C_1$–$C_4$ alkyl, $C_1$–$C_4$ dihydroxyalkyl, or halogen.

Embodiment 42. Compounds according to embodiment 41,
wherein
$R_6$ and $R_7$ are independently at each occurrence H, $C_1$–$C_6$ alkyl, $C_1$–$C_6$ alkoxy, $C_1$–$C_6$ alkoxy $C_1$–$C_6$ alkyl, $C_1$–$C_6$ alkoxycarbonyl, OH, $C_1$–$C_6$ hydroxyalkyl, $C_1$–$C_6$ dihydroxyalkyl, —($C_1$–$C_4$)alkyl-$CO_2$-alkyl, pyridyl $C_1$–$C_6$ alkyl, $C_1$–$C_6$ alkanoyl, benzyl, phenyl $C_1$–$C_6$ alkoxy, or phenyl $C_1$–$C_6$ alkanoyl, wherein each of the above is unsubstituted or substituted with 1, 2, or 3 groups that are independently, halogen, $C_3$–$C_6$ cycloalkyl, $C_1$–$C_6$ alkoxy, piperidinyl $C_1$–$C_6$ alkyl, morpholinyl $C_1$–$C_6$ alkyl, piperazinyl $C_1$–$C_6$ alkyl, OH, $NH_2$, NH(alkyl), N(alkyl)(alkyl), —O—$C_1$–$C_4$ alkanoyl, $C_1$–$C_4$ alkyl, $CF_3$, or $OCF_3$.

Embodiment 43. Compounds according to embodiment 42,
wherein
$X_a$ is hydrogen, methyl, fluorine, or chlorine;
$X_c$ and $X_d$ are both hydrogen;
$X_b$ is —$NR_6R_7$, —($C_1$–$C_4$ alkyl)-C(O)$NR_6R_7$, $R_6R_7N$—($C_1$–$C_6$ alkyl)-, —C(O)$NR_6R_7$; wherein
$R_6$ and $R_7$ are independently at each occurrence H, $C_1$–$C_6$ alkyl, $C_1$–$C_6$ hydroxyalkyl, $C_1$–$C_4$ dihydroxyalkyl, $C_1$–$C_6$ alkoxy, $C_1$–$C_6$ alkoxy $C_1$–$C_6$ alkyl, or $C_1$–$C_6$ alkanoyl, wherein each of the above is optionally substituted with 1, 2, or 3 groups that are independently OH, SH, halogen, or $C_3$–$C_6$ cycloalkyl.

Embodiment 44. Compounds according to embodiment 39,
wherein
$R_5$ is

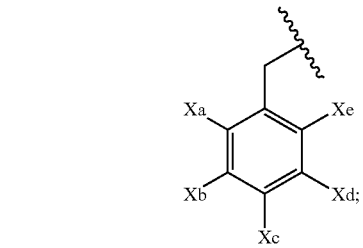

$X_a$ is H, fluoro, chloro, or methyl;
$X_e$ is hydrogen, halogen, or methyl; and
$X_b$ is H;
$X_d$ is H or halogen;

Embodiment 45. Compounds according to embodiment 44,
wherein
$X_c$ is —$SO_2NR_6R_7$, or halogen; wherein
$R_6$ and $R_7$ are independently at each occurrence H, $C_1$–$C_6$ alkyl, $C_1$–$C_6$ alkoxy, $C_1$–$C_6$ alkoxy $C_1$–$C_6$ alkyl, $C_1$–$C_6$ alkoxycarbonyl, OH, $C_1$–$C_6$ hydroxyalkyl, $C_1$–$C_6$ dihydroxyalkyl, —($C_1$–$C_4$)alkyl-$CO_2$-alkyl, pyridyl $C_1$–$C_6$ alkyl, $C_1$–$C_6$ alkanoyl, benzyl, phenyl $C_1$–$C_6$ alkoxy, or phenyl $C_1$–$C_6$ alkanoyl, wherein each of the above is unsubstituted or substituted with 1, 2, or 3 groups that are independently, halogen, $C_3$–$C_6$ cycloalkyl, $C_1$–$C_6$ alkoxy, piperidinyl $C_1$–$C_6$ alkyl, morpholinyl $C_1$–$C_6$ alkyl, piperazinyl $C_1$–$C_6$ alkyl, OH, SH, $NH_2$, NH(alkyl), N(alkyl)(alkyl), —O—$C_1$–$C_4$ alkanoyl, $C_1$–$C_4$ alkyl, $CF_3$, or $OCF_3$; or $R_6$, $R_7$, and the nitrogen to which they are attached form a morpholinyl, thiomorpholinyl, piperidinyl, pyrrolidinyl, or piperazinyl ring which is optionally substituted with 1 or 2 groups that are independently $C_1$–$C_4$ alkyl, $C_1$–$C_4$ alkoxy, hydroxy, hydroxy $C_1$–$C_4$ alkyl, $C_1$–$C_4$ dihydroxyalkyl, or halogen; or $X_c$ is fluoro, chloro, —$NH_2$, —NH($C_1$–$C_6$ alkyl), —N($C_1$–$C_6$ alkyl)($C_1$–$C_6$ alkyl), —$SO_2NH_2$, —$SO_2$NH ($C_1$–$C_6$ alkyl), —$SO_2$N($C_1$–$C_6$ alkyl)($C_1$–$C_6$ alkyl), or piperazinyl, wherein the piperazinyl group is optionally substituted with 1 or 2 groups that are independently $C_1$–$C_4$ alkyl, $C_1$–$C_4$ alkoxy, hydroxy, hydroxy $C_1$–$C_4$ alkyl, $C_1$–$C_4$ dihydroxyalkyl, or halogen.

Embodiment 46. Compounds according to embodiment 44,
wherein
$X_c$ is —C(O)$NR_6R_7$, —($C_1$–$C_6$ alkyl)-C(O)$NR_6R_7$, —$NR_6R_7$, or $R_6R_7$N—($C_1$–$C_6$ alkyl)-; wherein $R_6$ and $R_7$ are independently at each occurrence H, $C_1$–$C_6$ alkyl, $C_1$–$C_6$ alkoxy, $C_1$–$C_6$ alkoxy $C_1$–$C_6$ alkyl, $C_1$–$C_6$ alkoxycarbonyl, OH, $C_1$–$C_6$ hydroxyalkyl, $C_1$–$C_6$ dihydroxyalkyl, $C_1$–$C_6$ dihydroxyalkyl, —($C_1$–$C_4$) alkyl-$CO_2$-alkyl, pyridyl $C_1$–$C_6$ alkyl, $C_1$–$C_6$ alkanoyl, benzyl, phenyl $C_1$–$C_6$ alkoxy, or phenyl $C_1$–$C_6$ alkanoyl wherein each of the above is unsubstituted or substituted with 1, 2, or 3 groups that are independently, halogen, $C_3$–$C_6$ cycloalkyl, $C_1$–$C_6$ alkoxy, piperidinyl $C_1$–$C_6$ alkyl, morpholinyl $C_1$–$C_6$ alkyl, piperazinyl $C_1$–$C_6$ alkyl, OH, —$NH_2$, —NH (alkyl), —N(alkyl)(alkyl), —O—$C_1$–$C_4$ alkanoyl, $C_1$–$C_4$ alkyl, $CF_3$, or $OCF_3$; or $R_6$, $R_7$, and the nitrogen to which they are attached form a morpholinyl, thiomorpholinyl, piperidinyl, pyrrolidinyl, or piperazinyl ring which is optionally substituted with 1 or 2 groups that are independently $C_1$–$C_4$ alkyl, $C_1$–$C_4$ alkoxy, hydroxy, hydroxy $C_1$–$C_4$ alkyl, $C_1$–$C_4$ dihydroxyalkyl, or halogen.

Embodiment 47. Compounds according to embodiment 46,
wherein
$R_6$ is hydrogen; and
$R_7$ is $C_1$–$C_6$ alkyl or $C_1$–$C_6$ alkanoyl, each of which is optionally substituted with 1, 2, or 3 groups that are independently $NH_2$, NH($C_1$–$C_6$ alkyl), N($C_1$–$C_6$ alkyl)($C_1$–$C_6$ alkyl), OH, SH, cyclopropyl, or $C_1$–$C_4$ alkoxy;

Embodiment 48. Compounds according to embodiment 47,
wherein
$X_c$ is —C(O)$NR_6R_7$.

Embodiment 49. Compounds according to embodiment 47,
wherein
$X_c$ is $NR_6R_7$, or $R_6R_7$N—($C_1$–$C_6$ alkyl)-.

Embodiment 50. Compounds according to embodiment 38, wherein
$X_a$ is hydrogen;
two of $X_b$, $X_c$, and $X_d$ are hydrogen and the other is —C(O)$NR_6R_7$, —($C_1$–$C_6$ alkyl)-C(O)$NR_6R_7$, —$NR_6R_7$, $R_6R_7$N—($C_1$–$C_6$ alkyl)- or —$CO_2$—($C_1$–$C_6$)alkyl;

wherein
$R_6$ and $R_7$ are independently at each occurrence H, $C_1$–$C_6$ alkyl, $C_1$–$C_6$ alkoxy, $C_1$–$C_6$ alkoxy $C_1$–$C_6$ alkyl, $C_1$–$C_6$ alkoxycarbonyl, OH, $C_1$–$C_6$ hydroxyalkyl, $C_1$–$C_6$ dihydroxyalkyl, —($C_1$–$C_4$)alkyl-$CO_2$-alkyl, pyridyl $C_1$–$C_6$ alkyl, $C_1$–$C_6$ alkanoyl, benzyl, phenyl $C_1$–$C_6$ alkoxy, or phenyl $C_1$–$C_6$ alkanoyl, wherein each of the above is unsubstituted or substituted with 1, 2, or 3 groups that are independently, halogen, $C_3$–$C_6$ cycloalkyl, $C_1$–$C_6$ alkoxy, piperidinyl $C_1$–$C_6$ alkyl, morpholinyl $C_1$–$C_6$ alkyl, piperazinyl $C_1$–$C_6$ alkyl, OH, $NH_2$, NH(alkyl), N(alkyl)(alkyl), —O—$C_1$–$C_4$ alkanoyl, $C_1$–$C_4$ alkyl, $CF_3$, or $OCF_3$; or $R_6$, $R_7$, and the nitrogen to which they are attached form a morpholinyl, piperidinyl, pyrrolidinyl, or piperazinyl ring which is optionally substituted with 1 or 2 groups that are independently $C_1$–$C_4$ alkyl, $C_1$–$C_4$ alkoxy, hydroxy, hydroxy $C_1$–$C_4$ alkyl, $C_1$–$C_4$ dihydroxyalkyl, or halogen; and $X_c$ is hydrogen, methyl, $C_1$–$C_2$ alkoxy, or halogen.

Embodiment 51. Compounds according to embodiment 50,
wherein
$X_b$ is —C(O)$NR_6R_7$, —($C_1$–$C_6$ alkyl)-C(O)$NR_6R_7$, —$NR_6R_7$, or $R_6R_7$N—($C_1$–$C_6$ alkyl)- wherein
$R_6$ is hydrogen or $C_1$–$C_4$ alkyl;
$R_7$ is OH, $C_1$–$C_6$ alkyl or $C_1$–$C_6$ alkanoyl, wherein the alkyl and alkanoyl groups substituted with 1, 2, or 3 groups that are independently $NH_2$, NH($C_1$–$C_6$ alkyl), N($C_1$–$C_6$ alkyl)($C_1$–$C_6$ alkyl), $C_3$–$C_6$ cycloalkyl, OH, or $C_1$–$C_4$ alkoxy.

Embodiment 52. Compounds according to embodiment 38,
wherein
$X_a$ is halogen or methyl;
$X_b$ is H, —$NR_6R_7$, $R_6R_7$N—($C_1$–$C_6$ alkyl)-, —C(O)$NR_6R_7$, or —$CO_2$—($C_1$–$C_6$)alkyl;
$X_c$ is —$NR_6R_7$, $R_6R_7$N—($C_1$–$C_6$ alkyl)-, —C(O)$NR_6R_7$, halogen, —$CO_2$—($C_1$–$C_6$)alkyl, $NH_2$, NH($C_1$–$C_6$ alkyl), N($C_1$–$C_6$ alkyl)($C_1$–$C_6$ alkyl), —$SO_2NH_2$, —$SO_2$NH ($C_1$–$C_6$ alkyl), —$SO_2$N($C_1$–$C_6$ alkyl)($C_1$–$C_6$ alkyl), or piperazinyl, wherein the piperazinyl group is optionally substituted with 1 or 2 groups that are independently $C_1$–$C_4$ alkyl, $C_1$–$C_4$ alkoxy, hydroxy, hydroxy $C_1$–$C_4$ alkyl, $C_1$–$C_4$ dihydroxyalkyl, or halogen;
$X_d$ is hydrogen;
$X_e$ is H, methyl, $NH_2$, NH($C_1$–$C_6$ alkyl) or N($C_1$–$C_6$ alkyl)($C_1$–$C_6$ alkyl).

Embodiment 53. Compounds according to embodiment 38,
wherein
$X_1$, $X_2$, $X_a$, $X_b$, $X_c$, $X_d$, and $X_e$ are independently selected from H, OH, halogen, $CF_3$, alkyl, $OCF_3$, pyridyl, pyridazinyl, pyrimidyl, pyrazinyl, thienyl, furyl, pyrrolyl, piperidinyl, piperazinyl, or $C_3$–$C_7$ cycloalkyl, wherein each of the above is optionally substituted with —$NR_6R_7$, —C(O)$NR_6R_7$, —($C_1$–$C_4$ alkyl)-C(O)$NR_6R_7$, $R_6R_7$N—($C_1$–$C_6$ alkyl)-, $C_1$–$C_6$ alkyl, $C_1$–$C_6$ alkoxy, or halogen.

Embodiment 54. Compounds according to embodiment 37,
wherein
$R_5$ is a heteroaryl or heteroarylalkyl group, where each heteroaryl is pyrazolyl, imidazolyl, furanyl, pyridyl, pyridazinyl, pyrimidinyl, pyrazinyl, pyrazolyl, imidazolyl, dihydroindolyl, dihydroisoindolyl, indolon-2-yl, quinolinyl, isoquinolinyl, tetrahydroisoquinolinyl, dihydroisoquinolinyl, or indolyl, each of which is optionally substituted with 1, 2, 3, or 4 groups that are independently —C(O)NR$_6$R$_7$, —(C$_1$–C$_4$ alkyl)-C(O)NR$_6$R$_7$, —NR$_6$R$_7$, hydroxy(C$_1$–C$_4$)alkyl, C$_1$–C$_4$ dihydroxyalkyl, hydrogen, hydroxy, halogen, haloalkyl, alkyl, haloalkoxy, R$_6$R$_7$N—(C$_1$–C$_6$ alkyl)-, —CO$_2$—(C$_1$–C$_6$)alkyl, —N(R)C(O)NR$_6$R$_7$, or —N(R)C(O)—(C$_1$–C$_6$)alkoxy; wherein R$_6$ and R$_7$ are independently at each occurrence H, C$_1$–C$_6$ alkyl, C$_1$–C$_6$ alkoxy, C$_1$–C$_6$ alkoxy C$_1$–C$_6$ alkyl, C$_1$–C$_6$ alkoxycarbonyl, OH, C$_1$–C$_6$ hydroxyalkyl, C$_1$–C$_6$ dihydroxyalkyl, C$_1$–C$_6$ thiohydroxyalkyl, —(C$_1$–C$_4$)alkyl-CO$_2$-alkyl, pyridyl C$_1$–C$_6$ alkyl, C$_1$–C$_6$ alkanoyl, benzyl, phenyl C$_1$–C$_6$ alkoxy, or phenyl C$_1$–C$_6$ alkanoyl, wherein each of the above is unsubstituted or substituted with 1, 2, or 3 groups that are independently, halogen, C$_3$–C$_6$ cycloalkyl, C$_1$–C$_6$ alkoxy, piperidinyl C$_1$–C$_6$ alkyl, morpholinyl C$_1$–C$_6$ alkyl, piperazinyl C$_1$–C$_6$ alkyl, OH, SH, NH$_2$, NH(alkyl), N(alkyl)(alkyl), —O—C$_1$–C$_4$ alkanoyl, C$_1$–C$_4$ alkyl, CF$_3$, or OCF.

Embodiment 55. Compounds according to embodiment 54, wherein

Y$_2$, Y$_4$, and Y are independently halogen; and
Y$_1$ and Y$_3$ are both hydrogen.

Embodiment 56. Compounds according to embodiment 55, wherein

X$_1$ and X$_2$ are independently H, methyl, —NR$_6$R$_7$, R$_6$R$_7$N—(C$_1$–C$_6$ alkyl)-, —C(O)NR$_6$R$_7$, —(C$_1$–C$_4$ alkyl)-C(O)NR$_6$R$_7$, C$_1$–C$_6$ hydroxyalkyl, C$_1$–C$_6$ dihydroxyalkyl, or —(C$_1$–C$_4$ alkyl)-morpholinyl.

Embodiment 57. Compounds according to embodiment 56, wherein

R$_5$ is pyridyl C$_1$–C$_6$ alkyl, pyrimidinyl C$_1$–C$_6$ alkyl, or pyrazinyl C$_1$–C$_6$ alkyl, each of which is optionally substituted with 1, 2, or 3 groups that are independently hydroxy(C$_1$–C$_4$)alkyl, C$_1$–C$_4$ dihydroxyalkyl, OH, halogen, CF$_3$, (C$_1$–C$_4$)alkyl, OCF$_3$, —NR$_6$R$_7$, —(C$_1$–C$_4$ alkyl)-C(O)NR$_6$R$_7$, R$_6$R$_7$N—(C$_1$–C$_6$ alkyl)-, or —C(O)NR$_6$R$_7$.

Embodiment 58. Compounds according to embodiment 57, wherein

R$_5$ is of the formula:

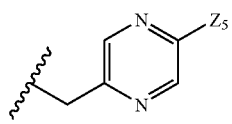

wherein

Z$_5$ is hydroxy(C$_1$–C$_4$)alkyl, C$_1$–C$_4$ dihydroxyalkyl, OH, halogen, CF$_3$, (C$_1$–C$_4$)alkyl, OCF$_3$, —NR$_6$R$_7$, R$_6$R$_7$N—(C$_1$–C$_6$ alkyl)-, —(C$_1$–C$_4$ alkyl)-C(O)NR$_6$R$_7$, or —C(O)NR$_6$R$_7$, wherein R$_6$ and R$_7$ at each occurrence are independently H, C$_1$–C$_6$ alkyl optionally substituted with 1, 2, or 3 groups that are independently C$_1$–C$_4$ alkoxycarbonyl, halogen, C$_3$–C$_6$ cycloalkyl, OH, SH, or C$_1$–C$_4$ alkoxy.

Embodiment 59. Compounds according to embodiment 57, wherein

R$_5$ is of the formula:

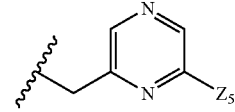

wherein

Z$_5$ is hydroxy(C$_1$–C$_4$)alkyl, C$_1$–C$_4$ dihydroxyalkyl, OH, halogen, CF$_3$, (C$_1$–C$_4$)alkyl, OCF$_3$, —NR$_6$R$_7$, R$_6$R$_7$N—(C$_1$–C$_6$ alkyl)-, —(C$_1$–C$_4$ alkyl)-C(O)NR$_6$R$_7$, or —C(O)NR$_6$R$_7$, wherein R$_6$ and R$_7$ at each occurrence are independently H, C$_1$–C$_6$ alkyl optionally substituted with 1, 2, or 3 groups that are independently C$_1$–C$_4$ alkoxycarbonyl, halogen, C$_3$–C$_6$ cycloalkyl, OH, SH, or C$_1$–C$_4$ alkoxy.

Embodiment 60. Compounds according to embodiment 57, wherein

R$_5$ is of the formula:

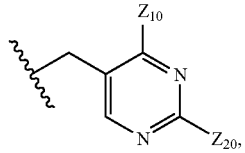

wherein

Z$_{10}$ H or methyl; and
Z$_{20}$ is —(C$_1$–C$_4$ alkyl)-C(O)NR$_6$R$_7$, hydroxy(C$_1$–C$_4$)alkyl, C$_1$–C$_4$ dihydroxyalkyl, OH, halogen, CF$_3$, (C$_1$–C$_4$)alkyl, OCF$_3$, —NR$_6$R$_7$, R$_6$R$_7$N—(C$_1$–C$_6$ alkyl)-, or —C(O)NR$_6$R$_7$, wherein R$_6$ and R$_7$ at each occurrence are independently H, C$_1$–C$_6$ alkyl optionally substituted with 1, 2, or 3 groups that are independently C$_1$–C$_4$ alkoxycarbonyl, halogen, C$_3$–C$_6$ cycloalkyl, OH, SH, or C$_1$–C$_4$ alkoxy.

Embodiment 61. Compounds according to embodiment 57, wherein

R$_5$ is of the formula:

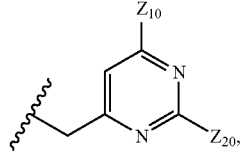

wherein

Z$_{10}$ is H or methyl; and
Z$_{20}$ is —(C$_1$–C$_4$ alkyl)-C(O)NR$_6$R$_7$, hydroxy(C$_1$–C$_4$)alkyl, C$_1$–C$_4$ dihydroxyalkyl, OH, halogen, CF$_3$, (C$_1$–C$_4$)alkyl, OCF$_3$, —NR$_6$R$_7$, R$_6$R$_7$N—(C$_1$–C$_6$ alkyl)-, or —C(O)NR$_6$R$_7$, wherein R$_6$ and R$_7$ at each occurrence are independently H, C$_1$–C$_6$ alkyl optionally substituted with 1, 2, or 3 groups that are independently C$_1$–C$_4$ alkoxycarbonyl, halogen, C$_3$–C$_6$ cycloalkyl, OH, SH, or C$_1$–C$_4$ alkoxy.

Embodiment 62. Compounds according to embodiment 57,
wherein
$R_5$ is of the formula:

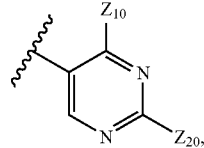

wherein
$Z_{10}$ is H or methyl; and
$Z_{20}$ is —($C_1$–$C_4$ alkyl)-C(O)$NR_6R_7$, hydroxy($C_1$–$C_4$)alkyl, $C_1$–$C_4$ dihydroxyalkyl, OH, halogen, $CF_3$, ($C_1$–$C_4$)alkyl, $OCF_3$, —$NR_6R_7$, $R_6R_7N$—($C_1$–$C_6$ alkyl)-, or —C(O)$NR_6R_7$, wherein
$R_6$ and $R_7$ at each occurrence are independently H, $C_1$–$C_6$ alkyl optionally substituted with 1, 2, or 3 groups that are independently $C_1$–$C_4$ alkoxycarbonyl, halogen, $C_3$–$C_6$ cycloalkyl, OH, SH, or $C_1$–$C_4$ alkoxy.

Embodiment 63. Compounds according to embodiment 57,
wherein
$R_5$ is of the formula:

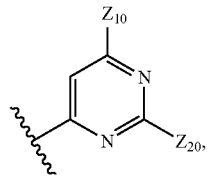

wherein
$Z_{10}$ H or methyl; and
$Z_{20}$ is —($C_1$–$C_4$ alkyl)-C(O)$NR_6R_7$, hydroxy($C_1$–$C_4$)alkyl, $C_1$–$C_4$ dihydroxyalkyl, OH, halogen, $CF_3$, ($C_1$–$C_4$)alkyl, $OCF_3$, —$NR_6R_7$, $R_6R_7N$—($C_1$–$C_6$ alkyl)-, or —C(O)$NR_6R_7$, wherein
$R_6$ and $R_7$ at each occurrence are independently H, $C_1$–$C_6$ alkyl optionally substituted with 1, 2, or 3 groups that are independently $C_1$–$C_4$ alkoxycarbonyl, halogen, $C_3$–$C_6$ cycloalkyl, OH, SH, or $C_1$–$C_4$ alkoxy.

Embodiment 64. Compounds according to embodiment 57,
wherein
$R_5$ is of the formula:

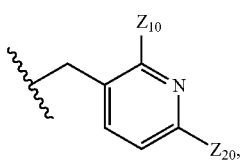

wherein
$Z_{10}$ H or methyl; and
$Z_{20}$ is —($C_1$–$C_4$ alkyl)-C(O)$NR_6R_7$, hydroxy($C_1$–$C_4$)alkyl, $C_1$–$C_4$ dihydroxyalkyl, OH, halogen, $CF_3$($C_1$–$C_4$)alkyl, $OCF_3$, —$NR_6R_7$, $R_6R_7N$—($C_1$–$C_6$ alkyl)-, or —C(O)$NR_6R_7$, wherein
$R_6$ and $R_7$ at each occurrence are independently H, $C_1$–$C_6$ alkyl optionally substituted with 1, 2, or 3 groups that are independently $C_1$–$C_4$ alkoxycarbonyl, halogen, $C_3$–$C_6$ cycloalkyl, OH, SH, or $C_1$–$C_4$ alkoxy.

Embodiment 65. Compounds according to embodiment 57,
wherein
$R_5$ is of the formula:

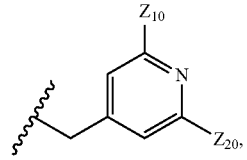

wherein
$Z_{10}$ H or methyl; and
$Z_{20}$ is —($C_1$–$C_4$ alkyl)-C(O)$NR_6R_7$, hydroxy($C_1$–$C_4$)alkyl, $C_1$–$C_4$ dihydroxyalkyl, OH, halogen, $CF_3$, ($C_1$–$C_4$)alkyl, $OCF_3$, —$NR_6R_7$, $R_6R_7N$—($C_1$–$C_6$ alkyl)-, or —C(O)$NR_6R_7$, wherein
$R_6$ and $R_7$ at each occurrence are independently H, $C_1$–$C_6$ alkyl optionally substituted with 1, 2, or 3 groups that are independently $C_1$–$C_4$ alkoxycarbonyl, halogen, $C_3$–$C_6$ cycloalkyl, OH, SH, or $C_1$–$C_4$ alkoxy.

Embodiment 66. Compounds according to embodiment 57,
wherein
$R_5$ is of the formula:

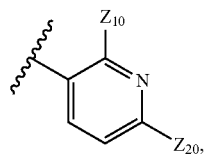

wherein
$Z_{10}$ H or methyl; and
$Z_{20}$ is —($C_1$–$C_4$ alkyl)-C(O)$NR_6R_7$, hydroxy($C_1$–$C_4$)alkyl, $C_1$–$C_4$ dihydroxyalkyl, OH, halogen, $CF_3$, ($C_1$–$C_4$)alkyl, $OCF_3$, —$NR_6R_7$, $R_6R_7N$—($C_1$–$C_6$ alkyl)-, or —C(O)$NR_6R_7$, wherein
$R_6$ and $R_7$ at each occurrence are independently H, $C_1$–$C_6$ alkyl optionally substituted with 1, 2, or 3 groups that are independently $C_1$–$C_4$ alkoxycarbonyl, halogen, $C_3$–$C_6$ cycloalkyl, OH, SH, or $C_1$–$C_4$ alkoxy.

Embodiment 67. Compounds according to embodiment 57,
wherein
$R_5$ is of the formula:

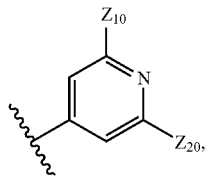

wherein
$Z_{10}$ H or methyl; and
$Z_{20}$ is —($C_1$–$C_4$ alkyl)-C(O)$NR_6R_7$, hydroxy($C_1$–$C_4$)alkyl, $C_1$–$C_4$ dihydroxyalkyl, OH, halogen, $CF_3$, ($C_1$–$C_4$)alkyl, $OCF_3$, —$NR_6R_7$, $R_6R_7N$—($C_1$–$C_6$ alkyl)-, or —C(O)$NR_6R_7$, wherein
$R_6$ and $R_7$ at each occurrence are independently H, $C_1$–$C_6$ alkyl optionally substituted with 1, 2, or 3 groups that are independently $C_1$–$C_4$ alkoxycarbonyl, halogen, $C_3$–$C_6$ cycloalkyl, OH, SH, or $C_1$–$C_4$ alkoxy.

Embodiment A7. Compounds according to embodiment 1 wherein $R_1$ is H, halogen, alkyl optionally substituted with $C_1$–$C_4$ alkoxycarbonyl, $C_2$–$C_6$ alkenyl optionally substituted with $C_1$–$C_4$ alkoxycarbonyl, $C_2$–$C_4$ alkynyl, $C_1$–$C_4$ haloalkyl, carboxaldehyde, $C_1$–$C_4$ hydroxyalkyl, phenyl ($C_1$–$C_6$)alkoxy, benzyl, phenethyl, phenpropyl, CN, or phenyl($C_1$–$C_6$)alkanoyl, wherein the phenyl groups are unsubstituted or substituted with 1, 2, or 3 groups that are independently halogen, $C_1$–$C_4$ alkyl, $C_1$–$C_4$ alkoxy, nitro, CN, $CF_3$, $OCF_3$ or $CO_2H$;

$R_2$ is OH, benzyloxy, phenyloxy, phenyloxy($C_1$–$C_6$)alkyl, phenyl($C_1$–$C_4$)thioalkoxy, —OC(O)NH(CH$_2$)phenyl, —OC(O)N(alkyl)(CH$_2$)$_n$phenyl, di($C_1$–$C_6$)alkylamino, $C_2$–$C_6$ alkynyl, pyridyl, pyrimidyl, pyridazyl, pyrazolyl, imidazolyl, pyrrolyl, tetrahydroquinolinyl, tetrahydroisoquinolinyl, tetrazolyl, pyrazinyl, benzimidazolyl, triazinyl, tetrahydrofuryl, piperidinyl, hexahydropyrimidinyl, thiazolyl, thienyl, or $CO_2H$, wherein n is 0, 1, 2, 3, 4, 5 or 6;

each of the above is unsubstituted or substituted with 1, 2, 3, 4, or 5 groups that are independently halogen, $NR_6R_7$, ($C_1$–$C_4$)haloalkyl, ($C_1$–$C_4$)haloalkoxy, ($C_1$–$C_6$)alkyl, pyridyl, —($C_1$–$C_6$)alkyl-N(R)—$CO_2R_{30}$, or $NR_6R_7$—($C_1$–$C_6$ alkyl)-, $R_4$ is H, alkyl optionally substituted with one or two groups that are independently $CO_2H$, —$CO_2$ alkyl, —C(O)NRR, —N($R_{30}$)C(O)NRR, —N($R_{30}$)C(O)—($C_1$–$C_6$)alkoxy, or —$NR_6R_7$, phenyl($C_1$–$C_6$)alkoxy, phenyl($C_1$–$C_6$)alkyl, hydroxyalkyl, wherein the phenyl groups are unsubstituted or substituted with 1, 2, 3, 4, or 5 groups that are independently halogen, hydroxy, alkoxy, alkyl, nitro, $CF_3$, or $OCF_3$; and $R_5$ is phenyl($C_1$–$C_6$)alkyl, ($C_1$–$C_6$)alkyl, phenyl, piperidinyl ($C_1$–$C_6$)alkyl, thienyl($C_1$–$C_6$)alkyl, indolyl, quinolinyl, isoquinolinyl, isoindolyl, indol-2-onyl, indazolyl, indolyl ($C_1$–$C_6$)alkyl, quinolinyl($C_1$–$C_6$)alkyl, isoquinolinyl ($C_1$–$C_6$)alkyl, isoindolyl($C_1$–$C_6$)alkyl, indol-2-onyl ($C_1$–$C_6$)alkyl, naphthyl($C_1$–$C_6$)alkyl, pyridyl($C_1$–$C_6$)alkyl, pyrimidyl($C_1$–$C_6$)alkyl, pyrazinyl($C_1$–$C_6$)alkyl, or wherein each of the above is unsubstituted or substituted with 1, 2, 3, 4, or 5 groups that are independently alkyl, halogen, alkoxy, benzyloxy, thioalkoxy, —$CO_2$($C_1$–$C_5$ alkyl), $CO_2H$, CN, amidinooxime, $NR_8R_9$, $NR_6R_7$—($C_1$–$C_6$ alkyl)-, —C(O)$NR_6R_7$, amidino, $CF_3$, or $OCF_3$;

$R_8$ is hydrogen, $C_1$–$C_6$ alkyl, $C_1$–$C_6$ alkanoyl, phenyl $C_1$–$C_6$ alkyl and phenyl $C_1$–$C_6$ alkanoyl; and $R_9$ is aminoalkyl, mono $C_1$–$C_6$ alkylamino $C_1$–$C_6$ alkyl, di $C_1$–$C_6$ alkylamino $C_1$–$C_6$ alkyl, $C_1$–$C_6$ alkyl, $C_1$–$C_6$ alkanoyl, phenyl $C_1$–$C_4$ alkyl, indazolyl, and phenyl $C_1$–$C_4$ alkanoyl.

In this embodiment, it is preferred that when $R_2$ is benzyloxy, $R_4$ is H, and $R_5$ is benzyl or methyl, $R_1$ is not hydrogen; and no more than two of $R_1$, $R_2$, $R_4$, and $R_5$ are simultaneously hydrogen.

Embodiment A8. Compounds according to embodiment A7 wherein $R_1$ is H, halogen, $C_1$–$C_4$ alkyl optionally substituted with $C_1$–$C_4$ alkoxycarbonyl, $C_2$–$C_4$ alkenyl optionally substituted with $C_1$–$C_4$ alkoxycarbonyl, $C_2$–$C_4$ alkynyl, or carboxaldehyde;

$R_2$ is benzyloxy, OH, phenyloxy, phenyloxy($C_1$–$C_6$)alkyl, phenyl($C_1$–$C_4$)thioalkoxy, or pyridyl; wherein each of the above is optionally substituted with 1, 2, 3, 4, or 5 groups that are independently halogen, —($C_1$–$C_6$)alkyl-N(R)—$CO_2R_{30}$, $NR_6R_7$, ($C_1$–$C_4$)haloalkyl, ($C_1$–$C_4$)haloalkoxy, ($C_1$–$C_6$)alkyl, pyridyl, or $NR_6R_7$—($C_1$–$C_6$ alkyl)-.

Embodiment A9. Compounds according to embodiment A7 wherein $R_4$ is H, ($C_1$–$C_6$)alkyl optionally substituted with one or two groups that are independently $CO_2H$, —$CO_2$ alkyl, —C(O)NRR, —N($R_{30}$)C(O)NRR, —N($R_{30}$)C(O)—($C_1$–$C_6$)alkoxy, or —$NR_6R_7$, phenyl($C_1$–$C_6$)alkoxy, or hydroxy($C_1$–$C_6$)alkyl, wherein the phenyl groups are unsubstituted or substituted with 1, 2, or 3 groups that are independently halogen, hydroxy, $C_1$–$C_4$ alkoxy, $C_1$–$C_4$ alkyl, nitro, $CF_3$, $OCF_3$; and $R_5$ is benzyl, phenethyl, phenpropyl, phenbutyl, ($C_1$–$C_6$) alkyl, phenyl, pyridyl, pyrimidyl, indolyl, indazolyl, indolyl($C_1$–$C_6$)alkyl, naphthyl($C_1$–$C_6$)alkyl, thienyl ($C_1$–$C_6$)alkyl, pyridyl($C_1$–$C_6$)alkyl, pyrimidyl($C_1$–$C_6$) alkyl, or pyrazinyl($C_1$–$C_6$)alkyl, and wherein each of the above is unsubstituted or substituted with 1, 2, or 3 groups that are independently alkyl, halogen, alkoxy, benzyloxy, thioalkoxy, —$CO_2$($C_1$–$C_5$ alkyl), $CF_3$, $OCF_3$, $CO_2H$, CN, amidinooxime.

In this embodiment, it is preferred that when $R_2$ is benzyloxy, $R_4$ is H, and $R_5$ is benzyl or methyl, $R_1$ is not hydrogen; and no more than two of $R_1$, $R_2$, $R_4$, and $R_5$ are simultaneously hydrogen.

Embodiment A10. Compounds according to embodiment A7, wherein $R_4$ is H, ($C_1$–$C_4$)alkyl optionally substituted with one or two groups that are independently $CO_2H$, —$CO_2$ alkyl, —C(O)NRR, —N($R_{30}$)C(O)NRR, —N($R_{30}$)C(O)—($C_1$–$C_6$)alkoxy, or —$NR_6R_7$, phenyl($C_1$–$C_6$)alkoxy, benzyl, phenethyl, phenpropyl, or hydroxy($C_1$–$C_6$)alkyl, wherein the phenyl groups are unsubstituted or substituted with 1, 2, or 3 groups that are independently halogen, hydroxy, $C_1$–$C_4$ alkoxy, $C_1$–$C_4$ alkyl, nitro, $CF_3$, $OCF_3$; and $R_5$ is indolyl, quinolinyl, isoquinolinyl, isoindolyl, indol-2-onyl, indolyl($C_1$–$C_6$)alkyl, quinolinyl($C_1$–$C_6$)alkyl, isoquinolinyl($C_1$–$C_6$)alkyl, isoindolyl($C_1$–$C_6$)alkyl, indol-2-onyl($C_1$–$C_6$)alkyl, each of which is unsubstituted or substituted with 1, 2, or 3 groups that are independently $C_1$–$C_4$ alkyl, halogen, $CF_3$, $OCF_3$, —$CO_2CH_3$, $C_1$–$C_4$ hydroxyalkyl, $C_1$–$C_4$ alkoxy, —$CO_2$($C_1$–$C_5$ alkyl), benzyloxy, —$NR_8R_9$, $NR_6R_7$—($C_1$–$C_6$ alkyl)-, —C(O)$NR_6R_7$, or amidinooxime;

wherein $R_6$ and $R_7$ are independently at each occurrence H, alkyl, hydroxyalkyl, alkoxy, alkoxyalkyl, alkanoyl, phenylalkyl, phenylalkoxy, or phenylalkanoyl, wherein each is unsubstituted or substituted with 1, 2, or 3 groups that are independently, halogen, hydroxy, $C_1$–$C_4$ alkoxy, OH, SH, $C_3$–$C_6$ cycloalkyl, $C_1$–$C_4$ alkyl, $CF_3$, or $OCF_3$; or $R_6$, $R_7$, and the nitrogen to which they are attached form a morpholinyl, thiomorpholinyl, or piperazinyl ring which is optionally substituted with 1 or 2 groups that are independently $C_1$–$C_4$ alkyl, hydroxy, hydroxy $C_1$–$C_4$ alkyl, or halogen.

Embodiment A11. Compounds according to embodiment A7
wherein
$R_1$ is chloro, bromo, iodo, or H; and
$R_5$ is benzyl, phenethyl, phenpropyl, phenyl, quinolinyl, indolyl, isoquinolinyl, isoindolyl, indol-2-onyl, indolyl $(C_1-C_6)$alkyl, quinolinyl$(C_1-C_6)$alkyl, isoquinolinyl $(C_1-C_6)$alkyl, isoindolyl$(C_1-C_6)$alkyl, indol-2-onyl $(C_1-C_6)$alkyl, piperidinyl $C_1-C_4$ alkyl, thienyl $C_1-C_4$ alkyl, —$CH_2$-pyridyl, or pyridyl, each of which is unsubstituted or substituted with 1, 2, or 3 groups that are independently $C_1-C_4$ alkyl, halogen, $CF_3$, $OCF_3$, $C_1-C_4$ hydroxyalkyl, $C_1-C_4$ alkoxy, —$CO_2(C_1-C_5$ alkyl), benzyloxy, $NR_8R_9$, $NR_6R_7C_1-C_4$ alkyl, —$C(O)NR_6R_7$, and amidinooxime;
wherein
  $R_6$ and $R_7$ are independently at each occurrence H, alkyl, hydroxyalkyl, alkoxy, alkoxyalkyl, alkanoyl, phenylalkyl, phenylalkoxy, or phenylalkanoyl, wherein each is unsubstituted or substituted with 1, 2, or 3 groups that are independently, halogen, hydroxy, $C_1-C_4$ alkoxy, OH, SH, $C_3-C_6$ cycloalkyl, $C_1-C_4$ alkyl, $CF_3$, or $OCF_3$; or
  $R_6$, $R_7$, and the nitrogen to which they are attached form a morpholinyl, thiomorpholinyl, or piperazinyl ring which is optionally substituted with 1 or 2 groups that are independently $C_1-C_4$ alkyl, hydroxy, hydroxy $C_1-C_4$ alkyl, or halogen.

Embodiment A12. Compounds according to embodiment A11, wherein
$R_5$ is benzyl, phenethyl, phenpropyl, or phenyl, each of which is unsubstituted or substituted with 1, 2, or 3 groups that are independently $C_1-C_4$ alkyl, halogen, $CF_3$, $OCF_3$, —$CO_2CH_3$, $C_1-C_4$ hydroxyalkyl, $C_1-C_4$ alkoxy, —$CO_2$ $(C_1-C_5$ alkyl), benzyloxy, $NR_8R_9$, $NR_6R_7C_1-C_4$ alkyl, —$C(O)NR_6R_7$, and amidinooxime.

Embodiment A13. Compounds according to embodiment A11, wherein
$R_5$ is quinolinyl, indolyl, isoquinolinyl, isoindolyl, indol-2-onyl, indolyl$(C_1-C_6)$alkyl, quinolinyl$(C_1-C_6)$alkyl, isoquinolinyl$(C_1-C_6)$alkyl, isoindolyl$(C_1-C_6)$alkyl, indol-2-onyl$(C_1-C_6)$alkyl, piperidinyl $C_1-C_4$ alkyl, thienyl $C_1-C_4$ alkyl, —$CH_2$-pyridyl, or pyridyl, each of which is unsubstituted or substituted with 1, 2, or 3 groups that are independently $C_1-C_4$ alkyl, halogen, $CF_3$, $OCF_3$, —$CO_2CH_3$, $C_1-C_4$ hydroxyalkyl, $C_1-C_4$ alkoxy, —$CO_2$ $(C_1-C_5$ alkyl), benzyloxy, $NR_8R_9$, $NR_6R_7C_1-C_4$ alkyl, —$C(O)NR_6R_7$, and amidinooxime.

Embodiment A14. Compounds according to any one of embodiments A11, A12, or A13 wherein
$R_2$ is benzyloxy, or phenethyloxy;
each of the above is unsubstituted or substituted with 1, 2, or 3, groups that are independently —$(C_1-C_6)$alkyl-N(R)—$CO_2R_{30}$, fluoro, chloro, bromo, $CF_3$, or $(C_1-C_4)$ alkyl.

Embodiment A15. Compounds according to any one of embodiments A11, A12 or A13 wherein
$R_2$ is phenyloxy$(C_1-C_6)$alkyl, wherein the phenyl group is unsubstituted or substituted with 1, 2, or 3, groups that are independently —$(C_1-C_6)$alkyl-N(R)—$CO_2R_{30}$, fluoro, chloro, bromo, $CF_3$, or $(C_1-C_4)$alkyl.

Embodiment A16. Compounds according to embodiment A1,
wherein
$R_1$ is H, halogen, $C_1-C_4$ alkyl optionally substituted with $C_1-C_4$ alkoxycarbonyl, $C_2-C_4$ alkenyl optionally substituted with $C_1-C_4$ alkoxycarbonyl, $C_2-C_4$ alkynyl, or carboxaldehyde.

Embodiment A17. Compounds according to embodiment A16, wherein
$R_2$ is benzyloxy, OH, phenyloxy, phenyloxy$(C_1-C_6)$alkyl, or phenyl$(C_1-C_4)$thioalkoxy, wherein each of the above is optionally substituted with 1, 2, 3, 4, or 5 groups that are independently halogen, —$(C_1-C_6)$alkyl-N(R)—$CO_2R_{30}$, $NR_6R_7$, $(C_1-C_4)$haloalkyl, $(C_1-C_4)$haloalkoxy, $(C_1-C_6)$ alkyl, pyridyl, or $NR_6R_7$—$(C_1-C_6$ alkyl)-.

Embodiment A18. Compounds according to embodiment A17, wherein
$R_4$ is H, or $(C_1-C_4)$alkyl optionally substituted with one or two groups that are independently $CO_2H$, —$CO_2$ alkyl, —$C(O)NRR$, —$N(R_{30})C(O)NRR$, —$N(R_{30})C(O)$— $(C_1-C_6)$alkoxy, OH, or —$NR_6R_7$ Embodiment A19. Compounds according to embodiment A18, wherein
$R_5$ is phenyl, naphthyl, indolyl, pyridyl, quinolinyl, isoquinolinyl, isoindolyl, indol-2-onyl, indolyl$(C_1-C_6)$ alkyl, quinolinyl$(C_1-C_6)$alkyl, isoquinolinyl$(C_1-C_6)$ alkyl, isoindolyl$(C_1-C_6)$alkyl, indol-2-onyl$(C_1-C_6)$alkyl, pyridazinyl, pyrimidinyl, or pyrazinyl, pyridazinyl $(C_1-C_6)$alkyl, pyrimidinyl$(C_1-C_6)$alkyl, or pyrazinyl $(C_1-C_6)$alkyl, each of which is unsubstituted or substituted with 1, 2, 3, 4 or 5 groups that are independently $C_1-C_4$ alkyl, halogen, $CF_3$, $OCF_3$, —$CO_2CH_3$, $C_1-C_4$ hydroxyalkyl, $C_1-C_4$ alkoxy, —$CO_2(C_1-C_5$ alkyl), benzyloxy, —$NR_8R_9$, —$C(O)NR_6R_7$, $NR_6R_7C_1-C_4$ alkyl, and amidinooxime; wherein
  $R_6$ and $R_7$ are independently at each occurrence H, $C_1-C_4$ alkyl, $C_1-C_4$ hydroxyalkyl, $C_1-C_4$ alkoxy, $C_1-C_4$ alkoxy $C_1-C_4$ alkyl, $C_1-C_4$ alkanoyl, phenyl $C_1-C_4$ alkyl, phenyl $C_1-C_4$ alkoxy, or phenyl $C_1-C_4$ alkanoyl, wherein each is unsubstituted or substituted with 1, 2, or 3 groups that are independently, halogen, hydroxy, $C_1-C_4$ alkoxy, $C_1-C_4$ alkyl, OH, SH, $C_3-C_6$ cycloalkyl, $CF_3$, or $OCF_3$; or
  $R_6$, $R_7$, and the nitrogen to which they are attached form a morpholinyl, thiomorpholinyl, or piperazinyl ring which is optionally substituted with 1 or 2 groups that are independently $C_1-C_4$ alkyl, hydroxy, hydroxy $C_1-C_4$ alkyl, or halogen.

Embodiment A20. Compounds according to embodiment A19, wherein
$R_1$ is H, halogen, methyl, ethyl, $C_2-C_4$ alkenyl $C_2-C_4$ alkynyl, or carboxaldehyde;
$R_2$ is benzyloxy, OH, phenyloxy, phenyloxy$(C_1-C_6)$alkyl, or phenyl$(C_1-C_4)$thioalkoxy, wherein each of the above is optionally substituted with 1, 2, 3, or 4 groups that are independently halogen, —$(C_1-C_6)$alkyl-N(R)—$CO_2R_{30}$, $NR_6R_7$, $NR_6R_7C_1-C_4$ alkyl, $(C_1-C_4)$haloalkyl, $(C_1-C_4)$ haloalkoxy, $(C_1-C_6)$alkyl, or pyridyl; and
$R_4$ is H, $(C_1-C_4)$alkyl optionally substituted with one or two groups that are independently $CO_2H$, —$CO_2$ alkyl, —$C(O)NRR$, —$N(R_{30})C(O)NRR$, —$N(R_{30})C(O)$— $(C_1-C_6)$alkoxy, OH, or —$NR_6R_7$.

Embodiment A21. Compounds according to embodiment A20, wherein
$R_5$ is phenyl optionally substituted with 1, 2, 3, 4, or 5 groups that are independently halogen, $C_1-C_6$ alkyl, —$NR_{10}R_{11}$, $C_1-C_4$ alkoxy, —$C(O)NR_{10}R_{11}$, —$CO_2H$, $NR_{10}R_{11}$, $C_1-C_4$ alkyl, $C_1-C_6$ alkyl, $C_1-C_6$ alkoxycarbonyl, $C_1-C_6$ alkoxy, CHO, —$SO_2NH_2$, $C_1-C_4$ haloalkyl, $C_1-C_6$ hydroxyalkyl, —$C_1-C_4$ alkyl-$NR_{12}C$ $(O)NR_{13}R_{14}$, —$C_1-C_4$ alkyl-$NR_{12}C(O)$—$(C_1-C_4$ alkyl)- $NR_{13}R_{14}$, —$C_1-C_4$ alkyl-$NR_{12}C(O)OR_{15}$, or —$C_1-C_4$ alkyl-$NR_{12}C(O)$—$(C_1-C_4$ alkyl)-$R_{15}$, wherein
  $R_{10}$ and $R_{11}$, at each occurrence are independently H, $C_1-C_6$ alkyl, amino $C_1-C_4$ alkyl, NH($C_1-C_6$ alkyl) alkyl, N($C_1-C_6$ alkyl)($C_1-C_6$ alkyl)$C_1-C_6$ alkyl, $C_1-C_6$ hydroxyalkyl, $C_1-C_6$ alkoxy $C_1-C_6$ alkyl, OH, —$SO_2$ $(C_1-C_6$ alkyl), or $C_1-C_6$ alkanoyl, or $R_{10}$ $R_{11}$, and the nitrogen to which they are attached form a piperidinyl, pyrrolidinyl, piperazinyl, or a morpholinyl ring optionally substituted with 1 or 2 groups that are independently alkyl or halogen, $R_{12}$ is H or $C_1$–$C_6$ alkyl;

$R_{13}$ and $R_{14}$ are independently H or $C_1$–$C_6$ alkyl; or $R_{13}$ and $R_{14}$ and the nitrogen to which they are attached form a morpholinyl ring; and $R_{15}$ is $C_1$–$C_6$ alkoxy; —OC(O)$C_1$–$C_6$ alkyl, OH.

Embodiment A22. Compounds according to embodiment A21, wherein $R_5$ is phenyl optionally substituted with 1, 2, 3, 4, or 5 groups that are independently halogen, $C_1$–$C_6$ alkyl, —NR$_{10}$,R$_{11}$NR$_{10}$R$_{11}$, $C_1$–$C_6$ alkyl, $C_1$–$C_4$ alkoxy, or —C(O)NR$_{10}$R$_{11}$, —CO$_2$H, —$C_1$–$C_4$ alkyl-NR$_{10}$R$_{11}$, $C_1$–$C_6$ alkyl, $C_1$–$C_6$ alkoxycarbonyl, $C_1$–$C_6$ alkoxy, CHO, —SO$_2$NH$_2$, $C_1$–$C_4$ haloalkyl, $C_1$–$C_6$ hydroxyalkyl, —$C_1$–$C_4$ alkyl-NR$_{12}$C(O)NR$_{13}$R$_{14}$, —$C_1$–$C_4$ alkyl-NR$_{12}$C(O)—($C_1$–$C_4$ alkyl)-NR$_{13}$R$_{14}$, —$C_1$–$C_4$ alkyl-NR$_{12}$C(O)OR$_{15}$, or —$C_1$–$C_4$ alkyl-NR$_{12}$C(O)—($C_1$–$C_4$ alkyl)-R$_{15}$ wherein $R_{10}$ and $R_{11}$ at each occurrence are independently H, $C_1$–$C_6$ alkyl, amino $C_1$–$C_4$ alkyl, NH($C_1$–$C_6$ alkyl)alkyl, N($C_1$–$C_6$ alkyl)($C_1$–$C_6$ alkyl)$C_1$–$C_6$ alkyl, $C_1$–$C_6$ hydroxyalkyl, $C_1$–$C_6$ alkoxy $C_1$–$C_6$ alkyl, OH, —SO$_2$($C_1$–$C_6$ alkyl), or $C_1$–$C_6$ alkanoyl, $R_{12}$ is H or $C_1$–$C_6$ alkyl;

$R_{13}$ and $R_{14}$ are independently H or $C_1$–$C_6$ alkyl; or $R_{13}$ and $R_{14}$ and the nitrogen to which they are attached form a morpholinyl ring; and $R_{15}$ is $C_1$–$C_6$ alkoxy; —OC(O)$C_1$–$C_6$ alkyl, OH.

Embodiment A23. Compounds according to embodiment A22, wherein $R_5$ is phenyl optionally substituted with 1, 2, 3, 4, or 5 groups that are independently halogen, $C_1$–$C_6$ alkyl, —NR$_{10}$R$_{11}$, NR$_{10}$R$_{11}$, $C_1$–$C_4$ alkyl, $C_1$–$C_4$ alkoxy, —C(O)NR$_{10}$R$_{11}$, wherein $R_{10}$ and $R_{11}$ at each occurrence are independently H, $C_1$–$C_6$ alkyl, amino $C_1$–$C_4$ alkyl, NH($C_1$–$C_6$ alkyl)alkyl, N($C_1$–$C_6$ alkyl)($C_1$–$C_6$ alkyl)$C_1$–$C_6$ alkyl, $C_1$–$C_6$ hydroxyalkyl, $C_1$–$C_6$ alkoxy $C_1$–$C_6$ alkyl, OH, —SO$_2$($C_1$–$C_6$ alkyl), $C_1$–$C_6$ alkanoyl.

Embodiment A24. Compounds according to embodiment A23, wherein $R_5$ is phenyl optionally substituted with 1, 2, 3, 4, or 5 groups that are independently halogen, $C_1$–$C_6$ alkyl, —NR$_{10}$R$_{11}$, or $C_1$–$C_4$ alkoxy.

Embodiment A25. Compounds according to embodiment A23, wherein $R_5$ is substituted with at least one —C(O)NR$_{10}$R$_{11}$.

Embodiment A26. Compounds according to embodiment A25, wherein $R_{10}$ and $R_{11}$ at each occurrence are independently H, $C_1$–$C_6$ alkyl, amino $C_1$–$C_4$ alkyl, NH($C_1$–$C_6$ alkyl)alkyl, N($C_1$–$C_6$ alkyl)($C_1$–$C_6$ alkyl)$C_1$–$C_6$ alkyl, $C_1$–$C_6$ hydroxyalkyl, $C_1$–$C_6$ alkoxy $C_1$–$C_6$ alkyl.

Embodiment 27. Compounds according to embodiment A26, wherein $R_{10}$ is H.

Embodiment A28. Compounds according to embodiment A25, wherein $R_{10}$ and $R_{11}$ at each occurrence are independently H, $C_1$–$C_6$ alkyl, OH, —SO$_2$ ($C_1$–$C_6$ alkyl), $C_1$–$C_6$ alkanoyl.

Embodiment A29. Compounds according to embodiment A20, wherein $R_5$ is phenyl optionally substituted with 1, 2, 3, 4, or 5 groups that are independently halogen, $C_1$–$C_6$ alkyl, NH$_2$, NH($C_1$–$C_6$ alkyl), N($C_1$–$C_6$ alkyl)($C_1$–$C_6$ alkyl), $C_1$–$C_4$ alkoxy, —C(O)NR$_{10}$R$_{11}$, wherein each of the above alkyl groups is optionally substituted with 1 or 2 groups that are independently OH, or methoxy; wherein $R_{10}$, $R_{11}$, and the nitrogen to which they are attached form a piperidinyl, pyrrolidinyl, piperazinyl, or a morpholinyl ring optionally substituted with 1 or 2 groups that are independently alkyl or halogen.

Embodiment A30. Compounds according to embodiment A20, wherein $R_5$ is phenyl optionally substituted with 1, 2, 3, 4, or 5 groups that are independently halogen, $C_1$–$C_6$ alkyl, $C_1$–$C_4$ alkoxy, —CO$_2$H, —$C_1$–$C_4$ alkyl-NR$_{10}$R$_{11}$, $C_1$–$C_6$ alkoxycarbonyl, $C_1$–$C_6$ alkoxy, CHO, —SO$_2$NH$_2$, $C_1$–$C_4$ haloalkyl, $C_1$–$C_6$ hydroxyalkyl, —$C_1$–$C_4$ alkyl-NR$_{12}$C(O)NR$_{13}$R$_{14}$, —$C_1$–$C_4$ alkyl —NR$_{12}$C(O)—($C_1$–$C_4$ alkyl)-NR$_{13}$R$_{14}$, —$C_1$–$C_4$ alkyl-NR$_{12}$C(O)OR$_{15}$, or -$C_1$–$C_4$ alkyl-NR$_{12}$C(O)—($C_1$–$C_4$ alkyl)-R$_{15}$, —OC(O)$C_1$–$C_6$ alkyl, or OH wherein $R_{12}$ is H or $C_1$–$C_6$ alkyl;

$R_{13}$ and $R_{14}$ are independently H or $C_1$–$C_6$ alkyl; or $R_{13}$ and $R_{14}$ and the nitrogen to which they are attached form a morpholinyl ring;

$R_{15}$ is $C_1$–$C_6$ alkoxy.

Embodiment A31. Compounds according to embodiment A30, wherein $R_5$ is phenyl optionally substituted with 1, 2, 3, 4, or 5 groups that are independently halogen, $C_1$–$C_4$ alkyl, $C_1$–$C_4$ alkoxy, —CO$_2$H, $C_1$–$C_4$ alkoxycarbonyl, $C_1$–$C_4$ alkoxy, CHO, —SO$_2$NH$_2$, $C_1$–$C_4$ haloalkyl, $C_1$–$C_4$ hydroxyalkyl.

Embodiment A32. Compounds according to embodiment A30, wherein $R_5$ is phenyl optionally substituted with 1, 2, 3, 4, or 5 groups that are independently halogen, $C_1$–$C_4$ alkyl, $C_1$–$C_4$ alkoxy, —CO$_2$H, —$C_1$–$C_4$ alkyl-NR$_{10}$R$_{11}$, —$C_1$–$C_4$ alkyl-NR$_{12}$C(O)NR$_{13}$R$_{14}$, —$C_1$–$C_4$ alkyl-NR$_{12}$C(O)—($C_1$–$C_4$ alkyl)-NR$_{13}$R$_{14}$, —$C_1$–$C_4$ alkyl-NR$_{12}$C(O)OR$_{15}$, or —$C_1$–$C_4$ alkyl-NR$_{12}$C(O)—($C_1$–$C_4$ alkyl)-R$_{15}$, or —OC(O)$C_1$–$C_6$ alkyl, wherein $R_{12}$ is H or $C_1$–$C_6$ alkyl;

$R_{13}$ and $R_{14}$ are independently H or $C_1$–$C_6$ alkyl; or $R_{13}$ and $R_{14}$ and the nitrogen to which they are attached form a morpholinyl ring;

$R_{15}$ is $C_1$–$C_6$ alkoxy.

Embodiment A33. Compounds according to embodiment A311, wherein $R_5$ is phenyl optionally substituted with 1, 2, 3, 4, or 5 groups that are independently halogen, $C_1$–$C_4$ alkyl, $C_1$–$C_4$ alkoxy, —CO$_2$H, —$C_1$–$C_4$ alkyl-NR$_{11}$R$_{11}$, —$C_1$–$C_4$ alkyl-NR$_{12}$C(O)NR$_{13}$R$_{14}$, —$C_1$–$C_4$ alkyl-NR$_{12}$C(O)—($C_1$–$C_4$ alkyl)-NR$_{13}$R$_{14}$, wherein $R_{12}$ is H or $C_1$–$C_6$ alkyl;

$R_{13}$ and $R_{14}$ are independently H or $C_1$–$C_6$ alkyl; or $R_{13}$ and $R_{14}$ and the nitrogen to which they are attached form a morpholinyl ring.

Embodiment A34. Compounds according to any one of embodiments A30, A31, A32, or A33, wherein the phenyl group is substituted with two groups that are meta to each other.

Embodiment A35. Compounds according to any one of embodiments A30, A31, A32, or A33, wherein the phenyl group is substituted with two groups that are para to each other.

Embodiment A36. Compounds according to embodiment A20, wherein $R_5$ is indolyl, pyridyl, pyridazinyl, pyrimidinyl, indazolyl, quinolinyl, isoquinolinyl, isoindolyl, indol-2-onyl, pyridazinyl, pyrimidinyl, or pyrazinyl, each of which is unsubstituted or substituted with 1, 2, 3, 4 or 5 groups that are independently $C_1$–$C_4$ alkyl, halogen, $CF_3$, $OCF_3$, —$CO_2CH_3$, $C_1$–$C_4$ hydroxyalkyl, $C_1$–$C_4$ alkoxy, —$CO_2$ ($C_1$–$C_5$ alkyl), benzyloxy, $NR_8R_9$, $NR_6R_7C_1$–$C_4$ alkyl, —$C(O)NR_6R_7$, or amidinooxime; wherein $R_6$ and $R_7$ are independently at each occurrence H, $C_1$–$C_4$ alkyl, $C_1$–$C_4$ hydroxyalkyl, $C_1$–$C_4$ alkoxy, $C_1$–$C_4$ alkoxy $C_1$–$C_4$ alkyl, $C_1$–$C_4$ alkanoyl, phenyl $C_1$–$C_4$ alkyl, phenyl $C_1$–$C_4$ alkoxy, or phenyl $C_1$–$C_4$ alkanoyl, wherein each is unsubstituted or substituted with 1, 2, or 3 groups that are independently, halogen, OH, SH, $C_3$–$C_6$ cycloalkyl, $C_1$–$C_4$ alkoxy, $C_1$–$C_4$ alkyl, OH, $CF_3$, or $OCF_3$; or $R_6$, $R_7$, and the nitrogen to which they are attached form a morpholinyl, thiomorpholinyl, or piperazinyl ring which is optionally substituted with 1 or 2 groups that are independently $C_1$–$C_4$ alkyl, hydroxy, hydroxy $C_1$–$C_4$ alkyl, or halogen.

Embodiment A38. Compounds according to embodiment A36, wherein $R_5$ is indolyl, pyridyl, pyrimidinyl, indazolyl, or pyrazinyl, each of which is unsubstituted or substituted with 1, 2, 3, or 4 groups that are independently $C_1$–$C_4$ alkyl, halogen, $CF_3$, $OCF_3$, —$CO_2CH_3$, $C_1$–$C_4$ hydroxyalkyl, $C_1$–$C_4$ alkoxy, —$CO_2(C_1$–$C_5$ alkyl), benzyloxy, —$C(O)NR_6R_7$, —$NR_8R_9$, $NR_6R_7C_1$–$C_4$ alkyl, and amidinooxime; wherein $R_6$ and $R_7$ are independently at each occurrence H, $C_1$–$C_4$ alkyl, $C_1$–$C_4$ hydroxyalkyl, $C_1$–$C_4$ alkoxy, $C_1$–$C_4$ alkoxy $C_1$–$C_4$ alkyl, $C_1$–$C_4$ alkanoyl, phenyl $C_1$–$C_4$ alkyl, phenyl $C_1$–$C_4$ alkoxy, or phenyl $C_1$–$C_4$ alkanoyl, wherein each is unsubstituted or substituted with 1, 2, or 3 groups that are independently, halogen, OH, SH, $C_3$–$C_6$ cycloalkyl, $C_1$–$C_4$ alkoxy, $C_1$–$C_4$ alkyl, OH, $CF_3$, or $OCF_3$.

Embodiment A39. Compounds according to embodiment A38, wherein $R_5$ is indolyl, pyridyl, or pyrazinyl, each of which is unsubstituted or substituted with 1, 2, 3, or 4 groups that are independently $C_1$–$C_4$ alkyl, halogen, $CF_3$, $OCF_3$, —$CO_2CH_3$, $C_1$–$C_4$ hydroxyalkyl, $C_1$–$C_4$ alkoxy, —$CO_2$ ($C_1$–$C_5$ alkyl), benzyloxy, —$C(O)NR_6R_7$, $NR_8R_9$, $NR_6R_7$—$C_1$–$C_4$ alkyl-, and amidinooxime; wherein $R_6$ and $R_7$ are independently at each occurrence H, $C_1$–$C_4$ alkyl, $C_1$–$C_4$ hydroxyalkyl, $C_1$–$C_4$ alkoxy, $C_1$–$C_4$ alkoxy $C_1$–$C_4$ alkyl, each of which is optionally substituted with 1, 2, or 3 groups that are independently halogen, OH, SH, $C_3$–$C_6$ cycloalkyl, $C_1$–$C_4$ alkoxy, $C_1$–$C_4$ alkyl, OH, $CF_3$, or $OCF_3$.

Embodiment A40. Compounds according to embodiment A36, wherein $R_5$ is indolyl, pyridyl, pyridazinyl, pyrimidinyl, or pyrazinyl, each of which is unsubstituted or substituted with 1, 2, 3, 4 or 5 groups that are independently $C_1$–$C_4$ alkyl, halogen, $CF_3$, $OCF_3$, —$CO_2CH_3$, $C_1$–$C_4$ hydroxyalkyl, $C_1$–$C_4$ alkoxy, —$CO_2(C_1$–$C_5$ alkyl), benzyloxy, —$C(O)NH_2$, —$C(O)NH(C_1$–$C_6$ alkyl) wherein the alkyl group is optionally substituted with OH or methoxy, —$C(O)N$($C_1$–$C_6$ alkyl)($C_1$–$C_6$ alkyl) wherein each alkyl group is independently and optionally substituted with OH or methoxy, —$C(O)NR_6R_7$, $NR_8R_9$, $NR_6R_7C_1$–$C_4$ alkyl, —$C_1$–$C_4$ alkyl-$NH_2$, —$C_1$–$C_4$ alkyl-$NH(C_1$–$C_6$ alkyl) wherein each alkyl group is independently and optionally substituted with OH or methoxy, —$C_1$–$C_4$ alkyl-$N(C_1$–$C_6$ alkyl)($C_1$–$C_6$ alkyl) wherein each alkyl group is independently and optionally substituted with OH or methoxy, and amidinooxime; wherein $R_6$, $R_7$, and the nitrogen to which they are attached form a morpholinyl, thiomorpholinyl, or piperazinyl ring which is optionally substituted with 1 or 2 groups that are independently $C_1$–$C_4$ alkyl, hydroxy, hydroxy $C_1$–$C_4$ alkyl, or halogen.

Embodiment A42. Compounds according to any one of embodiments A37, A38, A39, or A40, wherein $R_1$ is H, halogen, methyl, or carboxaldehyde;

$R_2$ is benzyloxy, phenyloxy, phenyloxy($C_1$–$C_6$)alkyl, or phenyl($C_1$–$C_4$)thioalkoxy, wherein each of the above is optionally substituted with 1, 2, 3, or 4 groups that are independently halogen, —$C_1$–$C_6$)alkyl-N(R)—$CO_2R_{30}$, $NR_6R_7$, ($C_1$–$C_4$)haloalkyl, ($C_1$–$C_4$)haloalkoxy, ($C_1$–$C_6$) alkyl, $NR_6R_7(C_1$–$C_6$)alkyl, pyridyl, morpholinyl, thiomorpholinyl, piperazinyl pyridyl($C_1$–$C_6$)alkyl, morpholinyl($C_1$–$C_6$)alkyl, thiomorpholinyl($C_1$–$C_6$)alkyl, or piperazinyl($C_1$–$C_6$)alkyl wherein the pyridyl, morpholinyl, thiomorpholinyl, and piperazinyl rings are optionally substituted with 1 or 2 groups that are independently $C_1$–$C_4$ alkyl, or halogen;

wherein $R_6$ and $R_7$ are independently at each occurrence H, $C_1$–$C_4$ alkyl optionally substituted with 1 or two groups that are independently OH, halogen or methoxy, $C_1$–$C_4$ hydroxyalkyl, $C_1$–$C_4$ alkoxy, $C_1$–$C_4$ alkoxy $C_1$–$C_4$ alkyl, $C_1$–$C_4$ alkanoyl, benzyl, benzyloxy, or phenyl $C_1$–$C_4$ alkanoyl, wherein each is unsubstituted or substituted with 1, 2, or 3 groups that are independently, halogen, OH, SH, $C_3$–$C_6$ cycloalkyl, $C_1$–$C_4$ alkoxy, $C_1$–$C_4$ alkyl, $CF_3$, or $OCF_3$, and $R_4$ is H, ($C_1$–$C_3$)alkyl optionally substituted with one or two groups that are independently $CO_2H$, —$CO_2$ alkyl, —$C(O)NRR$, —$N(R_{30})C(O)NRR$, —$N(R_{30})C(O)$—($C_1$–$C_6$)alkoxy, —$NR_6R_7$, $NR_6R_7C_1$–$C_4$ alkyl, or hydroxy($C_1$–$C_3$)alkyl.

Embodiment A43. Compounds according to embodiment A42, wherein $R_1$ is H or halogen.

Embodiment A44. Compounds according to embodiment A18, wherein $R_5$ is phenyl($C_1$–$C_6$)alkyl, ($C_1$–$C_6$)alkyl, piperidinyl($C_1$–$C_6$) alkyl, thienyl($C_1$–$C_6$)alkyl, indolyl($C_1$–$C_6$)alkyl, naphthyl($C_1$–$C_6$)alkyl, pyridyl($C_1$–$C_6$)alkyl, pyrimidyl ($C_1$–$C_6$)alkyl, quinolinyl($C_1$–$C_6$)alkyl, isoquinolinyl ($C_1$–$C_6$)alkyl, isoindolyl($C_1$–$C_6$)alkyl, indol-2-onyl ($C_1$–$C_6$)alkyl, pyridazinyl($C_1$–$C_6$)alkyl, pyrazinyl ($C_1$–$C_6$)alkyl, or pyrazinyl($C_1$–$C_6$)alkyl, wherein each of the above is unsubstituted or substituted with 1, 2, 3, 4, or 5 groups that are independently alkyl, halogen, alkoxy, benzyloxy, hydroxyalkyl, thioalkoxy, —$CO_2$ ($C_1$–$C_5$ alkyl), $CO_2H$, CN, amidinooxime, $NR_8R_9$, $NR_6R_7$—($C_1$–$C_6$ alkyl)-, —$C(O)NR_6R_7$, amidino, $CF_3$, or $OCF_3$;

$R_8$ is hydrogen, $C_1$–$C_6$ alkyl, $C_1$–$C_6$ alkanoyl, phenyl $C_1$–$C_6$ alkyl and phenyl $C_1$–$C_6$ alkanoyl; and $R_9$ is aminoalkyl, mono $C_1$–$C_6$ alkylamino $C_1$–$C_6$ alkyl, di $C_1$–$C_6$ alkylamino $C_1$–$C_6$ alkyl, $C_1$–$C_6$ alkyl, $C_1$–$C_6$ alkanoyl, phenyl $C_1$–$C_4$ alkyl, indazolyl, and phenyl $C_1$–$C_4$ alkanoyl.

In this embodiment, it is preferred that when $R_2$ is benzyloxy, $R_4$ is H, and $R_5$ is benzyl or methyl, $R_1$ is not hydrogen; and no more than two of $R_1$, $R_2$, $R_4$, and $R_5$ are simultaneously hydrogen.

Embodiment A45. Compounds according to embodiment A44, wherein $R_5$ is phenyl($C_1$–$C_6$)alkyl, which is unsubstituted or substituted with 1, 2, 3, 4, or 5 groups that are independently alkyl, halogen, alkoxy, benzyloxy, thioalkoxy, —$CO_2$($C_1$–$C_5$ alkyl), $CO_2H$, CN, amidinooxime, $NR_8R_9$, $NR_6R_7$—($C_1$–$C_6$ alkyl)-, —$C(O)NR_6R_7$, amidino, $CF_3$, or $OCF_3$; wherein $R_6$ and $R_7$ are independently at each occurrence H, $C_1$–$C_4$ alkyl, $C_1$–$C_4$ hydroxyalkyl, $C_1$–$C_4$ alkoxy, $C_1$–$C_4$ alkoxy $C_1$–$C_4$ alkyl, $C_1$–$C_4$ alkanoyl, phenyl $C_1$–$C_4$ alkyl, phenyl $C_1$–$C_4$ alkoxy, or phenyl $C_1$–$C_4$ alkanoyl, wherein each is unsubstituted or substituted with 1, 2, or 3 groups that are independently, halogen, OH, SH, $C_3$–$C_6$ cycloalkyl, $C_1$–$C_4$ alkoxy, $C_1$–$C_4$ alkyl, $CF_3$, or $OCF_3$; or $R_6$, $R_7$, and the nitrogen to which they are attached form a morpholinyl, thiomorpholinyl, or piperazinyl ring which is optionally substituted with 1 or 2 groups that are independently $C_1$–$C_4$ alkyl, hydroxy, hydroxy $C_1$–$C_4$ alkyl, or halogen;

$R_8$ is hydrogen, $C_1$–$C_6$ alkyl, $C_1$–$C_6$ alkanoyl, phenyl $C_1$–$C_6$ alkyl and phenyl $C_1$–$C_6$ alkanoyl; and $R_9$ is aminoalkyl, mono $C_1$–$C_6$ alkylamino $C_1$–$C_6$ alkyl, di $C_1$–$C_6$ alkylamino $C_1$–$C_6$ alkyl, $C_1$–$C_6$ alkyl, $C_1$–$C_6$ alkanoyl, phenyl $C_1$–$C_4$ alkyl, indazolyl, and phenyl $C_1$–$C_4$ alkanoyl.

Embodiment A46. Compounds according to embodiment A45, wherein $R_5$ is phenyl($C_1$–$C_6$)alkyl, which is unsubstituted or substituted with 1, 2, 3, 4, or 5 groups that are independently CN, halogen, $C_1$–$C_4$ alkoxy, $C_1$–$C_4$ thioalkoxy, $C_1$–$C_4$ haloalkyl, $C_1$–$C_4$ alkyl, $C_1$–$C_4$ haloalkyl, $C_1$–$C_4$ haloalkoxy, —$C(O)NR_{20}R_{21}$,
wherein $R_{20}$ and $R_{21}$ are independently H, $C_1$–$C_6$ alkyl, $C_1$–$C_6$ hydroxyalkyl, $C_1$–$C_6$ alkoxy $C_1$–$C_6$ alkyl, or $R_{20}$, $R_{21}$, and the nitrogen to which they are attached form a piperazinyl, or morpholinyl ring, each of which is optionally substituted with 1 or 2 groups that are independently alkyl or halogen.

Embodiment A47. Compounds according to embodiment A46, wherein $R_5$ is phenyl($C_1$–$C_4$)alkyl, which is unsubstituted or substituted with 1, 2, 3, 4, or 5 groups that are independently CN, halogen, $C_1$–$C_4$ alkoxy, $C_1$–$C_4$ haloalkyl, $C_1$–$C_4$ alkyl, $C_1$–$C_4$ haloalkoxy, —$C(O)NR_{20}R_{21}$, wherein $R_{20}$ and $R_{21}$ are independently H, $C_1$–$C_6$ alkyl, $C_1$–$C_6$ hydroxyalkyl, $C_1$–$C_6$ alkoxy $C_1$–$C_6$ alkyl, or $R_{20}$, $R_{21}$, and the nitrogen to which they are attached form a piperazinyl, or morpholinyl ring, each of which is optionally substituted with 1 or 2 groups that are independently alkyl or halogen.

Embodiment A48. Compounds according to embodiment A47, wherein $R_5$ is benzyl or phenethyl, each of which is unsubstituted or substituted with 1, 2, 3, 4, or 5 groups that are independently CN, halogen, $C_1$–$C_4$ alkoxy, $CF_3$, $OCF_3$, $C_1$–$C_4$ alkyl, —$C(O)NR_2OR_{21}$, wherein $R_{20}$ and $R_{21}$ are independently H, $C_1$–$C_6$ alkyl, $C_1$–$C_6$ hydroxyalkyl, $C_1$–$C_6$ alkoxy $C_1$–$C_6$ alkyl, or $R_{20}$, $R_{21}$, and the nitrogen to which they are attached form a piperazinyl, or morpholinyl ring, each of which is optionally substituted with 1 or 2 groups that are independently alkyl or halogen.

Embodiment A49. Compounds according to embodiment A48, wherein $R_5$ is benzyl or phenethyl, each of which is unsubstituted or substituted with 1, 2, 3, 4, or 5 groups that are independently halogen, methoxy, ethoxy, $CF_3$, $OCF_3$, methyl, ethyl, or —$C(O)NR_{20}R_{21}$, wherein $R_{20}$ and $R_{21}$ are independently H, $C_1$–$C_6$ alkyl, $C_1$–$C_6$ hydroxyalkyl, $C_1$–$C_6$ alkoxy $C_1$–$C_6$ alkyl, Embodiment A50. Compounds according to embodiment A48, wherein $R_5$ is benzyl or phenethyl, each of which is unsubstituted or substituted with 1, 2, 3, 4, or 5 groups that are independently halogen, methoxy, ethoxy, $CF_3$, $OCF_3$, methyl, ethyl, or —$C(O)NR_{20}R_{21}$, wherein $R_{20}$, $R_{21}$, and the nitrogen to which they are attached form a piperazinyl, or morpholinyl ring, each of which is optionally substituted with 1 or 2 groups that are independently alkyl or halogen.

Embodiment A51. Compounds according to embodiment A49, wherein $R_5$ is substituted on the phenyl ring with 1, 2, 3, 4, or 5 groups and wherein there is a group at the para position of the phenyl.

Embodiment A52. Compounds according to embodiment A43, wherein $R_5$ is piperidinyl($C_1$–$C_6$)alkyl, thienyl($C_1$–$C_6$)alkyl, indolyl($C_1$–$C_6$)alkyl, pyridyl($C_1$–$C_6$)alkyl, pyrimidyl($C_1$–$C_6$)alkyl, quinolinyl($C_1$–$C_6$)alkyl, isoquinolinyl($C_1$–$C_6$)alkyl, isoindolyl($C_1$–$C_6$)alkyl, indol-2-onyl($C_1$–$C_6$)alkyl, pyridazinyl($C_1$–$C_6$)alkyl, or pyrazinyl($C_1$–$C_6$)alkyl, or pyrazinyl($C_1$–$C_6$)alkyl, or pyrazinyl($C_1$–$C_6$)alkyl, wherein each of the above is unsubstituted or substituted with 1, 2, 3, 4, or 5 groups that are independently $C_1$–$C_6$ alkyl, halogen, $C_1$–$C_6$ alkoxy, $C_1$–$C_6$ hydroxyalkyl, benzyloxy, $C_1$–$C_6$ thioalkoxy, —$CO_2$($C_1$–$C_5$ alkyl), $CO_2H$, CN, amidinooxime, $NR_8R_9$, $NR_6R_7$—($C_1$–$C_6$ alkyl)-, —$C(O)NR_6R_7$, amidino, $CF_3$, or $OCF_3$;

$R_8$ is hydrogen, $C_1$–$C_6$ alkyl, $C_1$–$C_6$ alkanoyl, phenyl $C_1$–$C_6$ alkyl and phenyl $C_1$–$C_6$ alkanoyl; and $R_9$ is aminoalkyl, mono $C_1$–$C_6$ alkylamino $C_1$–$C_6$ alkyl, di $C_1$–$C_6$ alkylamino $C_1$–$C_6$ alkyl, $C_1$–$C_6$ alkyl, $C_1$–$C_6$ alkanoyl, phenyl $C_1$–$C_4$ alkyl, indazolyl, and phenyl $C_1$–$C_4$ alkanoyl.

In this embodiment, it is preferred that when $R_2$ is benzyloxy, $R_4$ is H, and $R_5$ is benzyl or methyl, $R_1$ is not hydrogen; and no more than two of $R_1$, $R_2$, $R_4$, and $R_5$ are simultaneously hydrogen.

Embodiment A53. Compounds according to embodiment A52, wherein $R_5$ is piperidinyl($C_1$–$C_4$)alkyl, thienyl($C_1$–$C_4$)alkyl, indolyl($C_1$–$C_4$)alkyl, pyridyl($C_1$–$C_4$)alkyl, pyrimidyl($C_1$–$C_4$)alkyl, or pyrazinyl($C_1$–$C_4$)alkyl, each of which is unsubstituted.

Embodiment A54. Compounds according to embodiment A52, wherein $R_5$ is indolyl($C_1$–$C_4$)alkyl, pyrimidyl($C_1$–$C_4$)alkyl, or pyrazinyl($C_1$–$C_4$)alkyl, wherein each of the above is unsubstituted or substituted with 1, 2, 3, or 4 groups that are independently $C_1$–$C_6$ alkyl, halogen, $C_1$–$C_6$ alkoxy, $C_1$–$C_6$ hydroxyalkyl, benzyloxy, $C_1$–$C_6$ thioalkoxy, —$CO_2$($C_1$–$C_5$ alkyl), $CO_2H$, CN, amidinooxime, $NR_8R_9$, $NR_6R_7$—($C_1$–$C_6$ alkyl)-, amidino, —$C(O)NR_{20}R_{21}$, $CF_3$, or $OCF_3$; wherein $R_6$ and $R_7$ are independently at each occurrence H, $C_1$–$C_4$ alkyl, $C_1$–$C_4$ hydroxyalkyl, $C_1$–$C_4$ alkoxy, $C_1$–$C_4$ alkoxy $C_1$–$C_4$ alkyl, $C_1$–$C_4$ alkanoyl, benzyl, benzyloxy, or phenyl $C_1$–$C_4$ alkanoyl, wherein each is unsubstituted or substituted with 1, 2, or 3 groups that are independently, halogen, OH, SH, $C_3$–$C_6$ cycloalkyl, $C_1$–$C_4$ alkoxy, $C_1$–$C_4$ alkyl, $CF_3$, or $OCF_3$; or $R_6$, $R_7$, and the nitrogen to which they are attached form a morpholinyl, thiomorpholinyl, or piperazinyl ring which is optionally substituted with 1 or 2 groups that are independently $C_1$–$C_4$ alkyl, hydroxy, hydroxy $C_1$–$C_4$ alkyl, or halogen;

$R_8$ is hydrogen, $C_1$–$C_6$ alkyl, $C_1$–$C_6$ alkanoyl, phenyl $C_1$–$C_4$ alkyl and phenyl $C_1$–$C_4$ alkanoyl; and $R_9$ is aminoalkyl, mono $C_1$–$C_6$ alkylamino $C_1$–$C_6$ alkyl, di $C_1$–$C_6$ alkylamino $C_1$–$C_6$ alkyl, $C_1$–$C_6$ alkyl, $C_1$–$C_6$ alkanoyl, phenyl $C_1$–$C_4$ alkyl, indazolyl, and phenyl $C_1$–$C_4$ alkanoyl;

$R_{20}$ and $R_2$, are independently H, $C_1$–$C_6$ alkyl, $C_1$–$C_6$ hydroxyalkyl, $C_1$–$C_6$ alkoxy $C_1$–$C_6$ alkyl, or $R_{20}$, $R_{21}$, and the nitrogen to which they are attached form a piperazinyl, or morpholinyl ring, each of which is optionally substituted with 1 or 2 groups that are independently alkyl or halogen Embodiment A55. Compounds according to embodiment A54, wherein $R_5$ is indolyl($C_1$–$C_4$)alkyl, or pyrazinyl($C_1$–$C_4$)alkyl, wherein each of the above is unsubstituted or substituted with 1, 2, 3, or 4 groups that are independently $C_1$–$C_6$ alkyl, halogen, $C_1$–$C_6$ alkoxy, $C_1$–$C_6$ hydroxyalkyl, benzyloxy, $C_1$–$C_6$ thioalkoxy, —$CO_2$($C_1$–$C_5$ alkyl), $CO_2H$, CN, —$C(O)NR_{20}R_{21}$, $CF_3$, or $OCF_3$; wherein $R_{20}$ and $R_{21}$ are independently H, $C_1$–$C_6$ alkyl, $C_1$–$C_6$ hydroxyalkyl, $C_1$–$C_6$ alkoxy $C_1$–$C_6$ alkyl, or $R_{20}$, $R_{21}$, and the nitrogen to which they are attached form a piperazinyl, or morpholinyl ring, each of which is optionally substituted with 1 or 2 groups that are independently alkyl or halogen.

Embodiment A56. Compounds according to embodiment A52, wherein $R_5$ is isoquinolinyl, isoindolyl, indol-2-onyl, quinolinyl ($C_1$–$C_6$)alkyl, isoquinolinyl($C_1$–$C_6$)alkyl, isoindolyl ($C_1$–$C_6$)alkyl, indol-2-onyl($C_1$–$C_6$)alkyl, wherein each of the above is unsubstituted or substituted with 1, 2, 3, 4, or 5 groups that are independently $C_1$–$C_6$ alkyl, halogen, $C_1$–$C_6$ alkoxy, $C_1$–$C_6$ hydroxyalkyl, benzyloxy, $C_1$–$C_6$ thioalkoxy, —$CO2$($C_1$–$C_5$ alkyl), $CO_2H$, CN, amidinooxime, $NR_8R_9$, $NR_6R_7$—($C_1$–$C_6$ alkyl)-, —$C(O)NR_6R_7$, amidino, $CF_3$, or $OCF_3$.

Embodiment A57. Compounds according to embodiment A1,
wherein $R_1$ is H, halogen, methyl, ethyl, $C_2$–$C_4$ alkenyl, $C_2$–$C_4$ alkynyl, or carboxaldehyde;

$R_2$ is benzyloxy, OH, phenyloxy, phenyloxy($C_1$–$C_6$)alkyl, or phenyl($C_1$–$C_4$)thioalkoxy, wherein each of the above is optionally substituted with 1, 2, 3, or 4 groups that are independently halogen, —($C_1$–$C_6$)alkyl-N(R)—$CO_2R_{30}$, $NR_6R_7$, ($C_1$–$C_4$)haloalkyl, ($C_1$–$C_4$)haloalkoxy, ($C_1$–$C_6$) alkyl, pyridyl, or $NR_6R_7$—($C_1$–$C_6$ alkyl)-; and $R_4$ is H, ($C_1$–$C_4$)alkyl optionally substituted with one or two groups that are independently $CO_2H$, —$CO_2$ alkyl, —$C(O)NRR$, —$N(R_{30})C(O)NRR$, —$N(R_{30})C(O)$—($C_1$–$C_6$)alkoxy, or —$NR_6R_7$, or hydroxy($C_1$–$C_4$)alkyl;

$R_5$ is $C_3$–$C_7$ cycloalkyl or $C_3$–$C_7$ cycloalkylalkyl, each of which is optionally substituted with 1 or 2 groups that are independently alkyl, alkoxy, halogen, —$NR_6R_7$, or $NR_6R_7$—($C_1$–$C_6$ alkyl)-, wherein each of the alkyl groups is optionally substituted with 1 or 2 groups that are independently OH, methoxy, $NH_2$, or halogen.

Embodiment A58. Compounds according to embodiment A57, wherein $R_5$ is $C_3$–$C_7$ cycloalkyl or $C_3$–$C_7$ cycloalkyl $C_1$–$C_4$ alkyl, each of which is optionally substituted with 1 or 2 groups that are independently $C_1$–$C_4$ alkyl, $C_1$–$C_4$ alkoxy, halogen, —$NR_6R_7$, or $NR_6R_7$—($C_1$–$C_6$ alkyl)- wherein each of the alkyl groups is optionally substituted with 1 or 2 groups that are independently OH, methoxy, or $NH_2$;

$R_6$ and $R_7$ are independently at each occurrence H, $C_1$–$C_4$ alkyl, $C_1$–$C_4$ hydroxyalkyl, $C_1$–$C_4$ alkoxy, $C_1$–$C_4$ alkoxy $C_1$–$C_4$ alkyl, $C_1$–$C_4$ alkanoyl, benzyl, benzyloxy, or phenyl $C_1$–$C_4$ alkanoyl, wherein each is unsubstituted or substituted with 1, 2, or 3 groups that are independently, halogen, OH, SH, $C_3$–$C_6$ cycloalkyl, $C_1$–$C_4$ alkoxy, $C_1$–$C_4$ alkyl, $CF_3$, or $OCF_3$; or $R_6$, $R_7$, and the nitrogen to which they are attached form a morpholinyl, thiomorpholinyl, or piperazinyl ring which is optionally substituted with 1 or 2 groups that are independently $C_1$–$C_4$ alkyl, hydroxy, hydroxy $C_1$–$C_4$ alkyl, or halogen.

Embodiment A59. Compounds according to embodiment A58, wherein $R_1$ is H, halogen, methyl, ethyl;

$R_2$ is benzyloxy, phenyloxy, phenyloxy($C_1$–$C_6$)alkyl, or phenyl($C_1$–$C_4$)thioalkoxy, wherein each of the above is optionally substituted with 1, 2, 3, or 4 groups that are independently halogen, —($C_1$–$C_6$)alkyl-N(R)—$CO_2R_{30}$, amino, mono or dialkylamino, —$NR_6R_7$, ($C_1$–$C_4$) haloalkyl, ($C_1$–$C_4$)haloalkoxy, ($C_1$–$C_6$)alkyl, or $NR_6R_7$—($C_1$–$C_6$ alkyl)-; and $R_4$ is H, methyl, ($C_1$–$C_4$)alkyl optionally substituted with one or two groups that are independently $CO_2H$, —$CO_2$ alkyl, —$C(O)NRR$, —$N(R_{30})C(O)NRR$, —$N(R_{30})C(O)$—($C_1$–$C_6$)alkoxy, or —$NR_6R_7$ or hydroxy($C_1$–$C_2$) alkyl.

Embodiment A60. Compounds according to embodiment A59, wherein $R_2$ is substituted with two halogens and is further optionally substituted with 1 or 2 groups that are independently halogen, —($C_1$–$C_6$)alkyl-N(R)—$CO_2R_{30}$, amino, mono or dialkylamino, —$NR_6R_7$, ($C_1$–$C_4$)haloalkyl, ($C_1$–$C_4$) haloalkoxy, ($C_1$–$C_6$)alkyl, or $NR_6R_7$—($C_1$–$C_6$ alkyl).

Embodiment A61. Compounds according to embodiment A1,
wherein $R_5$ is H, alkyl optionally substituted with 1, 2, or 3 groups that are independently phenylalkoxycarbonyl, —$NR_8R_9$, halogen, —$C(O)NR_8R_9$, alkoxycarbonyl, or alkanoyl, alkoxyalkyl optionally substituted with one trimethylsilyl group, alkoxycarbonyl, amino, hydroxyalkyl, alkenyl optionally substituted with alkoxycarbonyl, alkynyl, —$SO_2$-alkyl, or alkoxy optionally substituted with one trimethylsilyl group, wherein each of the above is unsubstituted or substituted with 1, 2, 3, 4, or 5 groups that are independently alkyl, halogen, alkoxy, phenylalkoxy, thioalkoxy, —$SO_2$ alkyl, alkoxycarbonyl, phenylalkoxycarbonyl, $CO_2H$, CN, OH, amidinooxime, $NR_8R_9$, $NR_6R_7$—($C_1$–$C_6$ alkyl)-, —$C(O)NR_6R_7$, amidino, hydroxyalkyl, carboxaldehyde, —$NR_6R_7$, haloalkyl, or haloalkoxy;

wherein $R_8$ is hydrogen, alkyl, alkanoyl, phenylalkyl and arylalkanoyl; and wherein $R_9$ is alkyl, alkanoyl, phenylalkyl, heteroaryl, aminoalkyl, monoalkylaminoalkyl, dialkylaminoalkyl, and arylalkanoyl.

In this embodiment, it is preferred that when $R_2$ is benzyloxy, $R_4$ is H, and $R_5$ is benzyl or methyl, $R_1$ is not hydrogen; and no more than two of $R_1$, $R_2$, $R_4$, and $R_5$ are simultaneously hydrogen.

Embodiment A62. Compounds according to embodiment A1, wherein $R_5$ is H, alkyl optionally substituted with 1, 2, or 3 groups that are independently phenylalkoxycarbonyl, —$NR_8R_9$, halogen, —C(O)$NR_8R_9$, alkoxycarbonyl, or alkanoyl, alkoxyalkyl optionally substituted with one trimethylsilyl group, alkoxycarbonyl, amino, hydroxyalkyl, alkenyl optionally substituted with alkoxycarbonyl, alkynyl, —$SO_2$-alkyl, alkoxy optionally substituted with one trimethylsilyl group, wherein each of the above is unsubstituted or substituted with 1, 2, 3, 4, or 5 groups that are independently alkyl, halogen, alkoxy, phenylalkoxy, thioalkoxy, —$SO_2$ alkyl, alkoxycarbonyl, phenylalkoxycarbonyl, $CO_2H$, CN, OH, amidinooxime, $NR_8R_9$, $NR_6R_7$—($C_1$–$C_6$ alkyl)-, —C(O)$NR_6R_7$, amidino, hydroxyalkyl, carboxaldehyde, —$NR_6R_7$, haloalkyl, or haloalkoxy;

wherein $R_8$ is hydrogen, alkyl, alkanoyl, phenylalkyl and arylalkanoyl; and wherein $R_9$ is alkyl, alkanoyl, phenylalkyl, heteroaryl, aminoalkyl, monoalkylaminoalkyl, dialkylaminoalkyl, and arylalkanoyl.

In this embodiment, it is preferred that when $R_2$ is benzyloxy, $R_4$ is H, and $R_5$ is benzyl or methyl, $R_1$ is not hydrogen; and no more than two of $R_1$, $R_2$, $R_4$, and $R_5$ are simultaneously hydrogen.

Embodiment A63. Compounds according to embodiment A62, wherein $R_1$ is H, halogen, methyl, ethyl, $C_2$–$C_4$ alkenyl, $C_2$–$C_4$ alkynyl, or carboxaldehyde;

$R_2$ is benzyloxy, OH, phenyloxy, phenyloxy($C_1$–$C_6$)alkyl, or phenyl($C_1$–$C_4$)thioalkoxy, wherein each of the above is optionally substituted with 1, 2, 3, or 4 groups that are independently halogen, —($C_1$–$C_6$)alkyl-N(R)—$CO_2R_{30}$, $NR_6R_7$, ($C_1$–$C_4$)haloalkyl, ($C_1$–$C_4$)haloalkoxy, ($C_1$–$C_6$) alkyl, pyridyl, or $NR_6R_7$—($C_1$–$C_6$ alkyl)-; and $R_4$ is H, ($C_1$–$C_4$)alkyl optionally substituted with one or two groups that are independently $CO_2H$, —$CO_2$ alkyl, —C(O)NRR, —N($R_{30}$)C(O)NRR, —N($R_{30}$)C(O)—($C_1$–$C_6$)alkoxy, or —$NR_6R_7$, or hydroxy($C_1$–$C_4$)alkyl.

Embodiment A64. Compounds according to embodiment A63, wherein $R_5$ is H, alkyl optionally substituted with 1, 2, or 3 groups that are independently phenylalkoxycarbonyl, —$NR_8R_9$, halogen, —C(O)$NR_8R_9$, alkoxycarbonyl, or alkanoyl, alkoxyalkyl optionally substituted with one trimethylsilyl group, alkoxycarbonyl, amino, hydroxyalkyl, alkenyl optionally substituted with alkoxycarbonyl, alkynyl, —$SO_2$-alkyl, alkoxy optionally substituted with one trimethylsilyl group, wherein wherein $R_8$ is hydrogen, $C_1$–$C_4$ alkyl, $C_1$–$C_4$ alkanoyl, phenyl $C_1$–$C_4$ alkyl and phenyl $C_1$–$C_4$ alkanoyl;

wherein $R_9$ is $C_1$–$C_4$ alkyl, $C_1$–$C_4$ alkanoyl, phenyl $C_1$–$C_4$ alkyl, pyridyl, aminoalkyl, monoalkylaminoalkyl, dialkylaminoalkyl, and phenyl $C_1$–$C_4$ alkanoyl.

Embodiment A65. Compounds according to embodiment A64, wherein $R_5$ is $C_1$–$C_6$ alkyl optionally substituted with 1, 2, or 3 groups that are independently phenyl $C_1$–$C_4$ alkoxycarbonyl, $NH_2$, mono $C_1$–$C_4$ alkylamino, di $C_1$–$C_4$ alkylamino, halogen, —C(O)$NH_2$, —C(O)NH($C_1$–$C_6$ alkyl) wherein the alkyl is optionally substituted with OH, $NH_2$, or methoxy, —C(O)N($C_1$–$C_6$ alkyl)($C_1$–$C_6$ alkyl) wherein each alkyl is optionally substituted with OH, $NH_2$, or methoxy, $C_1$–$C_4$ alkoxycarbonyl, and $C_1$–$C_4$ alkanoyl, or $R_5$ is $C_1$–$C_4$ alkoxy $C_1$–$C_4$ alkyl, $C_1$–$C_4$ alkoxycarbonyl, amino, $C_1$–$C_4$ hydroxyalkyl, $C_2$–$C_4$ alkenyl optionally substituted with $C_1$–$C_4$ alkoxycarbonyl, $C_2$–$C_4$ alkynyl, —$SO_2$—$C_1$–$C_4$ alkyl, or $C_1$–$C_4$ alkoxy.

Embodiment A66. A compound of the formula

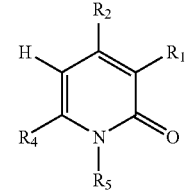

or a pharmaceutically acceptable salt thereof, wherein $R_1$ is halogen, $NO_2$, alkyl, carboxaldehyde, hydroxyalkyl, arylalkoxy, arylalkyl, CN, aryl, alkanoyl, alkoxy, alkoxyalkyl, haloalkyl, or arylalkanoyl, wherein the aryl portion of arylalkoxy, arylalkyl, and arylalkanoyl is unsubstituted or substituted with 1, 2, 3, 4, or 5 groups that are independently halogen, ($C_1$–$C_4$) alkyl, ($C_1$–$C_4$)alkoxy, nitro, CN, haloalkyl, haloalkoxy or $CO_2H$;

wherein the alkyl portion of the alkyl, hydroxyalkyl, arylalkoxy, arylalkyl, alkanoyl, alkoxy, alkoxyalkyl and arylalkanoyl groups is unsubstituted or substituted with 1, 2, or 3 groups that are independently halogen, $C_1$–$C_4$ alkoxy, $C_1$–$C_4$ alkoxycarbonyl, or spirocyclopropyl;

$R_2$ is aryl, heteroaryl, arylalkenyl, arylalkoxy, aryloxyalkyl, arylalkyl, OH, alkynyl, aryloxy, aryloxyalkyl, arylthioalkoxy, alkoxy, —OC(O)NH($CH_2$)aryl, —OC(O)N(alkyl)($CH_2$)$_n$aryl, —$OSO_2$($C_1$–$C_6$)alkyl, —$OSO_2$ aryl, alkyl, alkoxyalkoxy, $NR_8R_9$, or $CO_2H$, wherein n is 0, 1, 2, 3, 4, 5 or 6;

each of the above is unsubstituted or substituted with 1, 2, 3, 4, or 5 groups that are independently halogen, —($C_1$–$C_6$)alkyl-N(R)—$CO_2R_{30}$, alkoxy, alkoxycarbonyl, CN, $NR_6R_7$, haloalkyl, haloalkoxy, alkyl, heteroaryl, heteroarylalkyl, $NR_6R_7$—($C_1$–$C_6$ alkyl)-, phenyl, —$SO_2$-phenyl wherein the phenyl groups are optionally substituted with 1, 2, or 3 groups that are independently halogen or $NO_2$; or —OC(O)$NR_6R_7$, wherein $R_6$ and $R_7$ are independently at each occurrence H, alkyl, alkoxy, alkoxyalkyl, alkoxycarbonyl, —$SO_2$-alkyl, OH, hydroxyalkyl, —($C_1$–$C_4$)alkyl-$CO_2$-alkyl, heteroarylalkyl, alkanoyl, arylalkyl, arylalkoxy, or arylalkanoyl, wherein each of the above is unsubstituted or substituted with 1, 2, or 3 groups that are independently halogen, alkoxy, heterocycloalkyl, OH, SH, $C_3$–$C_6$ cycloalkyl, $NH_2$, NH(alkyl), N(alkyl)(alkyl), —O—alkanoyl, alkyl, haloalkyl, or haloalkoxy; or $R_6$, $R_7$, and the nitrogen to which they are attached form a morpholinyl, thiomorpholinyl, piperidinyl, pyrrolidinyl, or piperazinyl ring which is optionally substituted with 1 or 2 groups that are independently $C_1$–$C_4$ alkyl, $C_1$–$C_4$ alkoxy, hydroxy, hydroxy $C_1$–$C_4$ alkyl, or halogen;

R at each occurrence is independently H or $C_1$–$C_6$ alkyl;

$R_{30}$ is $C_1$–$C_6$ alkyl optionally substituted with 1 or 2 groups that are independently OH, SH, halogen, amino, monoalkylamino, dialkylamino or $C_3$–$C_6$ cycloalkyl;

$R_4$ is H, alkyl optionally substituted with one or two groups that are independently $CO_2H$, —$CO_2$ alkyl, —C(O)NRR, —N($R_{30}$)C(O)NRR, —N($R_{30}$)C(O)—($C_1$–$C_6$)alkoxy, or —$NR_6R_7$, arylalkoxy, arylalkyl, hydroxyalkyl, haloalkyl, alkoxy, carboxaldehyde, $CO_2H$, alkoxyalkyl, or alkoxyalkoxy, wherein the aryl portion of arylalkoxy, arylalkyl is unsubstituted or substituted with 1, 2, 3, 4, or 5 groups that are independently halogen, hydroxy, alkoxy, alkyl, nitro, haloalkyl, or haloalkoxy; and $R_5$ is H, arylalkyl, alkyl, aryl, alkoxy, heterocycloalkylalkyl, heteroarylalkyl, heterocycloalkyl, cycloalkyl, cycloalkylalkyl, -alkyl-S-aryl, -alkyl-$SO_2$-aryl, —($C_1$–$C_4$)alkyl-C(O)-heterocycloalkyl, —$SO_2$-aryl, or heteroaryl, wherein each of the above is unsubstituted or substituted with 1, 2, 3, 4, or 5 groups that are independently alkyl, halogen, alkoxy, aryl, arylalkoxy, thioalkoxy, alkoxycarbonyl, arylalkoxycarbonyl, OH, $CO_2H$, CN, amidinooxime, $NR_8R_9$, $NR_6R_7$—($C_1$–$C_6$ alkyl)-, —C(O)$NR_6R_7$, —($C_1$–$C_4$ alkyl)-C(O)$NR_6R_7$, amidino, hydroxyalkyl, —$SO_2$ alkyl, —$SO_2H$, —$SO_2NR_6R_7$, —$NR_6R_7$, alkanoyl wherein the alkyl portion is optionally substituted with OH, halogen or alkoxy, haloalkyl, —($C_1$–$C_4$ alkyl)-$NR_{15}$C(O)$NR_{16}R_{17}$, —($C_1$–$C_4$ alkyl)-$NR_{15}$C(O)$R_{18}$, —O—$CH_2$—O—, —O—$CH_2CH_2$—O—, or haloalkoxy; wherein $R_8$ at each occurrence is independently hydrogen, alkyl, alkanoyl, arylalkyl and arylalkanoyl wherein each of the above is optionally substituted with 1, 2, 3, 4, or 5 groups that are independently alkyl, alkoxy, alkoxycarbonyl, halogen, or haloalkyl; and $R_9$ at each occurrence is independently alkyl, alkanoyl, arylalkyl cycloalkyl, alkenyl, heteroaryl, cycloalkylalkyl, arylalkanoyl, —$SO_2$-phenyl, and aryl wherein each of the above is optionally substituted with 1, 2, 3, 4, or 5 groups that are independently alkyl, alkoxy, alkoxycarbonyl, halogen, or haloalkyl;

$R_{15}$ is H or $C_1$–$C_6$ alkyl;

$R_{16}$ and $R_{17}$ are independently H or $C_1$–$C_6$ alkyl; or $R_{16}$, $R_{17}$, and the nitrogen to which they are attached form a morpholinyl ring; and $R_{18}$ is $C_1$–$C_6$ alkyl optionally substituted with —O—($C_2$–$C_6$ alkanoyl, $C_1$–$C_6$ hydroxyalkyl, $C_1$–$C_6$ alkoxy, $C_1$–$C_6$ alkoxy $C_1$–$C_6$ alkyl; amino $C_1$–$C_6$ alkyl, mono or dialkylamino $C_1$–$C_6$ alkyl.

In this embodiment, it is preferred that:

$R_6$ and $R_7$ are not simultaneously OH;

$R_6$ and $R_7$ are not simultaneously —$SO_2$($C_1$–$C_6$ alkyl);

when $R_2$ is OH, $R_4$ is methyl and $R_5$ is phenyl, $R_1$ is not acetyl; and $R_4$ and $R_5$ are not simultaneously hydrogen.

Embodiment A71. Compounds according to embodiment A66 wherein $R_1$ is halogen, $C_1$–$C_6$ alkyl, phenyl, carboxaldehyde, $C_1$–$C_6$ hydroxyalkyl, phenyl $C_1$–$C_6$ alkoxy, phenyl $C_1$–$C_6$ alkyl, CN, $C_1$–$C_6$ alkanoyl, $C_1$–$C_6$ alkoxy, $C_1$–$C_6$ alkoxy $C_1$–$C_6$ alkyl, $C_1$–$C_6$ haloalkyl, or phenyl $C_1$–$C_6$ alkanoyl, wherein the above phenyl groups are unsubstituted or substituted with 1, 2, or 3 groups that are independently halogen, ($C_1$–$C_4$)alkyl, ($C_1$–$C_4$)alkoxy, nitro, CN, $C_1$–$C_4$ haloalkyl, $C_1$–$C_4$ haloalkoxy or $CO_2H$;

wherein the above alkyl groups are unsubstituted or substituted with 1, 2, or 3 groups that are independently halogen, methoxy, or ethoxy;

$R_2$ is phenylalkoxy, OH, phenyloxy, phenyloxy($C_1$–$C_6$) alkyl, phenylthio ($C_1$–$C_4$)alkoxy, alkoxy, alkenyl, phenethyl, —OC(O)NH($CH_2$)$_n$phenyl, —OC(O)N(alkyl)($CH_2$)$_n$phenyl, alkyl, alkoxyalkoxy, $NR_8R_9$, pyridyl, pyrimidyl, pyridazyl, pyrazolyl, imidazolyl, pyrrolyl, tetrahydroquinolinyl, amino, tetrahydroisoquinolinyl, tetrazolyl, pyrazinyl, benzimidazolyl, triazinyl, tetrahydrofuryl, piperidinyl, hexahydropyrimidinyl, thiazolyl, thienyl, or $CO_2H$, wherein n is 0, 1, 2, or 3;

each of the above is unsubstituted or substituted with 1, 2, 3, 4, or 5 groups that are independently halogen, —($C_1$–$C_6$)alkyl-N(R)—$CO_2R_{30}$, haloalkyl, haloalkoxy, alkyl, thienyl, pyridyl, or phenyl optionally substituted with 1, 2, or 3 halogens;

$R_6$ and $R_7$ are independently at each occurrence H, alkyl, alkoxy, alkoxyalkyl, hydroxyalkyl, alkoxycarbonyl, —($C_1$–$C_4$)alkyl-$CO_2$-alkyl, alkanoyl, phenylalkyl, phenylalkoxy, or phenylalkanoyl, wherein each of the above is unsubstituted or substituted with 1, 2, or 3 groups that are independently, halogen, OH, SH, $C_3$–$C_6$ cycloalkyl, alkoxy, $NH_2$, NH($C_1$–$C_6$ alkyl), N($C_1$–$C_6$ alkyl)($C_1$–$C_6$ alkyl), alkyl, $CF_3$ or $OCF_3$; or $R_6$, $R_7$, and the nitrogen to which they are attached form a morpholinyl, thiomorpholinyl, piperidinyl, pyrrolidinyl, or piperazinyl ring which is optionally substituted with 1 or 2 groups that are independently $C_1$–$C_4$ alkyl, hydroxy, hydroxy $C_1$–$C_4$ alkyl, or halogen;

$R_4$ is H, alkyl optionally substituted with one or two groups that are independently $CO_2H$, —$CO_2$ alkyl, —C(O)NRR, —N($R_{30}$)C(O)NRR, —N($R_{30}$)C(O)—($C_1$–$C_6$)alkoxy, or —$NR_6R_7$, phenylalkoxy, phenylalkyl, hydroxyalkyl, carboxaldehyde, haloalkyl, alkoxy, alkoxyalkyl, or alkoxyalkoxy, wherein the above phenyl groups are unsubstituted or substituted with 1, 2, or 3 groups that are independently halogen, hydroxy, alkoxy, alkyl, nitro, haloalkyl, or haloalkoxy; and $R_5$ is benzyl, phenethyl, ($C_1$–$C_6$)alkyl, phenyl, naphthyl, alkoxy, piperidinyl, pyrrolidinyl, imidazolidinyl, piperazinyl, isoquinolinyl, tetrahydroisoquinolinyl, indolyl, 1H-indazolyl, pyridyl, pyrimidyl, pyridazyl, pyrazinyl, piperidinyl($C_1$–$C_6$)alkyl, pyrrolidinyl($C_1$–$C_6$) alkyl, imidazolidinyl($C_1$–$C_6$)alkyl, piperazinyl($C_1$–$C_6$) alkyl, pyridyl($C_1$–$C_6$)alkyl, pyrimidyl($C_1$–$C_6$)alkyl, pyridazyl($C_1$–$C_6$)alkyl, pyrazinyl($C_1$–$C_6$)alkyl, isoquinolinyl($C_1$–$C_6$)alkyl, tetrahydroisoquinolinyl ($C_1$–$C_6$)alkyl, indolyl($C_1$–$C_6$)alkyl, or 1H-indazolyl ($C_1$–$C_6$)alkyl, and wherein each of the above is unsubstituted or substituted with 1, 2, 3, 4, or 5 groups that are independently alkyl, halogen, alkoxy, hydroxyalkyl, phenylalkoxy, thioalkoxy, alkoxycarbonyl, phenylalkoxycarbonyl, OH, $CO_2H$, CN, amidinooxime, $NR_8R_9$, $NR_6R_7$—($C_1$–$C_6$ alkyl)-, —C(O)NR$_6$R$_7$, amidino, piperazinyl, morpholinyl, —SO$_2$ (C$_1$–C$_6$)alkyl, —SO$_2$NH$_2$, —SO$_2$NH(C$_1$–C$_6$) alkyl, —SO$_2$N(C$_1$–C$_6$)alkyl(C$_1$–C$_6$)alkyl, haloalkyl, or haloalkoxy.

In this embodiment, it is preferred that when R$_2$ is OH, R$_4$ is methyl and R$_5$ is phenyl, R$_1$ is not acetyl; and R$_4$ and R$_5$ are not simultaneously hydrogen.

Embodiment A72. Compounds according to embodiment A71
wherein
R$_1$ is halogen, alkyl, carboxaldehyde, hydroxyalkyl, phenylalkoxy, phenyl, benzyl, phenethyl, phenpropyl, phenbutyl, CN, (C$_2$–C$_6$)alkanoyl, haloalkyl, or phenylCO—, phenylCH$_2$CO—, phenylCH$_2$CH$_2$CO—,
  wherein the above phenyl groups are unsubstituted or substituted with 1, 2, or 3 groups that are independently halogen, (C$_1$–C$_4$)alkyl, (C$_1$–C$_4$)alkoxy, nitro, CN, haloalkyl, haloalkoxy or CO$_2$H;
    wherein the above alkyl groups are unsubstituted or substituted with 1, 2, or 3 groups that are independently halogen, methoxy, or ethoxy,
R$_2$ is benzyloxy, phenethyloxy, phenpropyloxy, OH, phenyloxy, phenyloxy(C$_1$–C$_6$)alkyl, phenylthio(C$_3$–C$_4$) alkoxy, NR$_8$R$_9$, (C$_1$–C$_6$)alkyl, alkynyl, phenethyl, —OC(O)N(CH$_3$)CH$_2$ phenyl, alkoxyalkoxy, pyridyl, pyrimidyl, pyridazyl, pyrazolyl, imidazolyl, pyrrolyl, pyrazinyl, piperidinyl, hexahydropyrimidinyl, benzimidazolyl, or thienyl, wherein
    each of the above is unsubstituted or substituted with 1, 2, or 3 groups that are independently halogen, —(C$_1$–C$_6$)alkyl-N(R)—CO$_2$R$_{30}$, CF$_3$, OCF$_3$, (C$_1$–C$_4$)alkyl, thienyl, pyridyl, or phenyl optionally substituted with 1, 2, or 3 halogens;
  R$_6$ and R$_7$ are independently at each occurrence H, (C$_1$–C$_6$)alkyl, (C$_1$–C$_6$)alkoxy, (C$_1$–C$_6$)alkoxy(C$_1$–C$_6$) alkyl, (C$_1$–C$_6$)alkoxycarbonyl, hydroxy(C$_1$–C$_6$)alkyl, —(C$_1$–C$_4$)alkyl-CO$_2$-alkyl, (C$_1$–C$_6$)alkanoyl, phenyl (C$_1$–C$_6$)alkyl, phenyl(C$_1$–C$_6$)alkoxy, or phenyl(C$_1$–C$_6$) alkanoyl, wherein each of the above is unsubstituted or substituted with 1, 2, or 3 groups that are independently, halogen, (C$_1$–C$_6$)alkoxy, NH$_2$, OH, SH, C$_3$–C$_6$ cycloalkyl, (C$_1$–C$_6$)alkyl, CF$_3$ or OCF$_3$; or
  R$_6$, R$_7$, and the nitrogen to which they are attached form a morpholinyl., piperidinyl, pyrrolidinyl, or piperazinyl ring which is optionally substituted with 1 or 2 groups that are independently C$_1$–C$_4$ alkyl, hydroxy, hydroxy C$_1$–C$_4$ alkyl, or halogen;
R$_4$ is H, alkyl optionally substituted with one or two groups that are independently CO$_2$H, —CO$_2$ alkyl, —C(O)NRR, —N(R$_{30}$)C(O)NRR, —N(R$_{30}$)C(O)—(C$_1$–C$_6$)alkoxy, or —NR$_6$R$_7$, benzyloxy, phenethyloxy, phenpropyloxy, benzyl, phenethyl, phenpropyl, hydroxyalkyl, halo (C$_1$–C$_4$)alkyl, carboxaldehyde, alkoxy, alkoxyalkyl, or alkoxyalkoxy,
wherein
  the above phenyl groups are unsubstituted or substituted with 1, 2, or 3 groups that are independently halogen, hydroxy, alkoxy, alkyl, nitro, CF$_3$ or OCF$_3$; and
R$_5$ is benzyl, phenethyl, phenpropyl, phenbutyl, (C$_1$–C$_6$) alkyl, phenyl, piperidinyl, pyrrolidinyl, imidazolidinyl, piperidinyl(C$_1$–C$_6$)alkyl, pyrrolidinyl(C$_1$–C$_6$)alkyl, imidazolidinyl(C$_1$–C$_6$)alkyl, pyridyl, pyrimidinyl, pyridazyl, pyrazinyl, pyridyl(C$_1$–C$_6$)alkyl, pyrimidyl (C$_1$–C$_6$)alkyl, pyridazyl(C$_1$–C$_6$)alkyl, or pyrazinyl (C$_1$–C$_6$)alkyl wherein
  each of the above is unsubstituted or substituted with 1, 2, 3, 4, or 5 groups that are independently alkyl, halogen, haloalkyl, NR$_8$R$_9$, NR$_6$R$_7$—(C$_1$–C$_6$ alkyl)-, carboxaldehyde, morpholinyl, SO$_2$NH$_2$, SO$_2$NH (alkyl), SO$_2$N(alkyl)(alkyl), alkoxy, hydroxyalkyl, benzyloxy, thioalkoxy, OH, CO$_2$H, CN, —CO$_2$ (C$_1$–C$_5$ alkyl), phenylalkoxycarbonyl, amidinooxime, amidino, —C(O)NR$_6$R$_7$, CF$_3$, CF$_2$CF$_3$, ClCH$_2$, or OCF$_3$.

In this embodiment, it is preferred that when R$_2$ is OH, R$_4$ is methyl and R$_5$ is phenyl, R$_1$ is not acetyl.

Embodiment A73. Compounds according to embodiment A72
wherein
R$_1$ is halogen, alkyl, carboxaldehyde, hydroxy(C$_1$–C$_4$)alkyl, phenylalkoxy, benzyl, phenethyl, —C(O)CH$_3$, phenylCO—, or phenylCH$_2$CO—,
  wherein the above phenyl groups are unsubstituted or substituted with 1, 2, or 3 groups that are independently halogen, (C$_1$–C$_4$)alkyl, (C$_1$–C$_4$)alkoxy, nitro, CN, CF$_3$, or OCF$_3$;
    wherein the above alkyl groups are unsubstituted or substituted with 1, 2, or 3 groups that are independently halogen, methoxy, or ethoxy;
R$_2$ is benzyloxy, phenethyloxy, phenpropyloxy, OH, phenyloxy, phenyloxy(C$_1$–C$_6$)alkyl, phenethyl, NR$_8$R$_9$, —S-benzyl, or (C$_1$–C$_6$)alkyl, wherein
  each of the above is unsubstituted or substituted with 1, 2, or 3 groups that are independently halogen, —(C$_1$–C$_6$) alkyl-N(R)—CO$_2$R$_{30}$, CF$_3$, OCF$_3$, alkyl, thienyl, or pyridyl;
  R$_6$ and R$_7$ are independently at each occurrence H, (C$_1$–C$_6$)alkyl, (C$_1$–C$_6$)alkoxy, (C$_1$–C$_6$)alkoxy(C$_1$–C$_6$) alkyl, (C$_1$–C$_6$)alkoxycarbonyl, hydroxy(C$_1$–C$_6$)alkyl, —(C$_1$–C$_4$)alkyl-CO$_2$-alkyl, (C$_1$–C$_6$)alkanoyl, phenyl (C$_1$–C$_6$)alkyl, phenyl(C$_1$–C$_6$)alkoxy, or phenyl(C$_1$–C$_6$) alkanoyl, wherein each of the above is unsubstituted or substituted with 1, 2, or 3 groups that are independently, halogen, (C$_1$–C$_6$)alkoxy, NH$_2$, OH, SH, C$_3$–C$_6$ cycloalkyl, (C$_1$–C$_6$)alkyl, CF$_3$ or OCF$_3$; or
  R$_6$, R$_7$, and the nitrogen to which they are attached form a morpholinyl, piperidinyl, pyrrolidinyl, or piperazinyl ring which is optionally substituted with 1 or 2 groups that are independently C$_1$–C$_4$ alkyl, hydroxy, hydroxy C$_1$–C$_4$ alkyl, or halogen;
R$_4$ is H, alkyl optionally substituted with one or two groups that are independently CO$_2$H, —CO$_2$ alkyl, —C(O)NRR, —N(R$_{30}$)C(O)NRR, —N(R$_{30}$)C(O)—(C$_1$–C$_6$)alkoxy, or —NR$_6$R$_7$, benzyloxy, phenethyloxy, phenpropyloxy, benzyl, or hydroxyalkyl, wherein
  the above phenyl groups are unsubstituted or substituted with 1, 2, or 3 groups that are independently halogen, hydroxy, alkoxy, alkyl, nitro, CF$_3$ or OCF$_3$; and
R$_5$ is benzyl, phenethyl, phenpropyl, phenbutyl, (C$_1$–C$_6$) alkyl, phenyl, pyridyl, pyrazinyl, pyrimidinyl, pyrazinyl (C$_1$–C$_6$)alkyl, pyrimidinyl(C$_1$–C$_6$)alkyl, or pyridyl (C$_1$–C$_4$)alkyl, wherein
  each of the above is unsubstituted or substituted with 1, 2, 3, 4, or 5 groups that are independently alkyl, halogen, haloalkyl, morpholinyl, —SO$_2$ (C$_1$–C$_6$)alkyl, —SO$_2$NH$_2$, —SO$_2$NH(C$_1$–C$_6$), —SO$_2$N(C$_1$–C$_6$) (C$_1$–C$_6$), (C$_1$–C$_4$)alkoxy, phenyl(C$_1$–C$_4$)alkoxy, thio (C$_1$–C$_4$)alkoxy, (C$_1$–C$_4$)alkoxycarbonyl, OH, CO$_2$H, CN, amidinooxime, amidino, NR$_8$R$_9$, NR$_6$R$_7$—(C$_1$–C$_6$ alkyl)-, hydroxyalkyl, CONR$_6$R$_7$, CF$_3$, or OCF$_3$.

Embodiment A74. Compounds according to embodiment A73 wherein $R_1$ is halogen, alkyl, carboxaldehyde, or hydroxyalkyl;

$R_2$ is benzyloxy, phenethyloxy, phenpropyloxy, OH, phenyloxy, phenyloxy($C_1$–$C_6$)alkyl, phenethyl, phenylthioalkoxy, or ($C_1$–$C_6$)alkyl, wherein
  each of the above is unsubstituted or substituted with 1, 2, or 3 groups that are independently halogen, —($C_1$–$C_6$)alkyl —N(R)—$CO_2R_{30}$, $CF_3$, $OCF_3$, alkyl, thienyl, or pyridyl;

$R_4$ is H, ($C_1$–$C_4$)alkyl optionally substituted with one or two groups that are independently $CO_2H$, —$CO_2$ alkyl, —C(O)NRR, —N($R_{30}$)C(O)NRR, —N($R_{30}$)C(O)—($C_1$–$C_6$)alkoxy, or —$NR_6R_7$, benzyloxy, or phenethyloxy, wherein
  the above phenyl groups are unsubstituted or substituted with 1, 2, or 3 groups that are independently halogen, hydroxy, ($C_1$–$C_4$)alkoxy, ($C_1$–$C_4$)alkyl, nitro, $CF_3$ or $OCF_3$; and $R_5$ is benzyl, phenethyl, ($C_1$–$C_6$)alkyl, phenyl, indazolyl, or pyridyl, wherein each of the above is unsubstituted or substituted with 1, 2, 3, 4, or 5 groups that are independently ($C_1$–$C_4$)alkyl, halogen, OH, $CO_2H$, CN, ($C_1$–$C_4$)alkoxy, —C(O)pyrrolidine, —$SO_2$ ($C_1$–$C_6$)alkyl, benzyloxy, —$CO_2$($C_1$–$C_5$ alkyl), amidino, thio($C_1$–$C_4$)alkoxy, amidinooxime, $CF_3$, $NR_8R_9$, $NR_6R_7$—($C_1$–$C_6$ alkyl)-, $CONR_6R_7$, or $OCF_3$.

Embodiment A75. Compounds according to embodiment A74 wherein $R_1$ is chloro, bromo, iodo, methyl, $C_2$–$C_3$ alkenyl, $C_2$–$C_3$ alkynyl; and $R_5$ is benzyl, phenethyl, phenpropyl, phenyl, or pyridyl, each of which is unsubstituted or substituted with 1, 2, or 3 groups that are independently alkyl, OH, halogen, alkoxy, $NH_2$, NH($C_1$–$C_6$)alkyl, N($C_1$–$C_6$)alkyl($C_1$–$C_6$)alkyl, $NR_8R_9$, $NR_6R_7$—($C_1$–$C_6$ alkyl)-, $CONR_6R_7$, and amidinooxime; wherein
  $R_6$ and $R_7$ are independently H, $C_1$–$C_4$ alkyl, $C_1$–$C_6$ alkanoyl, wherein the alkyl and alkanoyl groups are optionally substituted with 1, 2, or 3 groups that are independently OH, halogen, or $C_3$–$C_7$ cyclopropyl.

Embodiment A76. Compounds according to embodiment A75 wherein $R_2$ is benzyloxy, phenethyl, phenyloxy($C_1$–$C_6$)alkyl, or phenethyloxy, each of which is unsubstituted or substituted with 1, 2, or 3 groups that are independently halogen, —($C_1$–$C_6$)alkyl-N(R)—$CO_2R_{30}$, $CF_3$, $OCF_3$, or ($C_1$–$C_4$)alkyl.

Embodiment A77. Compounds according to embodiment A66, wherein $R_5$ is benzyl, phenethyl, thienyl($C_1$–$C_6$ alkyl), piperidinyl($C_1$–$C_6$)alkyl, pyrrolidinyl($C_1$–$C_6$)alkyl, imidazolidinyl($C_1$–$C_6$)alkyl, piperazinyl($C_1$–$C_6$)alkyl, pyridyl($C_1$–$C_6$)alkyl, pyrimidyl($C_1$–$C_6$)alkyl, pyridazyl($C_1$–$C_6$)alkyl, pyrazinyl($C_1$–$C_6$)alkyl, isoquinolinyl($C_1$–$C_6$)alkyl, tetrahydroisoquinolinyl($C_1$–$C_6$)alkyl, indolyl($C_1$–$C_6$)alkyl, or 1H-indazolyl($C_1$–$C_6$)alkyl, wherein
  each of the above is unsubstituted or substituted with 1, 2, 3, 4, or 5 groups that are independently ($C_1$–$C_6$)alkyl, halogen, ($C_1$–$C_6$)alkoxy, ($C_1$–$C_6$)hydroxyalkyl, phenyl($C_1$–$C_6$)alkoxy, ($C_1$–$C_6$)thioalkoxy, ($C_1$–$C_6$)alkoxycarbonyl, phenyl($C_1$–$C_6$)alkoxycarbonyl, OH, $CO_2H$, CN, amidinooxime, $NR_8R_9$, $NR_6R_7$—($C_1$–$C_6$ alkyl)-, —C(O)$NR_6R_7$, amidino, piperazinyl, morpholinyl, —$SO_2$ ($C_1$–$C_6$)alkyl, —$SO_2NH_2$, —$SO_2NH$($C_1$–$C_6$)alkyl, —$SO_2N$($C_1$–$C_6$)alkyl($C_1$–$C_6$) alkyl, ($C_1$–$C_4$)haloalkyl, —($C_1$–$C_4$ alkyl)-$NR_{15}$C(O)$NR_{16}R_{17}$, —($C_1$–$C_4$ alkyl)-$NR_{15}$C(O)$R_{18}$, —O—$CH_2$—O—, —O—$CH_2CH_2$—O—, or ($C_1$–$C_4$) haloalkoxy; wherein
  $R_6$ and $R_7$ are independently at each occurrence H, ($C_1$–$C_6$)alkyl, ($C_1$–$C_6$)alkoxy, ($C_1$–$C_6$)alkoxy($C_1$–$C_6$) alkyl, ($C_1$–$C_6$)alkoxycarbonyl, ($C_1$–$C_6$) hydroxyalkyl, —($C_1$–$C_4$)alkyl-$CO_2$—($C_1$–$C_6$)alkyl, ($C_1$–$C_6$)alkanoyl, phenyl($C_1$–$C_6$)alkyl, phenyl ($C_1$–$C_6$)alkoxy, or phenyl($C_1$–$C_6$)alkanoyl, wherein each of the above is unsubstituted or substituted with 1, 2, or 3 groups that are independently, halogen, ($C_1$–$C_4$)alkoxy, $NH_2$, OH, SH, $C_3$–$C_6$ cycloalkyl, NH($C_1$–$C_6$ alkyl), N($C_1$–$C_6$ alkyl)($C_1$–$C_6$ alkyl), ($C_1$–$C_4$)alkyl, $CF_3$ or $OCF_3$; or
  $R_6$, $R_7$, and the nitrogen to which they are attached form a morpholinyl, thiomorpholinyl, piperidinyl, pyrrolidinyl, or piperazinyl ring which is optionally substituted with 1 or 2 groups that are independently $C_1$–$C_4$ alkyl, hydroxy, hydroxy $C_1$–$C_4$ alkyl, or halogen; and
  $R_{18}$ is $C_1$–$C_6$ alkyl optionally substituted with —O—($C_2$–$C_6$ alkanoyl, $C_1$–$C_6$ hydroxyalkyl, $C_1$–$C_6$ alkoxy, $C_1$–$C_6$ alkoxy $C_1$–$C_6$ alkyl; amino $C_1$–$C_6$ alkyl, mono or dialkylamino $C_1$–$C_6$ alkyl.

In this embodiment, it is preferred that $R_6$ and $R_7$ are not simultaneously OH; and $R_6$ and $R_7$ are not simultaneously —$SO_2$($C_1$–$C_6$ alkyl).

Embodiment A78. Compounds according to embodiment A77, wherein $R_1$ is halogen, methyl, ethyl, $C_2$–$C_4$ alkenyl, $C_2$–$C_4$ alkynyl, or carboxaldehyde;

$R_2$ is benzyloxy, OH, phenyloxy, phenyloxy($C_1$–$C_6$)alkyl, or phenyl($C_1$–$C_4$)thioalkoxy, wherein each of the above is optionally substituted with 1, 2, 3, or 4 groups that are independently halogen, —($C_1$–$C_6$)alkyl-N(R)—$CO_2R_{30}$, $NR_6R_7$, ($C_1$–$C_4$)haloalkyl, ($C_1$–$C_4$)haloalkoxy, ($C_1$–$C_6$) alkyl, or pyridyl; and $R_4$ is H, ($C_1$–$C_4$)alkyl optionally substituted with one or two groups that are independently $CO_2H$, —$CO_2$ alkyl, —C(O)NRR, —N($R_{30}$)C(O)NRR, —N($R_{30}$)C(O)—($C_1$–$C_6$)alkoxy, or —$NR_6R_7$, or hydroxy($C_1$–$C_4$)alkyl.

Embodiment A79. Compounds according to embodiment A78, wherein $R_5$ is benzyl, or phenethyl, wherein each is unsubstituted or substituted with 1, 2, 3, 4, or 5 groups that are independently ($C_1$–$C_6$)alkyl, halogen, ($C_1$–$C_6$)alkoxy, ($C_1$–$C_6$) hydroxyalkyl, phenyl($C_1$–$C_6$)alkoxy, ($C_1$–$C_6$)thioalkoxy, ($C_1$–$C_6$)alkoxycarbonyl, phenyl($C_1$–$C_6$)alkoxycarbonyl, OH, $CO_2H$, CN, amidinooxime, $NR_8R_9$, $NR_6R_7$—($C_1$–$C_6$ alkyl)-, —C(O)$NR_6R_7$, —($C_1$–$C_4$ alkyl)-C(O)$NR_6R_7$ amidino, piperazinyl, morpholinyl, —$SO_2$ ($C_1$–$C_6$)alkyl, —$SO_2NH_2$, —$SO_2NH$($C_1$–$C_6$)alkyl, —$SO_2N$($C_1$–$C_6$) alkyl($C_1$–$C_6$)alkyl, ($C_1$–$C_4$)haloalkyl, —($C_1$–$C_4$ alkyl)-$NR_{15}$C(O)$R_{18}$, —O—$CH_2$—O, —O—$CH_2CH_2$—O—, or ($C_1$–$C_4$)haloalkoxy; wherein
  $R_6$ and $R_7$ are independently at each occurrence H, ($C_1$–$C_6$)alkyl, ($C_1$–$C_6$)alkoxy, ($C_1$–$C_6$)alkoxy($C_1$–$C_6$) alkyl, ($C_1$–$C_6$)alkoxycarbonyl, ($C_1$–$C_6$)hydroxyalkyl, —($C_1$–$C_4$)alkyl-$CO_2$—($C_1$–$C_6$)alkyl, ($C_1$–$C_6$) alkanoyl, phenyl($C_1$–$C_6$)alkyl, phenyl($C_1$–$C_6$)alkoxy, or phenyl($C_1$–$C_6$)alkanoyl, wherein each of the above is unsubstituted or substituted with 1, 2, or 3 groups that are independently, halogen, ($C_1$–$C_4$)alkoxy, $NH_2$, OH, SH, $C_3$–$C_6$ cycloalkyl, NH($C_1$–$C_6$ alkyl), N($C_1$–$C_6$ alkyl)($C_1$–$C_6$ alkyl), ($C_1$–$C_4$)alkyl, $CF_3$ or $OCF_3$; or $R_6$, $R_7$, and the nitrogen to which they are attached form a morpholinyl, thiomorpholinyl, piperidinyl, pyrrolidinyl, or piperazinyl ring which is optionally substituted with 1 or 2 groups that are independently $C_1$–$C_4$ alkyl, hydroxy, hydroxy $C_1$–$C_4$ alkyl, or halogen; and $R_{18}$ is $C_1$–$C_6$ alkyl optionally substituted with —O—($C_2$–$C_6$ alkanoyl, $C_1$–$C_6$ hydroxyalkyl, $C_1$–$C_6$ alkoxy, $C_1$–$C_6$ alkoxy $C_1$–$C_6$ alkyl, amino $C_1$–$C_6$ alkyl, or mono or dialkylamino $C_1$–$C_6$ alkyl.

In this embodiment, it is preferred that $R_6$ and $R_7$ are not simultaneously OH; and $R_6$ and $R_7$ are not simultaneously —SO$_2$($C_1$–$C_6$ alkyl)

Embodiment A80. Compounds according to embodiment A79, wherein $R_5$ is benzyl or phenethyl, wherein each is optionally substituted with 1, 2, 3, 4, or 5 groups that are independently $C_1$–$C_6$ alkyl, —C(O)NR$_6$R$_7$, —($C_1$–$C_4$ alkyl)-C(O)NR$_6$R$_7$, NR$_8$R$_9$, halogen, $C_1$–$C_6$ alkoxy, CO$_2$H, —($C_1$–$C_4$ alkyl)-CO$_2$H, $C_1$–$C_6$ thioalkoxy, amidinooxime, $C_1$–$C_6$ alkoxycarbonyl, —($C_1$–$C_4$ alkyl)-$C_1$–$C_6$ alkoxycarbonyl, $C_1$–$C_6$ hydroxyalkyl, —($C_1$–$C_4$ alkyl)-CN, CN, phenyl $C_1$–$C_6$ alkoxy, OH, $C_1$–$C_4$ haloalkyl, $C_1$–$C_4$ haloalkoxy, NR$_6$R$_7$—($C_1$–$C_6$ alkyl)-, —($C_1$–$C_4$ alkyl)-NR$_{15}$C(O)R$_{18}$, amidinooxime, —SO$_2$($C_1$–$C_6$ alkyl), —O—CH$_2$—O—, —O—CH$_2$CH$_2$—O—, phenyl $C_1$–$C_4$ alkoxy, or phenyl; wherein $R_6$ and $R_7$ at each occurrence are independently H, OH, $C_1$–$C_6$ alkyl, amino $C_1$–$C_4$ alkyl, NH($C_1$–$C_6$ alkyl) alkyl, N($C_1$–$C_6$ alkyl)($C_1$–$C_6$ alkyl)$C_1$–$C_6$ alkyl, $C_1$–$C_6$ hydroxyalkyl, $C_1$–$C_6$ alkoxy $C_1$–$C_6$ alkyl, —SO$_2$($C_1$–$C_6$ alkyl) each of which is optionally substituted with 1, 2, or 3 groups that are independently halogen, OH, SH, $C_3$–$C_6$ cycloalkyl, $C_1$–$C_4$ alkoxy, $C_1$–$C_4$ alkyl, OH, CF$_3$, or OCF$_3$; or $R_6$, $R_7$, and the nitrogen to which they are attached form a piperidinyl, pyrrolidinyl, piperazinyl, or a morpholinyl, thiomorpholinyl, ring optionally substituted with 1 or 2 groups that are independently alkyl, hydroxy, hydroxy $C_1$–$C_4$ alkyl, or halogen, $R_{18}$ is $C_1$–$C_6$ alkyl optionally substituted with —O—($C_2$–$C_6$ alkanoyl, $C_1$–$C_6$ hydroxyalkyl, $C_1$–$C_6$ alkoxy, $C_1$–$C_6$ alkoxy $C_1$–$C_6$ alkyl; amino $C_1$–$C_6$ alkyl, mono or dialkylamino $C_1$–$C_6$ alkyl.

In this embodiment, it is preferred that $R_6$ and $R_7$ are not simultaneously OH; and $R_6$ and $R_7$ are not simultaneously —SO$_2$($C_1$–$C_6$ alkyl)

Embodiment A81. Compounds according to embodiment A80, wherein $R_5$ is benzyl or phenethyl, wherein each is optionally substituted with 1, 2, 3, 4, or 5 groups that are independently $C_1$–$C_6$ alkyl, —C(O)NR$_6$R$_7$, —($C_1$–$C_4$ alkyl)-C(O)NR$_6$R$_7$, halogen, $C_1$–$C_6$ alkoxy, CO$_2$H, —($C_1$–$C_4$ alkyl)-CO$_2$H, $C_1$–$C_6$ thioalkoxy, amidinooxime, $C_1$–$C_6$ alkoxycarbonyl, —($C_1$–$C_4$ alkyl)-$C_1$–$C_6$ alkoxycarbonyl, $C_1$–$C_6$ hydroxyalkyl, —($C_1$–$C_4$ alkyl)-CN, CN, phenyl $C_1$–$C_6$ alkoxy, OH, $C_1$–$C_4$ haloalkyl, $C_1$–$C_4$ haloalkoxy, NR$_6$R$_7$—($C_1$–$C_6$ alkyl)-, NR$_8$R$_9$, —($C_1$–$C_4$ alkyl)-NR$_{15}$C(O)R$_{18}$, amidinooxime, —SO$_2$($C_1$–$C_6$ alkyl), —O—CH$_2$—O—, —O—CH$_2$CH$_2$—O—, phenyl $C_1$–$C_4$ alkoxy, or phenyl; wherein $R_6$ and $R_7$ at each occurrence are independently H, OH, $C_1$–$C_6$ alkyl, amino $C_1$–$C_4$ alkyl, NH($C_1$–$C_6$ alkyl) alkyl, N($C_1$–$C_6$ alkyl)($C_1$–$C_6$ alkyl)$C_1$–$C_6$ alkyl, $C_1$–$C_6$ hydroxyalkyl, $C_1$–$C_6$ alkoxy $C_1$–$C_6$ alkyl, —SO$_2$($C_1$–$C_6$ alkyl) each of which is optionally substituted with 1, 2, or 3 groups that are independently halogen, OH, SH, $C_3$–$C_6$ cycloalkyl, $C_1$–$C_4$ alkoxy, $C_1$–$C_4$ alkyl, OH, CF$_3$, or OCF$_3$; and $R_{18}$ is $C_1$–$C_6$ alkyl optionally substituted with —O—($C_2$–$C_6$ alkanoyl, $C_1$–$C_6$ hydroxyalkyl, $C_1$–$C_6$ alkoxy, $C_1$–$C_6$ alkoxy $C_1$–$C_6$ alkyl; amino $C_1$–$C_6$ alkyl, mono or dialkylamino $C_1$–$C_6$ alkyl.

In this embodiment, it is preferred that $R_6$ and $R_7$ are not simultaneously OH; and $R_6$ and $R_7$ are not simultaneously —SO$_2$($C_1$–$C_6$ alkyl)

Embodiment A82. Compounds according to embodiment A81, wherein $R_5$ is benzyl which is optionally substituted with 1, 2, 3, 4, or 5 groups that are independently $C_1$–$C_4$ alkyl, —C(O)NR$_6$R$_7$, —($C_1$–$C_4$ alkyl)-C(O)NR$_6$R$_7$, halogen, $C_1$–$C_4$ alkoxy, CO$_2$H, $C_1$–$C_4$ thioalkoxy, $C_1$–$C_4$ alkoxycarbonyl, $C_1$–$C_6$ hydroxyalkyl, CN, OH, NR$_6$R$_7$—($C_1$–$C_6$ alkyl)-, NR$_8$R$_9$, —SO$_2$($C_1$–$C_6$ alkyl), or benzyloxy; wherein $R_6$ and $R_7$ at each occurrence are independently H, OH, $C_1$–$C_6$ alkyl, amino $C_1$–$C_4$ alkyl, NH($C_1$–$C_6$ alkyl) alkyl, N($C_1$–$C_6$ alkyl)($C_1$–$C_6$ alkyl)$C_1$–$C_6$ alkyl, $C_1$–$C_6$ hydroxyalkyl, $C_1$–$C_6$ alkoxy $C_1$–$C_6$ alkyl, —SO$_2$($C_1$–$C_6$ alkyl) each of which is optionally substituted with 1, 2, or 3 groups that are independently halogen, OH, SH, $C_3$–$C_6$ cycloalkyl, $C_1$–$C_4$ alkoxy, $C_1$–$C_4$ alkyl, OH, CF$_3$, or OCF$_3$.

In this embodiment, it is preferred that $R_6$ and $R_7$ are not simultaneously OH; and $R_6$ and $R_7$ are not simultaneously —SO$_2$($C_1$–$C_6$ alkyl).

Embodiment A83. Compounds according to embodiment A82, wherein $R_5$ is benzyl which is optionally substituted with 1, 2, 3, 4, or 5 groups that are independently $C_1$–$C_4$ alkyl, —C(O)NR$_6$R$_7$—($C_1$–$C_4$ alkyl)-C(O)NR$_6$R$_7$, halogen, $C_1$–$C_4$ alkoxy, $C_1$–$C_4$ thioalkoxy, $C_1$–$C_4$ alkoxycarbonyl, $C_1$–$C_6$ hydroxyalkyl, CN, NR$_8$R$_9$, or NR$_6$R$_7$—($C_1$–$C_6$ alkyl)-; wherein $R_6$ and $R_7$ at each occurrence are independently H, OH, $C_1$–$C_6$ alkyl, amino $C_1$–$C_4$ alkyl, NH($C_1$–$C_6$ alkyl) alkyl, N($C_1$–$C_6$ alkyl)($C_1$–$C_6$ alkyl)$C_1$–$C_6$ alkyl, $C_1$–$C_6$ hydroxyalkyl, or $C_1$–$C_4$ alkoxy $C_1$–$C_4$ alkyl each of which is optionally substituted with 1, 2, or 3 groups that are independently halogen, OH, SH, $C_3$–$C_6$ cycloalkyl, $C_1$–$C_4$ alkoxy, $C_1$–$C_4$ alkyl, OH, CF$_3$, or OCF$_3$.

In this embodiment, it is preferred that $R_6$ and $R_7$ are not simultaneously OH.

Embodiment A84. Compounds according to embodiment A83, wherein the $R_5$ group is disubstituted with two groups that are meta to each other.

Embodiment A86. Compounds according to embodiment A80, wherein $R_5$ is benzyl which is optionally substituted with 1, 2, 3, 4, or 5 groups that are independently $C_1$–$C_4$ alkyl, —C(O)NR$_6$R$_7$—($C_1$–$C_4$ alkyl)-C(O)NR$_6$R$_7$, NR$_8$R$_9$, NR$_6$R$_7$—($C_1$–$C_6$ alkyl)-, halogen, $C_1$–$C_4$ alkoxy, CO$_2$H, —($C_1$–$C_4$ alkyl)-CO$_2$H, —($C_1$–$C_4$ alkyl)-$C_1$–$C_6$ alkoxycarbonyl, —($C_1$–$C_4$ alkyl)-CN, CN, phenyl $C_1$–$C_6$ alkoxy, CF$_3$, OCF$_3$, —($C_1$–$C_4$ alkyl)-NR$_{15}$C(O)R$_{18}$, amidinooxime, —O—CH$_2$—O—, —O—CH$_2$CH$_2$—O—, or phenyl; wherein $R_6$ and $R_7$ at each occurrence are independently H, $C_1$–$C_4$ alkyl, amino $C_1$–$C_4$ alkyl, NH($C_1$–$C_4$ alkyl)alkyl, N($C_1$–$C_4$ alkyl)($C_1$–$C_4$ alkyl)$C_1$–$C_4$ alkyl, $C_1$–$C_6$ hydroxyalkyl, $C_1$–$C_4$ alkoxy $C_1$–$C_4$ alkyl, or OH, each of which is optionally substituted with 1, 2, or 3 groups that are independently halogen, OH, SH, $C_3$–$C_6$ cycloalkyl, $C_1$–$C_4$ alkoxy, $C_1$–$C_4$ alkyl, OH, $CF_3$, or $OCF_3$; and $R_{18}$ is $C_1$–$C_6$ alkyl, $C_1$–$C_6$ hydroxyalkyl, $C_1$–$C_6$ alkoxy, $C_1$–$C_4$ alkoxy $C_1$–$C_6$ alkyl; amino $C_1$–$C_6$ alkyl, mono or dialkylamino $C_1$–$C_6$ alkyl.

In this embodiment, it is preferred that $R_6$ and $R_7$ are not simultaneously OH.

Embodiment A87. Compounds according to embodiment A80, wherein $R_5$ is benzyl or phenethyl, wherein each is optionally substituted with 1, 2, 3, 4, or 5 groups that are independently $C_1$–$C_6$ alkyl, —C(O)$NR_6R_7$, —($C_1$–$C_4$ alkyl)-C(O)$NR_6R_7$, halogen, $C_1$–$C_6$ alkoxy, $CO_2H$, —($C_1$–$C_4$ alkyl)-$CO_2H$, $C_1$–$C_6$ thioalkoxy, amidinooxime, $C_1$–$C_6$ alkoxycarbonyl, —($C_1$–$C_4$ alkyl)-$C_1$–$C_6$ alkoxycarbonyl, $C_1$–$C_6$ hydroxyalkyl, —($C_1$–$C_4$ alkyl)-CN, CN, phenyl $C_1$–$C_6$ alkoxy, OH, $C_1$–$C_4$ haloalkyl, $C_1$–$C_4$ haloalkoxy, $NR_8R_9$, $NR_6R_7$—($C_1$–$C_6$ alkyl)-, —($C_1$–$C_4$ alkyl)-$NR_{15}C(O)R_{18}$, amidinooxime, —$SO_2$($C_1$–$C_6$ alkyl), —O—$CH_2$—O—, —O—$CH_2CH_2$—O—, phenyl $C_1$–$C_4$ alkoxy, or phenyl; wherein $R_6$, $R_7$, and the nitrogen to which they are attached form a piperidinyl, pyrrolidinyl, piperazinyl, or a morpholinyl, thiomorpholinyl, ring optionally substituted with 1 or 2 groups that are independently alkyl, hydroxy, hydroxy $C_1$–$C_4$ alkyl, or halogen, $R_{18}$ is $C_1$–$C_6$ alkyl optionally substituted with —O—($C_2$–$C_6$ alkanoyl, $C_1$–$C_6$ hydroxyalkyl, $C_1$–$C_6$ alkoxy, $C_1$–$C_6$ alkoxy $C_1$–$C_6$ alkyl; amino $C_1$–$C_6$ alkyl, mono or dialkylamino $C_1$–$C_6$ alkyl.

In this embodiment, it is preferred that $R_6$ and $R_7$ are not simultaneously OH; and $R_6$ and $R_7$ are not simultaneously —$SO_2$($C_1$–$C_6$ alkyl).

Embodiment A88. Compounds according to embodiment A87, wherein $R_5$ is benzyl which is optionally substituted with 1, 2, 3, 4, or 5 groups that are independently $C_1$–$C_4$ alkyl, —C(O)$NR_6R_7$, —($C_1$–$C_4$ alkyl)-C(O)$NR_6R_7$, halogen, $C_1$–$C_4$ alkoxy, $CO_2H$, $C_1$–$C_4$ thioalkoxy, $C_1$–$C_4$ alkoxycarbonyl, $C_1$–$C_6$ hydroxyalkyl, CN, OH, $NR_8R_9$, $NR_6R_7$—($C_1$–$C_6$ alkyl)-, —$SO_2$($C_1$–$C_6$ alkyl), or benzyloxy; and wherein $R_6$ and $R_7$ at each occurrence are independently H, OH, $C_1$–$C_6$ alkyl, amino $C_1$–$C_4$ alkyl, NH($C_1$–$C_6$ alkyl) alkyl, N($C_1$–$C_6$ alkyl)($C_1$–$C_6$ alkyl)$C_1$–$C_6$ alkyl, $C_1$–$C_6$ hydroxyalkyl, $C_1$–$C_6$ alkoxy $C_1$–$C_6$ alkyl, or —$SO_2$($C_1$–$C_6$ alkyl), each of which is optionally substituted with 1, 2, or 3 groups that are independently halogen, OH, SH, $C_3$–$C_6$ cycloalkyl, $C_1$–$C_4$ alkoxy, $C_1$–$C_4$ alkyl, OH, $CF_3$, or $OCF_3$.

In this embodiment, it is preferred that $R_6$ and $R_7$ are not simultaneously OH; and $R_6$ and $R_7$ are not simultaneously —$SO_2$($C_1$–$C_6$ alkyl)

Embodiment A89. Compounds according to embodiment A80, wherein $R_5$ is benzyl which is optionally substituted with 1, 2, 3, 4, or 5 groups that are independently $C_1$–$C_4$ alkyl, —C(O)$NR_6R_7$—($C_1$–$C_4$ alkyl)-C(O)$NR_6R_7$, $NR_6R_7$—($C_1$–$C_6$ alkyl)-, $NR_8R_9$, halogen, $C_1$–$C_4$ alkoxy, $C_1$–$C_4$ thioalkoxy, $C_1$–$C_4$ alkoxycarbonyl, $C_1$–$C_6$ hydroxyalkyl, or CN; wherein $R_6$ and $R_7$ at each occurrence are independently H, OH, $C_1$–$C_6$ alkyl, amino $C_1$–$C_4$ alkyl, NH($C_1$–$C_6$ alkyl) alkyl, N($C_1$–$C_6$ alkyl)($C_1$–$C_6$ alkyl)$C_1$–$C_6$ alkyl, $C_1$–$C_6$ hydroxyalkyl, or $C_1$–$C_4$ alkoxy $C_1$–$C_4$ alkyl, each of which is optionally substituted with 1, 2, or 3 groups that are independently halogen, OH, SH, $C_3$–$C_6$ cycloalkyl, $C_1$–$C_4$ alkoxy, $C_1$–$C_4$ alkyl, OH, $CF_3$, or $OCF_3$.

In this embodiment, it is preferred that $R_6$ and $R_7$ are not simultaneously OH.

Embodiment A90. Compounds according to embodiment A89, wherein the $R_5$ group is disubstituted with two groups that are meta to each other.

Embodiment A91. Compounds according to embodiment A78, wherein $R_5$ is phenyl, which is optionally substituted with 1, 2, 3, 4, or 5 groups that are independently $C_1$–$C_4$ alkyl, —C(O)$NR_6R_7$, —$NR_6R_7$, $NR_6R_7$($C_1$–$C_6$ alkyl), $NR_8R_9$, $C_1$–$C_6$ hydroxyalkyl, halogen, $C_1$–$C_4$ alkoxy, $CO_2H$, OH, $C_1$–$C_6$ alkoxycarbonyl, carboxaldehyde, $C_1$–$C_4$ haloalkyl, —($C_1$–$C_4$ alkyl)-$NR_{15}C(O)NR_{16}R_{17}$, —($C_1$–$C_4$ alkyl)-$NR_{15}C(O)R_{18}$; wherein $R_6$ and $R_7$ at each occurrence are independently H, OH, $C_1$–$C_6$ alkyl, amino $C_1$–$C_4$ alkyl, NH($C_1$–$C_6$ alkyl) alkyl, N($C_1$–$C_6$ alkyl)($C_1$–$C_6$ alkyl)$C_1$–$C_6$ alkyl, $C_1$–$C_6$ hydroxyalkyl, $C_1$–$C_6$ alkoxy $C_1$–$C_6$ alkyl, —$SO_2$($C_1$–$C_6$ alkyl), —$SO_2NH_2$, —$SO_2NH$($C_1$–$C_6$ alkyl), —$SO_2N$($C_1$–$C_6$ alkyl)($C_1$–$C_6$ alkyl), or $C_1$–$C_6$ alkanoyl, each of which is optionally substituted with 1, 2, or 3 groups that are independently halogen, OH, SH, $C_3$–$C_6$ cycloalkyl, $C_1$–$C_4$ alkoxy, $C_1$–$C_4$ alkyl, OH, $CF_3$, or $OCF_3$; or $R_6$, $R_7$, and the nitrogen to which they are attached form a piperidinyl, pyrrolidinyl, piperazinyl, or a morpholinyl ring optionally substituted with 1 or 2 groups that are independently alkyl, hydroxy, hydroxy $C_1$–$C_4$ alkyl, or halogen, $R_{15}$ is H or $C_1$–$C_6$ alkyl;

$R_{16}$ and $R_{17}$ are independently H or $C_1$–$C_6$ alkyl; or $R_{16}$, $R_{17}$, and the nitrogen to which they are attached form a morpholinyl ring;

$R_{18}$ is $C_1$–$C_6$ alkyl optionally substituted with —O—($C_2$–$C_6$ alkanoyl, $C_1$–$C_6$ hydroxyalkyl, $C_1$–$C_6$ alkoxy, $C_1$–$C_6$ alkoxy $C_1$–$C_6$ alkyl; amino $C_1$–$C_6$ alkyl, mono or dialkylamino $C_1$–$C_6$ alkyl.

In this embodiment, it is preferred that $R_6$ and $R_7$ are not simultaneously OH.

Embodiment A92. Compounds according to embodiment A91, wherein $R_5$ is phenyl, which is optionally substituted with 1,2, 3, 4, or 5 groups that are independently $C_1$–$C_4$ alkyl, —($C_1$–$C_4$ alkyl)-C(O)$NR_6R_7$, —C(O)$NR_6R_7$, —$NR_6R_7$, $NR_6R_7$($C_1$–$C_6$ alkyl), $NR_8R_9$, $C_1$–$C_6$ hydroxyalkyl, halogen, $C_1$–$C_4$ alkoxy, $CO_2H$, OH, $C_1$–$C_6$ alkoxycarbonyl, carboxaldehyde, $C_1$–$C_4$ haloalkyl, —($C_1$–$C_4$ alkyl)-$NR_{15}C(O)NR_{16}R_{17}$, —($C_1$–$C_4$ alkyl)-$NR_{15}C(O)R_{18}$; wherein $R_6$ and $R_7$ at each occurrence are independently H, OH, $C_1$–$C_6$ alkyl, amino $C_1$–$C_4$ alkyl, NH($C_1$–$C_6$ alkyl) alkyl, N($C_1$–$C_6$ alkyl)($C_1$–$C_6$ alkyl)$C_1$–$C_6$ alkyl, $C_1$–$C_6$ hydroxyalkyl, $C_1$–$C_6$ alkoxy $C_1$–$C_6$ alkyl, —$SO_2$($C_1$–$C_6$ alkyl), —$SO_2NH_2$, —$SO_2NH$($C_1$–$C_6$ alkyl), —$SO_2N$($C_1$–$C_6$ alkyl)($C_1$–$C_6$ alkyl), or $C_1$–$C_6$ alkanoyl each of which is optionally substituted with 1, 2, or 3 groups that are independently halogen, OH, SH, $C_3$–$C_6$ cycloalkyl, $C_1$–$C_4$ alkoxy, $C_1$–$C_4$ alkyl, OH, $CF_3$, or $OCF_3$;

$R_{15}$ is H or $C_1$–$C_6$ alkyl;

$R_{16}$ and $R_{17}$ are independently H or $C_1$–$C_6$ alkyl; or $R_{16}$, $R_{17}$, and the nitrogen to which they are attached form a morpholinyl ring;

$R_{18}$ is $C_1$–$C_6$ alkyl optionally substituted with —O—($C_2$–$C_6$ alkanoyl, $C_1$–$C_6$ hydroxyalkyl, $C_1$–$C_6$ alkoxy, $C_1$–$C_6$ alkoxy $C_1$–$C_6$ alkyl; amino $C_1$–$C_6$ alkyl, mono or dialkylamino $C_1$–$C_6$ alkyl.

Embodiment A93. Compounds according to embodiment A92, wherein $R_1$ is halogen, methyl, ethyl, $C_2$–$C_4$ alkenyl, $C_2$–$C_4$ alkynyl, or carboxaldehyde;

$R_2$ is benzyloxy, OH, phenyloxy, phenyloxy($C_1$–$C_6$)alkyl, or phenyl($C_1$–$C_4$)thioalkoxy, wherein each of the above is optionally substituted with 1, 2, 3, or 4 groups that are independently halogen, —($C_1$–$C_6$)alkyl-N(R)—$CO_2R_{30}$, $NR_6R_7$, ($C_1$–$C_4$)haloalkyl, ($C_1$–$C_4$)haloalkoxy, ($C_1$–$C_6$) alkyl, pyridyl, or $NR_6R_7$—($C_1$–$C_6$ alkyl)-; and $R_4$ is H, ($C_1$–$C_4$)alkyl optionally substituted with one or two groups that are independently $CO_2H$, —$CO_2$ alkyl, —C(O)NRR, —N($R_{30}$)C(O)NRR, —N($R_{30}$)C(O)—($C_1$–$C_6$)alkoxy, or —$NR_6R_7$, or hydroxy($C_1$–$C_4$)alkyl.

Embodiment A94. Compounds according to embodiment A93, wherein $R_5$ is phenyl, which is optionally substituted with 1, 2, 3, 4, or 5 groups that are independently $C_1$–$C_4$ alkyl, —C(O)$NR_6R_7$, —($C_1$–$C_4$ alkyl)-C(O)$NR_6R_7$, —$NR_6R_7$, $NR_6R_7$ ($C_1$–$C_6$ alkyl), $C_1$–$C_6$ hydroxyalkyl, halogen, $C_1$–$C_4$ alkoxy, $CO_2H$, OH, $C_1$–$C_6$ alkoxycarbonyl, carboxaldehyde, $C_1$–$C_4$ haloalkyl, wherein $R_6$ and $R_7$ at each occurrence are independently H, OH, $C_1$–$C_6$ alkyl, amino $C_1$–$C_4$ alkyl, NH($C_1$–$C_6$ alkyl) alkyl, N($C_1$–$C_6$ alkyl)($C_1$–$C_6$ alkyl)$C_1$–$C_6$ alkyl, $C_1$–$C_6$ hydroxyalkyl, $C_1$–$C_6$ alkoxy $C_1$–$C_6$ alkyl, —$SO_2$ ($C_1$–$C_6$ alkyl), —$SO_2NH_2$, —$SO_2NH(C_1$–$C_6$ alkyl), —$SO_2N(C_1$–$C_6$ alkyl)($C_1$–$C_6$ alkyl), or $C_1$–$C_6$ alkanoyl, each of which is optionally substituted with 1, 2, or 3 groups that are independently halogen, OH, SH, $C_3$–$C_6$ cycloalkyl, $C_1$–$C_4$ alkoxy, $C_1$–$C_4$ alkyl, OH, $CF_3$, or $OCF_3$.

Embodiment A101. Compounds according to embodiment A66, wherein $R_5$ is thienyl($C_1$–$C_6$ alkyl), piperidinyl($C_1$–$C_6$)alkyl, pyrrolidinyl($C_1$–$C_6$)alkyl, imidazolidinyl($C_1$–$C_6$)alkyl, piperazinyl($C_1$–$C_6$)alkyl, pyridyl($C_1$–$C_6$)alkyl, pyrimidyl ($C_1$–$C_6$)alkyl, pyridazyl($C_1$–$C_6$)alkyl, pyrazinyl($C_1$–$C_6$) alkyl, isoquinolinyl($C_1$–$C_6$)alkyl, tetrahydroisoquinolinyl ($C_1$–$C_6$)alkyl, indolyl($C_1$–$C_6$)alkyl, 1H-indazolyl($C_1$–$C_6$) alkyl, dihydroindolonyl($C_1$–$C_6$ alkyl), indolinyl($C_1$–$C_6$ alkyl), dihydroisoindolyl($C_1$–$C_6$ alkyl), dihydrobenzimdazolyl($C_1$–$C_6$ alkyl), or dihydrobenzoimidazolonyl($C_1$–$C_6$ alkyl), wherein each of the above is unsubstituted or substituted with 1, 2, 3, 4, or 5 groups that are independently ($C_1$–$C_6$)alkyl, halogen, ($C_1$–$C_6$)alkoxy, ($C_1$–$C_6$)hydroxyalkyl, phenyl ($C_1$–$C_6$)alkoxy, ($C_1$–$C_6$)thioalkoxy, ($C_1$–$C_6$) alkoxycarbonyl, phenyl($C_1$–$C_6$)alkoxycarbonyl, OH, $CO_2H$, CN, amidinooxime, $NR_8R_9$, $NR_6R_7$—($C_1$–$C_6$ alkyl)-, —C(O)$NR_6R_7$, —($C_1$–$C_4$ alkyl)-C(O)$NR_6R_7$, amidino, piperazinyl, morpholinyl, —$SO_2$ ($C_1$–$C_6$) alkyl, —$SO_2NH_2$, —$SO_2NH(C_1$–$C_6$)alkyl, —$SO_2N$ ($C_1$–$C_6$)alkyl($C_1$–$C_6$)alkyl, ($C_1$–$C_4$)haloalkyl, —($C_1$–$C_4$ alkyl)-$NR_{15}C(O)NR_{16}R_{17}$, —($C_1$–$C_4$ alkyl)-$NR_{15}C(O)R_{18}$, —O—$CH_2$—O, —O—$CH_2CH_2$—O—, or ($C_1$–$C_4$)haloalkoxy; wherein $R_6$ and $R_7$ are independently at each occurrence H, ($C_1$–$C_6$)alkyl, ($C_1$–$C_6$)alkoxy, ($C_1$–$C_6$)alkoxy($C_1$–$C_6$) alkyl, ($C_1$–$C_6$)alkoxycarbonyl, ($C_1$–$C_6$)hydroxyalkyl, —($C_1$–$C_4$)alkyl-$CO_2$—($C_1$–$C_6$)alkyl, ($C_1$–$C_6$) alkanoyl, phenyl($C_1$–$C_6$)alkyl, phenyl($C_1$–$C_6$)alkoxy, or phenyl($C_1$–$C_6$)alkanoyl, wherein each of the above is unsubstituted or substituted with 1, 2, or 3 groups that are independently, halogen, ($C_1$–$C_4$)alkoxy, OH, SH, $C_3$–$C_6$ cycloalkyl, $NH_2$, NH($C_1$–$C_6$ alkyl), N($C_1$–$C_6$ alkyl)($C_1$–$C_6$ alkyl), ($C_1$–$C_4$)alkyl, $CF_3$ or $OCF_3$; or $R_6$, $R_7$, and the nitrogen to which they are attached form a morpholinyl, thiomorpholinyl, piperidinyl, pyrrolidinyl, or piperazinyl ring which is optionally substituted with 1 or 2 groups that are independently $C_1$–$C_4$ alkyl, hydroxy, hydroxy $C_1$–$C_4$ alkyl, or halogen; and $R_{18}$ is $C_1$–$C_6$ alkyl optionally substituted with —O—($C_2$–$C_6$ alkanoyl, $C_1$–$C_6$ hydroxyalkyl, $C_1$–$C_6$ alkoxy, $C_1$–$C_6$ alkoxy $C_1$–$C_6$ alkyl; amino $C_1$–$C_6$ alkyl, mono or dialkylamino $C_1$–$C_6$ alkyl.

In this embodiment, it is preferred that $R_6$ and $R_7$ are not simultaneously OH; and $R_6$ and $R_7$ are not simultaneously —$SO_2(C_1$–$C_6$ alkyl)

Embodiment A102. Compounds according to embodiment A101, wherein $R_1$ is halogen, methyl, ethyl, $C_2$–$C_4$ alkenyl, $C_2$–$C_4$ alkynyl, or carboxaldehyde;

$R_2$ is benzyloxy, OH, phenyloxy, phenyloxy($C_1$–$C_6$)alkyl, or phenyl($C_1$–$C_4$)thioalkoxy, wherein each of the above is optionally substituted with 1, 2, 3, or 4 groups that are independently halogen, —($C_1$–$C_6$)alkyl-N(R)—$CO_2R_{30}$, $NR_6R_7$, ($C_1$–$C_4$)haloalkyl, ($C_1$–$C_4$)haloalkoxy, ($C_1$–$C_6$) alkyl, pyridyl, or $NR_6R_7$—($C_1$–$C_6$ alkyl)-; and $R_4$ is H, ($C_1$–$C_4$)alkyl optionally substituted with one or two groups that are independently $CO_2H$, —$CO_2$ alkyl, —C(O)NRR, —N($R_{30}$)C(O)NRR, —N($R_{30}$)C(O)—($C_1$–$C_6$)alkoxy, or —$NR_6R_7$, or hydroxy($C_1$–$C_4$)alkyl.

Embodiment A103. Compounds according to embodiment A102, wherein $R_5$ is thienyl($C_1$–$C_6$ alkyl), indolyl($C_1$–$C_6$ alkyl), pyridinyl ($C_1$–$C_6$ alkyl), piperazinyl($C_1$–$C_6$ alkyl), or pyrazinyl ($C_1$–$C_6$ alkyl) each of which is optionally substituted with 1, 2, or 3 groups that are independently $C_1$–$C_4$ alkyl, $C_1$–$C_4$ hydroxyalkyl, halogen, —C(O)$NR_6R_7$, —($C_1$–$C_4$ alkyl)-C(O)$NR_6R_7$, $C_1$–$C_6$ alkoxycarbonyl, —$NR_6R_7$, $NR_6R_7$—($C_1$–$C_6$ alkyl)-, haloalkyl, $C_1$–$C_6$ alkanoyl, $R_6$ and $R_7$ at each occurrence are independently H, $C_1$–$C_6$ alkyl optionally substituted with 1, 2, or 3 groups that are independently $C_1$–$C_4$ alkoxycarbonyl, halogen, $C_3$–$C_6$ cycloalkyl, OH, SH, or $C_1$–$C_4$ alkoxy; or $R_6$, $R_7$, and the nitrogen to which they are attached form a piperidinyl, pyrrolidinyl, piperazinyl, or a morpholinyl ring optionally substituted with 1 or 2 groups that are independently alkyl, hydroxy, hydroxy $C_1$–$C_4$ alkyl, or halogen.

Embodiment A104. Compounds according to embodiment A103, wherein $R_5$ is thienyl($C_1$–$C_6$ alkyl), indolyl($C_1$–$C_6$ alkyl), pyridinyl ($C_1$–$C_6$ alkyl), piperazinyl($C_1$–$C_6$ alkyl), or pyrazinyl ($C_1$–$C_6$ alkyl).

Embodiment A105. Compounds according to embodiment A103, wherein $R_4$ is H, methyl, ethyl, or —$CH_2OH$;

$R_5$ is pyridinyl($C_1$–$C_6$ alkyl), or pyrazinyl($C_1$–$C_6$ alkyl) each of which is optionally substituted with 1, 2, or 3 groups that are independently $C_1$–$C_4$ alkyl, $C_1$–$C_4$ hydroxyalkyl, halogen, —C(O)$NR_6R_7$, —($C_1$–$C_4$ alkyl)-C(O)$NR_6R_7$, $C_1$–$C_6$ alkoxycarbonyl, —$NR_6R_7$, $NR_6R_7$—($C_1$–$C_6$ alkyl)-, $CF_3$, $C_1$–$C_6$ alkanoyl, wherein $R_6$ and $R_7$ at each occurrence are independently H, $C_1$–$C_6$ alkyl optionally substituted with 1, 2, or 3 groups that are independently $C_1$–$C_4$ alkoxycarbonyl, halogen, $C_3$–$C_6$ cycloalkyl, OH, SH, or $C_1$–$C_4$ alkoxy;

or $R_6$, $R_7$, and the nitrogen to which they are attached form a piperidinyl, pyrrolidinyl, piperazinyl, or a morpholinyl ring optionally substituted with 1 or 2 groups that are independently alkyl, hydroxy, hydroxy $C_1$–$C_4$ alkyl, or halogen.

Embodiment A106. Compounds according to embodiment A105, wherein $R_4$ is H, alkyl substituted with one or two groups that are independently $CO_2H$, —$CO_2$—($C_1$–$C_6$)alkyl, —C(O)NRR, —N($R_{30}$)C(O)NRR, —N($R_{30}$)C(O)—($C_1$–$C_6$) alkoxy, or —$NR_6R_7$.

Embodiment A112. Compounds according to embodiment 16, wherein $R_1$ is halogen, or methyl;

$R_2$ is benzyloxy, which is optionally substituted with 1, 2, 3, or 4 groups that are independently halogen, —($C_1$–$C_6$) alkyl-N(R)—$CO_2R_{30}$, $CF_3$, $OCF_3$, or ($C_1$–$C_4$)alkyl; and $R_4$ is H, methyl, ethyl, —$CH_2OH$, —$CH_2CO_2$—($C_1$–$C_4$ alkyl), or $C_2$ hydroxyalkyl.

Embodiment A113. Compounds according to any one of embodiments A85, A95, A97, A98, A99, A100, 16 or 17, wherein $R_1$ is halogen, or methyl;

$R_2$ is benzyloxy, which is optionally substituted with 1, 2, 3, or 4 groups that are independently halogen, —($C_1$–$C_6$) alkyl-N(R)—$CO_2R_{30}$, $CF_3$, $OCF_3$, or ($C_1$–$C_4$)alkyl,; and $R_4$ is alkyl substituted with one group that is $CO_2H$, —$CO_2$—($C_1$–$C_6$)alkyl, —C(O)NRR, —N($R_{30}$)C(O)NRR, —N($R_{30}$)C(O)—($C_1$–$C_6$)alkoxy, or —$NR_6R_7$.

Embodiment A114. Compounds according to embodiment A66, wherein $R_5$ is isoquinolinyl($C_1$–$C_6$ alkyl), tetrahydroisoquinolinyl ($C_1$–$C_6$ alkyl), 1H-indazolyl($C_1$–$C_6$ alkyl), dihydroindolonyl($C_1$–$C_6$ alkyl), indolinyl($C_1$–$C_6$ alkyl), dihydroisoindolyl($C_1$–$C_6$ alkyl), dihydrobenzimdazolyl ($C_1$–$C_6$ alkyl), dihydrobenzoimidazolonyl($C_1$–$C_6$ alkyl), each of which is unsubstituted or substituted with 1, 2, or 3 groups that are independently alkyl, alkoxy, halogen, $C_1$–$C_6$ alkoxycarbonyl, alkanoyl optionally substituted with 1 or 2 groups that are independently selected from the group consisting of OH, $NH_2$, NH($C_1$–$C_6$ alkyl), and N($C_1$–$C_6$ alkyl)($C_1$–$C_6$ alkyl), —C(O)$NR_6R_7$, —($C_1$–$C_4$ alkyl)-C(O)$NR_6R_7$, $NR_6R_7$—($C_1$–$C_6$ alkyl)-, —$NR_6R_7$, or $SO_2H$; or piperidinyl $C_1$–$C_4$ alkyl optionally substituted with 1, 2, or 3 groups that are independently $C_1$–$C_4$ alkyl, $C_1$–$C_4$ alkoxy, halogen, —C(O)$NR_6R_7$, —($C_1$–$C_4$ alkyl)-C(O)$NR_6R_7$, $NR_6R_7$—($C_1$–$C_6$ alkyl)-, or —$NR_6R_7$, or $C_1$–$C_6$ alkoxycarbonyl.

Embodiment A115. Compounds according to embodiment A114, wherein $R_5$ is isoquinolinyl($C_1$–$C_4$ alkyl), piperidinyl $C_1$–$C_4$ alkyl, tetrahydroisoquinolinyl($C_1$–$C_4$ alkyl), 1H-indazolyl ($C_1$–$C_4$ alkyl), dihydroindolonyl($C_1$–$C_4$ alkyl), indolinyl ($C_1$–$C_4$ alkyl), dihydroisoindolyl($C_1$–$C_4$ alkyl), dihydrobenzimdazolyl($C_1$–$C_4$ alkyl), or dihydrobenzoimidazolonyl($C_1$–$C_4$ alkyl).

Embodiment A116. Compounds according to embodiment A114, wherein $R_5$ is piperidinyl $C_1$–$C_4$ alkyl optionally substituted with 1, 2, or 3 groups that are independently $C_1$–$C_4$ alkyl, $C_1$–$C_4$ alkoxy, halogen, or $C_1$–$C_6$ alkoxycarbonyl.

Embodiment A117. Compounds according to embodiment A66, wherein $R_5$ is pyrimidyl, indolinyl, indolyl, 1H-isoindolyl, isoquinolinyl, tetrahydroisoquinolinyl, benzimidazolyl, dihydro-1H-benzimidazolyl, pyrrolyl, imidazolyl, or each of which is optionally substituted with 1, 2, or 3 groups independently selected from the group consisting of $C_1$–$C_6$ alkoxycarbonyl, $C_1$–$C_4$ thioalkoxy, each of which is unsubstituted or substituted with 1, 2, or 3 groups that are independently —C(O)$NR_6R_7$, —($C_1$–$C_4$ alkyl)-C(O)$NR_6R_7$, $NR_6R_7$—($C_1$–$C_6$ alkyl)-, —$NR_6R_7$, alkyl, alkoxy, halogen, $C_1$–$C_6$ alkoxycarbonyl, or alkanoyl optionally substituted with 1 or 2 groups that are independently selected from the group consisting of OH, $NH_2$, NH($C_1$–$C_6$ alkyl), and N($C_1$–$C_6$ alkyl)($C_1$–$C_6$ alkyl), and $SO_2H$; or pyridyl, pyrazolyl, optionally substituted with 1, 2, or 3 groups that are independently —C(O)$NR_6R_7$, —($C_1$–$C_4$ alkyl)-C(O)$NR_6R_7$, $NR_6R_7$—($C_1$–$C_6$ alkyl)-, —$NR_6R_7$, $C_1$–$C_4$ alkyl, $C_1$–$C_4$ hydroxyalkyl, halogen, $C_1$–$C_6$ alkoxycarbonyl, —$NR_6R_7$, $NR_6R_7$—($C_1$–$C_6$ alkyl)-, $CF_3$, $C_1$–$C_6$ alkanoyl, wherein $R_6$ and $R_7$ at each occurrence are independently H, $C_1$–$C_6$ alkyl optionally substituted with 1, 2, or 3 groups that are independently $C_1$–$C_4$ alkoxycarbonyl, halogen, $C_3$–$C_6$ cycloalkyl, OH, SH, or $C_1$–$C_4$ alkoxy;

or $R_6$, $R_7$, and the nitrogen to which they are attached form a piperidinyl, pyrrolidinyl, piperazinyl, or a morpholinyl ring optionally substituted with 1 or 2 groups that are independently alkyl, hydroxy, hydroxy $C_1$–$C_4$ alkyl, or halogen.

Embodiment A118. Compounds according to embodiment A117, wherein $R_5$ is pyrimidyl, pyrrolyl, imidazolyl, or pyrazolyl, each of which is optionally substituted with 1, 2, or 3 groups independently selected from $C_1$–$C_6$ alkoxycarbonyl, $C_1$–$C_4$ thioalkoxy, each of which is unsubstituted or substituted with 1, 2, or 3 groups that are independently alkyl, alkoxy, halogen, $C_1$–$C_6$ alkoxycarbonyl, —C(O)$NR_6R_7$, —($C_1$–$C_4$ alkyl)-C(O)$NR_6R_7$, $NR_6R_7$—($C_1$–$C_6$ alkyl)-, or —$NR_6R_7$, or $C_1$–$C_4$ alkanoyl optionally substituted with 1 or 2 groups that are independently selected from the group consisting of OH, $NH_2$, NH($C_1$–$C_6$ alkyl), and N($C_1$–$C_6$ alkyl)($C_1$–$C_6$ alkyl), or $SO_2H$.

Embodiment A119. Compounds according to embodiment A117, wherein $R_5$ is pyridyl or pyrazolyl, optionally substituted with 1, 2, or 3 groups that are independently $C_1$–$C_4$ alkyl, $C_1$–$C_4$ hydroxyalkyl, halogen, —C(O)$NR_6R_7$, —($C_1$–$C_4$ alkyl)-C(O)$NR_6R_7$, $_{NR6}R_7$—($C_1$–$C_6$ alkyl)-, or —$NR_6R_7$, $C_1$–$C_6$ alkoxycarbonyl, —$NR_6R_7$, $NR_6R_7$—($C_1$–$C_6$ alkyl)-, $CF_3$, $C_1$–$C_6$ alkanoyl, wherein $R_6$ and $R_7$ at each occurrence are independently H, $C_1$–$C_6$ alkyl optionally substituted with 1, 2, or 3 groups that are independently $C_1$–$C_4$ alkoxycarbonyl, halogen, $C_3$–$C_6$ cycloalkyl, OH, SH, or $C_1$–$C_4$ alkoxy;

or $R_6$, $R_7$, and the nitrogen to which they are attached form a piperidinyl, pyrrolidinyl, piperazinyl, or a morpholinyl ring optionally substituted with 1 or 2 groups that are independently alkyl, hydroxy, hydroxy $C_1$–$C_4$ alkyl, or halogen.

Embodiment A120. Compounds according to embodiment A119, wherein $R_5$ is pyridyl or pyrazolyl, optionally substituted with 1, 2, or 3 groups that are independently $C_1$–$C_4$ alkyl, $C_1$–$C_4$ hydroxyalkyl, halogen, —C(O)$NR_6R_7$, —($C_1$–$C_4$ alkyl)-C(O)$NR_6R_7$ $NR_6R_7$—($C_1$–$C_6$ alkyl)-, —$NR_6R_7$, $C_1$–$C_6$ alkoxycarbonyl, $CF_3$, $C_1$–$C_6$ alkanoyl, wherein $R_6$ and $R_7$ at each occurrence are independently H, $C_1$–$C_6$ alkyl optionally substituted with 1, 2, or 3 groups that are independently $C_1$–$C_4$ alkoxycarbonyl, halogen, $C_3$–$C_6$ cycloalkyl, OH, SH, or $C_1$–$C_4$ alkoxy.

Embodiment A121. Compounds according to embodiment A119, wherein $R_5$ is pyridyl or pyrazolyl, optionally substituted with 1, 2, or 3 groups that are independently $C_1$–$C_4$ alkyl, $C_1$–$C_4$ hydroxyalkyl, halogen, —C(O)$NR_6R_7$, —($C_1$–$C_4$ alkyl)-C(O)$NR_6R_7$, $NR_6R_7$—($C_1$–$C_6$ alkyl)-, —$NR_6R_7$, $C_1$–$C_6$ alkoxycarbonyl, $CF_3$, $C_1$–$C_6$ alkanoyl, wherein $R_6$, $R_7$, and the nitrogen to which they are attached form a piperidinyl, pyrrolidinyl, piperazinyl, or a morpholinyl ring optionally substituted with 1 or 2 groups that are independently alkyl, hydroxy, hydroxy $C_1$–$C_4$ alkyl, or halogen.

Embodiment A122. Compounds according to any one of embodiments A114, A115, A116, or A117 wherein $R_1$ is halogen, methyl, ethyl, $C_2$–$C_4$ alkenyl, $C_2$–$C_4$ alkynyl, or carboxaldehyde;

$R_2$ is benzyloxy, OH, phenyloxy, phenyloxy($C_1$–$C_6$)alkyl, or phenyl($C_1$–$C_4$)thioalkoxy, wherein each of the above is optionally substituted with 1, 2, 3, or 4 groups that are independently halogen, —($C_1$–$C_6$)alkyl-N(R)—$CO_2R_{30}$, $NR_6R_7$, ($C_1$–$C_4$)haloalkyl, ($C_1$–$C_4$)haloalkoxy, ($C_1$–$C_6$) alkyl, pyridyl, or $NR_6R_7$—($C_1$–$C_6$ alkyl)-; and $R_4$ is H, ($C_1$–$C_4$)alkyl substituted with one group that is $CO_2H$, —$CO_2$—($C_1$–$C_6$)alkyl, —C(O)NRR, —N($R_{30}$)C(O)NRR, —N($R_{30}$)C(O)—($C_1$–$C_6$)alkoxy, or —$NR_6R_7$, hydroxy($C_1$–$C_4$)alkyl.

Embodiment A123. Compounds according to embodiment A66, wherein $R_5$ is $C_1$–$C_6$ alkyl optionally substituted with 1 or 2, groups that are independently $C_1$–$C_4$ alkoxycarbonyl, or halogen, or $R_5$ is $C_1$–$C_4$ alkoxy, ethyl, methyl, cyclopropylmethyl, cycloalkyl, or alkynyl, or $R_5$ is $C_2$–$C_6$ alkenyl optionally substituted with $C_1$–$C_4$ alkoxycarbonyl or cyclohexyl.

Embodiment A124. Compounds according to embodiment A123, wherein $R_1$ is halogen, methyl, ethyl, $C_2$–$C_4$ alkenyl, $C_2$–$C_4$ alkynyl, or carboxaldehyde;

$R_2$ is benzyloxy, OH, phenyloxy, phenyloxy($C_1$–$C_6$)alkyl, or phenyl($C_1$–$C_4$)thioalkoxy, wherein each of the above is optionally substituted with 1, 2, 3, or 4 groups that are independently halogen, —($C_1$–$C_6$)alkyl-N(R)—$CO_2R_{30}$, $NR_6R_7$, ($C_1$–$C_4$)haloalkyl, ($C_1$–$C_4$)haloalkoxy, ($C_1$–$C_6$) alkyl, pyridyl, or $NR_6R_7$—($C_1$–$C_6$ alkyl)-; and $R_4$ is H, ($C_1$–$C_4$)alkyl substituted with one group that is $CO_2H$, —$CO_2$—($C_1$–$C_6$)alkyl, —C(O)NRR, —N($R_{30}$)C(O)NRR, —N($R_{30}$)C(O)—($C_1$–$C_6$)alkoxy, or —$NR_6R_7$, hydroxy($C_1$–$C_4$)alkyl; wherein $R_6$ and $R_7$ at each occurrence are independently H, $C_1$–$C_6$ alkyl optionally substituted with 1, 2, or 3 groups that are independently $C_1$–$C_4$ alkoxycarbonyl, halogen, $C_3$–$C_6$ cycloalkyl, OH, SH, or $C_1$–$C_4$ alkoxy; ps or $R_6$, $R_7$, and the nitrogen to which they are attached form a piperidinyl, pyrrolidinyl, piperazinyl, or a morpholinyl ring optionally substituted with 1 or 2 groups that are independently alkyl, hydroxy, hydroxy $C_1$–$C_4$ alkyl, or halogen.

Embodiment A125. Compounds according to embodiment A124, wherein $R_5$ is $C_1$–$C_6$ alkyl optionally substituted with 1 or 2, groups that are independently $C_1$–$C_4$ alkoxycarbonyl, or halogen, or $R_5$ is $C_1$–$C_4$ alkoxy, ethyl, methyl, cyclopropylmethyl, cyclohexyl, cyclopentyl, $C_2$–$C_6$ alkynyl, or $R_5$ is $C_2$–$C_6$ alkenyl optionally substituted with $C_1$–$C_4$ alkoxycarbonyl or cyclohexyl.

Embodiment A126. Compounds according to embodiment A66, wherein $R_2$ is phenylalkynyl, —OC(O)NH($CH_2$)$_n$aryl, —OC(O)N(alkyl)($CH_2$)aryl, —$OSO_2$($C_1$–$C_6$)alkyl, —$OSO_2$ aryl, or $NR_8R_9$, wherein n is 0, 1, 2, 3, 4, 5 or 6;

each of the above is unsubstituted or substituted with 1, 2, 3, 4, or 5 groups that are independently halogen, —($C_1$–$C_6$)alkyl-N(R)—$CO_2R_{30}$, alkoxy, alkoxycarbonyl, CN, $NR_6R_7$, haloalkyl, haloalkoxy, alkyl, heteroaryl, heteroarylalkyl, $NR_6R_7$—($C_1$–$C_6$ alkyl)-, phenyl, —$SO_2$-phenyl wherein the phenyl groups are optionally substituted with 1, 2, or 3 groups that are independently halogen or $NO_2$; or —OC(O)$NR_6R_7$, wherein $R_6$ and $R_7$ are independently at each occurrence H, alkyl, alkoxy, alkoxyalkyl, alkoxycarbonyl, —$SO_2$-alkyl, OH, hydroxyalkyl, —($C_1$–$C_4$)alkyl-$CO_2$-alkyl, heteroarylalkyl, alkanoyl, arylalkyl, arylalkoxy, or arylalkanoyl, wherein each of the above is unsubstituted or substituted with 1, 2, or 3 groups that are independently, halogen, alkoxy, heterocycloalkyl, OH, $NH_2$, $C_3$–$C_6$ cycloalkyl, NH(alkyl), N(alkyl)(alkyl), —O—alkanoyl, alkyl, $C_1$–$C_4$ haloalkyl, or $C_1$–$C_4$ haloalkoxy; or $R_6$, $R_7$, and the nitrogen to which they are attached form a morpholinyl, thiomorpholinyl, piperidinyl, pyrrolidinyl, or piperazinyl ring which is optionally substituted with 1 or 2 groups that are independently $C_1$–$C_4$ alkyl, $C_1$–$C_4$ alkoxy, hydroxy, hydroxy $C_1$–$C_4$ alkyl, or halogen.

Embodiment A127. Compounds according to embodiment A126, wherein $R_1$ is halogen, methyl, ethyl, $C_2$–$C_4$ alkenyl, $C_2$–$C_4$ alkynyl, or carboxaldehyde; and $R_4$ is H, ($C_1$–$C_4$)alkyl substituted with one group that is $CO_2H$, —$CO_2$—($C_1$–$C_6$)alkyl, —C(O)NRR, —N($R_{30}$)C(O)NRR, —N($R_{30}$)C(O)—($C_1$–$C_6$)alkoxy, —$NR_6R_7$, $NR_6R_7$—($C_1$–$C_6$ alkyl)-, or hydroxy($C_1$–$C_4$)alkyl.

Embodiment A128. Compounds according to embodiment A127, wherein $R_5$ is phenyl, optionally substituted with 1, 2, 3, 4, or 5 groups that are independently halogen, $C_1$–$C_4$ alkyl, $C_1$–$C_4$ alkoxy, $CF_3$, $OCF_3$, —($C_1$–$C_4$ alkyl)-C(O)$NR_6R_7$, $NR_6R_7$—($C_1$–$C_6$ alkyl)-, —$NR_6R_7$, or C(O)$NR_6R_7$, wherein $R_6$ and $R_7$ are independently at each occurrence H, $C_1$–$C_6$ alkyl, $C_1$–$C_6$ alkoxy, $C_1$–$C_6$ alkoxy $C_1$–$C_6$ alkyl, $C_1$–$C_6$ alkoxycarbonyl, OH, $C_1$–$C_6$ hydroxyalkyl, —($C_1$–$C_4$)alkyl-$CO_2$-alkyl, pyridyl $C_1$–$C_6$ alkyl, $C_1$–$C_6$ alkanoyl, benzyl, phenyl $C_1$–$C_6$ alkoxy, or phenyl $C_1$–$C_6$ alkanoyl, wherein each of the above is unsubstituted or substituted with 1, 2, or 3 groups that are independently, halogen, $C_1$–$C_6$ alkoxy, piperidinyl $C_1$–$C_6$ alkyl, morpholinyl $C_1$–$C_6$ alkyl, piperazinyl $C_1$–$C_6$ alkyl, OH, SH, $C_3$–$C_6$ cycloalkyl, $NH_2$, NH(alkyl), N(alkyl)(alkyl), —O—$C_1$–$C_4$ alkanoyl, $C_1$–$C_4$ alkyl, $CF_3$, or $OCF_3$; or $R_6$, $R_7$, and the nitrogen to which they are attached form a morpholinyl, thiomorpholinyl, piperidinyl, pyrrolidinyl, or piperazinyl ring which is optionally substituted with 1 or 2 groups that are independently $C_1$–$C_4$ alkyl, $C_1$–$C_4$ alkoxy, hydroxy, hydroxy $C_1$–$C_4$ alkyl, or halogen; or $R_5$ is benzyl optionally substituted with 1,2,3,4, or 5 groups that are independently halogen, $C_1$–$C_6$ alkyl, $C_1$–$C_6$ alkoxy, CN, $CF_3$, $OCF_3$, —($C_1$–$C_4$ alkyl)-C(O)$NR_6R_7$, $NR_6R_7$—($C_1$–$C_6$ alkyl)-, —$NR_6R_7$, or C(O)$NR_6R_7$.

Embodiment A129. Compounds according to embodiment A128, wherein $R_2$ is $NR_8R_9$, or $NR_8R_9$—($C_1$–$C_4$ alkyl)-; wherein $R_8$ at each occurrence is independently hydrogen, $C_1$–$C_6$ alkyl, $C_1$–$C_6$ alkanoyl, phenyl($C_1$–$C_6$)alkyl or phenyl ($C_1$–$C_6$)alkanoyl wherein each of the above is optionally substituted with 1, 2, 3, 4, or 5 groups that are independently $C_1$–$C_6$ alkyl, $C_1$–$C_6$ alkoxy, $C_1$–$C_6$ alkoxycarbonyl, halogen, or $C_1$–$C_4$ haloalkyl; and $R_9$ at each occurrence is independently $C_1$–$C_6$ alkyl, $C_1$–$C_6$ alkanoyl, phenyl($C_1$–$C_6$)alkyl, $C_3$–$C_7$ cycloalkyl, $C_2$–$C_6$ alkenyl, pyridyl, pyridazinyl, pyrimidinyl, pyrazinyl, imidazolyl, $C_3$–$C_7$ cycloalkyl ($C_1$–$C_6$)alkyl, phenyl($C_1$–$C_6$)alkanoyl, —$SO_2$-phenyl, and phenyl wherein each of the above is optionally substituted with 1, 2, 3, 4, or 5 groups that are independently $C_1$–$C_6$ alkyl, $C_1$–$C_6$ alkoxy, $C_1$–$C_6$ alkoxycarbonyl, halogen, or $C_1$–$C_4$ haloalkyl.

Embodiment A130. Compounds according to embodiment A129, wherein $R_8$ is H.

Embodiment A131. Compounds according to embodiment A130, wherein $R_2$ is —NH-benzyl option substituted with 1, 2, or 3 groups that are independently halogen, $C_1$–$C_4$ alkyl, $C_1$–$C_4$ alkoxy, $CF_3$, $OCF_3$, or $R_2$ is —NH—C(O)phenyl, wherein the phenyl group is optionally substituted with 1, 2, or 3 groups that are independently halogen, $C_1$–$C_4$ alkyl, or $C_1$–$C_4$ alkoxy; or $R_2$ is —NH-allyl.

Embodiment A132. Compounds according to embodiment A131, wherein $R_1$ is chloro, bromo, iodo, or methyl; and $R_5$ is benzyl optionally substituted with 1,2,3,4, or 5 groups that are independently halogen, —($C_1$–$C_4$ alkyl)-C(O)$NR_6R_7$, $NR_6R_7$—($C_1$–$C_6$ alkyl)-, —$NR_6R_7$, $C_1$–$C_6$ alkyl, $C_1$–$C_6$ alkoxy, CN, $CF_3$, $OCF_3$, or C(O)$NR_6R_7$.

Embodiment A133. Compounds according to embodiment A131, wherein $R_1$ is chloro, bromo, iodo, or methyl; and $R_5$ is phenyl, optionally substituted with 1, 2, 3, 4, or 5 groups that are independently halogen, —($C_1$–$C_4$ alkyl)-C(O)$NR_6R_7$, $NR_6R_7$—($C_1$–$C_6$ alkyl)-, —$NR_6R_7$, $C_1$–$C_4$ alkyl, $C_1$–$C_4$ alkoxy, $CF_3$, $OCF_3$, or C(O)$NR_6R_7$.

Embodiment A134. A compound of the formula

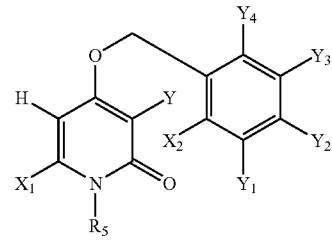

or pharmaceutically acceptable salts thereof, wherein $R_5$ is

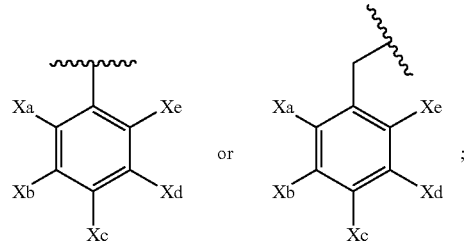

wherein $X_1$, $X_2$, $X_a$, $X_b$, $X_c$, $X_d$, and $X_e$ at are independently selected from —C(O)$NR_6R_7$, —$NR_6R_7$, hydroxy($C_1$–$C_4$)alkyl, H, OH, halogen, haloalkyl, alkyl, haloalkoxy, heteroaryl, heterocycloalkyl, $C_3$–$C_7$ cycloalkyl, $NR_6R_7$—($C_1$–$C_6$ alkyl)-, —$CO_2$—($C_1$–$C_6$)alkyl, —N(R)C(O)$NR_6R_7$, —N(R)C(O)—($C_1$–$C_6$)alkoxy, $CO_2$H—($C_1$–$C_6$ alkyl)-, or —$SO_2NR_6R_7$; wherein the heteroaryl and heterocycloalkyl groups are optionally substituted with —$NR_6R_7$, —C(O)$NR_6R_7$, $NR_6R_7$—($C_1$–$C_6$ alkyl)-, $C_1$–$C_6$ alkyl, $C_1$–$C_6$ alkoxy, or halogen;

$R_6$ and $R_7$ are independently at each occurrence H, $C_1$–$C_6$ alkyl, $C_1$–$C_6$ alkoxy, $C_1$–$C_6$ alkoxy $C_1$–$C_6$ alkyl, $C_1$–$C_6$ alkoxycarbonyl, OH, $C_1$–$C_6$ hydroxyalkyl, $C_1$–$C_6$ thiohydroxyalkyl, —($C_1$–$C_4$)alkyl-$CO_2$-alkyl, pyridyl $C_1$–$C_6$ alkyl, $C_1$–$C_6$ alkanoyl, benzyl, phenyl $C_1$–$C_6$ alkoxy, or phenyl $C_1$–$C_6$ alkanoyl, wherein each of the above is unsubstituted or substituted with 1, 2, or 3 groups that are independently, halogen, $C_3$–$C_6$ cycloalkyl, $C_1$–$C_6$ alkoxy, piperidinyl $C_1$–$C_6$ alkyl, morpholinyl $C_1$–$C_6$ alkyl, piperazinyl $C_1$–$C_6$ alkyl, OH, SH, $NH_2$, NH(alkyl), N(alkyl)(alkyl), —O—$C_1$–$C_4$ alkanoyl, $C_1$–$C_4$ alkyl, $CF_3$, or $OCF_3$; or $R_6$, $R_7$, and the nitrogen to which they are attached form a morpholinyl, thiomorpholinyl, piperidinyl, pyrrolidinyl, or piperazinyl ring which is optionally substituted with 1 or 2 groups that are independently $C_1$–$C_4$ alkyl, $C_1$–$C_4$ alkoxy, hydroxy, hydroxy $C_1$–$C_4$ alkyl, or halogen;

R at each occurrence is independently H or $C_1$–$C_6$ alkyl; and

Y, $Y_1$, $Y_2$, $Y_3$, and $Y_4$ are independently selected from H, halogen, alkyl, carboxaldehyde, hydroxyalkyl, alkenyl, alkynyl, CN, alkanoyl, alkoxy, alkoxyalkyl, haloalkyl, and carboxyl.

Embodiment A135. Compounds according to embodiment A134, wherein $Y_2$, $Y_4$, and Y are independently halogen; and $Y_1$ and $Y_3$ are both hydrogen.

Embodiment A136. Compounds according to embodiment A135, wherein $X_a$ is H, methyl, —$NR_6R_7$, $NR_6R_7$—($C_1$–$C_6$ alkyl)-, —C(O)$NR_6R_7$, $C_1$–$C_6$ hydroxyalkyl, or —($C_1$–$C_4$ alkyl)-morpholinyl.

Embodiment A137. Compounds according to embodiment A136, wherein $X_a$ and $X_e$ are independently halogen, is $NH_2$, NH($C_1$–$C_6$ alkyl), N($C_1$–$C_6$ alkyl)($C_1$–$C_6$ alkyl) or methyl.

Embodiment A138. Compounds according to embodiment A137, wherein $X_b$ or $X_c$ is —$NR_6R_7$, $NR_6R_7$—($C_1$–$C_6$ alkyl)-, —C(O)$NR_6R_7$, —$SO_2NR_6R_7$, or halogen; wherein $R_6$ and $R_7$ are independently at each occurrence H, $C_1$–$C_6$ alkyl, $C_1$–$C_6$ alkoxy, $C_1$–$C_6$ alkoxy $C_1$–$C_6$ alkyl, $C_1$–$C_6$ alkoxycarbonyl, OH, $C_1$–$C_6$ hydroxyalkyl, —($C_1$–$C_4$) alkyl-$CO_2$-alkyl, pyridyl $C_1$–$C_6$ alkyl, $C_1$–$C_6$ alkanoyl, benzyl, phenyl $C_1$–$C_6$ alkoxy, or phenyl $C_1$–$C_6$ alkanoyl, wherein each of the above is unsubstituted or substituted with 1, 2, or 3 groups that are independently, halogen, $C_3$–$C_6$ cycloalkyl, $C_1$–$C_6$ alkoxy, piperidinyl $C_1$–$C_6$ alkyl, morpholinyl $C_1$–$C_6$ alkyl, piperazinyl $C_1$–$C_6$ alkyl, OH, SH, $NH_2$, NH(alkyl), N(alkyl)(alkyl), —O—$C_1$–$C_4$ alkanoyl, $C_1$–$C_4$ alkyl, $CF_3$, or $OCF_3$; or $R_6$, $R_7$, and the nitrogen to which they are attached form a morpholinyl, thiomorpholinyl, piperidinyl, pyrrolidinyl, or piperazinyl ring which is optionally substituted with 1 or 2 groups that are independently $C_1$–$C_4$ alkyl, $C_1$–$C_4$ alkoxy, hydroxy, hydroxy $C_1$–$C_4$ alkyl, or halogen.

Embodiment A139. Compounds according to embodiment A138, wherein $R_6$, $R_7$, and the nitrogen to which they are attached form a morpholinyl, thiomorpholinyl, piperidinyl, pyrrolidinyl, or piperazinyl ring which is optionally substituted with 1 or 2 groups that are independently $C_1$–$C_4$ alkyl, $C_1$–$C_4$ alkoxy, hydroxy, hydroxy $C_1$–$C_4$ alkyl, or halogen.

Embodiment A140. Compounds according to embodiment A138, wherein $R_6$, $R_7$, and the nitrogen to which they are attached form a piperazinyl ring which is optionally substituted with 1 or 2 groups that are independently $C_1$–$C_4$ alkyl, $C_1$–$C_4$ alkoxy, hydroxy, hydroxy $C_1$–$C_4$ alkyl, or halogen.

Embodiment A141. Compounds according to embodiment A138, wherein $R_6$ and $R_7$ are independently at each occurrence H, $C_1$–$C_6$ alkyl, $C_1$–$C_6$ alkoxy, $C_1$–$C_6$ alkoxy $C_1$–$C_6$ alkyl, $C_1$–$C_6$ alkoxycarbonyl, OH, $C_1$–$C_6$ hydroxyalkyl, —($C_1$–$C_4$) alkyl-$CO_2$-alkyl, pyridyl $C_1$–$C_6$ alkyl, $C_1$–$C_6$ alkanoyl, benzyl, phenyl $C_1$–$C_6$ alkoxy, or phenyl $C_1$–$C_6$ alkanoyl, wherein each of the above is unsubstituted or substituted with 1, 2, or 3 groups that are independently, halogen, $C_3$–$C_6$ cycloalkyl, $C_1$–$C_6$ alkoxy, piperidinyl $C_1$–$C_6$ alkyl, morpholinyl $C_1$–$C_6$ alkyl, piperazinyl $C_1$–$C_6$ alkyl, OH, $NH_2$, NH(alkyl), N(alkyl)(alkyl), —O—$C_1$–$C_4$ alkanoyl, $C_1$–$C_4$ alkyl, $CF_3$, or $OCF_3$.

Embodiment A142. Compounds according to embodiment A138, wherein $R_6$ and $R_7$ are independently at each occurrence H, $C_1$–$C_6$ alkyl, $C_1$–$C_6$ hydroxyalkyl, $C_1$–$C_6$ alkoxy, $C_1$–$C_6$ alkoxy $C_1$–$C_6$ alkyl, or $C_1$–$C_6$ alkanoyl, wherein each of the above is optionally substituted with 1, 2 or 3 groups that are independently OH, SH, halogen, or $C_3$–$C_6$ cycloalkyl.

Embodiment A143. Compounds according to embodiment A137, wherein $X_a$ and $X_e$ are independently fluoro, chloro, or methyl; and $X_a$ is hydrogen or halogen.

Embodiment A144. Compounds according to embodiment A137, wherein $X_a$ is halogen;

$X_e$ is $NH_2$, NH($C_1$–$C_6$ alkyl) or N($C_1$–$C_6$ alkyl)($C_1$–$C_6$ alkyl);

$X_b$ and $X_d$ are both hydrogen.

Embodiment A145. Compounds according to embodiment A144, wherein $X_c$ is —$NR_6R_7$, $NR_6R_7C_1$–$C_6$ alkyl, —$SO_2NR_6R_7$, or halogen; wherein $R_6$ and $R_7$ are independently at each occurrence H, $C_1$–$C_6$ alkyl, $C_1$–$C_6$ alkoxy, $C_1$–$C_6$ alkoxy $C_1$–$C_6$ alkyl, $C_1$–$C_6$ alkoxycarbonyl, OH, $C_1$–$C_6$ hydroxyalkyl, —($C_1$–$C_4$) alkyl -$CO_2$-alkyl, pyridyl $C_1$–$C_6$ alkyl, $C_1$–$C_6$ alkanoyl, benzyl, phenyl $C_1$–$C_6$ alkoxy, or phenyl $C_1$–$C_6$ alkanoyl, wherein each of the above is unsubstituted or substituted with 1, 2, or 3 groups that are independently, halogen, $C_3$–$C_6$ cycloalkyl, $C_1$–$C_6$ alkoxy, piperidinyl $C_1$–$C_6$ alkyl, morpholinyl $C_1$–$C_6$ alkyl, piperazinyl $C_1$–$C_6$ alkyl, OH, SH, $NH_2$, NH(alkyl), N(alkyl)(alkyl), —O—$C_1$–$C_4$ alkanoyl, $C_1$–$C_4$ alkyl, $CF_3$, or $OCF_3$; or $R_6$, $R_7$, and the nitrogen to which they are attached form a morpholinyl, thiomorpholinyl, piperidinyl, pyrrolidinyl, or piperazinyl ring which is optionally substituted with 1 or 2 groups that are independently $C_1$–$C_4$ alkyl, $C_1$–$C_4$ alkoxy, hydroxy, hydroxy $C_1$–$C_4$ alkyl, or halogen.

Embodiment A146. Compounds according to embodiment A145, wherein $X_c$ is fluoro, chloro, $NH_2$, NH($C_1$–$C_6$ alkyl), N($C_1$–$C_6$ alkyl)($C_1$–$C_6$ alkyl), —$SO_2NH_2$, —$SO_2NH$($C_1$–$C_6$ alkyl), —$SO_2N$($C_1$–$C_6$ alkyl)($C_1$–$C_6$ alkyl), or piperazinyl, wherein the piperazinyl group is optionally substituted with 1 or 2 groups that are independently $C_1$–$C_4$ alkyl, $C_1$–$C_4$ alkoxy, hydroxy, hydroxy $C_1$–$C_4$ alkyl, or halogen.

Embodiment A147. Compounds according to either embodiment A137 or A144, wherein $X_c$ is —C(O)$NR_6R_7$, —($C_1$–$C_6$ alkyl)-C(O)$NR_6R_7$, $NR_6R_7$, or $NR_6R_7$—($C_1$–$C_6$ alkyl)-; wherein $R_6$ and $R_7$ are independently at each occurrence H, $C_1$–$C_6$ alkyl, $C_1$–$C_6$ alkoxy, $C_1$–$C_6$ alkoxy $C_1$–$C_6$ alkyl, $C_1$–$C_6$ alkoxycarbonyl, OH, $C_1$–$C_6$ hydroxyalkyl, —($C_1$–$C_4$) alkyl-$CO_2$-alkyl, pyridyl $C_1$–$C_6$ alkyl, $C_1$–$C_6$ alkanoyl, benzyl, phenyl $C_1$–$C_6$ alkoxy, or phenyl $C_1$–$C_6$ alkanoyl, wherein each of the above is unsubstituted or substituted with 1, 2, or 3 groups that are independently, halogen, $C_3$–$C_6$ cycloalkyl, $C_1$–$C_6$ alkoxy, piperidinyl $C_1$–$C_6$ alkyl, morpholinyl $C_1$–$C_6$ alkyl, piperazinyl $C_1$–$C_6$ alkyl, OH, $NH_2$, NH(alkyl), N(alkyl)(alkyl), —O—$C_1$–$C_4$ alkanoyl, $C_1$–$C_4$ alkyl, $CF_3$, or $OCF_3$; or $R_6$, $R_7$, and the nitrogen to which they are attached form a morpholinyl, thiomorpholinyl, piperidinyl, pyrrolidinyl, or piperazinyl ring which is optionally substituted with 1 or 2 groups that are independently $C_1$–$C_4$ alkyl, $C_1$–$C_4$ alkoxy, hydroxy, hydroxy $C_1$–$C_4$ alkyl, or halogen.

Embodiment A148. Compounds according to embodiment A147, wherein $R_6$ is hydrogen; and $R_7$ is $C_1$–$C_6$ alkyl or $C_1$–$C_6$ alkanoyl, each of which is optionally substituted with 1, 2, or 3 groups that are independently NH$_2$, NH(C$_1$–C$_6$ alkyl), N(C$_1$–C$_6$ alkyl)(C$_1$–C$_6$ alkyl), OH, SH, cyclopropyl, or C$_1$–C$_4$ alkoxy.

Embodiment A148a. Compounds according to embodiment A148, wherein

R$_7$ is C$_1$–C$_6$ alkanoyl optionally substituted with 1, 2, or 3 groups that are independently OH, cyclopropyl, or NH$_2$.

Embodiment A149. Compounds according to embodiment A135, wherein

X$_a$ is hydrogen;

X$_b$, X$_c$, or X$_d$ is —C(O)NR$_6$R$_7$, —(C$_1$–C$_6$ alkyl)-C(O)NR$_6$R$_7$, NR$_6$R$_7$, NR$_6$R$_7$—(C$_1$–C$_6$ alkyl)- or —CO$_2$—(C$_1$–C$_6$)alkyl; wherein R$_6$ and R$_7$ are independently at each occurrence H, C$_1$–C$_6$ alkyl, C$_1$–C$_6$ alkoxy, C$_1$–C$_6$ alkoxy C$_1$–C$_6$ alkyl, C$_1$–C$_6$ alkoxycarbonyl, OH, C$_1$–C$_6$ hydroxyalkyl, —(C$_1$–C$_4$) alkyl-CO$_2$-alkyl, pyridyl C$_1$–C$_6$ alkyl, C$_1$–C$_6$ alkanoyl, benzyl, phenyl C$_1$–C$_6$ alkoxy, or phenyl C$_1$–C$_6$ alkanoyl, wherein each of the above is unsubstituted or substituted with 1, 2, or 3 groups that are independently, halogen, C$_3$–C$_6$ cycloalkyl, C$_1$–C$_6$ alkoxy, piperidinyl C$_1$–C$_6$ alkyl, morpholinyl C$_1$–C$_6$ alkyl, piperazinyl C$_1$–C$_6$ alkyl, OH, NH$_2$, NH(alkyl), N(alkyl)(alkyl), —O—C$_1$–C$_4$ alkanoyl, C$_1$–C$_4$ alkyl, CF$_3$, or OCF$_3$; or R$_6$, R$_7$, and the nitrogen to which they are attached form a morpholinyl, piperidinyl, pyrrolidinyl, or piperazinyl ring which is optionally substituted with 1 or 2 groups that are independently C$_1$–C$_4$ alkyl, C$_1$–C$_4$ alkoxy, hydroxy, hydroxy C$_1$–C$_4$ alkyl, or halogen; and X$_e$ is hydrogen, methyl, C$_1$–C$_2$ alkoxy, or halogen.

Embodiment A150. Compounds according to embodiment A149, wherein

X$_b$ is NR$_6$R$_7$, or NR$_6$R$_7$—(C$_1$–C$_6$ alkyl)-, —C(O)NR$_6$R$_7$ or —CO$_2$—(C$_1$–C$_6$)alkyl; wherein R$_6$ is hydrogen or C$_1$–C$_4$ alkyl;

R$_7$ is OH, C$_1$–C$_6$ alkyl or C$_1$–C$_6$ alkanoyl, wherein the alkyl and alkanoyl groups substituted with 1, 2, or 3 groups that are independently NH$_2$, NH(C$_1$–C$_6$ alkyl), N(C$_1$–C$_6$ alkyl)(C$_1$–C$_6$ alkyl), C$_3$–C$_6$ cycloalkyl, OH, or C$_1$–C$_4$ alkoxy.

Embodiment A151. Compounds according to embodiment A137, wherein

X$_a$ is halogen;

X$_b$ is NR$_6$R$_7$, NR$_6$R$_7$—(C$_1$–C$_6$ alkyl)-, —C(O)NR$_6$R$_7$, or —CO$_2$—(C$_1$–C$_6$)alkyl;

X$_c$ is NR$_6$R$_7$, NR$_6$R$_7$—(C$_1$–C$_6$ alkyl)-, —C(O)NR$_6$R$_7$, halogen, —CO$_2$—(C$_1$–C$_6$)alkyl, NH$_2$, NH(C$_1$–C$_6$ alkyl), N(C$_1$–C$_6$ alkyl)(C$_1$–C$_6$ alkyl), —SO$_2$NH$_2$, —SO$_2$NH(C$_1$–C$_6$ alkyl), —SO$_2$N(C$_1$–C$_6$ alkyl)(C$_1$–C$_6$ alkyl), or piperazinyl, wherein the piperazinyl group is optionally substituted with 1 or 2 groups that are independently C$_1$–C$_4$ alkyl, C$_1$–C$_4$ alkoxy, hydroxy, hydroxy C$_1$–C$_4$ alkyl, or halogen;

X$_d$ is hydrogen;

X$_e$ is H, methyl, NH$_2$, NH(C$_1$–C$_6$ alkyl) or N(C$_1$–C$_6$ alkyl)(C$_1$–C$_6$ alkyl).

Embodiment A152. Compounds according to embodiment A135, wherein

X$_1$, X$_2$, X$_a$, X$_b$, X$_c$, X$_d$, and X$_e$ are independently selected from H, OH, halogen, CF$_3$, alkyl, OCF$_3$, pyridyl, pyridazinyl, pyrimidyl, pyrazinyl, thienyl, furyl, pyrrolyl, piperidinyl, piperazinyl, or C$_3$–C$_7$ cycloalkyl, wherein each of the above is optionally substituted with —NR$_6$R$_7$, —C(O)NR$_6$R$_7$, NR$_6$R$_7$—(C$_1$–C$_6$ alkyl)-, C$_1$–C$_6$ alkyl, C$_1$–C$_6$ alkoxy, or halogen.

Embodiment A153. Compounds according to embodiment A152, wherein at least three of X$_1$, X$_2$, X$_a$, X$_b$, X$_c$, X$_d$, and X$_e$ are hydrogen.

Embodiment A154. A compound of the formula:

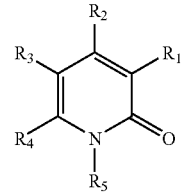

or a pharmaceutically acceptable salt thereof, wherein

R$_1$ is alkanoyl, halogen, arylalkanoyl, arylalkyl, alkoxyalkyl, hydroxyalkyl, or carboxaldehyde, wherein the aryl portion of arylalkyl, and arylalkanoyl is unsubstituted or substituted with 1, 2, 3, 4, or 5 groups that are independently halogen, C$_1$–C$_4$ alkyl, C$_1$–C$_4$ alkoxy, nitro, CN, haloalkyl, haloalkoxy or CO$_2$H;

the alkyl portion of the hydroxyalkyl, arylalkyl, alkanoyl, alkoxyalkyl and arylalkanoyl groups are unsubstituted or substituted with 1, 2, or 3 groups that are independently halogen, methoxy, ethoxy or spirocyclopropyl;

R$_2$ is arylalkoxy, aryloxy, phenyloxy(C$_1$–C$_6$)alkyl, OH, halogen, arylthioalkoxy, alkoxy, —OC(O)NH(CH$_2$)aryl, —OC(O)N(alkyl)(CH$_2$)$_n$aryl, alkyl, alkoxyalkoxy, dialkylamino, pyridyl, pyrimidyl, pyridazyl, pyrazolyl, imidazolyl, pyrrolyl, tetrahydroquinolinyl, tetrahydroisoquinolinyl, tetrazolyl, pyrazinyl, benzimidazolyl, triazinyl, tetrahydrofuryl, piperidinyl, hexahydropyrimidinyl, thiazolyl, thienyl, or CO$_2$H, wherein n is 0, 1, 2, 3, 4, 5 or 6;

the aryl portion of arylalkoxy, aryloxy, arylthioalkoxy, —OC(O)NH(CH$_2$)$_n$aryl, and —OC(O)N(alkyl)(CH$_2$)$_n$aryl or the heteroaryl and heterocycloalkyl groups is unsubstituted or substituted with 1, 2, 3, 4, or 5 groups that are independently halogen, —(C$_1$–C$_6$)alkyl-N(R)—CO$_2$R$_{30}$, haloalkyl, heteroaryl, heteroarylalkyl, NR$_6$R$_7$, NR$_6$R$_7$—(C$_1$–C$_6$ alkyl)-, —OC(O)NR$_6$R$_7$, wherein R$_6$ and R$_7$ are independently at each occurrence H, alkyl, alkoxy, alkanoyl, arylalkyl, arylalkoxy, or arylalkanoyl, wherein each of the above is unsubstituted or substituted with 1, 2, or 3 groups that are independently, halogen, OH, SH, C$_3$–C$_6$ cycloalkyl, alkoxy, alkyl, haloalkyl, or haloalkoxy; or R$_6$, R$_7$, and the nitrogen to which they are attached form a morpholinyl, thiomorpholinyl, thiomorpholinyl S-oxide, thiomorpholinyl S,S-dioxide, piperidinyl, or piperazinyl ring which is optionally substituted with 1 or 2 groups that are independently C$_1$–C$_4$ alkyl, alkoxycarbonyl, hydroxyl, hydroxyalkyl, or halogen;

R at each occurrence is independently H or C$_1$–C$_6$ alkyl;

R$_{30}$ is C$_1$–C$_6$ alkyl optionally substituted with 1 or 2 groups that are independently OH, SH, halogen, amino, monoalkylamino, dialkylamino or C$_3$–C$_6$ cycloalkyl;

R$_3$ is halogen, arylalkoxycarbonyl, aryloxycarbonyl, arylalkyl, —OC(O)NH(CH$_2$)aryl, arylalkoxy, —OC(O)N(alkyl)(CH$_2$)$_n$aryl, aryloxy, arylthio, thioalkoxy, arylthioalkoxy, alkenyl, NR$_6$R$_7$, NR$_6$R$_7$—(C$_1$–C$_6$ alkyl)-, or alkyl, wherein the aryl portion of arylalkoxycarbonyl, aryloxycarbonyl, arylalkyl, —OC(O)NH(CH$_2$)$_n$aryl, arylalkoxy, —OC(O)N(alkyl)(CH$_2$)$_n$aryl, and arylthioalkoxy, is unsubstituted or substituted with 1, 2, or 3 groups that are independently, halogen, alkoxy, alkyl, haloalkyl, or haloalkoxy, wherein n is 0, 1, 2, 3, 4, 5, or 6; or $R_4$ is H, alkyl substituted with one group selected from $CO_2H$, $-CO_2-(C_1-C_6)$alkyl, $-C(O)NRR$, $-N(R_{30})C(O)NRR$, $-N(R_{30}))C(O)-(C_1-C_6)$alkoxy, and $-NR_6R_7$, arylalkoxy, arylalkyl, hydroxyalkyl, haloalkyl, alkoxy, alkoxyalkyl, or alkoxyalkoxy, wherein the aryl portion of arylalkoxy, arylalkyl is unsubstituted or substituted with 1, 2, 3, 4, or 5 groups that are independently halogen, hydroxy, alkoxy, alkyl, nitro, haloalkyl, or haloalkoxy; and $R_5$ is arylalkyl, alkyl, aryl, alkoxy, heterocycloalkylalkyl, heteroarylalkyl, arylthioalkyl, heterocycloalkyl, or heteroaryl, wherein each of the above is unsubstituted or substituted with 1, 2, 3, 4, or 5 groups that are independently alkyl, halogen, alkoxy, arylalkoxy, thioalkoxy, alkoxycarbonyl, arylalkoxycarbonyl, $CO_2H$, $CN$, amidinooxime, $NR_6R_7$, $NR_6R_7-(C_1-C_6$ alkyl)-, $-C(O)NR_6R_7$, amidino, haloalkyl, or haloalkoxy.

Embodiment A160. Compounds according to embodiment A154 wherein $R_1$ is halogen, $(C_1-C_6)$alkanoyl, phenyl$(C_1-C_6)$alkanoyl, naphthyl$(C_1-C_6)$alkanoyl, naphthyl$(C_1-C_6)$alkyl, phenyl $(C_1-C_6)$alkyl, alkoxyalkyl, hydroxyalkyl, or carboxaldehyde, wherein the phenyl and naphthyl portions of the above are unsubstituted or substituted with 1, 2, 3, 4, or 5 groups that are independently halogen, $C_1-C_4$ alkyl, $C_1-C_4$ alkoxy, nitro, CN, $CF_3$, $OCF_3$ or $CO_2H$;

the alkyl portion of the above groups are unsubstituted or substituted with 1, 2, or 3 groups that are independently halogen, methoxy, or ethoxy.

$R_2$ is phenylalkoxy, aryloxy, phenyloxy$(C_1-C_6)$alkyl, OH, halogen, phenylthioalkoxy, alkoxy, alkyl, alkoxyalkoxy, $-OC(O)NH(CH_2)$phenyl, $-OC(O)N(alkyl)(CH_2)_n$phenyl, pyridyl, pyrimidyl, pyridazyl, pyrazolyl, or thienyl, wherein n is 0, 1, 2, 3, or 4, and the above groups are unsubstituted or substituted with 1, 2, 3, 4, or 5 groups that are independently halogen, $-(C_1-C_6)$alkyl-N(R)$-CO_2R_{30}$, halo$(C_1-C_4)$alkyl, or thienyl;

$R_3$ is halogen, phenylalkoxycarbonyl, phenyloxycarbonyl, phenyl$(C_1-C_6)$alkyl, phenylalkoxy, phenyloxy, phenylthio, thioalkoxy, arylthioalkoxy, $(C_2-C_6)$alkenyl, $NR_6R_7$, $NR_6R_7-(C_1-C_6$ alkyl)-, or alkyl, wherein the phenyl, naphthyl, and aryl portions of arylalkoxycarbonyl, aryloxycarbonyl, arylalkyl, $-OC(O)NH(CH_2)$aryl, arylthioalkoxy, arylalkoxy, and $-OC(O)N(alkyl)(CH_2)_n$aryl, are unsubstituted or substituted with 1, 2, or 3 groups that are independently, halogen, alkoxy, alkyl, $CF_3$, or $OCF_3$, wherein n is 0, 1, 2, 3, 4, 5, or 6; or $R_4$ is H, $(C_1-C_6)$alkyl substituted with one group that is $CO_2H$, $-CO_2-(C_1-C_6)$alkyl, $-C(O)NRR$, $-N(R_{30})C(O)NRR$, $-N(R_{30})C(O)-(C_1-C_6)$alkoxy, or $-NR_6R_7$, phenylalkoxy, phenyl$(C_1-C_6)$alkyl, hydroxyalkyl, haloalkyl, alkoxyalkyl, or alkoxyalkoxy, wherein the phenyl portion of the above groups are unsubstituted or substituted with 1, 2, 3, 4, or 5 groups that are independently halogen, hydroxy, alkoxy, alkyl, nitro, $CF_3$, or $OCF_3$.

$R_5$ is phenyl$(C_1-C_6)$alkyl, $(C_1-C_6)$alkyl, phenyl, naphthyl, pyridyl, $(C_1-C_6)$alkoxy, piperidinyl$(C_1-C_6)$alkyl, pyrrolyl$(C_1-C_6)$alkyl, imidazolidinyl$(C_1-C_6)$alkyl, pyrazolyl$(C_1-C_6)$alkyl, imidazolyl$(C_1-C_6)$alkyl, tetrahydropyridinyl$(C_1-C_6)$alkyl, thienyl$(C_1-C_6)$alkyl, phenylthio$(C_1-C_6)$alkyl, or pyridyl$(C_1-C_6)$alkyl, wherein each of the above is unsubstituted or substituted with 1, 2, or 3 groups that are independently $(C_1-C_4)$alkyl, fluoro, chloro, bromo, $(C_1-C_4)$alkoxy, phenyl$(C_1-C_4)$alkoxy, thio$(C_1-C_4)$alkoxy, $(C_1-C_4)$alkoxycarbonyl, phenyl $(C_1-C_4)$alkoxycarbonyl, $CO_2H$, CN, amidinooxime, $NR_6R_7$, $NR_6R_7-(C_1-C_6$ alkyl)-, $-C(O)NR_6R_7$, amidino, $CF_3$, $-CF_2CF_3$, $OCF_3$ or $OCF_2CF_3$.

Embodiment A161. Compounds according to embodiment A160 wherein $R_1$ is halogen, $(C_1-C_4)$alkanoyl, phenyl$(C_1-C_4)$alkanoyl, benzyl, phenethyl, phenpropyl, hydroxyalkyl, or carboxaldehyde, wherein the above phenyl groups are unsubstituted or substituted with 1, 2, or 3 groups that are independently halogen, $C_1-C_4$ alkyl, $C_1-C_4$ alkoxy, nitro, CN, $CF_3$, $OCF_3$ or $CO_2H$;

the alkyl portion of the above groups are unsubstituted or substituted with 1, 2, or 3 groups that are independently halogen, methoxy, or ethoxy;

$R_2$ is benzyloxy, phenethyloxy, phenpropyloxy, phenbutyloxy, phenyloxy, phenyloxy$(C_1-C_6)$alkyl, OH, halogen, phenylthioalkoxy, alkoxy, alkyl, alkoxyalkoxy, wherein n is 0, 1, 2, 3, or 4, and the above groups are unsubstituted or substituted with 1, 2, or 3, groups that are independently halogen, $-(C_1-C_6)$alkyl-N(R)$-CO_2R_{30}$, halo$(C_1-C_4)$alkyl, or thienyl;

$R_3$ is halogen, phenylalkoxycarbonyl, phenyloxycarbonyl, phenyl$(C_1-C_6)$alkyl, phenylalkoxy, phenyloxy, phenylthio, thioalkoxy, phenylthioalkoxy, $(C_2-C_6)$alkenyl, $NR_6R_7$, $NR_6R_7$ $C_1-C_6$ alkyl, or alkyl, wherein the above phenyl groups are unsubstituted or substituted with 1, 2, or 3 groups that are independently, halogen, alkoxy, $(C_1-C_4)$alkyl, $CF_3$, or $OCF_3$, $R_4$ is H, $(C_1-C_6)$alkyl substituted with one group that is $CO_2H$, $-CO_2-(C_1-C_6)$alkyl, $-C(O)NRR$, $-N(R_{30})C(O)NRR$, $-N(R_{30})C(O)-(C_1-C_6)$alkoxy, or $-NR_6R_7$, phenylalkoxy, benzyl, phenethyl, hydroxyalkyl, haloalkyl, alkoxyalkyl, or alkoxyalkoxy, wherein the phenyl portion of the above groups are unsubstituted or substituted with 1, 2, or 3 groups that are independently halogen, hydroxy, $(C_1-C_4)$alkoxy, $(C_1-C_4)$alkyl, nitro, $CF_3$, or $OCF_3$.

$R_5$ is benzyl, phenethyl, phenpropyl, phenbutyl, $(C_1-C_6)$ alkyl, phenyl, or pyridyl, wherein each of the above is unsubstituted or substituted with 1, 2, or 3 groups that are independently $(C_1-C_4)$alkyl, fluoro, chloro, bromo, $(C_1-C_4)$alkoxy, phenyl$(C_1-C_4)$alkoxy, thio$(C_1-C_4)$alkoxy, $(C_1-C_4)$alkoxycarbonyl, $CO_2H$, CN, amidinooxime, $NR_6R_7$, $NR_6R_7-(C_1-C_6$ alkyl)-, $-C(O)NR_6R_7$, amidino, $CF_3$, or $OCF_3$.

Embodiment A162. Compounds according to embodiment A161 wherein $R_1$ is bromo, phenyl$(C_1-C_4)$alkanoyl, benzyl, phenethyl, phenpropyl, hydroxyalkyl, or carboxaldehyde, wherein the above phenyl groups are unsubstituted or substituted with 1, 2, or 3 groups that are independently halogen, $C_1-C_4$ alkyl, $C_1-C_4$ alkoxy, nitro, CN, $CF_3$, $OCF_3$ or $CO_2H$;

$R_2$ is benzyloxy, phenethyloxy, phenpropyloxy, phenbutyloxy, phenyloxy, phenyloxy($C_1$–$C_6$)alkyl, OH, halogen, or phenylthioalkoxy, wherein n is 0, 1, 2, 3, or 4, and the above groups are unsubstituted or substituted with 1, 2, or 3, groups that are independently halogen, —($C_1$–$C_6$)alkyl-N(R)—$CO_2R_{30}$, halo ($C_1$–$C_4$)alkyl, or thienyl;

$R_3$ is bromo, phenylalkoxycarbonyl, phenyloxycarbonyl, phenyl($C_1$–$C_6$)alkyl, phenylalkoxy, phenyloxy, phenylthio, thioalkoxy, phenylthioalkoxy, ($C_2$–$C_6$) alkenyl, $NR_6R_7$, $NR_6R_7$ $C_1$–$C_6$ alkyl, or alkyl, wherein the above phenyl groups are unsubstituted or substituted with 1, 2, or 3 groups that are independently, halogen, alkoxy, ($C_1$–$C_4$)alkyl, $CF_3$, or $OCF_3$, $R_4$ is H, ($C_1$–$C_6$)alkyl substituted with one group that is $CO_2H$, —$CO_2$—($C_1$–$C_6$)alkyl, —C(O)NRR, —N($R_{30}$)C(O)NRR, —N($R_{30}$)C(O)—($C_1$–$C_6$)alkoxy, or —$NR_6R_7$, phenylalkoxy, benzyl, or phenethyl, wherein the phenyl portion of the above groups are unsubstituted or substituted with 1, 2, or 3 groups that are independently halogen, hydroxy, ($C_1$–$C_4$)alkoxy, ($C_1$–$C_4$)alkyl, nitro, $CF_3$, or $OCF_3$.

$R_5$ is benzyl, phenethyl, phenpropyl, ($C_1$–$C_6$)alkyl, phenyl, or pyridyl, wherein each of the above is unsubstituted or substituted with 1, 2, or 3 groups that are independently ($C_1$–$C_4$)alkyl, fluoro, chloro, bromo, ($C_1$–$C_4$)alkoxy, $CO_2H$, CN, amidinooxime, amidino, $CF_3$, $OCF_3$, $NR_6R_7$, $NR_6R_7$—($C_1$–$C_6$ alkyl)-, or —C(O)$NR_6R_7$; wherein $R_6$ and $R_7$ are independently hydrogen, OH, $C_1$–$C_4$ alkoxy, $C_1$–$C_6$ alkanoyl, or $C_1$–$C_6$ alkyl, wherein each of the above is optionally substituted with 1 or 2 groups that are independently OH, $NH_2$, $C_3$–$C_6$ cycloalkyl, or halogen; or $R_6$, $R_7$, and the nitrogen to which they are attached form a morpholinyl, piperidinyl, pyrrolidinyl, or piperazinyl ring which is optionally substituted with 1 or 2 groups that are independently $C_1$–$C_4$ alkyl, $C_1$–$C_4$ alkoxy, hydroxy, hydroxy $C_1$–$C_4$ alkyl, or halogen.

Embodiment A163. Compounds of the formula

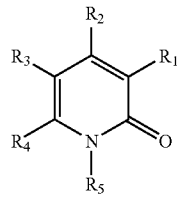

or pharmaceutically acceptable salts thereof, wherein $R_1$ is H, halogen, alkyl, carboxaldehyde, hydroxyalkyl, arylalkoxy, arylalkyl, CN, alkanoyl, alkoxy, alkoxyalkyl, or arylalkanoyl, wherein the aryl portion of arylalkoxy, arylalkyl, and arylalkanoyl is unsubstituted or substituted with 1, 2, 3, 4, or 5 groups that are independently halogen, $C_1$–$C_4$ alkyl, $C_1$–$C_4$ alkoxy, nitro, CN, haloalkyl, haloalkoxy or $CO_2H$;

wherein the alkyl portion of the alkyl, hydroxyalkyl, arylalkoxy, arylalkyl, alkanoyl, alkoxy, alkoxyalkyl and arylalkanoyl groups is unsubstituted or substituted with 1, 2, or 3 groups that are independently halogen, methoxy, ethoxy or spirocyclopropyl;

$R_2$ is H, arylthio, —OC(O)NH($CH_2$)$_n$aryl, arylalkyl, —OC(O)N(alkyl)($CH_2$)$_n$aryl, or arylthioalkoxy, wherein n is 1, 2, 3, 4, or 5; wherein the aryl groups are optionally substituted with 1, 2, 3, 4, or 5 groups that are independently halogen, —($C_1$–$C_6$)alkyl-N(R)—$CO_2R_{30}$, $C_1$–$C_4$ alkoxy, $C_1$–$C_4$ alkyl, $CF_3$, or $OCF_3$;

R at each occurrence is independently H or $C_1$–$C_6$ alkyl;

$R_{30}$ is $C_1$–$C_6$ alkyl optionally substituted with 1 or 2 groups that are independently OH, SH, halogen, amino, monoalkylamino, dialkylamino or $C_3$–$C_6$ cycloalkyl;

$R_3$ is halogen, alkoxycarbonyl, arylalkoxycarbonyl, aryloxycarbonyl, arylalkyl, —OC(O)NH($CH_2$)$_n$aryl, arylalkoxy, —OC(O)N(alkyl)($CH_2$)$_n$aryl, aryloxy, arylthio, thioalkoxy, arylthioalkoxy, alkenyl, $NR_6R_7$$C_1$–$C_6$ alkyl, $NR_6R_7$ or alkyl, wherein the aryl portion of arylalkoxycarbonyl, aryloxycarbonyl, arylalkyl, —OC(O)NH($CH_2$)aryl, arylalkoxy, —OC(O)N(alkyl)($CH_2$)$_n$aryl, and arylthioalkoxy, is unsubstituted or substituted with 1, 2, or 3 groups that are independently, halogen, alkoxy, alkyl, haloalkyl, or haloalkoxy, wherein n is 0, 1, 2, 3, 4, 5, or 6; or $R_4$ is H, alkyl substituted with one group that is $CO_2H$, —$CO_2$—($C_1$–$C_6$)alkyl, —C(O)NRR, —N($R_{30}$)C(O)NRR, —N($R_{30}$)C(O)—($C_1$–$C_6$)alkoxy, or —$NR_6R_7$, arylalkoxy, arylalkyl, hydroxyalkyl, haloalkyl, alkoxy, alkoxyalkyl, or alkoxyalkoxy, wherein the aryl portion of arylalkoxy, arylalkyl is unsubstituted or substituted with 1, 2, 3, 4, or 5 groups that are independently halogen, hydroxy, alkoxy, alkyl, nitro, haloalkyl, or haloalkoxy; and $R_5$ is arylalkyl, alkyl, aryl, alkoxy, heterocycloalkylalkyl, heteroarylalkyl, arylthioalkyl, heterocycloalkyl, or heteroaryl, wherein each of the above is unsubstituted or substituted with 1, 2, 3, 4, or 5 groups that are independently alkyl, halogen, alkoxy, arylalkoxy, thioalkoxy, alkoxycarbonyl, arylalkoxycarbonyl, $CO_2H$, CN, amidinooxime, $NR_6R_7$, $NR_6R_7$—($C_1$–$C_6$ alkyl)-, —C(O)$NR_6R_7$, amidino, haloalkyl, or haloalkoxy; wherein $R_6$ and $R_7$ are independently at each occurrence H, $C_1$–$C_6$ alkyl, $C_1$–$C_6$ alkoxy, $C_1$–$C_6$ alkoxy $C_1$–$C_6$ alkyl, $C_1$–$C_6$ alkoxycarbonyl, OH, $C_1$–$C_6$ hydroxyalkyl, —($C_1$–$C_4$) alkyl-$CO_2$-alkyl, pyridyl $C_1$–$C_6$ alkyl, $C_1$–$C_6$ alkanoyl, benzyl, phenyl $C_1$–$C_6$ alkoxy, or phenyl $C_1$–$C_6$ alkanoyl, wherein each of the above is unsubstituted or substituted with 1, 2, or 3 groups that are independently, halogen, $C_3$–$C_6$ cycloalkyl, $C_1$–$C_6$ alkoxy, piperidinyl $C_1$–$C_6$ alkyl, morpholinyl $C_1$–$C_6$ alkyl, piperazinyl $C_1$–$C_6$ alkyl, OH, SH, $NH_2$, NH(alkyl), N(alkyl)(alkyl), —O—$C_1$–$C_4$ alkanoyl, $C_1$–$C_4$ alkyl, $CF_3$, or $OCF_3$; or $R_6$, $R_7$, and the nitrogen to which they are attached form a morpholinyl, thiomorpholinyl, piperidinyl, pyrrolidinyl, or piperazinyl ring which is optionally substituted with 1 or 2 groups that are independently $C_1$–$C_4$ alkyl, $C_1$–$C_4$ alkoxy, hydroxy, hydroxy $C_1$–$C_4$ alkyl, or halogen.

Embodiment A168. Compounds according to embodiment A163 wherein $R_5$ is benzyl, phenethyl, phenpropyl, phenbutyl, alkyl, phenyl, alkoxy, pyridyl($C_1$–$C_6$)alkyl, phenyl($C_1$–$C_6$) thioalkyl, pyrrolyl, pyrrolyl($C_1$–$C_6$)alkyl, or pyridyl, wherein each of the above is unsubstituted or substituted with 1, 2, or 3 groups that are independently ($C_1$–$C_6$) alkyl, halogen, ($C_1$–$C_6$)alkoxy, phenyl($C_1$–$C_6$)alkoxy, ($C_1$–$C_6$)thioalkoxy, alkoxycarbonyl, $CO_2H$, CN, amidinooxime, amidino, $CF_3$, or $OCF_3$.

Embodiment A169. Compounds according to embodiment A163
wherein
$R_1$ is H, Cl, Br, $(C_1–C_6)$alkyl, carboxaldehyde, hydroxy $(C_1–C_6)$alkyl,
  wherein the alkyl portion of above is unsubstituted or substituted with 1, 2, or 3 groups that are independently halogen, methoxy, or ethoxy
$R_2$ is H, phenylthio, —OC(O)NH(CH$_2$)aryl, phenylalkyl, —OC(O)N(alkyl)(CH$_2$)aryl, or phenylthio$(C_1–C_6)$ alkoxy,
  wherein n is 1, 2, 3, or 4;
  wherein the aryl groups are optionally substituted with 1, 2, 3, 4, or 5 groups that are independently halogen, —$(C_1–C_6)$alkyl-N(R)—$CO_2R_{30}$, $C_1–C_4$ alkoxy, $C_1–C_4$ alkyl, $CF_3$, or $OCF_3$;
$R_3$ is bromo, alkoxycarbonyl, phenylalkoxycarbonyl, phenyloxycarbonyl, phenylalkyl, phenylalkoxy, phenyloxy, phenylthio, thioalkoxy, phenylthioalkoxy, alkenyl, $NR_6R_7$ or alkyl, wherein
  the phenyl portion of the above is unsubstituted or substituted with 1, 2, or 3 groups that are independently, halogen, $(C_1–C_4)$alkoxy, $(C_1–C_4)$alkyl, halo$(C_1–C_4)$ alkyl, or halo$(C_1–C_4)$alkoxy,
  wherein n is 0, 1, 2, 3, or 4;
$R_4$ is H, alkyl substituted with one group that is $CO_2H$, —$CO_2$—$(C_1–C_6)$alkyl, —C(O)NRR, —N(R$_{30}$)C(O)NRR, —N(R$_{30}$)C(O)—$(C_1–C_6)$alkoxy, or —$NR_6R_7$, phenylalkoxy, phenylalkyl, hydroxyalkyl, haloalkyl, alkoxy, alkoxyalkyl, or wherein
  the phenyl portion of phenylalkoxy, phenylalkyl is unsubstituted or substituted with 1, 2, or 3 groups that are independently halogen, hydroxy, alkoxy, alkyl, nitro, haloalkyl, or haloalkoxy
$R_5$ is benzyl, phenethyl, phenpropyl, phenbutyl, alkyl, phenyl, phenyl$(C_1–C_6)$thioalkyl, pyrrolyl, or pyridyl, wherein each of the above is unsubstituted or substituted with 1, 2, or 3 groups that are independently $(C_1–C_6)$ alkyl, halogen, $(C_1–C_6)$alkoxy, benzyloxy, $(C_1–C_6)$ thioalkoxy, alkoxycarbonyl, $CO_2H$, CN, amidinooxime, amidino, $CF_3$, or $OCF_3$;
  $R_6$ and $R_7$ are independently hydrogen, OH, $C_1–C_4$ alkoxy, $C_1–C_6$ alkanoyl, or $C_1–C_6$ alkyl, wherein each of the above is optionally substituted with 1 or 2 groups that are independently OH, $NH_2$, $C_3–C_6$ cycloalkyl, or halogen; or
  $R_6$, $R_7$, and the nitrogen to which they are attached form a morpholinyl, piperidinyl, pyrrolidinyl, or piperazinyl ring which is optionally substituted with 1 or 2 groups that are independently $C_1–C_4$ alkyl, $C_1–C_4$ alkoxy, hydroxy, hydroxy $C_1–C_4$ alkyl, or halogen.
Embodiment A170. Compounds according to embodiment 1

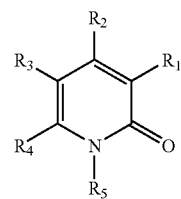

or a pharmaceutically acceptable salt thereof, wherein
$R_1$ is H, halogen, alkyl, carboxaldehyde, hydroxyalkyl, arylalkoxy, arylalkyl, CN, alkanoyl, alkoxy, alkoxyalkyl, or arylalkanoyl,
  wherein the aryl portion of arylalkoxy, arylalkyl, and arylalkanoyl is unsubstituted or substituted with 1, 2, 3, 4, or 5 groups that are independently halogen, $C_1–C_4$ alkyl, $C_1–C_4$ alkoxy, nitro, CN, haloalkyl, haloalkoxy or $CO_2H$;
  wherein the alkyl portion of the alkyl, hydroxyalkyl, arylalkoxy, arylalkyl, alkanoyl, alkoxy, alkoxyalkyl and arylalkanoyl groups is unsubstituted or substituted with 1, 2, or 3 groups that are independently halogen, methoxy, ethoxy or spirocyclopropyl;
$R_2$ is arylalkoxy, aryloxy, aryloxyalkyl, OH, halogen, arylthioalkoxy, alkoxy, —OC(O)NH(CH$_2$)$_n$aryl, —OC(O)N(alkyl)(CH$_2$)$_n$aryl, alkyl, alkoxyalkoxy, dialkylamino, or $CO_2H$, wherein
  n is 0, 1, 2, 3, 4, 5 or 6;
  the aryl portion of arylalkoxy, aryloxy, arylthioalkoxy, —OC(O)NH(CH$_2$)aryl, and —OC(O)N(alkyl)(CH$_2$)$_n$aryl or the heteroaryl and heterocycloalkyl groups is unsubstituted or substituted with 1, 2, 3, 4, or 5 groups that are independently halogen, —$(C_1–C_6)$alkyl-N(R)—$CO_2R_{30}$, haloalkyl, heteroaryl, heteroarylalkyl, $NR_6R_7$, $NR_6R_7$—$(C_1–C_6$ alkyl)-, —OC(O)$NR_6R_7$, wherein
  $R_6$ and $R_7$ are independently at each occurrence H, $C_1–C_6$ alkyl, $C_1–C_6$ alkoxy, $C_1–C_6$ alkoxy $C_1–C_6$ alkyl, $C_1–C_6$ alkoxycarbonyl, OH, $C_1–C_6$ hydroxyalkyl, —$(C_1–C_4)$ alkyl-$CO_2$-alkyl, pyridyl $C_1–C_6$ alkyl, $C_1–C_6$ alkanoyl, benzyl, phenyl $C_1–C_6$ alkoxy, or phenyl $C_1–C_6$ alkanoyl, wherein each of the above is unsubstituted or substituted with 1, 2, or 3 groups that are independently, halogen, $C_3–C_6$ cycloalkyl, $C_1–C_6$ alkoxy, piperidinyl $C_1–C_6$ alkyl, morpholinyl $C_1–C_6$ alkyl, piperazinyl $C_1–C_6$ alkyl, OH, SH, $NH_2$, NH(alkyl), N(alkyl)(alkyl), —O—$C_1–C_4$ alkanoyl, $C_1–C_4$ alkyl, $CF_3$, or $OCF_3$; or
  $R_6$, $R_7$, and the nitrogen to which they are attached form a morpholinyl, thiomorpholinyl, piperidinyl, pyrrolidinyl, or piperazinyl ring which is optionally substituted with 1 or 2 groups that are independently $C_1–C_4$ alkyl, $C_1–C_4$ alkoxy, hydroxy, hydroxy $C_1–C_4$ alkyl, or halogen;
R at each occurrence is independently H or $C_1–C_6$ alkyl;
$R_{30}$ is $C_1–C_6$ alkyl optionally substituted with 1 or 2 groups that are independently OH, SH, halogen, amino, monoalkylamino, dialkylamino or $C_3–C_6$ cycloalkyl;
$R_3$ is halogen, alkoxycarbonyl, arylalkoxycarbonyl, aryloxycarbonyl, arylalkyl, —OC(O)NH(CH$_2$)aryl, arylalkoxy, —OC(O)N(alkyl)(CH$_2$)$_n$aryl, aryloxy, arylthio, thioalkoxy, arylthioalkoxy, alkenyl, $NR_6R_7C_1–C_6$ alkyl, $NR_6R_7$ or alkyl, wherein
  the aryl portion of arylalkoxycarbonyl, aryloxycarbonyl, arylalkyl, —OC(O)NH(CH$_2$)$_n$aryl, arylalkoxy, —OC(O)N(alkyl)(CH$_2$)$_n$aryl, and arylthioalkoxy, is unsubstituted or substituted with 1, 2, or 3 groups that are independently, halogen, alkoxy, alkyl, haloalkyl, or haloalkoxy,
  wherein n is 0, 1, 2, 3, 4, 5, or 6; or
$R_4$ is H, alkyl substituted with one group that is $CO_2H$, —$CO_2$—$(C_1–C_6)$alkyl, —C(O)NRR, —N(R$_{30}$)C(O)NRR, —N(R$_{30}$)C(O)—$(C_1–C_6)$alkoxy, or —$NR_6R_7$, arylalkoxy, arylalkyl, hydroxyalkyl, haloalkyl, alkoxy, alkoxyalkyl, or alkoxyalkoxy, wherein
  the aryl portion of arylalkoxy, arylalkyl is unsubstituted or substituted with 1, 2, 3, 4, or 5 groups that are independently halogen, hydroxy, alkoxy, alkyl, nitro, haloalkyl, or haloalkoxy; and $R_5$ is aryl, heterocycloalkylalkyl, heteroarylalkyl, arylthioalkyl, heterocycloalkyl, or heteroaryl, wherein each of the above is unsubstituted or substituted with 1, 2, 3, 4, or 5 groups that are independently alkyl, halogen, alkoxy, arylalkoxy, thioalkoxy, alkoxycarbonyl, arylalkoxycarbonyl, $CO_2H$, CN, amidinooxime, $NR_6R_7$, $NR_6R_7$—($C_1$–$C_6$ alkyl)-, —C(O)$NR_6R_7$, amidino, haloalkyl, or haloalkoxy.

Embodiment A173. Compounds according to embodiment A170 wherein $R_1$ is H, halogen, alkyl, carboxaldehyde, hydroxyalkyl, benzyloxy, phenethyloxy, phenpropyloxy, benzyl, phenethyl, phenpropyl, CN, alkanoyl, alkoxy, or phenylC(O)—, phenylCH$_2$C(O)—, or phenylCH$_2$CH$_2$C(O),
  wherein the above phenyl groups are unsubstituted or substituted with 1, 2, or 3 groups that are independently halogen, $C_1$–$C_4$ alkyl, $C_1$–$C_4$ alkoxy, nitro, CN, $CF_3$, $OCF_3$ or $CO_2H$;
  wherein the above alkyl groups are unsubstituted or substituted with 1, 2, or 3 groups that are independently halogen, methoxy, or ethoxy;

$R_2$ is benzyloxy, phenethyloxy, phenpropyloxy, phenyloxy, phenyloxy($C_1$–$C_6$)alkyl, OH, halogen, phenylthioalkoxy, alkyl, alkoxy, —OC(O)NH(CH$_2$)$_n$phenyl, OC(O)N(alkyl)(CH$_2$)$_n$phenyl, dialkylamino, or $CO_2H$, wherein
  n is 0, 1, 2, 3, or 4;
  the above aryl groups are unsubstituted or substituted with 1, 2, 3, 4, or 5 groups that are independently halogen, —($C_1$–$C_6$)alkyl-N(R)—$CO_2R_{30}$, $CF_3$, pyridyl, thienyl, $NR_6R_7$ or $NR_6R_7$—($C_1$–$C_6$ alkyl)-, wherein
  $R_6$ and $R_7$ are independently at each occurrence H, alkyl, alkanoyl, benzyl, or phenylC(O)—, wherein the phenyl portion of the above is unsubstituted or substituted with 1, 2, or 3 groups that are independently, halogen, OH, $C_3$–$C_6$ cycloalkyl, alkoxy, alkyl, $CF_3$, or $OCF_3$;

$R_3$ is halogen, alkoxycarbonyl, phenylalkoxycarbonyl, phenyloxycarbonyl, phenylalkyl, —OC(O)NH(CH$_2$)$_n$phenyl, phenylalkoxy, —OC(O)N(alkyl)(CH$_2$)$_n$phenyl, phenyloxy, phenylthio, thioalkoxy, phenylthioalkoxy, alkenyl, $NR_6R_7$ or alkyl, wherein
  the phenyl portion of the above is unsubstituted or substituted with 1, 2, or 3 groups that are independently, halogen, alkoxy, alkyl, haloalkyl, or haloalkoxy,
  wherein n is 0, 1, 2, 3, or 4;

$R_4$ is H, alkyl substituted with one group that is $CO_2H$, —$CO_2$—($C_1$–$C_6$)alkyl, —C(O)NRR, —N($R_{30}$)C(O)NRR, —N($R_{30}$)C(O)—($C_1$–$C_6$)alkoxy, or —$NR_6R_7$, phenylalkoxy, phenylalkyl, hydroxyalkyl, haloalkyl, alkoxy, alkoxyalkyl, or alkoxyalkoxy, wherein
  the phenyl portion of the above is unsubstituted or substituted with 1, 2, or 3 groups that are independently halogen, hydroxy, alkoxy, alkyl, nitro, haloalkyl, or haloalkoxy; and $R_5$ is phenyl, naphthyl, pyrrolylalkyl, piperidinylalkyl pyridinylalkyl, pyrimidinylalkyl, phenylthioalkyl, pyrrolyl, piperidinyl, pyridyl, or thienylalkyl, wherein each of the above is unsubstituted or substituted with 1, 2, or 3 groups that are independently alkyl, halogen, alkoxy, phenylalkoxy, thioalkoxy, alkoxycarbonyl, phenylalkoxycarbonyl, $CO_2H$, CN, amidinooxime, $NR_6R_7$, $NR_6R_7$—($C_1$–$C_6$ alkyl)-, —C(O)$NR_6R_7$, amidino, haloalkyl, or haloalkoxy.

Embodiment A174. Compounds according to embodiment A173 wherein $R_1$ is H, halogen, alkyl, carboxaldehyde, hydroxyalkyl, benzyloxy, phenethyloxy, benzyl, phenethyl, CN, ($C_1$–$C_6$)alkanoyl, alkoxy, or phenylC(O)—, or phenylCH$_2$C(O)—,
  wherein the above phenyl groups are unsubstituted or substituted with 1, 2, or 3 groups that are independently halogen, $C_1$–$C_4$ alkyl, $C_1$–$C_4$ alkoxy, nitro, CN, $CF_3$, $OCF_3$ or $CO_2H$;

$R_2$ is benzyloxy, phenethyloxy, phenpropyloxy, phenyloxy, phenyloxy($C_1$–$C_6$)alkyl, halogen, phenyl($C_1$–$C_4$)thioalkoxy, —OC(O)NH(CH$_2$)$_n$phenyl, —OC(O)N(alkyl)(CH$_2$)$_n$phenyl, or dialkylamino, wherein
  n is 0, 1, 2, 3, or 4;
  the above phenyl groups are unsubstituted or substituted with 1, 2, or 3 groups that are independently halogen, $CF_3$, $NR_6R_7$, or $NR_6R_7$—($C_1$–$C_6$ alkyl)-, wherein
  $R_6$ and $R_7$ are independently at each occurrence H, ($C_1$–$C_6$)alkyl, acetyl, benzyl, or phenylC(O)—, wherein the phenyl portion of the above is unsubstituted or substituted with 1, 2, or 3 groups that are independently, halogen, OH, cyclopropyl, alkoxy, alkyl, $CF_3$, or $OCF_3$;

$R_3$ is halogen, alkoxycarbonyl, phenylalkoxycarbonyl, phenyloxycarbonyl, phenylalkyl, phenylalkoxy, phenyloxy, phenylthio, thioalkoxy, phenylthioalkoxy, alkenyl, $NR_6R_7$ or alkyl, wherein
  the phenyl portion of the above is unsubstituted or substituted with 1, 2, or 3 groups that are independently, halogen, alkoxy, alkyl, haloalkyl, or haloalkoxy,
  wherein n is 0, 1, 2, 3, or 4;

$R_4$ is H, alkyl substituted with one group that is $CO_2H$, —$CO_2$—($C_1$–$C_6$)alkyl, —C(O)NRR, —N($R_{30}$)C(O)NRR, —N($R_{30}$)C(O)—($C_1$–$C_6$)alkoxy, or —$NR_6R_7$, phenylalkoxy, phenylalkyl, hydroxyalkyl, haloalkyl, alkoxy, alkoxyalkyl, or alkoxyalkoxy, wherein
  the phenyl portion of the above is unsubstituted or substituted with 1, 2, or 3 groups that are independently halogen, hydroxy, alkoxy, alkyl, nitro, haloalkyl, or haloalkoxy; and $R_5$ is phenyl, phenyl($C_1$–$C_4$)thioalkyl, pyridyl, or thienyl ($C_1$–$C_4$)alkyl, wherein each of the above is unsubstituted or substituted with 1, 2, or 3 groups that are independently ($C_1$–$C_4$)alkyl, fluoro, chloro, bromo, ($C_1$–$C_4$)alkoxy, CN, amidinooxime, amidino, $CF_3$, or $OCF_3$.

Embodiment A175. Compounds according to embodiment A174 wherein $R_5$ is substituted with at least one group selected from fluoro, chloro, bromo, and methyl.

In another aspect, the invention provides pharmaceutical compositions comprising at least one pharmaceutically acceptable carrier, solvent, adjuvant or excipient and a compound of formula I, embodiment A66, or embodiment A154.

The invention further provides pharmaceutical compositions comprising at least one pharmaceutically acceptable carrier, solvent, adjuvant or excipient and compounds according to any of the preceding embodiments.

As noted above, the invention encompasses methods of treating a TNF mediated disorder, a p38 kinase mediated disorder, inflammation and/or arthritis in a subject, the method comprising treating a subject having or susceptible to such disorder or condition with a therapeutically-effective amount of a compound of formula I or embodiment A1.

More specifically, the invention provides methods for treating or preventing inflammation; arthritis, rheumatoid arthritis, spondylarthropathies, gouty arthritis, osteoarthritis, systemic lupus erthematosus, juvenile arthritis, and other arthritic conditions; neuroinflammation; allergy, Th2 mediated diseases; pain, neuropathic pain; fever; pulmonary disorders, lung inflammation, adult respiratory distress syndrome, pulmonary sarcoisosis, asthma, silicosis, chronic pulmonary inflammatory disease, and chronic obstructive pulmonary disease (COPD); cardiovascular disease, arteriosclerosis, myocardial infarction (including post-myocardial infarction indications), thrombosis, congestive heart failure, cardiac reperfusion injury, as well as complications associated with hypertension and/or heart failure such as vascular organ damage, restenosis; cardiomyopathy; stroke including ischemic and hemorrhagic stroke; reperfusion injury; renal reperfusion injury; ischemia including stroke and brain ischemia, and ischemia resulting from cardiac/coronary bypass; neurotrauma and brain trauma including closed head injury; brain edema; neurodegenerative disorders; liver disease and nephritis; gastrointestinal conditions, inflammatory bowel disease, Crohn's disease, gastritis, irritable bowel syndrome, ulcerative colitis; ulcerative diseases, gastric ulcers; ophthalmic diseases, retinitis, retinopathies, uveitis, ocular photophobia, acute injury to the eye tissue and ocular traumas such as post-traumatic glaucoma, traumatic optic neuropathy, and central retinal artery occlusion (CRAO); periodontal disease; ophthalmological conditions, retinitis, retinopathies (including diabetic retinopathy), uveitis, ocular photophobia, nonglaucomatous optic nerve atrophy, and age related macular degeneration (ARMD)(including ARMD-atrophic form), corneal graft rejection, ocular neovascularization, retinal neovascularization, neovascularization following injury or infection, retrolental fibroplasias, neovascular glaucoma; glaucoma including primary open angle glaucoma (POAG), juvenile onset primary open-angle glaucoma, angle-closure glaucoma, pseudoexfoliative glaucoma, anterior ischemic optic neuropathy (AION), ocular hypertension, Reiger's syndrome, normal tension glaucoma, neovascular glaucoma, ocular inflammation and corticosteroid-induced glaucoma; diabetes; diabetic nephropathy; skin-related conditions, psoriasis, eczema, burns, dermatitis, keloid formation, scar tissue formation, angiogenic disorders; viral and bacterial infections, sepsis, septic shock, gram negative sepsis, malaria, meningitis, HIV infection, opportunistic infections, cachexia secondary to infection or malignancy, cachexia secondary to acquired immune deficiency syndrome (AIDS), AIDS, ARC (AIDS related complex), pneumonia, herpes virus; myalgias due to infection; influenza; endotoxic shock; toxic shock syndrome; autoimmune disease, graft vs. host reaction and allograft rejections; treatment of bone resorption diseases, osteoporosis; multiple sclerosis; disorders of the female reproductive system, endometriosis; hemaginomas, infantile hemagionmas, angiofibroma of the nasopharynx, avascular necrosis of bone; benign and malignant tumors/neoplasia, cancer, colorectal cancer, brain cancer, bone cancer, epithelial call-derived neoplasia (epithelial carcinoma), basal cell carcinoma, adenocarcinoma, gastrointestinal cancer, lip cancer, mouth cancer, esophageal cancer, small bowel cancer, stomach cancer, colon cancer, liver cancer, bladder cancer, pancreas cancer, ovarian cancer, cervical cancer, lung cancer, breast cancer, skin cancer, squamus cell and/or basal cell cancers, prostate cancer, renal cell carcinoma, and other known cancers that affect epithelial cells throughout the body; leukemia; lymphoma; systemic lupus erthrematosis (SLE); angiogenesis including neoplasia; metastasis; central nervous system disorders, central nervous system disorders having an inflammatory or apoptotic component, Alzheimer's disease, Parkinson's disease, Huntington's disease, amyotrophic lateral sclerosis, spinal cord injury, and peripheral neuropathy; Canine B-Cell Lymphoma. Compounds of the invention are also useful for preventing the production or expression of cyclooxygenase-2, or cyclooxygenase-2 activity.

In this aspect, the invention encompasses methods of treating a p38 kinase or TNF-alpha mediated disorder comprising administering to a patient in need thereof a therapeutically effective amount of Compounds according to embodiment 1 and at least one pharmaceutically acceptable carrier, adjuvant, solvent or excipient.

Representative compounds of the invention are:

1-benzyl-4-(benzyloxy)-3-bromopyridin-2(1H)-one;

3-bromo-1-(4-fluorobenzyl)-4-[(4-fluorobenzyl)oxy] pyridin-2 (1H)-one;

3-bromo-4-[(2,4-difluorobenzyl)oxy]-1-(2,6-dimethylphenyl)-6-methylpyridin-2(1H)-one;

4-(benzyloxy)-3-bromo-1-(4-fluorobenzyl)pyridin-2 (1H)-one;

3-bromo-4-[(2,4-difluorobenzyl)oxy]-1-(3-fluorobenzyl) pyridin-2 (1H)-one;

3-bromo-4-[(2,4-difluorobenzyl)oxy]-6-methyl-1-(pyridin-3-ylmethyl)pyridin-2 (1H)-one;

4-bromo-2-(2,6-dichlorophenyl)-5-[(2,4-difluorobenzyl) oxy]pyridazin-3(2H)-one;

3-bromo-1-(2,6-dichlorophenyl)-4-[(2,4-difluorobenzyl) oxy]-6-methylpyridin-2 (1H)-one;

3-bromo-1-(3-fluorobenzyl)-4-[(3-methylbenzyl)oxy] pyridin-2(1H)-one;

3-bromo-4-[(2,4-difluorobenzyl)oxy]-6-methyl-1-(pyridin-4-ylmethyl)pyridin-2(1H)-one;

4-(benzyloxy)-3-bromo-1-(3-fluorobenzyl)pyridin-2 (1H)-one;

1-benzyl-4-(benzyloxy)-3-bromo-6-methylpyridin-2 (1H)-one;

3-bromo-4-[(2,4-difluorobenzyl)oxy]-1-(2-methoxy-6-methylphenyl)-6-methylpyridin-2 (1H)-one;

3-bromo-4-[(2,4-difluorobenzyl)oxy]-1-(2-fluorobenzyl) pyridin-2 (1H)-one;

3-bromo-4-[(4-fluorobenzyl)oxy]-6-methyl-1-(pyridin-3-ylmethyl)pyridin-2 (1H)-one;

3-bromo-1-(2,6-dichlorophenyl)-4-[(4-fluorobenzyl)oxy]-6-methylpyridin-2(1H)-one;

4-(benzyloxy)-3-bromo-1-(4-methylbenzyl)pyridin-2 (1H)-one;

4-(benzyloxy)-3-bromo-1-(4-chlorobenzyl)pyridin-2 (1H)-one;

3-bromo-4-[(2,4-difluorobenzyl)oxy]-1-(3-methoxybenzyl) pyridin-2(1H)-one;

4-{[4-(benzyloxy)-3-bromo-2-oxopyridin-1(2H)-yl] methyl}benzoic acid;

4-(benzyloxy)-3-bromo-1-(2-fluorobenzyl)pyridin-2 (1H)-one;

3-bromo-1-(2,6-dimethylphenyl)-4-[(4-fluorobenzyl)oxy]-6-methylpyridin-2(1H)-one;

4-(benzyloxy)-3-bromo-1-[4-(methylthio)benzyl]pyridin-2 (1H)-one;

1-benzyl-4-(benzyloxy)-3-chloropyridin-2(1H)-one;

4-{[4-(benzyloxy)-3-bromo-2-oxopyridin-1(2H)-yl] methyl}-N'-hydroxybenzenecarboximidamide;

methyl 4-{[4-(benzyloxy)-3-bromo-2-oxopyridin-1(2H)-yl] methyl}benzoate;

3-bromo-4-[(3-chlorobenzyl)oxy]-1-(3-fluorobenzyl) pyridin-2 (1H)-one;

3-bromo-1-(3-fluorobenzyl)-4-[(4-fluorobenzyl)oxy] pyridin-2(1H)-one;

4-{[4-(benzyloxy)-3-bromo-2-oxopyridin-1(2H)-yl] methyl}benzonitrile;

4-(benzyloxy)-3-bromo-1-(2,6-dichlorophenyl)-6-methylpyridin-2(1H)-one;
3-bromo-4-[(4-fluorobenzyl)oxy]-1-(pyridin-4-ylmethyl)pyridin-2(1H)-one;
4-(benzyloxy)-3-bromo-1-(4-bromobenzyl)pyridin-2(1H)-one;
4-{[3-bromo-4-[(4-fluorobenzyl)oxy]-2-oxopyridin-1(2H)-yl]methyl}benzonitrile;
1-(3-fluorobenzyl)-4-[(4-fluorobenzyl)oxy]-3-iodopyridin-2(1H)-one;
4-bromo-2-(2,6-dichlorophenyl)-5-{[2-(hydroxymethyl)benzyl]oxy}pyridazin-3(2H)-one;
3-bromo-4-[(4-fluorobenzyl)oxy]-1-(pyridin-3-ylmethyl)pyridin-2(1H)-one;
3-bromo-1-(2,4-difluorobenzyl)-4-[(2,4-difluorobenzyl)oxy]pyridin-2(1H)-one;
3-bromo-4-[(4-fluorobenzyl)oxy]-6-methyl-1-(pyridin-2-ylmethyl)pyridin-2(1H)-one; or a pharmaceutically acceptable salt thereof.

Embodiment 57. Compounds according to embodiment 1 or embodiment A1, which is
3-bromo-4-[(4-chlorobenzyl)oxy]-1-(4-fluorobenzyl)pyridin-2(1H)-one;
1-benzyl-3-bromo-4-[(4-chlorobenzyl)oxy]pyridin-2(1H)-one;
3-bromo-1-(4-chlorobenzyl)-4-[(4-chlorobenzyl)oxy]pyridin-2(1H)-one;
3-bromo-4-[(4-chlorobenzyl)oxy]-1-[2-(phenylthio)ethyl]pyridin-2(1H)-one;
3-bromo-4-[(4-chlorobenzyl)oxy]-1-(2-phenylethyl)pyridin-2(1H)-one;
3-bromo-4-hydroxy-1-(4-hydroxybenzyl)pyridin-2(1H)-one;
4-(benzyloxy)-3-bromo-1-(piperidin-3-ylmethyl)pyridin-2(1H)-one hydrochloride;
3-bromo-1-(4-methoxybenzyl)-4-phenoxypyridin-2(1H)-one;
1-benzyl-2-oxo-4-phenoxy-1,2-dihydropyridine-3-carbaldehyde;
3-bromo-4-[(4-chlorobenzyl)oxy]-1-(4-methoxybenzyl)pyridin-2 (1H)-one;
3-bromo-4-[(4-fluorobenzyl)oxy]-1-(3-phenylpropyl)pyridin-2 (1H)-one;
4-(benzyloxy)-1-[4-(benzyloxy)benzyl]-3-bromopyridin-2(1H)-one;
4-(benzyloxy)-3-bromo-1-[2-(trifluoromethyl)benzyl]pyridin-2(1H)-one;
4-(benzyloxy)-3-bromo-1-[3-(trifluoromethyl)benzyl]pyridin-2(1H)-one;
4-(benzyloxy)-3-bromo-1-(piperidin-4-ylmethyl)pyridin-2 (1H)-one hydrochloride;
1-benzyl-3-bromo-4-{[2-(trifluoromethyl)benzyl]oxy}pyridin-2(1H)-one;
1-benzyl-4-[(2,6-dichlorobenzyl)oxy]pyridin-2(1H)-one;
1-benzyl-4-(benzyloxy)-3-(hydroxymethyl)pyridin-2(1H)-one;
1-benzyl-3-bromo-4-[(2,6-dichlorobenzyl)oxy]pyridin-2 (1H)-one;
1-benzyl-4-[(3-chlorobenzyl)oxy]-6-methylpyridin-2(1H)-one;
1-benzyl-3-bromo-4-[(3-chlorobenzyl)oxy]-6-methylpyridin-2(1H)-one;
1-benzyl-3-bromo-4-[(2-chlorobenzyl)oxy]pyridin-2(1H)-one;
4-(benzyloxy)-3-bromo-1-ethylpyridin-2(1H)-one;
4-(benzyloxy)-1-(4-bromobenzyl)pyridin-2(1H)-one;
3-bromo-1-(4-methylbenzyl)-4-[(4-methylbenzyl)oxy]pyridin-2(1H)-one;
methyl 4-{[4-(benzyloxy)-3-bromo-2-oxopyridin-1(2H)-yl]methyl}benzoate;
4-(benzyloxy)-3-bromo-1-(2-thien-3-ylethyl)pyridin-2(1H)-one;
4-(benzyloxy)-3-bromo-1-(2-thien-2-ylethyl)pyridin-2 (1H)-one;
1-benzyl-4-[(3-chlorobenzyl)oxy]pyridin-2 (1H)-one;
3-bromo-1-(4-fluorobenzyl)-4-[(4-fluorobenzyl)oxy]pyridin-2 (1H)-one;
4-(benzyloxy)-1-(3-fluorobenzyl)pyridin-2 (1H)-one;
4-(benzyloxy)-1-(2-fluorobenzyl)pyridin-2 (1H)-one;
4-(benzyloxy)-3-bromo-1-methylpyridin-2(1H)-one hydrobromide;
4-(benzyloxy)-3-bromo-1-methylpyridin-2(1H)-one;
3-bromo-1-(3-chlorobenzyl)-4-[(4-chlorobenzyl)oxy]pyridin-2(1H)-one;
3-bromo-1-(3-chlorobenzyl)-4-[(4-fluorobenzyl)oxy]pyridin-2(1H)-one;
4-(benzyloxy)-1-(4-chlorobenzyl)pyridin-2 (1H)-one;
4-(benzyloxy)-3-bromo-1-[4-(trifluoromethoxy)benzyl]pyridin-2 (1H)-one;
4-(benzyloxy)-3-bromo-1-(4-tert-butylbenzyl)pyridin-2 (1H)-one;
1-benzyl-4-(benzyloxy)-6-methylpyridin-2 (1H)-one;
1-benzyl-4-(benzyloxy)-3,5-dibromo-6-methylpyridin-2 (1H)-one;
4-(benzyloxy)-3-bromo-1-[4-(trifluoromethyl)benzyl]pyridin-2 (1H)-one;
1-benzyl-4-[(2-chlorobenzyl)oxy]pyridin-2 (1H)-one;
1-(2-bromobenzyl)-3-[(2-bromobenzyl)oxy]pyridin-2 (1H)-one;
methyl 5-chloro-1-(4-chlorobenzyl)-6-oxo-1,6-dihydropyridine-3-carboxylate;
3-benzyl-4-hydroxy-1-(2-phenylethyl)pyridin-2(1H)-one;
5-bromo-1-(2-chloro-6-fluorobenzyl)-3-methylpyridin-2 (1H)-one;
1-(2-bromobenzyl)-3-[(2-bromobenzyl)oxy]pyridin-2(1H)-one;
1-benzyl-4-(benzyloxy)pyridin-2 (1H)-one;
1-benzyl-4-(benzyloxy)-3-bromopyridin-2(1H)-one;
1-benzyl-4-(benzyloxy)-2-oxo-1,2-dihydropyridine-3-carbaldehyde;
1-benzyl-4-chloro-2-oxo-1,2-dihydropyridine-3-carbaldehyde;
1-benzyl-4-hydroxy-2-oxo-1,2-dihydropyridine-3-carbaldehyde;
1-benzyl-4-(benzyloxy)-3-methylpyridin-2(1H)-one;
4-(benzyloxy)-1-(4-fluorobenzyl)pyridin-2(1H)-one;
1-benzyl-4-(benzyloxy)-3,5-dibromopyridin-2 (1H)-one;
4-(benzyloxy)-3-bromo-1-[4-(methylthio)benzyl]pyridin-2 (1H)-one;
4-(benzyloxy)-3-bromo-1-(4-fluorobenzyl)pyridin-2(1H)-one;
1-benzyl-4-(benzyloxy)-3-chloropyridin-2(1H)-one;
3-bromo-1-(4-fluorobenzyl)-4-[(4-fluorobenzyl)oxy]pyridin-2(1H)-one;
1-benzyl-3-bromo-2-oxo-1,2-dihydropyridin-4-yl methyl (phenyl)carbamate;
1-benzyl-3-bromo-4-(2-phenylethyl)pyridin-2 (1H)-one;
1-benzyl-3-bromo-4-(3-phenylpropyl)pyridin-2(1H)-one;
1-benzyl-3-methyl-4-(2-phenylethyl)pyridin-2 (1H)-one;
1-benzyl-3-methyl-4-(3-phenylpropyl)pyridin-2 (1H)-one;
1-benzyl-4-(benzylthio)-3-methylpyridin-2(1H)-one;
1-benzyl-4-(benzylthio)-3-bromopyridin-2 (1H)-one;
1-benzyl-2-oxo-1,2-dihydropyridin-4-yl methanesulfonate;
3-acetyl-4-hydroxy-6-methyl-1-[choro]phenylpyridin-2 (1H)-one;

6-(benzyloxy)-1-methyl-2-oxo-1,2-dihydropyridine-3-carbonitrile;
3-benzoyl-6-(benzyloxy)-1-methylpyridin-2(1H)-one;
3-benzyl-6-(benzyloxy)-1-methylpyridin-2 (1H)-one;
1-benzyl-4-hydroxypyridin-2(1H)-one;
1-benzyl-4-(benzylthio)pyridin-2(1H)-one
4-amino-1-benzylpyridin-2(1H)-one;
1-benzyl-4-(benzyloxy)pyridin-2(1H)-one;
1-benzyl-4-hydroxypyridin-2(1H)-one;
1-benzyl-2-oxo-1,2-dihydropyridin-4-yl methyl(phenyl)carbamate;
or a pharmaceutically acceptable thereof.

Embodiment 58. Compounds according to embodiment 1 or embodiment A1, which is
4-(benzyloxy)-1-(4-methylbenzyl)pyridin-2(1H)-one;
4-(benzyloxy)-3-bromopyridin-2(1H)-one;
methyl 4-{[4-(benzyloxy)-2-oxopyridin-1(2H)-yl]methyl}benzoate;
methyl-4-{[4-(benzyloxy)-3-bromo-2-oxopyridin-1(2H)-yl]methyl}benzoate;
4-{[4-(benzyloxy)-2-oxopyridin-1(2H)-yl]methyl}benzonitrile;
4-(benzyloxy)-1-(4-tert-butylbenzyl)pyridin-2(1H)-one;
4-(benzyloxy)-1-[4-(trifluoromethyl)benzyl]pyridin-2(1H)-one;
4-(benzyloxy)-3-bromo-1-[4-(trifluoromethyl)benzyl]pyridin-2(1H)-one;
4-(benzyloxy)-3-bromo-1-[3-(trifluoromethyl)benzyl]pyridin-2(1H)-one;
4-(benzyloxy)-3-bromo-1-[2-(trifluoromethyl)benzyl]pyridin-2(1H)-one;
4-(benzyloxy)-1-[4-(trifluoromethoxy)benzyl]pyridin-2(1H)-one;
4-(benzyloxy)-3-bromo-1-[4-(trifluoromethoxy)benzyl]pyridin-2(1H)-one;
1-benzyl-4-hydroxy-6-methylpyridin-2(1H)-one;
1-benzyl-6-methyl-2-oxo-1,2-dihydropyridin-4-yl 4-bromobenzenesulfonate;
1-benzyl-3-bromo-4-[(3-chlorobenzyl)oxy]-6-methylpyridin-2 (1H)-one;
1-benzyl-6-methyl-2-oxo-1,2-dihydropyridin-4-yl 4-bromobenzenesulfonate;
1-benzyl-3-bromo-4-[(3-chlorobenzyl)oxy]-6-methylpyridin-2 (1H)-one;
1-Benzyl-4-[2,6-(dichlorobenzyl)oxy]pyridin-2(1H)-one;
4-[(2,6-dichlororbenzyl)oxy]pyridine-1-oxide;
4-[(2,6-dichlorobenzyl)oxy]pyridine 1-oxide;
1-Benzyl-3-bromo-4-[2,6-(dichlorobenzyl)oxy]pyridin-2 (1H)-one;
1-Benzyl-3-bromo-4-[(4-methylbenzyl)oxy]pyridin-2(1H)-one;
1-Benzyl-4-[benzylthio]-3-bromopyridin-2 (1H)-one;
1-benzyl-4-(benzyloxy)-3-iodopyridin-2 (1H)-one;
1-benzyl-4-(benzyloxy)-3-vinylpyridin-2(1H)-one;
1-benzyl-4-(benzyloxy)-3-ethylpyridin-2(1H)-one;
3-acetyl-4-(benzyloxy)-1-(2-chlorophenyl)-6-methylpyridin-2(1H)-one;
3-acetyl-1-(2-chlorophenyl)-4-hydroxy-6-methylpyridin-2 (1H)-one;
1-benzyl-3-bromo-4-hydroxypyridin-2 (1H)-one;
1-benzyl-3-bromo-2-oxo-1,2-dihydropyridin-4-yl trifluoromethanesulfonate;
1-benzyl-3-bromo-4-(phenylethynyl)pyridin-2 (1H)-one;
3-bromo-1-(3-fluorobenzyl)-6-methyl-4-(2-phenylethyl)pyridin-2(1H)-one;
1-(3-fluorobenzyl)-4-hydroxy-6-methylpyridin-2(1H)-one;
3-bromo-1-(3-fluorobenzyl)-4-hydroxy-6-methylpyridin-2 (1H)-one;
3-bromo-1-(3-fluorobenzyl)-6-methyl-2-oxo-1,2-dihydropyridin-4-yl trifluoromethanesulfonate;
3-bromo-1-(3-fluorobenzyl)-6-methyl-4-(phenylethynyl)pyridin-2(1H)-one;
3-acetyl-1-(2,6-dichlorophenyl)-4-hydroxy-6-methylpyridin-2(1H)-one;
1-(2,6-dichlorophenyl)-4-hydroxy-6-methylpyridin-2 (1H)-one;
4-(benzyloxy)-1-(2,6-dichlorophenyl)-6-methylpyridin-2 (1H)-one;
3-bromo-1-(3-fluorobenzyl)-4-(2-phenylethyl)pyridin-2 (1H)-one;
3-bromo-1-(3-fluorobenzyl)-4-hydroxypyridin-2 (1H)-one;
3-bromo-1-(3-fluorobenzyl)-2-oxo-1,2-dihydropyridin-4-yl trifluoromethanesulfonate;
3-bromo-1-(3-fluorobenzyl)-4-(phenylethynyl)pyridin-2 (1H)-one;
4-(benzyloxy)-3-ethynyl-1-(3-fluorobenzyl)pyridin-2 (1H)-one;
4-(benzyloxy)-1-(3-fluorobenzyl)-3-iodopyridin-2(1H)-one;
4-(benzyloxy)-1-(3-fluorobenzyl)-3-[(trimethylsilyl)ethynyl]pyridin-2(1H)-one;
4-(benzylamino)-3-bromo-1-(3-fluorobenzyl)pyridin-2 (1H)-one;
1-(3-fluorobenzyl)-4-hydroxypyridin-2(1H)-one;
4-(benzylamino)-1-(3-fluorobenzyl)pyridin-2(1H)-one;
or a pharmaceutically acceptable salt thereof.

Embodiment 59. Compounds according to embodiment 1 or embodiment A1, which is
3-bromo-4-[(2,4-difluorobenzyl)oxy]-1-(2-fluorobenzyl)pyridin-2(1H)-one;
3-bromo-4-[(4-fluorobenzyl)oxy]-6-methyl-1-(pyridin-3-ylmethyl)pyridin-2 (1H)-one;
3-bromo-4-[(4-fluorobenzyl)oxy]-6-methyl-1-(pyridin-4-ylmethyl)pyridin-2(1H)-one;
3-bromo-1-(2,6-dichlorophenyl)-4-[(4-fluorobenzyl)oxy]-6-methylpyridin-2 (1H)-one;
3-bromo-4-[(2,4-difluorobenzyl)oxy]-1-(3-methoxybenzyl)pyridin-2(1H)-one;
3-bromo-1-(2,6-dimethylphenyl)-4-[(4-fluorobenzyl)oxy]-6-methylpyridin-2(1H)-one;
3-bromo-4-[(3-chlorobenzyl)oxy]-1-(3-fluorobenzyl)pyridin-2 (1H)-one;
3-bromo-4-[(4-fluorobenzyl)oxy]-1-(pyridin-4-ylmethyl)pyridin-2 (1H)-one;
3-bromo-1-(3-fluorobenzyl)-4-[(4-fluorobenzyl)oxy]pyridin-2(1H)-one;
4-{[3-bromo-4-[(4-fluorobenzyl)oxy]-2-oxopyridin-1(2H)-yl]methyl}benzonitrile;
1-(3-fluorobenzyl)-4-[(4-fluorobenzyl)oxy]-3-iodopyridin-2(1H)-one;
3-bromo-4-[(4-fluorobenzyl)oxy]-1-(pyridin-3-ylmethyl)pyridin-2(1H)-one;
3-bromo-1-(2,4-difluorobenzyl)-4-[(2,4-difluorobenzyl)oxy]pyridin-2 (1H)-one;
3-bromo-4-[(4-fluorobenzyl)oxy]-6-methyl-1-(pyridin-2-ylmethyl)pyridin-2 (1H)-one;
3-bromo-4-[(2,4-difluorobenzyl)oxy]-1-(3-fluorobenzyl)pyridin-2(1H)-one;
3-bromo-4-[(2,4-difluorobenzyl)oxy]-6-methyl-1-(pyridin-3-ylmethyl)pyridin-2(1H)-one;
3-bromo-1-(2,6-dichlorophenyl)-4-[(2,4-difluorobenzyl)oxy]-6-methylpyridin-2(1H)-one;
3-bromo-1-(3-fluorobenzyl)-4-[(3-methylbenzyl)oxy]piperidin-2-one; 3-bromo-4-[(2,4-difluorobenzyl)oxy]-6-methyl-1-(pyridin-4-ylmethyl)pyridin-2(1H)-one;

3-bromo-4-[(2,4-difluorobenzyl)oxy]-1-(2-methoxy-6-methylphenyl)-6-methylpyridin-2(1H)-one;
or a pharmaceutically acceptable salt thereof.

Embodiment 60. Compounds according to embodiment 1, which is 1-(1-acetyl-2,3-dihydro-1H-indol-5-yl)-3-chloro-4-[(2,4-difluorobenzyl)oxy]-6-methylpyridin-2(1H)-one;
3-chloro-4-[(2,4-difluorobenzyl)oxy]-1-(1-glycoloyl-2,3-dihydro-1H-indol-5-yl)-6-methylpyridin-2(1H)-one;
3-chloro-4-[(2,4-difluorobenzyl)oxy]-1-[1-(2-hydroxy-2-methylpropanoyl)-2,3-dihydro-1H-indol-5-yl]-6-methylpyridin-2(1H)-one;
3-chloro-4-[(2,4-difluorobenzyl)oxy]-6-methyl-1-[1-(N-methylglycyl)-2,3-dihydro-1H-indol-5-yl]pyridin-2(1H)-one;
3-chloro-4-[(2,4-difluorobenzyl)oxy]-1-[1-(3-hydroxypropanoyl)-2,3-dihydro-1H-indol-5-yl]-6-methylpyridin-2(1H)-one;
3-chloro-4-[(2,4-difluorobenzyl)oxy]-1-[1-(3-hydroxy-3-methylbutanoyl)-2,3-dihydro-1H-indol-5-yl]-6-methylpyridin-2(1H)-one;
5-[3-chloro-4-[(2,4-difluorobenzyl)oxy]-6-methyl-2-oxopyridin-1(2H)-yl]indoline-1-carboxamide;
3-chloro-4-[(2,4-difluorobenzyl)oxy]-6-methyl-1-[1-(methylsulfonyl)-2,3-dihydro-1H-indol-5-yl]pyridin-2(1H)-one;
1-(1-acetyl-1H-indol-5-yl)-3-chloro-4-[(2,4-difluorobenzyl)oxy]-6-methylpyridin-2(1H)-one;
3-chloro-4-[(2,4-difluorobenzyl)oxy]-1-(1-glycoloyl-1H-indol-5-yl)-6-methylpyridin-2(1H)-one;
3-chloro-4-[(2,4-difluorobenzyl)oxy]-1-[1-(2-hydroxy-2-methylpropanoyl)-1H-indol-5-yl]-6-methylpyridin-2(1H)-one;
3-chloro-4-[(2,4-difluorobenzyl)oxy]-6-methyl-1-[1-(N-methylglycyl)-1H-indol-5-yl]pyridin-2(1H)-one;
3-chloro-4-[(2,4-difluorobenzyl)oxy]-1-[1-(3-hydroxypropanoyl)-1H-indol-5-yl]-6-methylpyridin-2(1H)-one;
3-chloro-4-[(2,4-difluorobenzyl)oxy]-1-[1-(3-hydroxy-3-methylbutanoyl)-1H-indol-5-yl]-6-methylpyridin-2(1H)-one;
5-[3-chloro-4-[(2,4-difluorobenzyl)oxy]-6-methyl-2-oxopyridin-1(2H)-yl]-1H-indole-1-carboxamide;
3-chloro-4-[(2,4-difluorobenzyl)oxy]-6-methyl-1-[1-(methylsulfonyl)-1H-indol-5-yl]pyridin-2(1H)-one;
1-(2-acetyl-2,3-dihydro-1H-isoindol-5-yl)-3-chloro-4-[(2,4-difluorobenzyl)oxy]-6-methylpyridin-2(1H)-one;
3-chloro-4-[(2,4-difluorobenzyl)oxy]-1-(2-glycoloyl-2,3-dihydro-1H-isoindol-5-yl)-6-methylpyridin-2(1H)-one;
3-chloro-4-[(2,4-difluorobenzyl)oxy]-1-[2-(2-hydroxy-2-methylpropanoyl)-2,3-dihydro-1H-isoindol-5-yl]-6-methylpyridin-2(1H)-one;
3-chloro-4-[(2,4-difluorobenzyl)oxy]-6-methyl-1-[2-(N-methylglycyl)-2,3-dihydro-1H-isoindol-5-yl]pyridin-2(1H)-one;
3-chloro-4-[(2,4-difluorobenzyl)oxy]-1-[2-(3-hydroxypropanoyl)-2,3-dihydro-1H-isoindol-5-yl]-6-methylpyridin-2(1H)-one;
3-chloro-4-[(2,4-difluorobenzyl)oxy]-1-[2-(3-hydroxy-3-methylbutanoyl)-2,3-dihydro-1H-isoindol-5-yl]-6-methylpyridin-2(1H)-one;
5-[3-chloro-4-[(2,4-difluorobenzyl)oxy]-6-methyl-2-oxopyridin-1(2H)-yl]-1,3-dihydro-2H-isoindole-2-carboxamide;
3-chloro-4-[(2,4-difluorobenzyl)oxy]-6-methyl-1-[2-(methylsulfonyl)-2,3-dihydro-1H-isoindol-5-yl]pyridin-2(1H)-one;
1-(2-acetyl-1,2,3,4-tetrahydroisoquinolin-6-yl)-3-chloro-4-[(2,4-difluorobenzyl)oxy]-6-methylpyridin-2(1H)-one;
3-chloro-4-[(2,4-difluorobenzyl)oxy]-1-(2-glycoloyl-1,2,3,4-tetrahydroisoquinolin-6-yl)-6-methylpyridin-2(1H)-one;
3-chloro-4-[(2,4-difluorobenzyl)oxy]-1-[2-(2-hydroxy-2-methylpropanoyl)-1,2,3,4-tetrahydroisoquinolin-6-yl]-6-methylpyridin-2(1H)-one;
3-chloro-4-[(2,4-difluorobenzyl)oxy]-6-methyl-1-[2-(N-methylglycyl)-1,2,3,4-tetrahydroisoquinolin-6-yl]pyridin-2(1H)-one;
3-chloro-4-[(2,4-difluorobenzyl)oxy]-1-[2-(3-hydroxypropanoyl)-1,2,3,4-tetrahydroisoquinolin-6-yl]-6-methylpyridin-2(1H)-one;
3-chloro-4-[(2,4-difluorobenzyl)oxy]-1-[2-(3-hydroxy-3-methylbutanoyl)-1,2,3,4-tetrahydroisoquinolin-6-yl]-6-methylpyridin-2(1H)-one;
6-[3-chloro-4-[(2,4-difluorobenzyl)oxy]-6-methyl-2-oxopyridin-1(2H)-yl]-3,4-dihydroisoquinoline-2(1H)-carboxamide;
3-chloro-4-[(2,4-difluorobenzyl)oxy]-6-methyl-1-[2-(methylsulfonyl)-1,2,3,4-tetrahydroisoquinolin-6-yl]pyridin-2(1H)-one;
1-(2-acetyl-1,2,3,4-tetrahydroisoquinolin-7-yl)-3-chloro-4-[(2,4-difluorobenzyl)oxy]-6-methylpyridin-2(1H)-one;
3-chloro-4-[(2,4-difluorobenzyl)oxy]-1-(2-glycoloyl-1,2,3,4-tetrahydroisoquinolin-7-yl)-6-methylpyridin-2(1H)-one;
3-chloro-4-[(2,4-difluorobenzyl)oxy]-1-[2-(2-hydroxy-2-methylpropanoyl)-1,2,3,4-tetrahydroisoquinolin-7-yl]-6-methylpyridin-2(1H)-one;
3-chloro-4-[(2,4-difluorobenzyl)oxy]-6-methyl-1-[2-(N-methylglycyl)-1,2,3,4-tetrahydroisoquinolin-7-yl]pyridin-2(1H)-one;
3-chloro-4-[(2,4-difluorobenzyl)oxy]-1-[2-(3-hydroxypropanoyl)-1,2,3,4-tetrahydroisoquinolin-7-yl]-6-methylpyridin-2(1H)-one;
3-chloro-4-[(2,4-difluorobenzyl)oxy]-1-[2-(3-hydroxy-3-methylbutanoyl)-1,2,3,4-tetrahydroisoquinolin-7-yl]-6-methylpyridin-2(1H)-one;
7-[3-chloro-4-[(2,4-difluorobenzyl)oxy]-6-methyl-2-oxopyridin-1(2H)-yl]-3,4-dihydroisoquinoline-2(1H)-carboxamide;
3-chloro-4-[(2,4-difluorobenzyl)oxy]-6-methyl-1-[2-(methylsulfonyl)-1,2,3,4-tetrahydroisoquinolin-7-yl]pyridin-2(1H)-one;
1-(1-acetyl-1H-benzimidazol-5-yl)-3-chloro-4-[(2,4-difluorobenzyl)oxy]-6-methylpyridin-2(1H)-one;
3-chloro-4-[(2,4-difluorobenzyl)oxy]-1-(1-glycoloyl-1H-benzimidazol-5-yl)-6-methylpyridin-2(1H)-one;
3-chloro-4-[(2,4-difluorobenzyl)oxy]-1-[1-(2-hydroxy-2-methylpropanoyl)-1H-benzimidazol-5-yl]-6-methylpyridin-2(1H)-one;
3-chloro-4-[(2,4-difluorobenzyl)oxy]-6-methyl-1-[11 (N-methylglycyl)-1H-benzimidazol-5-yl]pyridin-2(1H)-one;
3-chloro-4-[(2,4-difluorobenzyl)oxy]-1-[1-(3-hydroxypropanoyl)-1H-benzimidazol-5-yl]-6-methylpyridin-2(1H)-one;
3-chloro-4-[(2,4-difluorobenzyl)oxy]-1-[1-(3-hydroxy-3-methylbutanoyl)-1H-benzimidazol-5-yl]-6-methylpyridin-2(1H)-one;
5-[3-chloro-4-[(2,4-difluorobenzyl)oxy]-6-methyl-2-oxopyridin-1(2H)-yl]-1H-benzimidazole-1-carboxamide;
3-chloro-4-[(2,4-difluorobenzyl)oxy]-6-methyl-1-[1-(methylsulfonyl)-1H-benzimidazol-5-yl]pyridin-2(1H)-one;

3-chloro-1-(1,3-diacetyl-2,3-dihydro-1H-benzimidazol-5-yl)-4-[(2,4-difluorobenzyl)oxy]-6-methylpyridin-2(1H)-one;

1-(3-acetyl-1-glycoloyl-2,3-dihydro-1H-benzimidazol-5-yl)-3-chloro-4-[(2,4-difluorobenzyl)oxy]-6-methylpyridin-2(1H)-one;

1-[3-acetyl-1-(2-hydroxy-2-methylpropanoyl)-2,3-dihydro-1H-benzimidazol-5-yl]-3-chloro-4-[(2,4-difluorobenzyl)oxy]-6-methylpyridin-2(1H)-one;

1-[3-acetyl-1-(N-methylglycyl)-2,3-dihydro-1H-benzimidazol-5-yl]-3-chloro-4-[(2,4-difluorobenzyl)oxy]-6-methylpyridin-2(1H)-one;

1-[3-acetyl-1-(3-hydroxypropanoyl)-2,3-dihydro-1H-benzimidazol-5-yl]-3-chloro-4-[(2,4-difluorobenzyl)oxy]-6-methylpyridin-2(1H)-one;

1-[3-acetyl-1-(3-hydroxy-3-methylbutanoyl)-2,3-dihydro-1H-benzimidazol-5-yl]-3-chloro-4-[(2,4-difluorobenzyl)oxy]-6-methylpyridin-2(1H)-one;

3-acetyl-5-[3-chloro-4-[(2,4-difluorobenzyl)oxy]-6-methyl-2-oxopyridin-1(2H)-yl]-2,3-dihydro-1H-benzimidazole-1-carboxamide;

1-(1-acetyl-3-glycoloyl-2,3-dihydro-1H-benzimidazol-5-yl)-3-chloro-4-[(2,4-difluorobenzyl)oxy]-6-methylpyridin-2(1H)-one;

3-chloro-4-[(2,4-difluorobenzyl)oxy]-1-(1,3-diglycoloyl-2,3-dihydro-1H-benzimidazol-5-yl)-6-methylpyridin-2(1H)-one;

3-chloro-4-[(2,4-difluorobenzyl)oxy]-1-[3-glycoloyl-1-(2-hydroxy-2-methylpropanoyl)-2,3-dihydro-1H-benzimidazol-5-yl]-6-methylpyridin-2(1H)-one;

3-chloro-4-[(2,4-difluorobenzyl)oxy]-1-[3-glycoloyl-1-(N-methylglycyl)-2,3-dihydro-1H-benzimidazol-5-yl]-6-methylpyridin-2(1H)-one;

3-chloro-4-[(2,4-difluorobenzyl)oxy]-1-[3-glycoloyl-1-(3-hydroxypropanoyl)-2,3-dihydro-1H-benzimidazol-5-yl]-6-methylpyridin-2(1H)-one;

5-[3-chloro-4-[(2,4-difluorobenzyl)oxy]-6-methyl-2-oxopyridin-1(2H)-yl]-3-glycoloyl-2,3-dihydro-1H-benzimidazole-1-carboxamide;

3-chloro-4-[(2,4-difluorobenzyl)oxy]-1-[3-glycoloyl-1-(3-hydroxy-3-methylbutanoyl)-2,3-dihydro-1H-benzimidazol-5-yl]-6-methylpyridin-2(1H)-one;

3-chloro-4-[(2,4-difluorobenzyl)oxy]-1-[3-glycoloyl-1-(methylsulfonyl)-2,3-dihydro-1H-benzimidazol-5-yl]-6-methylpyridin-2(1H)-one;

1-[1-acetyl-3-(2-hydroxy-2-methylpropanoyl)-2,3-dihydro-1H-benzimidazol-5-yl]-3-chloro-4-[(2,4-difluorobenzyl)oxy]-6-methylpyridin-2(1H)-one;

3-chloro-4-[(2,4-difluorobenzyl)oxy]-1-[1-glycoloyl-3-(2-hydroxy-2-methylpropanoyl)-2,3-dihydro-1H-benzimidazol-5-yl]-6-methylpyridin-2(1H)-one;

1-[1,3-bis(2-hydroxy-2-methylpropanoyl)-2,3-dihydro-1H-benzimidazol-5-yl]-3-chloro-4-[(2,4-difluorobenzyl)oxy]-6-methylpyridin-2(1H)-one;

3-chloro-4-[(2,4-difluorobenzyl)oxy]-1-[3-(2-hydroxy-2-methylpropanoyl)-1-(N-methylglycyl)-2,3-dihydro-1H-benzimidazol-5-yl]-6-methylpyridin-2(1H)-one;

3-chloro-4-[(2,4-difluorobenzyl)oxy]-1-[3-(2-hydroxy-2-methylpropanoyl)-1-(3-hydroxypropanoyl)-2,3-dihydro-1H-benzimidazol-5-yl]-6-methylpyridin-2(1H)-one;

3-chloro-4-[(2,4-difluorobenzyl)oxy]-1-[1-(3-hydroxy-3-methylbutanoyl)-3-(2-hydroxy-2-methylpropanoyl)-2,3-dihydro-1H-benzimidazol-5-yl]-6-methylpyridin-2(1H)-one;

5-[3-chloro-4-[(2,4-difluorobenzyl)oxy]-6-methyl-2-oxopyridin-1(2H)-yl]-3-(2-hydroxy-2-methylpropanoyl)-2,3-dihydro-1H-benzimidazole-1-carboxamide;

3-chloro-4-[(2,4-difluorobenzyl)oxy]-1-[3-(2-hydroxy-2-methylpropanoyl)-1-(methylsulfonyl)-2,3-dihydro-1H-benzimidazol-5-yl]-6-methylpyridin-2(1H)-one;

1-[1-acetyl-3-(N-methylglycyl)-2,3-dihydro-1H-benzimidazol-5-yl]-3-chloro-4-[(2,4-difluorobenzyl)oxy]-6-methylpyridin-2(1H)-one;

3-chloro-4-[(2,4-difluorobenzyl)oxy]-1-[1-glycoloyl-3-(N-methylglycyl)-2,3-dihydro-1H-benzimidazol-5-yl]-6-methylpyridin-2(1H)-one;

3-chloro-4-[(2,4-difluorobenzyl)oxy]-1-[1-(2-hydroxy-2-methylpropanoyl)-3-(N-methylglycyl)-2,3-dihydro-1H-benzimidazol-5-yl]-6-methylpyridin-2(1H)-one;

1-[1,3-bis(N-methylglycyl)-2,3-dihydro-1H-benzimidazol-5-yl]-3-chloro-4-[(2,4-difluorobenzyl)oxy]-6-methylpyridin-2(1H)-one;

3-chloro-4-[(2,4-difluorobenzyl)oxy]-1-[1-(3-hydroxypropanoyl)-3-(N-methylglycyl)-2,3-dihydro-1H-benzimidazol-5-yl]-6-methylpyridin-2(1H)-one;

3-chloro-4-[(2,4-difluorobenzyl)oxy]-1-[1-(3-hydroxy-3-methylbutanoyl)-3-(N-methylglycyl)-2,3-dihydro-1H-benzimidazol-5-yl]-6-methylpyridin-2(1H)-one;

5-[3-chloro-4-[(2,4-difluorobenzyl)oxy]-6-methyl-2-oxopyridin-1(2H)-yl]-3-(N-methylglycyl)-2,3-dihydro-1H-benzimidazole-1-carboxamide;

3-chloro-4-[(2,4-difluorobenzyl)oxy]-6-methyl-1-[3-(N-methylglycyl)-1-(methylsulfonyl)-2,3-dihydro-1H-benzimidazol-5-yl]pyridin-2(1H)-one;

1-[1-acetyl-3-(3-hydroxypropanoyl)-2,3-dihydro-1H-benzimidazol-5-yl]-3-chloro-4-[(2,4-difluorobenzyl)oxy]-6-methylpyridin-2(1H)-one;

3-chloro-4-[(2,4-difluorobenzyl)oxy]-1-[1-glycoloyl-3-(3-hydroxypropanoyl)-2,3-dihydro-1H-benzimidazol-5-yl]-6-methylpyridin-2(1H)-one;

3-chloro-4-[(2,4-difluorobenzyl)oxy]-1-[1-(2-hydroxy-2-methylpropanoyl)-3-(3-hydroxypropanoyl)-2,3-dihydro-1H-benzimidazol-5-yl]-6-methylpyridin-2(1H)-one;

3-chloro-4-[(2,4-difluorobenzyl)oxy]-1-[3-(3-hydroxypropanoyl)-1-(N-methylglycyl)-2,3-dihydro-1H-benzimidazol-5-yl]-6-methylpyridin-2(1H)-one;

1-[1,3-bis(3-hydroxypropanoyl)-2,3-dihydro-1H-benzimidazol-5-yl]-3-chloro-4-[(2,4-difluorobenzyl)oxy]-6-methylpyridin-2(1H)-one;

3-chloro-4-[(2,4-difluorobenzyl)oxy]-1-[1-(3-hydroxy-3-methylbutanoyl)-3-(3-hydroxypropanoyl)-2,3-dihydro-1H-benzimidazol-5-yl]-6-methylpyridin-2(1H)-one;

5-[3-chloro-4-[(2,4-difluorobenzyl)oxy]-6-methyl-2-oxopyridin-1(2H)-yl]-3-(3-hydroxypropanoyl)-2,3-dihydro-1H-benzimidazole-1-carboxamide;

3-chloro-4-[(2,4-difluorobenzyl)oxy]-1-[3-(3-hydroxypropanoyl)-1-(methylsulfonyl)-2,3-dihydro-1H-benzimidazol-5-yl]-6-methylpyridin-2(1H)-one;

1-[1-acetyl-3-(3-hydroxy-3-methylbutanoyl)-2,3-dihydro-1H-benzimidazol-5-yl]-3-chloro-4-[(2,4-difluorobenzyl)oxy]-6-methylpyridin-2(1H)-one;

3-chloro-4-[(2,4-difluorobenzyl)oxy]-1-[1-glycoloyl-3-(3-hydroxy-3-methylbutanoyl)-2,3-dihydro-1H-benzimidazol-5-yl]-6-methylpyridin-2(1H)-one;

3-chloro-4-[(2,4-difluorobenzyl)oxy]-1-[3-(3-hydroxy-3-methylbutanoyl)-1-(2-hydroxy-2-methylpropanoyl)-2,3-dihydro-1H-benzimidazol-5-yl]-6-methylpyridin-2(1H)-one;

3-chloro-4-[(2,4-difluorobenzyl)oxy]-1-[3-(3-hydroxy-3-methylbutanoyl)-1-(N-methylglycyl)-2,3-dihydro-1H-benzimidazol-5-yl]-6-methylpyridin-2(1H)-one;

3-chloro-4-[(2,4-difluorobenzyl)oxy]-1-[3-(3-hydroxy-3-methylbutanoyl)-1-(3-hydroxypropanoyl)-2,3-dihydro-1H-benzimidazol-5-yl]-6-methylpyridin-2(1H)-one;

1-[1,3-bis(3-hydroxy-3-methylbutanoyl)-2,3-dihydro-1H-benzimidazol-5-yl]-3-chloro-4-[(2,4-difluorobenzyl)oxy]-6-methylpyridin-2(1H)-one;

5-[3-chloro-4-[(2,4-difluorobenzyl)oxy]-6-methyl-2-oxopyridin-1(2H)-yl]-3-(3-hydroxy-3-methylbutanoyl)-2,3-dihydro-1H-benzimidazole-1-carboxamide;

3-chloro-4-[(2,4-difluorobenzyl)oxy]-1-[3-(3-hydroxy-3-methylbutanoyl)-1-(methylsulfonyl)-2,3-dihydro-1H-benzimidazol-5-yl]-6-methylpyridin-2(1H)-one;

3-acetyl-6-[3-chloro-4-[(2,4-difluorobenzyl)oxy]-6-methyl-2-oxopyridin-1(2H)-yl]-2,3-dihydro-1H-benzimidazole-1-carboxamide;

6-[3-chloro-4-[(2,4-difluorobenzyl)oxy]-6-methyl-2-oxopyridin-1(2H)-yl]-3-glycoloyl-2,3-dihydro-1H-benzimidazole-1-carboxamide;

6-[3-chloro-4-[(2,4-difluorobenzyl)oxy]-6-methyl-2-oxopyridin-1(2H)-yl]-3-(2-hydroxy-2-methylpropanoyl)-2,3-dihydro-1H-benzimidazole-1-carboxamide;

6-[3-chloro-4-[(2,4-difluorobenzyl)oxy]-6-methyl-2-oxopyridin-1(2H)-yl]-3-(N-methylglycyl)-2,3-dihydro-1H-benzimidazole-1-carboxamide;

6-[3-chloro-4-[(2,4-difluorobenzyl)oxy]-6-methyl-2-oxopyridin-1(2H)-yl]-3-(3-hydroxypropanoyl)-2,3-dihydro-1H-benzimidazole-1-carboxamide;

6-[3-chloro-4-[(2,4-difluorobenzyl)oxy]-6-methyl-2-oxopyridin-1(2H)-yl]-3-(3-hydroxy-3-methylbutanoyl)-2,3-dihydro-1H-benzimidazole-1-carboxamide;

5-[3-chloro-4-[(2,4-difluorobenzyl)oxy]-6-methyl-2-oxopyridin-1(2H)-yl]-1H-benzimidazole-1,3(2H)-dicarboxamide;

6-[3-chloro-4-[(2,4-difluorobenzyl)oxy]-6-methyl-2-oxopyridin-1(2H)-yl]-3-(methylsulfonyl)-2,3-dihydro-1H-benzimidazole-1-carboxamide;

1-[1-acetyl-3-(methylsulfonyl)-2,3-dihydro-1H-benzimidazol-5-yl]-3-chloro-4-[(2,4-difluorobenzyl)oxy]-6-methylpyridin-2(1H)-one;

3-chloro-4-[(2,4-difluorobenzyl)oxy]-1-[1-glycoloyl-3-(methylsulfonyl)-2,3-dihydro-1H-benzimidazol-5-yl]-6-methylpyridin-2(1H)-one;

3-chloro-4-[(2,4-difluorobenzyl)oxy]-1-[1-(2-hydroxy-2-methylpropanoyl)-3-(methylsulfonyl)-2,3-dihydro-1H-benzimidazol-5-yl]-6-methylpyridin-2(1H)-one;

3-chloro-4-[(2,4-difluorobenzyl)oxy]-6-methyl-1-[1-(N-methylglycyl)-3-(methylsulfonyl)-2,3-dihydro-1H-benzimidazol-5-yl]pyridin-2(1H)-one;

3-chloro-4-[(2,4-difluorobenzyl)oxy]-1-[1-(3-hydroxypropanoyl)-3-(methylsulfonyl)-2,3-dihydro-1H-benzimidazol-5-yl]-6-methylpyridin-2(1H)-one;

3-chloro-4-[(2,4-difluorobenzyl)oxy]-1-[1-(3-hydroxy-3-methylbutanoyl)-3-(methylsulfonyl)-2,3-dihydro-1H-benzimidazol-5-yl]-6-methylpyridin-2(1H)-one;

5-[3-chloro-4-[(2,4-difluorobenzyl)oxy]-6-methyl-2-oxopyridin-1(2H)-yl]-3-(methylsulfonyl)-2,3-dihydro-1H-benzimidazole-1-carboxamide;

1-[1,3-bis(methylsulfonyl)-2,3-dihydro-1H-benzimidazol-5-yl]-3-chloro-4-[(2,4-difluorobenzyl)oxy]-6-methylpyridin-2(1H)-one;

1-[3-acetyl-1-(methylsulfonyl)-2,3-dihydro-1H-benzimidazol-5-yl]-3-chloro-4-[(2,4-difluorobenzyl)oxy]-6-methylpyridin-2(1H)-one;

1-(1-acetyl-1H-pyrrol-3-yl)-3-chloro-4-[(2,4-difluorobenzyl)oxy]-6-methylpyridin-2(1H)-one;

3-chloro-4-[(2,4-difluorobenzyl)oxy]-1-(1-glycoloyl-1H-pyrrol-3-yl)-6-methylpyridin-2(1H)-one;

3-chloro-4-[(2,4-difluorobenzyl)oxy]-1-[1-(2-hydroxy-2-methylpropanoyl)-1H-pyrrol-3-yl]-6-methylpyridin-2(1H)-one;

3-chloro-4-[(2,4-difluorobenzyl)oxy]-6-methyl-1-[1-(N-methylglycyl)-1H-pyrrol-3-yl]pyridin-2(1H)-one;

3-chloro-4-[(2,4-difluorobenzyl)oxy]-1-[1-(3-hydroxypropanoyl)-1H-pyrrol-3-yl]-6-methylpyridin-2(1H)-one;

3-chloro-4-[(2,4-difluorobenzyl)oxy]-1-[1-(3-hydroxy-3-methylbutanoyl)-1H-pyrrol-3-yl]-6-methylpyridin-2(1H)-one;

3-[3-chloro-4-[(2,4-difluorobenzyl)oxy]-6-methyl-2-oxopyridin-1(2H)-yl]-1H-pyrrole-1-carboxamide;

3-chloro-4-[(2,4-difluorobenzyl)oxy]-6-methyl-1-[1-(methylsulfonyl)-1H-pyrrol-3-yl]pyridin-2(1H)-one;

1-(1-acetyl-1H-imidazol-4-yl)-3-chloro-4-[(2,4-difluorobenzyl)oxy]-6-methylpyridin-2(1H)-one;

3-chloro-4-[(2,4-difluorobenzyl)oxy]-1-(1-glycoloyl-1H-imidazol-4-yl)-6-methylpyridin-2(1H)-one;

3-chloro-4-[(2,4-difluorobenzyl)oxy]-1-[1-(2-hydroxy-2-methylpropanoyl)-1H-imidazol-4-yl]-6-methylpyridin-2(1H)-one;

3-chloro-4-[(2,4-difluorobenzyl)oxy]-6-methyl-1-[1-(N-methylglycyl)-1H-imidazol-4-yl]pyridin-2(1H)-one;

3-chloro-4-[(2,4-difluorobenzyl)oxy]-1-[1-(3-hydroxypropanoyl)-1H-imidazol-4-yl]-6-methylpyridin-2(1H)-one;

3-chloro-4-[(2,4-difluorobenzyl)oxy]-1-[1-(3-hydroxy-3-methylbutanoyl)-1H-imidazol-4-yl]-6-methylpyridin-2(1H)-one;

4-[3-chloro-4-[(2,4-difluorobenzyl)oxy]-6-methyl-2-oxopyridin-1(2H)-yl]-1H-imidazole-1-carboxamide;

3-chloro-4-[(2,4-difluorobenzyl)oxy]-6-methyl-1-[1-(methylsulfonyl)-1H-imidazol-4-yl]pyridin-2(1H)-one;

1-(1-acetyl-1H-pyrazol-4-yl)-3-chloro-4-[(2,4-difluorobenzyl)oxy]-6-methylpyridin-2(1H)-one;

3-chloro-4-[(2,4-difluorobenzyl)oxy]-1-(1-glycoloyl-1H-pyrazol-4-yl)-6-methylpyridin-2(1H)-one;

3-chloro-4-[(2,4-difluorobenzyl)oxy]-1-[1-(2-hydroxy-2-methylpropanoyl)-1H-pyrazol-4-yl]-6-methylpyridin-2(1H)-one;

3-chloro-4-[(2,4-difluorobenzyl)oxy]-6-methyl-1-[1-(N-methylglycyl)-1H-pyrazol-4-yl]pyridin-2(1H)-one;

3-chloro-4-[(2,4-difluorobenzyl)oxy]-1-[1-(3-hydroxypropanoyl)-1H-pyrazol-4-yl]-6-methylpyridin-2(1H)-one;

3-chloro-4-[(2,4-difluorobenzyl)oxy]-1-[1-(3-hydroxy-3-methylbutanoyl)-1H-pyrazol-4-yl]-6-methylpyridin-2(1H)-one;

4-[3-chloro-4-[(2,4-difluorobenzyl)oxy]-6-methyl-2-oxopyridin-1(2H)-yl]-1H-pyrazole-1-carboxamide;

3-chloro-4-[(2,4-difluorobenzyl)oxy]-6-methyl-1-[1-(methylsulfonyl)-1H-pyrazol-4-yl]pyridin-2(1H)-one;

3-chloro-4-[(2,4-difluorobenzyl)oxy]-1-isoquinolin-7-yl-6-methylpyridin-2(1H)-one;

3-chloro-4-[(2,4-difluorobenzyl)oxy]-1-(isoquinolin-6-ylmethyl)pyridin-2(1H)-one;

5-{[3-chloro-4-[(2,4-difluorobenzyl)oxy]-2-oxopyridin-1(2H)-yl]methyl}-1,3-dihydro-2H-indol-2-one;

3-chloro-4-[(2,4-difluorobenzyl)oxy]-1-(2,3-dihydro-1H-indol-5-ylmethyl)pyridin-2(1H)-one;

1-[(1-acetyl-2,3-dihydro-1H-indol-5-yl)methyl]-3-chloro-4-[(2,4-difluorobenzyl)oxy]pyridin-2(1H)-one;

3-chloro-4-[(2,4-difluorobenzyl)oxy]-1-[(1-glycoloyl-2,3-dihydro-1H-indol-5-yl)methyl]pyridin-2(1H)-one;

3-chloro-4-[(2,4-difluorobenzyl)oxy]-1-{[1-(2-hydroxy-2-methylpropanoyl)-2,3-dihydro-1H-indol-5-yl]methyl}pyridin-2(1H)-one;

3-chloro-4-[(2,4-difluorobenzyl)oxy]-1-{[1-(N-methylglycyl)-2,3-dihydro-1H-indol-5-yl]methyl}pyridin-2(1H)-one;

3-chloro-4-[(2,4-difluorobenzyl)oxy]-1-{[1-(3-hydroxypropanoyl)-2,3-dihydro-1H-indol-5-yl]methyl}pyridin-2(1H)-one;
3-chloro-4-[(2,4-difluorobenzyl)oxy]-1-{[1-(3-hydroxy-3-methylbutanoyl)-2,3-dihydro-1H-indol-5-yl]methyl}pyridin-2(1H)-one;
5-{[3-chloro-4-[(2,4-difluorobenzyl)oxy]-2-oxopyridin-1(2H)-yl]methyl}indoline-1-carboxamide;
3-chloro-4-[(2,4-difluorobenzyl)oxy]-1-{[-1-(methylsulfonyl)-2,3-dihydro-1H-indol-5-yl]methyl}pyridin-2(1H)-one;
3-chloro-4-[(2,4-difluorobenzyl)oxy]-1-(2,3-dihydro-1H-isoindol-5-ylmethyl)pyridin-2(1H)-one;
1-[(2-acetyl-2,3-dihydro-1H-isoindol-5-yl)methyl]-3-chloro-4-[(2,4-difluorobenzyl)oxy]pyridin-2(1H)-one;
3-chloro-4-[(2,4-difluorobenzyl)oxy]-1-[(2-glycoloyl-2,3-dihydro-1H-isoindol-5-yl)methyl]pyridin-2(1H)-one;
3-chloro-4-[(2,4-difluorobenzyl)oxy]-1-{[2-(2-hydroxy-2-methylpropanoyl)-2,3-dihydro-1H-isoindol-5-yl]methyl}pyridin-2(1H)-one;
3-chloro-4-[(2,4-difluorobenzyl)oxy]-1-{[2-(N-methylglycyl)-2,3-dihydro-1H-isoindol-5-yl]methyl}pyridin-2(1H)-one;
3-chloro-4-[(2,4-difluorobenzyl)oxy]-1-{[2-(3-hydroxypropanoyl)-2,3-dihydro-1H-isoindol-5-yl]methyl}pyridin-2(1H)-one;
3-chloro-4-[(2,4-difluorobenzyl)oxy]-1-{[2-(3-hydroxy-3-methylbutanoyl)-2,3-dihydro-1H-isoindol-5-yl]methyl}pyridin-2(1H)-one;
5-{[3-chloro-4-[(2,4-difluorobenzyl)oxy]-2-oxopyridin-1(2H)-yl]methyl}-1,3-dihydro-2H-isoindole-2-carboxamide;
3-chloro-4-[(2,4-difluorobenzyl)oxy]-1-{[2-(methylsulfonyl)-2,3-dihydro-1H-isoindol-5-yl]methyl}pyridin-2(1H)-one;
3-chloro-4-[(2,4-difluorobenzyl)oxy]-1-(1,2,3,4-tetrahydroisoquinolin-6-ylmethyl)pyridin-2(1H)-one;
1-[(2-acetyl-1,2,3,4-tetrahydroisoquinolin-6-yl)methyl]-3-chloro-4-[(2,4-difluorobenzyl)oxy]pyridin-2(1H)-one;
3-chloro-4-[(2,4-difluorobenzyl)oxy]-1-[(2-glycoloyl-1,2,3,4-tetrahydroisoquinolin-6-yl)methyl]pyridin-2(1H)-one;
3-chloro-4-[(2,4-difluorobenzyl)oxy]-1-{[2-(2-hydroxy-2-methylpropanoyl)-1,2,3,4-tetrahydroisoquinolin-6-yl]methyl}pyridin-2(1H)-one;
3-chloro-4-[(2,4-difluorobenzyl)oxy]-1-{[2-(N-methylglycyl)-1,2,3,4-tetrahydroisoquinolin-6-yl]methyl}pyridin-2(1H)-one;
3-chloro-4-[(2,4-difluorobenzyl)oxy]-1-{[2-(3-hydroxypropanoyl)-1,2,3,4-tetrahydroisoquinolin-6-yl]methyl}pyridin-2(1H)-one;
3-chloro-4-[(2,4-difluorobenzyl)oxy]-1-{[2-(3-hydroxy-3-methylbutanoyl)-1,2,3,4-tetrahydroisoquinolin-6-yl]methyl}pyridin-2(1H)-one;
6-{[3-chloro-4-[(2,4-difluorobenzyl)oxy]-2-oxopyridin-1(2H)-yl]methyl}-3,4-dihydroisoquinoline-2(1H)-carboxamide;
3-chloro-4-[(2,4-difluorobenzyl)oxy]-1-{[2-(methylsulfonyl)-1,2,3,4-tetrahydroisoquinolin-6-yl]methyl}pyridin-2(1H)-one;
3-chloro-4-[(2,4-difluorobenzyl)oxy]-1-(1,2,3,4-tetrahydroisoquinolin-5-ylmethyl)pyridin-2(1H)-one;
1-[(2-acetyl-1,2,3,4-tetrahydroisoquinolin-5-yl)methyl]-3-chloro-4-[(2,4-difluorobenzyl)oxy]pyridin-2(1H)-one;
3-chloro-4-[(2,4-difluorobenzyl)oxy]-1-[(2-glycoloyl-1,2,3,4-tetrahydroisoquinolin-5-yl)methyl]pyridin-2(1H)-one;
3-chloro-4-[(2,4-difluorobenzyl)oxy]-1-{[2-(2-hydroxy-2-methylpropanoyl)-1,2,3,4-tetrahydroisoquinolin-5-yl]methyl}pyridin-2(1H)-one;
3-chloro-4-[(2,4-difluorobenzyl)oxy]-1-{[2-(N-methylglycyl)-1,2,3,4-tetrahydroisoquinolin-5-yl]methyl}pyridin-2(1H)-one;
3-chloro-4-[(2,4-difluorobenzyl)oxy]-1-{[2-(3-hydroxypropanoyl)-1,2,3,4-tetrahydroisoquinolin-5-yl]methyl}pyridin-2(1H)-one;
3-chloro-4-[(2,4-difluorobenzyl)oxy]-1-{[2-(3-hydroxy-3-methylbutanoyl)-1,2,3,4-tetrahydroisoquinolin-5-yl]methyl}pyridin-2(1H)-one;
5-{[3-chloro-4-[(2,4-difluorobenzyl)oxy]-2-oxopyridin-1(2H)-yl]methyl}-3,4-dihydroisoquinoline-2(1H)-carboxamide;
3-chloro-4-[(2,4-difluorobenzyl)oxy]-1-{[2-(methylsulfonyl)-1,2,3,4-tetrahydroisoquinolin-5-yl]methyl}pyridin-2(1H)-one;
3-chloro-4-[(2,4-difluorobenzyl)oxy]-1-(2,3-dihydro-1H-benzimidazol-5-ylmethyl)pyridin-2(1H)-one;
1-[(1-acetyl-2,3-dihydro-1H-benzimidazol-5-yl)methyl]-3-chloro-4-[(2,4-difluorobenzyl)oxy]pyridin-2(1H)-one;
3-chloro-4-[(2,4-difluorobenzyl)oxy]-1-[(1-glycoloyl-2,3-dihydro-1H-benzimidazol-5-yl)methyl]pyridin-2(1H)-one;
3-chloro-4-[(2,4-difluorobenzyl)oxy]-1-{[1-(2-hydroxy-2-methylpropanoyl)-2,3-dihydro-1H-benzimidazol-5-yl]methyl}pyridin-2(1H)-one;
3-chloro-4-[(2,4-difluorobenzyl)oxy]-1-{-[1-(N-methylglycyl)-2,3-dihydro-1H-benzimidazol-5-yl]methyl}pyridin-2(1H)-one;
3-chloro-4-[(2,4-difluorobenzyl)oxy]-1-[1-(3-hydroxypropanoyl)-2,3-dihydro-1H-benzimidazol-5-yl]methyl}pyridin-2(1H)-one;
3-chloro-4-[(2,4-difluorobenzyl)oxy]-1-{[1-(3-hydroxy-3-methylbutanoyl)-2,3-dihydro-1H-benzimidazol-5-yl]methyl}pyridin-2(1H)-one;
5-{[3-chloro-4-[(2,4-difluorobenzyl)oxy]-2-oxopyridin-1(2H)-yl]methyl}-2,3-dihydro-1H-benzimidazole-1-carboxamide;
3-chloro-4-[(2,4-difluorobenzyl)oxy]-1-{[1-(methylsulfonyl)-2,3-dihydro-1H-benzimidazol-5-yl]methyl}pyridin-2(1H)-one;
1-[(3-acetyl-2,3-dihydro-1H-benzimidazol-5-yl)methyl]-3-chloro-4-[(2,4-difluorobenzyl)oxy]pyridin-2(1H)-one;
3-chloro-1-[(1,3-diacetyl-2,3-dihydro-1H-benzimidazol-5-yl)methyl]-4-[(2,4-difluorobenzyl)oxy]pyridin-2(1H)-one;
1-[(3-acetyl-1-glycoloyl-2,3-dihydro-1H-benzimidazol-5-yl)methyl]-3-chloro-4-[(2,4-difluorobenzyl)oxy]pyridin-2(1H)-one;
1-{[3-acetyl-1-(2-hydroxy-2-methylpropanoyl)-2,3-dihydro-1H-benzimidazol-5-yl]methyl}-3-chloro-4-[(2,4-difluorobenzyl)oxy]pyridin-2(1H)-one;
1-{[3-acetyl-1-(N-methylglycyl)-2,3-dihydro-1H-benzimidazol-5-yl]methyl}-3-chloro-4-[(2,4-difluorobenzyl)oxy]pyridin-2(1H)-one;
1-{[3-acetyl-1-(3-hydroxypropanoyl)-2,3-dihydro-1H-benzimidazol-5-yl]methyl}-3-chloro-4-[(2,4-difluorobenzyl)oxy]pyridin-2(1H)-one;
1-{[3-acetyl-1-(3-hydroxy-3-methylbutanoyl)-2,3-dihydro-1H-benzimidazol-5-yl]methyl}-3-chloro-4-[(2,4-difluorobenzyl)oxy]pyridin-2(1H)-one;
3-acetyl-5-{[3-chloro-4-[(2,4-difluorobenzyl)oxy]-2-oxopyridin-1(2H)-yl]methyl}-2,3-dihydro-1H-benzimidazole-1-carboxamide;
1-{[3-acetyl-1-(methylsulfonyl)-2,3-dihydro-1H-benzimidazol-5-yl]methyl}-3-chloro-4-[(2,4-difluorobenzyl)oxy]pyridin-2(1H)-one;
3-chloro-4-[(2,4-difluorobenzyl)oxy]-1-[(3-glycoloyl-2,3-dihydro-1H-benzimidazol-5-yl)methyl]pyridin-2(1H)-one;

1-[(1-acetyl-3-glycoloyl-2,3-dihydro-1H-benzimidazol-5-yl)methyl]-3-chloro-4-[(2,4-difluorobenzyl)oxy]pyridin-2(1H)-one;

3-chloro-4-[(2,4-difluorobenzyl)oxy]-1-[(1,3-diglycoloyl-2,3-dihydro-1H-benzimidazol-5-yl)methyl]pyridin-2(1H)-one;

3-chloro-4-[(2,4-difluorobenzyl)oxy]-1-{[3-glycoloyl-1-(2-hydroxy-2-methylpropanoyl)-2,3-dihydro-1H-benzimidazol-5-yl]methyl}pyridin-2(1H)-one;

3-chloro-4-[(2,4-difluorobenzyl)oxy]-1-{[3-glycoloyl-1-(N-methylglycyl)-2,3-dihydro-1H-benzimidazol-5-yl]methyl}pyridin-2(1H)-one;

3-chloro-4-[(2,4-difluorobenzyl)oxy]-1-{[3-glycoloyl-1-(3-hydroxypropanoyl)-2,3-dihydro-1H-benzimidazol-5-yl]methyl}pyridin-2(1H)-one;

3-chloro-4-[(2,4-difluorobenzyl)oxy]-1-{[3-glycoloyl-1-(3-hydroxy-3-methylbutanoyl)-2,3-dihydro-1H-benzimidazol-5-yl]methyl}pyridin-2(1H)-one;

5-{[3-chloro-4-[(2,4-difluorobenzyl)oxy]-2-oxopyridin-1(2H)-yl]methyl}-3-glycoloyl-2,3-dihydro-1H-benzimidazole-1-carboxamide;

3-chloro-4-[(2,4-difluorobenzyl)oxy]-1-{[3-glycoloyl-1-(methylsulfonyl)-2,3-dihydro-1H-benzimidazol-5-yl]methyl}pyridin-2(1H)-one;

3-chloro-4-[(2,4-difluorobenzyl)oxy]-1-{[3-(2-hydroxy-2-methylpropanoyl)-2,3-dihydro-1H-benzimidazol-5-yl]methyl}pyridin-2(1H)-one;

1-{[1-acetyl-3-(2-hydroxy-2-methylpropanoyl)-2,3-dihydro-1H-benzimidazol-5-yl]methyl}-3-chloro-4-[(2,4-difluorobenzyl)oxy]pyridin-2(1H)-one;

3-chloro-4-[(2,4-difluorobenzyl)oxy]-1-{[1-glycoloyl-3-(2-hydroxy-2-methylpropanoyl)-2,3-dihydro-1H-benzimidazol-5-yl]methyl}pyridin-2(1H)-one;

1-{[1,3-bis(2-hydroxy-2-methylpropanoyl)-2,3-dihydro-1H-benzimidazol-5-yl]methyl}-3-chloro-4-[(2,4-difluorobenzyl)oxy]pyridin-2(1H)-one;

3-chloro-4-[(2,4-difluorobenzyl)oxy]-1-{[3-(2-hydroxy-2-methylpropanoyl)-1-(N-methylglycyl)-2,3-dihydro-1H-benzimidazol-5-yl]methyl}pyridin-2(1H)-one;

3-chloro-4-[(2,4-difluorobenzyl)oxy]-1-{[3-(2-hydroxy-2-methylpropanoyl)-1-(3-hydroxypropanoyl)-2,3-dihydro-1H-benzimidazol-5-yl]methyl}pyridin-2(1H)-one;

3-chloro-4-[(2,4-difluorobenzyl)oxy]-1-{[1-(3-hydroxy-3-methylbutanoyl)-3-(2-hydroxy-2-methylpropanoyl)-2,3-dihydro-1H-benzimidazol-5-yl]methyl}pyridin-2(1H)-one;

5-{[3-chloro-4-[(2,4-difluorobenzyl)oxy]-2-oxopyridin-1(2H)-yl]methyl}-3-(2-hydroxy-2-methylpropanoyl)-2,3-dihydro-1H-benzimidazole-1-carboxamide;

3-chloro-4-[(2,4-difluorobenzyl)oxy]-1-{[3-(2-hydroxy-2-methylpropanoyl)-1-(methylsulfonyl)-2,3-dihydro-1H-benzimidazol-5-yl]methyl}pyridin-2(1H)-one;

3-chloro-4-[(2,4-difluorobenzyl)oxy]-1-{[3-(N-methylglycyl)-2,3-dihydro-1H-benzimidazol-5-yl]methyl}pyridin-2(1H)-one;

1-{[1-acetyl-3-(N-methylglycyl)-2,3-dihydro-1H-benzimidazol-5-yl]methyl}-3-chloro-4-[(2,4-difluorobenzyl)oxy]pyridin-2 (1H)-one;

3-chloro-4-[(2,4-difluorobenzyl)oxy]-1-{[1-glycoloyl-3-(N-methylglycyl)-2,3-dihydro-1H-benzimidazol-5-yl]methyl}pyridin-2(1H)-one;

3-chloro-4-[(2,4-difluorobenzyl)oxy]-1-{[1-(2-hydroxy-2-methylpropanoyl)-3-(N-methylglycyl)-2,3-dihydro-1H-benzimidazol-5-yl]methyl}pyridin-2(1H)-one;

1-{[1,3-bis(N-methylglycyl)-2,3-dihydro-1H-benzimidazol-5-yl]methyl}-3-chloro-4-[(2,4-difluorobenzyl)oxy]pyridin-2(1H)-one;

3-chloro-4-[(2,4-difluorobenzyl)oxy]-1-{[1-(3-hydroxypropanoyl)-3-(N-methylglycyl)-2,3-dihydro-1H-benzimidazol-5-yl]methyl}pyridin-2(1H)-one;

3-chloro-4-[(2,4-difluorobenzyl)oxy]-1-{[1-(3-hydroxy-3-methylbutanoyl)-3-(N-methylglycyl)-2,3-dihydro-1H-benzimidazol-5-yl]methyl}pyridin-2(1H)-one;

5-{[3-chloro-4-[(2,4-difluorobenzyl)oxy]-2-oxopyridin-1(2H)-yl]methyl}-3-(N-methylglycyl)-2,3-dihydro-1H-benzimidazole-1-carboxamide;

3-chloro-4-[(2,4-difluorobenzyl)oxy]-1-{[3-(N-methylglycyl)-1-(methylsulfonyl)-2,3-dihydro-1H-benzimidazol-5-yl]methyl}pyridin-2(1H)-one;

3-chloro-4-[(2,4-difluorobenzyl)oxy]-1-{[3-(3-hydroxypropanoyl)-2,3-dihydro-1H-benzimidazol-5-yl]methyl}pyridin-2(1H)-one;

1-{-[1-acetyl-3-(3-hydroxypropanoyl)-2,3-dihydro-1H-benzimidazol-5-yl]methyl}-3-chloro-4-[(2,4-difluorobenzyl)oxy]pyridin-2(1H)-one;

3-chloro-4-[(2,4-difluorobenzyl)oxy]-1-{[1-glycoloyl-3-(3-hydroxypropanoyl)-2,3-dihydro-1H-benzimidazol-5-yl]methyl}pyridin-2(1H)-one;

3-chloro-4-[(2,4-difluorobenzyl)oxy]-1-{[1-(2-hydroxy-2-methylpropanoyl)-3-(3-hydroxypropanoyl)-2,3-dihydro-1H-benzimidazol-5-yl]methyl}pyridin-2(1H)-one;

3-chloro-4-[(2,4-difluorobenzyl)oxy]-1-{[3-(3-hydroxypropanoyl)-1-(N-methylglycyl)-2,3-dihydro-1H-benzimidazol-5-yl]methyl}pyridin-2(1H)-one;

1-{[1,3-bis(3-hydroxypropanoyl)-2,3-dihydro-1H-benzimidazol-5-yl]methyl}-3-chloro-4-[(2,4-difluorobenzyl)oxy]pyridin-2(1H)-one;

3-chloro-4-[(2,4-difluorobenzyl)oxy]-1-{[1-(3-hydroxy-3-methylbutanoyl)-3-(3-hydroxypropanoyl)-2,3-dihydro-1H-benzimidazol-5-yl]methyl}pyridin-2(1H)-one;

5-{[3-chloro-4-[(2,4-difluorobenzyl)oxy]-2-oxopyridin-1(2H)-yl]methyl}-3-(3-hydroxypropanoyl)-2,3-dihydro-1H-benzimidazole-1-carboxamide;

3-chloro-4-[(2,4-difluorobenzyl)oxy]-1-{[3-(3-hydroxypropanoyl)-1-(methylsulfonyl)-2,3-dihydro-1H-benzimidazol-5-yl]methyl}pyridin-2(1H)-one;

3-chloro-4-[(2,4-difluorobenzyl)oxy]-1-{[3-(3-hydroxy-3-methylbutanoyl)-2,3-dihydro-1H-benzimidazol-5-yl]methyl}pyridin-2(1H)-one;

1-{[1-acetyl-3-(3-hydroxy-3-methylbutanoyl)-2,3-dihydro-1H-benzimidazol-5-yl]methyl}-3-chloro-4-[(2,4-difluorobenzyl)oxy]pyridin-2(1H)-one;

3-chloro-4-[(2,4-difluorobenzyl)oxy]-1-{[1-glycoloyl-3-(3-hydroxy-3-methylbutanoyl)-2,3-dihydro-1H-benzimidazol-5-yl]methyl}pyridin-2(1H)-one;

3-chloro-4-[(2,4-difluorobenzyl)oxy]-1-{[3-(3-hydroxy-3-methylbutanoyl)-1-(2-hydroxy-2-methylpropanoyl)-2,3-dihydro-1H-benzimidazol-5-yl]methyl}pyridin-2(1H)-one;

3-chloro-4-[(2,4-difluorobenzyl)oxy]-1-{[3-(3-hydroxy-3-methylbutanoyl)-1-(N-methylglycyl)-2,3-dihydro-1H-benzimidazol-5-yl]methyl}pyridin-2(1H)-one;

3-chloro-4-[(2,4-difluorobenzyl)oxy]-1-{[3-(3-hydroxy-3-methylbutanoyl)-1-(methylsulfonyl)-2,3-dihydro-1H-benzimidazol-5-yl]methyl}pyridin-2(1H)-one;

5-{[3-chloro-4-[(2,4-difluorobenzyl)oxy]-2-oxopyridin-1(2H)-yl]methyl}-3-(3-hydroxy-3-methylbutanoyl)-2,3-dihydro-1H-benzimidazole-1-carboxamide;

1-{[1,3-bis(3-hydroxy-3-methylbutanoyl)-2,3-dihydro-1H-benzimidazol-5-yl]methyl}-3-chloro-4-[(2,4-difluorobenzyl)oxy]pyridin-2(1H)-one;

3-chloro-4-[(2,4-difluorobenzyl)oxy]-1-{[3-(3-hydroxy-3-methylbutanoyl)-1-(3-hydroxypropanoyl)-2,3-dihydro-1H-benzimidazol-5-yl]methyl}pyridin-2(1H)-one;

6-{[3-chloro-4-[(2,4-difluorobenzyl)oxy]-2-oxopyridin-1(2H)-yl]methyl}-2,3-dihydro-1H-benzimidazole-1-carboxamide;

3-acetyl-6-{[3-chloro-4-[(2,4-difluorobenzyl)oxy]-2-oxopyridin-1(2H)-yl]methyl}-2,3-dihydro-1H-benzimidazole-1-carboxamide;

6-{[3-chloro-4-[(2,4-difluorobenzyl)oxy]-2-oxopyridin-1(2H)-yl]methyl}-3-glycoloyl-2,3-dihydro-1H-benzimidazole-1-carboxamide;

6-{[3-chloro-4-[(2,4-difluorobenzyl)oxy]-2-oxopyridin-1(2H)-yl]methyl}-3-(2-hydroxy-2-methylpropanoyl)-2,3-dihydro-1H-benzimidazole-1-carboxamide;

6-{[3-chloro-4-[(2,4-difluorobenzyl)oxy]-2-oxopyridin-1(2H)-yl]methyl}-3-(N-methylglycyl)-2,3-dihydro-1H-benzimidazole-1-carboxamide;

6-{[3-chloro-4-[(2,4-difluorobenzyl)oxy]-2-oxopyridin-1(2H)-yl]methyl}-3-(3-hydroxypropanoyl)-2,3-dihydro-1H-benzimidazole-1-carboxamide;

6-{[3-chloro-4-[(2,4-difluorobenzyl)oxy]-2-oxopyridin-1(2H)-yl]methyl}-3-(3-hydroxy-3-methylbutanoyl)-2,3-dihydro-1H-benzimidazole-1-carboxamide;

5-{[3-chloro-4-[(2,4-difluorobenzyl)oxy]-2-oxopyridin-1(2H)-yl]methyl}-1H-benzimidazole-1,3(2H)-dicarboxamide;

6-{[3-chloro-4-[(2,4-difluorobenzyl)oxy]-2-oxopyridin-1(2H)-yl]methyl}-3-(methylsulfonyl)-2,3-dihydro-1H-benzimidazole-1-carboxamide;

3-chloro-4-[(2,4-difluorobenzyl)oxy]-1-{[3-(methylsulfonyl)-2,3-dihydro-1H-benzimidazol-5-yl]methyl}pyridin-2(1H)-one;

1-{[1-acetyl-3-(methylsulfonyl)-2,3-dihydro-1H-benzimidazol-5-yl]methyl}-3-chloro-4-[(2,4-difluorobenzyl)oxy]pyridin-2(1H)-one;

3-chloro-4-[(2,4-difluorobenzyl)oxy]-1-{[1-glycoloyl-3-(methylsulfonyl)-2,3-dihydro-1H-benzimidazol-5-yl]methyl}pyridin-2(1H)-one;

3-chloro-4-[(2,4-difluorobenzyl)oxy]-1-{[1-(2-hydroxy-2-methylpropanoyl)-3-(methylsulfonyl)-2,3-dihydro-1H-benzimidazol-5-yl]methyl}pyridin-2(1H)-one;

3-chloro-4-[(2,4-difluorobenzyl)oxy]-1-{[1-(N-methylglycyl)-3-(methylsulfonyl)-2,3-dihydro-1H-benzimidazol-5-yl]methyl}pyridin-2(1H)-one;

3-chloro-4-[(2,4-difluorobenzyl)oxy]-1-{[1-(3-hydroxypropanoyl)-3-(methylsulfonyl)-2,3-dihydro-1H-benzimidazol-5-yl]methyl}pyridin-2(1H)-one;

3-chloro-4-[(2,4-difluorobenzyl)oxy]-1-{[1-(3-hydroxy-3-methylbutanoyl)-3-(methylsulfonyl)-2,3-dihydro-1H-benzimidazol-5-yl]methyl}pyridin-2(1H)-one;

5-{[3-chloro-4-[(2,4-difluorobenzyl)oxy]-2-oxopyridin-1(2H)-yl]methyl}-3-(methylsulfonyl)-2,3-dihydro-1H-benzimidazole-1-carboxamide;

1-{[1,3-bis(methylsulfonyl)-2,3-dihydro-1H-benzimidazol-5-yl]methyl}-3-chloro-4-[(2,4-difluorobenzyl)oxy]pyridin-2(1H)-one;

5-{[3-chloro-4-[(2,4-difluorobenzyl)oxy]-2-oxopyridin-1(2H)-yl]methyl}-1,3-dihydro-2H-benzimidazol-2-one;

1-acetyl-5-{[3-chloro-4-[(2,4-difluorobenzyl)oxy]-2-oxopyridin-1(2H)-yl]methyl}-1,3-dihydro-2H-benzimidazol-2-one;

5-{[3-chloro-4-[(2,4-difluorobenzyl)oxy]-2-oxopyridin-1(2H)-yl]methyl}-1-glycoloyl-1,3-dihydro-2H-benzimidazol-2-one;

5-{[3-chloro-4-[(2,4-difluorobenzyl)oxy]-2-oxopyridin-1(2H)-yl]methyl}-1-(2-hydroxy-2-methylpropanoyl)-1,3-dihydro-2H-benzimidazol-2-one;

5-{[3-chloro-4-[(2,4-difluorobenzyl)oxy]-2-oxopyridin-1(2H)-yl]methyl}-1-(N-methylglycyl)-1,3-dihydro-2H-benzimidazol-2-one;

5-{[3-chloro-4-[(2,4-difluorobenzyl)oxy]-2-oxopyridin-1(2H)-yl]methyl}-1-(3-hydroxypropanoyl)-1,3-dihydro-2H-benzimidazol-2-one;

5-{[3-chloro-4-[(2,4-difluorobenzyl)oxy]-2-oxopyridin-1(2H)-yl]methyl}-1-(3-hydroxy-3-methylbutanoyl)-1,3-dihydro-2H-benzimidazol-2-one;

5-{[3-chloro-4-[(2,4-difluorobenzyl)oxy]-2-oxopyridin-1(2H)-yl]methyl}-2-oxo-2,3-dihydro-1H-benzimidazole-1-carboxamide;

5-{[3-chloro-4-[(2,4-difluorobenzyl)oxy]-2-oxopyridin-1(2H)-yl]methyl}-1-(methylsulfonyl)-1,3-dihydro-2H-benzimidazol-H -one;

1-acetyl-6-{[3-chloro-4-[(2,4-difluorobenzyl)oxy]-2-oxopyridin-1(2H)-yl]methyl}-1,3-dihydro-2H-benzimidazol-2-one;

1,3-diacetyl-5-{[3-chloro-4-[(2,4-difluorobenzyl)oxy]-2-oxopyridin-1(2H)-yl]methyl}-1,3-dihydro-2H-benzimidazol-2-one;

3-acetyl-5-{[3-chloro-4-[(2,4-difluorobenzyl)oxy]-2-oxopyridin-1(2H)-yl]methyl}-1-glycoloyl-1,3-dihydro-2H-benzimidazol-2-one;

3-acetyl-5-{[3-chloro-4-[(2,4-difluorobenzyl)oxy]-2-oxopyridin-1(2H)-yl]methyl}-1-(2-hydroxy-2-methylpropanoyl)-1,3-dihydro-2H-benzimidazol-2-one;

3-acetyl-5-{[3-chloro-4-[(2,4-difluorobenzyl)oxy]-2-oxopyridin-1(2H)-yl]methyl}-1-(N-methylglycyl)-1,3-dihydro-2H-benzimidazol-2-one;

3-acetyl-5-{[3-chloro-4-[(2,4-difluorobenzyl)oxy]-2-oxopyridin-1(2H)-yl]methyl}-1-(3-hydroxypropanoyl)-1,3-dihydro-2H-benzimidazol-2-one;

3-acetyl-5-{[3-chloro-4-[(2,4-difluorobenzyl)oxy]-2-oxopyridin-1(2H)-yl]methyl}-1-(3-hydroxy-3-methylbutanoyl)-1,3-dihydro-2H-benzimidazol-2-one;

3-acetyl-5-{[3-chloro-4-[(2,4-difluorobenzyl)oxy]-2-oxopyridin-1(2H)-yl]methyl}-2-oxo-2,3-dihydro-1H-benzimidazole-1-carboxamide;

3-acetyl-5-{[3-chloro-4-[(2,4-difluorobenzyl)oxy]-2-oxopyridin-1(2H)-yl]methyl}-1-(methylsulfonyl)-1,3-dihydro-2H-benzimidazol-2-one;

6-{[3-chloro-4-[(2,4-difluorobenzyl)oxy]-2-oxopyridin-1(2H)-yl]methyl}-1-glycoloyl-1,3-dihydro-2H-benzimidazol-2-one;

1-acetyl-5-{[3-chloro-4-[(2,4-difluorobenzyl)oxy]-2-oxopyridin-1(2H)-yl]methyl}-3-glycoloyl-1,3-dihydro-2H-benzimidazol-2-one;

5-{[3-chloro-4-[(2,4-difluorobenzyl)oxy]-2-oxopyridin-1(2H)-yl]methyl}-1,3-diglycoloyl-1,3-dihydro-2H-benzimidazol-2-one;

5-{[3-chloro-4-[(2,4-difluorobenzyl)oxy]-2-oxopyridin-1(2H)-yl]methyl}-3-glycoloyl-1-(2-hydroxy-2-methylpropanoyl)-1,3-dihydro-2H-benzimidazol-2-one;

5-{[3-chloro-4-[(2,4-difluorobenzyl)oxy]-2-oxopyridin-1(2H)-yl]methyl}-3-glycoloyl-1-(N-methylglycyl)-1,3-dihydro-2H-benzimidazol-2-one;

5-{[3-chloro-4-[(2,4-difluorobenzyl)oxy]-2-oxopyridin-1(2H)-yl]methyl}-3-glycoloyl-1-(3-hydroxypropanoyl)-1,3-dihydro-2H-benzimidazol-2-one;

5-{[3-chloro-4-[(2,4-difluorobenzyl)oxy]-2-oxopyridin-1(2H)-yl]methyl}-3-glycoloyl-1-(3-hydroxy-3-methylbutanoyl)-1,3-dihydro-2H-benzimidazol-2-one;

5-{[3-chloro-4-[(2,4-difluorobenzyl)oxy]-2-oxopyridin-1(2H)-yl]methyl}-3-glycoloyl-2-oxo-2,3-dihydro-1H-benzimidazole-1-carboxamide;

5-{[3-chloro-4-[(2,4-difluorobenzyl)oxy]-2-oxopyridin-1(2H)-yl]methyl}-3-glycoloyl-1-(methylsulfonyl)-1,3-dihydro-2H-benzimidazol-2-one;

6-{[3-chloro-4-[(2,4-difluorobenzyl)oxy]-2-oxopyridin-1(2H)-yl]methyl}-1-(2-hydroxy-2-methylpropanoyl)-1,3-dihydro-2H-benzimidazol-2-one;

1-acetyl-5-{[3-chloro-4-[(2,4-difluorobenzyl)oxy]-2-oxopyridin-1(2H)-yl]methyl}-3-(2-hydroxy-2-methylpropanoyl)-1,3-dihydro-2H-benzimidazol-2-one;

5-{[3-chloro-4-[(2,4-difluorobenzyl)oxy]-2-oxopyridin-1(2H)-yl]methyl}-1-glycoloyl-3-(2-hydroxy-2-methylpropanoyl)-1,3-dihydro-2H-benzimidazol-2-one;

5-{[3-chloro-4-[(2,4-difluorobenzyl)oxy]-2-oxopyridin-1(2H)-yl]methyl}-1,3-bis(2-hydroxy-2-methylpropanoyl)-1,3-dihydro-2H-benzimidazol-2-one;

5-{[3-chloro-4-[(2,4-difluorobenzyl)oxy]-2-oxopyridin-1(2H)-yl]methyl}-3-(2-hydroxy-2-methylpropanoyl)-1-(N-methylglycyl)-1,3-dihydro-2H-benzimidazol-2-one;

5-{[3-chloro-4-[(2,4-difluorobenzyl)oxy]-2-oxopyridin-1(2H)-yl]methyl}-3-(2-hydroxy-2-methylpropanoyl)-1-(3-hydroxypropanoyl)-1,3-dihydro-2H-benzimidazol-2-one;

5-{[3-chloro-4-[(2,4-difluorobenzyl)oxy]-2-oxopyridin-1(2H)-yl]methyl}-1-(3-hydroxy-3-methylbutanoyl)-3-(2-hydroxy-2-methylpropanoyl)-1,3-dihydro-2H-benzimidazol-2-one;

5-{[3-chloro-4-[(2,4-difluorobenzyl)oxy]-2-oxopyridin-1(2H)-yl]methyl}-3-(2-hydroxy-2-methylpropanoyl)-2-oxo-2,3-dihydro-1H-benzimidazole-1-carboxamide;

5-{[3-chloro-4-[(2,4-difluorobenzyl)oxy]-2-oxopyridin-1(2H)-yl]methyl}-3-(2-hydroxy-2-methylpropanoyl)-1-(methylsulfonyl)-1,3-dihydro-2H-benzimidazol-2-one;

6-{[3-chloro-4-[(2,4-difluorobenzyl)oxy]-2-oxopyridin-1(2H)-yl]methyl}-1-(N-methylglycyl)-1,3-dihydro-2H-benzimidazol-2-one;

1-acetyl-5-{[3-chloro-4-[(2,4-difluorobenzyl)oxy]-2-oxopyridin-1(2H)-yl]methyl}-3-(N-methylglycyl)-1,3-dihydro-2H-benzimidazol-2-one;

5-{[3-chloro-4-[(2,4-difluorobenzyl)oxy]-2-oxopyridin-1(2H)-yl]methyl}-1-glycoloyl-3-(N-methylglycyl)-1,3-dihydro-2H-benzimidazol-2-one;

5-{[3-chloro-4-[(2,4-difluorobenzyl)oxy]-2-oxopyridin-1(2H)-yl]methyl}-1-(2-hydroxy-2-methylpropanoyl)-3-(N-methylglycyl)-1,3-dihydro-2H-benzimidazol-2-one;

5-{[3-chloro-4-[(2,4-difluorobenzyl)oxy]-2-oxopyridin-1(2H)-yl]methyl}-1,3-bis(N-methylglycyl)-1,3-dihydro-2H-benzimidazol-2-one;

5-{[3-chloro-4-[(2,4-difluorobenzyl)oxy]-2-oxopyridin-1(2H)-yl]methyl}-1-(3-hydroxypropanoyl)-3-(N-methylglycyl)-1,3-dihydro-2H-benzimidazol-2-one;

5-{[3-chloro-4-[(2,4-difluorobenzyl)oxy]-2-oxopyridin-1(2H)-yl]methyl}-1-(3-hydroxy-3-methylbutanoyl)-3-(N-methylglycyl)-1,3-dihydro-2H-benzimidazol-2-one;

5-{[3-chloro-4-[(2,4-difluorobenzyl)oxy]-2-oxopyridin-1(2H)-yl]methyl}-3-(N-methylglycyl)-2-oxo-2,3-dihydro-1H-benzimidazole-1-carboxamide;

5-{[3-chloro-4-[(2,4-difluorobenzyl)oxy]-2-oxopyridin-1(2H)-yl]methyl}-3-(N-methylglycyl)-1-(methylsulfonyl)-1,3-dihydro-2H-benzimidazol-2-one;

6-{[3-chloro-4-[(2,4-difluorobenzyl)oxy]-2-oxopyridin-1(2H)-yl]methyl}-1-(3-hydroxypropanoyl)-1,3-dihydro-2H-benzimidazol-2-one;

1-acetyl-5-{[3-chloro-4-[(2,4-difluorobenzyl)oxy]-2-oxopyridin-1(2H)-yl]methyl}-3-(3-hydroxypropanoyl)-1,3-dihydro-2H-benzimidazol-2-one;

5-{[3-chloro-4-[(2,4-difluorobenzyl)oxy]-2-oxopyridin-1(2H)-yl]methyl}-1-glycoloyl-3-(3-hydroxypropanoyl)-1,3-dihydro-2H-benzimidazol-2-one;

5-{[3-chloro-4-[(2,4-difluorobenzyl)oxy]-2-oxopyridin-1(2H)-yl]methyl}-1-(2-hydroxy-2-methylpropanoyl)-3-(3-hydroxypropanoyl)-1,3-dihydro-2H-benzimidazol-2-one;

5-{[3-chloro-4-[(2,4-difluorobenzyl)oxy]-2-oxopyridin-1(2H)-yl]methyl}-3-(3-hydroxypropanoyl)-1-(N-methylglycyl)-1,3-dihydro-2H-benzimidazol-2-one;

5-{[3-chloro-4-[(2,4-difluorobenzyl)oxy]-2-oxopyridin-1(2H)-yl]methyl}-1,3-bis(3-hydroxypropanoyl)-1,3-dihydro-2H-benzimidazol-2-one;

5-{[3-chloro-4-[(2,4-difluorobenzyl)oxy]-2-oxopyridin-1(2H)-yl]methyl}-1-(3-hydroxy-3-methylbutanoyl)-3-(3-hydroxypropanoyl)-1,3-dihydro-2H-benzimidazol-2-one;

5-{[3-chloro-4-[(2,4-difluorobenzyl)oxy]-2-oxopyridin-1(2H)-yl]methyl}-3-(3-hydroxypropanoyl)-2-oxo-2,3-dihydro-1H-benzimidazole-1-carboxamide;

5-{[3-chloro-4-[(2,4-difluorobenzyl)oxy]-2-oxopyridin-1(2H)-yl]methyl}-3-(3-hydroxypropanoyl)-1-(methylsulfonyl)-1,3-dihydro-2H-benzimidazol-2-one;

6-{[3-chloro-4-[(2,4-difluorobenzyl)oxy]-2-oxopyridin-1(2H)-yl]methyl}-1-(3-hydroxy-3-methylbutanoyl)-1,3-dihydro-2H-benzimidazol-2-one;

1-acetyl-5-{[3-chloro-4-[(2,4-difluorobenzyl)oxy]-2-oxopyridin-1(2H)-yl]methyl}-3-(3-hydroxy-3-methylbutanoyl)-1,3-dihydro-2H-benzimidazol-2-one;

5-{[3-chloro-4-[(2,4-difluorobenzyl)oxy]-2-oxopyridin-1(2H)-yl]methyl}-1-glycoloyl-3-(3-hydroxy-3-methylbutanoyl)-1,3-dihydro-2H-benzimidazol-2-one;

5-{[3-chloro-4-[(2,4-difluorobenzyl)oxy]-2-oxopyridin-1(2H)-yl]methyl}-3-(3-hydroxy-3-methylbutanoyl)-1-(2-hydroxy-2-methylpropanoyl)-1,3-dihydro-2H-benzimidazol-2-one;

5-{[3-chloro-4-[(2,4-difluorobenzyl)oxy]-2-oxopyridin-1(2H)-yl]methyl}-3-(3-hydroxy-3-methylbutanoyl)-1-(N-methylglycyl)-1,3-dihydro-2H-benzimidazol-2-one;

5-{[3-chloro-4-[(2,4-difluorobenzyl)oxy]-2-oxopyridin-1(2H)-yl]methyl}-3-(3-hydroxy-3-methylbutanoyl)-1-(3-hydroxypropanoyl)-1,3-dihydro-2H-benzimidazol-2-one;

5-{[3-chloro-4-[(2,4-difluorobenzyl)oxy]-2-oxopyridin-1(2H)-yl]methyl}-1,3-bis(3-hydroxy-3-methylbutanoyl)-1,3-dihydro-2H-benzimidazol-2-one;

5-{[3-chloro-4-[(2,4-difluorobenzyl)oxy]-2-oxopyridin-1(2H)-yl]methyl}-3-(3-hydroxy-3-methylbutanoyl)-2-oxo-2,3-dihydro-1H-benzimidazole-1-carboxamide;

5-{[3-chloro-4-[(2,4-difluorobenzyl)oxy]-2-oxopyridin-1(2H)-yl]methyl}-3-(3-hydroxy-3-methylbutanoyl)-1-(methylsulfonyl)-1,3-dihydro-2H-benzimidazol-2-one;

6-{[3-chloro-4-[(2,4-difluorobenzyl)oxy]-2-oxopyridin-1(2H)-yl]methyl}-2-oxo-2,3-dihydro-1H-benzimidazole-1-carboxamide;

3-acetyl-6-{[3-chloro-4-[(2,4-difluorobenzyl)oxy]-2-oxopyridin-1(2H)-yl]methyl}-2-oxo-2,3-dihydro-1H-benzimidazole-1-carboxamide;

6-{[3-chloro-4-[(2,4-difluorobenzyl)oxy]-2-oxopyridin-1(2H)-yl]methyl}-3-glycoloyl-2-oxo-2,3-dihydro-1H-benzimidazole-1-carboxamide;

6-{[3-chloro-4-[(2,4-difluorobenzyl)oxy]-2-oxopyridin-1(2H)-yl]methyl}-3-(2-hydroxy-2-methylpropanoyl)-2-oxo-2,3-dihydro-1H-benzimidazole-1-carboxamide;

6-{[3-chloro-4-[(2,4-difluorobenzyl)oxy]-2-oxopyridin-1(2H)-yl]methyl}-3-(N-methylglycyl)-2-oxo-2,3-dihydro-1H-benzimidazole-1-carboxamide;

6-{[3-chloro-4-[(2,4-difluorobenzyl)oxy]-2-oxopyridin-1(2H)-yl]methyl}-3-(3-hydroxypropanoyl)-2-oxo-2,3-dihydro-1H-benzimidazole-1-carboxamide;

6-{[3-chloro-4-[(2,4-difluorobenzyl)oxy]-2-oxopyridin-1(2H)-yl]methyl}-3-(3-hydroxy-3-methylbutanoyl)-2-oxo-2,3-dihydro-1H-benzimidazole-1-carboxamide;

5-{[3-chloro-4-[(2,4-difluorobenzyl)oxy]-2-oxopyridin-1(2H)-yl]methyl}-2-oxo-1H-benzimidazole-1,3(2H)-dicarboxamide;

6-{[3-chloro-4-[(2,4-difluorobenzyl)oxy]-2-oxopyridin-1(2H)-yl]methyl}-3-(methylsulfonyl)-2-oxo-2,3-dihydro-1H-benzimidazole-1-carboxamide;

6-{[3-chloro-4-[(2,4-difluorobenzyl)oxy]-2-oxopyridin-1(2H)-yl]methyl}-1-(methylsulfonyl)-1,3-dihydro-2H-benzimidazol-2-one;

1-acetyl-5-{[3-chloro-4-[(2,4-difluorobenzyl)oxy]-2-oxopyridin-1(2H)-yl]methyl}-3-(methylsulfonyl)-1,3-dihydro-2H-benzimidazol-2-one;

5-{[3-chloro-4-[(2,4-difluorobenzyl)oxy]-2-oxopyridin-1(2H)-yl]methyl}-1-glycoloyl-3-(methylsulfonyl)-1,3-dihydro-2H-benzimidazol-2-one;

5-{[3-chloro-4-[(2,4-difluorobenzyl)oxy]-2-oxopyridin-1(2H)-yl]methyl}-1-(2-hydroxy-2-methylpropanoyl)-3-(methylsulfonyl)-1,3-dihydro-2H-benzimidazol-2-one;

5-{[3-chloro-4-[(2,4-difluorobenzyl)oxy]-2-oxopyridin-1(2H)-yl]methyl}-1-(N-methylglycyl)-3-(methylsulfonyl)-1,3-dihydro-2H-benzimidazol-2-one;

5-{[3-chloro-4-[(2,4-difluorobenzyl)oxy]-2-oxopyridin-1(2H)-yl]methyl}-1-(3-hydroxypropanoyl)-3-(methylsulfonyl)-1,3-dihydro-2H-benzimidazol-2-one;

5-{[3-chloro-4-[(2,4-difluorobenzyl)oxy]-2-oxopyridin-1(2H)-yl]methyl}-1-(3-hydroxy-3-methylbutanoyl)-3-(methylsulfonyl)-1,3-dihydro-2H-benzimidazol-2-one;

5-{[3-chloro-4-[(2,4-difluorobenzyl)oxy]-2-oxopyridin-1(2H)-yl]methyl}-3-(methylsulfonyl)-2-oxo-2,3-dihydro-1H-benzimidazole-1-carboxamide;

5-{[3-chloro-4-[(2,4-difluorobenzyl)oxy]-2-oxopyridin-1(2H)-yl]methyl}-1,3-bis(methylsulfonyl)-1,3-dihydro-2H-benzimidazol-2-one;

3-benzyl-4-hydroxy-1-(2-phenylethyl)pyridin-2(1H)-one;

1-benzyl-4-hydroxy-2-oxo-1,2-dihydropyridine-3-carbaldehyde;

1-benzyl-4-chloro-2-oxo-1,2-dihydropyridine-3-carbaldehyde;

methyl 5-chloro-1-(4-chlorobenzyl)-6-oxo-1,6-dihydropyridine-3-carboxylate;

5-bromo-1-(2-chloro-6-fluorobenzyl)-3-methylpyridin-2(1H)-one;

3-bromo-1-(2,6-dichlorophenyl)-4-[(4-fluorophenyl)ethynyl]-6-methylpyridin-2(1H)-one;

3-bromo-1-(2,6-dichlorophenyl)-4-[(4-fluorophenyl)ethynyl]-6-methylpyridin-2(1H)-one;

methyl 3-chloro-4-[4-[(2,4-difluorobenzyl)oxy-6-methyl-2-oxopyridin-1(2H)-yl]benzoate;

4-[(2,4-difluorobenzyl)oxy]-1-(3-fluorobenzyl)-2-oxo-1,2-dihydropyridine-3-carbonitrile;

4-[(2,4-difluorobenzyl)oxy]-6-(hydroxymethyl)-1-(2,4,6-trifluorophenyl)pyridin-2(1H)-one;

4-[(2,4-difluorobenzyl)oxy]-6-methyl-1-[2-(trifluoromethyl)phenyl]pyridin-2(1H)-one;

3-[4-[(2,4-difluorobenzyl)oxy]-6-methyl-2-oxopyridin-1(2H)-yl]benzaldehyde;

4-[(2,4-difluorobenzyl)oxy]-1-(2,6-difluoro-4-morpholin-4-ylphenyl)-6-methylpyridin-2(1H)-one;

4-[(2,4-difluorobenzyl)oxy]-1-[2,6-difluoro-4-(4-methylpiperazin-1-yl)phenyl]-6-methylpyridin-2(1H)-one;

3-[3-bromo-4-[(2,4-difluorobenzyl)oxy]-6-methyl-2-oxopyridin-1(2H)-yl]benzoic acid;

4-[(2,4-difluorobenzyl)oxy]-1-[4-(dimethylamino)-2,6-difluorophenyl]-6-methylpyridin-2(1H)-one;

4-[(2,4-difluorobenzyl)oxy]-1-{2,6-difluoro-4-[(2-hydroxyethyl)(methyl)amino]phenyl}-6-methylpyridin-2(1H)-one;

methyl 3-[3-bromo-4-[(2,4-difluorobenzyl)oxy]-6-methyl-2-oxopyridin-1(2H)-yl]benzoate;

3-[4-[(2,4-difluorobenzyl)oxy]-6-methyl-2-oxopyridin-1(2H)-yl]-4-methylbenzoic acid;

4-[(2,4-difluorobenzyl)oxy]-1-(2,6-difluorophenyl)-6-(hydroxymethyl)pyridin-2(1H)-one;

3-bromo-1-{[5-(chloromethyl)pyrazin-2-yl]methyl}-4-[(2,4-difluorobenzyl)oxy]-6-methylpyridin-2(1H)-one;

1-[2-chloro-5-(hydroxymethyl)phenyl]-4-[(2,4-difluorobenzyl)oxy]-6-methylpyridin-2(1H)-one;

4-[(2,4-difluorobenzyl)oxy]-1-(2,6-difluoro-4-hydroxyphenyl)-6-methylpyridin-2(1H)-one;

3-bromo-4-[(2,4-difluorobenzyl)oxy]-1-[4-(hydroxymethyl)-2-methoxyphenyl]-6-methylpyridin-2(1H)-one;

methyl 3-[3-bromo-4-[(2,4-difluorobenzyl)oxy]-6-methyl-2-oxopyridin-1(2H)-yl]-4-methylbenzoate;

3-bromo-4-[(2,4-difluorobenzyl)oxy]-6-methyl-1-{3-[(4-methylpiperazin-1-yl)carbonyl]phenyl}pyridin-2(1H)-one;

3-[3-bromo-4-[(2,4-difluorobenzyl)oxy]-6-methyl-2-oxopyridin-1(2H)-yl]-N-[2-(dimethylamino)ethyl]benzamide;

3-[3-bromo-4-[(2,4-difluorobenzyl)oxy]-6-methyl-2-oxopyridin-1(2H)-yl]-N-(2-methoxyethyl)benzamide;

3-[3-bromo-4-[(2,4-difluorobenzyl)oxy]-6-methyl-2-oxopyridin-1(2H)-yl]-N-[2-(dimethylamino)ethyl]-N-methylbenzamide;

3-[3-bromo-4-[(2,4-difluorobenzyl)oxy]-6-methyl-2-oxopyridin-1(2H)-yl]-N-(2-hydroxyethyl)-N-methylbenzamide;

3-[3-bromo-4-[(2,4-difluorobenzyl)oxy]-6-methyl-2-oxopyridin-1(2H)-yl]-N-(2-methoxyethyl)-N-methylbenzamide;

4-[3-bromo-4-[(2,4-difluorobenzyl)oxy]-6-methyl-2-oxopyridin-1(2H)-yl]benzamide;

methyl 3-[3-chloro-4-[(2,4-difluorobenzyl)oxy]-6-methyl-2-oxopyridin-1(2H)-yl]-4-fluorobenzoate;

4-[4-[(2,4-difluorobenzyl)oxy]-6-methyl-2-oxopyridin-1(2H)-yl]-3-methylbenzoic acid;

1-(4-bromo-2-methylphenyl)-4-[(2,4-difluorobenzyl)oxy]-6-methylpyridin-2(1H)-one;

1-[(1-acetyl-1H-indol-5-yl)methyl]-3-chloro-4-[(2,4-difluorobenzyl)oxy]pyridin-2(1H)-one;

3-bromo-4-[(2,4-difluorobenzyl)oxy]-6-methyl-1-[(5-methylpyrazin-2-yl)methyl]pyridin-2(1H)-one;

methyl 2-{[3-bromo-1-(2,6-difluorophenyl)-6-methyl-2-oxo-1,2-dihydropyridin-4-yl]oxy}methyl)-3,5-difluorobenzylcarbamate;

3-bromo-4-[(2,4-difluorobenzyl)oxy]-1-{[5-(hydroxymethyl)pyrazin-2-yl]methyl}-6-methylpyridin-2(1H)-one;

4-{[3-bromo-4-[(2,4-difluorobenzyl)oxy]-6-methyl-2-oxopyridin-1(2H)-yl]methyl}-N,N-dimethylbenzamide;

3-[3-bromo-4-[(2,4-difluorobenzyl)oxy]-6-methyl-2-oxopyridin-1(2H)-yl]-N-(2-hydroxyethyl)-4-methylbenzamide;

3-bromo-4-[(2,4-difluorobenzyl)oxy]-6-methyl-1-{4-[(4-methylpiperazin-1-yl)carbonyl]benzyl}pyridin-2(1H)-one;

3-chloro-4-[(2,4-difluorobenzyl)oxy]-1-(1H-indol-5-ylmethyl)pyridin-2(1H)-one;

3-[3-bromo-4-[(2,4-difluorobenzyl)oxy]-6-methyl-2-oxopyridin-1(2H)-yl]-N-methylbenzamide;

3-[3-bromo-4-[(2,4-difluorobenzyl)oxy]-6-methyl-2-oxopyridin-1(2H)-yl]benzamide;

3-chloro-4-[(2,4-difluorobenzyl)oxy]-1-{[5-(hydroxymethyl)pyrazin-2-yl]methyl}-6-methylpyridin-2(1H)-one;

3-[3-bromo-4-[(2,4-difluorobenzyl)oxy]-6-methyl-2-oxopyridin-1(2H)-yl]-N-(2-methoxyethyl)-4-methylbenzamide;

3-[3-bromo-4-[(2,4-difluorobenzyl)oxy]-6-methyl-2-oxopyridin-1(2H)-yl]-N,4-dimethylbenzamide;

3-[3-bromo-4-[(2,4-difluorobenzyl)oxy]-6-methyl-2-oxopyridin-1(2H)-yl]-N,N,4-trimethylbenzamide;

3-bromo-4-[(2,4-difluorobenzyl)oxy]-6-methyl-1-[2-methyl-5-(morpholin-4-ylcarbonyl)phenyl]pyridin-2 (1H)-one;

3-bromo-4-[(2,4-difluorobenzyl)oxy]-1-[5-(1-hydroxy-1-methylethyl)-2-methylphenyl]-6-methylpyridin-2(1H)-one;

1-(2-bromobenzyl)-3-[(2-bromobenzyl)oxy]pyridin-2(1H)-one;

1-(2-bromobenzyl)-3-[(2-bromobenzyl)oxy]pyridin-2(1H)-one;

3-bromo-1-(4-methoxybenzyl)-4-phenoxypyridin-2(1H)-one;

1-benzyl-2-oxo-4-phenoxy-1,2-dihydropyridine-3-carbaldehyde;

3-Bromo-4-(2,4-difluoro-benzyloxy)-1-(3-dimethylaminomethyl-benzyl)-6-methyl-1H-pyridin-2-one;

N-{3-[3-Bromo-4-(2,4-difluoro-benzyloxy)-6-methyl-2-oxo-2H-pyridin-1-ylmethyl]-benzyl}-2-hydroxy-acetamide;

3-Bromo-4-(2,4-difluoro-benzyloxy)-6-methyl-1-[4-(piperidine-1-carbonyl)-benzyl]-1H-pyridin-2-one;

3-bromo-4-[(2,4-difluorobenzyl)oxy]-1-(2,6-difluorophenyl)-6-[(ethoxyamino)methyl]pyridin-2(1H)-one;

4-[3-Bromo-4-(2,4-difluoro-benzyloxy)-6-methyl-2-oxo-2H-pyridin-1-ylmethyl]-N-isopropyl-benzamide;

N-(3-aminopropyl)-4-{[3-bromo-4-[(2,4-difluorobenzyl)oxy]-6-methyl-2-oxopyridin-1(2H)-yl]methyl}benzamide hydrochloride;

3-[3-bromo-4-[(2,4-difluorobenzyl)oxy]-6-methyl-2-oxopyridin-1(2H)-yl]-N,4-dimethylbenzamide;

4-[3-Bromo-4-(2,4-difluoro-benzyloxy)-6-methyl-2-oxo-2H-pyridin-1-ylmethyl]-N,N-bis-(2-hydroxy-ethyl)-benzamide;

3-Bromo-4-(2,4-difluoro-benzyloxy)-6-methyl-1-[4-(pyrrolidine-1-carbonyl)-benzyl]-1H-pyridin-2-one;

4-[3-Bromo-4-(2,4-difluoro-benzyloxy)-6-methyl-2-oxo-2H-pyridin-1-ylmethyl]-N-hydroxy-benzamide;

4-[3-Bromo-4-(2,4-difluoro-benzyloxy)-6-methyl-2-oxo-2H-pyridin-1-ylmethyl]-N-methyl-benzamide;

4-[3-Bromo-4-(2,4-difluoro-benzyloxy)-6-methyl-2-oxo-2H-pyridin-1-ylmethyl]-N-(2-dimethylamino-ethyl)-benzamide;

3-bromo-4-[(2,4-difluorobenzyl)oxy]-1-(1H-indazol-5-ylmethyl)pyridin-2(1H)-one;

3-Bromo-4-(2,4-difluoro-benzyloxy)-6-methyl-1-[4-(4-methyl-piperazine-1-carbonyl)-benzyl]-1H-pyridin-2-one;

3-[3-bromo-4-[,(2,4-difluorobenzyl)oxy]-6-methyl-2-oxopyridin-1(2H)-yl]-4-methylbenzaldehyde;

3-Bromo-4-(2,4-difluoro-benzyloxy)-1-(4-dimethylaminomethyl-benzyl)-6-methyl-1H-pyridin-2-one;

3-[3-bromo-4-[(2,4-difluorobenzyl)oxy]-6-methyl-2-oxopyridin-1(2H)-yl]-N-(2-methoxyethyl)-4-methylbenzamide;

3-bromo-4-[(2,4-difluorobenzyl)oxy]-1-[2-(dimethylamino)-4,6-difluorophenyl]-6-methylpyridin-2(1H)-one hydrochloride;

N-(2-aminoethyl)-4-{[3-bromo-4-[(2,4-difluorobenzyl)oxy]-6-methyl-2-oxopyridin-1(2H)-yl]methyl}benzamide hydrochloride;

4-[3-Bromo-4-(2,4-difluoro-benzyloxy)-6-methyl-2-oxo-2H-pyridin-1-ylmethyl]-N-(2-hydroxy-ethyl)-benzamide;

3-Bromo-4-(2,4-difluoro-benzyloxy)-1-(4-hydroxymethyl-benzyl)-6-methyl-1H-pyridin-2-one;

3-chloro-4-[(2,4-difluorobenzyl)oxy]-1-[2,6-difluoro-4-(4-methylpiperazin-1-yl)phenyl]-6-methylpyridin-2 (1H)-one;

3-bromo-4-[(2,4-difluorobenzyl)oxy]-1-[2-(dimethylamino)-4,6-difluorophenyl]-6-methylpyridin-2(1H)-one;

3-bromo-4-[(2,4-difluorobenzyl)oxy]-1-[2,6-difluoro-4-(4-methylpiperazin-1-yl)phenyl]-6-methylpyridin-2 (1H)-one;

4-[3-Bromo-4-(2,4-difluoro-benzyloxy)-6-methyl-2-oxo-2H-pyridin-1-ylmethyl]-N-(2-methoxy-ethyl)-benzamide;

3-Bromo-4-(2,4-difluoro-benzyloxy)-1-{4-[(2-hydroxyethylamino)-methyl]-benzyl}-6-methyl-1H-pyridin-2-one;

3-bromo-4-[(2,4-difluorobenzyl)oxy]-1-(2,6-difluorophenyl)-6-[(dimethylamino)methyl]pyridin-2 (1H)-one;

3-bromo-4-[(2,4-difluorobenzyl)oxy]-6-methyl-1-[2-methyl-5-(morpholin-4-ylcarbonyl)phenyl]pyridin-2 (1H)-one;

3-Bromo-4-(2,4-difluoro-benzyloxy)-6-methyl-1-(4-methylaminomethyl-benzyl)-1H-pyridin-2-one;

3-Bromo-4-(2,4-difluoro-benzyloxy)-6-methyl-1-[4-(morpholine-4-carbonyl)-benzyl]-1H-pyridin-2-one;

N-(2-aminoethyl)-3-[3-bromo-4-[(2,4-difluorobenzyl)oxy]-6-methyl-2-oxopyridin-1(2H)-yl]benzamide;

N-(3-aminopropyl)-3-[3-bromo-4-[(2,4-difluorobenzyl)oxy]-6-methyl-2-oxopyridin-1(2H)-yl]benzamide hydrochloride;

4-[3-Bromo-4-(2,4-difluoro-benzyloxy)-6-methyl-2-oxo-2H-pyridin-1-ylmethyl]-N-(2-methoxy-ethyl)-N-methyl-benzamide;

1-(4-Aminomethyl-benzyl)-3-bromo-4-(2,4-difluoro-benzyloxy)-6-methyl-1H-pyridin-2-one;

3-bromo-4-[(2,4-difluorobenzyl)oxy]-6-methyl-1-[4-(piperazin-1-ylcarbonyl)benzyl]pyridin-2 (1H)-one hydrochloride;

3-Bromo-4-(2,4-difluoro-benzyloxy)-1-[4-(isopropylamino-methyl)-benzyl]-6-methyl-1H-pyridin-2-one;

3-bromo-4-[(2,4-difluorobenzyl)oxy]-1-(2,6-dimethylphenyl)-6-methylpyridin-2(1H)-one;

3-Bromo-4-(2,4-difluoro-benzyloxy)-1-{3-[(2-hydroxyethylamino)-methyl]-benzyl}-6-methyl-1H-pyridin-2-one;

1-(3-Aminomethyl-benzyl)-3-bromo-4-(2,4-difluoro-benzyloxy)-6-methyl-1H-pyridin-2-one;

3-Bromo-4-(2,4-difluoro-benzyloxy)-1-(4-hydroxy-benzyl)-6-methyl-1H-pyridin-2-one;

3-chloro-4-[(2,4-difluorobenzyl)oxy]-1-(2,6-difluorophenyl)-6-[(dimethylamino)methyl]pyridin-2 (1H)-one;

N-{3-[3-Bromo-4-(2,4-difluoro-benzyloxy)-6-methyl-2-oxo-2H-pyridin-1-ylmethyl]-benzyl}-acetamide;

3-bromo-4-[(2,4-difluorobenzyl)oxy]-1-{2,6-difluoro-4-[(2-hydroxyethyl)(methyl)amino]phenyl}-6-methylpyridin-2(1H)-one;

ethyl 3-[3-bromo-4-[(2,4-difluorobenzyl)oxy]-6-methyl-2-oxopyridin-1(2H)-yl]benzoate;

1-[3-(aminomethyl)benzyl]-3-bromo-4-[(2,4-difluorobenzyl)oxy]pyridin-2(1H)-one trifluoroacetate;

1-(3-{[Bis-(2-hydroxy-ethyl)-amino]-methyl}-benzyl)-3-bromo-4-(2,4-difluoro-benzyloxy)-6-methyl-1H-pyridin-2-one;

3-Bromo-4-(2,4-difluoro-benzyloxy)-1-[3-(isopropylamino-methyl)-benzyl]-6-methyl-1H-pyridin-2-one;

{3-[3-Bromo-4-(2,4-difluoro-benzyloxy)-2-oxo-2H-pyridin-1-ylmethyl]-benzyl}-carbamic acid tert-butyl ester;
3-[3-bromo-4-[(2,4-difluorobenzyl)oxy]-6-methyl-2-oxopyridin-1(2H)-yl]benzamide;
3-Bromo-4-(2,4-difluoro-benzyloxy)-1-[4-(1-hydroxy-1-methyl-ethyl)-benzyl]-6-methyl-1H-pyridin-2-one;
3-Bromo-4-(2,4-difluoro-benzyloxy)-1-(3-dimethylaminomethyl-benzyl)-1H-pyridin-2-one;
3-Bromo-4-(2,4-difluoro-benzyloxy)-6-methyl-1-(3-piperidin-1-ylmethyl-benzyl)-1H-pyridin-2-one;
3-bromo-4-[(2,4-difluorobenzyl)oxy]-1-(2,6-difluorophenyl)-6-{[(2-methoxyethyl)amino]methyl}pyridin-2(1H)-one;
3-[3-bromo-4-[(2,4-difluorobenzyl)oxy]-6-methyl-2-oxopyridin-1(2H)-yl]-N-methylbenzamide;
3-bromo-4-[(2,4-difluorobenzyl)oxy]-1-{2,4-difluoro-6-[(2-hydroxyethyl)(methyl)amino]phenyl}-6-methylpyridin-2(1H)-one;
3-Bromo-4-(2,4-difluoro-benzyloxy)-6-methyl-1-(3-morpholin-4-ylmethyl-benzyl)-1H-pyridin-2-one;
3-bromo-1-(2,6-dimethylphenyl)-6-methyl-4-[(2,4,6-trifluorobenzyl)oxy]pyridin-2(1H)-one;
3-bromo-1-(2,6-dimethylphenyl)-6-methyl-4-[(2,4,6-trifluorobenzyl)oxy]pyridin-2(1H)-one;
1-(4-{[Bis-(2-hydroxy-ethyl)-amino]-methyl}-benzyl)-3-bromo-4-(2,4-difluoro-benzyloxy)-6-methyl-1H-pyridin-2-one;
3-bromo-4-[(2,4-difluorobenzyl)oxy]-1-(2,6-difluoro-4-morpholin-4-ylphenyl)-6-methylpyridin-2(1H)-one;
4-Benzyloxy-3-bromo-1-(4-fluoro-benzyl)-1H-pyridin-2-one;
4-[3-Chloro-4-(2,4-difluoro-benzyloxy)-2-oxo-2H-pyridin-1-ylmethyl]-benzamide;
3-[3-bromo-4-[(2,4-difluorobenzyl)oxy]-6-methyl-2-oxopyridin-1(2H)-yl]-N,N,4-trimethylbenzamide;
3-[3-bromo-4-[(2,4-difluorobenzyl)oxy]-6-methyl-2-oxopyridin-1(2H)-yl]-N-isopropylbenzamide;
4-[3-Bromo-4-(2,4-difluoro-benzyloxy)-6-methyl-2-oxo-2H-pyridin-1-ylmethyl]-benzamide;
3-[3-Bromo-4-(2,4-difluoro-benzyloxy)-6-methyl-2-oxo-2H-pyridin-1-ylmethyl]-benzonitrile;
3-Bromo-4-(2,4-difluoro-benzyloxy)-6-methyl-1-(3-piperazin-1-ylmethyl-benzyl)-1H-pyridin-2-one;
4-[3-Bromo-4-(2,4-difluoro-benzyloxy)-6-methyl-2-oxo-2H-pyridin-1-ylmethyl]-N-(2-hydroxy-ethyl)-N-methyl-benzamide;
methyl 4-[3-bromo-4-[(2,4-difluorobenzyl)oxy]-6-methyl-2-oxopyridin-1(2H)-yl]-3-chlorobenzoate;
3-Bromo-4-(2,4-difluoro-benzyloxy)-6-methyl-1-[3-(morpholine-4-carbonyl)-benzyl]-1H-pyridin-2-one;
3-[3-Bromo-4-(2,4-difluoro-benzyloxy)-6-methyl-2-oxo-2H-pyridin-1-ylmethyl]-N,N-bis-(2-hydroxy-ethyl)-benzamide;
4-[3-Bromo-4-(2,4-difluoro-benzyloxy)-6-methyl-2-oxo-2H-pyridin-1-ylmethyl]-benzoic acid methyl ester;
3-[3-Bromo-4-(2,4-difluoro-benzyloxy)-6-methyl-2-oxo-2H-pyridin-1-ylmethyl]-N-hydroxy-benzamide;
3-Bromo-4-(2,4-difluoro-benzyloxy)-1-(3-hydroxymethyl-benzyl)-6-methyl-1H-pyridin-2-one;
3-bromo-4-[(2,4-difluorobenzyl)oxy]-1-(3-fluorobenzyl)pyridin-2(1H)-one;
3-Bromo-4-(2,4-difluoro-benzyloxy)-1-(3-fluoro-benzyl)-1H-pyridin-2-one;
N-{3-[3-Bromo-4-(2,4-difluoro-benzyloxy)-6-methyl-2-oxo-2H-pyridin-1-ylmethyl]-benzyl}-methanesulfonamide;
3-Bromo-4-(2,4-difluoro-benzyloxy)-6-methyl-1-[3-(pyrrolidine-1-carbonyl)-benzyl]-1H-pyridin-2-one;
3-bromo-4-[(2,4-difluorobenzyl)oxy]-6-methyl-1-(pyridin-3-ylmethyl)pyridin-2(1H)-one;
N-(3-aminopropyl)-3-{[3-bromo-4-[(2,4-difluorobenzyl)oxy]-6-methyl-2-oxopyridin-1(2H)-yl]methyl}benzamide hydrochloride;
3-bromo-4-[(2,4-difluorobenzyl)oxy]-6-methyl-1-(pyridin-3-ylmethyl)pyridin-2(1H)-one;
3-Bromo-4-(2,4-difluoro-benzyloxy)-1-(3-methylaminomethyl-benzyl)-1H-pyridin-2-one;
4-[3-bromo-4-[(2,4-difluorobenzyl)oxy]-6-methyl-2-oxopyridin-1(2H)-yl]-3,5-dichlorobenzenesulfonamide;
3-bromo-4-[(2,4-difluorobenzyl)oxy]-1-[4-(dimethylamino)-2,6-difluorophenyl]-6-methylpyridin-2(1H)-one;
3-Bromo-4-(2,4-difluoro-benzyloxy)-6-methyl-1-(4-piperidin-1-ylmethyl-benzyl)-1H-pyridin-2-one;
3-bromo-4-[(2,4-difluorobenzyl)oxy]-1-(pyridin-4-ylmethyl)pyridin-2(1H)-one;
N-(2-aminoethyl)-3-{[3-bromo-4-[(2,4-difluorobenzyl)oxy]-6-methyl-2-oxopyridin-1(2H)-yl]methyl}benzamide hydrochloride;
3-bromo-1-[2-chloro-5-(hydroxymethyl)phenyl]-4-[(2,4-difluorobenzyl)oxy]-6-methylpyridin-2(1H)-one;
3-bromo-4-[(2,4-difluorobenzyl)oxy]-1-(2,6-difluorophenyl)-6-methylpyridin-2(1H)-one;
3-chloro-1-[2-chloro-5-(hydroxymethyl)phenyl]-4-[(2,4-difluorobenzyl)oxy]-6-methylpyridin-2(1H)-one;
3-[3-bromo-4-[(2,4-difluorobenzyl)oxy]-6-methyl-2-oxopyridin-1(2H)-yl]-N-(2-hydroxyethyl)-4-methylbenzamide;
2-{3-[3-Bromo-4-(2,4-difluoro-benzyloxy)-2-oxo-2H-pyridin-1-ylmethyl]-phenyl}-acetamide;
3-bromo-4-[(2,4-difluorobenzyl)oxy]-6-methyl-1-[3-(piperazin-1-ylcarbonyl)benzyl]pyridin-2(1H)-one hydrochloride;
3-chloro-4-[(2,4-difluorobenzyl)oxy]-1-(2,6-difluorophenyl)-6-methylpyridin-2(1H)-one;
4-[3-Bromo-4-(2,4-difluoro-benzyloxy)-2-oxo-2H-pyridin-1-ylmethyl]-benzoic acid methyl ester;
1-(3-Aminomethyl-2-fluoro-benzyl)-3-bromo-4-(2,4-difluoro-benzyloxy)-1H-pyridin-2-one;
3-bromo-4-[(2,4-difluorobenzyl)oxy]-1-(2,6-difluorophenyl)-6-(morpholin-4-ylmethyl)pyridin-2(1H)-one;
4-(benzyloxy)-3-bromo-1-(4-fluorobenzyl)pyridin-2(1H)-one;
3-chloro-4-[(2,4-difluorobenzyl)oxy]-1-(1H-indol-5-ylmethyl)pyridin-2(1H)-one;
1-[3-(aminomethyl)benzyl]-3-bromo-4-[(4-fluorobenzyl)oxy]pyridin-2(1H)-one trifluoroacetate;
1-[3-(2-aminoethyl)benzyl]-3-bromo-4-[(2,4-difluorobenzyl)oxy]pyridin-2(1H)-one trifluoroacetate;
1-[3-(aminomethyl)benzyl]-3-bromo-4-[(4-fluorobenzyl)oxy]pyridin-2(1H)-one;
3-bromo-1-(2,6-dichlorophenyl)-4-[(2,4-difluorobenzyl)oxy]-6-methylpyridin-2(1H)-one;
3-[3-bromo-4-[(2,4-difluorobenzyl)oxy]-6-methyl-2-oxopyridin-1(2H)-yl]-N-(2-hydroxyethyl)benzamide;
3-bromo-4-[(2,4-difluorobenzyl)oxy]-6-methyl-1-(pyridin-4-ylmethyl)pyridin-2(1H)-one;
3-Bromo-4-(2,4-difluoro-benzyloxy)-1-(4-methoxy-benzyl)-6-methyl-1H-pyridin-2-one;
4-[3-Bromo-4-(2,4-difluoro-benzyloxy)-6-methyl-2-oxo-2H-pyridin-1-ylmethyl]-N,N-dimethyl-benzamide;
3-bromo-6-methyl-1-(pyridin-4-ylmethyl)-4-[(2,4,6-trifluorobenzyl)oxy]pyridin-2(1H)-one;

4-[3-Bromo-4-(2,4-difluoro-benzyloxy)-2-oxo-2H-pyridin-1-ylmethyl]-benzamide;
3-[3-Bromo-4-(2,4-difluoro-benzyloxy)-6-methyl-2-oxo-2H-pyridin-1-ylmethyl]-N-methyl-benzamide;
{3-[3-Bromo-4-(2,4-difluoro-benzyloxy)-6-methyl-2-oxo-2H-pyridin-1-ylmethyl]-benzyl}-carbamic acid methyl ester;
3-bromo-4-[(2,6-difluorobenzyl)oxy]-1-(2,6-dimethylphenyl)-6-methylpyridin-2(1H)-one;
4-[3-Bromo-4-(2,4-difluoro-benzyloxy)-6-methyl-2-oxo-2H-pyridin-1-ylmethyl]-benzonitrile;
3-bromo-4-[(2,4-difluorobenzyl)oxy]-6-methyl-1-(pyridin-4-ylmethyl)pyridin-2(1H)-one;
1-benzyl-4-(benzyloxy)-3-bromo-6-methylpyridin-2(1H)-one;
1-Benzyl-4-benzyloxy-3-bromo-6-methyl-1H-pyridin-2-one;
1-benzyl-4-(benzyloxy)-3-bromo-6-methylpyridin-2(1H)-one;
1-Benzyl-3-bromo-4-(2,4-difluoro-benzyloxy)-6-methyl-1H-pyridin-2-one;
{3-[3-Bromo-4-(2,4-difluoro-benzyloxy)-2-oxo-2H-pyridin-1-ylmethyl]-phenyl}-acetonitrile;
3-[3-Bromo-4-(2,4-difluoro-benzyloxy)-6-methyl-2-oxo-2H-pyridin-1-ylmethyl]-N-(2-hydroxy-ethyl)-benzamide;
3-Chloro-4-(2,4-difluoro-benzyloxy)-1-(3-fluoro-benzyl)-1H-pyridin-2-one;
1-Allyl-3-chloro-4-(2,4-difluoro-benzyloxy)-6-methyl-1H-pyridin-2-one;
3-Chloro-4-(2,4-difluoro-benzyloxy)-1-[4-(isopropylamino-methyl)-benzyl]-1H-pyridin-2-one;
methyl 3-[3-chloro-4-[(2,4-difluorobenzyl)oxy]-6-methyl-2-oxopyridin-1(2H)-yl]-4-methylbenzoate;
3-bromo-4-[(2,4-difluorobenzyl)oxy]-6-(hydroxymethyl)-1-(2,4,6-trifluorophenyl)pyridin-2(1H)-one;
3-Bromo-4-(2,4-difluoro-benzyloxy)-6-methyl-1-(4-piperazin-1-ylmethyl-benzyl)-1H-pyridin-2-one;
3-bromo-4-[(2,4-difluorobenzyl)oxy]-1-(2,6-difluorophenyl)-6-(hydroxymethyl)pyridin-2(1H)-one;
3-[3-Bromo-4-(2,4-difluoro-benzyloxy)-6-methyl-2-oxo-2H-pyridin-1-ylmethyl]-N,N-dimethyl-benzamide;
3-bromo-1-(3-fluorobenzyl)-4-[(3-methylbenzyl)oxy]pyridin-2(1H)-one;
3-Bromo-1-(3-fluoro-benzyl)-4-(3-methyl-benzyloxy)-1H-pyridin-2-one;
3-chloro-4-[(2,4-difluorobenzyl)oxy]-1-(1,2,3,4-tetrahydroisoquinolin-5-ylmethyl)pyridin-2(1H)-one;
3-bromo-1-(3-fluorobenzyl)-4-[(3-methylbenzyl)oxy]pyridin-2(1H)-one;
3-chloro-4-[(2,4-difluorobenzyl)oxy]-1-(isoquinolin-5-ylmethyl)pyridin-2(1H)-one trifluoroacetate;
3-[3-Bromo-4-(2,4-difluoro-benzyloxy)-6-methyl-2-oxo-2H-pyridin-1-ylmethyl]-benzamide;
3-bromo-4-[(2,4-difluorobenzyl)oxy]-6-methyl-1-({5-[(4-methylpiperazin-1-yl)carbonyl]pyrazin-2-yl}methyl)pyridin-2(1H)-one trifluoroacetate;
3-bromo-4-[(2,4-difluorobenzyl)oxy]-1-[5-(hydroxymethyl)-2-methylphenyl]-6-methylpyridin-2(1H)-one;
1-allyl-3-bromo-4-[(2,4-difluorobenzyl)oxy]-6-methylpyridin-2(1H)-one;
3-bromo-4-[(2,4-difluorobenzyl)oxy]-1-(pyridin-3-ylmethyl)pyridin-2(1H)-one;
3-bromo-4-[(2,4-difluorobenzyl)oxy]-1-(2-methoxy-6-methylphenyl)-6-methylpyridin-2(1H)-one;
3-bromo-4-[(2,4-difluorobenzyl)oxy]-1-(2-methoxy-6-methylphenyl)-6-methylpyridin-2(1H)-one;
3-[3-Bromo-4-(2,4-difluoro-benzyloxy)-2-oxo-2H-pyridin-1-ylmethyl]-benzamide;
3-chloro-4-[(2,4-difluorobenzyl)oxy]-6-(hydroxymethyl)-1-(2,4,6-trifluorophenyl)pyridin-2(1H)-one;
3-bromo-4-[(2,4-difluorobenzyl)oxy]-6-methyl-1-[2-(trifluoromethyl)phenyl]pyridin-2(1H)-one;
4-[3-Bromo-4-(2,4-difluoro-benzyloxy)-6-methyl-2-oxo-2H-pyridin-1-ylmethyl]-benzoic acid;
3-Bromo-4-(2,4-difluoro-benzyloxy)-6-methyl-1-(4-morpholin-4-ylmethyl-benzyl)-1H-pyridin-2-one;
4-(2,4-Difluoro-benzyloxy)-1-(3-fluoro-benzyl)-3-iodo-1H-pyridin-2-one;
3-bromo-4-[(2,4-difluorobenzyl)oxy]-6-methyl-1-(2,4,6-trifluorophenyl)pyridin-2(1H)-one;
3-[3-bromo-4-[(2,4-difluorobenzyl)oxy]-6-methyl-2-oxopyridin-1(2H)-yl]-N-hydroxybenzamide;
3-bromo-1-(2,6-dichlorophenyl)-4-[(2,6-difluorobenzyl)oxy]-6-methylpyridin-2(1H)-one;
3-(4-Benzyloxy-3-bromo-2-oxo-2H-pyridin-1-ylmethyl)-benzonitrile;
3-bromo-4-[(2,4-difluorobenzyl)oxy]-6-methyl-1-[3-(pyrrolidin-1-ylcarbonyl)phenyl]pyridin-2(1H)-one;
3-bromo-4-[(2,4-difluorobenzyl)oxy]-1-(2-fluorobenzyl)pyridin-2(1H)-one;
4-(benzyloxy)-3-bromo-1-(4-methylbenzyl)pyridin-2(1H)-one;
3-{[3-chloro-4-[(2,4-difluorobenzyl)amino]-6-methyl-2-oxopyridin-1(2H)-yl]methyl}benzonitrile;
3-[3-Bromo-4-(2,4-difluoro-benzyloxy)-6-methyl-2-oxo-2H-pyridin-1-ylmethyl]-N-isopropyl-benzamide;
3-bromo-1-(4-bromo-2,6-difluorophenyl)-4-[(2,4-difluorobenzyl)oxy]-6-methylpyridin-2(1H)-one;
3-bromo-4-[(4-fluorobenzyl)oxy]-6-methyl-1-(pyridin-3-ylmethyl)pyridin-2(1H)-one;
3-bromo-4-[(4-fluorobenzyl)oxy]-6-methyl-1-(pyridin-4-ylmethyl)pyridin-2(1H)-one;
3-bromo-4-[(4-fluorobenzyl)oxy]-6-methyl-1-(pyridin-4-ylmethyl)pyridin-2(1H)-one;
4-(benzyloxy)-3-bromo-1-(4-chlorobenzyl)pyridin-2(1H)-one;
4-Benzyloxy-3-bromo-1-(4-chloro-benzyl)-1H-pyridin-2-one;
3-bromo-1-(4-fluorobenzyl)-4-[(4-fluorobenzyl)oxy]pyridin-2(1H)-one;
3-bromo-1-(2,6-dichlorophenyl)-4-[(4-fluorobenzyl)oxy]-6-methylpyridin-2(1H)-one;
3-Bromo-1-(4-fluoro-benzyl)-4-(4-fluoro-benzyloxy)-1H-pyridin-2-one;
methyl 4-[3-bromo-4-[(2,4-difluorobenzyl)oxy]-6-methyl-2-oxopyridin-1(2H)-yl]benzoate;
4-(4-Benzyloxy-3-bromo-2-oxo-2H-pyridin-1-ylmethyl)-benzoic acid;
4-{[4-(benzyloxy)-3-bromo-2-oxopyridin-1(2H)-yl]methyl}benzoic acid;
3-chloro-4-[(2,4-difluorobenzyl)oxy]-6-methyl-1-(2,4,6-trifluorophenyl)pyridin-2(1H)-one;
4-(benzyloxy)-3-bromo-1-(2-fluorobenzyl)pyridin-2(1H)-one;
3-chloro-4-[(2,4-difluorobenzyl)oxy]-1-(2,6-difluorophenyl)-6-(hydroxymethyl)pyridin-2(1H)-one;
N-(2-aminoethyl)-4-[3-bromo-4-[(2,4-difluorobenzyl)oxy]-6-methyl-2-oxopyridin-1(2H)-yl]benzamide hydrochloride;
4-Benzyloxy-3-bromo-1-(4-methylsulfanyl-benzyl)-1H-pyridin-2-one;
1-Benzyl-4-benzyloxy-3-chloro-1H-pyridin-2-one;
4-(benzyloxy)-3-bromo-1-[4-(methylthio)benzyl]pyridin-2(1H)-one;

1-benzyl-4-(benzyloxy)-3-chloropyridin-2(1H)-one;
3-bromo-4-[(2,4-difluorobenzyl)oxy]-1-{[5-(hydroxymethyl)pyrazin-2-yl]methyl}-6-methylpyridin-2(1H)-one;
3-bromo-1-(2,6-dimethylphenyl)-4-[(4-fluorobenzyl)oxy]-6-methylpyridin-2(1H)-one;
3-bromo-1-(2,6-dimethylphenyl)-4-[(4-fluorobenzyl)oxy]-6-methylpyridin-2(1H)-one;
3-Bromo-4-(2,4-difluoro-benzyloxy)-1-[3-(isopropylamino-methyl)-benzyl]-1H-pyridin-2-one;
3-[3-Chloro-4-(2,4-difluoro-benzyloxy)-2-oxo-2H-pyridin-1-ylmethyl]-2-fluoro-benzamide;
5-{[3-bromo-4-[(2,4-difluorobenzyl)oxy]-6-methyl-2-oxopyridin-1(2H)-yl]methyl}-N-(2,3-dihydroxypropyl)pyrazine-2-carboxamide;
{3-[3-Bromo-4-(2,4-difluoro-benzyloxy)-2-oxo-2H-pyridin-1-ylmethyl]-phenyl}-acetic acid ethyl ester;
4-(4-Benzyloxy-3-bromo-2-oxo-2H-pyridin-1-ylmethyl)-N-hydroxy-benzamidine;
4-{[4-(benzyloxy)-3-bromo-2-oxopyridin-1(2H)-yl]methyl}-N'-hydroxybenzenecarboximidamide;
ethyl 5-{[3-chloro-4-[(2,4-difluorobenzyl)oxy]-6-methyl-2-oxopyridin-1(2H)-yl]methyl}pyrazine-2-carboxylate;
3-Bromo-4-(2,4-difluoro-benzyloxy)-1-(3-methoxy-benzyl)-1H-pyridin-2-one;
3-bromo-4-[(2,4-difluorobenzyl)oxy]-6-methyl-1-[(5-methylpyrazin-2-yl)methyl]pyridin-2(1H)-one;
3-bromo-4-[(2,4-difluorobenzyl)oxy]-1-(3-methoxybenzyl)pyridin-2(1H)-one;
4-(4-Benzyloxy-3-bromo-2-oxo-2H-pyridin-1-ylmethyl)-benzoic acid methyl ester;
3-Bromo-4-(2,4-difluoro-benzyloxy)-1-(4-dimethylaminomethyl-benzyl)-1H-pyridin-2-one;
3-Chloro-4-(2,4-difluoro-benzyloxy)-1-(3-methanesulfonyl-benzyl)-1H-pyridin-2-one;
4-(4-Benzyloxy-3-bromo-2-oxo-2H-pyridin-1-ylmethyl)-benzoic acid methyl ester;
methyl 4-{[4-(benzyloxy)-3-bromo-2-oxopyridin-1(2H)-yl]methyl}benzoate;
ethyl 5-{[3-bromo-4-[(2,4-difluorobenzyl)oxy]-6-methyl-2-oxopyridin-1(2H)-yl]methyl}pyrazine-2-carboxylate;
4-{[4-(benzyloxy)-3-bromo-2-oxopyridin-1(2H)-yl]methyl}benzonitrile;
4-(4-Benzyloxy-3-bromo-2-oxo-2H-pyridin-1-ylmethyl)-benzonitrile;
{3-[3-Bromo-4-(4-fluoro-benzyloxy)-2-oxo-2H-pyridin-1-ylmethyl]-benzyl}-carbamic acid tert-butylester;
3-bromo-4-[(2,4-difluorobenzyl)oxy]-1-[5-(1-hydroxy-1-methylethyl)-2-methylphenyl]-6-methylpyridin-2(1H)-one;
4-(benzyloxy)-3-bromo-1-(2,6-dichlorophenyl)-6-methylpyridin-2(1H)-one;
1-(3-Aminomethyl-benzyl)-4-benzyloxy-3-bromo-1H-pyridin-2-one;
3-bromo-4-[(4-fluorobenzyl)oxy]-1-(pyridin-4-ylmethyl)pyridin-2(1H)-one;
4-(benzyloxy)-3-bromo-1-(4-bromobenzyl)pyridin-2(1H)-one;
4-Benzyloxy-3-bromo-1-(4-bromo-benzyl)-1H-pyridin-2-one;
5-bromo-4-[(2,4-difluorobenzyl)oxy]-1-(2,6-difluorophenyl)-6-oxo-1,6-dihydropyridine-2-carbaldehyde;
3-chloro-4-[(2,4-difluorobenzyl)oxy]-1-{[5-(hydroxymethyl)pyrazin-2-yl]methyl}-6-methylpyridin-2(1H)-one;
4-(4-Benzyloxy-3-bromo-2-oxo-2H-pyridin-1-ylmethyl)-benzamide;
3-bromo-4-[(2,4-difluorobenzyl)oxy]-6-methyl-1-[3-(piperazin-1-ylcarbonyl)phenyl]pyridin-2(1H)-one hydrochloride;
3-bromo-4-[(2,4-difluorobenzyl)amino]-1-(3-fluorobenzyl)pyridin-2(1H)-one;
3-chloro-4-[(2,4-difluorobenzyl)oxy]-6-methyl-1-[(5-methylpyrazin-2-yl)methyl]pyridin-2(1H)-one;
3-chloro-4-[(2,4-difluorobenzyl)oxy]-1-[5-(hydroxymethyl)-2-methylphenyl]-6-methylpyridin-2(1H)-one;
3-bromo-1-(3-fluorobenzyl)-4-[(4-fluorobenzyl)oxy]pyridin-2(1H)-one;
3-Bromo-1-(3-fluoro-benzyl)-4-(4-fluoro-benzyloxy)-1H-pyridin-2-one;
3-bromo-4-[(2,4-difluorobenzyl)oxy]-6-methyl-1-[3-(morpholin-4-ylcarbonyl)phenyl]pyridin-2 (1H)-one;
3-(4-Benzyloxy-3-bromo-2-oxo-2H-pyridin-1-ylmethyl)-benzoic acid methyl ester;
3-bromo-1-(3-fluorobenzyl)-4-{[2-(hydroxymethyl)benzyl]oxy}pyridin-2(1H)-one;
3-Bromo-1-(3-fluoro-benzyl)-4-(2-hydroxymethyl-benzyloxy)-1H-pyridin-2-one;
1-Benzo[1,3]dioxol-5-ylmethyl-3-bromo-4-(2,4-difluoro-benzyloxy)-1H-pyridin-2-one;
3-bromo-4-[(2,6-difluorobenzyl)oxy]-6-methyl-1-(pyridin-4-ylmethyl)pyridin-2(1H)-one;
3-bromo-4-[(3-chlorobenzyl)oxy]-1-(3-fluorobenzyl)pyridin-2(1H)-one;
3-bromo-4-[(3-chlorobenzyl)oxy]-1-(3-fluorobenzyl)pyridin-2(1H)-one;
3-Bromo-4-(3-chloro-benzyloxy)-1-(3-fluoro-benzyl)-1H-pyridin-2-one;
4-(benzyloxy)-3-bromo-1-(3-fluorobenzyl)pyridin-2 (1H)-one;
4-Benzyloxy-3-bromo-1-(3-fluoro-benzyl)-1H-pyridin-2-one;
3-Bromo-4-(2,4-difluoro-benzyloxy)-6-methyl-1-[3-(piperidine-1-carbonyl)-benzyl]-1H-pyridin-2-one;
3-[3-bromo-4-[(2,4-difluorobenzyl)oxy]-6-methyl-2-oxopyridin-1(2H)-yl]-N,N-dimethylbenzamide;
3-[3-Chloro-4-(2,4-difluoro-benzyloxy)-2-oxo-2H-pyridin-1-ylmethyl]-2-fluoro-benzoic acid methyl ester;
1-(3-fluorobenzyl)-4-[(4-fluorobenzyl)oxy]-3-iodopyridin-2(1H)-one;
1-(3-Fluoro-benzyl)-4-(4-fluoro-benzyloxy)-3-iodo-1H-pyridin-2-one;
N-(3-aminopropyl)-4-[3-bromo-4-[(2,4-difluorobenzyl)oxy]-6-methyl-2-oxopyridin-1(2H)-yl]benzamide hydrochloride;
4-{[3-bromo-4-[(4-fluorobenzyl)oxy]-2-oxopyridin-1(2H)-yl]methyl}benzonitrile;
4-[3-Bromo-4-(4-fluoro-benzyloxy)-2-oxo-2H-pyridin-1-ylmethyl]-benzonitrile;
3-Bromo-1-(3-fluoro-benzyl)-4-(2,3,4-trifluoro-benzyloxy)-1H-pyridin-2-one;
1-benzyl-4-(benzyloxy)-3-bromopyridin-2(1H)-one;
5-{[3-bromo-4-[(2,4-difluorobenzyl)oxy]-6-methyl-2-oxopyridin-1(2H)-yl]methyl}-N-(2-hydroxyethyl)-N-methylpyrazine-2-carboxamide;
4-(4-Benzyloxy-3-bromo-2-oxo-2H-pyridin-1-ylmethyl)-benzonitrile;
3-bromo-1-(2,4-difluorobenzyl)-4-[(2,4-difluorobenzyl)oxy]pyridin-2(1H)-one;
3-Bromo-1-(2,4-difluoro-benzyl)-4-(2,4-difluoro-benzyloxy)-1H-pyridin-2-one;
4-[3-bromo-4-[(2,4-difluorobenzyl)oxy]-6-methyl-2-oxopyridin-1(2H)-yl]-N-(2-hydroxyethyl)benzamide;

3-bromo-4-[(4-fluorobenzyl)oxy]-1-(pyridin-3-ylmethyl) pyridin-2(1H)-one;
1-Benzyl-4-benzyloxy-3-bromo-1H-pyridin-2-one;
3-bromo-1-(cyclopropylmethyl)-4-[(2,4-difluorobenzyl) oxy]-6-methylpyridin-2(1H)-one;
1-(4-Aminomethyl-benzyl)-4-benzyloxy-3-bromo-1H-pyridin-2-one;
3-bromo-1-(4-fluorobenzyl)-4-[(4-fluorobenzyl)amino]-6-methylpyridin-2(1H)-one;
3-[3-Bromo-4-(2,4-difluoro-benzyloxy)-6-methyl-2-oxo-2H-pyridin-1-ylmethyl]-benzoic acid methyl ester;
5-{[3-bromo-4-[(2,4-difluorobenzyl)oxy]-6-methyl-2-oxopyridin-1(2H)-yl]methyl}-N,N-dimethylpyrazine-2-carboxamide;
3-bromo-4-[(4-fluorobenzyl)oxy]-6-methyl-1-(pyridin-2-ylmethyl)pyridin-2(1H)-one;
3-bromo-4-[(2,4-difluorobenzyl)oxy]-1-(2,6-dimethylphenyl)-6-methylpyridin-2(1H)-one;
3-bromo-1-(2,6-dichlorophenyl)-4-[(2,4-difluorobenzyl) oxy]-6-methylpyridin-2(1H)-one;
4-(benzyloxy)-1-(4-bromobenzyl)pyridin-2(1H)-one;
3-bromo-4-hydroxy-1-(4-hydroxybenzyl)pyridin-2 (1H)-one;
4-(benzyloxy)-3-bromo-1-[2-(trifluoromethyl)benzyl] pyridin-2 (1H)-one;
1-benzyl-4-[(3-chlorobenzyl)oxy]-6-methylpyridin-2 (1H)-one;
4-(benzyloxy)-3-bromo-1-(piperidin-3-ylmethyl)pyridin-2 (1H)-one hydrochloride;
1-benzyl-3-bromo-2-oxo-1,2-dihydropyridin-4-yl methyl (phenyl)carbamate;
4-(benzylamino)-1-(3-fluorobenzyl)-6-methyl-3-nitropyridin-2(1H)-one;
tert-butyl 4-[3-bromo-1-(3-fluorobenzyl)-2-oxo-1,2-dihydropyridin-4-yl]piperazine-1-carboxylate;
ethyl [4-(benzyloxy)-3-bromo-2-oxopyridin-1(2H)-yl] acetate;
N-[3-bromo-1-(3-fluorobenzyl)-2-oxo-1,2-dihydropyridin-4-yl]benzenesulfonamide;
3-bromo-4-[(4-tert-butylbenzyl)oxy]-1-(3-fluorobenzyl) pyridin-2 (1H)-one;
N-[3-bromo-1-(3-fluorobenzyl)-2-oxo-1,2-dihydropyridin-4-yl]-1-phenylmethanesulfonamide;
1-(biphenyl-2-ylmethyl)-3-bromo-4-[(4-fluorobenzyl)oxy] pyridin-2 (1H)-one;
4-(biphenyl-2-ylmethoxy)-3-bromo-1-(3-fluorobenzyl) pyridin-2 (1H)-one;
3-bromo-4-[(2,4-difluorophenyl)amino]-1-(3-fluorobenzyl) pyridin-2(1H)-one;
4-anilino-3-bromo-1-(3-fluorobenzyl)pyridin-2(1H)-one;
methyl 4-{[3-bromo-1-(3-fluorobenzyl)-2-oxo-1,2-dihydropyridin-4-yl]amino}benzoate;
3-bromo-1-(3-fluorobenzyl)-4-[(3,4,5-trimethoxyphenyl) amino]pyridin-2(1H)-one;
3-bromo-1-(3-fluorobenzyl)-4-[4-(4-fluorophenyl) piperazin-1-yl]pyridin-2(1H)-one;
3-bromo-1-(3-fluorobenzyl)-4-(4-methylpiperazin-1-yl) pyridin-2(1H)-one trifluoroacetate;
N-[3-bromo-1-(3-fluorobenzyl)-2-oxo-1,2-dihydropyridin-4-yl]-2,5-difluorobenzamide;
N-[3-bromo-1-(3-fluorobenzyl)-2-oxo-1,2-dihydropyridin-4-yl]-2,4-difluorobenzamide;
3-bromo-1-(cyclohexylmethyl)-4-[(4-fluorobenzyl)oxy] pyridin-2(1H)-one;
3-[4-(benzyloxy)-3-bromo-2-oxopyridin-1(2H)-yl] propanoic acid;
N-[3-bromo-1-(3-fluorobenzyl)-2-oxo-1,2-dihydropyridin-4-yl]-N'-(2,4-difluorophenyl)urea;
3-[4-(benzyloxy)-3-bromo-2-oxopyridin-1(2H)-yl] propanamide;
4-(benzyloxy)-3-bromo-1-(3-morpholin-4-yl-3-oxopropyl) pyridin-2(1H)-one;
N-(3-aminopropyl)-3-[4-(benzyloxy)-3-bromo-2-oxopyridin-1(2H)-yl]propanamide hydrochloride;
4-(benzyloxy)-3-bromo-1-(3-oxo-3-piperazin-1-ylpropyl) pyridin-2(1H)-one hydrochloride;
4-(benzyloxy)-3-bromo-1-(2-morpholin-4-ylethyl)pyridin-2 (1H)-one;
3-bromo-1-(3-fluorobenzyl)-4-{[4-fluoro-2-(trifluoromethyl)benzyl]amino}pyridin-2(1H)-one;
N-(2-aminoethyl)-3-[4-(benzyloxy)-3-bromo-2-oxopyridin-1(2H)-yl]propanamide hydrochloride;
[3-bromo-4-[(2,4-difluorobenzyl)oxy]-6-methyl-2-oxopyridin-1(2H)-yl]acetic acid;
3-bromo-4-[(2,4-difluorobenzyl)oxy]-6-methyl-1-(tetrahydrofuran-2-ylmethyl)pyridin-2(1H)-one;
4-[(2,4-difluorobenzyl)oxy]-6-methyl-1-(tetrahydrofuran-2-ylmethyl)pyridin-2(1H)-one;
methyl 3-bromo-4-[(2,4-difluorobenzyl)oxy]-6-methyl-2-oxopyridine-1(2H)-carboxylate;
1-allyl-3-(2,4-difluorobenzyl)-4-[(2,4-difluorobenzyl)oxy]-6-methylpyridin-2(1H)-one;
4-(benzyloxy)-1-(2,2-diethoxyethyl)pyridin-2(1H)-one;
methyl N-acetyl-3-[4-(benzyloxy)-2-oxopyridin-1(2H)-yl] alaninate;
benzyl N-acetyl-3-[4-(benzyloxy)-2-oxopyridin-1(2H)-yl] alaninate;
benzyl N-[(benzyloxy)carbonyl]-3-[4-(benzyloxy)-2-oxopyridin-1(2H)-yl]alaninate;
4-(benzyloxy)-1-(2-oxopropyl)pyridin-2(1H)-one;
5-{[4-(benzyloxy)-2-oxopyridin-1(2H)-yl]methyl}-5-methylimidazolidine-2,4-dione;
ethyl [4-(benzyloxy)-2-oxopyridin-1(2H)-yl]acetate;
2-[4-(benzyloxy)-2-oxopyridin-1(2H)-yl]acetamide;
1-benzyl-4-(benzyloxy)-3,5-dibromopyridin-2(1H)-one;
4-(benzyloxy)-1-ethylpyridin-2(1H)-one;
4-(benzyloxy)-1-(4-tert-butylbenzyl)pyridin-2(1H)-one;
4-{[4-(benzyloxy)-2-oxopyridin-1(2H)-yl]methyl}benzonitrile;
tert-butyl 3-{[4-(benzyloxy)-2-oxopyridin-1(2H)-yl] methyl}piperidine-1-carboxylate;
1,3-dibenzyl-4-hydroxy-6-methylpyridin-2(1H)-one;
1-benzyl-6-methyl-2-oxo-1,2-dihydropyridin-4-yl methanesulfonate;
4-(benzyloxy)-1-(4-bromobenzyl)pyridin-2(1H)-one;
4-(benzyloxy)-3-bromopyridin-2(1H)-one;
4-(benzyloxy)-3-bromo-1-[2-(trifluoromethyl)benzyl] pyridin-2(1H)-one;
1-benzyl-4-(1-naphthylmethoxy)pyridin-2(1H)-one;
1-benzyl-4-(benzylthio)-3,5-dibromopyridin-2(1H)-one;
1-benzyl-4-[(2,6-dichlorobenzyl)oxy]pyridin-2(1H)-one;
1-benzyl-3-[(benzylamino)methyl]-4-(benzyloxy)pyridin-2 (1H)-one;
1-benzyl-4-(benzyloxy)-3-{[(2-cyclohexylethyl)amino] methyl}pyridin-2(1H)-one;
1-benzyl-4-(benzylthio)-5-methylpyridin-2(1H)-one;
1-benzyl-3-bromo-6-methyl-2-oxo-1,2-dihydropyridin-4-yl methanesulfonate;
1-benzyl-3-bromo-6-methyl-4-{[2-(trifluoromethyl)benzyl] oxy}pyridin-2(1H)-one;
1-benzyl-6-methyl-2-oxo-1,2-dihydropyridin-4-yl 4-bromobenzenesulfonate;
1-benzyl-4-[(3-chlorobenzyl)oxy]-6-methylpyridin-2(1H)-one;
1-benzyl-3-bromo-6-methyl-2-oxo-1,2-dihydropyridin-4-yl 4-bromobenzenesulfonate;

4-phenoxy-1-{[2-(trimethylsilyl)ethoxy]methyl}pyridin-2 (1H)-one;
1-benzyl-4-phenoxypyridin-2(1H)-one;
1-(4-methoxybenzyl)-4-phenoxypyridin-2(1H)-one;
3-bromo-4-hydroxy-1-(4-hydroxybenzyl)pyridin-2(1H)-one hydrochloride;
4-(benzyloxy)-3-bromo-1-(piperidin-3-ylmethyl)pyridin-2 (1H)-one;
1-benzyl-4-[(2,6-dichlorobenzyl)oxy]pyridin-2(1H)-one;
1-benzyl-4-(benzyloxy)-3,5-dibromopyridin-2(1H)-one;
3-bromo-1-(3-fluorobenzyl)-4-[(E)-2-(4-fluorophenyl)vinyl]pyridin-2(1H)-one;
1-benzyl-4-(benzyloxy)-2-oxo-1,2-dihydropyridine-3-carbaldehyde;
1-benzyl-4-(benzyloxy)pyridin-2 (1H)-one;
1-benzyl-4-(benzyloxy)pyridin-2 (1H)-one;
1-benzyl-4-(benzylthio)pyridin-2 (1H)-one;
methyl 4-[3-chloro-4-[(2,4-difluorobenzyl)oxy]-2-oxopyridin-1(2H)-yl]benzoate;
benzyl(5-nitro-2,6-dioxo-3,6-dihydropyrimidin-1(2H)-yl)acetate;
ethyl 3-bromo-4-[(2,4-difluorobenzyl)oxy]-6-methyl-2-oxo-2H-1,2'-bipyridine-5'-carboxylate;
4-(benzyloxy)-1-(4-methylbenzyl)pyridin-2(1H)-one;
[5-bromo-4-[(2,4-difluorobenzyl)oxy]-1-(2,6-difluorophenyl)-2-methyl-6-oxo-1,6-dihydropyridin-3-yl]methyl carbamate;
4-(benzyloxy)-1-(4-chlorobenzyl)pyridin-2(1H)-one;
methyl(2E)-4-[4-[(2,4-difluorobenzyl)oxy]-6-methyl-2-oxopyridin-1(2H)-yl]but-2-enoate;
4-(benzyloxy)-1-(2-fluorobenzyl)pyridin-2 (1H)-one;
tert-butyl 4-{[4-(benzyloxy)-3-bromo-2-oxopyridin-1(2H)-yl]methyl}piperidine-1-carboxylate;
4-(benzyloxy)-1-(3-fluorobenzyl)pyridin-2(1H)-one;
3-bromo-4-[(2,4-difluorobenzyl)oxy]-1-(2,6-difluorophenyl)-5-(1,2-dihydroxyethyl)-6-methylpyridin-2(1H)-one;
1-benzyl-4-hydroxy-6-methylpyridin-2(1H)-one;
4-({[3-bromo-1-(3-fluorobenzyl)-2-oxo-1,2-dihydropyridin-4-yl]oxy}methyl)benzonitrile;
1-benzyl-4-(benzyloxy)-6-methylpyridin-2(1H)-one;
5-bromo-4-[(2,4-difluorobenzyl)oxy]-1-(2,6-difluorophenyl)-2-methyl-6-oxo-1,6-dihydropyridine-3-carbaldehyde oxime;
1-benzyl-4-(benzylthio)-3-methylpyridin-2(1H)-one;
1-benzyl-4-[(4-methylbenzyl)oxy]pyridin-2(1H)-one;
1-benzyl-4-(benzyloxy)-3,5-dibromo-6-methylpyridin-2 (1H)-one;
1-benzyl-4-(benzyloxy)-3,5-dibromo-6-methylpyridin-2 (1H)-one;
3-bromo-1-(3-fluorobenzyl)-4-(1-phenylethoxy)pyridin-2 (1H)-one;
4-(benzyloxy)-1-[4-(trifluoromethyl)benzyl]pyridin-2(1H)-one;
2-({[3-bromo-2-oxo-1-(pyridin-3-ylmethyl)-1,2-dihydropyridin-4-yl]oxy}methyl)-5-fluorobenzonitrile;
5-bromo-4-[(2,4-difluorobenzyl)oxy]-1-(2,6-difluorophenyl)-2-methyl-6-oxo-1,6-dihydropyridine-3-carbonitrile;
4-(benzyloxy)-1-(3-fluorobenzyl)-3-(trifluoromethyl)pyridin-2(1H)-one;
3-bromo-4-[(2,4-difluorobenzyl)oxy]-1-(2,6-difluorophenyl)-6-methyl-5-oxiran-2-ylpyridin-2(1H)-one;
1-benzyl-4-[(3-chlorobenzyl)oxy]pyridin-2(1H)-one;
1-benzyl-4-[(3-chlorobenzyl)oxy]pyridin-2(1H)-one;
5-bromo-4-[(2,4-difluorobenzyl)oxy]-1-(2,6-difluorophenyl)-2-methyl-6-oxo-1,6-dihydropyridine-3-carbaldehyde;

tert-butyl 3-{[4-(benzyloxy)-3-bromo-2-oxopyridin-1(2H)-yl]methyl}piperidine-1-carboxylate;
3-bromo-4-[(2,4-difluorobenzyl)oxy]-1-(2,6-difluorophenyl)-6-methyl-5-vinylpyridin-2(1H)-one;
4-(benzyloxy)-1-[4-(trifluoromethoxy)benzyl]pyridin-2 (1H)-one;
3-bromo-4-[(4-chlorobenzyl)oxy]-1-[2-(phenylthio)ethyl]pyridin-2 (1H)-one;
3-Bromo-4-(4-chloro-benzyloxy)-1-(2-phenylsulfanyl-ethyl)-1H-pyridin-2-one;
3-bromo-4-[(2,4-difluorobenzyl)oxy]-6-methyl-1-(2-morpholin-4-ylethyl)pyridin-2(1H)-one;
4-[(2,4-difluorobenzyl)oxy]-6-(hydroxymethyl)-1-(pyridin-3-ylmethyl)pyridin-2(1H)-one;
4-{[2-(Aminomethyl)-4-fluorobenzyl]oxy}-3-bromo-1-(2,6-difluorophenyl)-6-methylpyridin-2(1H)-one trifluoroacetate;
4-(benzyloxy)-1-(4-fluorobenzyl)pyridin-2(1H)-one;
4-(benzyloxy)-1-(4-fluorobenzyl)pyridin-2 (1H)-one;
4-Benzyloxy-3-bromo-1-methanesulfonyl-1H-pyridin-2-one;
tert-butyl 4-[4-(benzyloxy)-3-bromo-2-oxopyridin-1 (2H)-yl]piperidine-1-carboxylate;
1-benzyl-4-(benzyloxy)-3-vinylpyridin-2 (1H)-one;
4-(benzyloxy)-1-[4-(methylthio)benzyl]pyridin-2 (1H)-one;
3-Bromo-4-(2,4-difluoro-benzyloxy)-1-(2-methyl-4-methylamino-pyrimidin-5-ylmethyl)-1H-pyridin-2-one;
3-bromo-4-[(2,4-difluorobenzyl)oxy]-6-methylpyridin-2 (1H)-one;
1-benzyl-3-bromo-4-{[2-(trifluoromethyl)benzyl]oxy}pyridin-2 (1H)-one;
1-benzyl-3-bromo-4-{[2-(trifluoromethyl)benzyl]oxy}pyridin-2 (1H)-one;
4-[(2,4-difluorobenzyl)oxy]-1-[5-(hydroxymethyl)-2-methylphenyl]-6-methylpyridin-2 (1H)-one;
4-(benzyloxy)-1-[4-(methylsulfonyl)benzyl]pyridin-2(1H)-one;
4-Phenoxy-1H-pyridin-2-one;
1-benzyl-4-[(2-chlorobenzyl)oxy]pyridin-2(1H)-one;
1-benzyl-4-[(2-chlorobenzyl)oxy]pyridin-2(1H)-one;
methyl 4-{[4-(benzyloxy)-2-oxopyridin-1(2H)-yl]methyl}benzoate;
4-[(2,4-difluorobenzyl)oxy]-1-(2,6-difluorophenyl)-6-methylpyridin-2(1H)-one;
1-(3-fluorobenzyl)-4-(phenylethynyl)pyridin-2(1H)-one;
4-(benzyloxy)-3-bromo-1-(piperidin-4-ylmethyl)pyridin-2 (1H)-one hydrochloride;
4-(benzyloxy)-3-bromo-1-(piperidin-4-ylmethyl)pyridin-2 (1H)-one hydrochloride;
3-bromo-4-[(2,4-difluorobenzyl)oxy]-6-methyl-1-[2-(methylthio)pyrimidin-4-yl]pyridin-2(1H)-one;
4-(benzyloxy)-3-bromo-1-piperidin-4-ylpyridin-2(1H)-one hydrochloride;
4-Benzyloxy-1-difluoromethyl-1H-pyridin-2-one;
4-Benzyloxy-3-bromo-1-(2-chloro-phenyl)-6-methyl-1H-pyridin-2-one;
3-Bromo-6-methyl-1-pyridin-3-ylmethyl-4-[(pyridin-3-ylmethyl)-amino]-1H-pyridin-2-one;
1-(3,4-Dichloro-benzyl)-6-oxo-1,6-dihydro-pyridine-3-carboxylic acid (2,4-difluoro-phenyl)-amide;
1-(2,6-Dichloro-benzyl)-6-oxo-1,6-dihydro-pyridine-3-carboxylic acid (2,4-difluoro-phenyl)-amide;
5-Chloro-1-(2,6-dichloro-benzyl)-6-oxo-1,6-dihydro-pyridine-3-carboxylic acid (2,4-difluoro-phenyl)-amide;
5-Chloro-1-(2,6-dichloro-benzyl)-6-oxo-1,6-dihydro-pyridine-3-carboxylic acid methyl-phenyl-amide;
1-(2,6-Dichloro-benzyl)-6-oxo-1,6-dihydro-pyridine-3-carboxylic acid benzylamide;

1-(2,6-Dichloro-benzyl)-6-oxo-1,6-dihydro-pyridine-3-carboxylic acid (3-dimethylamino-propyl)-amide;
1-(2,6-Dichloro-benzyl)-6-oxo-1,6-dihydro-pyridine-3-carboxylic acid (2-morpholin-4-yl-ethyl)-amide;
N-[5-Acetyl-1-(4-chloro-benzyl)-6-methyl-2-oxo-1,2-dihydro-pyridin-3-yl]-4-chloro-benzamide;
1-(2,6-Dichloro-benzyl)-6-oxo-1,6-dihydro-pyridine-3-carboxylic acid N'-(3-chloro-5-trifluoromethyl-pyridin-2-yl)-hydrazide;
N-allyl-2-[(1-benzyl-6-oxo-1,6-dihydropyridin-3-yl)carbonyl]hydrazinecarbothioamide;
1-Benzyl-5-[5-(3,4-dichloro-benzylsulfanyl)-[1,3,4]oxadiazol-2-yl]-1H-pyridin-2-one;
N'-{[(1-benzyl-6-oxo-1,6-dihydropyridin-3-yl)carbonyl]oxy}pyridine-4-carboximidamide;
1-(2,6-Dichloro-benzyl)-6-oxo-1,6-dihydro-pyridine-3-carboxylic acid 3-trifluoromethyl-benzylamide;
1-Benzyl-6-oxo-1,6-dihydro-pyridine-3-carboxylic acid (2-morpholin-4-yl-ethyl)-amide;
5-[4-(3-Chloro-phenyl)-piperazine-1-carbonyl]-1-(3,4-dichloro-benzyl)-1H-pyridin-2-one;
5-Chloro-1-(2,6-dichloro-benzyl)-6-oxo-1,6-dihydro-pyridine-3-carboxylic acid benzylamide;
1-(4-Chloro-benzyl)-5-[3-(4-chloro-phenyl)-[1,2,4]oxadiazol-5-yl]-1H-pyridin-2-one;
1-(4-Chloro-benzyl)-5-[3-(4-chloro-phenyl)-[1,2,4]oxadiazol-5-yl]-1H-pyridin-2-one;
2-Chloro-N-[1-(2,6-dichloro-benzyl)-6-oxo-5-trifluoromethyl-1,6-dihydro-pyridin-3-yl]-4-fluoro-benzamide;
N-[1-(2,6-Dichloro-benzyl)-6-oxo-5-trifluoromethyl-1,6-dihydro-pyridin-3-yl]-4-isopropoxy-benzamide;
1-(2,6-Dichloro-benzyl)-6-oxo-1,6-dihydro-pyridine-3-carboxylic acid (4-trifluoromethoxy-phenyl)-amide;
1-(2,6-Dichloro-benzyl)-6-oxo-1,6-dihydro-pyridine-3-carboxylic acid (3-trifluoromethyl-phenyl)-amide;
5-Chloro-1-(2,6-dichloro-benzyl)-6-oxo-1,6-dihydro-pyridine-3-carboxylic acid (3-trifluoromethyl-phenyl)-amide;
1-(2,6-Dichloro-benzyl)-6-oxo-1,6-dihydro-pyridine-3-carboxylic acid (4-chloro-phenyl)-amide;
1-(2,6-Dichloro-benzyl)-6-oxo-1,6-dihydro-pyridine-3-carboxylic acid (2-dimethylamino-ethyl)-amide;
5-Methyl-1-phenyl-1H-pyridin-2-one;
3-Bromo-1-(3-fluoro-benzyl)-4-(3-methoxy-phenyl)-1H-pyridin-2-one;
3-Bromo-1-(3-fluoro-benzyl)-4-(3-isopropyl-phenyl)-1H-pyridin-2-one;
3'-Bromo-1'-(3-fluoro-benzyl)-6-methoxy-1'H-[3,4']bipyridinyl-2'-one;
4-Benzo[1,3]dioxol-5-yl-3-bromo-1-(3-fluoro-benzyl)-1H-pyridin-2-one;
3-Bromo-1-(3-fluoro-benzyl)-4-thiophen-3-yl-1H-pyridin-2-one;
3-Bromo-1-(3-fluoro-benzyl)-4-(3-trifluoromethyl-phenyl)-1H-pyridin-2-one;
3-Bromo-1-(3-fluoro-benzyl)-4-naphthalen-2-yl-1H-pyridin-2-one;
3-Bromo-1-(3-fluoro-benzyl)-4-(4-fluoro-phenyl)-1H-pyridin-2-one;
1-Benzenesulfonyl-4-benzyloxy-3-bromo-1H-pyridin-2-one;
4-[3-Amino-1-(2,4-difluoro-phenyl)-propoxy]-3-bromo-6-methyl-1-pyridin-3-ylmethyl-1H-pyridin-2-one;
1-(4-Bromo-2,6-difluoro-phenyl)-4-(2,4-difluoro-benzyloxy)-6-methyl-1H-pyridin-2-one;
2-[1-(4-Amino-2-methyl-pyrimidin-5-ylmethyl)-3-bromo-6-methyl-2-oxo-1,2-dihydro-pyridin-4-yloxymethyl]-5-fluoro-benzonitrile;
4-(2,4-Difluoro-benzyloxy)-6-methyl-1-(2,4,6-trifluoro-phenyl)-1H-pyridin-2-one;
1-(2-Chloro-4-hydroxy-phenyl)-4-(2,4-difluoro-benzyloxy)-6-methyl-1H-pyridin-2-one;
3-[4-(2,4-Difluoro-benzyloxy)-6-methyl-2-oxo-2H-pyridin-1-yl]-benzoic acid methyl ester;
3-Bromo-1-(2,6-difluoro-phenyl)-4-methoxy-6-methyl-5-vinyl-1H-pyridin-2-one;
3-Bromo-1-(2,6-difluoro-phenyl)-4-methoxy-6-methyl-5-styryl-1H-pyridin-2-one;
1-(2,6-Difluoro-phenyl)-4-methoxy-6-methyl-5-phenethyl-1H-pyridin-2-one;
3-Bromo-1-(2,6-difluoro-phenyl)-4-methoxy-6-methyl-5-phenethyl-1H-pyridin-2-one;
1-(1H-indazol-5-yl)-4-(1H-indazol-5-ylamino)-6-methylpyridin-2(1H)-one;
5-Bromo-4-(2,4-difluoro-benzyloxy)-1-(2,6-difluoro-phenyl)-2-[2-(2,4-difluoro-phenyl)-ethyl]-6-oxo-1,6-dihydro-pyridine-3-carbaldehyde;
4-[3-Bromo-4-(2,4-difluoro-benzyloxy)-6-methyl-2-oxo-2H-pyridin-1-yl]-pyrimidine-2-carbonitrile;
3-Bromo-4-(2,4-difluoro-benzyloxy)-6-methyl-2-oxo-2H-[1,2']bipyridinyl-5'-carboxylic acid;
3-Bromo-4-(5-carboxy-pyridin-2-yloxy)-6-methyl-2-oxo-2H-[1,2']bipyridinyl-5'-carboxylic acid;
3-Bromo-4-(2,4-difluoro-benzyloxy)-6,6'-dimethyl-2-oxo-2H-[1,2']bipyridinyl-3'-carbonitrile;
3-Bromo-4-(2,4-difluoro-benzyloxy)-6-methyl-2-oxo-2H-[1,2']bipyridinyl-5'-carboxylic acid methylamide;
3-Bromo-4-(2,4-difluoro-benzyloxy)-6-methyl-2-oxo-2H-[1,2']bipyridinyl-5'-carboxylic acid (2-hydroxy-ethyl)-amide;
3-Bromo-4-(2,4-difluoro-benzyloxy)-6-methyl-2-oxo-2H-[1,2']bipyridinyl-5'-carboxylic acid (2-methoxy-ethyl)-amide;
3-Bromo-1-(2,6-difluoro-phenyl)-4-methoxy-6-methyl-5-(4-methyl-benzyl)-1H-pyridin-2-one;
3-bromo-4-[(2,4-difluorobenzyl)oxy]-1-(2,6-difluorophenyl)-5-(1,2-dihydroxy-2-phenylethyl)-6-methylpyridin-2(1H)-one;
3-bromo-4-[(2,4-difluorobenzyl)oxy]-5'-(1-hydroxy-1-methylethyl)-6-methyl-2H-1,2'-bipyridin-2-one;
4-Benzyloxy-1H-pyridin-2-one;
4-Benzyloxy-3-methyl-1H-pyridin-2-one;
2-Oxo-6-phenethyl-1,2-dihydro-pyridine-3-carbonitrile;
2-Oxo-6-phenyl-1,2-dihydro-pyridine-3-carbonitrile;
6-Oxo-1,6-dihydro-[2,3']bipyridinyl-5-carbonitrile;
6-Oxo-1,6-dihydro-[2,3']bipyridinyl-5-carboxylic acid;
3-{[4-(benzyloxy)-3-bromo-2-oxopyridin-1 (2H)-yl]methyl}benzamide;
3-bromo-4-[(4-fluorobenzyl)oxy]-1-(4-methoxybenzyl)pyridin-2 (1H)-one;
3-bromo-4-[(4-fluorobenzyl)oxy]-1-(4-methoxybenzyl)pyridin-2 (1H)-one;
3-bromo-4-[(2,4-difluorobenzyl)oxy]-1-[2-fluoro-5-(hydroxymethyl)phenyl]-6-methylpyridin-2(1H)-one;
3-chloro-1-(4-fluorobenzyl)-4-[(4-fluorobenzyl)oxy]pyridin-2(1H)-one;
3-chloro-1-(4-fluorobenzyl)-4-[(4-fluorobenzyl)oxy]pyridin-2(1H)-one;
3-bromo-1-(3-chlorobenzyl)-4-[(4-fluorobenzyl)oxy]pyridin-2(1H)-one;
3-bromo-4-[(3,4-difluorobenzyl)oxy]-1-(3-fluorobenzyl)pyridin-2(1H)-one;
3-[3-bromo-4-[(2,4-difluorobenzyl)oxy]-6-methyl-2-oxopyridin-1(2H)-yl]-4-methylbenzoic acid;
3-bromo-1-(3-chlorobenzyl)-4-[(4-fluorobenzyl)oxy]pyridin-2(1H)-one;

3-bromo-1-(3-chlorobenzyl)-4-[(4-fluorobenzyl)oxy]pyridin-2(1H)-one;
4-{[3-chloro-4-[(2,4-difluorobenzyl)amino]-6-methyl-2-oxopyridin-1(2H)-yl]methyl}benzonitrile trifluoroacetate;
3-bromo-4-[(2,4-difluorobenzyl)oxy]-1-{[5-(1-hydroxy-1-methylethyl)pyrazin-2-yl]methyl}-6-methylpyridin-2(1H)-one;
4-(benzylamino)-3-bromo-1-(3-fluorobenzyl)pyridin-2(1H)-one;
4-(benzylamino)-3-bromo-1-(3-fluorobenzyl)pyridin-2(1H)-one;
2-{[3-bromo-4-[(2,4-difluorobenzyl)oxy]-6-methyl-2-oxopyridin-1(2H)-yl]methyl}benzonitrile;
3-bromo-4-[(2,4-difluorobenzyl)oxy]-1-[2-fluoro-6-(4-methylpiperazin-1-yl)phenyl]-6-methylpyridin-2(1H)-one trifluoroacetate;
4-[3-bromo-4-[(2,4-difluorobenzyl)oxy]-6-methyl-2-oxopyridin-1(2H)-yl]-N-methylbenzamide;
1-[2-(aminomethyl)benzyl]-3-bromo-4-[(2,4-difluorobenzyl)oxy]pyridin-2(1H)-one;
3-bromo-1-(4-fluorobenzyl)-4-[(4-fluorobenzyl)oxy]pyridin-2(1H)-one;
1-[2-(aminomethyl)benzyl]-3-bromo-4-[(2,4-difluorobenzyl)oxy]-6-methylpyridin-2(1H)-one;
3-bromo-4-[(2,4-difluorobenzyl)oxy]-6-methyl-1-[3-(piperidin-1-ylcarbonyl)phenyl]pyridin-2(1H)-one;
1-benzyl-3-bromo-4-[(4-chlorobenzyl)oxy]pyridin-2(1H)-one;
4-[(2,4-difluorobenzyl)oxy]-1-(3-fluorobenzyl)-3-methylpyridin-2(1H)-one;
4-(benzyloxy)-1-[4-(benzyloxy)benzyl]-3-bromopyridin-2(1H)-one;
4-[3-bromo-4-[(2,4-difluorobenzyl)oxy]-6-methyl-2-oxopyridin-1(2H)-yl]-N-hydroxybenzamide;
4-(benzyloxy)-3-bromo-1-[4-(trifluoromethyl)benzyl]pyridin-2(1H)-one;
3-bromo-1-(cyclopropylmethyl)-4-[(4-fluorobenzyl)oxy]pyridin-2(1H)-one;
3-bromo-1-(cyclopropylmethyl)-4-[(4-fluorobenzyl)oxy]pyridin-2(1H)-one;
1-benzyl-3-bromo-4-[(3-chlorobenzyl)oxy]-6-methylpyridin-2(1H)-one;
1-benzyl-3-bromo-4-[(3-chlorobenzyl)oxy]-6-methylpyridin-2(1H)-one;
1-benzyl-3-bromo-4-[(3-chlorobenzyl)oxy]-6-methylpyridin-2(1H)-one;
2-{[3-bromo-4-[(2,4-difluorobenzyl)oxy]-2-oxopyridin-1(2H)-yl]methyl}benzonitrile;
3-bromo-4-[(2,4-difluorobenzyl)oxy]-6-methyl-1-({5-[(methylamino)methyl]pyrazin-2-yl}methyl)pyridin-2(1H)-one trifluoroacetate;
3-bromo-1-(3-fluorobenzyl)-4-[(2-methylbenzyl)oxy]pyridin-2(1H)-one;
3-bromo-1-(3-fluorobenzyl)-4-[(2-methylbenzyl)oxy]pyridin-2(1H)-one;
methyl 3-{[3-bromo-4-[(2,4-difluorobenzyl)oxy]-2-oxopyridin-1(2H)-yl]methyl}benzoate;
3-bromo-1-(3-fluorobenzyl)-6-methyl-4-(2-phenylethyl)pyridin-2(1H)-one;
3-bromo-1-(3-fluorobenzyl)-6-methyl-4-(2-phenylethyl)pyridin-2(1H)-one;
1-benzyl-3-bromo-4-[(4-methylbenzyl)oxy]pyridin-2(1H)-one;
4-(benzyloxy)-1-(3-fluorobenzyl)-3-iodopyridin-2(1H)-one;
3-bromo-4-[(2,4-difluorobenzyl)oxy]-1-[3-(hydroxymethyl)phenyl]-6-methylpyridin-2(1H)-one;

4-(benzyloxy)-1-(3-fluorobenzyl)-3-iodopyridin-2(1H)-one;
3-{[3-bromo-4-[(2,4-difluorobenzyl)oxy]-6-methyl-2-oxopyridin-1(2H)-yl]methyl}benzoic acid;
3-bromo-4-[(4-fluorobenzyl)oxy]-1-[2-(hydroxymethyl)benzyl]pyridin-2(1H)-one;
3-bromo-4-[(2,4-difluorobenzyl)oxy]-1-[5-{[(2-hydroxyethyl)(methyl)amino]methyl}pyrazin-2-yl)methyl]-6-methylpyridin-2(1H)-one trifluoroacetate (salt);
4-(benzyloxy)-3-bromo-1-[(6-fluoropyridin-3-yl)methyl]pyridin-2(1H)-one;
3-bromo-4-[(4-chlorobenzyl)oxy]-1-(4-fluorobenzyl)pyridin-2(1H)-one;
3-bromo-4-[(4-chloro-2-fluorobenzyl)amino]-1-(3-fluorobenzyl)pyridin-2(1H)-one;
4-(benzyloxy)-3-bromo-1-ethylpyridin-2(1H)-one;
4-(benzyloxy)-3-bromo-1-ethylpyridin-2(1H)-one;
4-(benzyloxy)-3-bromo-1-ethylpyridin-2(1H)-one;
2-(2-{[3-bromo-4-[(2,4-difluorobenzyl)oxy]-2-oxopyridin-1(2H)-yl]methyl}phenyl)acetamide;
1-benzyl-3-bromo-4-[(2-chlorobenzyl)oxy]pyridin-2(1H)-one;
1-benzyl-3-bromo-4-[(2-chlorobenzyl)oxy]pyridin-2(1H)-one;
methyl 2-{[3-bromo-4-[(4-fluorobenzyl)oxy]-2-oxopyridin-1(2H)-yl]methyl}benzoate;
3-bromo-1-(2,6-dichlorophenyl)-4-[2-(4-fluorophenyl)ethyl]-6-methylpyridin-2(1H)-one;
3-bromo-1-(2,6-dichlorophenyl)-4-[2-(4-fluorophenyl)ethyl]-6-methylpyridin-2(1H)-one;
3-bromo-4-[(2,4-difluorobenzyl)oxy]-1-{5-[(isopropylamino)methyl]-2-methylphenyl}-6-methylpyridin-2(1H)-one hydrochloride;
3-bromo-1-(3-fluorobenzyl)-4-(2-phenylethyl)pyridin-2(1H)-one;
N-{3-[3-bromo-4-[(2,4-difluorobenzyl)oxy]-6-methyl-2-oxopyridin-1(2H)-yl]benzyl}-N'-methylurea;
3-chloro-4-[(2,4-difluorobenzyl)oxy]-1-[3-(hydroxymethyl)phenyl]-6-methylpyridin-2(1H)-one;
3-bromo-1-(3-fluorobenzyl)-4-[(3-fluorobenzyl)oxy]pyridin-2(1H)-one;
4-(benzyloxy)-3-bromo-1-[2-(2-thienyl)ethyl]pyridin-2(1H)-one;
4-(benzyloxy)-3-bromo-1-[2-(2-thienyl)ethyl]pyridin-2(1H)-one;
3-bromo-4-[(2,4-difluorobenzyl)amino]-1-(2,6-difluorophenyl)-6-methylpyridin-2(1H)-one trifluoroacetate;
3-bromo-4-[(2,4-difluorobenzyl)amino]-1-(2,6-difluorophenyl)-6-methylpyridin-2(1H)-one trifluoroacetate;
3-bromo-4-[(4-chlorobenzyl)oxy]-1-(4-methoxybenzyl)pyridin-2(1H)-one;
3-bromo-4-[(4-chlorobenzyl)oxy]-1-(4-methoxybenzyl)pyridin-2(1H)-one;
3-bromo-1-(4-chlorobenzyl)-4-[(4-chlorobenzyl)oxy]pyridin-2(1H)-one;
3-bromo-1-(3-fluorobenzyl)-4-[(4-methoxybenzyl)oxy]pyridin-2(1H)-one;
3-bromo-1-(3,5-dibromo-2,6-difluoro-4-hydroxyphenyl)-4-[(2,4-difluorobenzyl)oxy]-6-methylpyridin-2(1H)-one;
4-(benzyloxy)-3-bromo-1-[4-(trifluoromethoxy)benzyl]pyridin-2(1H)-one;
4-(benzyloxy)-3-bromo-1-[4-(trifluoromethoxy)benzyl]pyridin-2(1H)-one;
N'-{3-[3-bromo-4-[(2,4-difluorobenzyl)oxy]-6-methyl-2-oxopyridin-1(2H)-yl]benzyl}-N,N-dimethylurea;

3-bromo-4-[(4-fluorobenzyl)oxy]-1-[4-(trifluoromethyl)benzyl]pyridin-2(1H)-one;
2-{[3-bromo-4-[(2,4-difluorobenzyl)oxy]-6-methyl-2-oxopyridin-1(2H)-yl]methyl}benzamide;
N-{3-[3-bromo-4-[(2,4-difluorobenzyl)oxy]-6-methyl-2-oxopyridin-1(2H)-yl]benzyl}morpholine-4-carboxamide;
N-{3-[3-bromo-4-[(2,4-difluorobenzyl)oxy]-6-methyl-2-oxopyridin-1(2H)-yl]benzyl}methanesulfonamide;
4-[3-bromo-4-[(2,4-difluorobenzyl)oxy]-6-methyl-2-oxopyridin-1(2H)-yl]-N-isopropylbenzamide;
4-(allylamino)-3-bromo-1-(2,6-difluorophenyl)-5-iodo-6-methylpyridin-2(1H)-one;
4-(allylamino)-3-bromo-1-(2,6-difluorophenyl)-5-iodo-6-methylpyridin-2(1H)-one;
(4-{[4-(benzyloxy)-3-bromo-2-oxopyridin-1(2H)-yl]methyl}phenyl)acetic acid;
3-bromo-4-[(2,4-difluorobenzyl)oxy]-6-methyl-1-[4-(pyrrolidin-1-ylcarbonyl)phenyl]pyridin-2(1H)-one;
1-benzyl-4-(benzyloxy)-3-iodopyridin-2(1H)-one;
1-(biphenyl-4-ylmethyl)-3-bromo-4-[(4-fluorobenzyl)oxy]pyridin-2(1H)-one;
4-[3-bromo-4-[(2,4-difluorobenzyl)oxy]-6-methyl-2-oxopyridin-1(2H)-yl]benzoic acid;
4-(benzyloxy)-3-bromo-1-[2-(3-thienyl)ethyl]pyridin-2(1H)-one;
4-(benzyloxy)-3-bromo-1-[2-(3-thienyl)ethyl]pyridin-2(1H)-one;
3-bromo-4-[(4-fluorobenzyl)oxy]-1-[3-(trifluoromethyl)benzyl]pyridin-2(1H)-one;
N-[3-bromo-1-(3-fluorobenzyl)-2-oxo-1,2-dihydropyridin-4-yl]-4-fluorobenzamide;
methyl 3-[3-bromo-4-[(2,4-difluorobenzyl)oxy]-6-methyl-2-oxopyridin-1(2H)-yl]benzylcarbamate;
1-benzyl-4-(benzylthio)-3-bromopyridin-2(1H)-one;
4-(benzyloxy)-3-bromo-1-(4-tert-butylbenzyl)pyridin-2(1H)-one;
4-(benzyloxy)-3-bromo-1-(4-tert-butylbenzyl)pyridin-2(1H)-one;
N-{3-[3-bromo-4-[(2,4-difluorobenzyl)oxy]-6-methyl-2-oxopyridin-1(2H)-yl]benzyl}-2-methoxyacetamide;
3-bromo-4-[(2,4-difluorobenzyl)oxy]-1-({5-[(dimethylamino)methyl]pyrazin-2-yl}methyl)-6-methylpyridin-2(1H)-one trifluoroacetate;
3-bromo-4-[(2,4-difluorobenzyl)oxy]-6-methyl-1-[4-(piperazin-1-ylcarbonyl)phenyl]pyridin-2(1H)-one hydrochloride;
4-[3-bromo-4-[(2,4-difluorobenzyl)oxy]-6-methyl-2-oxopyridin-1(2H)-yl]-N,N-bis(2-hydroxyethyl)benzamide;
3-bromo-4-[(2,4-difluorobenzyl)oxy]-1-{5-[(dimethylamino)methyl]-2-methylphenyl}-6-methylpyridin-2(1H)-one hydrochloride;
1-benzyl-3-bromo-4-(2-phenylethyl)pyridin-2(1H)-one;
1-(3-fluorobenzyl)-4-[(4-fluorobenzyl)oxy]-3-methylpyridin-2(1H)-one;
4-(benzyloxy)-1-(piperidin-3-ylmethyl)pyridin-2(1H)-one trifluoroacetate;
3-bromo-4-[(2,4-difluorobenzyl)oxy]-6-methyl-1-[4-(morpholin-4-ylcarbonyl)phenyl]pyridin-2(1H)-one;
4-(benzyloxy)-1-(3-fluorobenzyl)-3-methylpyridin-2(1H)-one;
$N^1$-{3-[3-bromo-4-[(2,4-difluorobenzyl)oxy]-6-methyl-2-oxopyridin-1(2H)-yl]benzyl}glycinamide hydrochloride;
3-bromo-4-[(2,4-difluorobenzyl)oxy]-1-(2,6-difluorophenyl)-5-iodo-6-methylpyridin-2(1H)-one;
3-bromo-4-[(2,4-difluorobenzyl)oxy]-6-methyl-1-[4-(piperidin-1-ylcarbonyl)phenyl]pyridin-2(1H)-one;
N-[3-bromo-1-(3-fluorobenzyl)-2-oxo-1,2-dihydropyridin-4-yl]-2,6-difluorobenzamide;
2-{[4-(benzyloxy)-3-bromo-2-oxopyridin-1(2H)-yl]methyl}benzonitrile;
5-{[3-bromo-4-[(2,4-difluorobenzyl)oxy]-6-methyl-2-oxopyridin-1(2H)-yl]methyl}-N-methylpyrazine-2-carboxamide;
3-chloro-4-[(2,4-difluorobenzyl)amino]-1-(2,6-difluorophenyl)-6-methylpyridin-2(1H)-one;
3-[3-chloro-4-[(2,4-difluorobenzyl)oxy]-6-methyl-2-oxopyridin-1(2H)-yl]benzoic acid;
3-bromo-1-(3-fluorobenzyl)-4-[(3-fluorobenzyl)amino]pyridin-2(1H)-one;
3-bromo-1-(3-fluorobenzyl)-4-[(3-methoxybenzyl)oxy]pyridin-2(1H)-one;
3-bromo-1-(4-tert-butylbenzyl)-4-[(2,4-difluorobenzyl)oxy]pyridin-2(1H)-one;
N-{3-[3-bromo-4-[(2,4-difluorobenzyl)oxy]-6-methyl-2-oxopyridin-1(2H)-yl]benzyl}acetamide;
2-({3-[3-bromo-4-[(2,4-difluorobenzyl)oxy]-6-methyl-2-oxopyridin-1(2H)-yl]benzyl}amino)-2-oxoethyl acetate;
1-benzyl-4-(benzyloxy)-3-methylpyridin-2(1H)-one;
N-{3-[3-bromo-4-[(2,4-difluorobenzyl)oxy]-6-methyl-2-oxopyridin-1(2H)-yl]benzyl}urea;
1-benzyl-4-(benzyloxy)-3-ethylpyridin-2(1H)-one;
N-{3-[3-bromo-4-[(2,4-difluorobenzyl)oxy]-6-methyl-2-oxopyridin-1(2H)-yl]benzyl}-2-hydroxyacetamide;
3-bromo-4-[(4-chlorobenzyl)oxy]-1-(2-phenylethyl)pyridin-2(1H)-one;
3-bromo-1-(3-chlorobenzyl)-4-[(4-chlorobenzyl)oxy]pyridin-2(1H)-one;
1-[3-(aminomethyl)phenyl]-3-bromo-4-[(2,4-difluorobenzyl)oxy]-6-methylpyridin-2(1H)-one;
2-{[4-(benzyloxy)-3-bromo-2-oxopyridin-1(2H)-yl]methyl}benzamide;
1-(4-fluorobenzyl)-4-[(4-fluorobenzyl)oxy]pyridin-2(1H)-one;
1-[2-(aminomethyl)benzyl]-4-(benzyloxy)-3-bromopyridin-2(1H)-one;
methyl 3-[4-(benzyloxy)-3-bromo-2-oxopyridin-1(2H)-yl]propanoate;
1-benzyl-4-(benzyloxy)-3-methylpyridin-2(1H)-one;
4-(allylamino)-1-(2,6-difluorophenyl)-5-iodo-6-methylpyridin-2(1H)-one;
4-(allylamino)-1-(2,6-difluorophenyl)-5-iodo-6-methylpyridin-2(1H)-one;
3-bromo-1-(3-fluorobenzyl)-4-(phenylethynyl)pyridin-2(1H)-one;
4-[3-bromo-4-[(2,4-difluorobenzyl)oxy]-6-methyl-2-oxopyridin-1(2H)-yl]-N,N-dimethylbenzamide;
{4-[({4-(benzyloxy)-3-bromo-1-[4-(carboxymethyl)benzyl]-1,2-dihydropyridin-2-yl}oxy)methyl]phenyl}acetic acid;
4-(benzyloxy)-3-bromo-1-[3-(trifluoromethyl)benzyl]pyridin-2(1H)-one;
4-(benzyloxy)-3-ethynyl-1-(3-fluorobenzyl)pyridin-2(1H)-one;
3-bromo-4-[(2,4-difluorobenzyl)oxy]-1-{3-[(dimethylamino)methyl]phenyl}-6-methylpyridin-2(1H)-one;
4-(benzyloxy)-3-bromo-1-methylpyridin-2(1H)-one;
1-benzyl-3-bromo-4-(phenylethynyl)pyridin-2(1H)-one;
4-(benzyloxy)-3-bromo-1-methylpyridin-2(1H)-one;
3-bromo-1-(3-fluorobenzyl)-4-{[4-(trifluoromethyl)benzyl]oxy}pyridin-2(1H)-one;
4-(benzylamino)-3-bromo-1-(2,6-difluorophenyl)-5-iodo-6-methylpyridin-2(1H)-one;

4-[(2,4-difluorobenzyl)oxy]-1-(4-methoxybenzyl)-6-methylpyridin-2(1H)-one;
4-(benzyloxy)-3-bromo-1-methylpyridin-2(1H)-one hydrobromide;
4-(benzyloxy)-3-bromo-1-[4-(morpholin-4-ylcarbonyl)phenyl]pyridin-2(1H)-one;
5-bromo-4-[(2,4-difluorobenzyl)oxy]-1-(2,6-difluorophenyl)-6-oxo-1,6-dihydropyridine-2-carboxylic acid;
1-benzyl-3-bromo-4-[(2,6-dichlorobenzyl)oxy]pyridin-2(1H)-one;
3-[3-chloro-4-[(2,4-difluorobenzyl)oxy]-6-methyl-2-oxopyridin-1(2H)-yl]-2-methylbenzoic acid;
4-[4-(benzyloxy)-3-bromo-2-oxopyridin-1(2H)-yl]benzoic acid;
ethyl N-(5-{[3-bromo-4-[(2,4-difluorobenzyl)oxy]-6-methyl-2-oxopyridin-1(2H)-yl]methyl}-2-methylpyrimidin-4-yl)glycinate trifluoroacetate;
3-bromo-4-[(2,4-difluorobenzyl)oxy]-1-(2,6-difluorophenyl)-6-methyl-5-[(E)-2-phenylvinyl]pyridin-2(1H)-one;
3-bromo-1-(3-fluorobenzyl)-4-{[3-(trifluoromethyl)benzyl]amino}pyridin-2(1H)-one;
3-bromo-4-[(4-fluorobenzyl)oxy]-1-(3-phenylpropyl)pyridin-2(1H)-one;
3-bromo-1-(4-tert-butylbenzyl)-4-[(4-fluorobenzyl)oxy]pyridin-2(1H)-one;
4-(allylamino)-3-bromo-1-(2,6-difluorophenyl)-6-methylpyridin-2(1H)-one;
1-cyclohexyl-4-[(2,4-difluorobenzyl)oxy]-3,6-dimethylpyridin-2(1H)-one;
3-bromo-4-[(2,4-difluorobenzyl)oxy]-1-(2,6-difluorophenyl)-5-(hydroxymethyl)-6-methylpyridin-2(1H)-one;
1-benzyl-4-(benzyloxy)-2-oxo-1,2-dihydropyridine-3-carbaldehyde;
4-[(2,4-difluorobenzyl)oxy]-6-methyl-1-prop-2-yn-1-ylpyridin-2(1H)-one;
ethyl 3-[4-(benzyloxy)-3-bromo-2-oxopyridin-1(2H)-yl]propanoate;
1-benzyl-4-(benzyloxy)-3-(hydroxymethyl)pyridin-2(1H)-one;
or a pharmaceutically acceptable salt thereof.
3-Chloro-4-(2,4-difluoro-benzyloxy)-6-methyl-1-(5-methyl-pyrazin-2-ylmethyl)-1H-pyridin-2-one
3-Chloro-4-(2,4-difluoro-benzyloxy)-1-(5-hydroxymethyl-pyrazin-2-ylmethyl)-6-methyl-1H-pyridin-2-one
3-Bromo-4-(2,4-difluoro-benzyloxy)-1-(2,3-dihydro-1H-indol-5-ylmethyl)-1H-pyridin-2-one
3-Bromo-4-(2,4-difluoro-benzyloxy)-1-[1-(2-hydroxy-acetyl)-2,3-dihydro-1H-indol-5-ylmethyl]-6-methyl-1H-pyridin-2-one
3-Bromo-4-(2,4-difluoro-benzyloxy)-6-methyl-1-(1H-pyrazol-3-ylmethyl)-1H-pyridin-2-one
3-[3-Chloro-4-(2,4-difluoro-benzyloxy)-6-methyl-2-oxo-2H-pyridin-1-yl]-4,N-dimethyl-benzamide
3-[3-Chloro-4-(2,4-difluoro-benzyloxy)-6-methyl-2-oxo-2H-pyridin-1-yl]-4-methyl-benzamide
3-[3-Chloro-4-(2,4-difluoro-benzyloxy)-6-methyl-2-oxo-2H-pyridin-1-yl]-4-fluoro-N-methyl-benzamide
4-Chloro-3-[3-chloro-4-(2,4-difluoro-benzyloxy)-6-methyl-2-oxo-2H-pyridin-1-yl]-N-methyl-benzamide
3-[3-Chloro-4-(2,4-difluoro-benzyloxy)-6-methyl-2-oxo-2H-pyridin-1-yl]-4-fluoro-benzamide
4-[3-Chloro-4-(2,4-difluoro-benzyloxy)-6-methyl-2-oxo-2H-pyridin-1-yl]-3,N-dimethyl-benzamide
3-Chloro-4-(2,4-difluoro-benzyloxy)-1-[4-(1,2-dihydroxy-ethyl)-2-methyl-phenyl]-6-methyl-1H-pyridin-2-one
N-{4-[3-Chloro-4-(2,4-difluoro-benzyloxy)-6-methyl-2-oxo-2H-pyridin-1-ylmethyl]-phenyl}-2-hydroxy-acetamide
1-Hydroxy-cyclopropanecarboxylic acid 4-[3-chloro-4-(2,4-difluoro-benzyloxy)-6-methyl-2-oxo-2H-pyridin-1-ylmethyl]-benzylamide
N-{4-[3-Chloro-4-(2,4-difluoro-benzyloxy)-6-methyl-2-oxo-2H-pyridin-1-ylmethyl]-benzyl}-2-hydroxy-acetamide
N-{4-[3-Chloro-4-(2,4-difluoro-benzyloxy)-6-methyl-2-oxo-2H-pyridin-1-ylmethyl]-phenyl}-acetamide
{(2-[3-Bromo-1-(2,6-difluoro-phenyl)-6-methyl-2-oxo-1,2-dihydro-pyridin-4-yloxymethyl]-5-fluoro-benzyl}-carbamic acid ethyl ester The above names were generated using ChemDraw Ultra version 6.0.2, which is put out by CambridgeSoft.com, Cambridge, Mass; or ACD Namepro version 5.09, which is put out by ACDlabs.com.

Definitions

As used herein, the term "alkenyl" refers to a straight or branched hydrocarbon of a designed number of carbon atoms containing at least one carbon-carbon double bond. Examples of "alkenyl" include vinyl, allyl, and 2-methyl-3-heptene.

The term "alkoxy" represents an alkyl attached to the parent molecular moiety through an oxygen bridge. Examples of alkoxy groups include, for example, methoxy, ethoxy, propoxy and isopropoxy.

The term "thioalkoxy" represents an alkyl attached to the parent molecular moiety through a sulfur atom. Examples of thioalkoxy groups include, for example, thiomethoxy, thioethoxy, thiopropoxy and thioisopropoxy.

As used herein, the term "alkyl" includes those alkyl groups of a designed number of carbon atoms. Alkyl groups may be straight or branched. Examples of "alkyl" include methyl, ethyl, propyl, isopropyl, butyl, iso-, sec- and tert-butyl, pentyl, hexyl, heptyl, 3-ethylbutyl, and the like. "Cx-Cy alkyl" represents an alkyl group of the specified number of carbons. For example, $C_1$–$C_4$ alkyl includes all alkyl groups that include at least one and no more than four carbon atoms. It also contains subgroups, such as, for example, $C_2$–$C_3$ alkyl or $C_1$–$C_3$ alkyl.

The term "aryl" refers to an aromatic hydrocarbon ring system containing at least one aromatic ring. The aromatic ring may optionally be fused or otherwise attached to other aromatic hydrocarbon rings or non-aromatic hydrocarbon rings. Examples of aryl groups include, for example, phenyl, naphthyl, 1,2,3,4-tetrahydronaphthalene, indanyl, and biphenyl. Preferred examples of aryl groups include phenyl and naphthyl. The most preferred aryl group is phenyl. The aryl groups herein are unsubstituted or, as specified, substituted in one or more substitutable positions with various groups. Thus, such aryl groups can be optionally substituted with groups such as, for example, $C_1$–$C_6$ alkyl, $C_1$–$C_6$ alkoxy, halogen, hydroxy, cyano, nitro, amino, mono- or di-($C_1$–$C_6$)alkylamino, $C_2$–$C_6$ alkenyl, $C_2$–$C_6$ alkynyl, $C_1$–$C_6$ haloalkyl, $C_1$–$C_6$ haloalkoxy, amino($C_1$–$C_6$)alkyl, mono- or di($C_1$–$C_6$)alkylamino($C_1$–$C_6$)alkyl.

The term "arylalkyl" refers to an aryl group, as defined above, attached to the parent molecular moiety through an alkyl group, as defined above. Preferred arylalkyl groups include, benzyl, phenethyl, phenpropyl, and phenbutyl. More preferred arylalkyl groups include benzyl and phenethyl. The most preferred arylalkyl group is benzyl. The aryl portions of these groups are unsubstituted or, as specified, substituted in one or more substitutable positions with various groups. Thus, such aryl groups can be optionally substituted with groups such as, for example, $C_1$–$C_6$ alkyl, $C_1$–$C_6$ alkoxy, halogen, hydroxy, cyano, nitro, amino, mono- or di-($C_1$–$C_6$)alkylamino, $C_2$–$C_6$ alkenyl, $C_2$–$C_6$ alkynyl, $C_1$–$C_6$ haloalkyl, $C_1$–$C_6$ haloalkoxy, amino($C_1$–$C_6$)alkyl, mono- or di($C_1$–$C_6$)alkylamino($C_1$–$C_6$)alkyl.

The term "arylalkoxyl" refers to an aryl group, as defined above, attached to the parent molecular moiety through an alkoxy group, as defined above. Preferred arylaloxy groups include, benzyloxy, phenethyloxy, phenpropyloxy, and phenbutyloxy. The most preferred arylalkoxy group is benzyloxy.

The term "cycloalkyl" refers to a $C_3$–$C_8$ cyclic hydrocarbon. Examples of cycloalkyl include cyclopropyl, cyclobutyl, cyclopentyl, cyclohexyl, cycloheptyl and cyclooctyl. More preferred cycloalkyl groups include cyclopropyl.

The term "cycloalkylalkyl," as used herein, refers to a $C_3$–$C_8$ cycloalkyl group attached to the parent molecular moiety through an alkyl group, as defined above. Examples of cycloalkylalkyl groups include cyclopropylmethyl and cyclopentylethyl.

The terms "halogen" or "halo" indicate fluorine, chlorine, bromine, or iodine.

The term "heterocycloalkyl," refers to a non-aromatic ring system containing at least one heteroatom selected from nitrogen, oxygen, and sulfur, wherein the non-aromatic heterocycle is attached to the core. The heterocycloalkyl ring may be optionally fused to or otherwise attached to other heterocycloalkyl rings, aromatic heterocycles, aromatic hydrocarbons and/or non-aromatic hydrocarbon rings. Preferred heterocycloalkyl groups have from 3 to 7 members. Examples of heterocycloalkyl groups include, for example, piperazine, 1,2,3,4-tetrahydroisoquinoline, morpholine, piperidine, tetrahydrofuran, pyrrolidine, and pyrazole. Preferred heterocycloalkyl groups include piperidinyl, piperazinyl, morpholinyl, and pyrolidinyl. The heterocycloalkyl groups herein are unsubstituted or, as specified, substituted in one or more substitutable positions with various groups. Thus, such heterocycloalkyl groups can be optionally substituted with groups such as, for example, $C_1$–$C_6$ alkyl, $C_1$–$C_6$ alkoxy, halogen, hydroxy, cyano, nitro, amino, mono- or di-($C_1$–$C_6$)alkylamino, $C_2$–$C_6$ alkenyl, $C_2$–$C_6$ alkynyl, $C_1$–$C_6$ haloalkyl, $C_1$–$C_6$ haloalkoxy, amino ($C_1$–$C_6$)alkyl, mono- or di($C_1$–$C_6$)alkylamino($C_1$–$C_6$)alkyl.

The term "heteroaryl" refers to an aromatic ring system containing at least one heteroatom selected from nitrogen, oxygen, and sulfur. The heteroaryl ring may be fused or otherwise attached to one or more heteroaryl rings, aromatic or non-aromatic hydrocarbon rings or heterocycloalkyl rings. Examples of heteroaryl groups include, for example, pyridine, furan, thiophene, 5,6,7,8-tetrahydroisoquinoline and pyrimidine. Preferred examples of heteroaryl groups include thienyl, benzothienyl, pyridyl, quinolyl, pyrazinyl, pyrimidyl, imidazolyl, benzimidazolyl, furanyl, benzofuranyl, thiazolyl, benzothiazolyl, isoxazolyl, oxadiazolyl, isothiazolyl, benzisothiazolyl, triazolyl, tetrazolyl, pyrrolyl, indolyl, pyrazolyl, and benzopyrazolyl. Preferred heteroaryl groups include pyridyl. The heteroaryl groups herein are unsubstituted or, as specified, substituted in one or more substitutable positions with various groups. Thus, such heteroaryl groups can be optionally substituted with groups such as, for example, $C_1$–$C_6$ alkyl, $C_1$–$C_6$ alkoxy, halogen, hydroxy, cyano, nitro, amino, mono- or di-($C_1$–$C_6$)alkylamino, $C_2$–$C_6$ alkenyl, $C_2$–$C_6$ alkynyl, $C_1$–$C_6$ haloalkyl, $C_1$–$C_6$ haloalkoxy, amino($C_1$–$C_6$)alkyl, mono- or di($C_1$–$C_6$)alkylamino($C_1$–$C_6$)alkyl.

The term "heteroarylalkyl" refers to a heteroaryl group, as defined above, attached to the parent molecular moiety through an alkyl group, as defined above. Preferred heteroarylalkyl groups include, pyrazolemethyl, pyrazoleethyl, pyridylmethyl, pyridylethyl, thiazolemethyl, thiazoleethyl, imidazolemethyl, imidazoleethyl, thienylmethyl, thienylethyl, furanylmethyl, furanylethyl, isoxazolemethyl, isoxazoleethyl, pyrazinemethyl and pyrazineethyl. More preferred heteroarylalkyl groups include pyridylmethyl and pyridylethyl. The heteroaryl portions of these groups are unsubstituted or, as specified, substituted in one or more substitutable positions with various groups. Thus, such heteroaryl groups can be optionally substituted with groups such as, for example, $C_1$–$C_6$ alkyl, $C_1$–$C_6$ alkoxy, halogen, hydroxy, cyano, nitro, amino, mono- or di-($C_1$–$C_6$) alkylamino, $C_2$–$C_6$ alkenyl, $C_2$–$C_6$ alkynyl, $C_1$–$C_6$ haloalkyl, $C_1$–$C_6$ haloalkoxy, amino($C_1$–$C_6$)alkyl, mono- or di($C_1$–$C_6$)alkylamino($C_1$–$C_6$)alkyl.

If two or more of the same substituents are on a common atom, e.g., di($C_1$–$C_6$)alkylamino, it is understood that the nature of each group is independent of the other.

As used herein, the term "p38 mediated disorder" refers to any and all disorders and disease states in which p38 plays a role, either by control of p38 itself, or by p38 causing another factor to be released, such as but not limited to IL-1, IL-6 or IL-8. A disease state in which, for instance, IL-1 is a major component, and whose production or action, is exacerbated or secreted in response to p38, would therefore be considered a disorder mediated by p38.

As TNF-beta has close structural homology with TNF-alpha (also known as cachectin), and since each induces similar biologic responses and binds to the same cellular receptor, the synthesis of both TNF-alpha and TNF-beta are inhibited by the compounds of the present invention and thus are herein referred to collectively as "TNF" unless specifically delineated otherwise.

Non-toxic pharmaceutically acceptable salts include, but are not limited to salts of inorganic acids such as hydrochloric, sulfuric, phosphoric, diphosphoric, hydrobromic, and nitric or salts of organic acids such as formic, citric, malic, maleic, fumaric, tartaric, succinic, acetic, lactic, methanesulfonic, p-toluenesulfonic, 2-hydroxyethylsulfonic, salicylic and stearic. Similarly, pharmaceutically acceptable cations include, but are not limited to sodium, potassium, calcium, aluminum, lithium and ammonium. Those skilled in the art will recognize a wide variety of non-toxic pharmaceutically acceptable addition salts.

The compounds of this invention may contain one or more asymmetric carbon atoms, so that the compounds can exist in different stereoisomeric forms. These compounds can be, for example, racemates, chiral non-racemic or diastereomers. In these situations, the single enantiomers, i.e., optically active forms, can be obtained by asymmetric synthesis or by resolution of the racemates. Resolution of the racemates can be accomplished, for example, by conventional methods such as crystallization in the presence of a resolving agent; chromatography, using, for example a chiral HPLC column; or derivatizing the racemic mixture with a resolving reagent to generate diastereomers, separating the diastereomers via chromatography or selective crystallization, and removing the resolving agent to generate the original compound in enantiomerically enriched form. Any of the above procedures can be repeated to increase the enantiomeric purity of a compound.

The compounds of the invention may exist as atropisomers, i.e., chiral rotational isomers. The invention encompasses the racemic and the resolved atropisomers.

The following illustration generically shows a compound (Z) that can exist as atropisomers as well as its two possible atropisomers (A) and (B). This illustration also shows each of atropisomers (A) and (B) in a Fischer projection. In this illustration, $R_1$, $R_2$, and $R_4$ carry the same definitions as set forth for Formula I, $R_p$, is a substituent within the definition of $R_5$, and $R_p$ is a non-hydrogen substituent within the definition of $R_5$.

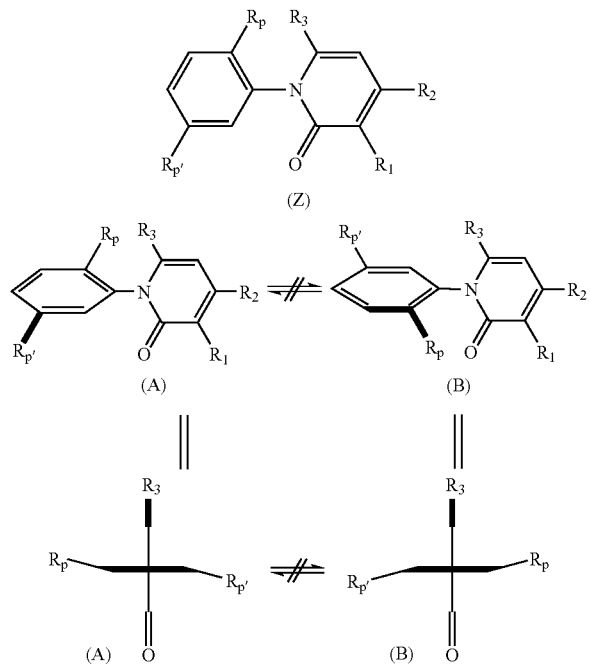

When the compounds described herein contain olefinic double bonds or other centers of geometric asymmetry, and unless otherwise specified, it is intended that the compounds include the cis, trans, Z- and E- configurations. Likewise, all tautomeric forms are also intended to be included.

The compounds of general Formula I may be administered orally, topically, parenterally, by inhalation or spray or rectally in dosage unit formulations containing conventional non-toxic pharmaceutically acceptable carriers, adjuvants and vehicles. The term parenteral as used herein includes percutaneous, subcutaneous, intravascular (e.g., intravenous), intramuscular, or intrathecal injection or infusion techniques and the like. In addition, there is provided a pharmaceutical formulation comprising a compound of general Formula I and a pharmaceutically acceptable carrier. One or more compounds of general Formula I may be present in association with one or more non-toxic pharmaceutically acceptable carriers and/or diluents and/or adjuvants, and if desired other active ingredients. The pharmaceutical compositions containing compounds of general Formula I may be in a form suitable for oral use, for example, as tablets, troches, lozenges, aqueous or oily suspensions, dispersible powders or granules, emulsion, hard or soft capsules, or syrups or elixirs.

For oral administration, the pharmaceutical composition may be in the form of, for example, a tablet, hard or soft capsule, lozenges, dispensable powders, suspension, or liquid. The pharmaceutical composition is preferably made in the form of a dosage unit containing a particular amount of the active ingredient. Examples of such dosage units are tablets or capsules.

Compositions intended for oral use may be prepared according to any method known to the art for the manufacture of pharmaceutical compositions and such compositions may contain one or more agents selected from the group consisting of sweetening agents, flavoring agents, coloring agents and preservative agents in order to provide pharmaceutically elegant and palatable preparations. Tablets contain the active ingredient in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques. In some cases such coatings may be prepared by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules, wherein the active ingredient is mixed with an inert solid diluent, for example, calcium carbonate, calcium phosphate, or kaolin, or as soft gelatin capsules wherein the active ingredient is mixed with water or an oil medium, for example peanut oil, liquid paraffin or olive oil.

Formulations for oral use may also be presented as lozenges.

Aqueous suspensions contain the active materials in admixture with excipients suitable for the manufacture of aqueous suspensions. Such excipients are suspending agents, for example sodium carboxymethylcellulose, methylcellulose, hydropropyl-methylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil, or coconut oil, or in a mineral oil such as liquid paraffin. The oily suspensions may contain a thickening agent, for example beeswax, hard paraffin, or cetyl alcohol. Sweetening agents and flavoring agents may be added to provide palatable oral preparations. These compositions may be preserved by the addition of an antioxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents or suspending agents are exemplified by those already mentioned above. Additional excipients, for example sweetening, flavoring, and coloring agents, may also be present.

Pharmaceutical compositions of the invention may also be in the form of oil-in-water emulsions. The oily phase may be a vegetable oil or a mineral oil or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol, glucose or sucrose. Such formulations may also contain a demulcent, a preservative, and flavoring and coloring agents. The pharmaceutical compositions may be in the form of a sterile injectable aqueous or oleaginous suspension. This suspension may be formulated according to the known art using those suitable dispersing or wetting agents and suspending agents that have been mentioned above. The sterile injectable preparation may also be a sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of general Formula I may also be administered in the form of suppositories, e.g., for rectal administration of the drug. These compositions can be prepared by mixing the drug with a suitable non-irritating excipient that is solid at ordinary temperatures but liquid at the rectal temperature and will therefore melt in the rectum to release the drug. Such materials include cocoa butter and polyethylene glycols.

Compounds of general Formula I may be administered parenterally in a sterile medium. The drug, depending on the vehicle and concentration used, can either be suspended or dissolved in the vehicle. Advantageously, adjuvants such as local anesthetics, preservatives, and buffering agents can be dissolved in the vehicle.

The active ingredient may also be administered by injection (IV, IM, subcutaneous or jet) as a composition wherein, for example, saline, dextrose, or water may be used as a suitable carrier. The pH of the composition may be adjusted, if necessary, with suitable acid, base, or buffer. Suitable bulking, dispersing, wetting or suspending agents, including mannitol and PEG 400, may also be included in the composition. A suitable parenteral composition can also include a compound formulated as a sterile solid substance, including lyophilized powder, in injection vials. Aqueous solution can be added to dissolve the compound prior to injection.

For disorders of the eye or other external tissues, e.g., mouth and skin, the formulations are preferably applied as a topical gel, spray, ointment or cream, or as a suppository, containing the active ingredients in a total amount of, for example, 0.075 to 30% w/w, preferably 0.2 to 20% w/w and most preferably 0.4 to 15% w/w. When formulated in an ointment, the active ingredients may be employed with either paraffinic or a water-miscible ointment base.

Alternatively, the active ingredients may be formulated in a cream with an oil-in-water cream base. If desired, the aqueous phase of the cream base may include, for example at least 30% w/w of a polyhydric alcohol such as propylene glycol, butane-1,3-diol, mannitol, sorbitol, glycerol, polyethylene glycol and mixtures thereof. The topical formulation may desirably include a compound, which enhances absorption or penetration of the active ingredient through the skin or other affected areas. Examples of such dermal penetration enhancers include dimethylsulfoxide and related analogs. The compounds of this invention can also be administered by a transdermal device. Preferably topical administration will be accomplished using a patch either of the reservoir and porous membrane type or of a solid matrix variety. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane. The transdermal patch may include the compound in a suitable solvent system with an adhesive system, such as an acrylic emulsion, and a polyester patch. The oily phase of the emulsions of this invention may be constituted from known ingredients in a known manner. While the phase may comprise merely an emulsifier, it may comprise a mixture of at least one emulsifier with a fat or oil or with both a fat and an oil. Preferably, a hydrophilic emulsifier is included together with a lipophilic emulsifier, which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base, which forms the oily, dispersed phase of the cream formulations. Emulsifiers and emulsion stabilizers suitable for use in the formulation of the present invention include Tween 60, Span 80, cetostearyl alcohol, myristyl alcohol, glyceryl monostearate, and sodium lauryl sulfate, among others. The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredients are dissolved or suspended in suitable carrier, especially an aqueous solvent for the active ingredients. The anti-inflammatory active ingredients are preferably present in such formulations in a concentration of 0.5 to 20%, advantageously 0.5 to 10% and particularly about 1.5% w/w. For therapeutic purposes, the active compounds of this combination invention are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

The amount of therapeutically active compounds that are administered and the dosage regimen for treating a disease condition with the compounds and/or compositions of this invention depends on a variety of factors, including the age, weight, sex and medical condition of the subject, the severity of the inflammation or inflammation related disorder, the route and frequency of administration, and the particular compound employed, and thus may vary widely. The pharmaceutical compositions may contain active ingredients in the range of about 0.1 to 1000 mg, preferably in the range of about 7.0 to 350 mg. A daily dose of about 0.01 to 100 mg/kg body weight, preferably between about 0.1 and about 50 mg/kg body weight and most preferably between about 0.5 to 30 mg/kg body weight, may be appropriate. The daily dose can be administered in one to four doses per day. In the case of skin conditions, it may be preferable to apply a topical preparation of compounds of this invention to the affected area two to four times a day.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

For administration to non-human animals, the composition may also be added to the animal feed or drinking water. It may be convenient to formulate the animal feed and drinking water compositions so that the animal takes in a therapeutically appropriate quantity of the composition along with its diet. It may also be convenient to present the composition as a premix for addition to the feed or drinking water.

The disclosures in this application of all articles and references, including patents, are incorporated herein by reference.

The invention is illustrated further by the following examples, which are not to be construed as limiting the invention in scope or spirit to the specific procedures described in them.

The starting materials and various intermediates may be obtained from commercial sources, prepared from commercially available compounds, or prepared using well-known synthetic methods.

The compound names in this application were created using ACD Name Pro version 5.09, or ChemDraw ultra version 6.0.2, software.

General Synthetic Procedures

Representative procedures for the preparation of compounds of the invention are outlined below in the Schemes The starting materials can be purchased or prepared using methods known to those skilled in the art. Similarly, the preparation of the various intermediates can be achieved using methods known in the art. The starting materials may be varied and additional steps employed to produce compounds encompassed by the invention, as demonstrated by the examples below. In addition, different solvents and reagents can typically be used to achieve the above transformations. Protection of reactive groups may also be necessary to achieve the above transformations. In general, the need for protecting groups, as well as the conditions necessary to attach and remove such groups, will be apparent to those skilled in the art of organic synthesis. When a protecting group is employed, deprotection will generally be required. Suitable protecting groups and methodology for protection and deprotection such as those described in *Protecting Groups in Organic Synthesis* by Greene and Wuts are known and appreciated in the art.

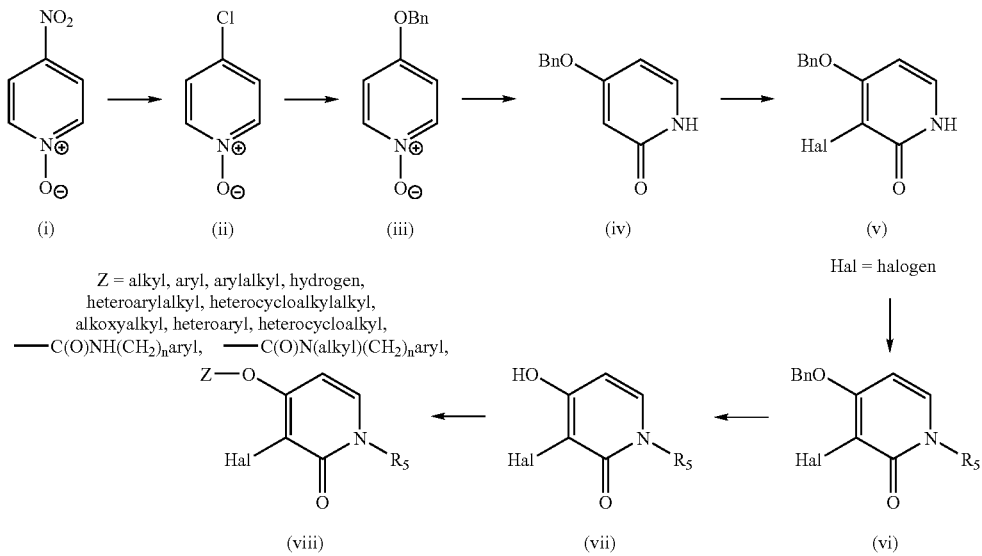

Scheme 1

In this scheme, $R_5$ is as defined above.

Alternatively, the compounds of the instant invention can be prepared according to the method outlined in Scheme 2.

Scheme 2

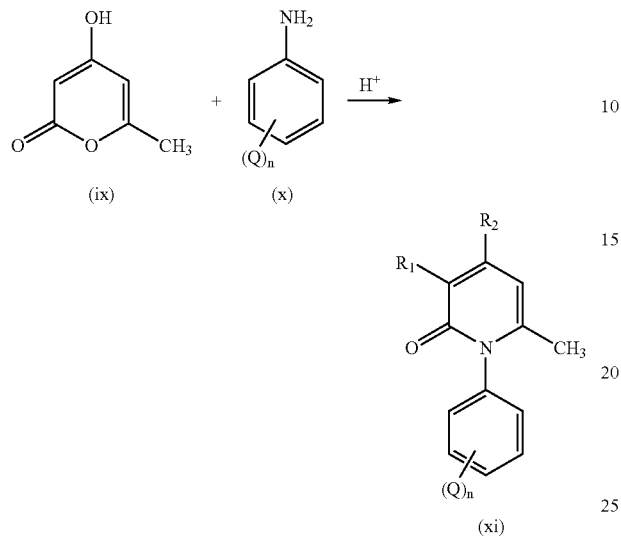

In Scheme 2, Q at each occurrence is independently alkyl, halogen, alkoxy, arylalkoxy, thioalkoxy, alkoxycarbonyl, arylalkoxycarbonyl, $CO_2H$, CN, amidinooxime, $NR_6R_7$, $NR_6R_7$ alkyl, $-C(O)NR_6R_7$, amidino, haloalkyl, or haloalkoxy; and n is 0, 1, 2, 3, 4, or 5.

Alternatively, compounds of the invention can be prepared using the procedures outlined in Schemes 3–25. In Schemes 3–25, the X, X', R, R', and R" substituents on groups such as aryl, heteroaryl, amine, and alkyl, carry the same definition described above for substituents on these groups.

Scheme 3

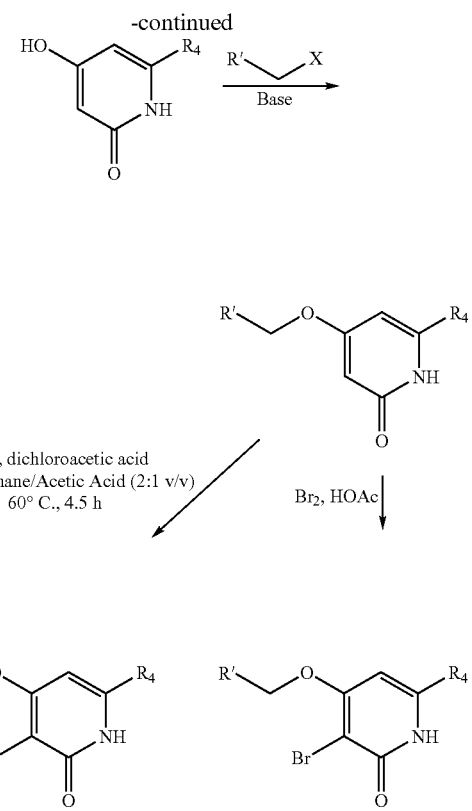

Scheme 4

Scheme 5

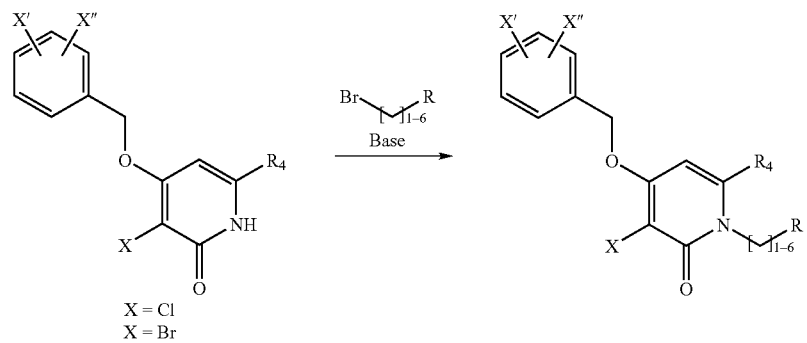

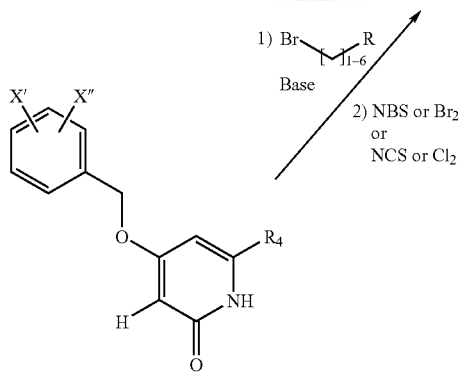
Scheme 6
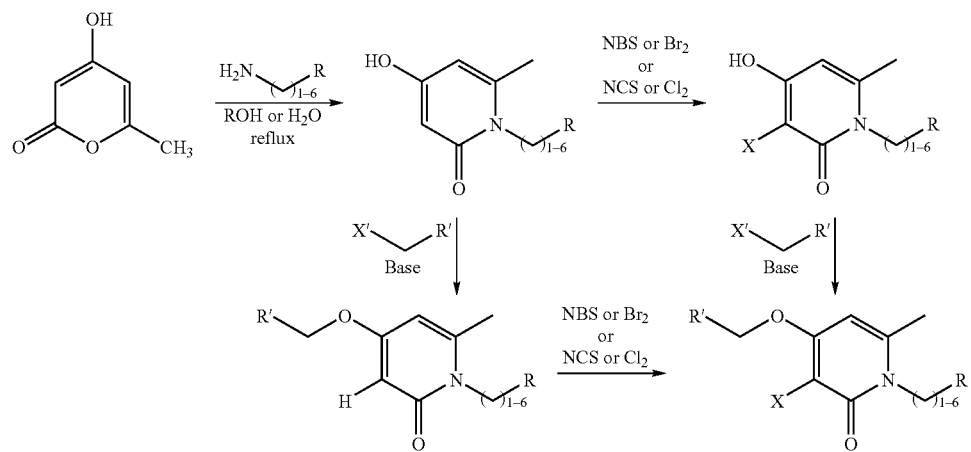
Scheme 7
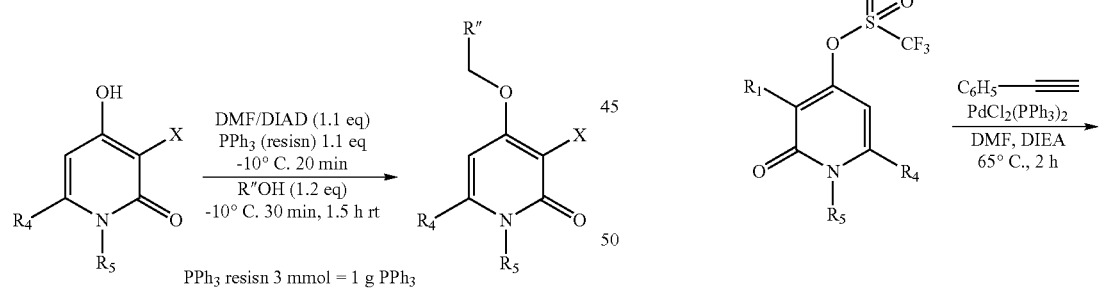
Scheme 8
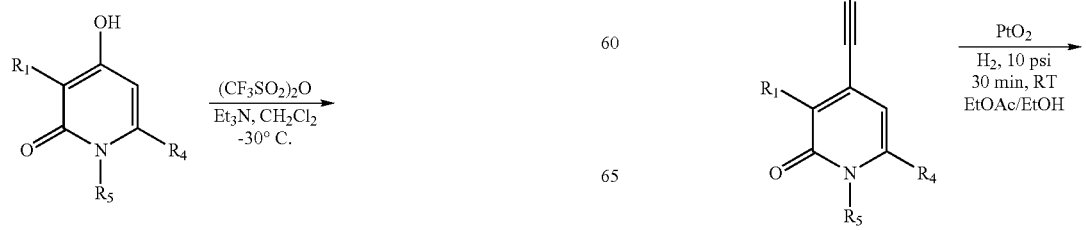

-continued
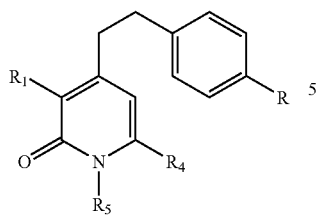
Scheme 9
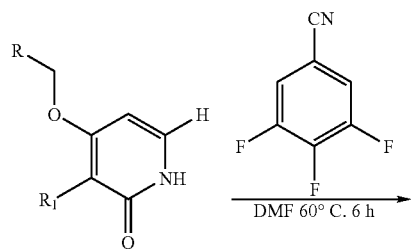
Scheme 10
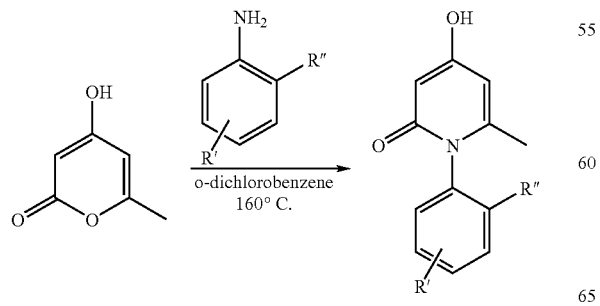
Scheme 11
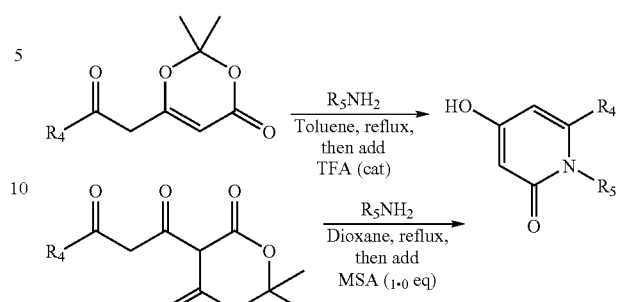
Scheme 12
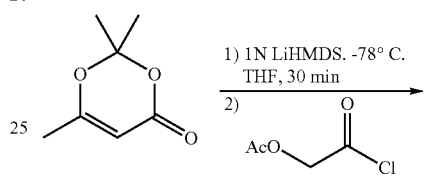
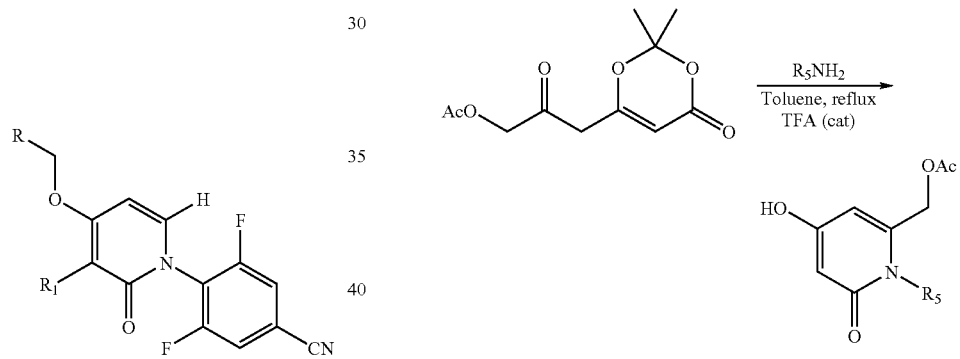
Scheme 13
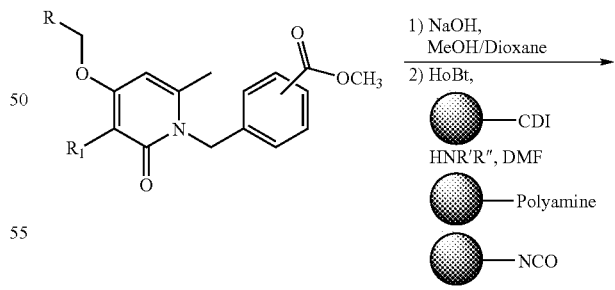

Scheme 14
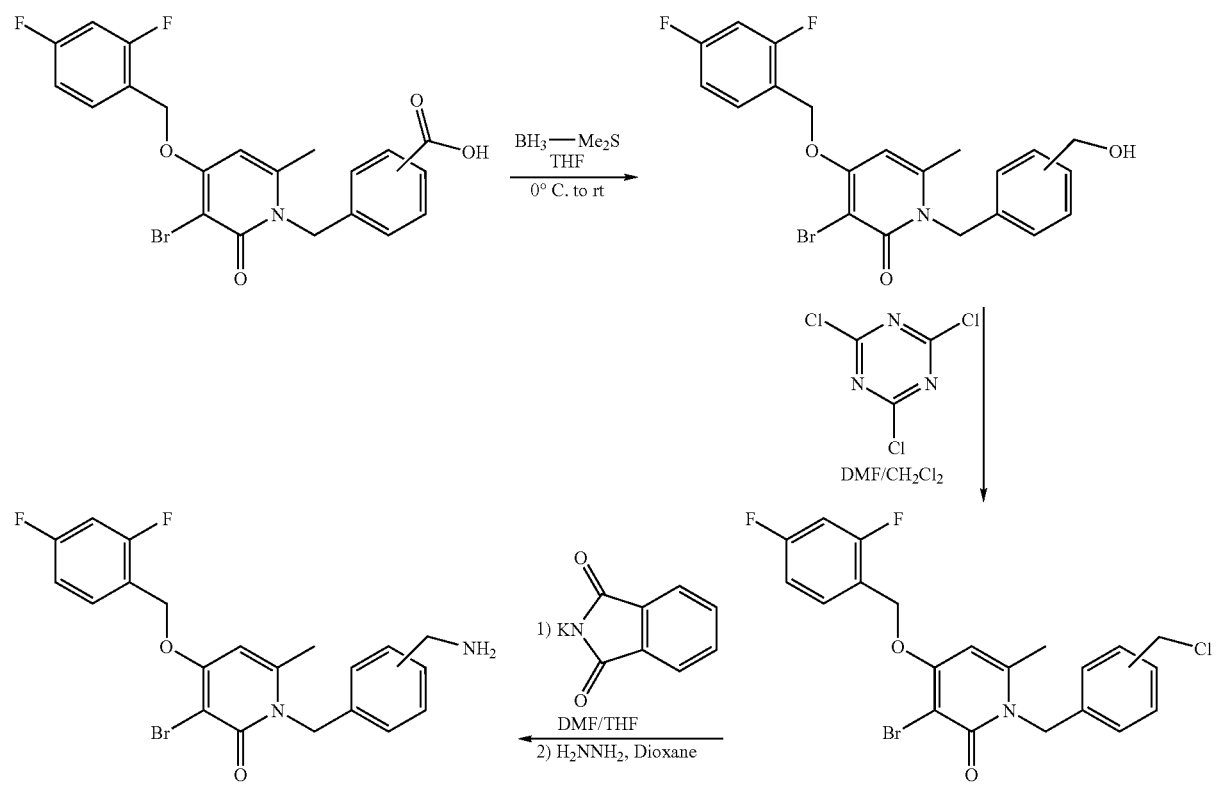
Scheme 15
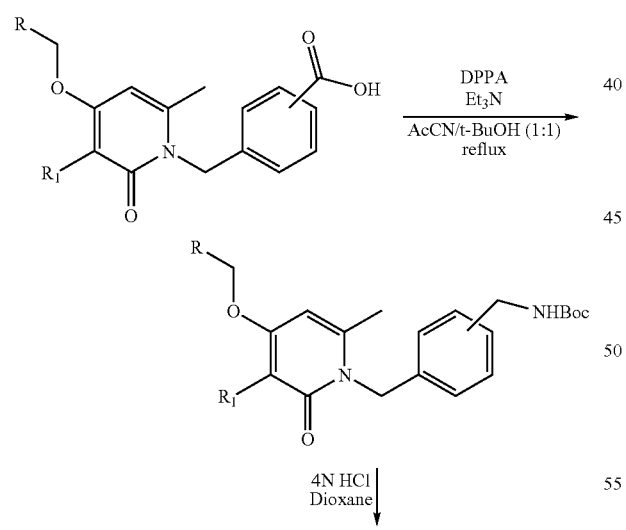
Scheme 16
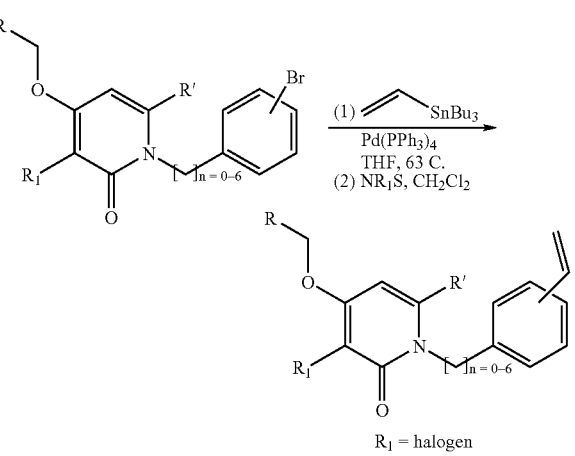
Scheme 17
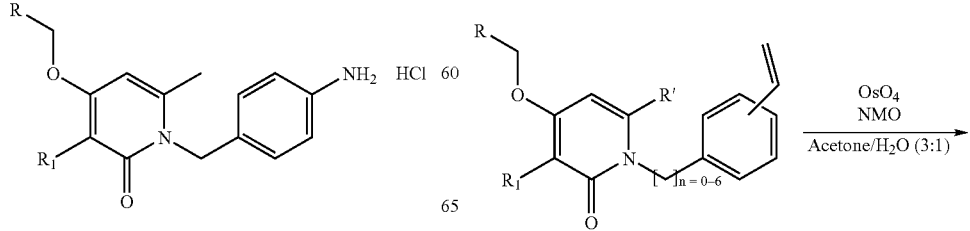

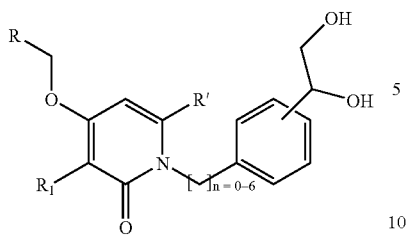
Scheme 18
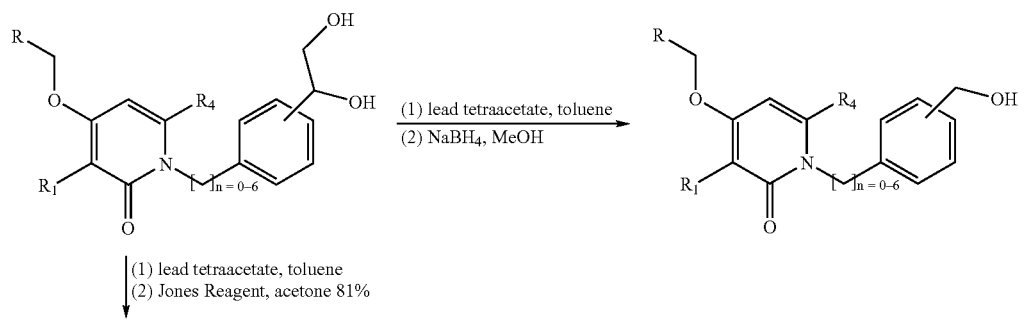
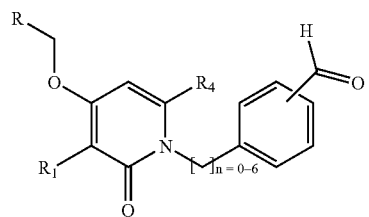
Scheme 19
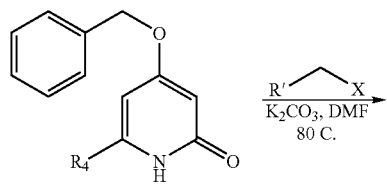
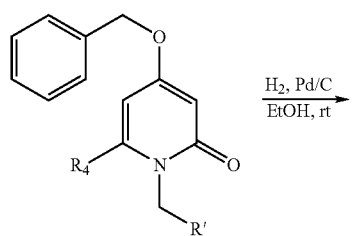
-continued
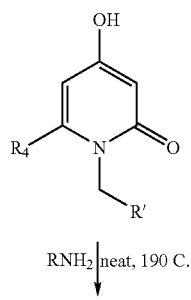
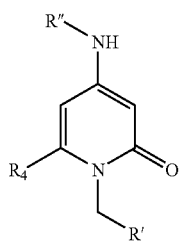

Scheme 20
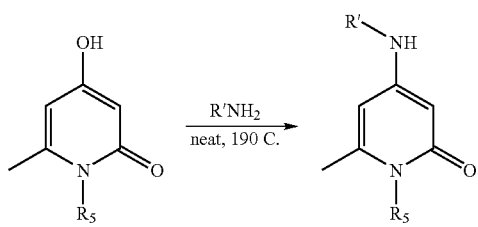
Scheme 21
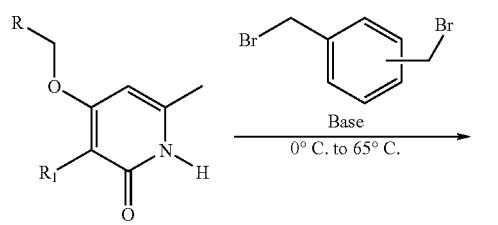
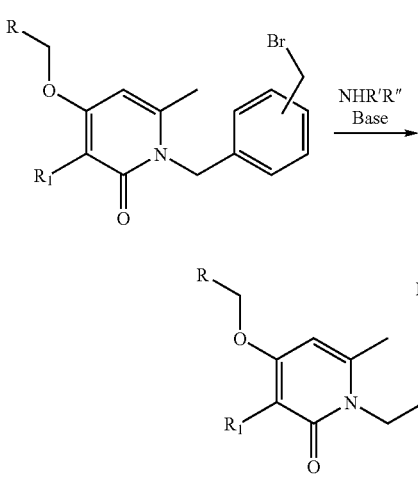
Scheme 22
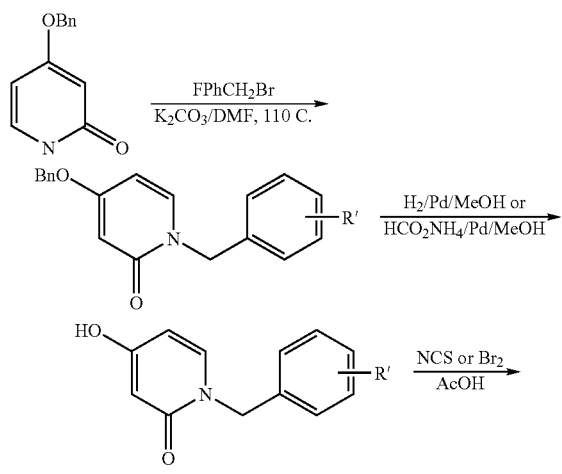
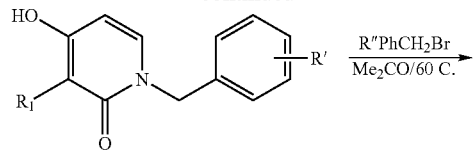
Scheme 23
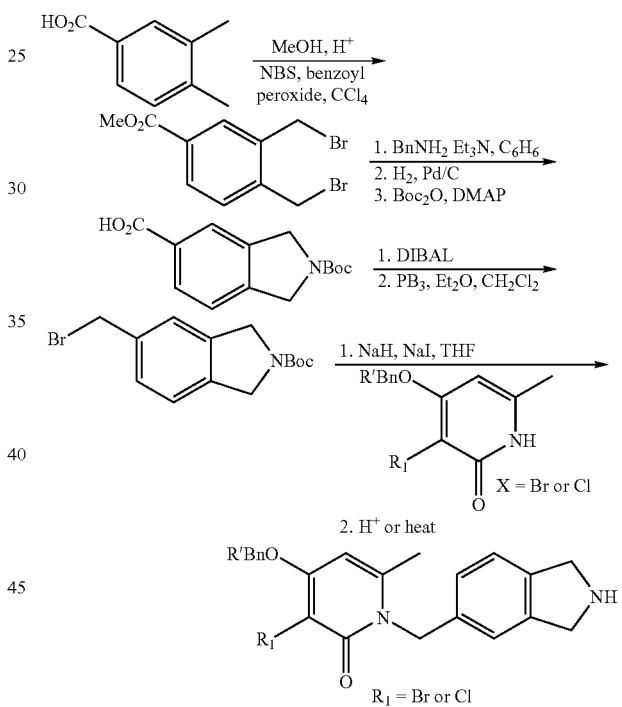
Scheme 24
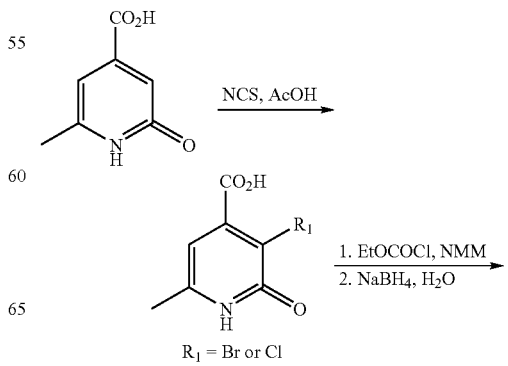

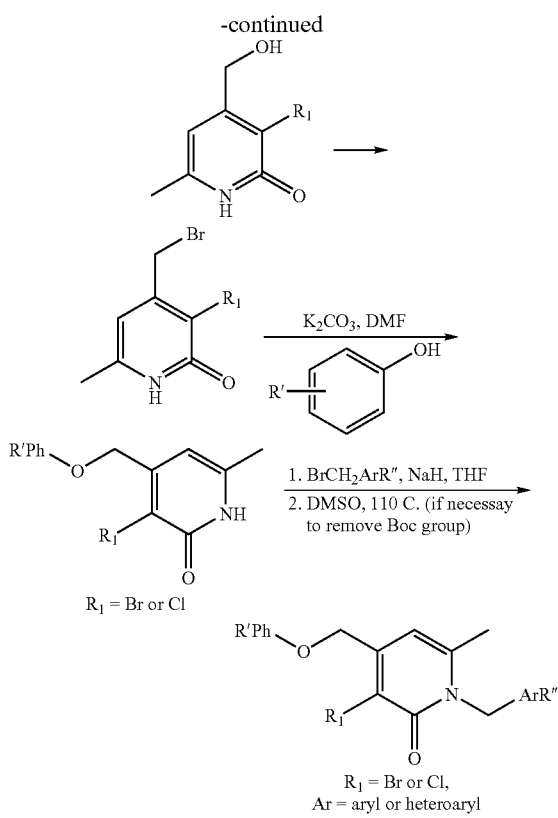

$R_1$ = Br or Cl $R_1$ = Br or Cl,
Ar = aryl or heteroaryl

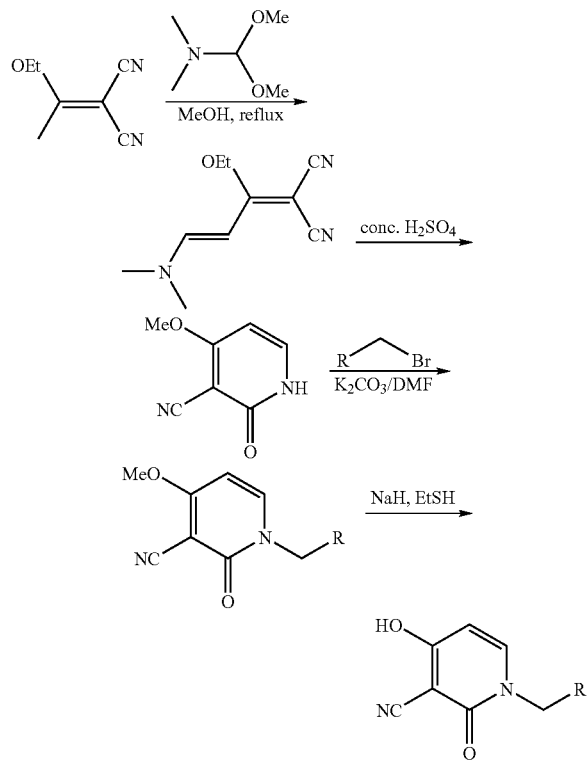

Scheme 25

The invention is illustrated further by the following examples, which are not to be construed as limiting the invention in scope or spirit to the specific procedures described in them. Those having skill in the art will recognize that the starting materials may be varied and additional steps employed to produce compounds encompassed by the invention, as demonstrated by the following examples. Those skilled in the art will also recognize that it may be necessary to utilize different solvents or reagents to achieve some of the above transformations. In some cases, protection of reactive functionalities may be necessary to achieve the above transformations. In general, such need for protecting groups, as well as the conditions necessary to attach and remove such groups, will be apparent to those skilled in the art of organic synthesis. When a protecting group is employed, adeprotection step may be required. Suitable protecting groups and methodology for protection and deprotection such as those described in *Protecting Groups in Organic Synthesis* by Greene and Wuts are well known and appreciated in the art.

Unless otherwise specified, all reagents and solvents are of standard commercial grade and are used without further purification. The appropriate atmosphere to run the reaction under, for example, air, nitrogen, hydrogen, argon and the like, will be apparent to those skilled in the art.

EXAMPLES

Example 1

4-(benzyloxy)-1-(4-methylbenzyl)pyridin-2(1H)-one

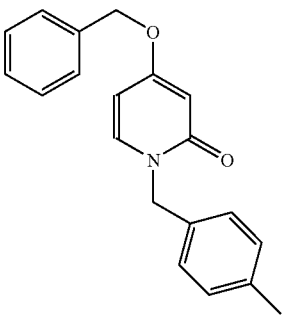

4-Benzyloxy-2(1H)-pyridone (3.0 g, 0.015 mol), 4-methylbenzyl bromide (3.15 g, 0.17 mol), and potassium carbonate (3.0 g, 0.022 mol) were heated at 80° C. for 2 hours. Contents were allowed to cool, diluted with water and a solid (5.52 g) was filtered. FABHRMS m/z 306.1494 (M+H, $C_{20}H_{20}NO_2$ requires 306.1494). $^1$H NMR (CDCl$_3$/ 300 MHz): 7.50–7.40 (m, 5H); 7.20–7.05 (m, 5H); 6.07–6.00 (m, 1H); 5.95–5.90 (m, 1H); 5.05 (s, 2H); 5.00 (s, 2H); 2.32 (s, 3H).

Anal. Calcd for $C_{20}H_{19}NO_2$: C, 78.66; H, 6.27; N, 4.59. Found: C, 78.54; H, 6.38; N, 4.58.

Example 2

4-(benzyloxy)-3-bromo-1-(4-methylbenzyl)pyridin-2 (1H)-one

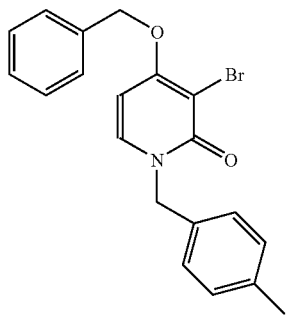

The material prepared in Example 1 (2.1 g, 0.007 mol) and sodium acetate (738 mg, 0.009 mol) in glacial acetic acid (15 mL) were cooled to 15° C. Bromine (0.412 mL, 0.008) in glacial acetic acid (5 mL) was added dropwise. Contents were stirred 2 hours, coming to room temperature. Water (200 mL) was added and a light yellow solid was filtered. Mp 150.4–151.2° C.

FAB HRMS m/z 384.0599 (M+H, $C_{20}H_{19}BrNO_2$ requires 384.0601). $^1$H NMR (CDCl$_3$/300 MHz) δ: 7.42–7.30 (m, 5H); 7.22–7.08 (m, 5H); 6.02 (d, 1H); 5.20 (s, 2H); 5.12 (s, 2H); 2.32 (s, 3H).

Anal. Calcd for $C_{20}H_{18}BrNO_2$: C, 62.51; H, 4.72; N, 3.65. Found: C, 62.11; H, 4.48; N, 3.54.

Examples 3–10

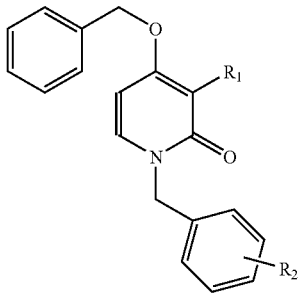

The compounds of Examples 3–10 are prepared essentially according to the procedure set forth above with respect to Example 1. Compounds wherein $R_1$=Br are prepared essentially according to the procedure of Example 2.

| Example No. | $R_1$ | $R_2$ | MF | M + H m/z Requires | FABHRMS m/z |
|---|---|---|---|---|---|
| Ex. 3 | —H | 4—Br | $C_{19}H_{16}BrNO_2$ | 370.0428 | 370.0443 |
| Ex. 4 | —Br | 4—Br | $C_{19}H_{15}Br_2NO_2$ | 447.9522 | 447.9548 |
| Ex. 5 | —H | 4—Cl | $C_{19}H_{16}ClNO_2$ | 326.0948 | 326.0893 |
| Ex. 6 | —Br | 4—Cl | $C_{19}H_{15}BrClNO_2$ | 404.0053 | 404.0035 |
| Ex. 7 | —H | 3—F | $C_{19}H_{16}FNO_2$ | 310.1243 | 310.1226 |
| Ex. 8 | —Br | 3—F | $C_{19}H_{15}BrFNO_2$ | | |
| Ex. 9 | —H | 2—F | $C_{19}H_{16}FNO_2$ | 310.1231 | 310.1243 |
| Ex. 10 | —Br | 2—F | $C_{19}H_{15}BrFNO_2$ | 388.0348 | 388.0373 |

NMR characterization of compounds of Examples 3–10

| Ex. No. | NMR Data |
|---|---|
| Ex. 3 | $^1$H NMR (CDCl$_3$/300 MHz) δ: 7.43(d, 2H); 7.40–7.33(m, 5H); 7.20–7.07(m, 3H); 6.04–6.01(m, 1H); 6.00–5.92(m, 1H); 5.03(s, 2H); 4.98(s, 2H) |
| Ex. 4 | $^1$H NMR (CDCl$_3$/300 MHz) δ: 7.50–7.15(m, 10H); 6.06(d, 1H); 5.20(s, 2H), 5.10(s, 2H) |
| Ex. 5 | $^1$H NMR (CDCl$_3$/300 MHz) δ: 7.40–7.32(m, 5H); 7.24(AB quartet, 4H); 7.10(d, 1H); 6.03–6.00(m, 1H); 5.98–5.92(m, 1H); 5.03(s, 2H); 4.99(s, 2H) |
| Ex. 6 | $^1$H NMR (CDCl$_3$/300 MHz): 7.43–7.20(m, 10H); 6.08(d, 1H); 5.20(s, 2H); 5.10(s, 2H) |
| Ex. 7 | $^1$H NMR (CDCl$_3$/300 MHz) δ: 7.45–7.25(m, 5H); 7.12(d, 1H); 7.07–6.93(m, 4H); 6.04–6.02(m, 1H); 6.00–5.94(m, 1H); 5.08(s, 2H); 5.00(s, 2H) |
| Ex. 8 | $^1$H NMR (CDCl$_3$/300 MHz) δ: 7.43–7.25(m, 6H); 7.21(d, 1H); 7.10–6.93(m, 3H); 6.08(d, 1H); 5.22(s, 2H); 5.12(s, 2H) |
| Ex. 9 | $^1$H NMR (CDCl$_3$/300 MHz) δ: 7.43–7.00(m, 10H); 6.01–5.92(m, 2H); 5.10(s, 2H); 4.99(s, 2H) |
| Ex. 10 | $^1$H NMR (CDCl$_3$/300 MHz): 7.52(d of t, 1H); 7.44–7.26(m, 7H); 7.15–7.00(m, 2H); 6.03(d, 1H); 5.20(s, 2H); 5.15(s, 2H) |

Example 11

4-(benzyloxy)-3-bromopyridin-2(1H)-one

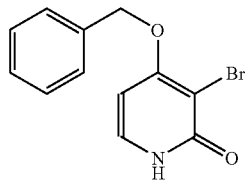

The material of Example 11 was prepared according to the procedure of Example 2. $^1$H NMR (CDCl$_3$/300 MHz) δ: 7.50–7.30 (m, 6H); 6.20 (d, 1H); 5.24 (s, 2H).

Anal. Calcd for $C_{12}H_{10}BrNO_2$ (0.3H$_2$O): C, 50.48; H, 3.74; N, 4.91. Found: C, 50.79; H, 3.41; N, 4.82.

Examples 12–19

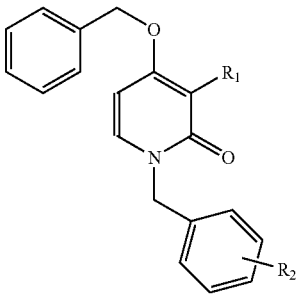

The compounds of Examples 12–19 are prepared essentially according to the procedures set forth above for Example 1. Compounds wherein $R_1$=Br are prepared essentially according to the procedure of Example 2.

| Example No. | R₁ | R₂ | MF | M+H Requires | FABHRMS m/z |
|---|---|---|---|---|---|
| Ex. 12 | —Br | 4-benzyloxy | $C_{26}H_{22}BrNO_3$ | 476.0861 | 476.0854 |
| Ex. 13 | —H | 4-CO₂Me | $C_{21}H_{19}NO_4$ | 350.1392 | 350.1391 |
| Ex. 14 | —Br | 4-CO₂Me | $C_{21}H_{18}BrNO_4$ | 428.0497 | 428.0480 |
| Ex. 15 | —Br | 4-CO₂H | $C_{20}H_{16}BrNO_4$ | 414.0341 | 414.0360 |
| Ex. 16 | —H | 4-CN | $C_{20}H_{16}N_2O_2$ | 317.1290 | 317.1270 |
| Ex. 17 | —Br | 4-CN | $C_{20}H_{15}BrN_2O_2$ | 395.0395 | 395.0376 |
| Ex. 18 | —H | 4-tButyl | $C_{23}H_{25}NO_2$ | 348.1964 | 348.1949 |
| Ex. 19 | —Br | 4-tButyl | $C_{23}H_{24}BrNO_2$ | 426.1069 | 426.1023 |

NMR characterization of compounds of Examples 12–19

| Ex. No. | NMR Data |
|---|---|
| Ex. 12 | ¹H NMR (CDCl₃/300 MHz): 7.45–7.15(m, 13H); 6.92(d, 2H); 6.01(d, 1H); 5.20(s, 2H); 5.08(s, 2H); 5.03(s, 2H) |
| Ex. 13 | ¹H NMR (CDCl₃/300 MHz): 8.00(d, 2H); 7.40–7.25(m, 7H); 7.10(d, 1H); 6.03–6.01(m, 1H); 6.00–5.93(m, 1H); 5.12, (s, 2H); 5.00(s, 2H); 3.95(s, 3H) |
| Ex. 14 | ¹H NMR (CDCl₃/300 MHz): 8.00(d, 2H); 7.42–7.31(m, 7H); 7.23(d, 1H); 6.08(d, 1H); 5.22(d, 2H); 5.20(s, 2H); 3.95(s, 3H) |
| Ex. 15 | ¹H NMR (DMSO-d₆/300 MHz): 8.00–7.80(m, 3H); 7.53–7.27 (m, 7H); 6.50(d, 1H); 5.32(s, 2H); 5.20(s, 2H) |
| Ex. 16 | ¹H NMR (CDCl₃/300 MHz) δ: 7.60(d, 2H); 7.42–7.30(m, 7H); 7.13(d, 1H); 6.05–5.98(m, 2H); 5.11(s, 2H); 5.00(s, 2H) |
| Ex. 17 | ¹H NMR (CDCl₃/300 MHz) δ: 7.61(d, 2H); 7.48–7.30(m, 6H); 7.23(d, 2H); 6.12(d, 1H); 5.22(s, 2H); 5.20(s, 2H) |
| Ex. 18 | ¹H NMR (CDCl₃/300 MHz): 7.40–7.28(m, 7H); 7.20(d, 2H); 7.10(d, 1H); 6.02(d, 1H); 5.97–5.90(m, 1H); 5.02(d, 2H); 4.98(d, 2H) |
| Ex. 19 | ¹H NMR (CDCl₃/300 MHz) δ: 7.43–7.20(m, 10H); 6.02 (d, 1H); 5.20(s, 2H); 5.10(s, 2H); 1.30(s, 9H) |

Example 20

4-(benzyloxy)-3-bromo-1-ethylpyridin-2(1H)-one

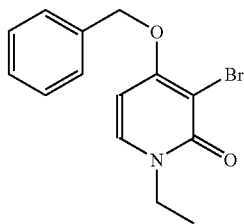

To 4-benzyloxy-2(1H)-pyridone (1.0 g, 0.005 mol) and potassium carbonate (1.0 g, 0.007 mol) in DMF (10 mL) was added bromoethane (0.82 mL, 0.011 mol). Contents were heated at 75° C. overnight. Contents were allowed to cool and partitioned between EtOAc and water. The EtOAc layer was dried over MgSO₄, filtered, and concentrated in vacuo leaving a waxy solid, which was recrystallized from EtOAc/hexanes to give a white solid (720 mg). To the white solid (700 mg, 0.003 mol) in glacial acetic acid (10 mL), bromine (0.17 mL, 0.00325 mol) in glacial acetic acid (5 mL) was added dropwise at 15° C. Contents were stirred one hour at room temperature and a yellow solid (1.1 g) was filtered. The solid was partitioned between EtOAc and 2.5N sodium hydroxide. The EtOAc layer was dried over MgSO₄, filtered, and concentrated in vacuo leaving a colorless oil (710 mg), which solidified.

FABHRMS m/z 310.0267 (M+H, $C_{14}H_{15}BrNO_2$ requires 310.0263). ¹H NMR (CDCl₃/300 MHz) δ: 7.45–7.30 (m, 6H); 7.22 (d, 1H); 6.07 (d, 1H); 5.20 (s, 2H); 4.00 (q, 2H); 1.32 (t, 3H).

Anal. Calcd for $C_{14}H_{14}BrNO_2$: C, 54.56; H, 4.58; N, 4.55. Found: C, 54.21; H, 4.38; N, 4.43.

Example 21

3-bromo-4-hydroxy-1-(4-hydroxybenzyl)pyridin-2(1H)-one

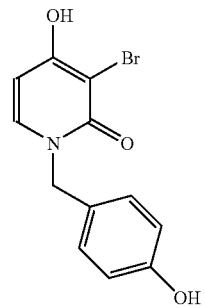

The material of Example 12 (120 mg, 0.25 mmol) and 10% palladium/carbon (30 mg) in glacial acetic acid (2 mL) were shaken at 55 lbs of hydrogen for 4 hours. Contents were filtered and the filtrate was concentrated in vacuo leaving an oil. FABHRMS m/z 295.9952 (M+H, $C_{12}H_{11}BrNO_3$ requires 295.9922).

¹H NMR (DMSO-d₆/300 MHz) δ: 11.40 (br s, 1H); 9.40 (br s, 1H); 7.60 (d, 1H); 7.10 (d, 2H); 6.70 (d, 2H); 6.02 (d, 1H); 4.93 (s, 2H).

Anal. Calcd for $C_{12}H_{10}BrNO_3$ (1.4H₂O): C, 44.85; H, 4.02; N, 4.36. Found: C, 45.07; H, 4.10; N, 4.35.

Example 22

4-(benzyloxy)-3-bromo-1-methylpyridin-2(1H)-one hydrobromide

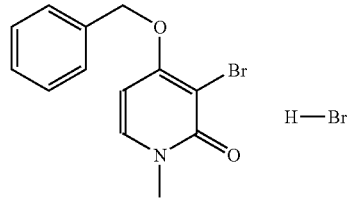

To 4-benzyloxy-2(1H)-pyridone (1.0 g, 0.005 mol) and potassium carbonate (760 mg, 0.0055 mol) in DMF (10 mL) was added methyl iodide (0.342 mL, 0.0055 mol). Contents were stirred overnight. Contents were partitioned between EtOAc and water. The EtOAc layer was dried over MgSO₄, filtered, and concentrated in vacuo leaving a white solid (960 mg).

To the white solid (332 mg, 0.0015 mol) in glacial acetic acid (10 mL), bromine (256 mg, 0.0016 mol) in glacial acetic acid (5 mL) was added dropwise at 15° C. Contents were stirred one hour at room temperature and the desired was filtered as a white solid, 262 mg (59% yield). mp 105.3–105.6° C. FABHRMS m/z 296.0097 (M+H, $C_{13}H_{13}BrNO_2$ requires 296.0110). ¹H NMR (CDCL₃/300 MHZ) δ: 7.45–7.30 (m, 6H); 7.22 (d, 1H); 6.07 (d,1H); 5.20 (s, 2H); 4.00 (q, 2H); 1.32 (t, 3H).

Anal. Calcd for $C_{13}H_{12}BrNO_2$ (HBr, 0.3H₂O): C, 41.04; H, 3.60; N, 3.68. Found: C, 41.00; H, 3.87; N, 3.52.

Example 23

4-(benzyloxy)-3-bromo-1-methylpyridin-2(1H)-one

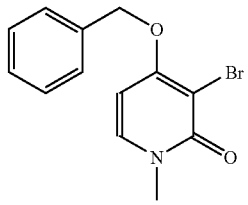

The material of Example 22 was partitioned between EtOAc and 2.5N sodium hydroxide. The EtOAc layer was dried over MgSO$_4$, filtered, and concentrated in vacuo leaving a red oil, which solidified. FABHRMS m/z 294.0112 (M+H, C$_{13}$H$_{13}$BrNO$_2$ requires 294.0130). $^1$H NMR (CDCl$_3$/300 MHz): 7.45–7.30 (m, 6H); 7.22 (d, 1H); 6.07 (d, 1H); 5.20 (s, 2H); 4.00 (q, 2H), 1.32 (t, 3H).

Anal. Calcd for C$_{13}$H$_{12}$BrNO$_2$: C, 53.08; H, 4.11; N, 4.76. Found: C, 53.06; H, 4.20; N, 4.74.

Example 24

4-{[4-(benzyloxy)-3-bromo-2-oxopyridin-1(2H)-yl]methyl}-N'-hydroxybenzenecarboximidamide

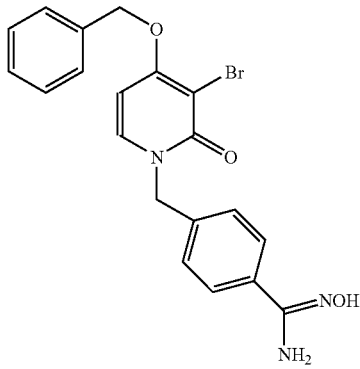

The material of Example 17 (500 mg, 0.00127 mol), hydroxylamine hydrochloride (90 mg, 0.0013 mol) and sodium bicarbonate (109 mg) were refluxed in ethanol (15 mL) overnight. Contents were allowed to cool and a solid was filtered and washed with water to give the desired as a white solid, 447 mg, (82% yield). mp 210.2–212.2° C. FABHRMS m/z 428.0634 (M+H, C$_{20}$H$_{19}$BrN$_3$O$_3$ requires 428.0610). $^1$H NMR (DMSO-d$_6$/300 MHz): 9.66 (s, 1H); 7.98 (d, 1H); 7.65 (d, 2H); 7.55–7.35 (m, 5H); 7.30 (d, 2H); 6.54 (d, 1H); 5.82 (s, 2H); 5.35 (s, 2H); 5.17 (s, 2H).

Anal. Calcd for C$_{20}$H$_{18}$BrN$_3$O$_3$: C, 56.09; H, 4.24; N, 9.81. Found: C, 55.92; H, 4.01; N, 9.52.

Example 25

4-(benzyloxy)-3-bromo-1-(piperidin-4-ylmethyl)pyridin-2(1H)-one hydrochloride

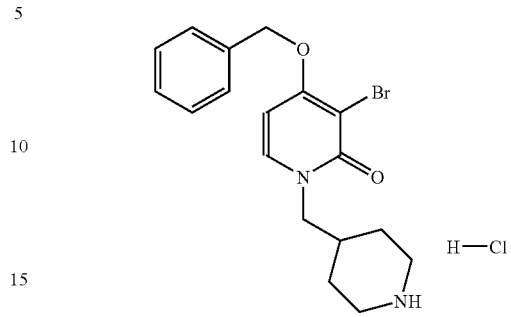

To the material of Example 11 (924 mg, 0.0033 mol) in DMF (5 mL) was added dropwise sodium bis(trimethylsilyl)amide (1M in THF, 3.6 mL). Contents were stirred one hour before adding dropwise a solution of 4-methanesulfonyloxymethyl-1-piperidine-1-carboxylic acid tert-butyl ester (*J. Labelled Compd, Radiopharm*, 38(7),. 1996, 595–606) (1.0 g, 0.0036 mol) in DMF (5 mL). Contents were heated at 75° C. overnight. Contents were allowed to cool and poured into water (100 mL). A solid was filtered and recrystallized from EtOAc to give white crystals (546 mg). The white crystals were refluxed in 4 N HCl/dioxane (10 mL) for 3 hours, allowed to cool and filtered to give the desired as a white solid, 415 mg (30% yield). mp 207.9° C. FABHRMS m/z 377.0852 (M+H, C$_{18}$H$_{23}$BrClN$_2$O$_2$ requires 377.0865). $^1$H NMR (DMSO-d$_6$/300 MHz) δ: 8.90 (br, 1H); 8.64 (br, 1H); 7.80 (d, 1H); 7.50–7.30 (m, 5H); 6.48 (d, 1H); 5.30 (s, 2H); 3.83 (d, 2H); 3.20 (d, 2H); 2.88–2.64 (m, 2H), 2.10–1.90 (m, 1H); 1.60 (d, 2H); 1.50–1.40 (m, 2H).

Anal. Calcd for C$_{18}$H$_{22}$BrClN$_2$O$_2$ (0.3H$_2$O): C, 51.58; H, 5.43; N, 6.68. Found: C, 51.59; H, 5.42; N, 6.81.

Example 26

4-(benzyloxy)-1-[4-(trifluoromethyl)benzyl]pyridin-2(1H)-one

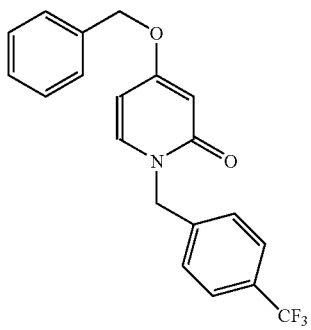

The material of Example 26 was prepared according to the procedure of Example 1. FABHRMS m/z 360.1213 (M+H, C$_{20}$H$_{17}$F$_3$NO$_2$ requires 360.1211). $^1$H NMR (CDCl$_3$/300 MHz) δ: 7.60 (d, 2H); 7.41–7.30 (m, 7H); 7.13 (d, 1H); 6.05–6.01 (m, 1H); 6.00–5.95 (m, 1H); 5.13 (s, 2H); 5.00 (s, 2H).

Anal. Calcd for C$_{20}$H$_{16}$F$_3$NO$_2$: C, 66.85; H, 4.49; N, 3.90. Found: C, 66.64; H, 4.26; N, 3.93.

Example 27

4-(benzyloxy)-3-bromo-1-[4-(trifluoromethyl)benzyl]pyridin-2(1H)-one

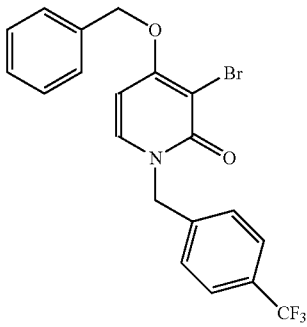

The material of Example 27 was prepared according to the procedure of Example 2. FABHRMS m/z 438.0308 (M+H, $C_{20}H_{16}BrF_3NO_2$ requires 438.0316). $^1$H NMR (CDCL$_3$/300 MHZ) δ: 7.65–7.20 (m, 10H); 6.13–6.03 (m, 1H); 5.30–5.13 (m, 4H).

Anal. Calcd for $C_{20}H_{15}BrF_3NO_2$: C, 54.81; H, 3.45; N, 3.20. Found: C, 54.69; H, 3.34; N, 3.19.

Example 28

4-(benzyloxy)-3-bromo-1-(piperidin-3-ylmethyl)pyridin-2(1H)-one hydrochloride

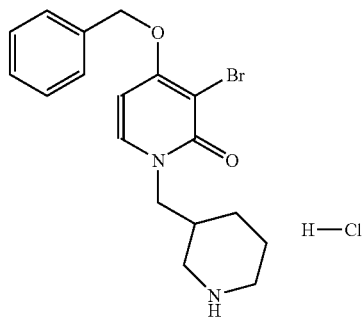

To the material of Example 11 (3.1 g, 0.011 mol) in DMF (20 mL) was added dropwise sodium bis(trimethylsilyl) amide (1M in THF, 12 mL). Contents were stirred one hour before adding dropwise a solution of 3-methanesulfonyloxymethyl-1-piperidine-1-carboxylic acid tert-butyl ester (*Bioorg.Med.Chem.Lett*, 8(13), 1998, 1595–1600) (4.2 g, 0.015 mol) in DMF (5 mL). Contents were heated at 75° C. overnight. Contents were allowed to cool, poured into water (100 mL) and a solid was filtered. The solid was stirred in 4 N HCl/dioxane (15 mL) for 3 hours and filtered to give the desired as a white solid, 752 mg (18% yield). mp 138.1–139.2° C. FABHRMS m/z 377.0859 (M+H, $C_{18}H_{22}BrN_2O_2$ requires 377.0865). $^1$H NMR (DMSO-d$_6$/300 MHz): 9.50–9.10 (br, 2H); 8.00 (d, 1H); 7.50–7.30 (m, 5H); 6.93 (d, 1H); 5.30 (s, 2H), 4.30–3.90 (m, 3H); 3.40–3.10 (m, 3H); 2.80–2.50 (m, 3H); 2.40–2.00 (m, 1H); 1.90–1.60 (m, 4H); 1.40–1.10 (m, 1H).

Anal. Calcd for $C_{18}H_{21}BrN_2O_2$ (2HCl, 0.25H$_2$O): C, 47.55; H, 5.21; N, 6.16. Found: C, 47.48; H, 5.46; N, 6.27.

Example 29

4-(benzyloxy)-3-bromo-1-(2-thien-3-ylethyl)pyridin-2(1H)-one

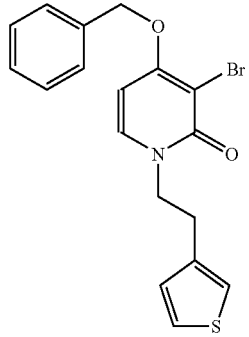

To the material of Example 11 (500 mg, 0.0018 mol) in DMF (5 mL) was added dropwise sodium bis(trimethylsilyl) amide (1M in THF, 2 mL). Contents were stirred one hour before adding dropwise a solution of methanesulfonic acid 2-thiophen-3-yl-ethyl ester (*J.A.C.S*, 109(6), 1987, 1858–1859) (412 mg, 0.002 mol) in DMF (5 mL). Contents were heated at 75° C. overnight. Contents were allowed to cool, poured into water (100 mL), and extracted into EtOAc, dried over MgSO$_4$, filtered, and concentrated in vacuo leaving a light yellow oil. The oil was purified by silica gel chromatography eluting with 50% EtOAc/hexanes to give the desired as a white solid, 199 mg (28% yield). mp 134.0–134.3° C.

FABHRMS m/z 390.0144 (M+H, $C_{18}H_{17}BrNO_2S$ requires 390.0163). $^1$H NMR (CDCl$_3$/300 MHz): 7.43–7.20 (m, 6H); 6.92–6.80 (m, 3H), 5.90 (d, 1H); 5.20 (s, 2H); 4.13 (t, 2H); 3.10 (t, 2H).

Anal. Calcd for $C_{18}H_{16}BrNO_2S$: C, 55.39; H, 4.13; N, 3.59. Found: C, 55.21; H, 3.87; N, 3.52.

Example 30

4-(benzyloxy)-3-bromo-1-(2-thien-2-ylethyl)pyridin-2(1H)-one

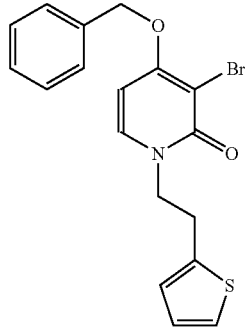

The title compound was prepared essentially according to the procedure of Example 29. mp 128.0–129.5° C. FAB-HRMS m/z 390.0160 (M+H, $C_{18}H_{17}BrNO_2S$ requires 390.0163). $^1$H NMR (CDCL$_3$/300 MHZ) δ: 7.48–7.30 (m, 5H); 7.12 (d, 1H); 6.95–6.80 (m, 2H); 6.75–6.68 (m 1H); 5.95 (d, 1H); 5.20 (s, 2H); 4.16 (t, 2H); 3.30 (t, 2H).

Anal. Calcd for $C_{18}H_{16}BrNO_2S$: C, 55.39; H, 4.13; N, 3.59. Found: C, 55.06; H, 4.01; N, 3.56.

Example 31

4-(benzyloxy)-3-bromo-1-[3-(trifluoromethyl)benzyl]pyridin-2(1H)-one

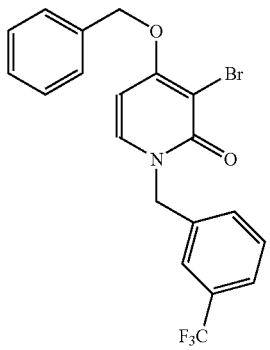

To the material of Example 11 (500 mg, 0.0018 mol) in DMF (5 mL) was added dropwise sodium bis(trimethylsilyl)amide (1M in THF, 2 mL). Contents were stirred one hour before adding dropwise a solution of 3-trifluoromethylbenzyl bromide (478 mg, 0.002 mol) in DMF (5 mL). Contents were heated at 75° C. for 2 hours. Contents were allowed to cool, poured into water (100 mL), and extracted with EtOAc, which was dried over $MgSO_4$, filtered, and concentrated in vacuo leaving a white solid.

FABHRMS m/z 438.0301 (M+H, $C_{20}H_{16}BrF_3NO_2$ requires 438.0316). $^1$H NMR ($CDCl_3$/300 MHz): 7.60–7.20 (m, 10H); 6.10 (d, 1H); 5.14 (s, 2H); 5.20 (s, 2H).

Anal. Calcd for $C_{20}H_{15}BrF_3NO_2$: C, 54.81; H, 3.45; N, 3.20. Found: C, 54.81; H, 3.36; N, 3.13.

Example 32

4-(benzyloxy)-3-bromo-1-[2-(trifluoromethyl)benzyl]pyridin-2(1H)-one

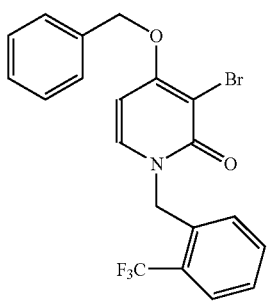

The material of Example 32 was prepared according to the procedure of Example 31.

FABHRMS m/z 438.0280 (M+H, $C_{20}H_{16}BrF_3NO_2$ requires 438.0316). $^1$H NMR ($CDCL_3$/300 MHZ) δ: 7.68 (d, 1H); 7.55–7.20 (m, 8H); 7.15 (d, 1H); 6.10 (d, 1H); 5.40 (s, 2H); 5.13 (s, 2H).

Anal. Calcd for $C_{20}H_{15}BrF_3NO_2$: C, 54.81; H, 3.45; N, 3.20. Found: C, 54.48; H, 3.36; N, 3.17.

Example 33

4-(benzyloxy)-1-[4-(trifluoromethoxy)benzyl]pyridin-2(1H)-one

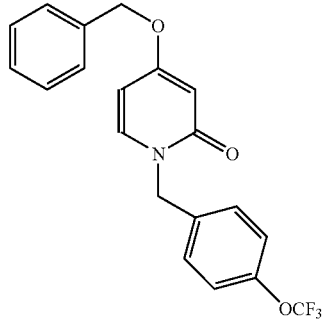

The material of Example 33 was prepared according to the procedure of Example 1.

FABHRMS m/z 376.1158 (M+H, $C_{20}H_{17}F_3NO_3$ requires 376.1161). $^1$H NMR ($CDCL_3$/300 MHZ) δ: 7.40–7.05 (m, 10H); 6.05–5.95 (m, 2H); 5.06 (s, 2H); 4.98 (s, 2H)

Anal. Calcd for $C_{20}H_{16}F_3NO_3$: C, 64.00; H, 4.30; N, 3.73. Found: C, 63.97; H, 4.26; N, 3.57.

Example 34

4-(benzyloxy)-3-bromo-1-[4-(trifluoromethoxy)benzyl]pyridin-2(1H)-one

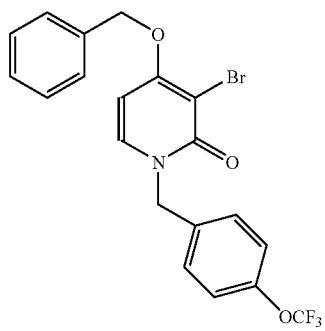

The material of Example 34 was prepared according to the procedure of Example 2.

FABHRMS m/z 454.0240 (M+H, $C_{20}H_{16}BrF_3NO_3$ requires 454.0266). $^1$H NMR ($CDCL_3$/300 MHZ) δ: 7.45–7.10 (m, 10H); 6.08 (d, 1H); 5.20 (s, 2H); 5.12 (s, 2H)

Anal. Calcd for $C_{20}H_{15}BrF_3NO_3$: C, 52.88; H, 3.33; N, 3.08. Found: C, 52.53; H, 3.09; N, 2.92.

Example 35

1-benzyl-4-(benzyloxy)-6-methylpyridin-2(1H)-one

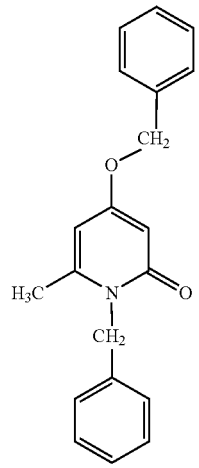

Step 1: Preparation of 1-benzyl-4-hydroxy-6-methylpyridin-2(1H)-one.

4-hydroxy-6-methyl-2-pyrone (0.2 mol, 25.2 g) and benzylamine (0.2 mol, 21.4 g) were added to water (800 mL) and heated to reflux with stirring for 2 hours. After cooling to room temperature, a light brown solid was collected by filtration. (33.4 g, 77%): $^1$H NMR (DMSO-d$_6$/300 MHz) δ: 10.5 (s, 1H), 7.4–7.1 (m, 5H), 5.8–5.6 (m, 2H), 5.2 (s, 2H), 5.1 (s, 2H), 2.2 (s, 3H). ES HRMS m/z 216.100 (M+H, C$_{12}$H$_{13}$NO$_2$ requires 216.102).

Step 2: Preparation of 1-benzyl-4-(benzyloxy)-6-methylpyridin-2(1H)-one.

1-benzyl-4-hydroxy-6-methylpyridin-2(1H)-one (10 mmol, 2.15 g), dichloromethane (100 mL), benzylbromide (11 mmol, 1.88 g), sodium hydroxide (2.5 N, 20 mmol, 8 mL), and benzyltriethylammonium chloride (0.5 g) were vigorously stirred at room temperature for 16 h. Hydrochloric acid (1 N) was added until the mixture produced an acidic reaction to pH paper. The mixture was then extracted with ethyl acetate (3×50 mL). The combined organic extracts were washed with brine, dried over magnesium sulfate, filtered, and concentrated. The product was obtained by flash chromatography eluting with ethyl acetate:hexanes (1:2). The appropriate fractions were concentrated to a clear oil. (1.3 g, 43%): $^1$H NMR (DMSO-d$_6$/300 MHz) δ: 7.4–7.1 (m, 10H), 6.0–5.9 (m, 2H), 5.2 (s, 2H), 5.1 (s, 2H), 2.2 (s, 3H). ES HRMS m/z 306.147 (M+H, C$_{20}$H$_{19}$NO$_2$ requires 306.149).

Example 36

1-benzyl-4-(benzyloxy)-3-bromo-6-methylpyridin-2(1H)-one

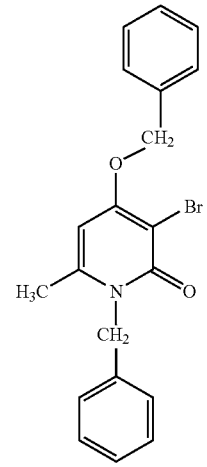

The product from example 35, 1-benzyl-4-(benzyloxy)-6-methylpyridin-2(1H)-one (4.2 mmol, 1.3 g), acetic acid (50 mL), and sodium acetate (5.0 mmol, 0.41 g) were stirred at room temperature. Bromine (4.2 mmol, 0.67 g) was added drop wise with stirring. After M hour, water (100 mL) was added and the mixture was extracted with ethyl acetate (3×50 mL). The combined organic extracts were washed with saturated aqueous sodium bicarbonate solution and brine. After drying over magnesium sulfate and concentrating, the mixture was purified by flash column chromatography eluting with ethyl acetate:hexanes (12). The appropriate fractions were concentrated to yield a light oil. (1.0 g, 62%): $^1$H NMR (DMSO-d$_6$/300 MHz) 7.4–7.0 (m, 10H), 6.5 (s, 1H), 5.29 (s, 2H), 5.27 (s, 2H), 2.2 (s, 3H). ES HRMS m/z 384.057 (M+H, C$_{20}$H$_{18}$NO$_2$Br requires 384.060).

Example 37

1-benzyl-4-(benzyloxy)-3,5-dibromo-6-methylpyridin-2(1H)-one

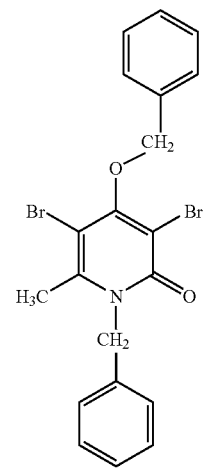

The product from example 35, 1-benzyl-4-(benzyloxy)-6-methylpyridin-2(1H)-one (4.2 mmol, 1.3 g), acetic acid (50 mL), and sodium acetate (5.0 mmol, 0.41 g) were stirred at room temperature. Bromine (4.2 mmol, 0.67 g) was added drop wise with stirring. After % hour, water (100 mL) was added and the mixture was extracted with ethyl acetate (3×50 mL).

The combined organics were washed with saturated aqueous sodium bicarbonate solution and brine. After drying over magnesium sulfate and concentrating, the mixture was purified by flash column chromatography eluting with ethyl acetate hexanes (1:2). The appropriate fractions were concentrated to yield a white solid. (0.3 g, 15%): $^1$H NMR (DMSO-$d_6$/300 MHz) 7.5–7.0 (m, 10H), 5.42 (s, 2H), 5.07 (s, 2H), 2.45 (s, 3H). ES HRMS m/z 463.966 (M+H, $C_{20}H_{17}NO_2Br_2$ requires 463.968).

Example 38

1-benzyl-4-[(3-chlorobenzyl)oxy]-6-methylpyridin-2 (1H)-one

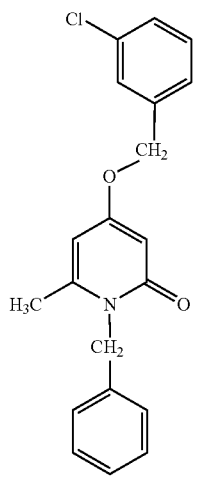

Step 1: Preparation of 1-benzyl-6-methyl-2-oxo-1,2-dihydropyridin-4-yl 4-bromobenzenesulfonate.

1-benzyl-4-hydroxy-6-methylpyridin-2(1H)-one (from example 35) (10 mmol, 2.15 g), N,N'-dimethylformamide (30 mL), potassium carbonate (20 mmol, 2.76 g), and 4-bromobenzenesulfonyl chloride (10 mmol, 2.55 g) were stirred at room temperature for 16 hours. Hydrochloric acid (1N) was added until the mixture was acidic to pH paper. Brine (50 mL) was added and the mixture extracted with ethyl acetate (3×50 mL). The combined organic extracts were washed with brine and dried over magnesium sulfate, and filtered. After concentrating, the material was purified by flash column chromatography eluting with ethyl acetate-:hexanes (1:2). The appropriate fractions were concentrated to a clear oil, which solidified upon standing several days to a white solid. (3.3 g, 76%): $^1$H NMR (DMSO-$d_6$/400 MHz) 7.9 (m, 4H), 7.32–7.00 (m, 5H), 7.3 (m, 1H), 6.12 (d, J=2.4 Hz, 1H), 6.02 (d, J=2.8 Hz, 1H), 5.20 (s, 2H), 2.2 (s, 3H). ES HRMS m/z 436.002 (M+H, $C_{19}H_{16}NO_4SBr$ requires 436.004).

Step 2: Preparation of 1-benzyl-4-[(3-chlorobenzyl)oxy]-6-methylpyridin-2(1H)-one.

1-benzyl-6-methyl-2-oxo-1,2-dihydropyridin-4-yl 4-bromobenzenesulfonate (3.0 mmol, 1.3 g), N,N'-dimethylformamide (30 mL), 3-chlorobenzyl alcohol (3.0 mmol, 0.43 g), and sodium hydroxide (60%, 3.3 mmol, 0.13 g) were stirred at room temperature under nitrogen for 4 hours. Hydrochloric acid (1 N, 10 mL) was added and the mixture extracted with ethyl acetate (3×25 mL). The combined organic extracts were washed with saturated aqueous sodium bicarbonate solution and brine. After drying over magnesium sulfate and concentrating, the mixture was purified by flash column chromatography eluting with ethyl acetate:hexanes (1:1) to obtain a light yellow oil. (14.3 g, 64%): $^1$H NMR (DMSO-$d_6$/300 MHz) δ: 7.4–7.0 (m, 10H), 6.0–5.8 (m, 2H), 5.2 (s, 2H), 5.0 (s, 2H), 2.1 (s, 3H). ES HRMS m/z 340.110 (M+H, $C_{20}H_{18}NO_2Cl$ requires 340.110).

Example 39

1-benzyl-3-bromo-4-[(3-chlorobenzyl)oxy]-6-methylpyridin-2(1H)-one

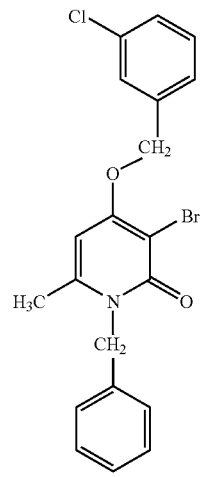

The product of example 38 (SC-83316), 1-benzyl-4-[(3-chlorobenzyl)oxy]-6-methylpyridin-2(1H)-one (0.91 mmol, 310 Mg), acetic acid (20 mL), and sodium acetate (0.91 mmol, 80 Mg) were stirred at room temperature when bromine (0.91 mmol, 145 Mg) was added. After stirring for one hour, the mixture was concentrated, dissolved in ethyl acetate, and washed successively with saturated aqueous sodium bicarbonate solution, brine, and water. After drying over magnesium sulfate and concentrating, the product was recrystallized from tetrahydrofuran/hexanes to yield a white solid. (240 Mg, 63%): $^1$H NMR (DMSO-$d_6$/300 MHz) 7.6–7.0 (m, 10H), 6.5 (s, 1H), 5.33 (s, 2H), 5.33 (s, 2H), 2.3 (s, 3H). ES HRMS m/z 420.019 (M+H, $C_{20}H_{17}NO_2BrCl$ requires 420.019).

EXAMPLE 40

1-Benzyl-4-[2,6-(dichlorobenzyl)oxy]pyridin-2(1H)-one

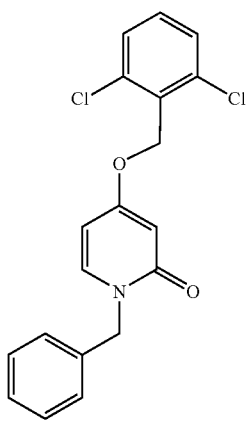

The title compound was prepared essentially as described in claim 1. mp 151.6–152.0° C. $^1$H NMR (CDCL$_3$/300 MHZ) δ: 7.31 (m, 8H), 7.12 (d, 1H, J=7.45 Hz), 6.13 (d, 1H, J=2.42 Hz), 5.90 (dd, 1H, J=2.62 Hz), 5.22 (s, 2H), 5.10 (s, 2H) ES HRMS m/z 360.0551 (M+H C$_{19}$H$_{15}$Cl$_2$NO$_2$ requires 360.0558).

EXAMPLE 41

1-Benzyl-3-bromo-4-[2,6-(dichlorobenzyl)oxy]pyridin-2(1H)-one

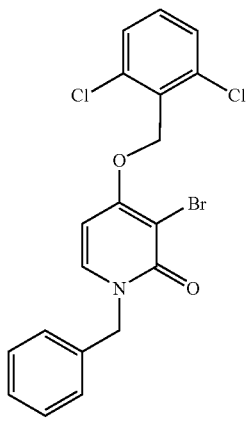

1-Benzyl-4-[2,6-(dichlorobenzyl)oxy]pyridin-2(1H)-one (0.400 g, 1.11 mmol) was dissolved in acetic acid (10 mL) Sodium acetate (0.091 g, 1.11 mmol was added, and the mixture was cooled to 15° C. Bromine (0.195 g, 1.22 mmol) was added via syringe. The reaction stirred at room temperature for 2 hours. Water (15 mL) was added, and the mixture transferred to a separatory funnel. Ethyl acetate (50 mL) was added and the layers were separated. The organic phase was washed with aqueous NaHCO$_3$ (2×25 mL), dried over MgSO$_4$, filtered, and evaporated to yield a white solid. $^1$H NMR (CDCL$_3$/300 MHZ) δ: 7.34 (m, 9H), 6.24 (d, 1H, J=7.65 Hz), 5.37 (s, 2H), 5.18 (s, 2H). ES HRMS m/z 439.9646 (M+H C$_{19}$H$_{14}$BrCl$_2$NO$_2$ requires 439.9641).

Example 42

1-Benzyl-4-[(2-chlorobenzyl)oxy]pyridin-2(1H)-one

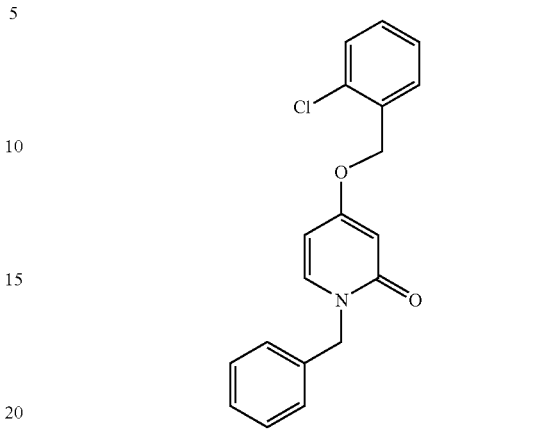

The title compound was prepared by a procedure similar to the one described in Example 1. mp 124.6–125.0° C. $^1$H NMR (CDCL$_3$/300 MHZ) δ: 7.36 (m, 9H), 7.14 (d, 1H, J=7.65 Hz), 6.04 (d, 1H, J=2.62 Hz), 5.98 (d, 1H, J=2.82 Hz), 5.10 (s, 2H), 5.09 (s, 2H). ES HRMS m/z 326.0950 (M+H C$_{19}$H$_{16}$ClNO$_2$ requires 326.0948).

Anal. Calc'd. for C$_{19}$H$_{16}$ClNO$_2$: C, 70.05; H, 4.95; N, 4.30; Cl, 10.88. Found: C, 69.87; H, 4.74; N, 4.42, Cl, 11.08.

EXAMPLE 43

1-Benzyl-3-bromo-4-[(2-chlorobenzyl)oxy]pyridin-2(1H)-one

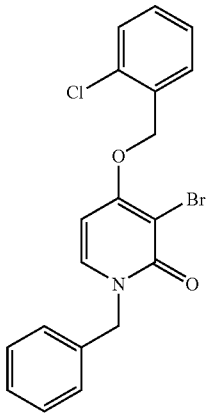

The title compound was prepared by a procedure similar to the one described in Example 2. mp 143.3–145.5° C. $^1$H NMR (CDCL$_3$/300 MHZ) δ: 7.63 (d, 2H, J=1.81 Hz), 7.44 (m, 9H), 6.06 (d, 1H, J=7.65 Hz), 5.29 (s, 2H), 5.17 (s, 2H). ES HRMS m/z 406.0036 (M+H C$_{19}$H$_{15}$BrClNO$_2$ requires 406.0032).

Anal. Calc'd. for C$_{19}$H$_{15}$Cl BrNO$_2$: C, 56.39; H, 3.74; N, 3.46; Cl, 8.76. Found: C, 56.01; H, 3.38; N, 3.36, Cl, 9.01.

EXAMPLE 44

1-Benzyl-3-bromo-4-[(4-methylbenzyl)oxy]pyridin-2(1H)-one

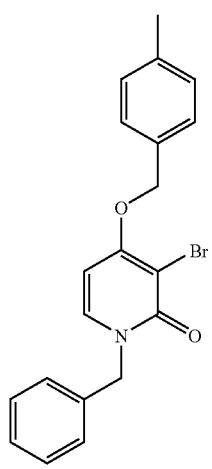

The title compound was prepared by a procedure similar to the one described in Example 2. mp 149.0–149.7° C. $^1$H NMR (CDCL$_3$/300 MHZ) δ: 7.25 (m, 10H), 6.04 (d, 1H, J=7.65 Hz), 5.17 (s, 2H), 5.15 (s, 2H), 2.34 (s, 3H). ES HRMS m/z 386.0583 (M+H C$_{20}$H$_{18}$BrNO$_2$ requires 386.0581).

EXAMPLE 45

1-Benzyl-4-[(3-chlorobenzyl)oxy]pyridin-2(1H)-one

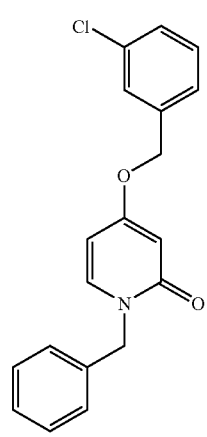

The title compound was prepared by a procedure similar to the one described in Example 1. mp 95.5–95.7° C. $^1$H NMR (CDCL$_3$/300 MHZ) δ: 7.34 (m, 9H), 7.13 (d, 1H, J=7.45 Hz), 5.96 (m, 1H), 5.95 (d, 1H, J=7.45 Hz), 5.09 (s, 2H), 4.96 (s, 2H). ES HRMS m/z 326.0977 (M+H C$_{19}$H$_{16}$ClNO$_2$ requires 326.0948).

EXAMPLE 46

1-Benzyl-4-[benzylthio]-3-bromopyridin-2(1H)-one

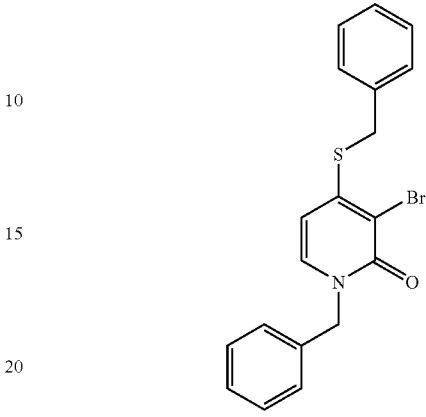

The title compound was prepared by a procedure similar to the one described in Example 2. mp 180.6–182.1° C. $^1$H NMR (CDCL$_3$/300 MHZ) δ: 7.33 (m, 10H), 7.14 (d, 1H, J=7.45 Hz), 6.08 (d, 1H, J=7.45 Hz), 5.13 (s, 2H), 4.15 (s, 2H). ES HRMS m/z 386.0211 (M+H C$_{19}$H$_{16}$BrNOS requires 386.0214).

EXAMPLE 47

1-Benzyl-3-bromo-4-{[2-(trifluoromethyl)benzyl]oxy}pyridin-2(1H)-one

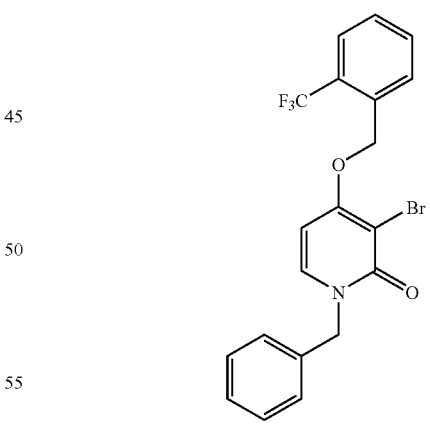

The title compound was prepared by a procedure similar to the one described in Example 2. mp 133.2–133.5° C. $^1$H NMR (CDCL$_3$/300 MHZ) δ: 7.81 (d, 1H, J=7.65 Hz), 7.68 (d, 1H, J=7.65 Hz), 7.61 (t, 1H, J=7.65 Hz), 7.38 (m, 7H), 6.01 (d, 1H, J=7.85 Hz), 5.39 (s, 2H), 5.16 (s, 2H). ES HRMS m/z 438.0313 (M+H C$_{20}$H$_{15}$BrF$_3$NO$_2$ requires 403.0316).

Example 48

1-benzyl-4-(benzyloxy)-3-iodopyridin-2(1H)-one

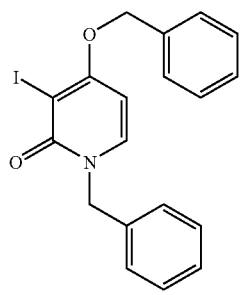

A mixture of N,O-dibenzyl-2-pyridone (2.0 g, 6.87 mmol), N-iodosuccinimide (1.7 g), dichloroacetic acid (0.15 mL) in acetonitrile (40.0 mL) was heated at 65° C. under argon atmosphere for 3.5 h, with constant stirring. The reaction mixture was concentrated to dryness, and the residue was purified by silica gel flash chromatography using EtOAc/hexanes 1:1 v/v to give the title compound 2.3 g (80%) as a flaky white solid: $^1$H-NMR (CDCl$_3$) δ: 7.4–7.2 (m, 10H), 7.19 (1H, d, J=7.6 Hz), 5.95 (d, 1H, J=7.6 Hz), 5.2 (s, 1H), 5.15 (s, 2H); ER-MS m/z=418 (MH$^+$); HR-MS m/z calcd C$_{19}$H$_{17}$NO$_2$ 418.0304, found 418.0277.

Example 49

1-benzyl-4-(benzyloxy)-3-vinylpyridin-2(1H)-one

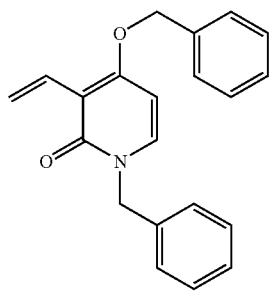

A solution of 1-benzyl-4-(benzyloxy)-3-iodopyridin-2(1H)-one (1.9 g, 4.56 mmol) and vinyl-tri-butyltin (2.5 mL) in acetonitrile (200 mL) containing DMF (2.0 mL) was degassed using house vacuum and purged with argon. Then added PdCl$_2$(PPh$_3$)$_2$ (0.3 g) and the mixture was heated at 65° C. under argon atmosphere for 4 h, with stirring. The solvents were distilled in vacuo, and the residue was triturated with EtOAc and filtered through a pad of celite. The filtrate was concentrated and the residue was purified by silica gel flash chromatography using 25% EtOAc in hexanes to give the title compound (0.75 g. 50%) as an orange colored solid.

$^1$H-NMR (CDCl$_3$) δ: 7.4–7.2 (m, 10H), 7.14 (d, 1H, J=7.6 Hz), 7.05 (dd, 1H, J=12.0 Hz), 6.47 (dd, 1H, J=2.8 Hz), 6.07 (d, 1H, J=7.6 Hz), 5.4 (dd, 1H, J=2.8 Hz), 5.13 (s, 4H); ER-MS m/z=418 (MH$^+$); ER-MS m/z=318 (MH$^+$); HR-MS m/z calcd C$_{21}$H$_{20}$NO$_2$ 318.1494, found 318.1480.

Example 50

1-benzyl-4-(benzyloxy)-3-ethylpyridin-2(1H)-one

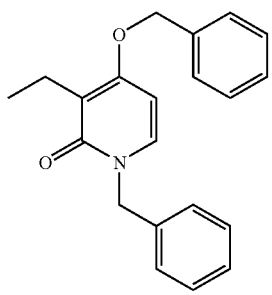

To a solution of 1-benzyl-4-(benzyloxy)-3-vinylpyridin-2(1H)-one (0.5 g, 1.6 mmol) in EtOH (10.0 mL) and EtOAc (10.0 mL) was added Pd/C (10%, 0.25 g) and stirred in an atmosphere of hydrogen gas at 30 psi for 16 h. The catalyst was removed by filtration, the filtrate was concentrated to dryness and the resulting residue was purified by silica gel flash chromatography using EtOAc/hexanes (1:1, v/v) to afford the title compound (0.32 g, 64%) as a pale yellow powder: $^1$H-NMR (CD$_3$OD) δ: 7.52 (d, 1H, J=7.6 Hz), 7.39–7.2 (m, 10H), 6.41 (d, 1 h, J=7.6 Hz), 5.18 (s, 2H), 5.15 (s, 2H), 2.58 (q, 2H, J=7.2 Hz), 1.03 (t, 3H, J=7.2 Hz), ER-MS m/z=320 (MH$^+$) HR-MS m/z calcd C$_{21}$H$_{22}$NO$_2$ 320.1651, found 320.1648.

Example 51

3-acetyl-4-(benzyloxy)-1-(2-chlorophenyl)-6-methylpyridin-2(1H)-one

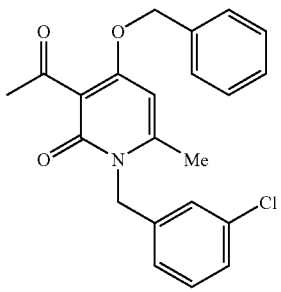

Step A
Preparation of 3-acetyl-1-(2-chlorophenyl)-4-hydroxy-6-methylpyridin-2(1H)-one

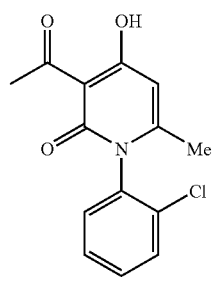

A mixture of 2-chlorophenylisocyanate (3.0 g, 19.53 mmol), and diketene (3.3 g, 39.28 mmol) in toluene (10.0 mL) containing triethylamine (0.05 mL) was heated to reflux for 6 h, under an atmosphere of argon. Toluene was distilled in vacuo and the resulting residue was purified by silica gel flash chromatography using 25% EtOAc in hexanes as the eluent to afford the title compound (0.85 g, see ref: *Heterocycles* 27 (9), 2063, 1988.) as a pale yellow solid: $^1$H-NMR (CD$_3$OD) δ: 7.63 (m, 1H), 7.52 (m, 2H), 7.4 (m, 1H), 6.14 (s, 1H), 2.58 (s, 3H), and 1.95 (s, 3H); ES-MS m/z=278 (MH$^+$).

Step B

Preparation of 3-acetyl-4-(benzyloxy)-1-(2-chlorophenyl)-6-methylpyridin-2(1H)-one To a solution of 3-acetyl-1-(2-chlorophenyl)-4-hydroxy-6-methylpyridin-2(1H)-one (0.56 g, 2.02 mmol) in DMF (5.0 mL), benzyl bromide (0.3 mL) and potassium carbonate (0.3 g, 2.16 mmol) were added. The mixture was stirred at room temperature for 3 h, and at 65° C. for 1 h under argon atmosphere. The reaction mixture was concentrated in vacuo and the residue was partitioned between 5% citric acid (25 mL) and EtOAc (50.0 mL). The organic phase was washed with brine, dried (Na$_2$SO$_4$), filtered, and concentrated to dryness. The resulting residue was purified by silica gel flash chromatography using 50% EtOAc in hexanes to afford the title compound (0.58 g, 75%) as a pale yellow amorphous substance: $^1$H-NMR (CD$_3$OD) δ: 7.65–7.3 (m, 9H), 6.5 (s, 1H), 5.31 (s, 2H), 2.42 (s, 3H), and 2.01 (s, 3H); ER-MS m/z=368 (MH $^+$); HR-MS m/z calcd C$_{21}$H$_{19}$NO$_3$Cl, 368.1060, found 368.1053.

Example 52

1-benzyl-3-bromo-4-(2-phenylethyl)pyridin-2(1H)-one

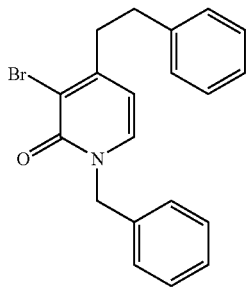

Step A

Preparation of 1-benzyl-3-bromo-4-hydroxypyridin-2(1H)-one

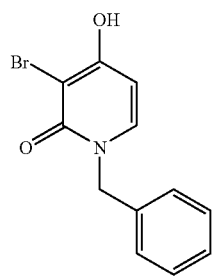

A suspension of N-benzyl-4-hydroxy-2-pyridone ((0.75 g, 3.7 mmol), NBS (0.7 g, 1.05 mmol) in dichloromethane was stirred at room temperature for 1.5 h under argon atmosphere. It was diluted with dichloromethane (25 mL), cooled and filtered. The solids were washed with dichloromethane and dried in vacuo. The filtrate and the washings were combined and washed with water, dried (Na$_2$SO$_4$), filtered, and concentrated to dryness. The resulting residue was washed with EtOAc, and dried in vacuo to give a combined mass of 0.65 g of the title compound as a white powder: $^1$H NMR (CD$_3$OD) δ: 7.54 (d, 1H, J=7.6 Hz), 7.27 (m, 5H), 6.12 (d, 1H, J=7.6 Hz), 5.15 (s, 2H); ES-MS: m/z=280 (MH$^+$).

Step B

Preparation of 1-benzyl-3-bromo-2-oxo-1,2-dihydropyridin-4-yl trifluoromethanesulfonate

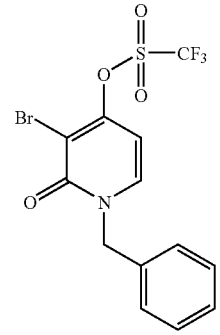

To a cold (−30° C.) suspension of 1-benzyl-3-bromo-4-hydroxypyridin-2(1H)-one (0.78 g, 2.8 mmol) in dichloromethane (10.0 mL), was added triethylamine (0.6 mL, 4.28 mmol), followed by the addition of triflic anhydride (0.7 mL, 4.17 mmol). The resulting mixture was stirred at −30° C. under argon atmosphere for 1 h. The reaction mixture was then poured into ice/water mixture (50 mL) and the products were extracted with dichloromethane (2×25 mL). The combined organic extracts were washed with water (2×20 mL), dried (Na$_2$SO$_4$), filtered, and concentrated to dryness. The residue was dried in vacuo to afford the desired trifluorosulfonate (1.0 g) as a pale yellow solid which used as such in the next step: 1H-NMR (CDCl$_3$) δ: 7.35 (m, 6H), 6.26 (d, 1H, J=8.0 Hz); $^{19}$F-NMR (CDCl$_3$) δ: −73.73 ppm; ES-MS: m/z=412 (MH$^+$).

Step C

Preparation of 1-benzyl-3-bromo-4-(phenylethynyl)pyridin-2(1H)-one.

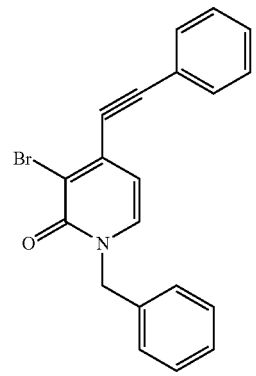

To a solution of 1-benzyl-3-bromo-2-oxo-1,2-dihydropyridin-4-yl trifluoromethanesulfonate (1.0 g) in DMF (5.0 mL) was added phenylacetylene (0.4 mL) and degassed using house vacuum. The reaction flask was then purged with argon, added diisopropylethylamine (0.53 mL), and PdCl$_2$(PPh$_3$)$_2$ (0.35 g) were added. The resulting mixture was stirred at room temperature for 15 min and heated at 65° C. under an argon atmosphere for 3 h. The dark colored reaction mixture was concentrated in vacuo, and the residue was partitioned between EtOAc (50 mL) and 5% aqueous citric acid (25 mL). The organic extracts were washed with water, dried (Na$_2$SO$_4$), filtered, and concentrated to dryness. The resulting material was purified by silica gel flash chromatography using 25% EtOAc in hexanes as the eluent. The appropriate fractions were combined, concentrated under reduced pressure. $^1$H NMR (CDCl$_3$) δ: 7.57 (m, 2H), 7.38 (m, 8H), 7.21 (d, 1H, J=6.8 Hz), 6.25 (d, 1H, J=6.8 Hz), and 5.16 (d, 2H), ES-MS: m/z=364 (MH$^+$);

HR-MS m/z (MH$^+$) calcd C$_{20}$H$_{15}$NOBr 364.0337, found 364.0337.

Step D

Preparation of 1-benzyl-3-bromo-4-(2-phenylethyl)pyridin-2(1H)-one.

A mixture of 1-benzyl-3-bromo-4-(phenylethynyl)pyridin-2(1H)-one (0.3 g), and platinum oxide (0.05 g) in a solvent mixture of EtOAc (10.0 mL) and EtOH (10.0 mL) was stirred in an atmosphere of hydrogen at 15 psi in a Fischer porter bottle for 45 min. The catalyst was removed by filtration, and filtrate was concentrated. The resulting residue was purified by silica gel flash chromatography using 25% EtOAc in hexanes as the eluent. The appropriate fractions (visualized under an UV lamp) were combined and concentrated under reduced pressure. $^1$H-NMR (CD$_3$OD) δ: 7.56 (d, 1H, J=6.8 Hz), 7.31–7.17 (m, 10H), 6.24 (d, 1H, J=6.8 Hz), 5.19 (s, 2H), 2.96 (m, 2H), and 2.91 (m, 2H); ES-MS m/z=368 (MH$^+$); HR-MS m/z (MH$^+$) calcd C$_{20}$H$_{19}$NOBr 368.0650, found 368.0630.

Example 53

3-bromo-1-(3-fluorobenzyl)-6-methyl-4-(2-phenylethyl)pyridin-2(1H)-one

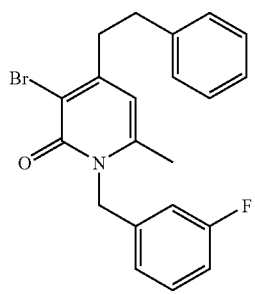

The title compound was prepared essentially according to the procedure of Example 52. $^1$H-NMR δ: (CD$_3$OD) δ: 7.35 (m, 1H), 7.31–7.16 (m, 5H), 6.99 (m, 1H), 6.91 (m, 1H), 6.81 (m, 1H), 6.20 (s, 1H), 5.41 (s, 2H), 2.94 (m, 4H), and 2.24 (s, 3H) $^{19}$F-NMR (CD$_3$OD) δ: -115.01 (m); ES-MS, m/z=400 (MH$^+$); HR-MS m/z calcd C$_{21}$H$_{20}$NOBrF 400.0712, found 400.0695.

Example 54

4-(benzyloxy)-3-bromo-1-(2,6-dichlorophenyl)-6-methylpyridin-2(1H)-one

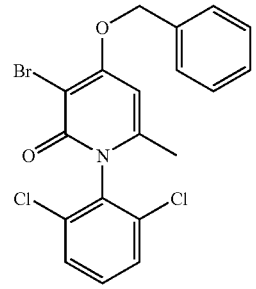

Step A

Preparation of 3-acetyl-1-(2,6-dichlorophenyl)-4-hydroxy-6-methylpyridin-2(1H)-one

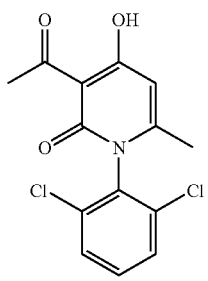

A mixture of 2,6 dichlorophenylisocyanate (4.8 g, 0.025 mol), and diketene (4.3 g, 0.05 mol) in toluene (15.0 mL) was heated to reflux for 4 h under an atmosphere of argon. After removal of the solvent in vacuo, the residue was purified by silica gel flash chromatography using EtOAc/hexanes (1:3 v/v). The appropriate fractions, as monitored by ES mass spectrometry (MH$^+$m/z=312) were combined and concentrated under reduced pressure. The resulting yellow solid (2.3 g) was further purified by reverse-phase HPLC using 10–90% acetonitrile/water gradient (45 min) at a flow rate of 100 mL/min. The appropriate fractions, as monitored by ES mass spectrometry (MH$^+$ m/z=312) were combined and concentrated to half the volume. The solid that separated was extracted with EtOAc (2×25 mL). The combined extracts were washed with water, dried (Na$_2$SO$_4$), filtered, and concentrated to dryness to give the title compound (0.77 g) as a pale yellow powder: $^1$H-NMR (CD$_3$OD) δ: 7.62 (m, 2H), 7.52 (m, 1H), 6.19 (s, 1H), 2.59 (s, 3H), and 1.96 (s, 3H); ES-MS m/z=312 (MH$^+$); HR-MS, m/z calc C$_{14}$H$_{12}$NO$_3$Cl$_2$ 312.0189, found 312.0214.

Step B.
Preparation of 1-(2,6-dichlorophenyl)-4-hydroxy-6-methylpyridin-2(1H)-one

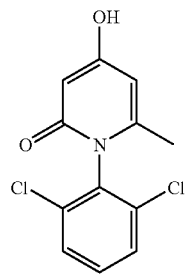

A mixture of 3-acetyl-1-(2,6-dichlorophenyl)-4-hydroxy-6-methylpyridin-2(1H)-one 0.7 g (0.002 mol) in n-butanol (3.0 mL) containing sulfuric acid (1.5 mL) was heated at 120° C. for 4 h. The dark reaction mixture was cooled, added ice/water (25 mL), and extracted with EtOAc (2×25 ml). The combined organic extracts were washed with water, dried (Na$_2$SO$_4$), filtered, concentrated under reduced pressure and the resulting material was purified by silica gel flash chromatography using 25% EtOAc in hexanes as the eluent to afford the title compound (0.14 g) as a pale yellow powder: $^1$H-NMR (CD$_3$OD) δ: 7.6 (m, 2H), 7.48 (m, 1H), 6.10 (dd, 1H), 5.78 (d, 1H, J=2.4 Hz), 1.91 (s, 3H); ES-MS m/z=270 (MH$^+$); HR-MS, m/z calc C$_{12}$H$_{10}$NO$_2$Cl$_2$ 270.0083, found 270.0103.

Step C
Preparation of 4-(benzyloxy)-1-(2,6-dichlorophenyl)-6-methylpyridin-2(1H)-one

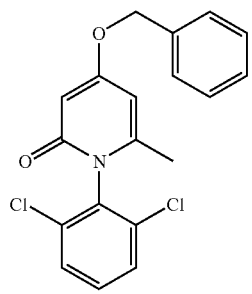

A mixture of 1-(2,6-dichlorophenyl)-4-hydroxy-6-methylpyridin-2(1H)-one (0.125 g, 0.46 mmol) and benzylbromide (0.1 mL) in DMF (2.5 mL) was stirred at room temperature for 16 h. The reaction mixture was diluted with water (10.0 mL) and extracted with EtOAc (2×20 mL). The combined organic extracts were washed with water, dried (Na$_2$SO$_4$), filtered, concentrated under reduced pressure and the resulting material was purified by silica gel flash chromatography using 25% EtOAc in hexanes to afford the title compound (0.11 g) as a pale yellow syrup: 1H-NMR (CD$_3$OD) δ: 7.61 (m, 2H), 7.55–7.3 (m, 6H), 6.23 (d, 1H, J=2.0 Hz), 6.01 (d, 1H, J=2.0 Hz), 5.12 (s, 2H), and 1.93 (s, 3H); ES-MS m/z=360 (MH$^+$); HR-MS, m/z calc C$_{19}$H$_{16}$NO$_2$Cl$_2$, 360.0553, found 360.0569.

Step D
Preparation of 4-(benzyloxy)-3-bromo-1-(2,6-dichlorophenyl)-6-methylpyridin-2(1H)-one
A mixture of 4-(benzyloxy)-1-(2,6-dichlorophenyl)-6-methylpyridin-2(1H)-one (0.1 g, 0.278 mmol) and N-bromosuccinimide (0.055 g, 0.3 mmol) in dichloroethane (3.0 mL) was stirred at room temperature for 1 h, and heated at 60° C. under argon for 30 min. The reaction mixture was then diluted with dichloroethane (15 mL), washed with water, dried (Na$_2$SO$_4$), filtered, and concentrated under reduced pressure. $^1$H NMR (CD$_3$OD) δ: 7.64 (m, 2H), 7.55 (m, 3H), 7.38 (m, 3H), 6.65 (s, 1H), 5.34 (s, 2H), and 2.00 (s, 3H); ES-MS m/z=439 (MH$^+$); HR-MS, m/z calc C$_{19}$H$_{16}$NO$_2$Cl$_2$Br, 439.9635, found 439.9669.

Example 55

3-bromo-1-(3-fluorobenzyl)-4-(2-phenylethyl)pyridin-2(1H)-one

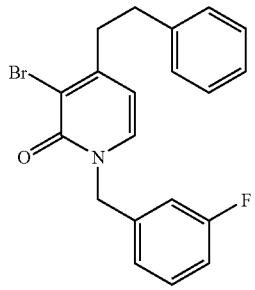

The title compound was prepared essentially according to the procedure of Example 52. $^1$H-NMR (CD$_3$OD) δ: 7.58 (d, 1H, J=6.8 Hz), 7.4–7.0 (m, 9H), 6.26 (d, 1H. J=6.8 Hz), 5.19 (s, 2H), 2.97 (m, 2H), and 2.90 (m, 2H); ES-MS m/z=386 (MH$^+$); HR-MS, m/z calc C$_{20}$H$_{18}$NOFBr, 386.0550, found 386.0585.

Example 56

1-benzyl-3-bromo-2-oxo-1,2-dihydropyridin-4-yl methyl(phenyl)carbamate

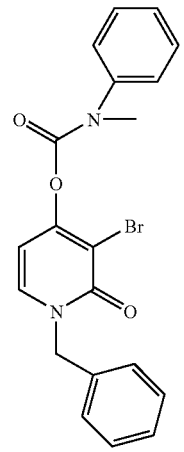

Step A

Preparation of 1-benzyl-2-oxo-1,2-dihydropyridin-4-yl methyl(phenyl)carbamate

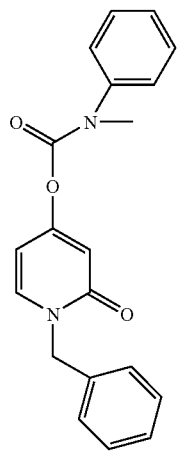

To a chilled solution of 1-benzyl-4-hydroxypyridin-2(1H)-one (0.375 g, 1.86 mmol) in anhydrous acetonitrile (10 mL) was added triethylamine (0.206 g, 2.04 mmol) followed by N-methyl-N-phenylcarbamoyl chloride (0.379 g, 2.24 mmol). The reaction mixture was stirred under nitrogen atmosphere at 0° C. for 30 min then at room temperature for 1 h. The reaction was monitored by TLC (5% methanol in dichloromethane). The solvent was removed under reduced pressure and the residue was washed with 10% citric acid and extracted with EtOAc. The organic extracts were combined, washed with water dried over anhydrous $Na_2SO_4$, and filtered. The solvent was removed under reduced pressure to afford a yellow syrup. The residue was purified by flash chromatography (silica gel) using 5% MeOH in $CH_2Cl_2$ to give the desired product (0.382 g, 61%) as a white semisolid.

MS and $^1$H-NMR were consistent with the desired structure. $^1$H-NMR ($d_6$-DMSO, 400 MHz) δ: 7.8 (d, 1H), 7.39 (m, 10H), 6.19 (s, 2H), 5.03 (s, 2H), 3.29 (s, 3H); HR-MS (ES) m/z calcd for $C_{20}H_{18}N_2O_3$ (MH$^+$)=335.1396, observed 335.1418.

Step B 1-benzyl-3-bromo-2-oxo-1,2-dihydropyridin-4-yl methyl (phenyl)carbamate

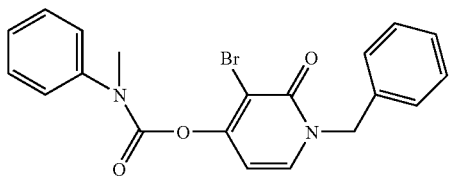

To a solution of 1-benzyl-2-oxo-1,2-dihydropyridin-4-yl methyl(phenyl)carbamate (0.38 g, 1.13 mmol) in anhydrous $CH_2Cl_2$ (7 mL) was added N-Bromosuccinimide (NBS, 0.24 g, 1.34 mmol). The reaction was stirred overnight at room temperature under nitrogen atmosphere. The reaction mixture was purified by flash chromatography (silica gel) using EtOAc/hexanes (1:1 v/v). The appropriate fractions were collected according to ES MS (M+H 413) and concentrated. The dried product showed about 14% of di-brominated product by analytical HPLC. The compounds were separated by reverse phase HPLC using a 10–90% acetonitrile in water, 30 min gradient at a 100 mL/min flow rate, to afford (after lyophilization) the salt of the desired compound. The salt was diluted in EtOAc and washed with $NaHCO_3$. The organic extracts were dried over anhydrous $Na_2SO_4$, filtered, and concentrated to afford the desired compound (0.271 g, 58%) as a beige solid.

MS and $^1$H-NMR were consistent with the desired structure. $^1$H-NMR ($d_6$-DMSO, 400 Hz) δ: 7.83 (d, 1H), 7.39 (m, 10H), 6.48 (s, 1H), 5.12 (s, 2H), 3.33 (s, 3H); HR-MS (ES) m/z calcd for $C_{20}H_{17}O_3Br$ (MH$^+$)=413.0495, observed 413.0496.

Example 57

4-(benzyloxy)-3-ethynyl-1-(3-fluorobenzyl)pyridin-2(1H)-one

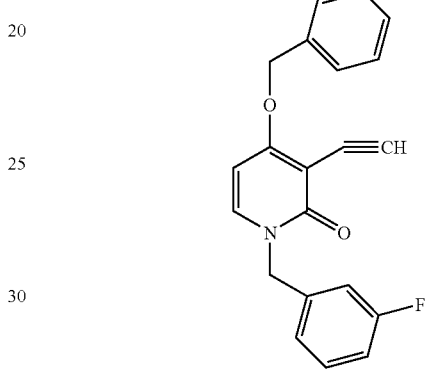

Step A

Preparation of 4-(benzyloxy)-1-(3-fluorobenzyl)-3-iodopyridin-2(1H)-one

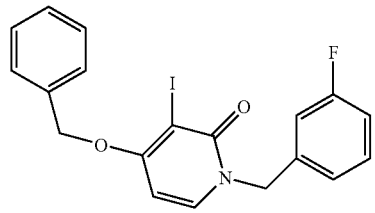

Heated a reaction mixture of 4-(benzyloxy)-1-(3-fluorobenzyl)pyridin-2(1H)-one (4.83 g, 15.6 mmol) in anhydrous acetonitrile (55 mL) and N-iodosuccinimide (NIS, 3.86 g, 17.1 mmol) under nitrogen atmosphere at 650 C for 4 h. The reaction mixture was concentrated under reduced pressure and the residue was purified by flash chromatography (silica gel) using EtOAc/hexanes (1:1 v:v). The appropriate fractions were collected according to ES MS (M+H 436) and washed with $Na_2SO_3$ to remove the color impurities. The fractions were concentrated under reduced pressure and dried in vacuo to afford the desired product (6.15 g, 90%) as a light yellow solid.

MS and $^1$H-NMR were consistent with the desired structure. $^1$H-NMR ($CD_3OD$, 400 Hz) δ: 7.73 (d, 1H), 7.47 (d, 2H), 7.39 (m, 4H), 7.08 (m, 3H), 6.39 (d, 1H), 5.29 (s, 2H), 5.19 (s, 2H); HR-MS (ES) m/z calcd for $C_{19}H_{15}NO_2FI$ (MH$^+$)=436.0210, observed 436.0196.

Step B
Preparation of 4-(benzyloxy)-1-(3-fluorobenzyl)-3-[(trimethylsilyl)ethynyl]pyridin-2(1H)-one

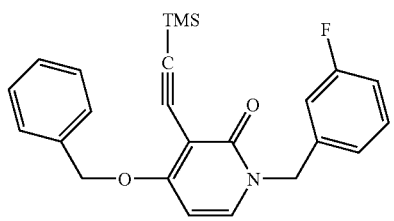

Degassed a solution of 4-(benzyloxy)-1-(3-fluorobenzyl)-3-iodopyridin-2(1H)-one (2.01 g, 4.62 mmol) in anhydrous acetonitrile (25 mL) under argon atmosphere. Triethylamine (1.11 g, 11 mmol) was added and quickly degassed. The reaction mixture was chilled in an ice bath for 15 minutes before adding bistriphenylphosphine-palladium chloride (0.34 g, 0.48 mmol) and cuprous iodide (0.2 g). The reaction was stirred at room temperature for 30 min before heating at 60° C. under an atmosphere of argon for 2 h. The reaction mixture was filtered through a bed of celite and the filtrate was concentrated under reduced pressure. The dark brown residue was diluted with $CH_2Cl_2$ (100 mL) and washed with water. The organic extracts were combined, dried over anhydrous $Na_2SO_4$, filtered, and concentrated under reduced pressure. The dark brown residue was purified by flash chromatography (silica gel) using 30% EtOAc in hexane. The appropriate fractions were combined and concentrated under reduced pressure to afford the desired product (1.34 g, 72%) as a light yellow solid.

MS and $^1$H-NMR were consistent with the desired structure. $^1$H-NMR (CD$_3$OD, 400 Hz) δ: 7.74 (d, 1H), 7.47 (d, 2H), 7.35 (m, 4H), 7.09 (m, 3H), 6.46 (d, 1H), 5.26 (s, 2H), 5.13 (s, 2H), 0.18 (s, 9H); HR-MS (ES) m/z calcd for $C_{24}H_{24}NO_2FSi$ (MH$^+$)=406.1638, observed 406.1610.

Step C
Preparation of 4-(benzyloxy)-3-ethynyl-1-(3-fluorobenzyl)pyridin-2(1H)-one

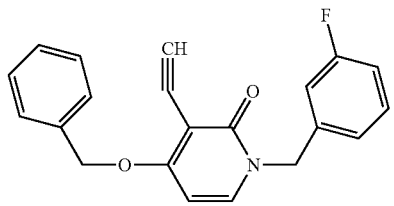

To a solution of 4-(benzyloxy)-1-(3-fluorobenzyl)-3-[(trimethylsilyl)ethynyl]pyridin-2(1H)-one (1.31 g, 3.2 mmol) in anhydrous acetonitrile (25 mL) at 0° C. was added tetrabutylammonium fluoride (0.611 g, 1.93 mmol). The reaction was stirred at 0° C. for 15 min then for 1 h at room temperature. The reaction was concentrated under reduced pressure and the residue was diluted with EtOAc and washed with water. The organic extracts were combined, dried over anhydrous $Na_2SO_4$, filtered, and concentrated under reduced pressure. The residue was purified by flash chromatography (silica gel) using EtOAc in hexanes (1:1 v/v). The appropriate fractions were combined and concentrated under reduced pressure to afford the desired product (0.779 g, 72%) as a gold solid.

MS and $^1$H-NMR were consistent with the desired structure. $^1$H-NMR (CD$_3$OD, 400 Hz) δ: 7.73 (d, 1H), 7.43 (d, 2H), 7.35 (m, 4H), 7.09 (m, 3H), 6.45 (d, 1H), 5.27 (s, 2H), 5.13 (s, 2H), 3.78 (s, 1H); HR-MS (ES) m/z calcd for $C_{21}H_{16}NO_2F$ (MH$^+$)=334.1243, observed 334.1234.

Example 58

4-(benzylamino)-3-bromo-1-(3-fluorobenzyl)pyridin-2(1H)-one

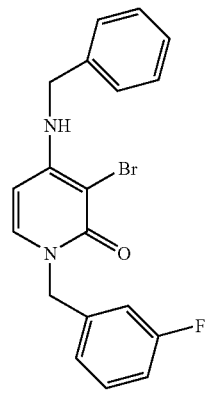

Step A
Preparation of 1-(3-fluorobenzyl)-4-hydroxypyridin-2(1H)-one

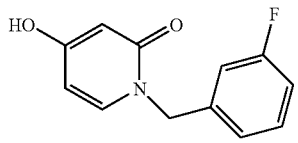

In a Fischer-Porter bottle, added a solution of 4-(benzyloxy)-1-(3-fluorobenzyl)pyridin-2(1H)-one (4.5 g, 14.56 mmol) in absolute ethanol-(20 mL). Flushed the solution with nitrogen then added palladium catalyst (1.05 g). Sealed bottle and evacuated system. The system was purged with hydrogen gas (2×15 psi) to check for leaks. The reaction was charged with hydrogen (35 psi) and stirred at room temperature for 45 min. The system was evacuated and flushed with nitrogen. The reaction was filtered and the catalyst was carefully washed with fresh ethanol. The filtrate was concentrated under reduced pressure.

MS and $^1$H-NMR were consistent with the desired structure. $^1$H-NMR (CD$_3$OD, 400 Hz) δ: 7.54 (d, 1H), 7.32 (m, 1H), 7.06 (m, 3H), 6.05 (dd, 1H), 5.83 (s, 1H), 5.09 (s, 2H); HR-MS (ES) m/z calcd for $C_{12}H_{10}NO_2F$ (MH$^+$)=220.0774, observed 220.0787.

Step B
Preparation of 4-(benzylamino)-1-(3-fluorobenzyl)pyridin-2(1H)-one

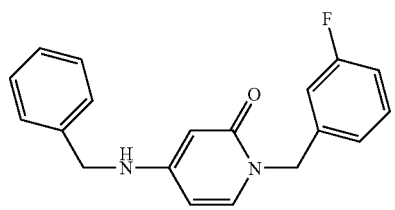

Heated a reaction mixture of 1-(3-fluorobenzyl)-4-hydroxypyridin-2(1H)-one (1.005 g, 4.5 mmol) in benzylamine (15 mL) at reflux (1850 C) under nitrogen atmosphere for 24 h. The reaction was monitored by ES-MS (MH+ 309). The solvent was removed by vacuum distillation to give a yellow residue.

MS and $^1$H-NMR were consistent with the desired structure. $^1$H-NMR (CD$_3$OD, 400 Hz) δ: 7.31 (m, 7H), 7.03 (m, 3H), 5.98 (dd, 1H), 5.45 (s, 1H), 5.00 (s, 2H), 4.30 (s, 2H); HR-MS (ES) m/z calcd for C$_{19}$H$_{17}$N$_2$O F. (MH$^+$)=309.1403, observed 309.1375.

Step C

Preparation of 4-(benzylamino)-3-bromo-1-(3-fluorobenzyl)pyridin-2(1H)-one

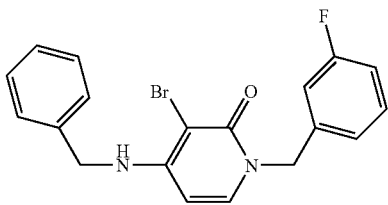

To a solution of 4-(benzylamino)-1-(3-fluorobenzyl) pyridin-2(1H)-one (0.50 g, 1.62 mmol) in anhydrous CH$_2$Cl$_2$ (10 mL) was added N-bromosuccinimide (NBS, 0.30 g, 1.7 mmol). The reaction was stirred at room temperature under a nitrogen atmosphere for 3 h. The reaction mixture was purified by flash chromatography (silica gel) using EtOAc in hexanes (1:1 v/v). The appropriate fractions were combined and concentrated.

MS and $^1$H-NMR were consistent with the desired structure. $^1$H-NMR (CD$_3$OD, 400 Hz) δ: 7.41 (d, 1H), 7.31 (m, 6H), 7.04 (m, 3H), 5.99 (d, 1H), 5.08 (s, 2H), 4.53 (s, 2H); HR-MS (ES) m/z calcd for C$_{19}$H$_{16}$N$_2$OFBr (MH$^+$)= 387.0508, observed 387.0504.

Example 59

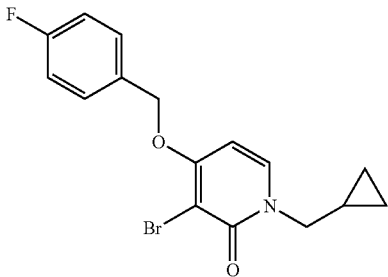

3-Bromo-1-cyclopropylmethyl-4-(4-fluorobenzyloxy)-1H-pyridin-2-one

Step 1. Preparation of 4-[(4-Fluorobenzyloxy]pyridine-1-oxide.

To an ice-cold solution of sodium hydride (1.9 g, of a 60% dispersion in mineral oil, 46 mmol) in DMF (39 mL) was added 4-fluorobenzyl alcohol (5.1 mL, 46 mmol). The reaction mixture was warmed to room temperature, 4-chloropyridine-1-oxide[1] (5.0 g, 39 mmol) was added, and the reaction mixture was stirred for 6 h. The reaction mixture was diluted with a 50% aqueous solution of brine, and extracted with CHCl$_3$ (7×50 mL). The combined organics were dried (MgSO$_4$), filtered, and concentrated under reduced pressure. Trituration with Et$_2$O afforded 4-[(4-fluorobenzyloxy]pyridine-1-oxide as an off-white solid (9.1 g, 90%), which was used in the next step without further purification or characterization.

Step 2. Preparation of 4-(4-Fluorobenzyloxy)-1H-pyridin-2-one.

A solution of 4-[(4-fluorobenzyloxy]pyridine-1-oxide (6.4 g, 29 mmol) in acetic anhydride (97 mL) was heated at reflux for 3 h. The reaction mixture was cooled to room temperature and the solvent was removed under reduced pressure. The residue was diluted with 1:1 MeOH/water (34 mL), and the mixture was stirred at room temperature for 1 h. The solvent was removed under reduced pressure. Trituration with Et$_2$O/hexanes afforded 4-(4-fluorobenzyloxy)-1H-pyridin-2-one as a brown solid (3.1 g, 48%): $^1$H NMR (300 MHz, CDCl$_3$) δ 7.40–7.36 (m, 2H), 7.22 (d, J=8 Hz, 1H), 7.09 (t, J=7 Hz, 2H), 6.03 (dd, J=7, 3 Hz, 1H), 5.94 (d, J=3 Hz, 1H), 4.98 (s, 2H).

Step 3. Preparation of 3-Bromo-4-(4-fluorobenzyloxy)-1H-pyridin-2-one.

To an ice-cold solution of 4-(4-fluorobenzyloxy)pyridine-2(1H)-one (3.1 g, 14 mmol) in AcOH (26 mL) was added a solution of bromine (0.79 mL, 15 mmol) in AcOH (51 mL), and the reaction mixture was stirred at room temperature for 2 h. The solvent was removed under reduced pressure, and purification by flash column chromatography (silica, 1:1 Et$_2$O/hexanes) to afford 3-bromo-4-(4-fluorobenzyloxy)-1H-pyridin-2-one as an orange solid (0.78 g, 48%): MS APCI m/z 298 [M+H]$^+$.

Step 4. Preparation of 3-Bromo-1-cyclopropylmethyl-4-(4-fluorobenzyloxy)-1H-pyridin-2-one.

To a solution of 3-bromo-4-(4-fluorobenzyloxy)-1H-pyridin-2-one (0.25 g, 0.84 mmol) in DMF (13 mL) was added K$_2$CO$_3$ (0.33 g, 1.7 mmol) and cyclopropylmethyl bromide (0.14 g, 1.0 mmol), and the reaction mixture was stirred at 110° C. for 2 h. The reaction mixture was cooled to room temperature, and the solvent was removed under reduced pressure. The residue was diluted with a 50% aqueous solution of brine, and extracted with CHCl$_3$ (3×50 mL). The combined organics were washed with water and then brine, dried (MgSO$_4$), filtered, and concentrated under reduced pressure. Purification by flash column chromatography (silica, 1:1 EtOAc/hexanes) afforded 3-bromo-1-cyclopropyl-methyl-4-(4-fluorobenzyloxy)-1H-pyridin-2-one as a yellow solid (0.12 g, 39%): mp 139–141° C.; $^1$H NMR (300 MHz, CDCl$_3$) δ 7.43–7.34 (m, 3H), 7.07 (t, J=9 Hz, 2H), 6.06 (d, J=6 Hz, 1H), 5.19 (s, 2H), 3.82 (d, J=9 Hz, 2H), 1.26–1.23 (m, 1H), 0.62–0.57 (m, 2H), 0.40–0.36 (m, 2H). ES HRMS m/z 352.0368 (M+H C$_{16}$H$_{16}$BrFNO$_2$ requires 352.0343).

Examples 60–69

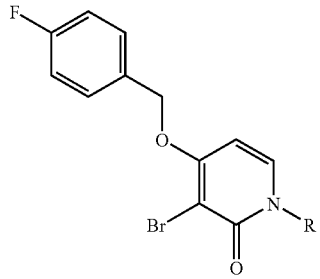

The compounds of Examples 60–69 are prepared essentially according to the procedures set forth above for Example 59.

| Example No. | R | MF | M + H Requires | ESHRMS m/z |
|---|---|---|---|---|
| Ex. 60 | pyridin-4-ylmethyl | | | |
| Ex. 61 | pyridin-3-ylmethyl | $C_{18}H_{14}BrFN_2O_2$ | 489.0296 | 489.0281 |
| Ex. 62 | 4-tert-butylbenzyl | $C_{23}H_{23}BrFNO_2$ | 444.0969 | 444.0971 |
| Ex. 63 | 3-trifluoromethylbenzyl | $C_{20}H_{14}BrF_4NO_2$ | 456.0217 | 456.0202 |
| Ex. 64 | Biphenyl-2-ylmethyl | $C_{25}H_{19}BrFNO_2$ | 464.0656 | 464.0656 |
| Ex. 65 | 4-methoxybenzyl | $C_{20}H_{17}BrFNO_3$ | 418.0449 | 418.0457 |
| Ex. 66 | 4-cyanobenzyl | $C_{20}H_{14}BrFN_2O_2$ | 413.0295 | 413.0287 |
| Ex. 67 | 4-trifluoromethylbenzyl | $C_{20}H_{14}BrF_4NO_2$ | 456.0217 | 456.0192 |
| Ex. 68 | Biphenyl-4-ylmethyl | $C_{25}H_{19}BrFNO_2$ | 464.0656 | 464.0653 |
| Ex. 69 | cyclohexylmethyl | $C_{19}H_{21}BrFNO_2$ | 394.0812 | 394.0797 |

NMR characterization of compounds of Examples 12–19

| Ex. No. | NMR Data |
|---|---|
| Ex. 60 | $^1$H NMR (300 MHz, CDCl$_3$) δ 8.57(dd, J=6, 3Hz, 2H), 7.43–7.38(m, 2H), 7.16(d, J=6Hz, 2H), 7.09(t, J=9Hz, 2H), 6.12(d, J=6Hz, 1H), 5.20(s, 2H), 5.16(s, 2H) |
| Ex. 61 | $^1$H NMR (300 MHz, CDCl$_3$) δ 8.58–8.55(m, 2H), 7.75(d, J=6Hz, 1H), 7.41–7.37(m, 2H), 7.31–7.26(m, 2H), 7.12–7.04(m, 2H), 5.17(d, J=6Hz, 1H), 5.18(s, 2H), 5.16(s, 2H) |
| Ex. 62 | $^1$H NMR (300 MHz, MeOD) δ 7.75(d, 1H, J=9Hz), 7.59(t, J=9Hz, 2H), 7.37(d, J=9Hz, 2H), 7.22(d, J=9Hz, 2H), 7.06–6.99(m, 2H), 6.52(d, J=9Hz, 1H), 5.29(s, 2H), 5.18(s, 2H), 1.28(s, 9H) |
| Ex. 63 | $^1$H NMR (300 MHz, CDCl$_3$) δ 7.58–7.37(m, 5H), 7.29–7.26(m, 2H), 7.08(t, J=7Hz, 2H), 6.10(d, J=7Hz, 1H), 5.20(s, 2H), 5.18(s, 2H) |
| Ex. 64 | $^1$H NMR (300 MHz, CDCl$_3$) δ 7.42–7.27(m, 11H), 7.07(t, J=6Hz, 2H), 6.72(d, J=7Hz, 1H), 5.88(d, J=9Hz, 1H), 5.16(s, 2H), 5.12(s, 2H) |
| Ex. 65 | $^1$H NMR (300 MHz, CDCl$_3$) δ 7.38–7.36(m, 2H), 7.27–6.84(m, 3H), 7.08(s, 2H), 6.86(d, J=7Hz, 2H), 6.01(d, J=6Hz, 1H), 5.15(s, 2H), 5.09(s, 2H), 3.78(s, 3H) |
| Ex. 66 | $^1$H NMR (300 MHz, CDCl$_3$) δ 7.64–7.61(m, 2H), 7.42–7.37(m, 4H), 7.27–7.25(m, 1H), 7.12–7.06(m, 2H), 6.11(d, J=6Hz, 1H), 5.19(s, 4H) |
| Ex. 67 | $^1$H NMR (300 MHz, CDCl$_3$) δ 7.59(d, J=6Hz, 2H), 7.43–7.37(m, 4H), 7.29–7.25(m, 1H), 7.08(t, J=6Hz, 2H), 6.08(d, J=9Hz, 1H), 5.20(s, 2H), 5.18(s, 2H) |
| Ex. 68 | $^1$H NMR (300 MHz, CDCl$_3$) δ 7.57–7.54(m, 4H), 7.45–7.34(m, 7H), 7.30–7.26(m, 1H), 7.08(t, J=9Hz, 2H), 6.06(d, J=6Hz, 1H), 5.20(s, 2H), 5.17(s, 2H) |
| Ex. 69 | $^1$H NMR (300 MHz, CDCl$_3$) δ 7.93(d, J=6Hz, 1H), 7.45–7.40(m, 2H), 7.29–7.26(m, 1H), 7.09(t, J=9Hz, 2H), 6.50(d, J=6Hz, 1H), 5.17(s, 2H), 4.14(d, J=6Hz, 2H), 1.90–1.74(m, 5H), 1.32–1.05(m, 5H) |

Example 70

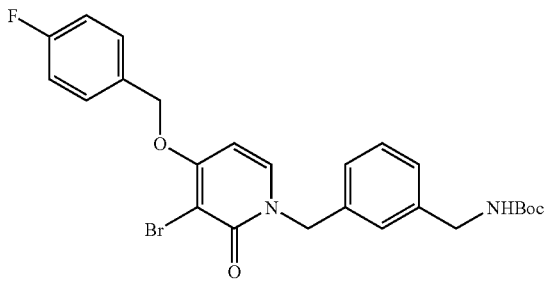

{3-[3-Bromo-4-(4-fluorobenzyloxy)-2-oxo-2H-pyridin-1-ylmethyl]benzyl}carbamic acid tert-Butyl ester Step 1. Preparation of 3-Hydroxymethylbenzonitrile.

To an ice-cold solution of 3-cyanobenzaldehyde (5.0 g, 38 mmol) in 1:1 MeOH/THF (90 mL) was added NaBH$_4$ (1.6 g, 42 mmol), and the reaction mixture was stirred for 3 h. The reaction mixture was diluted with brine, and the solvent was removed under reduced pressure. The residue was dissolved in water, and the aqueous layer was extracted with Et$_2$O (3×100 mL). The combined organics were washed with brine, dried (MgSO$_4$), filtered, and concentrated under reduced pressure to provide 3-hydroxymethyl-benzonitrile (4.95 g, 98%) as a clear oil, which was used in the next step without further purification or characterization.

Step 2. Preparation of 3-(tert -Butyldimethylsilyloxymethyl) benzonitrile.

To an ice-cold solution of 3-hydroxymethyl benzonitrile (4.95 g, 37 mmol) in CH$_2$Cl$_2$ (47 mL) was added imidazole (5.1 g, 74 mmol), DMAP (0.45 g, 3.7 mmol), and TBSCl (6.2 g, 41 mmol), and the reaction mixture was stirred for 12 h. The reaction mixture was diluted with water, and the aqueous layer was extracted with CH$_2$Cl$_2$ (3×150 mL). The combined organics were washed with brine, dried (MgSO$_4$), filtered, and concentrated under reduced pressure to provide 3-(tert -butyldimethylsilyloxymethyl)-benzonitrile (9.1 g, 99%) as a clear oil: $^1$H NMR (300 MHz, CDCl$_3$) δ 7.51 (s, 1H), 7.42 (d, J=6 Hz, 1H), 7.35–7.28 (m, 1H), 4.75 (s, 2H), 0.94 (s, 9H), 0.11 (s, 6H)

Step 3. Preparation of 3-(tert -Butyldimethylsilyloxymethyl) benzylamine.

To an ice-cold solution of 3-(tert -butyldimethylsilyloxymethyl)benzonitrile (4.5 g, 18 mmol) in THF (47 mL) was added LiAlH$_4$ (27 mL, of a 1 M solution in THF, 27 mmol), and the reaction mixture was stirred at reflux for 3 h. The reaction mixture was cooled to 0° C., and the reaction was quenched with water (25 mL) and 15% NaOH in water (75 mL). The reaction mixture was filtered, concentrated under reduced pressure, and the residue was dissolved in EtOAc. The organic solution was washed with water and then brine, dried (MgSO$_4$), filtered, and concentrated under reduced pressure to provide 3-(tert-Butyldimethylsilyloxymethyl)benzylamine (1.4 g, 30%) as a clear oil: $^1$H NMR (300 MHz, CDCl$_3$) δ 7.22–7.10 (m, 4H), 4.57 (s, 2H), 3.74 (s, 2H), 0.84 (s, 9H), 0.09 (s, 6H).

Step 4. Preparation of 3-(Hydroxymethyl)benzylcarbamic acid tert-butyl ester.

To a solution of 3-(tert-butyldimethylsilyloxymethyl)benzylamine (1.4 g, 5.5 mmol) and Et$_3$N (1.5 mL, 11 mmol) in CH$_2$Cl$_2$ (28 mL) was added di-tert-butyl dicarbonate (1.3 g, 5.8 mmol), and the reaction mixture was stirred for 12 h. The reaction mixture was diluted with water and extracted with CH$_2$Cl$_2$ (3×100 mL). The combined organics were washed with brine, dried (MgSO$_4$), filtered, and concentrated under reduced pressure. Purification by flash column chromatography (silica, CH$_2$Cl$_2$) to afford 3-(hydroxymethyl)benzylcarbamic acid tert-butyl ester as a yellow oil (1.4 g, 46%): $^1$H NMR (300 MHz, CDCl$_3$) δ 7.32–7.28 (m, 1H), 7.18 (d, J=8 Hz, 1H), 7.12 (s, 1H), 7.08–7.01 (m, 1H), 4.60 (s, 2H), 4.04 (d, J=6 Hz, 2H), 1.36 (s, 9H)

Step 5. Preparation of 3-(Bromomethyl)benzylcarbamic acid tert-butyl ester.

To an ice-cold solution of 3-(hydroxymethylbenzyl)carbamic acid tert-butyl ester (0.7 g, 3.0 mmol) and CBr$_4$ (1.0 g, 3.1 mmol) in THF (14 mL) was added Ph$_3$P (0.81 g, 3.1 mmol), and the reaction mixture was stirred for 18 h. The reaction mixture was filtered, and concentrated under reduced pressure. Purification by flash column chromatography (silica, eluent 5:95 to 15:85 EtOAc/hexanes) to afford the 3-(bromomethyl)benzyl-carbamic acid tert-butyl ester as a white solid (0.42 g, 51%): $^1$H NMR (300 MHz, MeOD) δ 7.55 (s, 1H), 7.32–7.27 (m, 2H), 7.21–7.19 (m, 1H), 4.54 (s, 2H), 4.21 (s, 2H), 1.28 (s, 9H).

Step 6. Preparation of 1{3-[3-Bromo-4-(4-fluorobenzyloxy)-2-oxo-2H-pyridin-1-ylmethyl]benzyl}carbamic acid tert-butyl ester.

To a solution of 3-bromo-4-(4-fluorobenzyloxy)pyridine-2(1H)-one (from Step 3, synthesis EXAMPLE 59) (0.2 g, 0.67 mmol) in DMF (11 mL) was added K$_2$CO$_3$ (0.26 g, 1.3 mmol) and 3-(bromomethyl)benzylcarbamic acid tert-butyl ester (0.23 g, 0.80 mmol), and the reaction mixture was stirred at 80° C. for 3 hours. The reaction mixture was cooled to room temperature, and concentrated under reduced pressure. The residue was diluted with a 50% aqueous solution of brine (24 mL), and extracted with CHCL$_3$ (4×50 mL). The combined organics was washed water and then brine, dried (MgSO$_4$), filtered, and concentrated under reduced pressure. Purification by flash column chromatography (silica, 3:7 EtOAc/hexanes) and recrystallization from MeOH afforded {3-[3-bromo-4-(4-fluorobenzyloxy)-2-oxo-2H-pyridin-1-ylmethyl]benzyl}carbamic acid tert-butyl ester as an off-white solid (0.07 g, 20%): mp 136–138° C.; $^1$H NMR (300 MHz, CDCl$_3$) δ 7.42–7.37 (m, 2H), 7.30–7.20 (m, 5H), 7.08 (t, J=9 Hz, 2H), 6.04 (d, J=9 Hz, 1H), 5.16 (s, 2H), 5.14 (s, 2H), 4.28 (d, J=6 Hz, 1H), 1.44 (s, 9H). ES HRMS m/z 517.1124 (M+H C$_{25}$H$_{27}$BrFN$_2$O$_4$ requires 517.1133).

Example 71

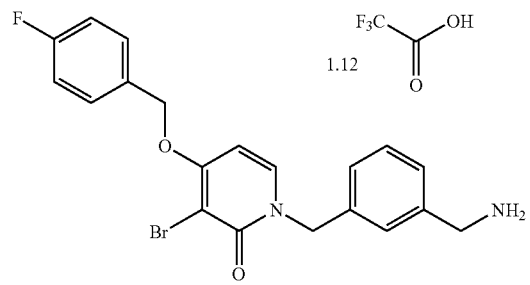

1-(3-Aminomethylbenzyl)-3-bromo-4-(4-fluorobenzyloxy)-1H-pyridin-2-one

To an ice-cold solution of 1-[3-{N-tert-Butoxycarbonyl}aminomethylbenzyl]-3-bromo-4-(4-fluorobenzyloxy)pyridine-2(1H)-one (Example 69) (0.05 g, 0.1 mmol) in CH$_2$Cl$_2$ (2 mL) was added TFA (2 mL), and the reaction mixture was stirred for 1 h. The solvent was removed under reduced pressure to provide 1-(3-aminomethylbenzyl)-3-bromo-4-(4-fluorobenzyloxy)-1H-pyridin-2-one as a tan solid (0.049 g, 100%), as the TFA salt: mp 127–139° C.; $^1$H NMR (300 MHz, DMSO-d$_6$) δ 8.13 (br s, 2H), 7.94 (d, J=6 Hz, 1H), 7.52–7.47 (m, 2H), 7.44–7.37 (m, 2H), 7.27 (t, J=8 Hz, 3H), 6.53 (d, J=8 Hz, 1H), 5.30 (s, 2H), 5.14 (s, 2H), 4.01 (d, J=6 Hz, 2H), 3.39 (br s, 2H); Anal. Calcd for C$_{20}$H$_{17}$BrF$_2$N$_2$·1.125 TFA: C, 48.99; H, 3.53; N, 5.13. Found: C, 48.80; H, 3.43; N, 4.75. ES HRMS m/z 417.0608 (M+H C$_{20}$H$_{19}$BrFN$_2$O$_2$ requires 417.0609).

Example 72

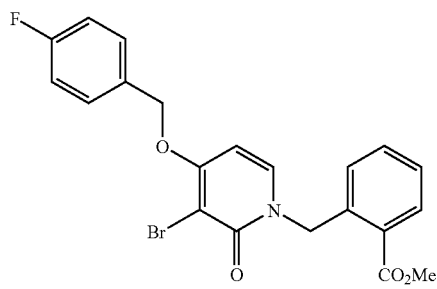

Methyl 2-[3-Bromo-4-(4-fluorobenzyloxy)-2-oxo-2H-pyridin-1-ylmethyl]benzoate

The title compound was prepared by a procedure similar to the one described for EXAMPLE 59 (0.36 g, 48%): mp 161–165° C.; $^1$H NMR (300 MHz, CDCl$_3$) δ 7.98 (d, J=6 Hz, 1H), 7.51–7.26 (m, 6H), 7.11–7.05 (m, 2H), 6.05 (d, J=8 Hz, 1H), 5.60 (s, 2H), 5.18 (s, 2H), 3.93 (s, 3H). ES HRMS m/z 446.0430 (M+H C$_{21}$H$_{18}$BrFNO$_4$ requires 418.0398).

Example 73

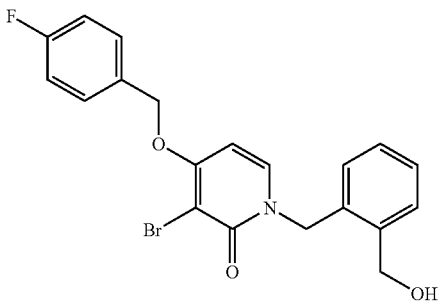

3-Bromo-4-(4-fluorobenzyloxy)-1-(2-hydroxymethylbenzyl)-1H-pyridin-2-one

To an ice-cold solution of 3-bromo-4-(4-fluorobenzyloxy)-1-(2-hydroxymethylbenzyl)-1H-pyridin-2-one (Example 72) (0.25 g, 0.56 mmol) in THF (1 mL) was added LiBH$_4$ (2.0 M solution in THF, 0.56 mmol), and the reaction mixture was stirred at 40° C. for 6 hours. The reaction mixture was cooled to room temperature, the solvent was removed under reduced pressure, and the residue was dissolved in EtOAc. The organic solution was washed with brine, dried (MgSO$_4$), filtered, and concemtrated under reduced pressure. $^1$H NMR (300 MHz, DMSO-d$_6$) δ 7.82 (d, J=8 Hz, 1H), 7.54–7.49 (m, 2H), 7.41 (d, J=7 Hz, 1H), 7.29–7.21 (m, 4H), 6.81 (d, J=7 Hz, 1H), 6.53 (d, J=8 Hz, 1H), 5.30–5.25 (m, 3H), 5.18 (s, 2H), 4.60 (d, J=7 Hz, 2H). ES HRMS m/z 418.0437 (M+H C$_{20}$H$_{18}$BrFNO$_3$ requires 418.0449).

Example 74

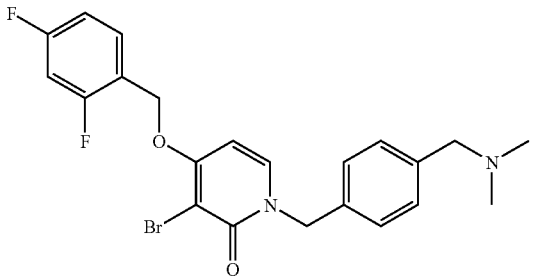

3-Bromo-4-(2,4-difluorobenzyloxy)-1-[(4-dimethylaminomethyl)benzyl]-1H-pyridin-2-one Step 1. Preparation of 4-(2,4-difluorobenzyloxy)pyridine-1-oxide.

To an ice-cold solution of sodium hydride (1.2 g of a 60% dispersion in mineral oil, 51 mmol) in DMF (43 mL) was added 2,4-difluorobenzyl alcohol (5.7 mL, 51 mmol). The reaction mixture was warmed to room temperature, 4-chloropyridine-1-oxide[1] (5.5 g, 43 mmol) was added, and the reaction mixture was stirred for 6 h. The reaction mixture was diluted with a 50% aqueous solution of brine, and extracted with CHCl$_3$ (7×50 mL). The combined organics were dried (MgSO$_4$), filtered, and the solvent was removed under reduced pressure. Trituration with Et$_2$O afforded 4-(2,4-difluorobenzyloxy)pyridine-1-oxide as an off-white solid (9.1 g, 90%): $^1$H NMR (300 MHz, CDCl$_3$) δ 8.16–8.08 (m, 1H), 7.47–7.36 (m, 1H), 6.97–6.81 (m, 1H), 5.09 (d, J=8 Hz, 1H)

Step 2. Preparation of 4-(2,4-Difluorobenzyloxy)-1H-pyridin-2-one.

A solution of 4-(2,4-difluorobenzyloxy)pyridine-1-oxide (13.4 g, 57 mmol) in acetic anhydride (30 mL) was stirred at reflux for 4 h. The solvent was removed under reduced pressure, the residue was diluted with 1:1 MeOH/water (60 mL), and the mixture was stirred at room temperature for 1 h. The solvent was removed under reduced pressure. Purification by flash column chromatography (silica, eluent methylene chloride to 9:1 methylene chloride/methanol) provided 4-(2,4-difluorobenzyloxy)-1H-pyridin-2-one as a light brown solid (4.2 g, 31%): $^1$H NMR (300 MHz, CDCl$_3$) δ 7.43 (q, J=8 Hz, 1H), 7.23 (d, J=7 Hz, 1H), 6.91–6.87 (m, 2H), 6.02 (dd, J=8, 2 Hz, 1H), 5.97 (d, J=2 Hz, 1H), 5.03 (s, 2H).

Step 3. Preparation of 3-Bromo-4-(2,4-difluorobenzyloxy)-1H-pyridin-2-one.

To an ice-cold solution of 4-(2,4-difluorobenzyloxy)-1H-pyridin-2-one (0.75 g, 3.1 mmol) in AcOH (12 mL) was added a solution of bromine (0.2 mL, 3.5 mmol) in AcOH (6 mL), and the reaction mixture was stirred 10 min. The solvent was removed under reduced pressure to afford 3-bromo-4-(2,4-difluorobenzyloxy)-1H-pyridin-2-one as a white solid (1.0 g, 100%): ESI MS m/z 299 [M+H]$^+$.

Step 4. Preparation of 3-Bromo-1-(4-chloromethylbenzyl)-4-(2,4-difluorobenzyloxy)-1H-pyridin-2-one.

To a solution of 3-bromo-4-(2,4-difluorobenzyloxy)-1H-pyridin-2-one (0.60 g, 2.5 mmol) in DMF (40 mL) was added K$_2$CO$_3$ (0.70 g, 5.1 mmol) and α,α'-dichloro-p-xylene (0.53 g, 3.0 mmol), and the reaction mixture was stirred at 110° C. for 2 h. The reaction mixture was cooled to room temperature, diluted with brine, and extracted with CHCl$_3$ (4×100 mL). The combined organics were washed water and then brine, dried (Na$_2$SO$_4$), filtered, and concentrated under reduced pressure to afford 3-bromo-1-(4-chloromethylbenzyl)-4-(2,4-difluorobenzyloxy)-1H-pyridin-2-one as an off-white solid (0.49 g, 43%): $^1$H NMR (300 MHz, CDCl$_3$) δ 7.54 (app q, J=8 Hz, 1H), 7.38–7.28 (m, 5H), 6.94 (td, J=8, 2 Hz, 1H), 6.85 (td, J=8, 2 Hz, 1H), 6.10 (d, J=9 Hz, 1H), 5.21 (s, 2H), 5.16 (s, 2H), 4.56 (s, 2H).

Step 5. Preparation of 3-Bromo-4-(2,4-difluorobenzyloxy)-1-[(4-dimethylaminomethyl) benzyl]-1H-pyridin-2-one.

To a sealed tube containing 3-bromo-1-(4-chloromethylbenzyl)-4-(2,4-difluoro-benzyloxy)-1H-pyridin-2-one (0.49 g, 1.1 mmol) was added a solution of dimethylamine (5.5 mL of a 2.0 M solution in THF, 11 mmol), and the reaction mixture was stirred for 15 h. The solvent was removed under reduced pressure. Purification by flash column chromatography (silica, eluent methylene chloride to 92:7.2:0.8 methylene chloride/methanol/ammonia) provided 3-bromo-4-(2,4-difluorobenzyloxy)-1-(4-dimethylaminomethylbenzyl)-1H-pyridin-2-one as a light yellow solid (0.23 g, 46%): mp 111–113° C.; $^1$H NMR (500 MHz, CDCl$_3$) δ 7.50–7.49 (m, 1H), 7.26–7.22 (m, 5H), 6.90–6.88 (m, 1H), 6.82–6.78 (m, 1H), 6.04 (d, J=6 Hz, 1H), 5.16 (s, 2H), 5.11 (s, 2H), 3.37 (s, 2H), 2.19 (s, 6H). ES HRMS m/z 463.0782 (M+H C$_{22}$H$_{22}$BrF$_2$N$_2$O$_2$ requires 463.0827).

Example 75

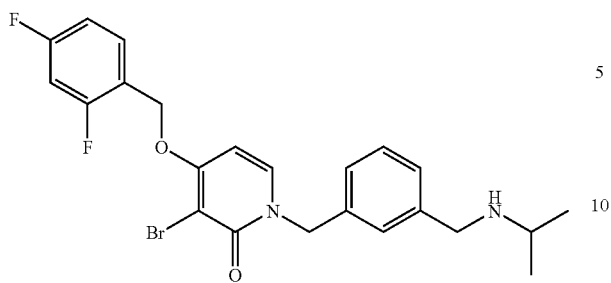

3-Bromo-4-(2,4-difluorobenzyloxy)-1-[3-(isopropylaminomethyl)benzyl]-1H-pyridin-2-one The title compound was prepared by a procedure similar to the one described for Example 74 (0.06 g, 35%): mp 109–110° C.; $^1$H NMR (300 MHz, CDCl$_3$) δ 7.54 (d, J=6 Hz, 1H), 7.33–7.20 (m, 5H), 6.94–6.81 (m, 2H), 6.10 (d, J=6 Hz, 1H), 5.20 (s, 2H), 5.14 (s, 2H), 3.77 (s, 2H), 2.88 (t, J=6 Hz, 1H), 1.13 (d, J=6 Hz, 6H). ES HRMS m/z 477.0955 (M+H C$_{23}$H$_{24}$BrF$_2$N$_2$O$_2$ requires 477.0984).

Example 76

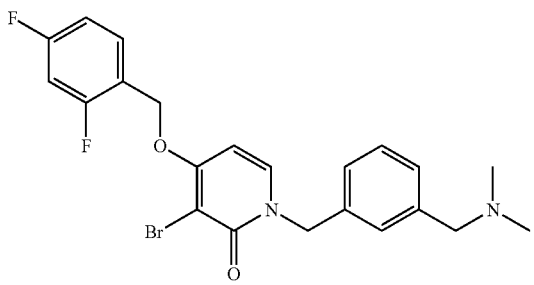

3-Bromo-4-(2,4-difluorobenzyloxy)-1-[(3-dimethylaminomethyl)benzyl]-1H-pyridin-2-one The title compound was prepared by a procedure similar to the one described for Example 74 (0.06 g, 25%): mp 103–107° C.;

$^1$H NMR (300 MHz, CDCl$_3$) δ 7.52 (d, J=8 Hz, 1H), 7.32–7.24 (m, 5H), 6.94 (td, J=9, 3 Hz, 1H), 6.84 (td, J=9, 3 Hz, 1H), 6.08 (d, J=8 Hz, 1H), 5.20 (s, 2H), 5.16 (s, 2H), 3.44 (s, 2H), 2.24 (s, 6H). ES HRMS m/z 463.0801 (M+H C$_{22}$H$_{22}$BrF$_2$N$_2$O$_2$ requires 463.0827).

Example 77

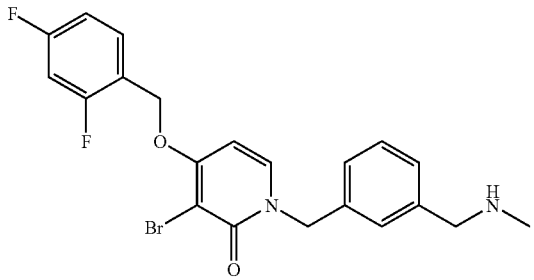

3-Bromo-4-(2,4-difluorobenzyloxy)-1-[(3-methylaminomethyl)benzyl]-1H-pyridin-2-one The title compound was prepared by a procedure similar to the one described for Example 74 (0.05 g, 16%): mp 107–111° C.;

$^1$H NMR (300 MHz, CDCl$_3$) δ 7.55 (d, J=6 Hz, 1H), 7.31–7.19 (m, 5H), 6.94–6.81 (m, 2H), 6.09 (d, J=6 Hz, 1H), 5.20 (s, 2H), 5.14 (s, 2H), 3.73 (s, 2H), 2.45 (s, 1H). ES HRMS m/z 449.0652 (M+H C$_{21}$H$_{20}$BrF$_2$N$_2$O$_2$ requires 449.0671).

Example 78

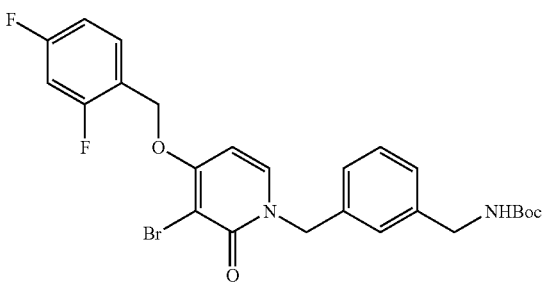

{3-[3-Bromo-4-(2,4-difluorobenzyloxy)-2-oxo-2H-pyridin-1-ylmethyl]benzyl}carbamic acid tert-butyl ester The title compound was prepared essentially according to the procedure described in Example 70. mp 80–84° C.;

$^1$H NMR (300 MHz, DMSO-d$_6$) δ 7.60–7.50 (m, 1H), 7.33–7.21 (m, 5H), 6.97–6.81 (m, 2H), 6.10 (dd, J=8, 2 Hz, 1H), 5.20 (s, 2H), 5.15 (s, 2H), 4.87 (br s, 2H), 4.30 (s, 2H), 1.45 (s, 9H). ES HRMS m/z 535.1019 (M+H C$_{25}$H$_{26}$BrF$_2$N$_2$O$_4$ requires 535.1039).

Example 79

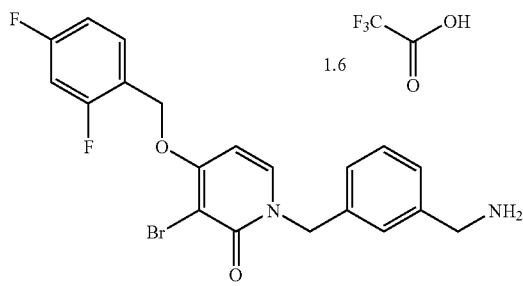

1-[(3-Aminomethyl)benzyl]-3-bromo-4-(2,4-difluorobenzyloxy)-1H-pyridin-2-one

Step 1. Preparation of 1-[(3-Aminomethyl)benzyl]-3-bromo-4-(2,4-difluorobenzyloxy)-1H-pyridin-2-one.

To an ice-cold solution of {3-[3-Bromo-4-(2,4-difluorobenzyloxy)-2-oxo-2H-pyridin-1-ylmethyl]benzyl}carbamic acid tert-butyl ester (Example 78) (0.05 g, 0.1 mmol) in CH$_2$Cl$_2$ (2 mL) was added TFA (2 mL), and the reaction mixture was stirred for 1 hour. The solvent was removed under reduced pressure to provide 1-[(3-aminomethyl)benzyl]-3-bromo-4-(2,4-difluorobenzyloxy)-1H-pyridin-2-one as a tan solid (0.049 g, 100%), as the TFA salt: mp 80–84° C.; $^1$H NMR (300 MHz, DMSO-d$_6$) δ 8.15 (br s, 3H), 7.97 (d, J=8 Hz, 1H), 7.79–7.60 (m, 1H), 7.44–7.30 (m, 4H), 7.20–7.15 (m, 1H), 6.61 (d, J=6 Hz, 1H), 5.31 (s, 2H), 5.16 (s, 2H), 4.03 (s, 2H); $^{19}$F NMR (282 MHz, DMSO-d$_6$) δ −74.56 (4.8F), −109.63 (1F), −113.61 (1F). ES HRMS m/z 435.0540 (M+H C$_{20}$H$_{18}$BrF$_2$N$_2$O$_2$ requires 435.0515).

Example 80

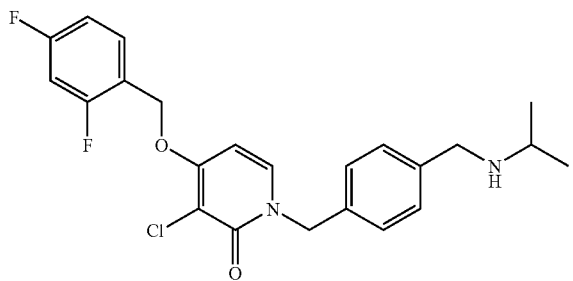

3-Chloro-4-(2,4-difluorobenzyloxy)-1-[4-(isopropylaminomethyl)benzyl]-1H-pyridin-2-one Step 1. Preparation of 3-Chloro-4-(2,4-difluorobenzyloxy)-1H-pyridin-2-one.

To a solution of 4-[(4-fluorobenzyl)oxy]pyridine-2(1H)-one (from Step 2, Example 74) (1.4 g, 5.9 mmol) in AcOH (25 mL) was added N-chlorosuccinimide (0.95 g, 7.1 mmol) and the reaction mixture was heated at reflux for 2 h. The solvent was removed under reduced pressure. $^1$H NMR (300 MHz, MeOD) δ 7.63–7.55 (m, 1H), 7.45 (d, J=8 Hz, 1H), 7.07–7.00 (m, 2H), 6.58 (d, J=8 Hz, 1H), 5.31 (d, J=8 Hz, 1H).

Step 2. Preparation of 3-Chloro-1-(4-chloromethylbenzyl)-4-(2,4-difluorobenzyloxy)-1H-pyridin-2-one.

3-Chloro-1-(4-chloromethylbenzyl)-4-(2,4-difluorobenzyloxy)-1H-pyridin-2-one was prepared by procedure similar to the one described for 3-bromo-1-(4-chloromethyl-benzyl)-4-(2,4-difluorobenzyloxy)-1H-pyridin-2-one (Step 3, as white solid (0.24 g, 34%): $^1$H NMR (300 MHz, CDCl$_3$) δ 7.53 (app q, J=9 Hz, 1H), 7.34 (app q, J=9 Hz, 1H), 7.23 (d, J=8 Hz, 1H), 6.94 (td, J=10, 2 Hz, 1H), 6.85 (td, J=10, 2 Hz, 1H), 6.14 (d, J=8 Hz, 1H), 5.20 (s, 2H), 5.16 (s, 2H), 4.56 (s, 2H).

Step 3. Preparation of 3-Chloro-4-(2,4-difluorobenzyloxy)-1-[4-(isopropylamino-methyl)benzyl]-1H-pyridin-2-one.

The title compound was prepared by a procedure similar to the one described for Example 74 (0.17 g, 69%): mp 146–151° C.; $^1$H NMR (300 MHz, CDCl$_3$) δ 7.52 (app q, J=9 Hz, 1H), 7.35–7.21 (m, 5H), 6.94 (td, J=8, 2 Hz, 1H), 6.85 (td, J=8, 2 Hz, 1H), 6.18 (d, J=8 Hz, 1H), 5.22 (s, 2H), 5.08 (s, 2H), 3.81 (s, 2H), 2.98 (br s, 1H), 1.20 (s, 6H). ES HRMS m/z 433.1481 (M+H C$_{23}$H$_{24}$ClF$_2$N$_2$O$_2$ requires 433.1489).

Example 81

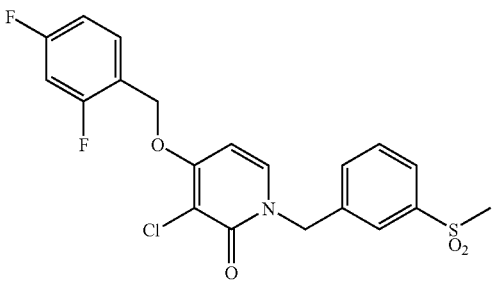

3-Chloro-4-(2,4-difluorobenzyloxy)-1-[(3-methanesulfonyl)benzyl]-1H-pyridin-2-one Step 1. Preparation of (3-Methanesulfonyl)phenyl methanol.

To an ice-cold solution of 3-(methylsulfonyl)benzoic acid (1.4 g, 7.1 mmol) in 2:1 Et$_2$O/THF (60 mL) was added LiAlH$_4$ (8.5 mL of 1.0 M solution in THF, 8.5 mmol), and the reaction mixture was heated at reflux for 1 h. The reaction mixture was cooled to 0° C., and the reaction was quenched with water (15 mL) and 15% NaOH in water (35 mL). The reaction mixture was filtered, concentrated under reduced pressure, and the residue was dissolved in EtOAc. The organic solution was washed with water and then brine, dried (MgSO$_4$), filtered, and concentrated under reduced pressure. Purification by flash column chromatography (silica, eluent 1:2 to 3:1 EtOAc/hexanes) provided (3-methanesulfonyl)phenyl methanol as a clear oil (0.56 g, 42%): $^1$H NMR (300 MHz, CDCl$_3$) δ 7.93 (s, 1H), 7.83 (d, J=7 Hz, 1H), 7.64 (d, J=7 Hz, 1H), 7.53 (t, J=7 Hz, 1H), 4.78 (d, J=6 Hz, 2H), 3.05 (s, 3H), 2.61 (br s, 1H).

Step 2. Preparation of 1-Chloromethyl-3-methanesulfonylbenzene.

A solution of (3-methanesulfonyl)phenyl methanol (0.21 g, 1.1 mmol) in thionyl chloride (3 mL) was heated at 80° C. for 3 h. The reaction mixture was cooled to room temperature, and the solvent was removed under reduced pressure to provide 1-chloromethyl-3-methanesulfonylbenzene as a yellow oil (0.23 g, 95%): $^1$H NMR (300 MHz, CDCl$_3$) δ 7.98 (s, 1H), 7.90 (d, J=8 Hz, 1H), 7.70 (d, J=8 Hz, 1H), 7.59 (t, J=8 Hz, 1H), 4.65 (s, 2H), 3.08 (s, 3H)

Step 3. Preparation of 3-Chloro-4-(2,4-difluorobenzyloxy)-1-[(3-methanesulfonyl)-benzyl]-1H-pyridin-2-one.

The title compound was prepared by a procedure similar to the one described for Example 80 (0.14 g, 78%): mp 155–157° C.; $^1$H NMR (300 MHz, CDCl$_3$) δ 7.88 (d, J=8 Hz, 1H), 7.83 (m, 1H), 7.67 (d, J=8 Hz, 1H), 7.58–7.48 (m, 2H), 7.31 (d, J=8 Hz, 1H), 6.95–6.83 (m, 2H), 6.22 (d, J=8 Hz, 1H), 5.22 (s, 4H), 3.08 (s, 3H). ES HRMS m/z 440.0525 (M+H C$_{20}$H$_{17}$ClF$_2$NO$_4$S requires 440.0529).

Example 82

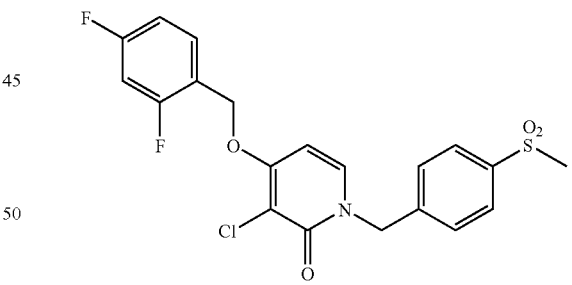

3-Chloro-4-(2,4-difluorobenzyloxy)-1-[(4-methanesulfonyl)benzyl]-1H-pyridin-2-one The title compound was prepared by a procedure similar to the one described for Example 81 (0.08 g, 73%): mp 223–225° C.; $^1$H NMR (300 MHz, CDCl$_3$) δ 7.91 (d, J=8 Hz, 2H), 7.53–7.47 (m, 3H), 7.30–7.26 (m, 1H), 6.94–6.86 (m, 2H), 6.22 (d, J=8 Hz, 1H), 5.23 (s, 4H), 3.03 (s, 3H). ES HRMS m/z 440.0512 (M+H C$_{20}$H$_{17}$ClF$_2$NO$_4$S requires 440.0529).

Example 83

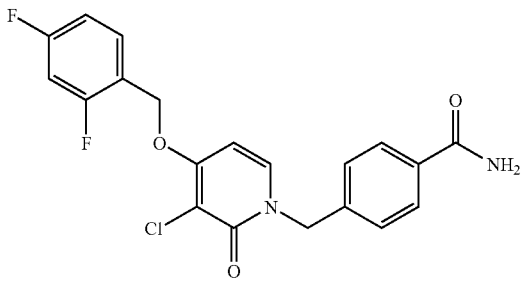

4-[3-Chloro-4-(2,4-difluorobenzyloxy)-2-oxo-2H-pyridin-1-ylmethyl]benzamide

Step 1. Preparation of Methyl 4-[3-chloro-4-(2,4-difluorobenzyloxy)-2-oxo-2H-pyridin-1-ylmethyl]benzoate.

Methyl 4-[3-Chloro-4-(2,4-difluorobenzyloxy)-2-oxo-2H-pyridin-1-ylmethyl]benzoate was prepared by a procedure similar to the one described for Example 81 (0.14 g, 60%): $^1$H NMR (300 MHz, CDCl$_3$) δ 8.01 (dd, J=8, 2 Hz, 1H), 7.52 (app q, J=8 Hz, 1H), 7.36 (d, J=9 Hz, 2H), 7.26–7.22 (m, 2H), 6.94 (td, J=8, 2 Hz, 1H), 6.85 (td, J=8, 2 Hz, 1H), 6.16 (d, J=9 Hz, 1H), 5.21 (s, 4H), 3.92 (s, 3H).

Step 2. Preparation of 4-[3-Chloro-4-(2,4-difluorobenzyloxy)-2-oxo-2H-pyridin-1-ylmethyl]benzamide.

A sealed tube containing a solution of 4-[3-Chloro-4-(2,4-difluorobenzyloxy)-2-oxo-2H-pyridin-1-ylmethyl]benzoic acid methyl ester (0.25 g, 0.60 mmol) and NH$_3$ (20 mL of a 7 N solution in MeOH, 140 mmol) was heated at 75° C. for 16 h. The reaction mixture was cooled to room temperature and the solvent was removed under reduced pressure. Trituration with Et$_2$O/MeOH afforded 4-[3-Chloro-4-(2,4-difluorobenzyloxy)-2-oxo-2H-pyridin-1-ylmethyl]benzamide as a white solid (0.14 g, 60%): mp 235–238° C.; $^1$H NMR (500 MHz, DMSO-d$_6$) δ 7.93 (d, J=8 Hz, 2H), 7.79 (d, J=8 Hz, 2H), 7.60 (app q, J=8 Hz, 1H), 7.35–7.27 (m, 4H), 7.20–7.10 (m, 1H), 6.61 (d, J=8 Hz, 1H), 5.28 (s, 2H), 5.14 (s, 2H). ES HRMS m/z 405.0788 (M+H C$_{20}$H$_{16}$ClF$_2$N$_2$O$_3$ requires 405.0812)

Example 84

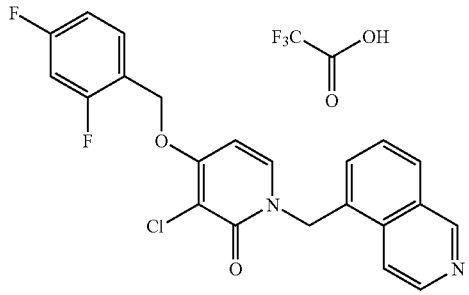

3-Chloro-4-(2,4-difluorobenzyloxy)-1-isoquinolin-5-ylmethyl-1H-pyridin-2-one

Step 1. Preparation of Isoquinolin-5-ylmethanol.

To an ice-cold solution of isoquinoline-5-carbaldehyde[2] (0.68 g, 4.3 mmol) in MeOH (15 mL) was added NaBH$_4$ (0.17 g, 4.6 mmol), and the reaction mixture was stirred for 15 min. The reaction was quenched with brine, the solvent was removed under reduced pressure, and the residue was dissolved in EtOAc. The organic solution was washed with water and then brine, dried (Na$_2$SO$_4$), filtered, and concentrated under reduced pressure to afford isoquinolin-5-ylmethanol as a brown solid (0.63 g, 93%): $^1$H NMR (300 MHz, DMSO-d$_6$) δ 9.87 (s, 1H), 8.82 (d, J=6 Hz, 1H), 8.57 (d, J=6 Hz, 1H), 8.47 (d, J=9 Hz, 1H), 8.30 (d, J=6 Hz, 1H), 7.95 (t, J=9 Hz, 1H), 5.34 (s, 2H).

Step 2. Preparation of 5-Bromomethylisoquinoline.

To a solution of isoquinolin-5-ylmethanol (0.63 g, 3.9 mmol) in AcOH (3.3 mL) was added HBr (6.6 mL, a 30% w/w solution in AcOH, 24 mmol), and the reaction mixture was stirred at 75° C. for 45 min. The reaction mixture was cooled to room temperature, and the precipitate was collected to provide the 5-bromomethylisoquinoline hydrobromide acid salt as a brown solid (1.1 g, 87%): $^1$H NMR (300 MHz, CDCl$_3$) δ 9.22 (s, 1H), 8.58 (d, J=6 Hz, 1H), 7.95–7.89 (m, 2H), 7.76 (d, J=9 Hz, 1H), 7.59 (dd, J=9, 6 Hz, 1H), 5.16 (s, 2H).

Step 3. Preparation of 3-Chloro-4-(2,4-difluorobenzyloxy)-1-isoquinolin-5-ylmethyl-1H-pyridin-2-one.

The title compound was prepared by a procedure similar to the one described for Example 81, as the TFA salt (0.13 g, 33%): mp 235–238° C.; $^1$H NMR (300 MHz, DMSO-d$_6$) δ 9.55 (s, 1H), 8.66 (d, J=6 Hz, 1H), 8.29 (d, J=6 Hz, 1H), 8.22 (d, J=8 Hz, 1H), 7.91 (d, J=8 Hz; 1H), 7.77 (t, J=8 Hz, 1H), 7.65–7.63 (m, 1H), 7.53 (d, J=7 Hz, 1H), 7.35–7.25 (m, 1H), 7.20–7.10 (m, 1H), 6.68 (d, J=8 Hz, 1H), 5.67 (s, 2H), 5.32 (s, 2H);
$^{19}$F NMR (282 MHz, DMSO-d$_6$) δ –74.79 (3F), –109.43 (1F), –113.62 (1F). ES HRMS m/z 413.0868 (M+H C$_{22}$H$_{16}$ClF$_2$N$_2$O$_3$ requires 413.0863).

Example 85

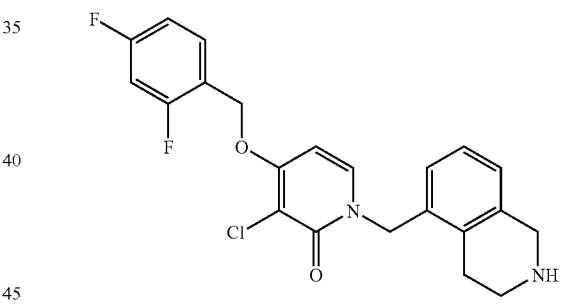

3-Chloro-4-(2,4-difluorobenzyloxy)-1-(1,2,3,4-tetrahydroisoquinolin-5-ylmethyl)-1H-pyridin-2-one Step 1. Preparation of 3-Chloro-4-(2,4-difluorobenzyloxy)-1-(1,2,3,4-tetrahydro-isoquinolin-5-ylmethyl)-1H-pyridin-2-one.

To a solution of 3-chloro-4-(2,4-difluorobenzyloxy)-1-isoquinolin-5-ylmethyl-1H-pyridin-2-one (Example 84) (0.14 g, 0.34 mmol) in AcOH (1.3 mL) was added NaCNBH$_3$ (0.09 g, 1.4 mmol), and the reaction mixture was stirred for 2 h. The reaction mixture was cooled to 0° C., and diluted with water(10 mL) and 40% aqueous NaOH (10 mL), and the aqueous layer was washed with EtOAc (3×50 mL). The combined organics were washed with brine, dried (Na$_2$SO$_4$), filtered, and concentrated under reduced pressure. Purification by flash column chromatography (silica, eluent 98:1.8:0.2 to 88:10.8:1.2 CH$_2$Cl$_2$/MeOH/NH$_3$) provided 3-chloro-4-(2,4-difluoro-benzyloxy)-1-(1,2,3,4-tetrahydroisoquinolin-5-ylmethyl)-1H-pyridin-2-one as a white solid (0.13 g, 92%): mp 180–184° C.; $^1$H NMR (300 MHz, MeOD) δ 7.65–7.55 (m, 2H), 7.16–7.00 (m, 4H), 6.90–6.80 (m, 1H), 6.60 (d, J=8 Hz, 1H), 5.31 (s, 2H), 5.20 (s, 2H), 4.06 (s, 2H), 3.21 (t, J=6 Hz, 2H), 2.82 (t, J=6 Hz, 2H). ES HRMS m/z 417.1173 (M+H $C_{22}H_{20}ClF_2N_2O_2$ requires 417.1176).

Example 86

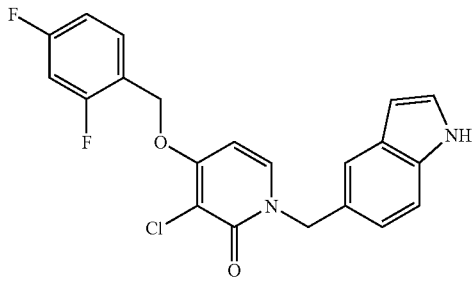

3-Chloro-4-(2,4-difluorobenzyloxy)-1-(1H-indol-5-ylmethyl)-1H-pyridin-2-one

Step 1. Preparation of 5-(Carboxymethyl)-indole-1-carbamic acid tert-butyl ester.

To a solution of methyl indole-5-carboxylate (6.9 g, 39 mmol) and Et$_3$N (6.0 mL, 43 mmol) in CH$_2$Cl$_2$ (150 mL) was added di-tert-butyl dicarbonate (19 g, 86 mmol), and the reaction mixture was stirred for 14 h. The reaction mixture was diluted with CH$_2$Cl$_2$, washed with water and then brine, dried (Na$_2$SO$_4$), filtered, and the solvent was removed under reduced pressure. Purification by flash column chromatography (silica, 3:7 EtOAc/hexanes) provided 5-(carboxymethyl)-indole-1-carbamic acid tert-butyl ester as a light yellow oil (11 g, 100%): $^1$H NMR (300 MHz, CDCl$_3$) δ 8.29 (s, 1H), 8.15 (d, J=9 Hz, 1H), 7.93 (d, J=9 Hz, 1H), 7.78 (d, J=3 Hz, 1H), 6.85 (d, J=3 Hz, 1H), 3.91 (s, 3H), 1.68 (s, 9H).

Step 2. Preparation of 5-Hydroxymethylindole-1-carbamic acid tert-butyl ester.

To a −78° C. solution of 5-(carboxymethyl)-indole-1-carbamic acid tert-butyl ester (10.8 g, 39 mmol) in THF (180 mL) was added DIBAL (127 mL of a 1 M solution in THF, 127 mmol), and the reaction mixture was stirred for 2.5 h. The reaction was quenched with 1:11 N HCl/MeOH (100 mL), the reaction mixture was warmed to room temperature, diluted with CH$_2$Cl$_2$ (100 mL), and separated. The organic solution was washed with saturated Rochelle salt, dried (Na$_2$SO$_4$), filtered, and concentrated under reduced pressure. Purification by flash column chromatography (silica, 1:1 EtOAc/hexanes) provided 5-hydroxymethylindole-1-carbamic acid tert-butyl ester as a yellow oil (6.5 g, 68%): $^1$H NMR (300 MHz, CDCl$_3$) δ 8.07 (d, J=9 Hz, 1H), 7.59 (d, J=6 Hz, 1H), 7.54 (s, 1H), 7.28 (d, J=9 Hz, 1H), 6.58 (d, J=6 Hz, 1H), 4.73 (s, 2H), 1.97 (s, 9H).

Step 3. Preparation of 5-Bromomethylindole-1-carbamic acid tert-butyl ester.

To an ice-cold solution of 5-hydroxymethylindole-1-carbamic acid tert-butyl ester (0.51 g, 2.1 mmol) in 4:1 Et$_2$O/CH$_2$Cl$_2$ (4 mL) was added PBr$_3$ (0.2 mL, 2.2 mmol), and the reaction mixture was stirred for 40 min. The reaction mixture was diluted with CH$_2$Cl$_2$, washed a saturated solution of NaHCO$_3$ (3×10 mL), dried (Na$_2$SO$_4$), filtered, and the solvent was removed under reduced pressure to provide 5-bromomethyl-indole-1-carbamic acid tert-butyl ester as a yellow solid (0.59 g, 93%). $^1$H NMR (300 MHz, CDCl$_3$) δ 8.07 (d, J=9 Hz, 1H), 7.68–7.62 (m, 2H) 7.33 (d, J=9 Hz, 1H), 6.60 (s, 1H), 4.68 (s, 2H), 1.67 (s, 9H).

Step 4. Preparation of 5-[3-Chloro-4-(2,4-difluorobenzyloxy)-2-oxo-2H-pyridin-1-ylmethyl]indole-1-carbamic acid tert-butyl ester.

5-[3-Chloro-4-(2,4-difluorobenzyloxy)-2-oxo-2H-pyridin-1-ylmethyl]indole-1-carbamic acid tert-butyl ester was prepared by a procedure similar to the one described for Example 81 as an off-white solid (0.54 g, 67%): $^1$H NMR (300 MHz, CDCl$_3$) δ 8.10 (d, J=8 Hz, 1H), 7.60 (d, J=3 Hz, 2H), 7.52 (m, 1H), 7.26 (m, 1H), 6.94 (td, J=9, 2 Hz, 1H), 6.84 (td, J=9, 2 Hz, 1H), 6.53 (d, J=2 Hz, 1H), 6.08 (d, J=8 Hz, 1H), 5.25 (s, 2H), 5.18 (s, 2H), 1.66 (s, 9H).

Step 5. Preparation of 3-Chloro-4-(2,4-difluorobenzyloxy)-1-(1H-indol-5-ylmethyl)-1H-pyridin-2-one.

A flask containing 5-[3-chloro-4-(2,4-difluorobenzyloxy)-2-oxo-2H-pyridin-1-ylmethyl]indole-1-carbamic acid tert-butyl ester (0.48 g, 0.96 mmol) was heated at 150° C. for 4 h. The reaction mixture was cooled to room temperature, and purification by preparatory HPLC (Phenomenex Luna C18(2) column, 250×21.20 mm, 10 µ

Solvent A: 0.05% TFA in 95:5H$_2$O/CH$_3$CN; Solvent B: 0.05% TFA in 95:5 CH$_3$CN/H$_2$O Eluent: 30–95% B over 20 min; flow 20.0 mL/min; UV Detector: 254 nm; Retention Time: 15.6 min) provided 3-chloro-4-(2,4-difluorobenzyloxy)-1-(1H-indol-5-ylmethyl)-1H-pyridin-2-one as an off-white solid (0.14 g, 36%): mp 152–153° C.; $^1$H NMR (300 MHz, DMSO-d$_6$) δ 11.11 (br s, 1H), 7.91 (d, J=8 Hz, 1H), 7.61 (app q, J=8 Hz, 1H), 7.51 (s, 1H), 7.36–7.33 (m, 3H), 7.16 (td, J=8, 2 Hz, 1H), 7.09 (dd, J=8, 2 Hz, 1H), 6.57 (d, J=8 Hz, 1H), 6.40 (br s, 1H), 5.28 (s, 2H), 5.16 (s, 2H) ES HRMS m/z 401.0845 (M+H $C_{21}H_{16}ClF_2N_2O_2$ requires 401.0863).

Example 87

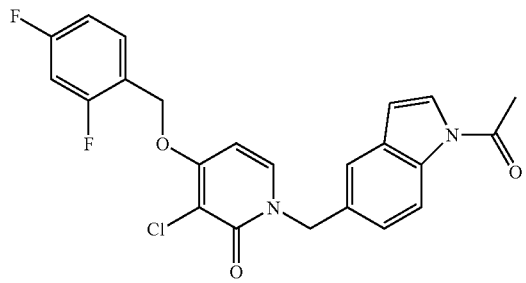

1-(1-Acetyl-1H-indol-5-ylmethyl)-3-chloro-4-(2,4-difluorobenzyloxy)-1H-pyridin-2-one To a solution of 3-chloro-4-(2,4-difluorobenzyloxy)-1-(1H-indol-5-ylmethyl)-1H-pyridin-2-one (Step 5, synthesis of Example 86) (0.22 g, 0.57 mmol) in CH$_3$CN (10 mL) was added acetic anhydride (0.06 mL, 0.58 mmol) and Et$_3$N (2 mL), and the reaction mixture was stirred at 86° C. for 6 h. The reaction mixture was cooled to room temperature, and partitioned between 1 N HCl and EtOAc. The organic solution was separated, washed with brine, dried (Na$_2$SO$_4$), filtered, and concentrated under reduced pressure. $^1$H NMR (300 MHz, MeOD) δ 8.35 (d, J=9 Hz, 1H), 7.77 (d, J=9 Hz, 1H), 7.70 (d, J=3 Hz, 1H), 7.54 (s, 2H), 7.31 (d, J=9 Hz, 1H), 7.01–6.99 (m, 2H), 6.66 (d, J=3 Hz, 1H), 6.59 (d, J=9 Hz, 1H), 5.29 (s, 4H), 2.63 (s, 3H). ES HRMS m/z 443.0965 (M+H $C_{23}H_{18}ClF_2N_2O_3$ requires 443.0969).

Example 88

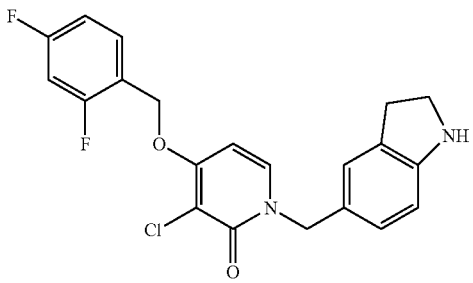

3-Chloro-4-(2,4-difluorobenzyloxy)-1-(2,3-dihydro-1H-indol-5-ylmethyl)-1H-pyridin-2-one To a solution of 3-chloro-4-(2,4-difluorobenzyloxy)-1-(1H-indol-5-ylmethyl)-1H-pyridin-2-one (Step 5, synthesis of Example 86) (0.24 g, 0.60 mmol) in ACOH (5 mL) was added NaCNBH$_3$ (0.06 g, 1.0 mmol), and the reaction mixture was stirred for 1 h. The reaction mixture was partitioned between water and EtOAc, and the precipitate was collected by filtration. Trituration with CH$_2$Cl$_2$ afforded 3-Chloro-4-(2,4-difluorobenzyl-oxy)-1-(2,3-dihydro-1H-indol-5-ylmethyl)-1H-pyridin-2-one as a white solid (0.2 g, 81%): mp 137–139° C.; $^1$H NMR (300 MHz, CDCl$_3$) δ 7.51 (app q, J=9 Hz, 1H), 7.21 (d, J=6 Hz, 1H), 7.11 (s, 1H), 6.99–6.80 (m, 3H), 6.57 (d, J=9 Hz, 1H), 6.08 (d, J=9 Hz, 1H), 5.18 (s, 2H), 5.02 (s, 2H), 3.83 (br s, 1H), 3.55 (t, J=9 Hz, 2H), 2.99 (t, J=9 Hz, 2H). ES HRMS m/z 403.1022 (M+H C$_{21}$H$_{18}$ClF$_2$N$_2$O$_2$ requires 403.1019).

The following example compounds were prepared by procedures similar to that described for Example 74. The yields and the analytical data of the title compounds are reported below.

Examples 89–101

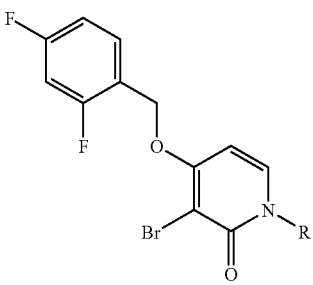

The compounds of Examples 89–101 are prepared essentially according to the procedures set forth above for Example 74. The yield (Y), molecular formula (MF) and analytical data for these compounds are shown below.

| Example No. | R | Y | MF | M + H Requires | ESHRMS m/z |
|---|---|---|---|---|---|
| Ex. 89 | pyridin-3-ylmethyl | 25 | C$_{18}$H$_{13}$BrF$_2$N$_2$O$_2$ | 407.0202 | 407.0197 |
| Ex. 90 | pyridin-4-ylmethyl | 6 | C$_{18}$H$_{13}$BrF$_2$N$_2$O$_2$ | 407.0202 | 407.0189 |
| Ex. 91 | pyridin-2-ylmethyl | 56 | C$_{18}$H$_{13}$BrF$_2$N$_2$O$_2$ | 407.0201 | 407.0184 |
| Ex. 92 | 4-tert-butyl)-benzyl | 32 | C$_{23}$H$_{22}$BrF$_2$NO$_2$ | 462.0875 | 462.0863 |
| Ex. 93 | 3-methoxy-benzyl | 50 | C$_{20}$H$_{16}$BrF$_2$NO$_3$ | 436.0354 | 436.0353 |
| Ex. 94 | Benzo[1,3]-dioxol-5-ylmethyl | 35 | C$_{20}$H$_{14}$BrF$_2$NO$_4$ | 450.0147 | 450.0136 |
| Ex. 95 | 2-fluorobenzyl | 42 | C$_{19}$H$_{14}$BrF$_3$NO$_2$ | 424.0155 | 424.0143 |

%): mp 179–182° C.; $^1$H NMR (300 MHz, CDCl$_3$) δ 7.58–7.53 (m, 3H), 7.33–7.26 (m, 1H), 7.14–7.02 (m, 2H), 6.96–6.82 (m, 2H), 6.11 (d, J=9 Hz, 1H), 5.20 (s, 2H), 5.18 (s, 2H). ES HRMS m/z (M+H requires).

Example 96

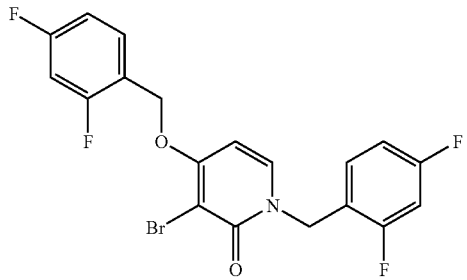

3-Bromo-4-(2,4-difluorobenzyloxy)-1-(2,4-difluorobenzyl)-1H-pyridin-2-one

Step 1. Preparation of 4-(2,4-Difluorobenzyloxy)-1-(2,4-difluorobenzyl)-1H-pyridin-2-one.

To a solution of 2,4-dihydroxypyridine (0.35 g, 3.2 mmol) in DMF (50 mL) was added K$_2$CO$_3$ (2.5 g, 13 mmol) and 2,4-difluorobenzyl bromide (1.0 mL, 7.6 mmol), and the reaction mixture was stirred at 110° C. for 4 h. The reaction mixture was cooled to room temperature, diluted with brine, and extracted with CHCl$_3$ (4×100 mL). The combined organics were washed with water and then brine, dried (Na$_2$SO$_4$), filtered, and concentrated under reduced pressure. $^1$H NMR (300 MHz, CDCl$_3$) δ 7.54 (app q, J=8 Hz, 1H), 7.38–7.28 (m, 5H), 6.94 (td, J=8, 2 Hz, 1H), 6.85 (td, J=8, 2 Hz, 1H), 6.10 (d, J=9 Hz, 1H), 5.21 (s, 2H), 5.16 (s, 2H), 4.56 (s, 2H).

Step 2. Preparation of 3-Bromo-4-(2,4-difluorobenzyloxy)-1-(2,4-fluorobenzyl)-1H-pyridin-2-one.

To an ice-cold solution of 4-(2,4-difluorobenzyloxy)-1-(2,4-difluorobenzyl)-1H-pyridin-2-one (0.72 g, 2.0 mmol) in AcOH (4.0 mL) was added a solution of bromine (0.11 mL, 2.2 mmol) in AcOH (7.2 mL), and the reaction mixture was stirred for 40 min. The solvent was removed under reduced pressure. $^1$H NMR (300 MHz, CDCl$_3$) δ 7.63–7.45 (m, 2H), 7.42 (d, J=6 Hz, 1H), 6.93–6.77 (m, 4H), 6.12 (d, J=6 Hz, 1H), 5.20 (s, 2H), 5.12 (s, 2H). ERMS m/z M+H 442.

Example 97

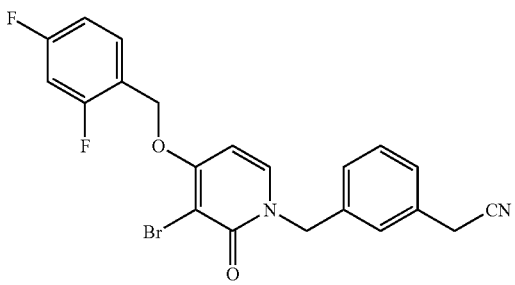

{3-[3-Bromo-4-(2,4-difluorobenzyloxy)-2-oxo-2H-pyridin-1-ylmethyl]-phenyl}acetonitrile Step 1. Preparation of Methyl 3-cyanomethylbenzoate.

To an ice-cold solution of methyl 3-bromomethylbenzoate (9.1 g, 40 mmol) in $CH_3CN$ (108 mL) was added tetrabutylammonium fluoride (17.3 mL, 60 mmol) and trimethylsilylcyanide (8.0 mL, 60 mmol), and the reaction mixture was heated at reflux for 20 h. The reaction mixture was cooled to room temperature, and the solvent was removed under reduced pressure. Purification by flash column chromatography (silica, 1:1 EtOAc/hexanes) provided methyl 3-cyanomethylbenzoate as a clear oil (3.0 g, 43%): $^1$H NMR (300 MHz, DMSO-$d_6$) δ 7.97 (s, 1H), 7.92 (d, J=8 Hz, 1H), 7.64 (d, J=8 Hz, 1H), 7.56 (t, J=8 Hz, 1H), 4.16 (s, 2H), 3.87 (s, 3H)

Step 2. Preparation of (3-Hydroxymethylphenyl)acetonitrile.

To an ice-cold solution of methyl 3-cyanomethylbenzoate (2.8 g, 18 mmol) in THF (23 mL) was added $LiBH_4$ (8.8 mL of a 2 M solution in THF, 18 mmol), and the reaction mixture was heated at reflux for 4 h. The reaction mixture was cooled to room temperature, the reaction was quenched with 1:1 water/1 N HCl, and the aqueous layer was washed with EtOAc (3×150 mL). The combined organics were washed with brine, dried ($MgSO_4$), filtered, and concentrated under reduced pressure.

Purification by flash column chromatography (silica, 2:1 EtOAc/hexanes) provided (3-hydroxymethylphenyl)-acetonitrile as a clear oil (0.97 g, 41%): $^1$H NMR (300 MHz, MeOD) δ 8.15–8.08 (m, 1H), 7.47–7.34 (m, 1H), 7.27 (s, 1H), 6.97–6.82 (m, 1H), 4.87 (s, 2H), 3.91 (s, 2H)

Step 3. Preparation of (3-Bromomethylphenyl)acetonitrile.

To an ice-cold solution of (3-hydroxymethylphenyl)acetonitrile (0.97 g, 7.3 mmol) in THF (35 mL) was added $CBr_4$ (2.5 g, 7.7 mmol) and $Ph_3P$ (2.0 g, 7.7 mmol), and the reaction mixture was stirred for 3 h. The reaction mixture was filtered, and concentrated under reduced pressure. Purification by flash column chromatography (silica, eluent 1:9 to 1:4 EtOAc/hexanes) provided (3-bromomethylphenyl)acetonitrile as a clear oil (0.89 g, 58%): $^1$H NMR (300 MHz, MeOD) δ 7.47–7.29 (m, 1H), 7.27 (s, 1H), 6.97–6.82 (m, 1H), 4.87 (s, 2H), 3.91 (s, 2H).

Step 4. Preparation of {3-[3-Bromo-4-(2,4-difluorobenzyloxy)-2-oxo-2H-pyridin-1-ylmethyl]phenyl}acetonitrile.

The title compound was prepared by a procedure similar to the one described for Example 74 (0.07 g, 10%): mp 120–121° C.; $^1$H NMR (300 MHz, CDCl$_3$) δ 7.60–7.50 (m, 1H), 7.37–7.27 (m, 5H), 6.96 (td, J=9, 3 Hz, 1H), 6.82 (td, J=9, 3 Hz, 1H), 6.13 (d, J=8 Hz, 1H), 5.21 (s, 2H), 5.16 (s, 2H). ES HRMS m/z 445.0381 (M+H $C_{21}H_{16}BrF_2N_2O_2$ requires 445.0358).

Example 98

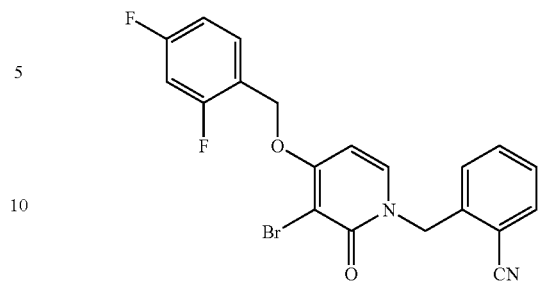

2-[3-Bromo-4-(2,4-difluorobenzyloxy)-2-oxo-2H-pyridin-1-ylmethyl]benzonitrile

The title compound was prepared by a procedure similar to the one described for Example 74 (0.13 g, 47%): mp 194–197° C.; $^1$H NMR (300 MHz, CDCl$_3$) δ 7.75 (d, J=9 Hz, 1H), 7.69–7.49 (m, 4H), 7.42 (t, J=8 Hz, 1H), 6.96–6.73 (m, 2H), 6.18 (d, J=8 Hz, H), 6.17 (s, 2H), 5.30 (s, 2H). ES HRMS m/z 431.0210 (M+H $C_{20}H_{14}BrF_2N_2O_2$ requires 431.0201.

Example 99

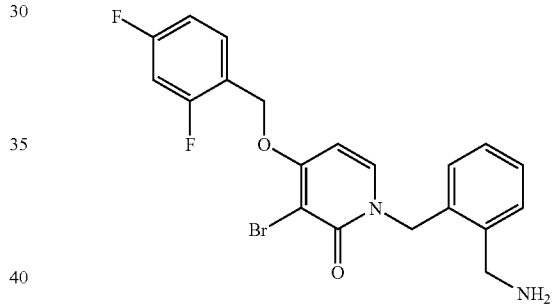

1-[(2-Aminomethyl)benzyl)]-3-bromo-4-(2,4-difluorobenzyloxy)-1H-pyridin-2-one

To a solution of 2-[3-bromo-4-(2,4-difluorobenzyloxy)-2-oxo-2H-pyridin-1-ylmethyl]-benzonitrile (0.11 g, 0.25 mmol) in THF (3 mL) was added $BH_3$-DMS (0.25 mL of a 2.0 M solution in THF, 0.5 mmol), and the reaction mixture was stirred at 70° C. for 1 h. The reaction mixture was cooled to 0° C., and the reaction was quenched with MeOH. The solvent was removed under reduced pressure, and the residue was partitioned between 2N NaOH and EtOAc. The organic solution was washed with brine, dried ($MgSO_4$), filtered, and concentrated under reduced pressure. Purification by flash column chromatography (silica, eluent methylene chloride to 90:9:1 methylene chloride/methanol/ammonia) provided 1-[(2-aminomethyl)benzyl]-3-bromo-4-(2,4-difluorobenzyloxy)-1H-pyridin-2-one as a white solid (0.15 g, 48%): $^1$H NMR (300 MHz, CDCl$_3$) δ 7.55 (app q, J=8 Hz, 1H), 7.40–7.26 (m, 4H), 7.14 (d, J=8 Hz, 1H), 6.94 (td, J=8, 2 Hz, 1H), 6.85 (td, J=8, 2 Hz, 1H), 6.08 (d, J=8 Hz, 1H), 5.31 (s, 2H), 5.21 (s, 2H), 4.03 (s, 2H). ES HRMS m/z 435.0517 (M+H $C_{20}H_{18}BrF_2N_2O_2$ requires 435.0514).

Example 100

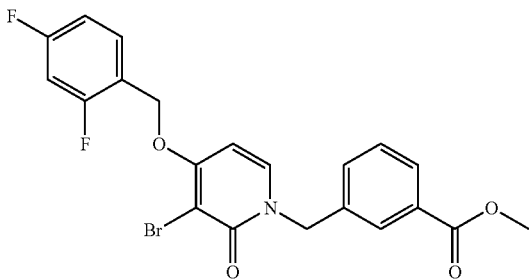

Methyl 3-[3-Bromo-4-(2,4-difluorobenzyloxy)-2-oxo-2H-pyridin-1-ylmethyl]benzoate The title compound was prepared by a procedure similar to the one described for Example 74 (0.05 g, 11%): mp 115–117° C.; $^1$H NMR (300 MHz, CDCl$_3$) δ 8.15–7.95 (m, 2H), 7.65–7.50 (m, 2H), 7.45–7.40 (m, 1H), 7.32 (d, J=6 Hz, 1H), 7.00–6.80 (m, 2H), 6.12 (d, J=9 Hz, 1H), 5.21 (s, 2H), 5.20 (s, 2H), 3.92 (s, 3H). ES HRMS m/z 464.0292 (M+H C$_{21}$H$_{17}$BrF$_2$NO$_4$ requires 464.0303).

Example 101

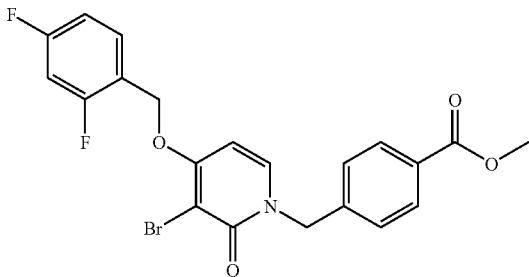

Methyl 4-[3-Bromo-4-(2,4-difluorobenzyloxy)-2-oxo-2H-pyridin-1-ylmethyl]-benzoate The title compound was prepared by a procedure similar to the one described for Example 74 (0.17 g, 46%): mp136–139° C.; $^1$H NMR (300 MHz, CDCl$_3$) δ 8.01 (d, J=8 Hz, 2H), 7.60–7.51 (m, 1H), 7.37 (d, J=8 Hz, 2H), 7.29–7.26 (m, 1H), 6.93 (td, J=9, 2 Hz, 1H), 6.84 (td, J=9, 2 Hz, 1H), 6.13 (d, J=8 Hz, 1H), 5.23 (s, 4H), 3.91 (s, 3H). ES HRMS m/z 464.0306 (M+H C$_{21}$H$_{17}$BrF$_2$NO$_2$ requires 464.0304).

Example 102

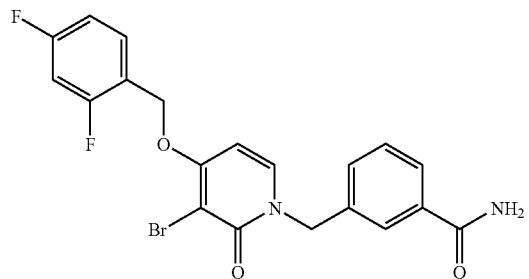

3-[3-Bromo-4-(2,4-difluorobenzyloxy)-2-oxo-2H-pyridin-1-ylmethyl]benzamide

A sealed tube containing a solution of methyl 3-[3-bromo-4-(2,4-difluorobenzyloxy)-2-oxo-2H-pyridin-1-ylmethyl]benzoate (0.1 g, 0.21 mmol) and NH$_3$ (3 mL of a 7 N solution in MeOH, 21 mmol) was heated at 75° C. for 16 h. The reaction mixture was cooled to room temperature and the solvent was removed under reduced pressure. Trituration with Et$_2$O/MeOH afforded a white solid (0.06 g, 64%): mp 198–201° C.; $^1$H NMR (300 MHz, DMSO-d$_6$) δ 8.02–8.00 (m, 2H), 7.85–7.75 (m, 2H), 7.70–7.60 (m, 1H), 7.45–7.30 (m, 4H), 7.17 (t, J=3 Hz, 1H), 6.60 (d, J=9 Hz, 1H), 5.32 (s, 2H), 5.18 (s, 2H). ES HRMS m/z 449.0295 (M+H C$_{20}$H$_{16}$BrF$_2$N$_2$O$_3$ requires 449.0307).

Example 103

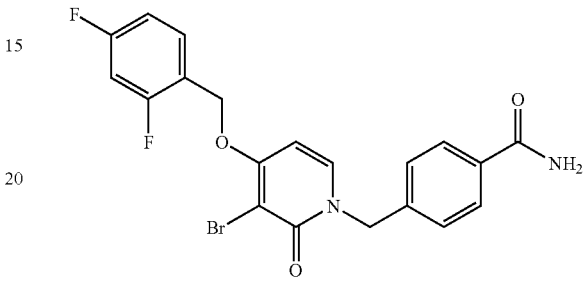

4-[3-Bromo-4-(2,4-difluorobenzyloxy)-2-oxo-2H-pyridin-1-ylmethyl]benzamide

The title compound was prepared by a procedure similar to the one described for Example 102 from Example 101 (0.04 g, 12%): mp 235–238° C.; $^1$H NMR (300 MHz, DMSO-d$_6$) δ 8.00 (d, J=8 Hz, 1H), 7.94 (br s, 1H), 7.78 (d, J=8 Hz, 1H), 7.64 (app q, J=8 Hz, 1H), 7.38–7.30 (m, 4H), 7.17 (td, J=6, 2 Hz, 1H), 6.60 (d, J=9 Hz, 1H), 5.27 (s, 2H), 5.14 (s, 2H). ES HRMS m/z 449.0291 (M+H C$_{20}$H$_{16}$BrF$_2$N$_2$O$_3$ requires 449.0307).

Example 104

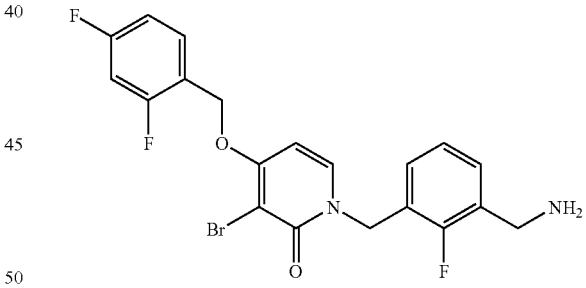

1-(3-Aminomethyl-2-fluorobenzyl)-3-bromo-4-(2,4-difluorobenzyloxy)-1H-pyridin-2-one Step 1. Preparation of 3-Bromo-1-(3-bromomethyl-2-fluorobenzyl)-4-(2,4-difluoro-benzyloxy)-1H-pyridin-2-one.

To a solution of 3-bromo-4-(2,4-difluorobenzyloxy)-1H-pyridin-2-one (from Step 3, Example 74) (0.3 g, 0.95 mmol) in DMF (26 mL) was added K$_2$CO$_3$ (0.26 g, 1.9 mmol) and 2,6-bis(bromomethyl)fluorobenzene (1.6 g, 5.7 mmol), and the reaction mixture was stirred at 110° C. for 3 h. The reaction mixture was cooled to room temperature, and the solvent was removed under reduced pressure. The residue was diluted with a 50% aqueous solution of brine, and the aqueous layer was extracted with EtOAc (3×50 mL). The combined organics were washed with water, dried (Na₂SO₄), filtered, and the solvent was removed under reduced pressure. Purification by flash column chromatography (silica, eluent 99:1 to 95:5 methylene chloride/methanol) afforded 3-bromo-1-(3-bromomethyl-2-fluorobenzyl)-4-(2,4-difluorobenzyloxy)-1H-pyridin-2-one as an off-white solid (0.24 g, 49%): $^1$H NMR (300 MHz, CDCl₃) δ 7.55–7.40 (m, 3H), 7.35–7.25 (m, 1H), 7.10–7.05 (m, 1H), 7.00–6.80 (m, 2H), 6.14 (d, J=6 Hz, 1H), 5.22 (s, 2H), 5.19 (s, 2H), 4.50 (s, 2H).

Step 2. Preparation of 1-(3-Aminomethyl-2-fluorobenzyl)-3-bromo-4-(2,4-difluoro-benzyloxy)-1H-pyridin-2-one.

A sealed tube containing a solution of 3-bromo-1-(3-bromomethyl-2-fluorobenzyl)-4-(2,4-difluorobenzyloxy)-1H-pyridin-2-one (0.24 g, 0.45 mmol) and NH₃ (24 mL of a 7 N solution in MeOH, 168 mmol) was heated at 80° C. for 1 h. The reaction mixture was cooled to room temperature and the solvent was removed under reduced pressure. Purification by flash column chromatography (silica, eluent 99.5:0.5 to 96:4 methylene chloride/methanol) afforded a white solid (0.12 g, 60%): mp 160–163° C.; $^1$H NMR (300 MHz, CDCl₃) δ 7.46–7.45 (m, 1H), 7.44–7.35 (m, 2H), 7.34–7.26 (m, 1H), 7.15–7.05 (m, 1H), 6.95–6.80 (m, 2H), 6.11 (d, J=9 Hz, 1H), 5.21 (s, 2H), 5.19 (s, 2H), 3.90 (s, 2H). ES HRMS m/z 453.0442 (M+H C₂₀H₁₇BrF₃N₂O₂ requires 453.0420).

Example 105

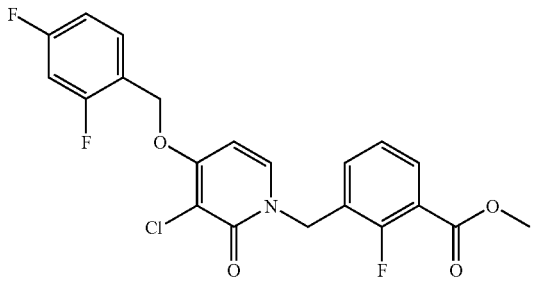

Methyl 3-[3-chloro-4-(2,4-difluorobenzyloxy)-2-oxo-2H-pyridin-1-ylmethyl]-2-fluoro-benzoate Step 1. Preparation of Methyl 2-fluoro-3-methylbenzoate.

To a solution of 2-fluoro-3-methyl benzoic acid (3.57 g, 23 mmol) in MeOH (40 mL) was added concentrated sulfuric acid (2.3 mL), and the reaction mixture was heated at reflux for 12 h. The reaction mixture was cooled, the solvent was removed under reduced pressure, and the residue was dissolved in EtOAc. The organic solution was washed with a saturated solution of NaHCO₃ and then brine, dried (Na₂SO₄), filtered and concentrated under reduced pressure to afford methyl 2-fluoro-3-methylbenzoate as a yellow oil (3.2 g, 82%): $^1$H NMR (300 MHz, CDCl₃) δ 7.76–7.71 (m, 1H), 7.39–7.34 (m, 1H), 7.08 (t, J=8 Hz, 1H), 3.98 (s, 3H), 2.31 (d, J=3 Hz, 3H).

Step 2. Preparation of Methyl 3-bromomethyl-2-fluorobenzoate.

To a mixture of methyl 2-fluoro-3-methylbenzoate (1.5 g, 8.9 mmol) and N-bromosuccinimide (1.67 g, 9.4 mmol) was added carbon tetrachloride (24 mL) and benzoyl peroxide (5 mg), and the mixture was heated at reflux for 16 h. The reaction mixture was cooled, filtered, and concentrated under reduced pressure. Purification by flash column chromatography (silica, eluent 5:95 to 60:40 EtOAc/hexanes) afforded methyl 3-bromomethyl-2-fluorobenzoate as a light yellow solid (0.91 g, 41%): $^1$H NMR (300 MHz, CDCl₃) δ 7.93–7.88 (m, 1H), 7.61–7.56 (m, 1H), 7.20 (t, J=8 Hz, 1H), 4.53 (d, J=3 Hz, 2H), 3.94 (s, 3H).

Step 3. Preparation of Methyl 3-[3-chloro-4-(2,4-difluorobenzyloxy)-2-oxo-2H-pyridin-1-ylmethyl]-2-fluorobenzoate.

Methyl 3-[3-chloro-4-(2,4-difluorobenzyloxy)-2-oxo-2H-pyridin-1-ylmethyl]-2-fluorobenzoate was prepared by a procedure similar to the one described for Example 81 (0.33 g, 69%): mp 171–174° C.; $^1$H NMR (300 MHz, CDCl₃) δ 7.89–7.84 (m, 2H), 7.60–7.45 (m, 2H), 7.25–7.15 (m, 1H), 7.00–6.80 (m, 2H), 6.17 (d, J=6.0 Hz, 1H), 5.21 (s, 2H), 5.19 (s, 2H), 3.93 (s, 3H). ES HRMS m/z 438.0747 (M+H C₂₁H₁₆ClF₃NO₄ requires 438.0714).

Example 106

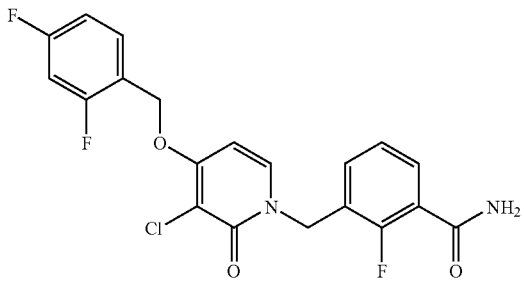

3-[3-Chloro-4-(2,4-difluorobenzyloxy)-2-oxo-2H-pyridin-1-ylmethyl]-2-fluoro-benzamide The title compound was prepared by a procedure similar to the one described for Example 99 (0.15 g, 62%): mp 252–254° C.; $^1$H NMR (300 MHz, DMSO-d₆) δ 8.04 (d, J=8 Hz, 1H), 7.92 (br s, 1H), 7.79–7.65 (m, 3H), 7.49–7.48 (m, 1H), 7.37–7.31 (m, 3H), 6.80 (d, J=8 Hz, 1H), 5.46 (s, 2H), 5.33 (s, 2H). ES HRMS m/z 423.0710 (M+H C₂₀H₁₅ClF₃N₂O₃ requires 423.0718).

Example 107

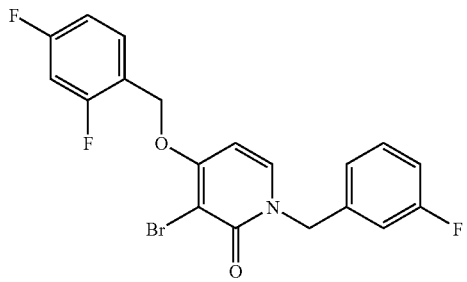

3-Bromo-4-(2,4-difluorobenzyloxy)-1-(3-fluorobenzyl)-1H-pyridin-2-one

Step 1. Preparation of 4-Benzyloxy-1-(3-fluorobenzyl)-1H-pyridin-2-one.

To a solution of 4-benzyloxy-1H-pyridin-2-one (1.0 g, 5 mmol) and K₂CO₃ (2.0 g, 9.9 mmol) in DMF (30 mL) was added 3-fluorobenzyl bromide (1.4 g, 7.5 mmol), and the reaction mixture was heated to 110° C. for 3 h. The reaction mixture was cooled to room temperature, and partitioned between EtOAc and water. The organic solution was washed with water and then brine, dried (Na₂SO₄), filtered and concentrated under reduced pressure. Purification by flash column chromatography (silica, eluent 97:3 to 93:7 methylene chloride/methanol) afforded 4-benzyloxy-1-(3-fluorobenzyl)-1H-pyridin-2-one (1.04 g, 67%): $^1$H NMR (300 MHz, CDCl₃) δ 7.45–7.25 (m, 5H), 7.13 (d, J=8 Hz, 1H), 7.10–6.90 (m, 3H), 6.10–5.95 (m, 2H), 5.07 (s, 2H), 5.00 (s, 2H).

Step 2. Preparation of 1-(3-Fluorobenzyl)-4-hydroxy-1H-pyridin-2-one.

To a solution of 4-benzyloxy-1-(3-fluorobenzyl)-1H-pyridin-2-one (1.79 g, 5.8 mmol) in EtOH (50 mL) was added 10% Pd/C (0.4 g), and reaction mixture was stirred under a hydrogen atmosphere for 1.5 h. The reaction mixture was filtered through diatomaceous earth and concentrated under reduced pressure to give 1-(3-fluorobenzyl)-4-hydroxy-1H-pyridin-2-one (0.92 g, 72%): ¹H NMR (300 MHz, CDCl₃) δ 7.55 (d, J=6 Hz, 1H), 7.40–7.30 (m, 1H), 7.10–6.95 (m, 3H), 6.07 (dd, J=6, 3 Hz, 1H), 5.85 (d, J=3 Hz, 1H), 5.11 (s, 2H).

Step 3. Preparation of 3-Bromo-1-(3-fluorobenzyl)-4-hydroxy-1H-pyridin-2-one.

To an ice-cold solution of 1-(3-fluorobenzyl)-4-hydroxy-1H-pyridin-2-one (0.67 g, 3.1 mmol) in AcOH (5.7 mL) was added a solution of bromine (0.52 g, 3.24 mmol) in AcOH (10.8 mL), and the reaction mixture was stirred for 5 min. The reaction mixture was warmed to room temperature and concentrated under reduced pressure to afford 3-bromo-1-(3-fluorobenzyl)-4-hydroxy-1H-pyridin-2-one as a yellow solid (1.07 g, crude): ¹H NMR (500 MHz, MeOD) δ 7.64 (d, J=8 Hz, 1H), 7.35–7.30 (m, 1H), 7.05–6.90 (m, 3H), 6.20 (d, J=8 Hz, 1H), 5.18 (s, 2H).

Step 4. Preparation of 3-Bromo-4-(2,4-difluorobenzyloxy)-1-(3-fluorobenzyl)-1H-pyridin-2-one.

To a solution of 3-bromo-1-(3-fluorobenzyl)-4-hydroxy-1H-pyridin-2-one (0.20 g, 0.67) and K₂CO₃ (0.27 g, 1.34 mmol) in acetone (10 mL) was added 2,4-difluorobenzyl bromide (0.16 g, 0.8 mmol), and the reaction mixture was heated at reflux for 1 h. The reaction mixture was cooled to room temperature, concentrated under reduced pressure, and the residue was dissolved in EtOAc. The organic solution was washed with water and then brine, dried (Na₂SO₄), filtered and concentrated under reduced pressure. ¹H NMR (300 MHz, CDCl₃) δ 7.65–7.55 (m, 1H), 7.40–7.25 (m, 2H), 7.15–6.80 (m, 5H), 6.14 (d, J=8 Hz, 1H), 5.22 (s, 2H), 5.16 (s, 2H). ES HRMS m/z 424.0159 (M+H C₁₉H₁₄BrF₃NO₂ requires 424.0155).

Example 108

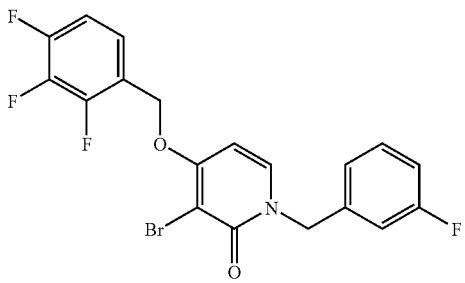

3-Bromo-1-(3-fluorobenzyl)-4-(2,3,4-trifluorobenzyloxy)-1H-pyridin-2-one

The title compound was prepared by a procedure similar to the one described for Example 107 (0.09 g, 39%): mp 176–178° C.; ¹H NMR (300 MHz, CDCl₃) δ 7.40–7.25 (m, 4H), 7.11–6.98 (m, 4H), 6.11 (d, J=9 Hz, 1H), 5.23 (s, 2H), 5.16 (s, 2H). ES HRMS m/z 442.0060 (M+H C₁₉H₁₃BrF₄NO₂ requires 442.0061).

Example 109

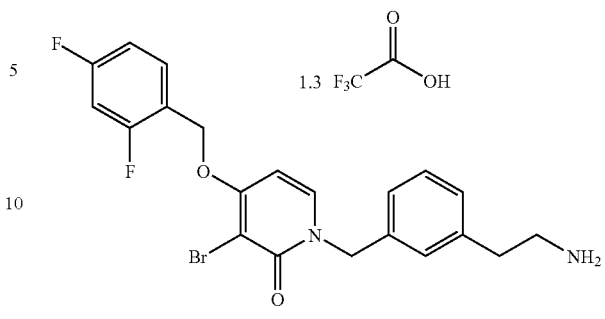

1-[3-(2-Aminoethyl) benzyl]-3-bromo-4-(2,4-difluorobenzyloxy)-1H-pyridin-2-one

The title compound was prepared from compound of Example 97 by a procedure similar to the one described for Example 99, as the TFA salt (0.13 g, 33%): mp 70–74° C.; ¹H NMR (300 MHz, DMSO-d₆) δ 8.21 (br s, 1H), 6.60–6.50 (m, 1H), 7.52 (d, J=6 Hz, 1H), 7.30–7.10 (m, 3H), 7.01 (d, J=9 Hz, 1H), 6.94–6.85 (m, 2H), 6.20 (d, J=6 Hz, 1H), 5.20 (s, 2H), 5.05 (s, 2H), 3.23 (br s, 2H), 2.97 (t, J=8 Hz, 2H), 2.05 (br s, 2H). ES HRMS m/z 449.0698 (M+H C₂₁H₂₀BrF₂N₂O₂ requires 449.0671).

Example 110

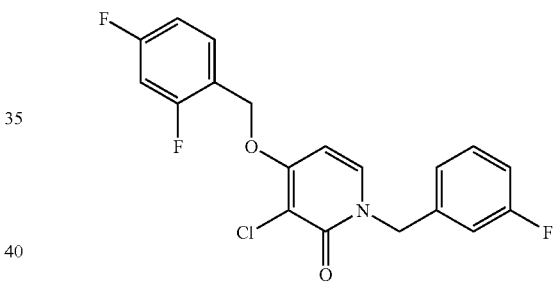

3-Chloro-4-(2,4-difluorobenzyloxy)-1-(3-fluorobenzyl)-1H-pyridin-2-one

Step 1. Preparation of 4-(2,4-difluorobenzyloxy)-1-(3-fluorobenzyl)-1H-pyridin-2-one.

To a solution of 1-(3-fluorobenzyl)-4-hydroxy-1H-pyridin-2-one (from Step 2 EXAMPLE 107) (0.92 g, 4.2 mmol) and K₂CO₃ (1.2 g, 8.4 mmol) in acetone (62 mL) was added 2,4-difluorobenzyl bromide (1.3 g, 6.3 mmol), and the reaction mixture was heated at reflux for 3 h. The reaction mixture was cooled room temperature, concentrated under reduced pressure, and the residue was partitioned between water and EtOAc. The organic solution was washed with brine, dried (Na₂SO₄), filtered, and concentrated under reduced pressure. Purification by flash column chromatography (silica, eluent methylene chloride to 95:5 methylene chloride/methanol) to provide 4-(2,4-difluorobenzyloxy)-1-(3-fluorobenzyl)-1H-pyridin-2-one as a white solid (1.21 g, 84%): ¹H NMR (300 MHz, CDCl₃) δ 7.45–7.20 (m, 2H), 7.14 (d, J=8 Hz, 1H), 7.05–6.75 (m, 5H), 6.05 (d, J=3 Hz, 1H), 5.95 (dd, J=5, 3 Hz, 1H), 5.08 (s, 2H), 5.00 (s, 2H).

Step 2. Preparation of 3-Chloro-4-(2,4-difluorobenzyloxy)-1-(3-fluorobenzyl)-1H-pyridin-2-one.

To a solution of 4-(2,4-difluorobenzyloxy)-1-(3-fluorobenzyl)-1H-pyridin-2-one (0.15 g, 0.4 mmol) in AcOH (3 mL) was added N-chlorosuccinimide (70 mg, 0.5 mmol), and the reaction mixture was heated at reflux for 10 min. The reaction mixture was cooled room temperature and the solvent was removed under reduced pressure. $^1$H NMR (300 MHz, CDCl$_3$) δ 7.60–7.50 (m, 1H), 7.45–7.20 (m, 2H), 7.10–6.80 (m, 5H), 6.16 (d, J=8 Hz, 1H), 5.21 (s, 2H), 5.15 (s, 2H). ES HRMS m/z 380.0641 (M+H C$_{19}$H$_{14}$ClF$_3$NO$_2$ requires 480.0660).

Examples 111–123

The following example compounds were prepared by procedures similar to that described for Example 107. The yields and the analytical data are described below.

Example 111

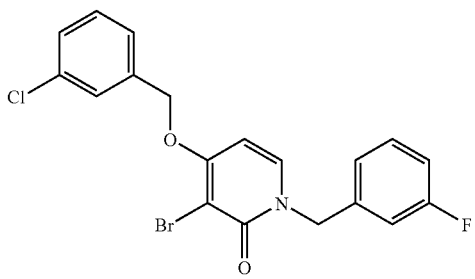

3-Bromo-4-(3-chlorobenzyloxy)-1-(3-fluorobenzyl)-1H-pyridin-2-one

The title compound was prepared by a procedure similar to the one described for EXAMPLE 107 (0.12 g, 42%): mp 149–153° C.; $^1$H NMR (300 MHz, CDCl$_3$) δ 7.40–7.23 (m, 6H), 7.09 (d, J=8 Hz, 1H), 7.05–6.95 (m, 2H), 6.05 (d, J=8 Hz, 1H), 5.19 (s, 2H), 5.14 (s, 2H). ES MS m/z M+H 442.

Example 112

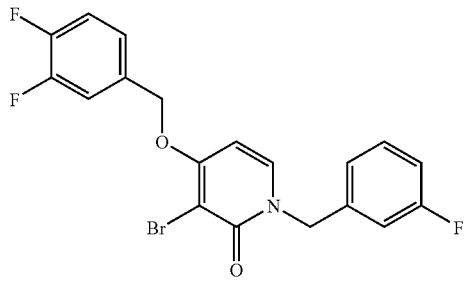

3-Bromo-4-(3,4-difluorobenzyloxy)-1-(3-fluorobenzyl)-1H-pyridin-2-one

The title compound was prepared by a procedure similar to the one described for EXAMPLE 107 (0.08 g, 48%): mp 172–174° C.; $^1$H NMR (300 MHz, CDCl$_3$) δ 7.40–6.95 (m, 8H), 6.05 (d, J=6 Hz, 1H), 5.16 (s, 4H). ES HRMS m/z 424.0111 (M+H C$_{19}$H$_{14}$BrF$_3$NO$_2$ requires 424.0155).

Example 113

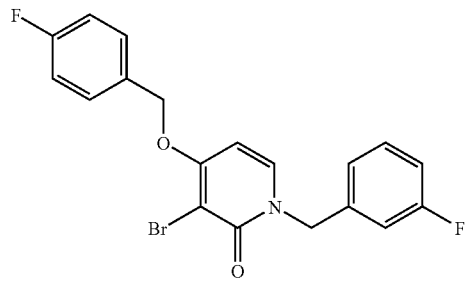

3-Bromo-1-(3-fluorobenzyl)-4-(4-fluorobenzyloxy)-1H-pyridin-2-one

The title compound was prepared by a procedure similar to the one described for EXAMPLE 107 (0.07 g, 35%): mp 180–183° C.; $^1$H NMR (300 MHz, CDCl$_3$) δ 7.50–7.25 (m, 5H), 7.15–7.00 (m, 4H), 6.07 (d, J=8 Hz, 1H), 5.18 (s, 2H), 5.14 (s, 2H). ES HRMS m/z 406.0258 (M+H C$_{19}$H$_{15}$BrF$_2$NO$_2$ requires 406.0249).

Example 114

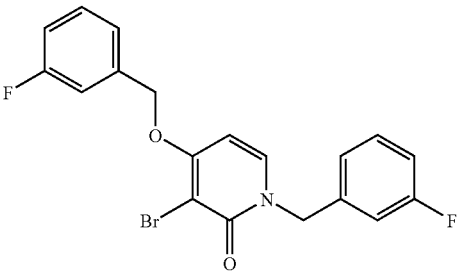

3-Bromo-1-(3-fluorobenzyl)-4-(3-fluorobenzyloxy)-1H-pyridin-2-one

To an ice-cold solution of 1-(3-fluorobenzyl)-4-(3-fluorobenzyloxy)-1H-pyridin-2-one (0.14 g, 0.43 mmol) in AcOH (2 mL) was added a solution of bromine (72 mg, 0.45 mmol) in AcOH (1 mL), and the reaction mixture was stirred for 5 min. The reaction mixture was warmed to room temperature and the solvent was removed under reduced pressure. $^1$H NMR (300 MHz, CDCl$_3$) δ 7.45–6.95 (m, 9H), 6.05 (d, J=8 Hz, 1H), 5.21 (s, 2H), 5.14 (s, 2H). ES HRMS m/z 406.0254 (M+H C$_{19}$H$_{15}$BrF$_2$NO$_2$ requires 406.0249).

Examples 115–123

The compounds of Examples 115–123 are prepared essentially according to the procedures set forth above for Example 107:

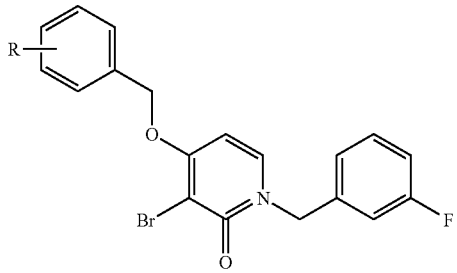

| Example No. | R | MF | M + H Requires | ESHRMS m/z |
|---|---|---|---|---|
| Ex. 115 | 3-methoxy | C₂₀H₁₇BrFNO₃ | 418.0449 | 418.0427 |
| Ex. 116 | 4-tert-butyl | C₂₃H₂₃BrFNO₂ | 444.0969 | 444.0977 |
| Ex. 117 | 3-methyl | C₂₀H₁₇BrFNO₂ | 402.0499 | 402.0513 |
| Ex. 118 | 4-trifluoromethyl | C₂₀H₁₄BrF₄NO₂ | 456.0217 | 456.0210 |
| Ex. 119 | 4-cyano | C₂₀H₁₄BrFN₂O₂ | 413.0295 | 413.0313 |
| Ex. 120 | 2-methyl | C₂₀H₁₇BrFNO₂ | 402.0499 | 402.0502 |
| Ex. 121 | 2-phenyl | C₂₅H₁₉BrFNO₂ | 464.0656 | 464.0654 |
| Ex. 122 | 4-methoxy | C₂₀H₁₇BrFNO₃ | 418.0449 | 418.0455 |
| Ex. 123 | 2-CO₂CH₃ | C₂₁H₁₇BrFNO₄ | 446.0398 | 446.0403 |

NMR characterization of compounds of Example 115–123

| Example No. | NMR Data |
|---|---|
| Ex. 115 | ¹H NMR (300 MHz, CDCl₃) δ 7.35–7.20(m, 4H), 7.15–6.85(m, 5H), 6.07(d, J=8Hz, 1H), 5.21(s, 2H), 5.13(s, 2H), 3.82(s, 3H) |
| Ex. 116 | ¹H NMR (300 MHz, CDCl₃) δ 7.45–7.20(m, 4H), 7.10–6.95(m, 3H), 6.11(d, J=8Hz, 1H), 5.19(s, 2H), 5.14(s, 2H), 1.32(s, 9H) |
| Ex. 117 | ¹H NMR (300 MHz, CDCl₃) δ 7.40–6.90(m, 9H), 6.08(d, J=8Hz, 1H), 5.19(s, 2H), 5.14(s, 2H), 2.37(s, 3H) |
| Ex. 118 | ¹H NMR (300 MHz, CDCl₃) δ 7.67–7.53(m, 4H), 7.31–724(m, 2H), 7.09–6.98(m, 3H), 6.04(d, J=8Hz, 1H), 5.26(s, 2H), 5.14(s, 2H) |
| Ex. 119 | ¹H NMR (300 MHz, CDCl₃) δ 7.71(dd, J=8, 2Hz, 2H), 7.58–7.55(m, 2H), 7.29–7.25(m, 2H), 7.09(d, J=8Hz, 1H), 7.03–6.98(m, 2H), 6.03(dd, J=8, 2Hz, 1H), 5.26(s, 2H), 5.15(s, 2H) |
| Ex. 120 | ¹H NMR (300 MHz, CDCl₃) δ 7.45–6.90(m, 9H), 6.15–6.10(m, 1H), 5.18(s, 2H), 5.15(s, 2H), 2.38(s, 3H) |
| Ex. 121 | ¹H NMR (300 MHz, CDCl₃) δ 7.70–7.65(m, 1H), 7.55–7.25(m, 9H) 7.14(d, J=8Hz, 1H), 7.10–6.95(m, 3H), 5.81(d, J=8Hz, 1H), 5.12(s, 2H), 5.08(s, 2H) |
| Ex. 122 | ¹H NMR (300 MHz, CDCl₃) δ 7.40–7.25(m, 3H), 7.15–6.90(m, 6H), 6.15–6.10(m, 1H), 5.16(s, 2H), 5.14(s, 2H), 3.82(s, 3H) |
| Ex. 123 | ¹H NMR (300 MHz, CDCl₃) δ 8.06(dd, J=8, 1Hz, 1H), 7.87(d, J=8Hz, 1H), 7.70–7.60(m, 1H), 7.50–7.25(m, 3H), 7.09(d, J=8Hz, 1H), 7.05–6.95(m, 2H), 6.19(d, J=8Hz, 1H), 5.65(s, 2H), 5.16(s, 2H), 3.91(s, 3H) |

Example 124

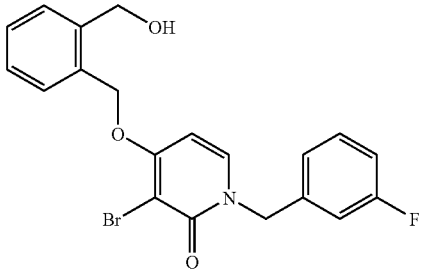

3-Bromo-1-(3-fluorobenzyl)-4-(2-hydroxymethylbenzyloxy)-1H-pyridin-2-one

Step 1. Preparation of 3-Bromo-1-(3-fluorobenzyl)-4-(2-hydroxymethylbenzyloxy)-1H-pyridin-2-one.

To an ice-cold solution of methyl 2-[3-bromo-1-(3-fluorobenzyl)-2-oxo-1,2-dihydro-pyridin-4-yloxymethyl]benzoate (0.12 g, 0.28 mmol) in THF (5 mL) was added LiBH₄ (0.15 mL of a 2.0 M solution in THF, 0.30 mmol), and the reaction mixture heated at reflux for 5 hours. The reaction mixture was cooled to room temperature, the solvent was removed under reduced pressure, and the residue dissolved in EtOAc. The organic solution was washed with brine, dried (Na₂SO₄), filtered, and concentrated under reduced pressure. ¹H NMR (300 MHz, DMSO-d₆) δ 7.98 (d, J=8 Hz, 1H), 7.46–7.28 (m, 5H), 7.15–7.10 (m, 3H), 6.56 (d, J=8 Hz, 1H), 5.35 (s, 2H), 5.25 (br s, 1H), 5.14 (s, 2H). ES HRMS m/z 418.0453 (M+H C₂₀H₁₈BrFNO₃ requires 418.0449).

Example 126

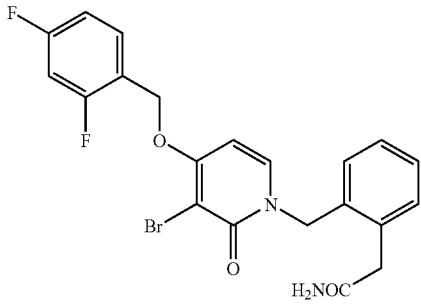

2-{2-[3-Bromo-4-(2,4-difluorobenzyloxy)-2-oxo-2H-pyridin-1-ylmethyl]-phenyl}acetamide Step 1. Preparation of (2-Bromomethylphenyl)acetic acid.

A solution of isochroman-3-one (1.5 g, 10 mmol) in 30% HBr in acetic acid (13 mL) was stirred at room temperature for 2 h, and 70° C. for 1 h. The reaction mixture was cooled to room temperature, and poured into ice-water. The precipitate was collected to afford (2-bromomethylphenyl)acetic acid as an off-white solid (2.15 g, 93%): ¹H NMR (300 MHz, DMSO-d₆) δ 7.45–7.23 (m, 4H), 4.73 (s, 2H), 3.73 (s, 2H).

Step 2. Preparation of Methyl(2-Bromomethylphenyl)acetate.

To an ice-cold solution of (2-bromomethylphenyl)acetic acid (1 g, 4.4 mmol) in THF (2.4 mL) was added trimethylsilyldiazomethane (3 mL of a 2 M solution in hexanes, 6 mmol), and the reaction mixture was stirred for 14 h. The reaction was quenched with AcOH, and the solvent was removed under reduced pressure. Purification by flash column chromatography (silica, eluent 98:2 to 94:6 methylene chloride/hexanes) afforded methyl(2-bromomethylphenyl) acetate as a light yellow solid (0.34 g, 32%): $^1$H NMR (300 MHz, CDCl$_3$) δ 7.40–7.20 (m, 4H), 4.59 (s, 2H), 3.81 (s, 2H), 3.71 (s, 3H).

Step 3. Preparation of Methyl {2-[3-bromo-4-(2,4-difluorobenzyloxy)-2-oxo-2H-pyridin-1-ylmethyl]phenyl}acetate.

Methyl {2-[3-bromo-4-(2,4-difluorobenzyloxy)-2-oxo-2H-pyridin-1-ylmethyl]-phenyl}acetate was prepared by a procedure similar to the one described for EXAMPLE 74 (0.41 g, 68%): $^1$H NMR (300 MHz, CDCl$_3$) δ 7.55–6.81 (m, 8H), 6.10 (d, J=6 Hz, 1H), 5.20 (s, 4H), 3.78 (s, 2H), 3.60 (s, 3H).

Step 4. Preparation of 2-{2-[3-Bromo-4-(2,4-difluorobenzyloxy)-2-oxo-2H-pyridin-1-ylmethyl]phenyl Acetamide.

2-{2-[3-Bromo-4-(2,4-difluorobenzyloxy)-2-oxo-2H-pyridin-1-ylmethyl]phenyl}-acetamide was prepared by a procedure similar to the one described for Example 102 (0.07 g, 72%): mp 178–183° C.; $^1$H NMR (300 MHz, DMSO-d$_6$) δ 7.89 (d, J=8 Hz, 1H), 7.66 (d, J=9 Hz, 1H), 7.54 (br s, 1H), 7.35 (br s, 1H), 7.30–7.15 (m, 4H), 6.98 (br s, 1H), 6.85 (d, J=7 Hz, 1H), 6.60 (d, J=8 Hz, 1H), 5.32 (s, 2H), 5.19 (s, 2H), 3.62 (s, 2H). ES HRMS m/z 463.0442 (M+H C$_{21}$H$_{18}$BrF$_2$N$_2$O$_3$ requires 463.0463).

Example 127

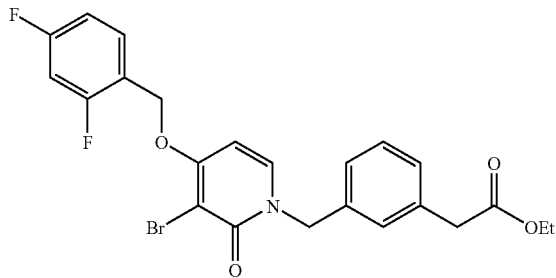

Ethyl {3-[3-Bromo-4-(2,4-difluorobenzyloxy)-2-oxo-2H-pyridin-1-ylmethyl]-phenyl}acetate Step 1. Preparation of Ethyl(3-bromomethylphenyl) Acetate.

To a mixture of m-tolylacetic acid ethyl ester (3.0 g, 16.8 mmol) and N-bromosuccinimide (3.0 g, 16.8 mmol) was added carbon tetrachloride (45 mL), followed by benzoyl peroxide (5 mg), and the reaction mixture was heated at reflux for 16 h. The reaction mixture was cooled to room temperature, filtered, and concentrated under reduced pressure. Purification by flash column chromatography (silica, eluent 5:95 to 2:3 EtOAc/hexanes) afforded ethyl(3-bromomethylphenyl) acetate as an off-white solid (0.89 g, 21%): $^1$H NMR (300 MHz, CDCl$_3$) δ 7.32–7.21 (m, 4H), 4.48 (s, 2H), 4.16 (q, J=6 Hz, 2H), 3.63, (s, 2H), 1.27 (t, J=6 Hz, 3H).

Step 2. Preparation of Ethyl {3-[3-Bromo-4-(2,4-difluorobenzyloxy)-2-oxo-2H-pyridin-1-ylmethyl]phenyl}acetate.

Ethyl {3-[3-Bromo-4-(2,4-difluorobenzyloxy)-2-oxo-2H-pyridin-1-ylmethyl]phenyl}-acetate was prepared by a procedure similar to the one described for EXAMPLE 74 (0.27 g, 69%): mp 95–98° C.; $^1$H NMR (300 MHz, CDCl$_3$) δ 7.65–7.55 (m, 1H), 7.40–7.20 (m, 5H), 7.00–6.80 (m, 2H), 6.09 (d, J=9 Hz, 1H), 5.21 (s, 2H), 5.16 (s, 2H), 4.14 (q, J=6 Hz, 2H), 3.60 (s, 2H), 1.25 (t, J=6 Hz, 3H). ES HRMS m/z 492.0655 (M+H C$_{23}$H$_{21}$BrF$_2$NO$_4$ requires 435.0617).

Example 128

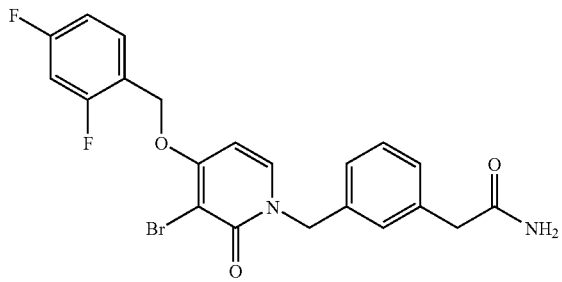

2-{3-[3-Bromo-4-(2,4-difluorobenzyloxy)-2-oxo-2H-pyridin-1-ylmethyl]phenyl}Acetamide The title compound was prepared by a procedure similar to the one described for EXAMPLE 102 (0.07 g, 28%): mp 164–167° C.; $^1$H NMR (300 MHz, DMSO-d$_6$) δ 7.96 (d, J=9 Hz, 1H), 7.70–7.60 (m, 1H), 7.60 (br s, 1H), 7.50–7.10 (m, 6H), 6.89 (br s, 1H), 6.58 (d, J=9 Hz, 1H), 5.31 (s, 2H), 5.12 (s, 2H), 3.32 (s, 2H). ES HRMS m/z 463.0485 (M+H C$_{21}$H$_{18}$BrF$_2$N$_2$O$_3$ requires 463.0464).

Example 129

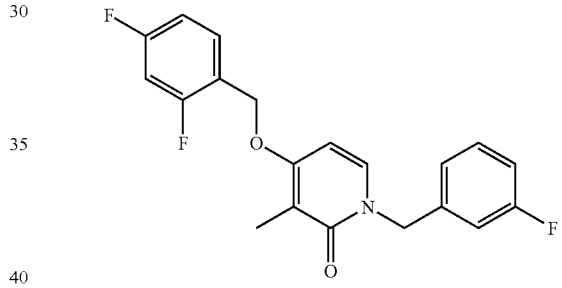

4-(2,4-Difluorobenzyloxy)-1-(3-fluorobenzyl)-3-methyl-1H-pyridin-2-one

Step 1. Preparation of 4-(2,4-Difluorobenzyloxy)-1-(3-fluorobenzyl)-3-methyl-1H-pyridin-2-one.

To a solution of 3-bromo-4-(2,4-difluorobenzyloxy)-1-(3-fluorobenzyl)-1H-pyridin-2-one (EXAMPLE 107) (0.14 g, 0.32 mmol), K$_2$CO$_3$ (88 mg, 0.64 mmol) and Cs$_2$CO$_3$ (0.10 g, 0.32 mmol) in dioxane (2 mL) was added Pd(PPh$_3$)$_4$ (18 mg, 0.12 mmol), followed by trimethylboroxine (40 mg, 0.32 mmol). The reaction mixture was degassed, purged with argon, and heated at reflux for 4 h. The reaction mixture was cooled to room temperature, and partitioned between water and EtOAc. The organic solution was washed with brine, dried (Na$_2$SO$_4$), filtered and concentrated under reduced pressure. Purification by flash column chromatography (silica, eluent methylene chloride to 97:3 methylene chloride/MeOH) afforded 4-(2,4-difluorobenzyloxy)-1-(3-fluorobenzyl)-3-methyl-1H-pyridin-2-one as a white solid (0.09 g, 79%): mp 127–129° C.; $^1$H NMR (300 MHz, CDCl$_3$) δ 7.50–7.40 (m, 1H), 7.35–7.25 (m, 1H), 7.17 (d, J=9 Hz, 1H), 7.06 (d, J=6 Hz, 1H), 7.00–6.80 (m, 4H), 6.12 (d, J=9 Hz, 1H), 5.12 (s, 4H), 2.07 (s, 3H). ES HRMS m/z 360.1180 (M+H C$_{20}$H$_{16}$F$_3$NO$_2$ requires 360.1206).

Example 130

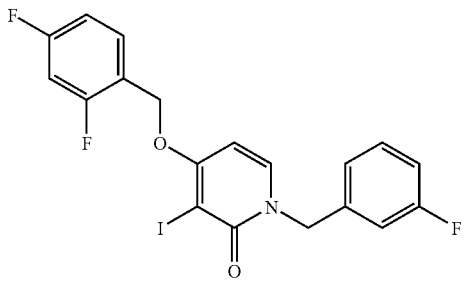

4-(2,4-Difluorobenzyloxy)-1-(3-fluorobenzyl)-3-iodo-1H-pyridin-2-one

Step 1. Preparation of 4-(2,4-Difluorobenzyloxy)-1-(3-fluorobenzyl)-1H-pyridin-2-one.

To a mixture of 1-(3-fluorobenzyl)-4-hydroxy-1H-pyridin-2-one (from Step 1, EXAMPLE 110) (0.92 g, 4.2 mmol) and $K_2CO_3$ (1.15 g, 8.4 mmol) in acetone (62 mL) was added 2,4-difluorobenzyl bromide (1.3 g, 6.3 mmol), and the reaction mixture was heated at reflux for 3 h. The reaction mixture was cooled to room temperature, concentrated under reduced pressure, and the residue was dissolved in EtOAc. The organic solution was washed with water and then brine, dried ($Na_2SO_4$), filtered, and concentrated under reduced pressure. Purification by flash column chromatography (silica, eluent methylene chloride to 95:5 methylene chloride/methanol) provided 4-(2,4-difluorobenzyloxy)-1-(3-fluorobenzyl)-1H-pyridin-2-one as a white solid (1.21 g, 84%): $^1$H NMR (300 MHz, $CDCl_3$) δ 7.45–7.20 (m, 2H), 7.14 (d, J=8 Hz, 1H), 7.05–6.75 (m, 5H), 6.05 (d, J=3 Hz, 1H), 5.95 (dd, J=5, 3 Hz, 1H), 5.08 (s, 2H), 5.00 (s, 2H).

Step 2. Preparation of 4-(2,4-Difluorobenzyloxy)-1-(3-fluorobenzyl)-3-iodo-1H-pyridin-2-one.

To a mixture of 4-(2,4-difluorobenzyloxy)-1-(3-fluorobenzyl)-1H-pyridin-2-one (0.15 g, 0.43 mmol) and N-iodosuccinimide (0.10 g, 0.46 mmol) in $CH_3CN$ (3 mL) was added dichloroacetic acid (13 mg, 0.10 mmol), and the reaction mixture was heated to 60° C. for 4 h. The reaction mixture was cooled to room temperature, concentrated under reduced pressure, and the residue was dissolved in methylene chloride. The organic solution was washed with a saturated solution of $NaHCO_3$ and then brine, dried ($Na_2SO_4$), filtered and concentrated under reduced pressure. Purification by flash column chromatography (silica, eluent 90:10 methylene chloride/hexanes to 99:1 methylene chloride/methanol) provided 4-(2,4-difluorobenzyloxy)-[(3-fluorobenzyl)-3-iodo-1H-pyridin-2-one as a white solid (0.15 g, 77%): mp 164–167° C.; $^1$H NMR (300 MHz, $CDCl_3$) δ 7.65–7.55 (m, 1H), 7.35–7.26 (m, 2H), 7.15–6.80 (m, 5H), 6.05 (d, J=6 Hz, 1H), 5.22 (s, 2H), 5.16 (s, 2H) ES HRMS m/z 472.0033 (M+H $C_{19}H_{14}F_3INO_2$ requires 472.0018).

Example 131

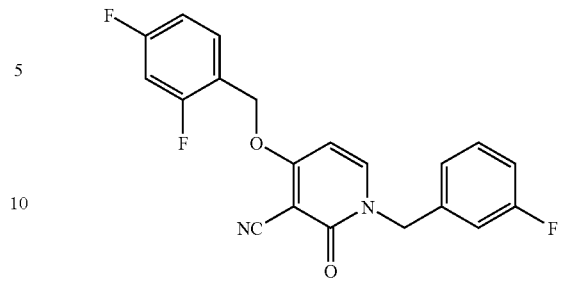

4-(2,4-Difluorobenzyloxy)-1-(3-fluorobenzyl)-2-oxo-1,2-dihydropyridine-3-carbonitrile Step 1. Preparation of 4-Methoxy-2-oxo-1,2-dihydropyridine-3-carbonitrile.

A solution of 2-(dimethylaminoethoxymethylene)malononitrile (1.97 g) in concentrated sulfuric acid (7.0 mL) was stirred at room temperature for 6.5 h. The reaction mixture was poured into water, and the precipitate was collected by filtration. $^1$H NMR (300 MHz, DMSO-$d_6$) δ 12.14 (br s, 1H), 7.79 (d, J=9 Hz, 1H), 6.35 (d, J=9 Hz, 1H), 3.98 (s, 3H).

Step 2. Preparation of 1-(3-Fluorobenzyl)-4-methoxy-2-oxo-1,2-dihydro-pyridine-3-carbonitrile.

1-(3-Fluorobenzyl)-4-methoxy-2-oxo-1,2-dihydropyridine-3-carbonitrile was prepared by a procedure similar to the one described for EXAMPLE 74 (0.56 g, 93%): $^1$H NMR (300 MHz, $CDCl_3$) δ 7.48 (d, J=9 Hz, 1H), 7.40–7.27 (m, 1H), 7.00–6.95 (m, 2H), 6.08 (d, J=9 Hz, 1H), 5.10 (s, 2H), 4.00 (s, 3H).

Step 3. Preparation of 1-(3-Fluorobenzyl)-4-hydroxy-2-oxo-1,2-dihydropyridine-3-carbonitrile.

To a solution of sodium hydride (92 mg of a 60% dispersion in mineral oil, 2.3 mmol) in DMF (7 mL) was added ethanethio](0.14 g, 2.2 mmol), followed by a solution of 1-(3-fluorobenzyl)-4-methoxy-2-oxo-1,2-dihydropyridine-3-carbonitrile (0.23 g, 0.89 mmol) in DMF (2 mL), and the reaction mixture was heated to 100° C. The reaction mixture was cooled to room temperature, acidified with 3 N HCl, and washed with EtOAc. The organic solution was washed with brine, dried ($Na_2SO_4$), filtered and concentrated under reduced pressure to give 1-(3-fluorobenzyl)-4-hydroxy-2-oxo-1,2-dihydro-pyridine-3-carbonitrile as an off-white solid (0.20 g, 91%): $^1$H NMR (300 MHz, MeOD) δ 8.00 (s, 1H), 7.82 (d, J=8 Hz, 1H), 7.40–7.30 (m, 1H), 7.15–7.00 (m, 2H), 6.13 (d, J=8 Hz, 1H), 5.11 (s, 2H)

Step 4. Preparation of 4-(2,4-Difluorobenzyloxy)-1-[(3-fluorobenzyl)-2-oxo-1,2-dihydro-pyridine-3-carbonitrile.

4-(2,4-Difluorobenzyloxy)-1-(3-fluorobenzyl)-2-oxo-1,2-dihydro-pyridine-3-carbonitrile was prepared by a procedure similar to the one described for EXAMPLE 107 (0.09 g, 30%): mp 187–190° C.; $^1$H NMR (300 MHz, $CDCl_3$) δ 7.60–7.45 (m, 2H), 7.40–7.30 (m, 1H), 7.10–6.50 (m, 5H), 6.13 (d, J=9 Hz, 1H), 5.27 (s, 2H), 5.10 (s, 2H).

Example 132

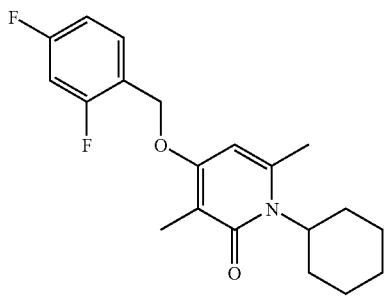

1-Cyclohexyl-4-(2,4-difluorobenzyloxy)-3,6-dimethyl-1H-pyridin-2-one

Step 1. Preparation of Methyl 1-cyclohexyl-4-hydroxy-2,5-dimethyl-6-oxo-1,6-dihydro-pyridine-3-carboxylate.

To a solution of 3-cyclohexylaminobut-2-enoic acid methyl ester (1.12 g, 5.72 mmol) in bromobenzene (20 mL) was added 2-methylmalonic acid bis-(2,4,6-trichlorophenyl)ester (2.71 g, 5.72 mmol) and the reaction mixture was heated at 170° C. for 3 h. The reaction mixture was cooled to room temperature, and concentrated under reduced pressure. Purification by flash column chromatography (silica, eluent methylene chloride to 94:6 methylene chloride/MeOH) and recrystallization from hot MeOH provided methyl 1-cyclohexyl-4-hydroxy-2,5-dimethyl-6-oxo-1,6-dihydropyridine-3-carboxylate as pale yellow crystals (0.34 g, 21%): $^1$H NMR (500 MHz, DMSO-$d_6$) δ 9.82 (s, 1H), 4.00–3.90 (m, 1H), 3.76 (s, 3H), 2.75–2.60 (m, 2H), 2.31 (s, 3H), 1.81 (s, 3H), 1.80–1.70 (m, 2H), 1.65–1.50 (m, 3H), 1.40–1.20 (m, 2H), 1.15–1.05 (m, 1H).

Step 2. Preparation of 1-Cyclohexyl-4-hydroxy-2,5-dimethyl-6-oxo-1,6-dihydro-pyridine-3-carboxylic acid.

A solution of methyl 1-cyclohexyl-4-hydroxy-2,5-dimethyl-6-oxo-1,6-dihydro-pyridine-3-carboxylate (0.35 g, 1.25 mmol) in 2 N NaOH (5 mL) was heated at reflux for 3.5 h. The reaction mixture was cooled room temperature, acidified to pH 1–2 with 1 N HCl, and washed with EtOAc. The organic solution was washed with brine, dried (MgSO$_4$), filtered and concentrated under reduced pressure to afford 1-cyclohexyl-4-hydroxy-2,5-dimethyl-6-oxo-1,6-dihydropyridine-3-carboxylic acid as a white solid (0.31 g, 94%): $^1$H NMR (300 MHz, MeOD) δ 4.30–4.00 (br s, 1H), 2.76 (br s, 5H), 1.90 (s, 3H), 1.90–1.80 (m, 2H), 1.75–1.60 (m, 3H), 1.50–1.15 (m, 3H).

Step 3. Preparation of 1-Cyclohexyl-4-hydroxy-3,6-dimethyl-1H-pyridin-2-one.

A solution of 1-cyclohexyl-4-hydroxy-2,5-dimethyl-6-oxo-1,6-dihydropyridine-3-carboxylic acid (0.15 g, 0.57 mmol) in concentrated HCl (5 mL) was heated at reflux for 4 h. The reaction mixture was cooled to room temperature, diluted with water and washed with EtOAc. The organic solution was washed with brine, dried (MgSO$_4$), filtered and concentrated under reduced pressure to give 1-cyclohexyl-4-hydroxy-3,6-dimethyl-1H-pyridin-2-one as a white solid (0.2 g, 77%): $^1$H NMR (300 MHz, DMSO-$d_6$) δ 9.81 (s, 1H), 5.73 (s, 1H), 3.95–3.75 (m, 1H), 2.80–2.55 (m, 2H), 2.25 (s, 3H), 1.85–1.40 (m, 5H), 1.72 (s, 3H), 1.38–1.05 (m, 3H).

Step 4. Preparation of 1-Cyclohexyl-4-(2,4-difluorobenzyloxy)-3,6-dimethyl-1H-pyridin-2-one.

1-Cyclohexyl-4-(2,4-difluorobenzyloxy)-3,6-dimethyl-1H-pyridin-2-one was prepared by a procedure similar to the one described for EXAMPLE 107 (0.05 g, 16%): mp 118–120° C.; $^1$H NMR (300 MHz, CDCl$_3$) δ 7.48–7.41 (m, 1H), 6.95–6.81 (m, 2H), 5.87 (s, 1H), 5.07 (s, 2H), 4.05–3.85 (m, 1H), 3.00–2.80 (m, 2H), 2.35 (s, 3H), 1.98 (s, 3H), 1.95–1.80 (m, 2H), 1.70–1.55 (m, 3H), 1.40–1.20 (m, 3H).

Example 133

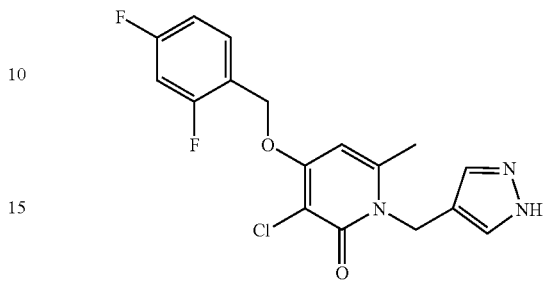

3-Chloro-4-(2,4-difluorobenzyloxy)-6-methyl-1-(1H-pyrazol-4-ylmethyl)-1H-pyridin-2-one Step 1. Preparation of 4-Methylpyrazole-1-carboxylic acid tert-butyl ester.

To a solution of 4-methyl-1H-pyrazole (1 g, 12 mmol) and DMAP (0.15 g, 1.2 mmol) in CH$_3$CN (20 mL) was added di-tert-butyl dicarbonate (2.8 g, 13 mmol), and the reaction mixture was stirred for 1 h. The reaction mixture was concentrated under reduced pressure, and the residue dissolved in EtOAc. The organic solution was washed with 1 N HCl, water and then brine, dried (MgSO$_4$), filtered, and concentrated under reduced pressure to provide 4-methyl-pyrazole-1-carboxylic acid tert-butyl ester as a light yellow oil (2.2 g, 100%): $^1$H NMR (300 MHz, CDCl$_3$) δ 7.83 (s, 1H), 7.53 (s, 1H), 2.09 (s, 3H), 1.64 (s, 9H).

Step 2. Preparation of 4-Bromomethylpyrazole-1-carboxylic acid tert-butyl ester.

To a solution of 4-methylpyrazole-1-carboxylic acid tert-butyl ester (1.0 g, 5.5 mmol) in carbon tetrachloride (20 mL) was added N-bromosuccinimide (1.0 g, 5.6 mmol) and benzoyl peroxide (50 mg), and the reaction mixture was heated at reflux for 16 h. The reaction mixture was cooled to room temperature, filtered, and concentrated under reduced pressure. Purification by flash column chromatography (silica, 1:4 EtOAc/hexanes) provided 4-bromomethylpyrazole-1-carboxylic acid tert-butyl ester as a light yellow oil (0.42 g, 30%): $^1$H NMR (300 MHz, CDCl$_3$) δ 8.10 (s, 1H), 7.74 (s, 1H), 4.39 (s, 2H), 1.65 (s, 9H)

Step 3. Preparation of 4-[3-Chloro-4-(2,4-difluorobenzyloxy)-6-methyl-2-oxo-2H-pyridin-1-ylmethyl]pyrazole-1-carboxylic acid tert-butyl ester.

4-[3-Chloro-4-(2,4-difluorobenzyloxy)-6-methyl-2-oxo-2H-pyridin-1-ylmethyl]pyrazole-1-carboxylic acid tert-butyl ester was prepared by a procedure similar to the one described for EXAMPLE 632: $^1$H NMR (300 MHz, CDCl$_3$) δ 8.09 (s, 1H), 7.72 (s 1H), 7.53 (app q, J=6 Hz, 1H), 6.97–6.82 (m, 2H), 6.00 (s, 1H), 5.19 (s, 2H), 5.13 (s, 2H), 2.43 (s, 3H), 1.63 (s, 9H).

Step 4. Preparation of 3-Chloro-4-(2,4-difluorobenzyloxy)-6-methyl-1-(1H-pyrazol-4-ylmethyl)-1H-pyridin-2-one.

4-[3-Chloro-4-(2,4-difluorobenzyloxy)-6-methyl-2-oxo-2H-pyridin-1-ylmethyl]pyrazole-1-carboxylic acid tert-butyl ester (0.16 g, 0.34 mmol) was heated to 140° C. for 16 h. The reaction mixture was cooled to room temperature. $^1$H NMR (300 MHz, CDCl$_3$) δ 8.33 (s, 2H), 7.68 (d, J=6 Hz, 1H), 7.52 (app q, J=6 Hz, 1H), 6.93–6.83 (m, 2H), 6.47 68 (d, J=9 Hz, 1H), 5.19 (s, 2H), 5.24 (s, 2H), 5.20 (s, 2H).

Example 134

4-{[4-(benzyloxy)-3-bromo-2-oxopyridin-1(2H)-yl]methyl}benzonitrile

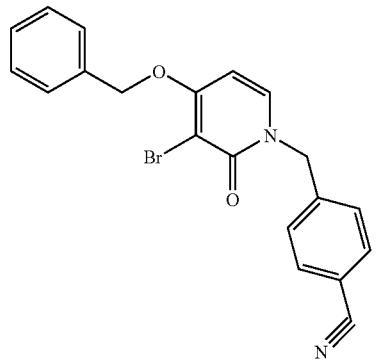

Preparation of 4-([4-(benzyloxy)-3-bromo-2-oxopyridin-1(2H)-yl]methyl}benzonitrile. 3-bromo-4-[(2,4-difluorobenzyl)oxy]-6-methylpyridin-2(1H)-one(1.0 g, 3.6 mmol) was dissolved in N,N-dimethylformamide (5 mL). α-Bromo-p-tolunitrile (0.85 g, 4.3 mmol) was added followed by $K_2CO_3$ (0.59 g, 4.3 mmol). The resulting mixture was heated to 80° C. for 16 h. The reaction was concentrated to an oil that was partitioned between water and ethyl acetate and extracted with ethyl acetate (3×100 ml). The organic extracts were combined, washed with brine, dried over $Na_2SO_4$, and filtered. The filtrate was concentrated to an oil, and purified by chromatography (silica gel, hexane/ethyl acetate) to yield a white solid (0.65 g, 46%). $^1$H NMR (400 MHz, $CDCl_3$) δ 7.62 (d, J=8.4 Hz, 2H), 7.41–7.31 (m, 7H), 7.23 (d, J=7.6 Hz, 1H), 6.11 (d, J=8.0 Hz, 1H), 5.24 (s, 2H), 5.18 (s, 2H). ES HRMS m/z 395.0404 (M+H $C_{20}H_{15}BrN_2O_2$ requires 395.0390).

Example 135

3-{[4-(benzyloxy)-3-bromo-2-oxopyridin-1(2H)-yl]methyl}benzonitrile

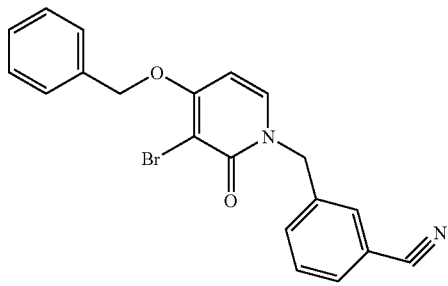

The title compound was prepared by a procedure essentially as described in example 134. $^1$H NMR (400 MHz, $CDCl_3$) δ 7.62–7.54 (m, 3H), 7.45 (d, J=7.6 Hz, 1H), 7.43–7.31 (m, 5H), 7.26 (d, J=1.6 Hz, 1H), 6.12 (d, J=1.6 Hz, 1H), 5.24 (s, 2H), 5.15 (s, 2H). ES HRMS m/z 395.0420 (M+H $C_{20}H_{15}BrN_2O_2$ requires 395.0390).

Example 136

2-{[4-(benzyloxy)-3-bromo-2-oxopyridin-1(2H)-yl]methyl}benzonitrile

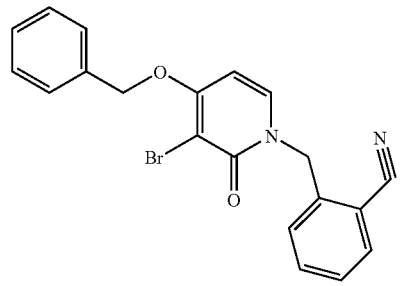

The title compound was prepared by a procedure essentially as described in example 134. $^1$H NMR (400 MHz, $CDCl_3$) δ 7.74 (d, J=8.4 Hz, 1H); 7.63 (dd, J=1.2, 8.0 Hz, 1H), 7.57 (dt, J=1.2, 8.4 Hz, 1H), 7.55 (d, J=8.0 Hz, 1H); 7.43–7.30 (m, 6H), 6.13 (d, J=8.0 Hz, 1H,), 5.33 (s, 2H), 5.23 (s, 2H). ES HRMS m/z 395.0398 (M+H $C_{20}H_{15}BrN_2O_2$ requires 395.0390).

Example 137

1-[4-(aminomethyl)benzyl]-4-(benzyloxy)-3-bromopyridin-2(1H)-one

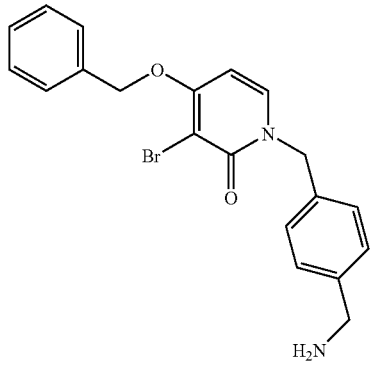

Preparation of 1-[4-(aminomethyl)benzyl]-4-(benzyloxy)-3-bromopyridin-2(1H)-one. EXAMPLE 134 (100 mg, 0.25 mmol) was dissolved in tetrahydrofuran (2 mL) under $N_2$. Borane dimethylsulfide complex (0.25 mL, 0.5 mmol, 2M in tetrahydrofuran) was added. The reaction was then heated to 70° C. and shaken overnight. The mixture was cooled and all the solvent was distilled under vacuum. The resulting residue was partitioned between ethyl acetate and 0.2 N NaOH, and extracted with ethyl acetate (3×10 mL). The organic extracts were combined, washed with brine, dried over $Na_2SO_4$, and filtered. The filtrate was concentrated to an oil, and triturated with dichloromethane and hexane to give an off-white solid. (80 mg, 80%). $^1$H NMR (400 MHz, $d_6$DMSO) δ 7.90 (d, J=7.6 Hz, 1H);

7.43–7.21 (m, 9H), 6.70 (d, J=7.6 Hz, 1H), 5.29 (s, 2H), 5.08 (s, 2H), 3.71 (s, 2H). ES HRMS m/z 399.0721 (M+H $C_{20}H_{19}BrN_2O_2$ requires 399.0703).

Example 138

1-[3-(aminomethyl)benzyl]-4-(benzyloxy)-3-bromopyridin-2(1H)-one

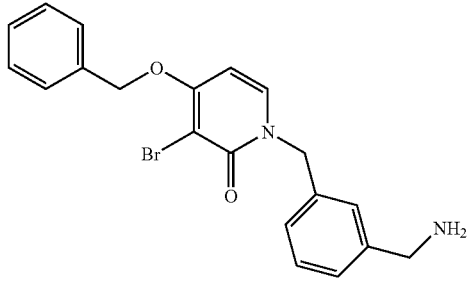

The title compound was prepared by a procedure essentially as described in Example 137 using the title compound of Example 135 as starting material. $^1$H NMR (400 MHz, $d_6$DMSO) δ 7.90 (d, J=7.6 Hz, 1H), 7.44–7.22 (m, 9H), 6.50 (d, J=7.6 Hz, 1H), 5.30 (s, 2H), 5.12 (s, 2H), 3.88 (s, 2H). ES HRMS m/z 399.0730 (M+H $C_{20}H_{19}BrN_2O_2$ requires 399.0703).

Example 139

1-[2-(aminomethyl)benzyl]-4-(benzyloxy)-3-bromopyridin-2(1H)-one

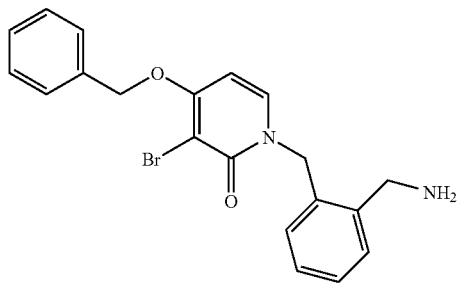

The title compound was prepared by a procedure essentially as described in Example 137 using the title compound of Example 136 as starting material. $^1$H NMR (400 MHz, $d_6$DMSO) δ 7.88 (d, J=8.0 Hz, 1H); 7.45–7.34 (m, 5H), 7.26–7.21 (m, 3H); 6.85 (d, J=7.2-Hz, 1H), 6.53 (d, J=7.6 Hz, 1H), 5.32 (s, 2H), 5.12 (s, 2H), 3.90 (s, 2H). ES HRMS m/z 399.0699 (M+H $C_{20}H_{19}BrN_2O_2$ requires 399.0703).

Example 140

4-{[4-(benzyloxy)-3-bromo-2-oxopyridin-1(2H)-yl]methyl}benzamide

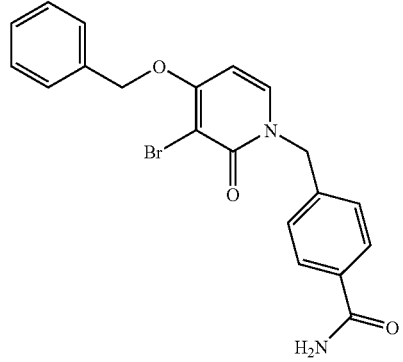

Preparation of 4-{[4-(benzyloxy)-3-bromo-2-oxopyridin-1(2H)-yl]methyl}benzamide. EXAMPLE 134 (100 mg, 0.25 mmol) was added to a suspension of potassium fluoride (40% on alumina) in t-butyl alcohol, heated to 85° C., and stirred for 20 h. The alumina was removed by filtration and washed with dichloromethane and water. The resulting filtrate was separated and the aqueous layer was extracted with dichloromethane (2×20 mL). The organic extracts were combined, dried over $Na_2SO_4$, and filtered. The filtrate was concentrated to an oil. Trituration with dichloromethane and hexane gave a solid (11.5 mg, 11%). $^1$H NMR (400 MHz, $d_6$DMSO) δ 7.94 (d, J=8.0 Hz 1H), 7.80 (d, J=8.4 Hz, 2H); 7.43–7.29 (m, 7H), 6.51 (d, J=7.6 Hz, 1H), 5.31 (s, 2H), 5.16 (s, 2H). ES HRMS m/z 413.0541 (M+H $C_{20}H_{17}BrN_2O_3$ requires 413.0495).

Example 141

3-{[4-(benzyloxy)-3-bromo-2-oxopyridin-1(2H)-yl]methyl}benzamide

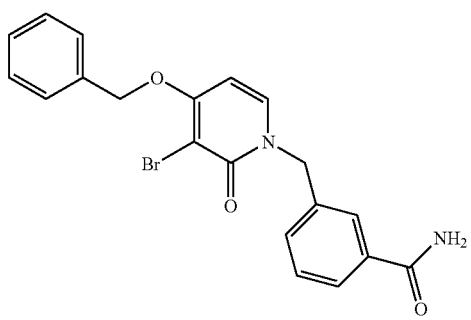

The title compound was prepared by a procedure essentially as described in Example 140 using the title compound of Example 135 as starting material. $^1$H NMR (400 MHz, $d_6$DMSO) δ 7.95 (d, J=7.6 Hz, 2H), 7.76 (m, 2H); 7.43–7.26 (m, 8H), 6.51 (d, J=7.6 Hz, 1H), 5.31 (s, 2H), 5.15 (s, 2H). ES HRMS m/z 413.0497 (M+H $C_{20}H_{17}BrN_2O_3$ requires 413.0495).

Example 142

2-{[4-(benzyloxy)-3-bromo-2-oxopyridin-1(2H)-yl]methyl}benzamide

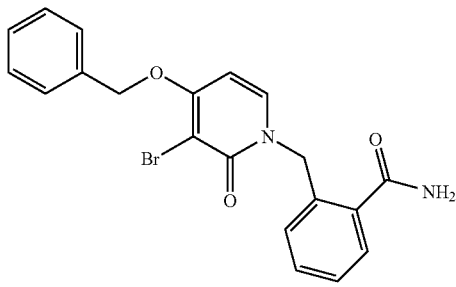

The title compound was prepared by a procedure essentially as described in Example 140 using the title compound of Example 136 as starting material. $^1$H NMR (400 MHz, d$_6$DMSO) δ 7.78 (d, J=7.6 Hz, 1H), 7.54 (dd, J=1.6, 7.6 Hz, 1H); 7.45 (d, J=7.6 Hz, 2H); 7.44–7.32 (m, 5H), 7.15 (d, J=7.6 Hz, 1H), 6.49 (d, J=7.6 Hz, 1H), 5.39 (s, 2H), 5.30 (s, 2H). ES HRMS m/z 4413.0506 (M+H C$_{20}$H$_{17}$BrN$_2$O$_3$ requires 413.0495).

Example 143

Methyl 3-{[4-(benzyloxy)-3-bromo-2-oxopyridin-1(2H)-yl]methyl}benzoate

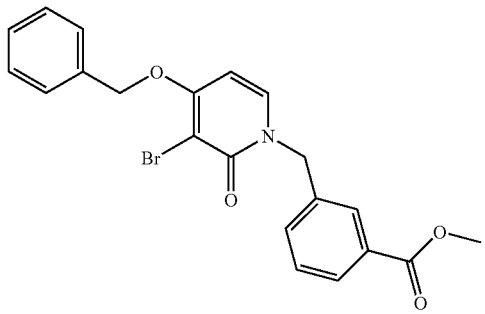

Preparation of Methyl 3-{[4-(benzyloxy)-3-bromo-2-oxopyridin-1(2H)-yl]methyl}benzoate. EXAMPLE 134 (100 mg, 0.25 mmol) was suspended in methanol and cooled to 0° C. HCl (g) was bubbled through the mixture until saturated (~30 minutes). The reaction was warmed to ambient temperature and stirred for 4 hours. HCl and methanol were removed in vacuo, yielding an oil, that was purified by chromatography (silica gel, hexane/ethyl acetate) to yield a white solid (3 mg, 3%). $^1$H NMR (400 MHz, CD$_3$OD) δ 7.98 (app d, J=8.0 Hz, 2H), 7.77 (app d, J=8.0 Hz, 1H); 7.55 (app d, J=8.0 Hz, 2H); 7.41–7.35 (m, 5H), 6.52 (d, J=7.6 Hz, 1H), 5.31 (s, 2H), 5.27 (s, 2H); 3.88, (s, 3H). API-ES MS m/z 429.0 (M+H C$_{21}$H$_{18}$BrNO$_4$ requires 428.0492).

Example 144

Methyl 4-{[4-(benzyloxy)-3-bromo-2-oxopyridin-1(2H)-yl]methyl}benzoate

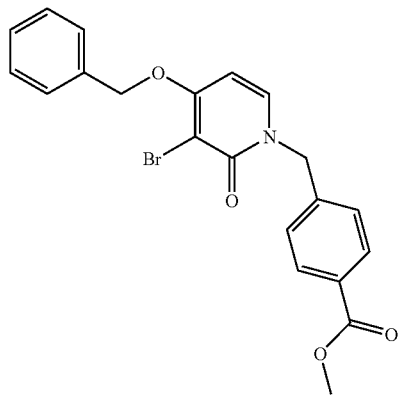

The title compound was prepared by a procedure essentially as described in Example 143 using the title compound of Example 134 as starting material. $^1$H NMR (400 MHz, CD$_3$OD) δ 7.94 (app d, J=8.4 Hz, 2H), 7.76 (app d, J=7.6 Hz, 1H); 7.46 (app d, J=8.0 Hz, 2H); 7.39–7.35 (m, 5H), 6.51 (d, J=7.6 Hz, 1H), 5.31 (s, 2H), 5.26 (s, 2H); 3.88, (s, 3H). ES HRMS m/z 428.0492 (M+H C$_{21}$H$_{18}$BrNO$_4$ requires 428.0492).

Example 145

4-(4-(benzyloxy)-3-bromo-2-oxopyridin-1(2H)-yl]benzonitrile

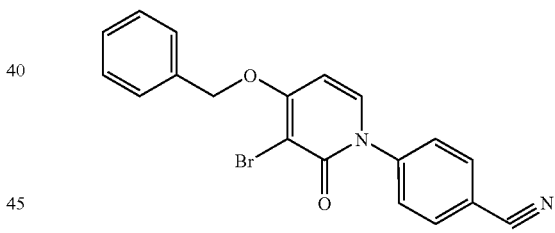

Preparation of 4-[4-(benzyloxy)-3-bromo-2-oxopyridin-1(2H)-yl]benzonitrile 3-bromo-4-[(2,4-difluorobenzyl)oxy]-6-methylpyridin-2(1H)-one(100 mg, 0.36 mmol) was suspended in dimethylsulfoxide (5 mL), cesium carbonate (375 mg, 1.15 mmol) was added and the reaction was shaken for 5 minutes. 4-Fluorobenzonitrile (52 mg, 0.43 mmol was then added, the reaction was heated to 80° C., and stirred. Reaction was monitored by LC/MS, and after 4 h was heated to 100° C. and stirred for 16 hours. Reaction mixture was partitioned between water and ethyl acetate and extracted with ethyl acetate (5×50 mL). The organic extracts were combined, washed with brine, dried over Na$_2$SO$_4$, and filtered. The filtrate was concentrated to an oil, and purified by chromatography (silica gel, hexane/ethyl acetate) to yield a white solid (40 mg, 29%). $^1$H NMR (400 MHz, CDCl$_3$) δ 7.77 (d, J=8.4 Hz, 2H), 7.52 (d, J=8.8 Hz, 2H), 7.44–7.42 (m, 4H), 7.28 (d, J=7.6 Hz, 1H), 7.26 (s, 1H), 6.24 (d, J=7.6 Hz, 1H); 5.31, (s, 2H). ES HRMS m/z 381.0230 (M+H C$_{19}$H$_{13}$BrN$_2$O$_2$ requires 381.0233).

Example 146

2-[4-(benzyloxy)-3-bromo-2-oxopyridin-1(2H)-yl]benzonitrile

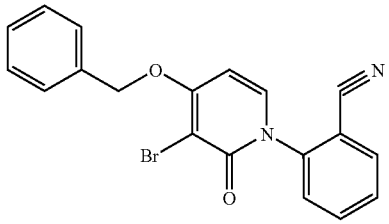

Preparation of 2-[4-(benzyloxy)-3-bromo-2-oxopyridin-1(2H)-yl]benzonitrile 3-bromo-4-[(2,4-difluorobenzyl)oxy]-6-methylpyridin-2(1H)-one(100 mg, 0.36 mmol) was suspended in dimethylsulfoxide (5 mL), cesium carbonate (375 mg, 1.15 mmol) was added and the reaction was shaken for 5 minutes. 4-Fluorobenzonitrile (52 mg, 0.43 mmol) was then added and the reaction was heated to 80° C. with stirring. Reaction was monitored by LC/MS, and after 4 h was heated to 100° C. and stirred for 16 hours. The reaction mixture was partitioned between water and ethyl acetate and extracted with ethyl acetate (5×50 mL). The organic extracts were combined, washed with brine, dried over $Na_2SO_4$, and filtered. The filtrate was concentrated to an oil, and purified by chromatography (silica gel, hexane/ethyl acetate) to yield a white solid (18 mg, 13%). $^1$H NMR (400 MHz, $CDCl_3$) δ 7.81 (dd, J=1.2, 8.4 Hz, 1H), 7.73 (dt, J=1.2, 8.0 Hz, 1H), 7.57 (dt, J -0.8, 8.0 Hz, 1H), 7.50–7.36 (m, 6H), 7.27 (d, J=8.0 Hz, 1H), 6.28 (d, J=8.0 Hz, 1H); 5.31 (s, 2H). ES HRMS m/z 381.0249 (M+H $C_{19}H_{13}BrN_2O_2$ requires 381.0233).

Example 147

(4-{[4-(benzyloxy)-3-bromo-2-oxopyridin-1(2H)-yl]methyl}phenyl)acetic acid

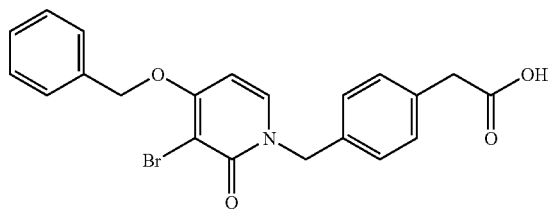

3-bromo-4-[(2,4-difluorobenzyl)oxy]-6-methylpyridin-2(1H)-one(0.5 g, 1.78 mmol) was dissolved in N,N-dimethylformamide (5 mL). 4-(Bromomethyl)phenylacetic acid (0.5 g, 2.14 mmol) was added followed by $K_2CO_3$ (0.3 g, 2.14 mmol). The reaction was heated to 80° C. and shaken for 16 hours, then heated to 100° C. and shaken for 16 hours more. The reaction mixture was partitioned between water and ethyl acetate and extracted with ethyl acetate (2×50 mL). The aqueous layer was acidified (pH 2) with 1N HCl and extracted with ethyl acetate (3×50 ml). The organic extracts were combined, washed with brine, dried over $Na_2SO_4$, and filtered. The filtrate was concentrated to an oil, and purified by chromatography (silica gel, hexane/ethyl acetate) followed by reversed phase chromatography ($C_{18}$, 0.1% aqueous trifluoroacetic acid /acetonitrile) to yield a white solid (25 mg, 3%). $^1$H NMR (400 MHz, $CDCl_3$) δ 7.40–7.38 (m, 3H), 7.25–7.20 (m, 7H), 6.05 (d, J=8.0 Hz, 1H), 5.21 (s, 2H); 5.13, (s, 2H); 3.62, (s, 2H). ES HRMS m/z 428.0510 (M+H $C_{21}H_{18}BrNO_4$ requires 428.0492).

Example 148

{4-[(4-(benzyloxy)-3-bromo-2-{[4-(carboxymethyl)benzyl]oxy}-1-lambda$^5$-pyridin-1-yl)methyl]phenyl}acetic acid

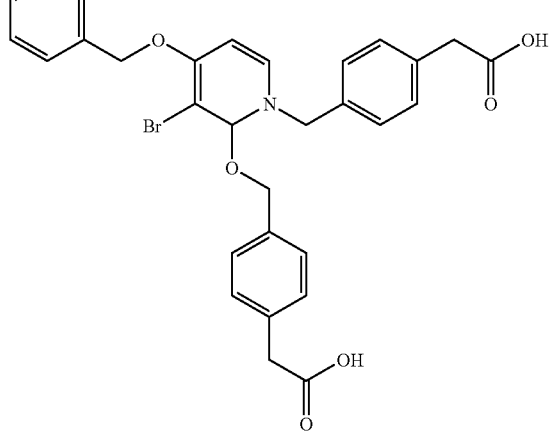

Preparation of {4-[(4-(benzyloxy)-3-bromo-2-{[4-(carboxymethyl)benzyl]oxy}-1-lambda$^5$-pyridin-1-yl)methyl]phenyl}acetic acid. The desired product was isolated by reversed phase chromatography ($C_{18}$, 0.1% aqueous trifluoroacetic acid/acetonitrile) using the preparation of Example 147 yielding a white solid (53 mg, 5%). $^1$H NMR (400 MHz, $CDCl_3$) δ 7.40–7.38 (m, 3H), 7.27–7.24 (m, 6H), 7.20 (d, J=7.6 Hz, 1H), 7.14 (d, J=8.0 Hz, 2H), 7.08 (d, J=8.4 Hz, 1H), 6.06 (d, J=7.6 Hz, 1H), 5.21 (s, 2H); 5.11 (s, 2H); 5.11 (s, 2H); 3.63 (s, 2H); 3.58 (s, 2H). ES HRMS m/z 576.1009(M+H $C_{30}H_{28}BrNO_6$ requires 576.1016).

Example 149

2-{[3-bromo-4-[(2,4-difluorobenzyl)oxy]-6-methyl-2-oxopyridin-1(2H)-yl]methyl}benzonitrile

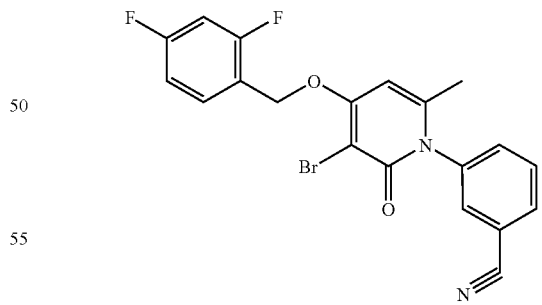

Preparation of 2-{[3-bromo-4-[(2,4-difluorobenzyl)oxy]-6-methyl-2-oxopyridin-1(2H)-yl]methyl}benzonitrile. 3-bromo-4-(2,4-difluorophenoxy)-6-methylpyridin-2(1H)-one (50 mg, 0.15 mmol) was dissolved in tetrahydrofuran (2 mL). α-Bromo-o-tolunitrile (44 mg, 0.23 mmol) was added followed by sodium hydride (7.2 mg, 0.18 mmol, 60% in mineral oil) and sodium iodide (56 mg, 0.38 mmol). The reaction was heated to 50° C. and stirred for 16 hours. The reaction was filtered through Celite® and the filtrate was concentrated to an oil that was partitioned between water and ethyl acetate and extracted with ethyl acetate (4×10 mL). The organic extracts were combined, washed with brine, dried over MgSO$_4$, and filtered. The filtrate was concentrated to an oil, and purified by chromatography (silica gel, hexane/ethyl acetate) to yield a white solid (25 mg, 37%). $^1$H NMR (400 MHz, CDCl$_3$) δ 7.68 (dd, J=8.0, 1.2 Hz, 1H); 7.58 (app q, J=8.8 Hz, 1H); 7.52 (dt, J=8.0 & 1.2 Hz, 1H), 7.38 (t, J=7.6 Hz, 1H); 7.08 (d, J=8.8 Hz, 1H), 7.00–6.93 (m, 1H); 6.89–6.84 (m, 1H); 6.05 (s, 1H), 5.57 (s, 2H), 5.22 (s, 2H); 2.28, (s, 3H). ES HRMS m/z 445.0335 (M+H C$_{21}$H$_{15}$BrF$_2$N$_2$O$_2$ requires 445.0358).

Example 150

3-{[3-bromo-4-[(2,4-difluorobenzyl)oxy]-6-methyl-2-oxopyridin-1(2H)-yl]methyl}benzonitrile

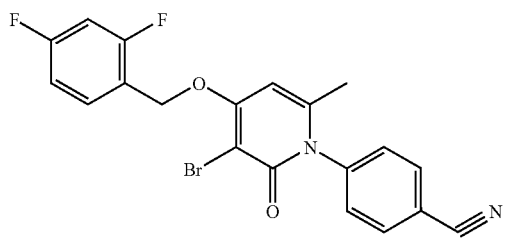

The title compound was prepared by a procedure essentially as described in Example 149 using 3-bromo-4-(2,4-difluorophenoxy)-6-methylpyridin-2(1H)-one (1 g, 3.0 mmol) as starting material. $^1$H NMR (CDCl$_3$, 400 MHz) δ 7.61–7.55 (m, 2H); 7.45–7.41 (m, 3H); 6.98–6.94 (m, 1H); 6.89–6.84 (m, 1H); 6.03 (s, 1H), 5.36 (s, 2H); 5.22 (s, 2H); 2.30, (s, 3H). ES HRMS m/z 445.0349 (M+H C$_{21}$H$_{15}$BrF$_2$N$_2$O$_2$ requires 445.0358).

Example 151

4-{[3-bromo-4-[(2,4-difluorobenzyl)oxy]-6-methyl-2-oxopyridin-1(2H)-yl]methyl}benzonitrile

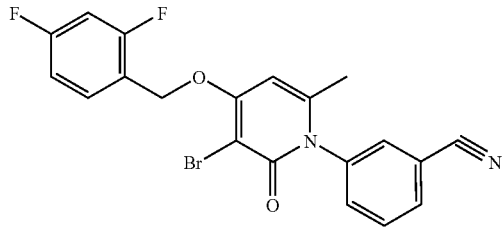

The title compound was prepared by a procedure essentially as described in Example 149 using 3-bromo-4-(2,4-difluorophenoxy)-6-methylpyridin-2(1H)-one (1 g, 3.0 mmol) as starting material. $^1$H NMR (400 MHz, CDCl$_3$) δ 7.61 (d, J=8.4 Hz, 2H); 7.62–7.56 (m, 1H); 7.27 (d, J=8.8 Hz, 2H); 6.95 (app t, J=8.4 Hz, 1H); 6.88–6.83 (m, 1H); 6.03 (s, 1H), 5.39 (s, 2H), 5.21 (s, 2H); 2.28 (s, 3H). ES HRMS m/z 445.0359 (M+H C$_{21}$H$_{15}$BrF$_2$N$_2$O$_2$ requires 445.0358).

Example 152

4-{[3-bromo-4-[(2,4-difluorobenzyl)oxy]-6-methyl-2-oxopyridin-1(2H)-yl]methyl}benzamide

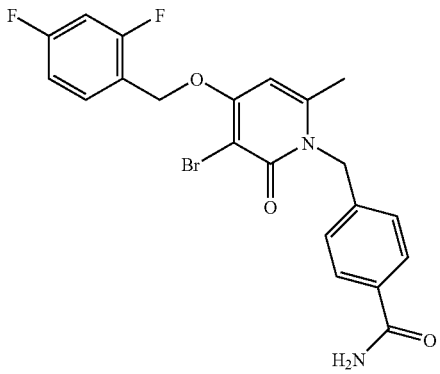

EXAMPLE 151 (50 mg, 0.11 mmol) was added to a suspension or potassium fluoride (40% on alumina) in t-butyl alcohol. The reaction was heated to 90° C. and stirred for 20 hours. Alumina was removed by filtration and washed with dichloromethane and water. The resulting filtrate was separated and the aqueous layer was extracted with dichloromethane (2×20 mL). The organic extracts were combined, dried over Na$_2$SO$_4$ and filtered. The filtrate was concentrated to an oil which was purified by chromatography (silica gel, hexane/ethyl acetate) to yield a white solid, yielding the product (13 mg, 25%). $^1$H NMR (400 MHz, CDCl$_3$) δ 7.75 (app d, J=8.4 Hz, 2H), 7.58 (app q, J=8.4 Hz, 1H); 7.24 (d, J=8.4 Hz, 2H); 6.98–6.94 (m, 1H), 6.89–6.83 (m, 1H), 6.01 (s, 1H); 5.40 (s, 2H), 5.21 (s, 2H); 2.28 (s, 3H). ES HRMS m/z 463.0486 (M+H C$_{21}$H$_{17}$BrF$_2$N$_2$O$_3$ requires 463.0463).

Example 153

Methyl 4-{[3-bromo-4-[(2,4-difluorobenzyl)oxy]-6-methyl-2-oxopyridin-1(2H)-yl]methyl}benzoate

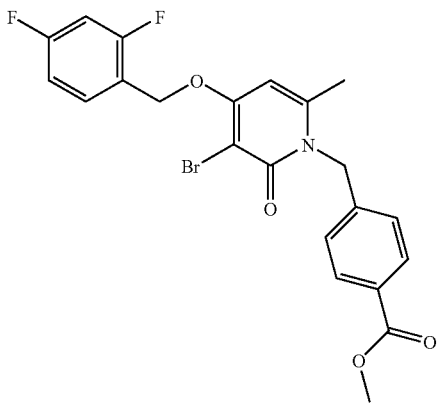

EXAMPLE 151 (50 mg, 0.11 mmol) was suspended in methanol and cooled to 0° C. HCl (g) was bubbled through the mixture until saturated (~30 minutes). Reaction was sealed, warmed to ambient temperature, and stirred for 2 hours. HCl and methanol were removed in vacuo, yielding an oil, that was purified by chromatography (silica gel, hexane/ethyl acetate) to yield a white solid (19 mg, 36%). $^1$H NMR (400 MHz, CDCl$_3$) δ 7.97 (app d, J=8.4 Hz, 2H), 7.58 (app q, J=8.0 Hz, 1H); 7.22 (d, J=8.4 Hz, 2H); 6.95 (app dt, J=1.5, 9.6 Hz, 1H), 6.89–6.83 (m, 1H), 6.00 (s, 1H); 5.41 (s, 2H), 5.21 (s, 2H); 3.90, (s, 3H); 2.27 (s, 3H). ES HRMS m/z 478.0461 (M+H C$_{22}$H$_{18}$BrNO$_4$ requires 478.0460).

Example 154

Methyl 3-{[3-bromo-4-[(2,4-difluorobenzyl)oxy]-6-methyl-2-oxopyridin-1(2H)-yl]methyl}benzoate

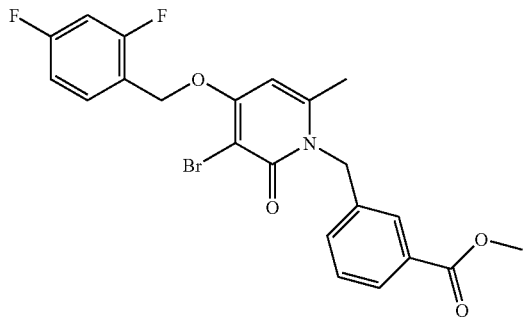

The title compound was prepared by a procedure essentially as described in Example 149 using the title compound of Example 150 as starting material. $^1$H NMR (400 MHz, CDCl$_3$) δ 7.95–7.92 (m, 1H); 7.84 (bs, 1H); 7.58 (app q, J=8.0 Hz, 1H); 7.39–7.37 (m, 2H); 6.95 (app dt, J=1.6, 8.4 Hz, 1H), 6.88–6.83 (m, 1H), 6.00 (s, 1H); 5.40 (s, 2H), 5.21 (s, 2H); 3.90, (s, 3H); 2.30 (s, 3H). ES HRMS m/z 478.0449 (M+H C$_{22}$H$_{18}$BrNO$_4$ requires 478.0460).

Example 155

3-{[3-bromo-4-[(2,4-difluorobenzyl)oxy]-6-methyl-2-oxopyridin-1(2H)-yl]methyl}benzamide

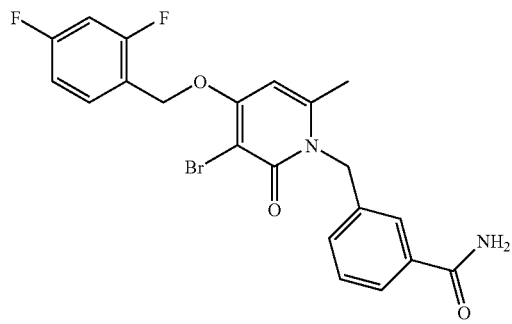

The title compound was prepared by a procedure essentially as described in Example 152 using the title compound of Example 150 as starting material. $^1$H NMR (400 MHz, CDCl$_3$) δ 7.68–7.66 (m, 2H), 7.57 (app q, J=8.4 Hz, 1H); 7.42–7.34 (m, 2H); 6.98–6.92 (m, 1H); 6.89–6.83 (m, 1H), 6.01 (s, 1H); 5.39 (s, 2H), 5.21 (s, 2H); 2.28 (s, 3H). ES HRMS m/z 463.0461 (M+H C$_{21}$H$_{17}$BrF$_2$N$_2$O$_3$ requires 463.0463).

Example 156

2-{[3-bromo-4-[(2,4-difluorobenzyl)oxy]-6-methyl-2-oxopyridin-1(2H)-yl]methyl}benzamide

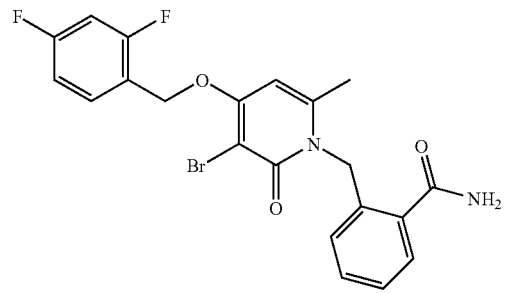

The title compound was prepared by a procedure essentially as described in Example 152 using the title compound of Example 149 as starting material. $^1$H NMR (400 MHz, CDCl$_3$) δ 7.68–7.66 (m, 2H), 7.57 (app q, J=8.4 Hz, 1H); 7.42–7.34 (m, 2H); 6.98–6.92 (m, 1H), 6.89–6.83 (m, 1H), 6.01 (s, 1H); 5.39 (s, 2H), 5.21 (s, 2H); 2.28 (s, 3H). ES HRMS m/z 463.0461 (M+H C$_{21}$H$_{17}$BrF$_2$N$_2$O$_3$ requires 463.0463). $^1$H NMR (400 MHz, CDCl$_3$) δ 7.56–7.55 (m, 2H); 7.32–7.25 (m, 2H); 7.00–6.94 (m, 1H), 6.88–6.84 (m, 1H); 6.81–6.79 (m, 1H), 6.11 (s, 1H); 5.51 (s, 2H), 5.24 (s, 2H); 2.43 (s, 3H). ES HRMS m/z 463.0467 (M+H C$_{21}$H$_{17}$BrF$_2$N$_2$O$_3$ requires 463.0463).

Example 157

1-[2-(aminomethyl)benzyl]-3-bromo-4-[(2,4-difluorobenzyl)oxy]-6-methylpyridin-2(1H)-one

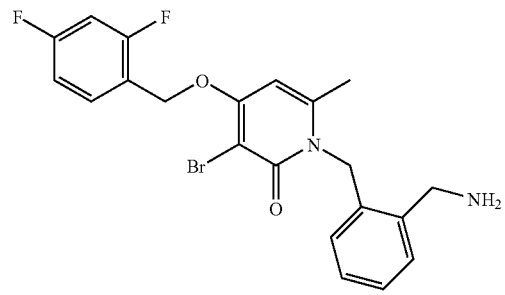

EXAMPLE 149 (50 mg, 0.11 mmol) was dissolved in tetrahydrofuran (2 mL) under N$_2$. Borane-methyl sulfide complex (0.11 mL, 0.22 mmol, 2M in tetrahydrofuran) was added. The reaction was then heated to 70° C. and shaken overnight. After cooling to ambient temperature, all the solvent was distilled under vacuum. The resulting residue was partitioned between ethyl acetate and 0.2 N NaOH, and extracted with ethyl acetate (3×20 mL). The organic extracts were combined, washed with brine, and dried over Na$_2$SO$_4$, and filtered. The filtrate was concentrated to an oil, and purified by chromatography (silica gel, hexane/ethyl acetate) to yield a white solid, to give product (19 mg, 39%). $^1$H NMR (400 MHz, CDCl$_3$) δ 7.56–7.55 (m, 2H); 7.32–7.25 (m, 2H); 7.00–6.94 (m, 1H), 6.88–6.84 (m, 1H); 6.81–6.79 (m, 1H); 6.11 (s, 1H); 5.44 (s, 2H), 5.17 (s, 2H); 4.59 (s, 2H); 2.18 (s, 3H). ES HRMS m/z 449.0692 (M+H C$_{21}$H$_{19}$BrF$_2$N$_2$O$_2$ requires 449.0671).

Example 158

3-bromo-1-[3-(bromomethyl)benzyl]-4-[(2,4-difluorobenzyl)oxy]-6-methylpyridin-2(1H)-one

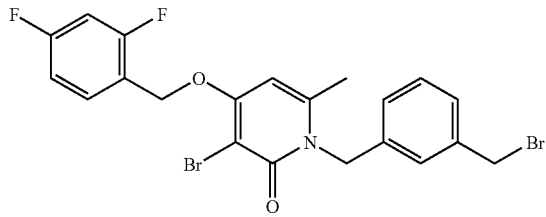

Preparation of 3-bromo-1-[3-(bromomethyl)benzyl]-4-[(2,4-difluorobenzyl)oxy]-6-methylpyridin-2(1H)-one.

3-bromo-4-[(2,4-difluorobenzyl)oxy]-6-methylpyridin-2(1H)-one (2 g, 6.06 mmol) was suspended in 1,4-dioxane (250 mL). α,α'-Dibromo-m-xylene (8 g, 30.3 mmol) was added followed by sodium hydride (0.3 g, 7.5 mmol, 60% in mineral oil). The reaction was heated to 60° C. and stirred for 16 hours. The reaction was filtered through Celite® and the filtrate was concentrated to an oil that was partitioned between water and dichloromethane and extracted with dichloromethane (4×250 mL). The organic extracts were combined, washed with brine, dried over $Na_2SO_4$, and filtered. The filtrate was concentrated to an oil, and purified by chromatography (silica gel, hexane/ethyl acetate) to yield a white solid (1.2 g, 38%). $^1$H NMR (400 MHz, $CDCl_3$) δ 7.57 (app q, J=7.6 Hz, 1H); 7.28–7.25 (m, 2H); 7.17 (s, 1H); 7.08 (m, 1H); 6.94 (app dt, J=1.2, 9.6 Hz, 1H), 6.87–6.82 (m, 1H); 5.99 (s, 1H), 5.34 (s, 2H), 5.20 (s, 2H); 4.43 (s, 2H); 2.29 (s, 3H). ES HRMS m/z 511.9672 (M+H $C_{21}H_{17}Br_2F_2NO_2$ requires 511.9667).

Example 159

3-bromo-1-[4-(bromomethyl)benzyl]-4-[(2,4-difluorobenzyl)oxy]-6-methylpyridin-2(1H)-one

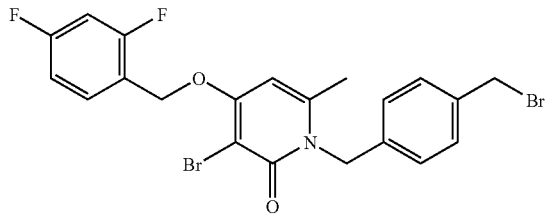

The title compound was prepared by a procedure essentially as described in Example 158. $^1$H NMR (400 MHz, $CDCl_3$) δ 7.68–7.66 (m, 2H), 7.57 (app q, J=8.4 Hz, 1H); 7.42–7.34 (m, 2H); 6.98–6.92 (m, 1H), 6.89–6.83 (m, 1H), 6.01 (s, 1H); 5.39 (s, 2H), 5.21 (s, 2H); 2.28 (s, 3H). ES HRMS m/z 463.0461 (M+H $C_{21}H_{17}BrF_2N_2O_3$ requires 463.0463). $^1$H NMR (400 MHz, $CDCl_3$) δ 7.56 (app q, J=7.6 Hz, 1H); 7.32 (d, J=8.0 Hz, 2H); 7.14 (d, J=8.0 Hz, 2H); 6.94 (app t, J=8.4 Hz, 1H), 6.87–6.82 (m, 1H); 5.98 (s, 1H), 5.33 (s, 2H), 5.19 (s, 2H); 4.44 (s, 2H); 2.29 (s, 3H). ES HRMS m/z 511.9683 (M+H $C_{21}H_{17}Br_2F_2NO_2$ requires 511.9667).

Example 160

1-[4-(aminomethyl)benzyl]-3-bromo-4-[(2,4-difluorobenzyl)oxy]-6-methylpyridin-2(1H)-one

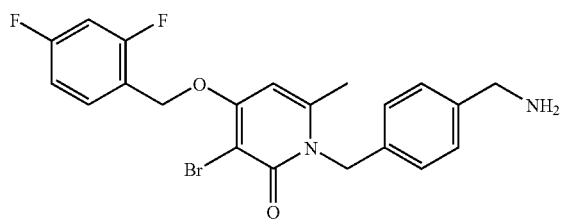

Example 159 (200 mg, 0.39 mmol) was suspended in methanol (3 mL) and cooled to −78° C. Ammonia (g) was bubbled through the mixture for 30 minutes. The reaction vessel was sealed, allowed to reach ambient temperature, and stirred for 4 hours. The solvent and ammonia were removed from the reaction in vacuo with stirring and the resulting oil was triturated with ether to yield a solid (174 mg, 99%). $^1$H NMR (400 MHz, $CD_3OD$) δ 7.61 (q, J=7.6 Hz, 1H); 7.40 (d, J=8.0 Hz, 2H); 7.20 (d, J=8.0 Hz, 2H); 7.03 (app t, J=8.8 Hz, 2H), 6.51 (s, 1H), 5.43 (s, 2H), 5.29 (s, 2H); 4.07 (s, 2H); 2.36 (s, 3H). ES HRMS m/z 449.0673 ($C_{21}H_{19}BrF_2N_2O_2$ requires 449.0671).

Examples 161–168

The compounds of Examples 161–168 are prepared essentially according to the procedures set forth above for Examples 158–160 or by using the compound of Example 158:

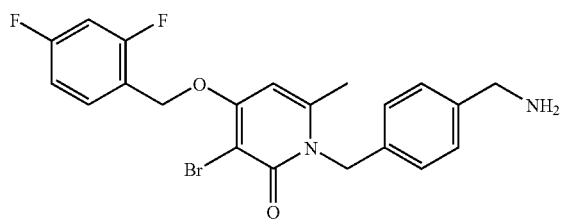

| Example No. | R | MF | M + H Requires | EHSRMS m/z |
|---|---|---|---|---|
| Ex. 161 | —$NH_2$ | $C_{21}H_{19}BrF_2N_2O_2$ | 449.0671 | 449.0694 |
| Ex. 162 | morpholin-4-yl | $C_{25}H_{25}BrF_2N_2O_3$ | 519.1089 | 519.1132 |
| Ex. 163 | dimethylamino | $C_{23}H_{23}BrF_2N_2O_2$ | 477.0984 | 477.0991 |
| Ex. 164 | isopropylamino | $C_{24}H_{25}BrF_2N_2O_2$ | 491.1140 | 491.1121 |
| Ex. 165 | piperidin-1-yl | $C_{26}H_{27}BrF_2N_2O_2$ | 517.1297 | 517.1341 |
| Ex. 166 | (2-hydroxyethyl)-amino | $C_{23}H_{23}BrF_2N_2O_3$ | 493.0933 | 493.0961 |
| Ex. 167 | bis(2-hydroxyethyl)amino | $C_{25}H_{27}BrF_2N_2O_4$ | 537.1195 | 537.1171 |
| Ex. 168 | piperazin-1-yl | $C_{25}H_{26}BrF_2N_2O_2$ | 518.1249 | 518.1280 |

NMR characterization of compounds of Examples 161–168

| Ex. No. | NMR Data |
|---|---|
| Ex. 161 | $^1$H NMR (400 MHz, $CD_3OD$) δ 7.61(q, J=7.6Hz, 1H); 7.42–7.35(m, 2H), 7.24–7.20(m, 2H), 7.03(app t, J=8.4Hz, 2H), 6.51(s, 1H), 5.43(s, 2H), 5.29(s, 2H); 4.07(s, 2H); 2.04(s, 3H) |

-continued

| Ex. 162 | ¹H NMR (400 MHz, CD₃OD) δ 7.58(app q, J=7.6Hz, 1H); 7.26–7.22(m, 2H), 7.15(s, 2H), 7.01(app d, J=6.4Hz, 2H), 6.95(app dt, J=1.2, 8.0Hz, 1H); 6.88–6.82(m, 1H); 5.98(s, 1H), 5.35(s, 2H), 5.20(s, 2H); 3.69(t, J=8.4Hz, 4H); 3.46(s, 2H); 2.41(m, 4H); 2.29(s, 3H) |
|---|---|
| Ex. 163 | ¹H NMR (400 MHz, CD₃OD) δ 7.61(app q, J=7.6Hz, 1H); 7.25–7.14(m, 3H); 7.01–6.92(m, 2H); 6.85(m, 1H); 5.97(s, 1H), 5.36(s, 2H), 5.20(s, 2H); 3.38(s, 2H); 2.28 (s, 3H); 2.21(s, 6H) |
| Ex. 164 | ¹H NMR (400 MHz, CDCl₃) δ 7.61(app q, J=8.0Hz, 1H); 7.25–7.22(m, 2H); 7.14(s, 1H), 6.99(app d, 6.8Hz, 1H), 6.94(app dt, J=2.0, 8.0Hz, 1H); 6.88–6.80(m, 1H); 5.97(s, 1H), 5.34(s, 2H), 5.19(s, 2H); 3.73(s, 2H); 2.28(s, 3H); 2.82(app heptet, J=6.0Hz, 1H), 1.07(d, J=6.0Hz, 6H) |
| Ex. 165 | ¹H NMR (400 MHz, CD₃OD) δ 7.61(app q, J=8.0Hz, 1H); 7.27(app t, J=8.0Hz, 1H); 7.20(app d, J=7.6Hz, 1H); 7.08(bs, 1H); 7.01(app t, J=8.0Hz, 2H); 6.48(s, 1H), 5.41(s, 2H), 5.28(s, 2H); 3.44(s, 2H); 2.35 (s, 3H); 2.40–2.30(m, 4H); 1.57–1.53(m, 4H); 1.48–1.38(m, 2H) |
| Ex. 166 | ¹H NMR (400 MHz, CDCl₃) δ 7.51(app q, J=8.0Hz, 1H); 7.22–7.14(m, 3H); 7.09(bs, 1H); 6.98(app d, J=7.2Hz, 1H); 6.89(app dt, J=1.6, 8.0Hz, 1H); 6.81–6.76(m, 1H); 5.92(s, 1H), 5.28(s, 2H), 5.14(s, 2H); 3.73 (s, 2H); 3.59(app t, J=4.8Hz, 2H); 2.73(app t, J=4.8Hz, 2H); 2.24(s, 3H) |
| Ex. 167 | ¹H NMR (400 MHz, CD₃OD) δ 7.61(app q, J=8.0Hz, 1H); 7.46(app d, J=8.8Hz, 2H); 7.31(bs, 1H); 7.27 (app t, J=8.0Hz, 1H); 7.03(app t, J=8.8Hz, 2H); 6.54(s, 1H), 5.44(s, 2H), 5.30(s, 2H); 4.47(s, 2H); 3.90–3.84(m, 4H); 3.40–3.25(m, 4H); 2.40(s, 3H) |
| Ex. 168 | ¹H NMR (400 MHz, CD₃OD) δ 7.62(app q, J=8.0Hz, 1H); 7.53–7.46(m, 2H); 7.36(bs, 1H); 7.30(app d, J=7.6Hz, 1H); 7.05–7.01(m, 2H), 6.55(s, 1H), 5.44(s, 2H), 5.30(s, 2H); 4.47(s, 2H); 3.58–3.53(m, 8H); 2.42(s, 3H) |

Example 169

3-{[3-bromo-4-[(2,4-difluorobenzyl)oxy]-6-methyl-2-oxopyridin-1(2H)-yl]methyl}benzoic acid

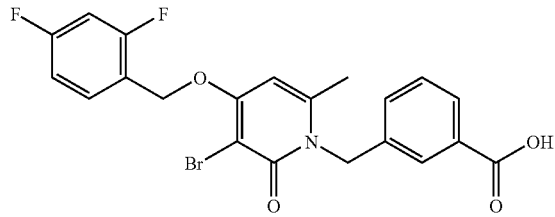

Preparation of 3-{[3-bromo-4-[(2,4-difluorobenzyl)oxy]-6-methyl-2-oxopyridin-1(2H)-yl]methyl}benzoic acid. EXAMPLE 154 (150 mg, 0.31 mmol) was dissolved in tetrahydrofuran (5 mL). Potassium trimethylsilanolate (80 mg, 0.62 mmol) was added and the reaction was stirred at ambient temperature for 4 hours. The reaction mixture was concentrated to an oil that was partitioned between water and ethyl acetate and extracted with ethyl acetate. The organic extracts were combined, washed with brine, dried over Na₂SO₄, and filtered. The filtrate was concentrated to an oil and purified by reversed phase chromatography (C₁₈, 0.1% aqueous trifluoroacetic acid/acetonitrile) to yield the product (64 mg, 44%) ¹H NMR (400 MHz, CD₃OD) δ 7.92 (app d, J=8.0 Hz, 1H); 7.78 (s, 1H), 7.62 (app q, J=8.0 Hz, 1H); 7.44 (t, J=7.6 Hz, 1H); 7.36 (app d, J=8.0 Hz, 1H); 7.02 (app t, J=7.6 Hz, 2H); 6.51 (s, 1H), 5.48 (s, 2H), 5.30 (s, 2H); 2.37 (s, 3H). ES HRMS m/z 464.0328 (C₂₁H₁₆BrF₂NO₄ requires 464.0304).

Examples 170–174

The compounds of Examples 170–174 are prepared using the compound of Example 159 or 161:

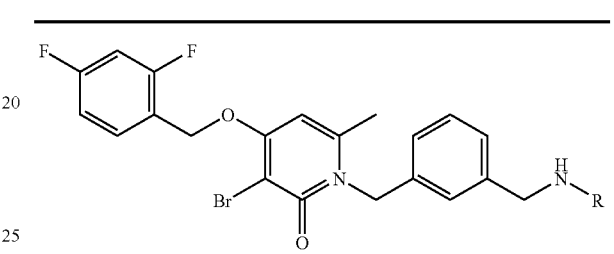

| Example No. | R | MF | M + H Requires | ESHRMS m/z |
|---|---|---|---|---|
| Ex. 170 | —C(O)CH₃ | C₂₃H₂₁BrF₂N₂O₃ | 491.0776 | 491.0772 |
| Ex. 171 | —C(O)OCH₃ | C₂₃H₂₁BrF₂N₂O₄ | 507.0726 | 507.0731 |
| Ex. 172 | —SO₂CH₃ | C₂₂H₂₁BrF₂N₂O₄S | 527.0446 | 527.0430 |
| Ex. 173 | —C(O)CH₂OH | C₂₃H₂₁BrF₂N₂O₄ | 507.0726 | 507.0712 |
| Ex. 174 | —C(O)NH₂ | C₂₂H₂₀BrF₂N₃O₃ | 492.0729 | 492.0751 |

NMR characteristics of compounds of Examples 170–174

| Ex. No. | NMR Data |
|---|---|
| Ex. 170 | ¹H NMR (400 MHz, CD₃OD) δ 7.61(app q, J=8.0Hz, 1H); 7.28(app t, J=8.0, 1H), 7.18(app d, J=8.0Hz, 1H), 7.05–7.00(m, 4H); 6.49(s, 1H), 5.41(s, 2H), 5.29(s, 2H); 2.37(s, 3H); 1.94(s, 3H) |
| Ex. 171 | ¹H NMR (400 MHz, CDCl₃) δ 7.57(app q, J=7.6Hz, 1H); 7.25(app t, J=8.0, 1H), 7.17(app d, J=8.0Hz, 1H), 7.06–7.02(m, 2H); 6.97–6.91(m, 1H); 6.87–6.82(m, 1H), 5.98(s, 1H), 5.33(s, 2H), 5.19(s, 2H); 4.30(d, J=6.0Hz, 2H); 3.67(s, 3H); 2.28(s, 3H) |
| Ex. 172 | ¹H NMR (400 MHz, CD₃CN) δ 7.58(app q, J=7.6Hz, 1H); 7.31(app t, J=8.0, 1H), 7.24(app d, J=8.0Hz, 1H), 7.11(s, 1H); 7.05–7.00(m, 3H); 6.32(s, 1H), 6.06(bs, 1H), 5.31(s, 2H), 5.23(s, 2H); 4.17(d, J=6.4Hz, 2H); 2.78(s, 3H); 2.28(s, 3H) |
| Ex. 173 | ¹H NMR (400 MHz, CDCl₃) δ 7.55(app q, J=8.0Hz, 1H); 7.23(aqpp t, J=7.6, 1H), 7.15(app d, J=7.2Hz, 1H), 7.05–7.00(m, 3H); 6.94(app dt, J=1.2, 8.8Hz, 1H); 6.88–6.81(m, 1H); 6.03(s, 1H), 5.27(s, 2H), 5.19(s, 2H); 4.39(d, J=6.4Hz, 2H); 4.05(s, 2H), 2.31(s, 3H) |
| Ex. 174 | ¹H NMR (400 MHz, CD₃OD) δ 7.62(app q, J=8.0Hz, 1H); 7.28(app t, J=8.0, 1H), 7.19(app d, J=8.0Hz, 1H), 7.05–6.96(m, 4H); 6.49(s, 1H), 5.41(s, 2H), 5.29(s, 2H); 4.25(s, 2H); 2.35(s, 3H) |

Examples 175–185

The compounds of Examples 175–175 are prepared using the compounds of Examples 159 or 160:

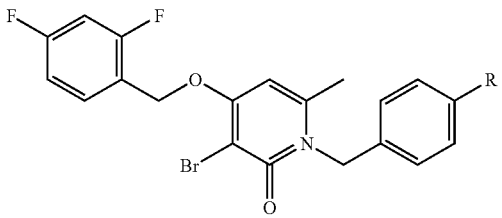

| Example No. | R | MF | M + H Requires | ESHRMS m/z |
|---|---|---|---|---|
| Ex. 175 | —CH$_2$NHCH(CH$_3$)$_2$ | C$_{24}$H$_{25}$BrF$_2$N$_2$O$_2$ | 491.1140 | 491.1143 |
| Ex. 176 | morpholin-4-ylmethyl | C$_{25}$H$_{25}$BrF$_2$N$_2$O$_3$ | 519.1089 | 519.1062 |
| Ex. 177 | —CH$_2$N(CH$_3$)$_2$ | C$_{23}$H$_{23}$BrF$_2$N$_2$O$_2$ | 477.0984 | 477.0931 |
| Ex. 178 | piperidin-1-ylmethyl | C$_{26}$H$_{27}$BrF$_2$N$_2$O$_2$ | 517.1297 | 517.1258 |
| Ex. 179 | [bis(2-hydroxyethyl)-amino]methyl | C$_{25}$H$_{27}$BrF$_2$N$_2$O$_4$ | 537.1195 | 537.1181 |
| Ex. 180 | —CH$_2$NHCH$_2$CH$_2$OH | C$_{23}$H$_{23}$BrF$_2$N$_2$O$_3$ | 493.0933 | 493.0907 |
| Ex. 181 | piperazin-1-ylmethyl | C$_{25}$H$_{26}$BrF$_2$N$_3$O$_2$ | 518.1249 | 518.1213 |
| Ex. 182 | —CH$_2$NHC(O)OCH$_3$ | C$_{23}$H$_{21}$BrF$_2$N$_2$O$_4$ | 507.0726 | 507.0752 |
| Ex. 183 | —CH$_2$NHC(O)CH$_3$ | C$_{23}$H$_{21}$BrF$_2$N$_2$O$_3$ | 491.0776 | 491.0793 |
| Ex. 184 | —CH$_2$NHSO$_2$CH$_3$ | C$_{22}$H$_{21}$BrF$_2$N$_2$O$_4$S | 527.0446 | 527.0431 |
| Ex. 185 | —CH$_2$NHC(O)NH$_2$ | C$_{22}$H$_{20}$BrF$_2$N$_3$O$_3$ | 492.0729 | 492.0720 |

NMR characterization of compounds of Examples 175–185

| Ex. No. | NMR Data |
|---|---|
| Ex. 175 | $^1$H NMR (400 MHz, CDCl$_3$) δ 7.56(q, J=8.0Hz, 1H); 7.25(d, J=8.0Hz, 2H), 7.10(d, J=8.0Hz, 2H), 6.94(app t, J=8.0Hz, 1H), 6.88–6.80(m, 1H); 5.97(s, 1H), 5.31(s, 2H), 5.19(s, 2H); 3.74(s, 2H); 2.82 (app heptet, J=6.0Hz, 1H), 2.28(s, 3H); 1.09(d, J=6.4Hz, 6H) |
| Ex. 176 | $^1$H NMR (400 MHz, CDCl$_3$) δ 7.56(q, J=8.0Hz, 1H); 7.25(d, J=8.0Hz, 2H), 7.11(d, J=8.0Hz, 2H), 6.94(app dt, J=2.0, 8.0Hz, 1H), 6.87–6.81(m, 1H); 5.97(s, 1H), 5.33(s, 2H), 5.19(s, 2H); 3.67(app t, J=4.8Hz, 4H); 3.44(s, 2H); 2.44–2.38(m, 4H), 2.29(s, 3H) |
| Ex. 177 | $^1$H NMR (400 MHz, CDCl$_3$) δ 7.56(q, J=8.0Hz, 1H); 7.23(d, J=8.0Hz, 2H), 7.11(d, J=8.0Hz, 2H), 6.93(app dt, J=2.0, 8.0Hz, 1H), 6.86–6.81(m, 1H); 5.96(s, 1H), 5.33(s, 2H), 5.18(s, 2H); 3.38(s, 2H); 2.29(s, 3H); 2.20(s, 6H) |
| Ex. 178 | $^1$H NMR (400 MHz, CDCl$_3$) δ 7.56(q, J=8.0Hz, 1H); 7.24–7.20(m, 2H), 7.10–7.07(m, 2H), 6.96–6.90(m, 1H), 6.86–6.81(m, 1H); 5.96(s, 1H), 5.32(s, 2H), 5.18(s, 2H); 3.34(s, 2H); 2.31(s, 3H); 2.31–2.28(m, 4H); 1.53–1.51(m, 4H); 1.39(m, 2H) |
| Ex. 179 | $^1$H NMR (400 MHz, CDCl$_3$) δ 7.57(q, J=8.0Hz, 1H); 7.25(d, J=8.0Hz, 2H); 7.12(d, J=8.0Hz, 2H); 6.94(dt, J=8.8Hz, 2H); 6.87–6.82(m, 1H), 5.98(s, 1H), 5.33(s, 2H), 5.19(s, 2H); 3.68(s, 2H); 3.61(t, J=5.2Hz, 4H); 2.70(t, J=5.2Hz, 4H); 2.29(s, 3H) |
| Ex. 180 | $^1$H NMR (400 MHz, CDCl$_3$) δ 7.57(q, J=8.0Hz, 1H); 7.25(d, J=8.0Hz, 2H), 7.12(d, J=8.0Hz, 2H); 6.94(app dt, J=8.8Hz, 2H); 6.87–6.82(m, 1H), 5.98(s, 1H), 5.33(s, 2H); 5.19(s, 2H); 3.68(s, 2H); 3.61(t, J=5.2Hz, 4H); 2.70(t, J=5.2Hz, 4H); 2.29(s, 3H) |
| Ex. 181 | $^1$H NMR (400 MHz, CDCl$_3$) δ 7.61(q, J=8.0Hz, 1H); 7.52(d, J=8.0Hz, 2H); 7.25(d, J=8.0Hz, 2H); 7.03(app t, J=8.0Hz, 2H), 6.53(s, 1H), 5.44(s, 2H), 5.30(s, 2H); 4.32(bs, 2H); 3.55–3.35(m, 8H); 2.39(s, 3H) |
| Ex. 182 | $^1$H NMR (400 MHz, CDCl$_3$) δ 7.56(app q, J=8.0Hz, 1H); 7.20(d, J=8.0Hz, 1H), 7.13(d, J=8.0Hz, 2H), 6.94(app dt, J=1.2, 8.0Hz, 1H), 6.87–6.81(m, 2H); 5.97(s, 1H), 5.32(s, 2H), 5.19(s, 2H); 4.31(d, J=6.0Hz, 2H); 3.68(s, 3H); 2.28(s, 3H) |
| Ex. 183 | $^1$H NMR (400 MHz, CDCl$_3$) δ 7.61(app q, J=8.0Hz, 1H); 7.23(d, J=8.0Hz, 2H), 7.08(d, J=8.0Hz, 2H), 7.04–6.99(m, 2H); 6.47(s, 1H), 5.39(s, 2H), 5.28(s, 2H); 4.30(s, 2H); 2.34(s, 3H); 1.95(s, 3H) |

-continued

| Ex. 184 | $^1$H NMR (400 MHz, CD$_3$OD) δ 7.62(app q, J=8.0Hz, 1H); 7.34(d, J=8.4Hz, 2H), 7.11(d, J=8.4Hz, 2H), 7.02(app t, J=8.8Hz, 2H), 6.48(s, 1H), 5.42(s, 2H), 5.28(s, 2H); 4.21(s, 2H); 2.82(s, 3H); 2.35(s, 3H) |
| --- | --- |
| Ex. 185 | $^1$H NMR (400 MHz, d$_7$DMF) δ 7.76(app q, J=8.0Hz, 1H); 7.28(d, J=8.0Hz, ), 7.14(d, J=8.0Hz, 2H), 7.34–7.26(m, 1H); 7.22–7.14(m, 1H); 6.62(s, 1H), 5.65(s, 2H), 5.39(s, 2H), 5.37(s, 2H); 4.26(d, J=6.0Hz, 2H); 2.40(s, 3H) |

Example 186

4-(4-{[3-bromo-4-[(2,4-difluorobenzyl)oxy]-6-methyl-2-oxopyridin-1(2H)-yl]methyl}benzoyl)piperazine-1-carboxamide

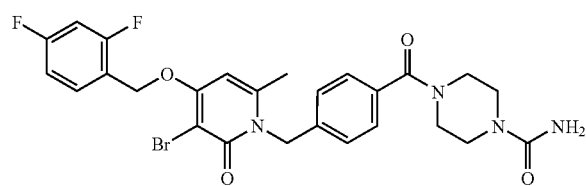

3-bromo-4-(2,4-difluorophenoxy)-6-methyl-1-[4-(piperazin-1-ylcarbonyl)benzyl]pyridin-2(1H)-one (300 mg, 0.54 mmol) was dissolved in N,N-dimethylacetamide (5 mL). Trimethylsilyl isocyanate (0.15 mL, 1.08 mmol) was added followed by N,N-diisopropylethylamine (0.23 mL, 1.3 mmol) and the reaction was stirred for 1 hour at ambient temperature. The reaction was then diluted with tetrahydrofuran (40 mL) and polyamine resin (1.3 g, 2.81 mmol/g) and methylisocyanate functionalized polystyrene (1 g, 1.38 mmol/g) were added. The mixture was shaken for 6 hours, filtered, and the resulting filtrate was concentrated to a white solid (279 mg, 90%). $^1$H NMR (400 MHz, CD$_3$OD) δ 7.61 (app q, J=8.0 Hz, 1H); 7.41 (d, J=8.0 Hz, 2H), 7.23 (d, J=8.0 Hz, 2H), 7.03 (app t, J=8.8 Hz, 2H); 6.51 (s, 1H), 5.46 (s, 2H), 5.30 (s, 2H), 3.75–3.35 (m, 8H); 2.37 (s, 3H). ES HRMS m/z 575.1104 (C$_{26}$H$_{25}$BrF$_2$N$_4$O$_4$ requires 575.1100).

Example 187

N-(4-{[3-bromo-4-[(2,4-difluorobenzyl)oxy]-6-methyl-2-oxopyridin-1(2H)-yl]methyl}benzyl)-2-methoxyacetamide

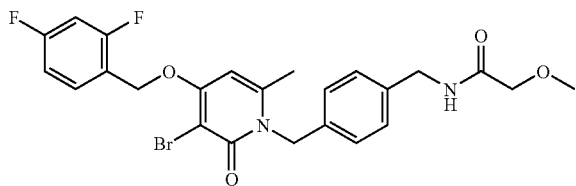

Polymer bound carbodiimide resin (2.3 g, 1.18 meq/g, 2.7 mmol) was suspended in N,N-dimethylformamide. Acetoxyacetic acid (120 mg, 1.33 mmol) was added, followed by 1-hydroxybenzotriazole (1M in N,N-dimethylformamide, 0.165 mL) and N,N-diisopropylethylamine (0.3 mL, 2.0 mmol). The reaction was shaken for 1 hour when EXAMPLE 159 (300 mg, 0.67 mmol) was added. The reaction was shaken for 16 hours and then diluted with tetrahydrofuran. Polyamine resin (1 g, 2.81 mmol/9) and methylisocyanate functionalized polystyrene (2 g, 1.38 mmol/g) were added and the mixture was shaken for 72 hours, filtered and the resulting filtrate concentrated. Trituration with water followed by trituration with ether yielded a white solid (125 mg, 36%). $^1$H NMR (400 MHz, CDCl$_3$) δ 7.56 (app q, J=8.0 Hz, 1H); 7.21 (d, J=8.0 (Hz, 2H), 7.13 (d, J=8.0 Hz, 2H), 6.94 (app t, J=8.8 Hz, 1H), 6.88–6.81 (m, 1H); 5.97 (s, 1H), 5.33 (s, 2H), 5.19 (s, 2H); 4.43 (d, J=6.0 Hz, 2H); 3.92 (s, 2H), 3.39 (s, 3H); 2.29 (s, 3H). ES HRMS m/z 521.0882 (C$_{24}$H$_{22}$BrF$_2$N$_2$O$_4$ requires 521.0882).

Examples 188–193

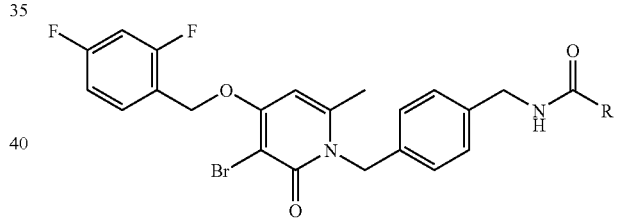

By following the general method for the preparation of Example 187 and substituting the appropriate carboxylic acid for acetoxyacetic acid, the compounds of Examples 188–193 are prepared. These compounds were triturated with water and again with ether and purified by chromatography (silica gel, hexane/ethyl acetate) as appropriate to yield off-white solids. Example 191 was prepared from its N-t-butoxycarbonyl protected intermediate. Deprotection was accomplished with 4N HCl in dioxane to afford the title compound as its hydrochloride salt (86 mg, 24%). Deprotection of the methyl ester from Ex. 188 was accomplished with K$_2$CO$_3$ in methanol/water to yield Ex. 192 as a white solid. The yields and analytical data are shown below.

| Compound No. | R | % Yield | MF | M + H Requires | ESHRMS m/z |
| --- | --- | --- | --- | --- | --- |
| Ex. 188 | CH$_2$OCOCH$_3$ | 49 | C$_{25}$H$_{23}$BrF$_2$N$_2$O$_5$ | 549.0831 | 549.0849 |
| Ex. 189 | C(CH$_3$)$_2$OH | 13 | C$_{25}$H$_{25}$BrF$_2$N$_2$O$_4$ | 535.1039 | 535.1035 |

-continued

| Compound No. | R | % Yield | MF | M + H Requires | ESHRMS m/z |
|---|---|---|---|---|---|
| Ex. 190 | C(—CH$_2$CH$_2$—)OH | 33 | C$_{25}$H$_{23}$BrF$_2$N$_2$O$_4$ | 535.0865 | 535.0876 |
| Ex. 191 | CH$_2$NH$_2$ | 24 | C$_{23}$H$_{22}$BrF$_2$N$_3$O$_3$ | 533.0882 | 533.0899 |
| Ex. 192 | CH$_2$OH | 25 | C$_{23}$H$_{21}$BrF$_2$N$_2$O$_4$ | 507.0726 | 507.0730 |
| Ex. 193 | CH$_2$NHCOCH$_3$ | 81 | C$_{25}$H$_{24}$BrF$_2$N$_3$O$_3$ | 548.0991 | 548.1000 |

Example 194

1-{4-[(4-acetylpiperazin-1-yl)carbonyl]benzyl}-3-bromo-4-[(2,4-difluorobenzyl)oxy]-6-methylpyridin-2(1H)-one

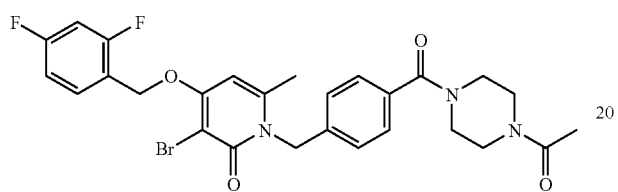

3-bromo-4-(2,4-difluorophenoxy)-6-methyl-1-[4-(piperazin-1-ylcarbonyl)benzyl]pyridin-2(1H)-one (200 mg, 0.36 mmol) was dissolved in N,N-dimethylformamide (5 mL). N,N-Diisopropylethylamine (0.25 mL, 1.44 mmol) was added followed by acetic anhydride (0.10 mL, 1.06 mmol). The reaction was stirred for 2 hours at ambient temperature and concentrated to an oil that was triturated in ether and again in water to yield an off-white solid (131 mg, 63%) $^1$H NMR (400 MHz, CD$_3$OD) δ 7.62 (app q, J=8.0 Hz, 1H); 7.42 (d, J=8.0 Hz, 2H), 7.23 (d, J=8.0 Hz, 2H), 7.62–7.02 (m, 1H); 7.02 (app t, J=8.0 Hz, 1H); 6.52 (s, 1H), 5.46 (s, 2H), 5.30 (s, 2H); 3.80–3.65 (m, 8H); 2.37 (s, 3H); 2.11 (s, 3H). ES HRMS m/z 574.1150 (C$_{27}$H$_{26}$BrF$_2$N$_3$O$_4$ requires 574.1148).

Example 195

3-bromo-4-[(2,4-difluorobenzyl)oxy]-6-methyl-1-(4-{[4-(methylsulfonyl)piperazin-1-yl]carbonyl}benzyl)pyridin-2(1H)-one

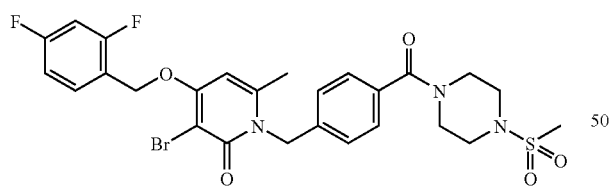

3-bromo-4-(2,4-difluorophenoxy)-6-methyl-1-[4-(piperazin-1-ylcarbonyl)benzyl]pyridin-2(1H)-one (300 mg, 0.54 mmol) was dissolved in N,N-dimethylformamide (5 mL). 4-Methylmorpholine (0.23 mL, 2.2 mmol) was added followed by methanesulfonyl chloride (0.10 mL, 1.33 mmol) and the reaction was stirred for 2 h. The reaction was then diluted with tetrahydrofuran (40 mL) and polyamine resin (1.3 g, 2.81 mmol/g) and methylisocyanate functionalized polystyrene (1 g, 1.38 mmol/g) were added. The mixture was shaken for 16 hours, filtered, and the resulting filtrate concentrated to an oil that was triturated with water. The resulting white solid was collected, washed with ether and dried (172 mg, 52%). $^1$H NMR (400 MHz, CDCl$_3$) δ 7.57 (app q, J=8.2 Hz, 1H); 7.34 (d, J=8.0 Hz, 2H), 7.20 (d, J=8.0 Hz, 2H), 7.02 (app dt, J=1.2, 8.8 Hz, 1H), 6.88–6.82 (m, 1H); 6.02 (s, 1H), 5.37 (s, 2H), 5.21 (s, 2H); 3.80–3.20 (m, 8H); 2.79 (s, 3H); 2.30 (s, 3H). ES HRMS m/z 610.0851 (C$_{26}$H$_{26}$BrF$_2$N$_3$O$_5$S requires 610.0817).

Example 196

Methyl-4-[4-(benzyloxy)-3-bromo-2-oxopyridin-1 (2H)-yl]benzoate.

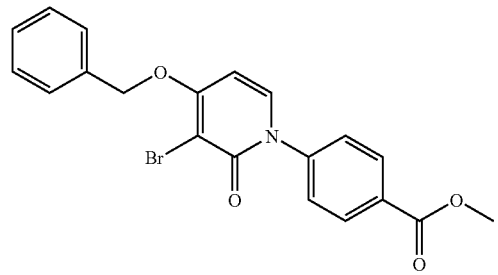

Step 1. Preparation of 4-[4-(benzyloxy)-2-oxopyridin-1 (2H)-yl]benzonitrile.

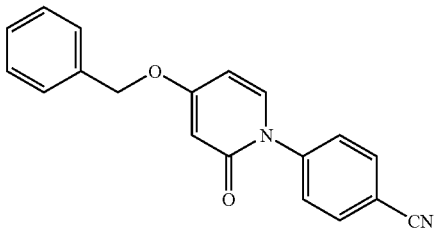

4-benzyloxy-2(1H)-pyridone (12.00 g, 59.63 mmol) was dissolved in dimethyl sulfoxide (100 mL). Potassium carbonate (10.99 g, 79.50 mmol) was added, followed by 4-fluorobenzonitrile (4.81 g, 39.75 mmol). The reaction was stirred at 100° C. for 18 hours. After cooling to room temperature the reaction was diluted with H$_2$O (150 mL) and the solids were collected by filtration washing with diethyl ether. Chromatography (silica gel, hexanes/ethyl acetate) provided an off-white solid (7.78 g, 65%). $^1$H NMR (300 MHz, CDCl$_3$) δ 7.79 (d, J=8.3 Hz, 2H), 7.54 (d, J=8.5 Hz, 2H), 7.44–7.41 (m, 5H), 7.22 (d, J=13.3 Hz, 1H), 6.13 (dd, J=2.6, 7.7 Hz, 1H), 6.06 (d, J=2.6 Hz, 1H), 5.07 (s, 2H)

Step 2. Preparation of 4-[4-(benzyloxy)-3-bromo-2-oxopyridin-1(2H)-yl]benzonitrile.

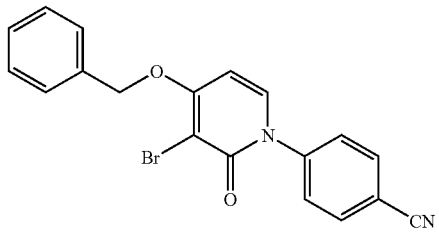

4-[4-(benzyloxy)-2-oxopyridin-1(2H)-yl]benzonitrile (Step 1) (2.76 g, 9.13 mmol) was suspended in acetonitrile (50 mL) and cooled in an ice-bath. N-bromosuccinimide (1.71 g, 9.54 mmol) was added. Once the addition was complete the cooling bath was removed. After stirring for 45 minutes the reaction was diluted with acetonitrile and solids were collected by filtration to give a white solid (3.13 g, 90%). $^1$H NMR (300 MHz, DMSO-d$_6$) δ 8.00 (d, J=8.5 Hz, 2H), 7.84 (d, J=7.9 Hz, 1H), 7.66 (d, J=8.5 Hz, 2H), 7.50–7.37 (m, 5H), 6.63 (d, J=7.9 Hz, 1H), 5.41 (s, 2H).

Step 3. Preparation of methyl-4-[4-(benzyl)oxy-3-bromo-2-oxopyridin-1(2H)-yl]benzoate. 4-[4-(benzyloxy)-3-bromo-2-oxopyridin-1(2H)-yl]benzonitrile (Step 2) (1.50 g, 3.93 mmol) suspended in methanol (50 mL) was cooled in an ice-bath. HCl (g) was then bubbled through the mixture for 5 minutes. The reaction was then stirred at room temperature overnight, at which time the reaction mixture was concentrated. The residue was suspended in 6N HCl (60 mL) and heated at reflux for 1.5 hours. After cooling to room temperature the solids were collected by filtration. Chromatography (silica gel, hexanes/ethyl acetate) provided an off-white shiny solid (0.540 g, 61%). $^1$H NMR (400 MHz, DMSO-d$_6$) δ 8.04 (d, J=8.5 Hz, 2H), 7.81 (d, J=7.8 Hz, 1H), 7.55 (d, J=8.6 Hz, 2H), 7.47–7.39 (m, 5H), 6.57 (d, J=7.9 Hz, 1H), 5.38 (s, 2H), 3.86 (s, 3H). ES-HRMS m/z 416.0355 (M+H caldc for C$_{20}$H$_{16}$BrNO$_4$ requires 414.0341).

Example 197

4-[4-(benzyloxy)-3-bromo-2-oxopyridin-1(2H)-yl]benzoic acid.

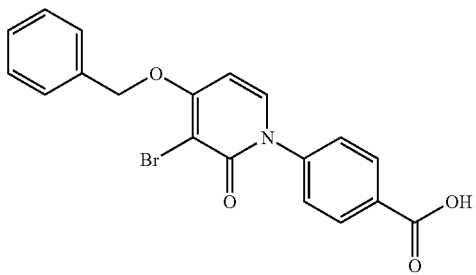

Preparation of 4-[4-(benzyloxy)-3-bromo-2-oxopyridin-1(2H)-yl]benzoic acid. EXAMPLE 196 (0.460 g, 1.11 mmol) was dissolved in tetrahydrofuran (5.0 mL). Potassium trimethylsilanolate (0.285 g, 2.22 mmol) was added. The reaction was stirred at room temperature for 3 hours at which time H$_2$O (10 mL) was added. The aqueous reaction mixture was acidified (pH-3) with 1N HCl. The tetrahydrofuran was evaporated, additional H$_2$O (50 mL) was added and the aqueous layer was extracted with ethyl acetate (2×50 mL). The combined organic layers were washed with brine (50 mL), dried over Na$_2$SO$_4$, filtered and evaporated to provide a rust colored solid (0.444 g, 100%). $^1$H NMR (400 MHz, DMSO-d$_6$) 68.02 (d, J=8.6 Hz, 2H), 7.80 (d, J=7.8 Hz, 1H), 7.55 (d, J=8.6 Hz, 2H), 7.50–7.34 (m, 5H), 6.57 (d, J=7.9 Hz, 1H), 5.38 (s, 2H). ES-HRMS m/z 400.0191 (M+H calcd for C$_{19}$H$_{14}$BrNO$_4$ requires 400.0184).

Example 198

4-[4-(benzyloxy)-3-bromo-2-oxopyridin-1(2H)-yl] benzamide.

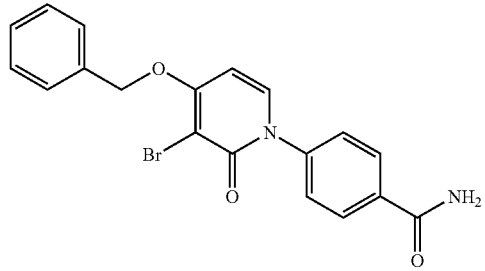

Preparation of 4-[4-(benzyloxy)-3-bromo-2-oxopyridin-1(2H)-yl]benzamide. STEP 2, EXAMPLE 196 (0.238 g, 0.624 mmol) was suspended in tert-butyl alcohol (3.0 mL). KF on 40 wt % Al$_2$O$_3$ (0.453 g, 3.12 mmol) was added. The reaction mixture was heated at reflux for 5 days. Additional KF on 40 wt % Al$_2$O$_3$ (0.453 g, 3.12 mmol) was added and heating was continued at reflux overnight. After cooling to room temperature chloroform and methanol were added and the solids were collected by filtration. Chromatography (reverse-phase, acetonitrile/H$_2$O) provided a tan solid (0.073 g, 30%). $^1$H NMR (400 MHz, DMSO-d$_6$) 68.07 (s, 1H), 7.95 (d, J=8.6 Hz, 2H), 7.79 (d, J=7.8 Hz, 1H), 7.47–7.34 (m, 7H), 6.56 (d, LJ=7.9 Hz, 1H), 5.38 (s, 2H). ES-HRMS m/z 399.0372 (M+H calcd for C$_{19}$H$_{15}$BrN$_2$O$_3$ requires 399.0344).

Example 199

1-[4-(aminomethyl)phenyl]-4-(benzyloxy)-3-bromopyridin-2(1H)-one.

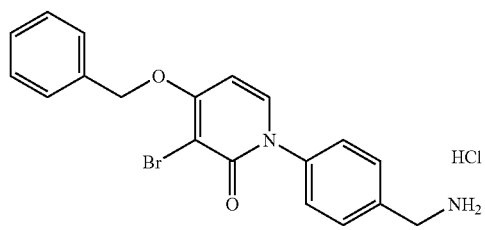

Preparation of 1-[4-(aminomethyl)phenyl]-4-(benzyloxy)-3-bromopyridin-2(1H)-one. STEP 2, EXAMPLE 196 (1.25 g, 3.28 mmol) was dissolved in tetrahydrofuran (15 mL). Borane-dimethylsulfide (3.44 mL, 6.89 mmol, 2.0 M in tetrahydrofuran) was added and the mixture heated at reflux. After 14.5 hours the solvent was evaporated. 0.5M NaOH (50 mL) was added followed by ethyl acetate. The aqueous layer was neutralized with 1N HCl. Methanol saturated with HCl was added and the mixture was heated at reflux for 5 hours. After cooling to room temperature, diethyl ether was added and the solids were collected by filtration. The solids were treated with 4N HCl in dixoane (5 mL) and methanol (1 mL) at room temperature for 1 hour, at which time diethyl ether was added and the solids were collected by filtration to give a tan solid (0.920 g, 67%). $^1$H NMR (300 MHz, DMSO-d$_6$) δ 8.67

(br s, 2H), 7.76 (d, J=7.6 Hz, 1H), 7.64 (d, J=8.3 Hz, 2H), 7.50–7.37 (m, 7H), 6.56 (d, J=7.6 Hz, 1H), 5.41 (s, 2H), 4.09 (br s, 2H). ES-HRMS m/z 385.0555 (M+H calcd for $C_{19}H17BrN_2O_2$ requires 385.0552).

Example 200
Methyl-4-[3-chloro-4-[(2,4-diflurobenzyl)oxy]-2-oxypyridin-1(2H)-yl]benzoate.

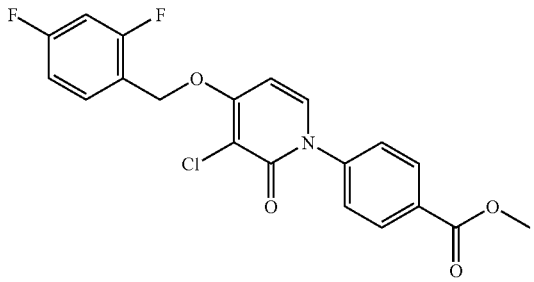

Step 1. Preparation of 4-[4-(benzyloxy)-2-oxopyridin-1(2H)-yl]benzonitrile.

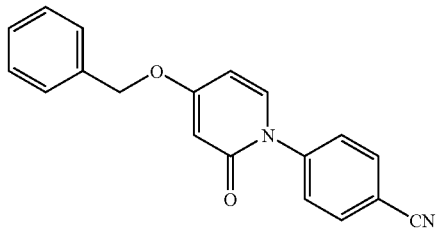

4-benzyloxy-2(1H)-pyridone (50.0 g, 248.47 mmol) was dissolved in dimethyl sulfoxide (300 mL). Potassium carbonate (68.68 g, 496.94 mmol) was added, followed by 4-fluorobenzonitrile (31.60 g, 260.89 mmol). The reaction was stirred at 100° C. for 20 hours. After cooling to room temperature the reaction was diluted with $H_2O$ (600 mL) and the solids were collected by filtration washing with diethyl ether. The solids were then washed with hot methanol to provide a tan solid (55.6 g, 74%). $^1$H NMR (300 MHz, $CDCl_3$) δ 7.79 (d, J=8.3 Hz, 2H), 7.54 (d, J=8.5 Hz, 2H), 7.44–7.41 (m, 5H), 7.22 (d, J=13.3, 1H), 6.13 (dd, J=2.6, 7.7 Hz, 1H), 6.06 (d, J=2.6 Hz, 1H), 5.07 (s, 2H).

Step 2. Preparation of 1-[4-nitrilephenyl]-4-hydroxy-2(1H)-pyridinone.

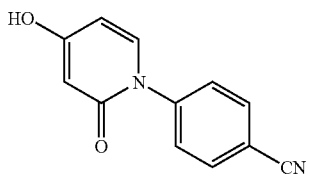

4-[4-(benzyloxy)-2-oxopyridin-1(2H)-yl]benzonitrile (Step 1) (20.0 g, 66.15 mmol) was dissolved in methanol (300 mL). Ammonium formate (8.34 g, 132.3 mmol) was added followed by 5% Pd/C (6.62 g). The resulting mixture was heated at reflux for 20 minutes at which time the reaction began to exotherm. The reaction was allowed to cool to room temperature at which time it was filtered through a pad of Celite® washing with methanol. The filtrate was evaporated to provide a pale yellow solid (16.2 g, >100%). $^1$H NMR (300 MHz, $CDCl_3$) δ 8.46 (s, 1H), 7,95 (d, J=8.5 Hz, 2H), 7.62 (d, J=8.5 Hz, 2H), 7.47 (d, J=7.7 Hz, 1H), 5.98 (dd, J=2.6, 7.7 Hz, 1H), 5.54 (d, J=2.4 Hz, 1H).

Step 3. Preparation of 4-[4-[(2,4-difluorobenzyloxy)]-2-oxopyridin-1(2H)-yl]benzonitrile.

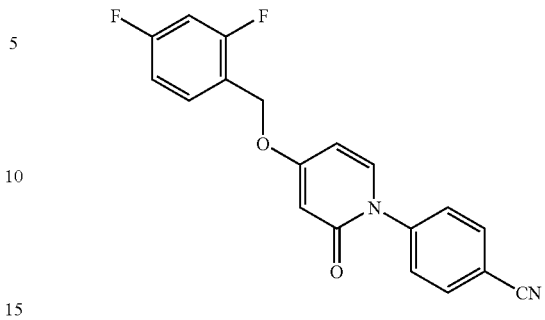

1-[4-Nitrilephenyl]-4-hydroxy-2(1H)-pyridinone (Step 2) (16.2 g) was dissolved in N,N-dimethylformamide (100 mL). Potassium carbonate (10.06 g, 72.77 mmol) was added followed by α-bromo-2,4-difluorotoluene (8.91 mL, 69.46 mmol). The resulting mixture was heated to 65° C. for 1 hour. Additional α-bromo-2,4-difluorotoluene (4.25 mL, 33.08 mmol) was added. The resulting mixture was heated to 65° C. for 5 hours. Additional α-bromo-2,4-difluorotoluene (2.12 mL, 16.54 mmol) was added. After stirring at 65° C. overnight the reaction was allowed to cool to room temperature. $H_2O$ (300 mL) was added and the solid was collected by filtration. A portion (8.0 g) of the solids were washed with hot methanol to give a pale yellow solid (6.22 g, 78%). $^1$H NMR (300 MHz, $CDCl_3$) δ 8.00 (d, J=8.5 Hz, 2H), 7.72–7.64 (m, 2H), 7.66 (d, J=8.5 Hz, 2H), 7.40–7.32 (m, 1H), 7.22–7.16 (m, 1H), 6.17–6.11 (m, 2H), 5.17 (s, 2H).

Step 4. Preparation of Methyl-4-[4-[(2,4-difluorobenzyl)oxy]-2-oxopyridin-1(2H)-yl]benzoate.

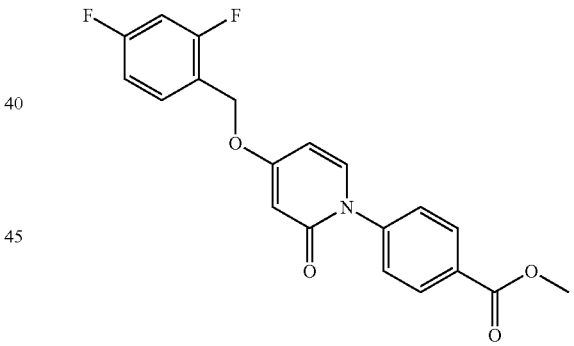

4-[4-[(2,4-difluorobenzyloxy)]-2-oxopyridin-1(2H)-yl]benzonitrile (Step 3) (2.00 g, 5.91 mmol) suspended in methanol (20 mL) and $H_2O$ (5 mL) was cooled in an ice-bath. HCl (g) was bubbled through the mixture until most of the solids dissolved. The resulting mixture was then heated at reflux for 3 hours. The reaction was then recooled in an ice-bath and HCl was bubbled through the mixture for 5 minutes. The mixture was heated at reflux for 2 hours and then the methanol was evaporated. Additional $H_2O$ (50 mL) was added and the aqueous reaction mixture was extracted with ethyl acetate (50 mL) and tetrahydrofuran (50 mL). The combined organic layers were washed with brine (50 mL), dried over $Na_2SO_4$, filtered and evaporated. Chromatography (silica gel, hexanes/ethyl acetate with 10% methanol) gave an off-white solid (0.630 g, 29%). $^1$H NMR (300 MHz, DMF-$d_6$) 68.15 (d, J=8.5 Hz, 2H), 7.80 (app q, J=7.9 Hz, 1H), 7.74–7.67 (m, 1H), 7.68 (d, J=8.5 Hz, 2H), 7.42–7.34

(app dt, J=2.4, 9.0 Hz, 1H), 7.28–7.22 (m, 1H), 6.20 (dd, J=2.6, 7.6 Hz, 1H), 6.15 (d, J=2.4 Hz, 1H), 5.28 (s, 2H), 3.98 (s, 3H)

Step 5. Preparation of methyl-4-[3-chloro-4-[(2,4-diflurobenzyl)oxy]-2-oxypyridin-[(2H)-yl]benzoate. Methyl-4-[4-[(2,4-difluorobenzyl)oxy]-2-oxopyridin-1(2H)-yl]benzoate (Step 4) (0.520 g, 1.40 mmol) was suspended in acetonitrile (10.0 mL). N-chlorosuccinimide (0.196 g, 1.47 mmol) was added followed by several drops of dichloroacetic acid. The resulting mixture was heated at reflux overnight. After cooling to room temperature additional acetonitrile was added and the precipitate was collected by filtration to give an off-white solid (0.331 g, 58%). $^1$H NMR (300 MHz, DMF-$d_6$) δ 8.34 (d, J=8.5 Hz, 2H), 8.12 (d, J=7.9 Hz, 1H), 8.04–7.96 (m, 1H), 7.88 (d, J=8.5 Hz, 2H), 7.59–7.53 (m, 1H), 7.52–7.41 (m, 1H), 7.05 (d, J=7.9 Hz, 1H), 5.70 (s, 2H), 4.15 (s, 3H). ES-HRMS m/z 406.0644 (M+H calcd for $C_{20}H_{14}ClF_2NO_4$ requires 406.0652).

Example 201

3-Bromo-4-[(2,4-diflurorbenzyl)oxy]-1-[3-(hydroxymethyl)phenyl]-6-methylpyridin-2(1H)-one.

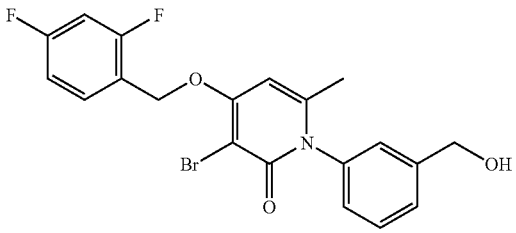

Step 1. Preparation of 4-Hydroxy-1-[3-(hydroxymethyl)phenyl]-6-methylpyridin-2(1H)-one.

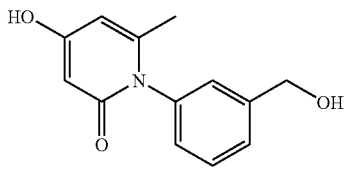

4-hydroxy-6-methyl-2-pyrone (10.0 g, 79.3 mmol) and 3-aminobenzyl alcohol (9.77 g, 79.3 mmol) were combined in $H_2O$ (100 mL) and heat at reflux. After 48 hours at reflux the reaction mixture was concentrated. The residue was treated with methanol and the precipitate was collected by filtration to give a pale yellow solid (3.04 g, 17%). $^1$H NMR (300 MHz, DMSO-$d_6$) δ 10.6 (br s, 1H), 7.46–7.35 (m, 2H), 7.09–7.03 (m, 2H), 5.88 (d, J=1.6 Hz, 1H), 5.55 (d, J=2.6 Hz, 1H), 4.54 (d, J=4.2 Hz, 2H), 1.83 (s, 3H)

Step 2. Preparation of 1-[3-(hydroxymethyl)phenyl]-4-[(2,4-difluorobenzyl)oxy]-6-methylpyridin-2(1H)-one.

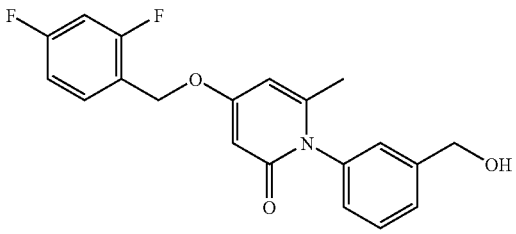

4-Hydroxy-1-[3-(hydroxymethyl)phenyl]-6-methylpyridin-2(1H)-one (Step 1) (0.674 g, 2.91 mmol) was suspended in acetone (10 mL). Cesium carbonate (1.04 g, 3.21 mmol) was added followed by α-bromo-2,4-difluorotoluene (0.392 mL, 3.06 mmol). After stirring at room temperature for 2 days the reaction was concentrated. The residue was portioned between $H_2O$ (30 mL) and ethyl acetate (30 mL). The aqueous layer was further extracted with ethyl acetate (30 mL). The combined organic layers were washed with brine (30 mL), dried over $Na_2SO_4$, filtered and concentrated. Chromatography (on silica, hexanes/ethyl acetate with 10% methanol) provided a white solid (0.531 g, 51%). $^1$H NMR (300 MHz, CDCl$_3$) δ 7.51–7.39 (m, 3H), 7.82 (s, 1H), 7.16 (d, J=26.8 Hz, 1H), 7.08–6.86 (m, 2H), 6.00 (d, J=2.6 Hz, 1H), 5.92 (d, J=2.6 Hz, 1H), 5.05 (s, 2H), 4.68 (s, 2H), 1.93 (s, 3H). ES-HRMS m/z 358.1256 (M+H calcd for $C_{20}H_{17}F_2NO_3$ requires 358.1249).

Step 3. Preparation of 3-bromo-4-[(2,4-diflurorbenzyl)oxy]-1-[3-(hydroxymethyl)phenyl]-6-methylpyridin-2(1H)-one . 1-[3-(hydroxymethyl)phenyl]-4-[(2,4-difluorobenzyl)oxy]-6-methylpyridin-2(1H)-one (Step 2) (0.460 g, 1.29 mmol) was suspended in acetonitrile (5.0 mL) and cooled in an ice-bath. N-bromosuccinimide (0.241 g, 1.35 mmol) was added. Once the addition was complete the cooling bath was removed. After stirring for 1.5 hours the reaction was diluted with acetonitrile and solids were collected by filtration to give a white solid (0.385 g, 68%). $^1$H NMR (300 MHz, DMSO-$d_6$) δ 7.70 (app q, J=7.9 Hz, 1H), 7.49–7.32 (m, 3H), 7.24–7.10 (m, 3H), 6.66 (s, 1H), 5.35 (s, 2H), 4.56 (d, J=5.6 Hz, 2H), 1.95 (s, 3H). ES-HRMS m/z 436.0384 (M+H calcd for $C_{20}H_{16}BrF_2NO_3$ requires 436.0354).

Example 202

Methyl-4-[3-bromo-4-[(difluorobenzyl)oxy]-6-methyl-2-oxopyridin-1(2H)-yl]benzoate.

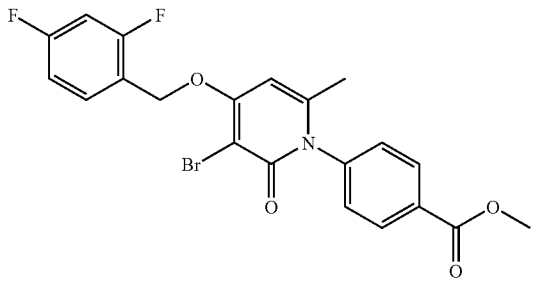

Step 1. Preparation of Methyl 4-(4-hydroxy-6-methyl-2-oxypyridin-[(2H)-yl)benzoate.

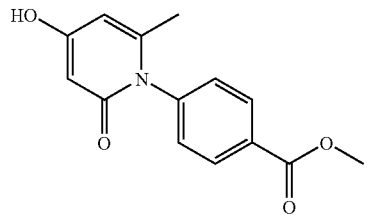

4-hydroxy-6-methyl-2-pyrone (21.00 g, 166.70 mmol) and 4-methylaminobenzoate (25.20 g, 166.70 mmol) were combined in 1,2-dichlorobenzene (50 mL) and rapidly heated to 160° C. After 15 minutes at 160° C. the reaction was allowed to cool to room temperature. The reaction was diluted with dichloromethane (50 mL) and extracted with saturated Na$_2$CO$_3$ (2×100 mL). The combined aqueous layers were acidified (pH-2) with concentrated HCl. The precipitate was collected by filtration and washed with diethyl ether to give a yellow/orange solid (10.9 g, 25%). $^1$H NMR (300 MHz, DMSO-d$_6$) δ 10.8 (s, 1H), 8.07 (d, J=8.5 Hz, 2H), 7.40 (d, J=8.5 Hz, 2H), 5.95 (d, J=2.4 Hz, 1H), 5.61 (d, J=2.4, 1H), 3.91 (s, 3H), 1.85 (s, 3H)

Step 2. Preparation of Methyl-4-[4-[(difluorobenzyl)oxy]-6-methyl-2-oxopyridin-1(2H)-yl]benzoate.

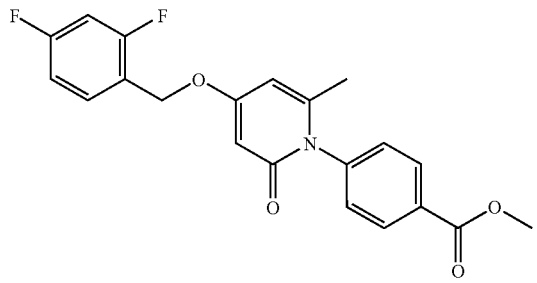

Methyl 4-(4-hydroxy-6-methyl-2-oxypyridin-[(2H)-yl] benzoate (Step 1) (10.90 g, 42.04 mmol) was dissolved in N,N-dimethylformamide (100 mL). Potassium carbonate (6.97 g, 50.45 mmol) was added, followed by 2,4-difluorobenzyl bromide (5.66 mL, 44.14 mmol). The reaction was stirred at room temperature for 3 days then diluted with H$_2$O (100 mL). The reaction mixture was extracted into ethyl acetate and tetrahydrofuran (2×100 mL). The precipitate was collected by filtration and the organic filtrate was washed with brine (50 mL), dried over Na$_2$SO$_4$, filtered and evaporated. The resulting solid was combined with the precipitate to provide a pale pink solid (6.77 g, 42%). $^1$H NMR (300 MHz, DMSO-d$_6$) δ 8.01 (d, J=8.3 Hz, 2H), 7.67 (q, J=7.9 Hz, 1H), 7.43 (d, J=8.3 Hz, 2H), 7.35 (m, 1H), 7.18 (app dt, J=1.6, 8.5 Hz, 1H), 6.08 (d, J=1.8 Hz, 1H), 5.98 (d, J=2.4 Hz, 1H), 5.14 (s, 2H), 3.91 (s, 3H), 1.87 (s, 3H).

Step 3. Preparation of methyl-4-[3-bromo-4-[(difluorobenzyl)oxy]-6-methyl-2-oxopyridin-1(2H)-yl] benzoate. Methyl-4-[4-[(difluorobenzyl)oxy]-6-methyl-2-oxopyridin-1(2H)-yl]benzoate (Step 2) (6.74 g, 17.49 mmol) suspended in acetonitrile (100 mL) was cooled in an ice-bath. N-bromosuccinimide (3.27 g, 18.36 mmol) was added. After 1 hour the ice-bath was removed and after an additional 30 minutes the reaction was diluted with acetonitrile (20 mL). The precipitate was collected by filtration to provide the title compound as an off-white solid (6.94 g, 85%). $^1$H NMR (300 MHz, CDCl$_3$) δ 8.20 (d, J=8.7 Hz, 2H), 7.61 (q, J=7.9 Hz, 1H), 7.30 (d, J=8.7 Hz, 2H), 7.02–6.96 (m, 1H), 6.90 (app dt, J=2.4, 9.5 Hz, 1H), 6.14 (s, 1H), 5.28 (s, 2H), 3.98 (s, 3H), 2.00 (s, 3H). ES-HRMS m/z 464.0304 (M+H calcd for C$_{21}$H$_{16}$BrF$_2$NO$_4$ requires 464.0301).

Example 203

4-[3-bromo-4-[(difluorobenzyl)oxy]-6-methyl-2-oxopyridin-1(2H)-yl]benzoic acid.

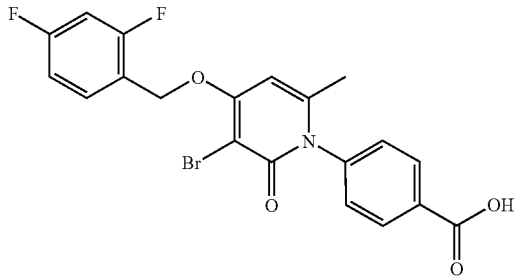

EXAMPLE 202 (7.43 g, 16.00 mmol) was dissolved in tetrahydrofuran (40 mL). Potassium trimethylsilanolate (4.10 g, 32.00 mmol) was added and the reaction mixture was stirred at room temperature for 22 hours. The tetrahydrofuran was evaporated and H$_2$O (50 mL) was added. The aqueous reaction mixture was acidified with 1N HCl and the precipitate was collected by filtration. The solids were washed with boiling methanol to give an off-white solid (5.05 g, 70%). $^1$H NMR (300 MHz, DMSO-d$_6$) δ 13,2 (br s, 1H), 8.10 (d, J=8.5 Hz, 2H), 7.72 (q, J=7.9 Hz, 1H), 7.45 (d, J=8.3 Hz, 2H), 7.38 (app dt, J=2.4, 9.9 Hz, 1H), 7.23 (app dt, J=1.8, 8.5 Hz, 1H), 6.72 (s, 1H), 5.37 (s, 2H), 1.97 (s, 3H). ES-HRMS m/z 450.0154 (M+H calcd for C$_{20}$H$_{14}$BrF$_2$NO$_4$ requires 450.0147).

Example 204

4-(Benzyloxy)-1-(3-fluorobenzyl)-3-(trifluoromethyl) pyridin-2(1H)-one.

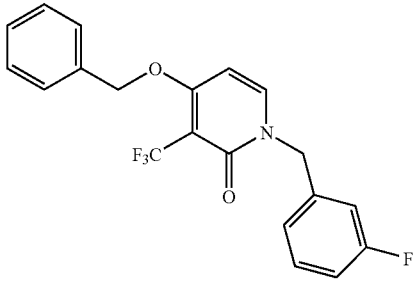

The starting material (0.250 g, 0.591 mmol) was dissolved in 1-methyl-2-pyrrolidinone (5.0 mL). Trifluoroacetic acid, sodium salt (0.322 g, 2.36 mmol) was added, followed by copper(I)iodide (0.225 g, 1.18 mmol). The resulting mixture was heated to 180° C. for 5 hours and then allowed to cool to room temperature. The reaction was diluted with H$_2$O (50 mL) and brine (50 mL), then extracted into ethyl acetate (2×50 mL). The combined organic layers were washed with brine (50 mL), dried over Na$_2$SO$_4$, filtered and evaporated. Chromatography (reverse-phase, acetonitrile/H$_2$O) provided an off-white solid (0.050 g, 22%). $^1$H NMR (400 MHz, CDCl$_3$) δ 7.40–7.27 (m, 8H), 7.06 (d, J=7.7 Hz, 1H), 6.97 (d, J=9.0 Hz, 1H), 6.07 (d, J=7.7 Hz, 1H), 5.20 (s, 2H), 5.06 (s, 2H). ES-HRMS m/z 378.1097 (M+H calcd for C$_{20}$H$_{15}$F$_4$NO$_2$ requires 378.1112).

Example 205

4-{[3-bromo-4-[(2,4-difluorobenzyl)oxy]-6-methyl-2-oxopyridin-1(2H)-yl]methyl}benzoic acid

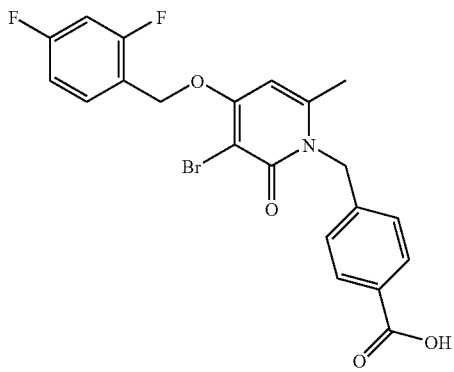

EXAMPLE 153 (50.0 g, 104.54 mmol) was dissolved in methanol (500 mL) and dioxane (100 mL). 1N NaOH (130 mL, 130 mmol) was added. The resulting mixture was heated to 50° C. for 5.5 hours. The reaction was partially concentrated and the heterogenous mixture was acidified (pH 2) with 1N HCl. The precipitate was collected by filtration to afford a white solid (49.2 g, >100%). $^1$H NMR (300 MHz, DMSO-$d_6$) δ 7.94 (d, J=8.3 Hz, 2H), 7.70 (app q, J=7.9 Hz, 1H), 7.35 (dt, J=2.2, 9.9 Hz, 1H), 7.18 (app d, J=8.3 Hz, 2H), 7.17–7.12 (m, 1H), 6.64 (s, 1H), 5.41 (s, 2H), 5.33 (s, 2H), 2.32 (s, 3H). ES-HRMS m/z 464.0327 (M+H calcd for $C_{21}H_{16}BrF_2NO_4$ requires 464.0304).

Example 206
3-Bromo-4-[(2,4-diflurobenzyl)oxy]-1-[4-(hydroxymethyl)benzyl]-6-methylpyridin-2(1H)-one.

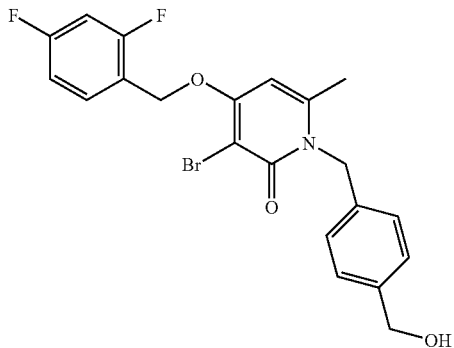

Example 205 (40.0 g, 86.16 mmol) suspended in tetrahydrofuran (300 mL) was cooled in an ice-bath. Borane dimethylsulfide (129.2 mL, 258.48 mmol, 2.0 M in tetrahydrofuran) was slowly added. The resulting mixture was slowly allowed to warm to room temperature overnight. The mixture was recooled in an ice-bath and quenched by the addition of small pieces of ice. After the evolution of gas ceased additional ice-water was added. The flask was fitted with a distillation apparatus and the dimethylsulfide was removed. After the reaction was cooled to room temperature, H$_2$O (300 mL), ethyl acetate (200 mL) and tetrahydrofuran (300 mL) were added. The precipitate that formed was collected by filtration and the filtrate was placed in a separatory funnel. The aqueous layer was further extracted with ethyl acetate (300 mL). The combined organic layers were washed with brine (300 mL). The organic phase was dried over Na$_2$SO$_4$ and evaporated which was combined with the precipitate to yield an off-white solid (37.8 g, 97%). $^1$H NMR (400 MHz, CDCl$_3$) δ 7.47 (app q, J=7.7 Hz, 1H), 7.23 (d, J=7.9 Hz, 2H), 7.05 (d, J=7.9 Hz, 2H), 6.86 (app dt, J=2.3, 8.6 Hz, 1H), 6.79 (app dt, J=2.4, 8.4 Hz, 1H), 6.00 (s, 1H), 5.28 (s, 2H), 5.16 (s, 2H), 4.57 (s, 2H), 2.25 (s, 3H). ES-HRMS m/z 450.0512 (M+H calcd for $C_{21}H_{18}BrF_2NO_3$ requires 450.0511).

Example 207

3-Bromo-4-[(2,4-diflurobenzyl)oxy]-1-[4-(1-hydroxy-1-methylethyl)benzyl]-6-methylpyridin-2(1H)-one.

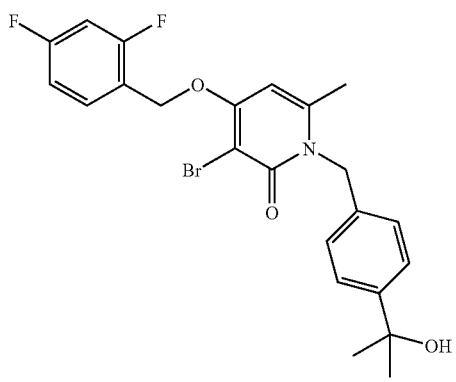

Preparation of 3-bromo-4-[(2,4-diflurobenzyl)oxy]-1-[4-(1-hydroxy-1-methylethyl)benzyl]-6-methylpyridin-2(1H)-one. EXAMPLE 153 (2.00 g, 4.18 mmol) suspended in tetrahydrofuran (20 mL) was cooled in the dry ice/acetone bath. Methyl magnesium bromide (4.32 mL, 12.96 mmol, 3.0 M in diethyl ether) was slowly added. The reaction was slowly allowed to warm to room temperature overnight. The reaction was then cooled in an ice bath and quenched by the addition of saturated NH$_4$Cl (50 mL). H$_2$O was added and the reaction was extracted with ethyl acetate. The combined organic layers were washed with brine, dried over Na$_2$SO$_4$, filerted and evaporated. The residue was subjected to chromatography (silica gel, hexanes/ethyl acetate with 10% methanol) to provide an off-white foam. The foam was dissolved in acetonitrile and cooled in an ice bath. N-bromosuccinimide (0.057 g, 0.320 mmol) was added. Once the addition was complete the cooling bath was removed. After 2.5 hours at room temperature the reaction was concentrated. Purification by chromatography (silica gel, hexanes/ethyl acetate with 10% methanol) provided a white foam. $^1$H NMR (400 MHz, CDCl$_3$) δ 7.56 (app q, J=7.7 Hz, 1H), 7.39 (d, J=78.3 Hz, 2H), 7.11 (d, J=8.2 Hz, 2H), 6.92 (app dt, J=1.7, 8.4 Hz, 1H), 6.86–6.81 (m, 1H), 5.97 (s, 1H), 5.31 (s, 2H), 5.18 (s, 2H), 2.29 (s, 3H), 1.52 (s, 6H). ES-HRMS m/z 478.0811 (M+H $C_{23}H_{22}BrF_2NO_3$ requires 478.0824).

Example 208
3-bromo-4-[(2,4-diflurobenzyl)oxy]-6-methyl-1-{4-[(methylamino)methyl]benzyl}pyridin-2(1H)-one.

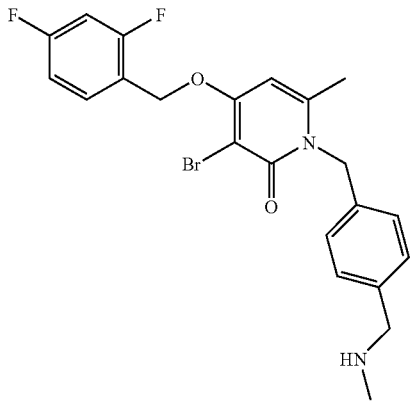

Step 1. Preparation of 4-{[3-bromo-4-[(2,4-difluorobenzyl)oxy]-6-methyl-2-oxopyridin-1(2H)-yl]methyl}benzaldehyde.

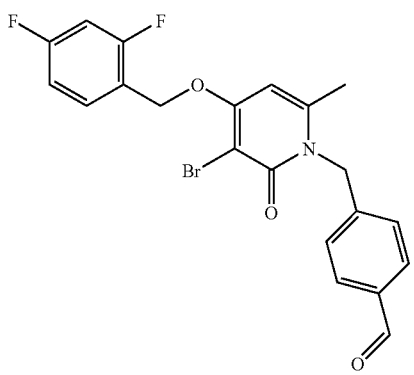

EXAMPLE 206 (1.30 g, 2.89 mmol) was suspended in acetonitrile (10 mL) and cooled in an ice-bath. 1-hydroxy-1,3-dihydro-3,3-bis(trifluoromethyl)-1,2-benziodoxole 1-oxide (0.580 g, 1.44 mmol) was added and the reaction mixture was stirred at room temperature overnight. Diethyl ether was added and the solid was collected by filtration to give a white solid (1.14 g, 88%). $^1$H NMR (400 MHz, CDCl$_3$) δ 9.96 (s, 1H), 7.80 (d, J=8.2 Hz, 2H), 7.56 (app q, J=7.7 Hz, 1H), 7.30 (d, J=8.2 Hz, 2H), 6.93 (app dt, J=1.6, 8.3 Hz, 1H), 6.87–6.82 (m, 1H), 6.02 (s, 1H), 5.41 (s, 2H), 5.20 (s, 2H), 2.27 (s, 3H)

Step 2. 3-bromo-4-[(2,4-diflurobenzyl)oxy]-6-methyl-1-{4-[(methylamino)methyl]benzyl}pyridin-2(1H)-one. 4-{[3-Bromo-4-[(2,4-difluorobenzyl)oxy]-6-methyl-2-oxopyridin-1(2H)-yl]methyl}benzaldehyde (Step 1) (1.53 g, 3.41 mmol) of step 1 was dissolved in N,N-dimethylformamie (5.0 mL). Methylamine (3.41 mL, 6.83 mmol, 2.0 M in tetrahydrofuran) was added followed by NaHB(OAc)3 (2.17 g, 10.23 mmol) in N,N-dimethylformamide (8.0 mL) and acetic acid (2.0 mL). The reaction was stirred at room temperature overnight at which time 1N NaOH (50 mL) was added and then extracted with ethyl acetate (2×50 mL). The organic layers were washed with brine (25 mL), dried over Na$_2$SO$_4$ and evaporated. Chromatography (on silica, ethyl acetate with 5% methanolic ammonia/hexanes) afforded a tan solid (0.810 g, 53%). $^1$H NMR (400 MHz, CDCl$_3$) δ 7.55 (app q, J=7.8 Hz, 1H), 7.22 (d, J=8.1 Hz, 2H), 7.11 (d, J=8.1 Hz, 2H), 6.92 (app dt, J=2.4, 8.3 Hz, 1H), 6.90–6.80 (m, 1H), 5.95 (s, 1H), 5.32 (s, 2H), 5.17 (s, 2H), 3.68 (s, 2H), 2.40 (s, 3H), 2.27 (s, 3H). ES-HRMS m/z 463.0838 (M+H calcd for C$_{22}$H$_{21}$BrF$_2$N$_2$O$_4$ requires 463.0827).

Example 209
4-[(2,4-diflurobenzyl)oxy]-1-(4-methoxybenzyl)-6-methylpyridin-2-(1H)-one.

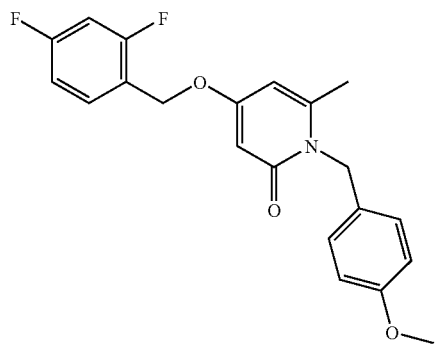

Step 1. Preparation of 1-(4-methoxybenzyl)-4-hydroxy-6-methylpyridin-2(1H)-one.

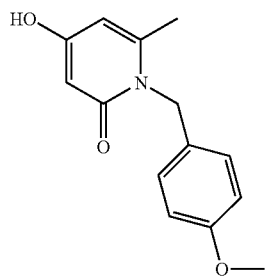

4-Hydroxy-6-methyl-2-pyrone (4.60 g, 36.45 mmol) and 4-methoxybenzylamine (5.00 g, 36.45 mmol) in H$_2$O (100 mL) were heated to reflux. After 15 hours at reflux the reaction was allowed to cool to room temperature. The precipitate was collected by filtration washing with H$_2$O to give a pale yellow solid (8.00 g, 89%). $^1$H NMR (400 MHz, DMSO-d$_6$) δ 7.2 (d, J=8.7 Hz, 2H), 6.85 (d, J=8.7 Hz, 2H), 5.74 (d, J=2.0 Hz, 1H), 5.56 (d, J=2.5 Hz, 1H), 5.08 (s, 2H), 3.68 (s, 3H), 2.14 (s, 3H).

Step 2. Preparation of 4-[(2,4-diflurobenzyl)oxy]-1-(4-methoxybenzyl)-6-methylpyridin-2(1H)-one. 1-(4-methoxybenzyl)-4-hydroxy-6-methylpyridin-2(1H)-one (Step 1) (7.97 g, 32.49 mmol) was dissolved in N,N-dimethylformamide (60 mL). Potassium carbonate (4.94 g, 35.74 mmol) was added, followed by α-bromo-2,4-difluorotoluene (4.38 mL, 34.11 mmol). The reaction was stirred at room temperature for 20 hours at which time the mixture was filtered through a pad of Celite® washing with acetonitrile and the filtrate was evaporated. The residue was dissolved in H$_2$O (150 mL) and extracted into ethyl acetate (2×100 mL). The organic phase was washed with brine (100 mL), dried over Na$_2$SO$_4$, filtered and evaporated. Chromatography (on silica, hexanes/ethyl acetate with 10% methanol) yielded an off-white solid (3.64 g, 30%). $^1$H NMR (300 MHz CDCl$_3$) δ 7.42 (app q, J=7.7 Hz, 1H), 7.13 (d, J=8.5 Hz, 2H), 6.96–6.84 (m 2H), 6.85 (app d, J=8.7 Hz, 2H), 6.01 (d, J=2.6 Hz, 1H), 5.82 (d, J=2.8 Hz, 1H), 5.23 (s, 2H), 5.02 (s, 2H), 3.79 (s, 3H), 2.25 (s, 3H). ES-HRMS m/z 372.1412 (M+H C$_{21}$H$_{19}$F$_2$NO$_3$ requires 372.1417).

Example 210

3-bromo-4-[(2,4-diflurobenzyl)oxy]-1-(4-methoxybenzyl)-6-methylpyridin-2(1H)-one

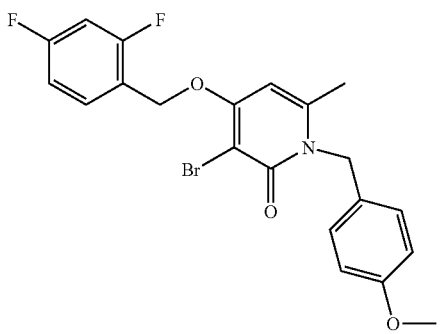

Preparation of 3-bromo-4-[(2,4-diflurobenzyl)oxy]-1-(4-methoxybenzyl)-6-methylpyridin-2(1H)-one. EXAMPLE 209 (0.200 g, 0.538 mmol) suspended in acetonitrile (3 mL) was cooled in an ice-bath. N-bromosuccinimide (0.101 g, 0.565 mmol) was added. Once the addition was complete the cooling bath was removed. After 1 hour the reaction was concentrated. Purification by chromatography (silica gel, hexanes/ethyl acetate) provided a white solid (0.240 g, 99%). $^1$H NMR (300 MHz, CDCl$_3$) δ 7.59 (app q, J=7.8 Hz, 1H), 7.16 (d, J=8.7 Hz, 2H), 6.97 (app dt, J=2.4, 8.6 Hz, 1H), 6.91–6.83 (m, 1H), 6.85 (app d, J=8.7 Hz, 2H), 5.98 (s, 1H), 5.31 (s, 2H), 5.21 (s, 2H), 3.79 (s, 3H), 2.34 (s, 3H). ES-HRMS m/z 450.0491 (M+H C$_{21}$H$_{18}$BrF$_2$NO$_3$ requires 450.0511).

Example 211

3-bromo-4-[(2,4-diflurobenzyl)oxy]-1-(4-hydroxybenzyl)-6-methylpyridin-2(1H)-one

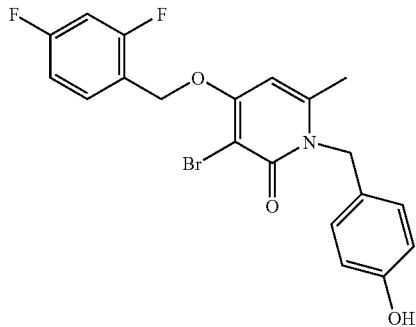

Preparation of 3-bromo-4-[(2,4-diflurobenzyl)oxy]-1-(4-hydroxybenzyl)-6-methylpyridin-2(1H)-one. EXAMPLE 210 (0.235 g, 0.522 mmol) was suspended in acetonitrile (3 mL). Cerric ammonium nitrate (1.14 g, 2.09 mmol) dissolved in H$_2$O (1 mL) was added. The reaction was stirred at room temperature for 1 hour and then diluted with dichloromethane (25 mL). The reaction was then washed with H$_2$O (10 mL). The aqueous phase was back extracted with dichloromethane (20 mL). The combined organic layers were dried over Na$_2$SO$_4$, filtered and evaporated. The residue was washed with hot ethyl acetate to give an off-white solid (0.134 g, 59%). $^1$H NMR (300 MHz, DMSO-d$_6$) δ 7.75 (app q, J=7.9 Hz, 1H), 7.65 (s, 1H), 7.45–7.36 (m, 1H), 7.36 (d, J=10.1 Hz, 2H), 7.27–7.20 (m, 1H), 6.49 (d, J=10.1 Hz, 2H), 5.60 (s, 2H), 5.07 (s, 2H), 2.63 (s, 3H). ES-HRMS m/z 436.0187 (M+H C$_{20}$H$_{16}$BrF$_2$NO$_3$ requires 436.0354).

Example 212

3-bromo-4-[(2,4-difluorobenzyl)oxy]-1{4-[(4-hydroxy-4-methylpiperidin-1-yl)carbonyl]benzyl}-6-methylpyridin-2(1H)-one

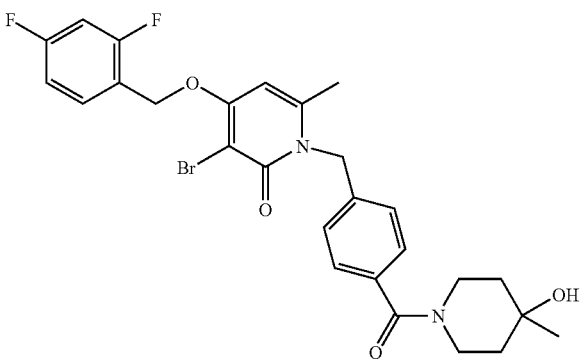

Step 1. Preparation of 4-hydroxy-4-methylpiperidine hydrochloride.

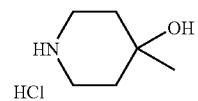

tert-Butyl-4-oxo-1-piperidine (10.0 g, 50.19 mmol) dissolved in diethyl ether (100 mL) was cooled in an ice-bath. Methyl magnesium bromide (18.40 mL, 55.21 mmol, 3.0 M in diethyl ether) was added. After slowly warming to room temperature the reaction was recooled in an ice-bath and quenched by the addition of saturated $NH_4Cl$ (75 mL).Additional $H_2O$ was added and the organic layer was removed. The aqueous layer was further extracted with diethyl ether (50 mL). The combined organic layers were washed with brine, dried over $Na_2SO_4$, filtered and concentrated. Chromatography (silica gel, hexanes/ethyl acetate) provided a clear oil. The resulting oil was dissolved in diethyl ether (10 mL) and treated with 4N HCl/dioxane (32.61 mL, 130.43 mmol). After stirring at room temperature for 1 hour the reaction mixture was concentrated to give a pale yellow solid (5.05 g, >100%).

Step 2. Preparation of 3-bromo-4-[(2,4-difluorobenzyl)oxy]-1{4-[(4-hydroxy-4-methylpiperidin-1-yl)carbonyl]benzyl}-6-methylpyridin-2(1H)-one. THE ACID (0.300 g, 0.646 mmol) was suspended in dichloromethane (6.0 mL). 1-hydroxybenzotriazole (0.044 g, 0.323 mmol) was added followed by 3-(1-cyclohexylcarbodiimide)propyl-functionalized silica gel (2.02 g, 1.29 mmol, loading=0.64 mmol/g), 3-(1-morpholine)propyl functionalized silica gel (1.84 g, 1.29 mmol, loading=0.7 mmol/g) and dichloromethane (2 mL). After stirring at room temperature for 15 minutes, 4-hydroxy-4-methylpiperidine hydrochloride (0.147 g, 0.969 mmol) was added. The resulting mixture was stirred at room temperature overnight, at which time dimethylamine-3-functionalized silica gel (1.7 g, 2.58 mmol, loading=1.5 mmol/g) was added followed by isocyanate-3-functionalized silica gel (1.3 g, 1.62 mmol, loading=1.22 mmol/g). The resulting mixture was stirred at room temperature for 3 hours. The reaction mixture was then filtered and concentrated. Chromatography (silica gel, hexanes/ethyl acetate with 10% methanol) provided a white foam (0.200 g, 55%). $^1$H NMR (300 MHz, $CDCl_3$) δ 7.58 (app q, J=7.7 Hz, 1H), 7.33 (d, J=8.1 Hz, 2H), 7.18 (d, J=8.1 Hz, 2H), 6.96 (app t, J=8.3 Hz, 1H), 6.87 (app dt, J=2.0, 9.5 Hz, 1H), 6.06 (s, 1H), 5.38 (s, 2H), 5.22 (s, 2H), 4.27 (br m, 1H), 3.41 (br m, 3H), 2.30 (s, 3H), 2.06 (s, 1H), 1.60 (br m, 4H), 1.28 (s, 3H). ES-HRMS m/z 561.1173 (M+H $C_{27}H_{27}BrF_2N_2O_4$ requires 561.1195).

Example 213

4-{[3-bromo-4-[(2,4-difluorobenzyl)oxy]-6-methyl-2-oxypyridin-1 (2H)-yl]methyl}-N-(2-hydroxy-2-methylpropyl)benzamide

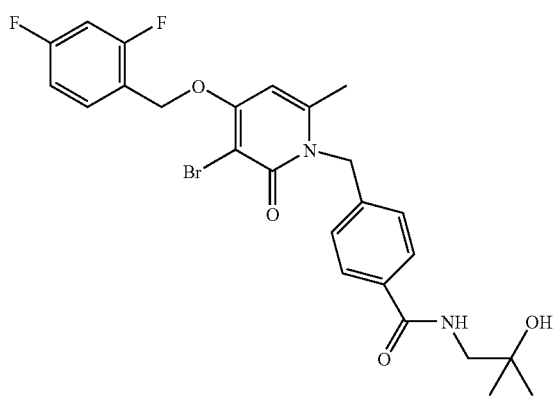

The title compound was by a procedure essentially as in Example 212 using 1-amino-2-methyl-2-propanol hydrochloride as starting material.

$^1$H NMR (400 MHz, $CDCl_3$) δ 7.70 (d, J=8.3 Hz, 2H), 7.53 (app q, J=7.8 Hz, 1H), 7.33 (t, J=5.8 Hz, 1H), 7.06 (d, J=8.3 Hz, 2H), 6.95–6.90 (m, 1H), 6.86–6.81 (m, 1H), 6.04 (s, 1H), 5.30 (s, 2H), 5.19 (s, 2H), 3.40 (d, J=5.9 Hz, 2H), 2.98 (br s, 1H), 2.24 (s, 3H), 1.21 (s, 6H). ES-HRMS m/z 535.1012 (M+H $C_{25}H_{25}BrF_2N_2O_4$ requires 535.1039).

Example 214

3-bromo-4-[(2,4-difluorobenzyl)oxy]-1{4-[(4-hydroxypiperidin-1-yl)carbonyl]benzyl}-6-methylpyridin-2(1H)-one

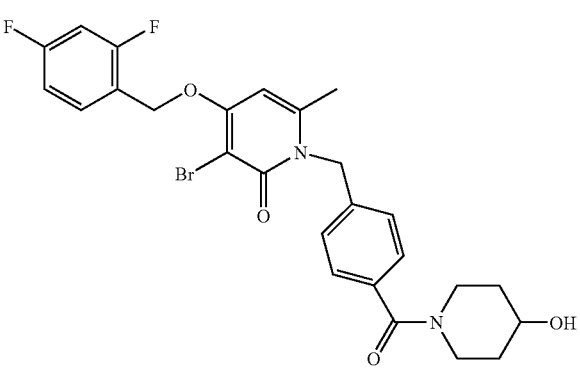

The title compound was produced essentially as in Example 212 using 4-hydroxypiperidine as starting material. $^1$H NMR (400 MHz, $CDCl_3$) δ 7.55 (app q, J=7.7 Hz, 1H), 7.30 (d, J=8.2 Hz, 2H), 7.15 (d, J=8.3 Hz, 2H), 6.94 (app dt, J=2.4, 8.4 Hz, 1H), 6.84 (app ddd, J=2.6, 8.9, 10.3 Hz, 1H), 6.01 (s, 1H), 5.36 (s, 2H), 5.19 (s, 2H), 4.12–4.07 (m, 1H), 3.96–3.90 (m, 1H), 3.60 (br s, 1H), 3.33 (br s, 1H), 3.13 (br s, 1H), 2.27 (s, 3H), 1.91 (br s, 3H), 1.77 (br s, 1H), 1.57 (br s, 1H), 1.44 (br s, 1H). ES-HRMS m/z 547.1006 (M+H $C_{26}H_{25}BrF_2N_2O_4$ requires 547.1039).

Example 215

4-{[3-bromo-4-[(2,4-difluorobenzyl)oxy]-6-methyl-2-oxopyridin-1(2H)-yl]methyl}-N-(2-hydroxyethyl)benzamide

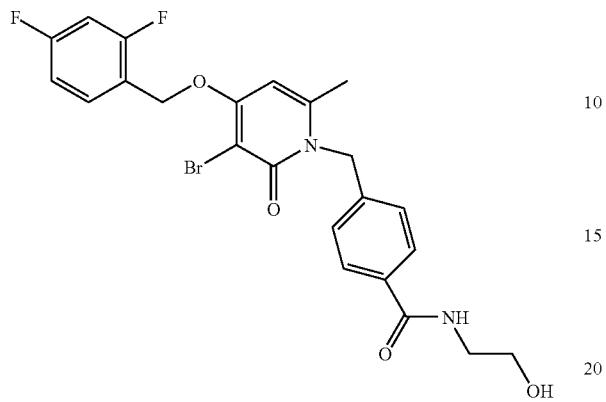

Preparation of 4-{[3-bromo-4-[(2,4-difluorobenzyl)oxy]-6-methyl-2-oxopyridin-1(2H)-yl]methyl}-N-(2-hydroxyethyl)benzamide. To a reaction vessel (borosilicate culture tube) was added EXAMPLE 205 (0.300 g, 0.646 mmol). A stock solution of 1-hydroxybenzotriazole in N,N-dimethylformamide (3 mL, 0.11 M) was added to the reaction vessel followed by approximately 1.10 g of the polymer bound carbodiimide resin (1.8 mmol/g). Additional N,N-dimethylformamide (2 mL) was then added to the reaction vessel. The parallel reaction apparatus was then orbitally shaken (Labline Benchtop Orbital Shaker) at approximately 200 RPM at room temperature for 15 minutes. Ethanolamine (0.06 mL, 0.994 mmol) was then added to the reaction vessel and the reaction apparatus was orbitally shaken at room temperature overnight. At this time the reaction was diluted with tetrahydrofuran (20 mL) and treated with approximately 2.0 g of polyamine resin (2.63 mmol/g) and approximately 2.6 g of methylisocyanate functionalized polystyrene (1.10 mmol/g) and the orbital shaking was continued at 200 RPM at room temperature for 3 hours. The reaction vessel was then opened and the solution phase product was separated from the insoluble quenched byproducts by filtration and collection into a vial. After partially evaporation the insoluble byproducts were rinsed further with tetrahydrofuran (2×10 mL) and combined with the partially reduced filtrate. The resulting filtrate was concentrated by blowing $N_2$ over the vial while heating (60° C.) in a reaction block (KEM-Lab Parallel Reactor) to give an off-white solid. (0.111 g, 34%) $^1$H NMR (400 MHz, DMF-$d_6$) δ 8.45 (t, J=5.4 Hz, 1H), 7.94 (d, J=8.2 Hz, 2H), 7.76 (app q, J=7.9 Hz, 1H), 7.33–7.27 (m, 1H), 7.27 (app d, J=7.9 Hz, 2H), 7.20 (app dt, J=2.4, 8.6 Hz, 1H), 6.65 (s, 1H), 5.47 (s, 2H), 5.38 (s, 2H), 4.83 (br s, 1H), 3.64–3.60 (m, 2H), 2.47–3.42 (m, 2H), 2.40 (s, 3H). ES-HRMS m/z 507.0742 (M+H $C_{23}H_{21}BrF_2N_2O_4$ requires 507.0726).

Example 216–231

Preparation of 3-bromo-4-(2,4-difluorophenoxy)-6-methyl-1-[4-(aminocarbonyl)benzyl]pyridin-2(1H)-one compounds

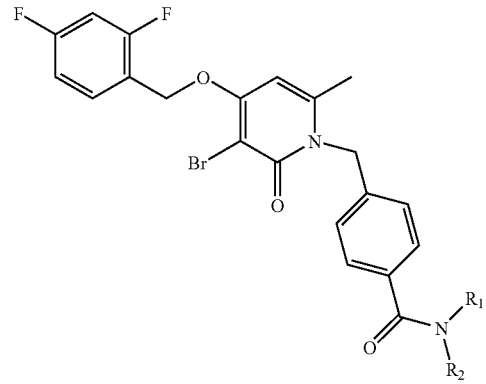

By following the method of Example 215 and substituting the appropriate amine, the compounds of Examples 216–231 are prepared. The deprotection of the protected intermediates was accomplished with 4N HCl in dioxane to afford the compounds as hydrochloride salts.

| Compound No. | $R_1$ | $R_2$ | % Yield | MF | M + H Requires | ESHRMS m/z |
|---|---|---|---|---|---|---|
| Ex. 216 | $CH_2CH_2NH-$ | $CH_2CH_2NH-$ | 73 | $C_{25}H_{24}BrF_2N_3O_4$ | 532.1042 | 532.1024 |
| Ex. 217 | H | $CH_2CH_2NH_2$ | 49 | $C_{23}H_{22}BrF_2N_3O_3$ | 506.0885 | 506.0883 |
| Ex. 218 | H | $CH_2CH_2CH_2NH_2$ | 31 | $C_{24}H_{24}BrF_2N_3O_3$ | 520.1042 | 520.1042 |
| Ex. 219 | H | OH | 53 | $C_{21}H_{17}BrF_2N_2O_4$ | 479.0413 | 479.0423 |
| Ex. 220 | H | $CH_3$ | 59 | $C_{22}H_{19}BrF_2N_2O_4$ | 477.0620 | 477.0605 |
| Ex. 221 | $CH_3$ | $CH_3$ | 51 | $C_{23}H_{21}BrF_2N_2O_3$ | 491.0776 | 491.0794 |
| Ex. 222 | $CH_2CH_2O-$ | $CH_2CH_2O-$ | 61 | $C_{25}H_{23}BrF_2N_2O_4$ | 533.0882 | 533.0901 |
| Ex. 223 | $CH_2CH_2OH$ | $CH_2CH_2OH$ | 69 | $C_{25}H_{25}BrF_2N_2O_5$ | 551.0988 | 551.0978 |
| Ex. 224 | $CH_2CH_2CH_2-$ | $CH_2CH_2CH_2-$ | 66 | $C_{26}H_{25}BrF_2N_2O_3$ | 531.1084 | 531.1089 |
| Ex. 225 | H | $CH(CH_3)_2$ | 50 | $C_{24}H_{23}BrF_2N_2O_3$ | 505.0933 | 505.0901 |
| Ex. 226 | $CH_2CH_2-$ | $CH_2CH_2-$ | 71 | $C_{25}H_{23}BrF_2N_2O_3$ | 517.0933 | 517.0908 |
| Ex. 227 | $CH_2CH_2N(CH_3)-$ | $CH_2CH_2N(CH_3)-$ | 83 | $C_{26}H_{26}BrF_2N_3O_3$ | 546.1198 | 546.1215 |
| Ex. 228 | H | $CH_2CH_2N(CH_3)_2$ | 81 | $C_{25}H_{26}BrF_2N_3O_3$ | 534.1198 | 534.1197 |
| Ex. 229 | H | $CH_2CH_2OCH_3$ | 79 | $C_{24}H_{23}BrF_2N_2O_4$ | 521.0882 | 521.0861 |
| Ex. 230 | $CH_3$ | $CH_2CH_2OH$ | 36 | $C_{24}H_{23}BrF_2N_2O_4$ | 521.0882 | 521.0893 |
| Ex. 231 | $CH_3$ | $CH_2CH_2OCH_3$ | 82 | $C_{25}H_{25}BrF_2N_2O_4$ | 535.1039 | 535.1028 |

Example 232

4-{[3-bromo-4-[(2,4-difluorobenzyl)oxy]-6-methyl-2-oxopyridin-1(2H)-yl]-N-(2-hydroxyethyl)benzamide

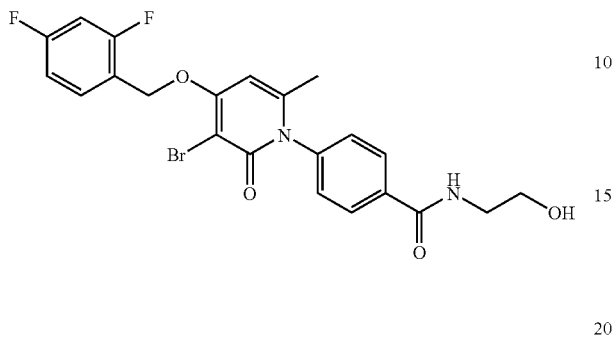

Preparation of 4-{[3-bromo-4-[(2,4-difluorobenzyl)oxy]-6-methyl-2-oxopyridin-1(2H)-yl]-N-(2-hydroxyethyl)benzamide. To a reaction vessel (borosilicate culture tube) was added EXAMPLE 203 (0.300 g, 0.666 mmol). A stock solution of 1-hydroxybenzotriazole in N,N-dimethylformamide (3 mL, 0.11 M) was added to the reaction vessel followed by approximately 1.13 g of the polymer bound carbodiimide resin (1.8 mmol/g). Additional N,N-dimethylformamide (2 mL) was then added to the reaction vessel. The parallel reaction apparatus was then orbitally shaken (Labline Benchtop Orbital Shaker) at approximately 200 RPM at room temperature for 15 minutes. Ethanolamine (0.06 mL, 0.994 mmol) was then added to the reaction vessel and the reaction apparatus was orbitally shaken at room temperature overnight. At this time the reaction was diluted with tetrahydrofuran (20 mL) and treated with approximately 2.0 g of polyamine resin (2.63 mmol/g) and approximately 2.7 g of methylisocyanate functionalized polystyrene (1.10 mmol/g) and the orbital shaking was continued at 200 RPM at room temperature for 3 hours. The reaction vessel was then opened and the solution phase products were separated from the insoluble quenched byproducts by filtration and collection into a vial. After partially evaporation the insoluble byproducts were rinsed further with tetrahydrofuran (2×10 mL) and combined with the partially reduced filtrate. The resulting filtrate was concentrated by blowing $N_2$ over the vial while heating (60° C.) in a reaction block (KEM-Lab Parallel Reactor). Purification by chromatography (silica gel) provided an off-white solid (0.155 g, 47%). $^1$H NMR (400 MHz, DMF-$d_6$) δ 8.58 (t, J=5.5 Hz, 1H), 8.10 (d, J=8.3 Hz, 2H), 7.79 (app q, J=7.9 Hz, 1H), 7.47 (d, J=8.3 Hz, 2H), 7.36–7.30 (m, 1H), 7.21 (app dt, J=2.4, 8.5 Hz, 1H), 6.73 (s, 1H), 5.43 (s, 2H), 3.68 (app t, J=5.9 Hz, 2H), 3.52–3.49 (m, 2H), 2.03 (s, 3H). ES-HRMS m/z 493.0597 (M+H $C_{22}H_{19}BrF_2N_2O_4$ requires 493.0569).

Examples 233–243

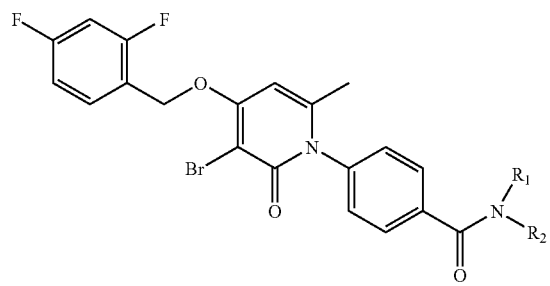

By following the method of Example 232 and substituting ethanolamine for the appropriate amine, the compounds of Examples 233–243 are prepared. The deprotection of the protected intermediates was accomplished with 4N HCl in dioxane to afford the compounds as hydrochloride salts.

| Compound No. | $R_1$ | $R_2$ | % Yield | MF | M + H Requires | ESHRMS m/z |
|---|---|---|---|---|---|---|
| Ex. 233 | $CH_2CH_2NH—$ | $CH_2CH_2NH—$ | 40.3 | $C_{24}H_{22}BrF_2N_3O_3$ | 518.0885 | 518.0866 |
| Ex. 234 | H | $CH_2CH_2NH_2$ | 57.1 | $C_{22}H_{20}BrF_2N_3O_3$ | 492.0729 | 492.0748 |
| Ex. 235 | H | $CH_2CH_2CH_2NH_2$ | 21.5 | $C_{23}H_{22}BrF_2N_3O_3$ | 506.0885 | 506.0915 |
| Ex. 236 | H | OH | 33.9 | $C_{20}H_{15}BrF_2N_2O_4$ | 465.0256 | 465.0259 |
| Ex. 237 | H | $CH_3$ | 20.7 | $C_{21}H_{17}BrF_2N_2O_3$ | 463.0463 | 463.0479 |
| Ex. 238 | $CH_3$ | $CH_3$ | 22.3 | $C_{22}H_{19}BrF_2N_2O_3$ | 477.0620 | 477.0643 |
| Ex. 239 | $CH_2CH_2O—$ | $CH_2CH_2O—$ | 84.4 | $C_{24}H_{21}BrF_2N_2O_3$ | 519.0726 | 519.0723 |
| Ex. 240 | $CH_2CH_2OH$ | $CH_2CH_2OH$ | 46.6 | $C_{24}H_{23}BrF_2N_2O_5$ | 537.0831 | 537.0854 |
| Ex. 241 | $CH_2CH_2CH_2—$ | $CH_2CH_2CH_2—$ | 76.5 | $C_{25}H_{23}BrF_2N_2O_3$ | 517.0933 | 517.0892 |
| Ex. 242 | H | $CH(CH_3)_2$ | 52.6 | $C_{23}H_{21}BrF_2N_2O_3$ | 491.0776 | 491.0781 |
| Ex. 243 | $CH_2CH_2—$ | $CH_2CH_2—$ | 47.2 | $C_{24}H_{21}BrF_2N_2O_4$ | 503.0776 | 503.0791 |

Example 244

4-[3-bromo-4-[(2,4-difluorobenzyl)oxy]-6-methyl-2-oxopyridin-1(2H)-yl]benzamide

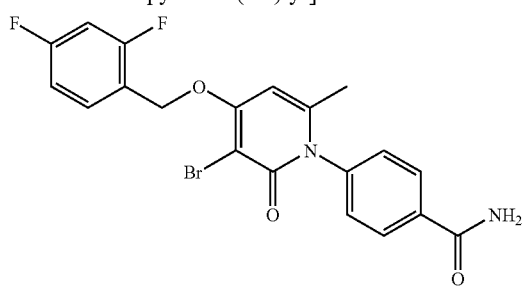

Preparation of 4-[3-bromo-4-[(2,4-difluorobenzyl)oxy]-6-methyl-2-oxopyridin-1(2H)-yl]benzamide EXAMPLE203 (0.500 g, 1.11 mmol) was suspended in tetrahydrofuran (5.0 mL). 2-Chloro-4,6-dimethoxy-1,3,5-triazine (0.234 g, 1.33 mmol) was added followed by 4-methylmorpholine (0.366 mL, 3.33 mmol). The resulting mixture was stirred at room temperature for 1.5 hours at which time NH$_4$OH (2.5 mL) was added. The resulting mixture was stirred at room temperature overnight. H$_2$O (25 mL) and tetrahydrofuran (25 mL) was added. The aqueous layer was further extracted with ethyl acetate (25 mL). The combined organic layers were washed with saturated sodium carbonate solution (25 mL), 1N HCl (25 mL), brine (25 mL), dried over Na$_2$SO$_4$, filtered and concentrated to provide a pale yellow solid (0.500 g, 100%). $^1$H NMR (400 MHz, DMF-d$_6$) δ 8.13 (s, 1H), 8.02 (d, J=8.5 Hz, 2H), 7.70 (app q, J=7.9 Hz, 1H), 7.40 (d, J=8.5 Hz, 2H), 7.41–7.34 (m, 1H), 7.22 (app dt, J=1.8, 8.5 Hz, 1H), 6.71 (s, 1H), 5.37 (s, 2H), 1.97 (s, 3H). ES-HRMS m/z 449.0281 (M+H C$_{20}$H$_{15}$BrF$_2$N$_2$O$_3$ requires 449.0307).

Example 245

4-(Benzyloxy)-3-bromo-1-[4-(morpholin-4-ylcarbonyl)phenyl]pyridin-2(1H)-one

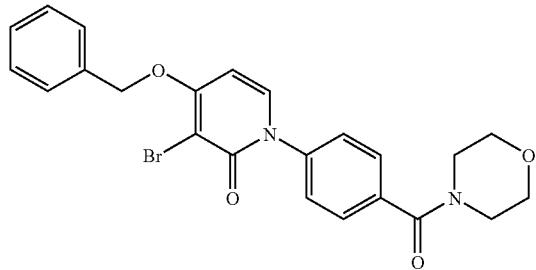

Preparation of 4-(Benzyloxy)-3-bromo-1-[4-(morpholin-4-ylcarbonyl)phenyl]pyridin-2(1H)-one. To a reaction vessel (borosilicate culture tube) was added EXAMPLE 197 (0.100 g, 0.250 mmol) which was dissolved in N,N-dimethylformamide (2.0 mL). 1-Hydroxybenzotriazole (0.017 g, 0.125 mmol) was added to the reaction vessel followed by approximately 0.423 g of the polymer bound carbodiimide resin (1.8 mmol/g). Additional N,N-dimethylformamide (2 mL) was then added to the reaction vessel. The parallel reaction apparatus was then orbitally shaken (Labline Benchtop Orbital Shaker) at approximately 200 RPM at room temperature for 15 minutes. Morpholine (0.033 g, 0.0375 mmol) dissolved in N,N-dimethlyformamide (0.5 mL) was then added to the reaction vessel and the reaction apparatus was orbitally shaken at room temperature overnight. At this time the reaction was diluted with N,N-dimethylformamide (2.0 mL) and dichloromethane (4.0 mL) and treated with approximately 0.770 g of polyamine resin (2.63 mmol/g) and approximately 1.0 g of methylisocyanate functionalized polystyrene (1.10 mmol/g) and the orbital shaking was continued at 200 RPM at room temperature for 3 hours. The reaction vessel was then opened and the solution phase product was separated from the insoluble quenched byproducts by filtration and collection into a vial. After partially evaporation the insoluble byproducts were rinsed with dichloromethane (2×10 mL). The filtrate was evaporated by blowing N$_2$ over the vial while heating (60° C.) in a reaction block (KEM-Lab Parallel Reactor) to give an off-white solid (0.092 g, 79%).

$^1$H NMR (400 MHz, CDCl$_3$) δ 7.50 (d, J=8.5 Hz, 2H), 7.48–7.33 (m, 7H), 7.27 (d, J=7.8 Hz, 1H), 6.19 (d, J=7.8 Hz, 1H), 5.29 (s, 2H), 3.76–3.47 (br m, 8H). ES-HRMS m/z 469.0733 (M+H C$_{23}$H$_{21}$BrN$_2$O$_4$ requires 469.0757).

Example 246

4-(Benzyloxy)-3-bromo-1-[4-(piperazin-1-ylcarbonyl)phenyl]pyridin-2(1H)-one hydrochloride

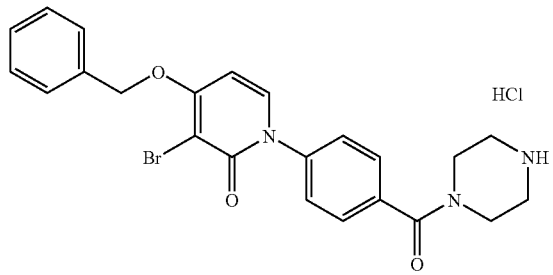

Preparation of 4-(benzyloxy)-3-bromo-1-[4-(piperazin-1-ylcarbonyl)phenyl]pyridin-2(1H)-one hydrochloride. By following the method of Ex. 245 and substituting N-tert-butyl carboxylate piperazine (0.070 g, 0.375 mmol) for morpholine the title compound was prepared as the N-t-butoxycarbonyl protected compound. The deprotection of the N-t-butoxycarbonyl intermediate was accomplished with 4N HCl in dioxane to afford the title compound as its hydrochloride salt (0.112 g, >100%). $^1$H NMR (400 MHz, DMSO-d$_6$) δ 9.55 (br s, 2H), 7.78 (d, J=7.8 Hz, 1H), 7.58 (d, J=8.5 Hz, 2H), 7.48–7.33 (m, 7H), 6.57 (d, J=7.8 Hz, 1H), 5.38 (s, 2H), 3.79–3.36 (br m, 4H), 3.30–3.14 (br s, 4H). ES-HRMS m/z 468.0940 (M+H C$_{23}$H$_{22}$BrN$_3$O$_3$ requires 468.0917).

Example 247

4-[4-(Benzyloxy)-3-bromo-2-oxopyridin-1(2H)-yl]-N-hydroxybenzamide

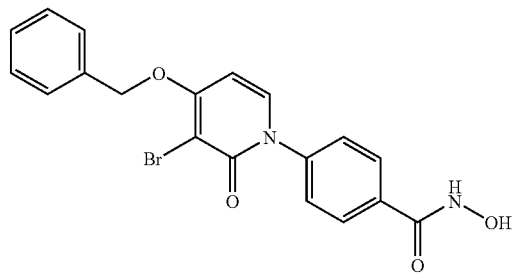

Preparation of 4-[4-(Benzyloxy)-3-bromo-2-oxopyridin-1(2H)-yl]-N-hydoxybenzamide. By following the method of EXAMPLE 245 and substituting O-(tetrahydro-2H-pyranyl-2-yl)hydroxylamine (0.044 g, 0.375 mmol) for morpholine the title compound was prepared as the tetrahydropyranly protected compound. The deprotection of the tetrahydropyranly intermediate was accomplished with 4N HCl in dioxane to afford the title compound (0.056 g, >71%). $^1$H NMR (400 MHz, DMSO-d$_6$) δ 11.03 (br s, 1H), 7.83 (d, J=8.6 Hz, 2H), 7.78 (d, J=7.8 Hz, 1H), 7.48–7.35 (m, 7H), 6.55 (d, J=7.8 Hz, 1H), 5.37 (s, 2H). ES-HRMS m/z 415.0278 (M+H C$_{19}$H$_{15}$BrN$_2$O$_4$ requires 415.0288).

Example 248

Methyl-4-{[3-chloro-4-[(2,4-difluorobenzyl)oxy]-6-methyl-2-oxopyridin-1(2H)-yl]methyl}benzoate.

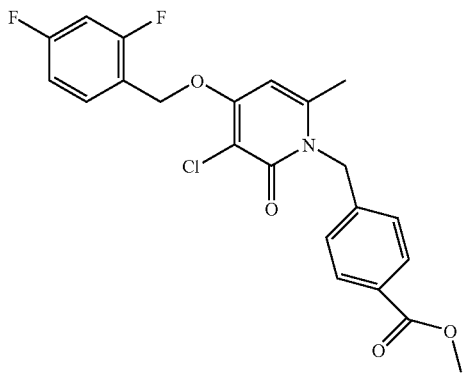

Step 1. Preparation of 3-chloro-4-[(2,4-difluorobenzyl)oxy]-6-methylpridin-2(1H)-one.

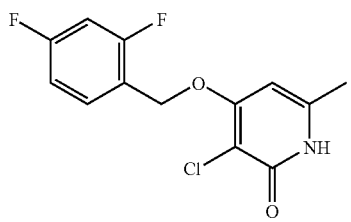

(5.00 g, 19.90 mmol) was suspended in 1,2-dichloroethane (100 mL). Dichloroacetic acid (0.082 mL, 0.995 mmol) was added, followed by N-chlorosuccinimide (3.19 g, 23.88 mmol). The reaction mixture was heated at 80° C. for 15.5 hours. The 1,2-dichloroethane was evaporated and the remaining solids were washed with acetonitrile to provide a tan solid (4.97 g, 88%).

Step 2. Preparation of methyl-4-{[3-chloro-4-[(2,4-difluorobenzyl)oxy]-6-methyl-2-oxopyridin-1(2H)-yl]methyl}benzoate. 3-Chloro-4-[(2,4-difluorobenzyl)oxy]-6-methylpridin-2(1H)-one (Step 1) (4.97 g, 17.40 mmol) suspended in tetrahydrofuran (50 mL) was cooled in an ice-bath. Methyl 4-(bromomethyl)benzoate (5.98 g, 26.10 mmol) was added, followed by sodium hydride (0.835 g, 20.88 mmol, 60% dispersion in mineral oil). Once the addition was complete the cooling bath was removed in the mixture was heated to 50° C. for 19 hours. After cooling to room temperature saturated NH$_4$Cl (50 mL) was added. Ethyl acetate was added and the precipitate was collected by filtration. The filtrate was further extracted with ethyl acetate. The combined organic layers were washed with brine (50 mL), dried over Na$_2$SO$_4$, filtered and evaporated. The resulting solid was combined with the precipitate and washed with hot ethyl acetate to give an off-white solid (5.24 g, 69%). $^1$H NMR (400 MHz, DMSO-d$_6$) δ 7.90 (d, J=8.5 Hz, 2H), 7.63 (app q, J=7.9 Hz, 1H), 7.31 (app dt, J=2.4, 9.9 Hz, 1H), 7.21 (d, J=8.3 Hz, 2H), 7.17–7.13 (m, 1H), 6.60 (s, 1H), 5.36 (s, 2H), 5.27 (s, 2H), 3.81 (s, 3H), 2.27 (s, 3H). ES-HRMS m/z 434.0931 (M+H C$_{22}$H$_{18}$BrF$_2$NO$_4$ requires 434.0965).

Example 249

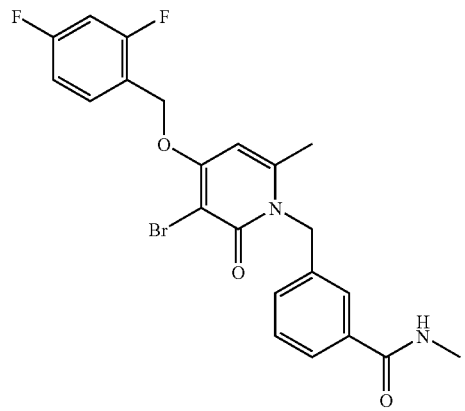

3-{[3-bromo-4-[(2,4-difluorobenzyl)oxy]-6-methyl-2-oxopyridin-1(2H)-yl]methyl}-N-methylbenzamide To a reaction vessel (borosilicate culture tube) was added EXAMPLE 169 (0.300 g, 0.646 mmol). A stock solution of 1-hydroxybenzotriazole in N,N-dimethylformamide (3 mL, 0.11 M) was added followed by approximately 1.10 g of the polymer bound carbodiimide resin (1.8 mmol/g). Additional N,N-dimethylformamide (2 mL) was then added to the reaction vessel. The parallel reaction apparatus was then orbitally shaken (Labline Benchtop Orbital Shaker) at approximately 200 RPM at room temperature for 15 minutes. N-Methylamine (0.50 mL, 0.999 mmol) was then added to the reaction vessel and the reaction apparatus was orbitally shaken at room temperature overnight. At this time the reaction was diluted with tetrahydrofuran (35 mL) and treated with approximately 2.0 g of polyamine resin (2.63 mmol/g) and approximately 2.6 g of methylisocyanate functionalized polystyrene (1.50 mmol/g) and the orbital shaking was continued at 200 RPM at room temperature for 4 hours. The reaction vessel was then opened and the solution phase products were separated from the insoluble quenched byproducts by filtration and collection into a vial. After partial evaporation the insoluble byproducts were rinsed with tetrahydrofuran (2×10 mL). The filtrate was evaporated by blowing N$_2$ over the vial while heating (60° C.) in a reaction block (KEM-Lab Parallel Reactor). Chromatography (C-18, acetonitrile/H$_2$O with 0.1% trifluoroacetic acid) afforded a white solid (0.178 g, 58%). $^1$H NMR (400 MHz, DMF-d$_6$) δ 7.65–7.53 (m, 3H), 7.37–7.28 (m, 2H), 6.97–6.82 (m, 2H), 6.00 (s, 1H), 5.36 (s, 2H), 5.19 (s, 3H), 2.96 (t, J=4.83 Hz, 3H), 2.29 (s, 3H). ES-HRMS m/z 477.0635 (M+H C$_{22}$H$_{19}$BrF$_2$N$_2$O$_3$ requires 477.0620).

Preparation of Examples 250–261

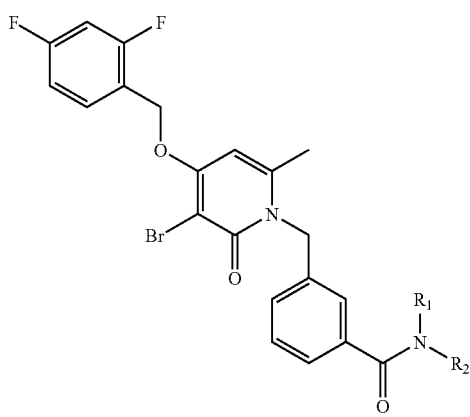

By following the method of Example 249 and replacing N-methylamine with the appropriate amine, the compounds of Examples 250–261 are prepared. The deprotection of the protected intermediates was accomplished with 4N HCl in dioxane to afford the compounds as hydrochloride salts.

| Compound No. | $R_1$ | $R_2$ | % Yield | MF | M + H Requires | ES-HRMS m/z |
|---|---|---|---|---|---|---|
| Ex. 250 | $CH_2CH_2NH-$ | $CH_2CH_2NH-$ | 89 | $C_{25}H_{24}BrF_2N_3O_4$ | 532.1042 | 532.1067 |
| Ex. 251 | H | $CH_2CH_2NH_2$ | 75 | $C_{23}H_{22}BrF_2N_3O_3$ | 506.0885 | 506.0900 |
| Ex. 252 | H | $CH_2CH_2CH_2NH_2$ | 84 | $C_{24}H_{24}BrF_2N_3O_3$ | 520.1042 | 520.1000 |
| Ex. 253 | H | OH | 45 | $C_{21}H_{17}BrF_2N_2O_4$ | 479.0413 | 479.0394 |
| Ex. 254 | $CH_3$ | $CH_3$ | 69 | $C_{23}H_{21}BrF_2N_2O_3$ | 491.0776 | 491.0731 |
| Ex. 255 | H | $CH_3$ | 58 | $C_{22}H_{19}BrF_2N_2O_3$ | 479.0602 | 479.0598 |
| Ex. 256 | $CH_2CH_2O-$ | $CH_2CH_2O-$ | 69 | $C_{25}H_{23}BrF_2N_2O_4$ | 533.0882 | 533.0857 |
| Ex. 257 | H | $CH_2CH_2OH$ | 51 | $C_{23}H_{21}BrF_2N_2O_4$ | 507.0726 | 507.0698 |
| Ex. 258 | $CH_2CH_2OH$ | $CH_2CH_2OH$ | 25 | $C_{25}H_{25}BrF_2N_2O_5$ | 551.0988 | 551.0972 |
| Ex. 259 | $CH_2CH_2CH_2-$ | $CH_2CH_2CH_2-$ | 62 | $C_{26}H_{25}BrF_2N_2O_3$ | 531.1089 | 531.1088 |
| Ex. 260 | H | $CH(CH_3)_2$ | 46 | $C_{24}H_{23}BrF_2N_2O_3$ | 505.0933 | 505.0918 |
| Ex. 261 | $CH_2CH_2-$ | $CH_2CH_2-$ | 60 | $C_{25}H_{23}BrF_2N_2O_3$ | 517.0933 | 517.0950 |

Example 262

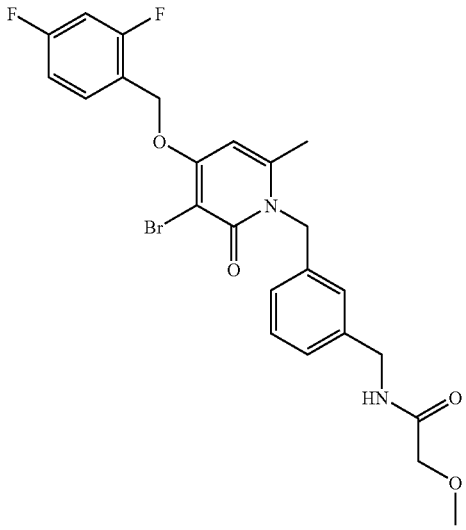

N-(3-{[3-bromo-4-[(2,4-difluorobenzyl)oxy]-6-methyl-2-oxopyridin-1(2H)-yl]methyl}benzyl)-2-methoxyacetamide To a reaction vessel (borosilicate culture tube) was added methoxyacetic acid (0.09 g, 1.00 mmol) A stock solution of 1-hydroxybenzotriazole (3 mL, 0.16 M) and N-methylmorpholine (3 mL, 0.43 M) in N,N-dimethylformamide were added to the reaction vessel followed by approximately 0.97 g of the polymer bound carbodiimide resin (1.38 mmol/g). Additional N,N-dimethylformamide (3 mL) was then added to the reaction vessel. The parallel reaction apparatus was then orbitally shaken (Labline Benchtop Orbital Shaker) at approximately 200 RPM at room temperature for 4 hours. 1-[3-(aminomethyl)benzyl]-3-bromo-4-[(2,4-difluorobenzyl)oxy]-6-methylpyridin-2(1H)-one (EXAMPLE 161) (0.30 g, 0.668 mmol) was then added to the reaction vessel followed by additional N,N-dimethylformamide (5.0 mL) and the reaction apparatus was orbitally shaken at room temperature overnight. At this time the reaction was diluted with tetrahydrofuran (20 mL) and treated with approximately 2.06 g of polyamine resin (2.63 mmol/g) and approximately 2.67 g of methylisocyanate functionalized polystyrene (1.10 mmol/g) and the orbital shaking was continued at 200 RPM at room temperature for 4 hours. The reaction vessel was then opened and the solution phase products were separated from the insoluble quenched byproducts by filtration and collection into a vial. After partial evaporation the insoluble byproducts were rinsed with tetrahydrofuran (2×10 mL). The filtrate was evaporated by blowing $N_2$ over the vial while heating (60° C.) in a reaction block (KEM-Lab Parallel Reactor) afforded a tan solid (0.321 g, 89.4%). $^1H$ NMR (400 MHz, DMF-$d_6$) δ 8.33 (br s, 1H), 7.81 (app q, J=7.85 Hz, 1H), 7.40–7.23 (m, 5H), 7.09 (d, J=7.25 Hz, 1H), 6.68 (s, 1H), 5.46 (s, 2H), 5.42 (s, 2H), 4.45 (d, J=6.24 Hz, 2H), 3.93 (s, 2H), 3.39 (s, 3H), 2.44 (s, 3H). ES-HRMS m/z 521.0891 (M+H $C_{24}H_{23}BrF_2N_2O_4$ requires 521.0882).

Preparation of Example 263–265

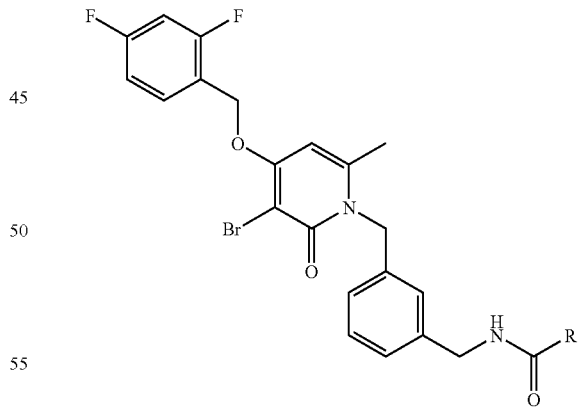

By following the method of Example 262 and replacing methoxyacetic acid with the appropriate acid, the compounds of Examples 263–265 are prepared. The deprotection of the protected intermediates was accomplished with 4N HCl in dioxane to afford the compounds as hydrochloride salts.

| Compound No. | R | % Yield | MF | M + H Requires | ES-HRMS m/z |
|---|---|---|---|---|---|
| Ex. 263 | CH$_2$NH$_2$ | 46.1 | C$_{23}$H$_{23}$BrF$_2$N$_3$O$_3$ | 506.0885 | 506.0870 |
| Ex. 264 | CH$_2$NHCOCH$_3$ | 70.4 | C$_{25}$H$_{24}$BrF$_2$N$_3$O$_4$ | 548.0991 | 548.1007 |
| Ex. 265 | CH$_2$OCOCH$_3$ | 42.7 | C$_{23}$H$_{21}$BrF$_2$N$_2$O$_4$ | 549.0831 | 549.0837 |

Example 266

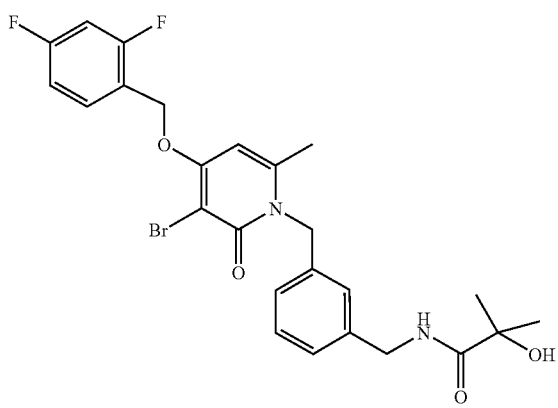

N-(3-{[3-bromo-4-[(2,4-difluorobenzyl)oxy]-6-methyl-2-oxopyridin-1(2H)-yl]methyl}benzyl)-2-hydroxy-2-methylpropanamide 1-[3-(aminomethyl)benzyl]-3-bromo-4-[(2,4-difluorobenzyl)oxy]-6-methylpyridin-2(1H)-one (EXAMPLE 161) (0.300 g, 0.668 mmol), 1-hydroxyisobutyric acid (0.215 g, 2.064 mmol), 1-hydroxybenzotriazole (0.112 g, 0.826 mmol), and 1-(3-dimethylaminopropyl)-3-ethylcarbodiimide hydrochloride (0.185 g, 0.963 mmol) were dissolved in N,N-dimethylacetamide (3 mL). N-methylmorpholine (0.209 g, 2.064 mmol) was added, and the reaction stirred for 1 hour at room temperature. The reaction was diluted with H$_2$O (50 mL) and the aqueous layer extracted with ethyl acetate (3×25 mL). The combined organics were then washed with 1N HCl (25 mL), saturated Na$_2$CO$_3$ (25 mL), brine (25 mL), dried over Na$_2$SO$_4$, and concentrated to yield an off-white solid (0.235 g, 64%). $^1$H NMR (400 MHz, DMF-d$_6$) δ 8.25 (br s, 1H), 7.81 (app q, J=7.92 Hz, 1H), 7.40–7.21 (m, 5H), 7.09 (d, J=6.84 Hz, 1H), 6.67 (s, 1H), 5.46 (s, 2H), 5.42 (s, 2H), 4.42 (d, J=6.24 Hz, 2H), 2.44 (s, 3H), 1.38 (s, 6H). ES-HRMS m/z 535.1024 (M+H C$_{25}$H$_{25}$BrF$_2$N$_2$O$_4$ requires 535.1039).

Example 267

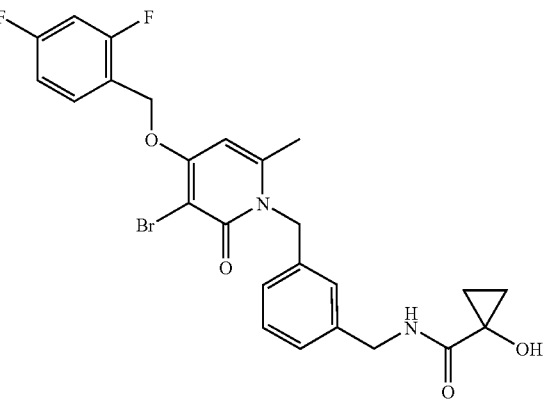

N-(3-{[3-bromo-4-[(2,4-difluorobenzyl)oxy]-6-methyl-2-oxopyridin-1(2H)-yl]methyl}benzyl)-1-hydroxycyclopropanecarboxamide By following the method of Example 266 and substituting 1-hydroxy-1-cyclopropane-carboxylic acid for 1-hydroxyisobutyric acid, the title compound was prepared (0.352 g, 96%). $^1$H NMR (400 MHz, DMF-d$_6$) δ 8.46 (app t, J=6.24 Hz, 1H), 7.81 (app q, J=7.92 Hz, 1H), 7.40–7.22 (m, 5H), 7.06 (d, J=7.05 Hz, 1H), 6.67 (s, 1H), 5.45 (s, 2H), 5.42 (s, 2H), 4.46 (d, J=6.44 Hz, 2H), 2.45 (s, 3H), 1.17–1.12 (m, 2H), 0.93 (app q, J=3.82 Hz, 2H). ES-HRMS m/z 533.0861 (M+H C$_{25}$H$_{23}$BrF$_2$N$_2$O$_4$ requires 533.0882).

Example 267

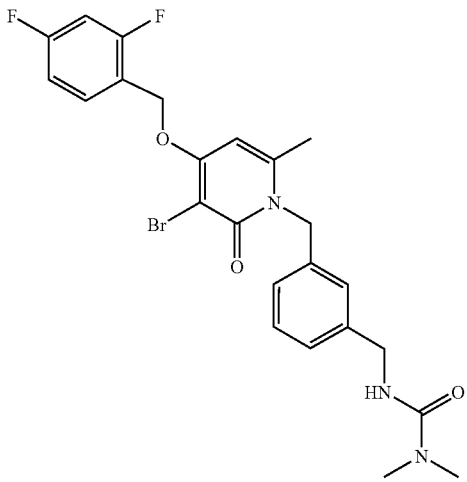

N'-(3-{[3-bromo-4-[(2,4-difluorobenzyl)oxy]-6-methyl-2-oxopyridin-1(2H)-yl]methyl}benzyl)-N,N-dimethylurea Step 1: Preparation of 4-nitrophenyl 3-{[3-bromo-4-[(2,4-difluorobenzyl)oxy]-6-methyl-2-oxopyridin-1(2H)-yl]methyl}benzylcarbamate.

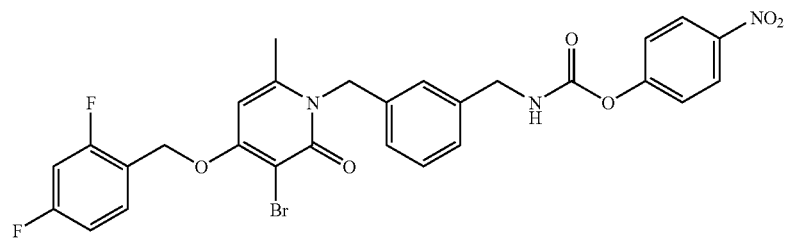

1-[3-(aminomethyl)benzyl]-3-bromo-4-[(2,4-difluorobenzyl)oxy]-6-methylpyridin-2(1H)-one (EXAMPLE 161) (2.00 g, 4.45 mmol) was suspended in dichloromethane (15 mL). Pyridine was added (0.43 mL, 5.34 mmol). After stirring for 10 minutes at room temperature, a stock solution of 4-nitrophenyl chloroformate (10.0 mL, 0.50 M) in dichloromethane was added dropwise. After stirring for 4.5 hours at room temperature, a stock solution of 4-nitrophenyl chloroformate (2.5 mL, 0.50 M) in dichloromethane was again added dropwise and stirring continued at 40° C. overnight. The reaction mixture was concentrated and subjected to chromatography (silica gel, ethyl acetate with 10% methanol/hexanes) to afford a yellow solid (1.11 g, 66%). $^1$H NMR (400 MHz, DMSO-d$_6$) δ 8.56 (app t, J=6.10 Hz, 1H), 8.24–8.21 (m, 2H), 7.62 (app q, J=7.88 Hz, 1H), 7.40–7.27 (m, 7H), 6.98 (d, J=7.52 Hz, 1H), 6.54 (s, 1H), 5.30 (s, 2H), 5.24 (s, 2H), 4.25 (d, J=6.18 Hz, 2H), 2.30 (s, 3H). ES-HRMS m/z 614.0753 (M+H C$_{28}$H$_{22}$BrF$_2$N$_3$O$_6$ requires 614.0733).

Step 2: Preparation of N'-(3-{[3-bromo-4-[(2,4-difluorobenzyl)oxy]-6-methyl-2-oxopyridin-1(2H)-yl]methyl}benzyl)-N,N-dimethylurea. To a reaction vessel (borosilicate culture tube) was added 4-nitrophenyl 3-{[3-bromo-4-[(2,4-difluorobenzyl)oxy]-6-methyl-2-oxopyridin-1(2H)-yl]methyl}benzylcarbamate (from step 1) (0.350 g, 0.570 mmol) dissolved in dichloromethane (6.0 mL). The parallel reaction apparatus was then orbitally shaken (Labline Benchtop Orbital Shaker) at approximately 200 RPM at room temperature for 15 minutes. A stock solution of N,N-dimethylamine in tetrahydorfuran (0.427 mL, 2.0 M) was then added to the reaction vessel and the reaction apparatus was orbitally shaken at room temperature overnight. The reaction mixture was concentrated and subjected to chromatography (silica gel, ethyl acetate with 10% methanol/hexanes) which afforded an off white solid (0.226 g, 63.3%). $^1$H NMR (400 MHz, DMF-d$_6$) δ 7.81 (app q, J=7.92 Hz, 1H), 7.40–7.19 (m, 5H), 7.06 (d, J=7.45 Hz, 1H), 6.88 (app t, J=5.84 Hz, 1H), 6.68 (s, 1H), 5.45 (s, 2H), 5.42 (s, 1H), 4.35 (d, J=5.84 Hz, 1H), 2.92 (s, 6H), 2.44 (s, 3H). ES-HRMS m/z 520.1065 (M+H C$_{24}$H$_{24}$BrF$_2$N$_3$O$_3$ requires 520.1042).

Preparation of Example 268–270

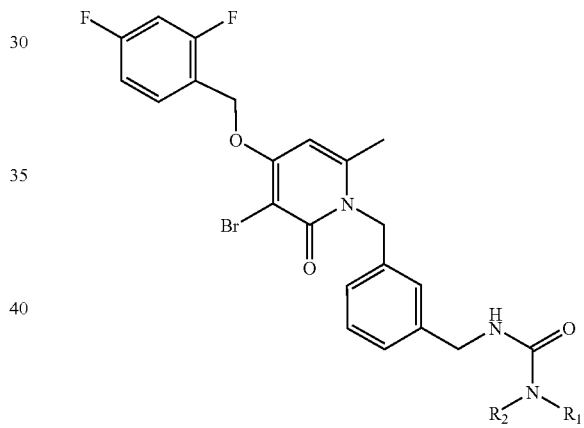

By following the method of Example 267 and replacing N,N-dimethylamine with the appropriate amine, the compounds of Examples 268–270 are prepared. The deprotection of the protected intermediates was accomplished with 4N HCl in dioxane to afford the compounds as hydrochloride salts.

| Compound No. | R$_1$ | R$_2$ | % Yield | MF | M + H Requires | ES-HRMS m/z |
| --- | --- | --- | --- | --- | --- | --- |
| Ex. 268 | CH$_2$CH$_2$N— | CH$_2$CH$_2$N— | 66.6 | C$_{26}$H$_{27}$BrF$_2$N$_4$O$_3$ | 561.1307 | 561.1309 |
| Ex. 269 | H | CH$_3$ | 27.0 | C$_{23}$H$_{22}$BrF$_2$N$_3$O$_3$ | 506.0885 | 506.0898 |
| Ex. 270 | CH$_2$CH$_2$O— | CH$_2$CH$_2$O— | 64.4 | C$_{26}$H$_{26}$BrF$_2$N$_3$O$_4$ | 562.1148 | 562.1137 |

Example 271

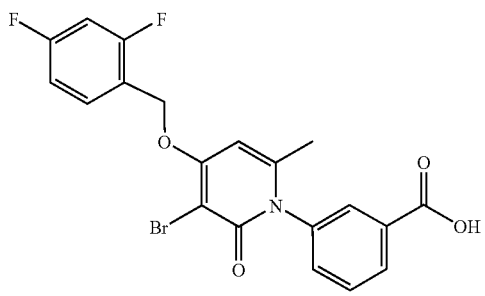

3-[3-bromo-4-[(2,4-difluorobenzyl)oxy]-6-methyl-2-oxopyridin-1(2H)-yl]benzoic acid Step 1: Preparation of methyl 3-(4-hydroxy-6-methyl-2-oxopyridin-1(2H)-yl)benzoate.

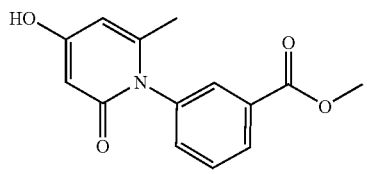

Methyl 3-aminobenzoate (75.00 g, 496.13 mmol) and 4-hydroxy-6-methyl-2-pyrone (62.57 g, 496.13 mmol) were suspended in 1,2-dichlorobenzene (150 mL) and heated to 165° C. for 15 minutes. The reaction was cooled to room temperature and extracted with 0.54M $K_2CO_3$ (4×250 mL). The aqueous layers were acidified (pH 2) with 4N HCl. The precipitate was collected by filtration to afford a yellow-orange solid (20.24 g, 16%). The resulting filtrate was extracted with ethyl acetate (3×1 L). The organic layers were washed with brine (500 mL), dried over $MgSO_4$ and evaporated. The resulting solid was washed with hot $H_2O$ to afford a yellow-orange solid (3.84 g, 3%). The two solids were then combined. $^1$H NMR (400 MHz, DMSO-$d_6$) δ 7.98 (dt, J=1.31, 7.79 Hz, 1H), 7.69 (app t, J=1.78 Hz, 1H), 7.62 (t, J=7.78 Hz, 1H), 7.49 (ddd, J=1.07, 1.07, 7.85 Hz, 1H), 5.89 (dd, J=0.87, 2.48 Hz, 1H), 5.55 (app d, J=0.94 Hz, 1H), 3.83 (s, 3H), 1.80 (s, 3H). ES-HRMS m/z 260.0895 (M+H $C_{14}H_{13}NO_4$ requires 260.0917).

Step 2: Preparation of methyl 3-[4-[(2,4-difluorobenzyl)oxy]-6-methyl-2-oxopyridin-1(2H)-yl]benzoate.

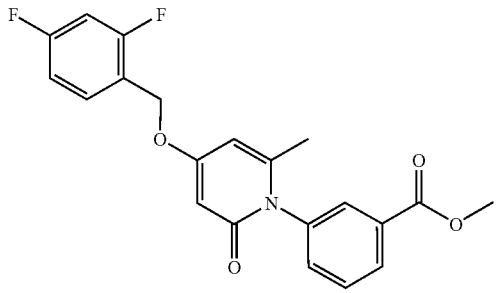

Methyl 3-(4-hydroxy-6-methyl-2-oxopyridin-1(2H)-yl)benzoate (from step 1) (24.00 g, 92.57 mmol) and $K_2CO_3$ (15.35 g, 111.08 mmol) were dissolved in N,N-dimethylformamide (220 mL). 2,4-Difluorobenzyl bromide (20.12 g, 97.20 mmol) was then added and the reaction mixture stirred for 48 hours at room temperature. The reaction mixture was diluted with $H_2O$ (1 L) and the precipitate collected by filtration to afford a white solid (4.08 g, 11%). The resulting oil was purified by chromatography (silica gel, ethyl acetate with 10% methanol/hexanes) to afford an off white solid (11.88 g, 33%). The two solids were combined. $^1$H NMR (400 MHz, CDCl$_3$) δ 8.11 (dt, J=1.41, 7.79 Hz, 1H), 7.87 (app t, J=1.78 Hz, 1H), 7.58 (app t, J=7.69 Hz, 1H), 7.45–7.38 (m, 2H), 6.94–6.84 (m, 2H), 5.97 (d, J=2.68 Hz, 1H), 5.90 (ddd, J=0.94, 1.74, 1.74 Hz, 1H), 5.97 (s, 1H), 3.90 (s, 3H), 1.89 (s, 3H). ES-HRMS m/z 386.1179 (M+H $C_{21}H_{17}F_2NO_4$ requires 386.1198).

Step 3: Preparation of methyl 3-[3-bromo-4-[(2,4-difluorobenzyl)oxy]-6-methyl-2-oxopyridin-1(2H)-yl]benzoate.

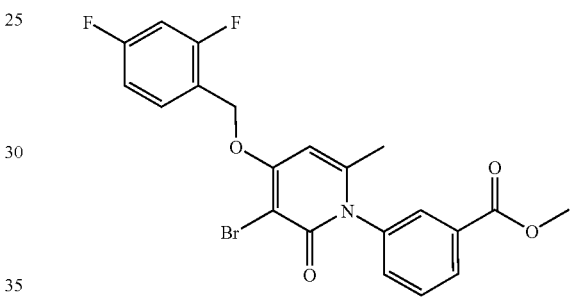

Methyl 3-[4-[(2,4-difluorobenzyl)oxy]-6-methyl-2-oxopyridin-1(2H)-yl]benzoate (from step 2) (15.85 g, 41.130 mmol) suspended in acetonitrile (165 mL) was cooled in an ice-bath. N-bromosuccinimide (7.687 g, 43.186 mmol) was added and the ice-bath was removed. The reaction mixture was stirred for 1.5 hours at room temperature. Reaction was concentrated and subjected to chromatography (silica gel, ethyl acetate with 10% methanol/hexanes) afforded an off white solid (17.63 g, 92%). $^1$H NMR (400 MHz, CDCl$_3$) δ 8.17 (dt, J=1.41, 7.85 Hz, 1H), 7.90 (t, J=1.81 Hz, 1H), 7.67–7.41 (m, 3H), 7.05–6.88 (m, 2H), 6.13 (s, 1H), 5.30 (s, 2H), 3.95 (s, 1H), 2.01 (s, 3H). ES-HRMS m/z 464.0286 (M+H $C_{21}H_{16}BrF_2NO_4$ requires 464.0304).

Step 4: Preparation of the title compound. Methyl 3-[3-bromo-4-[(2,4-difluorobenzyl)oxy]-6-methyl-2-oxopyridin-1(2H)-yl]benzoate (from step 3) (10.0 g, 21.539 mmol) was dissolved in methanol (36 mL) and tetrahydrofuran (14 mL). 4N NaOH (13.5 mL, 53.847 mmol) was added. The resulting mixture was stirred for 1.5 hours at room temperature. The reaction was acidified (pH 2) with 4N HCl. The precipitate was collected by filtration to afford an off white solid (7.83 g, 81%) $^1$H NMR (400 MHz, DMSO-$d_6$) δ 8.01 (dt, J=1.41, 7.65 Hz, 1H), 7.76 (app t, J=1.78 Hz, 1H), 7.76–7.15 (m, 5H), 6.66 (s, 1H), 5.32 (s, 2H), 1.92 (s, 3H) ES-HRMS m/z 450.0134 (M+H $C_{20}H_{14}BrF_2NO_4$ requires 450.0147).

Example 272

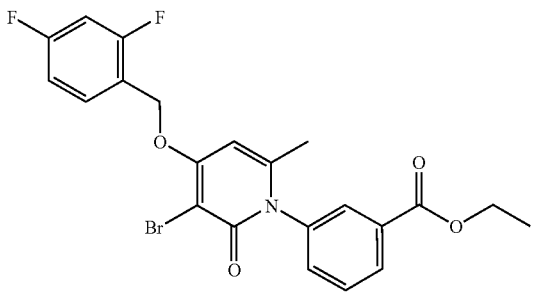

Ethyl 3-[3-bromo-4-[(2,4-difluorobenzyl)oxy]-6-methyl-2-oxopyridin-1(2H)-yl]benzoate By following the method of Example 271 and substituting ethyl 3-aminobenzoate for methyl 3-aminobenzoate, the title compound was prepared (2.66 g, 79%). $^1$H NMR (400 MHz, CDCl$_3$) δ 8.13 (dt, J=1.41, 7.85 Hz, 1H), 7.84 (t, J=1.88 Hz, 1H), 7.62–7.55 (m, 2H), 7.36 (app dq, J=1.07, 7.85 Hz, 1H), 6.96 (app dt, J=2.55, 8.35 Hz, 1H), 6.88–6.84 (m, 1H), 6.08 (s, 1H), 5.25 (s, 2H), 4.42–4.30 (m, 2H), 1.96 (s, 3H), 1.36 (t, J=7.12 Hz, 3H). ES-HRMS m/z 478.0482 (M+H C$_{22}$H$_{18}$BrF$_2$NO$_4$ requires 478.0460).

Example 273

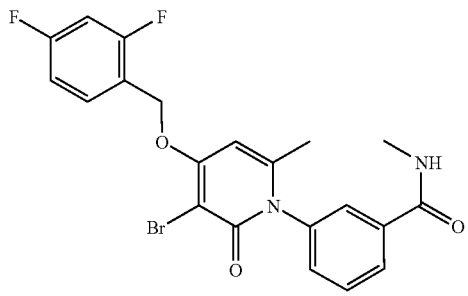

3-[3-bromo-4-[(2,4-difluorobenzyl)oxy]-6-methyl-2-oxopyridin-1(2H)-yl]-N-methylbenzamide To a reaction vessel (borosilicate culture tube) was added EXAMPLE 271 (0.300 g, 0.666 mmol). A stock solution of 1-hydroxybenzotriazole in N,N-dimethylformamide (3 mL, 0.11 M) was added to the reaction vessel followed by approximately 0.97 g of the polymer bound carbodiimide resin (1.38 mmol/g). Additional N,N-dimethylformamide (2 mL) was then added to the reaction vessel. The parallel reaction apparatus was then orbitally shaken (Labline Benchtop Orbital Shaker) at approximately 200 RPM at room temperature for 15 minutes. N-Methylamine in tetrahydrofuran (0.50 mL, 0.999 mmol) was then added to the reaction vessel and the reaction apparatus was orbitally shaken at room temperature overnight. At this time the reaction was diluted with tetrahydrofuran (30 mL) and treated with approximately 2.0 g of polyamine resin (2.63 mmol/g) and approximately 3.6 g of methylisocyanate functionalized polystyrene (1.10 mmol/g) and the orbital shaking was continued at 200 RPM at room temperature for 4 hours. The reaction vessel was then opened and the solution phase products were separated from the insoluble quenched byproducts by filtration and collection into a vial. After partial evaporation the insoluble byproducts were rinsed with tetrahydrofuran (2×10 mL). The filtrate was evaporated by blowing N$_2$ over the vial while heating (60° C.) in a reaction block (KEM-Lab Parallel Reactor) to give an off-white solid (0.189 g, 61%). $^1$H NMR (400 MHz, DMF-d$_6$) δ 8.56 (br d, J=4.16 Hz, 1H), 8.05–7.76 (m, 3H), 7.66 (t, J=7.79 Hz, 1H), 7.56–7.19 (m, 3H), 6.74 (s, 1H), 5.43 (s, 2H), 3.46 (s, 3H), 2.03 (s, 3H). ES-HRMS m/z 463.0476 (M+H C$_{21}$H$_{17}$BrF$_2$N$_2$O$_3$ requires 463.0463).

Preparation of Example 274–289

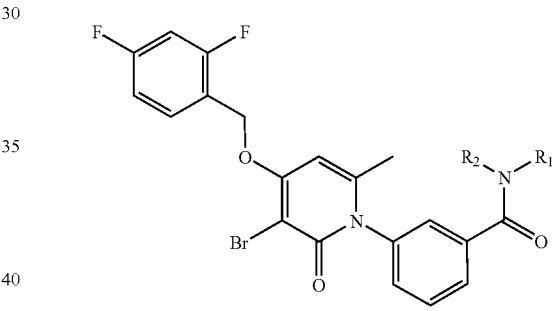

By following the method of Example 273 and replacing N-methylamine with the appropriate amine, the compounds of Examples 274–289 are prepared. The deprotection of the protected intermediates was accomplished with 4N HCl in dioxane to afford the compounds as their hydrochloride salts.

| Compound No. | R1 | R2 | % Yield | MF | M + H Requires | ES-HRMS m/z |
|---|---|---|---|---|---|---|
| Ex. 274 | CH2CH2NH— | CH2CH2NH— | 92.8 | C$_{24}$H$_{22}$BrF$_2$N$_3$O$_3$ | 518.0885 | 518.0865 |
| Ex. 275 | H | CH2CH2NH2 | 95.7 | C$_{22}$H$_{20}$BrF$_2$N$_3$O$_3$ | 492.0729 | 492.0711 |
| Ex. 276 | H | CH2CH2CH2NH2 | 97.8 | C$_{23}$H$_{22}$BrF$_2$N$_3$O$_3$ | 506.0885 | 506.0889 |
| Ex. 277 | H | OH | 91.0 | C$_{20}$H$_{15}$BrF$_2$N$_2$O$_4$ | 465.0256 | 465.0278 |
| Ex. 278 | CH3 | CH3 | 67.7 | C$_{22}$H$_{19}$BrF$_2$N$_2$O$_3$ | 477.0620 | 477.0626 |
| Ex. 279 | CH2CH2O— | CH2CH2O— | 86.7 | C$_{24}$H$_{21}$BrF$_2$N$_2$O$_4$ | 519.0726 | 519.0696 |
| Ex. 280 | H | CH2CH2OH | 78.3 | C$_{22}$H$_{19}$BrF$_2$N$_2$O$_4$ | 493.0569 | 493.0575 |
| Ex. 281 | CH2CH2CH2— | CH2CH2CH2— | 87.9 | C$_{25}$H$_{23}$BrF$_2$N$_2$O$_3$ | 517.0933 | 517.0918 |
| Ex. 282 | H | CH(CH3)2 | 80.6 | C$_{23}$H$_{21}$BrF$_2$N$_2$O$_3$ | 491.1076 | 491.1097 |
| Ex. 283 | CH2CH2— | CH2CH2— | 87.9 | C$_{24}$H$_{21}$BrF$_2$N$_2$O$_4$ | 503.0776 | 503.0732 |
| Ex. 284 | CH2CH2N(CH3)— | CH2CH2N(CH3)— | 75.8 | C$_{25}$H$_{24}$BrF$_2$N$_3$O$_3$ | 532.1042 | 532.1038 |
| Ex. 285 | H | CH2CH2N(CH3)2 | 86.1 | C$_{24}$H$_{24}$BrF$_2$N$_3$O$_3$ | 520.1042 | 520.1030 |
| Ex. 286 | H | CH2CH2OCH3 | 90.2 | C$_{23}$H$_{21}$BrF$_2$N$_2$O$_4$ | 507.0726 | 507.0680 |
| Ex. 287 | CH3 | CH2CH2N(CH3)2 | 60.0 | C$_{25}$H$_{26}$BrF$_2$N$_3$O$_3$ | 534.1198 | 534.1155 |

-continued

| Compound No. | R1 | R2 | % Yield | MF | M + H Requires | ES-HRMS m/z |
|---|---|---|---|---|---|---|
| Ex. 288 | CH3 | CH2CH2OH | 81.6 | $C_{23}H_{21}BrF_2N_2O_4$ | 507.0726 | 507.0694 |
| Ex. 289 | CH3 | CH2CH2OCH3 | 94.4 | $C_{24}H_{23}BrF_2N_2O_4$ | 521.0882 | 521.0862 |

Example 290

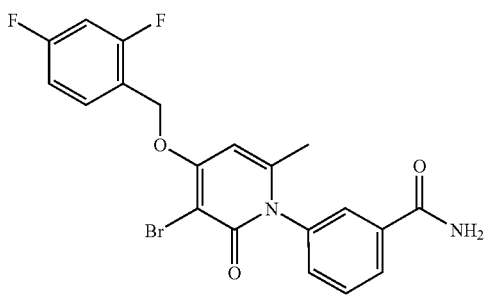

3-[3-bromo-4-[(2,4-difluorobenzyl)oxy]-6-methyl-2-oxopyridin-1(2H)-yl]benzamide

EXAMPLE 271 (2.00 g, 4.44 mmol) and 2-chloro-4,6-dimethoxy-1,3,5-triazine (0.94 g, 5.33 mmol) were suspended in tetrahydrofuran (20 mL). 4-Methylmorpholine (1.5 mL, 13.32 mmol) was added. The resulting mixture was stirred for 1.5 hours at room temperature. NH$_4$OH (10 mL, 148.00 mmol) was added and the reaction was stirred for 0.5 hours at room temperature. H$_2$O (50 mL) and tetrahydrofuran (50 mL) were added and the organic layer was separated. The aqueous phase was extracted with ethyl acetate (75 mL) and the combined organics were washed with saturated Na$_2$CO$_3$ (50 mL), 1N HCl (50 mL), and brine (50 mL). The organic phase was dried over Na$_2$SO$_4$ and evaporated. The resulting solid was washed with diethyl ether to give a white solid (1.86 g, 93%). $^1$H NMR (400 MHz, DMF-d$_6$) δ 8.20 (br s, 1H), 8.10–8.07 (m, 1H), 7.79 (s, 1H), 7.79 (app q, J=7.83 Hz, 1H), 7.66 (app t, J=7.79 Hz, 1H), 7.57–7.54 (m, 1H), 7.46 (br s, 1H), 7.36–7.19 (m, 2H), 6.74 (s, 1H), 5.43 (s, 2H), 2.04 (s, 3H). ES-HRMS m/z 449.0307 (M+H $C_{20}H_{15}BrF_2N_2O_3$ requires 449.0307).

Example 291

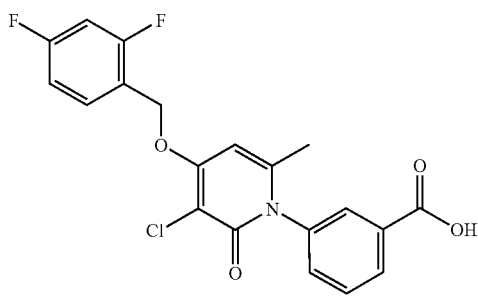

3-[3-chloro-4-[(2,4-difluorobenzyl)oxy]-6-methyl-2-oxopyridin-1(2H)-yl]benzoic acid Step 1: Preparation of methyl 3-[3-chloro-4-[(2,4-difluorobenzyl)oxy]-6-methyl-2-oxopyridin-1(2H)-yl]benzoate

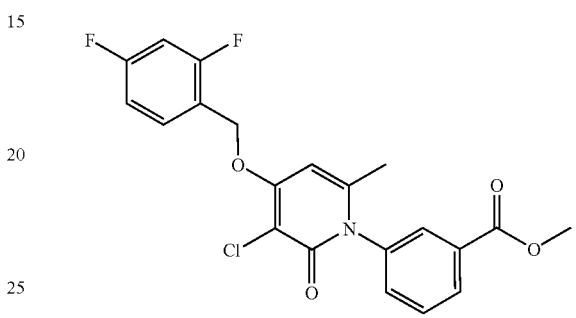

The product from step 2, Example 271 (4.54 g, 11.78 mmol) and N-chlorosuccinimide (1.65 g, 12.37 mmol) were suspended in dichloromethane (12 mL). Dichloroacetic acid (0.10 ml, 1.22 mmol) was added and the reaction mixture was stirred overnight at 40° C. The reaction was cooled to room temperature and a precipitate formed. The precipitate was collected by filtration and washed with dichloromethane (3×10 mL) to afford a white solid (1.75 g, 35%). The filtrate was concentrated and subjected to chromatography (silica gel, ethyl acetate with 10% methanol/hexanes) to afforded an off white solid (1.29 g, 26%). The two solids were then combined. $^1$H NMR (400 MHz, CDCl$_3$) δ 8.12 (dt, J=1.38, 7.83 Hz, 1H), 7.85 (t, J=1.74 Hz, 1H), 7.60–7.52 (m, 2H), 7.37 (dq, J=0.92, 7.92 Hz, 2H), 6.95 (app dt, J=2.55, 8.32 Hz, 1H), 6.89–6.83 (m, 1H), 6.11 (s, 1H), 5.24 (s, 2H), 3.90 (s, 3H), 1.96 (s, 3H). ES-HRMS m/z 420.0783 (M+H $C_{21}H_{16}ClF_2NO_4$ requires 420.0809).

Step 2: Methyl 3-[3-chloro-4-[(2,4-difluorobenzyl)oxy]-6-methyl-2-oxopyridin-1(2H)-yl]benzoate (from step 1) (2.90 g, 6.91 mmol) was dissolved in methanol (5 mL) and tetrahydrofuran (12 mL). 4N NaOH (4.3 mL, 17.27 mmol) was added. The resulting mixture was stirred for 1.5 hours at room temperature. The reaction was acidified (pH-2) with 4N HCl. The precipitate was collected by filtration to afford an off white solid (2.36 g, 84%). $^1$H NMR (400 MHz, DMSO-d$_6$) δ 8.01 (dt, J=1.41, 7.65 Hz, 1H), 7.76 (app t, J=1.68 Hz, 1H), 7.69–7.53 (m, 3H), 7.36–7.14 (m, 2H), 6.69 (s, 1H), 5.32 (s, 2H), 1.93 (s, 3H). ES-HRMS m/z 406.0662 (M+H $C_{20}H_{14}ClF_2NO_4$ requires 406.0652).

Example 292

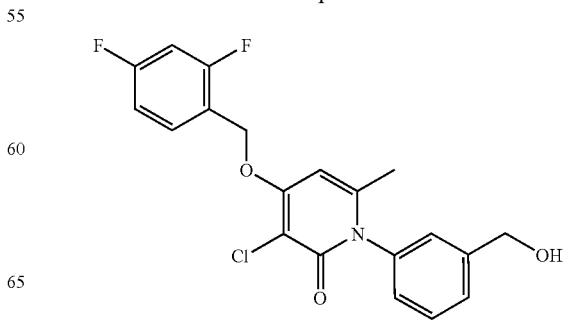

3-chloro-4-[(2,4-difluorobenzyl)oxy]-1-[3-(hydroxymethyl)phenyl]-6-methylpyridin-2(1H)-one The starting material (0.550 g, 1.540 mmol) and N-chlorosuccinimide (0.214 g, 1.602 mmol) were suspended in dichloromethane (15 mL). Dichloroacetic acid (0.01 ml, 0.154 mmol) was added and the reaction mixture heated to 40° C. for 9 hours. The reaction was cooled to room temperature and a precipitate formed. The precipitate was collected by filtration and washed with dichloromethane (3×10 mL) to afford a white solid (0.286 g, 47%). $^1$H NMR (400 MHz, DMSO-d$_6$) δ 7.38 (app q, J=7.35 Hz, 1H), 7.30–7.24 (m, 2H), 7.00 (br s, 1H), 6.85 (app dt, J=2.37, 6.24 Hz, 1H), 6.82–6.67 (m, 2H), 6.01 (s, 1H), 5.07 (s, 2H), 4.48 (d, J=5.24 Hz, 2H), 1.81 (app d, J=0.40 Hz, 3H). ES-HRMS m/z 392.0885 (M+H C$_{20}$H$_{16}$ClF$_2$NO$_3$ requires 392.0860).

Example 293

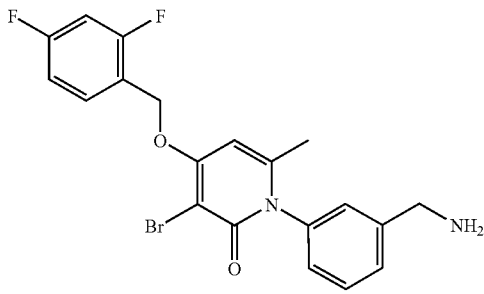

1-[3-(aminomethyl)phenyl]-3-bromo-4-[(2,4-difluorobenzyl)oxy]-6-methylpyridin-2(1H)-one Step 1: Preparation of 1-[3-(chloromethyl)phenyl]-4-[(2,4-difluorobenzyl)oxy]-6-methylpyridin-2(1H)-one.

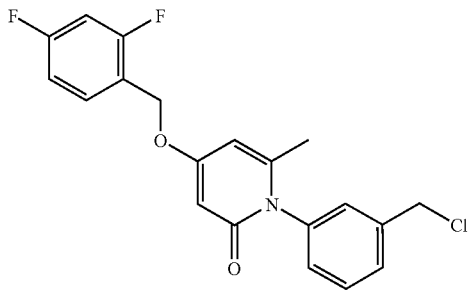

2,4,6-Trichloro-[1,3,5]-triazine (3.09 g, 16.78 mmol) was dissolved in N,N-dimethylformamide (45 mL). The reaction mixture was stirred at room temperature for 1 hour and then dichloromethane (90 mL) was added. The alcohol (5.72 g, 15.99 mmol) was then added. The reaction mixture was stirred at room temperature for 1 hour. The reaction mixture was diluted with dichloromethane (200 mL) and the organic phase was washed with H$_2$O (200 mL), saturated Na$_2$CO$_3$ (200 mL), 1N HCl (200 mL), and brine (200 mL). The organic phase was dried over MgSO$_4$ and evaporated to give an orange solid (5.95 g, 99%).

Step 2: Preparation of 1-[3-(aminomethyl)phenyl]-4-[(2,4-difluorobenzyl)oxy]-6-methylpyridin-2(1H)-one.

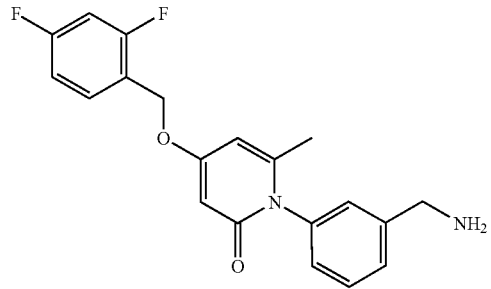

1-[3-(chloromethyl)phenyl]-4-[(2,4-difluorobenzyl)oxy]-6-methylpyridin-2(1H)-one from step 1 (1.00 g, 2.66 mmol) was suspended in methanol (5 mL). The suspension was then brought to −78° C. and NH$_3$ was bubbled through the reaction mixture for 10 minutes. The reaction was then slowly allowed to warm to room temperature and stirred at room temperature for 4 days. The reaction was concentrated and the residue taken up in CH$_2$Cl$_2$ and filtered to remove excess salt. The filtrate was concentrated to afford a tan solid (0.94 g, 99%).

Step 3: Preparation of title compound 1-[3-(aminomethyl)phenyl]-4-[(2,4-difluorobenzyl)oxy]-6-methylpyridin-2(1H)-one from step 3 (3.89 g, 10.93 mmol) suspended in acetonitrile (42 mL) was cooled in an ice-bath. N-bromosuccinimide (2.04 g, 11.47 mmol) was added and the ice-bath was removed. The reaction mixture was stirred for 1.5 hours at room temperature. The reaction was diluted with acetonitrile (100 mL) and the precipitate that formed was collected by filtration and washed with acetonitrile (3×30 mL) to afford an off-white solid (2.74 g, 58%). $^1$H NMR (400 MHz, DMSO-d$_6$) δ 7.67–7.59 (m, 3H), 7.34–7.31 (m, 2H), 7.04 (app t, J=8.72 Hz, 2H), 7.05–6.88 (m, 2H), 6.13 (s, 1H), 5.30 (s, 2H), 3.95 (s, 1H), 2.01 (s, 3H). ES-HRMS m/z 435.0538 (M+H C$_{20}$H$_{17}$BrF$_2$N$_2$O$_2$ requires 435.0514).

Example 294

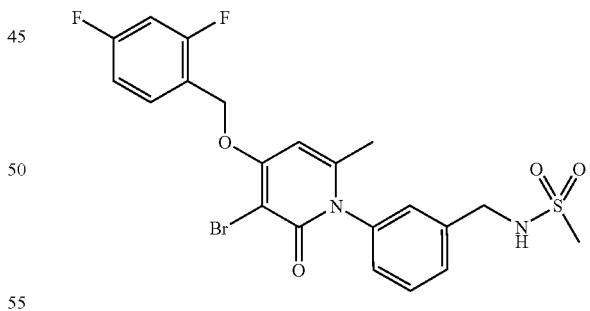

N-{3-[3-bromo-4-[(2,4-difluorobenzyl)oxy]-6-methyl-2-oxopyridin-1(2H)-yl]benzyl}methanesulfonamide To a reaction vessel (borosilicate culture tube) was added EXAMPLE 293 (0.200 g, 0.459 mmol) and N,N-dimethylformamide (4 mL). A stock solution of 4-methylmorpholine in N,N-dimethylformamide (1.8 mL, 1.0 M) was added to the reaction vessel and the parallel reaction apparatus was then orbitally shaken (Labline Benchtop Orbital Shaker) at approximately 200 RPM at room temperature for 10 minutes. A stock solution of methanesulfonyl chloride in N,N-dimethylformamide (4.50 mL, 0.15 M) was then added to the reaction vessel and the reaction apparatus was orbitally shaken at room temperature for 2 hours. At this time the reaction was diluted with dichloromethane (4 mL) and treated with approximately 2.1 g of polyamine resin (2.63 mmol/g) and approximately 0.8 g of methylisocyanate functionalized polystyrene (1.7 mmol/g) and the orbital shaking was continued at 200 RPM at room temperature overnight. The reaction vessel was then opened and the solution phase products were separated from the insoluble quenched byproducts by filtration and collection into a vial. After partial evaporation the insoluble byproducts were rinsed with dichloromethane (2×5 mL). The filtrate was evaporated by blowing $N_2$ over the vial while heating (60° C.) in a reaction block (KEM-Lab Parallel Reactor) to give a yellow solid (0.190 g, 81%). $^1$H NMR (400 MHz, $CD_3OD$) δ 7.63 (app q, J=7.00 Hz, 1H), 7.56–7.50 (m, 2H), 7.25 (m, 1H), 7.16 (dt, J=1.94, 7.25 Hz, 1H), 7.04 (app t, J=8.59 Hz, 2H), 6.58 (s, 1H), 5.34 (s, 2H), 4.30 (s, 2H), 2.87 (s, 3H), 2.03 (s, 3H). ES-HRMS m/z 513.0313 (M+H $C_{21}H_{19}BrF_2N_2O_4S$ requires 513.0290).

Preparation of Example 295–296

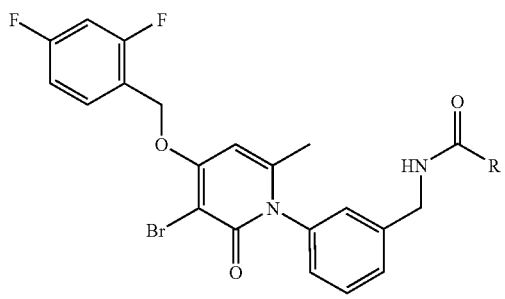

By following the method of Example 294 and replacing methanesulfonyl chloride with the appropriate acid chloride, the compounds of Examples 295–296 are prepared.

| Compound No. | R | % Yield | MF | M + H Requires | ES-HRMS m/z |
|---|---|---|---|---|---|
| Ex. 295 | $CH_3$ | 78.0 | $C_{22}H_{19}BrF_2N_2O_3$ | 477.0620 | 477.0640 |
| Ex. 296 | $OCH_3$ | 84.0 | $C_{22}H_{19}BrF_2N_2O_4$ | 493.0569 | 493.0591 |

Example 297

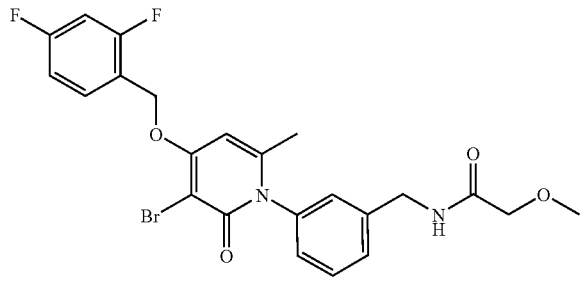

N-{3-[3-bromo-4-[(2,4-difluorobenzyl)oxy]-6-methyl-2-oxopyridin-1(2H)-yl]benzyl}-2-methoxyacetamide To a reaction vessel (borosilicate culture tube) was added approximately 2.87 g of polymer bound carbodiimide resin (0.96 mmol/g) followed by a stock solution of methoxyacetic acid (8.0 mL, 0.10 M) in N,N-dimethylacetamide. A stock solution of 1-hydroxybenzotriazole in N,N-dimethylacetamide (3.0 mL, 0.10 M) and N-methylmorpholine (6.0 mL, 0.10 M) in 1,2-dichloroethane were added to the reaction vessel. The parallel reaction apparatus was then orbitally shaken (Labline Benchtop Orbital Shaker) at approximately 200 RPM at room temperature for 4 hours. A stock solution of EXAMPLE 293 in N,N-dimethylacetamide (5.0 mL, 0.10 M) was then added to the reaction vessel and the reaction apparatus was orbitally shaken at room temperature overnight. At this time the reaction was diluted with 1,2-dichloroethane (10 mL) and treated with approximately 1.70 g of polyamine resin (2.63 mmol/g) and approximately 0.84 g of methylisocyanate functionalized polystyrene (1.50 mmol/g) and the orbital shaking was continued at 200 RPM at room temperature for 4 hours. The reaction vessel was then opened and the solution phase products were separated from the insoluble quenched byproducts by filtration and collection into a vial. After partial evaporation the insoluble byproducts were rinsed with N,N-dimethylacetamide (2×5 mL). The filtrate was evaporated by blowing $N_2$ over the vial while heating (60° C.) in a reaction block (KEM-Lab Parallel Reactor) and subjected to chromatography (silica gel, ethyl acetate with 10% methanol/hexanes) afforded an off white solid (0.081 g, 28%). $^1$H NMR (400 MHz, DMF-$d_6$) δ 7.59 (q, J=7.65 Hz, 1H), 7.46 (app t, J=7.55 Hz, 1H), 7.40–7.37 (m, 1H), 7.11–7.07 (m, 2H), 7.00 (t, J=8.56 Hz, 2H), 6.54 (s, 1H), 5.30 (s, 2H), 4.43 (s, 2H), 3.88 (s, 2H), 3.35 (app d, J=0.80 Hz, 2H), 1.97 (s, 3H). ES-HRMS m/z 507.0699 (M+H $C_{23}H_{21}BrF_2N_2O_4$ requires 507.0726).

Preparation of Examples 298–300

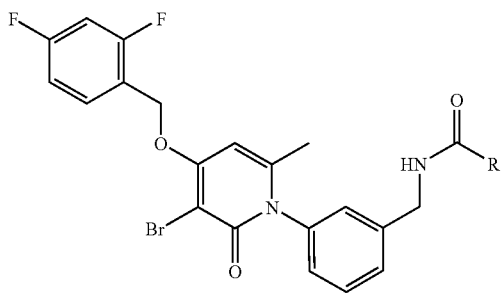

By following the method of and replacing methoxyacetic acid with the appropriate acid, the compounds of Examples 298–300 are prepared. The deprotection of the protected intermediates was accomplished with 4N HCl in dioxane or 1 M $K_2CO_3$ in methanol to afford the compounds as hydrochloride salts.

| Compound No. | R | % Yield | MF | M + H Requires | ES-HRMS m/z |
|---|---|---|---|---|---|
| Ex. 298 | CH$_2$OCOCH$_3$ | 35.5 | C$_{24}$H$_{21}$BrF$_2$N$_2$O$_5$ | 535.0675 | 535.0686 |
| Ex. 299 | CH$_2$NH$_2$ | 32.6 | C$_{22}$H$_{20}$BrF$_2$N$_3$O$_3$ | 492.0729 | 492.0744 |
| Ex. 300 | CH$_2$OH | 33.4 | C$_{22}$H$_{19}$BrF$_2$N$_2$O$_4$ | 493.0569 | 493.0578 |

Example 301

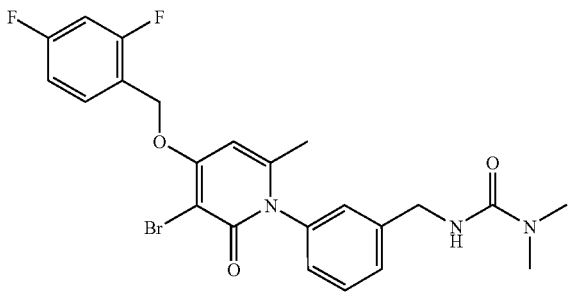

N'-[3-[3-bromo-4-[(2,4-difluorobenzyl)oxy]-6-methyl-2-oxopyridin-1(2H)-yl]benzyl}-N,N-dimethylurea Step 1: Preparation of 4-nitrophenyl 3-[3-bromo-4-[(2,4-difluorobenzyl)oxy]-6-methyl-2-oxopyridin-1(2H)-yl]benzylcarbamate.

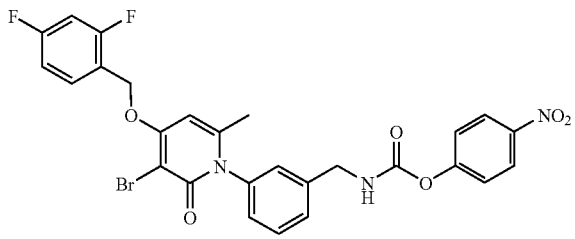

1-[3-(aminomethyl)phenyl]-3-bromo-4-[(2,4-difluorobenzyl)oxy]-6-methylpyridin-2(1H)-one (1.08 g, 2.48 mmol) was suspended in dichloromethane (7.5 mL). Pyridine was added (0.222 mL, 2.74 mmol). After stirring for 10 minutes at room temperature, a stock solution of 4-nitrophenyl chloroformate (5.0 mL, 0.50 M) in dichloromethane was added dropwise. After stirring for 4.5 hours at room temperature, a stock solution of 4-nitrophenyl chloroformate (2.5 mL, 0.50 M) in dichloromethane was again added dropwise and stirring continued at room temperature overnight. The reaction mixture was concentrated and subjected to chromatography (silica gel, ethyl acetate with 10% methanol/hexanes) afforded a yellow solid (0.85 g, 57%).

Step 2: Preparation of title compound. To a reaction vessel (borosilicate culture tube) was added 4-nitrophenyl 3-[3-bromo-4-[(2,4-difluorobenzyl)oxy]-6-methyl-2-oxopyridin-1(2H)-yl]benzylcarbamate (from step 1) (0.150 g, 0.250 mmol) and dichloromethane (2.5 mL). The parallel reaction apparatus was then orbitally shaken (Labline Benchtop Orbital Shaker) at approximately 200 RPM at room temperature for 15 minutes. A stock solution of N,N-dimethylamine in tetrahydorfuran (0.15 mL, 2.0 M) was then added to the reaction vessel and the reaction apparatus was orbitally shaken at room temperature overnight. The reaction mixture was concentrated and subjected to chromatography (silica gel, ethyl acetate with 10% methanol/hexanes) which afforded an off white solid (0.065 g, 51%). $^1$H NMR (400 MHz, DMF-d$_6$) δ 7.58 (app q, J=7.79 Hz, 1H), 7.42 (app t, J=7.65 Hz, 1H), 7.37 (app d, J=7.79 Hz, 1H), 7.08 (s, 1H), 7.03 (app dt, J=1.58, 5.37 Hz, 1H), 6.96 (app dt, J=2.55, 8.39 Hz, 1H), 6.88–6.83 (m, 1H), 6.06 (s, 1H), 5.24 (s, 2H), 4.95 (app t, J=5.57 Hz, 1H), 4.42 (app dddd, J=5.10, 5.71, 10.20, 15.17 Hz, 2H), 2.90 (s, 6H), 1.96 (s, 3H). ES-HRMS m/z 506.0848 (M+H C$_{23}$H$_{22}$BrF$_2$N$_3$O$_3$ requires 506.0885).

Preparation of Examples 302–303

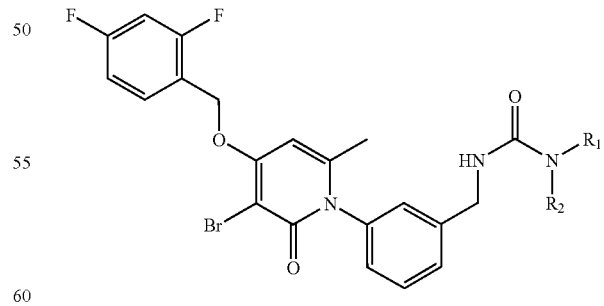

By following the method of Example 301 and substituting N,N-dimethylamine with the appropriate amine, the compounds of Examples 302–303 are prepared.

| Compound No. | R₁ | R₂ | % Yield | MF | M + H Requires | ES-HRMS m/z |
|---|---|---|---|---|---|---|
| Ex. 302 | H | CH₃ | 52.3 | C₂₂H₂₀BrF₂N₃O₃ | 492.0729 | 492.0737 |
| Ex. 303 | CH₂CH₂O— | CH₂CH₂O— | 50.7 | C₂₅H₂₄BrF₂N₃O₄ | 548.0991 | 548.0962 |

Example 304

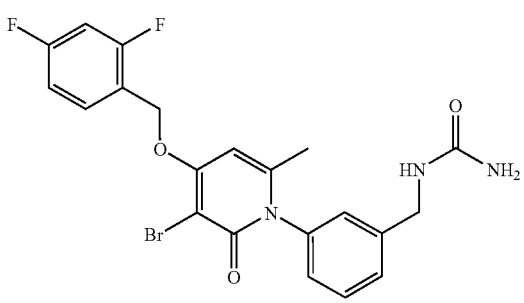

N-{3-[3-bromo-4-[(2,4-difluorobenzyl)oxy]-6-methyl-2-oxopyridin-1(2H)-yl]benzyl}urea To a reaction vessel (borosilicate culture tube) was added EXAMPLE 293 (0.200 g, 0.459 mmol) and tetrahydrofuran (4.0 mL). A stock solution of 4-methylmorpholine in tetrahydrofuran (1.8 mL, 1.0 M) was added to the reaction vessel and the parallel reaction apparatus was then orbitally shaken (Labline Benchtop Orbital Shaker) at approximately 200 RPM at room temperature for 10 minutes. A stock solution of trimethylsilyl isocyanate in tetrahydrofuran (4.0 mL, 0.2 M) was then added to the reaction vessel and the reaction apparatus was orbitally shaken at room temperature for two hours. At this time the reaction was diluted with tetrahydrofuran (4.0 mL) and the resulting precipitate collected by filtration. The solid was then washed with tetrahydrofuran (3×5 mL) to afford a white solid (0.214 g, 97%). ¹H NMR (400 MHz, CD₃OD) δ 7.72 (app q, J=7.83 Hz, 1H), 7.55 (app t, J=8.06 Hz, 1H), 7.46 (d, J=7.52 Hz, 1H), 7.25–7.14 (m, 4H), 6.65 (s, 1H), 5.65 (app t, J=0.80 Hz, 1H), 5.40 (s, 2H), 4.38 (s, 2H), 2.05 (s, 3H). ES-HRMS m/z 478.0594 (M+H C₂₁H₁₈BrF₂N₃O₃ requires 478.0572).

Example 305

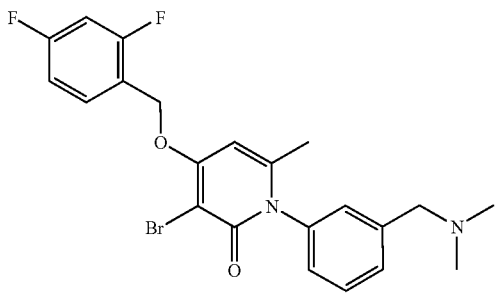

3-bromo-4-[(2,4-difluorobenzyl)oxy]-1-{3-[(dimethylamino)methyl]phenyl}-6-methylpyridin-2(1H)-one Step 1: Preparation of 4-[(2,4-difluorobenzyl)oxy]-1-{3-[(dimethylamino)methyl]phenyl}-6-methylpyridin-2(1H)-one.

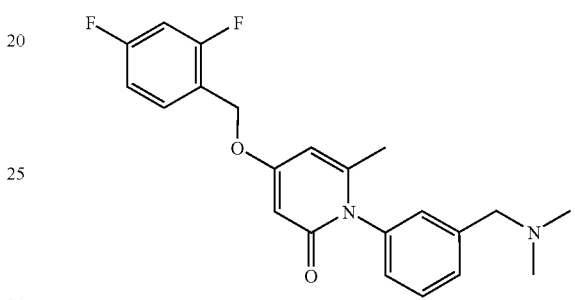

1-[3-(chloromethyl)phenyl]-4-[(2,4-difluorobenzyl)oxy]-6-methylpyridin-2(1H)-one (from step 1 of the synthesis of EXAMPLE 293) (0.500 g, 1.330 mmol) was suspended in a stock solution of N,N-dimethylamine in methanol (2.0 mL, 2.0 M) and stirred overnight at room temperature. Reaction was concentrated and the residue partitioned between H₂O (25 mL) and ethyl acetate (25 mL). The aqueous layer was further extracted with ethyl acetate (2×30 mL), and the combined organics were washed with brine (30 mL), dried over MgSO₄, and concentrated to afford an off-white solid (0.508 g, 99%).

Step 2: Preparation of the title compound. 4-[(2,4-difluorobenzyl)oxy]-1-{3-[(dimethylamino)methyl]phenyl}-6-methylpyridin-2(1H)-one from step 1 (0.200 g, 0.521 mmol) was suspended in acetonitrile (2.5 mL) and cooled in an ice-bath. N-bromosuccinimide (0.097 g, 0.547 mmol) was added and the ice-bath was removed. The reaction mixture was stirred for 1.5 hours at room temperature. The reaction was diluted with acetonitrile (100 mL). The precipitate that formed was collected by filtration and washed with acetonitrile (3×15 mL) to afford a yellow solid (0.160 g, 66%). Chromatography (C-18, acetonitrile/H₂O with 0.1% trifluoroacetic acid, followed by chromatography silica gel, ethyl acetate with 10% methanol/hexanes) afforded an off-white solid (0.024 g, 10%). ¹H NMR (400 MHz, CD₃OD) δ 7.68 (app q, J=7.85 Hz, 1H), 7.58 (app t, J=7.65 Hz, 1H), 7.50 (app d, J=7.85 Hz, 1H), 7.25–7.05 (m, 4H), 6.63 (s, 1H), 5.39 (s, 2H), 3.61 (app q, J=12.08 Hz, 2H), 2.32 (s, 6H), 2.08 (s, 3H). ES-HRMS m/z 463.0782 (M+H C₂₂H₂₁BrF₂N₂O₂ requires 463.0827).

Example 306

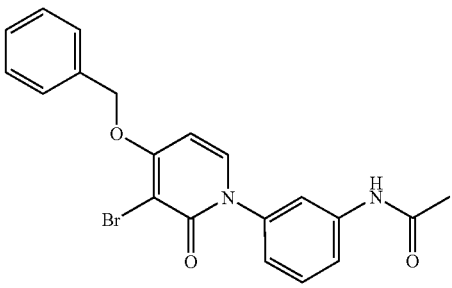

N-{4-[4-(benzyloxy)-3-bromo-2-oxopyridin-1(2H)-yl]benzyl}acetamide

1-[4-(aminomethyl)phenyl]-4-(benzyloxy)-3-bromopyridin-2(1H)-one hydrochloride (0.150 g, 0.389 mmol) was dissolved in N,N-dimethylformamide (3.5 mL). A stock solution of 4-methylmorpholine in N,N-dimethylformamide (1.5 mL, 1.0 M) was added and the reaction stirred at room temperature for 10 minutes. A stock solution of acetyl chloride in N,N-dimethylformamide (3.0 mL, 0.2 M) was then added to the reaction vessel and the reaction apparatus was orbitally shaken at 200 RPM for 2 hours at room temperature. At this time the reaction was diluted with dichloromethane (4 mL) and treated with approximately 1.8 g of polyamine resin (2.63 mmol/g) and approximately 0.8 g of methylisocyanate functionalized polystyrene (1.7 mmol/g) and the orbital shaking was continued at 200 RPM at room temperature overnight. The reaction vessel was then opened and the solution phase products were separated from the insoluble quenched byproducts by filtration and collection into a vial. After partial evaporation the insoluble byproducts were further rinsed with dichloromethane (3×5 mL) and combined with the partially concentrated filtrate. The resulting filtrate was concentrated by blowing $N_2$ over the vial while heating (60° C.) in a reaction block (KEM-Lab Parallel Reactor) to give an off-white solid (0.083 g, 50%). $^1$H NMR (400 MHz, $CD_3OD$) δ 7.59 (d, J=7.79 Hz, 1H), 7.48–7.29 (m, 9H), 6.55 (d, J=7.79 Hz, 1H), 5.35 (s, 2H), 4.39 (s, 2H), 1.98 (s, 3H) ES-HRMS m/z 427.0625 (M+H $C_{21}H_{19}BrN_2O_3$ requires 427.0652).

Example 307

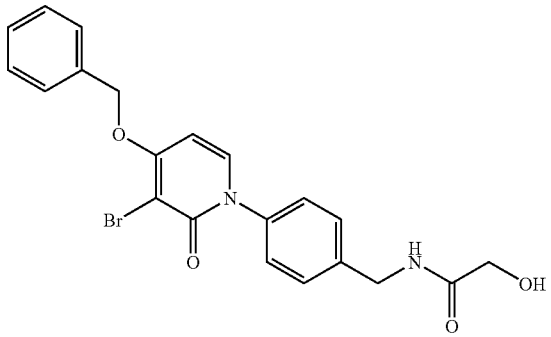

N-{4-[4-(benzyloxy)-3-bromo-2-oxopyridin-1(2H)-yl]benzyl}-2-hydroxyacetamide

To a reaction vessel (borosilicate culture tube) was added approximately 1.95 g of polymer bound carbodiimide resin (0.96 mmol/g) followed by a stock solution of glycolic acid (5.8 mL, 0.10 M) in N,N-dimethylacetamide. A stock solution of 1-hydroxybenzotriazole in N,N-dimethylacetamide (0.4 mL, 0.10 M) and N-methylmorpholine in 1,2-dichloroethane (3.9 mL, 0.10 M) were added to the reaction vessel. The parallel reaction apparatus was then orbitally shaken (Labline Benchtop Orbital Shaker) at approximately 200 RPM at room temperature for 2 hours. A stock solution of 1-[4-(aminomethyl)phenyl]-4-(benzyloxy)-3-bromopyridin-2(1H)-one hydrochloride in N,N-dimethylacetamide (0.05 M, 7.8 mL) was then added to the reaction vessel and the reaction apparatus was orbitally shaken at room temperature overnight. At this time the reaction was diluted with 1,2-dichloroethane (8 mL) and treated with approximately 1.17 g of polyamine resin (2.63 mmol/g) and approximately 0.58 g of methylisocyanate functionalized polystyrene (1.50 mmol/g) and the orbital shaking was continued at 200 RPM at room temperature for 4 hours. The reaction vessel was then opened and the solution phase products were separated from the insoluble quenched byproducts by filtration and collection into a vial. After partial evaporation the insoluble byproducts were rinsed with N,N-dimethylacetamide (2×5 mL) and combined with the partially concentrated filtrate. The filtrate was concentrated by blowing $N_2$ over the vial while heating (60° C.) in a reaction block (KEM-Lab Parallel Reactor) and subjected to chromatography (silica gel, ethyl acetate with 10% methanol/hexanes) which afforded an off white solid (0.081 g, 21%). $^1$H NMR (400 MHz, $CD_3OD$) δ 7.55–7.30 (m, 10H), 6.51 (d, J=7.85 Hz, 1H), 5.37 (s, 2H), 4.52 (s, 2H), 4.08 (s, 2H). ES-HRMS m/z 443.0605 (M+H $C_{21}H_{19}BrN_2O_4$ requires 443.0601).

Example 308

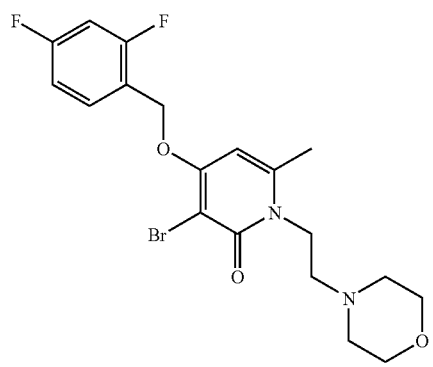

3-bromo-4-[(2,4-difluorobenzyl)oxy]-6-methyl-1-(2-morpholin-4-ylethyl)pyridin-2(1H)-one 3-bromo-4-[(2,4-difluorobenzyl)oxy]-6-methylpyridin-2(1H)-one (0.100 g, 0.303 mmol), cesium carbonate (0.296 g, 0.909 mmol), and 4-(2-chloroethyl)morpholine (0.059 g, 0.394 mmol) were suspended in acetonitrile (4 mL). The reaction was stirred at 60° C. overnight. $H_2O$ (25 mL) was added and the resulting precipitate was collected by filtration. The solid was subjected to chromatography (silica gel, ethyl acetate with 10% methanol) afforded an off-white solid (0.040 g, 30%). $^1$H NMR (400 MHz, $CDCl_3$) δ 7.55 (app q, J=7.92 Hz, 1H), 6.93 (app t, J=8.39 Hz, 1H), 6.84 (app t, J=9.40 Hz, 1H), 5.95 (s, 1H), 5.18 (s, 2H), 4.16 (app t, J=6.78 Hz, 2H), 3.68 (s, 4H), 2.65 (app t, J=6.38 Hz, 2H), 2.54 (s, 4H), 2.43 (s, 3H). ES-HRMS m/z 443.0743 (M+H $C_{19}H_{21}BrF_2N_2O_3$ requires 443.0776).

Example 309

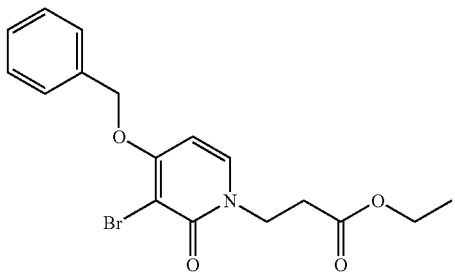

ethyl 3-[4-(benzyloxy)-3-bromo-2-oxopyridin-1 (2H)-yl]propanoate 3-bromo-4-[(2,4-difluorobenzyl)oxy]-6-methylpyridin-2 (1H)-one (0.50 g, 1.78 mmol) and cesium fluoride (0.0027 g, 0.178 mmol) were suspended in tetrahydrofuran (10 mL) followed by dropwise addition of tetraethylortho silicate (0.37 g, 1.78 mmol) at room temperature. After stirring for 10 minutes at room temperature, ethyl acrylate (0.23 g, 2.32 mmol) was added dropwise and the reaction stirred at room temperature overnight. The reaction mixture was filtered through a pad of Celite®. The filtrate was concentrated and the resulting residue subjected to chromatography (silica gel, ethyl acetate with 10% methanol/hexanes) to afford a white solid (0.62 g, 92%). $^1$H NMR (400 MHz, CDCl$_3$) δ 7.42 (d, J=7.79 Hz, 1H), 7.41–7.29 (m, 5H), 6.03 (d, J=7.65 Hz, 1H), 5.20 (s, 2H), 4.17 (t, J=5.98 Hz, 2H), 4.07 (q, J=7.16 Hz, 2H), 2.83 (t, J=5.98 Hz, 2H), 1.19 (t, J=7.18 Hz, 3H). ES-HRMS m/z 380.0523 (M+H C$_{17}$H$_{18}$BrNO$_4$ requires 380.0492).

Example 310

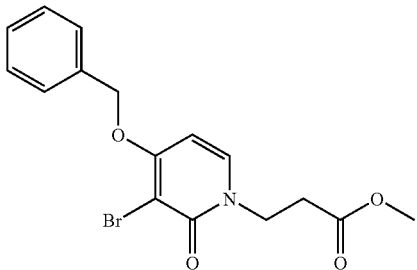

methyl 3-[4-(benzyloxy)-3-bromo-2-oxopyridin-1 (2H)-yl]propanoate 3-bromo-4-[(2,4-difluorobenzyl)oxy]-6-methylpyridin-2 (1H)-one (5.00 g, 17.85 mmol) and cesium fluoride (0.27 g, 1.78 mmol) were suspended in tetrahydrofuran (50 mL) followed by dropwise addition of tetramethylortho silicate (2.70 g, 17.85 mmol) at room temperature. After stirring for 10 minutes at room temperature, methyl acrylate (2.00 g, 23.20 mmol) was added dropwise and the reaction stirred at room temperature for 48 hours. The reaction mixture was filtered through a pad of Celite®. The filtrate was concentrated and the resulting residue subjected to chromatography (silica gel, ethyl acetate with 10% methanol/hexanes) to afford a white solid (6.10 g, 93%). $^1$H NMR (400 MHz, CDCl$_3$) δ 7.42 (d, J=7.65 Hz, 1H), 7.41–7.29 (m, 5H), 6.04 (d, J=7.65 Hz, 1H), 5.20 (s, 2H), 4.17 (t, J=5.91 Hz, 2H), 3.63 (s, 3H), 2.85 (t, J=5.91 Hz, 2H). ES-HRMS m/z 366.0350 (M+H C$_{16}$H$_{16}$BrNO$_4$ requires 366.0335).

Example 311

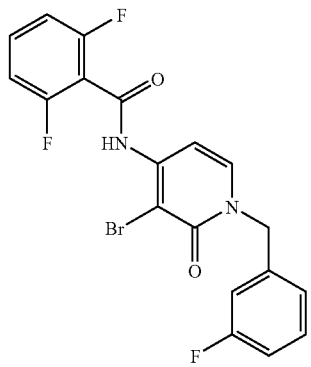

N-[3-bromo-1-(3-fluorobenzyl)-2-oxo-1,2-dihydropyridin-4-yl]-2,6-difluorobenzamide Step 1: Preparation of 3,4-dibromo-1-(3-fluorobenzyl) pyridin-2(1H)-one.

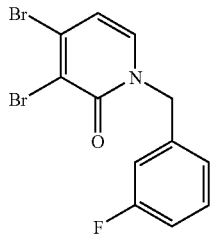

3-bromo-1-(3-fluorobenzyl)-2-oxo-1,2-dihydropyridin-4-yl trifluoromethanesulfonate (2.00 g, 4.65 mmol), KBr (5.53 g, 46.49 mmol), and 18-Crown-6 (0.10 g, 0.38 mmol) were dissolved in N,N-dimethylacetamide (26 mL) The reaction mixture was then heated at reflux for 16 hours. The reaction was concentrated and the resulting residue was partition between water (50 mL) and ethyl acetate (3×50 mL). The combined organics were washed with H$_2$O (2×30 mL), brine (50 mL), dried over MgSO$_4$, concentrated, and subjected to chromatography (silica gel, ethyl acetate with 10% methanol/hexane) to afford a brown solid (0.850 g, 51%).

Step 2: Preparation of 4-azido-3-bromo-1-(3-fluorobenzyl) pyridin-2(1H)-one.

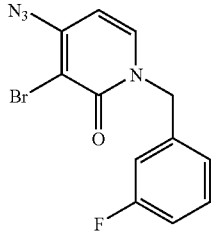

Sodium azide (1.08 g, 16.62 mmol) was suspended in N,N-dimethylformamide (10 mL) and a stock solution of 3,4-dibromo-1-(3-fluorobenzyl)pyridin-2(1H)-one (from step 1) in N,N-dimethylformamide (33.0 mL, 0.33 M) was added and the resulting mixture was heated to 60° C. for 4 hours. Ice water (30 mL) was added and the aqueous layer was extracted with ethyl acetate (4×50 mL). The combined organics were washed with H$_2$O (3×50 mL), brine (2×25 mL), dried over MgSO$_4$, concentrated, and subjected to chromatography (silica gel, ethyl acetate with 10% methanol/hexane) to afford an off-white solid (3.50 g, 98%).

Step 3: Preparation of 4-amino-3-bromo-1-(3-fluorobenzyl)pyridin-2(1H)-one hydrochloride

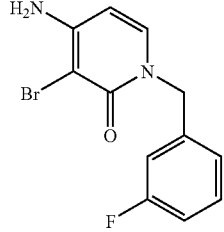

4-azido-3-bromo-1-(3-fluorobenzyl)pyridin-2 (1H)-one (from step 2) (4.00 g, 12.38 mmol) was suspended in ethyl acetate (300 mL) and Fe (2.07 g, 37.14 mmol) was added. A stock solution of NH$_4$Cl in H$_2$O (300 mL, 0.2 M) was added and the reaction mixture was stirred at room temperature for 36 hours. The reaction was filtered through a pad of Celite® and concentrated. The resulting solid was dissolved in ethyl acetate (150 mL) and washed with water (3×50 mL), brine (50 mL), dried over MgSO$_4$, and concentrated. $^1$H NMR (400 MHz, CD$_3$OD) δ 7.38–7.29 (m, 2H), 7.05 (d, J=7.79 Hz, 1H), 6.99 (d, J=8.99 Hz, 2H), 6.03 (d, J=7.39 Hz 1H), 5.09 (s, 2H). ES-HRMS m/z 297.0023 (M+H C$_{20}$H$_{17}$BrF$_2$N$_2$O$_2$ requires 297.0033).

Step 4: Preparation of the title compound. 4-amino-3-bromo-1-(3-fluorobenzyl)pyridin-2(1H)-one (from step 3) (0.30 g, 1.01 mmol) and 4-dimethylaminopyridine (0.002 g, 0.01 mmol) were suspended in acetonitrile (5 mL) followed by dropwise addition of triethylamine (0.2 mL, 1.41 mmol). This reaction mixture was stirred for 10 minutes at room temperature before being cooled to 0° C. 2,6-difluorobenzoyl chloride (0.37 g, 2.12 mmol) was added dropwise and the reaction was heated at reflux overnight. The reaction was cooled to room temperature and 1N NaOH (10 mL) was added. The reaction was then stirred for 45 minutes at room temperature. The reaction mixture was extracted with ethyl acetate (3×25 mL) and the organic layer washed with 1N NaOH (2×25 mL), H$_2$O (until pH neutral), brine (50 mL), dried over MgSO$_4$, concentrated, and subjected to chromatography (on C-18, acetonitrile/H$_2$O with 0.1% trifluoracetic acid) to afford a white solid (0.19 g, 43%). $^1$H NMR (400 MHz, CDCl$_3$) δ 8.42 (br s, 1H), 7.67 (d, J=7.65 Hz, 1H), 7.49 (app tt, J=6.31, 8.60 Hz, 1H), 7.33–28 (m, 2H), 7.10–6.97 (m, 5H), 5.17 (s, 2H). ES-HRMS m/z 437.0083 (M+H C$_{19}$H$_{12}$BrF$_3$N$_2$O$_2$ requires 437.0107).

Example 312

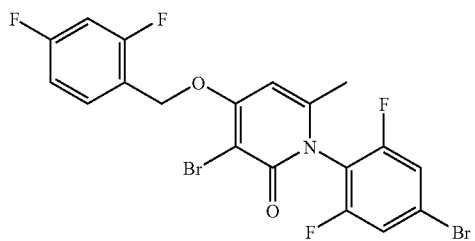

3-bromo-1-(4-bromo-2,6-difluorophenyl)-4-[(2,4-difluorobenzyl)oxy]-6-methylpyridin-2(1H)-one Step 1: Preparation of 1-(4-bromo-2,6-difluorophenyl)-4-hydroxy-6-methylpyridin-2(1H)-one.

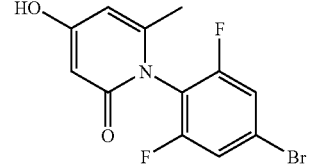

4-Hydroxy-6-methyl-2-pyrone (30.0 g, 238 mmol) and 4-bromo-2,6-difluoroaniline (49.5 g, 238 mmol) were suspended in 50 ml of 1,2-dichlorobenzene in a 250 ml, 3-necked, round bottom flask equipped with a J-Kem temperature controller probe, a Dean-Stark trap, and a heating mantle. The reaction was heated to 165° C. for 15 minutes, during which, water and some 1,2-dichlorobenzene was collected in the Dean-Stark trap. The reaction was allowed to cool to about 80° C. The flask was placed in an ice bath and about 25 ml of toluene was added and stirred. After about 10 minutes, a precipitate formed. The precipitate was filtered and washed 3 times with toluene, 3 times with hot water to remove excess pyrone, and dried in vacuo to give a tan solid (22.1 g, 29%). $^1$H NMR (400 MHz, DMSO-d$_6$) δ 11.00 (br s, 1H), 7.71 (d, J=6.98 Hz, 2H), 5.97 (t, J=0.88 Hz, 1H), 5.55 (d, J=2.28 Hz, 1H), 1.91 (s, 3H). LC/MS, t$_r$=1.96 minutes (5 to 95% acetonitrile/water over 5 minutes at 1 ml/min with detection 254 nm, at 50° C.). ES-MS m/z 316 (M+H). ES-HRMS m/z 315.9779 (M+H calcd for C$_{12}$H$_8$BrF$_2$NO$_2$ requires 315.9779).

Step 2: Preparation of 1-(4-bromo-2,6-difluorophenyl)-4-[(2,4-difluorobenzyl)oxy]-6-methylpyridin-2(1H)-one

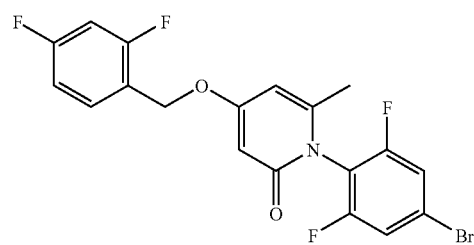

1-(4-bromo-2,6-difluorophenyl)-4-hydroxy-6-methylpyridin-2(1H)-one (from Step 1) (5.0 g, 15.8 mmol) was stirred briskly at room temperature with 2,4-difluorobenzyl bromide (2.23 ml, 17.4 mmol) and K$_2$CO$_3$ (3.27 g, 23.7 mmol) in 50 ml of dimethylformamide. After stirring overnight, the reaction was poured quickly into 900 ml of cold water. The resulting precipitate was filtered and washed with water and hexane. The product was purified using a Biotage silica chromatography system using 20% ethyl acetate/hexanes to give a beige solid (4.32 g, 62%). $^1$H NMR (400 MHz, CDCl$_3$) δ 7.41 (app q, J=6.31 Hz, 1H), 7.25 (dd, J=8.33, 1.74 Hz, 2H), 6.91 (dt, J=9.2, 0.8 Hz, 1H), 6.86 (dt, J=9.2, 0.8 Hz, 1H), 5.95 (d, J=2.56 Hz, 1H), 5.92 (dd, J=2.56, 0.94 Hz, 1H), 5.01 (s, 2H), 1.98 (s, 3H). LC/MS, t$_r$=3.04 minutes (5 to 95% acetonitrile/water over 5 minutes at 1 ml/min with detection 254 nm, at 50° C.). ES-MS m/z 442 (M+H). ES-HRMS m/z 442.0057 (M+H calcd for C$_{19}$H$_{12}$BrF$_4$NO$_2$ requires 442.0060).

Step 3: Preparation of the title compound. 1-(4-bromo-2,6-difluorophenyl)-4-[(2,4-difluorobenzyl)oxy]-6-methylpyridin-2(1H)-one (from Step 2) (500 mg, 1.13 mmol) was stirred at room temperature with N-bromosuccinimide (221 mg, 1.24 mmol) in 5 ml of $CH_2Cl_2$ for 1.5 hours. The reaction was evaporated on a rotary evaporator and the resulting solid was washed 4 times with acetonitrile and dried in vacuo to yield a white solid (478 mg, 92%). $^1$H NMR (300 MHz, $CDCl_3$) δ 7.62 (app q, J=6.64 Hz, 1H), 7.31 (d, J=6.85 Hz, 2H), 7.01 (app t, J=8.36 Hz, 1H), 6.96 (dt, J=9.46, 2.21 Hz, 1H), 6.19 (s, 1H), 5.30 (s, 2H), 2.10 (s, 3H); LC/MS, $t_r$=3.17 minutes (5 to 95% acetonitrile/water over 5 minutes at 1 ml/min with detection 254 nm, at 50° C.). ES-MS m/z 520 (M+H). ES-HRMS m/z 521.9134 (M+H calcd for $C_{19}H_{11}Br_2F_4NO_2$ requires 521.9146).

Example 313

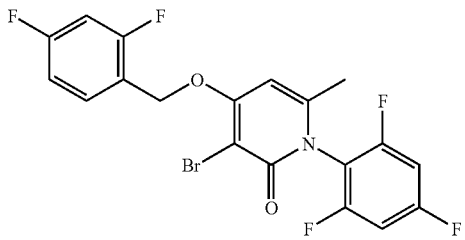

3-bromo-4-[(2,4-difluorobenzyl)oxy]-6-methyl-1-(2,4,6-trifluorophenyl)pyridin-2(1H)-one The title compound was produced essentially as in Example 313, using 2,4,6-trifluoroaniline instead of 4-bromo-2,6-difluoroaniline. $^1$H NMR (300 MHz, $CDCl_3$) δ 7.62 (app q, J=7.79 Hz, 1H), 7.01 (app dt, J=8.26, 2.01 Hz, 1H), 6.95–6.85 (m, 3H), 6.19 (s, 1H), 5.30 (s, 2H), 2.11 (s, 3H); LC/MS, $t_r$=2.81 minutes (5 to 95% acetonitrile/water over 5 minutes at 1 ml/min, at 254 nm, at 50° C.), ES-MS m/z 460 (M+H). ES-HRMS m/z 459.9954 (M+H calcd for $C_{19}H_{11}BrF_5NO_2$ requires 459.9966).

Example 314

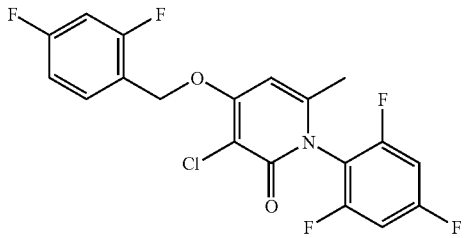

3-chloro-4-[(2,4-difluorobenzyl)oxy]-6-methyl-1-(2,4,6-trifluorophenyl)pyridin-2(1H)-one 4-[(2,4-difluorobenzyl)oxy]-6-methyl-1-(2,4,6-trifluorophenyl)pyridin-2(1H)-one (350 mg, 0.92 mmol) was refluxed with N-chlorosuccinimide (147 mg, 1.1 mmol) and dichloroacetic acid (0.038 ml, 0.46 mmol) in 5 ml of $CH_2Cl_2$ overnight. The reaction was evaporated on a rotary evaporator and the resulting solid was washed 4 times with acetonitrile and dried in vacuo to yield a white solid (217 mg, 57%). $^1$H NMR (300 MHz, $CDCl_3$) δ 7.60 (app q, J=7.75 Hz, 1H), 7.00 (app dt, J=8.23, 2.05 Hz, 1H), 6.93–6.86 (m, 3H), 6.22 (s, 1H), 5.30 (s, 2H), 2.12 (s, 3H); LC/MS, $t_r$=2.78 minutes (5 to 95% acetonitrile/water over 5 minutes at 1 ml/min, at 254 nm, at 50° C.), ES-MS m/z 416 (M+H). ES-HRMS m/z 416.0472 (M+H calcd for $C_{19}H_{11}ClF_5NO_2$ requires 416.0471).

Example 315

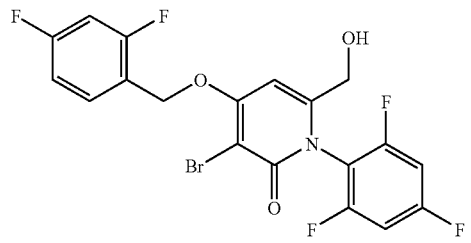

3-bromo-4-[(2,4-difluorobenzyl)oxy]-6-(hydroxymethyl)-1-(2,4,6-trifluorophenyl)pyridin-2(1H)-one Step 1: Preparation of 4-[(2,4-difluorobenzyl)oxy]-6-(hydroxymethyl)-1-(2,4,6-trifluorophenyl)pyridin-2(1H)-one.

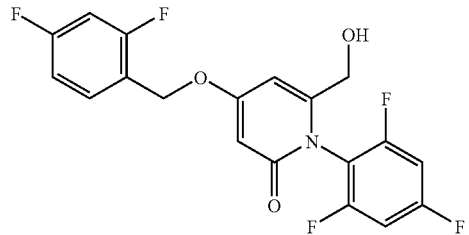

4-[(2,4-Difluorobenzyl)oxy]-6-methyl-1-(2,4,6-trifluorophenyl)pyridin-2(1H)-one (9.0 g, 23.6 mmol) was heated to 135° C. overnight with $SeO_2$ (13.1 g, 118 mmol) in 75 ml of 1,4-dioxane in a 350 ml sealed glass pressure vessel. The reaction mixture was cooled and placed on a plug of silica gel and washed with 5% methanol in $CH_2Cl_2$. The filtrate was evaporated and the resulting solid was washed with diethyl ether and dissolved in hot ethyl acetate. The insoluble Se salts were filtered off and the organic layer was evaporated. 7.01 g (17.6 mmol) of a 3:1 ratio of aldehyde to desired alcohol was isolated. The mixture was stirred with $NaBH_4$ (802 mg, 21.2 mmol) in 30 ml of methanol at room temperature for 1 hour. The reaction was evaporated and $CH_2Cl_2$ and acetonitrile were used to dissolve the bulk of the solid. The remaining insoluble solid was filtered off. The organic layer was washed 3 times with $NH_4Cl$, dried over $MgSO_4$ and evaporated. The resulting solid was washed 3 times with diethyl ether and dried in vacuo to yield a light orange solid (4.35 g, 46%). $^1$H NMR (300 MHz, DMSO-$d_6$) δ 7.68 (app q, J=7.92 Hz, 1H), 7.47 (app t, J=8.57 Hz, 2H), 7.35 (dt, J=9.87, 2.42 Hz, 1H), 7.18 (dt, J=8.31, 1.71 Hz, 1H), 6.21 (d, J=2.42 Hz, 1H), 6.07 (d, J=2.62 Hz, 1H), 5.67 (br s, 1H), 5.18 (s, 2H), 3.98 (s, 2H); LC/MS, $t_r$=2.31 minutes (5 to 95% acetonitrile/water over 5 minutes at 1 ml/min, at 254 nm, at 50° C.), ES-MS m/z 398 (M+H).

Step 2: Preparation of the title compound. 4-[(2,4-Difluorobenzyl)oxy]-6-(hydroxymethyl)-1-(2,4,6-trifluorophenyl)pyridin-2(1H)-one (from step 1) (2.1 g, 5.28 mmol) was stirred at room temperature with N-bromosuccinimide (1.13 g, 6.34 mmol) in 5 ml $CH_2Cl_2$ for 2 hours. The reaction was evaporated on a rotary evaporator and the resulting solid was washed 4 times with acetonitrile and dried in vacuo to yield a white solid (1.35 g, 54%). $^1$H NMR (300 MHz, $CD_3OD$) δ 7.69 (app q, J=6.65 Hz, 1H), 7.20 (app t, J=8.36 Hz, 2H), 7.09 (app t, J=8.46 Hz, 2H), 6.88 (s, 1H), 5.46 (s, 2H), 4.21 (s, 2H); LC/MS, $t_r$=2.48 minutes (5 to 95% acetonitrile/water over 5 minutes at 1 ml/min, at 254 nm, at 50° C.), ES-MS m/z 476 (M+H). ES-HRMS m/z 475.9907 (M+H calcd for $C_{19}H_{11}BrF_5NO_3$ requires 475.9915).

Example 316

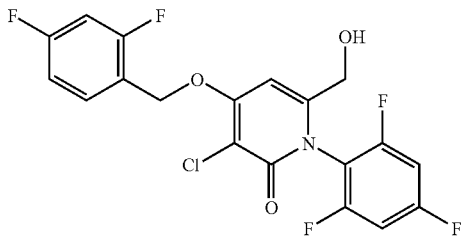

3-chloro-4-[(2,4-difluorobenzyl)oxy]-6-(hydroxymethyl)-1-(2,4,6-trifluorophenyl)pyridin-2(1H)-one 4-[(2,4-Difluorobenzyl)oxy]-6-(hydroxymethyl)-1-(2,4,6-trifluorophenyl)pyridin-2(1H)-one (2.1 g, 5.28 mmol) was refluxed with N-chlorosuccinimide (846 mg, 6.34 mmol) and dichloroacetic acid (0.87 ml, 10.56 mmol) in 5 ml $CH_2Cl_2$ overnight. The reaction was evaporated on a rotary evaporator and the resulting oil was triturated with diethyl ether to obtain a solid. The solid was washed 4 times with acetonitrile. Chromatography was done using a Biotage silica gel system with 60% ethyl acetate/hexanes. The recovery was poor from the column to give a white solid (109 mg, 5%). $^1$H NMR (300 MHz, $CD_3OD$) δ 7.67 (app q, J=7.85 Hz, 1H), 7.24–7.06 (m, 4H), 6.90 (s, 1H), 5.45 (s, 2H), 4.22 (s, 2H); LC/MS, $t_r$=2.71 minutes (5 to 95% acetonitrile/water over 5 minutes at 1 ml/min, at 254 nm, at 50° C.), ES-MS m/z 432 (M+H). ES-HRMS m/z 432.0413 (M+H calcd for $C_{19}H_{11}ClF_5NO_3$ requires 432.0420).

Example 317

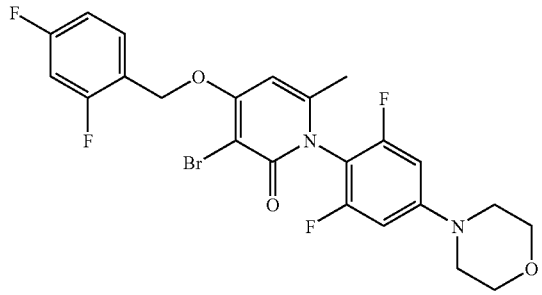

3-bromo-4-[(2,4-difluorobenzyl)oxy]-1-(2,6-difluoro-4-morpholin-4-ylphenyl)-6-methylpyridin-2(1H)-one Step 1: Preparation of 4-[(2,4-difluorobenzyl)oxy]-1-(2,6-difluoro-4-morpholin-4-ylphenyl)-6-methylpyridin-2(1H)-one.

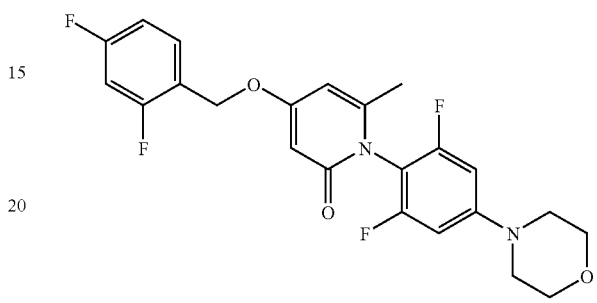

4-[(2,4-Difluorobenzyl)oxy]-6-methyl-1-(2,4,6-trifluorophenyl)pyridin-2(1H)-one (870 mg, 2.28 mmol) was heated to 100° C. with $K_2CO_3$ (630 mg, 4.56 mmol) in 5 ml of morpholine for 36 hours. The reaction was added to 200 ml of cold water and the resulting solid was washed with water and 50:50 diethyl ether/hexanes and dried in vacuo to give a beige solid (738 mg, 72%). $^1$H NMR (400 MHz, $CDCl_3$) δ 7.41 (app q, J=7.70 Hz, 1H), 6.93–6.85 (m, 2H), 6.49 (d, J=10.47 Hz, 2H), 5.96 (d, J=2.41 Hz, 1H), 5.89 (d, J=1.75 Hz, 1H), 5.00 (s, 2H), 3.83 (t, J=4.83 Hz, 4H), 3.19 (t, J=4.84 Hz, 4H), 1.99 (s, 3H); LC/MS, $t_r$=3.09 minutes (5 to 95% acetonitrile/water over 5 minutes at 1 ml/min, at 254 nm, at 50° C.), ES-MS m/z 449 (M+H). ES-HR/MS m/z 449.1485 (M+H calcd for $C_{23}H_{20}F_4N_2O_3$ requires 449.1483).

Step 2: Preparation of the title compound 0.4-[(2,4-Difluorobenzyl)oxy]-1-(2,6-difluoro-4-morpholin-4-ylphenyl)-6-methylpyridin-2(1H)-one (from step 1) (500 mg, 1.12 mmol) was stirred at room temperature with N-bromosuccinimide (236 mg, 1.33 mmol) in 5 ml of $CH_2Cl_2$ for 2 hours. The reaction was evaporated on a rotary evaporator and the resulting oil was triturated with diethyl ether to obtain a solid. The solid was washed 4 times with acetonitrile and dried in vacuo to yield a white solid (171 mg, 29%). $^1$H NMR (400 MHz, $CDCl_3$) δ 7.58 (app q, J=7.74 Hz, 1H), 6.96 (app t, J=8.39 Hz, 1H), 6.86 (dt, J=9.46, 2.28 Hz, 1H), 6.50 (d, J=10.74 Hz, 2H), 6.09 (s, 1H), 5.24 (s, 2H), 3.84 (t, J=4.84 Hz, 4H), 3.20 (t, J=4.83 Hz, 4H), 2.07 (s, 3H); LC/MS, $t_r$=3.18 minutes (5 to 95% acetonitrile/water over 5 minutes at 1 ml/min, at 254 nm, at 50° C.), ES-MS m/z 527 (M+H). ES-HRMS m/z 527.0570 (M+H calcd for $C_{23}H_{19}BrF_4N_2O_3$ requires 527.0588).

Example 318

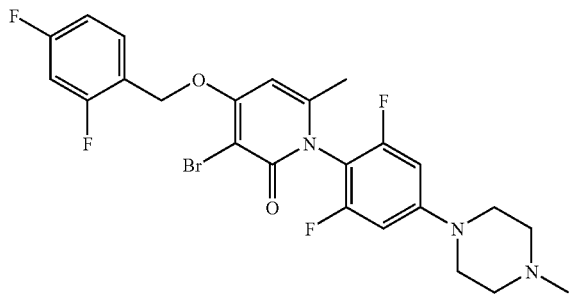

3-bromo-4-[(2,4-difluorobenzyl)oxy]-1-[2,6-difluoro-4-(4-methylpiperazin-1-yl)phenyl]-6-methylpyridin-2(1H)-one The title compound was prepared essentially as in Example 317, using 1-methylpiperazine instead of morpholine. $^1$H NMR (400 MHz, CDCl$_3$) δ 7.57 (app q, J=7.79 Hz, 1H), 6.96 (dt, J=8.19, 1.88 Hz, 1H), 6.86 (app dt, J=9.44, 2.48 Hz, 1H), 6.52 (d, J=10.61 Hz, 2H), 6.14 (s, 1H), 5.24 (s, 2H), 3.72 (br s, 4H), 3.51 (d, J=11.27 Hz, 2H), 3.07 (br s, 2H), 2.85 (d, J=4.29 Hz, 3H), 2.06 (s, 3H); LC/MS, t$_r$=2.50 minutes (5 to 95% acetonitrile/water over 5 minutes at 1 ml/min, at 254 nm, at 50° C.), ES-MS m/z 540 (M+H). ES-HRMS m/z 540.0930 (M+H calcd for C$_{24}$H$_{22}$BrF$_4$N$_3$O$_2$ requires 540.0904).

Example 320

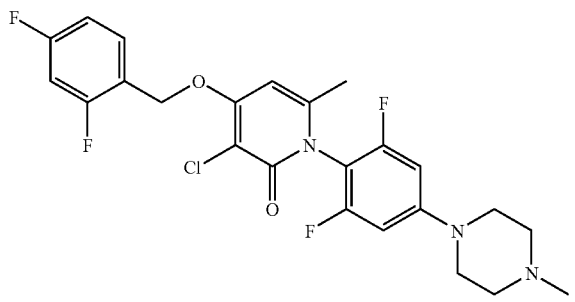

3-chloro-4-[(2,4-difluorobenzyl)oxy]-1-[2,6-difluoro-4-(4-methylpiperazin-1-yl)phenyl]-6-methylpyridin-2(1H)-one 4-[(2,4-Difluorobenzyl)oxy]-1-[2,6-difluoro-4-(4-methylpiperazin-1-yl)phenyl]-6-methylpyridin-2(1H)-one (1.3 g, 2.82 mmol) was stirred at reflux with N-chlorosuccinimide (451 mg, 3.38 mmol) and dichloroacetic acid (0.17 ml, 1.41 mmol) in 6 ml CH$_2$Cl$_2$ overnight. LC-MS showed 33% completion. More N-chlorosuccinimide (271 mg, 2.23 mmol) was added and refluxed overnight. The reaction was evaporated on a rotary evaporator and the resulting oil was triturated with ethyl acetate to obtain a solid. The solid was washed 4 times with ethyl acetate and with diethyl ether and dried in vacuo to obtain a white solid (606 mg, 43%). $^1$H NMR (400 MHz, DMSO-d$_6$) δ 7.66 (br q, J=7.74 Hz, 1H), 7.33 (br t, J=9.00 Hz, 1H), 7.16 (br t, J=7.65 Hz, 1H), 6.96 (d, J=11.81 Hz, 2H), 6.79 (s, 1H), 5.33 (s, 2H), 3.61 (br m, 4H), 3.25 (br m, 4H), 3.21 (br s, 3H), 2.04 (s, 3H); LC/MS, t$_r$=2.45 minutes (5 to 95% acetonitrile/water over 5 minutes at 1 ml/min, at 254 nm, at 50° C.), ES-MS m/z 496 (M+H). ES-HRMS m/z 496.1400 (M+H calcd for C$_{24}$H$_{22}$ClF$_4$N$_3$O$_2$ requires 496.1409).

Example 321

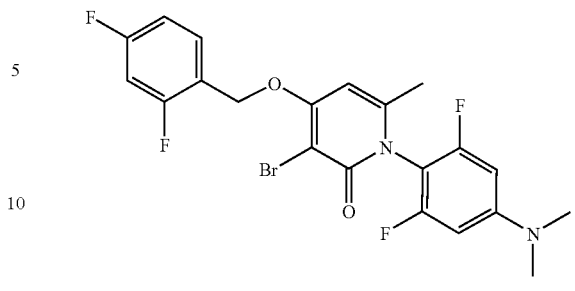

3-bromo-4-[(2,4-difluorobenzyl)oxy]-1-[4-(dimethylamino)-2,6-difluorophenyl]-6-methylpyridin-2(1H)-one The title compound was prepared essentially as described in Example 317, using dimethylamine instead of morpholine. $^1$H NMR (400 MHz, CDCl$_3$) δ 7.59 (q, J=7.74 Hz, 1H), 6.95 (dt, J=8.32, 1.61 Hz, 1H), 6.85 (app dt, J=9.54, 2.41 Hz, 1H), 6.27 (d, J=11.01 Hz, 2H), 6.08 (s, 1H), 5.23 (s, 2H), 2.98 (s, 3H), 2.07 (s, 3H); LC/MS, t$_r$=3.35 minutes (5 to 95% acetonitrile/water over 5 minutes at 1 ml/min, at 254 nm, at 50° C.), ES-MS m/z 485 (M+H). ES-HRMS m/z 485.0447 (M+H calcd for C$_{21}$H$_{17}$BrF$_4$N$_2$O$_2$ requires 485.0482).

Example 322

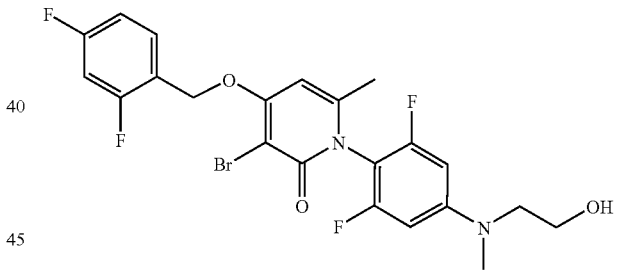

3-bromo-4-[(2,4-difluorobenzyl)oxy]-1-{2,6-difluoro-4-[(2-hydroxyethyl)(methyl)amino]phenyl}-6-methylpyridin-2(1H)-one The title compound was prepared essentially as in Example 317, using 2-(methylamino)ethanol instead of morpholine.

$^1$H NMR (400 MHz, CDCl$_3$) δ 7.58 (q, J=7.74 Hz, 1H), 6.95 (dt, J=8.24, 1.66 Hz, 1H), 6.85 (app dt, J=9.49, 2.37 Hz, 1H), 6.35 (d, J=11.01 Hz, 2H), 6.10 (s, 1H), 5.23 (s, 2H), 3.77 (t, J=5.77 Hz, 2H), 3.45 (t, J=5.78 Hz, 2H), 2.99 (s, 3H), 2.08 (s, 3H); LC/MS, t$_r$=2.96 minutes (5 to 95% acetonitrile/water over 5 minutes at 1 ml/min, at 254 nm, at 50° C.), ES-MS m/z 515 (M+H). ES-HRMS m/z 515.0576 (M+H calcd for C$_{22}$H$_{19}$BrF$_4$N$_2$O$_3$ requires 515.0588).

Example 323

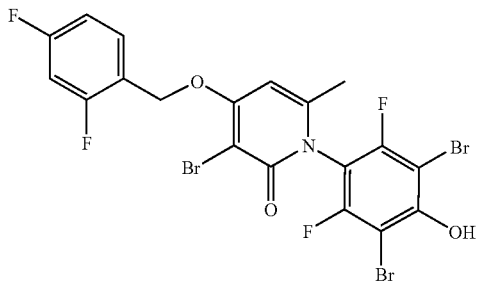

3-bromo-1-(3,5-dibromo-2,6-difluoro-4-hydroxyphenyl)-4-[(2,4-difluorobenzyl)oxy]-6-methylpyridin-2(1H)-one Step 1: Preparation of 4-[(2,4-difluorobenzyl)oxy]-1-(2,6-difluoro-4-hydroxyphenyl)-6-methylpyridin-2(1H)-one.

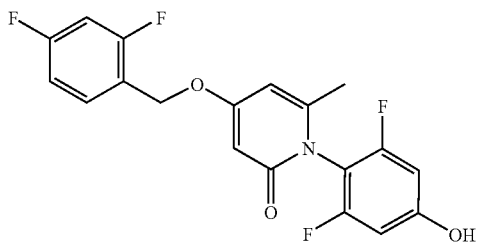

4-[(2,4-Difluorobenzyl)oxy]-6-methyl-1-(2,4,6-trifluorophenyl)pyridin-2(1H)-one (step 2 above) (10.0 g, 26.2 mmol) was heated to 45° C. with KOSiMe₃ (10.08 g, 78.6 mmol) in 50 ml of tetrahydrofuran for 4 days. The reaction was diluted with 30 ml of ethyl acetate and washed with 1N HCl and water, dried over MgSO₄, and evaporated to give an orange solid. The solid was stirred in hot 60% ethyl acetate/hexanes and filtered to give a white solid, which was dried in vacuo to obtain a white solid (3.79 g, 38%). The filtrate was found to contain a mixture of desired product and the ortho substituted regioisomer. ¹H NMR (400 MHz, CDCl₃) δ 7.42 (app q, J=7.70 Hz, 1H), 6.95–6.83 (m, 2H), 6.34 (d, J=9.40 Hz, 2H), 6.05 (app s, 2H), 5.06 (s, 2H), 2.01 (s, 3H); LC/MS, $t_r$=2.80 minutes (5 to 95% acetonitrile/water over 5 minutes at 1 ml/min, at 254 nm, at 50° C.), ES-MS m/z 380 (M+H). ES-HRMS m/z 380.0926 (M+H calcd for $C_{19}H_{13}F_4NO_3$ requires 380.0904).

Step 2: Preparation of the title compound. 4-[(2,4-Difluorobenzyl)oxy]-1-(2,6-difluoro-4-hydroxyphenyl)-6-methylpyridin-2(1H)-one (from step 1) (3.73 g, 8.14 mmol) was stirred as a suspension at room temperature with N-bromosuccinimide (1.52 g, 8.55 mmol) in 30 ml CH₂Cl₂ overnight. LC-MS showed a 60% starting material. The solid was filtered off, dissolved in 30 ml of CH₂Cl₂/N,N-dimethylformamide and stirred with more N-bromosuccinimide (0.76 g, 4.28 mmol) overnight. LC-MS showed the tri-brominated product as the major product. The reaction was poured into water and extracted with n-butanol. The combined organic layers were evaporated on a rotary evaporator and the resulting solid was washed with diethyl ether and dried in vacuo to yield a white solid (873 mg, 17%). ¹H NMR (400 MHz, CDCl₃) δ 7.67 (app q, J=7.80 Hz, 1H), 7.32 (dt, J=4.86, 2.11 Hz, 1H), 7.16 (dt, J=8.48, 1.84 Hz, 1H), 6.79 (s, 1H), 5.35 (s, 2H), 2.08 (s, 3H); LC/MS, $t_r$=3.26 minutes (5 to 95% acetonitrile/water over 5 minutes at 1 ml/min, at 254 nm, at 50° C.), ES-MS m/z 616 (M+H). ES-HRMS m/z 615.8234 (M+H calcd for $C_{19}H_{10}Br_3F_4NO_3$ requires 615.8200).

Example 324

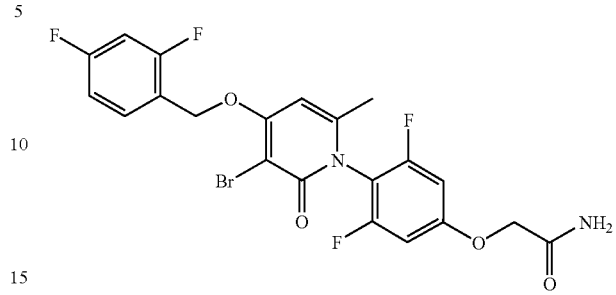

2-{4-[3-bromo-4-[(2,4-difluorobenzyl)oxy]-6-methyl-2-oxopyridin-1(2H)-yl]-3,5-difluorophenoxy}acetamide Step 1: Preparation of 3-bromo-4-[(2,4-difluorobenzyl)oxy]-1-(2,6-difluoro-4-hydroxyphenyl)-6-methylpyridin-2(1H)-one.

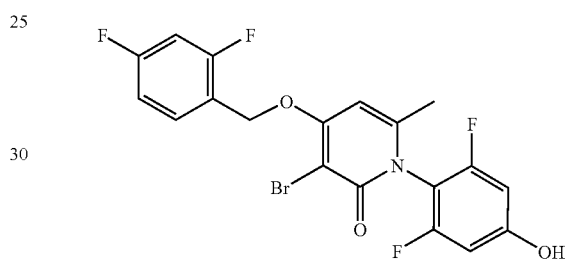

3-Bromo-4-[(2,4-difluorobenzyl)oxy]-6-methyl-1-(2,4,6-trifluorophenyl)pyridin-2(1H)-one (above) (7.5 g, 16.3 mmol) was heated to 45° C. with KOSiMe₃ (10.08 g, 78.6 mmol) in 50 ml of tetrahydrofuran for 48 hours. The reaction was diluted with 30 ml of ethyl acetate and washed with 1N HCl and water, dried over MgSO₄, and evaporated to give a black oil. The oil was dissolved in ethyl acetate. A precipitate formed upon standing, which was filtered, washed with ethyl acetate and dried in vacuo to obtain a white solid (2.80 g, 37%). The filtrate showed the presence of desired product and the ortho substituted regioisomer. ¹H NMR (400 MHz, DMSO-d₆) δ 7.66 (q, J=7.92 Hz, 1H), 7.32 (dt, J=8.77, 2.19 Hz, 1H), 7.15 (m, 1H), 6.73 (s, 1H), 6.67 (d, J=9.66 Hz, 2H), 5.33 (s, 2H), 2.03 (s, 3H); LC/MS, $t_r$=2.92 minutes (5 to 95% acetonitrile/water over 5 minutes at 1 ml/min, at 254 nm, at 50° C.), ES-MS m/z 458 (M+H). ES-HRMS m/z 457.9995 (M+H calcd for $C_{19}H_{12}BrF_4NO_3$ requires 458.0009).

Step 2: Preparation of the title compound. 3-Bromo-4-[(2,4-difluorobenzyl)oxy]-1-(2,6-difluoro-4-hydroxyphenyl)-6-methylpyridin-2(1H)-one (from step 1) (500 mg, 1.09 mmol) was stirred briskly with 2-bromoacetamide (196 mg, 1.43 mmol) and K₂CO₃ (282 mg, 2.05 mmol) in 5 ml of N,N-dimethylformamide at room temperature for 24 hours. The reaction was poured quickly into cold water and the resulting solid was filtered, washed with water, acetonitrile, and diethyl ether, and dried in vacuo to give a white solid (289 mg, 51%). ¹H NMR (400 MHz, DMSO-d₆) δ 7.66 (q, J=7.92 Hz, 1H), 7.61 (br s, 1H), 7.45 (br s, 1H), 7.33 (dt, J=10.07, 2.15 Hz, 1H), 7.16 (dt, J=8.53, 1.88 Hz, 1H), 6.99 (d, J=9.54 Hz, 2H), 6.76 (s, 1H), 5.34 (s, 2H), 2.03 (s, 3H); LC/MS, $t_r$=2.70 minutes (5 to 95% acetonitrile/water over 5 minutes at 1 ml/min, at 254 nm, at 50° C.), ES-MS m/z 515 (M+H). ES-HRMS m/z 515.0245 (M+H calcd for $C_{21}H_{15}BrF_4N_2O_4$ requires 515.0224).

Example 325

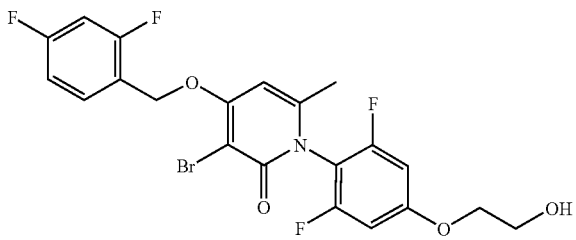

3-bromo-4-[(2,4-difluorobenzyl)oxy]-1-[2,6-difluoro-4-(2-hydroxyethoxy)phenyl]-6-methylpyridin-2(1H)-one The title compound was prepared by a procedure similar to the one described for Example 324. $^1$H NMR (400 MHz, DMSO-$d_6$) δ 7.66 (q, J=7.92 Hz, 1H), 7.33 (dt, J=10.04, 2.19 Hz, 1H), 7.17 (dt, J=8.68, 1.84 Hz, 1H), 6.99 (d, J=9.67 Hz, 2H), 6.75 (s, 1H), 5.34 (s, 2H), 4.92 (t, J=4.86 Hz, 1H), 4.07 (t, J=4.77 Hz, 2H), 3.70 (t, J=4.83 Hz, 2H), 2.03 (s, 3H); LC/MS, $t_r$=2.81 minutes (5 to 95% acetonitrile/water over 5 minutes at 1 ml/min, at 254 nm, at 50° C.), ES-MS m/z 502 (M+H). ES-HRMS m/z 502.0291 (M+H calcd for $C_{21}H_{16}BrF_4NO_4$ requires 502.0272).

Example 326

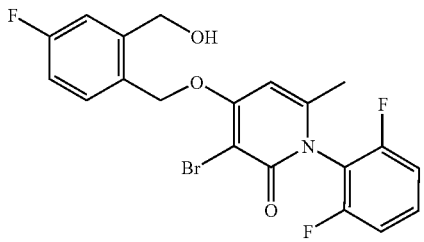

3-bromo-1-(2,6-difluorophenyl)-4-{[4-fluoro-2-(hydroxymethyl)benzyl]oxy}-6-methylpyridin-2(1H)-one Step 1: Preparation of 1-(2,6-difluorophenyl)-4-{[4-fluoro-2-(hydroxymethyl)benzyl]oxy}-6-methylpyridin-2(1H)-one

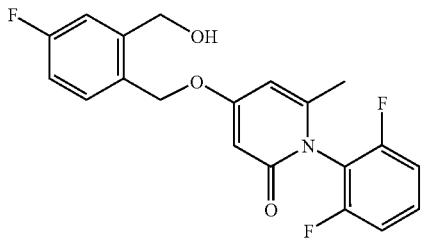

1-(2,6-Difluorophenyl)-4-hydroxy-6-methylpyridin-2(1H)-one (step 1) (3.0 g, 12.65 mmol) was dissolved in N,N-dimethylformamide and cooled to 0° C. Triphenylphosphine (3.98 g, 15.18 mmol) and diethyl azodicarboxylate (2.39 ml, 15.18 mmol) were added and stirred for 10 minutes. 1,2-Bis(hydroxymethyl)-4-fluorobenzene (2.57 g, 16.44 mmol) was added and stirred at 0° C. for 1 hour, then allowed to warm to room temperature and stirred overnight. LC-MS showed only 1 product, not a mixture of regioisomers, as expected. The reaction was added to water and extracted 3 times with ethyl acetate. The combined organic layers were dried over MgSO$_4$ and evaporated. A Biotage silica column was done using 60% ethyl acetate/hexanes as an eluent. Desired product, with a substantial impurity was obtained. Another Biotage silica column was ran using 30% ethyl acetate/hexanes to obtain pure product. The resulting oil was triturated with diethyl ether to obtain a white solid (720 mg, 15%). $^1$H NMR (300 MHz, CDCl$_3$) δ 7.51–7.39 (m, 2H), 7.26 (dd, J=9.62, 2.51 Hz, 1H), 7.13–7.01 (m, 3H), 6.03 (d, J=2.42 Hz, 1H), 5.96 (d, J=2.41 Hz, 1H), 5.06 (s, 2H), 4.73 (s, 2H), 2.81 (br s, 1H), 2.02 (s, 3H); LC/MS, $t_r$=2.37 minutes (5 to 95% acetonitrile/water over 5 minutes at 1 ml/min, at 254 nm, at 50° C.), ES-MS m/z 376 (M+H). ES-HR/MS m/z 376.1181 (M+H calcd for $C_{20}H_{16}F_3NO_3$ requires 376.1155). Identity of the positional isomer was determined from hmbc, 2-D NMR experiments using H to C 2- and 3-bond coupling.

Step 2: Preparation of the title compound. 1-(2,6-Difluorophenyl)-4-{[4-fluoro-2-(hydroxymethyl)benzyl]oxy}-6-methylpyridin-2(1H)-one (from step 1) (350 mg, 0.93 mmol) was stirred at room temperature with N-bromosuccinimide (199 mg, 1.12 mmol) in 1.5 ml CH$_2$Cl$_2$ for 1.5 hours. The reaction was evaporated on a rotary evaporator and the resulting solid was washed 4 times with acetonitrile and dried in vacuo to yield a white solid (197 mg, 47%). $^1$H NMR (300 MHz, CDCl$_3$) δ 7.53–7.43 (m, 2H), 7.25 (dd, J=9.46, 2.62 Hz, 1H), 7.11–7.03 (m, 3H), 6.25 (s, 1H), 5.31 (s, 2H), 4.81 (s, 2H), 2.28 (br s, 1H), 2.10 (s, 3H); LC/MS, $t_r$=2.38 minutes (5 to 95% acetonitrile/water over 5 minutes at 1 ml/min, at 254 nm, at 50° C.), ES-MS m/z 454 (M+H). ES-HRMS m/z 454.0247 (M+H calcd for $C_{20}H_{15}BrF_3NO_3$ requires 454.0260).

Example 327

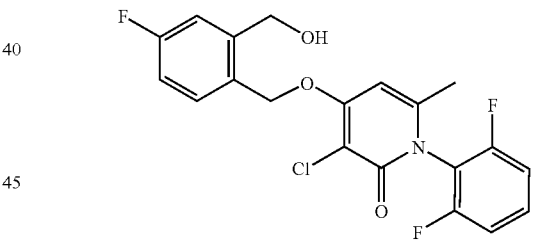

3-chloro-1-(2,6-difluorophenyl)-4-{[4-fluoro-2-(hydroxymethyl)benzyl]oxy}-6-methylpyridin-2(1H)-one 1-(2,6-Difluorophenyl)-4-{[4-fluoro-2-(hydroxymethyl)benzyl]oxy}-6-methylpyridin-2(1H)-one (step 1 above) (275 mg, 0.73 mmol) was stirred at reflux with N-chlorosuccinimide (117 mg, 0.88 mmol) and dichloroacetic acid (0.03 ml, 0.36 mmol) in 1.5 ml CH$_2$Cl$_2$ overnight. The reaction was evaporated on a rotary evaporator and the resulting solid was washed 4 times with ethyl acetate and with diethyl ether and dried in vacuo to obtain a white solid (65.5 mg, 22%). $^1$H NMR (300 MHz, CDCl$_3$) δ 7.52–7.43 (m, 2H), 7.26 (dd, J=9.38, 2.52 Hz, 1H), 7.12–7.04 (m, 3H), 6.27 (s, 1H), 5.32 (s, 2H), 4.82 (s, 2H), 2.29 (br s, 1H), 2.11 (s, 3H); LC/MS, $t_r$=2.32 minutes (5 to 95% acetonitrile/water over 5 minutes at 1 ml/min, at 254 nm, at 50° C.), ES-MS m/z 410 (M+H). ES-HRMS m/z 410.0755 (M+H calcd for $C_{20}H_{15}ClF_3NO_3$ requires 410.0765).

Example 328

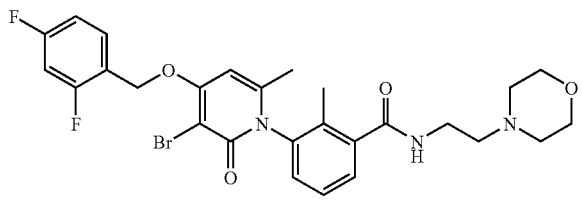

3-[3-bromo-4-[(2,4-difluorobenzyl)oxy]-6-methyl-2-oxopyridin-1(2H)-yl]-2-methyl-N-(2-morpholin-4-ylethyl)benzamide Step 1: Preparation of methyl 3-(4-hydroxy-6-methyl-2-oxopyridin-1(2H)-yl)-2-methylbenzoate.

4-Hydroxy-6-methyl-2-pyrone (72.6 g, 576 mmol) and methyl-3-amino-2-methylbenzoate (100 g, 605 mmol) were suspended in 75 ml of 1,2-dichlorobenzene in a 500 ml, 3-necked round bottom flask equipped with a J-Kem temperature controller probe, a Dean-Stark trap, and a heating mantle. The reaction was heated to 165° C. for 15 minutes, during which, water and some 1,2-dichlorobenzene was collected in the Dean-Stark trap. The reaction was allowed to cool to about 80° C. The flask was placed in an ice bath and about 300 ml of toluene was added and stirred. After about 30 minutes, a precipitate formed. The precipitate was filtered and washed 3 times with toluene, 3 times with hot water to remove excess pyrone, and dried in vacuo to give a tan solid (44.6 g, 28% yield). $^1$H NMR (400 MHz, DMSO-$d_6$) δ 10.66 (br s, 1H), 7.80 (dd, J=7.72, 1.28 Hz, 1H), 7.33 (dd, J=7.78, 1.34 Hz, 1H), 5.91 (dd, J=2.41, 0.69 Hz, 1H), 5.55 (d, J=2.42 Hz, 1H), 3.82 (s, 3H), 2.06 (s, 3H), 1.73 (s, 3H); LC/MS, $t_r$=1.85 minutes (5 to 95% acetonitrile/water over 5 minutes at 1 ml/min, at 254 nm, at 50° C.), ES-MS m/z 274 (M+H). ES-HRMS m/z 274.1078 (M+H calcd for $C_{15}H_{15}NO_4$ requires 274.1074).

Step 2: Preparation of methyl 3-[4-[(2,4-difluorobenzyl)oxy]-6-methyl-2-oxopyridin-1(2H)-yl]-2-methylbenzoate.

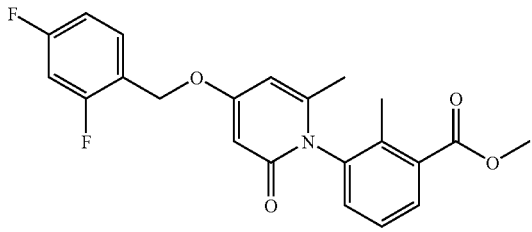

Methyl-3-(4-hydroxy-6-methyl-2-oxopyridin-1(2H)-yl)-2-methylbenzoate (from Step 1) (42.0 g, 154 mmol) was stirred briskly at room temperature with 2,4-difluorobenzyl bromide (19.7 ml, 154 mmol) and $K_2CO_3$ (31.8 g, 231 mmol) in 250 ml of N,N-dimethylformamide. After stirring overnight, the reaction was poured into 1 L of cold water. The solution was extracted 3 times with ethyl acetate and the organic layers were dried over $MgSO_4$, and evaporated. The product was carried on to the next step as a crude oil (60.4 g, 85%). $^1$H NMR (400 MHz, CDCl$_3$) δ 7.96 (dd, J=7.85, 1.28 Hz, 1H), 7.45–7.34 (m, 2H), 7.27–7.23 (m, 1H), 6.94–6.84 (m, 2H), 5.98 (d, J=2.68 Hz, 1H), 5.92 (dd, J=2.69, 0.81 Hz, 1H), 5.01 (s, 2H), 3.88 (s, 3H), 2.28 (s, 3H), 1.81 (s, 3H); LC/MS, $t_r$=2.96 minutes (5 to 95% acetonitrile/water over 5 minutes at 1 ml/min, at 254 nm, at 50° C.), ES-MS m/z 400 (M+H). ES-HRMS m/z 400.1341 (M+H calcd for $C_{22}H_{19}F_2NO_4$ requires 400.1355).

Step 3: Preparation of 3-[4-[(2,4-difluorobenzyl)oxy]-6-methyl-2-oxopyridin-1(2H)-yl]-2-methylbenzoic acid.

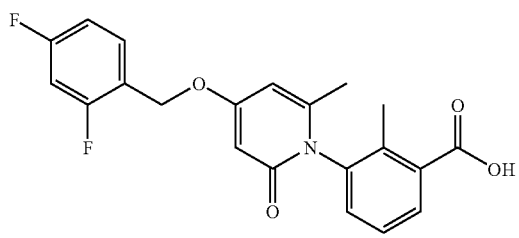

Methyl 3-[4-[(2,4-difluorobenzyl)oxy]-6-methyl-2-oxopyridin-1(2H)-yl]-2-methylbenzoate (from Step 2) (60.0 mg, 150 mmol) was stirred with 2.5 N NaOH (120 ml, 300 mmol) in 375 ml of tetrahydrofuran and 75 ml of water at room temperature overnight. The reaction was acidified with 1 N HCl, 350 ml of water was added and the solution was extracted 3 times with ethyl acetate. The combined organic layers were dried over $MgSO_4$, filtered and evaporated. The resulting solid was filtered, washed with ethyl acetate and dried in vacuo to yield a white solid 33.8 g, 58%). $^1$H NMR (400 MHz, CDCl$_3$) δ 7.98 (dd, J=7.92, 1.20 Hz, 1H), 7.43 (app q, J=7.70 Hz, 1H), 7.38 (t, J=7.72 Hz, 1H), 7.35 (dd, J=7.81, 1.21 Hz, 1H), 6.92–6.84 (m, 2H), 6.17 (d, J=2.56 Hz, 1H), 6.00 (dd, J=2.55, 0.81 Hz, 1H), 5.05 (s, 2H), 2.30 (s, 3H), 1.84 (s, 3H); LC/MS, $t_r$=2.61 minutes (5 to 95% acetonitrile/water over 5 minutes at 1 ml/min, at 254 nm, at 50° C.), ES-MS m/z 386 (M+H). ES-HR/MS m/z 386.1228 (M+H calcd for $C_{21}H_{17}F_2NO_4$ requires 386.1198).

Step 4: Preparation of 3-[3-bromo-4-[(2,4-difluorobenzyl)oxy]-6-methyl-2-oxopyridin-1(2H)-yl]-2-methylbenzoic acid.

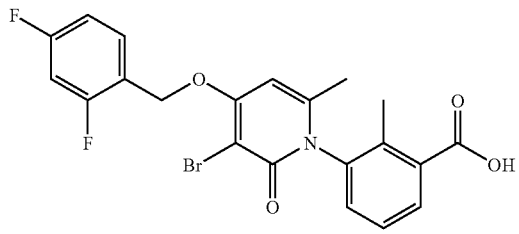

3-[4-[(2,4-Difluorobenzyl)oxy]-6-methyl-2-oxopyridin-1(2H)-yl]-2-methylbenzoic acid (from Step 3) (23.0 g, 59.7 mmol) was stirred at room temperature with N-bromosuccinimide (12.74 g, 71.6 mmol) in 120 ml of $CH_2Cl_2$ for 2 hours. The reaction was evaporated on a rotary evaporator and the resulting solid was stirred in acetonitrile for 1 hour, washed 7 times with acetonitrile and dried in vacuo to yield a white solid (19.14 g, 69%). $^1$H NMR (400 MHz, DMSO-$d_6$) δ 7.87 (dd, J=7.52, 1.61 Hz, 1H), 7.67 (app q, J=7.92 Hz, 1H), 7.45–7.37 (m, 2H), 7.33 (dt, J=9.87, 2.54 Hz, 1H), 7.17 (dt, J=8.50, 1.67 Hz, 1H), 6.71 (s, 1H), 5.32 (s, 2H), 2.08 (s, 3H), 1.86 (s, 3H); LC/MS, $t_r$=2.69 minutes (5 to 95% acetonitrile/water over 5 minutes at 1 ml/min, at 254 nm, at 50° C.), ES-MS m/z 464 (M+H). ES-HRMS m/z 464.0284 (M+H calcd for $C_{21}H_{16}BrF_2NO_4$ requires 464.0304).

Step 5: Preparation of the title compound. 3-[3-Bromo-4-[(2,4-difluorobenzyl)oxy]-6-methyl-2-oxopyridin-1(2H)-yl]-2-methylbenzoic acid (from Step 4 above) (500 mg, 1.08 mmol) was dissolved in 5 ml of $CH_2Cl_2$. 4-(2-Aminoethyl)morpholine (170 μl, 1.29 mmol) was added, followed, in order, by EDCI (247 mg, 1.29 mmol), 1-hydroxybenzotriazole (174 mg, 1.29 mmol) and triethylamine (301 μl, 2.16 mmol). The reaction was stirred at room temperature overnight. The reaction was quenched with $NH_4Cl$ and extracted 3 times with ethyl acetate. The combined organic layer was dried over $MgSO_4$ and evaporated. The resulting oil was triturated with diethyl ether/hexane to obtain a solid, which was dried in vacuo to give a white solid (472 mg, 76%). $^1$H NMR (400 MHz, DMSO-$d_6$) δ 7.64 (app q, J=7.79 Hz, 1H), 7.47 (dd, J=7.65, 1.01 Hz, 1H), 7.39 (t, J=7.75 Hz, 1H), 7.17 (dd, J=7.65, 0.81 Hz, 1H), 7.01 (dt, J=8.26, 1.61 Hz, 1H), 6.91 (dt, J=9.42, 2.32 Hz, 1H), 6.49 (t, J=5.04 Hz, 1H), 6.18 (s, 1H), 5.30 (s, 2H), 3.73 (t, J=4.53 Hz, 4H), 3.68–3.47 (m, 2H), 2.59 (t, J=5.94 Hz, 2H), 2.51 (t, J=4.33 Hz, 4H), 2.15 (s, 3H), 1.98 (s, 3H); LC/MS, $t_r$=2.27 minutes (5 to 95% acetonitrile/water over 5 minutes at 1 ml/min, at 254 nm, at 50° C.), ES-MS m/z 576 (M+H). ES-HRMS m/z 576.1313 (M+H calcd for $C_{27}H_{28}BrF_2N_3O_4$ requires 576.1304).

Examples 329–337

The following compounds are prepared essentially according to the procedure set forth for Example 328:

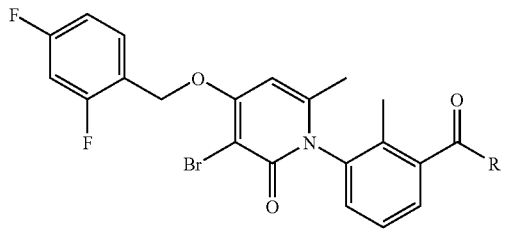

| Example No. | R | MF | M + H Requires | ESHRMS m/z |
|---|---|---|---|---|
| Ex. 329 | —NHCH$_2$CH$_2$OCH$_3$ | C$_{24}$H$_{22}$BrF$_2$N$_2$O$_4$ | 521.0882 | 521.0906 |
| Ex. 330 | —N(CH$_3$)$_2$ | C$_{23}$H$_{20}$BrF$_2$N$_2$O$_3$ | 491.0776 | 491.0752 |
| Ex. 331 | —NHCH$_2$CH$_2$OH | C$_{23}$H$_{20}$BrF$_2$N$_2$O$_4$ | 507.0726 | 507.0689 |
| Ex. 332 | —NHCH$_3$ | C$_{22}$H$_{18}$BrF$_2$N$_2$O$_3$ | 477.0620 | 477.0585 |
| Ex. 333 | —N(CH$_3$)CH$_2$CH$_2$OH | C$_{24}$H$_{22}$BrF$_2$N$_2$O$_4$ | 521.0882 | 521.0890 |
| Ex. 334 | 4-methylpiperazin-1-yl | C$_{26}$H$_{25}$BrF$_2$N$_3$O$_3$ | 546.1198 | 546.1187 |
| Ex. 335 | morpholin-4-yl | C$_{25}$H$_{22}$BrF$_2$N$_2$O$_4$ | 533.0882 | 533.0856 |
| Ex. 336 | —N(CH$_3$)CH$_2$CH$_2$OCH$_3$ | C$_{25}$H$_{24}$BrF$_2$N$_2$O$_4$ | 535.1039 | 535.1055 |
| Ex. 337 | —NH$_2$ | C$_{21}$H$_{16}$BrF$_2$N$_2$O$_3$ | 463.0463 | 463.0492 |

NMR characterization of compounds of Examples 329–337

| Example No. | NMR Data |
|---|---|
| Ex. 329 | $^1$H NMR (400 MHz, CDCl$_3$) δ 7.59(app q, J=7.79Hz, 1H), 7.47(dd, J=7.65, 1.08Hz, 1H), 7.34(t, J=7.72Hz, 1H), 7.12(dd, J=7.78, 0.94Hz, 1H), 6.96(app dt, J=7.92, 2.27Hz, 1H), 6.87(dt, J=9.46, 2.55Hz, 1H), 6.29(m, 1H), 6.12(s, 1H), 5.25(s, 2H), 3.73–3.65(m, 1H), 3.56–3.48(m, 3H), 3.35(d, J=3.09Hz, 3H), 2.09(s, 3H), 1.93(s, 3H) |
| Ex. 330 | $^1$H NMR (400 MHz, CDCl$_3$) δ 7.59(app q, J=7.79Hz, 1H), 7.34(t, J=7.66Hz, 1H), 7.28(dd, J=7.66, 1.21Hz, 1H), 7.07(dd, J=7.65, 1.08Hz, 1H), 6.96(app dt, J=8.52, 2.02Hz, 1H), 6.87(dt, J=9.46, 2.55Hz, 1H), 6.29(m, 1H), 6.12(s, 1H), 5.25(s, 2H), 3.11(s, 3H), 2.82(s, 3H), 1.96(s, 3H), 1.95(s, 3H) |
| Ex. 331 | $^1$H NMR (400 MHz, CDCl$_3$) δ 7.59(app q, J=7.4Hz, 1H), 7.46(d, J=6.71Hz, 1H), 7.32 (t, J=7.72Hz, 1H), 7.07(d, J=6.85Hz, 1H), 6.98(m, 2H), 6.87(dt, J=9.47, 2.41Hz, 1H), 6.15(s, 1H), 5.26(s, 2H), 3.71(t, J=4.97Hz, 2H), 3.60–3.45(m, 2H), 2.06(s, 3H), 1.95(s, 3H) |
| Ex. 332 | $^1$H NMR (400 MHz, CDCl$_3$) δ 7.59(app q, J=7.79Hz, 1H), 7.42(dd, J=7.66, 0.94Hz, 1H), 7.31(t, J=7.72Hz, 1H), 7.09(dd, J=7.79, 0.94Hz, 1H), 6.96(app dt, J=8.26, 1.61Hz, 1H), 6.87(dt, J=9.44, 2.49Hz, 1H), 6.12(s, 1H), 5.25(s, 2H), 2.96(d, J=4.83Hz, 3H), 2.07(s, 3H), 1.93(s, 3H) |
| Ex. 333 | $^1$H NMR (300 MHz, DMSO-$d_6$) δ 7.73(q, J=7.92Hz, 1H), 7.44–7.20(m, 5H), 6.75(s, 1H), 5.37(s, 2H), 4.83(br s, 1H), 3.65(br s, 2H), 3.45–3.33(m, 2H), 2.81(s, 3H), 1.93(d, J=3.42Hz, 3H), 1.85(d, J=8.06Hz, 3H) |
| Ex. 334 | $^1$H NMR (300 MHz, DMSO-$d_6$) δ 7.67(app q, J=7.92Hz, 1H), 7.40(t, J=7.78Hz, 1H), 7.34(dt, J=9.87, 2.55Hz, 1H), |

| | |
|---|---|
| | 7.27(d, J=7.52Hz, 1H), 7.24(d, J=7.79Hz, 1H), 7.17(dt, J=8.41, 1.97Hz, 1H), 6.71(s, 1H), 5.32(s, 2H), 3.63(m, 2H), 3.29(br s, 1H), 3.09(br s, 2H), 2.34(t, J=4.57Hz, 2H), 2.20(br s, 2H), 2.16(s, 3H), 1.88(d, J=8.86Hz, 3H), 1.80(d, J=4.83Hz, 3H) |
| Ex. 335 | $^1$H NMR (300 MHz, CDCl$_3$) δ 7.64(app q, J=7.79Hz, 1H), 7.42(t, J=7.65Hz, 1H), 7.33(d, J=7.66Hz, 1H), 7.14(d, J=7.65Hz, 1H), 7.00(dt, J=8.76, 2.21Hz, 1H), 6.91(dt, J=9.47, 2.42Hz, 1H), 6.17(s, 1H), 5.29(s, 2H), 3.98–3.92(m, 1H), 3.80–3.77(m, 3H), 3.59(br s, 2H), 3.29(t, J=4.43Hz, 2H), 2.04(s, 3H), 2.00(s, 3H) |
| Ex. 336 | $^1$H NMR (300 MHz, CDCl$_3$) δ 7.65(app q, J=7.79Hz, 1H); 7.43–7.32(m, 2H), 7.12(dd, J=7.66, 1.21Hz, 1H), 7.00(dt, J=9.06, 1.51Hz, 1H), 6.92(dt, J=9.42, 2.52Hz, 1H), 6.16(s, 1H), 5.30(s, 2H), 3.69(t, J=5.04Hz, 2H), 3.39(s, 3H), 3.26(s, 1H), 3.19(s, 1H), 2.91(s, 3H), 2.04(s, 3H), 2.00(s, 3H) |
| Ex. 337 | $^1$H NMR (300 MHz, DMSO-d$_6$) δ 7.91(br s, 1H), 7.73(app q, J=7.85Hz, 1H), 7.53–7.20(m, 5H), 6.74(s, 1H), 5.37(s, 2H), 1.99(s, 3H), 1.92(s, 3H) |

Example 338

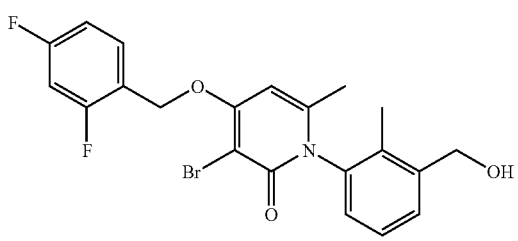

3-bromo-4-[(2,4-difluorobenzyl)oxy]-1-[3-(hydroxymethyl)-2-methylphenyl]-6-methylpyridin-2(1H)-one 3-[3-Bromo-4-[(2,4-difluorobenzyl)oxy]-6-methyl-2-oxopyridin-1(2H)-yl]-2-methylbenzoic acid (Step 4 above) (2.0 g, 4.31 mmol) was cooled to 0° C. in 10 ml of tetrahydrofuran. 19.5 ml of 1M BH$_3$.THF in tetrahydrofuran was added and stirred overnight, allowing the temperature to rise to room temperature. The reaction was cooled back down to 0° C. and ice chips were added to quench the reaction. The slurry was extracted 3 times with an ethyl acetate/tetrahydrofuran mixture. The combined organic layers were washed with brine, dried over MgSO$_4$, filtered and evaporated to give a white solid (1.73 g, 89%). $^1$H NMR (400 MHz, DMSO-d$_6$) δ 7.67 (app q, J=7.92 Hz, 1H), 7.46 (d, J=7.52 Hz, 1H), 7.32 (dt, J=10.74, 2.42 Hz, 1H), 7.30 (t, J=7.72 Hz, 1H), 7.17 (dt, J=8.46, 1.88 Hz, 1H), 7.03 (d, J=7.38 Hz, 1H), 6.68 (s, 1H), 5.32 (s, 2H), 4.51 (s, 2H), 3.29 (d, J=9.40 Hz, 1H), 1.85 (s, 3H), 1.81 (s, 3H), LC/MS, t$_r$=2.64 minutes (5 to 95% acetonitrile/water over 5 minutes at 1 ml/min, at 254 nm, at 50° C.), ES-MS m/z 450 (M+H). ES-HRMS m/z 450.0480 (M+H calcd for C$_{21}$H$_{18}$BrF$_2$NO$_3$ requires 450.0511).

Example 339

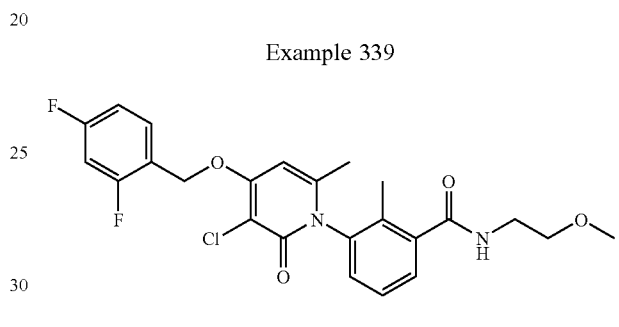

3-[3-chloro-4-[(2,4-difluorobenzyl)oxy]-6-methyl-2-oxopyridin-1(2H)-yl]-N-(2-methoxyethyl)-2-methylbenzamide Step 1: Preparation of 3-[3-chloro-4-[(2,4-difluorobenzyl)oxy]-6-methyl-2-oxopyridin-1(2H)-yl]-2-methylbenzoic acid.

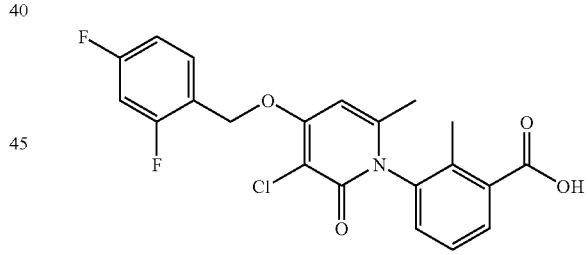

3-[4-[(2,4-Difluorobenzyl)oxy]-6-methyl-2-oxopyridin-1(2H)-yl]-2-methylbenzoic acid (Step 3 above) (10.0 g, 25.9 mmol) was refluxed with N-chlorosuccinimide (4.15 g, 31.1 mmol) and dichloroacetic acid (1.06 ml, 12.9 mmol) in 50 ml of CH$_2$Cl$_2$ overnight. The reaction was evaporated on a rotary evaporator and the resulting solid was stirred in acetonitrile for 30 minutes, washed 4 times with acetonitrile and dried in vacuo to yield a white solid (8.3 g, 78%). $^1$H NMR (300 MHz, DMSO-d$_6$) δ 7.93 (dd, J=7.15, 1.92 Hz, 1H), 7.72 (app q, J=7.92 Hz, 1H), 7.52–7.35 (m, 3H), 7.22 (dt, J=8.47, 2.01 Hz, 1H), 6.80 (s, 1H), 5.38 (s, 2H), 2.14 (s, 3H), 1.93 (s, 3H); LC/MS, t$_r$=2.64 minutes (5 to 95% acetonitrile/water over 5 minutes at 1 ml/min, at 254 nm, at 50° C.), ES-MS m/z 420 (M+H). ES-HRMS m/z 420.0806 (M+H calcd for C$_{21}$H$_{16}$ClF$_2$NO$_4$ requires 420.0809).

Step 5: Preparation of the title compound. 3-[3-Chloro-4-[(2,4-difluorobenzyl)oxy]-6-methyl-2-oxopyridin-1(2H)-yl]-2-methylbenzoic acid (from Step 1 above) (500 mg, 1.19 mmol) was dissolved in 5 ml of $CH_2Cl_2$. 2-Methoxyethylamine (129 µl, 1.49 mmol) was added, followed, in order, by EDCI (286 mg, 1.49 mmol), 1-hydroxybenzotriazole (202 mg, 1.49 mmol) and triethylamine (332 µl, 2.38 mmol). The reaction was stirred at room temperature overnight. The reaction was quenched with $NH_4Cl$ and extracted 3 times with ethyl acetate. The combined organic layer was dried over $MgSO_4$ and evaporated. The resulting solid was dried in vacuo to give a white solid (401 mg, 71%). $^1H$ NMR (400 MHz, $CDCl_3$) δ 7.56 (app q, J=7.74 Hz, 1H), 7.47 (d, J=6.98 Hz, 1H), 7.34 (t, J=7.72 Hz, 1H), 7.11 (d, J=7.25 Hz, 1H), 6.95 (dt, J=8.23, 1.66 Hz, 1H), 6.87 (dt, J=9.51, 2.46 Hz, 1H), 6.35 (br s, 1H), 6.15 (s, 1H), 5.25 (s, 2H), 3.72–3.63 (m, 1H), 3.58–3.49 (m, 3H), 3.35 (s, 3H), 2.09 (s, 3H), 1.93 (s, 3H); LC/MS, $t_r$=2.56 minutes (5 to 95% acetonitrile/water over 5 minutes at 1 ml/min, at 254 nm, at 50° C.), ES-MS m/z 477 (M+H). ES-HRMS m/z 477.1363 (M+H calcd for $C_{24}H_{23}ClF_2N_2O_4$ requires 477.1387).

Example 340

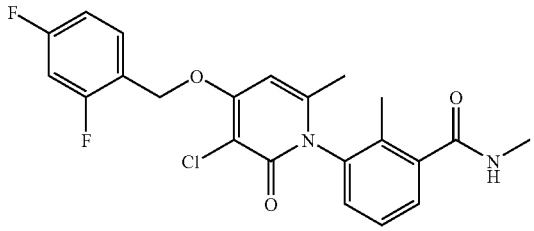

3-[3-chloro-4-[(2,4-difluorobenzyl)oxy]-6-methyl-2-oxopyridin-1(2H)-yl]-N,2-dimethylbenzamide The title compound was prepared by a procedure similar to the one described for Example 337, where methylamine was used as the amine and the product was obtained in 73% yield. $^1H$ NMR (300 MHz, DMSO-$d_6$) δ 8.37 (app d, J=4.64 Hz, 1H), 7.72 (app q, J=7.92 Hz, 1H), 7.44–7.35 (m, 4H), 7.22 (dt, J=8.54, 1.61 Hz, 1H), 6.78 (s, 1H), 5.37 (s, 2H), 2.79 (d, J=4.43 Hz, 3H), 1.95 (s, 3H), 1.94 (s, 3H); LC/MS, $t_r$=2.46 minutes (5 to 95% acetonitrile/water over 5 minutes at 1 ml/min, at 254 nm, at 50° C.), ES-MS m/z 433 (M+H). ES-HRMS m/z 433.1163 (M+H calcd for $C_{22}H_{19}ClF_2N_2O_3$ requires 433.1125).

Example 341

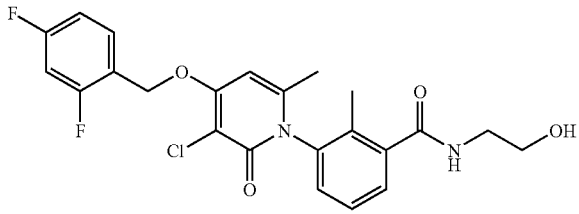

3-[3-chloro-4-[(2,4-difluorobenzyl)oxy]-6-methyl-2-oxopyridin-1(2H)-yl]-N-(2-hydroxyethyl)-2-methylbenzamide The title compound was prepared by a procedure similar to the one described for , where ethanolamine was used as the amine and the product was obtained in 65% yield. $^1H$ NMR (400 MHz, DMSO-$d_6$) δ 8.39 (t, J=5.51 Hz, 1H), 7.67 (app q, J=7.88 Hz, 1H), 7.43–7.33 (m, 3H), 7.23 (d, J=7.25 Hz, 1H), 7.17 (dt, J=8.39, 1.66 Hz, 1H), 6.74 (s, 1H), 5.32 (s, 2H), 3.48 (br s, 2H), 3.31–3.26 (m, 2H), 1.90 (s, 3H), 1.89 (s, 3H); LC/MS, $t_r$=2.34 minutes (5 to 95% acetonitrile/water over 5 minutes at 1 ml/min, at 254 nm, at 50° C.), ES-MS m/z 463 (M+H). ES-HRMS m/z 463.1220 (M+H calcd for $C_{23}H_{21}ClF_2N_2O_4$ requires 463.1231).

Example 342

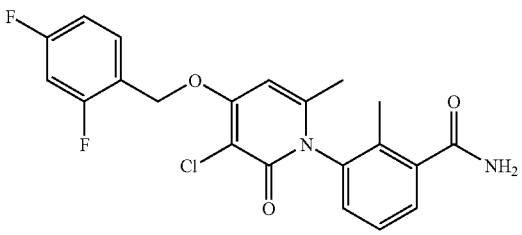

3-[3-chloro-4-[(2,4-difluorobenzyl)oxy]-6-methyl-2-oxopyridin-1(2H)-yl]-2-methylbenzamide 3-[3-Chloro-4-[(2,4-difluorobenzyl)oxy]-6-methyl-2-oxopyridin-1(2H)-yl]-2-methylbenzoic acid (Step 1 above) (500 mg, 1.19 mmol) was stirred with 2-chloro-4,6-dimethoxy-1,3,5-triazine (251 mg, 1.43 mmol) and N-methylmorpholine (392 µl, 3.57 mmol) in 5 ml of tetrahydrofuran at room temperature for 2 hours. 2.5 ml of $NH_4OH$ was added and stirred at room temperature for 2.5 hours. The reaction was diluted with tetrahydrofuran and ethyl acetate and extracted. The combined organic layers were washed with $NaHCO_3$, 1 N HCl, and brine, dried over $MgSO_4$, filtered and evaporated. The resulting solid was dried in vacuo to obtain a white solid (313 mg, 63%). $^1H$ NMR (400 MHz, DMSO-$d_6$) δ 7.87 (br s, 1H), 7.66 (q, J=7.83 Hz, 1H), 7.48–7.30 (m, 3H), 7.23 (d, J=7.52 Hz, 1H), 7.17 (t, J=7.65 Hz, 1H), 6.73 (s, 1H), 5.32 (s, 2H), 1.94 (s, 3H), 1.88 (s, 3H); LC/MS, $t_r$=2.44 minutes (5 to 95% acetonitrile/water over 5 minutes at 1 ml/min, at 254 nm, at 50° C.), ES-MS m/z 419 (M+H). ES-HRMS m/z 419.0963 (M+H calcd for $C_{21}H_{17}ClF_2N_2O_3$ requires 419.0969).

Example 343

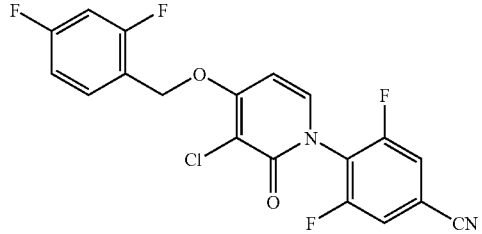

4-[3-chloro-4-[(2,4-difluorobenzyl)oxy]-2-oxopyridin-1(2H)-yl]-3,5-difluorobenzonitrile Step 1: Preparation of 4-[(2,4-difluorobenzyl)oxy]pyridine 1-oxide.

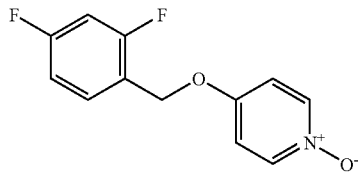

2,4-difluorobenzyl alcohol (100. g, 0.694 mol) and 4-nitropyridine N-oxide (98, g, 0.700 mol)are combined with 250 g $Cs_2CO_3$ (1.1 eq) in 2.5 L anhydrous dimethylformamide and heated to 80° C. with stirring. The reaction was followed by $^{19}$F-NMR (crude reaction mixture with external $D_2O$ reference) and complete after 40 h. The mixture was filtered hot; product crystallized out on cooling. 90.21 g (55%) of white plates were collected by filtration and washed with diethyl ether. The mother liquor was diluted with 2.5 L diethyl ether and stored in the freezer overnight, yielding a second crop 68.76 g (41%, combined yield 96%). $^1$H-NMR (400 MHz, DMSO-$d_6$) δ 8.06 (m, 2H), 7.61 (quartet, J=8.45 Hz, 1H), 7.30 (t, J=10.37 Hz, 1H), 7.12, (t, J=8.45 Hz, 1H), 7.09 (d, J=5.06 Hz, 2H), 5.14 (s, 2H). $^{19}$F-NMR (400 MHz, DMSO-$d_6$) δ−109.43 (quintet, J=7.78 Hz, 1F), −113.82 (quartet, J=9.55 Hz, 1F). LC/MS $t_r$=3.90 minutes (0–95% acetonitrile/water, 0.05% trifluoroacetic acid, over 6 minutes at 1 ml/min with detection at 215 nm, at 50° C.) ES-MS m/z 238 (M+H).

Step 2: Preparation of 4-[(2,4-difluorobenzyl)oxy]-pyridin-2(1H)-one (7).

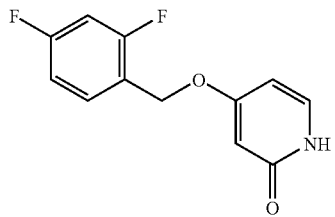

4-[(2,4-difluorobenzyl)oxy]pyridine 1-oxide (from Step 1) (30.0 g , 0.127 mol), anhydrous potassium acetate (25 g, 0.25 mol), acetic anydride (25 g, 0.25 mol), and 10 ml acetic acid were combined in a 250-ml round-bottomed flask with overhead stirring and heated to 130° C. for 4 hours. The mixture was concentrated under vacuum, the solids dissolved in 95 ml acetonitrile: 5 ml water, filtered through charcoal and poured into 600 ml ice with stirring. The mixture was allowed to stand overnight at room temperature, then 9.62 g (30%) product collected by filtration as a medium brown solid (adequate for the next step without purification). $^1$H-NMR (400 MHz, DMSO-$d_6$) δ 11.10 (s, 1H), 7.59 (quartet, J=9.91 Hz, 1H), 7.29 (t, J=10.36 Hz, 1H), 7.21 (d, J=8.20 Hz, 1H), 7.11 (t, J=8.48 Hz, 1H), 5.83 (m, 2H), 5.02 (s, 2H). $^{19}$F-NMR (400 MHz, DMSO-$d_6$) δ−109.57 (quintet, J=7.66 Hz, 1F)-113.88 (quartet, J=8.93 Hz, 1F). LC/MS $t_r$=4.29 minutes (0–95% acetonitrile/water, 0.05% trifluoroacetic acid, over 6 minutes at 1 ml/min with detection at 254 nm, at 50° C.) ES-MS m/z 238 (M+H).

Step 3: Preparation of 3-chloro-4-[(2,4-difluorobenzyl)oxy]pyridin-2 (1H)-one.

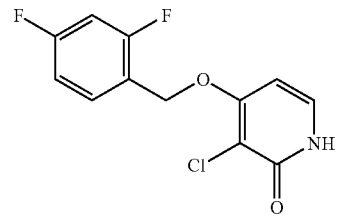

4-[(2,4-difluorobenzyl)oxy]-pyridin-2 (1H)-one (from Step 2) (8.60 g, 36.3 mmol) was stirred in 150 ml dimethylformamide and treated with N-chlorosuccinimide (5.4 g, 39.9 mmol). After 15 hours, the precipitate was collected by filtration (5.11 g, 52%) yeilding a lustrous white solid. The mother liquor was diluted to 500 ml with diethyl ether, providing 2.47 g (25%) in a second crop. $^1$H-NMR (400 MHz, DMSO-$d_6$) δ 11.87 (s, 1H), 7.60 (quartet, J=6.34 Hz, 1H), 7.43 (d, J=7.58 Hz, 1H), 7.31 (dt, J=10.08, 2.21 Hz, 1H), 7.14 (dt, J 8.65, 1.79 Hz, 1H), 6.44 (d, J=7.49 Hz, 1H), 5.28 (s, 1H). $^{19}$F-NMR (400 MHz, DMSO-$d_6$) δ−109.58 (quintet, J=7.75 Hz, 1F), −113.68 (quartet, J=8.68 Hz, 1F). LC/MS $t_r$=4.47 minutes (0–95% acetonitrile/water, 0.05% trifluoroacetic acid, over 6 minutes at 1 ml/min with detection at 254 nm, at 50° C.) ES-MS m/z 272, 274 3:1 (M+H).

Step 4: Preparation of the Title Compound.

3-chloro-4-[(2,4-difluorobenzyl)oxy]pyridin-2(1H)-one (from step 3) (3.25 g, 11.9 mmol) was combined with $Cs_2CO_3$ (3.93 g, 12.1 mmol) in 50 ml dimethylformamide and heated to 70° C., stirring under nitrogen. 3,4,5-trifluorobenzonitrile (1.83 g, 11.9 mmol) was added. After 4 hours, the mixture was filtered, concentrated in vacuo, washed thrice with hot cyclohexane, dissolved in tetrahydrofuran, treated with $MgSO_4$ and charcoal, and filtered. The solution was evaporated leaving a fine white solid (3.99 g, 82%). $^1$H-NMR (400 MHz, DMSO-$d_6$) δ 8.12 (d, J=7.59 Hz, 2H), 7.92 (d, J=8.31 Hz, 1H), 7.65 (quartet, J=6.77, 1H), 7.34 (dt, J=9.81, 2.71 Hz, 1H), 7.16 (dt, J=8.59, 2.50 Hz, 1H), 6.87 (d, J=8.01 Hz, 1H), 5.39 (s, 2H). $^{19}$F-NMR (400 MHz, DMSO-$d_6$) δ−109.17 (quintet, J=8.97 Hz, 1F), −113.51 (quartet, J=9.53 Hz, 1F), −116.32 (d, J=7.69 Hz, 2F). LC/MS $t_r$=5.51 minutes (0–95% acetonitrile/water, 0.05% trifluoroacetic acid, over 6 minutes at 1 ml/min with detection at 215 nm, at 50° C.) ES-MS m/z 409 (M+H). ES-HRMS m/z 409.0351 (M+H calcd for $C_{19}H_{10}ClF_4N_2O_2$ requires 409.0361).

Example 344

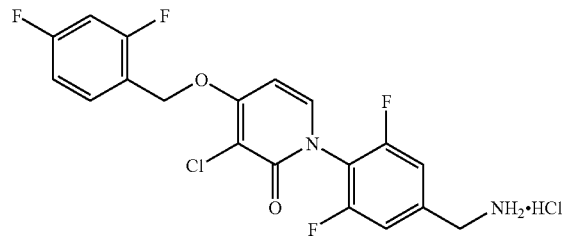

1-[4-(aminomethyl)-2,6-difluorophenyl]-3-chloro-4-
[(2,4-difluorobenzyl)oxy]pyridin-2(1H)-one
hydrochloride Step 1: Preparation of tert-butyl 4-[3-chloro-4-[(2,4-
difluorobenzyl)oxy]-2-oxopyridin-1(2H)-yl]-3,5-
difluorobenzylcarbamate.

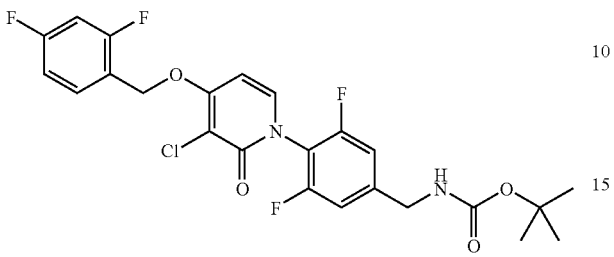

4-[3-chloro-4-[(2,4-difluorobenzyl)oxy]-2-oxopyridin-1
(2H)-yl]-3,5-difluorobenzonitrile 2.84 g, 6.95 mmol), di-t-
butyl-dicarbonate (3.18 g, 14.6 mmol), and nickel(II) chloride (0.90 g, 6.95 mmol) were combined with 40 ml methanol and 40 ml tetrahydrofuran and cooled to 0° C. stirring in an ice bath. Sodium borohydride (1.33 g, 35.2 mmol) was added in small portions over 10 minutes to control foaming, and the reaction was stirred 1 hour. Additional sodium borohydride (0.50 g, 13.2 mmol) was required to force the reaction to completion by LC. A color change from yellow to black persisted on completion. The mixture was filtered through a bed of charcoal layered on anhydrous $MgSO_4$ and evaporated to dryness. Excess di-t-butyl-dicarbonate and byproduct t-butanol were removed by repeated heating with water to 80° C. in vacuo, giving the product as a fine white powder (3.11 g, 87%). $^1$H-NMR (400 MHz, DMSO-$d_6$) δ 7.89 (d, J=8.04 Hz, 1H), 7.65 (quartet, J=6.73 Hz, 1H), 7.55 (t, J=6.73 Hz, 1H), 7.34, (dt, J=10.05, 2.51 Hz, 1H), 7.16 (m, 3H), 6.77 (d, J=8.18 Hz, 1H), 5.34 (s, 2H), 4.18 (d, J=5.68 Hz, 2H), 1.34 (s, 9H). $^{19}$F-NMR (400 MHz, DMSO-$d_6$) δ−109.26 (quintet, J=6.91 Hz, 1F), −113.53 (quartet, J=7.73 Hz, 1F), −120.32 (d, J=8.91 Hz, 2F). LC/MS $t_r$=5.90 minutes (0–95% acetonitrile/water, 0.05% trifluoroacetic acid, over 6 minutes at 1 ml/min with detection at 215 nm, at 50° C.) ES-MS m/z 513 (M+H). ES-HRMS m/z 513.1164 (M+H calcd for $C_{24}H_{22}ClF_4N_2O_4$ requires 513.1199).

Step 2: Preparation of the Title Compound.

tert-butyl 4-[3-chloro-4-[(2,4-difluorobenzyl)oxy]-2-oxopyridin-1(2H)-yl]-3,5-difluorobenzylcarbamate (from step 3) (1.39 g, 2.71 mmol) was dissolved in 20 ml tetrahydrofuran and treated with 4 ml concentrated hydrochloric acid. The solution was evaporated and dried in vacuo to a fine white solid (1.20 g, 99%). $^1$H-NMR (400 MHz, DMSO-$d_6$) δ 8.54 (m, 2H), 7.86 (d, J=7.57 Hz, 1H), 7.65 (quartet, J=7.62, 1H), 7.50 (d, J=9.25 Hz, 2H), 7.34 (dt, J=10.50, 2.45 Hz, 1H), 7.16 (dt, J=8.38, 2.55 Hz, 1H), 6.78 (d, J=7.86 Hz, 1H), 5.37 (s, 2H), 4.10 (br s, 2H), 4.97–3.14 (v br s, 3H). $^{19}$F-NMR (400 MHz, DMSO-$d_6$) δ−109.21 (quintet, J=7.77 Hz, 1F), −113.51 (quartet, j=8.95 Hz, 1F), −119.56 (d, J=9.44 Hz, 2F). LC/MS $t_r$=4.33 minutes (0–95% acetonitrile/water, 0.05% trifluoroacetic acid, over 6 minutes at 1 ml/min with detection at 215 nm, at 50° C.) ES-MS m/z 413 (M+H). ES-HRMS m/z 413.0712 (M+H calcd for $C_{19}H_{14}ClF_4N_2O_2$ requires 413.0674).

Example 345

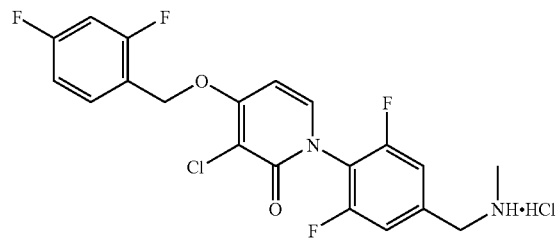

3-chloro-4-[(2,4-difluorobenzyl)oxy]-1-{2,6-
difluoro-4-[(methylamino)methyl]phenyl}pyridin-2
(1H)-one hydrochloride Step 1: Preparation of tert-butyl 4-[3-chloro-4-[(2,4-
difluorobenzyl)oxy]-2-oxopyridin-1(2H)-yl]-3,5-
difluorobenzyl(methyl)carbamate.

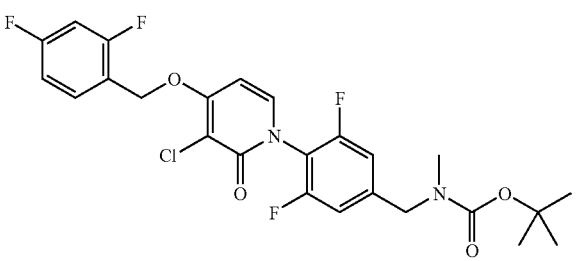

tert-butyl 4-[3-chloro-4-[(2,4-difluorobenzyl)oxy]-2-oxopyridin-1(2H)-yl]-3,5-difluorobenzylcarbamate (from Step 1) (252 mg, 0.491 mmol) and iodomethane (75 mg, 0.528 mmol) are combined in 8 ml anhydrous dimethylformamide. Sodium hydride 60% in mineral oil (30 mg, 0.75 mmol) was added and the mixture stirred under nitrogen at room temperaure for 1 hour. Saturated aqueous $NH_4Cl$ was added (4 ml) followed by 20 ml water and the product was extracted into ethyl acetate, washed with brine, dried over $MgSO_4$, filtered, and evaporated to give the product as a white powder (208 mg, 80%). $^1$H-NMR (400 MHz, DMSO-$d_6$) δ 7.87 (d, J=7.85 Hz, 1H), 7.64 (quartet, J=6.66 Hz, 1H), 7.32, (dt, J=9.39, 3.29 Hz, 1H), 7.13 (m, 3H), 6.77 (d, J=7.94 Hz, 1), 5.38 (s, 2H), 4.43 (s, 2H), 2.90 (s, 3H), 1.40 (br m, 9H). $^{19}$F-NMR (400 MHz, DMSO-$d_6$) δ−109.25 (quintet, J=8.93 Hz, 1F), −113.53 (quartet, J=9.73 Hz, 1F), −119.89 (d, J=9.35 Hz, 2F). LC/MS $t_r$=6.16 minutes (0–95% acetonitrile/water, 0.05% trifluoroacetic acid, over 6 minutes, then 95% acetonitrile for 2 minutes, at 1 ml/min with detection at 215 nm, at 50° C.) ES-MS m/z 527 (M+H). ES-HRMS m/z 527.1338 (M+H calcd for $C_{25}H_{24}ClF_4N_2O_4$ requires 527.1355).

Step 2: Preparation of the Title Compound.

tert-butyl 4-[3-chloro-4-[(2,4-difluorobenzyl)oxy]-2-oxopyridin-1(2H)-yl]-3,5-difluorobenzyl(methyl)carbamate from step 1) (188 mg, 0.357 mmol) was subjected to the conditions of Step 2, yielding a fine white solid (165 mg, 100%). $^1$H-NMR (400 MHz, DMSO-$d_6$) δ 9.30 (br s, 2H), 7.89 (d, J=7.99 Hz, 1H), 7.65 (quartet, J=7.64, 1H), 7.55 (d, J=8.66 Hz, 2H), 7.34 (dt, J=9.93, 2.57 Hz, 1H), 7.17 (dt, J=8.49, 2.48 Hz, 1H), 6.81 (d, J=8.01 Hz, 1H), 5.39 (s, 2H), 4.21 (s, 2H), 2.56 (s, 3H). $^{19}$F-NMR (400 MHz, DMSO-$d_6$) δ−109.20 (quintet, J=7.56 Hz, 1F), −113.52 (quartet, J=9.67 Hz, 1F), −119.21 (d, J=8.79 Hz, 2F). LC/MS $t_r$=4.30 minutes (0–95% acetonitrile/water, 0.05% trifluoroacetic acid, over 6 minutes at 1 ml/min with detection at 215 nm, at 50° C.)

ES-MS m/z 427 (M+H). ES-HRMS m/z 427.0816 (M+H calcd for $C_{20}H_{16}ClF_4N_2O_2$ requires 427.0831).

Example 346

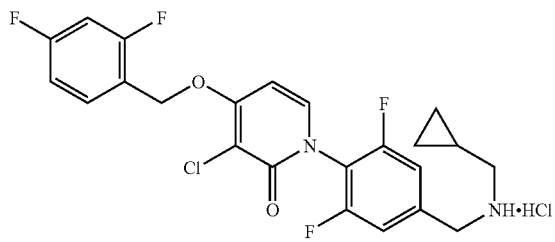

3-chloro-1-(4-{[(cyclopropylmethyl)amino]methyl}-2,6-difluorophenyl)-4-[(2,4-difluorobenzyl)oxy]pyridin-2(1H)-one hydrochloride The title compound was prepared by direct analogy with replacing iodomethane with bromocyclopropylmethane and extending the reaction time to 6 hours in Step 1.

Step 1:

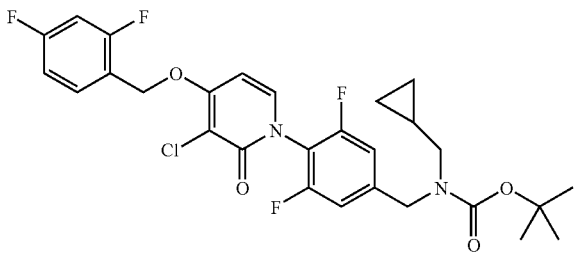

1 tert-butyl 4-[3-chloro-4-[(2,4-difluorobenzyl)oxy]-2-oxopyridin-1(2H)-yl]-3,5-difluorobenzyl(cyclopropylmethyl)carbamate $^1$H-NMR (400 MHz, DMSO-d$_6$) δ 7.89 (d, J=7.91 Hz, 1H), 7.65 (quartet, J=6.81 Hz, 1H), 7.33, (dt, J=9.90, 2.26 Hz, 1H), 7.17 (m, 3H), 6.77 (d, J=7.90 Hz, 1), 5.38 (s, 2H), 4.51 (s, 2H), 3.10 (br s, 2H), 1.36 (m, 9H), 0.97 (br s, 1H), 0.38 (m, 2H), 0.18 (m, 2H). $^{19}$F-NMR (400 MHz, DMSO-d$_6$) δ −109.25 (quintet, J=7.77 Hz, 1F), −113.54 (quartet, J=9.02 Hz, 1F), −120.24 (m, 2F). LC/MS t$_r$ 5.99 minutes (0–95% acetonitrile/water, 0.05% trifluoroacetic acid, over 6 minutes, then 95% acetonitrile for 2 minutes, at 1 ml/min with detection at 215 nm, at 50° C.) ES-MS m/z 567 (M+H). ES-HRMS m/z 567.1653 (M+H calcd for $C_{28}H_{28}ClF_4N_2O_4$ requires 567.1668).

Step 2: Title Compound.

$^1$H-NMR (400 MHz, DMSO-d$_6$) δ 9.51 (br s, 2H), 7.87 (d, J=7.96 Hz, 1H), 7.63 (m, 3H), 7.33 (dt, J=9.93, 2.65 Hz, 1H), 7.16 (dt, J=8.36, 2.32 Hz, 1H), 6.81 (d, J=7.92 Hz, 1H), 5.38 (s, 2H), 4.22 (br s, 2H), 2.82 (br s, 2H), 1.10 (m, 1H), 0.57 (m, 2H), 0.36 (m, 2H). $^{19}$F-NMR (400 MHz, DMSO-d$_6$) δ −109.25 (quintet, J=7.69 Hz, 1F), −113.54 (quartet, J=9.35 Hz, 1F), −120.24 (m, 2F). LC/MS t$_r$=4.55 minutes (0–95% acetonitrile/water, 0.05% trifluoroacetic acid, over 6 minutes at 1 ml/min with detection at 215 nm, at 50° C.) ES-MS m/z 467 (M+H). ES-HRMS m/z 467.1119 (M+H calcd for $C_{23}H_{20}ClF_4N_2O_2$ requires 467.1144).

Example 347

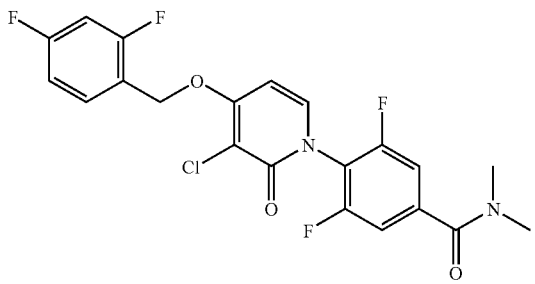

4-[3-chloro-4-[(2,4-difluorobenzyl)oxy]-2-oxopyridin-1(2H)-yl]-3,5-difluoro-N,N-dimethylbenzamide Step 1: Preparation of 4-[3-chloro-4-[(2,4-difluorobenzyl)oxy]-2-oxopyridin-1(2H)-yl]-3,5-difluorobenzamide.

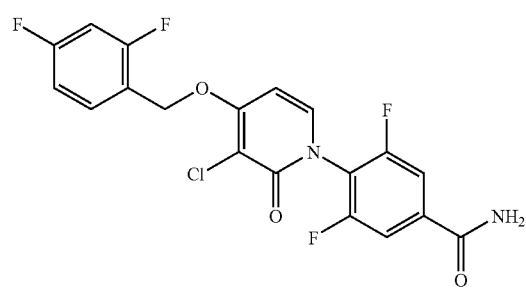

4-[3-chloro-4-[(2,4-difluorobenzyl)oxy]-2-oxopyridin-1(2H)-yl]-3,5-difluorobenzonitrile (540-mg, 1.32 mmol) and potassium trimethylsilonate 90% (375 mg, 2.63 mmol) are combined in 8 ml anhydrous toluene and heated to reflux with stirring. After 10 minutes, the mixture allowed to cool then partitioned between saturated aqueous ammonium chloride and ethyl acetate. The aqueous layer is extracted twice with ethyl acetate, the combined organics are washed with brine, dried over MgSO$_4$, and evaporated in vacuo. The crude product is taken up in tetrahydrofuran and filtered through charcoal layered over silica gel, and the solution evaporated in vacuo to give the product as a white powder (468 mg, 83%). $^1$H-NMR (400 MHz, DMSO-d$_6$) δ 8.22 (br s, 2H), 7.92 (d, J=7.84 Hz, 1H), 7.78 (d, J=8.45, 2H), 7.65 (quartet, J=8.40 Hz, 1H), 7.34, (dt, J=10.09, 2.58 Hz, 1H), 7.17 (dt, J=8.72, 2.30 Hz, 1H), 6.83 (d, J=7.91 Hz, 1H), 5.39 (s, 2H). $^{19}$F-NMR (400 MHz, DMSO-d$_6$) δ −109.21 (quintet, J=7.43 Hz, 1F), −113.52 (quartet, J=9.62 Hz, 1F), −118.74 (d, J=8.88 Hz, 2F). LC/MS t$_r$=4.67 minutes (0–95% acetonitrile/water, 0.05% trifluoroacetic acid, over 6 minutes, then 95% acetonitrile for 2 minutes, at 1 ml/min with detection at 215 nm, at 50° C.) ES-MS m/z 427 (M+H). ES-HRMS m/z 427.0454 (M+H calcd for $C_{19}H_{12}ClF_4N_2O_3$ requires 427.0467).

Step 2: Preparation of the Title Compound.

4-[3-chloro-4-[(2,4-difluorobenzyl)oxy]-2-oxopyridin-1(2H)-yl]-3,5-difluorobenzamide (from step 1) (243 mg, 0.357 mmol) was subjected to the conditions of Step 1, with the exception that two equivalents of sodium hydride 60% in mineral oil and iodomethane were used instead of one (46 mg, 0.69 mmol and 103 mg, 0.724 mmol respectively). $^1$H-NMR (400 MHz, DMSO-d$_6$) δ 7.92 (d, J=7.76 Hz, 1H), 7.66 (quartet, J=7.33, 1H), 7.44 (d, J=7.59 Hz, 2H), 7.34 (dt, J=9.88, 2.63 Hz, 1H), 7.17 (dt, J=8.35, 2.06 Hz, 1H), 6.83 (d, J=7.55 Hz, 1H), 5.39 (s, 2H), 2.98 (s, 3H), 2.91 (s, 3H).

$^{19}$F-NMR (400 MHz, DMSO-d$_6$) δ −109.22 (quintet, J=8.10 Hz, 1F), −113.53 (quartet, J=9.18 Hz, 1F), −118.88 (d, J=7.77 Hz, 2F). LC/MS t$_r$=5.13 minutes (0–95% acetonitrile/water, 0.05% trifluoroacetic acid, over 6 minutes at 1 ml/min with detection at 215 nm, at 50° C.) ES-MS m/z 455 (M+H). ES-HRMS m/z 455.0791 (M+H calcd for C$_{21}$H$_{16}$ClF$_4$N$_2$O$_3$ requires 455.0780).

Example 348

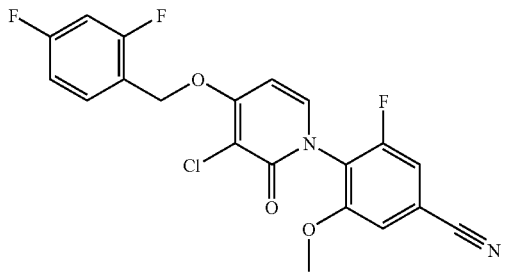

4-[3-chloro-4-[(2,4-difluorobenzyl)oxy]-2-oxopyridin-1(2H)-yl]-3-fluoro-5-methoxybenzonitrile Step 1: Preparation of 4-[3-chloro-4-[(2,4-difluorobenzyl)oxy]-2-oxopyridin-1(2H)-yl]-3-fluoro-5-hydroxybenzonitrile.

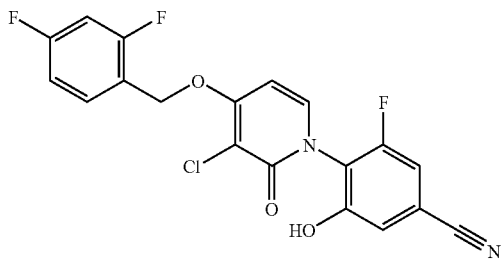

4-[3-chloro-4-[(2,4-difluorobenzyl)oxy]-2-oxopyridin-1(2H)-yl]-3,5-difluorobenzonitrile (522 mg, 1.28 mmol) and potassium trimethylsilonate 90% (655 mg, 4.60 mmol) are combined in 8 ml anhydrous tetrahydrofuran and stirred under nitrogen at room temperature for 2 hours. The precipitated potassium salt of was collected by filtration, washed with a minimum of tetrahydrofuran, and dried in vacuo. A portion of this salt (275 mg, 0.618 mmol) was dissolved in 5 ml water, the pH was adjusted below 6 with concentrated hydrochloric acid, the product collected by filtration, washed with water, sucked dry under a blanket of dry nitrogen, and dried further in vacuo overnight (251 mg, 100%, 98% overall). $^1$H-NMR (400 MHz, DMSO-d$_6$) δ 11.46 (br s, 1H), 7.74 (d, J=7.81 Hz, 1H), 7.67 (quartet, J=6.76 Hz, 1H), 7.52 (d, J=8.76 Hz, 1H), 7.364, (dt, J=10.18, 2.37 Hz, 1H), 7.24 (br s, 1H), 7.17 (br t, J=8.75 Hz, 1H), 6.74 (d, J=8.04 Hz, 1H), 5.39 (s, 2H).

$^{19}$F-NMR (400 MHz, DMSO-d$_6$) δ −109.26 (quintet, J=8.50 Hz, 1F), −113.52 (quartet, J=9.29 Hz, 1F), −118.06 (d, J=9.38 Hz, 1F). LC/MS t$_r$=5.13 minutes (0–95% acetonitrile/water, 0.05% trifluoroacetic acid, over 6 minutes, then 95% acetonitrile for 2 minutes, at 1 ml/min with detection at 215 nm, at 50° C.) ES-MS m/z 407 (M+H). ES-HRMS m/z 407.0381 (M+H calcd for C$_{19}$H$_{11}$ClF$_3$N$_2$O$_3$ requires 407.0405).

Step 2: Preparation of the Title Compound.

The potassium salt of 4-[3-chloro-4-[(2,4-difluorobenzyl)oxy]-2-oxopyridin-1(2H)-yl]-3-fluoro-5-hydroxybenzonitrile (from Step 1) (273 mg, 0.614 mmol) was stirred in 5 ml anhydrous dimethylformamide under nitrogen. Iodomethane (93 mg, 0.66 mmol) was added, and stirring continued for 2 hr. The mixture was diluted to 50 ml with ice-cold water, and the white precipitate collected by filtration. The precipitate was washed thrice with water, sucked dry under a blanket of nitrogen, and dried further in vacuo overnight (242 mg, 87%). $^1$H-NMR (400 MHz, DMSO-d$_6$) δ 7.73 (m, 2H), 7.65 (m, 2H), 7.34 (dt, J=9.90, 2.39 Hz, 1H), 7.17 (dt, J=8.75, 2.47 Hz, 1H), 6.75 (d, J=7.97 Hz, 1H), 5.37 (s, 2H), 3.84 (s, 3H). $^{19}$F-NMR (400 MHz, DMSO-d$_6$) δ −109.24 (quintet, J=7.85 Hz, 1F), −113.54 (quartet, J=9.83 Hz, 1F), −118.33 (d, J=7.77 Hz, 1F). LC/MS t$_r$=5.40 minutes (0–95% acetonitrile/water, 0.05% trifluoroacetic acid, over 6 minutes at 1 ml/min with detection at 215 nm, at 50° C.) ES-MS m/z 421 (M+H). ES-HRMS m/z 421.0522 (M+H calcd for C$_{20}$H$_{13}$ClF$_3$N$_2$O$_3$ requires 421.0561).

Example 349

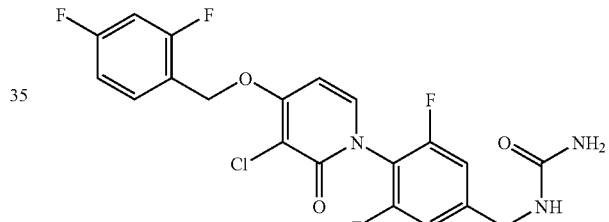

N-{4-[3-chloro-4-[(2,4-difluorobenzyl)oxy]-2-oxopyridin-1(2H)-yl]-3,5-difluorobenzyl}urea Step 1: Preparation of the Title Compound 1-[4-(aminomethyl)-2,6-difluorophenyl]-3-chloro-4-[(2,4-difluorobenzyl)oxy]pyridin-2(1H)-one hydrochloride (162 mg, 0.361 mmol) is dissolved in 4 ml 50% aqueous acetic acid and treated with potassium cyanate (59 mg, 0.72 mmol). The mixture was stirred 2 hr, then the mixture was diluted to 50 ml with cold water, and the crude product, contaminated with the acetamide, was purified by silica gel chromatography, eluting first with 20% ethanol in hexane then 40% ethanol in hexane. The 50% fractions were pooled by TLC and evaporated, giving the product as a fine white powder (65 mg, 40%). $^1$H-NMR (400 MHz, DMSO-d$_6$) δ 7.87 (d, J=8.07 Hz, 1H), 7.64 (quartet, J=6.53 Hz, 1H), 7.33, (dt, J=9.47, 1.99 Hz, 1H), 7.15 (m, 3H), 6.76 (d, J=7.97 Hz, 1H), 6.59 (m, 1H), 5.65 (br s, 2H), 5.38 (s, 2H), 4.22 (m, 2H). $^{19}$F-NMR (400 MHz, DMSO-d$_6$) δ −109.22 (quintet, J=7.86 Hz, 1F), −113.51 (quartet, J=9.40 1F), −120.65 (d, J=8.75 Hz, 2). LC/MS t$_r$=4.85 minutes (0–95% acetonitrile/water, 0.05% trifluoroacetic acid, over 6 minutes at 1 ml/min with detection at 215 nm, at 50° C.) ES-MS m/z 456 (M+H).

Example 350

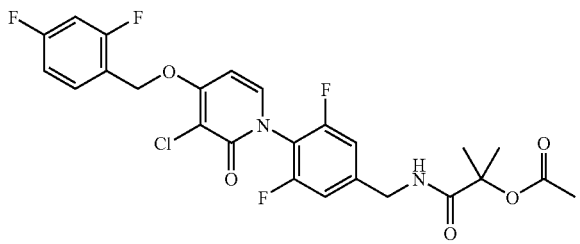

2-({4-[3-chloro-4-[(2,4-difluorobenzyl)oxy]-2-oxopyridin-1(2H)-yl]-3,5-difluorobenzyl}amino)-1,1-dimethyl-2-oxoethyl acetate Step 1: Preparation of the Title Compound 1-[4-(aminomethyl)-2,6-difluorophenyl]-3-chloro-4-[(2,4-difluorobenzyl)oxy]pyridin-2(1H)-one hydrochloride (225 mg, 0.501 mmol) is dissolved in a solution of 10 ml tetrahydrofuran and triethylamine (111 mg, 1.10 mmol). 2-acetoxy-2-methyl-propionyl chloride (85 mg, 0.516 mmol) is added, and the mixture stirred for 30 minutes before partitioning between saturated aqueous ammoniom chloride and ethyl acetate. The layers are seperated, and the aqueous phase extracted twice with ethyl acetate. The combined organics are washed with water and brine, then dried over MgSO$_4$, filtered, and evaporated in vacuo, giving the product as a fine white powder (254 mg, 94%). $^1$H-NMR (400 MHz, DMSO-d$_6$) δ 8.47 (t, J=6.16 Hz, 1H), 7.88 (d, J=7.71 Hz, 1H), 7.65 (quartet, J=7.24 Hz, 1H), 7.34, (dt, J=10.04, 2.49 Hz, 1H), 7.16 (m, 3H), 6.77 (d, J=7.78 Hz, 1H), 5.38 (s, 2H), 4.32 (d, J=5.93 2H), 2.02 (s, 3H), 1.48 (s, 6H). $^{19}$F-NMR (400 MHz, DMSO-d$_6$) δ−109.26 (quintet, J=9.00 Hz, 1F), 113.52 (quartet, J=9.52 Hz, 1F), −120.62 (d, J=9.09 Hz, 2F). LC/MS t$_r$=5.43 minutes (0–95% acetonitrile/water, 0.05% trifluoroacetic acid, over 6 minutes at 1 ml/min with detection at 215 nm, at 50° C.) ES-MS m/z 541 (M+H). ES-HRMS m/z 541.1128 (M+H calcd for C$_{25}$H$_{22}$ClF$_4$N$_2$O$_5$ requires 541.1148).

Example 351

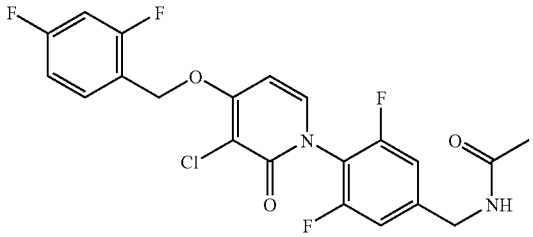

N-{4-[3-chloro-4-[(2,4-difluorobenzyl)oxy]-2-oxopyridin-1(2H)-yl]-3,5-difluorobenzyl}acetamide The compound was prepared in the following the produre for Example 350, substituting acetyl chloride (24 mg, 0.30 mmol) for 2-acetoxy-2-methyl-propionyl chloride. (128 mg, 96%). $^1$H-NMR (400 MHz, DMSO-d$_6$) δ 8.48 (br s, 1H), 7.87 (d, J=7.28 Hz, 1H), 7.64 (quartet, J=8.01 Hz, 1H), 7.33, (dt, J=9.87, 2.25 Hz, 1H), 7.17 (m, 3H), 6.76 (d, J=8.25 Hz, 1H), 5.38 (s, 2H), 4.30 (m, 2H), 1.88 (s, 3H). $^{19}$F-NMR (400 MHz, DMSO-d$_6$) δ−109.22 (quintet, J=8.04 Hz, 1F), −113.52 (quartet, J=9.91 Hz, 1F), −120.43 (d, J=8.77 Hz, 2F). LC/MS t$_r$=5.04 minutes (0–95% acetonitrile/water, 0.05% trifluoroacetic acid, over 6 minutes at 1 ml/min with detection at 215 nm, at 50° C.) ES-MS m/z 555 (M+H). ES-HRMS m/z 455.0824 (M+H calcd for C$_{21}$H$_{16}$ClF$_4$N$_2$O$_3$ requires 455.0780).

Example 352

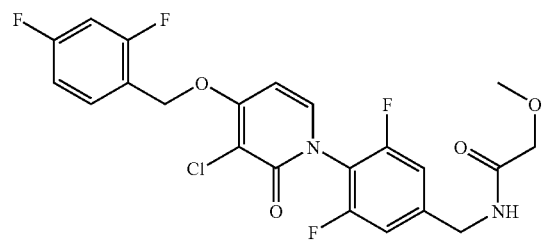

N-{4-[3-chloro-4-[(2,4-difluorobenzyl)oxy]-2-oxopyridin-1(2H)-yl]-3,5-difluorobenzyl}-2-methoxyacetamide The compound was prepared in the following the produre for EXAMPLE 350, substituting 2-methoxy-acetyl chloride (45 mg 0.415 mmol) for 2-acetoxy-2-methyl-propionyl chloride. (124 mg, 78%). $^1$H-NMR (400 MHz, DMSO-d$_6$) δ 8.56 (t, J=6.77 Hz, 1H), 7.90 (d, J=7.85 Hz, 1H), 7.67 (quartet, J=7.67 Hz, 1H), 7.36, (dt, J=10.03, 2.36 Hz, 1H), 7.20 (m, 3H), 6.79 (d, J=8.07 Hz, 1H), 5.40 (s, 2H), 4.37 (d, J=6.28 Hz, 2H), 3.91 (s, 2H), 3.35 (s, 3H). $^{19}$F-NMR (400 MHz, DMSO-d$_6$) δ−109.23 (quintet, J=8.29 Hz, 1F), −113.50 (quartet, J=9.36 Hz, 1F), −120.43 (d, J=9.07 Hz, 2F). LC/MS t$_r$=5.13 miinutes (0–95% acetonitrile/water, 0.05% trifluoroacetic acid, over 6 minutes at 1 ml/min with detection at 215 nm, at 50° C.) ES-MS m/z 485 (M+H). ES-HRMS m/z 485.0856 (M+H calcd for C$_{22}$H$_{18}$ClF$_4$N$_2$O$_4$ requires 485.0886).

Example 353

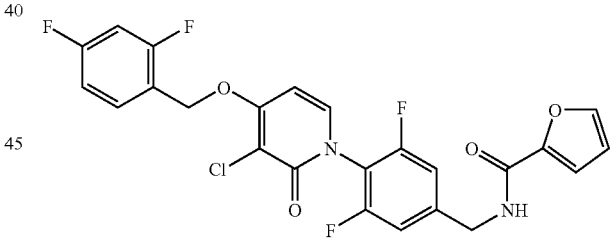

N-{4-[3-chloro-4-[(2,4-difluorobenzyl)oxy]-2-oxopyridin-1(2H)-yl]-3,5-difluorobenzyl}-2-furamide The compound was prepared in the following the produre for EXAMPLE 350, substituting furoyl chloride (62 mg, 0.48 mmol) for 2-acetoxy-2-methyl-propionyl chloride. Yield: 142 mg, 85%. $^1$H-NMR (400 MHz, DMSO-d$_6$) δ 9.07 (t, J=6.14 Hz, 1H), 7.90 (d, J=7.88 Hz, 1H), 7.87 (dd, J=1.69, 0.80 Hz, 1H), 7.67 (td, J=8.46, 6.80 Hz, 1H), 7.35, (dt, J=10.00, 2.81 Hz, 1H), 7.26 (d, J=8.78 Hz, 2H), 7.18 (ddt, J=8.58, 2.30, 1.07 Hz, 1H), 7.16 (dd, J=3.52, 0.77 Hz, 1H), 6.79 (d, J=8.07 Hz, 1H), 6.64 (dd, J=3.16, 1.73 Hz, 1H), 5.40 (s, 2H), 4.49 (d, J=6.13 Hz, 2H). $^{19}$F-NMR (400 MHz, DMSO-d$_6$) δ−109.23 (quintet, J=7.65 Hz, 1F), −113.50 (quartet, J=9.84 Hz, 1F), −120.29 (d, J=9.41 Hz, 2F). LC/MS t$_r$=5.32 minutes (0–95% acetonitrile/water, 0.05%

Example 354

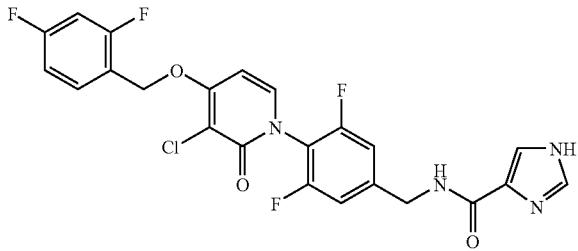

N-{4-[3-chloro-4-[(2,4-difluorobenzyl)oxy]-2-oxopyridin-1(2H)-yl]-3,5-difluorobenzyl}-1H-imidazole-4-carboxamide Step 1: Preparation of the Title Compound 1-[4-(aminomethyl)-2,6-difluorophenyl]-3-chloro-4-[(2,4-difluorobenzyl)oxy]pyridin-2(1H)-one hydrochloride (150 mg, 0.334 mmol) is dissolved in a solution of 4 ml tetrahydrofuran and triethylamine (35 mg, 0.35 mmol). 4-imidazolecarboxylic acid (62 mg, 0.56 mmol), 1-hydroxybenzotriazole hydrate (90 mg, 0.67 mmol), 1-[3-(dimethylamino)propyl]-3-ethylcarbodiimide hydrochloride (128 mg, 0.668 mmol), and triethylamine (100 mg, 0.989 mmol) were combined in 5 ml tetrahydrofuran and stirred under nitrogen. The solution containing 1-[4-(aminomethyl)-2,6-difluorophenyl]-3-chloro-4-[(2,4-difluorobenzyl)oxy]pyridin-2(1H)-one hydrochloride was added in one portion, rinsing with 2 ml tetrahydrofuran. Stirring was continued at room temperature overnight, then the reaction was poured into 90 ml of icewater, and the product collected by filtration and dired in vacuo (254 mg, 94%). $^1$H-NMR (400 MHz, DMSO-$d_6$) δ 12.55 (br s, 1H), 8.73 (t, J=6.57 Hz, 1H), 7.90 (d, J=7.87 Hz, 1H), 7.75 (s, 1H), 7.67 (m, 2H), 7.35, (dt, J=10.04, 2.54 Hz, 1H), 7.21 (m, 3H), 6.78 (d, J=8.04 Hz, 1H), 5.39 (s, 2H), 4.47 (m, 2H), 1$^9$F-NMR (400 MHz, DMSO-$d_6$) δ−109.26 (quintet, J=7.87 Hz, 1F), −113.52 (quartet, J=9.30 Hz, 1F), −120.59 (d, J=9.21 Hz, 2F). LC/MS $t_r$=4.48 minutes (0–95% acetonitrile/water, 0.05% trifluoroacetic acid, over 6 minutes at 1 ml/min with detection at 215 nm, at 50° C.) ES-MS m/z 507 (M+H). ES-HRMS m/z 507.0818 (M+H calcd for $C_{23}H_{16}ClF_4N_4O_3$ requires 507.0842).

Example 355

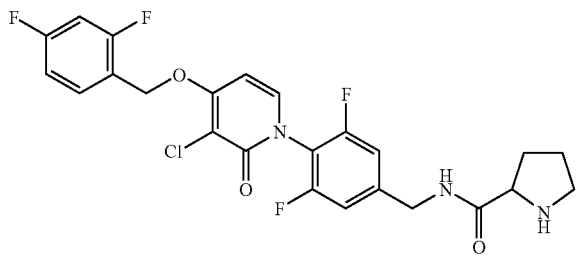

N-{4-[3-chloro-4-[(2,4-difluorobenzyl)oxy]-2-oxopyridin-1(2H)-yl]-3,5-difluorobenzyl}-5-oxoprolinamide Step 1: Preparation of the Title Compound The compound was prepared following the procedure for Example 354, substituting 2-pyrrolidone-5-carboxylic acid for 4-imidazolecarboxylic acid. $^1$H-NMR (400 MHz, DMSO-$d_6$) δ 8.67 (t, J=6.08 Hz, 1H), 7.88 (m, 1H), 7.65 (qr, J=7.57, 1H), 7.34, (dt, J=9.32, 2.63 Hz, 1H), 7.22 (d, J=9.36, 2H), 7.17 (dt, J=8.51, 2.55 Hz, 1H), 6.77 (d, J=7.66 Hz, 1H), 5.73 (s, 1H), 5.38 (s, 2H), 4.35 (d, J=5.74, 2H), 4.05 (m, 1H), 2.15 (m, 2H), 1.90 (m, 2H). $^{19}$F-NMR (400 MHz, DMSO-$d_6$) δ−109.25 (quintet, J=7.72 Hz, 1F), −113.52 (quartet, J=8.94 Hz, 1F), −120.39 (d, J=9.11 Hz, 2F). LC/MS $t_r$=4.81 minutes (0–95% acetonitrile/water, 0.05% trifluoroacetic acid, over 6 minutes at 1 ml/min with detection at 215 nm, at 50° C.) ES-MS m/z 524 (M+H). ES-HRMS m/z 524.0998 (M+H calcd for $C_{24}H_{19}ClF_4N_3O_4$ requires 524.0995).

Example 356

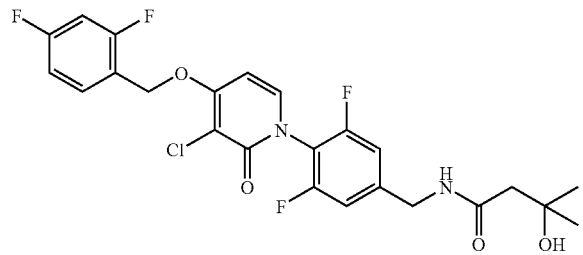

N-{4-[3-chloro-4-[(2,4-difluorobenzyl)oxy]-2-oxopyridin-1(2H)-yl]-3,5-difluorobenzyl}-3-hydroxy-3-methylbutanamide Step 1: Preparation of the Title Compound The compound was prepared following the procedure for substituting 2-hydroxy-2-methyl butyric acid for 4-imidazolecarboxylic acid. $^1$H-NMR (400 MHz, DMSO-$d_6$) δ 8.43 (t, J=6.04 Hz, 1H), 7.88 (d, J=8.01, 1H), 7.65 (qr, J=6.84, 1H), 7.34, (dt, J=10.13, 2.55 Hz, 1H), 7.22 (d, J=8.74, 2H), 7.16 (dt, J=8.57, 2.45 Hz, 1H), 6.77 (d, J=7.89 Hz, 1H), 5.38 (s, 2H), 4.75 (s, 0.5H(OH)), 4.35 (d, J=6.48, 2H), 2.28 (s, 2H), 1.47 (s, 0.5H(OH)), 1.16 (s, 6H). $^{19}$F-NMR (400 MHz, DMSO-$d_6$) δ−109.26 (quintet, J=7.79 Hz, 1F), −113.53 (quartet, J=9.23 Hz, 1F), −120.49 (d, J=9.39 Hz, 2F). LC/MS $t_r$=5.08 minutes (0–95% acetonitrile/water, 0.05% trifluoroacetic acid, over 6 minutes at 1 ml/min with detection at 215 nm, at 50° C.) ES-MS m/z 513 (M+H). ES-HRMS m/z 513.1177 (M+H calcd for $C_{24}H_{22}ClF_4N_2O_4$ requires 513.1199).

Example 357

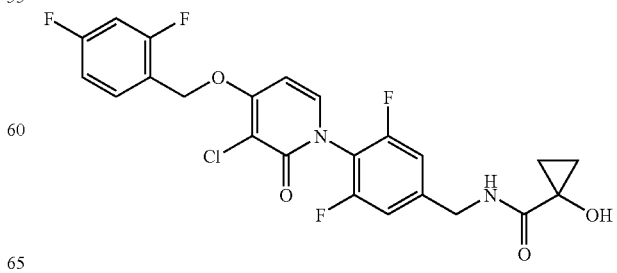

N-{4-[3-chloro-4-[(2,4-difluorobenzyl)oxy]-2-oxopyridin-1(2H)-yl]-3,5-difluorobenzyl}-1-hydroxycyclopropanecarboxamide Step 1: Preparation of the Title Compound The compound was prepared following the procedure for substituting 1-hydroxy-1-cyclopropanecarboxylic acid for 4-imidazolecarboxylic acid. $^1$H-NMR (400 MHz, DMSO-$d_6$) δ 8.70 (t, J=6.26 Hz, 1H), 7.89 (d, J=6.31, 1H), 7.65 (qr, J=6.83, 1H), 7.34 (t, J=10.58 Hz, 1H), 7.19 (m, 3H), 6.77 (d, J=7.70 Hz, 1H), 5.38 (s, 2H), 4.35 (d, J=5.66, 2H), 1.14 (s, 1H), 1.02 (m, 2H), 0.84 (m, 2H). $^{19}$F-NMR (400 MHz, DMSO-$d_6$) δ−109.25 (quintet, J=8.05 Hz, 1F), −113.53 (quartet, J=8.27 Hz, 1F), −120.59 (d, J=8.99 Hz, 2F). LC/MS $t_r$=5.01 minutes (0–95% acetonitrile/water, 0.05% trifluoroacetic acid, over 6 minutes at 1 ml/min with detection at 215 nm, at 50° C.) ES-MS m/z 497 (M+H). ES-HRMS m/z 497.0873 (M+H calcd for $C_{23}H_{18}ClF_4N_2O_4$ requires 497.0886).

Example 358

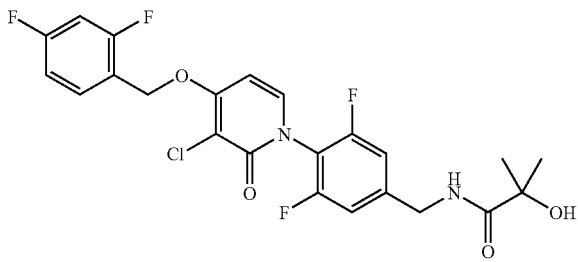

N-{4-[3-chloro-4-[(2,4-difluorobenzyl)oxy]-2-oxopyridin-1(2H)-yl]-3,5-difluorobenzyl}-2-hydroxy-2-methylpropanamide Step 1: Preparation of the Title Compound The compound was prepared following the procedure for substituting 2-hydroxyisobutyric acid for 4-imidazolecarboxylic acid. $^1$H-NMR (400 MHz, DMSO-$d_6$) δ 8.48 (t, J=6.41 Hz, 1H), 7.89 (d, J=7.78, 1H), 7.65 (qr, J=9.10, 1H), 7.33 (dt, J=10.12, 2.41 Hz, 1H), 7.17 (m, 3H), 6.77 (d, J=7.69 Hz, 1H), 5.38 (s, 2H), 4.31 (d, J=6.50, 2H), 1.41 (s, 1H), 1.33 (s, 6H). $^{19}$F-NMR (400 MHz, DMSO-$d_6$) δ−109.25 (quintet, J=7.49 Hz, 1F), −113.53 (quartet, J=9.64 Hz, 1F), −120.59 (d, J=8.68 Hz, 2F). LC/MS $t_r$=5.05 minutes (0–95% acetonitrile/water, 0.05% trifluoroacetic acid, over 6 minutes at 1 ml/min with detection at 215 nm, at 50° C.) ES-MS m/z 499 (M+H). ES-HRMS m/z 499.1020 (M+H calcd for $C_{23}H_{20}ClF_4N_2O_4$ requires 499.1042).

Example 359

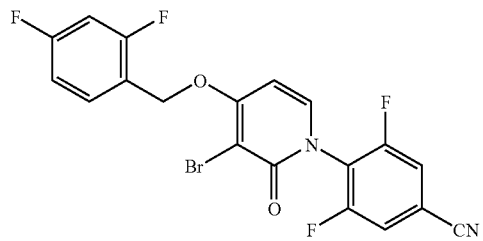

4-[3-bromo-4-[(2,4-difluorobenzyl)oxy]-2-oxopyridin-1(2H)-yl]-3,5-difluorobenzonitrile Step 1: Preparation of 3-bromo-4-[(2,4-difluorobenzyl)oxy]pyridin-2(1H)-one.

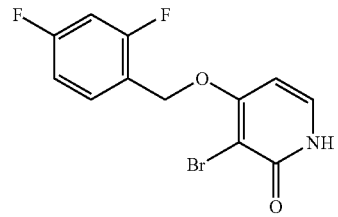

The compound was prepared in the following the produre for 3-chloro-4-[(2,4-difluorobenzyl)oxy]pyridin-2(1H)-one (, Step 3), substituting N-bromosuccinimide for N-chlorosuccinimide. $^1$H-NMR (400 MHz, DMSO-$d_6$) δ 11.85 (br s, 1H), 7.61 (m, 1H), 7.46 (d, J=7.36 Hz, 1H), 7.30, (m, 1H), 7.14 (m, 1H), 6.40 (d, J=7.71 Hz, 1H), 5.26 (s, 2H). $^{19}$F-NMR (400 MHz, DMSO-$d_6$) δ−109.69 (quintet, J=7.93 Hz, 1F), −113.63 (quartet, J=9.55 Hz, 1F). LC/MS $t_r$=4.48 minutes (0–95% acetonitrile/water, 0.05% trifluoroacetic acid, over 6 minutes at 1 ml/min with detection at 215 nm, at 50° C.) ES-MS m/z 316 (M+H).

Step 2: Preparation of the Title Compound.

The compound was prepared following the procedure for 4-[3-chloro-4-[(2,4-difluorobenzyl)oxy]-2-oxopyridin-1(2H)-yl]-3,5-difluorobenzonitrile (, Step 4), substituting 3-bromo-4-[(2,4-difluorobenzyl)oxy]pyridin-2(1H)-one (from step 1) (1.92 g, 6.06 mmol) for 3-chloro-4-[(2,4-difluorobenzyl)oxy]pyridin-2(1H)-one (, from Step 3). $^1$H-NMR (400 MHz, DMSO-$d_6$) δ 8.13 d, J=7.24 Hz, 2H), 7.95 (d, J=7.76 Hz, 1H), 7.66 (quartet, J=8.71 Hz, 1H), 7.34, (dt, J=9.94, 2.53 Hz, 1H), 7.17 (dt, J=8.64, 2.33 Hz, 1H), 6.82 (d, J=7.77 Hz, 1H), 5.39 (s, 2H). $^{19}$F-NMR (400 MHz, DMSO-$d_6$) δ−109.28 (quintet, J=7.98 Hz, 1F), −113.45 (quartet, J=9.29 Hz, 1F), −116.30 (d, J=7.44 Hz, 2F). LC/MS $t_r$=5.48 minutes (0–95% acetonitrile/water, 0.05% trifluoroacetic acid, over 6 minutes at 1 ml/min with detection at 215 nm, at 50° C.) ES-MS m/z 453 (M+H). ES-HRMS m/z 452.9836 (M+H calcd for $C_{19}H_{10}BrF_4N_2O_2$ requires 452.9856).

Example 360

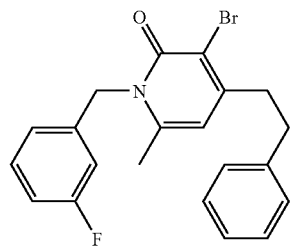

3-Bromo-1-(3-fluorobenzyl)-6-methyl-4-(2-phenylethyl)pyridin-2(1H)-one

Step 1: Preparation of 1-(3-fluorobenzyl)-4-hydroxy-6-methylpyridin-2(1H)-one

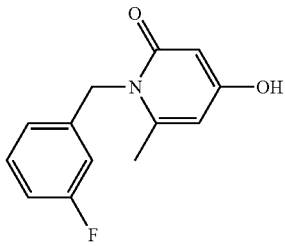

A mixture of 4-hydroxy-6-methyl-2-pyrone (2.5 g, 0.02 mol) and 3-fluorobenzylamine (2.5 g, 0.02 mol) in n-butanol (15.0 mL) was heated to reflux for 16 h under argon atmosphere. Butanol wad distilled in vacuo, the residue was triturated with EtOAc, cooled and filterd the precipitate. It was washed with cold EtOAc, and dried to give 0.86 g of the title compound as a pale yellow powder: 1H-NMR (CD$_3$OD/400 MHz) δ 7.31 (m, 1H), 7.0–6.85 (m, 2H), 6.83 (d, 1H, J=9.6 Hz), 5.96 (d, 1H, j=2.0 Hz), 5.80 (d, 1H, J=2.0 Hz), 5.30 (s, 2H), and 2,24 (s, 3H); ES MS m/z 234 (MH+).

Step 2: Preparation of 3-bromo-1-(3-fluorobenzyl)-4-hydroxy-6-methylpyridin-2(1H)-one

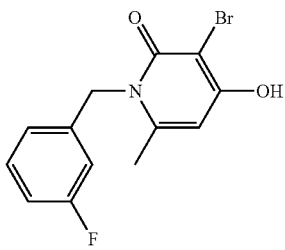

A mixture of 1-(3-fluorobenzyl)-4-hydroxy-6-methylpyridin-2(1H)-one (0.8 g, 0.0034 mol), NBS (0.64 g, 0.0036 mol) in dichloromethane (15.0 mL) was stirred at room temperature, under argon atmosphere. After 1.5 h, the reaction mixture was diluted with dichloromethane (15.0 mL), cooled and filterd the solids. The residue was washed with dichloromethane and dried in vacuo to give 0.93 g of the title compound as a white powder: 1H-NMR (CD$_3$OD/400 MHz) δ 7.33 (m, 1H), 7.2–6.8 (m, 3H), 6.07 (s, 1H), 5.34 (s, 2H), 2.26 (s, 3H); ES HRMS m/z 312.0016 (M+H C13H12NO2BrF requires 312.0035).

Step 3: Preparation of 3-bromo-1-(3-fluorobenzyl)-6-methyl-2-oxo-1,2-dihydropyridin-4-yl trifluoromethanesulfonate

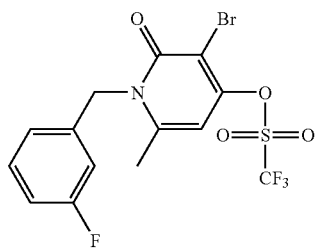

To a suspension of 3-bromo-1-(3-fluorobenzyl)-4-hydroxy-6-methylpyridin-2(1H)-one (0.86 g, 0.0028 mol) in dichloromethane (15.0 mL) cooled to −30° C., triethyl amine (0.5 mL, 0.004 mol) and trflic anhydride (0.7 mL, 0.0042 mol) were added and stirred for 1 h. The resulting orange solution was poured into ice cold water (25 mL) and extracted with dichloromethane (2×25 mL) The combined organic extracts were washed with water, dried (Na2SO4) and concentrated under reduced pressure. The resulting residue was purified by silica gel flash chromatography using 1:1 EtOAc/hexane v/v to afford 1.0 g (85%) the title compound as a light brown solid: 1H-NMR (CDCl$_3$/400 MHz) δ 7.32 (m, 1H), 7.0–6.85 (m, 3H), 6.18 (s, 1H), 5.32 (s, 2H), and 2.34 (s, 3H); ES HRMS m/z 443.9492 (M+H C14H11NO4BrF4S requires 443.9528).

Step 4: Preparation of 3-bromo-1-(3-fluorobenzyl)-6-methyl-4-(phenylethynyl)pyridin-2(1H)-one

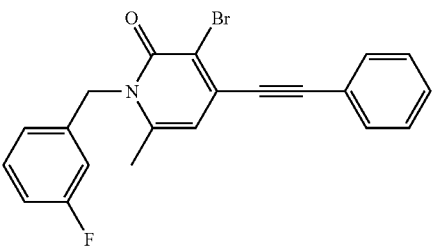

A solution of 3-bromo-1-(3-fluorobenzyl)-6-methyl-2-oxo-1,2-dihydropyridin-4-yl trifluoromethanesulfonate (1.0 g, 0.0022 mol) and phenylacetylene (0.3 mL, 0.0029 mol) in DMF (5.0 mL) was degassed using house vacuum, and purged with argon (3 cycles).

Then added diisopropylethylamine, (0.5 mL) followed by the addition of PdCl2(PPh3 (2 (0.36 g). The reaction mixture was heated at 65° C. for 1.5 h under argon atmosphere. The solvents were distilled in vacuo, and the residue was purified by silica gel flash chromatography using EtOAc/hexane (2:3 v/v) to afford 0.65 g (70%) of the title compound as a brown colored amorphous solid: 1H-NMR (CD$_3$OD/400 MHz) δ 7.59 (m, 2H), 7.45–7.3 (m, 4H), 7.05–6.85 (m, 3H), 6.44 (s, 1H), 5.41 (s, 2H), and 2.31 (s, 3H); 19F-NMR (CD$_3$OD/400 MHz) δ−116.33 (m); ES HRMS m/z 396.0373 (M+H C21H16NOBrF 396.0399).

Step 5: Preparation of 3-bromo-1-(3-fluorobenzyl)-6-methyl-4-(2-phenylethyl)pyridin-2(1H)-one To a solution of 3-bromo-1-(3-fluorobenzyl)-6-methyl-4-(phenylethynyl)pyridin-2(1H)-one (0.55 g, 0.0014 mol) in EtOAc (10.0 mL) and EtOH (10.0 mL) was added PtO2 (0.05 g) and stirred in an atmosphere of hydrogen gas at 15 psi for 30 min. The catalyst was removed by filtration, the filtrate was concentrated and the residue was purified by silica gel flash chromatography using 25% EtOAc in hexane as the eluent.

The appropriate fractions were combined (visualized under UV) and concentrated to dryness. 1H-NMR (CD$_3$OD/400 MHz) δ 7.35 (m, 1H), 7.31–7.16 (m, 5H), 6.99 (m, 1H), 6.91 (m, 1H), 6.81 (m, 1H), 6.20 (s, 1H), 5.41 (s, 2H), 2.94 (m, 4H), and. 2.24 (s, 3H); 19F-NMR (CD$_3$OD/400 MHz) δ−115.01 (m); ES HRMS m/z 400.0695 (M+H C21H20NOBrF 400.0712).

Example 361

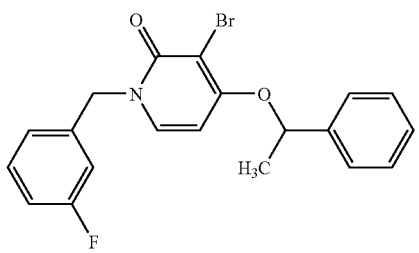

3-bromo-1-(3-fluorobenzyl)-4-(1-phenylethoxy) pyridin-2(1H)-one

A mixture of 3-bromo-1-(3-fluorobenzyl)-4-hydroxypyridin-2(1H)-one (0.2 g, 0.72 mmol), potassium carbonate (0.1 g, 0.72 mmol) and (1-bromoethyl)benzene (0.19 g, 1 mmol) in DMF (3.0 mL) was stirred at room temperature for 16 h. DMF was distilled in vacuo, and the residue was purified by flash chromatography (EtOAc in hexane (1:3 v/v) to give pale yellow syrup. This material was further purified by reverse-phase HPLC using 10–90% acetonitrile/water gradient (30 min), at flow rate of 100 mL/min. The appropriate fractions were combined, concentrated to a small volume (20 mL), added EtOAc (25 mL) and washed successively with satd. sod. bicarbonate, water, and dried ($Na_2SO_4$). EtOAc was removed under reduced pressure and residue was dried in vacuo to afford the title compound (0.15 g, 52%) as an amorphous substance: $^1$H NMR ($CD_3OD$/400 MHz) δ 7.56 (d, 1H, J=7.6 Hz), 7.4–7.2 (m, 5H), 7.0 (m, 3H), 6.28 (d, 1H, J=7.6 Hz), 5.65 (m, 1H), 5.19 (dxd, 2H, J=14.8 Hz), and 1.64 (d, 3H, J=6.4 Hz), ES-HRMS m/z 402.0492(M+H $C_{20}H_{18}NO_2Br$, requires 402.0499).

Example 362

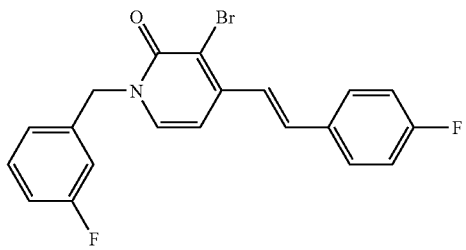

3-bromo-1-(3-fluorobenzyl)-4-[(E)-2-(4-fluorophenyl)ethenyl]pyridin-2(1H)-one

A mixture of 3-bromo-1-(3-fluorobenzyl)-2-oxo-1,2-dihydropyridin-4-yl trifluoromethanesulfonate (1.0 g, 0.0023 mol), and 4-fluorostyrene (0.33 mL, 0.0028 mol) in degassed DMF (100 ml) containing diisopropyl ethyl amine (0.37 g, 0.0029 mol) was treated with $PdCl_2(PPh_3)_2$ (0.32 g, 0.46 mmol) and heated at 65° C. under argon atmosphere for 16 h. DMF was distilled in vacuo, and the residue was purified by flash chromatography (EtOAc/hexane 1:4 v/v) to afford a yellow substance which was further purified by by reverse-phase HPLC using 10–90% acetonitrile/water gradient (30 min), at flow rate of 100 mL/min. The appropriate fractions were combined, concentrated to a small volume (20 mL), added EtOAc (25 mL) and washed successively with satd. sod. bicarbonate, water, and dried ($Na_2SO_4$). EtOAc was removed under reduced pressure and residue was dried in vacuo to afford the title compound (0.06 g, 6%) as yellow powder: $^1$H NMR ($CD_3OD$/400 MHz) δ 7.68 (m, 3H), 7.39 (m, 3H), 7.2–7.0 (m, 5H), 6.82 (d, 1H, J=7.2 Hz), and 5.22 (s, 2H); $^{19}$F NMR ($CD_3OD$/400 MHz) δ–113.9 (m) and −115 (m); ES-HRMS m/z 402.0305 (M+H $C_{20}H_{15}NOF_2Br$, requires 402.0300).

Example 363

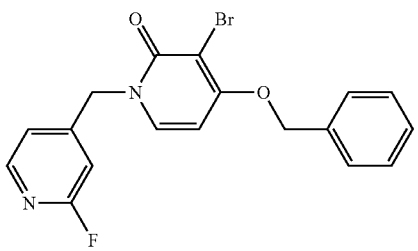

4-(Benzyloxy)-3-bromo-1-[(6-fluoropyridin-3-yl) methyl]pyridin-2(1H)-one

A mixture of 4-(benzyloxy)-3-bromopyridin-2(1H)-one (0.2 g, 0.00076 mol), 5-bromomethyl-2-fluoropyridine (0.25 g, 0.0013 mol) and pot. Carbonate (0.15 g, 0.0011 mol) in DMF (3.0 ml) was stirred at room temperature for 16 h under argon atmosphere. DMF was distilled in vacuo and the residue was partitioned between water (15 ml) and EtOAc (25 mL). The organic phase was washed with water, dried ($Na_2SO_4$) and concentrated under reduced pressure. $^1$H NMR ($CD_3OD$/400 MHz) δ 8.22 (m, 1H, 2.4 Hz), 7.92 (m, 1H), 7.82 (d, 1H, J=7.6 Hz), 7.44–7.31 (m 5H), 7.03 (m, 1H), 6.49 (d, 1H, J=7.6 Hz), 5.29 (s, 2H), and 5.20 (s, 2H); $^{19}$F NMR ($CD_3OD$/400 MHz) δ–72.30 (d, J=6.0 Hz) and −115 (m); ES-HRMS m/z 389.0295 (M+H $C_{18}H_{15}N_2O_2FBr$, requires 389.0309).

Example 364

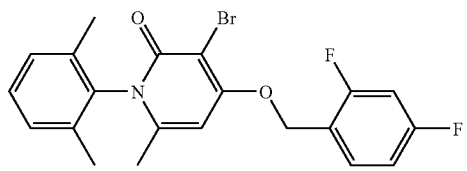

3-Bromo-4-[(2,4-difluorobenzyl)oxy]-1-(2,6-dimethylphenyl)-6-methylpyridin-2(1H)-one

STEP 1

Preparation of

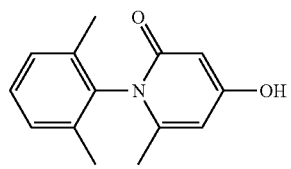

1-(2,6-dimethylphenyl)-4-hydroxy-6-methylpyridin-2(1H)-one

A mixture of 4-hydroxy-6-methyl-2-pyrone (2.5 g, 0.02 mol), 2,6 dimethylaniline (2.4 g, 0.02 mol), and p-toluenesulfonic acid (0.2 g) as heated at 140° C. for 3 h under nitrogen atmosphere. The reaction mixture was cooled, triturated with acetonitrile, cooled and filtered the solids. $^1$H NMR (CD$_3$OD/400 MHz) δ 7.22 (m, 3H), 6.12 (d, 1H, J=1.6 Hz), 5.83 (d, 1H, J=1.8 Hz), 2.00 (s, 6H), and 1.82 (s, 3H); ES MS m/z 229 (M+H).

Step 2

Preparation of

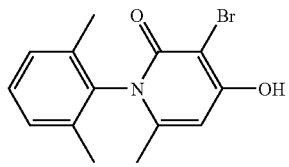

3-Bromo-1-(2,6-dimethylphenyl)-4-hydroxy-6-methylpyridin-2(1H)-one

A mixture of 1-(2,6-dimethylphenyl)-4-hydroxy-6-methylpyridin-2(1H)-one (0.4 g, 0.00175 mol), and NBS (0.35 g, 0.0019 mol) in dichloromethane (10.0 ml) was stirred at room temperature under nitrogen atmosphere. After 1 h, the solids were filtered, washed with dicholoromethane to give 0.42 g (78%) of the title compd as a pale yellow powder: $^1$H NMR (CD$_3$OD/400 MHz) δ 7.22 (m, 3H), 6.21 (s, 1H), 1.99 (s, 6H), and 1.82 (s, 3H); ES MS m/z 308/310 (M+H).

Step 3

A mixture of 3-Bromo-1-(2,6-dimethylphenyl)-4-hydroxy-6-methylpyridin-2(1H)-one (0.15 g, 0.00049 mol), 2,4 difluorobenzyl bromide (0.12 g, 0.00058 mol) and potassium carbonate (0.075 g, 0.00054 mol) in DMF 3.00 mL) was stirred at room temperature uder argon atmosphere for 2 h. It was then heated at 60° C. for 30 min and concentrated in vacuo. The residue was purified by flash chromatography. $^1$H NMR (CD$_3$OD/400 MHz) δ 7.62 (m, 1H), 7.28 (m, 3H), 7.04 (m, 2H), 6.68 (s, 1H), 5.35 (m, 1H), 1.98 (s, 6H), and 1.92 (s, 3H); ES-HRMS m/z 434.0574 (M+H C$_{21}$H$_{19}$NO$_2$F$_2$Br, requires 434.0562).

Example 365

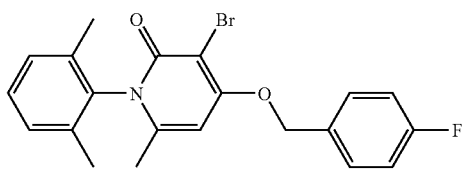

3-Bromo-1-(2,6-dimethylphenyl)-4-[(4-fluorobenzyl)oxy]-6-methylpyridin-2(1H)-one The title compound was prepared by a procedure similar to the one described for Example 364. $^1$H NMR (CD$_3$OD/400 MHz) δ 7.58 (m, 2H), 7.23 (m, 3H), 7.15 (m, 2H), 6.62 (s, 1H), 5.32 (s, 2H), 1.98 (m, 6H), and 1.91 (s, 3H); ES-HRMS m/z 416.0670. (M+H C$_{21}$H$_{20}$NO$_2$FBr, requires 416.0656).

Example 366

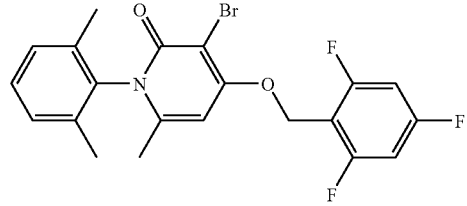

3-Bromo-1-(2,6-dimethylphenyl)-6-methyl-4-[(2,4,6-trifluorobenzyl)oxy]pyridin-2(1H)-one The title compound was prepared by a procedure similar to the one described for EXAMPLE 364. $^1$H NMR (CD$_3$OD/400 MHz) δ 7.19 (m, 3H), 6.95 (m, 2H), 6.69 (s, 1H), 5.29 (s, 2H), 1.95 (s, 6H), and 1.90 (s, 3H); ES-HRMS m/z 452.0471. (M+H C$_{21}$H$_{18}$NO$_2$F$_3$Br, requires 452.0468).

Example 367

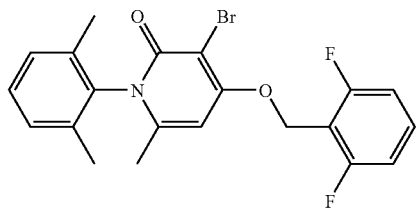

3-Bromo-4-[(2,6-difluorobenzyl)oxy]-1-(2,6-dimethylphenyl)-6-methylpyridin-2(1H)-one The title compound was prepared by a procedure similar to the one described for EXAMPLE 364. $^1$H NMR (CD$_3$OD/400 MHz) δ 7.46 (m, 1H), 7.24 (m, 3H), 7.08 (m, 2H), 6.74 (s, 1H), 5.38 (s, 2H), 1.99 (s, 6H), and 1.94 (s, 3H); ES-HRMS m/z 434.0589 (M+H C$_{21}$H$_{19}$NO$_2$F$_2$Br, requires 434.0562).

Example 368

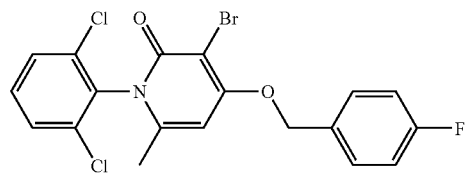

3-Bromo-1-(2,6-dichlorophenyl)-4-[(4-fluorobenzyl)oxy]-6-methylpyridin-2(1H)-one Step 1

Preparation of 1-(2,6-dichlorophenyl)-4-hydroxy-6-methylpyridin-2(1H)-one

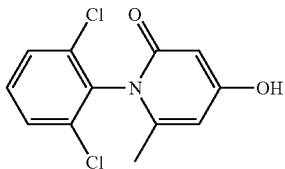

This compound was prepared by a procedure similar to the one described in step 1 for EXAMPLE 364. Yield: 28%, $^1$H NMR (CD3OD) δ 7.6 (m, 2H), 7.48 (m, 1H), 6.10 (dd, 1H), 5.78 (d, 1H, J=2.4 Hz), 1.91 (s, 3H); (ES-MS m/z=270 (MH$^+$);

Step 2

Preparation of 3-bromo-1-(2,6-dichlorophenyl)-4-hydroxy-6-methylpyridin-2(1H)-one

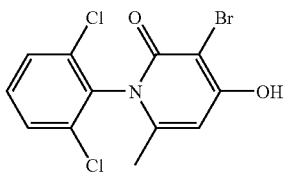

This compound was prepared by a procedure similar to the one described in step 2 for EXAMPLE 364. Yield: 78%, $^1$H NMR (400 MHz)CD$_3$OD δ 7.61 (m, 2H), 7.49 (m, 1H), 6.2 (s, 1H), and 1.91 (s, 3H); ES-MS, m/z=348 (MH$^+$).

Step 3

This compound was prepared by a procedure similar to the one described in step 3 for EXAMPLE 364. Yield: 44%, $^1$H NMR (CD$_3$OD) δ 7.62 (d, 2H,J=8.0 Hz), 7.51 (m, 3H), 7.15 (m, 2H), 6.64 (s, 1H), 5.33 (s, 2H), and 2.0 (s, 3H); $^{19}$F NMR (CD$_3$OD) δ−166.21 (m); ES-HRMS m/z 455.9541 (M+H C$_{19}$H$_{14}$NO$_2$Cl$_2$BrF, requires 455.9564).

Example 369

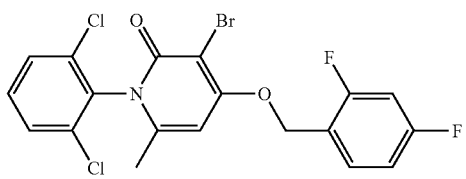

3-Bromo-1-(2,6-dichlorophenyl)-4-[(2,4-difluorobenzyl)oxy]-6-methylpyridin-2(1H)-one This compound was prepared by a procedure similar to the one described for EXAMPLE 368.

Yield: 64%, $^1$H NMR (CD$_3$OD/400 MHz 67.62 (m, 3H), 7.48 (m, 1H), 7.05 (m, 2H), 6.70 (s, 1H), 5.36 (s, 2H), and 2.02 (s, 3H), $^{19}$F NMR (CD$_3$OD) δ−111.43 (m) and −115.89 (m); ES-HRMS m/z 473.9450 (M+H C$_{19}$H$_{13}$NO$_2$Cl$_2$BrF$_2$, requires 473.9469).

Example 370

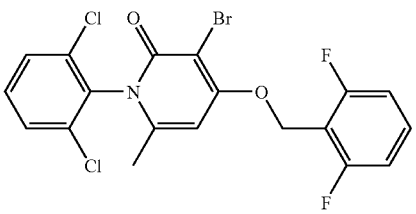

3-Bromo-1-(2,6-dichlorophenyl)-4-[(2,6-difluorobenzyl)oxy]-6-methylpyridin-2(1H)-one This compound was prepared by a procedure similar to the one described for EXAMPLE 368. Yield: 78%, $^1$H NMR (CD$_3$OD/400 MHz) δ 7.62 (d, 2H,J=8.0 Hz), 7.52 (m, 2H), 7.1 (m, 2H), 6.77 (s, 1H) and 2.04 (s, 3H); $^{19}$F NMR (CD$_3$OD) δ−117.04 (m); ES-HRMS m/z 473.9468 (M+H C$_{19}$H$_{13}$NO$_2$Cl$_2$BrF$_2$, requires 473.9469).

Example 371

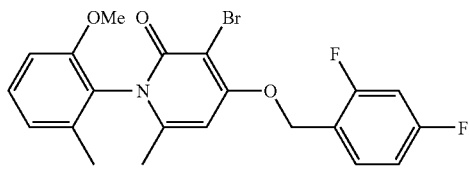

3-Bromo-4-[(2,4-difluorobenzyl)oxy]-1-(2-methoxy-6-methylphenyl)-6-methylpyridin-2(1H)-one Step 1

Preparation of 4-hydroxy-1-(2-methoxy-6-methylphenyl)-6-methylpyridin-2(1H)-one

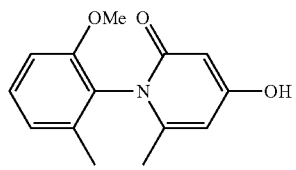

This compound was prepared by a procedure similar to the one described in step 1 for EXAMPLE 368. Yield: 21%, $^1$H NMR (CD$_3$OD/400 MHz) δ 7.31 (m, 1H), 6.94 (m, 2H), 6.05 (d, 1H, J=2.4 Hz), 5.78 (d, 1H, J=2.4 Hz), 3.76 (s, 3H), 2.00 (s, 3H), and 1.83 (s, 3H); ES-HRMS m/z 246.1092 (M+H C$_{14}$H$_{16}$NO$_3$, requires 246.1123).

Step 2

Preparation of 3-bromo-4-hydroxy-1-(2-methoxy-6-methylphenyl)-6-methylpyridin-2(1H)-one

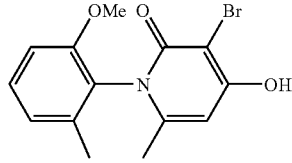

This compound was prepared by a procedure similar to the one described in step 2 for EXAMPLE 368. Yield: 58%, $^1$H NMR (CD$_3$OD/400 MHz) δ 7.34 (m, 1H), 6.96 m (2H), 6.15 (s, 1H), 3.76 (s, 3H), 1.99 (s, 3H), and 1.83 (s, 3H); ES MS m/z 324 (M+H).

Step 3

This compound was prepared by a procedure similar to the one described for EXAMPLE 368. Yield: 60%, $^1$H NMR (CD$_3$OD/400 MHz) δ 7.63 (m, 1H), 7.36 (m, 1H), 7.01 (m, 4H), 6.61 (s, 1H), 5.33 (s, 2H), 3.76 (s, 3H), 1.99 (s, 3H), and 1.95 (s, 3H); $^{19}$F NMR (CD$_3$OD/400 MHz) δ−111.64 (m), and −116.03 (m); ES-HRMS m/z 450.0532 (M+H C$_{21}$H$_{19}$NO$_3$Cl$_2$BrF$_2$, requires 450.0511).

Example 372

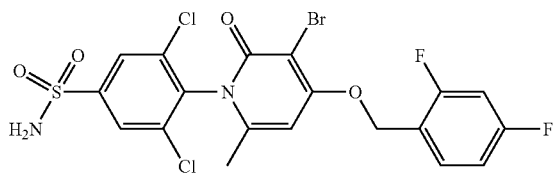

4-[3-bromo-4-[(2,4-difluorobenzyl)oxy]-6-methyl-2-oxopyridin-1(2H)-yl]-3,5-dichlorobenzenesulfonamide Step 1

Preparation of 3,5-dichloro-4-(4-hydroxy-6-methyl-2-oxopyridin-1(2H)-yl)benzenesulfonamide

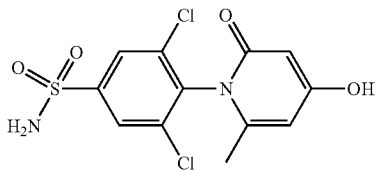

A mixture of 4-hydroxy-6-methylpyrone ((1.2 g, 0.0095 mol), and 2,6-dichlorosulphanilamide (2.4 g, 0.0099 mol) was heated at 170° C. under argon for 20 min. The resulting dark colored melt was cooled and the crude material was first purified by flash chromatography (EtOAc) to give partially purified material which contained the desired product. This was further purified by reverse-phase HPLC using 10–90% CH$_3$CN/Water (30 min gradient) at a flow rate of 100 mL/min. The appropriate fractions (m/z=349)were combined and freeze dried to afford 0.19 g of 3,5-dichloro-4-(4-hydroxy-6-methyl-2-oxopyridin-1(2H)-yl) benzenesulfonamide as pale yellow solid: $^1$H NMR (CD$_3$OD/400 MHz) δ 8.06 (s, 2H), 6.13 (d, 1H, J=1.6 Hz), 5.78 (d, 1H, J=1.6 Hz), and 1.94 (s, 3H)); ES-HRMS m/z 348.9819 (M+H C$_{12}$H$_{11}$N$_2$O$_4$SCl$_2$ requires 348.9811e).

Step 2

A mixture of 3,5-dichloro-4-(4-hydroxy-6-methyl-2-oxopyridin-1(2H)-yl)benzenesulfonamide (0.18 g, 0.0005 mol), N-bromosuccinimide (0.1 g, 0.00056 mol)in acetici acid (2.0 mL) was stirred at room temperature under argon atmosphere for 1 h. Acetic acid was removed in vacuo, the residue was dissolved in DMF (2.0 mL), and added 2,4 difluorobenzyl bromide (0.128 g, 0.0006 mol), potassium carbonate (0.1 g, 0.0007 mol). The resulting mixture was stirred at room temperature for 1 h. The solvents were distilled in vacuo, and the residue was purified by flash chromatography (EtOAc/hexane 1:3 v/v) to give 0.14 g of partially purified product. This was further purified by reverse-phase HPLC using 10–90% CH$_3$CN/Water (30 min gradient) at a flow rate of 100 mL/min. The appropriate fractions (m/z=553) were combined and freeze dried to afford 0.045 g of pale yellow powder. This was partitioned between EtOAc (25 ml) and 5% sod. bicarbonate. The organic phase was washed with water, dried (Na$_2$SO$_4$) and concentrated under reduced pressure. This material was dried invacuo to afford the title compound (0.033 g) as a white amorphous substance:

$^1$H NMR (CDCl$_3$/400 MHz) δ 7.99 (s, 2H), 7.59 (m, 1H), 6.98 (m, 1H), 6.85 (m, 1H), 6.23 (s, 1H), 5.69 (s, 2H), 5.28 (s, 2H), 1.97 (s, 3H), and 1,76 (br, 2H); ES-HRMS m/z 552.7214 (M+H C$_{19}$H$_{14}$BrCl$_2$N$_2$O$_4$S requires 552.9197).

Example 373

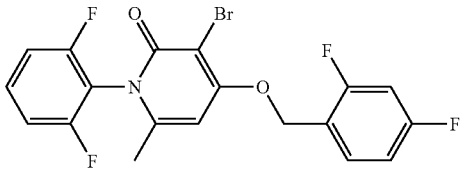

3-Bromo-4-[(2,4-difluorobenzyl)oxy]-1-(2,6-difluorophenyl)-6-methylpyridin-2(1H)-one Step 1

Preparation of 1-(2,6-difluorophenyl)-4-hydroxy-6-methylpyridin-2(1H)-one

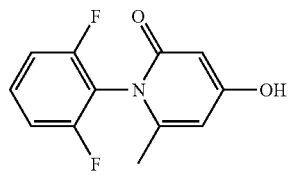

A mixture of 4-hydroxy-6-methyl-2-pyrone (10.0 g, 0.079 mol) and 2,6 difluoroaniline (9.5 g, 0.073 mol) was heated at 170° C. under argon atmosphere for 20 min. The water formed was removed using a Dean-stark apparatus. The melt was cooled, the dark solid was tritutrated with EtOAc., and filtered. This material was washed thoroughly with EtOAc to afford the desired product 1-(2,6-difluorophenyl)-4-hydroxy-6-methylpyridin-2(1H)-one 6.5 g (35%) as a light brown solid: $^1$H NMR (CD$_3$OD/400 MHz) δ 7.56 (m, 1H), 7.19 (m, 2H), 6.09 (m, 1H), 5.77 (d, 1H, J=2.4 Hz), and 1.99 (s, 3H); ES-HRMS m/z 238.0679 (M+H C$_{12}$H$_{10}$NO$_2$F$_2$ requires 238.0674).

Step 2

Preparation of 3-bromo-1-(2,6-difluorophenyl)-4-hydroxy-6-methylpyridin-2(1H)-one

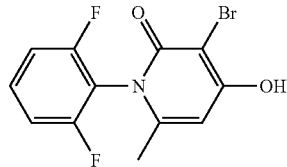

The title compound was prepared by a procedure described in step2 for EXAMPLE 364.

Yield: 79%, $^1$H NMR (CD$_3$OD/400 MHz) δ 7.58 (m, 1H), 7.21 (m, 2H), 6.19 (d, 1H, J=0.8 Hz), 1.99 (s, 3H); ES-HRMS m/z 315.9811 (M+H C$_{12}$H$_9$NO$_2$F$_2$Br requires 315.9779).

Step 3

This compound was prepared by a procedure described in step 3 for EXAMPLE 364.

Yield : 63%, $^1$H NMR (CD$_3$OD) δ 7.58 (m, 2H), 7.23 (m, 2H), 7,06 (m, 2H), 6.68 (s, 1H), 5.36 (s, 2H), and 2.10 (s, 3H); $^{19}$F NMR (CD$_3$OD) δ –111.50 (m), –115.96 (m), and –121.93 (m); ES-HRMS m/z 442.0061 (M+H C$_{19}$H$_{13}$NO$_2$F$_4$Br requires 442.0060).

Example 374

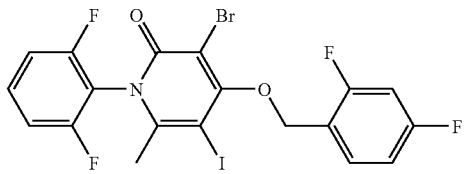

3-Bromo-4-[(2,4-difluorobenzyl)oxy]-1-(2,6-difluorophenyl)-5-iodo-6-methylpyridin-2(1H)-one A solution of 3-Bromo-4-[(2,4-difluorobenzyl)oxy]-1-(2,6-difluorophenyl)-6-methylpyridin-2(1H)-one (0.3 g, 0.00068 mol) and N-iodosuccinimide (0.22 g, 0.00098 mol) in dichloroethane, containing dichloroacetic acid (0.1 mL) was heated to reflux for 6 h under argon atmosphere. After the removal of the solvents under reduced pressure, the residue was partitioned between, dichloromethane (20 mL) and 5% sod. sulphite (10 mL). The organic phase was washed with water, dried (Na$_2$SO$_4$), and concentrated under reduced pressure. The residue was purified by flash chromatography (25% EtOAc in hexane) to afford the title compound (0.125 g, 32%) as a pale yellow powder: $^1$H NMR (CDCl$_3$/400 MHz) δ 7.68 (m, 1H), 7.46 (m, 1H), 7.11 (m, 2H), 6.95 (m, 1H), 6.85 (m, 1H), 5.23 (s, 2H), and 2.38 (s, 3H); $^{19}$F NMR (CDCl$_3$) δ–109.15 (m), –112.95 (m), –118.50 (m); ES-HRMS m/z 567.9014 (M+H C$_{19}$H$_{12}$NO$_2$F$_4$BrI requires 567.9027).

Example 375

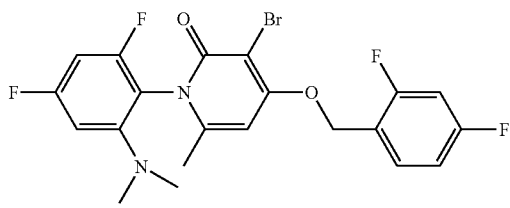

3-Bromo-4-[(2,4-difluorobenzyl)oxy]-1-[2-(dimethylamino)-4,6-difluorophenyl]-6-methylpyridin-2(1H)-one Step 1

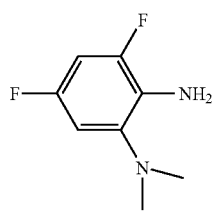

3,5-difluoro-N~1, N~1~-dimethylbenzene-1,2-diamine

To a solution of 2,4,6-trifluoronitrobenzene (2.58 g, 0.0145 mol) in THF (20.0 ml) was added a solution of N,N-dimethylamine in THF (8.5 mL of 2M soln) and stirred for 45 min at 0° C. It was then stirred at room temperature for 30 min and concentrated to dryness. The resulting material was dissolved in EtOH (25 mL), added Pd/C (10%, 0.6 g) and hydrogenated at 50 psi for 4 h. The catalyst was removed by filtration, and the filtrate was concentrated to dryness under reduced pressure. Te residue was partitioned between sod. bicarbonate (10%, 25 mL) and EtOAc (30 mL). The organic phase was washed with water, dried (Na$_2$SO$_4$), and concentrated to dryness to afford the title compound (1.3 g, 50%) as a dark colored solid: $^1$H NMR (CDCl$_3$/400 MHz) δ 6.52 (m, 2H), 3.64 (br, 2H), and 2.65 (s, 6H); ES-HRMS m/z 172.0772 (M+C$_8$H$_{10}$N$_2$F$_2$ requires 172.0810).

Step 2

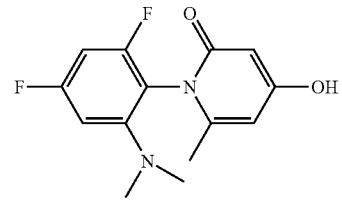

1-[2-(dimethylamino)-4,6-difluorophenyl]-4-hydroxy-6-methylpyridin-2(1H)-one

An intimate mixture of 4-hydroxy-6-methyl-2-pyrone (1.3 g, 0.0103 mol), and 3,5-difluoro-N,N-dimethylbenzene-1,2-diamine (1.4 g, 0.008 mol) was heated at 160° C. under argon for 15 min. The dark colored reaction mixture was cooled, triturated with EtOAc (15 ml), and filtered. The solids were washed with warm EtOAc, followed by hexane and dried to give the title compound as a light blue solid (0.4 g, 14%). Analalytically pure sample was prepared by reverse-phase HPLC purification using 10–90% CH$_3$CN/Water (30 min gradient) at a flow rate of 100 mL/min. The appropriate fractions were combined and freeze-dried to give the title compound: $^1$H NMR (CD$_3$OD/400 MHz) δ 6.61 (m, 2H), 6.08 (d, 1H, J=2.0 Hz), 6.78 (d, 1H, J=2.0 Hz), 2.69 (s, 6H), and 1.94 (s, 3H); ES-HRMS m/z 281.1084 (M+H C$_{14}$H$_{15}$N$_2$O$_2$F$_2$ requires 281.1096)

Step 2

Preparation of

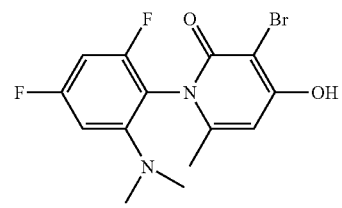

3-bromo-1-[2-(dimethylamino)-4,6-difluorophenyl]-4-hydroxy-6-methylpyridin-2(1H)-one The title compound was prepared by a procedure described in step2 for EXAMPLE 364. Yield:71%, $^1$H NMR (CD$_3$OD/400 MHz) δ 6.62 (m, 2H), 6.17 (s, 1H), 2.67 (s, 6H), and 1.94 (s, 3H); ES-HRMS m/z 359.0188 (M+H C$_{14}$H$_{14}$N$_2$O$_2$F$_2$Br requires 359.0201).

Step 3

This compound was prepared by a procedure described in step 3 for EXAMPLE 364.

Yield : 34%, $^1$H NMR (CDCl$_3$/400 MHz) δ 7.62 (m, 1H), 6.98 (m, 1H), 6.85 (m, 1H), 6.46 (m, 2H), 6.11 (s, 1H), 5.24 (s, 2H), 2.66 (s, 6H), and 1.98 (s, 3H); $^{19}$F NMR (CDCl$_3$/400 MHz) δ–108.06 (m), –109.60 (m), –115.02 (m), and –116.01 (m); ES-HRMS m/z 485.0451 (M+H C$_{21}$H$_{18}$N$_2$O$_2$F$_4$Br requires 485.0482).

The title compound was prepared by stirring a suspension of thet product of step 3, above, (0.14 g) with 4N HCl in dioxane (0.7 mL) at room temperature for 30 min. The mixture was concentrated to dryness. ¹H NMR (CD₃OD/400 MHz) δ 7.62 (m, 1H), 7.02 (m, 2H), 6.65 (m, 3H), 5.34 (s, 2H), 2.66 (s, 6H), and 2.05 (s, 3H); ES MS m/z=485.

Example 376

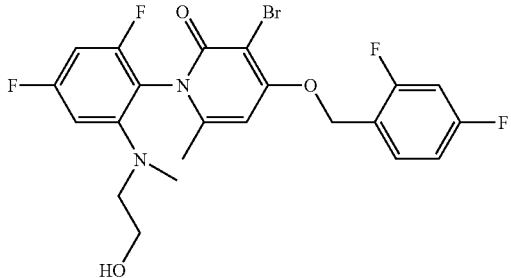

3-Bromo-4-[(2,4-difluorobenzyl)oxy]-1-{2,4-difluoro-6-[(2-hydroxyethyl)(methyl)amino]phenyl}-6-methylpyridin-2(1H)-one The title compound was prepared by a similar procedure described for EXAMPLE 375, replacing N,N-dimethyl group by N-Methyl-aminoethanol. ¹H NMR (CDCl₃/400 MHz) δ 7.59 (m, 1H), 6.98. (m, 1H), 6.85 (m, 1H), 6.61 (m, 1H), 6.52 (m, 1H), 6.17 (m, 1H), 5.25 (s, 2H), 3.63 (m, 1H), 3.53 (m, 1H), 3.26 (m, 1H), 3.0 (m, 1H), 2.66 (s, 6H), and 2.09 (s, 3H); ES-HRMS m/z 515.0512 (M+H C₂₂H₂₀N₂O₃F₄Br requires 515.0588).

Example 377

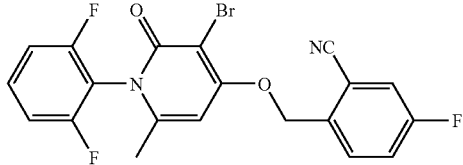

2-({[3-Bromo-1-(2,6-difluorophenyl)-6-methyl-2-oxo-1,2-dihydropyridin-4-yl]oxy}methyl)-5-fluorobenzonitrile Step 1

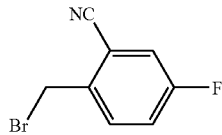

2-(Bromomethyl)-5-fluorobenzonitrile

A mixture of 5-fluoro-2-methylbenzonitrile (2.0 g, 0.015 mol), NBS (3.2 g, 0.018 mol) and benzoylperoxide (0.25 g) in carbontetrachloride (25.0 ml) was heated to reflux for 6 h, under argon atmosphere. The reaction mixture was cooled and filtered. The filtrate was concentrated under reduced pressure, and the residue was purified by flash chromatography (5% EtOAc in hexane) to afford 2-(Bromomethyl)-5-fluorobenzonitrile (1.9 g, 60%) as a colorless liquid: ¹H NMR (CDCl₃/400 MHz) δ 7.59 (m) 7.58 (m, 1H), 7.38 (m, 1H), and 7.25 (m, 1H)

Step 2

A mixture of 3-bromo-1-(2,6-difluorophenyl)-4-hydroxy-6-methylpyridin-2(1H)-one 1.0 g, 0.0032 mol), potassium carbonate (0.65 g, 0.0047 mol) and 2-(Bromomethyl) 5-fluorobenzonitrile (0.95 g, 0.0045 mol) in dimethylacetamide (15.0 ml) was stirred at room temperature under argon atmosphere. After 1 h, dimethylacetamide was distilled in vacuo and the residue was partitioned between dichloromethane (50 ml) and 55 citric acid (15 mL). The organic phase was washed with water, dried (Na₂SO₄), and concentrated to dryness. The resulting material was triturated with EtOAc, filtered, washed with EtOAc and dried to afford the title compound (0.86 g, 60%) as a white powder: ¹H NMR (DMSO-d₆/400 MHz) δ 7.95 (m, 1H), 7.81 (m, 1H), 7.68 (m, 2H), 7.37 (m, 2H), 6.79 (s, 1H), 5.45 (s, 2H), and 2.03 (s, 3H); ¹⁹F-NMR (DMSO-d₆) δ−111.31 (m), −120.34 (m); ES-HRMS m/z 449.0094 (M+H C₂₀H₁₃N₂O₂F₃Br requires 449.0107).

Example 378

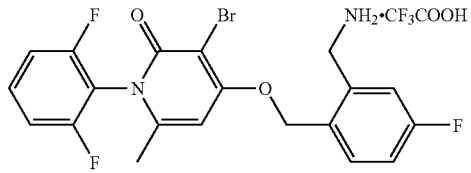

4-{[2-(Aminomethyl)-4-fluorobenzyl]oxy}-3-bromo-1-(2,6-difluorophenyl)-6-methylpyridin-2(1H)-one trifluoroacetate To a cold suspension of 2-({[3-Bromo-1-(2,6-difluorophenyl)-6-methyl-2-oxo-1,2-dihydropyridin-4-yl]oxy}methyl)-5-fluorobenzonitrile (0.3 g, 0.00066 mol) in THF (3.0 mL), was added BH₃.THF (1.0 mL). After stirring at room temperature for 15 min, the reaction mixture was heated to reflux for 30 min under argon atmosphere. The resulting clear solution cooled, added MeOH (2.0 mL), concentrated under reduced pressure, and the residue was purified by reverse-phase HPLC purification using 10–90% CH₃CN/Water (30 min gradient) at a flow rate of 100 mL/min. The appropriate fractions (m/z=453 M+H) were combined and freeze-dried to give the title compound (0.16 g, 43%) as its trifluoroacetate salt: ¹H NMR (DMSO-d₆/400 MHz) δ 8.19 (br, 3H), 7.65 (m, 2H), 7.37 (m, 4H), 6.78 (s, 1H), 5.42 (s, 2H), 4.21 (br, 2H), and 2.04 (s, 3H); ¹⁹F NMR (DMSO-d₆/400 MHz) δ−112.96 (m), and −120.41 (m); ES-HRMS m/z 453.0387 (M+H C₂₀H₁₇N₂O₃F₃Br requires 453.0420).

Example 379

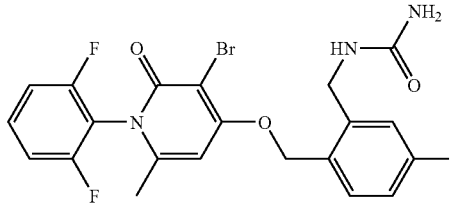

N-[2-({[3-bromo-1-(2,6-difluorophenyl)-6-methyl-2-oxo-1,2-dihydropyridin-4-yl]oxy}methyl)-5-fluorobenzyl]urea To a suspension of 4-{[2-(aminomethyl)-4-fluorobenzyl]oxy}-3-bromo-1-(2,6-difluorophenyl)-6-methylpyridin-2

(1H)-one trifluoroacetate (0.13 g, 0.00023 mol) in THF (3.0 mL), was added triethyl amine (0.07 mL, 0.0005 mol) followed by the addition of trimethylsilylisocyanate (0.066 mL). The reaction mixture was stirred at room temperature for 1 h, and the desired product was isolated by reverse-phase HPLC purification using 10–90% $CH_3CN$/Water (30 min gradient) at a flow rate of 100 mL/min. The appropriate fractions (m/z=496 M+H) were combined and freeze-dried, and the residue was partitioned between 5% sod. bicarbonate (20 mL) and dichloromethane (20 mL). The organic phase was washed with water, dried ($Na_2SO_4$) and concentrated to dryness under reduced pressure, to afford the title compound as a white amorphous powder (0.065 g): $^1H$ NMR (DMSO-$d_6$/400 MHz) δ 7.62 (m, 1H), 7.52 (m, 1H), 7.35 (m, 2H), 7.09 (m, 2H), 6.77 (s, 1H), 6.51 (t, 1H), 5.61 (s, 2H), 5.38 (s. 2H), 4.28 (d, 2H, J=6.0 Hz), and 2.02 (s, 3H); $^{19}F$ NMR (DMSO-$d_6$/400 MHz) δ–114.044 (m), and –120.31 (m); ES-HRMS m/z 496.0460 (M+H $C_{21}H_{18}N_3O_3F_3Br$ requires 496.0478).

Example 380

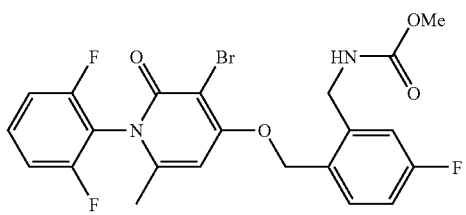

Methyl 2-({[3-bromo-1-(2,6-difluorophenyl)-6-methyl-2-oxo-1,2-dihydropyridin-4-yl]oxy}methyl)-5-fluorobenzylcarbamate To solution of 4-{[2-(aminomethyl)-4-fluorobenzyl]oxy}-3-bromo-1-(2,6-difluorophenyl)-6-methylpyridin-2 (1H)-one trifluoroacetate (0.12 g, 0.00021 mol) in dimethylacetamide (2.0 mL) at 0° C., was added triethylamine (0.06 mL, 0.00043 mol) followed by the addition of methylchloroformate (0.05 mL). The reaction mixture was stirred at room temperature for 30 min under argon atmosphere. Dimethylacetamide was distilled in vacuo and the residue was partitioned between dichloromethane (10 mL) and 5% citric acid (10 mL). The organic phase was washed with water, dried ($Na_2SO_4$) and concentrated to dryness. The resulting residue was purified by flash chromatography (60% EtOAc in hexane) to afford the title compound (0.09 g, 75%) as a white amorphous powder: $^1H$ NMR (DMSO-$d_6$/400 MHz) δ 7.68 (m, 1H), 7.62 (m, 1H), 7.59 (m, 1H) 7.38 (m, 2H), 7.115 (m, 2H), 6.78 (s, 1H), 5.38 (s, 2H), 4.31 (d, 2H, J=6.0 Hz), 3.53 (s, 3H), and 2.03 (s, 3H); $^{19}F$ NMR (DMSO-$d_6$/400 MHz) δ–113.77 (m), and –120.33 (m); ES-HRMS m/z 511.0508 (M+H $C_{22}H_{19}N_2O_4F_3Br$ requires 511.0475).

Example 381

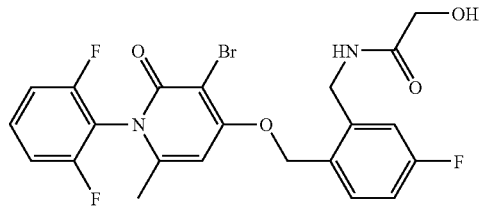

N-[2-({[3-bromo-1-(2,6-difluorophenyl)-6-methyl-2-oxo-1,2-dihydropyridin-4-yl]oxy}methyl)-5-fluorobenzyl]-2-hydroxyacetamide To a suspension of 4-{[2-(aminomethyl)-4-fluorobenzyl]oxy}-3-bromo-1-(2,6-difluorophenyl)-6-methylpyridin-2 (1H)-one trifluoroacetate (0.12 g, 0.00021 mol) in THF (2.0 mL) at 5° C., was added triethyl amine (0.036 g, 0.00035 mol) followed by the addition of acetoxyacetyl chloride (0.05 mL). The mixture was stirred at room temperature for 30 min, diluted with cold water (10 mL), and extracted the products with dichloromethane (2×10 mL). The combined organic extracts were washed with water, dried ($Na_2SO_4$) and concentrated to dryness. The residue was dissolved in ethanol (0.5 mL), added 1N NaoH (0.5 mL)and stirred at room temperature for 1 h. The resulting solution was diluted with water (15 mL), and extracted with dichloromethane (2×10 mL). The combined dichloromethane extracts were washed with water, dried ($Na_2SO_4$) and concentrated to dryness. The residue was purified by flash chromatography (1% MeOH in EtOAc) to afford the title compound (0.032 g, 30%) as a white amorphous powder: $^1H$ NMR ($CDCl_3$/400 Hz) δ 7.45 (m, 2H), 7.18 (m, 1H), 7.05 (m, 3H), 6.23 (s, 1H), 5.24 (s, 2H), 4.56 (d, 2H, J=6.4 Hz), 4.08 (d, 2H, J=5.2 Hz), 2.79 (t, 1H), and 2.08 (s, 3H;) $^{19}F$ NMR ($CDCl_3$/400 MHz) δ–111.88 (m), and –118.62 (m); ES-HRMS m/z 511.0482 (M+H $C_{22}H_{19}N_2O_4F_3Br$ requires 511.0475).

Example 382

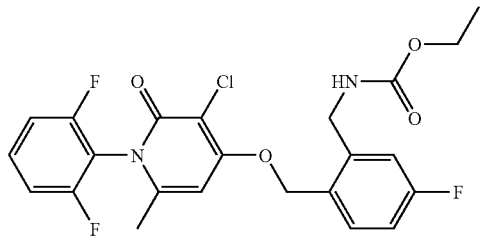

Ethyl 2-({[3-chloro-1-(2,6-difluorophenyl)-6-methyl-2-oxo-1,2-dihydropyridin-4-yl]oxy}methyl)-5-fluorobenzylcarbamate To solution of 4-{[2-(aminomethyl)-4-fluorobenzyl]oxy}-3-chloro-1-(2,6-difluorophenyl)-6-methylpyridin-2 (1H)-one trifluoroacetate (0.3 g, 0.00057 mol) in dimethylacetamide (3.0 mL) was added N-methymorpholine (0.064 g, 0.00064 mol), followed by addition of ethylchloroformate (0.06 mL) and stirred at –10° C., for 30 min. The solvents were distilled in vacuo and the residue was purified by reverse-phase HPLC purification using 10–90% $CH_3CN$/Water (30 min gradient) at a flow rate of 100 mL/min. The appropriate fractions (m/z=481 M+H) were combined and freeze-dried, and the residue was partitioned between 5% sod. bicarbonate (20 mL) and dichloromethane (20 mL). The organic phase was washed with water, dried (Na$_2$SO$_4$) and concentrated to dryness under reduced pressure, to afford the title compound as a white amorphous powder (0.15 g, 55%): $^1$H NMR (CD$_3$OD/400 MHz) δ 7.61 (m, 1H), 7.52 (m, 1H), 7.26 (~t, 2H, J=8.4 Hz), 7.12 (dd, 1H), 7.05 (3d, 1H, J=2.4 Hz), 6.74 (s, 1H), 5.40 (s, 2H), 4.42 (s, 2H), 4.05 (q, 2H, J=7.2 Hz), 2.12 (s, 3H), and 1.21 (t, 3H, J=7.2 Hz); ES-HRMS m/z 481.1118 (M+H C$_{23}$H$_{21}$N$_2$O$_4$F$_3$Cl requires 481.1136).

Example 383

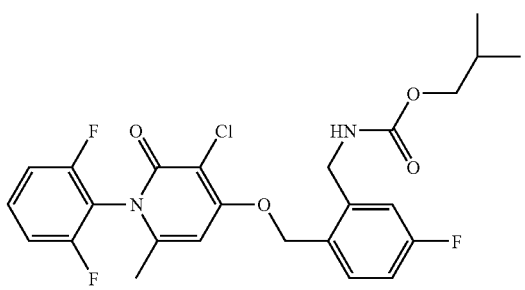

Isobutyl 2-({[3-chloro-1-(2,6-difluorophenyl)-6-methyl-2-oxo-1,2-dihydropyridin-4-yl]oxy}methyl)-5-fluorobenzylcarbamate The title compound was prepared by a procedure similar to the one described for EXAMPLE 382. Yield 57%; $^1$H NMR (CD$_3$OD/400 MHz) δ 7.61 (m, 1H), 7.51 (m, 1H), 7.24 (~t, 2H, J=8.0 Hz), 7.18 (m, 1H), 7.06 (m, 1H), 6.74 (s, 1H), 5.40 (s, 2H), 4.21 (s, 2H), 3.79 (d, 2H, J=6.8 Hz), 2.12 (s, 3H), 1.85 (m, 1H), and 0.91 (d, 6H, J=6.4 Hz); ES-HRMS m/z 509.1422 (M+H C$_{25}$H$_{25}$N$_2$O$_4$F$_3$Cl requires 509.1449).

Example 384

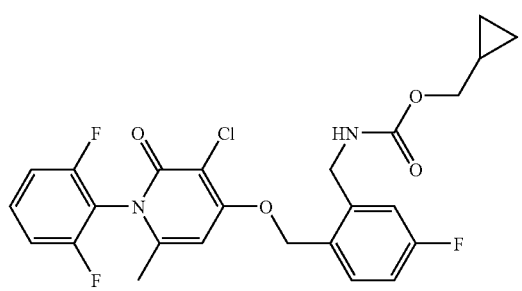

Cyclopropylmethyl 2-({[3-chloro-1-(2,6-difluorophenyl)-6-methyl-2-oxo-1,2-dihydropyridin-4-yl]oxy}methyl)-5-fluorobenzylcarbamate The title compound was prepared by a procedure similar to the one described for EXAMPLE 382. Yield 46%; $^1$H NMR (CD$_3$OD/400 Hz) δ 7.61 (m, 1H), 7.55 (m, 1H), 7.24 (~t, 2H, J=7.6 Hz), 7.18 (m, 1H), 7.05 (m, 1H), 6.73 (s, 1H), 5.40 (s, 2H), 4.42 (s, 2H), 3.83 (d, 2H, J=7.2 Hz), 2.12 (s, 3H), 1.1 (br, 1H), 0.58 (~d, 2H), and 0.22 (~d, 2H); ES-HRMS m/z 507.1316 (M+H C$_{25}$H$_{23}$N$_2$O$_4$F$_3$Cl requires 507.1293).

Example 385

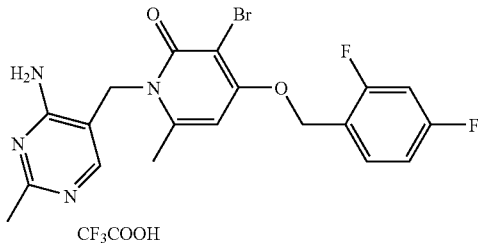

1-[(4-amino-2-methylpyrimidin-5-yl)methyl]-3-bromo-4-[(2,4-difluorobenzyl)oxy]-6-methylpyridin-2(1H)-one trifluoroacetate Step 1

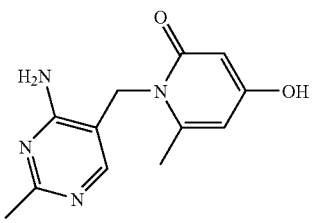

1-[(4-amino-2-methylpyrimidin-5-yl)methyl]-4-hydroxy-6-methylpyridin-2(1H)-one

A mixture of 4-hydroxy-6-methyl-2-pyrone (0.9 g, 0.007 mol) and 4-amino-5-aminomethyl-2-methylpyrimidine (1.0 g, 0.007 mol) in water (10.0 ml) was heated at 100° C. for 1 h under argon atmosphere. The reaction mixture was cooled, and filtered the yellow precipitate. It was washed successively with cold water, ethanol, and dried in vacuo to afford the title compound (1.01 g, 51%) as a pale yellow powder: $^1$H NMR (DMSO-d$_6$/400 MHz) δ 7.62 (s, 1H), 7.04 (s, 1H), 5.83 (d, 1H, J=2.0 Hz), 5.58 (d, 1H, J=2.0 Hz), 4.92 (s, 2H), 2.24 (s, 3H), and 2.22 (s, 3H); ES-HRMS m/z 325.0304 (M+H C$_{12}$H$_{14}$N$_4$O$_2$Br requires 325.0295).

Step 2

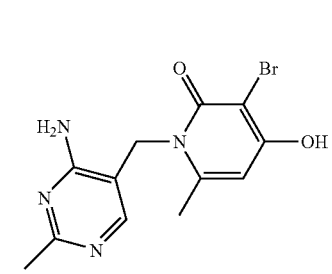

1-[(4-amino-2-methylpyrimidin-5-yl)methyl]-3-bromo-4-hydroxy-6-methylpyridin-2(1H)-one A mixture of 1-[(4-amino-2-methylpyrimidin-5-yl)methyl]-4-hydroxy-6-methylpyridin-2(1H)-one (0.5 g, 0.002 mol), and NBS (0.4 g, 0.002 mol)in glacial acetic acid (5.0 ml) was stirred at room temperature for 1 h under argon atmosphere. Acetic acid was removed in vacuo, residue was triturated with EtOAc containing 10% EtOH, and filtered. The pale yellow precipitate was washed with EtOAc containing 10% EtOH and dried in vacuo to afford the title compound (0.47 g, 725) as a pale yellow powder:

$^1$H NMR (CD$_3$OD/400 MHz) δ 7.62 (s, 1H), 6.09 (s, 1H), 5.15 (s, 2H), 2.42 (s, 3H), and 2.33 (s, 3H); ES-HRMS m/z 247.1160 (M+H C$_{12}$H$_{15}$N$_4$O$_2$ requires 247.1190)

Step 3

To suspension of 1-[(4-amino-2-methylpyrimidin-5-yl)methyl]-3-bromo-4-hydroxy-6-methylpyridin-2(1H)-one (1.0 g, 0.0031 mol) and potassium carbonate (0.0 g, 0.004 mol) in dimethylacetamide (10.0 mL) was added 2,4 difluorobenzyl bromide (0.62 mL, 0.0048 mol) and stirred at room temperature for 2 hours. Dimethylacetamide was distilled in vacuo and the residue was purified by reverse-phase HPLC using 10–90% CH$_3$CN/Water (30 min gradient) at a flow rate of 100 mL/min. The appropriate fractions (m/z=566)were combined and freeze dried to afford 0.65 g (37%) of the title compound as its trifluoroacetate salt: $^1$H NMR (CD$_3$OD/400 MHz) δ 7.65 (s, 1H), 7.58 (m, 1H), 7.05 (m, 2H), 6.61 (s, 1H), 5.31 (s, 2H), 5.18 (s, 2H), 2.51 (s, 3H), and 2.46 (s, 3H); $^1$H NMR (CD$_3$OD/400 MHz) δ–111.39 (m), and –115.98 (m); ES-HRMS m/z 451.0590 (M+H C$_{19}$H$_{18}$N$_4$O$_2$BrF$_2$ requires 451.0576).

Example 386

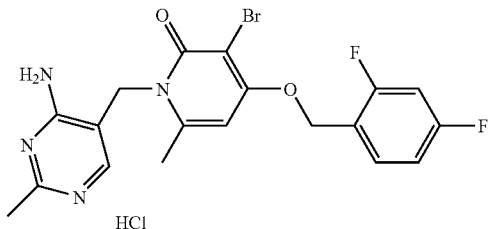

1-[(4-amino-2-methylpyrimidin-5-yl)methyl]-3-bromo-4-[(2,4-difluorobenzyl)oxy]-6-methylpyridin-2(1H)-one hydrochloride Ion exchange (25 g) BioRad AG 2×8 resin (200–400 mesh chloride form) was washed with 1M HCl (150 mL), and equilibrated for 2.5 h. This resin was loaded onto a column, and added a solution of Example 385 (3.3 g, 5.8 mmol) in water/CH$_3$CN (1:1). The column was eluted slowly over 1 h, fractions were collected, and freeze dried to afford the desired HCl salt (2.2 g, 72%) as a white solid: $^1$H-NMR (CD$_3$OD, 400 Hz) δ 7.60 (m, 2H), 7.21 (m, 2H), 6.62 (s, 1H), 5.31 (s, 2H), 5.18 (s, 2H), 2.52 (s, 3H), 2.47 (s, 3H); ES-HRMS m/z 451.0544/453.0577 (M+H C$_{19}$H$_{17}$N$_4$O$_2$F$_2$Br requires 451.0581/453.0563).

Example 387

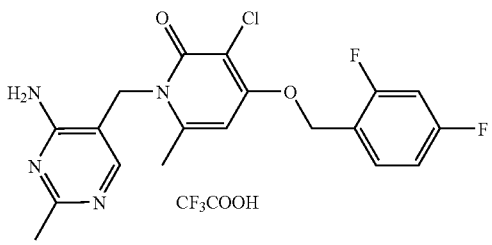

1-[(4-amino-2-methylpyrimidin-5-yl)methyl]-3-chloro-4-[(2,4-difluorobenzyl)oxy]-6-methylpyridin-2(1H)-one trifluoroacetate Step 1. Preparation of 1-[(4-amino-2-methylpyrimidin-5-yl)methyl]-3-chloro-4-hydroxy-6-methylpyridin-2(1H)-one

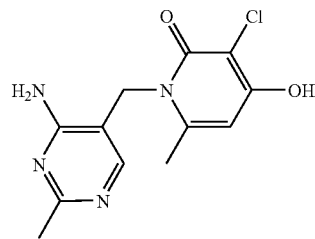

$^1$H NMR (CD$_3$OD, 400 Hz) δ 7.62 (m, 1H), 6.11 (s, 1H), 5.13 (s, 2H), 2.66 (s, 3H), 2.42 (s, 3H); ES-HRMS m/z 281.0793 (M+H C$_{12}$H$_{13}$N$_4$O$_2$Cl requires 281.0800).

Step 2. Preparation of 1-[(4-amino-2-methylpyrimidin-5-yl)methyl]-3-chloro-4-[(2,4-difluorobenzyl)oxy]-6-methylpyridin-2 (1H)-one trifluoroacetate The title compound was prepared by a procedure similar to the one described for Example 385 step 2. $^1$H NMR (CD$_3$OD, 400 Hz) δ 7.59 (m, 2H), 7.03 (m, 2H), 6.63 (s, 1H), 5.31 (s, 2H), 5.17 (s, 2H), 2.48 (s, 3H), 2.46 (s, 3H); ES-HRMS m/z 407.1097 (M+H C$_{19}$H$_{17}$N$_4$O$_2$ClF$_2$ requires 407.1081).

Example 388

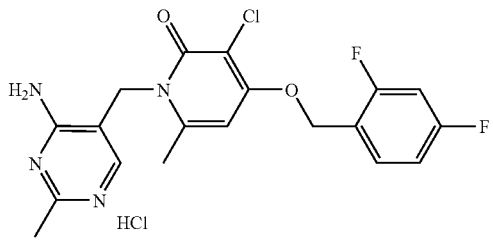

1-[(4-amino-2-methylpyrimidin-5-yl)methyl]-3-chloro-4-[(2,4-difluorobenzyl) oxy]-6-methylpyridin-2 (1H)-one hydrochloride Ion exchange (12.5 g) BioRad AG 2×8 resin (200–400 mesh chloride form) was washed with 1M HCl (150 mL), and equilibrated for 2.5 h. This resin was loaded onto a column, and added a solution of EXAMPLE 387 (1.2 g, 2.4 mmol) in water/CH$_3$CN (1:1). The column was eluted slowly over 1 h, fractions were collected, and freeze dried to afford the desired HCl salt (1.03 g, 97%) as a white solid: $^1$H NMR (CD$_3$OD, 400 Hz) δ 7.60 (m, 2H), 7.04 (m, 2H), 6.64 (s, 1H), 5.31 (s, 2H), 5.17 (s, 2H), 2.50 (s, 3H), 2.47 (s, 3H); ES-HRMS m/z 407.1079 (M+H C$_{19}$H$_{17}$N$_4$O$_2$ClF$_2$ requires 407.1081).

Example 389

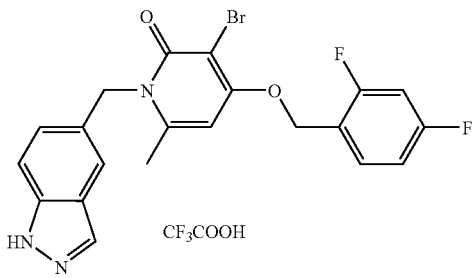

3-Bromo-4-[(2,4-difluorobenzyl)oxy]-1-(1H-indazol-5-ylmethyl)-6-methylpyridin-2(1H)-one trifluoroacetate To a mixture of 3-bromo-4-[(2,4-difluorobenzyl)oxy]-6-methylpyridin-2(1H)-one (0.55 g, 0.0017 mol) and 5-(bromomethyl)-1-tetrahydro-2H-pyran-2-yl-1H-indazole (0.5 g, 0.0017 mol) in THF (10.0 mL) was added NaH (0.045 g, 0.0019 mol) and heated at 60° C. for 16 h under argon atmosphere. THF was distilled under reduced pressure, and the residue was suspended in EtOAc, added acetic acid (0.5 mL) and the product was purified by flash chromatography (80% EtOAc in hexane). The appropriate fractions were combined and concentrated to give an amorphous substance (0.31 g). This was stirred with trifluoroacetic (0.5 mL) for 30 min, the solution was diluted with acetonitrile (5 mL) and the product was isolated by reverse-phase HPLC using 10–90% CH$_3$CN/Water (30 min gradient) at a flow rate of 100 mL/min. The appropriate fractions (m/z=460) were combined and freeze dried to afford 0.14 g (52%) of the title compound as its trifluoroacetate salt: $^1$H NMR (CD$_3$OD/400 MHz) δ 7.97 (s, 1H), 7.62 (m, 1H), 7.51 (m, 1H), 7.45 (s, 1H), 7.25 (m, 1H), 7.03 (t, 2H), 6.49 (s, 1H), 5.53 (s, 2H), 5.29 (s, 2H), and 2.40 (s, 3H); $^{19}$F NMR (CD$_3$OD/400 MHz) δ −111.69 (m), −116.09 (m); ES-HRMS m/z 460.0432 (M+H C$_{21}$H$_{17}$N$_3$O$_2$BrF$_2$ requires 460.0467).

Example 390

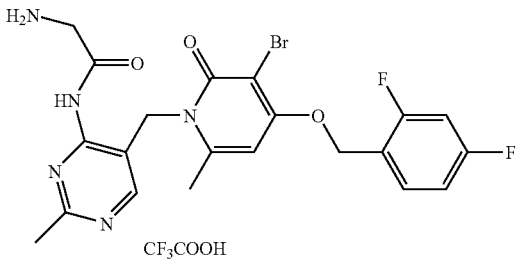

N~1~-(5-{[3-bromo-4-[(2,4-difluorobenzyl)oxy]-6-methyl-2-oxopyridin-1(2H)-yl]methyl}-2-methylpyrimidin-4-yl)glycinamide trifluoroacetate To a solution of BOC-Gly-OH (0.19 g, 0.0011 mol) in DMF (2.0 mL), was added N-methylmorpholine (0.14 mL, 0.0011 mol), followed by the addition of isobutylchloroformate (0.15 mL, 0.0011 mol) and stirred at −10° C. for 15 min. Then added a solution of 1-[(4-amino-2-methylpyrimidin-5-yl)methyl]-3-bromo-4-[(2,4-difluorobenzyl)oxy]-6-methylpyridin-2(1H)-one trifluoroacetate (0/125 g, 0.00022 mol) in DMF (2.0 mL) containing diisopropylethylamine (0.1 g, 0.006 mL) and the resulting mixture was stirred for 16 h, at room temperature. The solvents were distilled in vacuo and the residue was purified by by reverse-phase HPLC using 10–90% CH$_3$CN/Water (30 min gradient) at a flow rate of 100 mL/min. The appropriate fractions (m/z=608/610) were combined and freeze dried to afford 0.025 g of white powder. This was stirred with trifluoroacetic acid (0.5 mL) for 1 h and product was isolated by reverse-phase HPLC using 10–90% CH$_3$CN/Water (30 min gradient) at a flow rate of 100 mL/min. The appropriate fractions (m/z=508/510) were combined and freeze dried to afford the title compound (0.02 g) as a white powder: $^1$H NMR (CD$_3$OD/400 MHz) δ 8.18 (s, 1H), 7.61 (m, 1H), 7.02 (m, 2H), 6.59 (s, 1H), 5.30 (s, 4H), 4.23 (s, 2H), 2.60 (s, 3H), and 2.47 (s, 3H); ES-HRMS m/z 508.0797 (M+H C$_{21}$H$_{21}$N$_5$O$_3$BrF$_2$ requires 508.0790).

Example 391

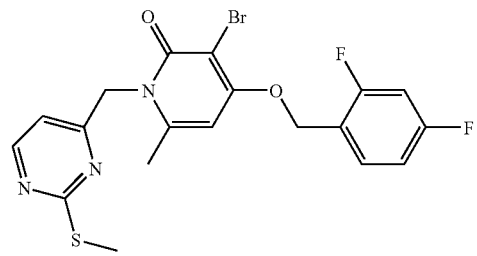

3-bromo-4-[(2,4-difluorobenzyl)oxy]-6-methyl-1-{[2-(methylthio)pyrimidin-4-yl]methyl}pyridin-2(1H)-one Step 1

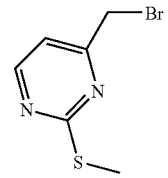

4-(Bromomethyl)-2-(methylthio)pyrimidine

To a solution of 4-methyl-2-methylthiopyrimidine (12.6 g, 0.09 mol) in acetic acid (50.0 mL) was added bromine (5.5 mL, 0.11 mol) and heated at 80° C. under argon atmosphere for 2 h. Acetic acid was distilled in vacuo, the residue was triturated with dichloromethane (100.0 mL) and poured into satd. sod.bicarbonate solution (200.0 mL). Additional dichloromethane (100.0 ml) was added and stirred for 15 min. The organic phase was washed with water (3×100 mL), dried (Na$_2$SO$_4$), and concentrated under reduced pressure. The dark colored residue was purified by flash chromatography (EtOAc/hexane 1:4 v/v) to afford 4-(bromomethyl)-2-(methylthio)pyrimidine (10.9 g, 55%) as a dark colored liquid: $^1$H NMR (CDCl$_3$/400 MHz) δ 8.50 (d, 1H, J=4.8 Hz), 7.09 (d, 1H, J=4.8 Hz), 4.34 (s, 2H), and 2.56 (s, 3H); ES MS m/z 219 (M+H).

Step 2

To a mixture of 3-bromo-4-[(2,4-difluorobenzyl)oxy]-6-methylpyridin-2(1H)-one 5.0 g, 0.015 mol) and 4-(Bromomethyl)-2-(methylthio)pyrimidine (4.0 g, 0.018 mol) in THF (50.0 mL) was added NaH (0.4 g, 0.0017 mol) and stirred at 55° C. under argon for 16 h. The reaction mixture was concentrated under reduced pressure and the residue was partitioned between 5% citric acid (25 mL) and EtOAc (50 mL). A precipitate was formed, it was filtered, washed with water, EtOAc, and dried in vacuo to afford the title compound (4.2 g, 59%) as a light brown powder, $^1$H NMR (CD$_3$OD/400 MHz) δ 8.45 (d, 1H, J=5.2 Hz), 7.6 (m, 1H), 7.06 (d over m, 2H, J=5.2 Hz), 6.54 (s, 1H), 5.39 (s, 2H), 5.32 (s, 2H), 2.43 (s, 3H), 2.33 (s, 3H); ES-HRMS m/z 468.0173 (M+H C$_{19}$H$_{17}$N$_3$O$_2$BrSF$_2$ requires 468.0187).

Example 392

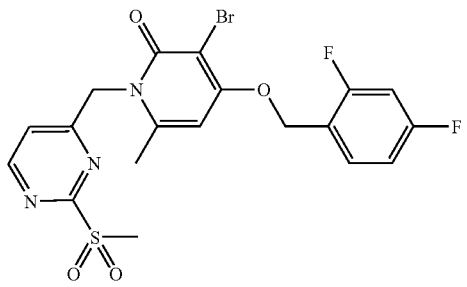

3-Bromo-4-[(2,4-difluorobenzyl)oxy]-6-methyl-1-{[2-(methylsulfonyl)pyrimidin-4-yl]methyl}pyridin-2(1H)-one A suspension of 3-bromo-4-[(2,4-difluorobenzyl)oxy]-6-methyl-1-{[2-(methylthio)pyrimidin-4-yl]methyl}pyridin-2(1H)-one 0.28 g, 0.0006 mol), and magnesium monoperoxyphthalate hexahydrate 90.6 g, 0.0012 mol) in acetonitrile (8.0 ml) and water (2.0 ml) was stirred at room temperature for 16 h. The resulting clear solution was concentrated under reduced pressure, and the residue was partitioned between dichloromethane (30 mL) and water (20 mL). The organic phase was washed with water, dried (Na$_2$SO$_4$) and concentrated to afford the title compound (0.27 g, 90%) as a pale yellow substance: $^1$H NMR (CD$_3$OD/400 MHz) δ 8.91 (d, 1H, J=5.2 Hz), 7.63 (d over m, 2H, J=5.2 Hz), 7.03 (m, 2H), 6.58 (s, 1H), 5.54 (s, 2H), 5.33 (s, 2H), 3.28 (s, 3H), and 2.49 (s, 3H); $^{19}$F NMR (CD$_3$OD/400 MHz) δ−111.58 (m), −115.98 (m); ES-HRMS m/z 500.0113 (M+H C$_{19}$H$_{17}$N$_3$O$_4$BrSF$_2$ requires 500.0086).

Example 393

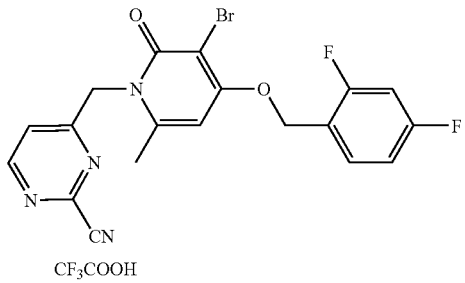

4-{[3-Bromo-4-[(2,4-difluorobenzyl)oxy]-6-methyl-2-oxopyridin-1(2H)-yl]methyl}pyrimidine-2-carbonitrile trifluoroacetate A mixture of 3-Bromo-4-[(2,4-difluorobenzyl)oxy]-6-methyl-1-{[2-(methylsulfonyl)pyrimidin-4-yl]methyl}pyridin-2(1H)-one (1.0 g, 0.002 mol) and NaCN (0.15 g, 0.0031 mol) in DMF (5.0 mL) was stirred at room temperature for 2 h under argon atmosphere. DMF was distilled in vacuo, the residue was triturated with acetonitrile (10 mL) and water (10 mL), and filtered the red colored precipitate. It was washed with acetonitrile and dried to afford the title compound (0.26 g). The washings and the fitrate were combined and purified by reverse-phase HPLC using 10–90% acetonitrile/water gradient (30 min) at a flow rate of 100 mL/min to give an additional 0.5 g of the title compound: $^1$H NMR (CD$_3$OD/400 MHz) δ 8.83 (d, 1H, J=5.2 Hz), 7.62 (d over m, 2H, J=5.2 Hz), 7.00 (m, 2H), 6.58 (s, 1H), 5.46 (s, 2H), 5.33 (s, 2H), and 2.47 (s, 3H); $^{19}$F NMR (CD$_3$OD/400 MHz) δ−111.64 (m), −116.03 (m); ES-HRMS m/z 447.0278 (M+H C$_{19}$H$_{14}$N$_4$O$_2$BrF$_2$ requires 447.0263).

Example 394

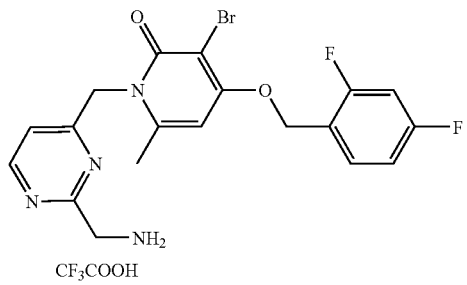

4-{[2-(Aminomethyl)-4-fluorobenzyl]oxy}-3-bromo-1-(2,6-difluorophenyl)-6-methylpyridin-2(1H)-one trifluoroacetate To a solution of 4-{[3-Bromo-4-[(2,4-difluorobenzyl)oxy]-6-methyl-2-oxopyridin-1(2H)-yl]methyl}pyrimidine-2-carbonitrile trifluoroacetate (0.3 g. 0.00066 mol) in a solvent mixture of EtOAc (15.0 mL) and acetic acid (5.0 mL), was added Pd/C (10% , 0.18 g) and stirred in an atmosphere of hydrogen at 15 psi for 2 h. The catalyst was removed by filtration . The filtrate was concentrated to dryness and the residue was residue was purified by reverse-phase HPLC using 10–90% acetonitrile/water gradient (30 min) at a flow rate of 100 mL/min. The appropriate fractions (m/z=451) were combined and freeze dried to afford (0.32 g, 645) of the title compound as its trifluoroacetate salt: $^1$H NMR (DMSO-d$_6$/400 MHz) δ 8.78 (d, 1H, J=5.2 Hz), 8.28 (br, 2H), 7.62 (m, 1H), 7.38 (m, 1H), 7.25 (d, 1H, J=5.2 Hz), 7.18 (m 1H), 6.62 (s, 1H), 5.32 (s, 2H), 5.29 (s, 2H), 4.24 (s, 2H), and 2.46 (s, 3H); $^{19}$F NMR (DMSO-d$_6$/400 MHz) δ−109.59 (m), −113.67 (m); ES-HRMS m/z 451.0530 (M+H C$_{19}$H$_{18}$N$_4$O$_2$BrF$_2$ requires 451.0576).

Example 395

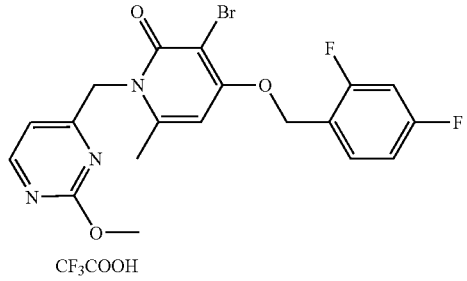

3-Bromo-4-[(2,4-difluorobenzyl)oxy]-1-[(2-methoxypyrimidin-4-yl)methyl]-6-methylpyridin-2(1H)-one trifluoroacetate A solution of 4-{3-Bromo-4-[(2,4-difluorobenzyl)oxy]-6-methyl-2-oxopyridin-1(2H)-yl]methyl}pyrimidine-2- carbonitrile trifluoroacetate (0.13 g, 0.00023 mol) in MeOH (2.0 mL) was treated with 1N NaOH (0.5 mL). After stirring at room temperature for 3 h, it was heated at 60° C. for an additional 3 h and left overnight room temperature. The resulting solution was diluted with acetonitrile, and purified by reverse-phase HPLC using 10–90% acetonitrile/water gradient (30 min) at a flow rate of 100 mL/min. The appropriate fractions (m/z=452) were combined and freeze dried to afford the title compound (0.015 g) as a white powder: $^1$H NMR (CD$_3$OD) δ 8.84 (d, 1H, J=5.2 Hz)

7.62 (d, 1H, J=5.2 Hz), 7.05 (m, 2H), 6.57 (s, 1H), 5.49 (s, 2H), 5.32 (s, 2H), 3.96 (s, 3H), and 2.49 (s, 3H); ES-HRMS m/z 452.0440 (M+H C$_{19}$H$_{17}$N$_3$O$_3$BrF$_2$ requires 452.0416).

Example 396

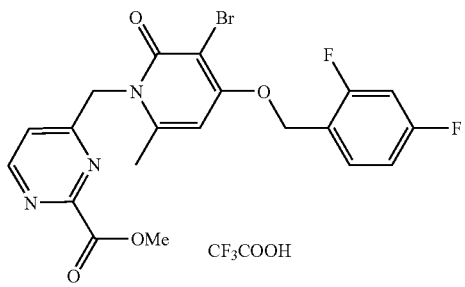

Methyl 4-{[3-bromo-4-[(2,4-difluorobenzyl)oxy]-6-methyl-2-oxopyridin-1(2H)-yl]methyl}pyrimidine-2-carboxylate trifluoroacetate The title compound was obtained as a second product in the formation of 3-Bromo-4-[(2,4-difluorobenzyl)oxy]-1-[(2-methoxypyrimidin-4-yl)methyl]-6-methylpyridin-2(1H)-one trifluoroacetate. $^1$H NMR (CD$_3$OD/400 MHz) δ 8.46 (d, 1H, J=5.2 Hz), 7.62 (m, 1H), 7.00 (m 2H), 6.93 (d, 1H, J=5.2 Hz), 6.55 (s, 1H), 5.39 (s, 2H), 5.32 (s, 2H), 3.85 (s, 3H), and 2.44 (s, 3H); ES-HRMS m/z 480.0340 (M+H C$_{20}$H$_{17}$N$_3$O$_4$BrF$_2$ requires 480.0365).

Example 397

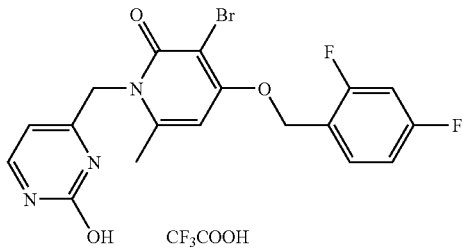

3-Bromo-4-[(2,4-difluorobenzyl)oxy]-1-[(2-hydroxypyrimidin-4-yl)methyl]-6-methylpyridin-2(1H)-one trifluoroacetate A mixture of 4-{[3-Bromo-4-[(2,4-difluorobenzyl)oxy]-6-methyl-2-oxopyridin-1(2H)-yl]methyl}pyrimidine-2-carbonitrile trifluoroacetate (0.2 g, 0.00035 mol) potassium fluoride on aluminum oxide (0.25 g) in t-butanol (5.0 mL) was refluxed for 4 h under argon atmosphere. The reaction mixture was cooled, filtered the precipitate and washed with ethanol. The combined filtrate and washings were concentrated to dryness and the residue was purified by reverse-phase HPLC using 10–90% acetonitrile/water gradient (30 min) at a flow rate of 100 mL/min. The appropriate fractions (m/z=452) were combined and freeze dried to afford the title compound (0.05 g) as a white powder:

$^1$H NMR (DMSO-d$_6$/400 Mz) δ 7.85 (d, 1H J=6.4 Hz), 7.64 (m, 1H), 7.30 (m 1H), 7.15 (m 1H), 6.55 (s, 1H), 6.22 (d, 1H, J=6.4 Hz), 5.28 (s, 2H), 5.12 (d, 2H), and 2.29 (s, 3H); $^{19}$F-NMR (DMSO-d$_6$/400 MHz) δ–109.69 (m), and –113.67 (m); ES-HRMS m/z 438.0228 (M+H C$_{18}$H$_{15}$N$_3$O$_3$BrF$_2$ requires 438.0259).

Example 398

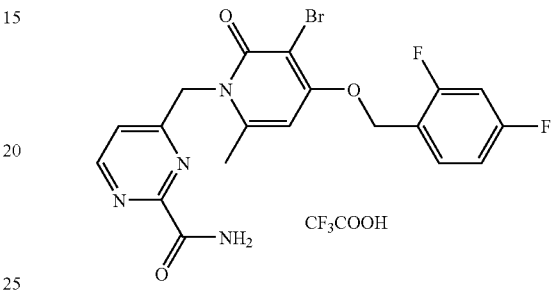

4-{[3-bromo-4-[(2,4-difluorobenzyl)oxy]-6-methyl-2-oxopyridin-1(2H)-yl]methyl}pyrimidine-2-carboxamide trifluoroacetate The title compound was obtained by a procedure described for Example 397. $^1$H NMR (DMSO-d$_6$/400 MHz) δ 8.82 (d, 1H J=5.2 Hz), 8.01 (br, 1H), 7.79 (br 1H), 7.64 (m, 1H), 7.34 (m , 2H), 7.16 (m 1H), 6.62 (s, 1H), 5.36 (s, 2H), 5.30 (s, 2H), and 2.38 (s, 3H); $^{19}$F NMR (DMSO-d$_6$/400 MHz) δ–109.64 (m), and –113.66 (m) ES-HRMS m/z 465.0385 (M+H C$_{19}$H$_{16}$N$_4$O$_3$BrF$_2$ requires 465.0368).

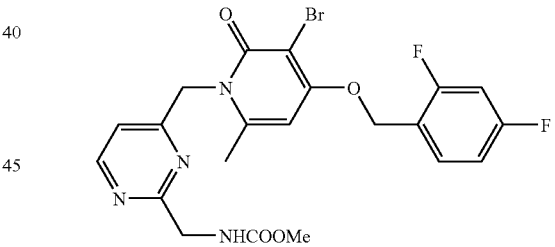

Example 399

Methyl (4-{[3-bromo-4-[(2,4-difluorobenzyl)oxy]-6-methyl-2-oxopyridin-1(2H)-yl]methyl}pyrimidin-2-yl)methylcarbamate To a solution of 4-{[2-(Aminomethyl)-4-fluorobenzyl]oxy}-3-bromo-1-(2,6-difluorophenyl)-6-methylpyridin-2(1H)-one trifluoroacetate (0.13 g, 0.00023 mol) in dimethylacetamide (1.0 mL), was added triethylamine (0.04 mL, 0.0003 mol), followed by the addition of methylchloroformate (0.05 mL) and stirred at 0° C. for 30 min under argon atmosphere. The reaction mixture was diluted with water (10 mL) and extracted with EtOAc (2×20 mL), The combined organic extracts were washed with water, dried (Na$_2$SO$_4$) and concentrated to dryness. The resulting residue was purified by flash chromatography (5% MeOH in EtOAc) to afford the title compound (0.055 g, 37%) as pale yellow powder: $^1$H NMR (DMSO-$d_6$/400 MHz) δ 8.65 (d, 1H J 5.6 Hz), 7.63 (1H), 7.5 (m, 1H), 7.28 (m 1H), 7.13 (m, 2H), 6.59 (s, 1H), 5.28 (s, 4H), 5.26 (d, 2H, J=6.0 Hz), and 2.46 (s, 3H); $^{19}$F NMR (DMSO-$d_6$/400 MHz) δ−109.64 (m), and −113.71 (m); ES-HRMS m/z 509.0621 (M+H $C_{21}H_{20}N_4O_4BrF_2$ requires 509.0630).

Example 400

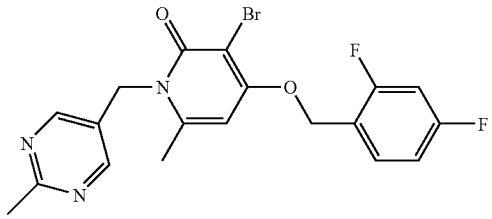

3-Bromo-4-[(2,4-difluorobenzyl)oxy]-6-methyl-1-[(5-methylpyrazin-2-yl)methyl]pyridin-2(1H)-one Step 1

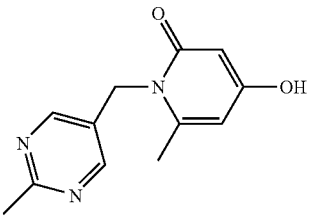

4-hydroxy-6-methyl-1-[(5-methylpyrazin-2-yl)methyl]pyridin-2(1H)-one

A mixture of 4-hydroxy-6-methyl-2-pyrone (5.0 g, 0.04 mol) and 5-aminomethyl-2-methylpyrazine (5.0 g, 0.041 mol) in water (25.0 ml) was heated at 100° C. for 1 h under argon atmosphere. The reaction mixture was cooled, and filtered the yellow precipitate. It was washed with ethanol, and dried in vacuo to afford the title compound (5.8 g, 63%) as a pale yellow powder: $^1$H NMR (DMSO-$d_6$/400 MHz) δ 10.43 (br, 1H), 8.38 (d, 2H, J=5.2 Hz), 5.77 (d, 1H, J=2.0 Hz), 5.58 (d, 1H, J=2.0 Hz), 4.92 (s, 2H), 2.24 (s, 3H), and 2.22 (s, 3H); ES MS m/z 232 (M+H)

Step 2

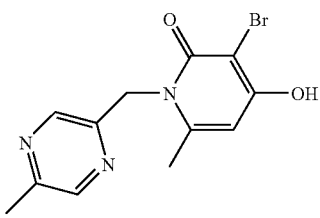

3-Bromo-4-hydroxy-6-methyl-1-[(5-methylpyrazin-2-yl)methyl]pyridin-2(1H)-one

The title compound was prepared by a procedure described in step 2 for Example 385.

Yield: 64%, $^1$H NMR (CD$_3$OD/400 MHz) δ 8.47 (s, 1H), 8.42 (s, 1H), 6.07 (s, 1H), 5.38 (s, 2H), 2.51 (s, 3H), and 2.44 (s, 3H), ES MS m/z 310 and 312 (M+H)

Step 3

To a mixture of 3-Bromo-4-hydroxy-6-methyl-1-[(5-methylpyrazin-2-yl)methyl]pyridin-2(1H)-one (0.45 g, 0.0015 mol), and potassium carbonate (0.25 g, 0.0018 mol) in dimethylacetamide (5.0 mL) was added 2,4 difluorobenzyl bromide (0.25 mL. 0.0019 mol)and stirred at room temperature under argon for 1 h. Dimethylacetamide was distilled in vacuo and the residue was partitioned between CH$_2$Cl$_2$ (20 mL) and water (20 mL). The organic phase was washed with water, dried (Na$_2$SO$_4$) and concentrated under reduced pressure. The resulting material was purified by flash chromatography (EtOAc/hexane 4:1 v/v) as the eluent. The appropriate fractions (m/z=451/453) were combined and concentrated under reduced pressure to give a white (0.25 g, 38%)solid. $^1$H NMR (CD$_3$OD/400 MHz) δ 8.49 (s, 1H), 8.40 (s, 1H), 7.60 (m, 1H), 6.99 (m, 2H), 6.51 (s, 1H), 5.42 (s, 2H), 5.29 (s, 2H), 2.54 (s, 3H), and 2.50 (s, 3H); $^{19}$F NMR (CD$_3$OD/400 MHz) δ−117.70 (m), and −116.09 (m); ES-HRMS m/z 436.0439 (M+H $C_{19}H_{17}N_3O_2BrF_2$ requires 436.0467).

Example 401

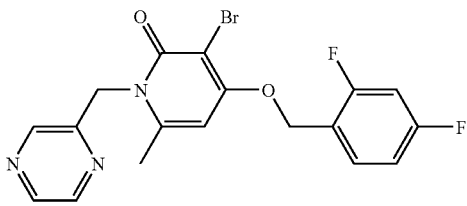

3-bromo-4-[(2,4-difluorobenzyl)oxy]-6-methyl-1-(pyrazin-2-ylmethyl)pyridin-2(1H)-one Step 1

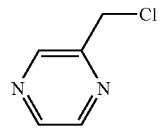

2-Chloromethylpyrazine

A mixture of 2-methylpyrazine (3.5 g, 0.037 mol), NCS (6.3 g, 0.047 mol) and benzoyl peroxide (0.05 g) was heated to reflux for 16 h under argon atmosphere. It was filtered and the filtrate was concentrated to dryness. The resulting residue was purified by flash chromatography using 30% EtOAc in hexane to afford 2-chloromethylpyrazine as a dark colored liquid (1.7 g, 365): $^1$H NMR (CD$_3$OD/400 MHz) δ 8.75 (d, 1H, J=1.2 Hz), 8.58 (m, 1H), 8.56 (m, 1H), and 4.75 (s, 2H); ES MS m/z=129 (M+H).

Step 2

3-Bromo-4-[(2,4-difluorobenzyl)oxy]-6-methylpyridin-2 (1H)-one (1.8 g, 0.0055 mol) and 2-chloropyrazine (0.8 g, 0.00625) were suspended in THF (25 mL), then added NaH (0.15 g, 0.0062 mol), KI (0.1 g) and the mixture was heated at 65° C. under argon atmosphere for 16 h. The reaction mixture was cooled, added acetic acid (0.5 mL) and concentrated to dryness under reduced pressure. The residue was stirred with a mixture of water (50 mL) and EtoAc (25 mL) and filtered the precipitate. It was washed with water, and acetonitrile an dried in vacuo to afford 1.7 g of light brown powder. $^1$H NMR (CD$_3$OD/400 MHz) δ 8.65 (d, 1H), 8.49 (m, 1H), 8.47 (m, 1H), 7.61 (~q, 1H), 7.02 (m, 2H), 6.52 (s, 1H), 5.47 (s, 2H), 5.23 (s, 2H), and 2.53 (s, 3H); $^{19}$F NMR (CD$_3$OD/400 MHz) δ −111.72 (m), and −116.07 (m); ES-HRMS m/z 422.0283 (M+H C$_{18}$H$_{15}$N$_3$O$_2$BrF$_2$ requires 422.0310).

Example 402

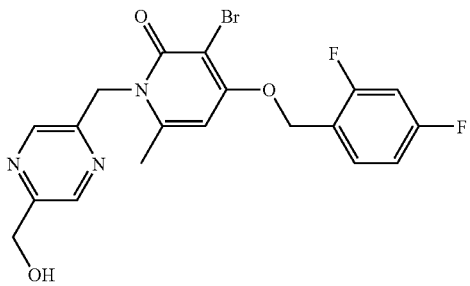

3-Bromo-4-[(2,4-difluorobenzyl)oxy]-1-{[5-(hydroxymethyl)pyrazin-2-yl]methyl}-6-methylpyridin-2(1H)-one Step 1

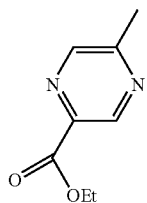

Ethyl 5-methylpyrazine-2-carboxylate

A solution of 5-methylpyrazine-2-carboxylic acid (15.0 g, 0.109 mol) in ethanol (70.0 mL) containing (1.5 g, 0.0079 mol) was heated to reflux for 4 h under argon atmosphere. The dark colored solution was cooled, added sod.bicarbonate (1.0 g) and concentrated under reduced pressure. The residue was partitioned between water (50 mL) and EtOAc (100 mL). The organic layer was washed with water (2×25 mL), dried (Na$_2$SO$_4$), and concentrated under reduced pressure to afford ethyl 5-methylpyrazine-2-carboxylate (12.05 g, 67%) as an orange colored liquid: $^1$H NMR (CD$_3$OD/400 MHz) δ 9.1 (d, 1H, J=1.2 Hz), 8.62 (d, 1H, J=1.2 Hz), 4.45 (q, 2H, J=7.2 Hz), 2.63 (s, 3H), and 1,41 (t, 3H, J=7.2 Hz); ES MS m/z 167 (M+H).

Step 2

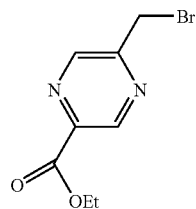

Ethyl 5-(bromomethyl)pyrazine-2-carboxylate

A solution of ethyl 5-methylpyrazine-2-carboxylate (12.0 g, 0.072 mol) in glacial acetic acid (60 mL) containing bromine (4.0 mL) was heated at 80° C. under anhydrous conditions for 45 min. After the removal of acetic acid in vacuo, the residue was partitioned between saturated, bicarbonate (100 mL) and EtOAc (3×30 mL). The combined EtOAc extracts were washed with water (2×25 mL), dried (Na$_2$SO$_4$), and concentrated under reduced pressure. The resulting liquid was purified by flash chromatography (20% EtOAc in hexane) to afford ethyl-(5-bromomethylpyrazine-2-carboxylate (7.7 g, 44%) as an orange colored liquid: $^1$H NMR (CD$_3$OD/400 MHz) δ 9.18 (d. 1H, J=1.2 Hz) 8.85 (d, 1H, J=1.2 Hz), 4.71 (d, 2H), 4.47 (q, 2H, J=7.2 Hz), and 1.42 (t, 3H, J=7.2 Hz); ES-HRMS m/z 244.9942 (M+H C$_8$H$_{10}$N$_2$O$_2$Br requires 244.9920).

Step 3

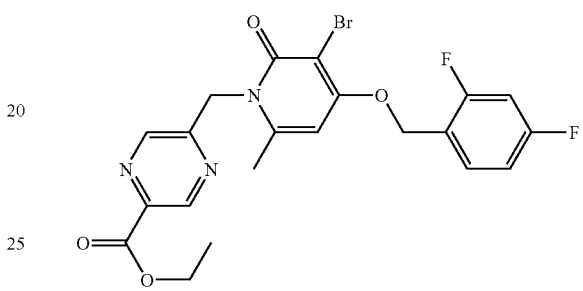

Ethyl 5-{[3-bromo-4-[(2,4-difluorobenzyl)oxy]-6-methyl-2-oxopyridin-1(2H)-yl]methyl}pyrazine-2-carboxylate To a mixture of 3-bromo-4-[(2,4-difluorobenzyl)oxy]-6-methylpyridin-2(1H)-one (6.0 g, 0.018 mol) and ethyl 5-(bromomethyl)pyrazine-2-carboxylate (4.9 g, 0.02 mol) in THF (50.0 mL) was added NaH (0.5 g) and heated at 55° C. under argon atmosphere for 3 h. The reaction mixture was cooled, added acetic acid (1.2 ml)and concentrated under reduced pressure. The residue was triturated with water and filtered the solid. It was washed with water, followed by ethanol and dried in vacuo to afford the title compound (3.0 g, 78%)as alight brown powder: $^1$H NMR (CD$_3$OD/400 MHz) δ 9.10 (d. 1H, J=1.2 Hz), 8.77 (d, 1H, J=1.2 Hz), 7.61 (m, 1H), 7.01 (m 2H), 6.54 (s, 1H), 5.54 (s, 2H), 5.30 (s, 2H), 4.43 (q, 2H, J=6.8 Hz), 2.52 (s, 3H), and 1,39 (t, 3H, J=6.8 Hz); $^{19}$F NMR (CD$_3$OD/400 MHz) δ−111.64 (m), and −116.04 (m); ES-HRMS m/z 494.0482 (M+H C$_{21}$H$_{19}$N$_3$O$_4$BrF$_2$ requires 494.0522).

Step 4

To a suspension of ethyl 5-{[3-bromo-4-[(2,4-difluorobenzyl)oxy]-6-methyl-2-oxopyridin-1(2H)-yl]methyl}pyrazine-2-carboxylate (2.0 g, 0.004 mol) in t-butanol (15,0 mL and THF (5.0 mL) was added NaBH$_4$ (0.18 g, 0.0047 mol) and the mixture was stirred at room temperature for 16 h under argon atmosphere. It was cooled, added MeOH (5.0 mL) and acetic acid (1.0 mL) and concentrated to dryness. The residue was triturated with water and filtered. It was washed with water, dried in vacuo and purified by flash chromatography (1% MeOH in EtOAc to afford the title compound (0.75 g, 41%) as a pale yellow powder: $^1$H NMR (CD$_3$OD/400 MHz) δ 8.58 (d. 1H, J=1.6 Hz), 8.56 (d, 1H, J=1.6 Hz), 7.6 (m, 1H), 7.01 (m, 2H), 6.52 (s, 1H), 5.46 (s, 2H), 5.29 (s, 2H), 4.71 (s, 2H), and 2.54 (s, 3H); $^{19}$F NMR (CD$_3$OD/400 MHz) δ−111.70 (m), and −116.06 (m); ES-HRMS m/z 452.0394 (M+H C$_{19}$H$_{17}$N$_3$O$_3$BrF$_2$ requires 452.0416).

Example 403

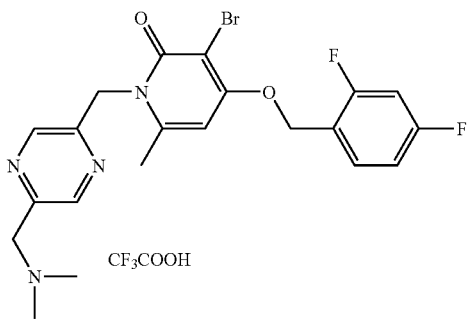

3-Bromo-4-[(2,4-difluorobenzyl)oxy]-1-({5-[(dimethylamino)methyl]pyrazin-2-yl}methyl)-6-methylpyridin-2(1H)-one trifluoroacetate Step 1

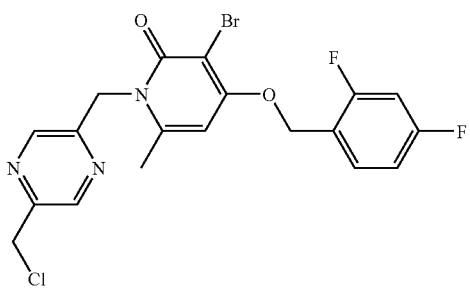

3-Bromo-1-{[5-(chloromethyl)pyrazin-2-yl]methyl}-4-[(2,4-difluorobenzyl)oxy]-6-methylpyridin-2(1H)-one Cyanurylchloride (0.42 g, .0023 mol) was added to DMF (0.52 mL) and stirred at room temperature for 15 min. Then added dichloromethane (15 mL) followed by the addition of 3-Bromo-4-[(2,4-difluorobenzyl)oxy]-1-{[5-(hydroxymethyl)pyrazin-2-yl]methyl}-6-methylpyridin-2(1H)-one 1.0 g, 0.0022 mol) and reaction mixture was stirred at room temperature under argon atmosphere. After 1 h, an additional 1.0 mL of DMF was added and the reaction was allowed to proceed for another hour, when a clear solution was obtained. The solution was diluted with dichloromethane (20 mL) and washed with water, dried (Na$_2$SO$_4$), and concentrated to dryness under reduced pressure. The residue was triturated with EtOAc, filtered, washed with EtOAc and dried to afford 0.79 g (77%) of the title compound as a pale yellow powder: $^1$H NMR (CD$_3$OD/400 MHz) δ 8.66 (s, 2H), 7.73 (m, 1H), 7.05 (m, 2H), 6.56 (s, 1H), 5.52 (s, 2H), 5.33 (s, 2H), 4.74 (s, 2H), and 2.57 (s, 3H); ES-HRMS m/z 470.0051 (M+H C$_{19}$H$_{16}$N$_3$O$_2$BrClF$_2$ requires 470.0077).

Step 2

A suspension of 3-Bromo-1-{[5-(chloromethyl)pyrazin-2-yl]methyl}-4-[(2,4-difluorobenzyl)oxy]-6-methylpyridin-2(1H)—one (0.25 g, 0.00053 mol) in THF (1.0 mL) was treated with N, N,-dimethyl amine (1.0 mL of 2M soln in THF) and stirred at room temperature for 16 h. The reaction mixture was concentrated and the title compound was isolated by reverse-phase HPLC using 10–90% acetonitrile/water gradient (30 min) at a flow rate of 100 mL/min. The appropriate fractions (m/z=479) were combined and freeze dried to afford the title compound (0.27 g, 87%) as a white powder: $^1$H NMR (CD$_3$OD/400 MHz) δ 8.78 (d. 1H, J Hz), 8.56 (d, 1H, J=1.2 Hz), 7.61 (m 1H), 7.01 (m, 2H), 6.55 (s, 1H), 5.49 (s, 2H), 5.30 (s, 2H), 4.52 (s, 2H), 2.94 (s, 6H) and 2.57 (s, 3H); $^{19}$F NMR (CD$_3$OD)=δ−111.56 (m) and −116.02 (m); ES-HRMS m/z 479.0885 (M+H C$_{21}$H$_{22}$N$_4$O$_2$BrF$_2$ requires 479.0889).

Example 404

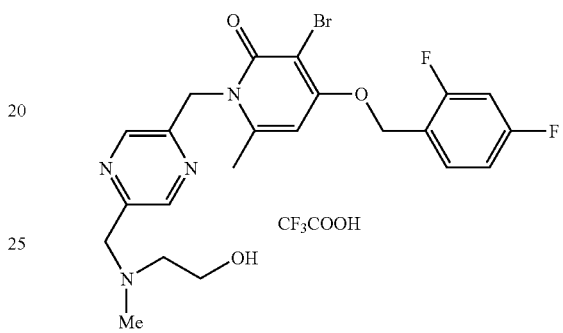

3-Bromo-4-[(2,4-difluorobenzyl)oxy]-1-[(5-{[(2-hydroxyethyl)(methyl)amino]-methyl}pyrazin-2-yl)methyl]-6-methylpyridin-2(1H)-one trifluoroacetate The title compound was prepared in a similar manner as described for Example 403, substituting N-methylaminoethanol for N,N-dimethylamine. Yield= 78%, $^1$H NMR (CD$_3$OD/400 MHz) δ 8.78 (d. 1H, J Hz), 8.59 (d. 1H, J=1.2 Hz), 7.6 (m, 1H), 7.01 (m, 2H), 6.55 (s, 1H), 5.49 (s, 2H), 5.30 (s, 2H), 3.89 (~t, 2H), 2.97 (s, 3H), and 2.57 (s, 3H); $^{19}$F NMR (CD$_3$OD/400 MHz)=δ−111.56 (m) and −116.04 (m); ES-HRMS m/z 509.0964 (M+H C$_{22}$H$_{24}$N$_4$O$_3$BrF$_2$ requires 509.0994).

Example 405

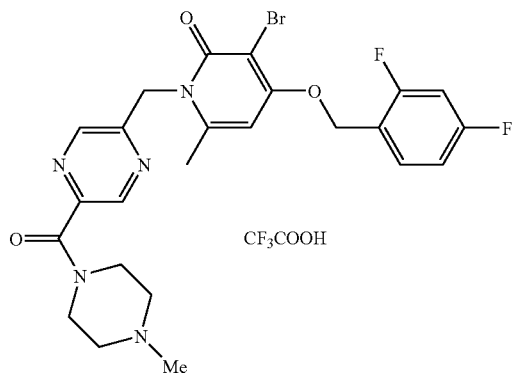

3-Bromo-4-[(2,4-difluorobenzyl)oxy]-6-methyl-1-({5-[(4-methylpiperazin-1-yl)carbonyl]pyrazin-2-yl}methyl)pyridin-2(1H)-one trifluoroacetate Step 1

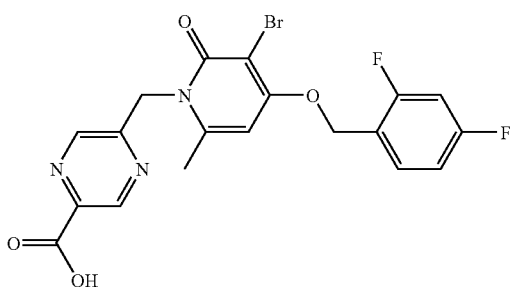

5-{[3-Bromo-4-[(2,4-difluorobenzyl)oxy]-6-methyl-2-oxopyridin-1(2H)-yl]methyl}pyrazine-2-carboxylic acid A suspension of ethyl 5-{[3-bromo-4-[(2,4-difluorobenzyl)oxy]-6-methyl-2-oxopyridin-1(2H)-yl]methyl}pyrazine-2-carboxylate (0.18 g, 0.002 mol) and 1N NaOH (0.6 mL in 1:1 v/v EtOH/Water) was stirred at room temperature for 1.5 h. The reaction mixture was acidified with 5% citric acid and filtered the precipitate. It was washed with water, followed by ethanol and dried in vacuo to afford the title compound (0.14 g, 77%) as a light brown powder: $^1$H NMR (CD$_3$OD/400 MHz)=δ 9.03 (s. 1H), 8.60 (s, 1H), 7.61 (m. 1H), 7.00 (m, 2H), 6.52 (s, 1H), 5.51 (s, 2H), 5.30 (s. 2H), and 2.52 (s, 3H); $^{19}$F NMR (CD$_3$OD/400 MHz)= δ−111.75 (m) and −116.06 (m); ES-HRMS m/z 466.0209 (M+H C$_{19}$H$_{15}$N$_4$O$_3$BrF$_2$ requires 466.0209).

Step 2

To a solution of 5-{[3-Bromo-4-[(2,4-difluorobenzyl)oxy]-6-methyl-2-oxopyridin-1(2H)-yl]methyl}pyrazine-2-carboxylic acid (0.28 g, 0.0006 mol) in DMF (3.0 mL), at −15° C., was added isobutylchloroformate (0.082 g, 0.0006 mol), followed by the addition of N-methylmorpholine (0.06 g, 0.00063 mol) and stirred under argon for 15 min. N-methylpiperazine (0.072 g, 0.00072 mol) in DMF (2.0 mL) was then added to the reaction and the mixture was stirred at room temperature for 3 h. After the removal of the solvents in vacuo, the residue was purified by reverse-phase HPLC using 10–90% acetonitrile/water gradient (30 min) at a flow rate of 100 mL/min. The appropriate fractions (m/z=548) were combined and freeze dried to afford the title compound (0.32 g, 80%) as a white powder: $^1$H NMR (CD$_3$OD/400 MHz) δ 8.89 (d. 1H, J=1.6 Hz), 8.73 (d, 1H, J=1.6 Hz), 7.61 (m, 1H), 7.01 (m, 2H), 6.56 (s, 1H), 5.50 (s, 2H), 5.30 (s, 2H), 2.9 (s, 3H), and 2.57 (s, 3H); $^{19}$F NMR (CD$_3$OD/400 MHz)=δ−109.36 (m) and −114.91 (m); ES-HRMS m/z 548.1090 (M+H C$_{24}$H$_{25}$N$_5$O$_3$BrF$_2$ requires 548.1103).

Example 406

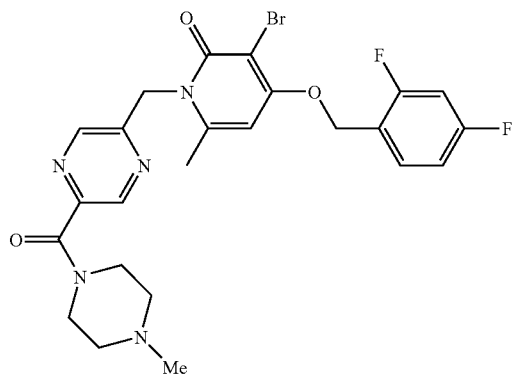

3-Bromo-4-[(2,4-difluorobenzyl)oxy]-6-methyl-1-({5-[(4-methylpiperazin-1-yl)carbonyl]pyrazin-2-yl}methyl)pyridin-2(1H)-one A solution of 3-Bromo-4-[(2,4-difluorobenzyl)oxy]-6-methyl-1-({5-[(4-methylpiperazin-1-yl)carbonyl]pyrazin-2-yl}methyl)pyridin-2(1H)-one trifluoroacetate (0.17 g, 0.00026 mol) in 0.1N NaOH (25 mL) was stirred at room temperature for 15 min. and extracted the product in ethyl acetate (2×20 mL). The combined organic extracts were washed with water (2×20 mL), dried (Na$_2$SO$_4$) and concentrated to dryness. The residue was dried in vacuo to afford the title product (0.09 g, 64%) as a white powder: $^1$H NMR (CD$_3$OD/400 MHz) δ 8.69 (d. 1H, J=1.2 Hz), 8.67 (d, 1H, J=1.2 Hz), 7.60 (m, 1H), 7.00 (m, 2H), 6.54 (s, 1H), 5.50 (s, 2H), 5.30 (s, 2H), 3.78 (t, 2H, J=4.8 Hz), 3.58 (t, 2H, J=4.8 Hz), 2.526 (s, 3H), 2.53 (t, 2H, J=4.8 Hz), 2.44 (t, 2H, J=4.8 Hz), and 2.31 (s, 3H); $^{19}$F NMR (CD$_3$OD/400 MHz)=δ− 111.65 (m) and −116.06 (m); ES-HRMS m/z 548.1123 (M+H C$_{24}$H$_{25}$N$_5$O$_3$BrF$_2$ requires 548.1103).

Example 407

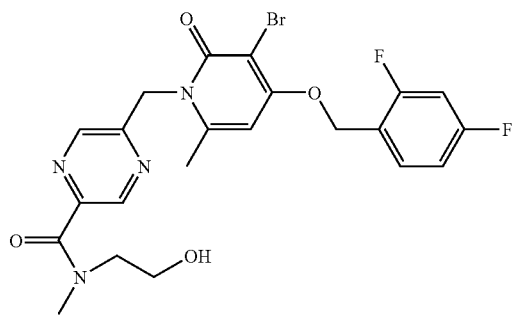

5-{[3-Bromo-4-[(2,4-difluorobenzyl)oxy]-6-methyl-2-oxopyridin-1(2H)-yl]methyl}-N-(2-hydroxyethyl)-N-methylpyrazine-2-carboxamide The title compound was prepared in a similar manner as described for Example 405, substituting N-methylpiperazine by N-methylethanolamine. Yield=60%, $^1$H NMR (CD$_3$OD/400 MHz) δ 8.69 (d. 1H, J=1.2 Hz), 8.64 (d. 1H, J=1.2 Hz), 7.61 (m, 1H), 7.00 (m, 2H), 6.54 (s, 1H), 5.49 (s. 2H), 5.30 (s, 2H), 3.81 (~t, 1H), 3.66 (m, 2H), 3.56 (t, 1H, J=5.2 Hz), 3.12 (d, 3H J=7.6 Hz), 2.56 (s, 3H); $^{19}$F NMR (CD$_3$OD/400 MHz) δ−109.64 (m) and −113.66 (m); ES-HRMS m/z 523.0743 (M+H C$_{22}$H$_{22}$N$_4$O$_4$BrF$_2$ requires 523.0797).

Example 408

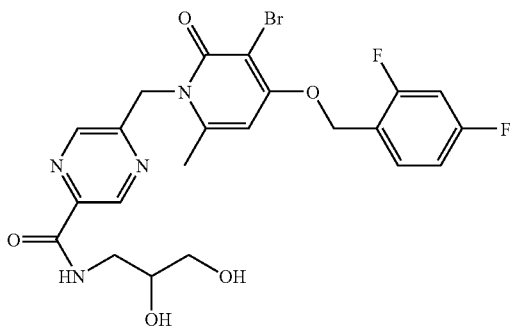

5-{[3-Bromo-4-[(2,4-difluorobenzyl)oxy]-6-methyl-
2-oxopyridin-1(2H)-yl]methyl}-N-(2,3-
dihydroxypropyl)pyrazine-2-carboxamide The title compound was prepared in a similar manner as described for EXAMPLE 405, substituting N-methylpiperazine by 3-amino-1,2-propanediol. Yield= 56%; $^1$H NMR (CD$_3$OD/400 MHz) δ 9.09 (d. 1H, J=1.2 Hz), 8.70 (d. 1H, J=1.2 Hz), 7.60 (m, 1H), 7.00 (m, 2H), 6.54 (s, 1H), 5.53 (s. 2H), 5.30 (s, 2H), 3.80 (m, 1H), 3.61 (dd, 1H), 5.53 (d, 2H), J=5.2 Hz), 3.42 (dd, 1H), and 2.55 (s, 3H); $^{19}$F NMR (CD$_3$OD/400 MHz) δ−109.65 (m), and −113.67 (m); ES-HRMS m/z 539.0703 (M+H C$_{22}$H$_{22}$N$_4$O$_4$BrF$_2$ requires 539.0736).

Example 409

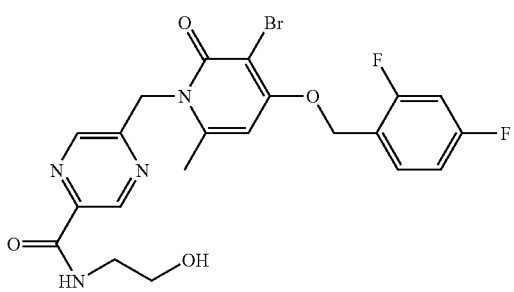

5-{[3-Bromo-4-[(2,4-difluorobenzyl)oxy]-6-methyl-
2-oxopyridin-1(2H)-yl]methyl}-N-(2-hydroxyethyl)
pyrazine-2-carboxamide The title compound was prepared in a similar manner as described for EXAMPLE 405, substituting N-methylpiperazine by 2-aminoethanol. Yield=46%; $^1$H NMR (CD$_3$OD/400 Hz) δ 9.08 (d. 1H, J=1.2 Hz), 8.70 (d, 1H, J=1.2 Hz), 7.601 (m, 1H), 7.01 (m, 2H), 6.54 (s, 1H), 5.53 (s, 2H), 5.30 (s, 2H), 3.69 (t, 2H, J=6.0 Hz), 3.53 (t, 2H, J=6.0 Hz), 2.55 (s, 3H); $^{19}$F NMR (CD$_3$OD/400 Hz) δ−111.67 (m) and −116.07 (m); ES-HRMS m/z 509.0616, (M+H C$_{21}$H$_{20}$N$_4$O$_4$BrF$_2$ requires 509.0630).

Example 410

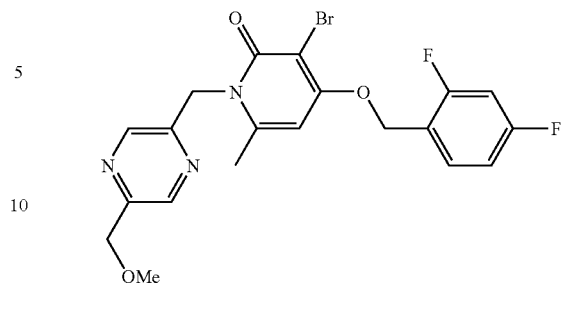

3-Bromo-4-[(2,4-difluorobenzyl)oxy]-1-{[5-
(methoxymethyl)pyrazin-2-yl]methyl}-6-
methylpyridin-2(1H)-one To a solution of 3-Bromo-4-[(2,4-difluorobenzyl)oxy]-1-{[5-(hydroxymethyl)pyrazin-2-yl]methyl}-6-methylpyridin-2(1H)-one (0.35 g, 0.00078 mol) in DMF at 0° C., was added NaH (0.022 g, 0.00092 mol) and stirred for 10 min. Iodomethane (0.05 mL) was added to the reaction and the mixture was stirred at 10° C. for 3 h. DMF was distilled in vacuo and the residue was partitioned between 5% citric acid and EtOAc (15.0 mL). The organic phase was washed with water, dried (Na$_2$SO$_4$) and concentrated to dryness. The residue was purified by flash chromatography (EtOAc), and the appropriate fractions were combined and concentrated to a pale yellow powder.

$^1$H NMR (CD$_3$OD/400 MHz) δ 8.59 (s), 8.55 (s, 1H), 7.60 (m, 1H), 6.99 (m, 2H), 6.52 (s, 1H), 5.47 (s, 2H), 5.30 (s, 2H), 4.57 (s, 2H), 3.44 (s, 2H), and 2.54 (s, 3H); $^{19}$F NMR (CD$_3$OD/400 Hz) δ−111.69 (m) and −116.09 (m); ES-HRMS m/z 466.0577 (M+H C$_{21}$H$_{19}$N$_3$O$_3$BrF$_2$ requires 466.0572).

Example 411

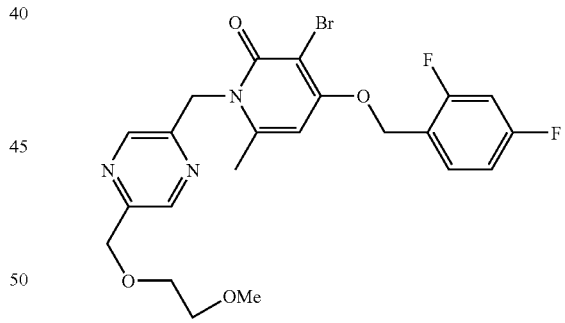

3-Bromo-4-[(2,4-difluorobenzyl)oxy]-1-({5-[(2-
methoxyethoxy)methyl]pyrazin-2-yl}methyl)-6-
methylpyridin-2(1H)-one To a solution of 3-Bromo-4-[(2,4-difluorobenzyl)oxy]-1-{[5-(hydroxymethyl)pyrazin-2-yl]methyl}-6-methylpyridin-2(1H)-one (0.25 g, 0.00055 mol) in dimethyl acetamide at 0° C., was added NaH (0.016 g, 0.00067 mol) and stirred for 15 min. 2-Methoxyethyl bromide (0.09 g, 0.00–65 mol) was then added , and the mixture was stirred at room temperature for 6 h. Dimethylacetamide was distilled in vacuo and the product was purified by reverse-phase HPLC using 10–90% acetonitrile/water gradient (30 min) at a flow rate of 100 mL/min. The appropriate fractions (m/z=510) were combined and freeze dried to afford the title compound (0.32 g, 80%) as a white powder:

$^1$H NMR (CD$_3$OD/400 Hz) δ 8.59 (s. 1H), 8.58 (s, 1H), 7.60 (m , 1H), 7.02 (m, 2H), 6.52 (s, 1H), 5.45 (s, 2H), 5.29 (s, 2H), 4.67 (s, 2H), 3.71 (~t, 2H,), 3.57 (~t, 2H), 3.34 (s, 3H), and 2.54 (s, 3H); ES-HRMS m/z 510.0852 (M+H C$_{20}$H$_{18}$N$_4$O$_4$BrF$_2$ requires 510.0835).

Example 412

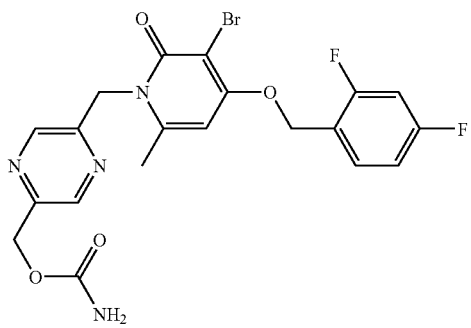

(5-{[3-Bromo-4-[(2,4-difluorobenzyl)oxy]-6-methyl-2-oxopyridin-1(2H)-yl]methyl}pyrazin-2-yl)methyl carbamate To a suspension of 3-Bromo-4-[(2,4-difluorobenzyl)oxy]-1-{[5-(hydroxymethyl)pyrazin-2-yl]methyl}-6-methylpyridin-2(1H)-one (0.21 g, 0.00055 mol) in THF (5.0 mL) and DMF (2.0 mL), was added 4-nitrophenylchloroformate (0.1 g, 0.0005 mol) and cooled to 0° C. triethylamine (0.052 g, 0.0005 mol) was then added, stirred at room temperature for 1 h, and at 65° C. for an additional 1 h. It was cooled in an ice bath and added 2M ammonia in propanol (1.0 mL) and stirred at room temperature for 2 h. After the removal of the solvents under reduced pressure, the residue was partitioned between 5% sod. bicarbonate, and EtOAc (25 mL). The organic phase was washed with 5% sod. bicarbonate, (3×25 mL), water (3×25 mL), dried (Na$_2$SO$_4$) and concentrated under reduced pressure. The resulting substance was purified by isolated by reverse-phase HPLC using 10–90% CH$_3$CN/Water (30 min gradient) at a flow rate of 100 mL/min. The appropriate fractions (m/z=495 M+H) were combined and freeze-dried, and the residue was partitioned between 5% sod. bicarbonate (20 mL) and EtOAc (25 mL). The organic phase was washed with water, dried (Na$_2$SO$_4$) and concentrated to dryness under reduced pressure, to afford the title compound as a white powder (0.065 g):

$^1$H NMR (CD$_3$OD/400 MHz) δ 8.61 (br s, 1H), 8.54 (br s, 1H), 7.60 )m 1H), 7.02 (m, 2H), 6.52 (s, 1H), 5.47 (s, 2H), 5.29 (s, 2H), 5.15 (s, 2H), and 2.54 (s, 3H): $^{19}$F NMR (CD$_3$OD) δ –111.70 (m), and –116.09 (m); ES-HRMS m/z 495.0449 (M+H C$_{20}$H$_{18}$N$_4$O$_4$BrF$_2$ requires 495.0474).

Example 413

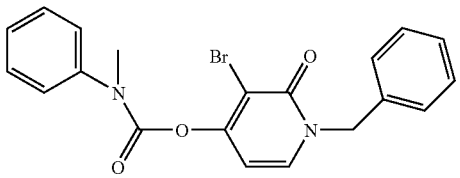

1-benzyl-3-bromo-2-oxo-1,2-dihydropyridin-4-yl methyl(phenyl)carbamate

Step 1. Preparation of 1-benzyl-2-oxo-1,2-dihydropyridin-4-yl methyl(phenyl)carbamate

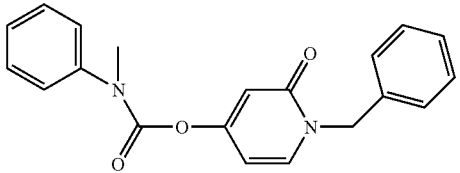

To a chilled solution of 1-benzyl-4-hydroxypyridin-2 (1H)-one (0.375 g, 1.86 mmol) in anhydrous acetonitrile (10 mL) was added triethylamine (0.206 g, 2.04 mmol) followed by N-methyl-N-phenylcarbamoyl chloride (0.379 g, 2.24 mmol). The reaction mixture was stirred under nitrogen atmosphere at 0° C. for 30 minutes then at room temperature for 1 hour. The reaction was monitored by TLC (5% methanol in dichloromethane). The solvent was removed under reduced pressure and the residue was washed with 10% citric acid and extracted with ethyl acetate. The organic extracts were combined, washed with water and dried over anhydrous Na$_2$SO$_4$. The solvent was removed under reduced pressure to afford a yellow syrup. The residue was purified by flash chromatography (silica gel) using 5% MeOH in CH$_2$Cl$_2$ to give the desired product (0.382 g, 61%) as a white semisolid. $^1$H-NMR (d$_6$-DMSO, 400 MHz) δ 7.8 (d, 1H, J=7.2 Hz), 7.39 (m, 10H), 6.19 (s, 2H), 5.03 (s, 2H), 3.29 (s, 3H); ES-HRMS m/z 335.1396 (M+H calculated for C$_{20}$H$_{19}$N$_2$O$_3$ requires 335.1418).

Step 2. Preparation of 1-benzyl-3-bromo-2-oxo-1,2-dihydropyridin-4-yl methyl(phenyl)carbamate

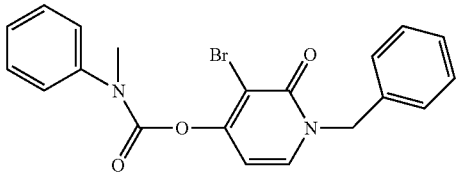

To a solution of 1-benzyl-2-oxo-1,2-dihydropyridin-4-yl methyl(phenyl)carbamate (0.38 g, 1.13 mmol) in anhydrous CH$_2$Cl$_2$ (7 mL) was added N-Bromosuccinimide (NBS, 0.24 g, 1.34 mmol). The reaction was stirred overnight at room temperature under nitrogen atmosphere. The reaction mixture was purified by flash chromatography (silica gel) using ethyl acetate/hexane (1:1 v/v). The appropriate fractions were collected according to ES MS (M+H 413) and concentrated. The dried product showed about 14% of di-bromonated product by analytical HPLC. The compounds were separated by reverse phase HPLC using a 10–90% acetonitrile in water (30 minute gradient) at a 100 mL/min flow rate to afford (after lyophilization) the salt of the desired compound. The salt was diluted in ethyl acetate and washed with NaHCO₃. The organic extracts were dried over anhydrous Na₂SO₄ and concentrated to afford the desired compound (0.271 g, 58%) as a beige solid. ¹H-NMR (d₆-DMSO, 400 MHz) δ 7.94 (d, 1H, J=7.2 Hz), 7.29 (m, 10H), 6.48 (s, 1H), 5.12 (s, 2H), 3.33 (s, 3H); ES-HRMS m/z 413.0495 (M+H calculated for $C_{20}H_{18}O_3Br$ requires 413.0496).

Example 414

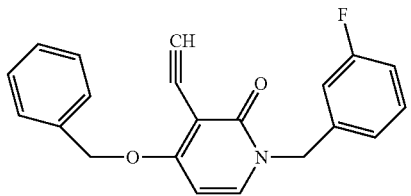

4-(benzyloxy)-3-ethynyl-1-(3-fluorobenzyl)pyridin-2(1H)-one

Step 1. Preparation of 4-(benzyloxy)-1-(3-fluorobenzyl)-3-iodopyridin-2(1H)-one

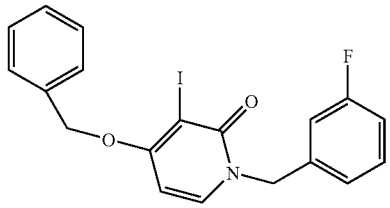

A mixture of 4-(benzyloxy)-1-(3-fluorobenzyl)pyridin-2(1H)-one (4.83 g, 15.6 mmol) in anhydrous acetonitrile (55 mL) and N-iodosuccinimide (NIS, 3.86 g, 17.1 mmol) was heated at 65° C. under nitrogen for 4 hours. The reaction mixture was concentrated under reduced pressure and the residue was purified by flash chromatography (silica gel) using ethyl acetate/hexane (1:1 v:v). The appropriate fractions were collected according to ES MS (M+H 436) and washed with Na₂SO₃ to remove the color impurities. The fractions were concentrated under reduced pressure and dried in vacuo to afford the desired product (6.15 g, 90%) as a light yellow solid. ¹H-NMR (CD₃OD, 400 MHz) δ 7.73 (d, 1H, J=7.6 Hz), 7.47 (d, 2H, J=7.2 Hz), 7.39 (m, 4H), 7.08 (m, 3H), 6.39 (d, 1H, J=8.0 Hz), 5.29 (s, 2H), 5.19 (s, 2H); ES-HRMS m/z 436.0210 (M+H calculated for $C_{19}H_{16}NO_2FI$ requires 436.0196).

Step 2. Preparation of 4-(benzyloxy)-1-(3-fluorobenzyl)-3-[(trimethylsilyl)ethynyl]pyridin-2(1H)-one

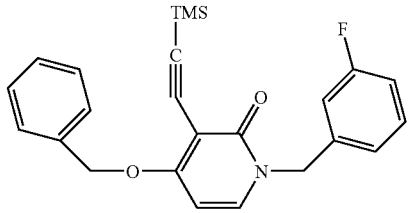

Degassed a solution of 4-(benzyloxy)-1-(3-fluorobenzyl)-3-iodopyridin-2(1H)-one (2.01 g, 4.62 mmol) in anhydrous acetonitrile (25 mL) under argon atmosphere. Triethylamine (1.11 g, 11 mmol) was added and quickly degassed. The reaction mixture was chilled in an ice bath for 15 minutes before adding bistriphenylphosphine-palladium chloride (0.34 g, 0.48 mmol) and cuprous iodide (0.2 g). The reaction was stirred at room temperature for 30 minutes before heating at 60° C. under an atmosphere of argon for 2 hours. The reaction mixture was filtered through a bed of celite and the filtrate was concentrated under reduced pressure. The dark brown residue was diluted with CH₂Cl₂ (100 mL) and washed with water. The organic extracts were combined, dried over anhydrous Na₂SO₄, and concentrated under reduced pressure. The dark brown residue was purified by flash chromatography using 30% ethyl acetate in hexane. The appropriate fractions were combined and concentrated under reduced pressure to afford the desired product (1.34 g, 72%) as a light yellow solid. ¹H-NMR (CD₃OD, 400 MHz) δ 7.74 (d, 1H, J=7.6 Hz), 7.47 (d, 2H, J=7.6 Hz), 7.35 (m, 4H), 7.09 (m, 3H), 6.46 (d, 1H, J=7.6 Hz), 5.26 (s, 2H), 5.13 (s, 2H), 0.18 (s, 9H); ES-HRMS m/z 406.1638 (M+H calculated for $C_{24}H_{25}NO_2FSi$ requires 406.1610).

Step 3. Preparation of 4-(benzyloxy)-3-ethynyl-1-(3-fluorobenzyl)pyridin-2(1H)-one

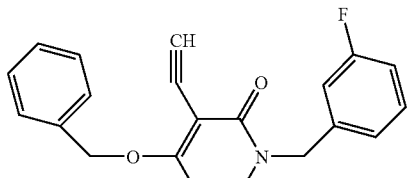

To a solution of 4-(benzyloxy)-1-(3-fluorobenzyl)-3-[(trimethylsilyl)ethynyl]pyridin-2(1H)-one (1.31 g, 3.2 mmol) in anhydrous acetonitrile (25 mL) at 0° C. was added tetrabutylammoniun fluoride (0.611 g, 1.93 mmol). The reaction was stirred at 0° C. for 15 minutes then for 1 hour at room temperature. The reaction was concentrated under reduced pressure and the residue was diluted with ethyl acetate and washed with water. The organic extracts were combined, dried over anhydrous Na₂SO₄ and concentrated under reduced pressure. The residue was purified by flash chromatography (silica gel) using ethyl acetate in hexane (1:1 v/v). The appropriate fractions were combined and concentrated under reduced pressure to afford the desired product (0.779 g, 72%) as a gold solid. ¹H-NMR (CD₃OD, 400 MHz) δ 7.73 (d, 1H, J=7.6 Hz), 7.43 (d, 2H, J=7.2 Hz), 7.35 (m, 4H), 7.09 (m, 3H), 6.45 (d, 1H, J=7.6 Hz), 5.27 (s, 2H), 5.13 (s, 2H), 3.78 (s, 1H); ES-HRMS m/z 334.1243 (M+H calculated for $C_{21}H_{17}NO_2F$ requires 334.1234).

Example 415

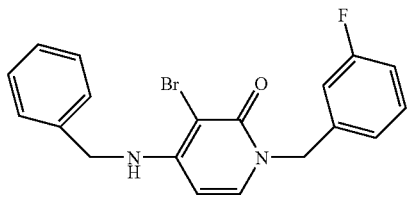

4-(benzylamino)-3-bromo-1-(3-fluorobenzyl) pyridin-2(1H)-one

Step 1. Preparation of 1-(3-fluorobenzyl)-4-hydroxypyridin-2(1H)-one

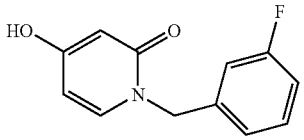

In a Fischer-Porter bottle, added a solution of 4-(benzyloxy)-1-(3-fluorobenzyl)pyridin-2(1H)-one (4.5 g, 14.56 mmol) in absolute ethanol (20 mL). Flushed the solution with nitrogen then added palladium catalyst (1.05 g, 10% Pd/C). Sealed bottle and evacuated system. The system was purged with hydrogen gas (2×15 psi) to check for leaks. The reaction was charged with hydrogen (35 psi) and stirred at room temperature for 45 minutes. The system was evacuated and flushed with nitrogen. The reaction was filtered and the catalyst was carefully washed with fresh ethanol. The filtrate was concentrated under reduced pressure. $^1$H-NMR (CD$_3$OD, 400 MHz) δ 7.54 (d, 1H, J=7.6 Hz), 7.32 (m, 1H), 7.06 (d, 1H, J=7.6 Hz), 6.99 (m, 2H), 6.05 (dd, 1H, J=2.4 Hz, 2.8 Hz), 5.83 (d, 1H, J=2.4 Hz), 5.09 (s, 2H); ES-HRMS m/z 220.0774 (M+H calculated for C$_{12}$H$_{11}$NO$_2$F requires 220.0787).

Step 2. Preparation of 4-(benzylamino)-1-(3-fluorobenzyl)pyridin-2(1H)-one

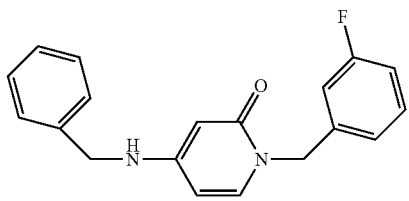

A mixture of 1-(3-fluorobenzyl)-4-hydroxypyridin-2(1H)-one (1.005 g, 4.5 mmol) in benzylamine (15 mL) was heated at reflux (185° C.) under nitrogen atmosphere for 24 hours. The reaction was monitored by ES-MS (MH+ 309). The solvent was removed by vacuum distillation to give a yellow residue. $^1$H-NMR (CD$_3$OD, 400 MHz) δ 7.31 (m, 7H), 7.03 (m, 3H), 5.98 (d, 1H, J=7.2 Hz), 5.45 (s, 1H), 5.00 (s, 2H), 4.30 (s, 2H); ES-HRMS m/z 309.1403 (M+H calculated for C$_{19}$H$_{18}$N$_2$°F. requires 309.1375).

Step 3. Preparation of 4-(benzylamino)-3-bromo-1-(3-fluorobenzyl)pyridin-2(1H)-one

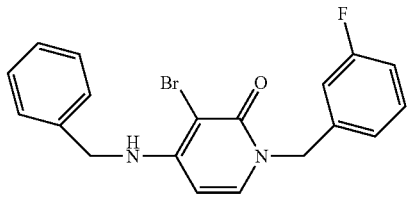

To a solution of 4-(benzylamino)-1-(3-fluorobenzyl) pyridin-2(1H)-one (0.50 g, 1.62 mmol) in anhydrous CH$_2$Cl$_2$ (10 mL) was added N-bromosuccinimide (NBS, 0.30 g, 1.7 mmol). The reaction was stirred at room temperature under a nitrogen atmosphere for 3 hours. The reaction mixture was purified by flash chromatography (silica gel) using ethyl acetate in hexane (1:1 v/v). The appropriate fractions were combined and concentrated. $^1$H-NMR (CD$_3$OD, 400 MHz) δ 7.41 (d, 1H, J=7.6 Hz), 7.31 (m, 6H), 7.04 (m, 3H), 5.99 (d, 1H, J=7.6 Hz), 5.08 (s, 2H), 4.53 (s, 2H); ES-HRMS m/z 387.0508 (M+H calculated for C$_{19}$H$_{17}$N$_2$OBrF requires 387.0504).

Example 416

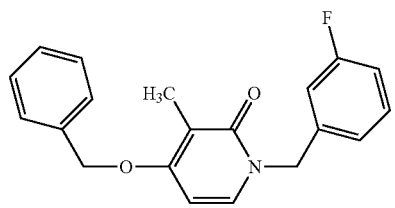

4-(benzyloxy)-1-(3-fluorobenzyl)-3-methylpyridin-2(1H)-one

Step 1. Preparation of 4-(benzyloxy)-1-(3-fluorobenzyl)-3-iodopyridin-2(1H)-one

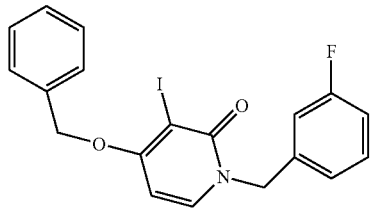

A mixture of 4-(benzyloxy)-1-(3-fluorobenzyl)pyridin-2(1H)-one (4.83 g, 15.6 mmol) and N-iodosuccinimide (NIS, 3.86 g, 17.1 mmol) in anhydrous acetonitrile (55 mL) was heated at 65° C. for 4 hours under nitrogen atmosphere. The reaction mixture was concentrated under reduced pressure and the residue was purified by flash chromatography (ethyl acetate/hexane 1:1 v/v). The appropriate fractions were collected according to ES MS (M+H 436) and washed with Na$_2$SO$_3$ to remove the color impurities. The fractions were concentrated under reduced pressure and dried in vacuo to afford the desired product (6.15 g, 90%) as a light yellow solid. $^1$H-NMR (CD$_3$OD, 400 MHz) δ 7.73 (d, 1H, J=7.6 Hz), 7.36 (m, 6H), 7.08 (m, 3H), 6.39 (d, 1H, J=8.0 Hz), 5.28 (s, 2H), 5.19 (s, 2H); ES-HRMS m/z 436.0196 (M+H calculated for C$_{19}$H$_{16}$NO$_2$FI requires 436.0210).

Step 2. Preparation of 4-(benzyloxy)-1-(3-fluorobenzyl)-3-methylpyridin-2(1H)-one

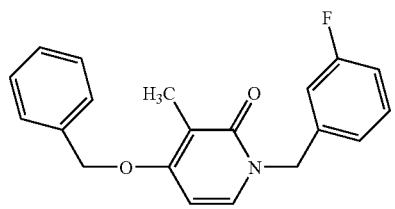

To a degassed solution of 4-(benzyloxy)-1-(3-fluorobenzyl)-3-iodopyridin-2(1H)-one (1.03 g, 2.36 mmol) in anhydrous DMF (15 mL) under argon atmosphere was added triethylamine (1.11 g, 11 mmol). The reaction mixture was chilled in an ice bath for 15 minutes before adding tetramethyl tin (2.10 g, 11.75 mmol) followed by bistriphenylphosphine-palladium chloride (0.166 g, 0.24 mmol). The reaction was stirred at room temperature for 30 minutes before heating at 950 C under an atmosphere of argon for 3 hours. The reaction mixture was filtered through a bed of celite and the filtrate was concentrated under reduced pressure. The dark brown residue was diluted with ethyl acetate (100 mL) and washed with water. The organic extracts were combined, dried over anhydrous $Na_2SO_4$, and concentrated under reduced pressure. The dark brown residue was purified by flash chromatography (30% ethyl acetate in hexane). The appropriate fractions were combined and concentrated under reduced pressure to afford the desired product (0.1758 g, 22%) as a light yellow solid. The product was further purified by reverse phase HPLC using a 10–90% acetonitrile/water (30 minute gradient) at a 100 mL/min flow rate, to afford a cleaner product as a light yellow solid (0.0975 g, 8%). $^1$H-NMR ($CD_3OD$, 400 MHz) δ 7.58 (d, 1H, J=7.6 Hz)), 7.35 (m, 6H), 6.98 (m, 3H), 6.46 (d, 1H, J=7.6 Hz), 5.19 (s, 2H), 5.15 (s, 2H), 2.0 (s, 3H); ES-HRMS m/z 324.1366 (M+H calculated for $C_{20}H_{19}NO_2F$ requires 324.1394).

Example 417

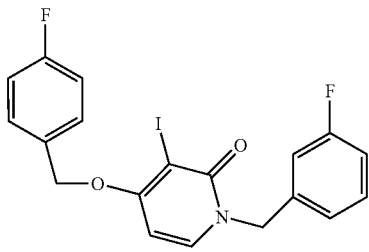

1-(3-fluorobenzyl)-4-[(4-fluorobenzyl)oxy]-3-iodopyridin-2(1H)-one

Step 1: Preparation of 1-(3-fluorobenzyl)-4-hydroxy-3-iodopyridin-2(1H)-one

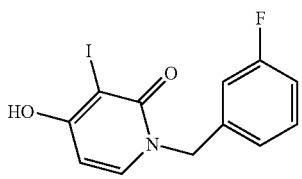

To a mixture of 1-(3-fluorobenzyl)-4-hydroxypyridin-2(1H)-one (1.1 g, 5 mmol) in acetonitrile (15 mL) was added N-iodosuccinimide (1.1 g, 5.5 mmol) along with a ca. amount of dichloroacetic acid (0.1 mL). The reaction mixture stirred at room temperature for 1 hour under nitrogen. The mixture was chilled in an ice bath and filtered cold with fresh $MeCl_2$. The beige solid was dried to afford the desired iodinated intermediate (1.21 g, 69%). ES-LRMS m/z 346.

Step 2: Preparation of 1-(3-fluorobenzyl)-4-[(4-fluorobenzyl)oxy]-3-iodopyridin-2(1H)-one To a mixture of 1-(3-fluorobenzyl)-4-hydroxy-3-iodopyridin-2(1H)-one (0.5 g, 1.44 mmol) in DMF (5 mL) was added $K_2CO_3$ (0.199 g, 1.44 mmol) followed by the addition of 4-fluorobenzyl bromide (0.189 mL, 1.51 mmol). The reaction mixture stirred at room temperature for 30 minutes. The mixture was diluted with ethyl acetate (50 mL) and washed with water. The organic extracts were dried over anhydrous $Na_2SO_4$ and concentrated to dryness. $^1$H-NMR ($CD_3OD$, 400 MHz) δ 7.75 (d, 1H, J=7.6 Hz), 7.49 (q, 2H), 7.34 (q, 1H), 7.11 (m, 5H), 6.40 (d, 1H, J=7.6 Hz), 5.26 (s, 2H), 5.19 (s, -2H); ES-HRMS m/z 454.0098 (M+H calculated for $C_{19}H_{15}NO_2F_2I$ requires 454.0110).

Example 418

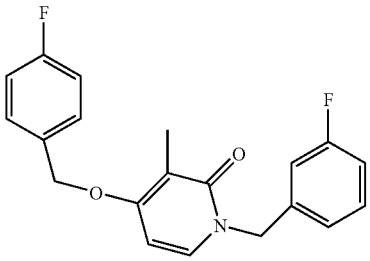

1-(3-fluorobenzyl)-4-[(4-fluorobenzyl)oxy]-3-methylpyridin-2(1H)-one

To a degassed solution of 1-(3-fluorobenzyl)-4-[(4-fluorobenzyl)oxy]-3-iodopyridin-2(1H)-one (0.804 g, .7 mmol) in DMF (10 mL) and LiCl (0.25 g, .9 mmol) was added tetramethyltin (0.49 mL, 3.54 mmol) followed by bistriphenylphosphine-palladium chloride catalyst (0.124 g, 0.177 mmol). The reaction mixture was heated in an oil bath (85°–90° C.) under nitrogen for 3 hours. The solvent was concentrated and the residue was diluted with ethyl acetate and washed with water. The organic extracts were dried over anhydrous $Na_2SO_4$ and concentrated to dryness. The residue was purified by flash column chromatography (20% ethyl acetate in hexane). The appropriate fractions were concentrated. $^1$H-NMR ($CD_3OD$, 400 MHz) δ 7.59 (d, 1H, J=7.6 Hz), 7.46 (m, 2H), 7.34 (m, 1H), 7.10 (m, 4H), 6.46 (d, 1H, J=7.6 Hz), 5.17 (s, 2H), 5.15 (s, 2H), 1.99 (s, 3H); ES-HRMS m/z 342.1314 (M+H calculated for $C_{20}H_{18}NO_2F_2$ requires 342.1300).

Example 419

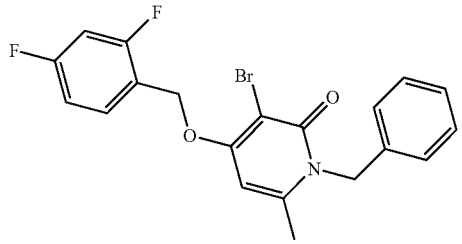

1-benzyl-3-bromo-4-[(2,4-difluorobenzyl)oxy]-6-methylpyridin-2(1H)-one

To a degassed cold solution of DMF (10 mL) and $PPh_3$ (resin, 0.93 g, 2.75 mmol) was added DEAD (0.44 mL, 2.75 mmol). The reaction mixture stirred at −10° C. for 20 minutes under nitrogen. A solution of 1-benzyl-3-bromo-4-hydroxy-6-methylpyridin-2(1H)-one (0.62 g, 2.1 mmol) and 2,4-difluorobenzylalcohol (0.283 mL, 2.5 mmol) in DMF (10 mL) was added to the resin suspension. The reaction mixture stirred at −10° C. for 30 minutes and then allowed to stir at room temperature for 1 hour. The resin was filtered and rinsed with fresh MeOH and the filtrate was concentrated. The residue was dissolved in ethyl acetate and purified by flash column chromatography (ethyl acetate/hexane 1:1 v/v). The appropriate fractions were concentrated. $^1$H-NMR ($CD_3OD$, 400 MHz) δ 7.62 (m, 1H), 7.31 (m, 3H), 7.1 (d, 2H, J=7.2 Hz), 7.02 (t, 2H, J=8.6 Hz), 6.48 (s, 1H), 5.42 (s, 2H), 5.28 (s, 2H), 2.34 (s, 3H); ES-HRMS m/z 420.0399/422.0380 (M+H calculated for $C_{20}H_{17}NO_2F_2Br$ requires 420.0405/422.0387).

Example 420

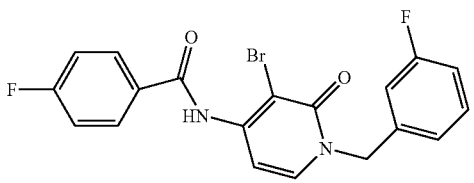

N-[3-bromo-1-(3-fluorobenzyl)-2-oxo-1,2-dihydropyridin-4-yl]-4-fluorobenzamide

Step 1. Preparation of 4-amino-1-(3-fluorobenzyl)pyridin-2(1H)-one

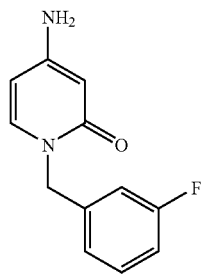

In a Fischer-Porter bottle, added a solution of 4-(benzylamino)-1-(3-fluorobenzyl)pyridin-2(1H)-one (2.5 g, 8.11 mmol) in glacial acetic acid (20 mL). After the solution was flushed with nitrogen, catalyst was added (10% Pd/C, 2.0 g). The vessel was sealed, evacuated, and purged with hydrogen gas. The system was charged with hydrogen gas (50 psi) and the mixture stirred at room temperature for 4 hours. The system was evacuated and flushed with nitrogen. The reaction mixture was filtered through a bed of celite and washed with fresh ethanol. The filtrate was concentrated under reduced pressure and the residue was purified by flash column chromatography (hexane/ethyl acetate 3:4 v/v). The filtrate was concentrated. $^1$H-NMR (CD$_3$OD, 400 MHz) δ 7.32 (q, 1H), 7.02 (m, 3H), 5.93 (dd, 1H, J=2.4 Hz, 2.8 Hz), 5.58 (d, 1H, J=2.4 Hz); ES-HRMS m/z 219.0966 (M+H calculated for C$_{12}$H$_{12}$N$_2$O F. requires 219.0928).

Step 2. Preparation of 4-fluoro-N-[1-(3-fluorobenzyl)-2-oxo-1,2-dihydropyridin-4-yl]benzamide

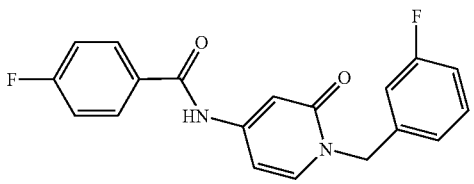

To a solution of 4-amino-1-(3-fluorobenzyl)pyridin-2(1H)-one (0.263 g, 1.2 mmol) inacetonitrile (7 mL) was added a DMAP (ca.), triethylamine (0.25 mL, 1.8 mmol) and 4-fluorobenzoyl chloride (0.213 mL, 1.8 mmol). The reaction mixture stirred at 0° C. for 25 minutes and then filtered. The solid was washed with 10% citric acid and water to afford the desired compound (0.326 g, 79%) after drying. $^1$H-NMR (d$_6$DMSO, 400 MHz) δ 7.98 (m, 2H), 7.71 (d, 1H, J=7.6 Hz), 7.35 (m, 3H), 7.08 (m, 3H), 6.98 (d, 1H, J=2.4 Hz), 6.61 (dd, 1H, J=2.4 Hz, 2.4 Hz), 5.03 (s, 2H); ES LRMS m/z 341.1.

Step 3. Preparation of N-[3-bromo-1-(3-fluorobenzyl)-2-oxo-1,2-dihydropyridin-4-yl]-4-fluorobenzamide To a mixture of 4-fluoro-N-[1-(3-fluorobenzyl)-2-oxo-1,2-dihydropyridin-4-yl]benzamide (0.305 g, 0.89 mmol) in acetonitrile (7 mL) was added NBS (0.159 g, 0.89 mmol). The reaction mixture stirred at room temperature for 1.5 hours. The filtrate was removed under reduced pressure and the residue was purified by flash column chromatography (ethyl acetate/hexane 1:1 v/v). The fractions were concentrated. $^1$H-NMR (CD$_3$OD, 400 MHz) δ 8.03 (m, 2H), 7.79 (d, 1H, J=7.6 Hz), 7.47 (d, 1H, J=8.0 Hz), 7.28 (m, 3H), 7.12 (m, 3H), 5.23 (s, 2H); ES-HRMS m/z 419.0202/421.0191 (M+H calculated for C$_{19}$H$_{14}$N$_2$O$_2$F$_2$Br requires 419.0201/421.0183).

Example 421

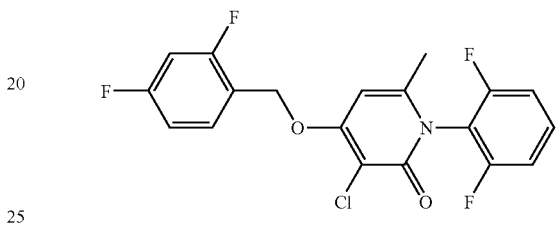

3-chloro-4-[(2,4-difluorobenzyl)oxy]-1-(2,6-difluorophenyl)-6-methylpyridin-2(1H)-one Step 1. Preparation of 3-chloro-1-(2,6-difluorophenyl)-4-hydroxy-6-methylpyridin-2(1H)-one

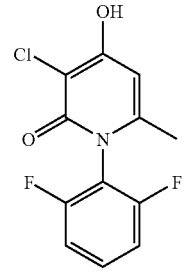

To a mixture of 1-(2,6-difluorophenyl)-4-hydroxy-6-methylpyridin-2(1H)-one (0.30 g, 1.26 mmol) in dichloromethane (5 mL) was added NCS (2.52 g, 1.90 mmol). The reaction mixture stirred at room temperature under nitrogen for 4.5 hours. The suspension was cooled in ice bath, filtered, and the solid was rinsed with fresh dichloromethane to afford the desired product (0.271 g, 79%) as a white solid. $^1$H-NMR (CD$_3$OD, 400 MHz) δ 7.58 (m, 1H), 7.22 (m, 2H), 6.20 (s 1H), 2.00 (s, 3H); ES-HRMS m/z 272.0287 (M+H calculated for C$_{12}$H$_9$NO$_2$F$_2$Cl requires 272.0290).

Step 2. Preparation of 3-chloro-4-[(2,4-difluorobenzyl)oxy]-1-(2,6-difluorophenyl)-6-methylpyridin-2(1H)-one To a solution of 3-chloro-1-(2,6-difluorophenyl)-4-hydroxy-6-methylpyridin-2(1H)-one (0.27 g, 1.00 mmol) in DMA (5 mL) was added K$_2$CO$_3$ followed by the addition of 2,4-difluorobenzyl bromide (0.128 mL, 1 mmol). The reaction mixture stirred at room temperature for 2 hours and then was diluted in water. The reaction mixture was extracted with ethyl acetate, the organic extracts were dried over Na$_2$SO$_4$ and the filtrate was concentrated. The resulting residue was purified by flash column chromatography (ethyl acetate/hexane 3:4 v/v) to afford the desired product. $^1$H-NMR (CD$_3$OD, 400 MHz) δ 7.60 (m, 2H), 7.25 (m, 2H), 7.04 (m, 2H), 6.71 (s, 1H), 5.36 (s, 2H), 2.11 (s, 3H);

ES-HRMS m/z 398.0551 (M+H calculated for C₁₉H₁₃NO₂F₄Cl requires 398.0571).

Example 422

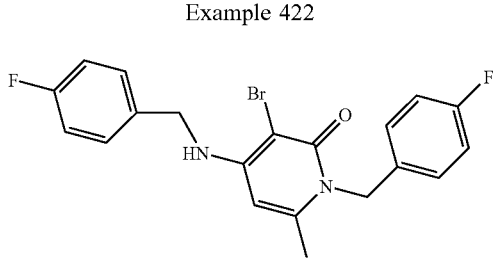

3-bromo-1-(4-fluorobenzyl)-4-[(4-fluorobenzyl)amino]-6-methylpyridin-2(1H)-one

Step 1: Preparation of 1-(4-fluorobenzyl)-4-[(4-fluorobenzyl)amino]-6-methylpyridin-2(1H)-one

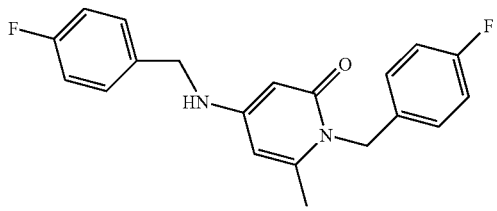

A mixture of 4-hydroxy-6-methylpyrone (5.0 g, 0.04 mol) and 4-fluorobenzylamine (10.0 g. 0.08 mol) in n-butanol (25.0 mL) was heated to reflux for 24 hours under argon atmosphere. The resulting solution was concentrated to dryness under reduced pressure. The residue was triturated with ethyl acetate and filtered. It was thoroughly washed with ethyl acetate and dried to afford the title compound as a pale yellow powder (4.1 g. 30%). ¹H-NMR (CD₃OD, 400 MHz) δ 7.33 (q, 2H), 7.04 (m, 5H), 5.85 (d, 1H, J=2.0 Hz), 5.44 (d, 2H, J=2.4 Hz), 5.20 (s, 1H), 4.29 (s, 2H), 2.17 (s, 3H); ES-HRMS m/z 341.1488 (M+H calculated for C₂₀H₁₉N₂OF₂ requires 341.1460).

Step 2: Preparation of 3-bromo-1-(4-fluorobenzyl)-4-[(4-fluorobenzyl)amino]-6-methylpyridin-2(1H)-one To a solution of 1-(4-fluorobenzyl)-4-[(4-fluorobenzyl)amino]-6-methylpyridin-2(1H)-one (0.2857 g, 0.84 mmol) in MeCl₂ was added NBS (0.156 g, 0.88 mmol). The reaction stirred at room temperature under nitrogen for 45 minutes. The reaction mixture was diluted with MeCl₂ and washed with NaHCO₃. The organic extracts were washed with water, dried over Na₂SO₄, and concentrated to afford the desired product (0.3242 g, 92%) as a yellow solid. ¹H-NMR (CD₃OD, 400 MHz) δ 7.32 (q, 2H), 7.04 (m, 6H), 5.91 (s, 1H), 5.28 (s, 2H), 4.50 (s, 2H), 2.17 (s, 3H); ES-HRMS m/z 419.0549/421.0537 (M+H calculated for C₂₀H₁₈N₂OBrF₂ requires 419.0565/421.0547).

Example 423

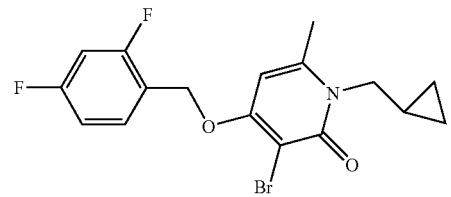

3-bromo-1-(cyclopropylmethyl)-4-[(2,4-difluorobenzyl)oxy]-6-methylpyridin-2(1H)-one To a mixture of 3-bromo-1-(cyclopropylmethyl)-4-hydroxy-6-methylpyridin-2(1H)-one (0.276 g, 1.07 mmol) and K₂CO₃ (0.148 g, 1.07 mmol) in DMA (4 mL) was added 2,4-difluorobenzyl bromide (0.14 ml, 1.07 mmol). The mixture stirred at room temperature for 1.5 hours. The reaction mixture was diluted in water and extracted with ethyl acetate. The organic extracts were dried over Na₂SO₄ and concentrated. The residue was purified by flash column chromatography (ethyl acetate/hexane 1:1 v/v). The appropriate fractions were combined, and concentrated. ¹H-NMR (CD₃OD, 400 MHz) δ 7.60 (q, 1H), 7.04 (m, 2H), 6.42 (s, 1H), 5.26 (s, 2H), 4.06 (s, 1H), 4.04 (s, 1H), 2.50 (s, 3H), 0.53 (m, 2H), 0.43 (m, 2H); ES-HRMS m/z 384.0392 (M+H calculated for C₁₇H₁₇N₂OBrF₂ requires 384.0405).

Example 424

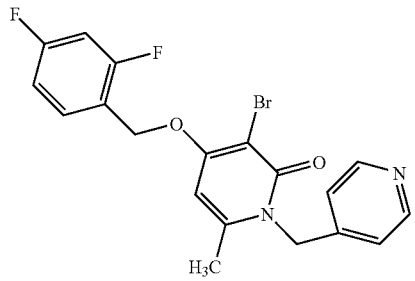

3-bromo-4-[(2,4-difluorobenzyl)oxy]-6-methyl-1-(pyridin-4-ylmethyl)pyridin-2(1H)-one Step 1. Preparation of 3-bromo-4-hydroxy-6-methyl-1-(pyridin-4-ylmethyl)pyridin-2(1H)-one

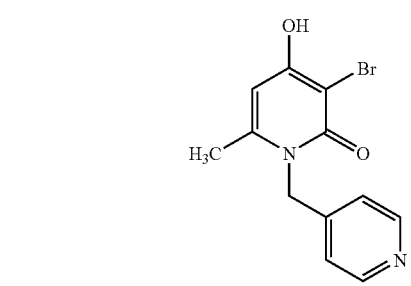

Commercially available 4-hydroxy-6-methylpyrone (10 g, 79.3 mmol) was condensed with commercially available 4-(aminomethyl) pyridine (8 mL, 79.3 mmol) in water (50 mL). The mixture was heated in an oil bath at reflux for 1 hour under nitrogen. The solvent was evaporated. MS and $^1$H-NMR were consistent with the desired desbrominated structure. $^1$H-NMR (CD$_3$OD, 400 MHz) δ 8.45 (dd, 2H, J=1.6 Hz, 1.6 Hz), 7.15 (d, 2H, J=6.0 Hz), 6.00 (d, 1H, J=2.0 Hz), 5.80 (d, 1H, J=2.4 Hz), 5.34 (s, 2H), 2.23 (s, 3H); ES-LRMS (M+H) m/z 217.

To a suspension of the above compound (0.801 g, 3.7 mmol) in MeCl$_2$ (10 mL) was added NBS (0.725 g, 4.07 mmol). The reaction mixture stirred at room temperature for 30 minutes under nitrogen. The suspension was chilled in an ice bath and filtered. The solid was washed with fresh MeCl$_2$ and dried to afford a beige solid (0.9663 g, 88%) after drying. $^1$H-NMR (CD$_3$OD, 400 MHz) δ 8.47 (d, 2H, J=5.2 Hz), 7.16 (d, 2H, J=6.0 Hz), 6.09 (s, 1H), 5.40 (s, 2H), 2.24 (s, 3H); ES-LRMS (M+H) m/z 295/297.

Step 2. Preparation of 3-bromo-4-[(2,4-difluorobenzyl)oxy]-6-methyl-1-(pyridin-4-ylmethyl)pyridin-2(1H)-one

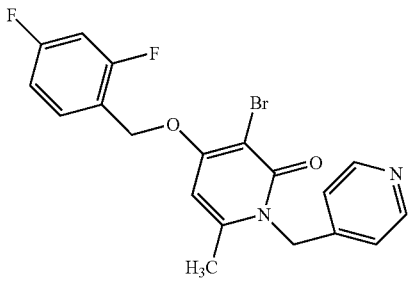

To a cold solution of 2,4-difluorobenzylalcohol (0.569 mL, 5.1 mmol) in THF (5 mL) was added PPh$_3$ (resin, 2.55 g, 7.65 mmol) followed by the addition of DIAD (1.48 mL, 7.65 mmol). The reaction mixture stirred at −10° C. for 15 minutes under nitrogen. A solution of 3-bromo-4-hydroxy-6-methyl-1-(pyridin-4-ylmethyl)pyridin-2(1H)-one (1.0 g, 3.4 mmol), in DMF (10 mL) was added to the resin suspension. The reaction mixture stirred at 0° C. for 1.5 hours and then allowed to stir at room temperature overnight. The resin was filtered and rinsed with fresh MeOH and the filtrate was concentrated. The residue was dissolved in ethyl acetate and purified by flash column chromatography (ethyl acetate). The appropriate fractions were concentrated. $^1$H-NMR (CD$_3$OD, 400 MHz) δ 8.47 (d, 2H, J=5.6 Hz), 7.63 (q, 1H), 7.15 (d, 1H, J=5.6 Hz), 7.05 (m, 2H), 6.55 (s, 1H), 5.45 (s, 2H), 5.31 (s, 2H), 2.35 (s, 3H); ES-HRMS m/z 421.0366/423.0355 (M+H calculated for C$_{19}$H$_{16}$N$_2$O$_2$F$_2$Br requires 421.0358/423.0339).

Example 428

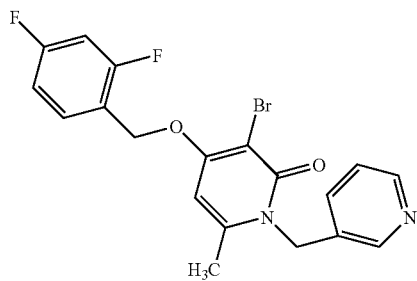

3-bromo-4-[(2,4-difluorobenzyl)oxy]-6-methyl-1-(pyridin-3-ylmethyl)pyridin-2(1H)-one Step 1. Preparation of 3-bromo-4-hydroxy-6-methyl-1-(pyridin-3-ylmethyl)pyridin-2(1H)-one

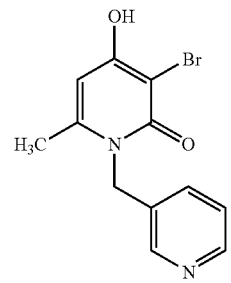

Commercially available 4-hydroxy-6-methylpyrone (15 g, 119.0 mmol) was condensed with commercially available 3-(aminomethyl) pyridine (12.10 mL, 119.0 mmol) in water (75 mL). The mixture was heated in an oil bath at reflux for 1 hour under nitrogen. The solvent was evaporated. $^1$H-NMR (CD$_3$OD, 400 MHz) δ 8.43 (d, 1H, J=4.8 Hz), 8.38 (s, 1H), 7.60 (d, 1H, J=8.0 Hz), 7.39 (dd, 1H, J=4.8 Hz, 4.8 Hz), 5.97 (d, 1H, J=2.0 Hz), 5.79 (d, 1H, J=2.4 Hz), 5.33 (s, 2H), 2.28 (s, 3H); ES-LRMS (M+H) m/z 217.

To a suspension of the above compound (5.01 g, 23.1 mmol) in MeCl$_2$ (50 mL) was added NBS (4.53 g, 25.4 mmol). The reaction mixture stirred at room temperature for 30 minutes under nitrogen. The suspension was chilled in an ice bath and filtered. The solid was washed with fresh MeCl$_2$ and dried to afford a beige solid (7.89 g, 114%) after drying. $^1$H-NMR (CD$_3$OD, 400 MHz) δ 8.44 (d, 1H, J=4.4 Hz), 8.39 (s, 1H), 7.62 (d, 1H, J=7.6 Hz), 7.39 (dd, 1H, J=5.2 Hz, 4.4 Hz), 6.07 (s, 1H), 5.39 (s, 2H), 2.29 (s, 3H); ES-LRMS (M+H) m/z 295/297.

Step 2. Preparation of 3-bromo-4-[(2,4-difluorobenzyl)oxy]-6-methyl-1-(pyridin-3-ylmethyl)pyridin-2(1H)-one

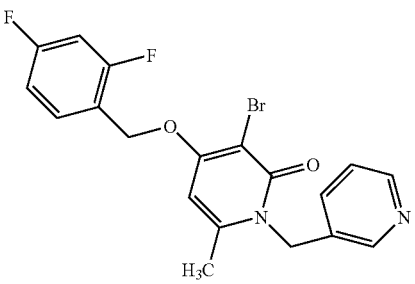

The compound was prepared essentially as described in Step 2 of example 424 using 3-bromo-4-hydroxy-6-methyl-1-(pyridin-3-ylmethyl)pyridin-2(1H)-one. ¹H-NMR (CD₃OD, 400 MHz) δ 8.45 (d, 1H, J=4.4 Hz), 8.41 (s, 1H), 7.63 (m, 2H), 7.41 (dd, 1H, J=5.2 Hz, 4.8 Hz), 7.02 (m, 2H), 6.52 (s, 1H), 5.44 (s, 2H), 5.29 (s, 2H), 2.40 (s, 3H); ES-HRMS m/z 421.0355/423.0358 (M+H calculated for $C_{19}H_{16}N_2O_2F_2Br$ requires 421.0358/423.0339).

Example 435

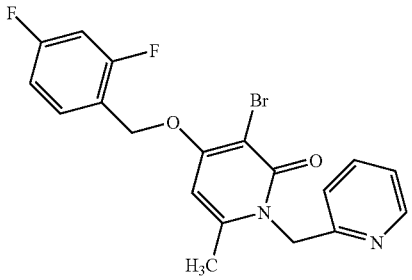

3-bromo-4-[(2,4-difluorobenzyl)oxy]-6-methyl-1-(pyridin-2-ylmethyl)pyridin-2(1H)-one Step 1. Preparation of 3-bromo-4-hydroxy-6-methyl-1-(pyridin-2-ylmethyl)pyridin-2(1H)-one

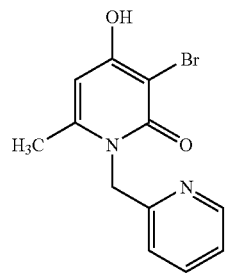

Commercially available 4-hydroxy-6-methylpyrone (5 g, 39.6 mmol) was condensed with commercially available 2-(aminomethyl) pyridine (4.03 mL, 39.6 mmol) in water (25 mL). The mixture was heated in an oil bath at reflux for 1.5 hour under nitrogen. The solvent was evaporated. MS and ¹H-NMR were consistent with the desired desbromonated structure. ¹H-NMR (CD₃OD, 400 MHz) δ 8.47 (d, 1H, J=4.8 Hz), 7.75 (ddd, 1H, J=2.0 Hz, 1.6 Hz, 1.6 Hz), 7.28 (dd, 1H, J=4.8 Hz, 4.8 Hz), 7.11 (d, 1H, J=7.6 Hz), 5.98 (d, 1H, J=2.4 Hz), 5.77 (d, 1H, J=2.4 Hz), 5.35 (s, 2H), 2.28 (s, 3H); ES-LRMS (M+H) m/z 217.

To a suspension of the above compound (3.0 g, 13.8 mmol) in MeCl₂ (30 mL) was added NBS (2.71 g, 15.18 mmol). The reaction mixture stirred at room temperature for 2.5 hours under nitrogen. The suspension was chilled in an ice bath and filtered. The solid was washed with fresh MeCl₂ and dried to afford a beige solid (3.18 g, 77%) after drying. ¹H-NMR (CD₃OD, 400 MHz) δ 8.46 (d, 1H, J=4.8 Hz), 7.76 (ddd, 1H, J=2.0 Hz, 1.6 Hz, 1.6 Hz), 7.29 (dd, 1H, J=5.2 Hz, 5.2 Hz), 7.17 (d, 1H, J=8.0 Hz), 6.07 (s, 1H), 5.40 (s, 2H), 2.30 (s, 3H); ES-LRMS (M+H) m/z 295/297.

Step 2. Preparation of 3-bromo-4-[(2,4-difluorobenzyl)oxy]-6-methyl-1-(pyridin-2-ylmethyl)pyridin-2(1H)-one

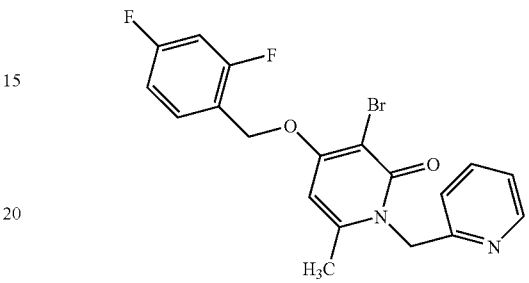

The compound was prepared essentially as described in Step 2 of example 424 using 3-bromo-4-hydroxy-6-methyl-1-(pyridin-2-ylmethyl)pyridin-2(1H)-one ¹H-NMR (CD₃OD, 400 MHz) δ 8.45 (d, 1H, J=4.4 Hz), 7.76 (ddd, 1H, J=2.0 Hz, 2.0 Hz, 1.6 Hz), 7.62 (q, 1H), 7.29 (dd, 1H, J=5.2 Hz, 5.6 Hz), 7.21 (d, 1H, J=8.0 Hz), 7.04 (m, 2H), 6.51 (s, 1H), 5.45 (s, 2H), 5.29 (s, 2H), 2.42 (s, 3H); ES-HRMS m/z 421.0354/423.0332 (M+H calculated for $C_{19}H_{16}N_2O_2F_2Br$ requires 421.0358/423.0339).

Examples 425–427, 429–435, 436–437

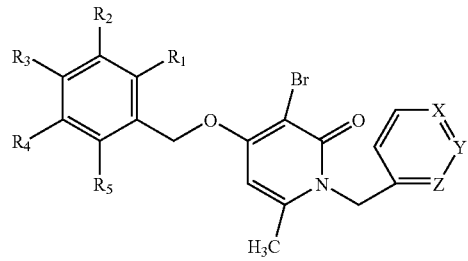

The following compounds were prepared essentially according to the procedures set forth above for Example 424, using the products of Step 1 of Examples 424, 428, or 435.

| Ex. No. | R₁ | R₂ | R₃ | R₄ | R₅ | X | Y | Z | MF | M + H m/z required | ES-HRMS m/z |
|---|---|---|---|---|---|---|---|---|---|---|---|
| 425 | H | H | F | H | H | N | CH | CH | $C_{19}H_{16}N_2O_2FBr$ | 403.0452/405.0434 | 403.0444/405.0414 |
| 426 | F | H | F | H | F | N | CH | CH | $C_{19}H_{14}N_2O_2F_3Br$ | 439.0264/441.0245 | 439.0270/441.0274 |
| 427 | F | H | H | H | F | N | CH | CH | $C_{19}H_{15}N_2O_2F_2Br$ | 421.0358/423.0339 | 421.0378/423.0368 |
| 429 | H | H | F | H | H | CH | N | CH | $C_{19}H_{16}N_2O_2FBr$ | 403.0487/405.0438 | 403.0487/405.0438 |
| 430 | F | H | F | H | F | CH | N | CH | $C_{19}H_{14}N_2O_2F_3Br$ | 439.0264/441.0245 | 439.0267/441.0241 |
| 431 | F | H | H | H | H | CH | N | CH | $C_{19}H_{16}N_2O_2FBr$ | 403.0452/405.0434 | 403.0489/405.0474 |
| 432 | F | H | F | F | H | CH | N | CH | $C_{19}H_{14}N_2O_2F_3Br$ | 439.0264/441.0245 | 439.0266/441.0231 |
| 433 | F | H | Cl | H | H | CH | N | CH | $C_{19}H_{15}N_2O_2FClBr$ | 437.0062/439.0041 | 437.0068/439.0041 |
| 434 | Cl | H | F | H | H | CH | N | CH | $C_{19}H_{15}N_2O_2FClBr$ | 437.0062/439.0041 | 437.0048/439.0043 |
| 435 | F | H | H | H | F | CH | N | CH | $C_{19}H_{15}N_2O_2F_2Br$ | 421.0358/423.0339 | 421.0371/423.0336 |

-continued

| Ex. No. | R₁ | R₂ | R₃ | R₄ | R₅ | X | Y | Z | MF | M + H m/z required | ES-HRMS m/z |
|---|---|---|---|---|---|---|---|---|---|---|---|
| 436 | H | H | F | H | H | CH | CH | N | $C_{19}H_{16}N_2O_2FBr$ | 403.0452/405.0434 | 403.0454/405.0379 |
| 437 | F | H | H | H | F | CH | CH | N | $C_{19}H_{14}N_2O_2F_3Br$ | 439.0264/441.0245 | 439.0266/441.0242 |
| 438 | F | H | F | H | H | CH | CH | N | $C_{19}H_{14}N_2O_2F_3Br$ | 439.0264/441.0245 | 439.0264/441.0241 |

NMR characterization of compounds of Examples 425–427, 429–435, 436–437

| Ex. No. | NMR Data |
|---|---|
| 425 | ¹H-NMR (CD₃OD, 400 MHz) δ 8.47(d, 2H, J=5.6Hz), 7.50(q, 2H), 7.14(m, 4H), 6.49(s, 1H), 5.44(s, 2H), 5.27(s, 2H), 2.32(s, 3H) |
| 426 | ¹H-NMR (CD₃OD, 400 MHz) δ 8.48(dd, 2H, J=1.6Hz), 7.15(d, 2H, J=6.0Hz), 6.98(t, 2H, J=1.2Hz), 6.60(s, 1H), 5.45(s, 2H), 5.29(s, 2H), 2.36(s, 3H) |
| 427 | ¹H-NMR (CD₃OD, 400 MHz) δ 8.47(d, 2H, J=1.6Hz), 7.45(m, 1H), 7.16(d, 2H, J=5.6Hz), 7.06(t, 2H, J=8.4Hz), 6.62(s, 1H), 5.46(s, 2H), 5.34(s, 2H), and 2.37(s, 3H) |
| 429 | ¹H-NMR (CD₃OD, 400 MHz) δ 8.45(d, 1H, J=4.4Hz), 8.40(s, 1H), 7.62(d, 1H, J=8.0Hz), 7.49(q, 2H), 7.41(dd, 1H, J=4.8Hz, 4.8Hz), 7.14(t, 2H, J=8.8Hz), 6.46(s, 1H), 5.43(s, 2H), 5.26(s, 2H), 2.38(s, 3H) |
| 430 | ¹H-NMR (CD₃OD, 400 MHz) δ 8.45(d, 1H, J=3.6Hz), 8.42(d, 1H, J=1.2Hz), 7.60(d, 1H, J=8.4Hz), 7.41(dd, 1H, J=5.2Hz, 4.8Hz), 6.97(m, 2H), 6.57(s, 1H), 5.45(s, 2H), 5.27(s, 2H), 2.42(s, 3H) |
| 431 | ¹H-NMR (CD₃OD, 400 MHz) δ 8.45(d, 1H, J=4.4Hz), 8.41(d, 1H, J=1.6Hz), 7.58(m, 2H), 7.41(m, 2H), 7.22(m, 2H), 6.51(s, 1H), 5.44(s, 2H), 5.34(s, 2H), 2.39(s, 3H) |
| 432 | ¹H-NMR (CD₃OD, 400 MHz) δ 8.45(d, 1H, J=4.0Hz), 8.41(d, 1H, J=1.6Hz), 7.63(d, 1H, J=7.6Hz), 7.53(m, 1H), 7.41(dd, 1H, J=5.6Hz, 5.2Hz), 7.26(m, 1H), 6.51(s, 1H), 5.45(s, 2H), 5.29 (s, 2H), 2.40(s, 3H) |
| 433 | ¹H-NMR (CD₃OD, 400 MHz) δ 8.45(d, 1H, J=4.0Hz), 8.41(d, 1H, J=1.6Hz), 7.60(m, 2H), 7.39(dd, 1H, J=5.2Hz), 7.28(s, 1H), 7.26(s, 1H), 6.50(s, 1H), 5.44(s, 2H), 5.31(s, 2H), 2.40(s, 3H) |
| 434 | ¹H-NMR (CD₃OD, 400 MHz) δ 8.45(d, 1H, J=4.0Hz), 8.41(d, 1H, J=1.6Hz), 7.68(m, 2H), 7.39(dd, 1H, J=4.8Hz, 4.8Hz), 7.31(dd, 1H, J=2.4Hz, 2.8Hz), 7.16(ddd, 1H, J=2.8Hz, 2.8Hz, 2.8Hz), 6.50(s, 1H), 5.45(s, 2H), 5.32(s, 2H), 2.41(s, 3H) |
| 435 | ¹H-NMR (CD₃OD, 400 MHz) δ 8.45(d, 1H, J=4.0Hz), 8.42(s, 1H), 7.60(d, 1H, J=8.0Hz), 7.47(m, 1H), 7.40(dd, 1H, J=5.2Hz, 4.8Hz), 7.07(m, 2H), 6.59(s, 1H), 5.45(s, 2H), 5.32(s, 2H), 2.41(s, 3H) |
| 436 | ¹H-NMR (CD₃OD, 400 MHz) δ 8.45(d, 1H, J=4.8Hz), 7.76(ddd, 1H, J=2.0Hz, 1.6Hz, 1.6Hz), 7.51(q, 2H), 7.30(dd, 1H, J=5.2Hz), 7.19(d, 1H, J=7.6Hz), 7.14(t, 2H, J=8.8Hz), 6.46(s, 1H), 5.44(s, 2H), 5.26(s, 2H), 2.40(s, 3H) |
| 437 | ¹H-NMR (CD₃OD, 400 MHz) δ 8.46(d, 1H, J=4.8Hz), 7.76(ddd, 1H, J=2.0Hz, 1.6Hz, 1.6Hz), 7.29(dd, 1H, J=4.8Hz, 5.2Hz), 7.21 (d, 1H, J=7.6Hz), 6.69(dd, 2H, J=8.0Hz, 7.6Hz), 6.57(s, 1H), 5.46(s, 2H), 5.28(s, 2H), 2.43(S, 3H) |
| 438 | ¹H-NMR (CD₃OD, 400 MHz) δ 8.45(d, 1H, J=4.4Hz), 7.76(ddd, 1H, J=2.0Hz, 1.6Hz, 1.6Hz), 7.55(m, 1H), 7.26(m, 3H), 6.50(s, 1H), 5.46(s, 2H), 5.29(s, 2H), 2.42(s, 3H) |

Example 439

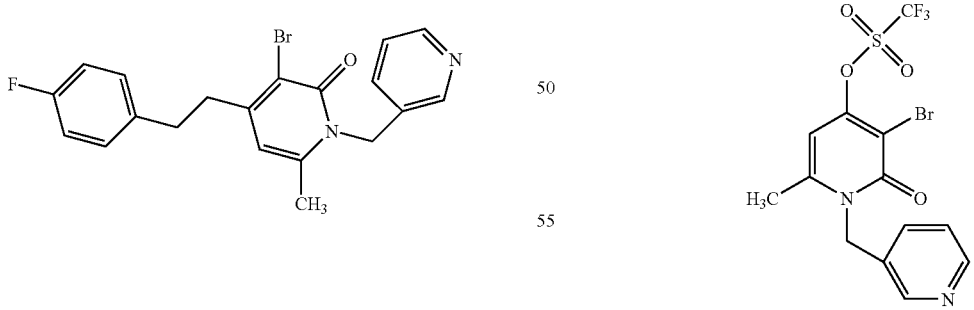

3-bromo-4-[2-(4-fluorophenyl)ethyl]-6-methyl-1-(pyridin-3-ylmethyl)pyridin-2(1H)-one Step 1. Preparation of 3-bromo-6-methyl-2-oxo-1-(pyridin-3-ylmethyl)-1,2-dihydropyridin-4-yl trifluoromethanesulfonate To a chilled suspension (−30° C.) of 3-bromo-4-hydroxy-6-methyl-1-(pyridin-3-ylmethyl)pyridin-2(1H)-one (0.481 g, 1.63 mmol) in dichloromethane (6 mL) was added triethylamine (0.28 mL, 2.04 mmol), followed by the addition of a solution of trifluoromethanesulfonic anhydride (0.4 mL, 2.44 mmol) in dichloromethane (3 mL). The reaction mixture stirred at −30° C. under nitrogen for 1 hour. The reaction mixture was diluted with dichloromethane and washed with cold NaHCO$_3$/water. The organic extracts were dried over Na$_2$SO$_4$ and the filtrate was concentrated under reduced pressure to afford the desired compound as a yellow semisolid (0.6675 g, 95%) after drying. ES-LRMS (M+H) m/z 427.1/429.1.

Step 2. Preparation of 3-bromo-4-[(4-fluorophenyl) ethynyl]-6-methyl-1-(pyridin-3-ylmethyl)pyridin-2(1H)-one

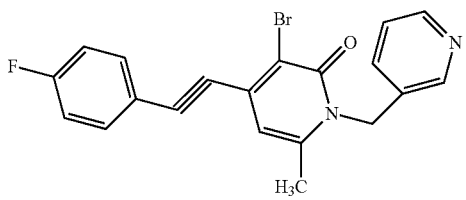

To a degassed solution of 3-bromo-6-methyl-2-oxo-1-(pyridin-3-ylmethyl)-1,2-dihydropyridin-4-yl trifluoromethanesulfonate (0.6675 g, 1.56 mmol) in DMF (9 mL), DIEA (0.35 mL, 2.03 mmol), 4-fluorophenylacetylene (0.235 mL, 1.95 mmol) and PdCl$_2$(PPh$_3$)$_2$ (0.11 g) were added. The reaction mixture stirred at room temperature under nitrogen for 1 hour and then heated in an oil bath (65° C.) under nitrogen overnight. The solvents were distilled in vacuo and the residue was purified by flash column chromatography (5% methanol in ethyl acetate). The extracts were concentrated to afford the desired compound (0.432 g, 69%) after drying. $^1$H-NMR (CD$_3$OD, 400 MHz) δ 8.45 (s, 2H), 7.96 (s, 1H), 7.64 (m, 3H), 7.41 (dd, 1H, J=4.8 Hz, 4.8 Hz), 7.18 (t, 2H, J=8.8 Hz), 6.46 (s, 1H), 5.45 (s, 2H), 2.37 (s, 3H); ES-HRMS m/z 397.0361/399.0310 (M+H calculated for C$_{20}$H$_{15}$N$_2$OFBr requires 397.0346/399.0328).

Step 3. Preparation of 3-bromo-4-[2-(4-fluorophenyl)ethyl]-6-methyl-1-(pyridin-3-ylmethyl)pyridin-2(1H)-one

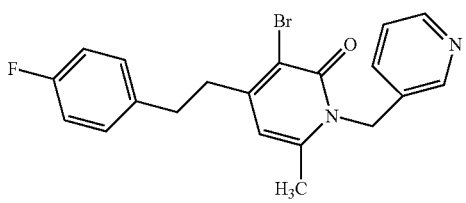

A suspension of 3-bromo-4-[(4-fluorophenyl)ethynyl]-6-methyl-1-(pyridin-3-ylmethyl)pyridin-2(1H)-one (0.430 g, 1.01 mmol) in Ethyl acetate (5 mL) and EtOH (5 mL), containing PtO$_2$ (0.015 g) was stirred in an atmosphere of hydrogen (15 psi) in a Fischer-Porter bottle for 2 hours. The reaction mixture was filtered and the filtrate was concentrated to reduce volume. The material was purified by flash column chromatography (ethyl acetate). The appropriate fractions were combined and concentrated under reduced pressure to afford the desired product (0.0943 g, 22%) as a sticky semisolid after drying. $^1$H-NMR (CD$_3$OD, 400 MHz) δ 8.46 (d, 2H, J=26.4 Hz), 7.60 (d, 1H, J=8.0 Hz), 7.41 (dd, 1H, J=4.8 Hz, 4.8 Hz), 7.21 (m, 2H), 6.97 (t, 2H, J=8.8 Hz), 6.24 (s, 1H), 5.43 (s, 2H), 2.93 (m, 4H), 2.31 (s, 3H); ES-HRMS m/z 401.0645/403.0603 (M+H calculated for C$_{20}$H$_{19}$N$_2$OFBr requires 401.0659/403.0641).

Example 440

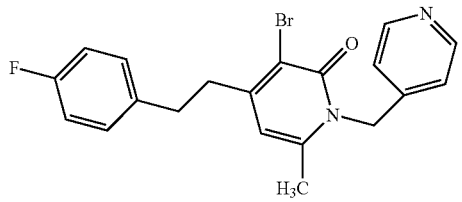

3-bromo-4-[2-(4-fluorophenyl)ethyl]-6-methyl-1-(pyridin-4-ylmethyl)pyridin-2(1H)-one The title compound was prepared by a procedure similar to the one described for step 1 to step3 (0.374 g, 25%). MS and $^1$H-NMR for step 1 were consistent with the desired structure. $^1$H-NMR (CD$_3$OD, 400 MHz) δ 8.80 (d, 2H, J=6.8 Hz), 7.89 (d, 2H, J=6.8 Hz), 6.61 (s, 1H), 5.66 (s, 2H), 2.45 (s, 3H); ES-HRMS m/z 427.9645/429.9625 (M+H calculated for C$_{13}$H$_{11}$N$_2$O$_4$SF$_3$Br requires 427.9599/429.9578).

MS and $^1$H-NMR for step 3 were consistent with the desired structure. $^1$H-NMR (CD$_3$OD, 400 MHz) δ 8.48 (d, 2H, J=5.2 Hz), 7.21 (m, 2H), 7.13 (d, 2H, J=5.2 Hz), 6.98 (t, 2H, J=9.0 Hz), 6.26 (s, 1H), 5.43 (s, 2H), 2.95 (m, 4H), 2.25 (s, 3H); ES-HRMS m/z 401.0682/403.0636 (M+H calculated for C$_{20}$H$_{19}$N$_2$OFBr requires 401.0659/403.0641).

Example 441

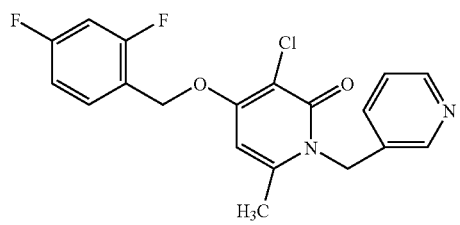

3-chloro-4-[(2,4-difluorobenzyl)oxy]-6-methyl-1-(pyridin-3-ylmethyl)pyridin-2 (1H)-one Step 1. Preparation of 3-chloro-4-hydroxy-6-methyl-1-(pyridin-3-ylmethyl)pyridin-2 (1H)-one

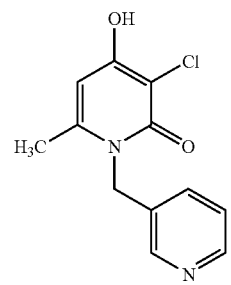

To a suspension of 4-hydroxy-6-methyl-1-(pyridin-3-ylmethyl)pyridin-2(1H)-one (1.016 g, 4.7 mmol) in MeCl$_2$ (10 mL) was added NCS (1.21 g, 1.78 mmol). The reaction mixture stirred at room temperature for 24 hours under nitrogen. The suspension was chilled in an ice bath and filtered. The solid was washed with fresh MeCl$_2$ and dried to afford a yellow solid (1.00 g, 85%) after drying. $^1$H-NMR (CD$_3$OD, 400 MHz) δ 8.54 (m, 2H), 7.85 (d, 1H, J=1.6 Hz), 7.61 (m, 1H), 6.10 (s, 1H), 5.41 (s, 2H), 2.33 (s, 3H); ES-LRMS (M+H) m/z 251/253.

Step 2. Preparation of 3-chloro-4-[(2,4-difluorobenzyl)oxy]-6-methyl-1-(pyridin-3-ylmethyl)pyridin-2 (1H)-one

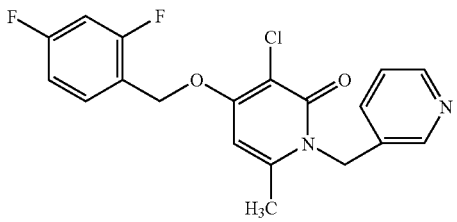

To a degassed cold solution of DMF (10 mL) and PPh₃ (resin, 2.2 g, 6.6 mmol) was added DEAD (1.038 mL, 6.6 mmol). The reaction mixture stirred at −10° C. for 20 minutes under nitrogen. A solution of 3-chloro-4-hydroxy-6-methyl-1-(pyridin-3-ylmethyl)pyridin-2(1H)-one (1.00 g, 4.0 mmol) and 2,4-difluorobenzylalcohol (0.66 mL, 6.0 mmol) in DMF (10 mL) was added to the resin suspension. The reaction mixture stirred at −10° C. for 30 minutes and then allowed to stir at room temperature for 1 hour. The resin was filtered and rinsed with fresh MeOH and the filtrate concentrated. The residue was dissolved in ethyl acetate and purified by flash column chromatography (5% methanol in ethyl acetate). The appropriate fractions were concentrated. $^1$H-NMR (CD₃OD, 400 MHz) δ 8.45 (ddd, 2H, J=1.6 Hz, 1.6 Hz, 1.6 Hz), 7.61 (m, 2H), 7.41 (dd, 1H, J=4.4 Hz, 4.8 Hz), 7.02 (m, 2H), 6.55 (s, 1H), 5.43 (s, 2H), 5.29 (s, 2H), 2.41 (s, 3H); ES-HRMS m/z 377.0882/379.0840 (M+H calculated for $C_{19}H_{16}N_2O_2F_2Cl$ requires 377.0863/379.0840).

Example 442

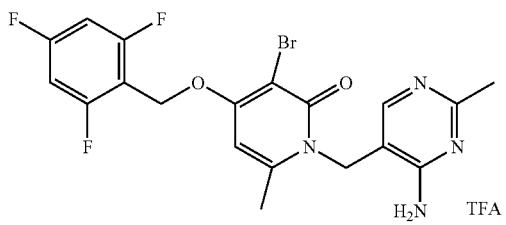

1-[(4-amino-2-methylpyrimidin-5-yl)methyl]-3-bromo-6-methyl-4-[(2,4,6-trifluorobenzyl)oxy]pyridin-2(1H)-one trifluoroacetate The title compound was prepared by a procedure similar to the one described for Example 385, step 2 (0.142 g, 9%). $^1$H NMR (CD₃OD, 400 MHz) δ 7.64 (s, 1H), 7.00 (m, 2H), 6.66 (s, 1H), 5.29 (s, 2H), 5.18 (s, 2H), 2.50 (s, 3H), 2.47 (s, 3H) ES-HRMS m/z 469.0488/471.0464 (M+H calculated for $C_{19}H_{17}N_4O_2F_3Br$ requires 469.0481/471.0463).

Example 443

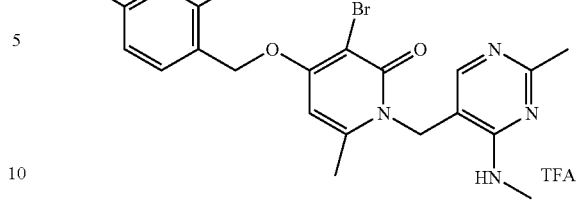

3-bromo-4-[(2,4-difluorobenzyl)oxy]-6-methyl-1-{[2-methyl-4-(methylamino)pyrimidin-5-yl]methyl}pyridin-2(1H)-one trifluoroacetate To a solution of 1-[(4-amino-2-methylpyrimidin-5-yl)methyl]-3-bromo-4-[(2,4-difluorobenzyl)oxy]-6-methylpyridin-2(1H)-one hydrochloride (0.15 g, 0.3 mmol) in DMF (3 mL) was added DBU (0.09 mL, 0.6 mmol). The solution was cooled in an ice bath and iodomethane (0.019 mL, 0.3 mmol) was added. The reaction mixture stirred at room temperature under nitrogen for 2 hours. The reaction was purified by reverse phase HPLC 10–90% CH3CN/water (30 minute gradient) at a flow rate of 100 mL/min. The appropriate fractions (m/z=465 M+H) were combined and freeze dried to afford the desired product (0.036 g, 25%) as a white powder. $^1$H NMR (CD₃OD, 400 MHz) δ 7.72 (s, 1H), 7.60 (m, 1H), 7.03 (m, 2H), 6.62 (s, 1H), 5.31 (s, 2H), 5.16 (s, 2H), 3.77 (s, 3H), 2.60 (s, 3H), 2.47 (s, 3H); ES-HRMS m/z 465.0717/467.0712 (M+H calculated for $C_{20}H_{20}N_4O_2F_2Br$ requires 465.0732/467.0714).

Example 444

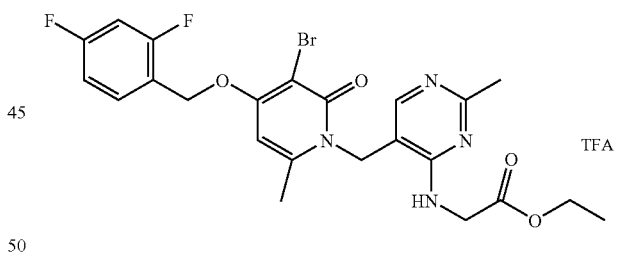

ethyl N-(5-{[3-bromo-4-[(2,4-difluorobenzyl)oxy]-6-methyl-2-oxopyridin-1(2H)-yl]methyl}-2-methylpyrimidin-4-yl)glycinate trifluoroacetate The title compound was prepared by a procedure similar to the one described for Example 442 with the exception that the reaction mixture had to be heated at oil bath temperature 70° C. for 2 days (0.1384 g, 51%). $^1$H NMR (CD₃OD, 400 MHz) δ 7.78 (s, 1H), 7.61 (m, 1H), 7.03 (m, 2H), 6.61 (s, 1H), 5.30 (s, 2H), 5.18 (s, 2H), 5.03 (s, 2H), 4.27 (q, 2H), 2.55 (s, 3H), 2.46 (s, 3H), 1.28 (t, 3H, J=7.0 Hz); ES-HRMS m/z 537.0936/539.0932 (M+H calculated for $C_{23}H_{24}N_4O_4F_2Br$ requires 537.0943/539.0926).

Example 445

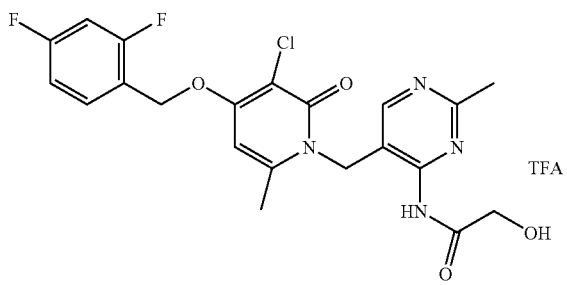

N-(5-{[3-chloro-4-[(2,4-difluorobenzyl)oxy]-6-methyl-2-oxopyridin-1(2H)-yl]methyl}-2-methylpyrimidin-4-yl)-2-hydroxyacetamide trifluoroacetate To a chilled solution of 1-[(4-amino-2-methylpyrimidin-5-yl)methyl]-3-chloro-4-[(2,4-difluorobenzyl)oxy]-6-methylpyridin-2(1H)-one trifluoroacetate (0.200 g, 0.38 mmol) in DMF (20 mL) and a catalytic amount of DMAP was added triethylamine (0.064 mL, 0.38 mmol). The reaction stirred at −20° C. and acetoxyacetyl chloride (0.082 mL, 0.76 mmol) was added. The reaction stirred cold for 15 minutes and then allowed to warm up to room temperature for 3 hours. The reaction was monitored by LR-ES MS m/z=466. The reaction was incomlete after 3 hours. Added acetoxyacetyl chloride (0.05 mL, 0.466 mmol), and triethylamine (0.2 mL, 1.43 mmol) to the reaction mixture and continued to stir overnight at room temperature. The next morning the reaction heated at 65° C. for 3 hours. The solvent was removed in vacuo and 1N LiOH (2.5 mL) was added to the residue. The reaction was heated at 60° C. for 5 hours. The reaction was diluted with acetonitrile and water (1:1) and purified by reverse phase HPLC in 10–90% CH$_3$CN/water (30 minute gradient) at a flow rate of 50 mL/min. The appropriate fractions were freeze dried to afford the desired product (0.020 g, 9%). $^1$H NMR (CD$_3$OD, 400 MHz) δ 8.04 (s, 1H), 7.6 (m, 1H), 7.02 (m, 1H), 6.59 (s, 1H), 5.30 (s, 2H), 5.24 (s, 2H), 4.26 (s, 1H), 2.60 (s, 3H), 2.43 (s, 3H); ES-HRMS m/z 465.1161 (M+H calculated for C$_{21}$H$_{20}$N$_4$O$_4$F$_2$Cl requires 465.1136).

Example 446

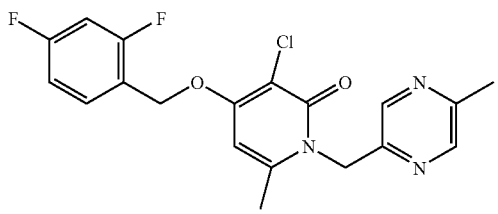

3-chloro-4-[(2,4-difluorobenzyl)oxy]-6-methyl-1-[(5-methylpyrazin-2-yl)methyl]pyridin-2(1H)-one Step 1. Preparation of 3-chloro-4-hydroxy-6-methyl-1-[(5-methylpyrazin-2-yl)methyl]pyridin-2(1H)-one

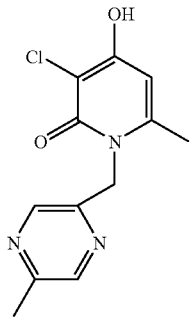

To a solution of 4-hydroxy-6-methyl-1-[(5-methylpyrazin-2-yl)methyl]pyridin-2(1H)-one (1.00 g, .3 mmol) in glacial acetic acid (10 mL) was added NCS (0.79 g, 5.94 mmol). The reaction mixture stirred at 60° C. for 6 hours. The solvent was removed under reduced pressure and the resulting residue was triturated with ethyl acetate. The desired product was filtered and dried (0.80 g, 69%). $^1$H NMR (CD$_3$OD, 400 MHz) δ 8.47 (s, 1H), 8.42 (s, 1H), 6.08 (s, 1H), 5.36 (s, 2H), 2.50 (s, 3H), 2.43 (s, 3H); ES-HRMS m/z 266.0691 (M+H calculated for C$_{12}$H$_{13}$N$_3$O$_2$Cl requires 266.0691).

Step 2. Preparation of 3-chloro-4-[(2,4-difluorobenzyl)oxy]-6-methyl-1-[(5-methylpyrazin-2-yl)methyl]pyridin-2(1H)-one To a solution of 3-chloro-4-hydroxy-6-methyl-1-[(5-methylpyrazin-2-yl)methyl]pyridin-2(1H)-one (2.48 g, 9.3 mmol) in DMA (7 mL) was added K$_2$CO$_3$ (1.54 g, 11.0 mmol) followed by 2,4-difluorobenzyl bromide (1.2 mL, 9.3 mmol). The reaction mixture stirred at room temperature under nitrogen for 1.5 hours. The solvent was distilled in vacuo. The resulting residue was diluted in dichloromethane and washed with water. The organic extracts were concentrated and the resulting residue was purified by flash column chromatography (ethyl acetate). The appropriate fractions were combined, and concentrated. $^1$H NMR (CD$_3$OD, 400 MHz) δ 8.49 (d, 1H, J=1.2 Hz), 8.40 (s, 1H), 7.59 (m, 1H), 7.04 (m, 2H), 6.54 (s, 1H), 5.41 (s, 2H), 5.28 (s, 2H), 2.54 (s, 3H), 2.40 (s, 3H); ES-HRMS m/z 392.1014 (M+H calculated for C$_{19}$H$_{17}$N$_3$O$_2$ClF$_2$ requires 392.0972).

Example 447

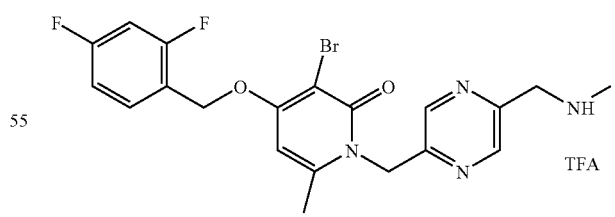

3-bromo-4-[(2,4-difluorobenzyl)oxy]-6-methyl-1-({5-[(methylamino)methyl]pyrazin-2-yl}methyl)pyridin-2(1H)-one trifluoroacetate To a suspension of 3-bromo-1-{5-(chloromethyl)pyrazin-2-yl]methyl}-4-[(2,4-difluorobenzyl)oxy]-6-methylpyridin-2(1H)-one (0.25 g, 0.53 mmol) in THF was added methylamine (1 mL, 2.1 mmol). The reaction was sealed and stirred at room temperature overnight. The reaction mixture was diluted in water:acetonitrile (1:1) and purified by reverse phase HPLC 10–90% CH₃CN/water (30 minute gradient) at a flow rate of 70 mL/min. The appropriate fractions were combined and freeze dried to afford the desired product (0.22 g, 71%) as an amorphous solid. $^1$H NMR (CD$_3$OD, 400 MHz) δ 8.73 (s, 1H), 8.55 (s, 1H), 7.6 (m, 2H), 7.02 (m, 1H), 6.54 (s, 1H), 5.47 (s, 2H), 5.29 (s, 2H), 4.37 (s, 2H), 2.78 (s, 3H), 2.56 (s, 3H). ES-HRMS m/z 465.0732/467.0709 (M+H calculated for C$_{20}$H$_{20}$N$_4$O$_2$BrF$_2$ requires 465.0732/467.0714).

Example 448

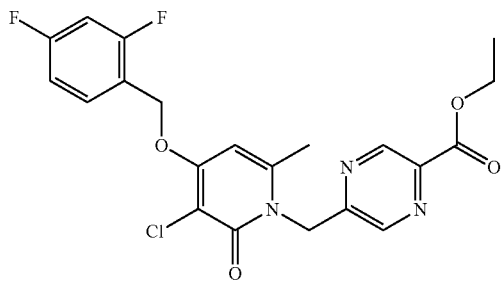

Ethyl 5-{[3-chloro-4-[(2,4-difluorobenzyl)oxy]-6-methyl-2-oxopyridin-1(2H)-yl]methyl}pyrazine-2-carboxylate To a mixture of 3-chloro-4-[(2,4-difluorobenzyl)oxy]-6-methylpyridin-2(1H)-one (0.59 g, 2.07 mmol) and ethyl 5-(bromomethyl)pyrazine-2-carboxylate (0.62 g, 2.4 mmol) in THF (15 mL) was added NaH (0.06 g, 2.4 mmol). The reaction stirred at 60° C. for 3.5 hours. The solvent was removed under reduced pressure and the residue was partitioned over dichloromethane and citric acid (5%). The organic extracts were washed with water and dried over Na$_2$SO$_4$ (anhydrous). The organic extracts were concentrated and the residue was purified by flash column chromatography (100% ethyl acetate). The appropriate fractions were combined and concentrated under reduced pressure to remove solvent. $^1$H NMR (CD$_3$OD, 400 MHz) δ 9.11 (d, 1H, J=1.6 Hz), 8.77 (s, 1H), 7.52 (m, 1H), 7.02 (m, 2H), 6.57 (s, 1H), 5.53 (s, 2H), 5.30 (s, 2H), 4.49 (q, 2H), 2.52 (s, 3H), 1.39 (t, 3H, J=7.2 Hz); ES-HRMS m/z 450.1045 (M+H calculated for C$_{21}$H$_{19}$N$_3$O$_4$ClF$_2$ requires 450.01027).

Example 449

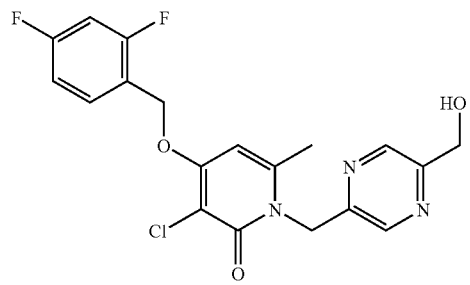

3-chloro-4-[(2,4-difluorobenzyl)oxy]-1-{[5-(hydroxymethyl)pyrazin-2-yl]methyl}-6-methylpyridin-2(1H)-one To a suspension of ethyl 5-{[3-chloro-4-[(2,4-difluorobenzyl)oxy]-6-methyl-2-oxopyridin-1(2H)-yl]methyl}pyrazine-2-carboxylate (4.0 g, 8.9 mmol) in THF:t-butanol (1:1) (10 mL) was added NaBH$_4$ (0.46 g, 12.4 mmol). The reaction stirred at room temperature under argon overnight. The reaction mixture was quenched with acetic acid (2 mL) and the solvent was removed in vacuo. The residue was triturated with water and filtered. The solid was washed with fresh water followed by ethanol. The solid was purified by flash column chromatography (100% ethyl acetate). The appropriate fractions were combined and concentrated under reduced pressure to afford the desired compound (1.58 g, 44%) as a white solid. $^1$H NMR (CD$_3$OD, 400 MHz) δ 8.59 (s, 1H), 8.56 (s, 1H), 7.52 (m, 1H), 7.01 (m, 2H), 6.55 (m, 1H), 5.45 (s, 2H), 5.29 (s, 2H), 4.71 (2H), 2.54 (s, 3H); ES-HRMS m/z 408.0940 (M+H calculated for C$_{19}$H$_{17}$N$_3$O$_3$ClF$_2$ requires 408.0921).

Example 450

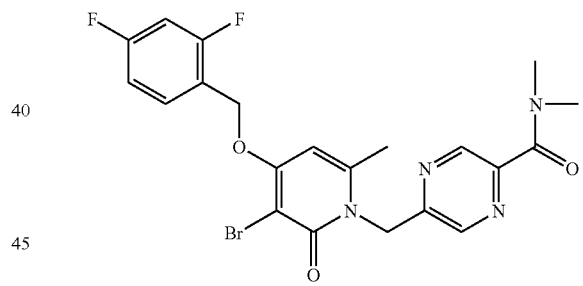

5-{[3-bromo-4-[(2,4-difluorobenzyl)oxy]-6-methyl-2-oxopyridin-1(2H)-yl]methyl}-N,N-dimethylpyrazine-2-carboxamide To a cold solution of 5-{[3-bromo-4-[(2,4-difluorobenzyl)oxy]-6-methyl-2-oxopyridin-1(2H)-yl]methyl}pyrazine-2-carboxylic acid (0.175 g, 0.37 mmol) in DMF (5 mL, −10° C.) was added IBCF (0.046 mL, 0.35 mmol) followed by NMM (0.041 mL 0.37 mmol). The reaction was activated for 20 minutes at −15° C. after which dimethylamine (0.375 mL, 0.74 mmol) was added. The reaction stirred at −10° C. to room temperature for 45 minutes. The solvent was removed in vacuo and the residue was purified by reverse phase HPLC 10–90% CH$_3$CN/water (30 minute gradient) at a flow rate of 70 mL/min. The appropriate fractions were combined and freeze dried to afford the desired product (0.140 g, 75%) as a white solid. $^1$H NMR (CD$_3$OD, 400 MHz) δ 8.68 (s, 1H), 8.67 (s, 1H), 7.52 (m, 1H), 7.02 (m, 2H), 6.54 (s, 1H), 5.50 (s, 2H), 5.30 (s, 2H), 3.11 (s, 3H), 3.07 (s, 3H), 2.55 (s, 3H); ES-HRMS m/z 493.0680/495.0657 (M+H calculated for C$_{21}$H$_{20}$N$_4$O$_3$BrF$_2$ requires 493.0680/495.0657).

Example 451

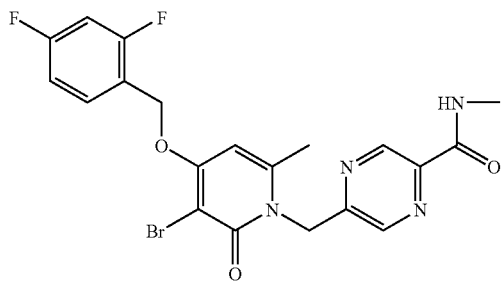

5-{[3-bromo-4-[(2,4-difluorobenzyl)oxy]-6-methyl-
2-oxopyridin-1(2H)-yl]methyl}-N-methylpyrazine-
2-carboxamide The title compound was prepared essentially as in Ex. 450, substituting dimethylamine with methylamine. $^1$H NMR (CD$_3$OD, 400 MHz) δ 9.07 (s, 1H), 8.68 (s, 1H), 7.54 (m, 1H), 7.02 (m, 2H), 6.54 (s, 1H), 5.52 (s, 2H), 5.30 (s, 2H), 2.94 (s, 3H), 2.54 (s, 3H); ES-HRMS m/z 479.0542/481.0518 (M+H calculated for C$_{20}$H$_{18}$N$_4$O$_3$BrF$_2$ requires 479.0525, 481.0507).

Example 452

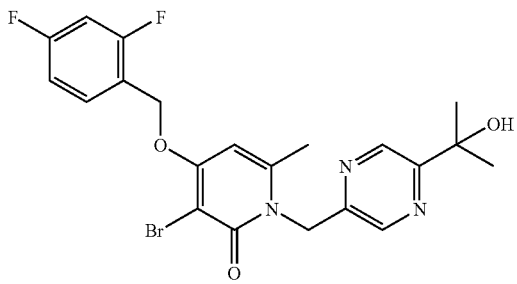

3-bromo-4-[(2,4-difluorobenzyl)oxy]-1-{[5-(1-
hydroxy-1-methylethyl)pyrazin-2-yl]methyl}-6-
methylpyridin-2(1H)-one To a cold flask of MeMgBr (1.59 mL, 1.0 mmol) was added a suspension of ethyl 5-{[3-bromo-4-[(2,4-difluorobenzyl)oxy]-6-methyl-2-oxopyridin-1(2H)-yl]methyl}pyrazine-2-carboxylate (0.5 g, 1.0 mmol) in THF (20 mL). The reaction stirred at 0° C. for 1.5 hours and then at room temperature overnight. The reaction was quenched with cold citric acid (25 mL, 5%) and extracted with ethyl acetate (2×100 mL). The organic extracts were washed with fresh water. The organic extracts were concentrated and purified by reverse phase HPLC 10–90% CH$_3$CN/water (30 minute gradient) at a flow rate of 70 mL/min. The appropriate fractions were combined and freeze dried to afford the desired product (29.9 mg, 6%). $^1$H NMR (CD$_3$OD, 400 MHz) δ 8.76 (d, 1H, J=1.6 Hz), 8.54 (d, 1H, J=1.2 Hz), 7.52 (m, 1H), 7.02 (m, 2H), 6.52 (s, 1H), 5.45 (s, 2H), 5.29 (s, 2H), 2.55 (s, 3H), 1.52 (s, 6H); ES-HRMS m/z 480.0745/482.0722 (M+H calculated for C$_{21}$H$_{21}$N$_3$O$_3$BrF$_2$ requires 480.0729/482.0711).

Example 453

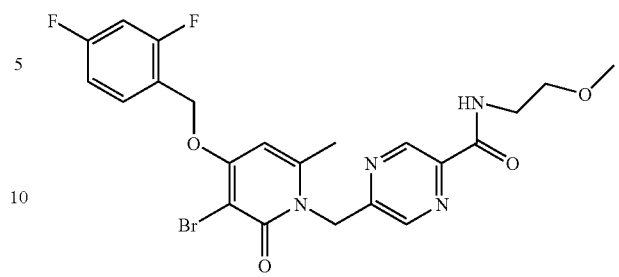

5-{[3-bromo-4-[(2,4-difluorobenzyl)oxy]-6-methyl-
2-oxopyridin-1(2H)-yl]methyl}-N-(2-methoxyethyl)
pyrazine-2-carboxamide The title compound was prepared essentially as in Ex. 450, substituting dimethylamine with 2-methoxyethylamine. $^1$H NMR (CD$_3$OD, 400 MHz) δ 9.08 (d, 1H, J=1.2 Hz), 8.70 (d, 1H, J=1.2 Hz), 7.61 (m, 1H), 7.04 (m, 2H), 6.54 (s, 1H), 5.53 (s, 2H), 5.30 (s, 2H), 3.56 (m, 4H), 3.30 (s, 3H), 2.54 (s, 3H); ES-HRMS m/z 523.0822/525.0810 (M+H calculated for C$_{22}$H$_{22}$N$_4$O$_4$BrF$_2$ requires 523.0787/525.0770).

Example 454

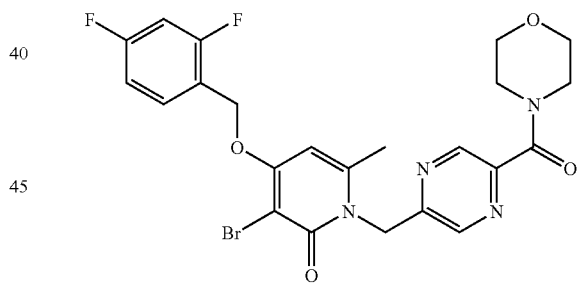

3-bromo-4-[(2,4-difluorobenzyl)oxy]-6-methyl-1-{
[5-(morpholin-4-ylcarbonyl)pyrazin-2-yl]
methyl}pyridin-2(1H)-one The title compound was prepared essentially as in Ex. 450, substituting dimethylamine with morpholine. $^1$H NMR (CD$_3$OD, 400 MHz) δ 8.77 (d, 1H, J=1.6 Hz), 8.67 (s, 1H), 7.54 (m, 1H), 7.02 (m, 2H), 6.54 (s, 1H), 5.50 (s, 2H), 5.30 (s, 2H), 3.75 (s, 4H), 3.59 (dd, 4H, J=5.6 Hz, 5.2 Hz), 2.55 (s, 3H); ES-HRMS m/z 535.0816/537.0817 (M+H calculated for C$_{23}$H$_{22}$N$_4$O$_4$BrF$_2$ requires 535.0787/537.0770).

Example 455

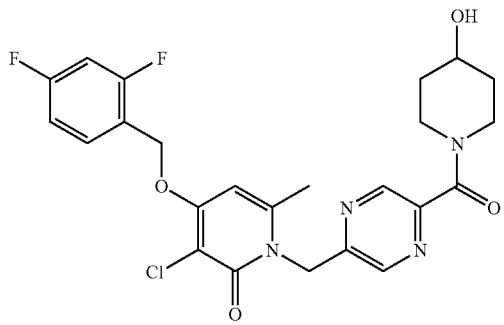

3-chloro-4-[(2,4-difluorobenzyl)oxy]-1-({5-[(4-hydroxypiperidin-1-yl)carbonyl]pyrazin-2-yl}methyl)-6-methylpyridin-2(1H)-one Step 1. Preparation of 5-{[3-chloro-4-[(2,4-difluorobenzyl)oxy]-6-methyl-2-oxopyridin-1(2H)-yl]methyl}pyrazine-2-carboxylic acid

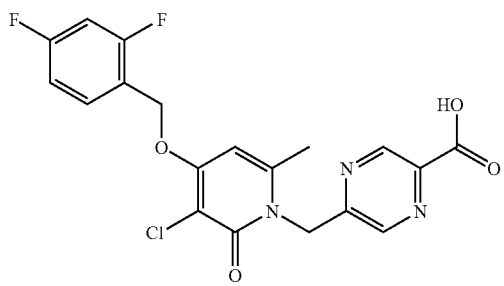

A mixture of ethyl 5-{[3-chloro-4-[(2,4-difluorobenzyl)oxy]-6-methyl-2-oxopyridin-1(2H)-yl]methyl}pyrazine-2-carboxylate (1.03 g, 2.3 mmol) in 1N NaOH (3.4 ml, 3.45 mmol, EtOH/water 1:1 v/v) stirred at room temperature for 2 hours. The reaction mixture was quenched with 5% citric acid and filtered. The solid was washed with water and dried to afford the desired product (1.011 g, 100%) as a white solid. $^1$H NMR (CD$_3$OD, 400 MHz) δ 9.02 (s, 1H), 8.60 (s, 1H), 7.60 (m, 1H), 7.04 (m, 2H), 6.55 (s, 1H), 5.50 (s, 2H), 5.30 (s, 2H), 2.52 (s, 3H); ES-HRMS m/z 422.0732 (M+H calculated for $C_{19}H_{15}N_3O_4ClF_2$ requires 422.0714).

Step 2. Preparation of 3-chloro-4-[(2,4-difluorobenzyl)oxy]-1-({5-[(4-hydroxypiperidin-1-yl)carbonyl]pyrazin-2-yl}methyl)-6-methylpyridin-2(1H)-one The title compound was prepared by a procedure similar to the one described for Example 453 (0.1396 g, 47%). $^1$H NMR (CD$_3$OD, 400 MHz) δ 8.67 (s, 2H), 7.59 (m, 1H), 7.02 (m, 2H), 6.57 (s, 1H), 5.49 (s, 2H), 5.30 (s, 2H), 4.16 (m, 1H), 3.89 (septet, 1H), 3.72 (m, 1H), 3.38 (m, 2H), 2.56 (s, 3H), 1.93 (m, 1H), 1.83 (m, 1H), 1.45 (m, 2H); ES-HRMS m/z 505.1485 (M+H calculated for $C_{24}H_{24}N_4O_4ClF_2$ requires 505.1449).

Example 456

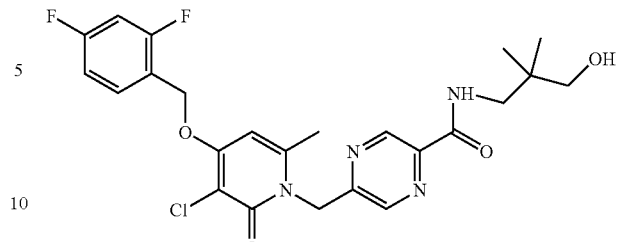

5-{(3-chloro-4-[(2,4-difluorobenzyl)oxy]-6-methyl-2-oxopyridin-1(2H)-yl]methyl}-N-(3-hydroxy-2,2-dimethylpropyl)pyrazine-2-carboxamide The title compound was prepared by a procedure similar to the one described for Example 455 (0.215 g, 71%). $^1$H NMR (CD$_3$OD, 400 MHz) δ 9.08 (d, 1H, J=1.2 Hz), 8.71 (d, 1H, J=1.6 Hz), 7.58 (m, 1H), 7.02 (m, 2H), 6.57 (s, 1H), 5.52 (s, 1H), 5.30 (s, 1H), 3.31 (s, 4H), 2.55 (s, 3H), 0.912 (s, 6H); ES-HRMS m/z 507.1630 (M+H calculated for $C_{24}H_{26}N_4O_4ClF_2$ requires 507.1605).

Example 457

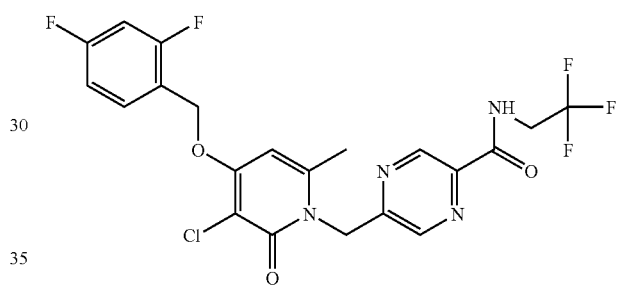

5-{[3-chloro-4-[(2,4-difluorobenzyl)oxy]-6-methyl-2-oxopyridin-1(2H)-yl]methyl}-N-(2,2,2-trifluoroethyl)pyrazine-2-carboxamide The title compound was prepared by a procedure similar to the one described for Example 455 except no purification was required, only a NaHCO$_3$/ethyl acetate extraction was needed (0.2176 g, 73%). $^1$H NMR (CD$_3$OD, 400 MHz) δ 9.11 (d, 1H, J=1.6 Hz), 8.73 (d, 1H, J=1.3 Hz), 7.59 (m, 1H), 7.02 (m, 2H), 6.57 (s, 1H), 5.53 (s, 2H), 5.30 (s, 2H), 4.01 (q, 2H), 2.54 (s, 3H); ES-HRMS m/z 503.0930 (M+H calculated for $C_{21}H_{17}N_4O_3ClF_5$ requires 503.0904).

Example 458

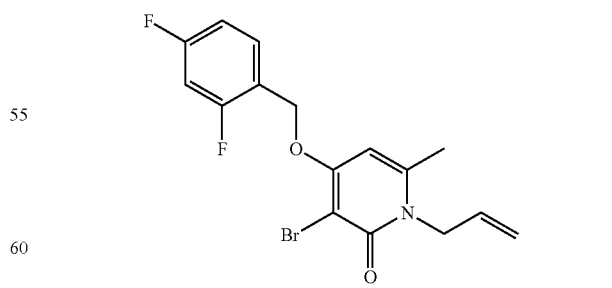

1-allyl-3-bromo-4-[(2,4-difluorobenzyl)oxy]-6-methylpyridin-2(1H)-one

Step 1: 1-allyl-4-hydroxy-6-methylpyridin-2(1H)-one. 4-hydroxy-6-methyl-2-pyrone (2 g, 16 mmol) was stirred in water (25 mL). Allylamine (1.2 ml, 16 mmol) was added to the reaction. The reaction was then heated to 100° C. at which point the reaction became homogeneous. The reaction was stirred at 100° C. for 2 h. The reaction was then allowed to cool to rt after which a white precipitate formed. The precipitate was isolated by suction filtration. After additional washing with water, 1.8 g (69%) of an off-white solid was obtained.

Step 2: 1-allyl-4-[(2,4-difluorobenzyl)oxy]-6-methylpyridin-2(1H)-one. To a stirred solution of the above pyrone(4.0 g, 24 mmol) in DMF(75 ml) was added $Cs_2CO_3$ (7.8 g, 4 mmol) followed by addition of 2,4-diflurorbenzyl bromide(3.4 mmol, 26.4 mmol). The resulting mixture was stirred at rt for 2 h. Additional $Cs_2CO_3$ (1 g) and bromide (1 ml) was added and the reaction was stirred for an additional 2 h. The $Cs_2CO_3$ was removed by suction filtration. The DMF was removed under vacuum and the crude material was purified by flash chromatography. Elution with ethyl acetate-hexanes (2:1 to 1:1) afforded 1.5 g (21%) of the desired compound.

Step 3: 1-allyl-3-bromo-4-[(2,4-difluorobenzyl)oxy]-6-methylpyridin-2(1H)-one. To a stirred suspension of the above pyridinone (1 g, 3.4 mmol) in $CH_3CN$ (10 ml) was added n-bromosuccinimide (670 mg, 3.8 mmol). The reaction mixture was stirred, at rt, for 3 h. The product was obtained by filtration of the reaction mixture and washing of the solid with diethyl ether. $^1$H-NMR (DMSO$_{d6}$/400 MHz) δ 7.62 (app q, J=8.8 hz, 1H), 7.31 (ddd, J=12.0, 9.6, 2.8 hz, 1H); 7.15 (app dtd, J=8.4, 2.4, 0.8 Hz, 1H); 6.50 (s, 1H); 5.87 (ddt, J=12.4, 10.4, 5.6 Hz, 1H), 5.30 (s, 2H), 5.10 (dd, J=10, 1.6 Hz, 1H), 4.87 (dd, J=17.6, 1.6 Hz, 1H), 4.64 (m, 2H), 2.34 (s, 3H); 19F-NMR (DMSO$_{d6}$/282.2 MHz) −109.68 (quin, J=1H), −113.66 (quar, J=1H); HRMS m/z 370.0255 (M+H calcd for $C_{16}H_{15}BrF_2NO_2$=370.0246).

Example 459

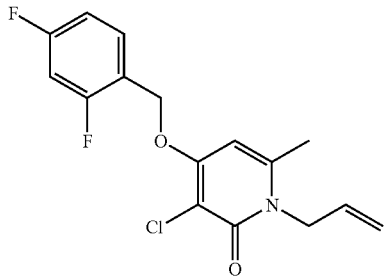

1-allyl-3-chloro-4-[(2,4-difluorobenzyl)oxy]-6-methylpyridin-2(1H)-one

Step 1: 1-allyl-3-chloro-4-hydroxy-6-methylpyridin-2(1H)-one. To a stirred solution of 1-allyl-4-hydroxy-6-methylpyridin-2(1H)-one (500 mg, 3.0 mmol) in $CH_3CN$(10 ml), at rt, was added sequentially n-bromosuccinimide (440 mg, 3.3 mmol) and dichloroacetic acid (546 μl, 6.62 mmol). The resulting mixture was stirred for 2 h. The heterogeneous mixture was filtered and the solid was washed with additional $CH_3CN$ to give 350 mg (59%) of the desired product as a tan solid. $^1$H-NMR (DMSO$_{d6}$/300 MHz) δ 11.16 (s, 1H), 5.98–5.86 (m, 2H), 5.12 (dd, J=10.5, 1.5 Hz, 1H), 4.89 (dd, J=17.1, 1.5 Hz, 1H), 4.63–4.61 (m, 2H), 2.29 (s, 3H). ES-HRMS m/z 200.050 (M+H calcd for $C_9H_{11}ClNO_2$=200.0470)

Step 2: 1-allyl-3-chloro-4-[(2,4-difluorobenzyl)oxy]-6-methylpyridin-2(1H)-one. The title compound was prepared by the procedure outline in the synthesis of Example 458, step 3. $^1$H-NMR (DMSO$_{d6}$/300 MHz) δ 7.67 (app q, J=8.4 hz, 1H), 7.36 (app dt, J=10.2, 2.7 hz, 1H); 7.15 (m, 1H); 6.58 (s, 1H); 5.93 (ddt, J=15.3, 9.6, 4.8 Hz, 1H), 5.30 (s, 2H), 5.15 (dd, J=10.2, 1.2 Hz, 1H), 4.92 (dd, J=17.4, 1.2 Hz, 1H), 4.69–467 (m, 2H), 2.41 (s, 3H). ES-HRMS m/z 326.0760 (M+H calcd for $C_{16}H_{15}ClF_2NO_2$=326.0790).

Example 460

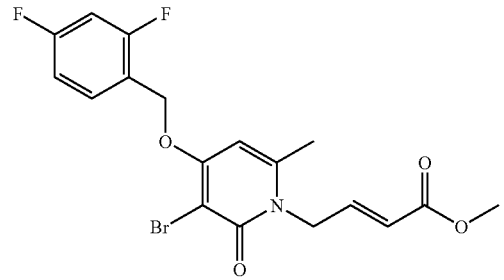

Methyl (2E)-4-[3-bromo-4-[(2,4-difluorobenzyl)oxy]-6-methyl-2-oxopyridin-1(2H)-yl]but-2-enoate To a stirred suspension of NaH (277 mg, 11 mmol) in anhydrous THF (30 ml), which was cooled to 0° C., was slowly added 3-bromo-4-[(2,4-difluorobenzyl)oxy]-6-methylpyridin-2(1H)-one (3.3 g, 10 mmol). The resulting slurry was stirred for 15 min, after which methyl 4-bromocrotonate (1.4 ml, 12 mmol) was added to the reaction. The ice bath was removed and the reaction was heated to reflux for 16 h. The reaction was quenched by the addition of 1N $NH_4Cl$. The layers were separated and the aqueous layer was extracted with $CH_2Cl_2$ (5×). The organics were combined, dried, and concentrated in vacuo. The crude yellowish material was then triturated with $Et_2O$ to give, after filtration and drying, 1.8 g (43%) of a white solid. $^1$H-NMR (DMSO$_{d6}$/300 MHz) δ 7.65 (app q, J=8.7 hz, 1H), 7.36 (app dt, J=12.0, 3.0 hz, 1H); 7.17 (dt, J=8.4, 1.8 Hz, 1H); 6.94 (dt, J=15.9, 4.5 Hz, 1H); 6.57 (s, 1H), 5.52 (d, J=15.9 Hz, 1H), 5.29 (s, 2H), 4.84 (m, 2H), 3.63 (s, 3H), 2.33 (s, 3H). ES-HRMS m/z 428.0301 (M+H calcd for $C_{18}H_{17}BrF_2NO_4$=428.0310).

Example 461

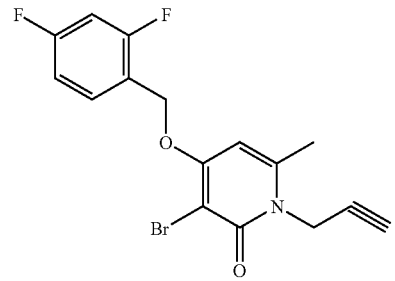

3-bromo-4-[(2,4-difluorobenzyl)oxy]-6-methyl-1-prop-2-ynylpyridin-2(1H)-one

Step 1: 4-[(2,4-difluorobenzyl)oxy]-6-methyl-1-prop-2-ynylpyridin-2(1H)-one. The title compound was prepared by alkylation of 4-[(2,4-difluorobenzyl)oxy]-6-methylpyridin- 2(1H)-one (2.5 g, 10 mmol) with propargyl bromide (1.3 ml, 11.0 mmol) as described above to give 1.3 g (44%) of the desired product. $^1$H-NMR (DMSO$_{d6}$/300 MHz) δ 7.60 (app q, J=8.4 hz, 1H), 7.35–7.27 (m, 1H); 7.16–7.10 (m, 1H); 5.94 (d, J=2.1 Hz, 1H), 5.88 (d, J=3.0 Hz, 1H), 5.03 (s, 2H), 4.76 (d, J=2.4, Hz, 2H), 3,31 (s, 3H), 3.24 (t, J=2.4 Hz, 1H), 2.39 (s, 3H); ES-HRMS m/z 290.0994 (M+H calcd for $C_{16}H_{14}F_2NO_2$=290.0993).

Step 2: Bromination of 4-[(2,4-difluorobenzyl)oxy]-6-methyl-1-prop-2-ynylpyridin-2(1H)-one (500 mg, 1.67 mmol) with NBS (300 mg, 1.67 mmol) was carried out in the manner described above to give 350 mg (57%) of the desired compound. $^1$H-NMR (DMSO$_{d6}$/300 MHz) δ 7.67 (app q, J=9.0 hz, 1H), 7.36 (app dt, J=10.5, 2.4 hz, 1H); 7.23–7.16 (m, 1H); 6.60 (s, 1H), 5.29 (s, 2H), 4.90 (d, J=2.4, Hz, 1H), 3.35 (s, 3H), 3.32 (s, 1H), 2.53 (s, 3H); ES-HRMS m/z 368.0107 (M+H calcd for $C_{16}H_{13}BrF_2NO_2$=368.0098).

Example 462

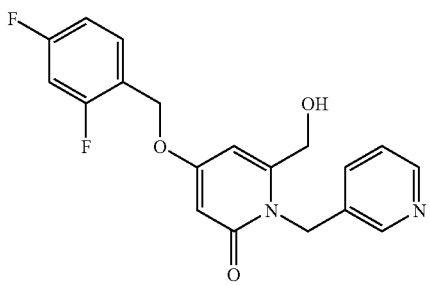

4-[(2,4-difluorobenzyl)oxy]-6-(hydroxymethyl)-1-(pyridin-3-ylmethyl)pyridin-2(1H)-one Step 1: To a suspension of (4-[(2,4-difluorobenzyl)oxy]-6-methyl-1-(pyridin-3-ylmethyl)pyridin-2(1H)-one) (710 mg, 2 mmol) in dioxane (10 mL) was added selenium dioxide (1.1 g 10 mmol). The resulting mixture was heated to 160° C. in a 125 mL sealed tube for 1 h. The reaction was filtered through a fritted funnel. The filtrate was washed with (10:1)CH$_2$Cl$_2$-MeOH. The organics were combined and concentrated in vacuo. The crude material was purified by flash chromatography. Elution with (50:50→0:100)hexanes yielded 450 mg (63%) of the aldehyde. $^1$H-NMR (DMSO$_{d6}$/400 MHz). δ 9.48 (s, 1H, CHO).

Step 2: The aldehyde (350 mg, 1 mmol) was dissolved in MeOH (4 mL) and cooled to 0° C. . To this mixture was added NaBH$_4$ (28 mg, 1 mmol) in one portion. After 30 min, additional NaBH4 (20 mg) was added to the reaction. The MeOH was then removed under vacuum. The residue was diluted with 1N NH$_4$Cl and then extracted with CH$_2$Cl$_2$(4×). The organics were combined, dried, and concentrated in vacuo. The yellowish crude product was then taken up in (1:1)CH$_2$Cl$_2$-Et$_2$O. After sitting for a period of time a white precipitate resulted. Filtration and washing with additional Et$_2$O yielded, after drying, 250 mg (55%) of the desired alcohol. $^1$H-NMR (DMSO$_{d6}$/400 MHz). δ 8.42 (dd, J=4.4, 1.6 Hz, 1H), 8.37 (d, J=1.6 Hz, 1H), 7.61 (app q, J=8.0 Hz, 1H), 7.45 (d, J=8.0 Hz, 1H), 7.32–7.27 (M, 2H), 7.12 (dt, J=8.4, 1.6 Hz, 1H), 6.07 (d, J=2.8 Hz, 1H), 5.99 (d, J=12.8 Hz, 1H), 5.63 (br s, 1H), 5.18 (s, 2H), 5.09 (s, 2H), 4.29 (s, 2H). LC/MS, t$_r$=1.19 minutes (5 to 95% acetonitrile/water over 5 minutes at 1 ml/min with detection 254 nm, at 50° C.). ES-MS m/z 359.1 (M+H).

Example 463

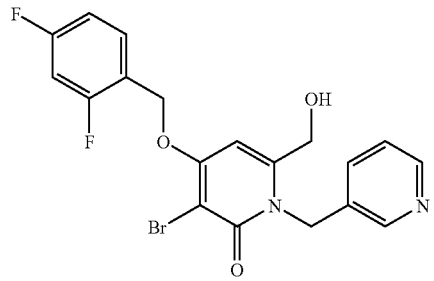

3-Bromo-4-[(2,4-difluorobenzyl)oxy]-6-(hydroxymethyl)-1-(pyridin-3-ylmethyl)pyridin-2(1H)-one The title compound was prepared by bromination of as described above to give a 60% yield. $^1$H-NMR (DMSO$_{d6}$/300 MHz). δ 7.93 (d, J=7.8 Hz, 1H), 7.73–7.65 (m, 3H), 7.38 (dt, J=10.2, 2.4 Hz, 1H), 7.21 (app t, J=8.7 Hz, 2H), 6.74 (s, 1H), 5.38–5.36 (m, 4H), 4.50 (s, 2H); ES-HRMS m/z 437.0311 (M+H cacld for $C_{19}H_{16}BrF_2N_2O_2$=437.0313).

Example 464

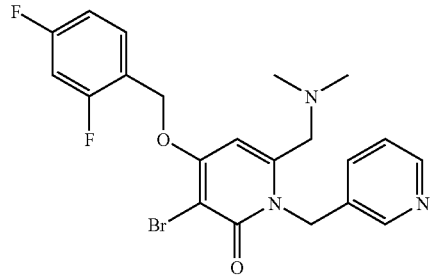

3-bromo-4-[(2,4-difluorobenzyl)oxy]-6-[(dimethylamino)methyl]-1-(pyridin-3-ylmethyl)pyridin-2(1H)-one The title compound was prepared in a similar manner to the procedure outlined below for 3-bromo-4-[(2,4-difluorobenzyl)oxy]-1-(2,6-difluorophenyl)-6-[(dimethylamino) -methyl]pyridin-2(1H)-one using the aldehyde (300 mg, 0.85 mmol) described above and 2.0 N THF solution of dimethylamine (500 μL, 1 mmol) to give 110 mg (34%) of a colorless oil. The oil was then dissolved in MeOH (1 mL) and stirred with fumaric acid (25 mg) for 1 h. The resulting precipitate was filtered, washed with diethyl ether, and dried to give the pure product as it's fumurate salt. $^1$H-NMR (DMSO$_{d6}$/400 MHz). δ 8.43–8.41

(m, 1H), 8.35 (s, 1H), 7.67–7.61 (m, 1H), 7.44–7.40 (m, 1H), 7.35–7.29 (m, 2H), 7.17–7.12 (m, 1H), 6.62 (s, 1H), 6.60 (s, 1H), 5.41 (s, 2H), 5.32 (s, 2H), 3.13 (s, 2H), 2.12 (s, 6H). LC/MS, t$_r$=1.55 minutes (5 to 95% acetonitrile/water over 5 minutes at 1 ml/min with detection 254 nm, at 50° C.). ES-MS m/z 464 (M+H).

Example 465

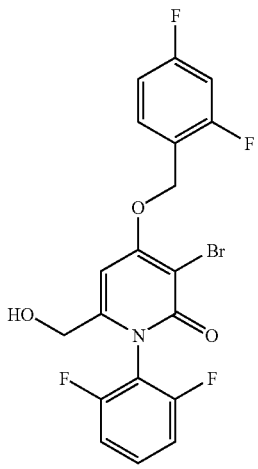

3-bromo-4-[(2,4-difluorobenzyl)oxy]-1-(2,6-difluorophenyl)-6-(hydroxymethyl)pyridin-2(1H)-one Step 1: 4-[(2,4-difluorobenzyl)oxy]-1-(2,6-difluorophenyl)-6-oxo-1,6-dihydropyridine-2-carbaldehyde.

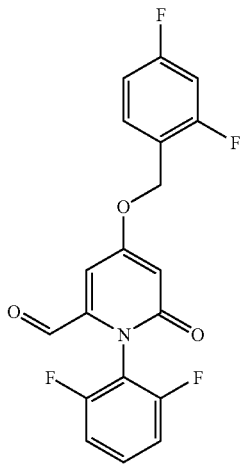

In a 300 ml high-pressure glass reaction vessel (16.3 g, 45 mmol) was dissolved in 1,4-dioxane (90 mL). The reaction vessel was sealed and immersed in a preheated oil bath at 170° C. The reaction was heated at 170° C. (165–170° C.) for 1.5 hours and then cooled to room temperature. The reaction was worked up by filtering the reaction mixture through a plug of celite and silica gel. The plug was then washed with 500 ml of methanol-CH$_2$Cl$_2$ mixture (1:5). The filtrate was evaporated to give 14.2 g of the desired crude aldehyde.

Step 2: Preparation of 4-[(2,4-difluorobenzyl)oxy]-1-(2,6-difluorophenyl)-6-(hydroxymethyl)pyridin-2(1H)-one.

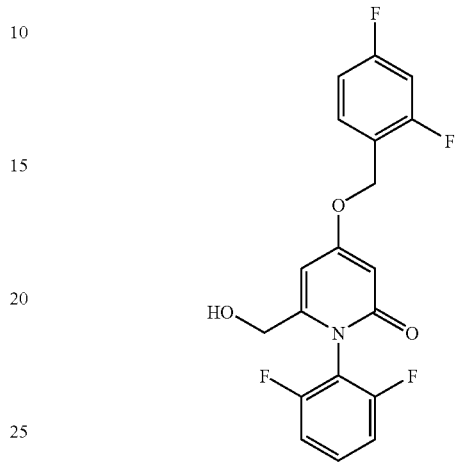

In a 500 ml three neck round bottom flask equipped with a stir bar of 4-[(2,4-difluorobenzyl)oxy]-1-(2,6-difluorophenyl)-6-oxo-1,6-dihydropyridine-2-carbaldehyde (14.2 g, 37.7 mmol) was dissolved in methanol (200 mL). The reaction mixture was cooled to 0° C. and to this was added sodium borohydride (2.13 g, 56.30 mmol) in a slow portion-wise fashion. The reaction was stirred at 0° C. for 2 hour. Excess amount of sodium borohydride was added to drive the reaction to completion. After stirring for approximately 2.5 hours, the reaction was allowed to warm to room temperature and then concentrated to dryness. The residue was taken up in ethyl acetate (100 mL) and washed with dilute HCl (pH of aqueous layer was approximately 4). Organic extracts were washed with brine (1×50 ml), dried over MgSO$_4$, and concentrated in vacuo. The crude product was recrystallized from ethyl acetate and hexane to yield 7.56 g(44% yield-starting from step 1) of the desired alcohol.

Step 3: Preparation of the Title Compound.

In a 100 ml round bottom flask of 4-[(2,4-difluorobenzyl)oxy]-1-(2,6-difluorophenyl)-6-(hydroxymethyl)pyridin-2 (1H)-one (2.49 g, 6.56 mmol), from step 2, was dissolved in acetonitrile (35 mL). The reaction mixture was cooled to 0° C. in ice bath for 10 min. and then charged with N-bomosuccinamide (1.17 g, 6.6 mmol). The mixture was allowed to stir, at 0° C., under nitrogen atmosphere for 2 hours. The reaction was the worked up by removing the acetonitrile under vacuum. The resulting residue was then filtered, with washing from a small amount of acetonitrile, to give a yellow solid. $^1$H NMR (400 MHz, DMSO-d$_6$) δ 7.695–7.588 (m, 2H), 7.368–7.314 (m, 3H), 7.175 (dt, J=8.5, 2.5, Hz, 1H), 6.760 (s, 1H), 5.712 (t, J=5.674 Hz, 1H), 5.384 (s, 2H), 4.004–3.990 (m, 2H); ES-HRMS m/z 458.0013 (M+H-calcd for C$_{19}$H$_{13}$BrF$_4$NO$_3$, requires 458.0013).

Example 466

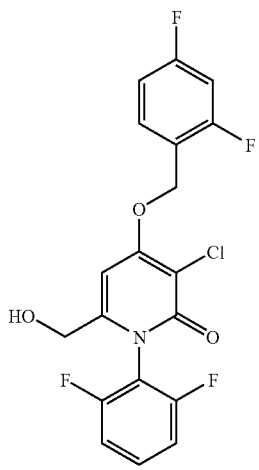

3-chloro-4-[(2,4-difluorobenzyl)oxy]-1-(2,6-difluorophenyl)-6-(hydroxymethyl)pyridin-2(1H)-one The title compound was prepared by taking 4-[(2,4-difluorobenzyl)oxy]-1-(2,6-difluorophenyl)-6-(hydroxymethyl)pyridin-2(1H)-one (1.5 g, 3.9 mmol) in acetonitrile (15 mL) and adding to that N-chlorosuccinimide (580 mg, 4.3 mmol). The reaction was stirred at rt for 3 h afterwhich a small amount of additional N-chlorosuccinimide (50 mg, 0.4 mmol) was added to the reaction. Stirring was continued for 1 h. The reaction mixture was filtered through a fritted funnel to obtain the crude material. $^1$H NMR (400 MHz, DMSO-$d_6$) δ 7.69–7.61 (m, 2H), 7.37–7.31 (m, 3H), 7.17 (dt, J=8.8, 2.0 Hz, 1H), 6.80 (s, 1H), 5.70 (t, J=6.0 Hz, 1H), 5.38 (s, 2H), 4.01 (d, J=6.0 Hz, 2H); ES-HRMS m/z 414.0515 (M+H calcd for $C_{19}H_{13}ClF_4NO_3$, requires 414.0520).

Example 467

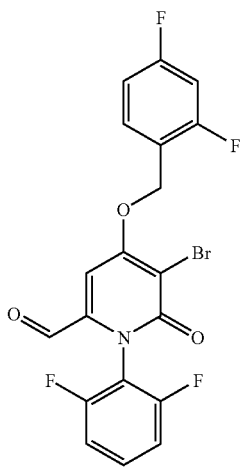

5-bromo-4-[(2,4-difluorobenzyl)oxy]-1-(2,6-difluorophenyl)-6-oxo-1,6-dihydropyridine-2-carbaldehyde Preparation of the title compound. In a 50 ml one neck round bottom flask 4-[(2,4-difluorobenzyl)oxy]-1-(2,6-difluorophenyl)-6-oxo-1,6-dihydropyridine-2-carbaldehyde (0.36 g, 0.95 mmol) was dissolved in acetonitrile (5 mL). The reaction mixture was cooled to 0° C. in ice bath and charged with N-bromosuccinamide (0.17 g, 0.95 mmol). The mixture was allowed to stir at 0° C. for 2 hours under nitrogen atmosphere After 2 hours, the solvent was evaporated under vacuum. $^1$H NMR (400 MHz, DMSO-$d_6$) δ 9.53 (s, 1H), 7.73–7.67 (m, 2H), 7.62–7.54 (m, 1H), 7.35 (dt, J=10.40, 2.56 Hz, 1H), 7.27 (t, J=8.35 Hz, 2H), 7.19 (dt, J=8.60, 2.44 Hz, 1H), 5.72 (s, 1H), 5.50 (s, 2H); ES-MS m/z 455.9836 (M+H calcd for $C_{19}H_{11}BrF_4NO_3$, requires 455.9859).

Example 468

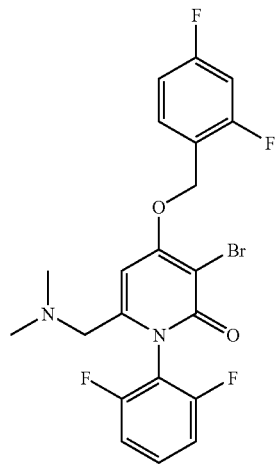

3-bromo-4-[(2,4-difluorobenzyl)oxy]-1-(2,6-difluorophenyl)-6-[(dimethylamino)methyl]pyridin-2(1H)-one In a 50 ml round bottom flask 5-bromo-4-[(2,4-difluorobenzyl)oxy]-1-(2,6-difluorophenyl)-6-oxo-1,6-dihydropyridine-2-carbaldehyde (0.456 gm, 1.0 mmol) was stirred in dichloromethane (5 mL). To this mixture was added a 2M THF solution of dimethyl amine (1.25 ml, 2.5 mmol). The mixture was allowed to stir under nitrogen atmosphere and at room temperature for 2 hours. To this mixture was then added triacetoxy sodium borohydride (0.37 g, 1.75 mmol) followed by two to three drops of acetic acid. The mixture was then stirred at rt overnight. The solvents were then removed by evaporation and the residue was taken up in ethyl acetate (30 ml) and washed with aqueous sodium bicarbonate and brine. The organics were then combined, dried over MgSO$_4$, and concentrated in vacuo. The crude product was purified by flash column chromatography using a solvent gradient of (3:1) ethyl acetate-hexane to (0:100) ethyl acetate to give 0.14 g (30% yield) of the desired product. $^1$H NMR (300 MHz, DMSO-$d_6$) δ 7.73–7.58 (m, 2H), 7.42–7.30 (m, 3H), 7.22 (dt, J=8.73, 2.60 Hz, 1H), 6.81 (s, 1H), 5.44 (s, 2H), 3.04 (s, 2H), 1.96 (s, 6H); ES-MS m/z 485.0 (M+H). ES-HRMS m/z 485.0457 (M+H calcd for $C_{21}H_{18}BrF_4N_2O_2$, requires 485.0489).

Example 469

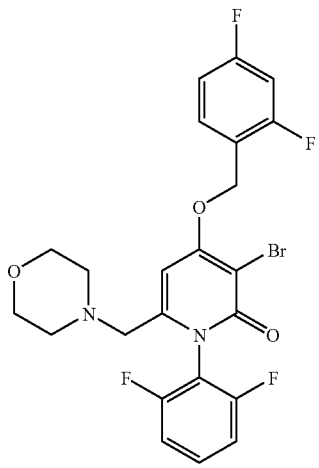

3-bromo-4-[(2,4-difluorobenzyl)oxy]-1-(2,6-difluorophenyl)-6-(morpholin-4-ylmethyl)pyridin-2(1H)-one The title compound was prepared by reacting 5-bromo-4-[(2,4-difluorobenzyl)oxy]-1-(2,6-difluorophenyl)-6-oxo-1,6-dihydropyridine-2-carbaldehyde (0.456 g, 1 mmol) with morpholine (0.13 ml, 1.5 mmol) and triacetoxy sodium borohydride (0.42 g, 2.0 mmol) in dichloromethane (7 mL) by using a similar procedure to the one described for Example 468. The crude product was purified by flash column chromatography. Elution with (50:50→0:100) hexanes-ethyl acetate to give 0.15 g (29% yield) of the desired product. $^1$H NMR (300 MHz, DMSO-$d_6$) δ 7.75–7.57 (m, 2H), 7.43–7.31 (m, 3H), 7.20 (dt, J=8.64, 2.48 Hz, 2H), 6.85 (s, 1H), 5.44 (s, 2H), 3.37 (app t, J=4.37 Hz, 4H), 3.13 (s, 2H), 2.08 (t, J=4.19 Hz, 4H); ES-HRMS m/z 527.0600 (M+H calcd for $C_{23}H_{20}BrF_4N_2O_3$ requires 527.0594).

Example 470

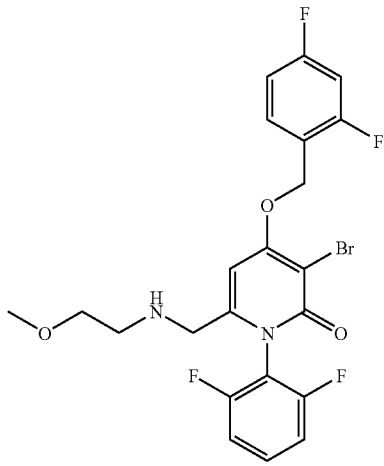

3-bromo-4-[(2,4-difluorobenzyl)oxy]-1-(2,6-difluorophenyl)-6-{[(2-methoxyethyl)amino]methyl}pyridin-2(1H)-one The title compound was prepared by reacting 5-bromo-4-[(2,4-difluorobenzyl)oxy]-1-(2,6-difluorophenyl)-6-oxo-1,6-dihydropyridine-2-carbaldehyde -(0.319 g, 0.7 mmol) with 2-methoxy ethylamine (0.086 ml, 1.0 mmol) and triacetoxy sodium borohydride (0.42 g, 2.0 mmol) in dichloromethane (4 mL) by using a procedure, similar to the one described for Example 468. The crude product was purified by flash column chromatography. Elution with (50:50→40:100) hexanes-ethyl acetate to give 0.13 g of the desired product.

$^1$H NMR (400 MHz, CDCl$_3$) δ 7.54 (q, J=6.89 Hz, 1H), 7.41–7.33 (m, 1H), 7.19 (s, 1H), 6.99 (t, J=7.90 Hz, 2H), 6.90 (dt, J=7.90, 2.78, Hz, 1H), 6.80 (dt, J=10.60, 2.34 Hz, 1H), 6.51 (s, 1H), 5.24 (s, 2H), 3.33 (t, J=4.69 Hz, 1H), 3.30 (s, 3H), 2.57 (t, J=4.86 Hz, 2H), 1.53 (s, 2H); ES-HRMS m/z 515.0548 (M+H calcd for $C_{22}H_{20}BrF_4N_2O_3$, requires 515.0594).

Example 471

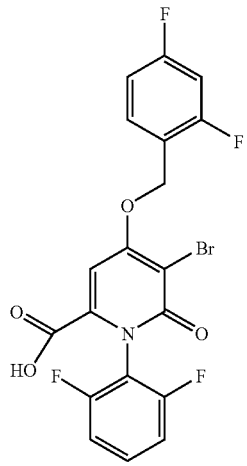

5-bromo-4-[(2,4-difluorobenzyl)oxy]-1-(2,6-difluorophenyl)-6-oxo-1,6-dihydropyridine-2-carboxylic acid In a 100 ml round bottom flask, 3-bromo-4-[(2,4-difluorobenzyl)oxy]-1-(2,6-difluorophenyl)-6(hydroxymethyl)pyridin-2(1H)-one (1.70 g, 3.7 mmol) was dissolved in acetone (10 mL) and cooled to 0° C. in ice bath. To the reaction was added 1M acetone solution of Jones (5 ml, excess amount). Additional Jones reagent was added over time (approximately 6 hours) until the reaction was complete. The reaction was then concentrated down to dryness. The residue was then taken up in ethyl acetate (10 mL) and washed with brine. The dark yellow to brown colored crude product was purified by dissolving in 1N aqueous NaOH. The remaining organic impurities were removed by extracting with diethyl ether. The organic layers were discarded and the aqueous layer was acidified with dilute HCl (til $_p$H app 1) to precipitate the pure acid which was then filtered and triturated with ether to obtain 1.17 g (65%) of the desired product. $^1$H NMR (400 MHz, DMSO-$d_6$) δ 7.66 (q, J=9.41 Hz, 1H), 7.57–7.50 (m, 1H), 7.34 (dt, J=10.11, 2.78 Hz, 1H), 7.28–7.23 (m, 3H), 7.18 (dt, 8.90, 2.42 Hz, 1H), 5.47 (s, 2H). ES-HRMS m/z 471.9814 (M+H calcd for $C_{19}H_{11}BrF_4NO_4$, requires 471.9808).

Example 472

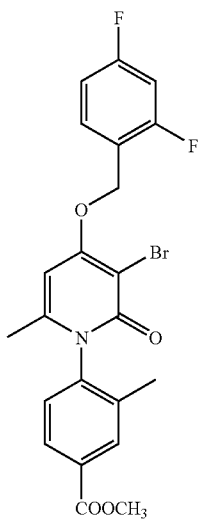

Methyl 4-[3-bromo-4-[(2,4-difluorobenzyl)oxy]-6-methyl-2-oxopyridin-1(2H)-yl]-3-methylbenzoate Step 1: Preparation of methyl 4-(4-hydroxy-6-methyl-2-oxopyridin-1(2H)-yl)-3-methylbenzoate.

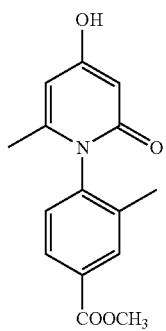

In a 50 ml one neck round bottom flask equipped with a stir bar, Dean Stark trap, and condenser 4-amino-2-methyl methylbenzoate (1.19 g, 11.63 mmol) and 4-hydroxy-6-methyl-2H-pyran-2-one (1.611 g, 12.78 mmol) were mixed together and dissolved in 1,2-dichlorobenzene (5 mL). The mixture was vigorously stirred and then placed in a pre-heated oil bath at 165° C. The reaction was maintained at 165° C. for 1.5 hour and cooled to room temperature. The reaction was worked up by diluting with toluene (10 mL) and then stirring at room temperature for 2 hours. A light brown precipitate resulted. The crude product was isolated by filtration and then triturated with ether. $^1$H NMR (400 MHz, DMSO-$d_6$) δ 10.64 (s, 1H), 7.93 (s, 1H), 7.85 (dd, 8.46 Hz, 1H), 7.26 (d, J=8.12 Hz, 1H), 5.91 (d, J=2.32 Hz, 1H), 5.54 (d, J=2.32 Hz, 1H), 3.84 (s, 3H), 1.99 (s, 3H), 1.73 (s, 3H). ES-HRMS m/z 272.0880 (M−H calcd for $C_{15}H_{14}NO_4$, requires 272.1001).

Step 3: Preparation of Methyl 4-(3-bromo-4-hydroxy-6-methyl-2-oxopyridin-1 (2H)-yl)-3-methylbenzoate

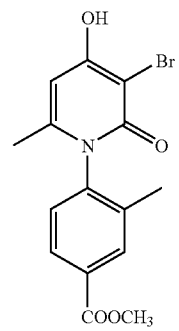

Methyl 4-(3-bromo-4-hydroxy-6-methyl-2-oxopyridin-1 (2H)-yl)-3-methylbenzoate was prepared by reacting— methyl 4-(4-hydroxy-6-methyl-2-oxopyridin-1(2H)-yl)-3-methylbenzoate with N-bomosuccinamide in acetonitrile by following a procedure, similar to the one described in Example 465—step 3. $^1$H NMR (400 MHz, DMSO-$d_6$) δ 7.95 (s, 1H), 7.87 (dd, J=7.76, 2.02 Hz, 1H), 7.31 (d, J=8.54, 1H), 6.09 (s, 1H), 3.85 (s, 3H), 1.99 (s, 3H), 1.74 (s, 1H). ES-HRMS m/z 352.0195 (M+H calcd for $C_{15}H_{14}BrNO_4$, requires 352.0185).

Step 4: The title compound was prepared by taking methyl 4-(3-bromo-4-hydroxy-6-methyl-2-oxopyridin-1(2H)-yl)-3-methylbenzoate (0.92 g, 2.61 mmol) and dissolving in dry DMF (5 mL). Potassium carbonate (0.432 g, 3.13 mmol) and 2,4 Difluuorobenzyl bromide (0.335 ml, 2.61 mmol) were then added. The mixture was allowed to stir at room temperature for 2 hours.

The reaction was then worked up by pouring it into 100 ml of ice-water which resulted in a precipitate forming which was isolated by filtering through a fritted funnel. The crude product was washed with ether and dried in vacuum to give 0.85 g (76.20%) of pure product. $^1$H NMR (400 MHz, DMSO-$d_6$) δ 7.98 (d, J=1.6 Hz, 1H), 7.88 (dd, J=8.04, 2.0 Hz, 1H), 7.69 (q, J=8.6 Hz, 1H), 7.36–7.30 (m, 2H), 7.17 (dt, J=8.7, 2.3 Hz, 1H), 6.71 (s, 1H), 5.32 (s, 2H), 3.86 (s, 3H), 2.00 (s, 3H), 1.86 (s, 3H). ES-HRMS m/z 478.0459 (M+H calcd for $C_{22}H_{19}BrF_2NO_4$ requires 478.0466).

Examples 473–476

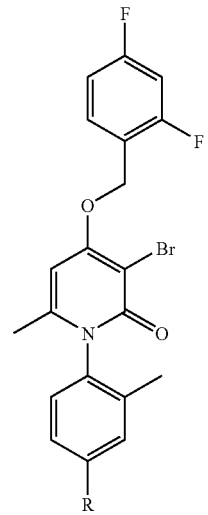

The compounds of Examples 473–476 are prepared by derivitazion of the compounds of Example 472.

| Compound No. | R | MF | M + H Requires | ESHRMS m/z |
|---|---|---|---|---|
| Ex. 473 | —CO₂H | C₂₁H₁₆BrF₂NO₄ | 464.0310 | 464.0324 |
| Ex. 474 | —CH₂OH | C₂₁H₁₈BrF₂NO₃ | 450.0500 | 450.0517 |
| Ex. 475 | C(O)NH(CH₂)₂OCH₃ | C₂₄H₂₂BrF₂N₂O₄ | 521.0888 | 521.0865 |
| Ex. 476 | C(O)NHCH₃ | C₂₂H₂₀BrF₂N₂O₃ | 477.0626 | 477.0609 |

NMR characterization of compounds of Examples 473–476

| Ex. No. | NMR Data |
|---|---|
| 473 | ¹H-NMR (400 MHz, DMSO-d₆) δ 13.11(s, 1H), 7.95(d, J=1.70Hz, 1H), 7.86(dd, J=7.88, 1.91Hz, 1H), 7.67(dq, J=8.47, 1.89Hz, 1H), 7.36–7.30(m, 2H), 7.17(dt, J=8.54, 2.48Hz, 1H), 6.71(s, 1H), 5.32(s, 2H), 1.99(s, 3H), 1.87(s, 3H) |
| 474 | ¹H NMR (400 MHz, DMSO-d₆) δ 7.67(q, J=8.5Hz, 1H), 7.34(dd, J=10.04, 2.77Hz, 1H), 7.32(s, 1H), 7.24(dd, J=8.39, 1.47Hz, 1H), 7.17(dt, J=8.84, 2.6Hz, 1H), 7.08(d, J=7.94Hz, 1 H), 6.66(s, 1H), 5.30(s, 2H), 5.25(t, J=6.01Hz, 1H), 4.5(d, J=6.68Hz, 2H), 1.91(s, 3H), 1.86(s, 3H) |
| 475 | ¹H NMR (400 MHz, DMSO-d₆) δ 8.58(app t, J=5.4Hz, 1H), 7.84(s, 1H), 7.76(dd, J=8.06, 1.63Hz, 1H), 7.68(dq, J=8.77, 2.04Hz, 1H), 7.33(dt, J=9.76, 2.03Hz, 1H), 7.27(d, J=8.34Hz, 1H), 7.17(ddt, J=8.51, 2.63, 0.91Hz, 1H), 6.70(s, 1H), 5.31(s, 2H), 4.50(t, J=5.6Hz, 1H), 3.47–3.36(m, 4H), 3.24(s, 3H), 1.97(s, 3H), 1.87(s, 3H) |
| 476 | ¹H NMR (400 MHz, DMSO-d₆) δ 8.50–8.49(m, 1H), 7.82(s, 1H), 7.74 (dd, J=8.22, 1.79Hz, 1H), 7.69(q, J=6.75Hz, 1H), 7.33(dt, J=9.88, 2.57Hz, 1H), 7.26(d, J=8.52Hz, 1H), 7.17(dt, J=8.93, 2.16Hz, 1H), 6.69(s, 1H), 5.31(s, 2H), 2.77(d, J=4.58Hz, 3H), 1.97(s, 3H), 1.86(s, 3H) |

Example 477

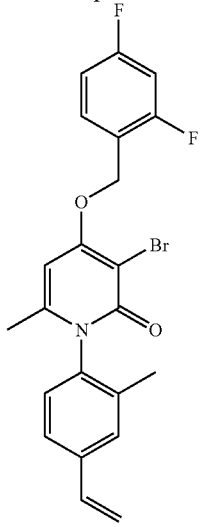

3-bromo-4-[(2,4-difluorobenzyl)oxy]-6-methyl-1-(2-methyl-4-vinylphenyl)pyridin-2(1H)-one Step 1—Preparation of –1-(4-bromo-2-methylphenyl)-4-hydroxy-6-methylpyridin-2(1H)-one

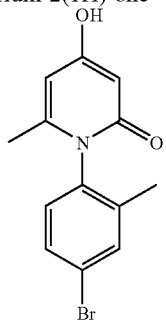

The title compound was prepared in a similar manner to the procedure outlined above for 4-(4-hydroxy-6-methyl-2-oxopyridin-1(2H)-yl)-3-methylbenzoate. ¹H NMR (400 MHz, DMSO-d₆) δ 10.61 (s, 1H), 7.59 (d, J=2.84 Hz, 1H), 7.45 (dd, J=8.39, 2.44 Hz, 1H), 7.06 (d, J=7.44, 1H), 5.89 (d, J=2.73 Hz, 1H), 5.53 (d, J=2.30, 1H), 1.91 (s, 3H), 1.75 (s, 3H). ES-HRMS m/z 294.0127 (M+H calcd for C₁₃H₁₃BrNO₃, requires 294.0130).

Step 2—Preparation of –1-(4-bromo-2-methylphenyl)-4-[(2,4-difluorobenzyl)oxy]-6-methylpyridin-2(1H)-one

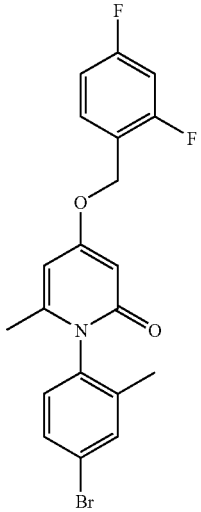

1-(4-bromo-2-methylphenyl)-4-hydroxy-6-methylpyridin-2-(1H)-one (7.35 g, 25.0 mmol) was dissolved in DMF (15 mL) and stirred with potassium carbonate (4.14 g, 30.0 mmol) and 2,4 difluorobenzyl bromide (3.21 ml (25.0 mmol) at room temperature for 2 hours. The reaction was worked up by pouring in to 300 ml ice water under continuous stirring. A white precipitate was obtained which was isolated by filtering and further purified by triturating with ether to give 3.06 g (29%) of the desired product. $^1$H NMR (400 MHz, DMSO-$d_6$) δ 7.65–7.59 (m, 2H), 7.49 (dd, J=8.45, 2.22 Hz, 1H), 7.31 (dt, J=9.79, 2.22 Hz, 1H), 7.16–7.08 (m, 2H), 6.05 (d, J=2.58 Hz, 1H), 5.93 (d, J=2.66 Hz, 1H), 5.08 (s, 2H), 1.93 (s, 3H), 1.77 (s, 3H). ES-HRMS m/z 420.0390 (M+H calcd for $C_{20}H_{17}BrF_2NO_2$, requires 420.0411).

Step 3: Preparation of 4-[(2,4-difluorobenzyl)oxy]-6-methyl-1-(2-methyl-4-vinylphenyl)pyridin-2(1H)-one.

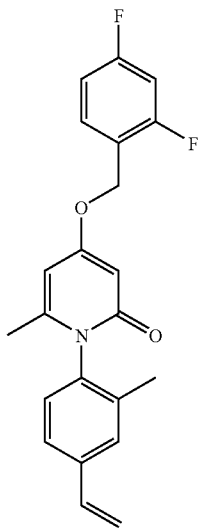

In a 50 ml round bottom flask previously evacuated and filled with nitrogen, 1-(4-bromo-2-methylphenyl)-4-[(2,4-difluorobenzyl)oxy]-6-methylpyridin-2 (1H)-one (0.420 g, 1.0 mmol) was dissolved in dry THF (10 mL). To this mixture was added Pd (PPh$_3$)$_4$ (0.173 g, 0.15 mmol). The reaction flask was sealed with a rubber septum, evacuated and filled with nitrogen. Under a nitrogen atmosphere, tributyl(vinyl)tin (0.35 ml, 1.2 mmol) was added to the sealed reaction mixture and stirred overnight at 50° C.

The reaction was worked up by quenching with water and extraction of the product with ethyl acetate. The crude product was purified by column chromatography. Elution with ethyl acetate-hexanes (50:50→0:100) gave 0.32 g (69%) of the desired product.

Step 4: The title compound was prepared by reacting 4-[(2,4-difluorobenzyl)oxy]-6-methyl-1-(2-methyl-4-vinylphenyl)pyridin-2(1H)-one (0.64 g, 1.74 mmol) with N-bromosuccinamide (0.325 g, 1.83 mmol) in acetonitrile (9 mL) at 0° C. using a similar procedure as described in step 3 of Example 465, to give 0.423 g (54.5% after recrystallization) of the desired product. $^1$H NMR (400 MHz, DMSO-$d_6$) δ 7.67 (app q, J=7.59 Hz, 1H), 7.48 (s, 1H), 7.42 (dd, J=8.21, 1.98 Hz, 1H), 7.33 (dt, J=10.00, 2.27 Hz, 1H), 7.17 (dt, J=8.51, 2.44 Hz, 1H), 7.13 (d, J=7.88 Hz, 1H), 6.74 (dd, J=11.29, 6.34 Hz, 1H), 6.67 (s, 1H), 5.88 (d, J=17.85, 1H), 5.32–5.30 (m, 2H), 1.92 (s, 3H), 1.88 (s, 3H). ES-HRMS m/z 446.0579 (M+H calcd for $C_{22}H_{19}BrF_2NO_2$, requires 446.0568).

Example 478

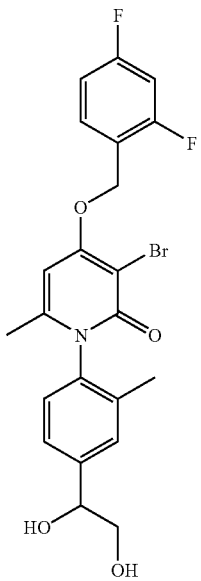

3-bromo-4-[(2,4-difluorobenzyl)oxy]-1-[4-(1,2-dihydroxyethyl)-2-methylphenyl]-6-methylpyridin-2 (1H)-one 3-bromo-4-[(2,4-difluorobenzyl)oxy]-6-methyl-1-(2-methyl-4-vinylphenyl)pyridin-2(1H)-one (0.126 g, 0.28 mmol) was dissolved in a mixture of acetone (3 mL) and water (1 mL). To this was added 4-methylmorpholine N-oxide (0.032 g, 0.28 mmol) and catalytic amount (approximately 5 mgs) of osmium tetroxide was added, and stirred under nitrogen atmosphere. After approximately 2 hours, the reaction was worked up by evaporation of the acetone. The product was extracted into ethyl acetate and concentrated to give a dark colored solid which was further purified by column chromatography to give 0.049 g (37% yield)of charcoal colored solid. $^1$H NMR (400 MHz, DMSO-$d_6$) δ 7.67 (q, J=8.24 Hz, 1H), 7.37–7.23 (m, 3H), 7.17 (dt, J=8.62, 2.62 Hz, 1H), 7.07 (dd, J=9.36, 2.24 Hz, 1H), 6.65 (s, 1H), 5.30 (s, 2H), 4.74 (t, J=6.16 Hz, 1H), 4.57–4.50 (m, 1H), 3.45 (app t, J=6.12 Hz, 2H), 3.41–3.37 (m, 1H), 1.91 (s, 3H), 1.85 (s, 3H). ES-HRMS m/z 480.0625 (M+H calcd for $C_{22}H_{21}BrF_2NO_4$, requires 480.0623).

Example 479

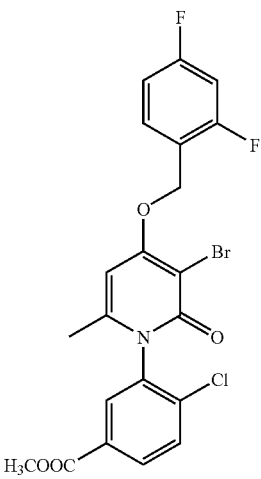

methyl 3-[3-bromo-4-[(2,4-difluorobenzyl)oxy]-6-methyl-2-oxopyridin-1(2H)-yl]-4-chlorobenzoate Step 1: Preparation of methyl 4-chloro-3-(4-hydroxy-6-methyl-2-oxopyridin-1(2H)-yl)benzoate.

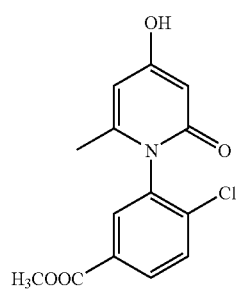

A condensation reaction with methyl 3-amino-4-chlorobenzoate (14.5 g, 78.2 mmol) and 4-hydroxy-6-methyl pyranone under reaction condition similar to the one described in Example 465—step 3 gave 12.32 (53.8%) of desired product.

Step 3—Preparation of methyl-4-chloro-3-[4-[(2,4-difluorobenzyl)oxy]-6-methyl-2-oxopyridin-1(2H)-yl]benzoate.

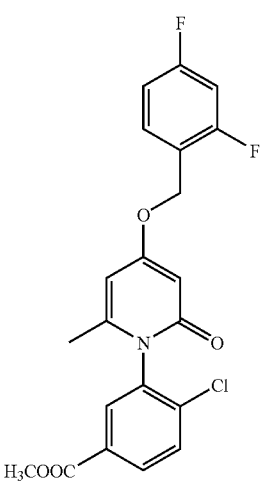

In a 250 ml round bottom flask, methyl 4-chloro-3-(4-hydroxy-6-methyl-2-oxopyridin-1(2H)-yl)benzoate (5.28 g, 18.0 mmol) from step 1 was reacted with 2,4-difluorobenzylbromide (3.72 g, 18.0 mmol) in DMF using similar procedure as in Example 472 step 3. After aqueous work up and chromatographic purification, 2.3 g (30%) pure product was obtained.

Step 4: methyl 3-[3-bromo-4-[(2,4-difluorobenzyl)oxy]-6-methyl-2-oxopyridin-1(2H)-yl]-4-chlorobenzoate was prepared by reacting methyl-4-chloro-3-[4-[(2,4-difluorobenzyl)oxy]-6-methyl-2-oxopyridin-1(2H)-yl] benzoate (2.3 g, 5.47 mmol) with N-bromosuccinamide (0.97 g, 5.47 mmol) in acetonitrile (10 mL) at 0° C., using a similar procedure as described in step 3 of Example 465, to give 1.80 g (66.2%) of the desired product. $^1$H NMR (400 MHz, DMSO-$d_6$) δ 8.06–8.03 (m, 2H), 7.86 (d, J=9.70 Hz, 1H), 7.68 (q, J=7.62, 1H), 7.34 (dt, J=10.07, 2.46 Hz, 1H), 7.17 (dt, J=8.72, 2.90 Hz, 1H), 6.73 (s, 1H), 5.33 (s, 2H), 3.85 (s, 3H), 1.91 (s, 3H). ES-MS m/z 495.9757 (M–H calcd for $C_{21}H_{14}BrClF_2NO_4$, requires 495.9795).

Example 480

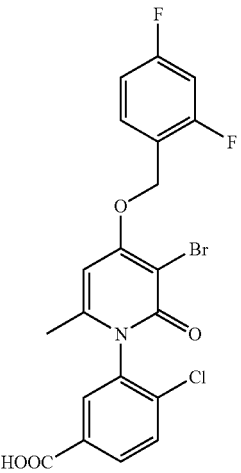

3-[3-bromo-4-[(2,4-difluorobenzyl)oxy]-1–6-methyl-2-oxopyridin-1(2H)-yl]-4-chlorobenzoic acid In a 50 ml round bottom flask, methyl-4-chloro-3-[4-[(2,4-difluorobenzyl)oxy]-6-methyl-2-oxopyridin-1(2H)-yl]benzoate (0.450 g, 0.90 mmol) was stirred in THF (5 mL). To this mixture was added NaOH (0.120 g, 3.0 mmol) as a solution in water (1.5 mL). The reaction mixture was stirred at room temperature overnight. The THF was evaporated and the residue was acidified with dilute HCl. A white precipitate was obtained. The product was filtered, washed with water and dried in vacuum to give 0.375 g (86% yield) of the desired product. $^1$H NMR (400 MHz, DMSO-$d_6$) δ 7.89 (dd, J=7.78, 1.73 Hz, 1H), 7.71–7.65 (m, 2H), 7.53 (d, J=9.08 Hz, 1H), 7.33 (dt, J=9.95, 2.59 Hz, 1H), 7.17 (dt, J=8.22, 2.59 Hz, 1H), 6.68 (s, 1H), 5.32 (s, 2H), 1.89 (s, 3H). ES-MS m/z 481.9585 (M–H calcd for $C_{20}H_{12}BrClF_2NO_4$, requires 481.9601).

Example 481

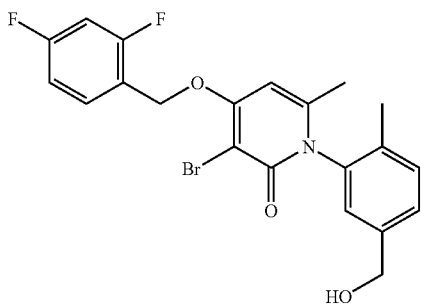

3-bromo-4-[(2,4-difluorobenzyl)oxy]-1-[5-(hydroxymethyl)-2-methylphenyl]-6-methylpyridin-2(1H)-one Step 1: Preparation of 4-hydroxy-1-[5-(hydroxymethyl)-2-methylphenyl]-6-methylpyridin-2(1H)-one.

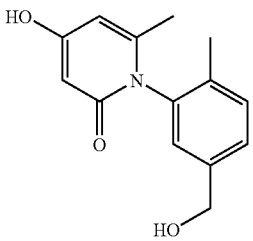

4-Hydroxy-6-methyl-2-pyrone (23.0 g, 182.2 mmol) and 3-Amino-4-methylbenzyl alcohol (25.0 g, 182.2 mmol) were taken up in 25 ml of 1,2-dichlorobenzene. The solution was heated to 165° C. in a 250 ml round bottom flask equipped with a J-Kem temperature controller probe, and a heating mantle. In a separate 250 ml round bottom flask 4-Hydroxy-6-methyl-2-pyrone (23.0 g, 182.2 mmol) was suspended in 25 ml of 1,2-dichlorobenzene and also heated to 165° C. The pyrone solution was poured into the flask containing the aniline and the reaction stirred at 165° C. for 20 minutes. The reaction was allowed to cool to room temperature. Reaction contents were washed with saturated NaHCO$_3$ (aq.). Separated the organic and aqueous layers. Aqueous layer was made acidic with dropwise addition of concentrated HCl. The product was extracted from the acidic aqueous layer with n-BuOH. N-BuOH removed in vacuo to produce a reddish brown oil. (8.5 g, 19%). Contents carried forward to next reaction with no further purification. $^1$H NMR (300 MHz, CD$_3$OD) δ 7.35 (m, 2H), 7.08 (s, 1H), 6.08 (br s, 1H), 5.81 (br s, 1H), 4.60 (s, 2H), 2.01 (s, 3H), 1.87 (s, 3H). LC/MS, t$_r$=1.42 minutes (5 to 95% acetonitrile/water over 5 minutes at 1 ml/min with detection 254 nm, at 50° C.). ES-MS m/z 246.1131 (M+H). ES-HRMS m/z 246.1107 (M+H calcd for C$_{14}$H$_{16}$NO$_3$ requires 246.1125).

Step 2: 4-[(2,4-difluorobenzyl)oxy]-1-[5-(hydroxymethyl)-2-methylphenyl]-6-methyl-pyridin-2(1H)-one.

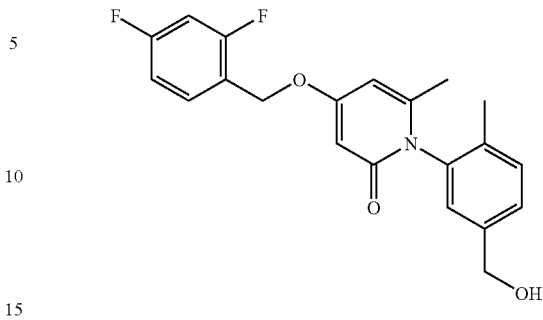

4-hydroxy-1-[5-(hydroxymethyl)-2-methylphenyl]-6-methyl pyridin-2(1H)-one (from Step 1) (8.0 g, 32.6 mmol) was stirred briskly at room temperature with 2,4-difluorobenzyl bromide (4.2 ml, 32.6 mmol) and K$_2$CO$_3$ (4.5 g, 32.6 mmol) in 50 ml of dimethylformamide. After stirring for 8 hours, H$_2$O (100 ml) was added to reaction mixture. The product was extracted with ethyl acetate. Ethyl acetate layer was separated and dried over Na$_2$SO$_4$. Ethyl acetate was removed in vacuo. A yellow oil was obtained. The oil was passed through a plug of silica gel first eluting with 500 ml of ethyl acetate/hexane (1:1). This eluent was set aside. Next, ethyl acetate (100%) was passed through the plug until desired product was completely flushed from silica (3 liters). Solvent was removed in vacuo. Light yellow oil obtained (7.5 g, 62%). $^1$H NMR (300 MHz, CD$_3$OD) δ 7.60 (app q, J=6.44 Hz, 1H), 7.42 (d, J=0.81 Hz, 2H), 7.15 (s, 1H), 7.06 (m, 2H), 6.21 (dd, J=1.61, 1.00 Hz, 1H), 6.12 (d, J=2.62 Hz, 1H), 5.16 (s, 2H), 4.65 (s, 2H), 2.07 (s, 3H), 1.93 (s, 3H); LC/MS, t$_r$=2.38 minutes (5 to 95% acetonitrile/water over 5 minutes at 1 ml/min with detection 254 nm, at 50° C.). ES-MS m/z 372 (M+H).

Step 3: Preparation of the title compound. 4-[(2,4-difluorobenzyl)oxy]-1-[5-(hydroxymethyl)-2-methylphenyl]-6-methyl-pyridin-2(1H)-one (from Step 2) (4.0 g, 10.8 mmol) was stirred at room temperature with N-bromosuccinimide (2.1 g, 11.9 mmol) in 100 ml of CH$_2$Cl$_2$ for 2.0 hours. The reaction was evaporated on a rotary evaporator and the resulting solid was washed with acetonitrile and dried in vacuo to yield a white solid (3.9 g, 80%). $^1$H NMR (300 MHz, CDCl$_3$) δ 7.67 (app q, J=6.24 Hz, 1H), 7.35 (d, J=1.01 Hz, 2H), 7.10 (s, 1H), 7.04 (m, 1H), 6.91 (ddd, J=11.08, 8.66, 2.42 Hz, 1H), 6.15 (d, J=0.63 Hz, 2H), 5.29 (s, 2H), 4.66 (s, 2H), 2.08 (s, 3H), 1.97 (s, 3H); ES-MS m/z 450 (M+H). ES-HRMS m/z 450.0467 (M+H calcd for C$_{21}$H$_{19}$BrF$_2$NO$_3$ requires 450.0511).

Example 482

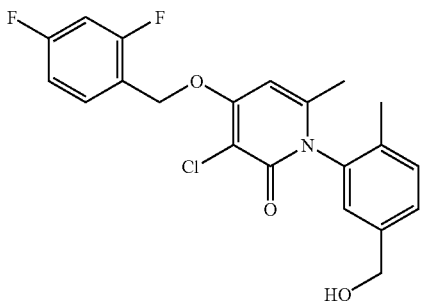

3-chloro-4-[(2,4-difluorobenzyl)oxy]-1-[5-(hydroxymethyl)-2-methylphenyl]-6-methylpyridin-2(1H)-one The title compound was prepared by a procedure similar to the one described for Example 481, except that the product from Step 2, Example 481 was chlorinated instead of being brominated. The procedure is as follows: 4-[(2,4-difluorobenzyl)oxy]-1-[5-(hydroxymethyl)-2-methylphenyl]-6-methyl-pyridin-2(1H)-one (from Step 2, Example 481 above) (7.0 g, 18.8 mmol) was refluxed with N-chlorosuccinimide (2.5 g, 18.8 mmol) in 50 ml of $CH_2Cl_2$ overnight. The reaction was evaporated on a rotary evaporator and the resulting solid was stirred in MeOH. The precipitate was collected on a filter pad, washed with MeOH and dried in vacuo to yield a white solid (1.6 g, 21%). $^1$H NMR (300 MHz, DMF-$d_7$) δ 7.85 (app q, J=6.44 Hz, 1H), 7.43 (d, J=0.81, 1H), 7.42–7.23 (m, 3H), 6.84 (s, 1H), 5.48 (s, 2H), 4.67 (s, 2H), 2.05 (s, 3H), 2.03 (s, 3H); ES-MS m/z 406 (M+H). ES-HRMS m/z 406.1033 (M+H calcd for $C_{21}H_{16}ClF_2NO_4$ requires 406.1016).

Example 483

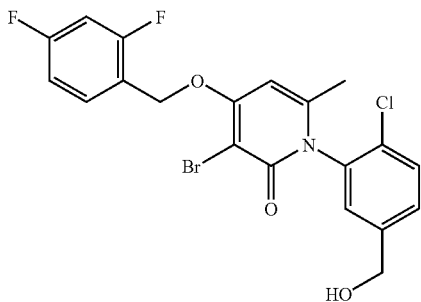

3-bromo-4-[(2,4-difluorobenzyl)oxy]-1-[5-(hydroxymethyl)-2-methylphenyl]-6-methylpyridin-2(1H)-one Step 1: Preparation of 3-amino-4-chloro-benzyl alcohol.

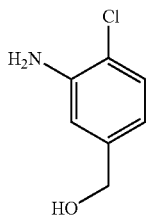

3-Nitro-4-chloro-benzyl alcohol (23.0 g, 122.6 mmol) is taken up in isopropyl alcohol (175 ml) and water (35 ml). Iron powder (<10 micron) (68.0 g, 1.2 moles) and NH$_4$Cl (66.0 g, 1.2 moles) are added. The suspension is stirred overhead at 70° C. in a three neck round bottom flask equipped with a heating mantle and a J-Kem temperature controller probe. After 4 hours, isopropyl alcohol was removed in vacuo. Water (100 ml) and concentrated HCl (10 ml) was added to mixture. Contents are transferred to a separatory funnel and ethyl acetate is used to extract the aqueous layer of impurities. The aqueous layer was then basified with 50% aqueous NaOH. The product was extracted from the basic aqueous layer with ethyl acetate. The ethyl acetate layer was dried over Na$_2$SO$_4$ and then removed in vacuo. The remaining residue was taken up in 50% ethyl acetate/hexane and the precipitate was collected on a filter pad. Precipitate was washed with 50% ethyl acetate/hexane to yield a flocculent brown solid (8.4 g, 44%). $^1$H NMR (300 MHz, CD$_3$OD) δ 7.17 (d, J=8.26 Hz, 1H), 6.86 (d, J=2.01 Hz, 1H), 6.66 (dd, J=2.01, 0.61 Hz, 1H), 4.51 (s, 2H); LC/MS, t$_r$=0.32 minutes (5 to 95% acetonitrile/water over 5 minutes at 1 ml/min with detection 254 nm, at 50° C.); ES-MS m/z 158 (M+H).

Step 2: 1-[2-chloro-5-(hydroxymethyl)phenyl]-4-hydroxy-6-methylpyridin-2(1H)-one.

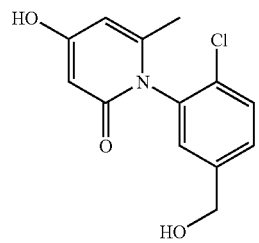

3-amino-4-chloro-benzyl alcohol (8.0 g, 51.0 mmol) and 4-hydroxy-6-methyl-2-pyrone (6.4 g, 51.0 mmol) were taken up in 1,2-dichlorobenzene (50 ml). The mixture was plunged into a 165° C. oil bath where it stirred for 20 minutes. The reaction was cooled to room temperature and the reaction was worked up by washing with saturated NaHCO$_3$ (aq.) and extracting impurities with ethyl acetate. The product remained in the aqueous layer. The basic aqueous layer was made acidic with concentrated HCl. The product was extracted from the acidic aqueous layer with ethyl acetate. The ethyl acetate layer was dried over Na$_2$SO$_4$ and the solvent removed in vacuo. The product was obtained as a yellow oil in a 26% yield and was carried through to the next step with no further purification.

$^1$H NMR (300 MHz, CD$_3$OD) δ 7.62 (d, J=8.26 Hz, 2H), 7.51 (dd, J=8.46, 2.22 Hz, 1H), 7.36 (d, J=2.01 Hz, 1H), 6.13 (br s, 1H), 5.84 (d, J=2.42 Hz, 1H), 4.68 (s, 2H), 1.97 (s, 3H); LC/MS, t$_r$=0.25 minutes and 1.41 minutes (tautomer), (5 to 95% acetonitrile/water over 5 minutes at 1 ml/min with detection 254 nm, at 50° C.). ES-MS m/z 266 (M+H).

Step 3: 1-[2-chloro-5-(hydroxymethyl)phenyl]-4-[(2,4-difluorobenzyl)oxy]-6-methylpyridin-2(1H)-one.

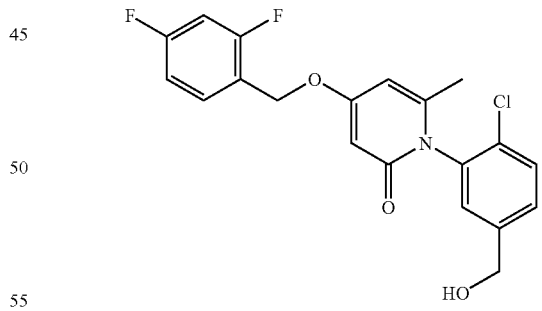

1-[2-chloro-5-(hydroxymethyl)phenyl]-4-hydroxy-6-methylpyridin-2(1H)-one (from step 2) (3.5 g, 13.2 mmol) was taken up in DMF (10 ml) and cooled to 0° C. 2,4-Difluorobenzyl bromide (1.7 ml, 13.2 mmol) and K$_2$CO$_3$ (1.8 g, 13.2 mmol) were added and the reaction stirred for 6 hours. The reaction was worked up by adding saturated NaHCO$_3$ (aq.) and extracting with ethyl acetate. The ethyl acetate extraction was washed with water, and the aqueous layer was extracted with ethyl acetate. The organic layers were combined and dried over Na$_2$SO$_4$, filtered, and the solvent removed in vacuo. The product was obtained in 83% crude yield and carried through to the next step as a brown oil. LC/MS, $t_r$=2.48 minutes (5 to 95% acetonitrile/water over 5 minutes at 1 ml/min with detection 254 nm, at 50° C.). ES-MS m/z 392 (M+H). ES-HRMS m/z 392.0853 (M+H calcd for $C_{20}H_{17}ClF_2NO_3$ requires 392.0860).

Step 4: The title compound was prepared from 1-[2-chloro-5-(hydroxymethyl)phenyl]-4-[(2,4-difluorobenzyl)oxy]-6-methylpyridin-2(1H)-one (from step 3) (1.8 g, 4.6 mmol) and N-bromosuccinimide (0.82 g, 4.6 mmol) by dissolving them in $CH_2Cl_2$ (10 ml) and stirring for 2 hours at room temperature. The solvent was removed in vacuo and the residue was taken up in $CH_3CN$. The precipitate was collected on a filter pad and rinsed with $CH_3CN$ to yield a white solid (370 mg, 17%). $^1$H NMR (300 MHz, $CDCl_3$) δ 7.65 (app q, J=6.24 Hz, 1H), 7.52 (d, J=8.26 Hz, 1H), 7.40 (dd, J=8.26, 2.01 Hz 1H), 7.26 (d, J=0.81 Hz, 1H), 7.03 (m, 1H), 6.91 (ddd, J=11.08, 8.66, 2.42 Hz, 1H), 6.17 (d, J=0.81 1H), 5.29 (s, 2H), 4.63 (s, 2H), 2.02 (s, 3H); ES-MS m/z 471 (M+H). ES-HRMS m/z 471.9953 (M+H calcd for $C_{20}H_{16}BrClF_2NO_3$ requires 471.9944).

Example 484

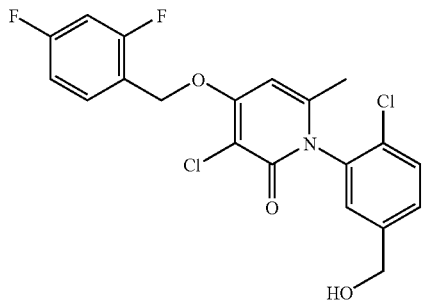

3-chloro-4-[(2,4-difluorobenzyl)oxy]-1-[5-(hydroxymethyl)-2-methylphenyl]-6-methylpyridin-2(1H)-one The title compound was prepared from 1-[2-chloro-5-(hydroxymethyl)phenyl]-4-[(2,4-difluorobenzyl)oxy]-6-methylpyridin-2(1H)-one (2.4 g, 6.1 mmol) and NCS (815.0 mg, 6.1 mmol) in 65° C. dichloroethane (20 ml). A catalytic amount of dichloroacetic acid (2 drops) was added. After two hours the solvent was removed in vacuo and the residue was taken up in diethyl ether. The precipitate was collected on a filter pad and then taken up in 50% ethyl acetate/hexanes to remove residual succinimide. The precipitate was collected on a filter pad and then dried in vacuo to produce a white powder (180 mg, 6.9%). $^1$H NMR (300 MHz, $CDCl_3$) δ 7.61 (app q, J=6.44 Hz, 1H), 7.52 (d, J=8.26 Hz, 1H), 7.40 (dd, J=8.26, 2.01 Hz 1H), 7.27 (d, J=2.01 Hz, 1H), 7.00 (m, 1H), 6.91 (m, 1H), 6.20 (s, 1H), 5.29 (s, 2H), 4.65 (s, 2H), 2.03 (s, 3H); ES-MS m/z 426 (M+H). ES-HRMS m/z 426.0453 (M+H calcd for $C_{20}H_{16}Cl2F_2NO_3$ requires 426.0470).

Example 485

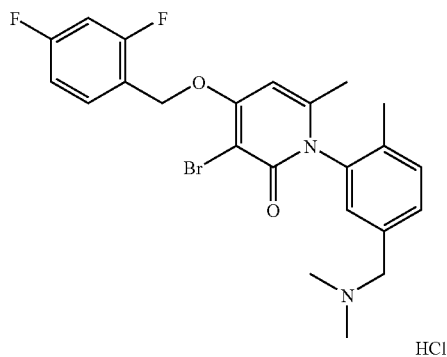

3-bromo-4-[(2,4-difluorobenzyl)oxy]-1-{5-[(dimethylamino)methyl]-2-methylphenyl}-6-methylpyridin-2(1H)-one hydrochloride Step 1: Preparation of 3-[3-bromo-4-[(2,4-difluorobenzyl)oxy]-6-methyl-2-oxopyridin-1(2H)-yl]-4-methylbenzaldehyde.

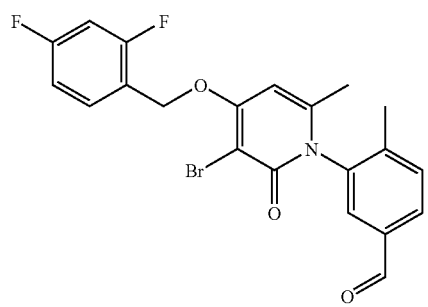

3-bromo-4-[(2,4-difluorobenzyl)oxy]-1-[5-(hydroxymethyl)-2-methylphenyl]-6-methylpyridin-2(1H)-one (1.5 g, 3.33 mmol) was dissolved in 75% $CH_3CN$/$CH_2Cl_2$ (20 ml) and cooled to 0° C. Dess-Martin Periodinane(2.8 g, 6.66 mmol) was added and the reaction stirred for four hours. At this time, the reaction was quenched with 5% sodium bisulfite (aq.). The product was extracted with ethyl acetate. The combined organic extracts were then washed with saturated $NaHCO_3$ (aq.). The aqueous layer was extracted with ethyl acetate. The combined organic extracts were dried over $Na_2SO_4$, filtered, and concentrated. The resulting residue was taken up in diethyl ether and the precipitate was collected on a filter pad and washed with more diethyl ether to yield a white solid (1.35 g, 91%). $^1$H NMR (300 MHz, $CDCl_3$) δ 10.00 (s, 1H), 7.91 (dd, J=7.65, 1.61 Hz, 1H), 7.65 (m, 2H), 7.57 (d, J=7.85 Hz, 1H), 7.03 (m, 1H), 6.95 (ddd, J=12.69, 8.86, 2.62 Hz, 1H), 6.19 (s, 1H), 5.31 (s, 2H), 2.20 (s, 3H), 1.96 (s, 3H); ES-MS m/z 448 (M+H). ES-HRMS m/z 448.0347 (M+H calcd for $C_{21}H_{17}BrF_2NO_3$ requires 448.0354).

Step 2: Preparation of the title compound. 3-[3-bromo-4-[(2,4-difluorobenzyl)oxy]-6-methyl-2-oxopyridin-1(2H)-yl]-4-methylbenzaldehyde (from step 1) (0.50 g, 1.11 mmol) was dissolved in $CH_2Cl_2$ (10 ml). N,N-dimethylamine (2.0 M in THF) (1.11 ml, 2.22 mmol) was added. This mixture stirred for at room temperature for 12 hours. Next, sodium tri-acetoxyborohydride (0.47 g, 2.22 mmol) was added and the reaction stirred for two more hours. The reaction was washed with 1 N NaOH (aq.) and then extracted with $CH_2Cl_2$. The combined organic extracts were washed with water. The aqueous layer was separated and extracted with CH$_2$Cl$_2$. The combined organic extracts were dried over Na$_2$SO$_4$, filtered and concentrated in vacuo. The resulting residue was taken up in diethyl ether. 1M HCl in diethyl ether (5 ml) was added and the precipitate was collected on a filter pad. This precipitate was hygroscopic. The hygroscopic solid was then taken up in hot ethyl acetate. Hexane was added until a precipitate crashed out. The precipitate was collected on a filter pad to yield a white solid (150 mg, 26%). $^1$H NMR (400 MHz, D$_2$O) δ 7.42 (m, 3H), 7.17 (s, 1H), 6.86 (m, 2H), 6.53 (s, 1H), 5.20 (s, 2H), 4.18 (s, 1H), 2.72 (s, 6H), 1.85 (s, 3H), 1.82 (s, 3H); ES-MS m/z 477 (M+H). ES-HRMS m/z 477.0955 (M+H calcd for C$_{23}$H$_{24}$BrF$_2$N$_2$O$_2$ requires 477.0984).

Example 486

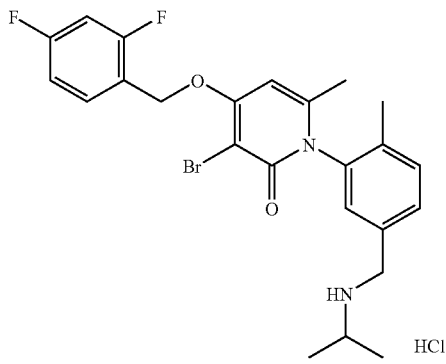

3-bromo-4-[(2,4-difluorobenzyl)oxy]-1-{5-[(isopropylamino)methyl]-2-methylphenyl}-6-methylpyridin-2(1H)-one hydrochloride The title compound was prepared by reductive amination of 3-[3-bromo-4-[(2,4-difluorobenzyl)oxy]-6-methyl-2-oxopyridin-1(2H)-yl]-4-methylbenzaldehyde (from step 1) (0.50 g, 1.11 mmol) with iso-propyl amine (0.13 g, 2.22) according to the procedure described above for Example 485 (Step 2) to give the desired compound (0.49 g, 84%). $^1$H NMR (400 MHz, CD$_3$OD) δ 7.64 (app quartet, J=6.58 Hz, 1H), 7.53 (m, 2H), 7.29 (br s, 1H), 7.03 (m, 1H), 6.68 (s, 1H), 5.36 (s, 2H), 4.22 (s, 2H), 3.46 (m, 1H), 2.06 (s, 3H), 2.01 (s, 3H), 1.37 (d, J=6.58 Hz, 6H); ES-MS m/z 491 (M+H). ES-HRMS m/z 491.1107 (M+H calcd for C$_{24}$H$_{26}$BrF$_2$N$_2$O$_2$ requires 491.1140).

Example 487

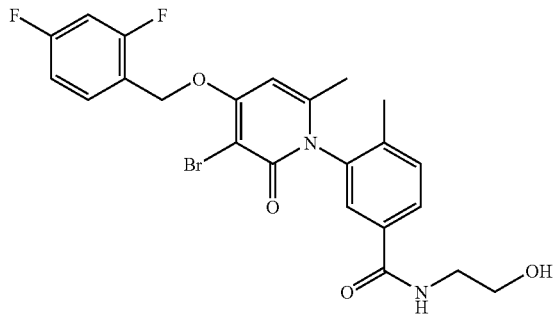

3-[3-bromo-4-[(2,4-difluorobenzyl)oxy]-6-methyl-2-oxopyridin-1(2H)-yl]-N-(2-hydroxyethyl)-4-methylbenzamide

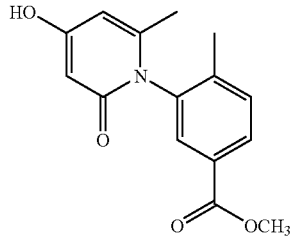

Step 1: Preparation of methyl 3-(4-hydroxy-6-methyl-2-oxopyridin-1(2H)-yl)-4-methylbenzoate.

4-Hydroxy-6-methyl-2-pyrone (22.9 g, 181.6 mmol) and methyl-3-amino-2-methylbenzoate (25 g, 151.3 mmol) were suspended in 50 ml of 1,2-dichlorobenzene in a 250 ml, 3-necked round bottom flask equipped with a J-Kem temperature controller probe, a Dean-Stark trap, and a heating mantle. The reaction was heated to 165° C. for 15 minutes, during which, water and some 1,2-dichlorobenzene was collected in the Dean-Stark trap. The reaction was allowed to cool to about 110° C. At this point, 200 ml of toluene was added. The flask was plunged into a 0° C. ice bath while stirring. "Oiling out" occurred. Perhaps too much toluene was added so some of the solvent was removed in vacuo. The oil went back into solution and a light brown precipitate remained. The toluene mixture was allowed to stir for 72 hours at room temperature. A precipitate was collected on a filter pad. The precipitate was filtered and washed 3 times with toluene, 3 times with 50° C. water to remove excess pyrone, and dried in vacuo to give a tan solid (16.5 g, 40% yield). $^1$H NMR (300 MHz, CD$_3$OD) δ 8.06 (dd, J=8.06, 1.61 Hz, 1H), 7.80 (d, J=1.61 Hz, 1H), 7.56 (d, J=8.06, Hz, 1H), 6.15 (dd, J=2.42, 0.81 Hz, 1H), 5.86 (d, J=2.42 1H), 3.94 (s, 3H), 2.15 (s, 3H), 1.91 (s, 3H); ES-MS m/z 274 (M+H). ES-HRMS m/z 274.1066 (M+H calcd for C$_{15}$H$_{16}$NO$_4$ requires 274.1074).

Step 2: Preparation of methyl 3-[4-[(2,4-difluorobenzyl)oxy]-6-methyl-2-oxopyridin-1(2H)-yl]-4-methylbenzoate.

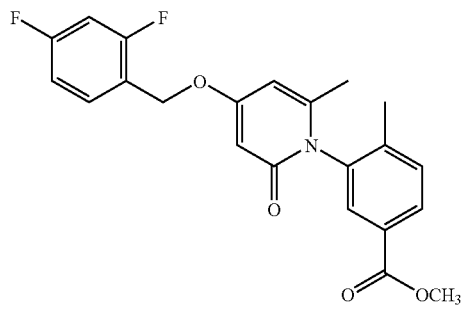

Methyl 3-(4-hydroxy-6-methyl-2-oxopyridin-1(2H)-yl)-4-methylbenzoate (from Step 1) (16.5 g, 60.4 mmol) 2,4-difluorobenzyl bromide (7.8 ml, 60.4 mmol) were taken up in 250 ml of N,N-dimethylformamide and the mixture was cooled to 0° C. K$_2$CO$_3$ (8.3 g, 60.4 mmol) was added and reaction stirred for 12 hours during which time the reaction was allowed to warm to room temperature. LC/MS indicated the presence of starting material after 12 hours. An excess of K$_2$CO$_3$ was added at room temperature along with 0.50 ml of 2,4-difluorobenzyl bromide. The reaction stirred for an additional two hours. Saturated NaHCO$_3$ (aq.) was poured into reaction vessel. The solution was extracted with ethyl acetate and the organic layers were combined then washed with water. The organic layer was separated and the aqueous layer was extracted with ethyl acetate. The organic layers were combined and dried over $Na_2SO_4$, and evaporated. The product was carried on to the next step as a crude oil (24.1 g, quantitative yield). $^1H$ NMR (300 MHz, $CDCl_3$) δ 8.06 (dd, J=7.85, 1.61 Hz, 1H), 7.82 (d, J=1.61, 1H), 7.52–7.44 (m, 2H), 7.01–6.88 (m, 2H), 6.05 (d, J=2.62 Hz, 1H), 5.97 (dd, J=2.62, 0.81 Hz, 1H), 5.08 (s, 2H), 3.93 (s, 3H), 2.20 (s, 3H), 1.89 (s, 3H); ES-MS m/z 400 (M+H). ES-HRMS m/z 400.1374 (M+H calcd for $C_{22}H_{20}F_2NO_4$ requires 400.1355).

Step 3: Preparation of 3-[4-[(2,4-difluorobenzyl)oxy]-6-methyl-2-oxopyridin-1(2H)-yl]-4-methylbenzoic acid.

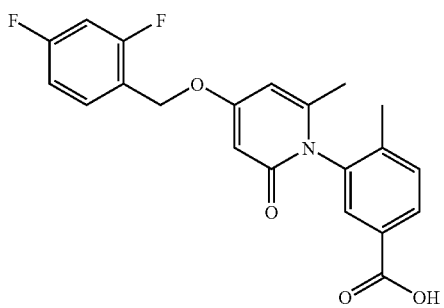

Methyl 3-[4-[(2,4-difluorobenzyl)oxy]-6-methyl-2-oxopyridin-1(2H)-yl]-4-methylbenzoate (14 g, 35.0 mmol) (from step 2) was taken up in THF (25 ml) and $H_2O$. 2.5 N NaOH (aq.) was added and the reaction stirred for 30 minutes at room temperature. The reaction was made acidic via the addition of concentrated HCl. The product was extracted with ethyl acetate. The ethyl acetate extraction was dried over $Na_2SO_4$, filtered, and the solvent removed in vacuo. Upon vacuum removal of the solvent, the product crashed out of the ethyl acetate. This precipitate was collected on a filter pad and washed with a 50 ethyl acetate/hexanes to yield a white powder (9 g, 7%). $^1H$ NMR (300 MHz, $CDCl_3$) δ 8.01 (dd, J=, 1.61 Hz, 1H), 7.84 (d, J=1.61 Hz, 1H), 7.52–7.47 (app q, J=8.26, 1H), 7.43 (d, J=8.06 Hz, 1H), 7.00–6.88 (m, 2H), 6.19 (d, J=2.62 Hz, 1H), 6.05 (dd, J=2.62, 1.81 Hz, 1H), 5.17 (s, 2H), 2.19 (s, 3H), 1.90 (s, 3H); ES-HR/MS m/z 386.12 (M+H calcd for $C_{21}H_{18}F_2NO_4$ requires 386.1198).

Step 4: Preparation of 3-[3-bromo-4-[(2,4-difluorobenzyl)oxy]-6-methyl-2-oxopyridin-1(2H)-yl]-4-methylbenzoic acid.

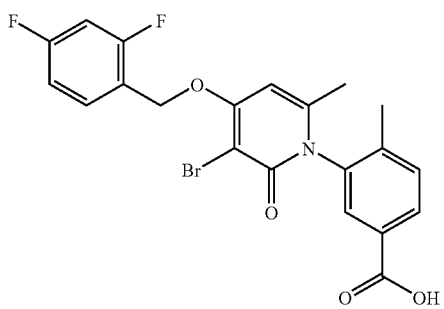

3-[4-[(2,4-difluorobenzyl)oxy]-6-methyl-2-oxopyridin-1 (2H)-yl]-4-methylbenzoic acid (5.9 g, 15.2 mmol) (from step 3 above) was taken up in dichloromethane (25 ml). N-Bromosuccinimide was added and the reaction stirred for 14 hours. The dichloromethane was removed in vacuo and the residue was taken up in acetonitrile. The precipitate was collected on a filter pad and rinsed with acetonitrile to yield the desired product as a white solid (5.2 g, 74%). $^1H$ NMR (300 MHz, $CD_3OD$) δ 7.87 (dd, J=7.85, 1.61,Hz, 1H), 7.82 (d, J=1.81 Hz, 1H), 7.69 (app q, J=8.06 Hz 1H), 7.57 (d, J=8.06 Hz, 1H), 7.09 (dt, J=8.66, 2.22 Hz, 1H), 6.70 (s, 1H), 5.40 (s, 2H), 2.14 (s, 3H), 2.02 (s, 3H); ES-MS m/z 464 (M+H). ES-HRMS m/z 464.0275 (M+H calcd for $C_{21}H_{17}BrF_2NO_4$ requires 464.0304).

Step 5: Preparation of the title compound. 3-[3-bromo-4-[(2,4-difluorobenzyl)oxy]-6-methyl-2-oxopyridin-1(2H)-yl]-4-methylbenzoic acid (from Step 4 above) (1.9 g, 4.10 mmol) was dissolved in 20 ml of $CH_2Cl_2$. Ethanolamine (297 μl, 4.92 mmol) was added, followed, in order, by EDCI (0.764 g, 4.92 mmol), 1-hydroxybenzotriazole (0.665 g, 4.92 mmol) and triethylamine (1.14 ml, 8.20 mmol). The reaction was stirred at room temperature overnight. The reaction was quenched with $NH_4Cl$ and extracted 3 times with ethyl acetate. The combined organic layer was then washed with saturated $NaHCO_3$ (aq.) and extracted 3 times with ethyl acetate. The organic layers were combined and washed with $H_2O$ and extracted 3 times with ethyl acetate. The organic layers were combined and dried over $Na_2SO_4$ and evaporated. The resulting residue was triturated with diethyl ether/hexane to obtain a solid, which was dried in vacuo to give a white solid (1.5 g, 72%). $^1H$ NMR (300 MHz, $CDCl_3$) δ 7.93 (dd, J=7.85, 1.61 Hz, 1H), 7.65 (d, J=1.61 Hz, 1H), 7.62 (app q, J=8.26 Hz, 1H), 7.40 (d, J=8.06 Hz, 1H), 7.39–7.30 (m, 1H), 7.03–6.97 (m, 1H), 6.88–6.81 (m, 1H), 6.25 (s, 1H), 5.20 (s, 2H), 3.70–3.52 (m, 1H), 3.16–3.12 (m, 2H), 2.10 (s, 3H), 1.98 (s, 3H); ES-MS m/z 507 (M+H). ES-HRMS m/z 507.0719 (M+H calcd for $C_{23}H_{22}BrF_2N_2O_4$ requires 507.0726).

Examples 488–491

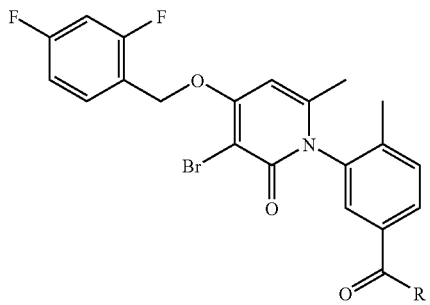

The compounds of Examples 488–491–476 are prepared essentially according to the procedures set forth for Example 487.

| Compound No. | R | % Yield | MF | M + H Requires | ESHRMS m/z |
|---|---|---|---|---|---|
| Ex. 488 | —NH(CH$_2$)$_2$OCH$_3$ | 84 | C$_{24}$H$_{24}$BrF$_2$N$_2$O$_4$ | 528.0882 | 521.0868 |
| Ex. 489 | —NHCH$_3$ | 79 | C$_{22}$H$_{20}$BrF$_2$N$_2$O$_3$ | 477.0620 | 477.0602 |
| Ex. 490 | —N(CH$_3$)$_2$ | 54 | C$_{23}$H$_{22}$BrF$_2$N$_2$O$_3$ | 491.0776 | 491.0753 |
| Ex. 491 | -morpholine | 65 | C$_{25}$H$_{24}$BrF$_2$N$_2$O$_4$ | 533.0858 | 533.0882 |

Example 492

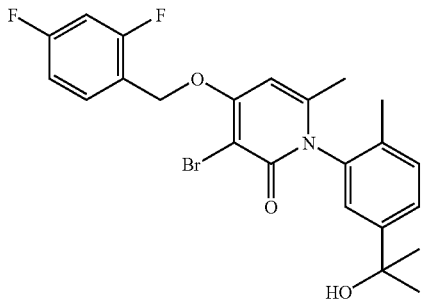

3-bromo-4-[(2,4-difluorobenzyl)oxy]-1-[5-(1-hydroxy-1-methylethyl)-2-methylphenyl]-6-methylpyridin-2(1H)-one Step 1: Preparation of methyl 3-[3-bromo-4-[(2,4-difluorobenzyl)oxy]-6-methyl-2-oxopyridin-1(2H)-yl]-4-methylbenzoate.

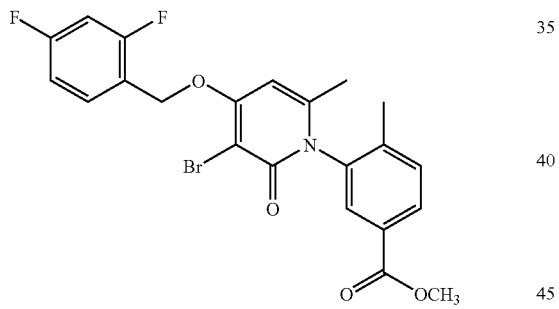

Methyl 3-[4-[(2,4-difluorobenzyl)oxy]-6-methyl-2-oxopyridin-1(2H)-yl]-4-methylbenzoate (as prepared above) (1.8 g, 4.51 mmol) was taken up in CH$_2$Cl$_2$ (10 ml). N-bromosuccinimide (0.80 g, 4.51 mmol) was added and the mixture stirred at room temperature for two hours. The CH$_2$Cl$_2$ is removed in vacuo and the residue is taken up in CH$_3$CN. The resulting precipitate is collected on a filter pad and washed with CH$_3$CN to yield a white solid (0.30 g, 14%, first crop)

$^1$H NMR (300 MHz, CDCl$_3$) δ 8.06 (dd, J=8.06, 1.61 Hz, 1H), 7.80 (d, J=1.61 Hz, 2H), 7.65 (app q, J=8.46 Hz, 1H), 7.48 (d, J=8.06, 1H), 7.05–6.99 (m, 1H), 6.96–6.89 (m, 1H), 6.16 (s, 1H), 5.31 (s, 2H), 3.93 (s, 3H), 2.17 (s, 3H), 1.96 (s, 3H). ES-HRMS m/z 478.0476 (M+H calcd for C$_{22}$H$_{19}$BrF$_2$NO$_4$ requires 478.0476).

Step 2: Preparation of the title compound. Methyl 3-[3-bromo-4-[(2,4-difluorobenzyl)oxy]-6-methyl-2-oxopyridin-1(2H)-yl]-4-methylbenzoate (0.22 g, 0.46 mmol) was taken up in THF and cooled to 0° C. MeMgCl (3.0 M in THF) (0.73 ml, 2.2 mmol) was slowly added to the 0° C. solution.

The reaction was allowed to proceed without maintaining the 0° C. bath temperature. The reaction was complete within two hours. At this time the mixture was quenched with saturated NH$_4$Cl (aq.) and extracted with ethyl acetate. The organic layers were combined, washed with H$_2$O, and extracted with ethyl acetate. The organic layers were combined and dried over Na$_2$SO$_4$, filtered, and evaporated. The residue was taken up in 50% ethyl acetate/hexanes. The precipitate was collected on a filter pad and washed with 50% ethyl acetate/hexanes to yield a white solid (0.10 g, 45%). $^1$H NMR (300 MHz, CD$_3$OD) δ 7.70 (app q, J=8.26, Hz, 1H), 7.54 (dd, J=8.06, 2.01 Hz, 1H), 7.40 (d, J=1.81 Hz, 1H), 7.12–7.06 (m, 2H), 6.68 (s, 1H), 5.40 (s, 2H), 2.05 (s, 3H), 2.02 (s, 3H), 1.57 (s, 6H). ES-HRMS m/z 478.0785 (M+H calcd for C$_{23}$H$_{23}$BrF$_2$NO$_3$ requires 478.0824).

Example 493

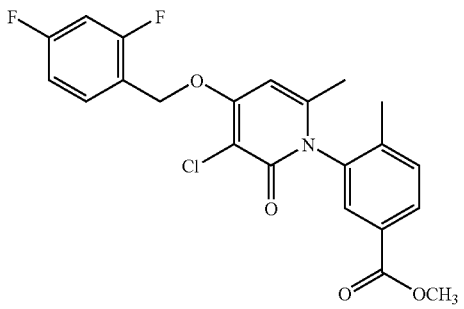

methyl 3-[3-chloro-4-[(2,4-difluorobenzyl)oxy]-6-methyl-2-oxopyridin-1(2H)-yl]-4-methylbenzoate The title compound was prepared by taking up methyl 3-[4-[(2,4-difluorobenzyl)oxy]-6-methyl-2-oxopyridin-1(2H)-yl]-4-methylbenzoate (1.46 g, 3.66 mmol) in dichloroethane (25 ml) and adding N-chlorosuccinimide (0.49 g, 3.66 mmol), dichloroacetic acid (catalytic), and heating to 50° C. for 6 hours. At this time, the solvent was removed in vacuo and the residue taken up in diethyl ether. The precipitate was collected on a filter pad. $^1$H NMR (300 MHz, CDCl$_3$) δ 8.07 (dd, J=7.85, 1.61 Hz, 1H), 7.80 (d, J=1.81 Hz, 2H), 7.62 (app q, J=8.46 Hz, 1H), 7.48 (d, J=7.85, 1H), 7.05–6.95 (m, 1H), 6.93–6.89 (m, 1H), 6.19 (s, 1H), 5.30 (s, 2H), 3.93 (s, 3H), 2.17 (s, 3H), 1.97 (s, 3H). ES-HRMS m/z 434.0932 (M+H calcd for C$_{22}$H$_{19}$ClF$_2$NO$_4$ requires 434.0965).

Example 494

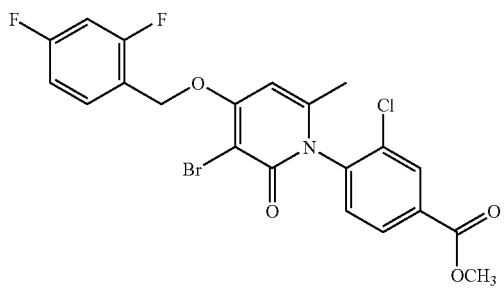

methyl 4-[3-bromo-4-[(2,4-difluorobenzyl)oxy]-6-methyl-2-oxopyridin-1(2H)-yl]-3-chlorobenzoate Step 1: Preparation of methyl 3-chloro-4-(4-hydroxy-6-methyl-2-oxopyridin-1(2H)-yl)benzoate.

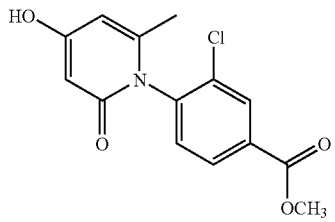

4-Hydroxy-6-methyl-2-pyrone (24.5 g, 193.9 mmol) and methyl-3-amino-2-chlorobenzoate (30 g, 161.6 mmol) were suspended in 75 ml of 1,2-dichlorobenzene in a 250 ml, 3-necked round bottom flask equipped with a J-Kem temperature controller probe, a Dean-Stark trap, and a heating mantle. The reaction was heated to 175° C. for 20 minutes, during which, water and some 1,2-dichlorobenzene was collected in the Dean-Stark trap. The reaction was allowed to cool to about 110° C. At this point, 200 ml of toluene was added. The toluene mixture was allowed to stir for 72 hours at room temperature. A precipitate was collected on a filter pad. The precipitate was filtered and washed 3 times with toluene, 3 times with 50° C. water to remove excess pyrone, and dried in vacuo to give a tan solid (13.0 g, 27% yield). $^1$H NMR (300 MHz, CD$_3$OD) δ 8.26 (d, J=1.81 Hz, 1H), 8.14 (dd, J=8.26, 1.81 Hz, 1H) 7.54 (d, J=8.26, Hz, 1H), 6.14 (dd, J=2.42, 1.0 Hz, 1H), 5.83 (d, J=2.42 1H), 4.00 (s, 3H), 1.96 (s, 3H); LC/MS, t$_r$=1.81 minutes (5 to 95% acetonitrile/water over 5 minutes at 1 ml/min with detection 254 nm, at 50° C.). ES-MS m/z 294 (M+H).

Step 2: Preparation of methyl 3-chloro-4-[4-[(2,4-difluorobenzyl)oxy]-6-methyl-2-oxopyridin-1(2H)-yl]benzoate.

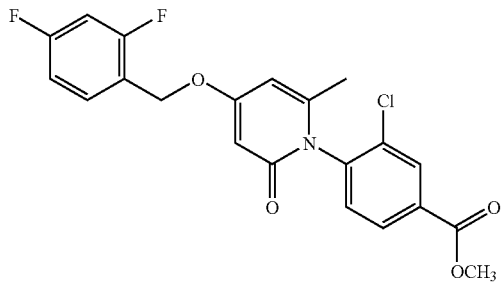

Methyl 3-chloro-4-(4-hydroxy-6-methyl-2-oxopyridin-1(2H)-yl)benzoate (from Step 1) (2.4 g, 8.17 mmol) was taken up in DMF (10 ml). 2,4-difluorobenzylbromide (1.05 ml, 8.17 mmol) and K$_2$CO$_3$ (1.13 g, 8.17 mmol) were added. The reaction stirred for 6 hours at room temperature. At this time, the reaction was poured into water (200 ml) and extracted with ethyl acetate. The ethyl acetate layer was dried over Na$_2$SO$_4$, filtered, and the solvent removed in vacuo to give amber oil (2.62 g, 77% crude yield). LC/MS, t$_r$=2.79 minutes (5 to 95% acetonitrile/water over 5 minutes at 1 ml/min with detection 254 nm, at 50° C.). ES-MS m/z 294 (M+H)

Step 3: Preparation of the title compound. Methyl 3-chloro-4-[4-[(2,4-difluorobenzyl)oxy]-6-methyl-2-oxopyridin-1(2H)-yl]benzoate (from step 2) (2.60 g, .21 mmol) was taken up in CH$_2$Cl$_2$ (20 ml). N-bromosuccinimide (1.11 g, 6.21 mmol) was added and the mixture stirred at room temperature for 4 hours. The CH$_2$Cl$_2$ is removed in vacuo and the residue is taken up in CH$_3$CN. The resulting precipitate is collected on a filter pad and washed with CH$_3$CN to yield a white solid (0.75 g, 24%). $^1$H NMR (300 MHz, CDCl$_3$) δ 8.22 (d, J=1.88 Hz, 1H), 8.06 (dd, J=8.19, 1.75 Hz, 1H), 7.59 (app q, J=8.46 Hz, 1H), 7.33 (d, J=8.19, 1H), 6.96 (dt, J=8.06, 1.21 Hz, 1H), 6.89–6.84 (m, 1H), 6.13 (s, 1H), 5.26 (s, 2H), 3.95 (s, 3H), 1.95 (s, 3H). ES-HRMS m/z 497.9892 (M+H calcd for C$_{22}$H$_{16}$BrClF$_2$NO$_4$ requires 497.9914).

Example 495

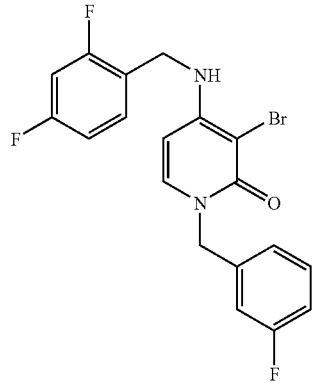

3-bromo-4-[(2,4-difluorobenzyl)amino]-1-(3-fluorobenzyl)pyridin-2(1H)-one

Step 1

Preparation of 4-(benzyloxy)-[(3-fluorobenzyl)pyridin-2(1H)-one.

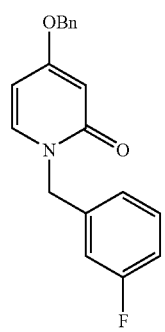

A 100 mL round bottomed flask equipped with stirbar and nitrogen inlet was charged with 4-benzyloxy-2(1H)-pyridinone (20 g, 99.6 mmol) and N,N-dimethyl formamide (50 mL). K$_2$CO$_3$ (13.7 g, 99.6 mmol) and KI (1.6 g, 9.6 mmol) were added followed by 3-fluorobenzyl bromide (14.6 mL, 119.4 mmol). The reaction mixture was heated for 18 h at 80 C. The reaction mixture was concentrated in vacuo and treated with hot ethyl acetate. The solids were filtered off, the filtrate was poured into water and was extracted with ethyl acetate. The organic extract was washed with brine, dried with anhydrous Na$_2$SO$_4$, and concentrated in vacuo. The residue was dissolved in hot ethyl acetate and precipitated with hexanes to give the title compound (10 g, 33%). $^1$H NMR (400 MHz, CD$_3$OD) δ 7.57 (d, J=8.4 Hz, 1H), 7.37 (m, 5H), 7.07 (d, J=8.4 Hz, 1H), 7.01 (app d, J=8.4 Hz, 2H), 6.17 (d, J=2.68 and 7.6 Hz, 1H), 6.04 (d, J=2.68 Hz, 1H), 5.10 (s, 2H), 5.08 (s, 2H) ppm. $^{19}$F NMR (400 MHz, CD$_3$OD) δ–114.88 (1 F) ppm. ES-HRMS m/z 310.1271 (M+H calcd for C$_{19}$H$_{17}$FNO$_2$ requires 310.1238).

Step 2

Preparation of 1-(3-fluorobenzyl)-4-hydroxypyridin-2(1H)-one

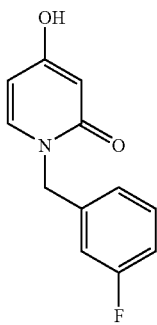

A small Parr bottle was charged with SC-82484 (10 g, 32.3 mmol), ethanol (175 mL) and 10% Pd/C (0.5 g). The system was flushed twice with both nitrogen and hydrogen. The reaction mixture was hydrogenated at 30 psi until no starting material was visible by LC-MS. The reaction mixture was slurried with Celite and then was filtered through a pad of celite. The filtrate and ensuing ethanol washes were concentrated in vacuo to give a beige solid. $^1$H NMR (400 MHz, CD$_3$OD) δ 7.53 (d, J=7.67 Hz, 1H), 7.32 (m, 1H), 7.06 (d, J=7.6 Hz, 1H), 6.98 (d, J=8.4 Hz, 2H), 6.05 (dd, J=2.58 and 7.67 Hz, 1H), 5.83 (d, J=2.0 Hz, 2H), 5.10 (s, 2H) ppm. $^{19}$F NMR (400 MHz, CD$_3$OD) δ –115.33 (1 F) ppm. ES-HRMS m/z 218.0641 (M+H calcd for C$_{12}$H$_{11}$FNO$_2$ requires 218.0612)

Step 3

Preparation of 4-[(2,4-difluorobenzyl)amino]-1-(3-fluorobenzyl)pyridin-2(1H)-one

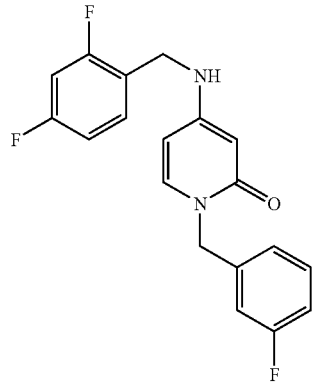

The product from Step 2 (0.5 g, 2.28 mmol) and 2,4-difluoro benzylamine (4 mL, 33.6 mmol) were combined in a nitrogen flushed culture tube. The tube was capped and heated at 180 C for 24 h. The excess amine was distilled in vacuo and the residue was chromatographed on silica (95:5 ethyl acetate: methanol). The final compound was isolated as a light yellow solid (0.16 g, 36%). $^1$H NMR (400 MHz, CD$_3$OD) δ 7.33 (m, 3H), 7.03 (d, J=8 Hz, 1H), 6.96 (m, 3H), 6.95 (m, 1H), 5.97 (dd, J=3.2 and 8.0 Hz, 1H), 5.48 (d, J=2.56 Hz, 1H), 5.02 (s, 2H), 4.33 (s, 2H) ppm. $^{19}$F NMR (400 MHz, CD$_3$OD) δ–113.88 (1 F), –115.33 (1 F), –116.78 (1 F) ppm. ES-HRMS m/z 345.1221 (M+H calcd for C$_{19}$H$_{17}$F$_3$N$_2$O requires 345.1209).

Step 4 Preparation of 3-bromo-4-[(2,4-difluorobenzyl)amino]-1-(3-fluorobenzyl)pyridin-2(1H)-one

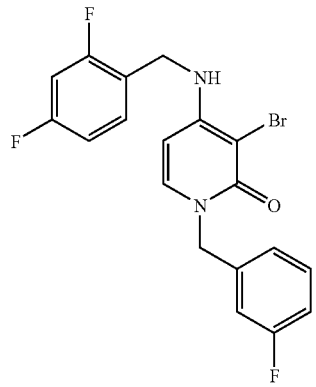

N-Bromo succinimide (81 mg, 0.46 mmol) was added to a solution of the product from Step 3 (0.15 g, 0.44 mmol) in methylene chloride (10 mL). After stirring at 25 C for 1 h, the reaction was complete by LC-MS. The reaction mixture was poured into saturated aqueous NaHCO$_3$. The aqueous mixture was extracted with ethyl acetate. The organic layer was washed with brine, dried with anhydrous MgSO$_4$, and concentrated in vacuo. $^1$H NMR (400 MHz, CDCl$_3$) δ 7.3–7.2 (m, 4H), 7.07 (app t, J=7.6 Hz, 2H), 6.97 (m, 2H), 6.80 (m, 2H), 5.78 (d, J=7.6 Hz, 1H), 5.30 (br s, 1H), 5.08 (s, 2H), 4.46 (d, J=6 Hz, 2H) ppm. $^{19}$F NMR (400 MHz, CDCl$_3$) δ–110.64 (1 F), –112.75 (1F), –114.79 (1 F) ppm. ES-HRMS m/z 423.0275 (M+H calcd for C$_{19}$H$_{15}$BrF$_3$N$_2$O requires 423.0314).

Example 496

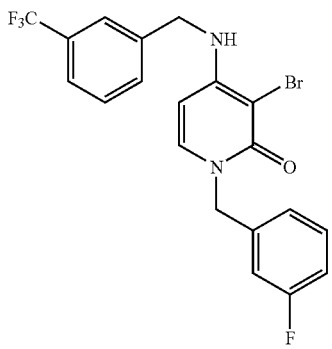

3-bromo-1-(3-fluorobenzyl)-4-{[3-(trifluoromethyl)benzyl]amino}pyridin-2(1H)-one The title compound was prepared essentially as in Example 495. $^1$H NMR (400 MHz, CDCl$_3$) δ 7.54 (m, 2H), 7.48 (m, 2H), 7.27 (q, J=3.1, 9.0 Hz, 1H), 6.96 (app t, J=8.8 Hz, 2H), 5.71 (d, J=7.6 Hz, 1H), 5.4 (br m, 1H), 5.08 (s, 2H), 4.52 (d, J=5.6 Hz, 2H) ppm. $^{19}$F NMR (400 MHz, CDCl$_3$) δ −63 (3 F), −112 (1 F) ppm. ES-HRMS m/z 455.0388 (M+H calcd for C$_{20}$H$_{16}$BrF$_4$N$_2$O requires 455.0377).

Example 497

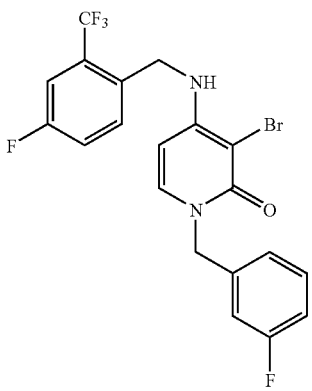

3-bromo-1-(3-fluorobenzyl)-4-{[4-fluoro-2-(trifluoromethyl)benzyl]amino}pyridin-2(1H)-one The title compound was prepared essentially as in Example 495. $^1$H NMR (400 MHz, CDCl$_3$) δ 7.43 (m, 2H), 7.27 (m, 3H), 7.07 (m, 2H), 6.99 (m, 2H), 5.65 (d, J=10 Hz, 1H), 5.46 (br s, 1H), 5.09 (s, 2H), 4.64 (s, 2H) ppm. $^{19}$F NMR (400 MHz, CDCl$_3$) δ −61.31 (3 F), −112.69 (1 F), 112.97 (1 F) ppm. ES-HRMS m/z 473.0246 (M+H calcd for C$_{20}$H$_{15}$BrF$_5$N$_2$O requires 473.0282).

Example 498

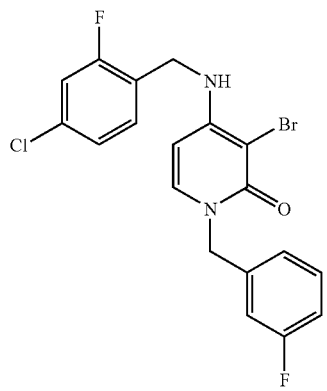

Preparation of -bromo-4-[(4-chloro-2-fluorobenzyl)amino]-1-(3-fluorobenzyl)pyridin-2(1H)-one The title compound was prepared essentially as in Example 495. $^1$H NMR (400 MHz, CDCl$_3$) δ 7.27 (m, 1H), 7.19 (app t, J=8.8 Hz, 1H), 7.10 (m, 4H), 6.95 (app t, J=8.8 Hz, 2H), 5.74 (d, J=8 Hz, 1H), 5.40 (br s, 1H), 5.08 (s, 2H), 4.47 (d J=6 Hz, 2H) ppm. $^{19}$F NMR (400 MHz, CDCl$_3$) δ −112.67 (1 F), −116.39 (1 F) ppm. ES-HRMS m/z 439.0047 (M+H calcd for C$_{19}$H$_{15}$ClBrF$_2$N$_2$O requires 439.0019).

Example 499

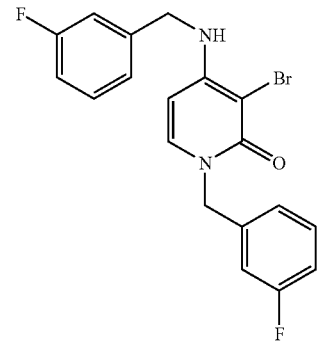

The title compound was prepared essentially as in Example 495. $^1$H NMR (400 MHz, CDCl$_3$) δ 7.35–7.2 (m, 1H), 7.27 (dd, J=2.5 and 8 Hz, 1H), 7.05 (app d, J=7.2 Hz, 3H), 6.97 (m, 4H), 5.72 (d, J=7.6 Hz, 1H), 5.41 (br s, 1H), 5.08 (s, 2H), 4.46 (d, J=6.4 Hz, 2H) ppm. $^{19}$F NMR (400 MHz, CDCl$_3$) δ −112.5 (1 F), −113 (1 F) ppm. ES-HRMS m/z 405.0431 (M+H calcd for C$_{19}$H$_{16}$BrF$_2$N$_2$O requires 405.0409).

Example 500

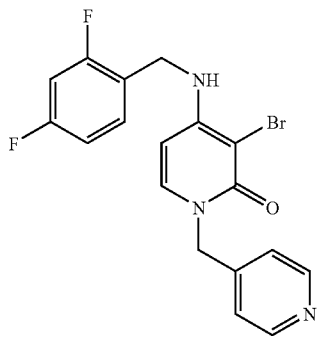

Preparation of 3-bromo-4-[(2,4-difluorobenzyl)amino]-6-methyl-1-(pyridin-4-ylmethyl)pyridin-2(1H)-one Step 1 Preparation of 4-[(2,4-difluorobenzyl)amino]-6-methyl-1-(pyridin-4-ylmethyl)pyridin-2(1H)-one

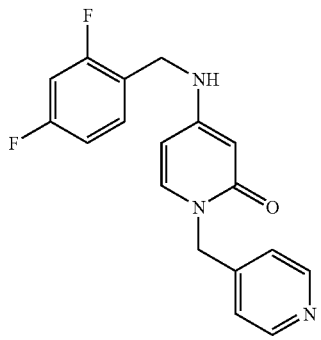

(0.3 g, 1.39 mmol) and 2,4-difluoro benzylamine (1 mL, 8.4 mmol) were combined in a nitrogen flushed culture tube. The tube was capped and heated at 180 C for 24 h. The excess amine was distilled in vacuo. $^1$H NMR (400 MHz, CD$_3$OD) δ 8.44 (dd, J=1.7 and 4.8 Hz, 2H), 7.38 (q, J=10 and 15 Hz, 1H), 7.14 (d, J=4.8 Hz, 2H), 6.95 (m, 2H), 5.90 (dd, J=1 and 2.5 Hz, 1H), 5.47 (d, J=2, 1H), 5.28 (s, 2H), 4.33 (s, 2H), 2.27 (s, 3H) ppm. $^{19}$F NMR (400 MHz, CD$_3$OD) δ–113.73 (1 F), –116.66 (1 F) ppm. ES-HRMS m/z 342.1422 (M+H calcd for C$_{19}$H$_{18}$F$_2$N$_3$O requires 342.1418).

Step 2 Preparation of 3-bromo-4-[(2,4-difluorobenzyl)amino]-6-methyl-1-(pyridin-4-ylmethyl)pyridin-2(1H)-one

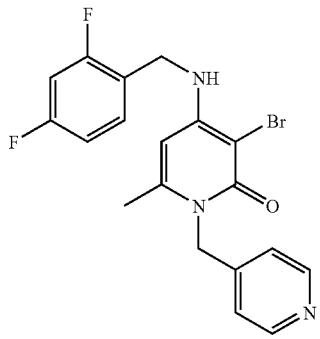

N-Bromo succinimide (77 mg, 0.43 mmol) was added to a solution of the product of Step 1 (0.14 g, 0.41 mmol) in methylene chloride (10 mL). After stirring at 25 C for 1 h, the reaction was complete by LC-MS. The reaction mixture was poured into saturated aqueous NaHCO$_3$. The aqueous mixture was extracted with ethyl acetate. The organic layer was washed with brine, dried with anhydrous Na$_2$SO$_4$, filtered and concentrated in vacuo. The residue was triturated with hexanes to give the title compound as a yellow solid (81 mg, 47%). $^1$H NMR (400 MHz, CDCl$_3$) δ 8.47 (dd, J=1.6 and 4.8 Hz, 2H), 7.24 (q, J=6.4 and 13.6 Hz, 1H), 7.01 (d, J=6.4 Hz, 2H), 6.83 (m, 2H), 5.68 (s, 1H), 5.25 (s, 2H), 4.45 (d, J=6.4 Hz, 2H), 2.12 (s, 3H) ppm. $^{19}$F NMR (400 MHz, CDCl$_3$) δ–110.51 (m, 1 F), –(M+H calcd for C$_{19}$H$_{17}$BrF$_2$N$_3$O requires 420.0523).

Example 501

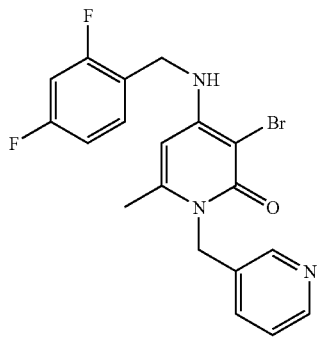

Preparation of 3-bromo-4-[(2,4-difluorobenzyl)amino]-6-methyl-1-(pyridin-3-ylmethyl)pyridin-2(1H)-one The title compound was prepared essentially as in Example 500.

$^1$H NMR (400 MHz, CDCl$_3$) δ 8.45 (d, J=4.8 Hz, 2H), 7.55 (app t, J=6 Hz, 1H), 7.21 (m, 2H), 6.83 (m, 2H), 5.65 (s, 1H), 5.34 (d, J=5.2 Hz, 1H), 5.27 (s, 2H), 4.45 (s, 2H), 2.10 (d, J=4.8 Hz, 3H) ppm. $^{19}$F NMR (400 MHz, CDCl$_3$) δ–110.74 (1 F), –114.86 (1 F) ppm. ES-HRMS m/z 420.0533 (M+H calcd for C$_{19}$H$_{17}$BrF$_2$N$_3$O requires 420.0523).

Example 502

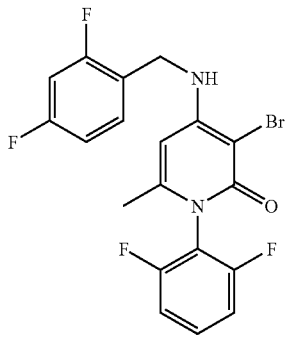

Preparation of 3-bromo-4-[(2,4-difluorobenzyl)amino]-1-(2,6-difluorophenyl)-6-methylpyridin-2(1H)-one Step 1 Preparation of 4-[(2,4-difluorobenzyl)amino]-1-(2,6-difluorophenyl)-6-methylpyridin-2(1H)-one

413

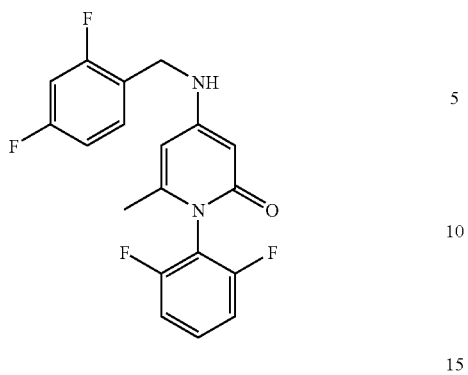

1-(2,6-difluorophenyl)-4-hydroxy-6-methylpyridin-2(1H)-one (0.3 g, 1.26 mmol) and 2,4-difluoro benzylamine (1 mL, 8.4 mmol) were combined in a nitrogen flushed culture tube. The tube was capped and heated at 180 C for 24 h. The excess amine was distilled in vacuo and the residue was chromatographed on silica (1:1 hexanes:ethyl acetate). The compound was approximately 50% pure and was carried on without further purification (0.633 g). $^1$H NMR (400 MHz, CD$_3$OD) δ 7.53 (m, 1H), 7.41 (m, 1H), 7.16 (t, J=8.8 Hz, 2H), 6.93 (m, 2H), 6.00 (s, 1H), 5.42 (s, 1H), 5.42 (s, 1H), 4.37 (s, 2H), 1.93 (s, 3H) ppm. LC/MS, t$_r$=4.65 minutes (5 to 95% acetonitrile/water over 8 minutes at 1 ml/min with detection 254 nm, at 50° C.). ES-MS m/z 363 (M+H).

Step 2 Preparation of 3-bromo-4-[(2,4-difluorobenzyl)amino]-1-(2,6-difluorophenyl)-6-methylpyridin-2(1H)-one

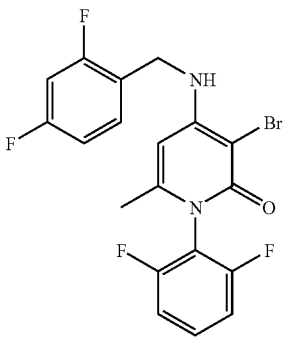

N-Bromo succinimide (168 mg, 0.945 mmol) was added to a solution of the product of Step 1 (0.633 g) in methylene chloride (10 mL). After stirring at 25 C for 1 h, the reaction was 50% complete by LC-MS. Additional N-bromo succinimide (150 mg) was added and the reaction was stirred at 25 C for 12 h. The reaction mixture was poured into saturated aqueous NaHCO$_3$. The aqueous mixture was extracted with ethyl acetate. The organic layer was washed with brine, dried with anhydrous Na$_2$SO$_4$, and concentrated in vacuo. The residue was purified by reverse phase chromatography (60:40 Acetonitrile: water with 0.05% trifluoroacetic acid). The title compound was isolated as the TFA salt (0.161 g, 23%). $^1$H NMR (400 MHz, CD$_3$OD) δ 7.53 (m, 1H), 7.35 (q, J=8, 15.6 Hz, 1H), 7.16 (t, J=8 Hz, 2H), 6.96 (app q, J=8, 16.4 Hz, 2H), 6.12 (s, 1H), 4.86 (s, 2H), 1.94 (s, 3H) ppm. $^{19}$F NMR (400 MHz, CD$_3$OD) δ −77.33 (1 F), −113.60 (1 F), −116.63 (1 F), −121.50 (1 F) ppm. ES-HRMS m/z 441.0231 (M+H calcd for C$_{19}$H$_{14}$BrF$_4$N$_2$O requires 441.0220).

414

Example 503

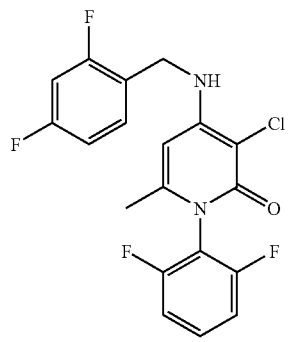

Preparation of 3-chloro-4-[(2,4-difluorobenzyl)amino]-1-(2,6-difluorophenyl)-6-methylpyridin-2(1H)-one 1-(2,6-difluorophenyl)-4-hydroxy-6-methylpyridin-2(1H)-one (0.3 g, 1.26 mmol) and 2,4-difluoro benzylamine (1 mL, 84 mmol) were combined in an nitrogen flushed culture tube. The tube was capped and heated at 180 C for 24 h. The excess amine was distilled in vacuo and the residue was used without further purification. N-Chloro succinimide (168 mg, 1.26 mmol) was added to a solution of the residue in methylene chloride (10 mL). After stirring at 25 C for 1 h, the reaction mixture was poured into saturated aqueous NaHCO$_3$. The aqueous mixture was extracted with ethyl acetate. The organic layer was washed with brine, dried with anhydrous Na$_2$SO$_4$, and concentrated in vacuo. The residue was chromatographed on silica (25:75 hexanes: ethyl acetate) to give the title compound (32 mg, 6%). $^1$H NMR (400 MHz, CD$_3$OD) δ 7.55 (m, 1H), 7.36 (q, J=9.2 and 15.2 Hz, 1H), 7.18 (t, J=7.6 Hz, 2H), 6.98 (m, 2H), 6.15 (s, 1H), 4.62 (s, 2H), 1.96 (s, 3H) ppm. 19 F NMR (400 MHz, CD$_3$OD) δ−113.78 (1 F), −116.72 (1 F), −121.57 (1 F) ppm. ES-HRMS m/z 397.0752 (M+H calcd for C$_{19}$H$_{14}$ClF$_4$N$_2$O requires 397.0725).

Example 504

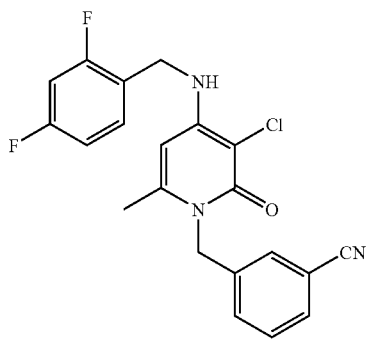

Preparation of 3-{[3-chloro-4-[(2,4-difluorobenzyl)amino]-6-methyl-2-oxopyridin-1(2H)-yl]methyl}benzonitrile Step 1 Preparation of 3-phthalimidomethyl-benzonitrile

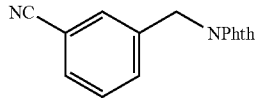

3-Phthalimidomethyl-benzonitrile was prepared as described in the literature. (Bookser, B. C.; Bruice, T. C. J. Am. Chem. Soc. 1991, 113, 4208–18.)

Step 2 Preparation of 3-(aminomethyl)benzonitrile

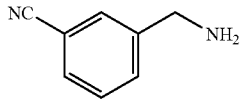

3-(Aminomethyl)benzonitrile was prepared as described in the literature. (Bookser, B. C.; Bruice, T. C. J. Am. Chem. Soc. 1991, 113, 4208–18.)

Step 3 Preparation of 3-[(4-hydroxy-6-methyl-2-oxopyridin-1(2H)-yl)methyl]benzonitrile

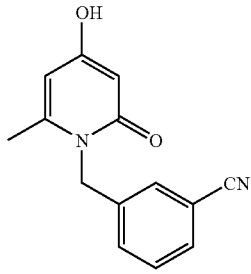

A nitrogen flushed pyrex reaction tube was charged with 3-(aminomethyl)benzonitrile (1 g, 7.9 mmol), 4-hydroxy-6-methyl-2-pyrone (1 g, 7.9 mmol) and water (20 mL). The tube was capped and was heated to reflux. After 1.5 h, the product precipitated from solution. The reaction mixture was cooled to room temperature, filtered and washed with water. The product was used without further purification (1.67 g, 88%).

$^1$H NMR (400 MHz, dmso-d$_6$) δ 10.53 (s, 1H), 7.61 (d, J=8 Hz, 1H), 7.52 (t, J=8 Hz, 2H), 7.38 (d, J=8 Hz, 1H), 5.79 (dd, J=1 and 2.5 Hz, 1H), 5.56 (d, J=2.7 Hz, 1H), 5.18 (s, 2H), 2.14 (s, 3H) ppm. ES-HRMS m/z 241.0968 (M+H calcd for C$_{14}$H$_{13}$N$_2$O$_2$ requires 241.0972).

Step 5 Preparation of 3-{[4-[(2,4-difluorobenzyl)amino]-6-methyl-2-oxopyridin-1(2H)-yl]methyl}benzonitrile

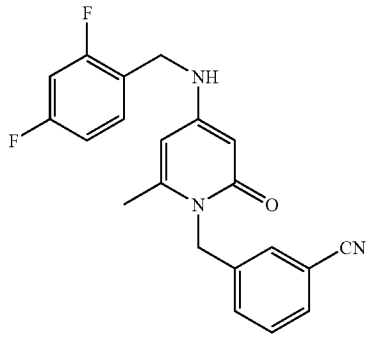

The product from Step 4 (0.5 g, 2.08 mmol) and 2,4-difluoro benzylamine (2 mL, 16.8 mmol) were combined in a nitrogen flushed culture tube. The tube was capped and heated at 180 C for 24 h. The excess amine was distilled in vacuo and the residue was triturated with ethyl acetate/hexanes to precipitate the starting materials. The residue was chromatographed on reverse phase (1:1 water:acetonitrile with 0.05% trifluoroacetic acid). The product of Step 5 was isolated as a white semi-solid (0.125 g, 15%). $^1$H NMR (400 MHz, CD$_3$OD) δ 7.6 d, J=8 Hz, 1H), 7.49 (t, J=8 Hz, 1H), 7.41 (m, 3H), 6.94 (m, 2H), 5.89 (dd, J=0.8 and 2.7 Hz, 1H), 5.47 (d, J=2.8 Hz, 1H), 5.27 (s, 2H), 4.34 (s, 2H), 2.18 (s, 3H) ppm. LC/MS, t$_r$=4.87 minutes (5 to 95% acetonitrile/water over 8 minutes at 1 ml/min with detection 254 nm, at 50° C.). ES-MS m/z 366 (M+H).

Step 6 Preparation of 3-{[3-chloro-4-[(2,4-difluorobenzyl)amino]-6-methyl-2-oxopyridin-1(2H)-yl]methyl}benzonitrile

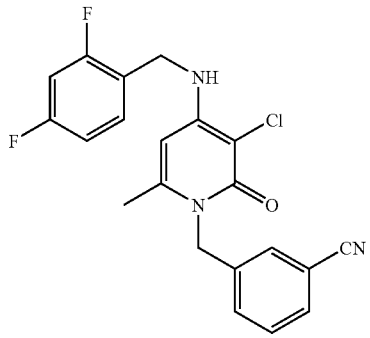

N-Chloro succinimide (36 mg, 0.27 mmol) was added to a solution of the product of Step 5 (0.125 g, 0.26 mmol) in methylene chloride (10 mL). After stirring at 25 C for 2 h, the reaction was complete by LC-MS. The reaction mixture was poured into saturated aqueous NaHCO$_3$. The aqueous mixture was extracted with ethyl acetate. The organic layer was washed with brine, dried with anhydrous Na$_2$SO$_4$, and concentrated in vacuo. The residue was triturated with acetonitrile to give the title compound as a tan solid (20 mg, 13%). $^1$H NMR (400 MHz, CD$_3$OD) δ 7.61 (d, J=8.4 Hz, 1H), 7.49 (m, 2H), 7.40 (d, J=8.4 Hz, 1H), 7.33 (q, J=8.4 and 14.8 Hz, 1H), 6.94 (m, 2H), 6.00 (s, 1H), 5.34 (s, 2H), 4.56 (s, 2H), 2.21 (s, 3H) ppm. $^{19}$F NMR (400 MHz, CD$_3$OD) δ –114.00 (1 F), –116.89 (1 F) ppm. LC/MS, t$_r$=5.49 minutes (5 to 95% acetonitrile/water over 8 minutes at 1 ml/min with detection 254 nm, at 50° C.). ES-MS m/z 400 (M+H).

Example 505

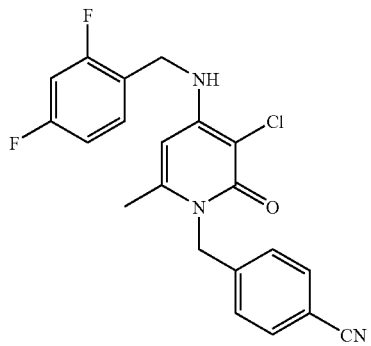

Preparation of 4-{[3-chloro-4-[(2,4-difluorobenzyl)amino]-6-methyl-2-oxopyridin-1(2H)-yl]methyl}benzonitrile The title compound was prepared essentially as in Example 504. $^1$H NMR (400 MHz, CD$_3$OD) δ 7.66 (d, J=8 Hz, 2H), 7.33 (q, J=8 and 15.2 Hz, 1H), 7.25 (d, J=8 Hz, 2H), 6.94 (m, 2H), 6.01 (s, 1H), 5.36 (s, 2H), 4.55 (s, 2H), 2.19 (s, 3H) ppm. $^{19}$F NMR (400 MHz, CD$_3$OD) δ −77.52 (1 F), −113.89 (1 F), −116.71 (1 F) ppm. LC/MS, t$_r$=5.49 minutes (5 to 95% acetonitrile/water over 8 minutes at 1 ml/min with detection 254 nm, at 50° C.). ES-MS m/z 400 (M+H).

Example 506

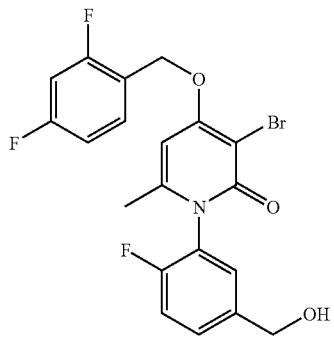

Preparation of 3-bromo-4-[(2,4-difluorobenzyl)oxy]-1-[2-fluoro-5-(hydroxymethyl)phenyl]-6-methylpyridin-2(1H)-one

Step 1 Preparation of (3-amino-4-fluorophenyl)methanol

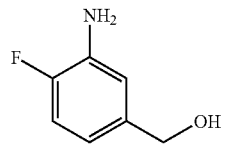

A flask equipped with overhead stirrer was charged with 4-fluoro-3-nitrobenzyl alcohol (20 g, 0.117 mol) and 200 mL of 5:1 isopropanol:water. Ammonium chloride (62 g, 1.17 mol) was added followed by iron filings (65 g, .17 mol). The mixture was stirred at 70 C for 1.5 H when it was shown to be complete by LC-MS. The liquid was decanted and the solids were washed with additional isopropanol:water. The isopropanol was removed and the residue was diluted with 0.5 N HCl and was extracted with ethyl acetate. The aqueous layer was brought to pH 12–14 with 2.5 N NaOH and was extracted with ethyl acetate. The organic layer was dried with anhydrous Na$_2$SO$_4$ and concentrated in vacuo. 3-Amino-4-fluorophenyl methanol was isolated as a brown solid (4.5 g, 27%) and was used without further purification. LC/MS, t$_r$=2.40 minutes (5 to 95% acetonitrile/water over 8 minutes at 1 ml/min with detection 254 nm, at 50° C.). ES-MS m/z 142 (M+H). ES-HRMS m/z 142.0692 (M+H calcd for C$_7$H$_8$FNO requires 142.0663).

Step 2 Preparation of 1-[2-fluoro-5-(hydroxymethyl)phenyl]-4-hydroxy-6-methylpyridin-2(1H)-one

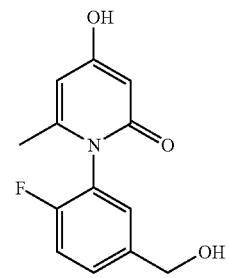

A 100 mL round bottomed flask equipped with stirbar, Dean-Stark trap and reflux condenser was charged with (3-amino-4-fluorophenyl)methanol (4.5 g, 31.9 mmol), 4-hydroxy-6-methyl-2-pyrone (4 g, 31.9 mmol) and o-dichlorobenzene (5 mL). The system was immersed in a 170 C oil bath for 10 minutes. The solvent was removed in vacuo and the residue was chromatographed on reverse phase (75:25 water:acetonitrile with 0.05% TFA). The product contained some starting materials after purification and was used without further purification (1.27 g, 15%). $^1$H NMR (400 MHz, dmso-d$_6$) δ 7.39 (m, 1H), 7.20 (dd, J=2.2 and 7.6 Hz, 1H), 6.74 (dd, J=2.7 and 9.6 Hz, 1H), 5.93 (dd, J=1.2 and 2.2 Hz, 1H), 5.22 (dd, J=0.4 and 2.2 Hz, 1H), 2.12 (s, 3H) ppm. ES-HRMS m/z 250.0862 (M+H calcd for C$_{13}$H$_{13}$FNO$_3$ requires 250.0874).

Step 3 Preparation of 4-[(2,4-difluorobenzyl)oxy]-1-[2-fluoro-5-(hydroxymethyl)phenyl]-6-methylpyridin-2(1H)-one

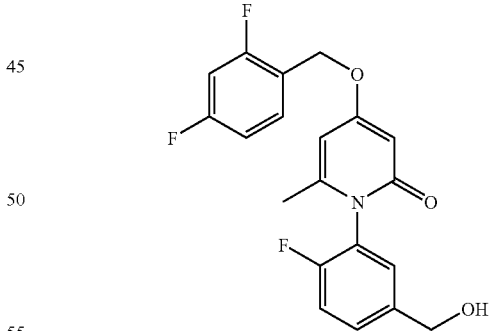

A 100 mL roundbottomed flask (nitrogen purged) was charged with 1-[2-fluoro-5-(hydroxymethyl)phenyl]-4-hydroxy-6-methylpyridin-2(1H)-one (1.2 g, 4.82 mmol) and N,N-dimethyl formamide (10 mL). Potassium carbonate (0.6 g, 4.4 mmol) and 2,4-difluorobenzyl bromide (0.56 mL, 4.4 mmol) was added and the reaction mixture was stirred at room temperature overnight. The reaction mixture was diluted with saturated aqueous NaHCO$_3$ and extracted with ethyl acetate. The organic layer was concentrated in vacuo and the residue was chromatographed on silica (9:1 methylene chloride:ethanol). The impure oil (0.3 g, 17%) was carried on without further purification. ¹H NMR (400 MHz, CD₃OD) δ 7.54 (m, 2H), 7.30 (m, 2H), 7.02 (m, 2H), 6.17 (dd, J=1 and 2.8 Hz, 1H), 6.03 (d, J=2.8 Hz, 1H), 5.14 (s, 2H), 4.62 (s, 2H), 2.14 (s, 3H) ppm. ¹⁹F NMR (400 MHz, CD₃OD) δ −111.35 (1 F), −115.97 (1 F), −127.31 (1 F) ppm. LC/MS, $t_r$=5.05 minutes (5 to 95% acetonitrile/water over 8 minutes at 1 ml/min with detection 254 nm, at 50° C.). ES-MS m/z 375 (M+H).

Step 4 Preparation of 3-bromo-4-[(2,4-difluorobenzyl)oxy]-1-[2-fluoro-5-(hydroxymethyl)phenyl]-6-methylpyridin-2(1H)-one

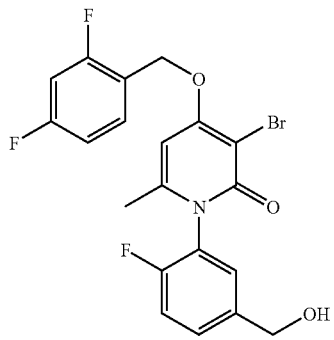

N-Bromo succinimide (50 mg, 0.3 mmol) was added to a solution of the product of Step 3 (0.12 g, 0.32 mmol) in N,N-dimethyl formamide (4 mL). After stirring at 25 C for 2 h, trifluoroacetic acid (50 µL) was added. After 1 h, additional N-Bromo succinimide (30 mg) was added. After 1 h, the reaction was complete by LC-MS. The reaction mixture was poured into brine and was extracted with ethyl acetate. The organic layer was washed with brine, dried with anhydrous Na₂SO₄, and concentrated in vacuo. The residue was chromatographed on reverse phase (95:5 methylene chloride: ethanol). The title compound was isolated as the TFA salt (38 mg, 26%). ¹H NMR (400 MHz, CD₃OD) δ 7.64 (q, J=7.6 and 14.8 Hz, 1H), 7.51 (m, 1H), 7.31 (app t, J=8.4 Hz, 1H), 7.04 (t, J=8.4 Hz, 2H), 6.63 (s, 1H), 5.34 (s, 2H), 4.62 (s, 2H), 2.06 (s, 3H) ppm. ¹⁹F NMR (400 MHz, CD₃OD) δ −111.48 (1 F), −115.92 (1 F), −127.23 (1 F) ppm. ES-HRMS m/z 454.0228 (M+H calcd for C₂₀H₁₆BrF₃NO₃ requires 454.0260).

Example 507

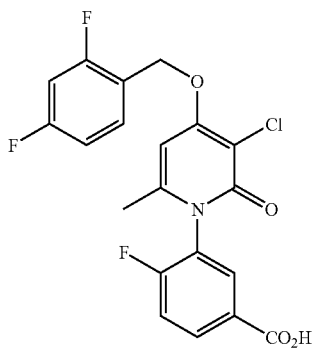

Preparation of 3-[3-chloro-4-[(2,4-difluorobenzyl)oxy]-6-methyl-2-oxopyridin-1(2H)-yl]-4-fluorobenzoic acid Step 1 Preparation of methyl 4-fluoro-3-nitrobenzoate

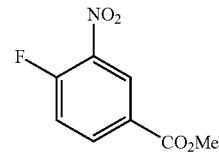

A 1 L 3-necked round bottomed flask equipped with a nitrogen inlet, stirbar, addition funnel and thermocouple was charged with 4-fluoro-3-nitrobenzoic acid (50 g, 0.27 mol) and methanol (300 mL). The system was cooled to 0 C and acetyl choride (27 mL, 0.37 mol) was added dropwise. The system was warmed to room temperature, the addition funnel was replaced with a reflux condensor, and was heated to reflux for 1.5 h. The reaction mixture was cooled to room temperature, quenched with saturated aqueous NaHCO₃, and extracted with ethyl acetate. The organic extract was washed with brine, dried with Na₂SO₄ and concentrated in vacuo to give methyl 4-fluoro-3-nitrobenzoate as an orange solid (40.6 g, 75%). ¹H NMR (400 MHz, CD₃OD) δ 8.67 ((dd, J=2.2 and 6.8 Hz, 1H), 8.34 (dddd, J=2.2, 4.4, 6.4 and 8.8 Hz, 1H), 7.55 (dd, J=8.8 and 10.8 Hz, 1H), 3.94 (s, 3H) ppm. ES-HRMS m/z 200.02446 (M+H calcd for C₈H₇FNO₄ requires 200.0354).

Step 2 Preparation of methyl 3-amino-4-fluorobenzoate

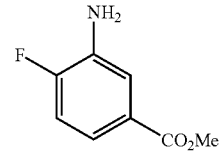

A Parr bottle was charged with the product of Step 1 (40 g, 0.2 mol), ethanol (400 mL) and 10% Pd/C (1 g g). The system was flushed twice with nitrogen and hydrogen. The reaction mixture was hydrogenated at 40 psi until no starting material was visible by LC-MS. The reaction mixture was slurried with Celite and then was filtered through a pad of celite. The filtrate and ensuing ethanol washes were concentrated in vacuo to give methyl 3-amino-4-fluorobenzoate as an orange solid (30.6 g, 91%). ¹H NMR (400 MHz, CD₃OD) δ 7.54 (d, J=8.7 Hz, 1H), 7.35 (m, 1H), 7.06 (t, J=8.7 Hz, 1H), 3.09 (s, 3H) ppm. ¹⁹F NMR (400 MHz, CD₃OD) δ −131.02 (1 F) ppm. ES-HRMS m/z 199.0281 (M+H calcd for C₈H₇FNO₄ requires 199.02).

Step 3 Preparation of methyl 4-fluoro-3-(4-hydroxy-6-methyl-2-oxopyridin-1(2H)-yl)benzoate

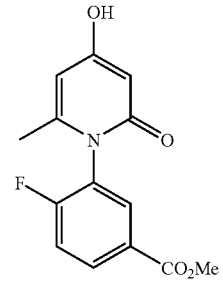

A 250 mL round bottomed flask equipped with stirbar, Dean-Stark trap and reflux condenser was charged with the product of Step 3 (30 g, 0.18 mol), 4-hydroxy-6-methyl-2-pyrone (22.6 g, 0.18 mol), and o-dichlorobenzene (90 mL). The system was immersed in a 170 C oil bath for 30 minutes and was then cooled to room temperature. The reaction mixture was washed with aqueous $Na_2CO_3$ (38 g, 0.36 mol, 300 mL water) The aqueous layer was washed with ethyl acetate and then was acidified to pH 1–2 with concentrated HCl. This was extracted with ethyl acetate, which was then dried with $MgSO_4$ and concentrated in vacuo. The viscous orange oil was used without further purification (14.4 g, 28%). $^1$H NMR (400 MHz, $CD_3OD$) δ 8.18 (dddd, J=2.3, 5.2, 7.2 and 8.8 Hz, 1H), 7.97 (dd, J=2 and 7.2 Hz, 1H), 7.44 (t, J=8.8 Hz, 1H), 6.09 (d, J=1.8 Hz, 1H), 5.78 (d, J=2.4 Hz, 1H), 3.9 (s, 3H), 2.14 (s, 3H) ppm. $^{19}$F NMR (400 MHz, $CD_3OD$) δ–117.29 (1 F) ppm. ES-HRMS m/z 278.0796 (M+H calcd for $C_{14}H_{13}FNO_4$ requires 278.0823).

Step 4 Preparation of methyl 3-[4-[(2,4-difluorobenzyl)oxy]-6-methyl-2-oxopyridin-1(2H)-yl]-4-fluorobenzoate

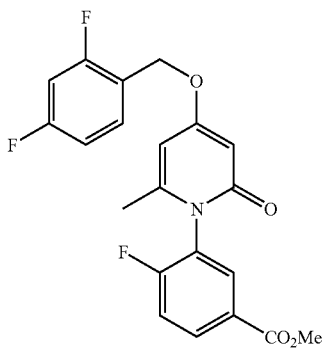

A 100 mL round bottomed flask equipped with stirbar and nitrogen inlet was charged with the product of Step 3 (14.4 g, 51.9 mmol) and N,N-dimethyl formamide (40 mL). 1,8-diazabicyclo[5.4.0]undec-7-ene (10.9 mL, 72.8 mmol) was added followed by 2,4-difluorobenzyl bromide (9.3 mL, 72.8 mmol). The reaction mixture was stirred at 65 C for 18 h, was poured into saturated aqueous $NaHCO_3$ and was extracted with ethyl acetate. The organic layer was washed with brine, dried with $Na_2SO_4$ and concentrated in vacuo to give the title product, as an orange oil (21.5 g), which was carried on to the next reaction without further purification. $^1$H NMR (400 MHz, $CD_3OD$) δ 8.20 (dddd, J=2.2, 4.8, 7.2 and 8.8 Hz, 1H), 8.00 (dd, J=2.2 and 7.2 Hz, 1H), 7.56 (td, J=2.4, 6.4 and 9.2 Hz, 1H), 7.46 (t, J=9.2 Hz, 1H), 7.02 (m, 2H), 6.18 (dd, J=0.8 and 2.6 Hz, 1H), 6.04 (d, J=2.7 Hz, 1H), 5.14 (s, 2H), 3.90 (s, 3H), 1.98 (s, 3H) ppm. $^{19}$F NMR (400 MHz, $CD_3OD$) δ–111.34 (1 F), –116.00 (1 F), –117.35 (1 F) ppm. ES-HRMS m/z 404.1104 (M+H calcd for $C_{21}H_{17}F_3NO_4$ requires 404.1104).

Step 5 Preparation of methyl 3-[3-chloro-4-[(2,4-difluorobenzyl)oxy]-6-methyl-2-oxopyridin-1(2H)-yl]-4-fluorobenzoate

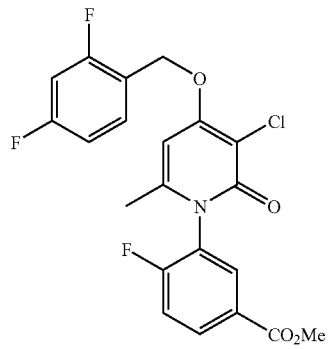

A 250 mL round bottomed flask equipped with stirbar and nitrogen inlet was charged with the product of Step 4 (21 g, 52 mmol) and N-methyl-2-pyrrolidine (100 mL). N-Chloro succinimide (8.3 g, 62 mmol) was added and the reaction mixture was stirred at 65 C for 2 h. The mixture was then cooled to room temperature, poured into saturated aqueous $NaHCO_3$ and extracted with ethyl acetate. The organic layer was washed with brine, dried with $Na_2SO_4$, and concentrated in vacuo. The residue was triturated with diethyl ether and filtered to give the title compound, as a white powder (5.9 g, 25%). $^1$H NMR (400 MHz, $CD_3OD$) δ 8.22 (dddd, J=2, 4.8, 6.8 and 8.8 Hz, 1H), 8.03 (dd, J=2 and 7.2 Hz, 1H), 7.62 (q, J=8.4 and 14.8 Hz, 1H), 7.48 (t, J=14 Hz, 1H), 7.04 (m, 2H), 6.69 (s, 1H), 5.36 (s, 2H), 3.91 (s, 3H), 2.08 (s, 3H) ppm. $^{19}$F NMR (400 MHz, $CD_3OD$) δ–111.38 (1 F), –115.97 (1 F), –117.43 (1 F) ppm. ES-HRMS m/z 438.0723 (M+H calcd for $C_{21}H_{16}ClF_3NO_4$ requires 438.0714).

Step 6 Preparation of 3-[3-chloro-4-[(2,4-difluorobenzyl)oxy]-6-methyl-2-oxopyridin-1(2H)-yl]-4-fluorobenzoic acid

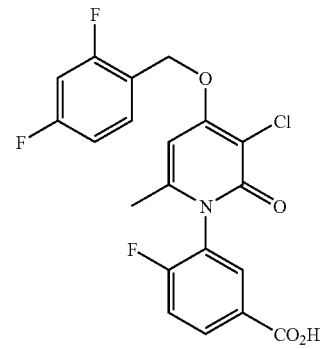

A 100 mL round bottomed flask was charged with the product of Step 5 (2.5 g, 5.72 mmol), tetrahydrofuran (40 mL), methanol (10 mL), and water (10 mL). To this slurry was added 2.5 N NaOH (4.6 mL, 11.4 mmol). The reaction mixture became clear after 5 minutes and the reaction was complete in 35 minutes by LC-MS. The organics were removed on the rotary evaporator and the remaining solution was acidified to pH 3 with 6N HCl. The desired compound was precipitated by the addition of diethyl ether and subsequent filtration. The title compound was isolated as a white powder (2.5 g, 98%). $^1$H NMR (400 MHz, dmso-$d_6$) δ 8.10 (dddd, J=2.1, 4.8, 7.2 and 8.4 Hz, 1H), 8.00 (dd, J=2.1 and 7.6 Hz, 1H), 7.66 (q, J=9.2 and 15.6 Hz, 1H), 7.57 (t, J=8.8 Hz, 1H), 7.34 (td, J=2.4 and 10.4 Hz, 1H), 7.17 (tdd, J=1, 2.7 and 8.4 Hz, 1H), 6.76 (s, 1H), 5.33 (s, 2H), 1.98 (s, 3H) ppm. $^{19}$F NMR (400 MHz, dmso-$d_6$) δ–109.32 (1 F), –113.64 (1 F), –117.22 (1 F) ppm. ES-HRMS m/z 424.0575 (M+H calcd for $C_{20}H_{14}ClF_3NO_4$ requires 424.0558).

Example 508

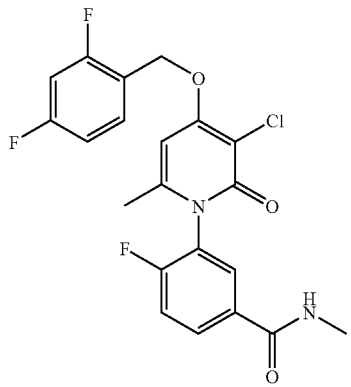

Preparation of 3-[3-chloro-4-[(2,4-difluorobenzyl)oxy]-6-methyl-2-oxopyridin-1(2H)-yl]-4-fluoro-N-methylbenzamide To a reaction vessel (borosilicate culture tube) was added 3-[3-chloro-4-[(2,4-difluorobenzyl)oxy]-6-methyl-2-oxopyridin-1(2H)-yl]-4-fluorobenzoic acid (0.300 g, 0.708 mmol) and 1-hydroxybenzotriazole (0.048 g, 0.45 mmol). N,N-Dimethylformamide (3 mL) was added to the reaction vessel followed by approximately 1.2 g of the polymer bound carbodiimide resin (1.38 mmol/g). Additional N,N-dimethylformamide (2 mL) was then added to the reaction vessel. The parallel reaction apparatus was then orbitally shaken (Labline Benchtop Orbital Shaker) at approximately 200 RPM at room temperature for 15 minutes. N-Methyl amine (1 mL, 2 mmol) was then added to the reaction vessel and the reaction apparatus was orbitally shaken at room temperature overnight. At this time the reaction was diluted with tetrahydrofuran (20 mL) and treated with approximately 2.17 g of polyamine resin (2.63 mmol/g) and approximately 2.8 g of methylisocyanate functionalized polystyrene (1.5 mmol/9) and the orbital shaking was continued at 200 RPM at room temperature for 3 hours. The reaction vessel was then opened and the solution phase product was separated from the insoluble quenched byproducts by filtration and collection into a vial. After partially evaporation the insoluble byproducts were rinsed with tetrahydrofuran (2×10 mL). The filtrate was evaporated by blowing $N_2$ over the vial and the resulting solid was triturated with diethyl ether to give an off-white solid. (0.168 g, 59%) $^1$H NMR (400 MHz, $CD_3OD$) δ 8.02 (dddd, J=2, 4.4, 7.2 and 8.4 Hz, 1H), 7.80 (dd, J=2 and 6.8 Hz, 1H), 7.62 (q, J=8 and 14.4 Hz, 1H), 7.34 (t, J=8.8 Hz, 1H), 7.04 (m, 2H), 6.69 (s, 1H), 5.36 (s, 2H), 3.29 (s, 3H), 1.98 (s, 3H) ppm. $^{19}$F NMR (400 MHz, $CD_3OD$) δ−108.94 (1 F), −113.55 (1 F), −117.76 (1 F) ppm. ES-HRMS m/z 437.0861 (M+H calcd for $C_{21}H_{17}ClF_3N_2O_3$ requires 437.0874).

Examples 509–518

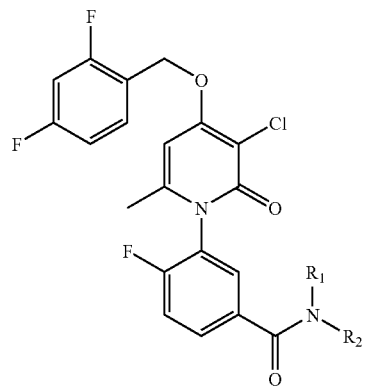

By following the method of Example 508 and replacing N-methylamine with the appropriate amine, the compounds of Examples 509–518 are prepared.

| Example No. | $R_1$ | $R_2$ | % Yield | MF | M + H Requires | ESHRMS m/z |
| --- | --- | --- | --- | --- | --- | --- |
| Ex. 509 | $CH_3$ | $CH_3$ | 59 | $C_{22}H_{19}ClF_3N_2O_3$ | 451.1031 | 451.1016 |
| Ex. 510 | H | $CH_2CH_2OH$ | 70 | $C_{22}H_{19}ClF_3N_2O_4$ | 467.0980 | 467.0985 |
| Ex. 511 | $CH_2CH_2N(CH_3)$— | $CH_2CH_2N(CH_3)$— | 70 | $C_{25}H_{24}ClF_3N_3O_3$ | 506.1453 | 506.1447 |
| Ex. 512 | $CH_2CH_2O$— | $CH_2CH_2O$— | 19 | $C_{24}H_{21}ClF_3N_2O_4$ | 493.1101 | 493.1136 |
| Ex. 513 | H | $CH_2CH_2OCH_3$ | 59 | $C_{23}H_{21}ClF_3N_2O_4$ | 481.1136 | 481.1136 |
| Ex. 514 | $CH_3$ | $CH_2CH_2OH$ | 63 | $C_{23}H_{21}ClF_3N_2O_4$ | 481.1136 | 481.1131 |
| Ex. 515 | H | $CH_2CH_2CH_2OH$ | 51 | $C_{23}H_{21}ClF_3N_2O_4$ | 481.1136 | 481.1121 |
| Ex. 516 | H | $CH_2CH(OH)CH_2OH$ | 64 | $C_{23}H_{21}ClF_3N_2O_5$ | 497.1086 | 497.1102 |
| Ex. 517 | H | $C(CH_3)_2CH_2OH$— | 54 | $C_{24}H_{23}ClF_3N_2O_4$ | 495.1293 | 495.1303 |
| Ex. 518 | $CH_2CH_2NH$— | $CH_2CH_2NH$— | 34 | $C_{23}H_{22}ClF_3N_3O_3$ | 491.89 | |

Example 519

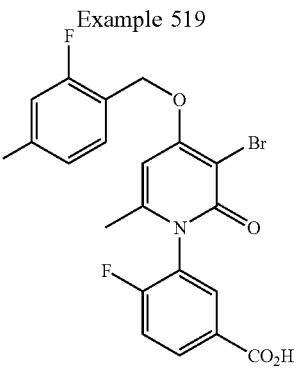

5 Preparation of 3-[3-bromo-4-[(2,4-difluorobenzyl)oxy]-6-methyl-2-oxopyridin-1(2H)-yl]-4-fluorobenzoic acid Step 1 Preparation of methyl 3-[3-bromo-4-[(2,4-difluorobenzyl)oxy]-6-methyl-2-oxopyridin-1(2H)-yl]-4-fluorobenzoate

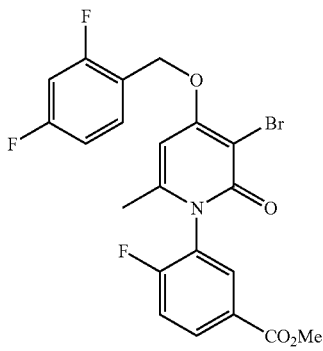

A 100 mL round bottomed flask equipped with stirbar and nitrogen inlet was charged with methyl 3-[4-[(2,4-difluorobenzyl)oxy]-6-methyl-2-oxopyridin-1(2H)-yl]-4-fluorobenzoate (7.3 g, 18 mmol) and N-methyl-2-pyrrolidine (20 mL). N-Bromo succinimide (3.5 g, 19.8 mmol) was added and the reaction mixture was stirred at room temperature for 30 minutes. The mixture poured into saturated aqueous NaHCO$_3$ and extracted with ethyl acetate. The organic layer was washed with brine, dried with Na$_2$SO$_4$, and concentrated in vacuo. The residue was triturated with diethyl ether and filtered to give the title compound as a white powder (3.49 g). $^1$H NMR (400 MHz, CD$_3$OD) δ 8.16 (qd, J=3, 6.8 and 15.6 Hz, 1H), 7.84 (d, J=2.12 Hz, 1H), 7.64 (q, J=8.4 and 14.8 Hz, 1H), 7.29 (d, J=8.4 Hz, 1H), 7.04 (m, 2H), 6.60 (s, 1H), 5.34 (s, 2H), 3.87 (s, 3H), 2.00 (s, 3H) ppm. $^{19}$F NMR (400 MHz, CD$_3$OD) δ−111.51 (1 F), −115.98 (1 F), −117.43 (1 F) ppm. ES-HRMS m/z 494.0387(M+H calcd for C$_{22}$H$_{19}$BrF$_2$NO$_5$ requires 494.0409).

Step 2 Preparation of 3-[3-bromo-4-[(2,4-difluorobenzyl)oxy]-6-methyl-2-oxopyridin-1(2H)-yl]-4-fluorobenzoic acid

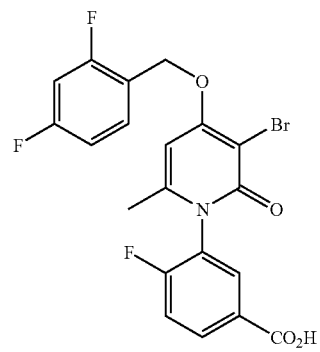

A 100 mL round bottomed flask was charged with the product of Step 2 (3.4 g, 7.05 mmol), tetrahydrofuran (40 mL), methanol (10 mL), and water (10 mL). To this slurry was added 2.5 N NaOH (5.6 mL, 14.1 mmol). The reaction mixture became clear after 5 minutes and the reaction was complete in 1 h by LC-MS. The organics were removed on the rotary evaporator and the remaining solution was acidified to pH 1–2 with 6N HCl. The desired compound was precipitated by the addition of water and diethyl ether and subsequent filtration. The title compound was isolated as a white powder (2.64 g, 80%). $^1$H NMR (400 MHz, CD$_3$OD) δ 8.21 (dddd, J=2.4, 5.2, 7.2 and 9.2 Hz, 1H), 8.00 (dd, J=2.0 and 7.2 Hz, 1H), 7.65 (q, J=8.4 and 14.8 Hz, 1H), 7.45 (t, J=8.4 Hz, 1H), 7.04 (appt, J=9.6 Hz, 1H), 6.65 (s, 1H), 5.36 (s, 2H), 2.07 (s, 3H) ppm. $^{19}$F NMR (400 MHz, CD$_3$OD) δ−111.40 (1 F), −116.00 (1 F), −118.36 (1 F) ppm. ES-HRMS m/z 480.0259 (M+H calcd for C$_{21}$H$_{17}$BrF$_2$NO$_5$ requires 480.0253).

Example 520

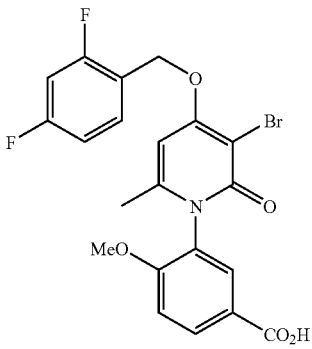

Preparation of 3-[3-bromo-4-[(2,4-difluorobenzyl)oxy]-6-methyl-2-oxopyridin-1(2H)-yl]-4-methoxybenzoic acid Step 1 Preparation of methyl 3-amino-4-methoxybenzoate

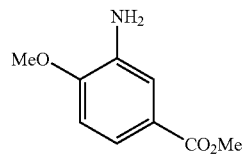

A 1 L 3-necked round bottomed flask equipped with a nitrogen inlet, stirbar, addition funnel and thermocouple was charged with 3-amino-4-methoxy benzoic acid (50 g, 0.299 mol) and methanol (300 mL). The system was cooled to 0 C and acetyl choride (30 mL, 0.42 mol) was added dropwise. The system was warmed to room temperature, the addition funnel was replaced with a reflux condenser, and was heated to reflux for 1.5 h. The reaction mixture was cooled to room temperature, quenched with saturated aqueous NaHCO$_3$, and extracted with ethyl acetate. The organic extract was washed with brine, dried with Na$_2$SO$_4$ and concentrated in vacuo to give methyl 3-amino-4-methoxybenzoate as a dark solid (47.9 g, 88%). $^1$H NMR (400 MHz, CD$_3$OD) δ 7.40 (t, J=268 Hz, 1H), 7.37 (t, J=2.0 Hz, 1H), 6.86 (d, J=8.8 Hz, 1H), 3.98 (s, 3H), 3.81 (s, 3H) ppm. ES-HRMS m/z 182.0826 (M+H calcd for C$_9$H$_{12}$ClNO$_3$ requires 182.0812).

Step 2 Preparation of methyl 3-(4-hydroxy-6-methyl-2-oxopyridin-1(2H)-yl)-4-methoxybenzoate

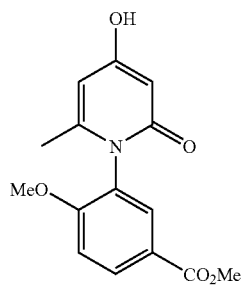

A 250 mL round bottomed flask equipped with stirbar, Dean-Stark trap and reflux condenser was charged with the product of Step 1 (23.5 g, 0.129 mol), 4-hydroxy-6-methyl-2-pyrone (17.8 g, 0.14 mol), and o-dichlorobenzene (200 mL). The system was immersed in a 170 C oil bath for 2 h and was then cooled to room temperature. The reaction mixture was washed with aqueous $Na_2CO_3$ (28 g, 0.26 mol, 500 mL water). The aqueous layer was washed with ethyl acetate and then was acidified to pH 1–2 with concentrated HCl. This was extracted with ethyl acetate, which was then dried with $Na_2SO_4$ and concentrated in vacuo. The viscous orange oil was triturated with MeOH to give the title compound as a yellow solid (1.61 g, 4%). $^1$H NMR (400 MHz, $CD_3OD$) δ 8.14 (dd, J=2.2 and 8.8 Hz, 1H), 7.79 (d, J=2.2 Hz, 1H), 7.27 (d, J=8.8 Hz, 1H), 6.05 (d, J=2.3 Hz, 1H), 5.77 (d, J=2.3 Hz, 1H), 3.88 (s, 3H), 3.87 (s, 3H), 1.90 (s, 3H) ppm. ES-HRMS m/z 290.0997 (M+H calcd for $C_{15}H_{16}NO_5$ requires 290.1023).

Step 3 Preparation of methyl 3-[4-[(2,4-difluorobenzyl)oxy]-6-methyl-2-oxopyridin-1(2H)-yl]-4-methoxybenzoate

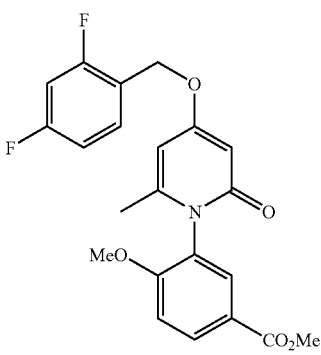

A 100 mL round bottomed flask equipped with stirbar and nitrogen inlet was charged with the product of Step 2 (1.6 g, 5.5 mmol) and N,N-dimethyl formamide (10 mL). 1,8-diazabicyclo[5.4.0]undec-7-ene (0.91 mL, 6 mmol) was added followed by 2,4-difluorobenzyl bromide (0.77 mL, 6 mmol). The reaction mixture was stirred at 60 C for 4 h, was poured into saturated aqueous $NaHCO_3$ and was extracted with ethyl acetate. The organic layer was washed with brine, dried with $Na_2SO_4$ and concentrated in vacuo to give the title compound as an orange foam (2.13 g, 93%), which was carried on to the next reaction without further purification. $^1$H NMR (400 MHz, $CD_3OD$) δ 8.17 (dd, J=2.64 and 11.6 Hz, 1H), 7.82 (td, J=2.7 and 6.8 Hz, 1H), 7.57 (m, 1H), 7.29 (d, J=11.6 Hz, 1H), 7.02 (m, 2H), 6.16 (m, 1H), 6.03 (d, J=3.5 Hz, 1H), 5.14 (s, 2H), 3.89 (s, 6H), 1.93 (s, 3H) ppm. $^{19}$F NMR (400 MHz, $CD_3OD$) δ −111.43 (1 F), −116.04 (1 F) ppm. ES-HRMS m/z 416.1310 (M+H calcd for $C_{22}H_{20}F_2NO_5$ requires 416.1304).

Step 4 Preparation of methyl 3-[3-bromo-4-[(2,4-difluorobenzyl)oxy]-6-methyl-2-oxopyridin-1(2H)-yl]-4-methoxybenzoate

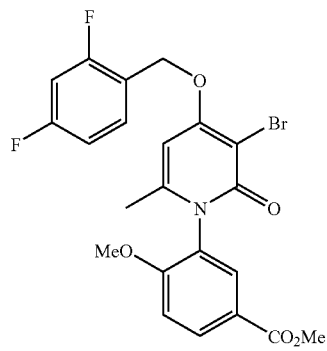

A 100 mL round bottomed flask equipped with stirbar and nitrogen inlet was charged with the product of Step 3 (2.1 g, 5.06 mmol) and N-methyl-2-pyrrolidine (10 mL). N-Bromo succinimide (1 g, 5.56 mmol) was added and the reaction mixture was stirred at room temperature for 1 h. The mixture poured into saturated aqueous $NaHCO_3$ and extracted with ethyl acetate. The organic layer was washed with brine, dried with $Na_2SO_4$, and concentrated in vacuo. The residue was chromatographed on silica (1:1 hexanes:ethyl acetate) to give the title compound as an orange oil (0.77 g, 31%). $^1$H NMR (400 MHz, $CD_3OD$) δ 8.16 (app qd, J=2.5 and 7.2 Hz, 1H), 7.84 (d, J=2.6 Hz, 1H), 7.64 (m, 1H), 7.30 (d, J=9.2 Hz, 1H), 7.04 (appt, J=8.4 Hz, 2H), 6.60 (s, 1H), 5.33 (s, 2H), 3.80 (s, 6H), 1.99 (s, 3H) ppm. $^{19}$F NMR (400 MHz, $CD_3OD$) δ−111.56 (1 F), −116.00 (1 F) ppm. ES-HRMS m/z 494.0398 (M+H calcd for $C_{22}H_{19}BrF_2NO_5$ requires 494.0409).

Step 5 Preparation of 3-[3-bromo-4-[(2,4-difluorobenzyl)oxy]-6-methyl-2-oxopyridin-1(2H)-yl]-4-methoxybenzoic acid

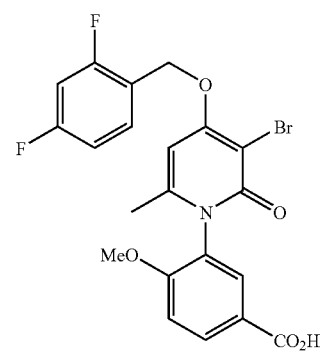

A 100 mL round bottomed flask was charged with the product of Step 4 (0.77 g, 1.55 mmol), tetrahydrofuran (10 mL), methanol (5 mL), and water (5 mL). To this slurry was added 2.5 N NaOH (1.2 mL, 3.1 mmol). The reaction mixture became clear after 30 minutes and the reaction was complete in 1 h by LC-MS. The organics were removed on the rotary evaporator and the remaining solution was acidified to pH 2–3 with 6N HCl. The desired compound was precipitated by the addition of water and diethyl ether and subsequent filtration. The title compound was isolated as a white powder (0.60 g, 81%). $^1$H NMR (400 MHz, $CD_3OD$) δ 8.17 (dd, J=2.2 and 8.8 Hz, 1H), 7.82 (d, J=2.2 Hz, 1H), 7.64 (q, 1H), 7.29 (d, J=8.8 Hz, 1H), 7.34 (t, J=8.8 Hz, 2H), 6.60 (s, 1H), 5.34 (s, 2H), 3.87 (s, 3H), 2.01 (s, 3H) ppm. ES-HRMS m/z 480.0259 (M+H calcd for $C_{21}H_{17}BrF_2NO_5$ requires 480.0253).

Example 521

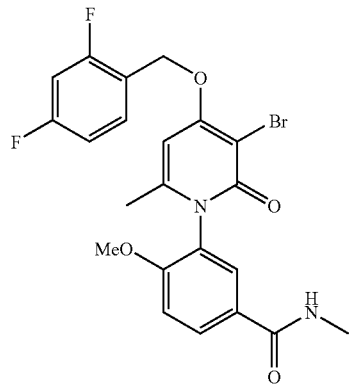

Preparation of 3-[3-bromo-4-[(2,4-difluorobenzyl)oxy]-6-methyl-2-oxopyridin-1(2H)-yl]-4-methoxy-N-methylbenzamide Step 1

To a reaction vessel (borosilicate culture tube) was added Example 520 (0.300 g, 0.624 mmol) and 1-hydroxybenzotriazole (0.042 g, 0.31 mmol). N,N-Dimethylformamide (3 mL) was added to the reaction vessel followed by approximately 1.06 g of the polymer bound carbodiimide resin (1.38 mmol/g). Additional N,N-dimethylformamide (2 mL) was then added to the reaction vessel. The parallel reaction apparatus was then orbitally shaken (Labline Benchtop Orbital Shaker) at approximately 200 RPM at room temperature for 15 minutes. N-Methyl amine (2 mL, 4 mmol) was then added to the reaction vessel and the reaction apparatus was orbitally shaken at room temperature overnight. At this time the reaction was diluted with tetrahydrofuran (20 mL) and treated with approximately 2 g of polyamine resin (2.63 mmol/g) and approximately 2.5 g of methylisocyanate functionalized polystyrene (1.5 mmol/g) and the orbital shaking was continued at 200 RPM at room temperature for 3 hours. The reaction vessel was then opened and the solution phase product was separated from the insoluble quenched byproducts by filtration and collection into a vial. After partially evaporation the insoluble byproducts were rinsed with tetrahydrofuran (2×10 mL). The filtrate was evaporated by blowing $N_2$ over the vial and the resulting solid was triturated with diethyl ether to give the desired product as an off-white solid (0.094 g, 31%). $^1$H NMR (400 MHz, $CD_3OD$) δ 7.98 (dd, J=2.2 and 8.8 Hz, 1H), 7.64 (m, 2H), 7.28 (d, J=9.2 Hz, 1H), 7.04 (t, J=9.2 Hz, 2H), 6.60 (s, 1H), 5.34 (s, 2H), 3.86 (s, 3H), 2.88 (s, 3H), 2.01 (s, 3H) ppm. $^{19}$F NMR (400 MHz, $CD_3OD$) δ–111.59 (1 F), –116.01 (1 F) ppm. ES-HRMS m/z 493.0593 (M+H calcd for $C_{22}H_{20}BrF_2N_2O_4$ requires 493.0569).

Example 522

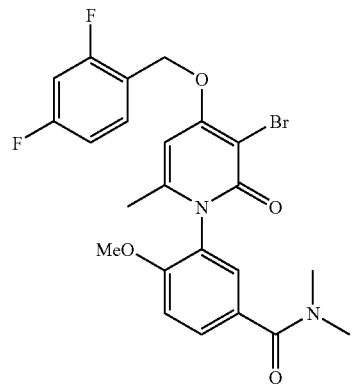

Preparation of 3-[3-bromo-4-[(2,4-difluorobenzyl)oxy]-6-methyl-2-oxopyridin-1(2H)-yl]-4-methoxy-N,N-dimethylbenzamide The title compound was prepared essentially as in Example 521. $^1$H NMR (400 MHz, $CD_3OD$) δ 7.64 (m, 1H), 7.61 (dd, J=2 and 8.8 Hz, 1H), 7.33 (d, J=2.2 Hz, 1H), 7.27 (d, J=8 Hz, 1H), 7.04 (t, J=8 Hz, 2H), 6.59 (s, 1H), 5.33 (s, 2H), 3.85 (s, 3H), 3.07 (s, 6H), 2.02 (s, 3H) ppm. $^{19}$F NMR (400 MHz, $CD_3OD$) δ–111.60 (1 F), –116.01 (1 F) ppm. ES-HRMS m/z 507.0716 (M+H calcd for $C_{23}H_{22}BrF_2N_2O_4$ requires 507.0726).

Example 523

1-[5-(aminomethyl)-2-fluorophenyl]-3-chloro-4-[(2,4-difluorobenzyl)oxy]-6-methylpyridin-2(1H)-one hydrochloride

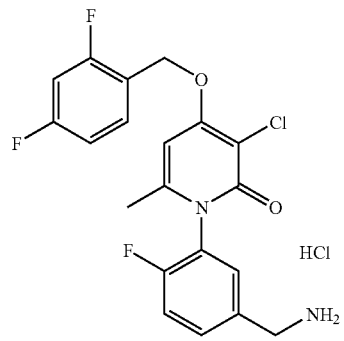

Preparation of 3-[3-chloro-4-[(2,4-difluorobenzyl)oxy]-6-methyl-2-oxopyridin-1(2H)-yl]-4-fluorobenzamide

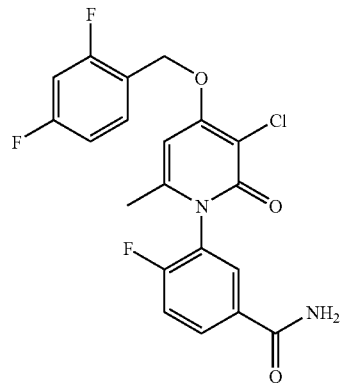

A 250 mL round bottomed flask equipped with stirbar and nitrogen inlet was charged with 3-[3-chloro-4-[(2,4-difluorobenzyl)oxy]-6-methyl-2-oxopyridin-1(2H)-yl]-4-fluorobenzoic acid (2.58 g, 6.1 mmol), 4-methylmorpholine (2.0 mL, 18.3 mmol), 2-chloro-4,6-dimethoxy-1,3,5-triazine (1.28 g, 7.3 mmol) and tetrahydrofuran (30 mL). After stirring the mixture for 30 min at 25° C., NH$_4$OH (15.0 mL) was added. The mixture was stirred for 30 min and diluted with water. The product precipitated from solution. The precipitated was filtered and washed with water and diethyl ether to give the title compound (2.55 g, 8%) as a white solid. $^1$H NMR (400 MHz, (CD$_3$)$_2$SO) δ 8.10 (m, 1H), 7.9 (dd, J=2.1 and 5.2 Hz, 1H), 7.65 (q, 6.7 and 8.5 Hz, 1H), 7.56 (t, J=9.1 Hz, 1H), 7.35 (td, J=2.4 and 8.2 Hz, 1H), 7.17 (td, J=2 and 6.6 Hz, 1H), 6.78 (s, 1H), 5.36 (s, 2H), 2 (s, 3H) ppm. ES-HRMS m/z 423. 0719 (M+H calcd for C$_{20}$H$_{15}$ClF$_3$N$_2$O$_3$ requires 423.0718).

Step 2

Preparation of 1-[5-(aminomethyl)-2-fluorophenyl]-3-chloro-4-[(2,4 difluorobenzyl)oxy]-6-methylpyridin-2(1H)-one hydrochloride

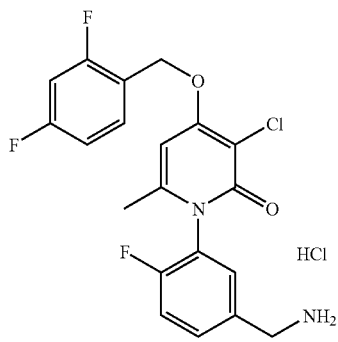

A 100 mL round bottomed flask equipped with stirbar and nitrogen inlet was charged with the product from step 1 (1.5 g, 3.5 mmol), BH$_3$·THF complex (7.4 mL, 7.4 mmol), and tetrahydrofuran (15 mL). The mixture was refluxed for 6 h, allowed to cool to room temperature and quenched with HCl 6N. The organics were evaporated and the remaining aqueous solution was saturated with NaOH 2.5N and extracted with dichloromethane. The organic phase was dried with Na$_2$SO$_4$ and concentrated in vacuo. HCl 6N was added, and concentrated in vacuo. $^1$H NMR (400 MHz, (CD$_3$)$_2$SO) δ 8.2 (m, 1H), 7.6 (m, 1H), 7.5 (m, 1H), 7.3 (t, J=9.8 Hz, 1H), 7.16 (t, J=8.6 Hz, 1H), 6.78 (s, 1H), 5.36 (s, 2H), 4.05 (d, J=5.8 Hz, 2H), 2 (s, 3H) ppm. ES-HRMS m/z 409.0940 (M+H calcd for C$_{20}$H$_{17}$ClF$_3$N$_2$O$_2$ requires 409.0925).

Example 524

3-[3-chloro-4-[(2,4-difluorobenzyl)oxy]-6-methyl-2-oxopyridin-1(2H)-yl]-4-fluoro-N-[2-hydroxy-1-(hydroxymethyl)ethyl]benzamide

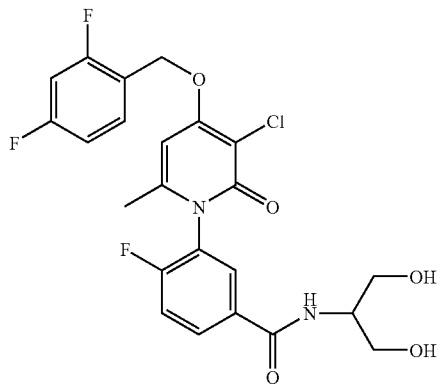

Preparation of 3-[3-chloro-4-[(2,4-difluorobenzyl)oxy]-6-methyl-2-oxopyridin-1(2H)-yl]-4-fluoro-N-[2-hydroxy-1-(hydroxymethyl)ethyl]benzamide The title compound was prepared essentially as in Example 521. $^1$H NMR (400 MHz, CD$_3$OD) δ 8.1 (m, 1H), 7.8 (dd, J=2.3 and 5.1 Hz, 1H), 7.6 (q, J=7.4 and 7.0 Hz, 1H), 7.41 (t, J=8.9 Hz, 1H), 7.04 (m, 2H), 6.7 (s, 1H), 5.36 (s, 2H), 4.1 (t, J=5.8 Hz, 1H), 3.7 (d, J=5.1 Hz, 4H), 2.1 (s, 3H) ppm. ES-HRMS m/z 497.1045 (M+H calcd for C$_{23}$H$_{21}$ClF$_3$N$_2$O$_5$ requires 497.1086).

Examples 525–528

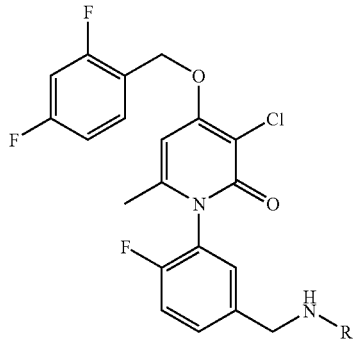

The compounds of Examples 525–528 are prepared by derivitazion of Example 523. The analytical data are shown below.

| Ex. No. | R | MF | M + H Requires | ESHRMS m/z |
|---|---|---|---|---|
| Ex. 525 | —C(O)CH₃ | C₂₂H₁₈ClF₃N₂O₃ | 451.1031 | 451.1010 |
| Ex. 526 | —C(O)CH₂OCH₃ | C₂₃H₂₀ClF₃N₂O₄ | 481.1136 | 481.1132 |
| Ex. 527 | —SO₂CH₃ | C₂₁H₁₈ClF₃N₂O₄S | 487.0701 | 487.0679 |
| Ex. 528 | —C(O)NH₂ | C₂₁H₁₆ClF₃N₃O₃ | 452.0983 | 452.0987 |

NMR characterization of compounds of Examples 525–528

| Ex. No. | NMR Data |
|---|---|
| 525 | ¹H NMR (400 MHz, CD₃OD) δ 7.6(q, J=7.8 and 7.0Hz, 1H), 7.5(m, 1H), 7.3(t, J=9.0Hz, 1H), 7.2(dd, J=1.9 and 5.1Hz, 1H), 7.05(m, 2H), 6.65(s, 1H), 5.36(s, 2H), 4.39(s, 2H), 2.1(s, 3H), 1.98(s, 3H) ppm |
| 526 | ¹H NMR (400 MHz, CD₃Cl₃) δ 7.45(q, J=8.6 and 6.2Hz, 1H), 7.3 (m, 1H), 7.1(m, 2H), 6.85(q, J=6.5 and 1.9Hz, 1H), 6.78(td, J=2.7 and 7.8Hz, 1H), 6.2(s, 1H), 5.2(s, 2H), 4.39(d, J=6.2Hz, 2H), 4.0(s, 3H) 2.3(s, 2H), 2.0(s, 3H), 1.98(s, 3H) ppm |
| 527 | ¹H NMR (400 MHz, CD₃OD) δ 7.49(q, J=8.2 and 6.3Hz, 1H), 7.33 (m, 1H), 7.23(m, 1H), 7.1(t, J=8.9, 1H), 6.9(td, J=0.78 and 6.6 1H), 6.8(td, J=2.7 and 6.25Hz, 1H), 6.2(s, 1H), 5.2(s, 2H), 4.2(s, 2H), 2.8(s, 3H) 2.0(s, 3H) ppm |
| 528 | ¹H NMR (400 MHz, (CD₃)₂SO) δ 7.61(q, J=8.9 and 6.6Hz, 1H), 7.38(d, J=7.8Hz, 1H), 7.3(d, J=10.2Hz, 1H) 7.21(d, J=7.4Hz, 1H), 7.1(t, J=8.6Hz, 1H), 6.71(s, 1H), 6.5(t, J=5.8Hz, 1H), 5.56(s, 2H), 5.3(s, 2H), 4.18(d, J=6.25Hz, 2H), 3.61(s, 1H), 1.98(s, 3H) ppm |

Example 529

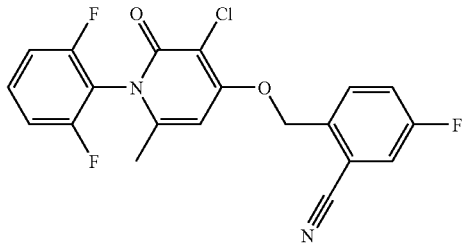

2-({[3-chloro-1-(2,6-difluorophenyl)-6-methyl-2-oxo-1,2-dihydropyridin-4-yl]oxy}methyl)-5-fluorobenzonitrile 2-(bromomethyl)-5-fluorobenzonitrile (3.47 g, 16.2 mmol), 3-chloro-1-(2,6-difluorophenyl)-4-hydroxy-6-methylpyridin-2 (1H)-one (3.15 g, 11.6 mmol), K₂CO₃ (2.56 g, 18.6 mmol), and 18-crown-6 (0.15 g) were dissolved in N,N-dimethylacetamide (25 mL). Reaction mixture stirred on 60° C. oil bath for 4 hours. Solvent removed by distillation. Reaction neutralized with 5% citric acid. The solid product was washed with hexane followed by 30% EtOAc/hexane. Filtered a brown solid (5.2 g, 79% yield).

¹H NMR (CD₃OD/400 MHz) δ 7.82 (m, 2H), 7.61 (m, 4H), 6.75 (s, 1H), 5.49 (s, 2H), 2.13 (s, 3H). ES HRMS m/z 405.0616 (M+H C₂₀H₁₃ClF₃N₂O₂ requires 405.0612).

Example 530

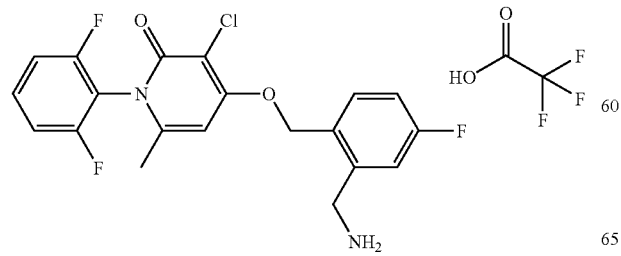

4-{[2-(aminomethyl)-4-fluorobenzyl]oxy}-3-chloro-1-(2,6-difluorophenyl)-6-methylpyridin-2(1H)-one trifluoroacetate BH₃THF (17.8 mL, 17.8 mmol) was added dropwise to a chilled (0° C.) solution of 2-({[3-chloro-1-(2,6-difluorophenyl)-6-methyl-2-oxo-1,2-dihydropyridin-4-yl]oxy}methyl)-5-fluorobenzonitrile (3.61 g, 8.92 mmol) in THF (30 mL). Following the addition, the reaction was heated at 60° C. for 1.5 hours. The reaction was quenched with MeOH, the solvent evaporated, and the crude product purified by prep HPLC. The product was isolated by freeze-drying and evaporation of the solvent to give a white solid (1.52 g, 32.6%). ¹H NMR (CD₃OD/400 MHz) δ 7.62 (m, 2H), 7.32 (m, 1H), 7.25 (tr, 2H, J=8.00 Hz), 7.18 (m, 1H), 6.78 (s, 1H), 5.43 (s, 1H), 4.22 (s, 1H), 2.14 (s, 3H). ES HRMS m/z 409.0900 (M+H C₂₀H₁₇N₂O₂F₃Cl requires 409.0925).

Examples 531–551

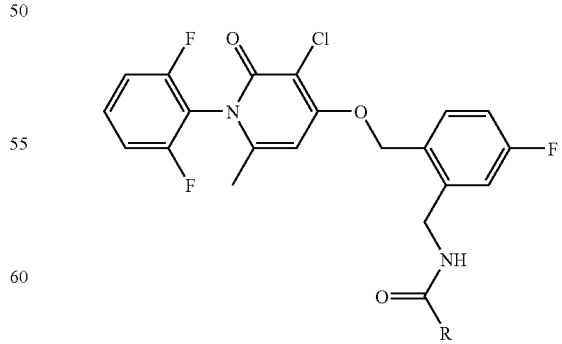

The compounds of Examples 531–551 are prepared by derivitazion of Example 530. The analytical data are shown below.

| Compound No. | R | MF | M + H Requires | ESHRMS m/z |
|---|---|---|---|---|
| Ex. 531 | —OCH$_3$ | C$_{22}$H$_{18}$ClF$_3$N$_2$O$_4$ | 467.0980 | 467.0985 |
| Ex. 532 | —CF$_3$ | C$_{22}$H$_{15}$ClF$_6$N$_2$O$_3$ | 505.0748 | 505.0754 |
| Ex. 533 | —O-isopropyl | C$_{24}$H$_{22}$ClF$_3$N$_2$O$_4$ | 495.1293 | 495.1304 |
| Ex. 534 | —NH—CH$_2$CH$_3$ | C$_{23}$H$_{21}$ClF$_3$N$_3$O$_3$ | 480.1296 | 480.1277 |
| Ex. 535 | —O-tetrahydrofuran-3-yl | C$_{25}$H$_{22}$ClF$_3$N$_2$O$_5$ | 523.1242 | 523.1282 |
| Ex. 536 | —O-propyl | C$_{24}$H$_{22}$ClF$_3$N$_2$O$_4$ | 495.1293 | 495.1338 |
| Ex. 537 | —O—CH$_2$CH=CH$_2$ | C$_{24}$H$_{20}$ClF$_3$N$_2$O$_4$ | 493.1136 | 493.1116 |
| Ex. 538 | —O—CH$_2$C≡CH | C$_{24}$H$_{18}$ClF$_3$N$_2$O$_4$ | 491.0980 | 491.0961 |
| Ex. 539 | —O-tButyl | C$_{25}$H$_{24}$ClF$_3$N$_2$O$_4$ | 509.1449 | 509.1436 |
| Ex. 540 | —NH-tButyl | C$_{25}$H$_{25}$ClF$_3$N$_3$O$_3$ | 508.1609 | 508.1574 |
| EX. 541 | —SO$_2$CH$_2$CH$_2$CH$_3$ | C$_{23}$H$_{22}$ClF$_3$N$_2$O$_4$S | 515.1014 | 515.0979 |
| Ex. 542 | —SO$_2$CH$_2$CH$_3$ | | | |
| Ex. 543 | —NH-isopropyl | C$_{24}$H$_{23}$ClF$_3$N$_3$O$_3$ | 494.1453 | 494.1456 |
| Ex. 544 | —CH$_2$OCH$_3$ | C$_{23}$H$_{20}$ClF$_3$N$_2$O$_4$ | 481.1136 | 481.1174 |
| Ex. 545 | —NHCH$_3$ | C$_{22}$H$_{20}$ClF$_3$N$_3$O$_3$ | 466.1140 | 466.1141 |
| Ex. 546 | —N(CH$_3$)(tButyl) | C$_{26}$H$_{27}$ClF$_3$N$_3$O$_3$ | 522.1766 | 522.1737 |
| Ex. 547 | —NH(cyclopropyl) | C$_{24}$H$_{21}$ClF$_3$N$_3$O$_3$ | 492.1296 | 492.1285 |
| Ex. 548 | —NHCH$_2$CF$_3$ | C$_{23}$H$_{17}$ClF$_6$N$_3$O$_3$ | 534.1014 | 534.1005 |
| Ex. 549 | NHCH$_2$(cyclopropyl) | C$_{25}$H$_{23}$ClF$_3$N$_3$O$_3$ | 506.1453 | 506.1432 |
| Ex. 550 | —NHCH$_2$(tButyl) | C$_{26}$H$_{27}$ClF$_3$N$_3$O$_3$ | 522.1766 | 522.1740 |
| Ex. 551 | —N(CH$_3$)$_2$ | C$_{23}$H$_{22}$ClF$_3$N$_3$O$_3$ | 480.1296 | 480.1307 |

NMR characterization of compounds of Examples 531–551

| Ex. No. | NMR data |
|---|---|
| 531 | $^1$H NMR (CD$_3$OD/400 MHz) δ 7.61(m, 1H), 7.53(m, 1H), 7.24(t, 2H, J=8.00Hz), 7.14(m, 1H), 7.05(m, 1H), 6.74(s, 1H), 5.40(s, 2H), 4.42(s, 2H), 3.63(s, 3H), 2.12(s, 3H) |
| 532 | $^1$H NMR (CD$_3$OD/400 MHz) δ 7.59(m, 2H), 7.24(t, 2H, J=8.00Hz), 7.11(m, 2H), 6.73(s, 1H), 5.43(s, 2H), 4.62(s, 2H), 2.12(s, 3H) |
| 533 | $^1$H NMR (CD$_3$OD/400 MHz) δ 7.61(m, 1H), 7.53(m, 1H), 7.24(t, 2H, J=7.60Hz), 7.13(m, 1H), 7.05(m, 1H), 6.74(s, 1H), 5.40(s, 2H), 4.81(m, 1H), 4.41(s, 2H), 2.12(s, 3H), 1.21(d, 6H, J=6.00Hz) |
| 534 | $^1$H NMR (CD$_3$OD/400 MHz) δ 7.61(m, 1H), 7.52(m, 1H), 7.24(t, 2H, J=0.80Hz), 7.13(m, 1H), 7.03(m, 1H), 6.73(s, 1H), 5.39(s, 2H), 4.44(s, 2H), 3.12(q, 2H, J=7.20Hz), 2.12(s, 3H), 1.08(t, 3H, J=7.20Hz) |
| 535 | $^1$H NMR (CD$_3$OD/300 MHz) δ 7.62(m, 1H), 7.54(m, 1H), 7.25(t, 2H, J=8.4Hz), 7.15(m, 1H), 7.07(m, 1H), 6.75(s, 1H), 5.41(s, 2H), 5.15(s br, 1H), 4.44(s, 2H), 3.82(m, 4H), 2.13(s, 4H), 2.03(s br, 1H) |
| 536 | $^1$H NMR (CD$_3$OD/300 MHz) δ 7.62(m, 1H), 7.54(m, 1H), 7.25(t, 2H, J=8.1Hz), 7.15(m, 1H), 7.06(m, 1H), 6.74(s, 1H), 5.41(s, 2H), 4.43(s, 2H), 3.98(t, 2H, J=6.6Hz), 2.13(s, 3H), 1.63(m, 2H), 0.94(t, 3H, J=7.2Hz) |
| 537 | $^1$H NMR (CD$_3$OD/300 MHz) δ 7.62(m, 1H), 7.54(m, 1H), 7.25(t, 2H, J=8.4Hz), 7.14(m, 1H), 7.07(m, 1H), 6.74(s, 1H), 5.92(m br, 1H), 5.41(s, 2H), 5.29(d, 1H, J=17.7Hz), 5.17(d, 1H, J=10.5Hz), 4.63(s, 1H), 4.53(d, 2H, J=5.4Hz), 4.44(s, 2H), 2.13(s, 3H) |
| 538 | $^1$H NMR (CD$_3$OD/400 MHz) δ 7.61(m, 1H), 7.53(m, 1H), 7.24(t, 2H, J=7.6Hz), 7.14(m, 1H), 7.06(m, 1H), 6.74(s, 1H), 5.41(s, 2H), 4.65(d, 2H, J=2.4Hz), 4.44(s, 2H), 2.86(t, 1H, J=2.4Hz), 2.12(s, 3H) |
| 539 | $^1$H NMR (CD$_3$OD/400 MHz) δ 7.61(m, 1H), 7.53(m, 1H), 7.24(tr, 2H, J=8.40), 7.12(m, 1H), 7.05(m, 1H), 6.74(s, 1H), 5.39(s, 2H), 4.36(s, 2H), 2.12(s, 3H), 1.43(s, 9H) |

-continued

| | |
|---|---|
| 540 | $^1$H NMR (CD$_3$OD/400 MHz) δ 7.61(m, 1H), 7.53(m, 1H), 7.24(tr, 2H, J=8.00Hz), 7.12(m, 1H), 7.04(m, 1H), 6.73(s, 1H), 5.37(s, 2H), 4.39(s, 2H), 2.12(s, 3H), 1.28(s, 9H) |
| 541 | $^1$H NMR (CD$_3$OD/300 MHz) δ 7.59(m, 2H), 7.26(m, 3H), 7.11(m, 1H), 6.75(s, 1H), 5.46(s, 2H), 4.40(s, 2H), 3.02(m, 2H), 2.12(s, 3H), 1.80(m, 2H), 1.03(tr, 3H, J=7.50 MHz) |
| 542 | $^1$H NMR (CD$_3$OD/400 MHz) δ 7.58(m, 2H), 7.26(m, 3H), 7.10(m, 1H), 6.74(s, 1H), 5.45(s, 2H), 4.39(s, 2H), 3.06(q, 2H, J=7.60Hz), 2.11(s, 3H), 1.31(t, 3H, J=7.2Hz) |
| 543 | $^1$H NMR (CD$_3$OD/400 MHz) δ 7.61(m, 1H), 7.52(m, 1H), 7.24(t, 2H, J=8.40Hz), 7.12(m, 1H), 7.04(m, 1H), 6.73(s, 1H), 5.39(s, 2H), 4.44(s, 2H), 3.77(m, 1H), 2.12(s, 3H), 1.10(d, 6H, J=6.40Hz) |
| 544 | $^1$H NMR (CD$_3$OD/400 MHz) δ 7.61(m, 1H), 7.54(m, 1H), 7.24(t, 2H, J=7.6Hz), 7.15(m, 1H), 7.06(m, 1H), 6.74(s, 1H), 5.43(s, 2H), 4.55(s, 2H), 3.92(s, 2H), 3.40(s, 3H), 2.12(s, 3H) |
| 545 | $^1$H NMR (CD$_3$OD/300 MHz) δ 7.63(m, 1H), 7.54(m, 1H), 7.26(t, 2H, J=8.7Hz), 7.15(m, 1H), 7.05(m, 1H), 6.75(s, 1H), 5.42(s, 2H), 4.47(s, 2H), 2.70(s, 3H), 2.14(s, 3H) |
| 546 | $^1$H NNMR (CD$_3$OD/300 MHz) δ 7.63(m, 1H), 7.53(m, 1H), 7.25(t, 2H, J=9.0Hz), 7.14(m, 1H), 7.04(m, 1H), 6.76(s, 1H), 5.41(s, 2H), 4.44(s, 2H), 2.90(s, 3H), 2.13(s, 3H), 1.39(s, 9H) |
| 547 | $^1$H NNMR (CD$_3$OD/400 MHz) δ 7.61(m, 1H), 7.52(m, 1H), 7.24(t, 2H, J=7.6Hz), 7.14(m, 1H), 7.03(m, 1H), 6.74(s, 1H), 5.41(s, 2H), 4.47(s, 2H), 2.46(m, 1H), 2.12(s, 3H), 0.68(q, 2H, J=5.2Hz), 0.46(m, 2H) |
| 548 | $^1$H NNMR (CD$_3$OD/400 MHz) δ 7.61(m, 1H), 7.53(m, 1H), 7.24(t, 2H, J=8.0Hz), 7.12(m, 1H), 7.04(m, 1H), 6.73(s, 1H), 5.39(s, 2H), 4.47(s, 2H), 3.79(q, 2H, J=9.6Hz), 2.12(s, 3H) |
| 549 | $^1$H NNMR (CD$_3$OD/400 MHz) δ 7.61(m, 1H), 7.52(m, 1H), 7.24(t, 2H, J=8.4Hz), 7.14(m, 1H), 7.04(m, 1H), 6.73(s, 1H), 5.39(s, 2H), 4.45(s, 2H), 2.96(d, 2H, J=6.8Hz), 2.12(s, 3H), 0.93(m, 1H), 0.44(m, 2H), 0.16(q, 2H, J=4.8Hz) |
| 550 | $^1$H NNMR (CD$_3$OD/400 MHz) δ 7.61(m, 1H), 7.53(m, 1H), 7.24(t, 2H, J=8.0Hz), 7.14(m, 1H), 7.04(m, 1H), 6.73(s, 1H), 5.39(s, 2H), 4.46(s, 2H), 2.92(d, 2H, J=4.8Hz), 2.12(s, 3H), 0.87(s, 9H) |
| 551 | $^1$H NNMR (CD$_3$OD/300 MHz) δ 7.62(m, 1H), 7.52(m, 1H), 7.25(t, 2H, J=8.7Hz), 7.15(m, 1H), 7.04(m, 1H), 6.75(s, 1H), 5.42(s, 2H), 4.48(s, 2H), 2.90(s, 6H), 2.14(s, 3H) |

$^1$H NMR (CD$_3$OD/400 MHz) δ 7.58 (m, 2H), 7.26 (m, 3H), 7.10 (m, 1H), 6.74 (s, 1H), 5.45 (s, 2H), 4.39 (s, 2H), 306 (q, 2H, J=7.60 Hz), 2.11 (s, 3H), 1.31 (t, 3H, J=7.2 Hz)$^1$H NMR (CD$_3$OD/300 MHz) δ 7.63 (m, 1H), 7.54 (m, 1H), 7.26 (t, 2H, J=8.7 Hz), 7.15 (m, 1H), 7.05 (m, 1H), 6.75 (s, 1H), 5.42 (s, 2H), 4.47 (s, 2H), 2.70 (s, 3H), 2.14 (s, 3H). ES HRMS m/z 466.1141 (M+H C$_{22}$H$_{20}$ClF$_3$N$_3$O$_3$ requires 466.1140).

Example 552

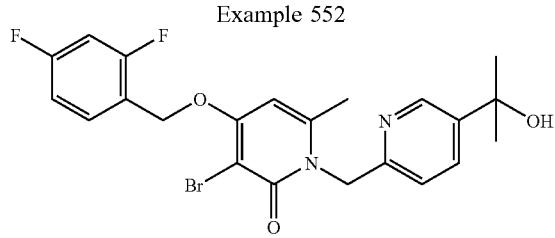

3-bromo-4-[(2,4-difluorobenzyl)oxy]-1-{[5-(1-hydroxy-1-methylethyl)pyridin-2-yl]methyl}-6-methylpyridin-2(1H)-one Step 1: Preparation of methyl 6-methylnicotinate 1-oxide.

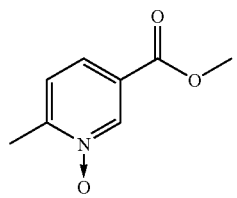

Methyl 6-methylnicotinate (6.0 g, 39.7 mmol) was added into dichloromethane (100 mL) in the round bottom flask under nitrogen. 3-chloroperoxybenzoic acid (10.0 g, 57.9 mmol) was then added into the flask and stirred for 5 hour. Saturated sodium bicarbonate solution (100 ml) was added into the reaction and the mixture was transferred to separatory funnel. Additional 200 mL of dichloromethane was added into the funnel and obtained the organic layer. The organic layer was washed with water (150 mL) and dried over anhydrous magnesium sulfate. The resulting solution was evaporated to yield white solid (6 g, 90%). LC/MS, t$_r$=0.33 minutes (5 to 95% acetonitrile/water over 5 minutes at 1 ml/min with detection 254 nm, at 50° C.). ES-MS m/z 168 (M+H). ES-HRMS m/z 168.0628 (M+H calcd for C$_8$H$_{10}$NO$_3$ requires 168.0655).

Step 2: Preparation of methyl 6-(chloromethyl)nicotinate.

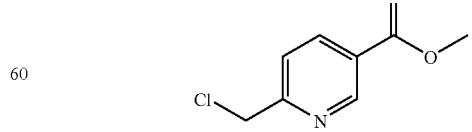

Methyl 6-methylnicotinate 1-oxide (from Step 1) (6.0 g, 35.9 mmol) was was added into the p-toluenesulfonyl chloride (10 g, 52.4 mmol) in 100 mL of 1,4-dioxane. The mixture was heated to reflux for 20 hours. Saturated sodium bicarbonate solution (200 ml) was added into the reaction and the mixture was transferred to separatory funnel. The compound was extracted using ethyl acetate (300 ml×2) and the combined ethyl acetate solution was dried over magnesium sulfate and evaporated to black solid (5.2 g, 78%). LC/MS, t$_r$=1.52 minutes (5 to 95% acetonitrile/water over 5 minutes at 1 ml/min with detection 254 nm, at 50° C.). ES-MS m/z 186 (M+H). ES-HRMS m/z 186.0314 (M+H calcd for C$_8$H$_9$ClNO$_2$ requires 186.0316).

Step 3: Preparation of methyl 6-{[4-[(2,4-difluorobenzyl)oxy]-6-methyl-2-oxopyridin-1(2H)-yl]methyl}nicotinate.

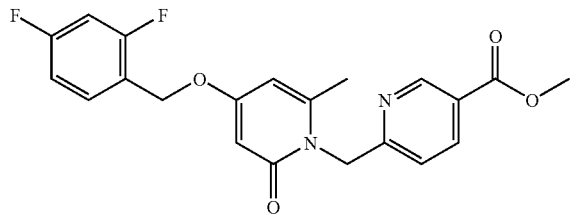

Methyl 6-(chloromethyl)nicotinate (from step 2). (2 g, 10.8 mmol) was added into 4-[(2,4-difluorobenzyl)oxy]-6-methylpyridin-2(1H)-one in 20 mL of dimethyl formamide followed by addition of cesium carbonate (5 g, 5.3 mmol). The mixture was heated to 100 C for 20 hours. It was cooled to room temperature and added 400 mL of water. Brown precipitate came out of from solution. It was filtered and rinsed with water (200 mL×3) and dried to obtain 4 g of solid. The product was purified using a Gilson Reversed Phase preparative chromatography to obtain white solid (1.4 g, 32%). $^1$H NMR (400 MHz, CDCl$_3$) δ 9.09 (d, J=1.48 Hz, 1H), 8.19 (dd, J=6.04, 2.15 Hz, 1H), 7.37 (app q, J=8.32 Hz, 1H), 7.25 (d, J=8.33 Hz, 1H), 6.84 (m, 2H), 5.94 (d, J=2.82 Hz, 1H), 5.83 (d, J=2.15 Hz, 1H), 5.36 (s, 2H), 4.97 (s, 2H), 3.90 (s, 3H), 2.27 (s, 3H); LC/MS, t$_r$=2.30 minutes (5 to 95% acetonitrile/water over 5 minutes at 1 ml/min with detection 254 nm, at 50° C.). ES-MS m/z 401 (M+H). ES-HRMS m/z 401.1307 (M+H calcd for C$_{21}$H$_{19}$ F$_2$N$_2$O$_4$ requires 401.1307).

Step 4: Preparation of the Title Compound.

3 molar solution of methyl magnesium bromide in ether (5 mL, 15 mmol) was added into 5 ml of anhydrous tetrahydrofuran in the round bottom flaks under nitrogen. The mixture was cooled to 0° C. Methyl 6-{[4-[(2,4-difluorobenzyl)oxy]-6-methyl-2-oxopyridin-1(2H)-yl]methyl}nicotinate (from Step 3) (300 mg, 0.75 mmol)was dissolved in 5 ml of anhydrous tetrahydrofuran in dropper funnel and the solution was slowly added into cold methyl magnesium bromide solution in the round bottom flask. After the addition, the mixture was continue stirring at 0 C for 30 minute and cold solution of saturated ammonium chloride (100 ml) was added slowly into the reaction mixture. The mixture was transferred to separatory funnel and the product was extracted with ethyl acetate (200 ml×2). The combined ethyl acetate solution was dried over anhydrous magnesium sulfate and evaporated to dryness. The resulting residue (220 mg) was added into 10 ml of dichloromethane followed by addition of N-bromo succinimide (100 mg, 0.56 mmol). The solution was stirred at room temperature for 3 hours. Saturated sodium bicarbonate solution (100 ml) was added into the reaction mixture and it was transferred to separatory funnel. The product was extracted with ethyl acetate (200 ml×2). The combined ethyl acetate solution was dried over anhydrous magnesium sulfate and evaporated to dryness.

$^1$H NMR (400 MHz, CDCl$_3$) δ 8.61 (d, J=1.88 Hz, 1H), 7.73 (dd, J=5.77, 2.42 Hz, 1H), 7.55 (app q, J=6.31 Hz, 1H), 7.30 (d, J=8.19 b Hz, 1H), 6.93 (m, 1H), 6.84 (m, 1H), 6.00 (s, 1H), 5.37 (s, 2H), 5.19 (s, 2H), 2.48 (s, 3H), 1.56 (s, 6H); LC/MS, t$_r$=2.29 minutes (5 to 95% acetonitrile/water over 5 minutes at 1 ml/min with detection 254 nm, at 50° C.). ES-MS m/z 479 (M+H). ES-HRMS m/z 479.0791 (M+H calcd for C$_{22}$H$_{22}$BrF$_2$N$_2$O$_3$ requires 479.0776).

Example 553

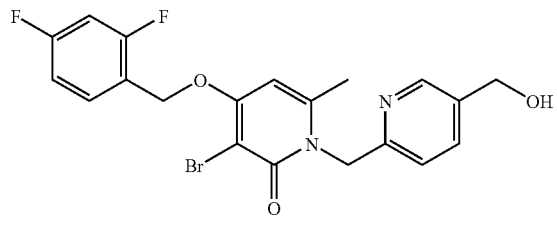

3-bromo-4-[(2,4-difluorobenzyl)oxy]-1-{[5-(hydroxymethyl)pyridin-2-yl]methyl}-6-methylpyridin-2(1H)-one Step 1: Preparation of 4-[(2,4-difluorobenzyl)oxy]-1-{[5-(hydroxymethyl)pyridin-2-yl]methyl}-6-methylpyridin-2(1H)-one

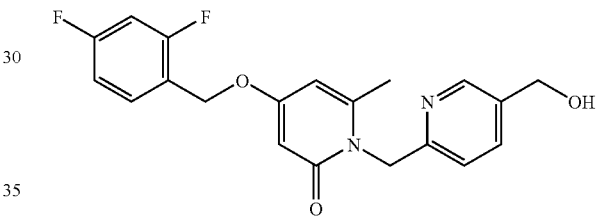

Methyl 6-{[4-[(2,4-difluorobenzyl)oxy]-6-methyl-2-oxopyridin-1(2H)-yl]methyl}nicotinate (from preparation of step 3) (350 mg, 0.87 mmol) was added into anhydrous tetrahydrofuran (15 ml) and the solution was cooled to −78° C. Into the cold solution, was added lithium aluminum hydride (100 mg, 2.6 mmol). After the addition, the reaction mixture was warm to 0 C and continue stirring for one additional hour. Potassium hydrogen sulfate (1 N solution, 150 ml) was added slowly into the reaction mixture to quench the reaction. The resulting mixture was transferred to a separatory funnel and the product was extracted with ethyl acetate (200 ml×2). The combine ethyl acetate solution was dried over anhydrous magnesium sulfate and evaporated to dryness. LC/MS, t$_r$=1.88 minutes (5 to 95% acetonitrile/water over 5 minutes at 1 ml/min with detection 254 nm, at 50° C.). ES-MS m/z 373 (M+H)

Step 2: Preparation of the Title Compound.

4-[(2,4-difluorobenzyl)oxy]-1-{[5-(hydroxymethyl)pyridin-2-yl]methyl}-6-methylpyridin-2(1H)-one (from step 1). (230 mg, 0.62 mmol) was added into 10 ml of dichloromethane followed by addition of N-bromo succinimide (110 mg, 0.62 mmol). The solution was stirred at room temperature for 3 hours. Saturated sodium bicarbonate solution (100 ml) was added into the reaction mixture and it was transferred to a separatory funnel. The product was extracted with ethyl acetate (200 ml×2). The combined ethyl acetate solution was dried over anhydrous magnesium sulfate and evaporated to dryness. $^1$H NMR (400 MHz, CDCl$_3$) δ 8.47 (app s, 1H), 7.64 (dd, J=5.77, 2.29 Hz, 1H), 7.55 (app q, J=6.45 Hz, 1H), 7.33 (d, J=6.05 Hz, 1H), 6.93 (m, 1H), 6.84

(m, 1H), 6.00 (s, 1H), 5.39 (s, 2H), 5.19 (s, 2H), 4.68 (s, 2H), 2.46 (s, 3H); LC/MS, $t_r$=2.01 minutes (5 to 95% acetonitrile/water over 5 minutes at 1 ml/min with detection 254 nm, at 50° C.). ES-MS m/z 451 (M+H).

Example 554

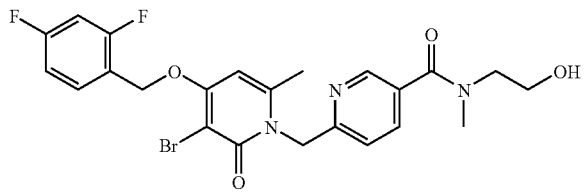

6-{[3-bromo-4-[(2,4-difluorobenzyl)oxy]-6-methyl-2-oxopyridin-1(2H)-yl]methyl}-N-(2-hydroxyethyl)-N-methylnicotinamide Step 1: Preparation of methyl 6-{[3-bromo-4-[(2,4-difluorobenzyl)oxy]-6-methyl-2-oxopyridin-1(2H)-yl]methyl}nicotinate.

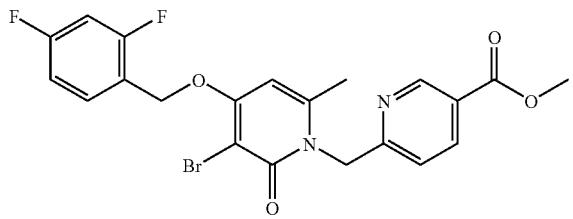

Methyl 6-{[4-[(2,4-difluorobenzyl)oxy]-6-methyl-2-oxopyridin-1(2H)-yl]methyl}nicotinate (350 mg, 0.87 mmol) (1.0 g, 2.5 mmol) was added into 150 ml of dichloromethane followed by addition of N-bromo succinimide (500 mg, 2.8 mmol). The solution was stirred at room temperature for 3 hours. Saturated sodium bicarbonate solution (300 ml) was added into the reaction mixture and it was transferred to a separatory funnel. The product was extracted with ethyl acetate (500 ml×2). The combined ethyl acetate solution was dried over anhydrous magnesium sulfate and evaporated to dryness. $^1$H NMR (400 MHz, CDCl$_3$) δ 9.08 (app d, J=2.15 Hz, 1H), 8.21 (dd, J=6.04, 2.15 Hz, 1H), 7.55 (app qt, J=6.31 Hz, 1H), 7.41 (d, J=6.31 Hz, 1H), 6.91 (m, 1H), 6.84 (m, 1H), 6.02 (1, 1H), 5.42 (s, 2H), 5.19 (s, 2H), 3.91 (s, 3H), 2.45 (s, 3H); LC/MS, $t_r$=2.85 minutes (5 to 95% acetonitrile/water over 5 minutes at 1 ml/min with detection 254 nm, at 50° C.). ES-MS m/z 479 (M+H). ES-HRMS m/z 479.0415 (M+H calcd for C$_{21}$H$_{18}$BrF$_2$N$_2$O$_4$ requires 479.0413).

Step 2: Preparation of 6-{[3-bromo-4-[(2,4-difluorobenzyl)oxy]-6-methyl-2-oxopyridin-1(2H)-yl]methyl}nicotinic acid.

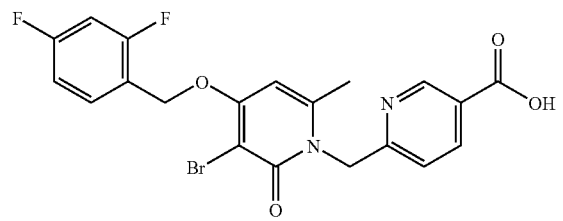

Methyl 6-{[3-bromo-4-[(2,4-difluorobenzyl)oxy]-6-methyl-2-oxopyridin-1(2H)— yl]methyl}nicotinate (from step 1) (1.0 g, 2.1 mmol) was added into the mixture of 100 ml tetrahydrofuran and 10 ml of methanol followed by addition of 2.5 N sodium hydroxide(0.85 ml, 2.1 mmol). The solution was heated to 50 C for 2 hours. After the solution was cooled to room temperature and evaporate to completely dried residue. The residue was added into 50 ml of tetrahydrofuran and 4 N HCl in 1,4-dioxane (0.52 ml, 2.1 mmol) and stirred the mixture for 30 minute. The mixture was evaporate to dryness. The residue was added 20 ml water and the aqueous solution was neutralized to exactly ph 7 by addition of saturated sodium bicarbonate solution drop wise. The resulting heterogeneous mixture was left standed for 20 hours. Filtered, rinsed with water (30 ml×3) and dried over high vacuum oven to afford white solid(950 mg, 97%). $^1$H NMR (400 MHz, CDCl$_3$ and CD$_3$OD) δ 8.98 (app br s, 1H), 8.15 (dd, J=6.17, 2.02 Hz, 1H), 7.45 (app q, J=6.58 Hz, 1H), 7.21 (d, J=8.19 Hz, 1H), 6.84 (m, 1H), 6.76 (m, 1H), 6.04 (s, 1H), 5.35 (s, 2H), 5.12 (s, 2H), 2.32 (s, 3H); LC/MS, $t_r$=2.48 minutes (5 to 95% acetonitrile/water over 5 minutes at 1 ml/min with detection 254 nm, at 50° C.). ES-MS m/z 465 (M+H). ES-HRMS m/z 465.0254 (M+H calcd for C$_{20}$H$_{16}$BrF$_2$N$_2$O$_4$ requires 465.0256).

Step 3: Preparation of the Title Compound.

6-{[3-bromo-4-[(2,4-difluorobenzyl)oxy]-6-methyl-2-oxopyridin-1(2H)-yl]methyl}nicotinic acid (from step 2)(230 mg, 0.5 mmol) was added into the 1-hydroxybenzotriazole (101 mg, 0.75 mmol) in 5 ml of N,N-dimethylforamide. 4-methyl morpholine (0.16 ml, 1.5 mmol) was added into the mixture followed by addition of 1-(3-(dimethylamino) propyl-3-ethylcarbodiimide hydrochloride (143 mg, 0.75 mmol). Stirred the mixture for 30 minute to become homogenous solution. To that homogenous solution, was added 2-(methylamino) ethanol (0.06 ml, 0.75 mmol) and the mixture was stirred for 20 hours. Water (150 ml) was added into the reaction mixture and the product was extracted using ethyl acetate (400 ml×2). The combined ethyl acetate solution was dried over anhydrous magnesium sulfate and evaporated to dryness. $^1$H NMR (400 MHz, DMSO-d$_6$) δ 8.47 (app br s, 1H), 7.80 (br d, J=7.92 Hz, 1H), 7.64 (app q, J=6.58 Hz, 1H), 7.30 (m, 2H), 7.15 (m, 1H), 6.56 (s, 1H), 5.39 (s, 2H), 5.28 (s, 2H), 3.46 (m, 2H), 3.23 (m, 2H), 2.93 (m, 3H), 2.36 (s, 3H); LC/MS, $t_r$=2.29 minutes (5 to 95% acetonitrile/water over 5 minutes at 1 ml/min with detection 254 nm, at 50° C.). ES-HRMS m/z 522.0850 (M+H calcd for C$_{23}$H$_{23}$BrF$_2$N$_3$O$_4$ requires 522.0835).

Example 555

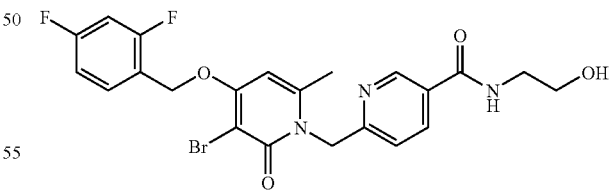

6-{[3-bromo-4-[(2,4-difluorobenzyl)oxy]-6-methyl-2-oxopyridin-1(2H)-yl]methyl}-N-(2-hydroxyethyl)nicotinamide Following the method of Example 554 (step 3) and substituting 2-(methylamino)ethanol for the ethanolamine obtained the title compound as a white solid (79% yield). $^1$H NMR (400 MHz, CD$_3$OD) δ 8.93 (d, J=2.01 Hz, 1H), 8.21 (dd, J=6.04, 2.21 Hz, 1H), 7.67 (app q, J=6.44 Hz, 1H), 7.39

(d, J=8.06 Hz, 1H), 7.08 (m, 2H), 6.58 (s, 1H), 5.55 (s, 2H), 5.35 (s, 2H), 3.74 (app t, J=5.73 Hz, 2H), 3.53 (app t, J=5.73 Hz, 2H), 2.49 (s, 3H); LC/MS, t$_r$=2.26 minutes (5 to 95% acetonitrile/water over 5 minutes at 1 ml/min with detection 254 nm, at 50° C.). ES-HRMS m/z 508.0673 (M+H calcd for C$_{22}$H$_{21}$BrF$_2$N$_3$O$_4$ requires 508.0678).

Example 556

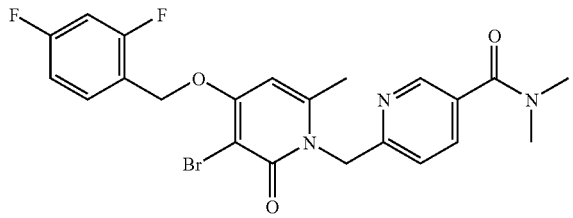

6-{[3-bromo-4-[(2,4-difluorobenzyl)oxy]-6-methyl-2-oxopyridin-1(2H)-yl]methyl}-N,N-dimethylnicotinamide Following the method of Example 554 (step 3) and substituting dimethylamine for the ethanolamine obtained the title compound as a white solid (75% yield). $^1$H NMR (400 MHz, CDCl$_3$) δ 8.55 (d, J=1.62 Hz, 1H), 7.68 (dd, J=5.77, 2.15 Hz, 1H), 7.55 (app q, J=6.45 Hz, 1H), 7.37 (d, J=8.06 Hz, 1H), 6.93 (m, 1H), 6.84 (m, 1H), 6.02 (s, 1H), 5.40 (s, 2H), 5.20 (s, 2H), 3.09 (s, 3H), 2.97 (s, 3H), 2.45 (s, 3H); LC/MS, t$_r$=2.45 minutes (5 to 95% acetonitrile/water over 5 minutes at 1 ml/min with detection 254 nm, at 50° C.). ES-HRMS m/z 492.0710 (M+H calcd for C$_{22}$H$_{21}$BrF$_2$N$_3$O$_3$ requires 492.0729).

Example 557

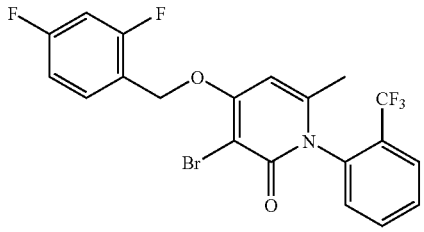

3-bromo-4-[(2,4-difluorobenzyl)oxy]-6-methyl-1-[2-(trifluoromethyl)phenyl]pyridin-2(1H)-one Step 1: Preparation of 4-hydroxy-6-methyl-1-[2-(trifluoromethyl)phenyl]pyridin-2(1H)-one.

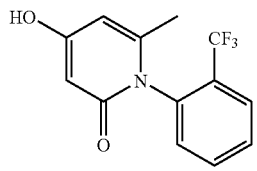

4-hydroxy-6-methyl-2-pyrone (10 g, 79.3 mmol) was added into the 2-(trifluoromethyl)aniline (14 ml, 111.3 mmol) in 10 ml of 1,2-dichlorobenzene in a round bottom flask. The mixture was then placed in a pre-heated oil bath at 165 C. After 30 minute of heating, the mixture was cooled to room temperature and added 250 ml of saturated sodium bicarbonate solution. The mixture was stirred at room temperature for 15 minutes and transferred to a separatory funnel. Ethyl acetate (300 ml) was added into the separatory funnel and partitions the layers. The aqueous layer was obtained and the organic layer was added 200 ml of saturated sodium bicarbonate solution. The aqueous layer was obtained again and the combined aqueous solution was neutralized with HCl solution. Upon neutralization, white solid precipitated out of the solution. Filtered the solid, rinsed with water (100 ml×5) and dried over high vacuum oven to obtain the white solid (7.5 g, 35.5%). LC/MS, t$_r$=1.77 minutes (5 to 95% acetonitrile/water over 5 minutes at 1 ml/min with detection 254 nm, at 50° C.). ES-MS m/z 270 (M+H).

Step 2: Preparation of 4-[(2,4-difluorobenzyl)oxy]-6-methyl-1-[2-(trifluoromethyl)phenyl]pyridin-2(1H)-one.

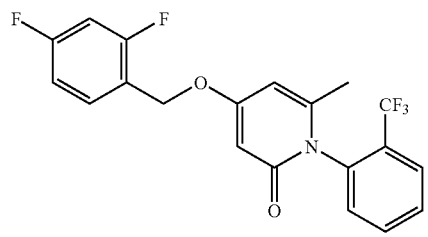

4-hydroxy-6-methyl-1-[2-(trifluoromethyl)phenyl]pyridin-2(1H)-one (from Step 1) (7.3 g, 27.1 mmol) was added into 3,4-difluorobenzyl bromide (5.5 g, 26.5 mmol) in 60 ml of dimethyl formamide. The mixture was cooled to 0 C. and cesium carbonate (20 g, 1.3 mmol) was added into the mixture. After the addition, the mixture was warmed to room temperature and stirred for 4 hours. Water (500 ml) was added into the reaction mixture. Yellow solid came out of solution. Filtered and rinsed with water (200 ml×2) to obtain the yellow solid. Dissolved the solid in ethyl acetate (500 ml) and water (300 ml) and transfer to a separatory funnel and obtained the organic layer. The organic layer was washed again with water (200 ml) and dried over anhydrous magnesium sulfate. The organic solution was evaporated to dryness. $^1$H NMR (400 MHz, CDCl$_3$) δ 7.82 (d, J=7.65 Hz, 1H), 7.7 (t, J=7.52 Hz, 1H), 7.58 (t, J=7.65 Hz, 1H), 7.42 (q, J=6.45 Hz, 1H), 7.27 (d, J=7.78 Hz, 2H), 6.89 (m, 2H), 5.95 (app d, J=2.42 Hz, 1H), 5.90 (app d, J=2.42 Hz, 1H), 5.01 (app d, J=2.94 Hz, 2H), 1.86 (s, 3H); LC/MS, t$_r$=2.74 minutes (5 to 95% acetonitrile/water over 5 minutes at 1 ml/min with detection 254 nm, at 50° C.). ES-MS m/z 396 (M+H).

Step 3: Preparation of the Title Compound.

N-bromosuccinimide (0.24 g, 1.36 mmol) was added into 4-[(2,4-difluorobenzyl)oxy]-6-methyl-1-[2-(trifluoromethyl)phenyl]pyridin-2(1H)-one (0.54 g, 1.36 mmol) in 20 ml of dichloromethane. The mixture was stirred at room temperature for 2 hours. Saturated sodium bicarbonate solution (150 ml) was added into the reaction mixture and the combine solution was transferred to a separatory funnel. The product was extracted with ethyl acetate (250 ml). The ethyl acetate solution was dried over anhydrous magnesium sulfate and evaporated to dryness. $^1$H NMR (400 MHz, CDCl$_3$) δ 7.82 (d, J=7.25 Hz, 1H), 7.7 (app t, J=7.66 Hz, 1H), 7.60 (m, 2H), 7.26 (s, 1H), 6.97 (m, 1H), 6.87 (m, 1H), 6.09 (s, 1H), 5.25 (app d, J=3.35 Hz, 2H), 1.94 (s, 3H); LC/MS, t$_r$=2.84 minutes (5 to 95% acetonitrile/ water over 5 minutes at 1 ml/min with detection 254 nm, at 50° C.). ES-HRMS m/z 474.0113 (M+H calcd for $C_{20}H_{14}BrF_5NO_2$ requires 474.0123).

Example 558

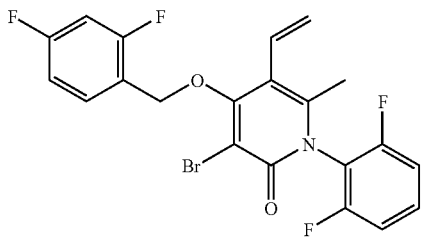

3-bromo-4-[(2,4-difluorobenzyl)oxy]-1-(2,6-difluorophenyl)-6-methyl-5-vinylpyridin-2(1H)-one Step 1: To a room temperature solution of 3-bromo-4-[(2,4-difluorobenzyl)oxy]-1-(2,6-difluorophenyl)-5-iodo-6-methylpyridin-2(1H)-one (1.00 g, 1.76 mmol) in anhydrous THF (12 mL) was added, sequentially, tributyl(vinyl)tin (1.21 g, 3.81 mmol) and tetrakis(triphenylphosphine) palladium (236 mg, 0.204 mmol) under an argon stream. The reaction vessel was then equipped with a reflux condenser and the reaction system purged with an argon flow. The resulting yellow solution was heated to 68° C. and stirred under a positive pressure of argon for 12.0 hours until complete disappearance of starting material by LCMS analysis. The reaction mixture was concentrated in vacuo and the resulting dark residue was subjected to $SiO_2$ chromatography with ethyl acetate/hexanes (3:7) to furnish a reddish solid. $^1$H NMR (400 MHz, $CDCl_3$) δ 7.62 (app q, J=7.8 Hz, 1H), 7.45 (app tt, J=8.4, 6.2, 1H), 7.09 (app t, J=8.8 Hz, 2H), 6.90 (app t, J=8.0 Hz, 1H), 6.83 (app dt, J=6.8, 2.5 Hz, 1H), 6.51 (dd, J=17.7, 11.4 Hz, 1H), 5.53 (dd, J=11.4, 1.5 Hz, 1H), 5.41 (dd, J=17.8, 1.5 Hz, 1H), 5.09 (br s, 2H), 2.09 (s, 3H); LC/MS C-18 column, $t_r$=3.20 minutes (5 to 95% acetonitrile/water over 5 minutes at 1 ml/min with detection 254 nm, at 50° C.). ES-MS m/z 468 (M+H). ES-HRMS m/z 468.0210 (M+H calcd for $C_{21}H_{15}BrF_4NO_2$ requires 468.0217).

Example 560

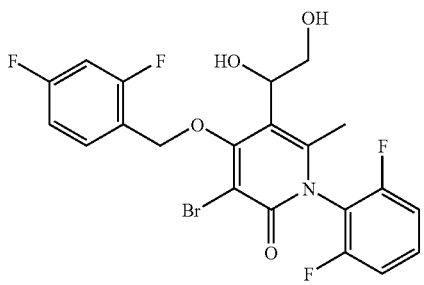

3-bromo-4-[(2,4-difluorobenzyl)oxy]-1-(2,6-difluorophenyl)-5-(1,2-dihydroxyethyl)-6-methylpyridin-2(1H)-one Step 1: To a room temperature solution of 3-bromo-4-[(2,4-difluorobenzyl)oxy]-1-(2,6-difluorophenyl)-6-methyl-5-vinylpyridin-2(1H)-one (0.970 g, 2.07 mmol) in water/acetone 1:3 (8.7 mL) was added, sequentially, osmium tetroxide (0.110 g, 0.433 mmol) and N-methyl morpholine oxide (1.32 g, 11.2 mmol). The resulting solution was stirred for one hour until complete consumption of starting material by LCMS analysis, and the reaction was concentrated in vacuo. The resulting dark residue was subjected to $SiO_2$ chromatography with ethyl acetate/hexanes (3:7) to furnish a solid. $^1$H NMR (400 MHz, $CDCl_3$) δ 7.59 (app q, J=8.2 Hz, 1H), 7.45 (ddd, J=14.7, 8.5, 6.8 Hz, 1H), 7.08 (app t, J=8.5 Hz, 2H), 6.94 (app t, J=8.2 Hz, 1H), 6.88 (app t, J=8.5 Hz, 1H), 5.31 (AB-q, J=10.6 Hz, Δ=38.3 Hz, 2H), 5.07 (dd, J=9.1, 3.8 Hz, 1H), 3.83 (t, J=10.8 Hz, 1H), 3.60 (dd, J=11.4, 3.9 Hz, 1H), 2.94 (br s, 1H), 2.16 (s, 3H); LC/MS C-18 column, $t_r$=2.26 minutes (5 to 95% acetonitrile/water over 5 minutes at 1 ml/min with detection 254 nm, at 50° C.). ES-MS m/z 502 (M+H). ES-HRMS m/z 502.0276 (M+H calcd for $C_{21}H_{17}BrF_4NO_4$ requires 502.0272).

Example 561

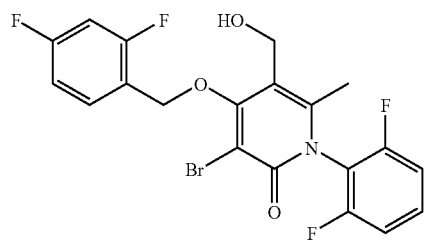

3-bromo-4-[(2,4-difluorobenzyl)oxy]-1-(2,6-difluorophenyl)-5-(hydroxymethyl)-6-methylpyridin-2(1H)-one Step 1: To a −20° C. solution of 5-bromo-4-[(2,4-difluorobenzyl)oxy]-1-(2,6-difluorophenyl)-2-methyl-6-oxo-1,6-dihydropyridine-3-carbaldehyde (0.659 g, 1.40 mmol) in methanol (10 mL) was added, portionwise, solid sodium borohyride (3.6 g, 96 mmol) over one hour until complete consumption of starting material by LCMS analysis. Next, the reaction mixture was diluted with 500 mL of ethyl acetate and washed with 3×200 mL of water. The resulting organic extract was $Na_2SO_4$ dried, filtered, and concentrated in vacuo to approximately 100 mL volume. The resulting liquid was diluted with hexanes (100 mL) to furnish an amorphous solid that was collected and dried at 1 mm Hg vacuum to furnish (620 mg, 94%) of the desired product. $^1$H NMR (400 MHz, $d_4$-MeOH) δ 7.70 (app q, J=8.3 Hz, 1H), 7.62 (app tt, J=10.4, 6.3 Hz, 1H), 7.25 (app t, J=8.6 Hz, 2H), 7.03 (app t, J=8.6 Hz, 1H), 6.88 (app t, J=8.5 Hz, 1H), 5.31 (s, 2H), 4.58 (s, 2H), 2.17 (s, 3H); LC/MS C-18 column, $t_r$=2.49 minutes (5 to 95% acetonitrile/water over 5 minutes at 1 ml/min with detection 254 nm, at 50° C.). ES-MS m/z 472 (M+H). ES-HRMS m/z 472.0152 (M+H calcd for $C_{20}H_{15}BrF_4NO_3$ requires 472.0166).

Example 562

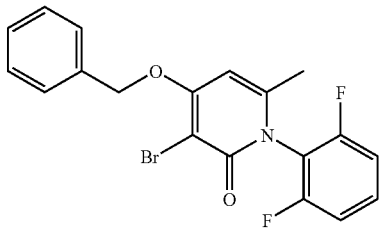

4-(benzyloxy)-3-bromo-1-(2,6-difluorophenyl)-6-methylpyridin-2(1H)-one

Step 1: Preparation of 4-(benzyloxy)-1-(2,6-difluorophenyl)-6-methylpyridin-2(1H)-one.

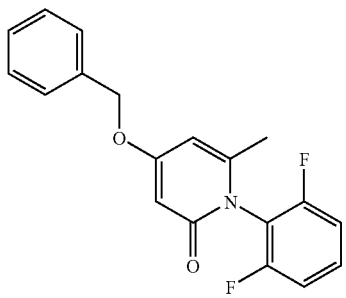

To a briskly stirred room temperature solution of 1-(2,6-difluorophenyl)-4-hydroxy-6-methylpyridin-2(1H)-one (1.43 g, 6.03 mmol) in dimethylformamide (4.6 mL) was added sequentially $K_2CO_3$ (2.01 g, 14.5 mmol) and benzyl bromide (2.40 mL, 20.2 mmol). The resulting suspension was stirred for 6.5 hours until complete consumption of starting material by LCMS analysis. The reaction was then diluted with ethyl acetate (200 mL) and brine washed (3×200 mL). The resulting organic extract was $Na_2SO_4$ dried, filtered, and concentrated in vacuo to approximately 100 mL volume. The resulting mother liquor rapidly precipitated and furnished an amorphous solid that was collected and dried at 1 mm Hg vacuum to provide a solid (1.62 g, 82%). $^1$H NMR (300 MHz, $d_4$-MeOH) δ 7.62 (app tt, J=8.6, 6.4 Hz, 1H), 7.52–7.32 (m, 4H), 7.30–7.12 (m, 3H), 6.27 (d, J=1.6 Hz, 1H), 6.04 (d, J=2.6 Hz, 1H), 5.18 (s, 2H), 2.06 (s, 3H). LC/MS C-18 column, $t_r$=2.51 minutes (5 to 95% acetonitrile/water over 5 minutes at 1 ml/min with detection 254 nm, at 50° C.). ES-MS m/z 328 (M+H). ES-HRMS m/z 328.1179 (M+H calcd for $C_{19}H_{16}F_2NO_2$ requires 328.1144).

Step 2: To a room temperature solution of 4-(benzyloxy)-1-(2,6-difluorophenyl)-6-methylpyridin-2(1H)-one (1.52 g, 4.64 mmol) in methylene chloride (15 mL) was added solid N-bromosuccinimide (2.01 g, 11.3 mmol) and the resulting reddish solution was stirred for 4.0 hours. At this time the reaction was diluted with ethyl acetate (400 mL) and washed with sodium sulfite (5% aqueous solution, 100 mL) and brine (3×200 mL). The resulting organic extracts were $Na_2SO_4$ dried, filtered, and concentrated in vacuo to approximately 60 mL volume. The resulting mother liquor rapidly precipitated and furnished an amorphous solid that was collected and dried at 1 mm Hg vacuum to provide a solid (1.70 g, 91%). $^1$H NMR (300 MHz, $d_4$-MeOH) δ 7.64 (app tt, J=8.6, 6.4 Hz, 1H), 7.57 (br d, J=7.1 Hz, 1H), 7.50–7.34 (m, 4H), 7.27 (app t, J=8.0 Hz, 1H), 7.26–7.21 (m, 1H), 6.66 (s, 1H), 5.40 (s, 2H), 2.12 (s, 3H); LC/MS C-18 column, $t_r$=2.63 minutes (5 to 95% acetonitrile/water over 5 minutes at 1 ml/min with detection 254 nm, at 50° C.). ES-MS m/z 406 (M+H). ES-HRMS m/z 406.0228 (M+H calcd for $C_{19}H_{15}BrF_2NO_2$ requires 406.0249).

Example 563

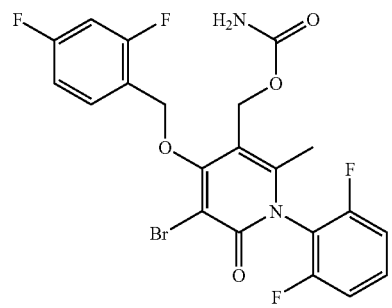

5-bromo-4-[(2,4-difluorobenzyl)oxy]-1-(2,6-difluorophenyl)-2-methyl-6-oxo-1,6-dihydropyridin-3-yl]methyl carbamate Step 1: To a room temperature solution of 3-bromo-4-[(2,4-difluorobenzyl)oxy]-1-(2,6-difluorophenyl)-5-(hydroxymethyl)-6-methylpyridin-2(1H)-one (76.2 mg, 0.161 mmol) in methylene chloride (0.4 mL) was added a solution of trichloroacetyl isocyanate (toluene, 0.60 M, 0.5 mL, 0.30 mmol). The resulting solution was stirred for one hour until complete consumption of starting material by LCMS analysis. The reaction mixture was then directly applied to $Al_2O_3$ (0.5 g of Broeckman-activity type I) and the slurry was matured for three hours. At this time, the $Al_2O_3$ plug was flushed with ethyl acetate/methanol (95:5) and the resulting mother liquor was concentrated to a residue that was subjected to $SiO_2$ chromatography using ethyl acetate/hexanes (1:1) to furnish a white solid (71.0 mg, 85%). $^1$H NMR (400 MHz, $d_4$-MeOH) δ 7.71–7.59 (m, 2H), 7.26 (app t, J=8.5 Hz, 2H), 7.02 (app t, J=9.2 Hz, 2H), 5.32 (s, 2H), 5.02 (s, 2H), 2.15 (s, 3H); LC/MS C-18 column, $t_r$=2.35 minutes (5 to 95% acetonitrile/water over 5 minutes at 1 ml/min with detection 254 nm, at 50° C.). ES-MS m/z 515 (M+H). ES-HRMS m/z 515.0188 (M+H calcd for $C_{21}H_{16}BrF_4N_2O_4$ requires 515.0224).

Example 564

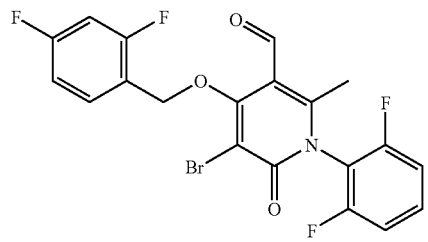

5-bromo-4-[(2,4-difluorobenzyl)oxy]-1-(2,6-difluorophenyl)-2-methyl-6-oxo-1,6-dihydropyridine-3-carbaldehyde Step 1: To a room temperature solution of 3-bromo-4-[(2,4-difluorobenzyl)oxy]-1-(2,6-difluorophenyl)-5-(1,2-dihydroxyethyl)-6-methylpyridin-2(1H)-one (550 mg, 1.10 mmol) in toluene (10.0 mL) was added lead(IV) acetate (810 mg, 1.82 mmol). The resulting dark brown solution was stirred for two hours until complete consumption of starting material by LCMS analysis. The reaction mixture was then diluted with ethyl acetate (400 mL), water washed (3×100 mL), and brine washed (3×300 mL). The resulting organic extract was separated, Na$_2$SO$_4$ dried, and concentrated. The resulting dark residue was subjected to SiO$_2$ chromatography with ethyl acetate/hexanes (1:1) to furnish a light yellow solid (321 mg, 62%). $^1$H NMR (400 MHz, CDCl$_3$) δ 10.08 (s, 1H), 7.56–7.48 (m, 2H), 7.12 (app t, J=7.3 Hz, 2H), 6.94 (app t, J=8.5 Hz, 1H), 6.88 (app t, J=8.7 Hz, 1H), 5.33 (s, 2H), 2.45 (s, 3H); LC/MS C-18 column, t$_r$=2.94 minutes (5 to 95% acetonitrile/water over 5 minutes at 1 ml/min with detection 254 nm, at 50° C.). ES-MS m/z 470 (M+H). ES-HRMS m/z 469.9996 (M+H calcd for C$_{20}$H$_{13}$BrF$_4$NO$_3$ requires 470.0009).

Example 565

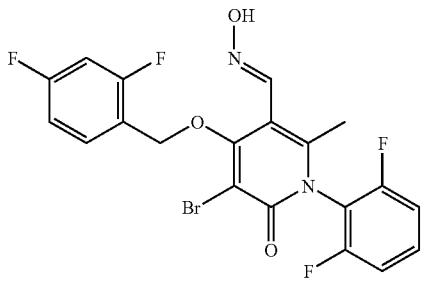

5-bromo-4-[(2,4-difluorobenzyl)oxy]-1-(2,6-difluorophenyl)-2-methyl-6-oxo-1,6-dihydropyridine-3-carbaldehyde oxime Step 1: To a room temperature solution of 5-bromo-4-[(2,4-difluorobenzyl)oxy]-1-(2,6-difluorophenyl)-2-methyl-6-oxo-1,6-dihydropyridine-3-carbaldehyde (316.5 mg, 0.673 mmol) in methanol (10.0 mL) was added solid NH$_2$OH.H$_2$O (300.0 mg, 4.32 mmol) and sodium acetate (480.0 mg, 5.85 mmol). The resulting suspension was stirred for 1.5 hours until complete consumption of starting material by LCMS analysis. The reaction mixture was then concentrated in vacuo and the resulting residue was diluted with methylene chloride (300 mL) and water washed (2×100 mL). The resulting organic extract was separated, Na$_2$SO$_4$ dried, and concentrated to furnish a light yellow solid (390 mg, 99%). $^1$H NMR (400 MHz, d$_4$-MeOH with CDCl$_3$) δ 8.06 (s, 1H), 7.51–7.40 (m, 2H), 7.06 (app dd, J=8.6, 7.4 Hz, 2H), 6.88 (app dt, J=8.3, 2.4 Hz, 1H), 6.83 (app dt, J=9.2, 2.4 Hz, 1H), 5.13 (s, 2H), 2.76 (s, 3H); LC/MS C-18 column, t$_r$=2.61 minutes (5 to 95% acetonitrile/water over 5 minutes at 1 ml/min with detection 254 nm, at 50° C.). ES-MS m/z 485 (M+H). ES-HRMS m/z 485.0093 (M+H calcd for C$_{20}$H$_{14}$BrF$_4$N$_2$O$_3$ requires 485.0118).

Example 566

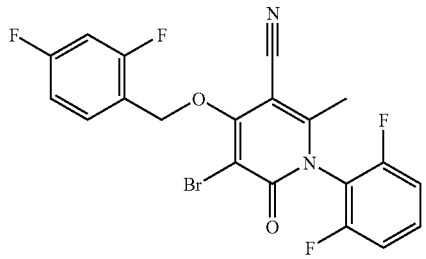

5-bromo-4-[(2,4-difluorobenzyl)oxy]-1-(2,6-difluorophenyl)-2-methyl-6-oxo-1,6-dihydropyridine-3-carbonitrile Step 1: To a room temperature solution of 5-bromo-4-[(2,4-difluorobenzyl)oxy]-1-(2,6-difluorophenyl)-2-methyl-6-oxo-1,6-dihydropyridine-3-carbaldehyde oxime (340.0 mg, 0.701 mmol) in methylene chloride (8.0 mL) was added solid 1,1' carbonyl diimidazole (290.0 mg, 1.79 mmol) and sodium acetate (480.0 mg, 5.85 mmol). The resulting solution was stirred for 1.5 hours until complete consumption of starting material by LCMS analysis. The reaction mixture was then concentrated in vacuo and the resulting residue was directly applied to SiO$_2$ chromatography with ethyl acetate/hexanes (3:7) to furnish a white solid (262 mg, 90%). $^1$H NMR (400 MHz, CDCl$_3$) δ 7.61 (app q, J=7.4 Hz, 1H), 7.52 (app tt, J=8.4, 6.3 Hz, 1H), 7.14 (app dd, J=8.6, 7.4 Hz, 2H), 6.94 (app dt, J=8.5, 2.5 Hz, 1H), 6.88 (app dt, J=8.5, 2.4 Hz, 1H), 5.43 (s, 2H), 2.32 (s, 3H); LC/MS C-18 column, t$_r$=2.95 minutes (5 to 95% acetonitrile/water over 5 minutes at 1 ml/min with detection 254 nm, at 50° C.). IR (neat) 3111, 3067, 3032, 2914, 2840, 2215 (nitrile stretch), 1678, 1587, 1470 cm$^{-1}$; ES-MS m/z 467 (M+H). ES-HRMS m/z 467.0037 (M+H calcd for C$_{20}$H$_{12}$BrF$_4$N$_2$O$_2$ requires 467.0013).

Example 567

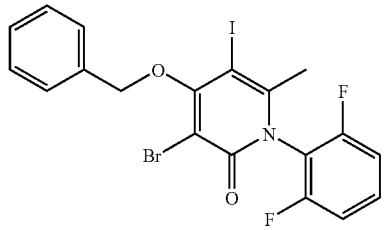

4-(benzyloxy)-3-bromo-1-(2,6-difluorophenyl)-5-iodo-6-methylpyridin-2(1H)-one

Step 1: A solution of 4-(benzyloxy)-3-bromo-1-(2,6-difluorophenyl)-6-methylpyridin-2(1H)-one (1.42 g, 3.50 mmol) in 1,2 dichloroethane (18 mL) was treated with solid N-iodosuccinimide (1.59 g, 7.06 mmol) and dichloroacetic acid (0.260 g, 2.01 mmol). The resulting solution was stirred and heated to 50° C. for 2.5 hours until complete consumption of starting material by LCMS. At this time the reaction was diluted with ethyl acetate (400 mL) and washed with sodium sulfite (5% aqueous solution, 100 mL) and brine (3×200 mL). The resulting organic extracts were Na$_2$SO$_4$ dried, filtered, and concentrated in vacuo to approximately 30 mL volume. The resulting mother liquor rapidly precipitated and furnished an amorphous solid that was collected and dried at 1 mm Hg vacuum to provide a solid (1.49 g, 82%). ¹H NMR (400 MHz, CDCl₃) δ 7.62 (app d, J=6.8 Hz, 2H), 7.51–7.38 (m, 4H), 7.09 (app t, J=8.0 Hz, 2H), 5.20 (s, 2H), 2.39 (s, 3H); LC/MS C-18 column, t$_r$=3.28 minutes (5 to 95% acetonitrile/water over 5 minutes at 1 ml/min with detection 254 nm, at 50° C.). ES-MS m/z 532 (M+H) ES-HRMS m/z 531.9196 (M+H calcd for $C_{19}H_{14}BrF_{21}NO_2$ requires 531.9215).

Example 568

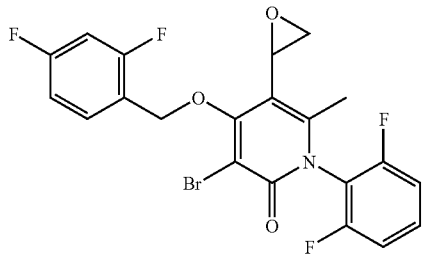

3-bromo-4-[(2,4-difluorobenzyl)oxy]-1-(2,6-difluorophenyl)-6-methyl-5-oxiran-2-ylpyridin-2(1H)-one Step 1: A sample of 3-bromo-4-[(2,4-difluorobenzyl)oxy]-1-(2,6-difluorophenyl)-6-methyl-5-vinylpyridin-2(1H)-one (10.0 mg, 0.0214 mmol) was treated with a solution of dimethyl dioxirane in acetone (approx. 0.1 M, 5 mL, 0.5 mmol). The reaction vessel was capped and sealed, and the resulting solution was stirred 6.0 hours. At this time the reaction was concentrated in vacuo and the resulting residue was subjected to SiO₂ chromatography with ethyl acetate/hexanes (4:6) to furnish a semi-solid (5.0 mg, 48%). ¹H NMR (400 MHz, CDCl₃) δ 7.57 (app q, J=7.4 Hz, 1H), 7.46 (app tt, J=8.5, 6.2, 1H), 7.11 (app t, J=8.0 Hz, 2H), 6.94 (app t, J=8.2 Hz, 1H), 6.83 (app t, J=9.2 Hz, 1H), 5.31 (AB-q, J=10.9 Hz, Δ=29.0 Hz, 2H), 3.63 (app t, J=3.5 Hz, 1H), 3.03 (dd, J=9.4, 5.0, 1H), 2.85 (dd, J=5.2, 2.7, 1H), 2.14 (s, 3H); LC/MS C-18 column, t$_r$=2.26 minutes (5 to 95% acetonitrile/water over 5 minutes at 1 ml/min with detection 254 nm, at 50° C.). ES-MS m/z 484 (M+H) and 502 (M+H₃O). ES-HRMS m/z 502.0273 (M+H₃O calcd for $C_{21}H_{17}BrF_4NO_4$ requires 502.0272).

Example 569

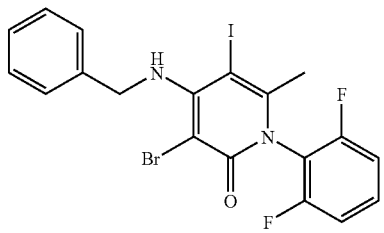

4-(benzylamino)-3-bromo-1-(2,6-difluorophenyl)-5-iodo-6-methylpyridin-2(1H)-one

Step 1: A slurry of 3-bromo-4-[(2,4-difluorobenzyl)oxy]-1-(2,6-difluorophenyl)-5-iodo-6-methylpyridin-2(1H)-one (80.0 mg, 0.141 mmol) and benzyl amine (300 mg, 2.80 mmol) was heated to 63° C. and stirred for 1.0 hours until complete disappearance of starting material by LCMS analysis. The reaction mixture was then diluted with ethyl acetate (300 mL) and brine washed (3×200 mL). The resulting organic extracts were Na₂SO₄ dried, filtered, and concentrated in vacuo to a residue that was then subjected to SiO₂ chromatography with ethyl acetate/hexanes (3:7) to furnish a brown solid (60.0 mg, 81%). ¹H NMR (400 MHz, CDCl₃) δ 7.43–7.22 (m, 6H), 7.04 (app t, J=8.4 Hz, 2H), 5.02 (br t, J=1.6 Hz, 1H), 4.86 (d, J=5.5 Hz, 2H), 2.37 (s, 3H); LC/MS C-18 column, t$_r$=3.02 minutes (5 to 95% acetonitrile/water over 5 minutes at 1 ml/min with detection 254 nm, at 50° C.). ES-MS m/z 531 (M+H). ES-HRMS m/z 530.9344 (M+H calcd for $C_{19}H_{15}BrF_{21}N_2O$ requires 530.9375).

Example 570

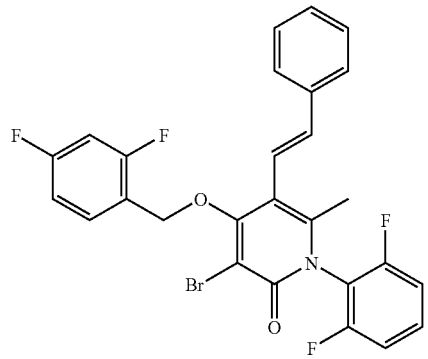

3-bromo-4-[(2,4-difluorobenzyl)oxy]-1-(2,6-difluorophenyl)-6-methyl-5-[(E)-2-phenylethenyl]pyridin-2(1H)-one Step 1: To an anhydrous -78° C. solution of β-bromostyrene (1.80 g, 10.0 mmol) in ether (18 mL) was added sequentially a solution of zinc chloride (10.0 mL, 1.0 M ether, 10.0 mmol) over 1.0 minute and a solution of tert-butyl lithium (15.0 mL, 1.6 M pentanes, 24.0 mmol) over 8.0 minutes. The resulting solution became cloudy and the reaction mixture was allowed to warm to room temperature on its own accord (over 30 minutes). After an additional 1.0 hour, the suspension was transferred by syringe directly to a separate vessel containing a solution of 3-bromo-4-[(2,4-difluorobenzyl)oxy]-1-(2,6-difluorophenyl)-5-iodo-6-methylpyridin-2(1H)-one (1.50 g, 2.64 mmol) and tetrakis(tripheylphosphine)palladium (294 mg, 0.254 mmol) in anhydrous THF (4 mL). This resulting suspension was heated to 55° C. for 40 minutes and cooled to room temperature, whereby it was stirred under a positive pressure of argon for an additional 4.0 hours until complete disappearance of starting material by LCMS analysis. The reaction suspension was subsequently treated with NaHCO₃ and brine (100 and 200 mL, respectively). The resulting emulsion was extracted with ethyl acetate (3×300 mL) and the organic extracts were Na₂SO₄ dried, filtered, and concentrated in vacuo to a residue that was then subjected to SiO₂ chromatography with ethyl acetate/hexanes (3:7) to furnish a reddish solid (1.25 g, 86%). ¹H NMR (400 MHz, CDCl₃) δ 7.51–7.39 (m, 2H), 7.38–7.24 (m, 5H), 7.10 (app t, J=8.5 Hz, 2H), 6.84 (d, J=17.2 Hz, 1H), 6.82–6.75 (m, 1H), 6.74–6.68 (m, 1H), 6.69 (d, J=17.2 Hz, 1H), 5.11 (br s, 2H), 2.15 (s, 3H); LC/MS C-18 column, t$_r$=3.74 minutes (5 to 95% acetonitrile/water over 5 minutes at 1 ml/min with detection 254 nm, at 50° C.). ES-MS m/z 544 (M+H).

ES-HRMS m/z 544.0565 (M+H calcd for $C_{27}H_{19}BrF_4NO_2$ requires 544.0530).

Example 574

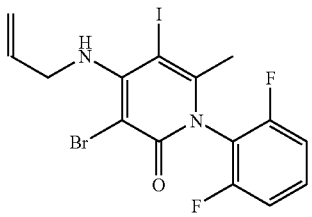

4-(allylamino)-3-bromo-1-(2,6-difluorophenyl)-5-iodo-6-methylpyridin-2(1H)-one

Step 1: A slurry of 3-bromo-4-[(2,4-difluorobenzyl)oxy]-1-(2,6-difluorophenyl)-5-iodo-6-methylpyridin-2(1H)-one (1.40 g, 2.46 mmol) and allyl amine (1.98 mg, 34.6 mmol) was heated to 50° C. and stirred for 1.0 hours until complete disappearance of starting material by LCMS analysis. The reaction mixture was then concentrated in vacuo (1.0 mm Hg) for 2 days at 50° C. to furnish a brown solid (1.18 g, 99%). $^1$H NMR (300 MHz, CDCl$_3$) δ 7.43 (app tt, J=8.4, 6.2, 1H), 7.09 (app t, J=8.4 Hz, 2H), 6.02 (app dq, J=11.0, 6.2 Hz, 1H), 5.39 (dd, J=16.9, 1.8 Hz, 1H), 5.30 (dd, J=11.0, 1.8 Hz, 1H), 4.84 (br s, 1H), 4.35 (br s, 2H), 2.42 (s, 3H); LC/MS C-18 column, t$_r$=2.71 minutes (5 to 95% acetonitrile/water over 5 minutes at 1 ml/min with detection 254 nm, at 50° C.). ES-MS m/z 481 (M+H). ES-HRMS m/z 480.9261 (M+H calcd for $C_{15}H_{13}BrF_2I N_2O$ requires 480.9219).

Example 575

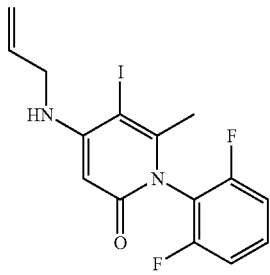

4-(allylamino)-1-(2,6-difluorophenyl)-5-iodo-6-methylpyridin-2(1H)-one

Step 1: A solution of 4-(allylamino)-3-bromo-1-(2,6-difluorophenyl)-5-iodo-6-methylpyridin-2(1H)-one (1.00 g, 2.07 mmol) and tetrakis(tripheylphosphine)palladium (420 mg, 0.363 mmol) in anhydrous THF (10 mL) under an argon stream was heated to 64° C. and stirred for 12 hours until complete disappearance of starting material by LCMS analysis. The reaction suspension was subsequently treated with brine (600 mL). The resulting emulsion was extracted with ethyl acetate (3×400 mL) and the organic extracts were anhy. Na$_2$SO$_4$ dried, filtered, and concentrated in vacuo to a residue that was then subjected to SiO$_2$ chromatography with ethyl acetate/hexanes (gradient 3:7) to furnish a solid (376 mg, 45%). $^1$H NMR (400 MHz, d$_4$-MeOH) δ 7.55 (app tt, J=8.7, 6.3, 1H), 7.18 (app t, J=7.6 Hz, 2H), 5.89 (app ddd, J=15.4, 10.3, 5.1 Hz, 1H), 5.01 (app d, J=17.0, Hz, 1H), 5.50 (s, 1H), 5.22 (app d, J=11.0 Hz, 1H), 4.35 (app d, J=5.0 Hz, 2H), 2.36 (s, 3H); LC/MS C-18 column, t$_r$=2.33 minutes (5 to 95% acetonitrile/water over 5 minutes at 1 ml/min with detection 254 nm, at 50° C.). ES-MS m/z 403 (M+H). ES-HRMS m/z 403.0133 (M+H calcd for $C_{15}H_{14}F_2I N_2O$ requires 403.0113).

Example 576

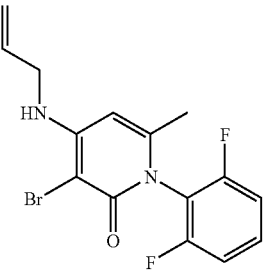

4-(allylamino)-1-(2,6-difluorophenyl)-5-iodo-6-methylpyridin-2(1H)-one

Step 1: A solution of 3-bromo-4-[(2,4-difluorobenzyl)oxy]-1-(2,6-difluorophenyl)-6-methylpyridin-2(1H)— one (197 mg, 0.445 mmol) and allyl amine (1.32 mg, 23.1 mmol) in THF (6.0 mL) was heated to 68° C. and stirred for 74.0 hours. The reaction mixture was then concentrated in vacuo (30 mm Hg) to furnish a residue that was subjected to SiO$_2$ chromatography with ethyl acetate/hexanes (3:7) to furnish a solid (36.0 mg, 23%). $^1$H NMR (400 MHz, d$_4$-MeOH) δ 7.55 (app tt, J=8.5, 6.5, 1H), 7.18 (app t, J=8.5 Hz, 2H), 6.14 (s, 1H), 5.91 (app dq, J=11.5, 6.4 Hz, 1H), 5.23 (dd, J=17.0, 1.5 Hz, 1H), 5.19 (dd, J=11.0, 1.6 Hz, 1H), 4.00 (app d, J=4.7 Hz , 2H), 1.98 (s, 3H); LC/MS C-18 column, t$_r$=2–0.24 minutes (5 to 95% acetonitrile/water over 5 minutes at 1 ml/min with detection 254 nm, at 50° C.). ES-MS m/z 355 (M+H). ES-HRMS m/z 355.0257 (M+H calcd for $C_{15}H_{14}F_2BrF_2N_2O$ requires 355.0252).

Example 577

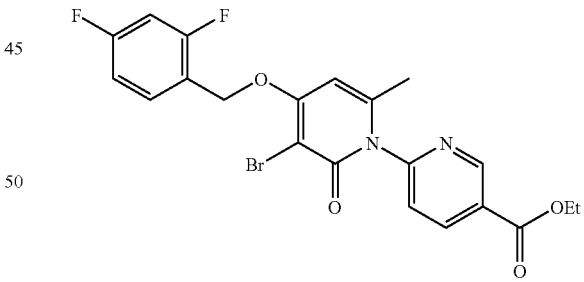

ethyl 3-bromo-4-[(2,4-difluorobenzyl)oxy]-6-methyl-2-oxo-2H-1,2'-bipyridine-5'-carboxylate Step 1: To a room temperature suspension of 3-bromo-4-[(2,4-difluorobenzyl)oxy]-6-methylpyridin-2(1H)-one (500.0 mg, 1.51 mmol) and Cs$_2$CO$_3$ (1.50 g, 4.60 mmol) in 1-methyl-2-pyrrolidinone (3.0 mL) was added ethyl 6-chloronicotinate (900 mg, 4.85 mmol). The resulting suspension was stirred and heated to 106° C. for 36 hours until complete consumption of starting material by LCMS analysis. The reaction mixture was then diluted with ethyl acetate (400 mL), water washed (3×200 mL). The resulting organic extract was separated, Na₂SO₄ dried, and concentrated. The resulting dark residue was subjected to SiO₂ chromatography with ethyl acetate/hexanes (3:7) to furnish a solid. $^1$H NMR (400 MHz, d₄-MeOH) δ 8.68 (app d, J=2.5 Hz, 1H), 8.39 (dd, J=8.7, 2.3 Hz, 1H), 7.62 (app q, J=8.2 Hz, 1H), 7.15 (d, J=8.6 Hz, 1H), 7.08 (s, 1H), 7.08–6.99 (m, 2H), 5.31 (s, 2H), 4.37 (q, J=7.1 Hz, 2H), 2.43 (s, 3H), 1.37 (t, J=7.1 Hz, 3H); LC/MS C-18 column, $t_r$=3.44 minutes (5 to 95% acetonitrile/water over 5 minutes at 1 ml/min with detection 254 nm, at 50° C.). ES-MS m/z 479 (M+H). ES-HRMS m/z 479.0401 (M+H calcd for $C_{21}H_{18}BrF_2N_2O_4$ requires 479.0431).

Example 578

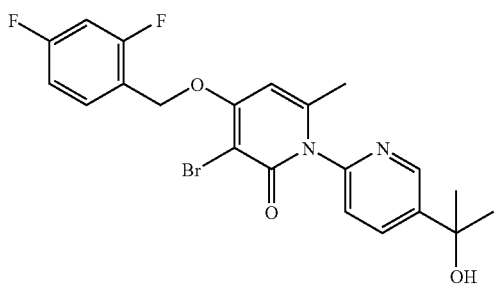

3-bromo-4-[(2,4-difluorobenzyl)oxy]-5'-(1-hydroxy-1-methylethyl)-6-methyl-2H-1,2'-bipyridin-2-one Step 1: To a 0° C. solution of methyl magnesium bromide (3.0 M, 3.5 mL, 10.5 mmol) was added dropwise over 15 minutes a solution of ethyl 3-bromo-4-[(2,4-difluorobenzyl)oxy]-6-methyl-2-oxo-2H-1,2'-bipyridine-5'-carboxylate (500.0 mg, 1.05 mmol) in THF (4.0 mL). The internal temperature of the reaction was never allowed to exceed 0° C. The resulting solution was maintained for 30 minutes until complete consumption of starting material by LCMS analysis. Next, a solution of ammonium chloride (saturated aqueous, 160 mL) was added. The reaction mixture was extracted with ethyl acetate (3×100 mL) and the resulting organic extracts were separated, Na₂SO₄ dried, and concentrated in vacuo to a residue that was subjected to SiO₂ chromatography with ethyl acetate/hexanes (gradient 3:7 to 6:4) to furnish a solid (386 mg, 79%). $^1$H NMR (400 MHz, d₄-MeOH) δ 8.23 (app d, J=2.8 Hz, 1H), 7.97 (dd, J=8.6, 2.3 Hz, 1H), 7.61 (app q, J=8.2 Hz, 1H), 7.06–7.00 (m, 3H), 7.00 (s, 1H), 5.30 (s, 2H), 2.38 (s, 3H), 1.54 (s, 6H); LC/MS C-18 column, $t_r$=2.75 minutes (5 to 95% acetonitrile/water over 5 minutes at 1 ml/min with detection 254 nm, at 50° C.). ES-MS m/z 465 (M+H). ES-HRMS m/z 465.0615 (M+H calcd for $C_{21}H_{20}BrF_2N_2O_3$ requires 465.0620). IR(neat) 3366, 3030, 2974, 1600, 1507, 1362, 1232 cm$^{-3}$. $^{13}$C NMR (400 MHz, d₄-MeOH, visible peaks with carbon fluorine coupling present) δ 164.4, 160.7, 158.9, 157.6, 143.6, 141.6, 137.5, 131.61, 131.56, 131.51, 131.46, 119.29, 119.25, 119.15, 119.11, 112.23, 111.55, 111.52, 111.33, 111.29, 106.0, 103.9, 103.7, 103.4, 96.8, 70.3, 64.9, 64.8, 30.5, 22.6.

Example 579

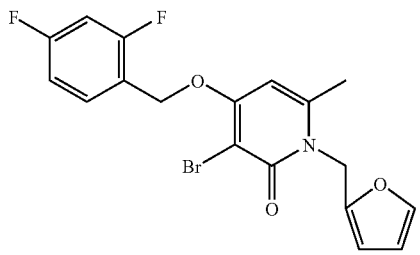

3-bromo-4-[(2,4-difluorobenzyl)oxy]-1-(2-furylmethyl)-6-methylpyridin-2(1H)-one

Step 1: Preparation of the title compound. To a room temperature suspension of 3-bromo-4-[(2,4-difluorobenzyl)oxy]-6-methylpyridin-2(1H)-one (330.0 mg, 1.00 mmol)) and NaH (48.0 mg, 2.0 mmol) in THF (3.0 mL) was added 2-(chloromethyl)furan (461 mg, 3.97 mmol). The resulting suspension was stirred and heated to 68° C. for 9 hours until complete consumption of starting material by LCMS analysis. The reaction mixture was then diluted with ethyl acetate (400 mL), water washed (3×200 mL). The resulting organic extract was separated, Na₂SO₄ dried, and concentrated. The resulting dark residue was subjected to SiO₂ chromatography with ethyl acetate/hexanes (4:6) to furnish a solid. $^1$H NMR (300 MHz, d₄-MeOH) δ 7.62 (app q, J=8.4 Hz, 1H), 7.46 (s, 1H), 7.06 (app t, J=8.7 Hz, 2H), 6.51 (s, 1H), 6.41–6.37 (m, 2H), 5.37 (s, 2H), 5.32 (s, 2H), 2.61 (s, 3H); LC/MS C-18 column, $t_r$=2.63 minutes (5 to 95% acetonitrile/water over 5 minutes at 1 ml/min with detection 254 nm, at 50° C.). ES-MS m/z 410 (M+H). ES-HRMS m/z 410.0177 (M+H calcd for $C_{18}H_{15}BrF_2NO_3$ requires 410.0198).

Example 580

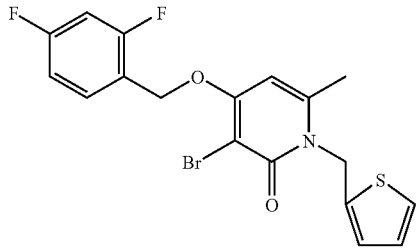

3-bromo-4-[(2,4-difluorobenzyl)oxy]-6-methyl-1-(thien-2-ylmethyl)pyridin-2(1H)-one Step 1: To a room temperature suspension of 3-bromo-4-[(2,4-difluorobenzyl)oxy]-6-methylpyridin-2(1H)-one (330.0 mg, 1.00 mmol)) and NaH (48.0 mg, 2.0 mmol) in THF (3.0 mL) was added 2-(chloromethyl)thiophene (461 mg, 3.97 mmol). The resulting suspension was stirred and heated to 68° C. for 12 hours until complete consumption of starting material by LCMS analysis. The reaction mixture was then diluted with ethyl acetate (400 mL), water washed (3×200 mL). The resulting organic extract was separated, $Na_2SO_4$ dried, and concentrated. The resulting dark residue was subjected to $SiO_2$ chromatography with ethyl acetate/hexanes (4:6) to furnish a solid. $^1H$ NMR (400 MHz, $d_4$-MeOH) δ 7.58 (app q, J=8.2 Hz, 1H), 7.30 (app dd, J=5.1, 1.2 Hz, 1H), 7.05 (d, J=2.6 Hz, 1H), 7.01 (app t, J=8.1 Hz, 2H), 6.93 (dd, J=5.1, 3.4 Hz, 1H), 6.43 (s, 1H), 5.49 (s, 2H), 5.25 (s, 2H), 2.51 (s, 3H); LC/MS C-18 column, $t_r$=2.74 minutes (5 to 95% acetonitrile/water over 5 minutes at 1 ml/min with detection 254 nm, at 50° C.). ES-MS m/z 426 (M+H). ES-HRMS m/z 425.9936 (M+H calcd for $C_{18}H_{15}BrF_2NO_2S$ requires 425.9969).

Example 581

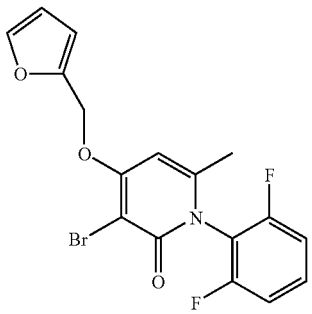

3-bromo-1-(2,6-difluorophenyl)-4-(2-furylmethoxy)-6-methylpyridin-2(1H)-one

Step 1: To a suspension of 3-bromo-4-[(2,4-difluorobenzyl)oxy]-1-(2,6-difluorophenyl)-6-methylpyridin-2(1H)— one (250 mg, 0.445 mmol) and furfuryl alcohol (198 mg, 2.0 mmol) in THF (2.5 mL) was added solid NaH (46.0 mg, 1.92 mmol). Following the evolution of gas, the resulting suspension laws heated to 60° C. and stirred for 3.5 hours until complete consumption of starting material by LCMS analysis. The reaction mixture was then diluted with ammonium chloride (saturated aqueous, 100 mL) and extracted with ethyl acetate (3×100 mL). The resulting organic extracts were separated, $Na_2SO_4$ dried, and concentrated to provide a residue that was subjected to $SiO_2$ chromatography with ethyl acetate/hexanes (3:7) to furnish a solid (110.0 mg, 49%). $^1H$ NMR (400 MHz, $d_4$-MeOH) δ 7.63 (app tt, J=8.5, 6.2, 1H), 7.62–7.61 (m, 1H), 7.28 (app t, J=8.5 Hz, 2H), 6.77 (s, 1H), 6.68 (d, J=4.1 Hz, 1H), 6.51 (dd, J=4.2, 3.9 Hz, 1H), 5.34 (s, 2H), 2.15 (s, 3H); LC/MS C-18 column, $t_r$=2.43 minutes (5 to 95% acetonitrile/water over 5 minutes at 1 ml/min with detection 254 nm, at 50° C.). ES-MS m/z 396 (M+H). ES-HRMS m/z 396.0044 (M+H calcd for $C_{17}H_{13}BrF_2NO_3$ requires 396.0041).

Example 582

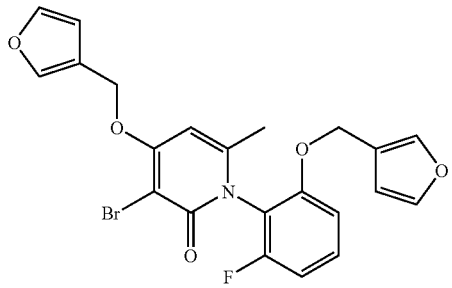

3-bromo-1-[2-fluoro-6-(3-furylmethoxy)phenyl]-4-(3-furylmethoxy)-6-methylpyridin-2(1H)-one By following the method of preparation of 3-bromo-1-(2,6-difluorophenyl)-4-(2-furylmethoxy)-6-methylpyridin-2(1H)-one (Example 581) and substituting 3-furylmethanol for furfuryl alcohol, the title compound was prepared in 55% chemical yield. $^1H$ NMR (400 MHz, $d_4$-MeOH) δ 7.64 (s, 1H), 7.55–7.42 (m, 3H), 7.40 (app t, J=1.4 Hz, 1H), 7.12 (d, J=9.0 Hz, 1H), 6.92 (app t, J=8.4 Hz, 1H), 6.58 (s, 2H), 6.34 (br s, 1H), 5.21 (s, 2H), 5.03 (AB-q, J=14.0 Hz, Δ=58.0 Hz, 2H), 1.99 (s, 3H); LC/MS C-18 column, $t_r$=2.67 minutes (5 to 95% acetonitrile/water over 5 minutes at 1 ml/min with detection 254 nm, at 50° C.). ES-MS m/z 474 (M+H). ES-HRMS m/z 474.0346 (M+H calcd for $C_{22}H_{18}BrFNO_5$ requires 474.0347).

Example 583

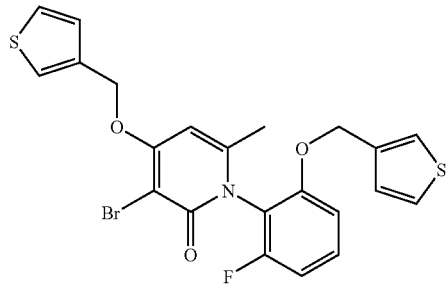

3-bromo-1-[2-fluoro-6-(thien-3-ylmethoxy)phenyl]-6-methyl-4-(thien-3-ylmethoxy)pyridin-2(1H)-one By following the method of preparation of 3-bromo-1-(2,6-difluorophenyl)-4-(2-furylmethoxy)-6-methylpyridin-2(1H)-one Example 581 and substituting thien-3-ylmethanol for furfuryl alcohol, the title compound was prepared in 38% chemical yield. $^1H$ NMR (400 MHz, $d_4$-MeOH) δ 7.50–7.42 (m, 3H), 7.33 (dd, J=5.0, 3.0 Hz, 1H), 7.26 (br d, J=2.0 Hz, 1H), 7.19 (dd, J=5.0, 1.2 Hz, 1H), 7.09 (d, J=8.6 Hz, 1H), 6.98 (dd, J=14.9, 1.3 Hz, 1H), 6.93 (dt, J=8.7, 1.0 Hz, 1H), 6.53 (br s, 1H), 5.33 (s, 2H), 5.14 (AB-q, J=12.1 Hz, Δ=50.0 Hz, 2H), 1.97 (s, 3H); LC/MS C-18 column, $t_r$=2.93 minutes (5 to 95% acetonitrile/water over 5 minutes at 1 ml/min with detection 254 nm, at 50° C.). ES-MS m/z 506 (M+H). ES-HRMS m/z 505.9881 (M+H calcd for $C_{22}H_{18}BrFNO_3S_2$ requires 505.9890).

Example 584

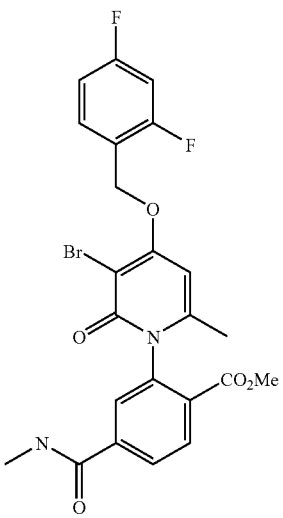

methyl 2-[3-bromo-4-[(2,4-difluorobenzyl)oxy]-6-methyl-2-oxopyridin-1(2H)-yl]-4-[(methylamino)carbonyl]benzoate Step 1: Preparation of 3-(4-hydroxy-6-methyl-2-oxopyridin-1(2H)-yl)-4-(methoxycarbonyl)benzoic acid.

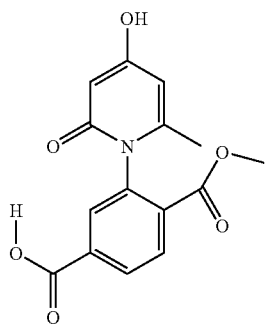

4-Hydroxy-6-methyl-2-pyrone (75.0 g, 595 mmol) and 3-amino-4-(methoxycarbonyl)benzoic acid (40.0 g, 0.205 mmol) were suspended in 56 ml of 1,2-dichlorobenzene in a 500 ml, 3-necked, round bottom flask equipped with a J-Kem temperature controller probe, a Dean-Stark trap, and a heating mantle. The reaction was heated to 180° C. over a period of 26 minutes during which time all solids dissolved. Upon reaching an internal temperature of 180° C., the reaction was allowed to maintain this temperature for an additional 25.0 minutes during which time the evolution of water from the reaction mixture was evident. Next, the heating apparatus was removed and the reaction was allowed to cool on its own accord to about 100° C. The reaction was then diluted with 160 ml of toluene and stirred. After about 10 minutes, the reaction reached room temperature and a gummy solid had formed. The precipitate was filtered, washed with EtOAc (400 mL) and water (200 mL, 55° C.), and dried in vacuo to give a tan solid (30.5 g, 49%). $^1$H NMR (400 MHz, $d_4$-MeOH) δ 8.20–8.09 (m, 2H), 7.84 (s, 1H), 6.08 (app d, J=1.0 Hz, 1H), 5.76 (app d, J=2.3 Hz, 1H), 3.76 (s, 3H), 1.91 (s, 3H). LC/MS, C-18 column, $t_r$=1.96 minutes (5 to 95% acetonitrile/water over 5 minutes at 1 ml/min with detection 254 nm, at 50° C.). ES-MS m/z 304 (M+H). ES-HRMS m/z 304.0803 (M+H calcd for $C_{15}H_{14}NO_6$ requires 304.0816).

Step 2: Preparation of methyl 2-(4-hydroxy-6-methyl-2-oxopyridin-1(2H)-yl)-4-[(methylamino)carbonyl]benzoate.

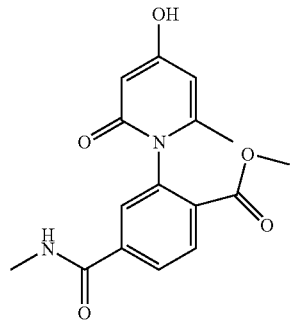

To a solution of 3-(4-hydroxy-6-methyl-2-oxopyridin-1(2H)-yl)-4-(methoxycarbonyl)benzoic acid (from Step 1) (1.00 g, 3.30 mmol) in dimethylformamide (10 mL) and THF (10 mL) was added cyclohexylcarbodiimide-derivatized silica gel (a product of Silicycle chemical division Quebec, Canada) with a loading of 0.60 mmol/g (15.2 g, 9.73 mmol). After stirring for 30 minutes, a solution of methylamine (2.0 M, THF, 2.9 mL, 5.8 mmol) was added followed by the addition of 1-hydroxy-benzotriazole (20.0 mg, 0.15 mmol). The reaction suspension was allowed to stir for 24 hours until the complete disappearance of starting material by LCMS analysis. The silica suspension was filtered and washed with 300 mL ethyl acetate/methanol (9:1) and 300 mL ethyl acetate/methanol (1:1). The resulting mother liquor was concentrated to furnish a brown semi-solid (898 mg, 86%). $^1$H NMR (300 MHz, $d_4$-MeOH) δ 8.22 (d, J=8.0 Hz, 1H), 8.04 (dd, J=8.3, 1.9 Hz, 1H), 7.73 (d, J=1.6 Hz, 1H), 6.13 (d, J=1.5 Hz, 1H), 5.80 (d, J=2.2 Hz, 1H), 3.80 (s, 3H), 3.03 (s, 3H), 1.97 (s, 3H). LC/MS, C-18 column, $t_r$=1.31 minutes (5 to 95% acetonitrile/water over 5 minutes at 1 ml/min with detection 254 nm, at 50° C.). ES-MS m/z 317 (M+H). ES-HRMS m/z 317.1142 (M+H calcd for $C_{16}H_{17}N_2O_5$ requires 317.1132).

Step 3: Preparation of methyl 2-(3-bromo-4-hydroxy-6-methyl-2-oxopyridin-1(2H)-yl)-4-[(methylamino)carbonyl]benzoate.

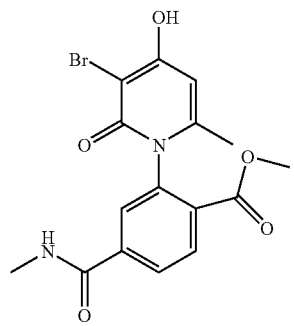

To a room temperature suspension of methyl 2-(4-hydroxy-6-methyl-2-oxopyridin-1(2H)-yl)-4-[(methylamino)carbonyl]benzoate (from Step 2) (406.0 mg, 1.28 mmol) in $CH_2Cl_2$ (8 mL) was added solid N-bromosuccinimide (251 mg, 1.41 mmol) and stirred for 10 minutes until complete consumption of starting material by LCMS analysis. The reaction was next diluted with $CH_2Cl_2$ (5 mL), ethyl acetate (5 mL), and hexanes (1 mL). After approximately 30 minutes the resulting white precipitate was filtered and washed with ethyl acetate (5 mL) to furnish a solid (298 mg, 62%). $^1$H NMR (400 MHz, $d_4$-MeOH) δ 8.20 (d, J=8.2 Hz, 1H), 8.01 (d, J=8.1 Hz, 1H), 7.69 (s, 1H), 6.18 (s 1H), 3.75 (s, 3H), 2.91 (s, 3H), 1.91 (s, 3H); LC/MS, $t_r$=1.27 minutes (5 to 95% acetonitrile/water over 5 minutes at 1 ml/min with detection 254 nm, at 50° C.). ES-MS m/z 395 (M+H). ES-HRMS m/z 395.0237 (M+H calcd for $C_{16}H_{16}BrN_2O_5$ requires 395.0237).

Step 4: Preparation of the Title Compound

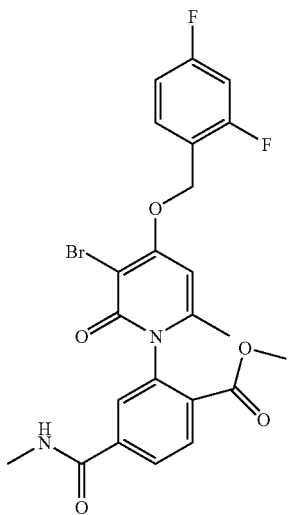

To a solution of methyl 2-(3-bromo-4-hydroxy-6-methyl-2-oxopyridin-1(2H)-yl)-4-[(methylamino)carbonyl] benzoate (from Step 3) (241 mg, 0.610 mmol) in dimethylformamide (0.5 mL) was added sequentially $K_2CO_3$ (240 mg, 1.73 mmol) and 2,4 difluorobenzyl bromide (0.085 mL, 0.66 mmol). The resulting suspension was stirred for 6.5 hours until complete consumption of starting material by LCMS analysis. The reaction was then diluted with ethyl acetate (200 mL) and brine washed (3×200 mL). The resulting organic extract was $Na_2SO_4$ dried, filtered, and concentrated in vacuo to approximately 5 mL volume. The resulting mother liquor rapidly precipitated and furnished an amorphous solid that was collected. $^1$H NMR (400 MHz, $d_4$-MeOH) δ 8.22 (d, J=8.2 Hz, 1H), 8.03 (dd, J=8.2, 1.7 Hz, 1H), 7.71 (d, J=1.8 Hz, 1H), 7.67 (app q, J=8.3 Hz, 1H), 7.05 (app t, J=8.6 Hz, 2H), 6.64 (s, 1H), 5.37 (s, 2H), 3.74 (s, 3H), 2.90 (s, 3H), 2.01 (s, 3H). LC/MS C-18 column, $t_r$=2.87 minutes (5 to 95% acetonitrile/water over 5 minutes at 1 ml/min with detection 254 nm, at 50° C.). ES-MS m/z 521 (M+H). ES-HRMS m/z 521.0491 (M+H calcd for $C_{23}H_{20}BrF_2N_2O_5$ requires 521.0518).

Example 585

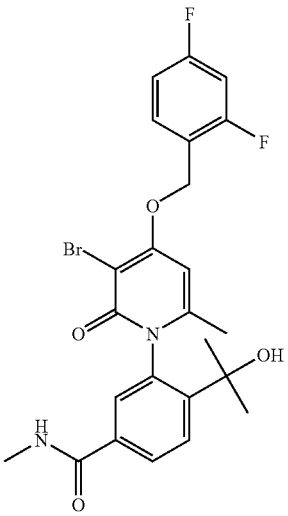

3-[3-bromo-4-[(2,4-difluorobenzyl)oxy]-6-methyl-2-oxopyridin-1(2H)-yl]-4-(1-hydroxy-1-methylethyl)-N-methylbenzamide Step 1: To a −10° C. solution of methyl magnesium bromide (3.0 M, 0.60 mL, 1.8 mmol) was added dropwise over 10 minutes a solution of methyl 2-[3-bromo-4-[(2,4-difluorobenzyl)oxy]-6-methyl-2-oxopyridin-1(2H)-yl]-4-[(methylamino)carbonyl]benzoate (85.0 mg, 0.163 mmol) in THF (1.0 mL). The internal temperature of the reaction was never allowed to exceed 0° C. The resulting solution was maintained for 10 minutes. Next, a solution of ammonium chloride (saturated aqueous, 100 mL) was added. The reaction mixture was removed from the bath and resulting emulsion was extracted with ethyl acetate (3×100 mL) and the resulting organic extracts were separated, $Na_2SO_4$ dried, and concentrated in vacuo to a residue that was subjected to $SiO_2$ chromatography with ethyl acetate/hexanes (gradient 3:7 to 6:4) to furnish a solid (16 mg, 19%). $^1$H NMR (400 MHz, $d_4$-MeOH) δ 7.89 (d, J=8.5 Hz, 1H), 7.78 (d, J=8.4 Hz, 1H), 7.61 (app q, J=8.2 Hz, 1H), 7.41 (s, 1H), 7.03–6.99 (m, 2H), 6.57 (s, 1H), 5.30 (s, 2H), 2.83 (s, 3H), 2.05 (s, 3H), 1.51 (s, 3H), 1.39 (s, 3H); LC/MS C-18 column, $t_r$=2.28 minutes (5 to 95% acetonitrile/water over 5 minutes at 1 ml/min with detection 254 nm, at 50° C.). ES-MS m/z 521 (M+H). ES-HRMS m/z 521.0860 (M+H calcd for $C_{24}H_{24}BrF_2N_2O_4$ requires 521.0882).

Example 586

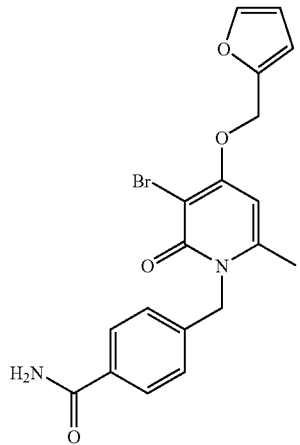

3-bromo-1-[2-fluoro-6-(thien-3-ylmethoxy)phenyl]-6-methyl-4-(thien-3-ylmethoxy)pyridin-2(1H)-one By following the method of preparation of 3-bromo-1-(2,6-difluorophenyl)-4-(2-furylmethoxy)-6-methylpyridin-2(1H)-one Example 581 and substituting 4-{[3-bromo-4-[(2,4-difluorobenzyl)oxy]-6-methyl-2-oxopyridin-1(2H)-yl]methyl}benzamide for 3-bromo-4-[(2,4-difluorobenzyl)oxy]-1-(2,6-difluorophenyl)-6-methylpyridin-2(1H)-one, the title compound was prepared in 76% chemical yield. $^1$H NMR (400 MHz, d$_4$-MeOH) δ 7.83 (d, J=8.1 Hz, 2H), 7.54 (app d, J=1.1 Hz, 1H), 7.19 (d, J=8.1 Hz, 2H), 6.57 (d, J=3.2 Hz, 1H), 6.53 (s, 1H), 6.43 (dd, J=3.1, 1.8 Hz, 1H), 5.45 (br s, 2H), 5.22 (s, 2H), 2.34 (s, 3H); LC/MS C-18 column, t$_r$=1.98 minutes (5 to 95% acetonitrile/water over 5 minutes at 1 ml/min with detection 254 nm, at 50° C.). ES-MS m/z 417 (M+H). ES-HRMS m/z 417.0469 (M+H calcd for C$_{19}$H$_{18}$BrN$_2$O$_4$ requires 417.0444).

Example 587

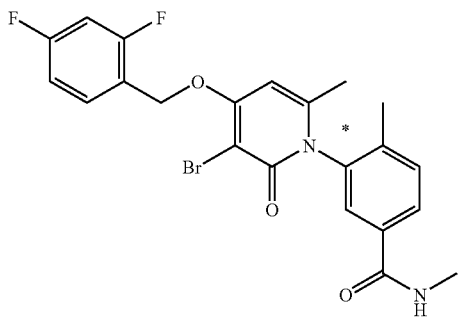

(−)-3-[3-bromo-4-[(2,4-difluorobenzyl)oxy]-6-methyl-2-oxopyridin-1(2H)-yl]-N, 4-dimethylbenzamide Example 489 (1.78 g, 4.36 mmol) were separated using a Chiral Technologies Chiralpak AD column (21 mm×250 mm, 20 μm) eluting with 100% ethanol (isocratic, 20 ml/min), loading 10 mg per injection. Fractions of the early-eluting atropisomer were pooled and concentrated in vacuo to the title compound (718 mg, 80%). Analytical chiral LC (Chiralpak AD, 4.6 mm×50 mm, 10 μm particle size, 0.5 ml/min ethanol) Retention time: 1.70 min, ee 94%. [α]$_D$=−23.8 ° (5 mg/ml DMSO, 22° C.). $^1$H NMR (400 MHz, DMSO-d$_6$) δ 8.42 (br qr, J=4.51 Hz, 1H), 7.82 (dd, J=7.92, 1.70 Hz, 1H), 7.68 (dt, J=8.24, 6.58 Hz, 1H), 7.58 (d, J=1.59 Hz, 1H), 7.48 (d, J=7.98 Hz, 1H), 7.34 (dt, J=9.90, 2.50 Hz, 1H), 7.18 (dt, J=8.53, 2.57 Hz, 1H), 6.71 (s, 1H), 5.33 (s, 2H), 2.74 (s, 3H), 1.98 (s, 3H), 1.88 (s, 3H). $^{19}$F-NMR (400 MHz, DMSO-d$_6$) δ−109.58 (quintet, J=7.49 Hz, 1 F), −113.65 (quartet, J=9.11 Hz, 1 F). ES-HRMS m/z 477.0612 (M+H calcd for C$_{22}$H$_{20}$BrF$_2$N$_2$O$_3$ requires 477.0620).

Example 588

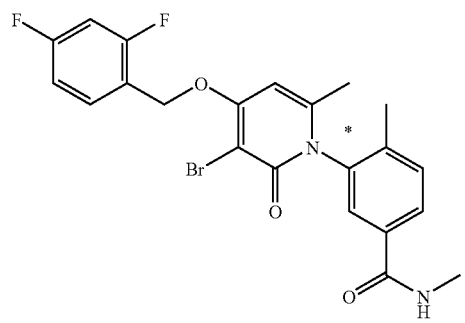

(+)-3-[3-bromo-4-[(2,4-difluorobenzyl)oxy]-6-methyl-2-oxopyridin-1(2H)-yl]-N,4-dimethylbenzamide The title compound was prepared as in Example 587, pooling the late-eluting atropisomer (722 mg, 81%). Analytical chiral LC (Chiralpak AD, 4.6 mm×50 mm, 10 μm particle size, 0.5 ml/min ethanol) Retention time: 2.00 min, ee 98%. [α]$_D$=+28.2° (5 mg/ml DMSO, 22° C.). $^1$H NMR (400 MHz, DMSO-d$_6$) δ 8.42 (br qr, J=4.51 Hz, 1H), 7.82 (dd, J=7.92, 1.70 Hz, 1H), 7.68 (dt, J=8.24, 6.58 Hz, 1H), 7.58 (d, J=1.59 Hz, 1H), 7.48 (d, J=7.98 Hz, 1H), 7.34 (dt, J=9.90, 2.50 Hz, 1H), 7.18 (dt, J=8.53, 2.57 Hz, 1H), 6.71 (s, 1H), 5.33 (s, 2H), 2.74 (s, 3H), 1.98 (s, 3H), 1.88 (s, 3H). $^{19}$F-NMR (400 MHz, DMSO-d$_6$) δ−109.58 (quintet, J=7.49 Hz, 1 F), −113.65 (quartet, J=9.11 Hz, 1 F). ES-HRMS m/z 477.0614 (M+H calcd for C$_{22}$H$_{20}$BrF$_2$N$_2$O$_3$ requires 477.0620).

Example 589

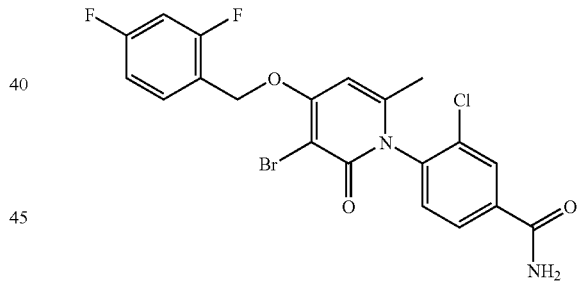

4-[3-bromo-4-[(2,4-difluorobenzyl)oxy]-6-methyl-2-oxopyridin-1(2H)-yl]-3-chlorobenzamide Step 1: Preparation of methyl 3-chloro-4-(4-hydroxy-6-methyl-2-oxopyridin-1(2H)-yl)benzoate.

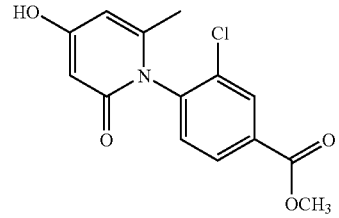

4-Hydroxy-6-methyl-2-pyrone (24.5 g, 193.9 mmol) and methyl-3-amino-2-chlorobenzoate (30 g, 161.6 mmol) were suspended in 75 ml of 1,2-dichlorobenzene in a 250 ml, 3-necked round bottom flask equipped with a J-Kem temperature controller probe, a Dean-Stark trap, and a heating mantle. The reaction was heated to 175° C. for 20 minutes, during which, water and some 1,2-dichlorobenzene was collected in the Dean-Stark trap. The reaction was allowed to cool to about 110° C. At this point, 200 ml of toluene was added. The toluene mixture was allowed to stir for 72 hours at room temperature. A precipitate was collected on a filter pad. The precipitate was filtered and washed 3 times with toluene, 3 times with 50° C. water to remove excess pyrone, and dried in vacuo to give a tan solid (13.0 g, 27% yield). $^1$H NMR (300 MHz, CD$_3$OD) δ 8.26 (d, J=1.81 Hz, 1H), 8.14 (dd, J=8.26, 1.81 Hz, 1H), 7.54 (d, J=8.26, Hz, 1H), 6.14 (dd, J=2.42, 1.0 Hz, 1H), 5.83 (d, J=2.42 1H), 4.00 (s, 3H), 1.96 (s, 3H); LC/MS, t$_r$=1.81 minutes (5 to 95% acetonitrile/water over 5 minutes at 1 ml/min with detection 254 nm, at 50° C.). ES-MS m/z 294 (M+H)

Step 2: Preparation of methyl 3-chloro-4-[4-[(2,4-difluorobenzyl)oxy]-6-methyl-2-oxopyridin-1(2H)-yl]benzoate.

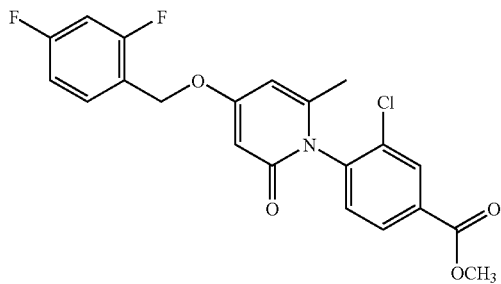

Methyl 3-chloro-4-(4-hydroxy-6-methyl-2-oxopyridin-1(2H)-yl)benzoate (from Step 1) (2.4 g, 8.17 mmol) was taken up in DMF (10 ml). 2,4-difluorobenzylbromide (1.05 ml, 8.17 mmol) and K$_2$CO$_3$ (1.13 g, 8.17 mmol) were added. The reaction stirred for 6 hours at room temperature. At this time, the reaction was poured into water (200 ml) and extracted with ethyl acetate. The ethyl acetate layer was dried over Na$_2$SO$_4$, filtered, and the solvent removed in vacuo to give amber oil (2.62 g, 77% crude yield). LC/MS, t$_r$=2.79 minutes (5 to 95% acetonitrile/water over 5 minutes at 1 ml/min with detection 254 nm, at 50° C.). ES-MS m/z 294 (M+H).

Step 3: Preparation of methyl 4-[3-bromo-4-[(2,4-difluorobenzyl)oxy]-6-methyl-2-oxopyridin-1(2H)-yl]-3-chlorobenzoate.

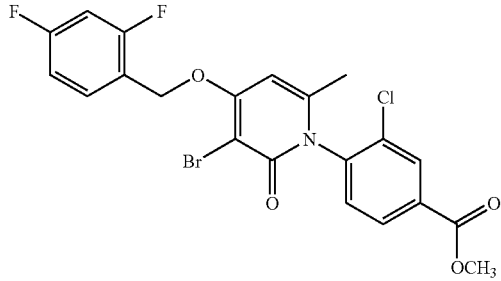

Methyl 3-chloro-4-[4-[(2,4-difluorobenzyl)oxy]-6-methyl-2-oxopyridin-1(2H)-yl]benzoate (from step 2) (2.60 g, .21 mmol) was taken up in CH$_2$Cl$_2$ (20 ml). N-bromosuccinimide (1.11 g, 6.21 mmol) was added and the mixture stirred at room temperature for 4 hours. The CH$_2$Cl$_2$ is removed in vacuo and the residue is taken up in CH$_3$CN.

The resulting precipitate is collected on a filter pad and washed with CH$_3$CN to yield a white solid (0.75 g, 24%). $^1$H NMR (300 MHz, CDCl$_3$) δ 8.22 (d, J=1.88 Hz, 1H), 8.06 (dd, J=8.19, 1.75 Hz, 1H), 7.59 (app q, J=8.46 Hz, 1H), 7.33 (d, J=8.19, 1H), 6.96 (dt, J=8.06, 1.21 Hz, 1H), 6.89–6.84 (m, 1H), 6.13 (s, 1H), 5.26 (s, 2H), 3.95 (s, 3H), 1.95 (s, 3H); ES-MS m/z 478 (M+H). ES-HRMS m/z 497.9892 (M+H calcd for C$_{22}$H$_{16}$BrClF$_2$NO$_4$ requires 497.9914).

Step 4: Preparation of 4-[3-bromo-4-[(2,4-difluorobenzyl)oxy]-6-methyl-2-oxopyridin-1(2H)-yl]-3-chlorobenzoic acid.

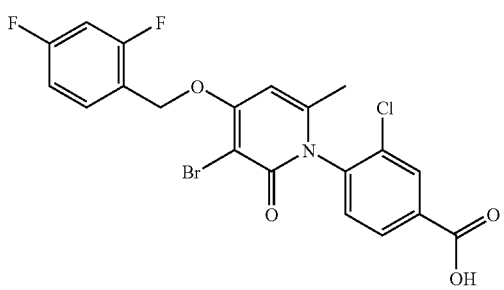

Methyl-4-[3-bromo-4-[(2,4-difluorobenzyl)oxy]-6-methyl-2-oxopyridin-1(2H)-yl]-3-chlorobenzoate (2.30 g, 4.61 mmol) was taken up in THF (20 ml) and H$_2$O (4 ml). 2.5 N NAOH (9.2 ml) was added to the vessel and the reaction stirred overnight to completion. Concentrated HCl was added dropwise until reaction was made acidic (pH=1). H$_2$O (100 ml) and THF (100 ml) were added to the mixture. The contents were poured into a separatory funnel and the aqueous layer was extracted with ethyl acetate. The organic layer was dried over Na$_2$SO$_4$, the solvent removed in vacuo, and the residue was taken up in a 50% mixture of ethyl acetate/hexane. The precipitate was collected on a filter pad to yield a white powder (1.5 g, 67%). $^1$H NMR (300 MHz, DMSO) δ 13.59 (1H), 8.16 (d, J=1.81 Hz, 1H), 8.06 (dd, J=6.24, 1.81 Hz, 1H), 7.73 (app q, J=8.46, 1H), 7.68 (d, J=8.26 Hz, 1H), 7.38 (dt, J=9.48, 2.62 Hz, 1H), 7.26–7.18 (m, 1H), 6.80 (s, 1H), 5.39 (s, 2H), 3.93 (s, 3H), 1.96 (s, 3H); ES-MS m/z 483 (M+H). ES-HRMS m/z 483.9749 (M+H calcd for C$_{20}$H$_{14}$BrClF$_2$NO$_4$ requires 483.9757).

Step 5: 4-[3-Bromo-4-[(2,4-difluorobenzyl)oxy]-6-methyl-2-oxopyridin-1(2H)-yl]-3-chlorobenzoic acid (0.5 g, 1.03 mmol) was taken up in THF (10 ml). 2-Chloro-4,6-dimethoxy-1,3,5-triazine (0.22 g, 1.24 mmol) and N-methyl morpholine (0.34 ml, 3.09 mmol) were added. The mixture stirred at room temperature for 1 hour. At this time, NH$_4$OH (2.5 ml) was added and the reaction stirred at room temperature for one more hour. To the reaction mixture was added more THF (50 ml) and water (200 ml). The mixture was extracted with ethyl acetate. The ethyl acetate extraction was washed with saturated brine solution. The brine layer was extracted with ethyl acetate. The organic layers were combined, dried over Na$_2$SO$_4$, filtered and the solvent was removed in vacuo. The residue was taken up in ethyl acetate and the resulting precipitate was collected on a filter pad to yield a white powder (0.38 g, 76%) $^1$H NMR (300 MHz, CD$_3$OD) δ 8.18 (d, J=1.81 Hz, 1H), 8.02 (dd, J=8.26, 2.01 Hz, 1H), 7.69 (app q, J=8.26 Hz, 1H), 7.55 (d, J=8.06 Hz, 1H), 7.12–7.06 (m, 2H), 6.71 (s, 1H), 5.40 (s, 2H), 2.07 (s, 3H). ES-MS m/z 482 (M+H). ES-HRMS m/z 482.9919 (M+H calcd for C$_{20}$H$_{15}$BrClF$_2$N$_2$O$_3$ requires 482.9917).

Example 590

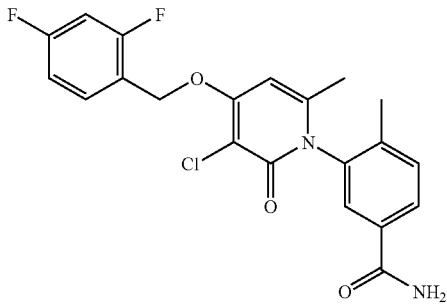

3-[3-chloro-4-(2,4-difluorobenzyl)oxy]-6-methyl-2-oxopyridin-1(H)-yl]-4-methylbenzamide Step 1: Preparation of 3-[3-chloro-4-[(2,4-difluorobenzyl)oxy]-6-methyl-2-oxopyridin-1(2H)-yl]-4-methylbenzoic acid.

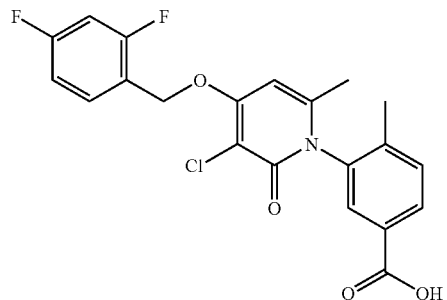

3-[4-[(2,4-Difluorobenzyl)oxy]-6-methyl-2-oxopyridin-1(2H)-yl]-4-methylbenzoic acid (from above) (7.5 g, 19.4 mmol) and NCS (2.6 g, 19.4 mmol) were taken up in 65° C. dichloroethane (100 ml). A catalytic amount of dichloroacetic acid (2 drops) was added. After two hours the solvent was removed in vacuo and the residue was taken up in diethyl ether. The precipitate was collected on a filter pad and then taken up in 50% ethyl acetate/hexanes to remove residual succinimide. The precipitate was collected on a filter pad and then dried in vacuo to produce a white powder (4.2 g, 52%). $^1$H NMR (300 MHz, CD$_3$OD) δ 8.10 (dd, J=7.85 1.81 Hz, 1H), 7.83 (d, J=8.26, 1.81 Hz, 1H), 7.40 (app q, J=8.26 Hz, 1H), 7.58 (d, J=7.85 Hz, 1H), 7.13–7.06 (m, 2H), 6.74 (s, 1H), 5.40 (s, 2H), 2.14 (s, 3H), 2.04 (s, 3H); ES-MS m/z 420 (M+H). ES-HRMS m/z 420.0786 (M+H calcd for C$_{21}$H$_{17}$ClF$_2$NO$_4$ requires 420.0809).

Step 2: 3-[3-chloro-4-[(2,4-difluorobenzyl)oxy]-6-methyl-2-oxopyridin-1(2H)-yl]-4-methylbenzoic acid (1.5 g, 3.57 mmol) was taken up in THF (30 ml). 2-Chloro-4,6-dimethoxy-1,3,5-triazine (0.75 g, 4.28 mmol) and N-methyl morpholine (1.18 ml, 10.72 mmol) were added. The mixture stirred at room temperature for 1 hour. At this time, NH$_4$OH (7.5 ml) was added and the reaction stirred at room temperature for one more hour. To the reaction mixture was added more THF (100 ml) and water (150 ml). The mixture was extracted with ethyl acetate. The ethyl acetate extraction was washed with saturated brine solution. The brine layer was extracted with ethyl acetate. The organic layers were combined, dried over Na$_2$SO$_4$, filtered and the solvent was removed in vacuo. The residue was taken up in ethyl acetate and the resulting precipitate was collected on a filter pad to yield a white powder (1.32 g, 88%) $^1$H NMR (300 MHz, CD$_3$OD) δ 7.96 (dd, J=7.85, 1.81 Hz, 1H), 7.71 (d, J=1.81 Hz, 1H), 7.67 (app q, J=8.06 Hz, 1H), 7.56 (d, J=8.06 Hz, 1H), 7.12–7.06 (m, 2H), 6.74 (s, 1H), 5.40 (s, 2H), 2.13 (s, 3H), 2.05 (s, 3H). ES-MS m/z 419 (M+H). ES-HRMS m/z 419.0979 (M+H calcd for C$_{21}$H$_{18}$ClF$_2$N$_2$O$_3$ requires 419.0969).

Example 591

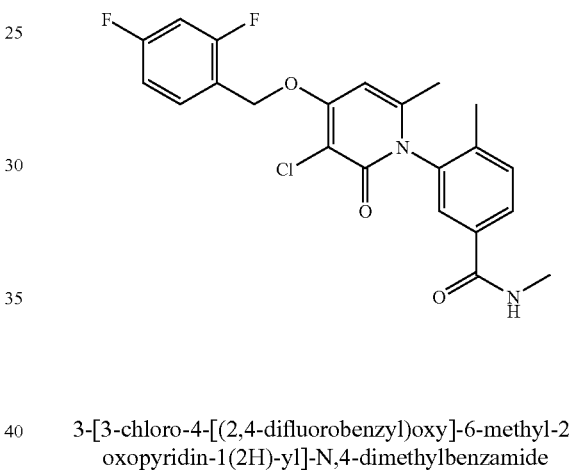

3-[3-chloro-4-[(2,4-difluorobenzyl)oxy]-6-methyl-2-oxopyridin-1(2H)-yl]-N,4-dimethylbenzamide The title compound was prepared from 3-[3-chloro-4-[(2,4-difluorobenzyl)oxy]-6-methyl-2-oxopyridin-1(2H)-yl]-4-methylbenzoic acid (from step 1 above) (1.5 g, 3.57 mmol) in dichloromethane (35 ml). To this mixture, 2.0 M methyl amine in THF (3.6 ml, 7.14 mmol) was added, followed, in order, by EDCI (0.67 g, 4.28 mmol), 1-hydroxybenzotriazole (0.58 g, 4.28 mmol) and triethylamine (0.99 ml, 7.14 mmol). The reaction was stirred at room temperature overnight. The reaction was quenched with NH$_4$Cl and extracted 3 times with ethyl acetate. The combined organic layer was then washed with saturated NaHCO$_3$ (aq.) and extracted 3 times with ethyl acetate. The organic layers were combined and washed with H$_2$O and extracted 3 times with ethyl acetate. The organic layers were combined and dried over Na$_2$SO$_4$ and evaporated. The resulting residue was triturated with diethyl ether/hexane to obtain a solid, which was dried in vacuo to give a white solid (1.5 g, 72%). $^1$H NMR (300 MHz, CD$_3$OD) δ 7.90 (dd, J=8.06, 1.81 Hz, 1H), 7.67 (app q, J=6.44 Hz, 1H), 7.55 (d, J=8.06 Hz, 1H), 7.13–7.06 (m, 2H), 6.74 (s, 1H), 5.40 (s, 2H), 2.93 (s, 3H), 2.13 (s, 3H), 2.04 (s, 3H); ES-MS m/z 433 (M+H). ES-HRMS m/z 433.1153 (M+H calcd for C$_{22}$H$_{20}$ClF$_2$N$_2$O$_3$ requires 433.1125).

Example 592

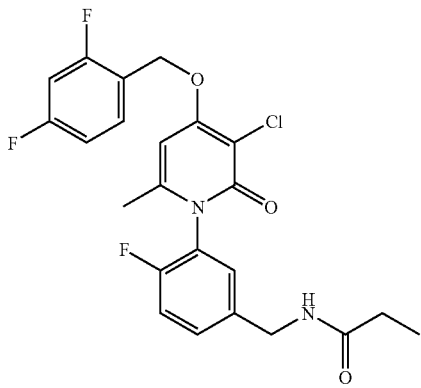

N-{3-[3-chloro-4-[(2,4-difluorobenzyl)oxy]-6-methyl-2-oxopyridin-1(2H)-yl]-4-fluorobenzyl}propanamide A 10 mL round bottomed flask equipped with stirbar and nitrogen inlet was charged with 1-[5-(aminomethyl)-2-fluorophenyl]-3-chloro-4-[(2,4 difluorobenzyl)oxy]-6-methylpyridin-2(1H)-one hydrochloride (250 mg, 0.56 mmol), propionyl chloride (49 μL, 0.56 mmol), triethylamine (195 μL, 1.4 mmol) and tetrahydrofuran (4.0 mL). After stirring at 25° C. for 5 min the reaction was completed by LC-MS. The reaction mixture was poured into a saturated aqueous $NH_4Cl$ solution. The aqueous mixture was extracted with ethyl acetate. The organic phase was dried with $Na_2SO_4$ and concentrated in vacuo to obtain (240 mg, 91%) as a yellow solid. $^1$H NMR (400 MHz, $(CD_3)_2SO$) δ 8.3 (t, J=5.8 Hz, 1H), 7.6 (q, J=8.7 and 6.58 Hz, 1H), 7.38 (d, J=7.78 Hz, 1H), 7.3 (dd, J=2.6 and 7.6 Hz, 1H), 7.22 (d, J=7.51 Hz, 1H), 7.12 (td, J=2.0 and 6.5 Hz, 1H), 6.65 (s, 1H), 5.3 (s, 2H), 4.23 (d, J=3.6 Hz, 2H), 2.1 (q, J=7.7 Hz 2H), 1.98 (s, 3H), 0.98 (t, J=7.5 Hz, 3H) ppm. ES-HRMS m/z 465.1203 (M+H calcd for $C_{23}H_{21}ClF_3N_2O_3$ requires 465.1187).

Example 593

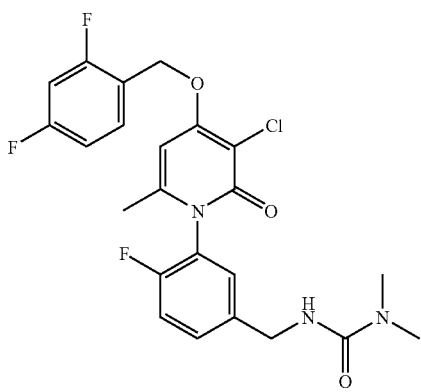

N-{3-[3-chloro-4-[(2,4-difluorobenzyl)oxy]-6-methyl-2-oxopyridin-1(2H)-yl]-4-fluorobenzyl}dimethylurea A 10 mL round bottomed flask equipped with stirbar and nitrogen inlet was charged with 1-[5-(aminomethyl)-2-fluorophenyl]-3-chloro-4-[(2,4 difluorobenzyl)oxy]-6-methylpyridin-2(1H)-one hydrochloride (250 mg, 0.56 mmol), dimethylcarbamyl chloride (52 μL, 0.56 mmol), triethylamine (195 μL, 1.4 mmol) and tetrahydrofuran (4.0 mL). After stirring at 25° C. for 5 min the reaction was completed by LC-MS. The reaction mixture was poured into a saturated aqueous $NH_4Cl$ solution. The aqueous mixture was extracted with ethyl acetate. The organic phase was dried with $Na_2SO_4$ and concentrated in vacuo to obtain the desired product (245 mg, 86%) as a white solid. $^1$H NMR (400 MHz, $(CD_3OD)$ δ 7.61 (q, J=7.9 and 6.7 Hz, 1H), 7.4 (m, 1H), 7.3 (d, J=9.3 Hz, 1H), 7.21 (m, 1H), 7.1 (m, 2H), 6.65 (s, 1H), 5.35 (s, 2H), 4.38 (s, 2H), 2.9 (s, 6H), 2.1 (s, 3H) ppm. ES-HRMS m/z 480.1269 (M+H calcd for $C_{23}H_{22}ClF_3N_3O_3$ requires 480.1296).

Example 594

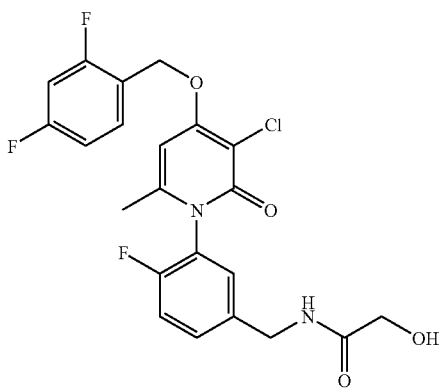

N-{3-[3-chloro-4-[(2,4-difluorobenzyl)oxy]-6-methyl-2-oxopyridin-1(2H)-yl]-4-fluorobenzyl}-2-hydroxyacetamide A 10 mL round bottomed flask equipped with stirbar and nitrogen inlet was charged with 1-[5-(aminomethyl)-2-fluorophenyl]-3-chloro-4-[(2,4 difluorobenzyl)oxy]-6-methylpyridin-2(1H)-one hydrochloride (250 mg, 0.56 mmol), acetoxyacetyl chloride (66 μL, 0.62 mmol), triethylamine (195 μL, 1.4 mmol) and tetrahydrofuran (4.0 mL). After stirring at 25° C.for 5 min the reaction was completed by LC-MS. NaOH (2.5M, 2.24 mmol, 1.0 mL) and MeOH (2.0 mL) was added and stirred for 10 min to give the title compound. The reaction mixture was acidified with concentrated HCl and extracted with ethyl. The organic phase was dried with $Na_2SO_4$ and concentrated in vacuo to obtain (217 mg, 78%) of the desired product as a yellow solid. $^1$H NMR (400 MHz, $(CD_3OD)$ δ 7.6 (q, J=7.6 and 6.9 Hz, 1H), 7.44 (m, 1H), 7.34 (m, 2H), 7.22 (m, 2H), 6.63 (s, 1H), 5.35 (s, 2H), 4.41 (s, 2H), 4.0 (s, 2H), 2.05 (s, 3H) ppm. ES-HRMS m/z 467.0957 (M+H calcd for $C_{22}H_{19}ClF_3N_2O_4$ requires 467.0980).

Example 595

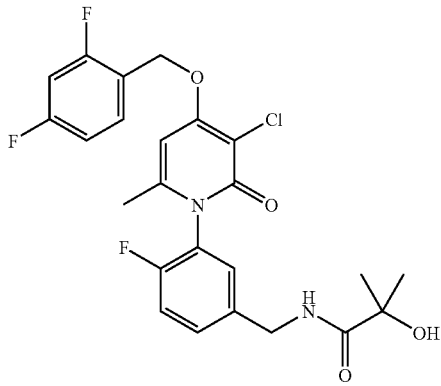

N-{3-[3-chloro-4-[(2,4-difluorobenzyl)oxy]-6-methyl-2-oxopyridin-1(2H)-yl]-4-fluorobenzyl)-2-hydroxy-2-methylpropanamide The title compound was prepared essentially as described in Example 594, with 1-chlorocarbonyl-1-methylethyl acetate substituting acetoxyacetyl chloride $^1$H NMR (400 MHz, (CDCl$_3$) δ 9.9 (q, J=8.2 and 6.5 Hz, 1H), 9.7 (t, J=2.6 Hz, 1H), 9.5 (t, J=8.9 Hz, 2H), 9.3 (m, 1H), 9.2 (m, 1H), 8.6 (s, 1H), 7.6 (s, 2H), 6.8 (d, J=15 Hz, 1H), 6.63 (d, J=15 Hz, 1H), 4.42 (d, J=3.2 Hz, 6H), 3.99 (s, 3H) ppm. ES-HRMS m/z 495.1271 (M+H calcd for C$_{24}$H$_{23}$ClF$_3$N$_2$O$_4$ requires 495.1293).

Example 596

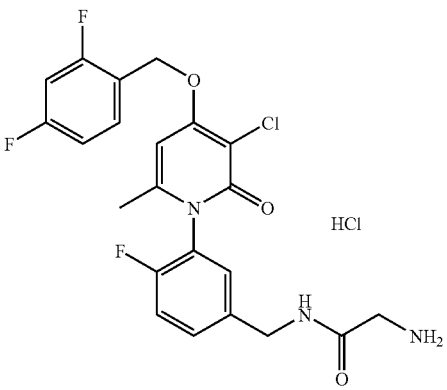

N$^1$-{3-[3-chloro-4-[(2,4-difluorobenzyl)oxy]-6-methyl-2-oxopyridin-1(2H)-yl]-4-fluorobenzyl}glycinamide hydrochloride A 25 mL round bottomed flask equipped with stirbar and nitrogen inlet was charged with boc-glycine (105 mg, 0.6 mmol) and 8 mL of DMF. The mixture was cooled to 0° C. and isboutylchloroformate (77.5 μL, 0.6 mmol) was added and stirred for 20 min. 1-[5-(aminomethyl)-2-fluorophenyl]-3-chloro-4-[(2,4 difluorobenzyl)oxy]-6-methylpyridin-2 (1H)-one hydrochloride (250 mg, 0.6 mmol) was added and stirred for 3 h. After completion of the reaction by LC-MS, concentrated HCl (2 mL) and 2 mL of methanol was added to remove the boc group. The reaction was stirred for 24 h, neutralized with 2M NaOH and extracted with ethyl acetate. The organic phase was dried with Na$_2$SO$_4$ and concentrated in vacuo to obtain (196 mg, 66%) of the desired product as a the HCl salt. $^1$H NMR (400 MHz, (CD$_3$OD) δ 7.6 (q, J=8 and 6.5 Hz, 1H), 7.5 (m, 1H), 7.3 (m, 2H), 7.0 (m, 2H), 6.63 (s, 1H), 5.35 (s, 2H), 4.4 (q, J=15 and 13.6 Hz, 2H), 3.7 (s, 2H), 2.05 (s, 3H) ppm. ES-HRMS m/z 466.1157 (M+H calcd for C$_{22}$H$_{20}$ClF$_3$N$_3$O$_3$ requires 466.1140).

Example 597

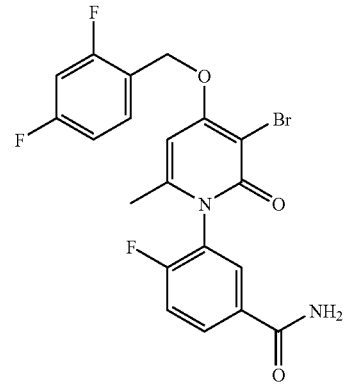

3-[3-bromo-4-[(2,4-difluorobenzyl)oxy]-6-methyl-2-oxopyridin-1(2H)-yl]-4-fluorobenzamide A 250 mL round bottomed flask equipped with stirbar and nitrogen inlet was charged with 3-[3-bromo-4-[(2,4-difluorobenzyl)oxy]-6-methyl-2-oxopyridin-1(2H)-yl]-4-fluorobenzoic acid (3.65 g, 7.8 mmol), 4-methylmorpholine (2.6 mL, 23.4 mmol), 2-chloro-4,6-dimethoxy-1,3,5-triazine (1.64 g, 9.36 mmol) and tetrahydrofuran (40 mL). After stirring the mixture for 30 min at 250 C, NH$_4$OH (20.0 mL) was added. The mixture was stirred for 30 min and diluted with water. The product precipitated from solution. The precipitated was filtered and washed with water and diethyl ether to give the title compound (2.37 g, 65%) as a white solid. $^1$H NMR (400 MHz, (CD$_3$)$_2$SO) δ 7.9 (d, J=7.3 Hz, 1H), 7.61 (q, J=8.6 and 6.7 Hz, 1H), 7.5 (m, 2H), 7.3 (t, J=9.6 Hz, 1H), 7.15 (t, J=8.7 Hz, 1H), 6.7 (s, 1H), 5.36 (s, 2H), 2 (s, 3H) ppm. ES-HRMS m/z 469.0172 (M+H calcd for C$_{20}$H$_{15}$BrF$_3$N$_2$O$_3$ requires 469.0195).

Example 598

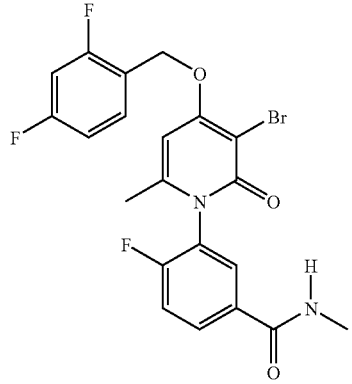

3-[3-bromo-4-[(2,4-difluorobenzyl)oxy]-6-methyl-2-oxopyridin-1(2H)-yl]-4-fluoro-N-methylbenzamide A solution of 3-[3-bromo-4-[(2,4-difluorobenzyl)oxy]-6-methyl-2-oxopyridin-1(2H)-yl]-4-fluorobenzoic acid (1 g, 2.1 mmol) in N,N-dimethylformamide (20 mL) was cooled to −10 C. Isobutyl chloroformate (0.27 mL, 2.1 mmol) and N-methyl morpholine (0.23 mL, 2.1 mmol) were added to the reaction vessel. After stirring at −10 C for 20 minutes, a solution of N-methyl amine (2.1 mL, 4.2 mmol, 2 M in THF) was added and the reaction mixture was warmed to room temperature as it stirred for 18 hours. The reaction mixture was concentrated in vacuo, suspended in water, filtered and washed with water, ethyl acetate and diethyl ether. $^1$H NMR (400 MHz, CD$_3$OD) δ 8.03 (dddd, J=3.0, 6.4, 9.2 and 11.6 Hz, 1H), 7.81 (dd, J 3.0 and (0.2 Hz, 1H), 7.66 (q, J=10.4 Hz, 1H), 7.47 (t, J=12 Hz, 1H), 7.06 (t, J=12 Hz, 2H), 6.67 (s, 1H), 5.38 (s, 2H), 2.91 (s, 3H), 2.10 (s, 3H) ppm. $^{19}$F NMR (400 MHz, CD$_3$OD) δ−111.50 (1 F), −115.97 (1 F), −120.16 ppm. ES-HRMS m/z 481.0346 (M+H calcd for C$_{21}$H$_{17}$BrF$_3$N$_2$O$_3$ requires 481.0369).

Example 599

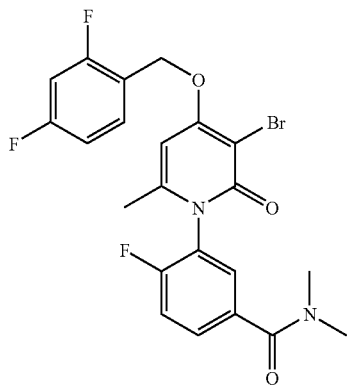

3-[3-bromo-4-[(2,4-difluorobenzyl)oxy]-6-methyl-2-oxopyridin-1(2H)-yl]-4-fluoro-N,N-dimethylbenzamide A solution of 3-[3-bromo-4-[(2,4-difluorobenzyl)oxy]-6-methyl-2-oxopyridin-1(2H)-yl]-4-fluorobenzoic acid (1 g, 2.1 mmol) in N,N-dimethylformamide (20 mL) was cooled to −10 C. Isobutyl chloroformate (0.27 mL, 2.1 mmol) and N-methyl morpholine (0.23 mL, 2.1 mmol) were added to the reaction vessel. After stirring at −10 C for 20 minutes, a solution of N-methyl amine (2.1 mL, 4.2 mmol, 2 M in THF) was added and the reaction mixture was warmed to room temperature as it stirred for 18 hours. The reaction mixture was concentrated in vacuo and partitioned between water and ethyl acetate. The organic layer was washed with brine and concentrated in vacuo. The solid was chromatographed on silica (95:5 methylene chloride : isopropyl alcohol) to give the desired product as a white powder (0.31 g, 30%). $^1$H NMR (400 MHz, CD$_3$OD) δ 7.64 (m, 1H), 7.50 (dd, J=2.4 and 7.2 Hz, 1H), 7.45 (t, J=9.6 Hz, 1H), 7.04 (t, J=9.2 Hz, 2H), 6.65 (s, 1H), 5.36 (s, 2H), 3.09 (s, 3H), 3.05 (s, 3H), 2.10 (s, 3H) ppm. $^{19}$F NMR (400 MHz, CD$_3$OD) δ−111.51 (1 F), −115.88 (1 F), −121.90 (1 F) ppm. ES-HRMS m/z 495.0508 (M+H calcd for C$_{22}$H$_{19}$BrF$_3$N$_2$O$_3$ requires 495.0526).

Example 600

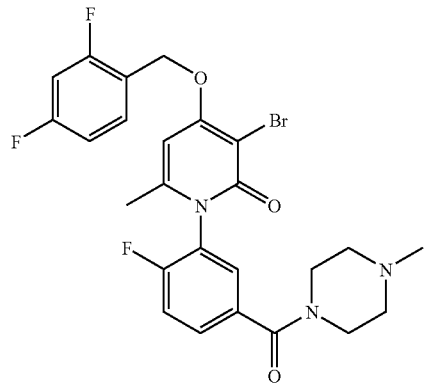

3-bromo-4-[(2,4-difluorobenzyl)oxy]-1-{2-fluoro-5-[(4-methylpiperazin-1-yl)carbonyl]phenyl}-6-methylpyridin-2(1H)-one Step 1 Preparation of 3-bromo-4-[(2,4-difluorobenzyl)oxy]-1-{2-fluoro-5-[(4-methylpiperazin-1-yl)carbonyl]phenyl}-6-methylpyridin-2(1H)-one

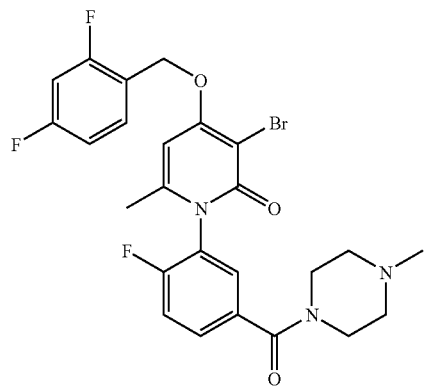

To a reaction vessel (borosilicate culture tube) was added 3-[3-bromo-4-[(2,4-difluorobenzyl)oxy]-6-methyl-2-oxopyridin-1(2H)-yl]-4-fluorobenzoic acid (0.300 g, 0.623 mmol) and 1-hydroxybenzotriazole (0.042 g, 0.45 mmol). N,N-Dimethylformamide (3 mL) was added to the reaction vessel followed by approximately 1.1 g of the polymer bound carbodiimide resin (1.38 mmol/g). Additional N,N-dimethylformamide (2 mL) was then added to the reaction vessel. The parallel reaction apparatus was then orbitally shaken (Labline Benchtop Orbital Shaker) at approximately 200 RPM at room temperature for 15 minutes. N-Methyl amine (1 mL, 2 mmol) was then added to the reaction vessel and the reaction apparatus was orbitally shaken at room temperature overnight. At this time the reaction was diluted with tetrahydrofuran (20 mL) and treated with approximately 2.0 g of polyamine resin (2.63 mmol/g) and approximately 2.5 g of methylisocyanate functionalized polystyrene (1.5 mmol/g) and the orbital shaking was continued at 200 RPM at room temperature for 3 hours. The reaction vessel was then opened and the solution phase product was separated from the insoluble quenched byproducts by filtration and collection into a vial. After partially evaporation the insoluble byproducts were rinsed with tetrahydrofuran (2×10 mL). The filtrate was evaporated by blowing $N_2$ over the vial and the resulting solid was triturated with diethyl ether to give an off-white solid. (0.14 g, 41%)

$^1$H NMR (400 MHz, $CD_3OD$) δ 7.63 (m, 1H), 7.51 (dd, J=2.2 and 7.2 Hz, 1H), 7.45 (t, J=8.4 Hz, 1H), 7.03 (m, 2H), 6.65 (s, 1H), 5.34 (s, 2H), 3.74 (s, 2H), 3.51 (s, 2H), 2.80 (s, 4H), 2.08 (s, 3H) ppm. $^{19}$F NMR (400 MHz, $CD_3OD$) δ–111.31 (1 F), –115.72 (1 F), –121.41 (1 F) ppm. ES-HRMS m/z 550.0946 (M+H calcd for $C_{25}H_{24}ClF_3N_3O_3$ requires 550.0948).

Example 601–603

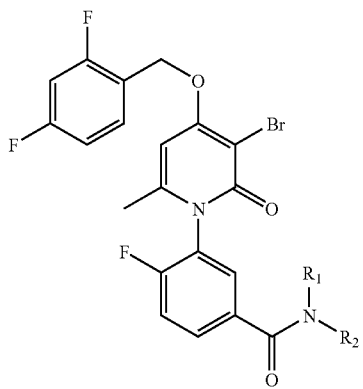

By following the method of Example 600 and replacing N-methylamine with the appropriate amine, the compounds of Examples 601–603 are prepared.

methyl 4-[3-bromo-4-[(2,4-difluorobenzyl)oxy]-6-methyl-2-oxopyridin-1(2H)-yl]-3-fluorobenzoate Step 1 Preparation of 4-amino-3-fluorobenzoic acid

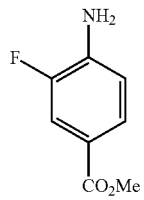

3-Fluoro-4-aminobenzoic acid was prepared as described in the literature. (Schmelkes, F. C.; Rubin, M. J. Am. Chem. Soc. 1944, 66, 1631–2.)

Step 2 Preparation of methyl 4-amino-3-fluorobenzoate

| Compound No. | $R_1$ | $R_2$ | % Yield | MF | M + H Requires | ESHRMS m/z |
|---|---|---|---|---|---|---|
| Ex. 601 | $CH_2CH_2O$— | $CH_2CH_2$— | 98 | $C_{24}H_{21}BrF_3N_2O_4$ | 537.0631 | 537.0620 |
| Ex. 602 | $CH_3$ | $CH_2CH_2OH$ | 43 | $C_{23}H_{21}BrF_3N_2O_4$ | 525.0631 | 525.0618 |
| Ex. 603 | H | $CH_2C(CH_3)_2OH$ | 65 | $C_{24}H_{23}BrF_3N_2O_4$ | 539.0783 | 539.0788 |

Example 604

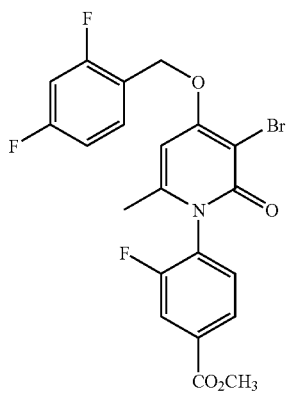

A 250 mL 3-necked round bottomed flask equipped with a nitrogen inlet, stirbar, addition funnel and thermocouple was charged with 4-amino-3-fluorobenzoic acid (11.8 g, 76 mol) and methanol (100 mL). The system was cooled to 0 C. and acetyl choride (7.6 mL, 107 mol) was added dropwise. The system was warmed to room temperature, the addition funnel was replaced with a reflux condenser, and was heated to reflux for 6 h. The reaction mixture was cooled to room temperature, quenched with saturated aqueous $NaHCO_3$, and extracted with ethyl acetate. The organic extract was washed with brine and concentrated in vacuo to give methyl methyl 4-amino-3-fluorobenzoate as an tan solid (8.2 g, 64%). $^1$H NMR (400 MHz, $CD_3OD$) δ 7.56 (dd, J=1.6 and 8.0 Hz, 1H), 7.52 (dd, J=1.9 and 12 Hz, 1H), 6.76 (t, J=8.4 Hz, 1H), 3.81 (s, 3H) ppm. $^{19}$F NMR (400 MHz, $CD_3OD$) δ–139.05 (1 F) ppm. ES-HRMS m/z 170.0565 (M+H calcd for $C_8H_9FNO_2$ requires 170.0612).

Step 3 Preparation of methyl 3-fluoro-4-(4-hydroxy-6-methyl-2-oxopyridin-1(2H)-yl)benzoate

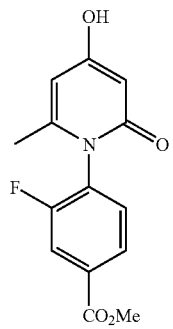

A 250 mL round bottomed flask equipped with stirbar, Dean-Stark trap and reflux condensor was charged with the product of Step 2 (8 g, 47.3 mmol), 4-hydroxy-6-methyl-2-pyrone (12 g, 84.6 mmol), and N-methyl-2-pyrrolidine (8 mL). The system was immersed in a 150 C. oil bath for 2 hours and was then cooled to room temperature. The reaction mixture was washed with aqueous $K_2CO_3$ (8.5 g, 200 mL water). The aqueous layer was washed with ethyl acetate and then was acidified to pH 4–5 with glacial HOAc. This was extracted with ethyl acetate, which was then concentrated in vacuo. The viscous oil was triturated with acetonitrile and filtered to the title compound as a tan solid (2.3 g, 17%). $^1$H NMR (400 MHz, $CD_3OD$) δ 7.98 (dd, J=1.8 and 8.0 Hz, 1H), 7.91 (dd, J=1.7 and 10 Hz, 1H), 7.46 (t, J=8 Hz, 1H), 6.09 (dd, J=0.9 and 2.4 Hz, 1H), 5.77 (d, J=2.7 Hz, 1H), 3.94 (s, 3H), 1.97 (s, 3H) ppm. $^{19}$F NMR (400 MHz, $CD_3OD$) δ–123.00 (1 F) ppm. ES-HRMS m/z 278.0781 (M+H calcd for $C_{14}H_{13}FNO_4$ requires 278.0823).

Step 4 Preparation of methyl 4-[4-[(2,4-difluorobenzyl)oxy]-6-methyl-2-oxopyridin-1(2H)-yl]-3-fluorobenzoate

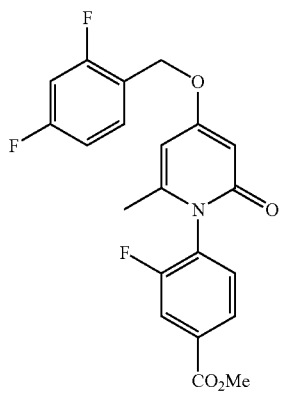

A 100 mL round bottomed flask equipped with stirbar and nitrogen inlet was charged with the product of Step 4 (2.3 g, 8.3 mmol) and N,N-dimethyl formamide (20 mL). 1,8-diazabicyclo[5.4.0]undec-7-ene (1.4 mL, 9.1 mmol) was added followed by 2,4-difluorobenzyl bromide (1.2 mL, 9.1 mmol). The reaction mixture was stirred at 60 C. for 3 h, was poured into saturated aqueous $NaHCO_3$ and was extracted with ethyl acetate. The organic layer was washed with brine and concentrated in vacuo. The solid was triturated with acetonitrile and filtered to give the title compound (2.15 g, 64%). $^1$H NMR (400 MHz, $CD_3OD$) δ 7.99 (dd, J=1.7 and 8.4 Hz, 1H), 7.93 (dd, J=1.8 and 10.4 Hz, 1H), 7.55 (m, 1H), 7.48 (t, J=6.8 Hz, 1H), 7.02 (m, 2H), 6.18 (d, J=1.3 and 2.76 Hz, 1H), 6.02 (d, J=2.7 Hz, 1H), 5.14 (s, 2H), 3.94 (s, 3H), 1.98 (s, 3H) ppm. $^{19}$F NMR (400 MHz, $CD_3OD$) δ–111.34 (1 F), –115.97 (1 F), –122.98 (1 F) ppm. ES-HRMS m/z 404.1133 (M+H calcd for $C_{21}H_{17}F_3NO_4$ requires 404.1104).

Step 5 Preparation of methyl 4-[3-bromo-4-[(2,4-difluorobenzyl)oxy]-6-methyl-2-oxopyridin-1(2H)-yl]-3-fluorobenzoate

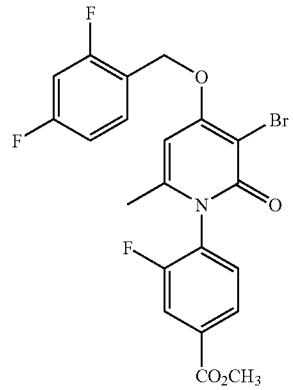

A 100 mL round bottomed flask equipped with stirbar and nitrogen inlet was charged with the product of Step 4 (2.15 g, 5.3 mmol) and N-methyl-2-pyrrolidine (15 mL). After cooling to 0 C., a solution of N-bromo succinimide (1.03 g, 5.8 mmol) in 10 mL of N-methyl-2-pyrrolidine was added over 15 minutes. After 15 additional minutes, the reaction mixture was warmed to room temperature and was stirred for 1 hour. The mixture was then poured into saturated aqueous $NaHCO_3$ and extracted with ethyl acetate. The organic layer was washed with brine and concentrated in vacuo. The residue was triturated with acetonitrile and filtered to give the title compound as a white powder (1.5 g, 59%). $^1$H NMR (400 MHz, $CD_3OD$) δ 8.00 (dd, J=2.0 and 8.4 Hz, 1H), 7.95 (dd, J=1.7 and 10 Hz, 1H), 7.64 (q, J=8.8 and 14.4 Hz, 1H), 7.51 (t, J=7.6 Hz, 1H), 7.04 (t, J=8, 4 Hz, 2H), 6.66 (s, 1H), 5.36 (s, 2H), 3.95 (s, 3H), 2.01 (s, 3H) ppm. $^{19}$F NMR (400 MHz, $CD_3OD$) δ–111.50 (1 F), –115.97 (1 F), –123.01 (1 F) ppm. ES-HRMS m/z 484.0169 (M+H calcd for $C_{21}H_{16}BrF_3NO_4$ requires 484.0192).

Example 605

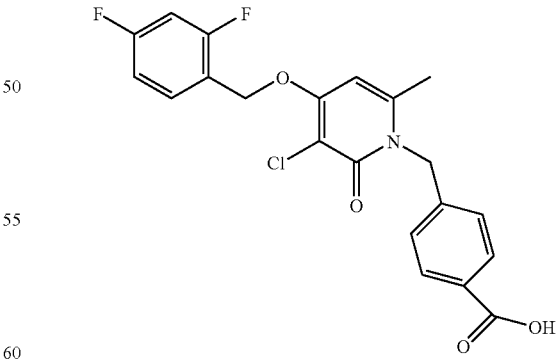

4-{[3-chloro-4-[(2,4-difluorobenzyl)oxy]-6-methyl-2-oxopyridin-1(2H)-yl]methyl}benzoic acid Preparation of 4-{[3-chloro-4-[(2,4-difluorobenzyl)oxy]-6-methyl-2-oxopyridin-1(2H)-yl]methyl}benzoic acid.

Methyl-4-{[3-chloro-4-[(2,4-difluorobenzyl)oxy]-6-methyl-2-oxopyridin-1(2H)-yl]methyl}benzoate (30.4 g, 70.1 mmol) was suspended in methanol (150 mL) and dioxane (150 mL). 2.5N NaOH (30.8 mL, 77.08 mmol) was added. The resulting mixture was heated to 50° C. for 8.0 hours. The reaction was partially concentrated and the heterogenous mixture was acidified (pH 2) with 1N HCl. The precipitate was collected by filtration washing with H$_2$O and diethyl ether to afford a white solid (29.2 g, 99%). $^1$H NMR (400 MHz, DMSO-d$_6$) δ 7.88 (d, J=8.3 Hz, 2H), 7.63 (app q, J=7.9 Hz, 1H), 7.31 (dt, J=2.4, 9.9 Hz, 1H), 7.18 (app d, J=8.3 Hz, 2H), 7.17–7.12 (m, 1H), 6.60 (s, 1H), 5.35 (s, 2H), 5.27 (s, 2H), 2.28 (s, 3H). ES-HRMS m/z 420.0821 (M+H calcd for C$_{21}$H$_{17}$ClF$_2$NO$_4$ requires 420.0809).

Example 606

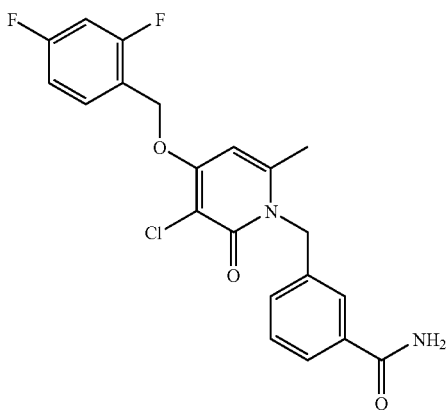

4-{[3-chloro-4-[(2,4-difluorobenzyl)oxy]-6-methyl-2-oxopyridin-1(2H)-yl]methyl}benzamide

Preparation of 4-{[3-chloro-4-[(2,4-difluorobenzyl)oxy]-6-methyl-2-oxopyridin-1(2H)-yl]methyl}benzamide. 4-{[3-chloro-4-[(2,4-difluorobenzyl)oxy]-6-methyl-2-oxopyridin-1(2H)-yl]methyl}benzoic acid (12.0 g, 28.58 mmol) was suspended in tetrahydrofuran (100 mL). 2-Chloro-4,6-dimethoxy-1,3,5-triazine (6.02 g, 34.3 mmol) was added followed by 4-methylmorpholine (9.43 mL, 85.74 mmol). The resulting mixture was stirred at room temperature for 1.5 hours at which time NH$_4$OH (50.0 mL) was added. The resulting mixture was stirred at room temperature for 1 hour and then partially concentrated. The precipitate was collected by filtration washing with H$_2$O and diethyl ether to provide an off-white solid (12.11 g, >100%). $^1$H NMR (400 MHz, DMSO-d$_6$) δ 7.91 (br s, 1H), 7.80 (d, J=8.3 Hz, 2H), 7.63 (app q, J=7.9 Hz, 1H), 7.31 (dt, J=2.6, 10.5 Hz, 1H), 7.17–7.12 (m, 1H), 7.13 (app d, J=8.3 Hz, 2H), 6.59 (s, 1H), 5.32 (s, 2H), 5.27 (s, 2H), 2.28 (s, 3H). ES-HRMS m/z 419.0968 (M+H calcd for C$_{21}$H$_{18}$ClF$_2$N$_2$O$_3$ requires 419.0969).

Example 607

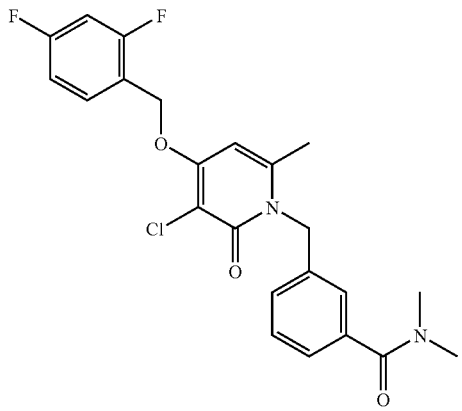

4-{[3-chloro-4-[(2,4-difluorobenzyl)oxy]-6-methyl-2-oxopyridin-1(2H)-yl]methyl}-N,N-dimethylbenzamide

Preparation of 4-{[3-chloro-4-[(2,4-difluorobenzyl)oxy]-6-methyl-2-oxopyridin-1(2H)-yl]methyl}-N,N-dimethylbenzamide. 4-{[3-chloro-4-[(2,4-difluorobenzyl)oxy]-6-methyl-2-oxopyridin-1(2H)-yl]methyl}benzoic acid (2.00 g, 4.76 mmol) was suspended in N,N-dimethylformamide (20 mL). 1-Hydroxybenzotriazole (0.773 g, 5.72 mmol) was added followed by 4-methylmorpholine (1.57 mL, 14.28 mmol), dimethylamine (7.14 mL, 2.0 M in tetrahydrofuran, 14.28 mmol) and then 1-[3-(dimethylamino)propyl]-3-ethylcarbodiimide hydrochloride (1.28 g, 6.66 mmol). The resulting mixture was stirred at room temperature for 3 hours at which time the reaction was diluted with H$_2$O (75 mL). The reaction mixture was then extracted with ethyl acetate. The combined organic extracts were washed with saturated NaHCO$_3$, brine, dried over Na$_2$SO$_4$, filtered and concentrated. The resulting solid was washed with ethyl acetate to provide the title compound as a white solid (1.67 g, 78%). $^1$H NMR (400 MHz, CDCl$_3$) δ 7.53 (app q, J=7.8 Hz, 1H), 7.33 (d, J=8.3 Hz, 2H), 7.16 (d, J=8.3 Hz, 2H), 6.95–6.90 (m, 1H), 6.84 (app dt, J=2.5, 9.4 Hz, 1H), 6.02 (s, 1H), 5.35 (s, 2H), 5.19 (s, 2H), 2.97–2.93 (br m, 6H), 2.26 (s, 3H). ES-HRMS m/z 447.1246 (M+H calcd for C$_{23}$H$_{22}$ClF$_2$N$_2$O$_3$ requires 447.1282).

Example 608

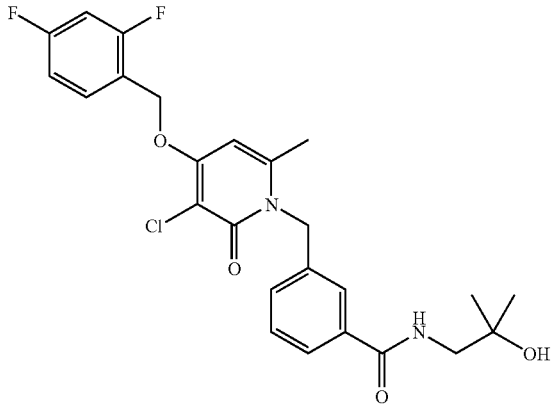

4-{[3-chloro-4-[(2,4-difluorobenzyl)oxy]-6-methyl-2-oxopyridin-1(2H)-yl]methyl}-N-(2-hydroxy-2-methylpropyl)benzamide

Preparation of 4-{[3-chloro-4-[(2,4-difluorobenzyl)oxy]-6-methyl-2-oxopyridin-1(2H)-yl]methyl}-N-(2-hydroxy-2-methylpropyl)benzamide. 4-{[3-chloro-4-[(2,4- difluorobenzyl)oxy]-6-methyl-2-oxopyridin-1(2H)-yl]methyl}benzoic acid (2.00 g, 4.76 mmol) was suspended in N,N-dimethylformamide (10 mL). 1-Hydroxybenzotriazole (0.772 g, 5.71 mmol) was added followed by 4-methylmorpholine (1.57 mL, 14.28 mmol), 1-amino-2-methyl-2-propanol hydrochloride (1.49 g, 11.90 mmol) and then 1-[3-(dimethylamino)propyl]-3-ethylcarbodiimide hydrochloride (1.28 g, 6.66 mmol). The resulting mixture was stirred at room temperature for 2 days at which time the reaction was diluted with H$_2$O (50 mL). The reaction mixture was then extracted with ethyl acetate. The combined organic extracts were washed with saturated NaHCO$_3$, brine, dried over Na$_2$SO$_4$, filtered and concentrated. The resulting solid was washed with diethyl ether to provide the title compound as a tan solid (2.08 g, 89%). $^1$H NMR (400 MHz, CDCl$_3$) δ 7.72 (d, J=8.2 Hz, 2H), 7.51 (app q, J=7.7 Hz, 1H), 7.25–7.21 (m, 1H), 7.10 (d, J=8.2 Hz, 2H), 6.93 (app dt, J=1.6, 8.3, 9.4 Hz, 1H), 6.87–6.82 (m, 1H), 6.01 (s, 1H), 5.32 (s, 2H), 5.19 (s, 2H), 3.42 (d, J=5.9 Hz, 2H), 2.26 (s, 3H), 1.23 (s, 6H). ES-HRMS m/z 491.1522 (M+H calcd for C$_{25}$H$_{26}$ClF$_2$N$_2$O$_4$ requires 491.1544).

Example 609

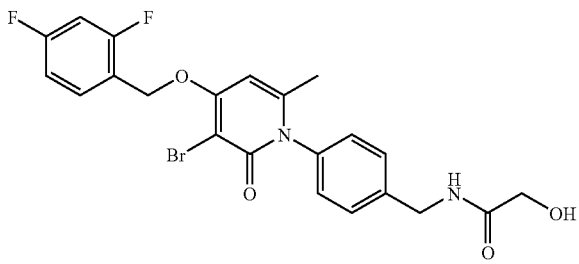

N-{4-[3-bromo-4-[(2,4-difluorobenzyl)oxy]-6-methyl-2-oxopyridin-1(2H)-yl]benzyl}-2-hydroxyacetamide Step 1. Preparation of 1-[4-(aminomethyl)phenyl]-3-bromo-4-[(2,4-difluorobenzyl)oxy]-6-methylpyridin-2(1H)-one.

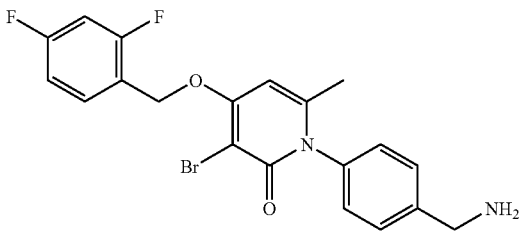

Example 244 (0.250 g, 0.556 mmol) was suspended in tetrahydrofuran (2.0 mL) and cooled in an ice-bath. Borane dimethyl sulfide (0.500 mL, 2.0 M in tetrahydrofuran, 1.00 mmol) was added. The resulting mixture was heated to reflux overnight and then cooled in an ice-bath. The reaction was quenched by the addition of 6.0 N HCl (5.0 mL) then washed with ethyl acetate. The aqueous layer was made alkaline with 2.5 N NaOH and extracted with ethyl acetate. The combined organic layers were washed with brine, dried over Na$_2$SO$_4$, filtered and concentrated to provide an off-white solid (0.180 g, 74%). $^1$H NMR (400 MHz, CDCl$_3$) δ 7.58 (app q, J=7.8 Hz, 1H), 7.44 (app d, J=8.2 Hz, 2H), 7.10 (d, J=8.2 Hz, 2H), 6.95 (app dt, J=1.5, 8.5 Hz, 1H), 6.88–6.83 (m, 1H), 6.06 (s, 1H), 5.24 (s, 2H), 3.93 (s, 2H), 1.96 (s, 3H).

Step 2. Preparation of 2-({4-[3-bromo-4-[(2,4-difluorobenzyl)oxy]-6-methyl-2-oxopyridin-1(2H)-yl]benzyl}amino)-2-oxoethyl.

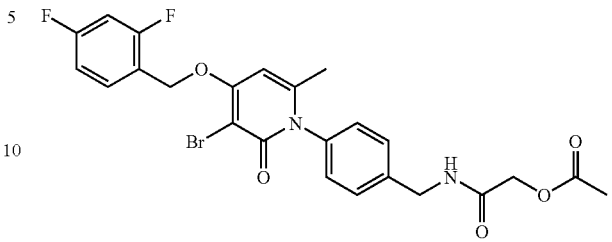

Acetoxyacetic acid (0.037 g, 0.310 mmol) was dissolved in dichloromethane (2.0 mL). 1-hydroxybenzotriazole (0.021 g, 0.155 mmol) was added followed by 3-(1-cyclohexylcarbodiimide)propyl-functionalized silica gel (1.00 g, 0.620 mmol, loading =0.64 mmol/g). After stirring at room temperature for 15 minutes, 1-[4-(aminomethyl)phenyl]-3-bromo-4-[(2,4-difluorobenzyl)oxy]-6-methylpyridin-2(1H)-one (Step 1) (0.180 g, 0.310 mmol) in dichloromethane (2.0 mL) was added. The resulting mixture was stirred at room temperature overnight, at which time the reaction mixture was filtered and concentrated. Chromatography (silica gel, hexanes/ethyl acetate with 10% methanol) provided a white solid (0.130 g, 78%). $^1$H NMR (400 MHz, CDCl$_3$) δ 7.58 (app q, J=7.8 Hz, 1H), 7.33 (d, J=8.3 Hz, 2H), 7.05 (app d, J=8.3 Hz, 2H), 6.97–6.92 (m, 1H), 6.88–6.83 (m, 1H), 6.08 (s, 1H), 5.24 (s, 2H), 4.58 (s, 2H), 4.44 (d, J=6.0 Hz, 2H), 2.13 (s, 3H), 1.95 (s, 3H).

Step 3. Preparation of N-{4-[3-bromo-4-[(2,4-difluorobenzyl)oxy]-6-methyl-2-oxopyridin-1(2H)-yl]benzyl}-2-hydroxyacetamide. 2-({4-[3-bromo-4-[(2,4-difluorobenzyl)oxy]-6-methyl-2-oxopyridin-1(2H)-yl]benzyl}amino)-2-oxoethyl (Step 2) (0.130 g, 0.243 mmol) was dissolved in methanol (5 mL) and H$_2$O (1 mL). K$_2$CO$_3$ (0.055 g, 0.398 mmol) was added and the resulting mixture was stirred at room temperature for 2 hours. The mixture was then concentrated and the residue was partitioned between H$_2$O and ethyl acetate. The organic layer was removed and the aqueous layer was further extracted with ethyl acetate. The combined organic layer were washed with brine, dried over Na$_2$SO$_4$, filtered and concentrated to provide an off-white solid (0.100 g, 84%). $^1$H NMR (400 MHz, CDCl$_3$) δ 7.56 (app q, J=7.7 Hz, 1H), 7.43 (t, J=5.8 Hz, 1H), 7.33 (d, J=8.2 Hz, 2H), 7.04 (app d, J=8.3 Hz, 2H), 6.98–6.93 (m, 1H), 6.88–6.83 (m, 1H), 6.11 (s, 1H), 5.24 (s, 2H), 4.41 (d, J=6.0 Hz, 2H), 3.87 (s, 2H), 1.96 (s, 3H). ES-HRMS m/z 493.0575 (M+H calcd for C$_{22}$H$_{20}$BrF$_2$N$_2$O$_4$ requires 493.0569).

Example 610

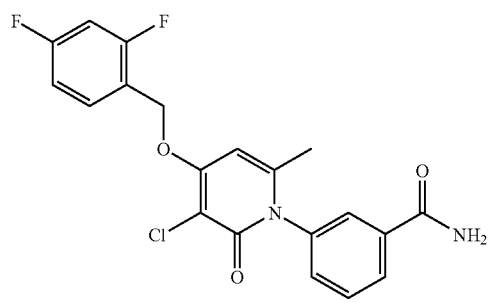

3-[3-chloro-4-[(2,4-difluorobenzyl)oxy]-6-methyl-2-oxopyridin-1(2H)-yl]benzamide Example 291 (2.00 g, 4.93 mmol) and 2-chloro-4,6-dimethoxy-1,3,5-triazine (1.04 g, 5.91 mmol) were suspended in tetrahydrofuran (20 mL). 4-Methylmorpholine (1.6 mL, 14.79 mmol) was added. The resulting mixture was stirred for 1.5 hours at room temperature. NH$_4$OH (10 mL, 148.00 mmol) was added and the reaction was stirred for 0.5 hours at room temperature. H$_2$O (50 mL) and tetrahydrofuran (50 mL) were added and the organic layer was separated. The aqueous phase was extracted with ethyl acetate (75 mL) and the combined organics were washed with saturated Na$_2$CO$_3$ (50 mL), 1N HCl (50 mL), and brine (50 mL). The organic phase was dried over Na$_2$SO$_4$ and evaporated. The resulting solid was washed with diethyl ether to give a white solid (1.96 g, 98%). $^1$H NMR (400 MHz, DMF-d$_6$) δ 8.24 (br s, 1H), 8.10 (dt, J=1.21, 7.79 Hz, 1H), 7.90 (t, J=1.88 Hz, 1H), 7.79 (app dt, J=6.58, 8.59 Hz, 1H), 7.66 (t, J=7.79 Hz, 1H), 7.57–7.55 (m, 1H), 7.46 (br s, 1H), 7.33 (ddd, J=2.55, 9.26, 11.82 Hz, 1H), 7.24–7.19 (m, 1H), 6.78 (s, 1H), 5.44 (s, 2H), 2.04 (s, 3H). ES-HRMS m/z 405.0835 (M+H calcd for C$_{20}$H$_{16}$BrF$_2$N$_2$O$_3$ requires 405.0812).

Example 611

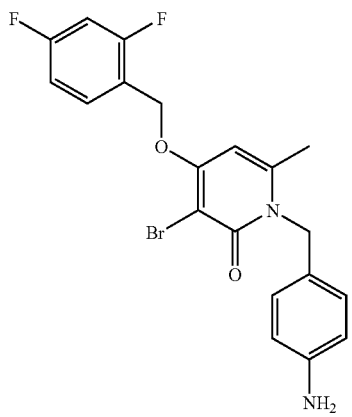

1-(4-aminobenzyl)-3-bromo-4-[(2,4-difluorobenzyl)oxy]-6-methylpyridin-2(1H)-one

Step 1: Preparation of 1-tert-butyl-4-{[3-bromo-4-[(2,4-difluorobenzyl)oxy]-6-methyl-2-oxopyridin-1(2H)-yl]methyl}phenylcarbamate.

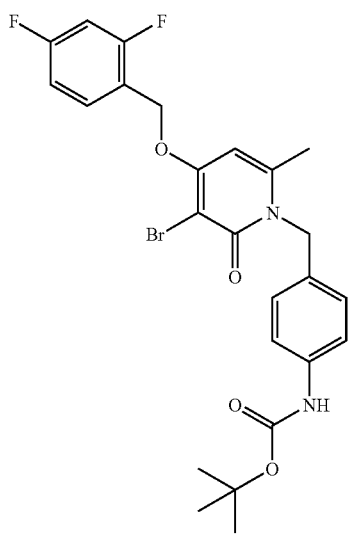

4-{[3-bromo-4-[(2,4-difluorobenzyl)oxy]-6-methyl-2-oxopyridin-1(2H)-yl]methyl}benzoic acid (8.00 g, 17.23 mmol) was suspended in 1:1 acetonitrile:t-butanol (172 mL). Diphenylphosphoryl azide (5.69 g, 20.68 mmol) and triethylamine (2.08 g, 20.68 mmol) were added. The reaction was heated to reflux for 1.5 hours. The reaction mixture was cooled to room temperature, concentrated and subjected to chromatography (on silica, ethyl acetate with 10% methanol/hexanes) to afford an off-white solid (6.14 g, 66%).

Step 2: 1-tert-butyl-4-{[3-bromo-4-[(2,4-difluorobenzyl)oxy]-6-methyl-2-oxopyridin-1(2H)-yl]methyl}phenylcarbamate (Step 1) (6.14 g, 11.47 mmol) was suspended in 4N HCl in dioxane (5.74 mL, 22.94 mmol). The reaction mixture was stirred at room temperature for 1 hour then diluted with diethyl ether. The precipitate was collected by filtration and washed with diethyl ether (3×30 mL) to afford a tan solid (3.45 g, 69%). $^1$H NMR (400 MHz, DMF-d$_6$) δ 7.64 (app dt, J=6.58, 8.59 Hz, 1H), 7.31 (ddd, J=2.55, 9.53, 10.61 Hz, 1H), 7.29–7.12 (m, 5H), 6.56 (s, 1H), 5.28 (s, 2H), 5.27 (s, 2H), 2.28 (s, 3H) ES-HRMS m/z 435.0516 (M+H calcd for C$_{20}$H$_{18}$BrF$_2$N$_2$O$_2$ requires 435.0514).

Example 612

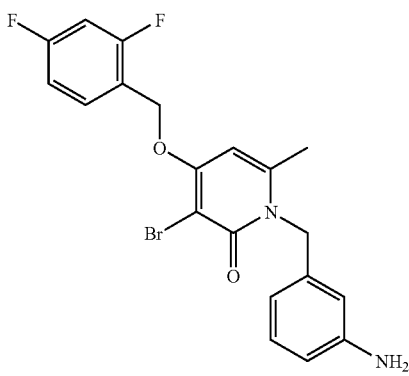

1-(3-aminobenzyl)-3-bromo-4-[(2,4-difluorobenzyl)oxy]-6-methylpyridin-2(1H)-one

By following the method for Example 611 and substituting 3-{[3-bromo-4-[(2,4-difluorobenzyl)oxy]-6-methyl-2-oxopyridin-1(2H)-yl]methyl}benzoic acid for 4-{[3-bromo-4-[(2,4-difluorobenzyl)oxy]-6-methyl-2-oxopyridin-1(2H)-yl]methyl}benzoic acid, the title compound was prepared (2.65 g, 67%). $^1$H NMR (400 MHz, DMF-d$_6$) δ 7.64 (app dt, J=6.58, 8.59 Hz, 1H), 7.39 (t, J=7.79 Hz, 1H), 7.32 (ddd, J=2.55, 9.53, 10.61 Hz, 1H), 7.18–7.08 (m, 3H), 6.96 (s, 1H), 6.58 (s, 1H), 5.30 (s, 2H), 5.27 (s, 2H), 2.29 (s, 3H). ES-HRMS m/z 435.0513 (M+H calcd for C$_{20}$H$_{18}$BrF$_2$N$_2$O$_2$ requires 435.0514).

Example 613

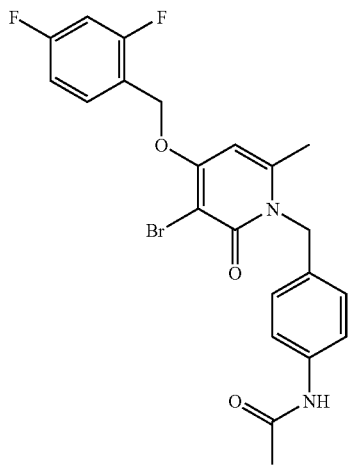

N-(4-{[3-bromo-4-[(2,4-difluorobenzyl)oxy]-6-methyl-2-oxopyridin-1(2H)-yl]methyl}phenyl)acetamide To a reaction vessel (borosilicate culture tube) was added Example 611 (0.300 g, 0.689 mmol) and dichloromethane (3.0 mL). A stock solution of N-methylmorpholine (0.30 M, 3.0 mL) was added and the parallel reaction apparatus was then orbitally shaken (Labline Benchtop Orbital Shaker) at approximately 200 RPM at room temperature for 10 minutes. Acetyl chloride (0.074 mL, 1.033 mmol) was then added to the reaction vessel and the reaction apparatus was orbitally shaken at room temperature for 1.5 hours. At this time the reaction was diluted with dichloromethane (15 mL) and treated with approximately 2.1 g of polyamine resin (2.63 mmol/g) and approximately 3.8 g of methylisocyanate functionalized polystyrene (1.10 mmol/g) and the orbital shaking was continued at 200 RPM at room temperature overnight. The reaction vessel was then opened and the solution phase products were separated from the insoluble quenched byproducts by filtration and collection into a vial. After partial evaporation the insoluble byproducts were rinsed with dichloromethane (2×10 mL). The filtrate was evaporated by blowing $N_2$ over the vial to afford a white solid (0.135 g, 41%). $^1$H NMR (400 MHz, DMF-$d_6$) δ 7.75 (app dt, J=6.58, 8.59 Hz, 1H), 7.63 (d, J=8.59 Hz, 1H), 7.30 (ddd, J=2.55, 9.53, 10.61 Hz, 1H), 7.22–7.14 (m, 3H), 6.60 (s, 1H), 5.37 (s, 4H), 2.40 (s, 3H), 2.06 (s, 3H). ES-HRMS m/z 477.0600 (M+H calcd for $C_{22}H_{21}BrF_2N_2O_3$ requires 477.0620).

Preparation of Examples 614–616

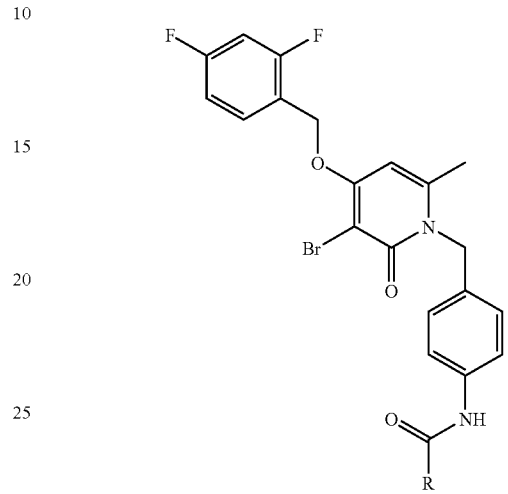

By following the method for Example 613 and replacing acetyl chloride with the appropriate acid chloride or sulfamoyl chloride, the compounds of Examples 614–616 are prepared. The deprotection of the protected intermediate was accomplished with 1M $K_2CO_3$ in methanol to afford the title compound.

| Compound No. | R | % Yield | MF | M + H Requires | ES-HRMS m/z |
|---|---|---|---|---|---|
| Ex. 614 | $CH_2OH$ | 65 | $C_{22}H_{20}BrF_2N_2O_4$ | 493.0569 | 493.0593 |
| Ex. 615 | $CH_2OCOCH_3$ | 43 | $C_{24}H_{22}BrF_2N_2O_5$ | 535.0675 | 535.0702 |
| Ex. 616 | $SO_2N(CH_3)_2$ | 43 | $C_{22}H_{23}BrF_2N_3O_4S$ | 542.0555 | 542.0572 |

Example 617

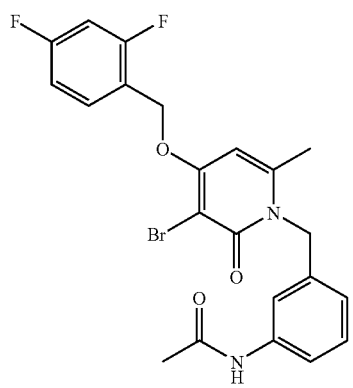

N-(3-{[3-bromo-4-[(2,4-difluorobenzyl)oxy]-6-methyl-2-oxopyridin-1(2H)-yl]methyl}phenyl)acetamide To a reaction vessel (borosilicate culture tube) was added Example 612 (0.300 g, 0.689 mmol) and dichloromethane (3.0 mL). A stock solution of N-methylmorpholine (0.30 M, 3.0 mL) was added and the parallel reaction apparatus was then orbitally shaken (Labline Benchtop Orbital Shaker) at approximately 200 RPM at room temperature for 10 minutes. Acetyl chloride (0.074 mL, 1.033 mmol) was then added to the reaction vessel and the reaction apparatus was orbitally shaken at room temperature for 1.5 hours. At this time the reaction was diluted with dichloromethane (15 mL) and treated with approximately 2.1 g of polyamine resin (2.63 mmol/g) and approximately 3.8 g of methylisocyanate functionalized polystyrene (1.10 mmol/g) and the orbital shaking was continued at 200 RPM at room temperature overnight. The reaction vessel was then opened and the solution phase products were separated from the insoluble quenched byproducts by filtration and collection into a vial. After partial evaporation the insoluble byproducts were rinsed with dichloromethane (2×10 mL). The filtrate was evaporated by blowing $N_2$ over the vial to afford a white solid (0.167 g, 51%). $^1$H NMR (400 MHz, DMF-$d_6$) δ 7.77 (app dt, J=6.58, 8.59 Hz, 1H), 7.69 (d, J=8.32 Hz, 1H), 7.41 (br s, 1H), 7.34–7.17 (m, 3H), 6.88 (d, J=7.65 Hz, 1H), 6.63 (s, 1H), 5.39 (s, 3H), 5.38 (s, 2H), 2.40 (s, 3H), 2.06 (s, 3H). ES-HRMS m/z 477.0620 (M+H calcd for $C_{22}H_{21}BrF_2N_2O_3$ requires 477.0620).

Preparation of Example 618–620

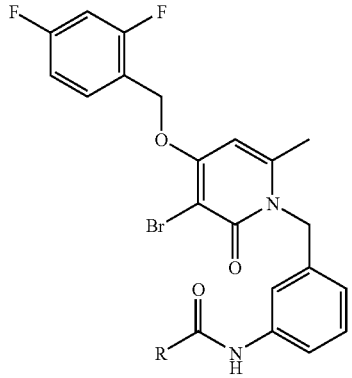

By following the method for Example 617 and replacing acetyl chloride with the appropriate acid chloride or sulfamoyl chloride, the compounds of Examples 618–620 are prepared. The deprotection of the protected intermediate was accomplished with 1M $K_2CO_3$ in methanol to afford the title compound.

Example 621

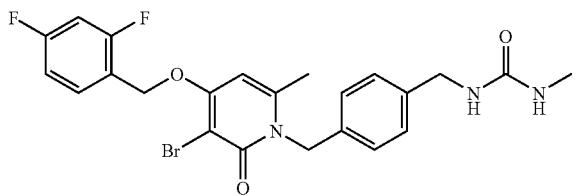

N-(4-{[3-bromo-4-[(2,4-difluorobenzyl)oxy]-6-methyl-2-oxopyridin-1(2H)-yl]methyl}benzyl)-N'-methylurea Preparation of (4-{[3-bromo-4-[(2,4-difluorobenzyl)oxy]-6-methyl-2-oxopyridin-1(2H)-yl]methyl}benzyl)-N'-methylurea. EXAMPLE 159 (150 mg, 0.33 mmol) was dissolved in N,N-dimethylacetamide (5 mL) and cooled to 0° C. 4-Nitrophenyl chloroformate (100 mg, 0.5 mmol) was added, followed by N,N-diisopropylethylamine (0.15 mL, 0.85 mmol) and the reaction was stirred at 0° C. for 5 minutes. N-Methylamine (0.5 mL, 1.0 mmol, 2M in tetrahydrofuran) was added and the reaction was allowed to reach ambient temperature and stirred for 1 hour. The reaction was then diluted with tetrahydrofuran (40 mL) and polyamine resin (1.3 g, 2.81 mmol/g) and methylisocyanate functionalized polystyrene (1 g, 1.38 mmol/g) were added. The mixture was shaken for 16 hours at ambient temperature, filtered, and the resulting filtrate concentrated to an oil that was triturated with ether. The resulting white solid was collected, washed with ether, and dried (87 mg, 52%). $^1$H NMR (400 MHz, $CD_3OD$) δ 7.61 (app q, J=8.4 Hz, 1H); 7.24 (d, J=8.0 Hz, 2H), 7.07 (d, J=8.0 Hz, 2H), 7.02 (app t, J=8.4 Hz, 2H), 6.47 (s, 1H), 5.39 (s, 2H), 5.28 (s, 2H), 4.26 (s, 2H); 2.68 (s, 3H); 2.34 (s, 3H). ES-HRMS m/z 506.0862 (M+H calcd for $C_{23}H_{23}BrF_2N_3O_3$ requires 506.0885).

Example 622

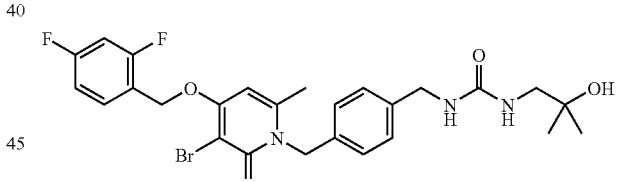

N-(4-{[3-bromo-4-[(2,4-difluorobenzyl)oxy]-6-methyl-2-oxopyridin-1(2H)-yl]methyl}benzyl)-N'-(2-hydroxy-2-methylpropyl)urea Preparation of N-(4-{[3-bromo-4-[(2,4-difluorobenzyl)oxy]-6-methyl-2-oxopyridin-1(2H)-yl]methyl}benzyl)-N'-(2-hydroxy-2-methylpropyl)urea. EXAMPLE 159 (300 mg,

| Compound No. | R | % Yield | MF | M + H Requires | ES-HRMS m/z |
|---|---|---|---|---|---|
| Ex. 618 | $CH_2OH$ | 72 | $C_{22}H_{20}BrF_2N_2O_4$ | 493.0569 | 493.0604 |
| Ex. 619 | $CH_2OCOCH_3$ | 53 | $C_{24}H_{22}BrF_2N_2O_5$ | 535.0675 | 535.0692 |
| Ex. 620 | $SO_2N(CH_3)_2$ | 21 | $C_{22}H_{23}BrF_2N_3O_4S$ | 542.0555 | 542.0567 |

0.67 mmol) was dissolved in N,N-dimethylacetamide (5 mL) and cooled to 0° C. 4-Nitrophenyl chloroformate (200 mg, 1.0 mmol) was added, followed by N,N-diisopropylethylamine (0.3 mL, 1.7 mmol) and the reaction was stirred at 0° C. for 5 minutes. 3-Amino-2-methyl-2-propanol (248 mg, 2.0 mmol) was added and the reaction was allowed to reach ambient temperature and stirred for 3 h. The reaction was then diluted with tetrahydrofuran (40 mL) and polyamine resin (1.3 g, 2.81 mmol/g) and methylisocyanate functionalized polystyrene (1 g, 1.38 mmol/g) were added. The mixture was shaken for 16 hours at ambient temperature, filtered, and the resulting filtrate concentrated to an oil that was triturated with ether. The resulting white solid was purified by chromatography (silica gel, hexane/ethyl acetate/methanol) followed by reversed phase chromatography ($C_{18}$, 0.1% aqueous trifluoroacetic acid/acetonitrile) to yield an off-white solid (43 mg, 11%). $^1$H NMR (400 MHz, CDCl$_3$) δ 7.56 (app q, J=8.0 Hz, 1H); 7.12 (d, J=8.4 Hz, 2H), 6.97 (d, J=8.0 Hz, 2H), 7.02 (app dt, J=1.6, 8.0 Hz, 2H), 6.83–6.88 (m, 1H), 6.06 (s, 1H), 5.26 (s, 2H), 5.21 (s, 2H); 4.22 (s, 2H); 3.09 (s, 2H); 2.30 (s, 3H); 1.14 (s, 6H). ES-HRMS. m/z 564.1279 (M+H calcd for $C_{26}H_{29}BrF_2N_3O_4$ requires 564.1304).

Example 623

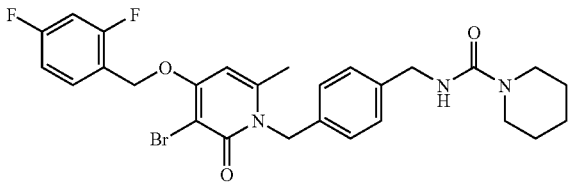

N-(4-{[3-bromo-4-[(2,4-difluorobenzyl)oxy]-6-methyl-2-oxopyridin-1(2H)-yl]methyl}benzyl)piperidine-1-carboxamide By following the general method for Example 622 and substituting piperidine (170 mg, 2.0 mmol) for 3-amino-2-methyl-2-propanol the title compound was prepared and purified by chromatography (silica gel, hexane/ethyl acetate/methanol) yielding an oil that was triturated with ether to afford a white solid (107 mg, 28%). $^1$H NMR (400 MHz, CDCl$_3$) δ 7.56 (app q, J=8.0 Hz, 1H); 7.23 (d, J=8.4 Hz, 2H), 7.11 (d, J=8.0 Hz, 2H), 7.02 (app t, J=8.0 Hz, 2H), 6.81–6.88 (m, 1H), 5.97 (s, 1H), 5.32 (s, 2H), 5.19 (s, 2H); 4.37 (s, 2H); 3.34–3.28 (m, 4H); 2.29 (s, 3H); 1.68–1.50 (m, 6H). ES-HRMS m/z 560.1365 (M+H calcd for $C_{27}H_{29}BrF_2N_3O_3$ requires 560.1355).

Example 624

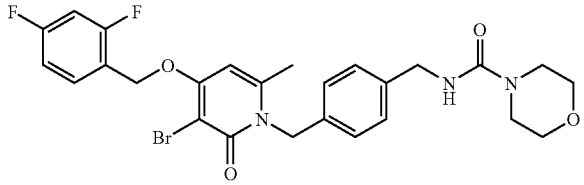

N-(4-{[3-bromo-4-[(2,4-difluorobenzyl)oxy]-6-methyl-2-oxopyridin-1(2H)-yl]methyl}benzyl)morpholine-4-carboxamide By following the general method for Example 622 and substituting morpholine (175 mg, 2.0 mmol) for 3-amino-2-methyl-2-propanol the title compound was prepared and purified by chromatography (silica gel, hexane/ethyl acetate/methanol) followed by reversed phase chromatography ($C_{18}$, 0.1% aqueous trifluoroacetic acid/acetonitrile) to yield an off-white solid (51 mg, 13%). $^1$H NMR (400 MHz, CDCl$_3$) δ 7.55 (app q, J=8.0 Hz, 1H); 7.17 (d, J=8.4 Hz, 2H), 7.01 (d, J=8.0 Hz, 2H), 6.94 (app dt, J=2.4, 8.0 Hz, 2H), 6.82–6.87 (m, 1H), 6.02 (s, 1H), 5.27 (s, 2H), 5.19 (s, 2H); 4.33 (s, 2H); 3.65–3.62 (m, 4H); 3.34–3.36 (m, 4H); 2.28 (s, 3H). ES-HRMS m/z 562.1152 (M+H calcd for $C_{26}H_{27}BrF_2N_3O_4$ requires 562.1148).

Example 625

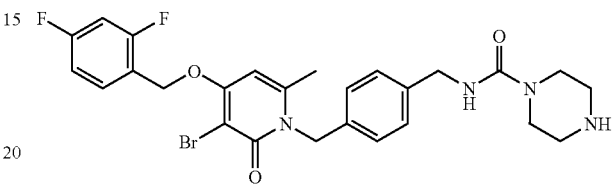

N-(4-{[3-bromo-4-[(2,4-difluorobenzyl)oxy]-6-methyl-2-oxopyridin-1(2H)-yl]methyl}benzyl)piperazine-1-carboxamide hydrochloride By following the general method for Example 622 and substituting 1-Boc-piperazine (372 mg, 2.0 mmol) for 3-amino-2-methyl-2-propanol the title compound was prepared from its N-t-butoxycarbonyl protected intermediate that was purified by chromatography (silica gel, hexane/ethyl acetate/methanol). Deprotection was accomplished with 4N HCl in dioxane to afford the title compound as its hydrochloride salt (78 mg, 19%). $^1$H NMR (400 MHz, CD$_3$OD) δ 7.61 (app q, J=7.6 Hz, 1H); 7.26 (d, J=8.4 Hz, 2H), 7.07 (d, J=8.4 Hz, 2H), 7.08–7.00 (m, 2H), 6.48 (s, 1H), 5.41 (s, 2H), 5.28 (s, 2H); 4.31 (s, 2H); 3.65–362 (m, 4H); 3.21–3.17 (m, 4H); 2.35 (s, 3H). ES-HRMS m/z 561.1318 (M+H calcd for $C_{26}H_{28}BrF_2N_4O_3$ requires 561.1307).

Example 626

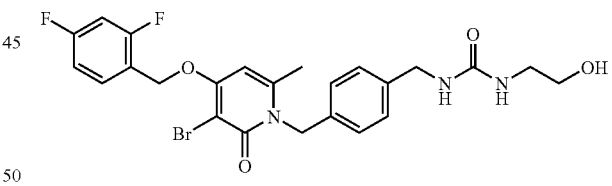

N-(4-{[3-bromo-4-[(2,4-difluorobenzyl)oxy]-6-methyl-2-oxopyridin-1(2H)-yl]methyl}benzyl)-N'-(2-hydroxyethyl)urea By following the general method for Example 622 and substituting ethanolamine (121 mg, 2.0 mmol) for 3-amino-2-methyl-2-propanol the title compound was prepared and purified by chromatography (silica gel, hexane/ethyl acetate/methanol) to yield an off-white solid (130 mg, 36%). $^1$H NMR (400 MHz, CDCl$_3$) δ 7.54 (app q, J=7.6 Hz, 1H); 7.13 (d, J=8.4 Hz, 2H), 6.95 (d, J=8.0 Hz, 2H), 6.96–6.92 (m, 1H); 6.83–6.88 (m, 1H), 6.09 (s, 1H), 5.26 (s, 2H), 5.21 (s, 2H); 4.24 (s, 2H); 3.56 (t, J=4.8 Hz, 2H); 3.21 (t, J=4.8 Hz, 2H); 2.31 (s, 3H). ES-HRMS m/z 536.0948 (M+H calcd for $C_{24}H_{25}BrF_2N_3O_4$ requires 536.0991).

Example 627

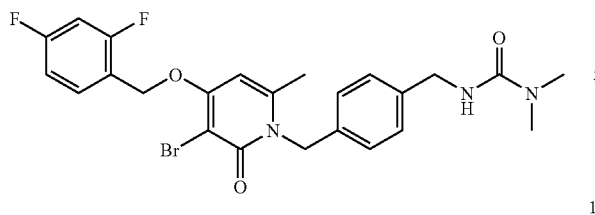

N'-(4-{[3-bromo-4-[(2,4-difluorobenzyl)oxy]-6-methyl-2-oxopyridin-1(2H)-yl]methyl}benzyl)-N,N-dimethylurea By following the general method for Example 622 and substituting N,N-dimethylamine (1.0 mL, 2.0 mmol, 2M in tetrahydrofuran) for 3-amino-2-methyl-2-propanol the title compound was prepared and purified by chromatography (silica gel, hexane/ethyl acetate/methanol) yielding an oil that was triturated with ether to afford a white solid (65 mg, 19%). $^1$H NMR (400 MHz, CDCl$_3$) δ 7.56 (app q, J=8.0 Hz, 1H); 7.22 (d, J=8.0 Hz, 2H), 7.10 (d, J=8.0 Hz, 2H), 6.93 (app dt, J=2.0, 8.0 Hz, 1H); 6.87–6.81 (m, 1H); 5.97 (s, 1H), 5.31 (s, 2H), 5.19 (s, 2H); 4.36 (s, 2H); 2.89 (s, 6H); 2.28 (s, 3H). ES-HRMS m/z 520.1072 (M+H calcd for C$_{24}$H$_{25}$BrF$_2$N$_3$O$_3$ requires 520.1042).

Example 628

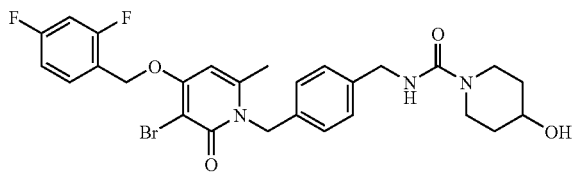

N-(4-{[3-bromo-4-[(2,4-difluorobenzyl)oxy]-6-methyl-2-oxopyridin-1(2H)-yl]methyl}benzyl)-4-hydroxypiperidine-1-carboxamide By following the general method for Example 622 and substituting 4-Hydroxypiperidine (202 mg, 2.0 mmol) for 3-amino-2-methyl-2-propanol the title compound was prepared and purified by chromatography (silica gel, hexane/ethyl acetate/methanol) yielding an oil that was triturated with ether to afford a white solid (41 mg, 11%). $^1$H NMR (400 MHz, CDCl$_3$) δ 7.56 (app q, J=8.0 Hz, 1H); 7.20 (d, J=7.6 Hz, 2H), 7.06 (d, J=8.0 Hz, 2H), 6.94 (app t, J=8.0 Hz, 1H); 6.84 (app t, J=8.0 Hz, 1H); 5.99 (s, 1H), 5.29 (s, 2H), 5.19 (s, 2H); 4.34 (s, 2H); 3.84–3.70 (m, 3H); 3.04–2.92 (m, 3H) 2.28 (s, 3H); 1.84–1.81 (m, 2H); 1.47–1.44 (m, 2H). ES-HRMS m/z 576.1348 (M+H calcd for C$_{27}$H$_{29}$BrF$_2$N$_3$O$_4$ requires 576.1304).

Example 629

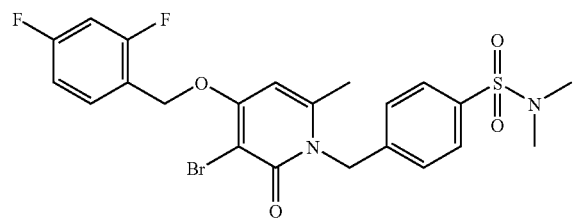

4-{[3-bromo-4-[(2,4-difluorobenzyl)oxy]-6-methyl-2-oxopyridin-1(2H)-yl]methyl}-N,N-dimethylbenzenesulfonamide Step 1: Preparation of 4-Bromomethyl-N,N-dimethylbenzenesulfonamide

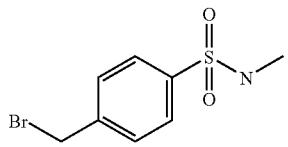

4-(Bromomethyl)benzenesulfonyl chloride (5.0 g, 18.6 mmol) was dissolved in tetrahydrofuran. N,N-dimethylamine (7.7 mL, 15.5 mmol, 2M in tetrahydrofuran) and and N,N-diisopropylethylamine (3.5 mL, 20.1 mmol) were added, and the reaction was allowed to stir at ambient temperature for 2 hours. The reaction was concentrated to an oil that was partitioned between water and ethyl acetate and extracted with ethyl acetate. The organic extracts were combined, washed with brine, dried over Na$_2$SO$_4$, and filtered. The resulting filtrate was concentrated to an oil which deposited needles that were a mixture of the title compound and 4-chloromethyl N,N-dimethylbenzenesulfonamide. The resulting needles were collected. and dried (2.3 g, 44%). ES-MS m/z 534 (M+H) and 578 (M+H)

Step 2: Preparation of 4-{[3-bromo-4-[(2,4-difluorobenzyl)oxy]-6-methyl-2-oxopyridin-1(2H)-yl]methyl}-N,N-dimethylbenzenesulfonamide. 3-bromo-4-(2,4-difluorophenoxy)-6-methylpyridin-2(1H)-one (300 mg, 0.91 mmol) was suspended in 1,4-dioxane (50 mL). 4-(Bromomethyl)-N,N-dimethylbenzenesulfonamide (from step1) (300 mg, 1.09 mmol) was added followed by sodium hydride (45 mg, 1.09 mmol, 60% in mineral oil). The reaction was heated to 80° C. and stirred for 16 hours after which more sodium hydride (45 mg, 1.09 mmol, 60% in mineral oil) and sodium iodide (150 mg, 1.0 mmol) were added. The reaction was allowed to stir at 80° C. for 4 hours more. The reaction was then filtered through Celite® and the filtrate was concentrated to an oil that was purified by chromatography (silica gel, hexane/ethyl acetate) followed by reversed phase chromatography (C$_{18}$, 0.1% aqueous trifluoroacetic acid/acetonitrile) to yield an off-white solid (41 mg, 8%). $^1$H NMR (400 MHz, CDCl$_3$) δ 7.71 (d, J=8.4

Hz, 2H); 7.57 (app q, J=7.6 Hz, 1H); 7.29 (d, J=8.0 Hz, 2H); 6.95 (app dt, J=2.0, 8.0 Hz, 1H), 6.88–6.83 (m, 1H); 6.05 (s, 1H), 5.42 (s, 2H), 5.22 (s, 2H); 2.69 (s, 6H); 2.29 (s, 3H). ES-HRMS m/z 527.0439 (M+H calcd for $C_{22}H_{22}Br_2F_2N_2O_4S$ requires 527.0446).

Example 630

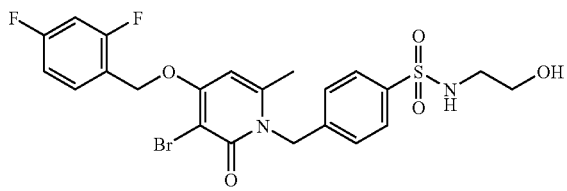

4-{[3-bromo-4-[(2,4-difluorobenzyl)oxy]-6-methyl-2-oxopyridin-1(2H)-yl]methyl}-N-(2-hydroxyethyl)benzenesulfonamide Step 1: Preparation of 4-Bromomethyl-N-(2-hydroxyethyl) benzenesulfonamide

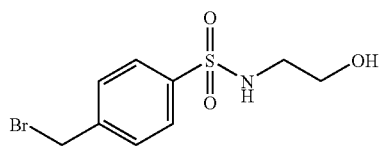

4-(Bromomethyl)benzenesulfonyl chloride (5.0 g, 18.6 mmol) was dissolved in tetrahydrofuran. Ethanolamine (1.1 mL, 18.6 mmol) and and N,N-diisopropylethylamine (3.9 mL, 22.3 mmol) were added, and the reaction was allowed to stir at ambient temperature for 30 minutes. The reaction was concentrated to an oil that was partitioned between water and ethyl acetate and extracted with ethyl acetate. The organic extracts were combined, washed with brine, dried over $Na_2SO_4$, and filtered. The resulting filtrate was concentrated to an oil that was a mixture of the title compound and 4-chloromethyl N-(2-hydroxyethyl) benzenesulfonamide. The resulting oil was dried in vacuo (3.7 g, 68%). ES-MS m/z 250 (M+H) and 294 (M+H).

Step 2: Preparation of 4-{[3-bromo-4-[(2,4-difluorobenzyl)oxy]-6-methyl-2-oxopyridin-1(2H)-yl]methyl}-N-(2-hydroxyethyl)benzenesulfonamide.

The title compound was prepared essentially according to the procedure described in Step 2 of Example 629, using 4-Bromomethyl-N-(2-hydroxyethyl) benzenesulfonamide (from step 1). $^1$H NMR (400 MHz, CDCl$_3$) δ 7.81 (d, J=8.4 Hz, 2H); 7.61 (app q, J=7.6 Hz, 1H); 7.30 (d, J=8.4 Hz, 2H); 6.95 (app t, J=8.4 Hz, 2H), 6.53 (s, 1H), 5.49 (s, 2H), 5.30 (s, 2H); 3.50 (t, J=6.0 Hz, 2H); 2.92 (t, J=6.0 Hz, 2H); 2.36 (s, 3H). ES-HRMS m/z 543.0453 (M+H calcd for $C_{22}H_{22}Br_2F_2N_2O_5S$ requires 543.0395).

Example 631

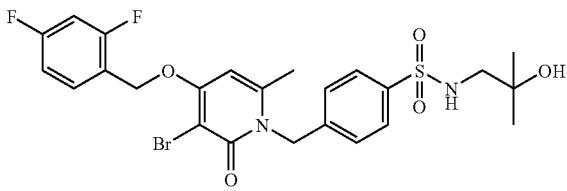

4-{[3-bromo-4-[(2,4-difluorobenzyl)oxy]-6-methyl-2-oxopyridin-1(2H)-yl]methyl}-N-(2-hydroxy-2-methylpropyl)benzenesulfonamide Step 1: Preparation of 4-Bromomethyl-N-(2-hydroxy-2-methylpropyl) benzenesulfonamide

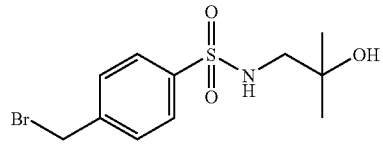

4-(Bromomethyl)benzenesulfonyl chloride (2.0 g, 7.3 mmol) was dissolved in tetrahydrofuran. 3-Amino-2-methyl-2-propanol (1.0 g, 8 mmol) and and N,N-diisopropylethylamine (1.5 mL, 8.8 mmol) were added, and the reaction was allowed to stir at ambient temperature for 30 minutes. The reaction was concentrated to an oil that was partitioned between water and ethyl acetate and extracted with ethyl acetate. The organic extracts were combined, washed with brine, dried over $Na_2SO_4$, and filtered. The resulting filtrate was concentrated to an oil that was a mixture of the title compound and 4-chloromethyl-N-(2-hydroxy-2-methylpropyl) benzenesulfonamide. The resulting oil was dried in vacuo (1.9 g, 81%).

Step 2: Preparation of 4-{[3-bromo-4-[(2,4-difluorobenzyl)oxy]-6-methyl-2-oxopyridin-1(2H)-yl]methyl}-N-(2-hydroxy-2-methylpropyl)benzenesulfonamide.

The title compound was prepared essentially according to the procedure described in Step 2 of Example 629, using 4-Bromomethyl-N-(2-hydroxy-2-methylpropyl) benzenesulfonamide (from step 1). $^1$H NMR (400 MHz, CDCl$_3$) δ 7.78 (d, J=8.4 Hz, 2H); 7.56 (app q, J=7.6 Hz, 1H); 7.26 (d, J=8.4 Hz); 6.95 (app t, J=8.4 Hz, 1H), 6.86–6.83 (m, 1H); 6.07 (s, 1H), 5.41 (s, 2H), 5.22 (s, 2H); 4.98 (t, J=6.4 Hz, 1H); 2.84 (d, J=6.4 Hz, 2H); 2.29 (s, 3H); 1.21 (s, 6H). ES-HRMS m/z 571.0684 (M+H calcd for $C_{24}H_{26}Br_2F_2N_2O_5S$ requires 571.0708).

Example 632

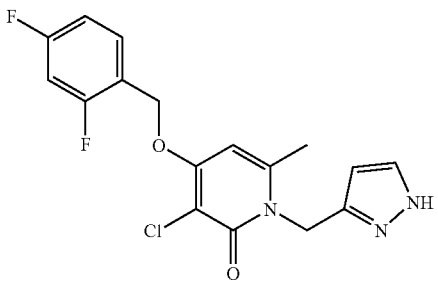

3-Chloro-4-(2,4-difluorobenzyloxy)-6-methyl-1-(1H-pyrazol-3-ylmethyl)-1H-pyridin-2-one Step 1. Preparation of 4-Hydroxy-6-methyl-1H-pyridin-2-one.

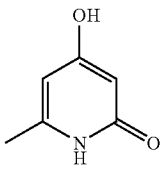

4-Hydroxy-6-methyl-pryan-2-one (25.8 g, 0.2 mol) was dissolved in 180 ml of concentrated ammonium hydroxide. The reaction was heated at refluxed for 4 hours. The reaction was cooled to room temperature and evaporated on a rotary evaporator to a quarter of the original volume. The resulting solid was filtered, washed with cold water, hexanes, and dried in a vacuum oven overnight to give a white solid (25 g, 98%): $^1$H NMR (300 MHz, DMSO-$d_6$) δ 10.94 (br s, 1H), 10.34 (s, 1H), 5.59 (d, J=1.4 Hz, 1H), 5.32 (d, J=2.0 Hz, 1H), 2.07 (s, 3H).

Step 2. Preparation of 3-Chloro-4-hydroxy-6-methyl-1H-pyridin-2-one.

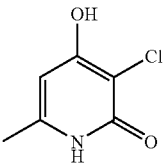

4-Hydroxy-6-methyl-1H-pyridin-2-one (25 g, 0.2 mol) and N-chlorosuccinimide (29.4 g, 0.22 mol) were dissolved in 200 mL of acetic acid. The reaction was heated at 115° C. for 6 hours. The reaction was cooled to room temperature, the solid was filtered, and washed with acetic acid and hexanes. The solid was dried in a vacuum oven overnight to give a white solid (19.2 g, 60%): $^1$H NMR (300 MHz, DMSO-$d_6$) δ 11.46 (br s, 1H), 11.04 (s, 1H), 5.79 (s, 1H), 2.09 (s, 3H).

Step 3. Preparation of 3-Chloro-4-(2,4-difluorobenzyloxy)-6-methyl-1H-pyridin-2-one.

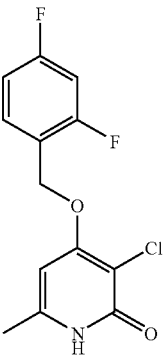

3-Chloro-4-hydroxy-6-methyl-1H-pyridin-2-one (19.2 g, 0.12 mol) and DBU (19.9 mL, 0.13 mol) were dissolved in 70 mL of NMP, 2,4-Difluorobenzylbromide (17 mL, 0.13 mol) was added dropwise and the reaction was heated at 80° C. for 6 hours. The reaction was cooled to room temperature, the solid was filtered, and washed with NMP and hexanes. The solid was dried in a vacuum oven overnight to give a white solid (4.4 g, 13%): $^1$H NMR (300 MHz, DMSO-$d_6$) δ 11.88 (br s, 1H), 7.63 (app q, J=9 Hz, 1H), 7.33 (app t, J=10 Hz, 1H), 7.16 (app t, J=9 Hz, 1H), 6.37 (s, 1H), 5.24 (s, 2H), 2.20 (s, 3H).

Step 4. Preparation of 3-Methylpyrazole-1-carboxylic acid tert-butyl ester.

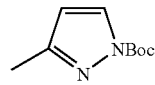

3-Methyl-1H-pyrazole (5.3 g, 65 mmol), DMAP (0.79 g, 6.5 mmol), and di-tert-butyl dicarbonate (2.8 g, 13 mmol) were at room temperature in 90 mL of $CH_3CN$ for 1 hour. The reaction was evaporated on a rotary evaporator, and the resulting solid dissolved in EtOAc, washed with 1 N HCl, water and brine, dried ($MgSO_4$), filtered, and evaporated on a rotary evaporator to give a light yellow oil (11.4 g, 96%): $^1$H NMR (300 MHz, CDCl$_3$) δ 7.96 (d, J=2.7 Hz, 1H), 6.17 (d, J=2.7 Hz, 1H), 2.32 (s, 3H), 1.63 (s, 9H).

Step 5. Preparation of 3-Bromomethylpyrazole-1-carboxylic acid tert-butyl ester.

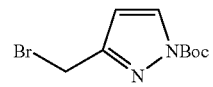

3-Methylpyrazole-1-carboxylic acid tert-butyl ester (6.0 g, 33 mmol), N-bromosuccinimide (1.0 g, 5.6 mmol) and benzoyl peroxide (50 mg) were dissolved in 20 mL of carbon tetrachloride. The reaction was heated at reflux for 16 h. The reaction was cooled to room temperature, filtered, and concentrated under reduced pressure. Purification by flash column chromatography (silica, 1:4 EtOAc/hexanes) gave a light yellow oil (4.5 g, 53%): $^1$H NMR (300 MHz, CDCl$_3$) δ 8.03 (d, J=2.6 Hz, 1H), 6.47 (d, J=2.6 Hz, 1H), 4.48 (s, 2H), 1.64 (s, 9H).

Step 6. Preparation of 3-[3-Chloro-4-(2,4-difluorobenzyloxy)-6-methyl-2-oxo-2H-pyridin-1-ylmethyl]pyrazole-1-carboxylic acid tert-butyl ester.

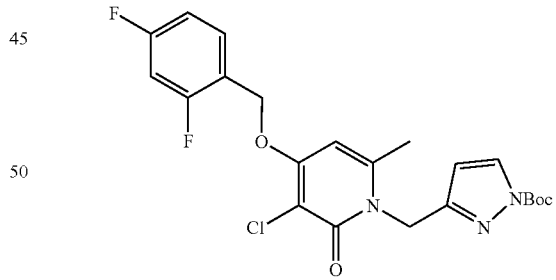

3-[3-Chloro-4-(2,4-difluorobenzyloxy)-6-methyl-2-oxo-2H-pyridin-1-ylmethyl]pyrazole-1-carboxylic acid tert-butyl ester was prepared by a procedure similar to the one described for Example 401 gave a yellow solid (1.4 g, 39%): $^1$H NMR (300 MHz, CDCl$_3$) δ 7.53–7.49 (m, 2H), 6.97–6.81 (m, 2H), 6.35 (d, J=2.0 Hz, 1H), 6.01 (s, 1H), 5.32 (s, 2H), 5.26 (s, 2H), 2.52 (s, 3H), 1.62 (s, 9H).

Step 7. Preparation of the title compound Example 632 3-[3-Chloro-4-(2,4-difluorobenzyloxy)-6-methyl-2-oxo-2H-pyridin-1-ylmethyl]pyrazole-1-carboxylic acid tert-butyl ester (0.16 g, 0.34 mmol) was heated to 140° C. for 16 h. The reaction mixture was cooled to room temperature.

Recrystallization from methylene chloride/hexanes provided an off-white solid (1.0 g, 91%): $^1$H NMR (300 MHz, DMSO-d$_6$) δ 12.67 (br s, 1H), 7.67–7.60 (m, 2H), 7.34 (dt, J=10.5, 2.5 Hz, 1H), 7.17 (dt, J=8.5, 1.6 Hz, 1H), 6.52 (s, 1H), 6.10 (d, J=1.9 Hz, 1H), 5.27 (s, 2H), 5.20 (s, 2H), 2.48 (s, 2H).

Example 633

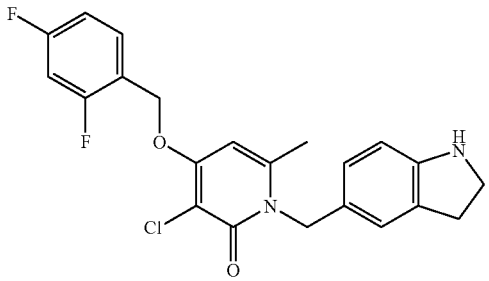

3-Chloro-4-(2,4-difluorobenzyloxy)-6-methyl-1-(2,3-dihydro-1H-indol-5-ylmethyl)-1H-pyridin-2-one Step 1. Preparation of 5-[3-Chloro-4-(2,4-difluorobenzyloxy)-6-methyl-2-oxo-2H-pyridin-1-ylmethyl]indole-1-carbamic acid tert-butyl ester

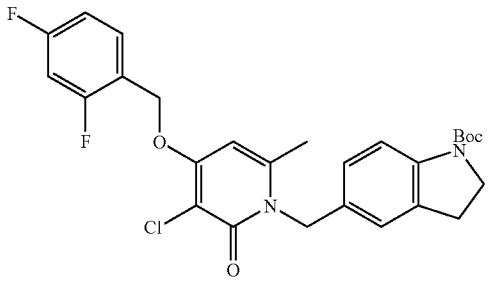

5-[3-Chloro-4-(2,4-difluorobenzyloxy)-2-oxo-2H-pyridin-1-ylmethyl]indole-1-carbamic acid tert-butyl ester was prepared by a procedure similar to the one described for Example 632 as an off-white solid (2.5 g, 61%): $^1$H NMR (300 MHz, DMSO-d$_6$) δ 8.00 (d, J=8.5 Hz, 1H), 7.70–7.62 (m, 2H), 7.39–7.32 (m, 2H), 7.21–7.13 (m, 2H), 6.70 (d, J=3.8 Hz, 1H), 6.66 (s, 1H), 5.40 (s, 2H), 5.29 (s, 2H), 2.33 (s, 3H), 1.62 (s, 9H).

Step 2. Preparation of 3-Chloro-4-(2,4-difluorobenzyloxy)-6-methyl-1-(1H-indol-5-ylmethyl)-1H-pyridin-2-one.

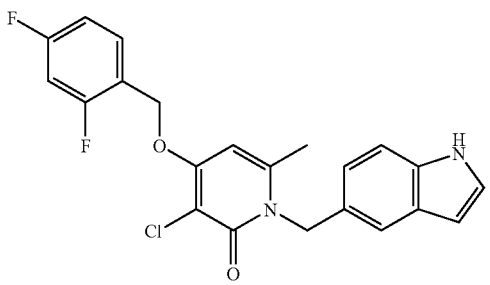

5-[3-Chloro-4-(2,4-difluorobenzyloxy)-6-methyl-2-oxo-2H-pyridin-1-ylmethyl]indole-1-carbamic acid tert-butyl ester (1.08 g, 2.1 mmol) dissolved in 40 mL of DMSO was stirred at 120° C. for 20 hours. The reaction was cooled to room temperature, diluted with water, and washed 5 times with ethyl acetate. The combined organics were washed 1 time with brine, dried (MgSO$_4$), filtered, and concentrated under reduced pressure. $^1$H NMR (300 MHz, DMSO-d$_6$) δ 11.1 (br s, 1H), 7.67 (d, J=6.7 Hz, 1H), 7.36–7.32 (m, 2H), 7.23 (s, 1H), 7.18 (d, J=2.3 Hz, 1H), 6.93 (dd, J=8.4, 1.2 Hz, 1H), 6.57 (s, 1H), 6.38 (s, 1H), 5.37 (s, 2H), 5.29 (s, 2H), 2.35 (s, 3H).

Step 3.3-Chloro-4-(2,4-difluorobenzyloxy)-6-methyl-1-(1H-indol-5-ylmethyl)-1H-pyridin-2-one (, from Step 2) (1.7 g, 4.1 mmol) was stirred in 26 mL of acetic acid and NaCNBH$_3$ (0.27 g, 4.3 mmol) was added portionwise. The reaction was stirred for 1 hour. The reaction was diluted water, and washed 5 times with ethyl acetate. The combined organics were washed 1 time with brine, dried (MgSO$_4$), filtered, and concentrated under reduced pressure. Purification by flash column chromatography (silica, 100% EtOAc) gave a white solid (1.2 g, 71%): $^1$H NMR (300 MHz, DMSO-d$_6$) δ 7.64 (app q, J=8.5 Hz, 1H), 7.34 (dt, J=9.5, 2.6 Hz, 1H), 7.17 (app t, J=8.5, 1H), 6.82 (s, 1H), 6.72 (d, J=8.0 Hz, 1H), 6.53 (s, 1H), 6.42 (d, J=8.0 Hz, 1H), 5.48 (br s, 1H), 5.27 (s, 2H), 5.13 (s, 2H), 3.37 (t, J=8.3 Hz, 2H), 2.82 (t, J=8.3 Hz, 2H), 2.35 (s, 3H).

Example 634

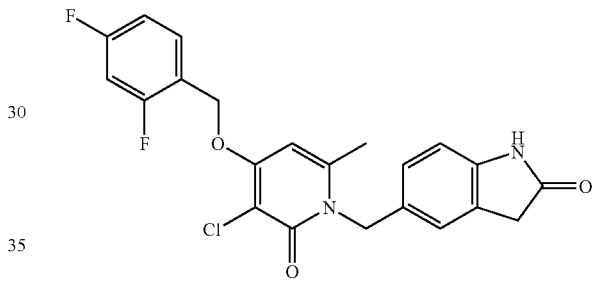

5-[3-Chloro-4-(2,4-difluorobenzyloxy)-6-methyl-2-oxo-2H-pyridin-1-ylmethyl]-1,3-dihydro-indol-2-one Step 1. Preparation of 5-[3-Chloro-4-(2,4-difluorobenzyloxy)-6-methyl-2-oxo-2H-pyridin-1-ylmethyl]-3,3-dibromo-1H-indol-2-one.

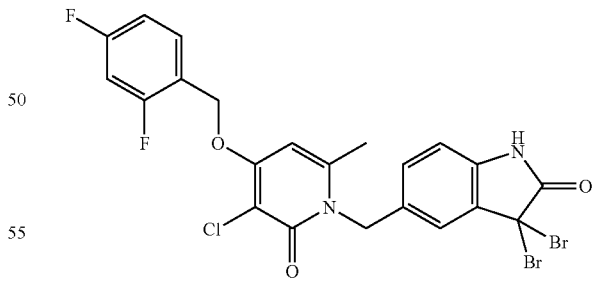

3-Chloro-4-(2,4-difluorobenzyloxy)-6-methyl-1-(1H-indol-5-ylmethyl)-1H-pyridin-2-one (0.45 mg, 1.1 mmol) (example 633, step 2) was suspended in 11 mL of tert-butanol and pyridinium bromide perbromide (1.04 g, 3.3 mmol) was added portionwise. The reaction was stirred for 16 hours. The reaction was diluted with water, and washed 4 times with ethyl acetate. The combined organics were washed 1 time with brine, dried (MgSO$_4$), filtered, and concentrated under reduced pressure. Trituration with meth ylene chloride gave an off-white solid (0.25 g, 39%): $^1$H NMR (300 MHz, DMSO-$d_6$) δ 11.26 (br s, 1H), 7.66 (app q, J=8.6 Hz, 1H), 7.48 (s, 1H), 7.35 (dt, J=10.5, 2.5 Hz, 1H), 7.18 (dt, J=8.7, 1.9, 1H), 7.05 (dd, J=8.2, 1.5, 1H), 6.88 (d, J=8.1 Hz, 1H), 6.61 (s, 1H), 5.29 (s, 4H), 2.36 (s, 3H).

Step 2.5-[3-Chloro-4-(2,4-difluorobenzyloxy)-6-methyl-2-oxo-2H-pyridin-1-ylmethyl]-3,3-dibromo-1H-indol-2-one (0.2 g, 0.34 mmol) was suspended in 5 mL of acetic acid, and zinc metal (0.22 g, 3.4 mmol) was added. The reaction was stirred for 48 hours. The reaction was diluted with water, and washed 2 times with ethyl acetate. The combined organics were washed 1 time with brine, dried (MgSO$_4$), filtered, and concentrated under reduced pressure. Purification by flash column chromatography (silica, 100% EtOAc) gave a white solid (0.12 g, 82%): $^1$H NMR (300 MHz, DMSO-$d_6$) δ 10.37 (br s, 1H), 7.65 (app q, J=6.9 Hz, 1H), 7.34 (dt, J=8.2, 2.5 Hz, 1H), 7.18 (dt, J=7.1, 1.9, 1H), 6.98 (br s, 2H), 6.77 (d, J=8.4 Hz, 1H), 6.57 (s, 1H), 5.28 (s, 2H), 5.23 (s, 2H), 3.44 (s, 2H), 2.34 (s, 3H).

Example 635

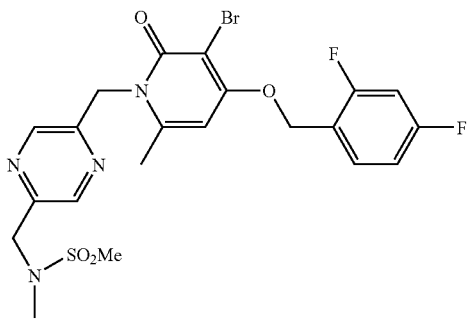

N-[(5-{[3-Bromo-4-[(2,4-difluorobenzyl)oxy]-6-methyl-2-oxopyridin-1(2H)-yl]methyl}pyrazin-2-yl)methyl]-N -methylmethanesulfonamide To a suspension of 3-bromo-4-[(2,4-difluorobenzyl)oxy]-6-methyl-1-({5-[(methylamino)methyl]pyrazin-2-yl}methyl)pyridin-2(1H)-one (0.16 g, 0.34 mmol) in acetonitrile at 0° C. was added triethylamine (0.043 g, 0.42 mmol), followed by the addition of methane sulfonylchloride (0.047 g, 0.41 mmol) and stirred at room temperature for 1 h under argon atmosphere. The solvents were removed in vacuo and the residue was triturated with water and filtered. It was washed with water an, acetonitrile and dried in vacuo to afford 0.11 g of material. $^1$H NMR (CD$_3$OD/400 MHz) δ 8.62 (s, 1H), 8.55 (s, 1H), 7.61 (m, 1H), 7.0 (m, 2H), 6.53 (s, 1H), 5.47 (s, 2H), 5.29 (s, 2H), 4.49 (s, 2H), 2.95 (s, 3H), 2.85 (s, 3H), and 2.55 (s, 3H); $^{19}$F NMR (CD$_3$OD/400 MHz) −111.70 (m) and −116.07 (m); ES-HRMS m/z 543.0515 (M+H calcd for C$_{21}$H$_{22}$BrF$_2$N$_4$O$_4$S requires 543.0508).

Example 636

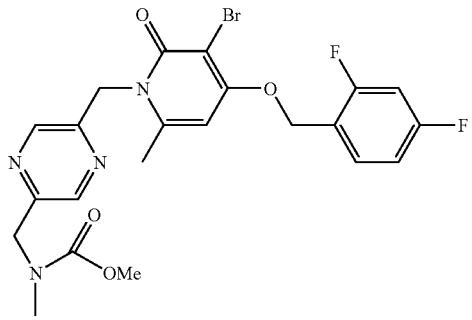

Methyl (5-{[3-Bromo-4-[(2,4-difluorobenzyl)oxy]-6-methyl-2-oxopyridin-1(2H)-yl]methyl}pyrazin-2-yl)methyl(methyl)carbamate To a cold (5° C.) solution of 3-bromo-4-[(2,4-difluorobenzyl)oxy]-6-methyl-1-({5-[(methylamino)methyl]pyrazin-2-yl}methyl)pyridin-2(1H)-one (0.20 g, 0.4 mmol) in DMF (2.0 ml), was added methylchloroformate (0.049 g, 0.52 mmol), followed by the addition of triethylamine (0.072 g, 0.71 mmol). The mixture was stirred at 5° C. for 30 min and at room temperature for an additional 30 min and concentrated in vacuo. The residue was partitioned between water (5.0 mL) and EtOAc (10.0 mL). The organic extract was washed with water, dried (Na$_2$SO$_4$), and concentrated to dryness. The resulting material was purified by reverse-phase HPLC using 10–90% CH$_3$CN/Water gradient (60 min) at a flow rate of 70 mL/min. The appropriate fractions (m/z=523 M+H) were combined and freeze dried to give a white powder. This was partitioned between 5% NaHCO$_3$ (10 mL) and EtOAc (15 mL). The organic layer was washed with water, dried (Na$_2$SO$_4$), and concentrated to dryness to afford the title compound (0.12 g, 53%) as a white powder: $^1$H NMR (CD$_3$OD/400 MHz) δ 8.59 (s, 1H), 8.41 (m, 1H), 7.60 (m, 1H), 7.05 (m, 2H), 6.52 (s, 1H), 5.45 (s, 2H), 5.29 (s, 2H), 4.58 (s, 2H), 3.69 and 3.64 (s, 3H), 2.97 (s, 3H), 2.85 (s, 3H), and 2.55 (s, 3H); $^{19}$F NMR(CD$_3$OD/ 400 MHz) −111.69 (m) and −116.09 (m); ES-HRMS m/z 523.0775(M+H calcd for C$_{22}$H$_{22}$BrF$_2$N$_4$O$_4$ requires 523.0787).

Example 637

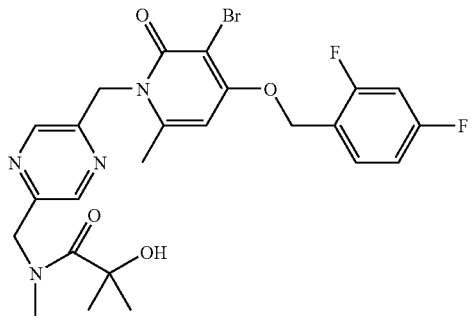

N-[(5-{[3-Bromo-4-[(2,4-difluorobenzyl)oxy]-6-methyl-2-oxopyridin-1(2H)-yl]methyl}pyrazin-2-yl)methyl]-2-hydroxy-N,2-dimethylpropanamide To a cold (5° C.) solution of 3-bromo-4-[(2,4-difluorobenzyl)oxy]-6-methyl-1-({5-[(methylamino)methyl]pyrazin-2-yl}methyl)pyridin-2(1H)-one (0.24 g, 0.52 mmol) in DMF (2.0 ml), was added 2-acetoxyisobutyryl chloride (0.093 g, 0.56 mmol), followed by the addition of triethylamine (0.072 g, 0.71 mmol). The mixture was stirred at room temperature for an additional 2 h and concentrated in vacuo. The residue was partitioned between water (5.0 mL) and EtOAc (15.0 mL). The EtOAc extract was washed with water, dried (Na$_2$SO$_4$), and concentrated to dryness. The resulting material (0.2 g) was stirred with 1M. LiOH (0.5 mL, MeOH/Water 1:1 v/v) at room temperature for 3 h, cooled, acidified with trifluoroacetic acid and the product was purified by reverse-phase HPLC using 10–90% CH$_3$CN/Water gradient (60 min) at a flow rate of 70 mL/min. The appropriate fractions (m/z=551 M+H) were combined and freeze dried to give a white powder. This was partitioned between 5% NaHCO$_3$ (10 mL) and EtoAc (15 mL). The organic layer was washed with water, dried (Na$_2$SO$_4$), and concentrated to dryness to afford the title compound (0.075 g) as a white powder: $^1$H NMR (CD$_3$OD/400 MHz) δ 8.59 (s, 1H), 8.41 (br, 1H), 7.60 (m, 2H), 7.01 (m, 2H), 6.52 (s, 1H), 5.45 (s, 2 h), 5.29 (s, 2H), Example 638

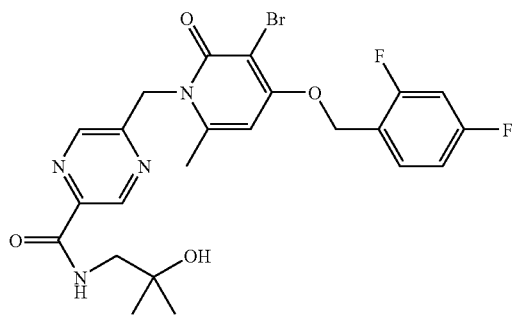

5-{[3-Bromo-4-[(2,4-difluorobenzyl)oxy]-6-methyl-2-oxopyridin-1(2H)-yl]methyl}-N-(2-hydroxy-2-methylpropyl)pyrazine-2-carboxamide To a solution of 5-{[3-bromo-4-[(2,4-difluorobenzyl)oxy]-6-methyl-2-oxopyridin-1(2H)-yl]methyl}pyrazine-2-carboxylic acid (0.42 g, 0.9 mmol) in DMF (3.0 mL) was added isobutylchloroformate (0.126 g, 0.13 mmol) followed by the addition of N-methylmorpholine (0.11 g, 1.1 mmol) and stirred at −10° C., under argon atmosphere. After 20 min, added a solution of 1,1 dimethyl-2-aminoethanol hydrochloride (0.135 g, 1.1 mmol) in DMF (2.0 mL) containing N-methylmorpholine (0.11 g, 1.1 mmol). The mixture was stirred at room temperature for 1 h, and concentrated to dryness in vacuo. The resulting residue was purified by reverse-phase HPLC using 10–90% CH$_3$CN/Water gradient (60 min) at a flow rate of 70 mL/min. The appropriate fractions (m/z=537 M+H) were combined and freeze dried to give a white powder. This was partitioned between 5% NaHCO$_3$ (10 mL) and EtOAc (15 mL). The organic layer was washed with water, dried (Na$_2$SO$_4$), and concentrated to dryness to afford the title compound (0.35 g, 75%) as a white powder: $^1$H NMR (CD$_3$OD/400 MHz) δ 9.1 (d, 1H, J=1.6 Hz), 8.71 (d, 1H, J=1.6 Hz), 7.61 (m 1H), 7.02 (m, 2H), 6.54 (s, 1H), 5.54 (s, 2H), 5.30 (s, 2 h). 3.30 (s, 2 h), 2.55 (s, 3H), and 1.21 (s, 6H); $^{19}$F NMR (CD$_3$OD/400 MHz) −111.67 (m) and −116.05 (m); ES-HRMS m/z 537.0948 (M+H calcd for C$_{23}$H$_{24}$BrF$_2$N$_4$O$_4$ requires 537.0943).

Example 639

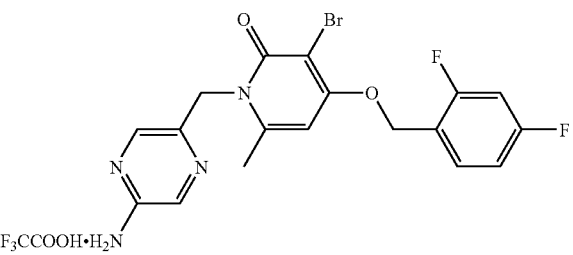

1-[(5-Aminopyrazin-2-yl)methyl]-3-bromo-4-[(2,4-difluorobenzyl)oxy]-6-methylpyridin-2(1H)-one trifluoroacetate A mixture of 5-{[3-bromo-4-[(2,4-difluorobenzyl)oxy]-6-methyl-2-oxopyridin-1(2H)-yl]methyl}pyrazine-2-carboxylic acid (0.70 g, 1.5 mmol) diphenylphosphoryl azide (0.51 g, 1.8 mmol) in dimethylacetamide (15.0 mL) and t-butanol (5.0 mL) containing triethylamine (0.18 g, 1.8 mmol) was heated at 90° C. for 6 h under argon atmosphere. The reaction mixture was cooled, filtered the precipitate. It was washed with acetonitrile and dried to obtain 0.22 g of the unreacted acid. The combilned filtrate and the washings were concentrated in vacuo and the resulting material was purified by reverse-phase HPLC using 10–90% CH$_3$CN/Water gradient (60 min) at a flow rate of 70 mL/min. The appropriate fractions (m/z=437 M+H were combined and freeze dried to give the title compound (0.21 g, 7%) as a white powder: $^1$H NMR (DMSO-d$_6$/400 MHz) δ 7.88 (d, 1H, J=1.2 Hz), 7.75 (d, 1H, J=1.2 Hz), 7.61 (m 1H), 7.34 (m, 1H), 7.18 (m, 1H), 6.49 (s, 1H), 5.25 (s, 2H), 5.10 (s, 2H), and 2.49 (s, 3H); $^{19}$F NMR (CD$_3$OD/400 MHz) −111.72 (m) and −116.11 (m); ES-HRMS m/z 437.0402(M+H calcd for C$_{18}$H$_{16}$BrF$_2$N$_4$O$_2$ requires 437.0419).

Example 640

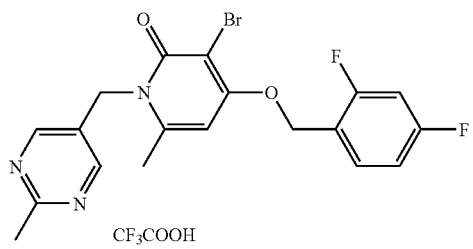

503

3-Bromo-4-[(2,4-difluorobenzyl)oxy]-6-methyl-1-[(3-methyl-1,2,4-triazin-6-yl)methyl]pyridin-2(1H)-one trifluoroacetate Step 1: Preparation of (2-methylpyrimidin-5-yl)methanol trifluoroacetate

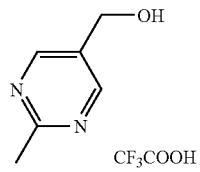

To solution of methyl 2-methylpyrimidinecarboxylate (2.6 g, 17.1 mmol) in THF was added dropwise diisobutylaluminumhydride (39.5 mL, 1M solution in THF) and stirred at −20° C. under argon atmosphere for 1.5 h, and at room temperature for 2 h. The reaction was quenched by the addition of powdered sodiumsulphate decahydrate (25 g), added THF (25 mL) and stirred at room temperature for 1 h. This mixture was allowed to stand in the refrigerator overnight and filtered through a celite pad. The precipitate was thoroughly with warm THF (100 mL) containing 10% ethanol. The combined washings and the filtrate were concentrated to afford ayellow syrup, which was purified by reverse-phase HPLC using 10–90% CH$_3$CN/Water gradient (60 min) at a flow rate of 70 mL/min. The appropriate fractions (m/z=125 M+H) were combined and lyophilized to give the title compound (0.67 g, 32%) as its trifluoroacetate salt: $^1$H NMR (CD$_3$OD/400 MHz) δ 8.65 (s, 2H), 4.62 (s, 2H), and 2.66 (s, 3H); ES-HRMS m/z 125.0678 (M+H calcd for C$_6$H$_9$N$_2$O requires 125.0709).

Step 2: Preparation of 3-bromo-4-[(2,4-difluorobenzyl)oxy]-6-methyl-1-[(3-methyl-1,2,4-triazin-6-yl)methyl]pyridin-2(1H)-one trifluoroacetate To a solution of (2-methylpyrimidin-5-yl)methanol trifluoroacetate (0.9 g, 3.76 mmol) in dichloromethane (10 mL) at 0° C., was added triethylamine (0.95 g, 9.41 mmol), followed by the addition of methanesulfonyl chloride (0.59 g, 5.17 mmol) and stirred at 0° C. for 1 h. After stirring for 1 h at room temperature, additional triethylamine (0.22 g) and methanesulfonyl chloride (0.15 g)were added and the mixture was stirred at room temperature for another hour under argon atmosphere. The reaction was quenched by the addition of cold water (15 mL) and stirred for 15 min. The organic layer was washed with water, followed by 5% sod. bicarbonate (2×15 mL), water, and dried (Na$_2$SO$_4$). After the removal of the solvent under reduced pressure, the residue was dried in a desiccator under vacuum for 4 h. This material was suspended in THF (10 mL) and DMF (5.0 mL), added 3-bromo-4-(2,4-difluorophenoxy)-6-methylpyridin-2(1H)-one (0.5 g, 1.52 mmol) and NaH (0.04 g). The resulting mixture was heated at 65° C. for 16 h under argon atmosphere. The solvents were distilled under vacuum and the residue was purified by reverse-phase HPLC using 10–90% CH$_3$CN/Water gradient (60 min) at a flow rate of 70 mL/min. The appropriate fractions (m/z=436 M+H) were combined and freeze dried to give the title compound (0.045 g,) as its trifluoroacetate salt: $^1$H NMR (CD$_3$OD/400 MHz) δ 8.58 (s, 2H), 7.61 (m, 1H), 7.01 (m, 2H), 6.53 (s, 1H), 5.37 (s, 2 h), 5.29 (s, 2H), 2.65 (s, 3H), and 2.46 (s, 3H); $^{19}$F NMR (CD$_3$OD/400 MHz) −111.62 (m), and −116.08 (m); ES-HRMS m/z 436.0433(M+H calcd for C$_{19}$H$_{17}$BrF$_2$N$_3$O$_2$ requires 436.0467).

504

Example 641

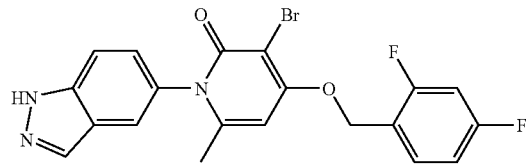

3-Bromo-4-[(2,4-difluorobenzyl)oxy]-1-(1H-indazol-5-yl)-6-methylpyridin-2(1H)-one Step 1: Preparation of 4-hydroxy-1-(1H-indazol-5-yl)-6-methylpyridin-2(1H)-one

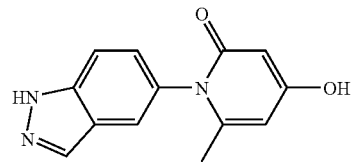

A mixture of 4-hydroxy-6-methyl-2-pyrone (3.75 g, 0.029 mol) and 5-aminoindazole (4.0 g, 0.03 mol) in water (70 ml) was heated at 90° C. under argon for 1 h. The mixture was cooled, decanted the supernatant and residue was triturated with ethanol, cooled and filtered the solid. It was washed with cold ethanol, and dried. $^1$H NMR (CD$_3$OD/400 MHz) δ 8.11 (s, 1H), 7.64 (m, 2H), 7.18 (d, 1H, J=2.0 Hz), 7.16 (d, 1H, J=2.0 Hz), 6.07 (m, 1H), 5.81 (d, 1H, J=2.8 Hz), and 1.94 (s, 3H); ES-HRMS m/z 242.0962 (M+H calcd for C$_{13}$H$_{12}$N$_3$O$_2$ requires 242.0924).

Step 2:

A mixture of 4-hydroxy-1-(1H-indazol-5-yl)-6-methylpyridin-2(1H)-one (0.2 g, 0.83 mmol), N-bromosuccinimide (0.15 g, 0.84 mmol) in dichloromethane (4.0 mL) and acetic acid (1.0 mL) was stirred at room temperature under argon atmosphere for 2.5 h. After the removal of the solvents, the residue was dried in vacuo for 4 h in a desiccator. It was then suspended in DMF (3.0 mL), potassium carbonate (0.1 g), and 2,4 difluorobenzyl bromide were added and mixture was stirred at room temperature for 3 h. DMF was distilled in vacuo and the residue was purified by reverse-phase HPLC using 10–90% CH$_3$CN/Water gradient (60 min) at a flow rate of 70 mL/min. The appropriate fractions (m/z=537 M+H) were combined and freeze dried to give a white powder. This was partitioned between 5% NaHCO$_3$ (10 mL) and EtOAc (15 mL). The organic layer was washed with water, dried (Na$_2$SO$_4$), and concentrated to dryness to afford the title compound (0.075 g) as a white powder: $^1$H NMR (CD$_3$OD/400 MHz) δ 8.13 (s, 1H), 7.68 (m, 3H), 7.20 (2d, 1H, J=1.2 Hz), 7.05 (m, 2H), 6.61 (s, 1H), 5.35 (s, 2H), and 2.05 (s, 3H); $^{19}$F NMR (CD$_3$OD/400 MHz) −111.62 (m) and −116.02 (m); ES-HRMS m/z 446.0305 (M+H calcd for C$_{20}$H$_{15}$BrF$_2$N$_3$O$_2$ requires 446.0310).

Example 642

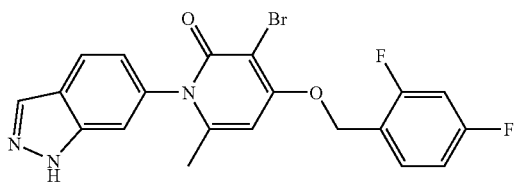

3-bromo-4-[(2,4-difluorobenzyl)oxy]-1-(1H-indazol-6-yl)-6-methylpyridin-2(1H)-one Step 1: Preparation of 4-hydroxy-1-(1H-indazol-6-yl)-6-methylpyridin-2(1H)-one

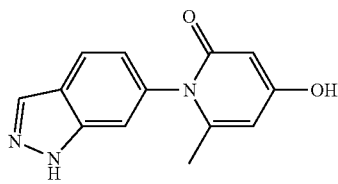

The title compound was prepared by a similar procedure described for 4-hydroxy-1-(1H-indazol-5-yl)-6-methylpyridin-2(1H)-one. Yield=12%; $^1$H NMR (CD$_3$OD/400 MHz) δ 8.12 (s, 1H), 7.90 (d, 1H, J=8.0 Hz), 7.42 (s, 1H), 6.94 (d, 1H, J=8.8 Hz), 6.08 (br s, 1H), 5.81 (d, 1H, J=2.4 Hz), and 1.96 (s, 3H); ES-HRMS m/z 242.0946 (M+H calcd for C$_{13}$H$_{12}$N$_3$O$_2$ requires 242.0924).

Step 2:

The title was prepared by a similar procedure described for 3-Bromo-4-[(2,4-difluorobenzyl)oxy]-1-(1H-indazol-5-yl)-6-methylpyridin-2(1H)-one. $^1$H NMR (CD$_3$OD/400 MHz) δ 8.14 (s, 1H), 7.93 (d, 1H, J=8.4 Hz), 7.61 (m, 1H), 7.46 (s, 1H), 7.04 (m, 2H), 6.98 (m, 1H), 6.62 (s, 1H), 5.36 (s, 2H), and 2.06 (s, 3H); $^{19}$F NMR (CD$_3$OD/400 MHz) –111.62 (m) and –116.03 (m); ES-HRMS m/z 446.0302 (M+H calcd for C$_{13}$H$_{12}$N$_3$O$_2$ requires 446.0310).

Example 643

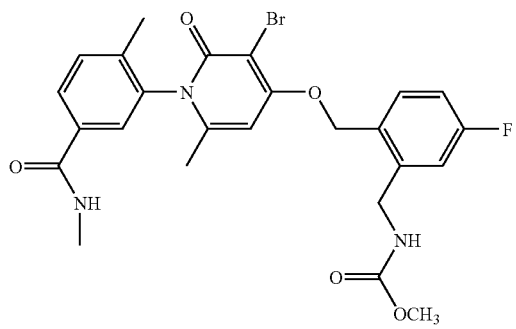

methyl 2-{[(3-bromo-6-methyl-1-{2-methyl-5-[(methylamino)carbonyl]phenyl}-2-oxo-1,2-dihydropyridin-4-yl)oxy]methyl}-5-fluorobenzylcarbamate Step 1: Preparation of methyl 3-[4-[(2-cyano-4-fluorobenzyl)oxy]-6-methyl-2-oxopyridin-1(2H)-yl]-4-methylbenzoate.

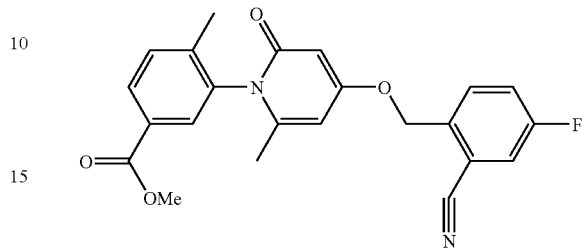

To a cooled (0° C.) solution of 2-(bromomethyl)-5-fluorobenzonitrile (4.31 g, 20.1 mmol) and methyl 3-(4-hydroxy-6-methyl-2-oxopyridin-1(2H)-yl)-4-methylbenzoate (5.00 g, 18.3 mmol) in DMF (20 mL) was added K$_2$CO$_3$ (3.00 g, 22.0 mmol). The reaction was allowed to warm to RT and stirred overnight. Additional 2-(bromomethyl)-5-fluorobenzonitrile (0.39 g, 1.83 mmol) and K$_2$CO$_3$ (0.25 g, 1.83 mmol) were added and the reaction heated at 60° C. for 2 h. Solvent removed by distillation. Reaction neutralized with 5% citric acid (50 mL). Organic products were extracted in DCM (3×25 mL), dried over Na$_2$SO$_4$, filtered, and concentrated to a thick dark brown oil. Purified by silica gel flash column chromatography using EtOAc as the eluent to give the product as a brown solid, dried in vacuo (6.18 g, 76%). $^1$H NMR (CD$_3$OD/400 MHz) δ 8.03 (m, 1H), 7.76 (m, 2H), 7.66 (m, 1H), 7.52 (m, 2H), 6.24 (s, 1H), 6.09 (s, 1H), 5.27 (s, 2H), 3.89 (s, 3H), 2.12 (s, 3H), 1.90 (s, 3H). ES HRMS m/z 407.1408 (M+H calculated for C$_{23}$H$_{20}$FN$_2$O$_4$ requires 407.1402).

Step 2: Preparation of methyl 3-[4-{[2-(aminomethyl)-4-fluorobenzyl]oxy}-6-methyl-2-oxopyridin-1(2H)-yl]-4-methylbenzoate trifluoroacetate

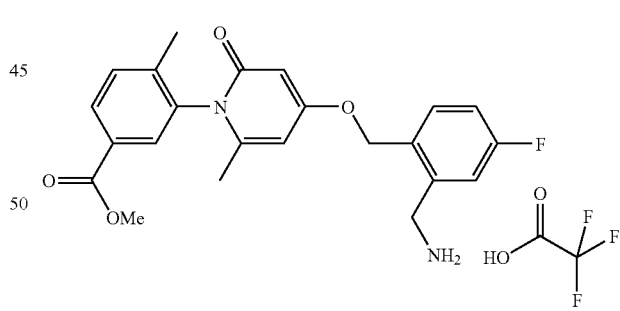

To a cooled (0° C.) solution of methyl 3-[4-[(2-cyano-4-fluorobenzyl)oxy]-6-methyl-2-oxopyridin-1(2H)-yl]-4-methylbenzoate (from Step 1) (0.510 g, 1.25 mmol) in THF (5 mL) was added dropwise BH$_3$THF (2.51 mL, 2.51 mmol). The reaction was then stirred at RT for 2.5 h. Reaction cooled (0° C.), quenched by the slow addition of MeOH, concentrated, and purified by preparatory HPLC. The product was isolated by freeze-drying and evaporation of the solvent to give a white solid, dried in vacuo (0.39 g, 76%). $^1$H NMR (CD$_3$OD/400 MHz) δ 8.04 (m, 1H), 7.75 (s, 1H), 7.63 (m, 1H), 7.55 (d, 1H, J=8.4 Hz), 7.32 (m, 1H), 7.24 (m, 1H), 6.25 (s, 1H), 6.12 (s, 1H), 5.23 (s, 2H), 4.25

(s, 2H), 3.90 (s, 3H), 2.11 (s, 3H), 1.90 (s, 3H). ES HRMS m/z 411.1691 (M+H calculated for $C_{23}H_{24}FN_2O_4$ requires 411.1715).

Step 3: Preparation of methyl 3-[4-[(4-fluoro-2-{[(methoxycarbonyl)amino]methyl}benzyl)oxy]-6-methyl-2-oxopyridin-1(2H)-yl]-4-methylbenzoate.

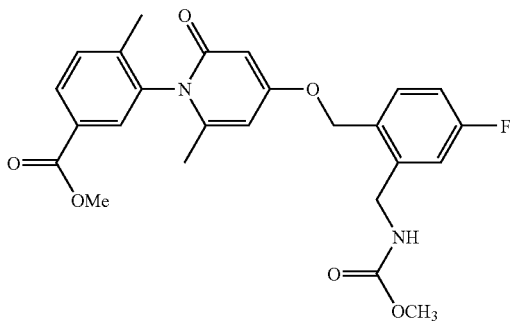

To a cooled (0° C.) solution of methyl 3-[4-{[2-(aminomethyl)-4-fluorobenzyl]oxy}-6-methyl-2-oxopyridin-1(2H)-yl]-4-methylbenzoate trifluoroacetate (from Step 2) (0.50 g, 0.95 mmol) in DMA (4 mL) was added 4-methylmorpholine (0.21 mL, 1.9 mmol) and methyl chloroformate (0.08 mL, 1.0 mmol). Reaction was stirred at RT for 1 h. Solvent removed by distillation. Crude product purified by preparatory HPLC. Acetonitrile was evaporated and the solution washed with 5% $NaHCO_3$ (30 mL) and extracted in DCM (3×25 mL). The organic extracts were dried over $Na_2SO_4$, filtered, and concentrated to a white solid, dried in vacuo (0.36 g, 81%). $^1$H NMR ($CD_3OD$/400 MHz) δ 8.03 (m, 1H), 7.77 (s, 1H), 7.53 (d, 1H, J=7.6 Hz), 7.47 (m, 1H), 7.12 (m, 1H), 7.03 (m, 1H), 6.21 (s, 1H), 6.08 (s, 1H), 5.18 (s, 2H), 4.38 (s, 2H), 3.89 (s, 3H), 3.65 (s, 3H), 2.12 (s, 3H), 1.89 (s, 3H). ES HRMS m/z 469.1767 (M+H calculated for $C_{25}H_{26}FN_2O_6$ requires 469.1769).

Step 4: Preparation of 3-[4-[(4-fluoro-2-{[(methoxycarbonyl)amino]methyl}benzyl)oxy]-6-methyl-2-oxopyridin-1(2H)-yl]-4-methylbenzoic acid.

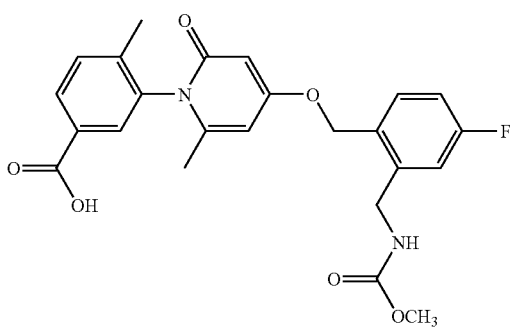

To methyl 3-[4-[(4-fluoro-2-{[(methoxycarbonyl)amino]methyl}benzyl)oxy]-6-methyl-2-oxopyridin-1(2H)-yl]-4-methylbenzoate (from Step 3) (0.17 g, 0.36 mmol) was added 1.5 N NaOH solution in 1:1 MeOH:water (0.39 mL, 0.59 mmol). The reaction mixture was stirred at 60° C. for 2.5 h. The solution was cooled (0° C.), neutralized by the slow addition of 5% citric acid, and organic products extracted in DCM. A white solid suspended in the organic layer was filtered, washed with DCM and water, dried in vacuo, and found to be the desired product (0.090 g, 55%). $^1$H NMR ($CD_3OD$/400 MHz) δ 8.03 (m, 1H), 7.75 (s, 1H), 7.52 (d, 1H, J=8.0 Hz), 7.47 (m, 1H), 7.12 (m, 1H), 7.03 (m, 1H), 6.21 (s, 1H), 6.08 (s, 1H), 5.18 (s, 2H), 4.38 (s, 2H), 3.65 (s, 3H), 2.12 (s, 3H), 1.90 (s, 3H). ES HRMS m/z 455.1632 (M+H calculated for $C_{24}H_{24}FN_2O_6$ requires 455.1613)

Step 5: Preparation of 3-[3-bromo-4-[(4-fluoro-2-{[(methoxycarbonyl)amino]methyl}benzyl)oxy]-6-methyl-2-oxopyridin-1(2H)-yl]-4-methylbenzoic acid.

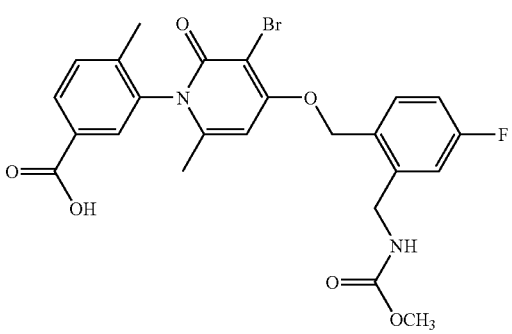

NBS (0.69 g, 3.85 mmol) was added to a solution of 3-[4-[(4-fluoro-2-{[(methoxycarbonyl)amino]methyl}benzyl)oxy]-6-methyl-2-oxopyridin-1(2H)-yl]-4-methylbenzoic acid (from Step 4) (1.75 g, 3.85 mmol) in DCM (45 mL). After 1.5 h, solvent removed on rotary evaporator. Solid dissolved in EtOAc and hexane added, resulting in a solid precipitate. Solid filtered. Solid subsequently dissolved in DCM and washed with water. Organic layer dried over $Na_2SO_4$, filtered, and concentrated. Pale yellow solid dried in vacuo (1.47 g, 72%).

$^1$H NMR ($CD_3OD$/400 MHz) δ 8.04 (m, 1H), 7.77 (s, 1H), 7.54 (m, 2H), 7.13 (m, 1H), 7.05 (m, 1H), 6.68 (s, 1H), 5.40 (s, 2H), 4.44 (s, 2H), 3.64 (s, 3H), 2.09 (s, 3H), 1.99 (s, 3H). ES HRMS m/z 533.0700 and 535.0677 (M+H calculated for $C_{24}H_{23}BrFN_2O_6$ requires 533.0718 and 535.0701).

Step 6: Preparation of the Title Compound.

To a cooled (−10° C.) solution of 3-[3-bromo-4-[(4-fluoro-2-{[(methoxycarbonyl)amino]methyl}benzyl)oxy]-6-methyl-2-oxopyridin-1(2H)-yl]-4-methylbenzoic acid (0.07 g, 0.13 mmol) in DMF (2.0 mL) was added isobutyl chloroformate (0.02 mL, 0.16 mmol) and 4-methylmorpholine (0.02 mL, 0.16 mmol). After 15 min, 2.0M methylamine in THF (0.01 mL, 0.20 mmol) was added. Solvent removed by distillation after 30 min. Crude product purified by preparatory HPLC. Acetonitrile was evaporated and the solution washed with 5% $NaHCO_3$ (30 mL) and extracted in DCM (3×25 mL). The organic extracts were dried over $Na_2SO_4$, filtered, concentrated, and dried in vacuo to give a white foam, (0.061 g, 86%). $^1$H NMR ($CD_3OD$/400 MHz) δ 7.85 (m, 1H), 7.54 (m, 3H), 7.14 (m, 1H), 7.05 (m, 1H), 6.68 (s, 1H), 5.40 (s, 2H), 4.43 (s, 2H), 3.64 (s, 3H), 2.89 (s, 3H), 2.08 (s, 3H), 1.99 (s, 3H). ES HRMS m/z 546.0987 and 548.1018 (M+H calculated for $C_{25}H_{26}BrFN_3O_5$ requires 546.1034 and 548.1018).

Example 644

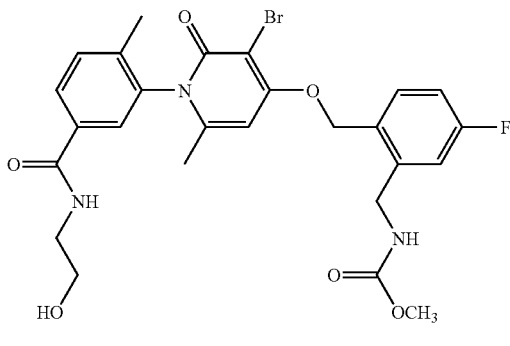

methyl 2-({[3-bromo-1-(5-{[(2-hydroxyethyl)amino]carbonyl}-2-methylphenyl)-6-methyl-2-oxo-1,2-dihydropyridin-4-yl]oxy}methyl)-5-fluorobenzylcarbamate The title compound was prepared using a procedure similar to that used in the preparation of Example 643. $^1$H NMR (CD$_3$OD/400 MHz) δ 7.88 (m, 1H), 7.61 (s, 1H), 7.53 (m, 2H), 7.13 (m, 1H), 7.04 (m, 1H), 6.68 (s, 1H), 5.41 (s, 2H), 4.43 (s, 2H), 3.68 (t, 2H, J=5.6 Hz), 3.64 (s, 3H), 3.48 (t, 2H, J=5.6 Hz), 2.08 (s, 3H), 2.00 (s, 3H). ES HRMS m/z 576.1101 and 578.1072 (M+H calculated for C$_{26}$H$_{28}$BrFN$_3$O$_6$ requires 576.1140 and 578.1124).

Example 645

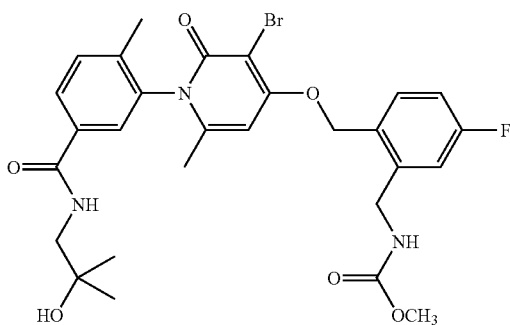

methyl 2-({[3-bromo-1-(5-{[(2-hydroxy-2-methylpropyl)amino]carbonyl}-2-methylphenyl)-6-methyl-2-oxo-1,2-dihydropyridin-4-yl]oxy}methyl)-5-fluorobenzylcarbamate The title compound was prepared using a procedure similar to that used in the preparation of Example 643. $^1$H NMR (CD$_3$OD/400 MHz) δ 7.89 (m, 1H), 7.63 (s, 1H), 7.54 (m, 2H), 7.13 (m, 1H), 7.04 (m, 1H), 6.69 (s, 1H), 5.41 (s, 2H), 4.43 (s, 2H), 3.64 (s, 3H), 3.38 (s, 2H), 2.09 (s, 3H), 2.01 (d, 6H, J=3.2 Hz), 1.21 (s, 3H). ES HRMS m/z 604.1412 and 606.1418 (M+H calculated for C$_{28}$H$_{32}$BrFN$_3$O$_6$ requires 604.1453 and 606.1438).

Example 646

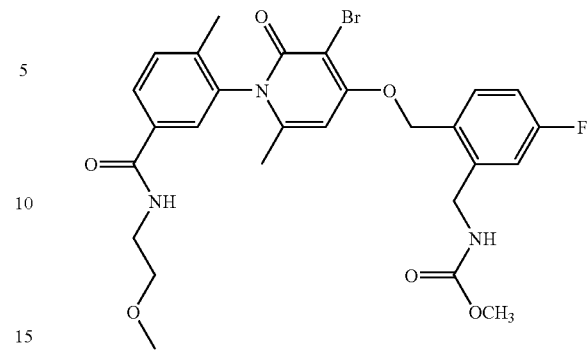

methyl 2-({[3-bromo-1-(5-{[(2-methoxyethyl)amino]carbonyl}-2-methylphenyl)-6-methyl-2-oxo-1,2-dihydropyridin-4-yl]oxy}methyl)-5-fluorobenzylcarbamate The title compound was prepared using a procedure similar to that used in the preparation of Example 643. $^1$H NMR (CD$_3$OD/400 MHz) δ 7.87 (m, 1H), 7.59 (s, 1H), 7.53 (m, 2H), 7.14 (m, 1H), 7.05 (m, 1H), 6.68 (s, 1H), 5.41 (s, 2H), 4.44 (s, 2H), 3.64 (s, 3H), 3.54 (s, 4H), 3.35 (s, 3H), 2.08 (s, 3H), 2.00 (s, 3H). ES HRMS m/z 590.1267 and 592.1219 (M+H calculated for C$_{27}$H$_{30}$BrFN$_3$O$_6$ requires 590.1297 and 592.1281).

Example 647

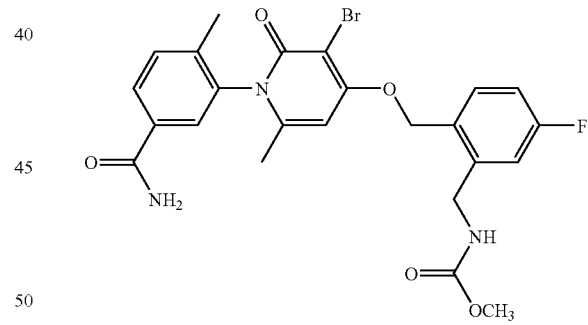

methyl 2-[({1-[5-(aminocarbonyl)-2-methylphenyl]-3-bromo-6-methyl-2-oxo-1,2-dihydropyridin-4-yl}oxy)methyl]-5-fluorobenzylcarbamate The title compound was prepared using a procedure similar to that used in the preparation of Example 643. $^1$H NMR (CD$_3$OD/400 MHz) δ 7.91 (m, 1H), 7.64 (s, 1H), 7.54 (m, 2H), 7.14 (m, 1H), 7.05 (m, 1H), 6.68 (s, 1H), 5.40 (s, 2H), 4.44 (s, 2H), 3.64 (s, 3H), 2.09 (s, 3H), 2.00 (s, 3H). ES HRMS m/z 532.0836 and 534.0787 (M+H calculated for C$_{24}$H$_{24}$BrFN$_3$O$_5$ requires 532.0878 and 534.0861).

Example 648

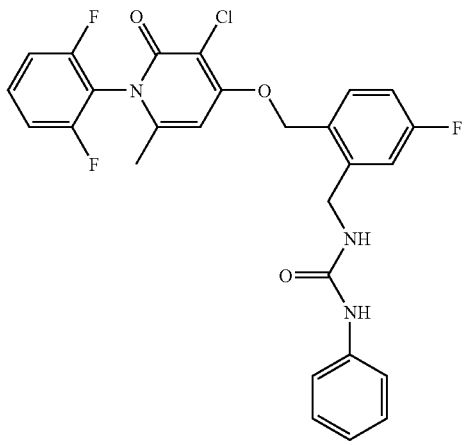

N-[2-({[3-chloro-1-(2,6-difluorophenyl)-6-methyl-2-oxo-1,2-dihydropyridin-4-yl]oxy}methyl)-5-fluorobenzyl]-N'-phenylurea To a cooled (0° C.) solution of 4-{[2-(aminomethyl)-4-fluorobenzyl]oxy}-3-chloro-1-(2,6-difluorophenyl)-6-methylpyridin-2(1H)-one trifluoroacetate (0.25 g, 0.48 mmol) in DMA (2.0 mL) was added 4-methylmorpholine (0.06 mL, 0.53 mmol) and phenyl isocyanate (0.06 mL, 0.53 mmol). The reaction was stirred at RT for 1.5 h. Solvent distilled and crude product purified by preparatory HPLC. Acetonitrile was evaporated and the solution washed with 5% NaHCO$_3$ (30 mL) and extracted in DCM (3×25 mL). The organic extracts were dried over Na$_2$SO$_4$, filtered, and concentrated to a white solid, dried in vacuo (0.18 g, 71%). $^1$H NMR (CD$_3$OD/400 MHz) δ 7.60 (m, 1H), 7.54 (m, 1H), 7.33 (d, 2H, J=7.6 Hz), 7.22 (m, 5H), 7.06 (m, 1H), 6.95 (t, 1H, J=7.2 Hz), 6.73 (s, 1H), 5.44 (s, 2H), 4.53 (s, 2H), 2.07 (s, 3H). ES HRMS m/z 528.1304 (M+H calculated for C$_{27}$H$_{22}$ClF$_3$N$_3$O$_3$ requires 528.1296).

Example 649

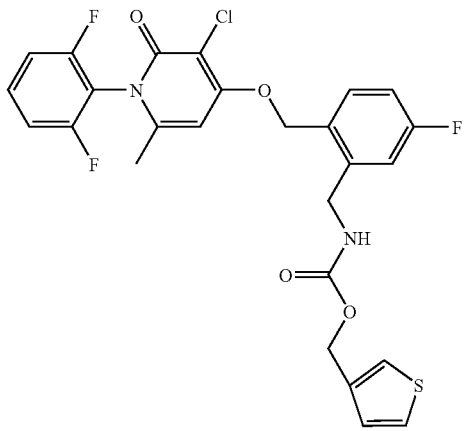

thien-3-ylmethyl 2-({[3-chloro-1-(2,6-difluorophenyl)-6-methyl-2-oxo-1,2-dihydropyridin-4-yl]oxy}methyl)-5-fluorobenzylcarbamate To a cooled (0° C.) solution of 4-{[2-(aminomethyl)-4-fluorobenzyl]oxy}-3-chloro-1-(2,6-difluorophenyl)-6-methylpyridin-2(1H)-one trifluoroacetate (0.26 g, 0.50 mmol) and 1,1-carbonyldiimidazole (0.10 g, 0.60 mmol) in DMA (2.0 mL) was added 4-methylmorpholine (0.06 mL, 0.55 mmol). After 1 h at RT, 3-thiophenemethanol (0.09 mL, 0.99 mmol) was added. No product was observed after 2 h at RT. NaH (0.01 g, 0.50 mmol) was added and the reaction stirred at 60° C. Reaction was complete after 20 min. The reaction mixture was cooled (0° C.) and acetic acid added to quench the reaction. Solvent removed by distillation. Crude product purified by preparatory HPLC. Acetonitrile was evaporated and the solution washed with 5% NaHCO$_3$ (30 mL) and extracted in DCM (3×25 mL). The organic extracts were dried over Na$_2$SO$_4$, filtered, and concentrated to a white foam, dried in vacuo (0.20 g, 73%). $^1$H NMR (CD$_3$OD/400 MHz) δ 7.61 (m, 1H), 7.52 (m, 1H), 7.34 (s, 2H), 7.23 (t, 3H, J=8.4 Hz), 7.10 (m, 2H), 6.71 (s, 1H), 5.40 (s, 2H), 5.07 (s, 2H), 4.43 (s, 2H), 2.10 (s, 3H). ES HRMS m/z 549.0858 (M+H calculated for C$_{26}$H$_{21}$ClF$_3$N$_2$O$_4$S requires 549.0857).

Example 650

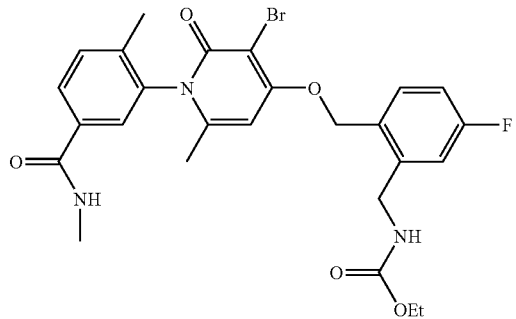

ethyl 2-{[(3-bromo-6-methyl-1-{2-methyl-5-[(methylamino)carbonyl]phenyl}-2-oxo-1,2-dihydropyridin-4-yl)oxy]methyl}-5-fluorobenzylcarbamate Step 1: Preparation of methyl 3-[4-[(2-{[(ethoxycarbonyl)amino]methyl}-4-fluorobenzyl)oxy]-6-methyl-2-oxopyridin-1(2H) yl]-4-methylbenzoate.

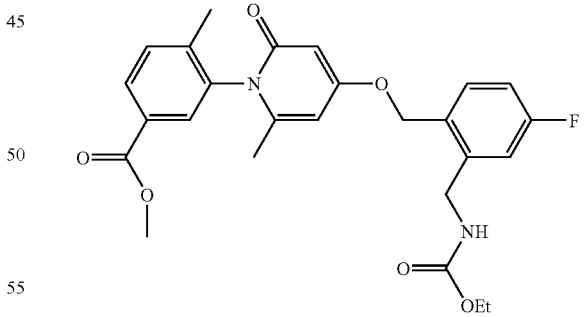

Prepared using a procedure similar to that used in the preparation of methyl 3-[4-[(4-fluoro-2-{[(methoxycarbonyl)amino]methyl}benzyl)oxy]-6-methyl-2-oxopyridin-1(2H)-yl]-4-methylbenzoate. $^1$H NMR (CD$_3$OD/400 MHz) δ 8.03 (m, 1H), 7.76 (s, 1H), 7.53 (d, 1H, J=8.0 Hz), 7.47 (m, 1H), 7.12 (m, 1H), 7.03 (m, 1H), 6.21 (s, 1H), 6.08 (s, 1H), 5.18 (s, 2H), 4.38 (s, 2H), 4.08 (q, 2H, J=6.8 Hz), 3.89 (s, 3H), 2.12 (s, 3H), 1.89 (s, 3H), 1.23 (t, 3H, J=6.8 Hz). ES HRMS m/z 483.1900 (M+H calculated for C$_{26}$H$_{28}$FN$_2$O$_6$ requires 483.1926).

Step 2: Preparation of 3-[4-[(2-{[(ethoxycarbonyl)amino]methyl}-4-fluorobenzyl)oxy]-6-methyl-2-oxopyridin-1(2H)-yl]-4-methylbenzoic acid.

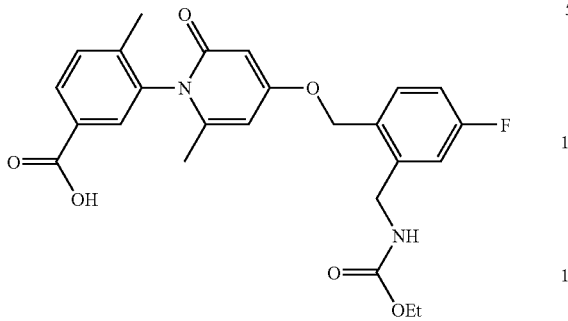

Prepared using a procedure similar to that used in the preparation of 3-[4-[(4-fluoro-2-{[(methoxycarbonyl)amino]methyl}benzyl)oxy]-6-methyl-2-oxopyridin-1(2H)-yl]-4-methylbenzoic acid. $^1$H NMR (CD$_3$OD/400 MHz) δ 8.03 (m, 1H), 7.74 (s, 1H), 7.48 (m, 2H), 7.11 (m, 1H), 7.03 (m, 1H), 6.21 (s, 1H), 6.08 (s, 1H), 5.18 (s, 2H), 4.38 (s, 2H), 4.08 (q, 2H, J=7.2 Hz), 2.11 (s, 3H), 1.90 (s, 3H), 1.23 (t, 3H, J=7.2 Hz). ES HRMS m/z 469.1738 (M+H calculated for C$_{25}$H$_{26}$FN$_2$O$_6$ requires 469.1769).

Step 3: Preparation of 3-[3-bromo-4-[(2-{[(ethoxycarbonyl)amino]methyl}-4-fluorobenzyl)oxy]-6-methyl-2-oxopyridin-1(2H)-yl]-4-methylbenzoic acid.

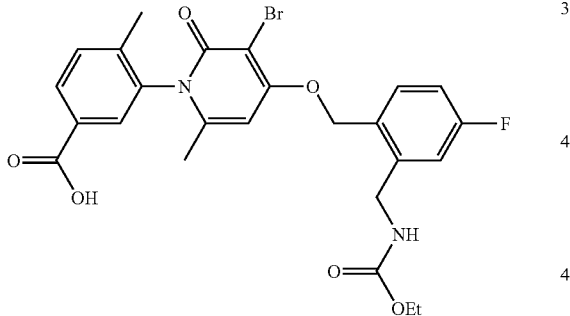

Prepared using a procedure similar to that used in Step 5 of the synthesis of Example 643. $^1$H NMR (CD$_3$OD/400 MHz) δ 8.04 (m, 1H), 7.76 (s, 1H), 7.55 (m, 2H), 7.13 (m, 1H), 7.05 (m, 1H), 6.68 (s, 1H), 5.40 (s, 2H), 4.43 (s, 2H), 4.07 (m, 2H), 2.09 (s, 3H), 1.99 (s, 3H), 1.22 (t, 3H, J=7.2 Hz). ES HRMS m/z 547.0842 and 549.0818 (M+H calculated for C$_{25}$H$_{25}$BrFN$_2$O$_6$ requires 547.0875 and 549.0858).

Step 4:

Prepared using a procedure similar to that used in the preparation of Example 643. $^1$H NMR (CD$_3$OD/400 MHz) δ 7.85 (m, 1H), 7.54 (m, 3H), 7.13 (m, 1H), 7.04 (m, 1H), 6.68 (s, 1H), 5.40 (s, 2H), 4.43 (s, 2H), 4.07 (q, 2H), 2.89 (s, 3H), 2.08 (s, 3H), 1.99 (s, 3H), 1.23 (t, 3H, J=7.2 Hz). ES HRMS m/z 560.1215 and 562.1193 (M+H calculated for C$_{26}$H$_{28}$BrFN$_3$O$_5$ requires 560.1191 and 562.1175).

Example 651

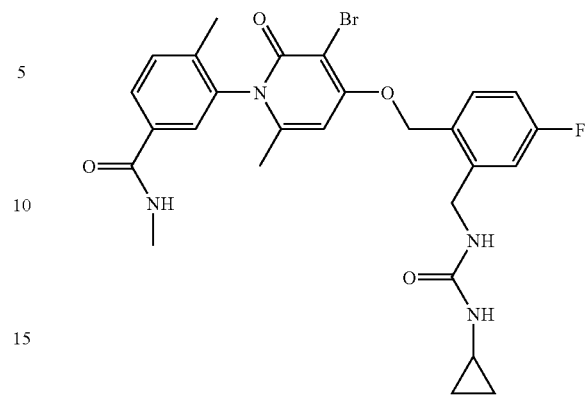

3-[3-bromo-4-([2-({[(cyclopropylamino)carbonyl]amino}methyl)-4-fluorobenzyl]oxy}-6-methyl-2-oxopyridin-1(2H)-yl]-N,4-dimethylbenzamide Step 1: Preparation of methyl 3-[4-{[2-({[(cyclopropylamino)carbonyl]amino}methyl)-4-fluorobenzyl]oxy}-6-methyl-2-oxopyridin-1(2H)-yl]-4-methylbenzoate.

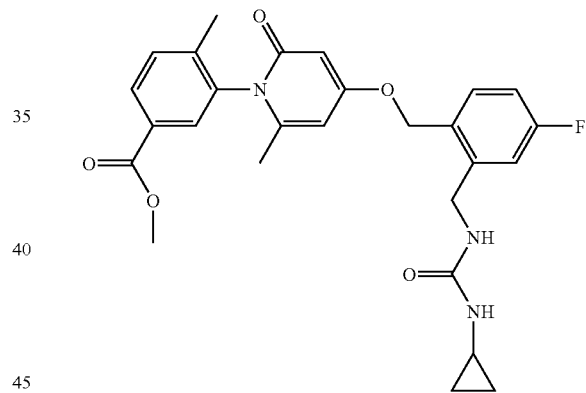

To a cooled (0° C.) solution of methyl 3-[4-{[2-(aminomethyl)-4-fluorobenzyl]oxy}-6-methyl-2-oxopyridin-1(2H)-yl]-4-methylbenzoate trifluoroacetate ( ) (1.13 g, 2.16 mmol) and 1,1-carbonyldiimidazole (0.42 g, 2.59 mmol) in DMA (8.0 mL) was added 4-methylmorpholine (0.36 mL, 3.2 mmol). Reaction was stirred at RT for 2 h. DMA removed by distillation. Crude product purified by preparatory HPLC. Acetonitrile was evaporated and the solution washed with 5% NaHCO$_3$ (30 mL) and extracted in DCM (3×25 mL). The organic extracts were dried over Na$_2$SO$_4$, filtered, concentrated, and dried in vacuo (0.78 g, 73%). $^1$H NMR (CD$_3$OD/400 MHz) δ 8.03 (m, 1H), 7.76 (s, 1H), 7.53 (d, 1H, J=8.0 Hz), 7.46 (m, 1H), 7.12 (m, 1H), 7.01 (m, 1H), 6.22 (s, 1H), 6.08 (s, 1H), 5.19 (s, 2H), 4.44 (s, 2H), 3.89 (s, 3H), 2.48 (m, 2H), 2.12 (s, 3H), 1.89 (s, 3H), 0.70 (m, 2H), 0.47 (m, 2H). ES HRMS m/z 494.2076 (M+H calculated for C$_{27}$H$_{29}$FN$_3$O$_5$ requires 494.2085).

Step 2: Preparation of 3-[4-{[2-({[(cyclopropylamino)carbonyl]amino}methyl)-4-fluorobenzyl]oxy}-6-methyl-2-oxopyridin-1(2H)-yl]-4-methylbenzoic acid.

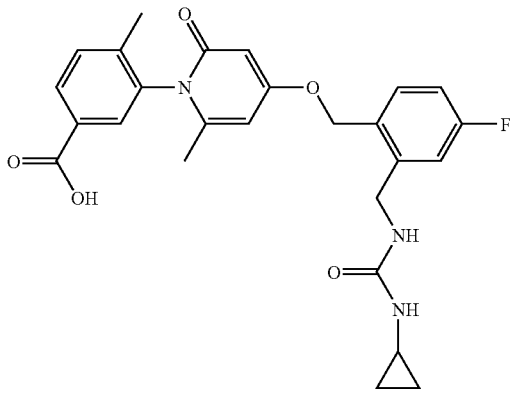

Prepared using a procedure similar to that used in the preparation of 3-[4-[(4-fluoro-2-{[(methoxycarbonyl)amino]methyl}benzyl)oxy]-6-methyl-2-oxopyridin-1(2H)-yl]-4-methylbenzoic acid. $^1$H NMR (CD$_3$OD/400 MHz) δ 8.02 (m, 1H), 7.74 (s, 1H), 7.48 (m, 2H), 7.12 (m, 1H), 7.01 (m, 1H), 6.22 (s, 1H), 6.08 (s, 1H), 5.19 (s, 2H), 4.44 (s, 2H), 2.48 (m, 1H), 2.11 (s, 3H), 1.90 (s, 3H), 0.69 (m, 2H), 0.47 (m, 2H). ES HRMS m/z 480.1921 (M+H calculated for C$_{26}$H$_{27}$FN$_3$O$_5$ requires 480.1929).

Step 3: Preparation of 3-[3-bromo-4-{[2-({[(cyclopropylamino)carbonyl]amino}methyl)-4-fluorobenzyl]oxy}-6-methyl-2-oxopyridin-1(2H)-yl]-4-methylbenzoic acid

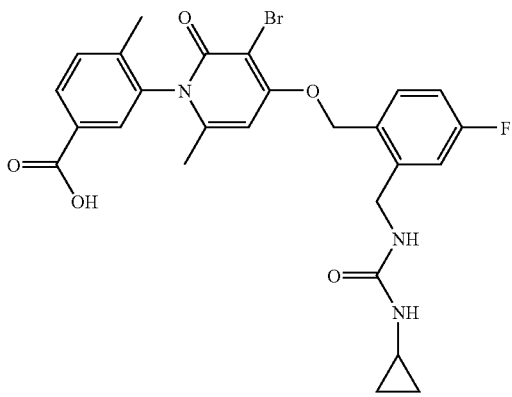

Prepared using a procedure similar to that used in Step 5 of the synthesis of Example 643. $^1$H NMR (DMSO-d$_6$/400 MHz) δ 7.92 (m, 1H), 7.67 (s, 1H), 7.54 (m, 2H), 7.12 (m, 2H), 6.71 (s, 1H), 5.37 (s, 2H), 4.31 (d, 2H, J=6.4 Hz), 2.40 (m, 1H), 2.00 (s, 3H), 1.88 (s, 3H), 0.56 (m, 2H), 0.33 (m, 2H). ES HRMS m/z 558.0988 and 560.0981 (M+H calculated for C$_{26}$H$_{26}$BrFN$_3$O$_5$ requires 558.1034 and 560.1018).

Step 4:

Prepared using a procedure similar to that used in the preparation of Example 643. $^1$H NMR (CD$_3$OD/400 MHz) δ 7.85 (m, 1H), 7.54 (m, 3H), 7.14 (m, 1H), 7.03 (m, 1H), 6.69 (s, 1H), 5.41 (s, 2H), 4.48 (s, 2H), 2.89 (s, 3H), 2.48 (m, 1H), 2.08 (s, 3H), 1.99 (s, 2H), 0.70 (m, 2H), 0.47 (m, 2H). ES HRMS m/z 571.1348 and 573.1355 (M+H calculated for C$_{27}$H$_{29}$BrFN$_4$O$_4$ requires 571.1351 and 573.1335).

Example 652

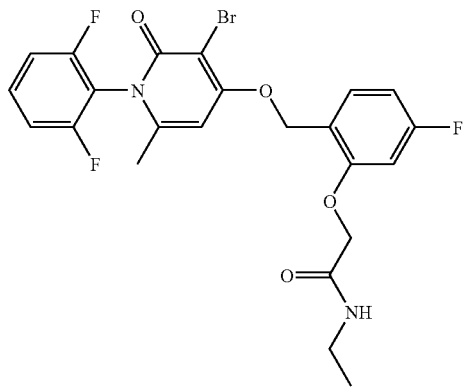

3-[3-bromo-4-{[2-({[(cyclopropylamino)carbonyl]amino}methyl)-4-fluorobenzyl]oxy}-6-methyl-2-oxopyridin-1(2H)-yl]-4-methylbenzoic acid Step 1: Preparation of ethyl(5-fluoro-2-methylphenoxy)acetate.

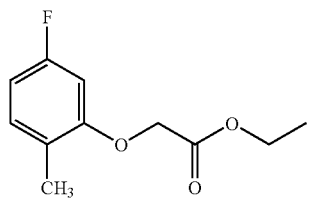

To a solution of 5-fluoro-2-methylphenol (1.00 g, 7.93 mmol) and ethylbromoacetate (1.59 g, 9.51 mmol) in DMF (15 mL) was added K$_2$CO$_3$ (1.10 g, 7.93 mmol). After 30 min at RT, DMF was removed by distillation. The crude product was washed with 5% citric acid (30 mL) and water (30 mL), extracted in DCM (3×20 mL), dried over Na$_2$SO$_4$, filtered, concentrated, and dried in vacuo. Desired product obtained as yellow oil (1.30 g, 77%). $^1$H NMR (CD$_3$OD/400 MHz) δ 7.09 (t, 1H, J=8.8 Hz), 6.58 (m, 1H), 6.56 (m, 1H), 4.71 (s, 2H), 4.23 (q, 2H, J=7.2 Hz), 2.18 (s, 3H), 1.27 (t, 3H, J=7.2 Hz). ES HRMS m/z 212.0847 (M+H calculated for C$_{11}$H$_{13}$FO$_3$ requires 212.0849).

Step 2: Preparation of ethyl [2-(bromomethyl)-5-fluorophenoxy]acetate.

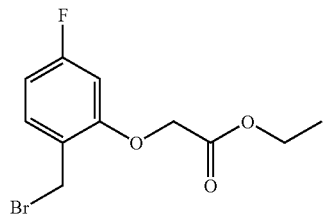

A solution of ethyl(5-fluoro-2-methylphenoxy)acetate (from Step 1) (0.65 g, 3.06 mmol), NBS (0.65 g, 3.68 mmol), and benzoyl peroxide (0.05 g, 0.21 mmol) in CCl4 (7.0 mL) were refluxed at 90° C. for 2.5 h. Additional NBS (0.16 g, 0.92 mmol) added, and reaction continued overnight. Solid filtered and filtrate concentrated onto silica gel. Purified by flash column chromatography using hexane and 2.5% EtOAc/hexane as eluent. Product obtained as yellow liquid (0.27 g, 30%). $^1$H NMR (CD$_3$OD/400 MHz) δ 7.37

(m, 1H), 6.69 (m, 2H), 4.80 (s, 2H), 4.60 (s, 2H), 4.23 (q, 2H, J=7.2 Hz), 1.27 (t, 3H, J=7.2 Hz).

Step 3: Preparation of ethyl [2-({[3-bromo-1-(2,6-difluorophenyl)-6-methyl-2-oxo-1,2-dihydropyridin-4-yl]oxy}methyl)-5-fluorophenoxy]acetate.

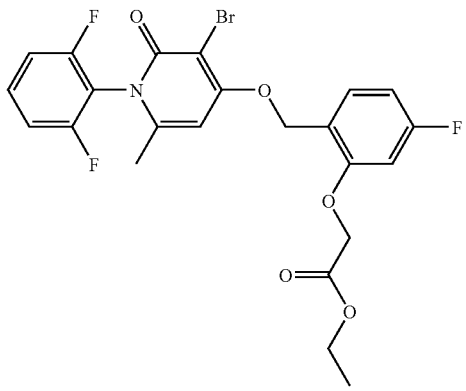

To a solution of ethyl [2-(bromomethyl)-5-fluorophenoxy]acetate (from Step 2) (0.59 g, 2.03 mmol) and 3-bromo-1-(2,6-difluorophenyl)-4-hydroxy-6-methylpyridin-2(1H)-one (0.61 g, 1.93 mmol) in DMF (3.0 mL) was added K$_2$CO$_3$ (0.34 g, 2.43 mmol). After 2 h at RT, DMF was removed by distillation. The crude product was washed with 5% citric acid, extracted in DCM, dried over Na$_2$SO$_4$, filtered, and concentrated onto silica gel. Purified by flash column chromatography using 50% EtOAc/hexane as the eluent. Obtained product as a pale yellow solid (0.45 g, 42%). $^1$H NMR (CD$_3$OD/400 MHz) δ 7.21 (q, 3H, J=8.4 Hz), 6.80 (m, 2H), 6.69 (s, 1H), 6.15 (s, 1H), 5.40 (s, 2H), 4.84 (s, 2H), 4.23 (q, 2H, J=6.8 Hz), 2.08 (s, 3H), 1.26 (t, 3H, J=6.8 Hz). ES HRMS m/z 526.0446 and 528.0414 (M+H calculated for C$_{23}$H$_{20}$BrF$_3$NO$_5$ requires 526.0471 and 528.0454).

Step 4: Preparation of [2-({[3-bromo-1-(2,6-difluorophenyl)-6-methyl-2-oxo-1,2-dihydropyridin-4-yl]oxy}methyl)-5-fluorophenoxy]acetic acid.

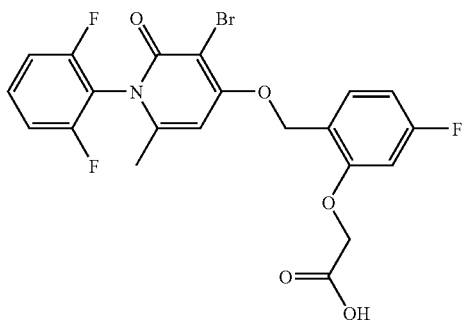

A solution of ethyl [2-({[3-bromo-1-(2,6-difluorophenyl)-6-methyl-2-oxo-1,2-dihydropyridin-4-yl]oxy}methyl)-5-fluorophenoxy]acetate (from Step 3) (0.62 g, 1.18 mmol), 1.5 N NaOH solution in 1:1 MeOH:water (1.2 mL, 1.77 mmol), and THF (1.2 mL) were refluxed at 60° C. for 1 h. The solution was concentrated on a rotary evaporator, cooled, and 5% citric acid added. The solid precipitate was filtered and dried in vacuo. Product obtained as a pale yellow solid (0.35 g, 60%).

$^1$H NMR (CD$_3$OD/400 MHz) δ 7.59 (m, 1H), 7.49 (m, 1H), 7.22 (m, 2H), 6.75 (m, 2H), 6.72 (s, 1H), 5.43 (s, 2H), 4.66 (s, 2H), 2.07 (s, 3H). ES HRMS m/z 498.0143 and 500.0186 (M+H calculated for C$_{21}$H$_{16}$BrF$_3$NO$_5$ requires 498.0158 and 500.0141).

Step 5: Preparation of 2-[2-({[3-bromo-1-(2,6-difluorophenyl)-6-methyl-2-oxo-1,2-dihydropyridin-4-yl]oxy}methyl)-5-fluorophenoxy]-N-ethylacetamide.

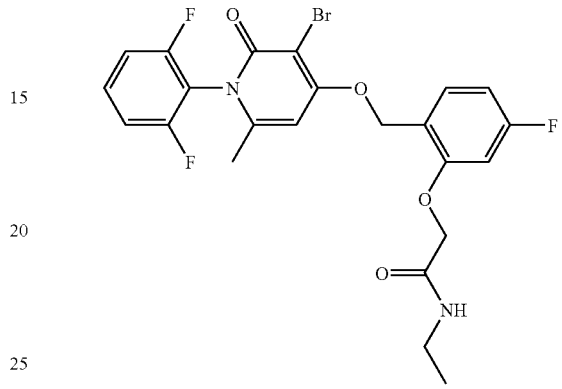

To a cooled (−10° C.) solution of [2-({[3-bromo-1-(2,6-difluorophenyl)-6-methyl-2-oxo-1,2-dihydropyridin-4-yl]oxy}methyl)-5-fluorophenoxy]acetic acid (from Step 4) (0.15 g, 0.30 mmol) in DMA (2.0 mL) was added 4-methylmorpholine (0.04 mL, 0.36 mmol) and isobutyl chloroformate (0.05 mL, 0.36 mmol). Ethylamine (0.04 mL, 0.45 mmol) was added after 20 minutes. DMF removed by distillation after 1 h. Crude product purified by preparatory HPLC. Acetonitrile was evaporated and the solution washed with 5% NaHCO$_3$ (30 mL) and extracted in DCM (3×25 mL). The organic extracts were dried over Na$_2$SO$_4$, filtered, concentrated, and dried in vacuo to give a white solid (0.080 g, 51%). $^1$H NMR (CD$_3$OD/400 MHz) δ 7.60 (m, 1H), 7.53 (t, 1H, J=8.0 Hz), 7.23 (t, 2H, J=8.4 Hz), 6.82 (m, 2H), 6.71 (s, 1H), 5.42 (s, 2H), 4.61 (s, 2H), 3.31 (q, 2H, J=6.4 Hz), 2.10 (s, 3H), 1.09 (t, 3H, J=7.2 Hz). ES HRMS m/z 525.0616 and 527.0568 (M+H calculated for C$_{23}$H$_{21}$BrF$_3$N$_2$O$_4$ requires 525.0631 and 527.0614).

Example 653

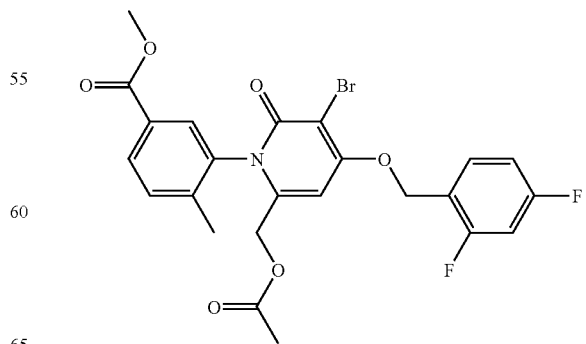

methyl 3-[6-[(acetyloxy)methyl]-3-bromo-4-[(2,4-difluorobenzyl)oxy]-2-oxopyridin-1(2H)-yl]-4-methylbenzoate Step 1: Preparation of 3-(2,2-dimethyl-4-oxo-4H-1,3-dioxin-6-yl)-2-oxopropyl acetate.

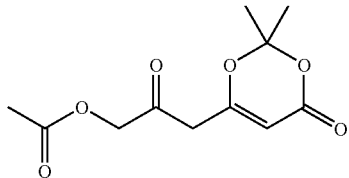

A solution of 2,2,6-trimethyl-4H-1,3-dioxin-4-one (20 g, 141 mmol) in dry THF (400 mL) was cooled to −78° C. To this solution was slowly added a LiHMDS (1M-THF, 160 mL, 160 mmol). The resulting solution was maintained at −78° C. with stirring for 30 min. To the reaction mixture was added acetoxy acetylchloride (17 mL, 160 mmol) and the resulting mixture was maintained at −78° C. for at 1 h. The reaction was then allowed to slowly warm to rt and stir for an additional 1 h. The reaction was then quenched with addition of a 1N solution of ammonium chloride. The layers were sperated and the aqueous layer was extracted with ethyl acetate (5×). The organics were combined, dried, and concentrated in vacuo. The crude product was purified using a medium pressure liquid chromatography biotage system. Elution with hexanes-ethyl acetate (3:1) gave 13.1 g (38%) of a red-brown oil. The product looks clean by NMR. $^1$H NMR (300 MHz, CDCl$_3$) δ 5.42 (s, 1H), 4.75 (s, 2H), 3.41 (s, 2H), 2.22 (s, 3H), 1.75 (s, 6H).

Step 2: Preparation of methyl 3-[6-[(acetyloxy)methyl]-4-hydroxy-2-oxopyridin-1(2H)-yl]-4-methylbenzoate.

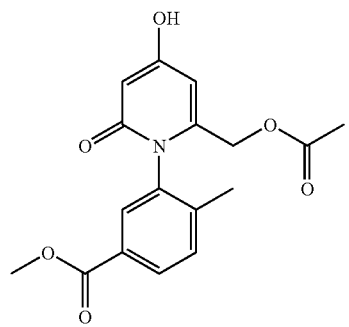

To a 100 mL RBF containing methyl 3-amino,4-methylbenzoate (1.65 g, 10 mmol) was added the enone from Step 1 (2.6 g, 10.7 mmol). The mixture was then dissolved in toluene (40 mL), fitted with a reflux condenser, and placed in an oil bath preset to 115° C. The mixture was heated to reflux for 1.5 h. The reaction flask was removed from the oil bath and a catalytic amount of TFA (5–6 drops) was added. The reaction was placed back in the oil bath and heated to reflux for an additional 2 h. The reaction was then allowed to cool to 0° C. The toluene was then removed under vacuum to give a thick brown residue. The residue was then dissolved in acetonitrile (10–15 mL) and allowed to stand. After 20–30 min a precipitate results which was filtered and washed with diethyl ether. After drying, an off-white solid (1.9 g, 57% yield) was obtained. $^1$H NMR (300 MHz, DMSO-d$_6$) δ 7.94 (dd, J=7.8, 1.5 Hz, 1H), 7.73 (s, 1H), 7.54 (d, J=8.1 Hz, 1H), 6.19 (s, 1H), 5.73–5.71 (m, 1H), 4.47 (AB quar, J=10.5 Hz, 2H), 3.87 (s, 3H), 2.09 (s, 3H), 1.91 (s, 3H). ES-HRMS m/z 332.1096 (M+H calcd for C$_{17}$H$_{18}$NO$_6$ requires 332.1129).

Step 3: Preparation of methyl 3-[6-[(acetyloxy)methyl]-3-bromo-4-hydroxy-2-oxopyridin-1(2H)-yl]-4-methylbenzoate.

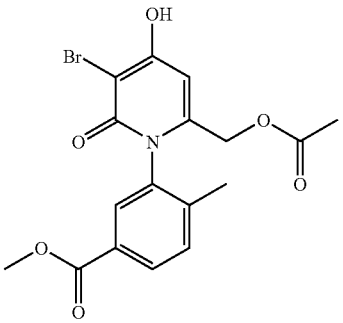

To a slurry of the phenol (2.5 g, 7.5 mmol) in dry acetonitrile (50 mL), at rt, was added n-bromosuccinimide (1.33 g, 7.5 mmol). The resulting homogeneous mixture was stirred at rt for 3 h. The resulting precipitate was filtered and washed sequentially with acetonitrile and the diethyl ether. The product was dried in a vacuum oven to yield an off-white solid (2.5 g, 81%). $^1$H NMR (300 MHz, DMSO-d$_6$) δ 11.82 (s, 1H), 7.97 (dd, J=7.8, 1.5 Hz, 1H), 97.80 (d, J=1.5 Hz, 1H), 7.57 (d, J=8.1 Hz, 1H), 6.38 (s, 1H), 4.49 (AB quar, J=13.8 Hz, 2H), 3.87 (s, 3H), 2.08 (s, 3H), 1.92 (s, 3H). ES-HRMS m/z 410.0225 (M+H calcd for C$_{17}$H$_{17}$NBrO$_6$ requires 410.0234).

Step 4: Preparation of the title compound. To a solution of the above phenol (2.5 g, 6.0 mmol) in dry DMF (25 mL) was added solid potassium carbonate (804 mg, 6.0 mmol). To this mixture was then added, via syringe, 2,4-diflourobenzyl bromide (783 μL, 6.0 mmol). The resulting mixture was allowed to stir at rt overnight. The reaction was then poured into ice water and stirred vigorously. The resulting precipitate was filtered and washed sequentially with water and diethyl ether. The solid was dried in a vacuum oven to yield an off-white solid (3.3 g, 99%). $^1$H NMR (400 MHz, DMSO-d$_6$) δ 7.97 (dd, J=7.6,1.2 Hz, 1H), 7.83 (d, J=1.6 Hz, 1H), 7.71 (q, J=8.8 Hz, 1H), 7.57 (d, J=8.0 Hz, 1H), 7.37 (dt, J=10.4, 2.4 Hz, 1H), 7.21 (dt, J=8.4, 2.0 Hz, 1H), 6.90 (s, 1H), 5.40 (s, 2H), 4.57 (AB quar, J=13.6 Hz, 2H), 3.86 (s, 3H), 2.07 (s, 3H), 1.90 (s, 3H). ES-HRMS m/z 536.0484 (M+H calcd for C$_{24}$H$_{21}$NF$_2$BrO$_6$ requires 536.0515).

Example 654

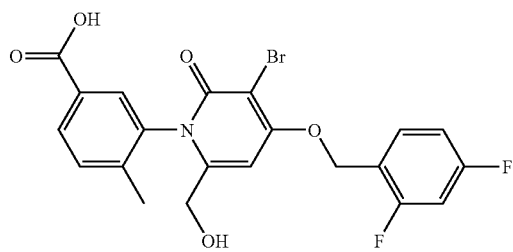

3-[3-bromo-4-[(2,4-difluorobenzyl)oxy]-6-(hydroxymethyl)-2-oxopyridin-1(2H)-yl]-4-methylbenzoic acid To a stirred suspension, at rt, of the Example 643 (2.0 g, 3.7 mmol) in THF (10 mL) was added a solution of 2.5N NaOH (3 mL, 7.5 mmol). The resulting homogeneous solution was stirred for 2 h. The reaction was judged complete and 1N HCl was added dropwise until a pH ~4 was obtained. The reaction was then diluted with CH₂Cl₂ (10 mL). The resulting precipitate was filtered with additional washing from CH₂Cl₂. The solid was dried in a vacuum oven to yield a pure white solid (1.8 g, 99%). ¹H NMR (300 MHz, DMSO-d₆) δ 7.95 (dd, J=7.8, 1.8 Hz, 1H), 7.74–7.66 (m, 2H), 7.54 (d, J=8.1 Hz, 1H), 7.37 (dq, J=7.8, 2.7 Hz, 1H), 7.24–7.17 (m, 1H), 6.72 (s, 1H), 5.39 (s, 2H), 3.83 (AB quar, J=15.6 Hz, 2H), 2.02 (s, 3H). ES-HRMS m/z 480.0253 (M+H calcd for C₂₁H₁₇NF₂BrO₅ requires 480.0253).

Example 655

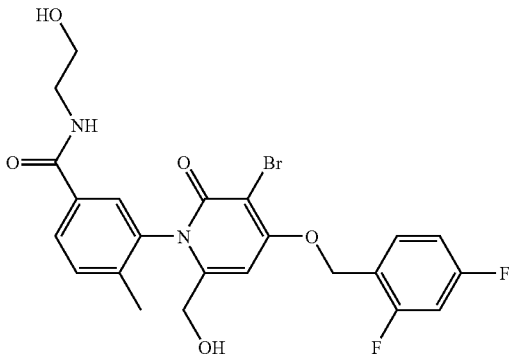

3-[3-bromo-4-[(2,4-difluorobenzyl)oxy]-6-(hydroxymethyl)-2-oxopyridin-1(2H)-yl]-N-(2-hydroxyethyl)-4-methylbenzamide To a slurry of Example 654 (500 mg, 1.04 mmol) in anhydrous CH₂Cl₂ was added Et₃N (218 μL, 1.56 mmol) and the resulting homogeneous mixture was stirred at rt. To this mixture was then added ethanolamine (70 μL, 1.14 mmol) via syringe. HOBt (155 mg, 1.14 mmol) was then added followed by addition of EDC (217 mg, 1.14 mmol). The reaction was allowed to stir overnight at rt. The reaction was quenched by addition of a solution of 1N NH₄Cl. The biphasic mixture was separated and the aqueous layer was extracted with CH₂Cl₂ (4×). The organics were combined, dried, and concentrated in vacuo. The resulting residue was purified by flash chromatography on a 16 g Michele-Miller column. Elution with CH₂Cl₂-MeOH (10:1→12:1) resulted in obtaining the desired product as a viscous oil. The oil was then dissolved in a CH₃CN-Et₂O combination. After 5–10 minutes, a precipitate resulted which upon filtration and drying yielded a pure white solid (210 mg, 40%). ¹H NMR (300 MHz, DMSO-d₆) δ 8.46 (t, J=5.2 Hz, 1H), 7.88 (dd, J=8.0, 2.0 Hz, 1H), 7.72–7.65 (m, 2H), 7.50 (d, J=8.4 Hz, 1H), 7.37 (dq, J=9.6, 2.4 Hz, 1H), 7.20 (dq, J=7.6, 1.6 Hz, 1H), 6.71 (s, 1H), 5.68 (t, J=5.6 Hz, —OH), 5.40 (s, 2H), 4.73 (t, J=5.6 Hz, —OH), 4.02 (dd, J=16.4, 5.6 Hz, 1H), 3.70 (dd, J=16.4, 5.6 Hz, 1H), 3.52–3.48 (m, 2H), 3.39–3.25 (m, 2H), 2.00 (s, 3H). ES-HRMS m/z 523.0674 (M+H calcd for C₂₃H₂₂N₂F₂BrO₅ requires 523.0675).

Example 656

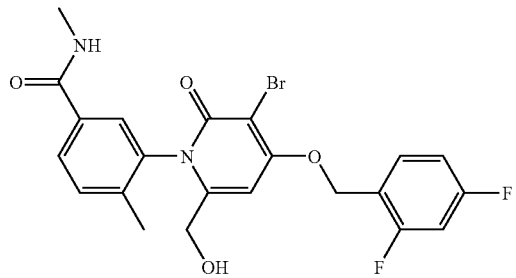

3-[3-bromo-4-[(2,4-difluorobenzyl)oxy]-6-(hydroxymethyl)-2-oxopyridin-1(2H)-yl]-N,4-dimethylbenzamide The titled compound was prepared from the acid Example 654 (550 mg, 1.07 mmol) in a similar manner to the amide described above using EDC (245 mg, 1.28 mmol), HOBt (171 μL, 1.28 mmol), Et₃N (225 mL, 1.6 mmol), and 2.0M MeNH₂-THF (1.2 μL, 2.48 mmol). Following work-up with 1N NH₄Cl the product was precipitated out of the biphasic mixture after dilution with additional CH₂Cl₂ to give a white solid (250 mg, 51% yield). ¹H NMR (300 MHz, DMSO-d₆) δ 8.48 (quar, J=4.5 Hz, 1H), 7.88 (dd, J=8.1, 1.8 Hz, 1H), 7.72 (app quar, J=6.6 Hz, 1H), 7.63 (d, J=1.8 Hz, 1H), 7.52 (d, J=8.1 Hz, 1H), 7.37 (dt, J=10.2, 2.4 Hz, 1H), 7.20 (app dt, J=8.4, 1.8 Hz, 1H), 6.74 (s, 1H), 5.71 (t, J=5.4 Hz, 1H), 5.42 (s, 2H), 4.03 (dd, J=13.8, 5.1 Hz, 1H), 3.72 (dd, J=16.4, 5.1 Hz, 1H), 2.78 (d, J=4.5 Hz, 3H), 2.02 (s, 3H). ES-HRMS m/z 493.0575 (M+H calcd for C₂₂H₂₀N₂F₂BrO₄ requires 493.0569).

Example 657

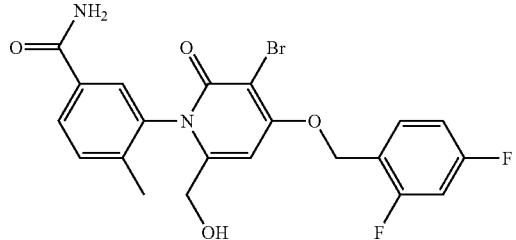

3-[3-bromo-4-[(2,4-difluorobenzyl)oxy]-6-(hydroxymethyl)-2-oxopyridin-1(2H)-yl]-4-methylbenzamide To a stirred suspension, at rt, of the carboxylic acid Example 654 (400 mg, 0.80 mmol) in anhydrous THF (4 mL) was added 4-methylmorpholine (274 μL, 2.5 mmol). To the resulting heterogeneous solution was then added 2-Chloro-4,6-dimethyltriazine (170 mg, 1.0 mmol) and the mixture was allowed to stir for 1 h at rt. Ammonium hydroxide solution (28–32%, 2 mL) was then added to the reaction and it was allowed to stir at rt overnight. The reaction was then worked up by diluting with H₂O (2–3 mL) and stirring vigorously. The resulting precipitate was filtered and washed with H2O and then diethyl ether. After drying with a vacuum oven an off-white solid (140 mg, 32%) was obtained. %). ¹H NMR (300 MHz, DMSO-d₆) δ 7.99–7.80 (m, 2H), 7.76 (m, 3H), 7.52 (d, J=8.1 Hz, 1H), 7.43–7.39 (m, 2H), 7.52 (d, J=8.1 Hz, 1H), 7.43–7.36 (m, 2H), 7.20 (dt, J=8.7, 1.8 Hz, 1H), 6.74 (s, 1H), 5.41 (s, 2H), 4.02–3.62 (m, 2H), 2.03 (s, 3H). ES-HRMS m/z 479.0411 (M+H calcd for $C_{21}H_{18}N_2F_2BrO_4$ requires 479.0413).

Example 658

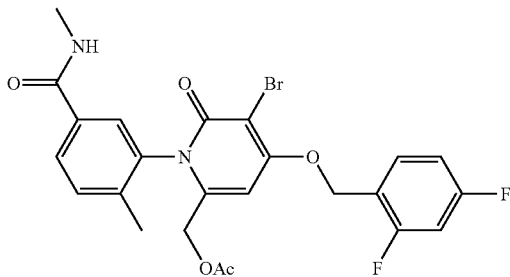

(5-bromo-4-[(2,4-difluorobenzyl)oxy]-1-{2-methyl-5-[(methylamino)carbonyl]phenyl}-6-oxo-1,6-dihydropyridin-2-yl)methyl acetate To a solution of 3-[3-bromo-4-[(2,4-difluorobenzyl)oxy]-6-(hydroxymethyl)-2-oxopyridin-1(2H)-yl]-N,4-dimethylbenzamide, (225 mg, 0.50 mmol) stirred in $CH_2Cl_2$ was added pyridine (55 μL, 0.69 mmol). To the resulting homogeneous solution was then added acetic anhydride (47 μL, 0.51 mmol). The mixture was stirred at rt for 3 h. Additional pyridine (150 μL, 1.8 mmol) and acetic anhydride (100 μL, 1.05 mmol) were then added and the reaction was allowed to stir overnight at rt. The reaction was then quenched with 1N $NHCl_4$ and diluted with $CH_2Cl_2$. The layers were separated and the organic layer was then extracted with $CH_2Cl_2$ (3×). The organics were then combined, dried, and concentrated in vacuo. The residue was then triturated with $Et_2O$ and filtered to give (150 mg, 61%) an off-white solid. $^1H$ NMR (300 MHz, DMSO-$d_6$) δ 8.48 (br s, 1H), 7.87 (app d, J=7.8 Hz, 1H), 7.74–7.69 (m, 2H), 7.52 (d, J=7.5 Hz, 1H), 7.40 (app t, J=8.1 Hz, 1H), 7.28–7.19 (m, 1H), 6.91 (s, 1H), 5.43 (s, 2H), 4.60 (s, 2H), 2.79 (s, 3H), 2.06 (s, 3H), 1.94 (s, 3H). ES-HRMS m/z 535.0676 (M+H calcd for $C_{24}H_{22}N_2F_2BrO_5$ requires 535.0675).

Example 659

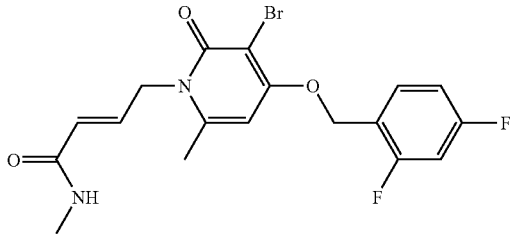

(2E)-4-[3-bromo-4-[(2,4-difluorobenzyl)oxy]-6-methyl-2-oxopyridin-1(2H)-yl]-N-methylbut-2-enamide Step 1, (2E)-4-[3-bromo-4-[(2,4-difluorobenzyl)oxy]-6-methyl-2-oxopyridin-1(2H)-yl]but-2-enoic acid: The carboxylic acid compo was prepared by stirring the ester (900 mg, 2.1 mmol) in THF (10 mL). To this solution was added 1N NaOH (1 mL) and the resulting mixture was stirred at rt. After 2 h, additional NaOH (1 mL) was added to the reaction and then allowed to stir at rt overnight. The THF was then concentrated under vacuum. The remaining aqueous layer was then acidified to pH ~4 after which a white precipitate resulted. Filtration and drying under vacuum gave rise to a white solid (900 mg) that was used as in the next step.

The titled compound was prepared by stirring the above acid (480 mg, 1.16 mmol) in $CH_2Cl_2$ at rt. To this mixture was added sequentially $Et_3N$ (244 μL), HOBt (188 mg, 1.4 mmol), $MeNH_2$ (2.0M-THF, 700 mL, 1.4 mmol), and finally EDC (266 mg, 1.4 mmol). The homogeneous mixture was then allowed to stir at rt overnight. The reaction was quenched with 1N HCl. The layers were separated and the aqueous layer was extracted with $CH_2Cl_2$ (4×). The organics were combined, dried, and concentrated in vacuo. The crude residue was triturated in $CH_3CN$-$Et_2O$ combination and filtered to give a pure white solid (330 mg, 67%). $^1H$-NMR (DMSO$_{d6}$/300 MHz) δ 8.20–7.90 (m, 1H), 7.68 (q, J=8.4 hz, 1H); 7.37 (dt, J=10.2, 2.4 Hz, 1H); 7.20 (dt, J=15.6, 4.2 Hz, 1H); 6.60 (s, 1H), 5.63 (d, J=15.6 Hz, 1H), 5.31 (s, 2H), 4.81 (d, J=2.7 Hz, 2H), 3.33 (d, J=6.9 Hz, 1H), 2.61 (d, J=4.8 Hz, 3H), 2.37 (s, 3H). ES-HRMS m/z 427.0493 (M+H calcd for $C_{18}H_{18}BrF_2N_2O_3$=427.0463).

Example 660

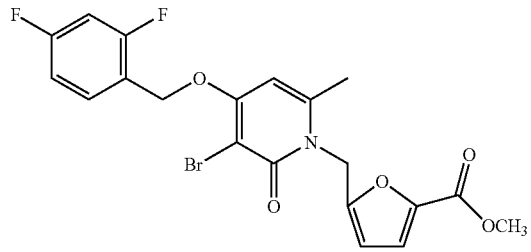

methyl 5-{[3-bromo-4-[(2,4-difluorobenzyl)oxy]-6-methyl-2-oxopyridin-1(2H)-yl]methyl}-2-furoate Step 1: To a room temperature suspension of 3-bromo-4-[(2,4-difluorobenzyl)oxy]-6-methylpyridin-2(1H)-one (330.1 mg, 1.00 mmol)) and NaH (48.0 mg, 2.0 mmol) in THF (1.6 mL) was added methyl-5-chloromethyl-2-furate (400 mg, 2.30 mmol). The resulting suspension was stirred and heated to 68° C. for 8 hours until complete consumption of starting material by LCMS analysis. The reaction mixture was then diluted with ammonium chloride (saturated aqueous solution, 10 mL) and water (100 mL). This resulting emulsion was then extracted with ethyl acetate (3×300 mL). The resulting organic extract was separated, $Na_2SO_4$ dried, and concentrated. The resulting dark residue was subjected to $SiO_2$ chromatography with ethyl acetate/hexanes (3:7) to furnish a solid. $^1H$ NMR (400 MHz, $CDCl_3$) δ 7.53 (app q, J=8.2 Hz, 1H), 7.07 (d, J=3.5 Hz, 1H), 6.93 (app dt, J=8.4, 1.5 Hz, 1H), 6.84 (app ddd, J=10.2, 8.7, 2.4 Hz, 1H), 6.53 (d, J=3.4 Hz, 1H), 6.00 (s, 1H), 5.27 (s, 2H), 5.18 (s, 2H), 3.85 (s, 3H), 2.54 (s, 3H); LC/MS C-18 column, $t_r$=2.64 minutes (5 to 95% acetonitrile/water over 5 minutes at 1 ml/min with detection 254 nm, at 50° C.). ES-MS m/z 468 (M+H). ES-HRMS m/z 468.0276 (M+H calcd for $C_{20}H_{17}BrF_2NO_5$ requires 468.0253).

Example 661

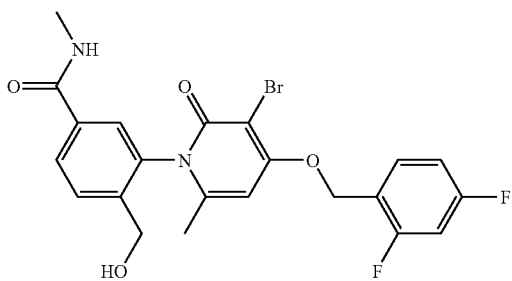

3-[3-bromo-4-[(2,4-difluorobenzyl)oxy]-6-methyl-2-oxopyridin-1(2H)-yl]-4-(hydroxymethyl)-N-methylbenzamide Step 1: Preparation of 2-[3-bromo-4-[(2,4-difluorobenzyl)oxy]-6-methyl-2-oxopyridin-1(2H)-yl]-4-[(methylamino)carbonyl]benzoic acid.

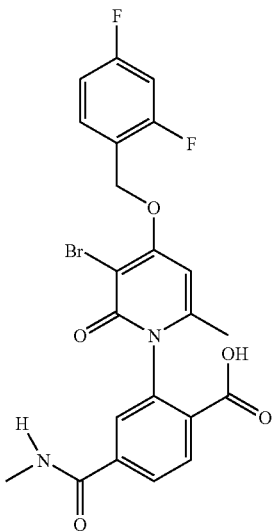

To a room temperature solution of methyl 2-[3-bromo-4-[(2,4-difluorobenzyl)oxy]-6-methyl-2-oxopyridin-1(2H)-yl]-4-[(methylamino)carbonyl]benzoate (1.05 g, 2.02 mmol) in THF (10.0 mL) was added dropwise an aqueous solution of sodium hydroxide (3.0 M, 3.5 mL, 10 mmol). The reaction was then heated to 60° C. for 8.0 hours. The resulting suspension was then diluted with 500 mL of ethyl acetate and neutralized with an aqueous solution of hydrochloric acid (2.0 N, 5.0 mL, 10 mmol). The resulting biphasic solution was separated and the resulting aqueous layer was further extracted with ethyl acetate (2×200 mL). The resulting combined organic extracts were $Na_2SO_4$ dried, filtered and concentrated in vacuo to a volume of 50 mL. At this time a white solid began to form and the resulting solid suspension was allowed to sit until precipitation appeared to stop (approximately 1.0 hour). The precipitate was collected and dried in vacuo (1.0 mm Hg) to furnish the solid acid as an intermediate (806 mg, 78%). $^1H$ NMR (400 MHz, $d_7$-DMF) δ 13.19 (s, 1H), 8.63 (app d, J=4.5 Hz, 1H), 8.09 (d, J=8.0 Hz, 1H), 8.00 (dd, J=8.0, 1.6 Hz, 1H), 7.71–7.67 (m, 2H), 7.34 (app dt, J=9.6, 1.6 Hz, 1H), 7.16 (app dt, J=8.7, 1.8 Hz, 1H), 6.66 (s, 1H), 5.33 (s, 2H), 3.29 (s, 3H), 1.92 (s, 3H); LC/MS C-18 column, $t_r$=2.15 minutes (5 to 95% acetonitrile/water over 5 minutes at 1 ml/min with detection 254 nm, at 50° C.). ES-MS m/z 507 (M+H). ES-HRMS m/z 507.0344 (M+H calcd for $C_{22}H_{18}BrF_2N_2O_5$ requires 507.0362).

Step 2: Preparation of the title compound. To a 0° C. solution of 2-[3-bromo-4-[(2,4-difluorobenzyl)oxy]-6-methyl-2-oxopyridin-1(2H)-yl]-4-[(methylamino)carbonyl]benzoic acid (500 mg, 0.986 mmol) in THF (6.8 mL) was added dropwise a solution of borane-dimethyl sulfide complex (THF solution, 2.0 M, 2.0 mL, 4.0 mmol). The internal temperature of the reaction was never allowed to exceed 0° C. The resulting solution was maintained for 4.0 hours, at which time the cooling bath was removed and the reaction was maintained at room temperature for an additional two hours. Next, a solution of ammonium chloride (saturated aqueous, 300 mL) was added. The resulting emulsion was extracted with ethyl acetate (3×300 mL) and the resulting organic extracts were separated, $Na_2SO_4$ dried, and concentrated in vacuo to a residue that was subjected to $SiO_2$ chromatography with ethyl acetate/hexanes (6:4) to furnish a solid (392 mg, 81%). $^1H$ NMR (400 MHz, $d_4$-MeOH) δ 7.96 (dd, J=8.0, 1.9 Hz, 1H), 7.75 (d, J=8.1 Hz, 1H), 7.65 (app q, J=8.0 Hz, 1H), 7.58 (d, J=1.7 Hz, 1H), 7.05 (app t, J=8.5 Hz, 2H), 6.64 (s, 1H), 5.36 (s, 2H), 4.35 (AB-q, J=14.1 Hz, Δ=60.8 Hz, 2H), 2.90 (s, 3H), 2.03 (s, 3H); LC/MS C-18 column, $t_r$=2.16 minutes (5 to 95% acetonitrile/water over 5 minutes at 1 ml/min with detection 254 nm, at 50° C.). ES-MS m/z 493 (M+H). ES-HRMS m/z 493.0590 (M+H calcd for $C_{22}H_{20}BrF_2N_2O_4$ requires 493.0596).

Example 662

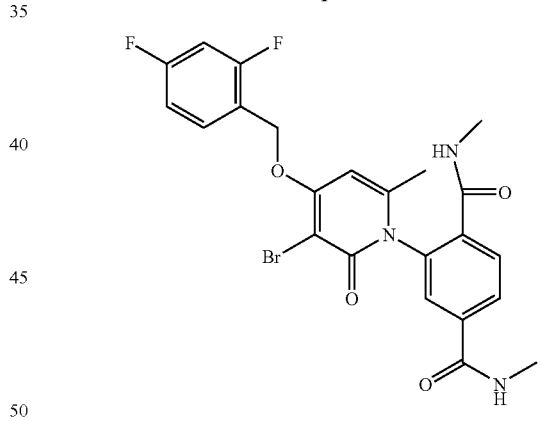

2-[3-bromo-4-[(2,4-difluorobenzyl)oxy]-6-methyl-2-oxopyridin-1(2H)-yl]-N,N'-dimethylterephthalamide Step 1: To a room temperature solution of 2-[3-bromo-4-[(2,4-difluorobenzyl)oxy]-6-methyl-2-oxopyridin-1(2H)-yl]-4-[(methylamino)carbonyl]benzoic acid (500 mg, 0.986 mmol) in DMF (5.0 mL) was added 1-(3-dimethylaminopropyl)-ethylcarbodiimide hydrochloride (EDC-HCl, 350.0 mg, 1.83 mmol) and 1-hydroxybenzotriazole (HOBT, 100.0 mg, 0.74 mmol) sequentially. To this resulting suspension was then added a solution of methylamine (2.0 M THF, 1.0 mL, 2.0 mmol). The reaction was stirred for 16.0 hours, at which time the reaction was diluted with ethyl acetate (600 mL). The mixture was washed with (3×200 mL) of water and the organic extract was separated, Na$_2$SO$_4$ dried, and concentrated in vacuo to a volume of approximately 60 mL. At this time a solid precipitate formed and was collected to furnish (289 mg, 56%). $^1$H NMR (300 MHz, d$_4$-MeOH) δ 8.06 (br d, J=8.0 Hz, 1H), 7.81 (d, J=8.1 Hz, 1H), 7.73 (s, 1H), 7.70 (app q, J=7.4 Hz, 1H), 7.09 (app t, J=8.0 Hz, 2H), 6.65 (s, 1H), 5.39 (s, 2H), 2.96 (s, 3H), 2.79 (s, 3H), 2.13 (s, 3H); LC/MS C-18 column, t$_r$=2.13 minutes (5 to 95% acetonitrile/water over 5 minutes at 1 ml/min with detection 254 nm, at 50° C.). ES-MS m/z 520 (M+H). ES-HRMS m/z 520.0700 (M+H calcd for C$_{23}$H$_{21}$BrF$_2$N$_3$O$_4$ requires 520.0678).

Example 663

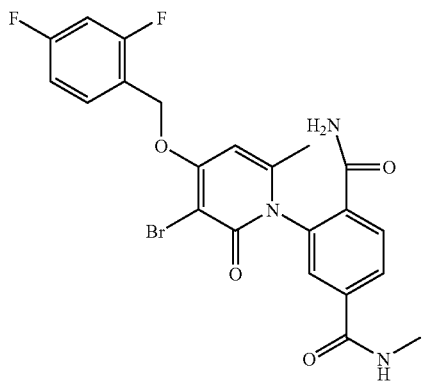

2-[3-bromo-4-[(2,4-difluorobenzyl)oxy]-6-methyl-2-oxopyridin-1(2H)-yl]-N-(4-methylterephthalamide Step 1: To a room temperature suspension of 2-[3-bromo-4-[(2,4-difluorobenzyl)oxy]-6-methyl-2-oxopyridin-1(2H)-yl]-4-[(methylamino)carbonyl]benzoic acid (302 mg, 0.595 mmol) in THF (1.8 mL) was added 2-chloro-4,6 dimethoxy-1,3,5 triazine (140.5 mg, 0.800 mmol) and N-methyl morpholine (NMM, 184 mg, 1.824 mmol) sequentially. The resulting solution was matured for 2 hours and then a saturated aqueous solution of ammonium hydroxide (0.60 mL) was added. The reaction was allowed to continue for 1 additional hour at which time a precipitate formed which was collected, washed with 20 mL of diethyl ether, and dried in vacuo to furnish a solid (201 mg, 66%). $^1$H NMR (400 MHz, d$_6$-DMSO) δ 8.59 (br d, J=8.0, 1H), 7.96 (d, J=8.0 Hz, 1H), 7.83 (s, 1H), 7.72 (d, J=9.0, 1H), 7.69–7.64 (m, 2H), 7.39–7.31 (m, 1H), 7.19 (app t, J=8.0 Hz, 1H), 6.60 (s, 1H), 5.31 (s, 2H), 3.85 (s, 1H), 2.78 (br d, J=8.0 Hz, 3H), 1.96 (s, 3H); LC/MS C-18 column, t$_r$=2.20 minutes (5 to 95% acetonitrile/water over 5 minutes at 1 ml/min with detection 254 nm, at 50° C.). ES-MS m/z 506 (M+H). ES-HRMS m/z 506.0550 (M+H calcd for C$_{22}$H$_{19}$BrF$_2$N$_3$O$_4$ requires 506.0522).

Example 664

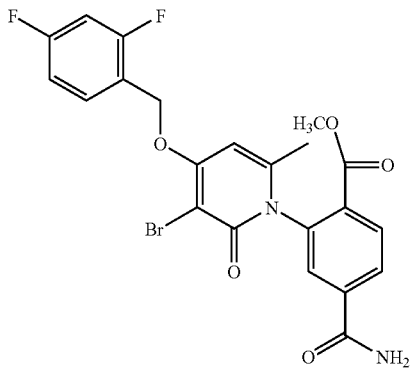

methyl 4-(aminocarbonyl)-2-[3-bromo-4-[(2,4-difluorobenzyl)oxy]-6-methyl-2-oxopyridin-1(2H)-yl]benzoate Step 1: To a room temperature solution of 3-(4-hydroxy-6-methyl-2-oxopyridin-1(2H)-yl)-4-(methoxycarbonyl) benzoic acid (3.01 g, 9.93 mmol) in DMF (20 mL) was added 1-(3-dimethylaminopropyl)-ethylcarbodiimide hydrochloride (EDC-HCl, 2.00 g, 10.4 mmol) and 1-hydroxy-benzotriazole (HOBT, 50.0 mg, 0.367 mmol) sequentially. To this resulting suspension was then added a solution of ammonia (0.5 M 1,4 dioxane, 30.0 mL, 15.0 mmol). The reaction was stirred for 16.0 hours until complete consumption of starting material was seen by LCMS analysis. At this time the reaction vessel was placed on a roto-evaporator at 30 mm Hg vacuum and maintained at 30° C. for 30 minutes to strip off any residual ammonia from the reaction mixture. The reaction vessel was removed from the roto-evaporator and subsequently charged with solid N-bromosuccinimide (1.790 g, 10.06 mmol) and the resulting reddish solution was stirred for 3.0 hours. At this time the reaction was charged with K$_2$CO$_3$ (3.00 g, 21.7 mmol) and 2,4 difluorobenzyl bromide (1.95 mL, 15.2 mmol). The resulting suspension was stirred for 16.0 hours. At this time the reaction suspension was diluted with water (400 mL) and extracted with ethyl acetate (3×300 mL). The organic extracts were separated, Na$_2$SO$_4$ dried, and concentrated to a residue that was subjected to SiO$_2$ chromatography using ethyl acetate/hexanes/methanol (6:3.5:0.5) to furnish an off white solid (1.09 g, 21%). $^1$H NMR (400 MHz, d$_4$-MeOH) δ 8.21 (dd, J=8.5, 1.5 Hz, 1H), 8.09 (dd, J=7.6, 2.0 Hz, 1H), 7.78 (br s, 1H), 7.65 (app q, J=7.9 Hz, 1H), 7.03 (app t, J=8.0 Hz, 2H), 6.63 (s, 1H), 5.37 (s, 2H), 3.75 (s, 3H), 2.02 (s, 3H); LC/MS C-18 column, t$_r$=2.28 minutes (5 to 95% acetonitrile/water over 5 minutes at 1 ml/min with detection 254 nm, at 50° C.). ES-MS m/z 507 (M+H). ES-HRMS m/z 507.0385 (M+H calcd for C$_{22}$H$_{18}$BrF$_2$N$_2$O$_5$ requires 507.0362).

Example 665

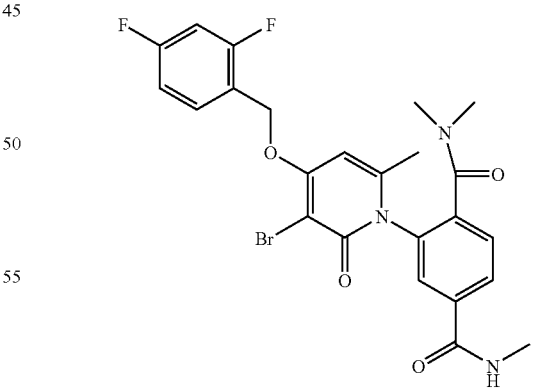

2-[3-bromo-4-[(2,4-difluorobenzyl)oxy]-6-methyl-2-oxopyridin-1(2H)-yl]-N$^1$,N$^1$,N$^4$-trimethylterephthalamide Step 1: To a room temperature solution of 2-[3-bromo-4-[(2,4-difluorobenzyl)oxy]-6-methyl-2-oxopyridin-1(2H)-yl]-4-[(methylamino)carbonyl]benzoic acid (300 mg, 0.591 mmol) in DMF (1.8 mL) was added 1-(3-dimethylaminopropyl)-ethylcarbodiimide hydrochloride (EDC-HCl, 190.0 mg, 1.0 mmol) and 1-hydroxybenzotriazole (HOBT, 26.0 mg, 0.191 mmol) sequentially. To this resulting suspension was then added a solution of dimethylamine (2.0 M THF, 0.50 mL, 1.0 mmol). The reaction was stirred for 16.0 hours, at which time the reaction mixture was directly applied to $SiO_2$ chromatography with ethyl acetate/hexanes (6:4) to furnish a solid (206 mg, 65%). $^1$H NMR (400 MHz, $d_4$-MeOH) δ 8.01 (dd, J=8.2, 1.5 Hz, 1H), 7.73 (app d, J=8.1 Hz, 1H), 7.61 (app q, J=7.2 Hz, 1H), 7.60 (app d, J=9.5 Hz, 1H), 7.04 (app t, J=8.0 Hz, 2H), 6.65 (s, 1H), 5.32 (s, 2H), 3.64 (s, 3H), 2.92 (s, 6H), 2.13 (s, 3H); LC/MS C-18 column, $t_r$=2.20 minutes (5 to 95% acetonitrile/water over 5 minutes at 1 ml/min with detection 254 nm, at 50° C.). ES-MS m/z 534 (M+H). ES-HRMS m/z 534.0820 (M+H calcd for $C_{24}H_{23}BrF_2N_3O_4$ requires 534.0835).

Example 666

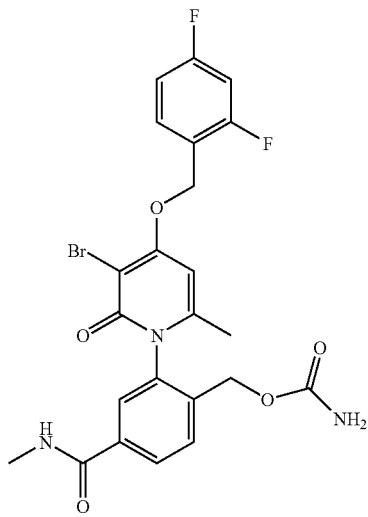

2-[3-bromo-4-[(2,4-difluorobenzyl)oxy]-6-methyl-2-oxopyridin-1(2H)-yl]-4-[(methylamino)carbonyl] benzyl carbamate Step 1: To a room temperature solution of 3-[3-bromo-4-[(2,4-difluorobenzyl)oxy]-6-methyl-2-oxopyridin-1(2H)-yl]-4-(hydroxymethyl)-N-methylbenzamide (493 mg, 1.00 mmol) in methylene chloride (5.0 mL) was added a solution of trichloroacetyl isocyanate (toluene, 0.53 M, 1.9 mL, 1.0 mmol). The resulting solution was stirred for one hour until complete consumption of starting material by LCMS analysis. The reaction mixture was then directly applied to $Al_2O_3$ (0.5 g of activity type I) and the slurry was matured for three hours. At this time, the $Al_2O_3$ plug was flushed with ethyl acetate/methanol (95:5) and the resulting mother liquor was concentrated to a residue that was subjected to $SiO_2$ chromatography using ethyl acetate/hexanes/methanol (6:3.5:0.5) to furnish a white solid (396 mg, 74%). $^1$H NMR (300 MHz, $d_4$-MeOH) δ 8.00 (dd, J=8.0, 1.7 Hz, 1H), 7.75 (d, J=8.2 Hz, 1H), 7.72–7.64 (m, 2H), 7.09 (app t, J=8.5 Hz, 2H), 6.69 (s, 1H), 5.40 (s, 2H), 4.85 (m, 2H), 2.90 (s, 3H), 2.10 (s, 3H); LC/MS C-18 column, $t_r$=2.15 minutes (5 to 95% acetonitrile/water over 5 minutes at 1 ml/min with detection 254 nm, at 50° C.) ES-MS m/z 536 (M+H). ES-HRMS m/z 536.0617 (M+H calcd for $C_{23}H_{21}BrF_2N_3O_5$ requires 536.0627).

Example 667

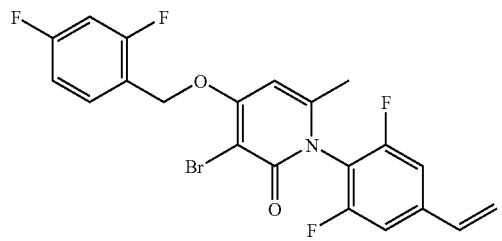

3-bromo-4-[(2,4-difluorobenzyl)oxy]-1-(2,6-difluoro-4-vinylphenyl)-6-methylpyridin-2(1H)-one
Step 1: Preparation of 4-[(2,4-difluorobenzyl)oxy]-1-(2,6-difluoro-4-vinylphenyl)-6-methylpyridin-2(1H)-one.

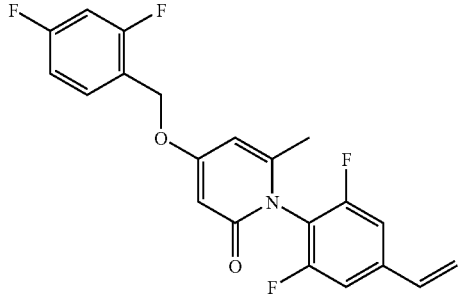

To a room temperature solution of 1-(4-bromo-2,6-difluorophenyl)-4-[(2,4-difluorobenzyl)oxy]-6-methylpyridin-2(1H)-one (4.01 g, 9.06 mmol) in anhydrous THF (30 mL) was added, sequentially, tributyl(vinyl)tin (5.00 g, 15.7 mmol) and tetrakis(tripheylphosphine) palladium (1.00 g, 0.865 mmol) under an argon stream. The reaction vessel was then equipped with a reflux condenser and the reaction system purged with an argon flow. The resulting yellow solution was heated to 68° C. and stirred under a positive pressure of argon for 12.0 hours until complete disappearance of starting material by LCMS analysis. The reaction mixture was diluted with 300 mL of brine and extracted with ethyl acetate (3×300 mL). The organic extracts were separated, $Na_2SO_4$ dried, and concentrated in vacuo and the resulting dark residue was subjected to $SiO_2$ chromatography with ethyl acetate/hexanes (1:1) to furnish a yellowish solid (3.18 g, 90%). $^1$H NMR (400 MHz, $CDCl_3$) δ 7.41 (app q, J=8.0 Hz, 1H), 7.08 (app d, J=8.3 Hz, 2H), 6.90 (app t, J=7.2 Hz, 1H), 6.85 (app t, J=7.4 Hz, 1H), 6.63 (dd, J=17.5, 10.9 Hz, 1H), 5.96 (app d, 15.8 Hz, 1H), 5.94 (app d, J=15.8 Hz, 1H), 5.79 (d, J=17.4 Hz, 1H), 5.43 (d, J=10.9 Hz, 1H), 5.01 (br s, 2H), 1.99 (s, 3H); LC/MS C-18 column, $t_r$=2.93 minutes (5 to 95% acetonitrile/water over 5 minutes with detection 254 nm, at 50° C.). ES-MS m/z 390 (M+H). ES-HRMS m/z 390.1095 (M+H calcd for $C_{21}H_{16}F_4NO_2$ requires 390.1112).
Step 2: To a briskly stirred room temperature solution of 4-[(2,4-difluorobenzyl)oxy]-1-(2,6-difluoro-4-vinylphenyl)-6-methylpyridin-2(1H)-one (721 mg, 1.85 mmol) in methylene chloride (10 mL) was added solid N-bromosuccinimide (330 mg, 1.86 mmol) and the resulting reddish solution was stirred for 10 minutes. At this time the reaction was diluted with ethyl acetate (100 mL) and washed with sodium sulfite (5% aqueous solution, 50 mL) The resulting organic extracts were $Na_2SO_4$ dried, filtered, and concentrated in vacuo to approximately 50 mL volume. The resulting mother liquor rapidly precipitated and furnished an amorphous solid that was collected and dried at 1 mm Hg vacuum to provide a solid (610 mg, 70%). $^1$H NMR (400 MHz, CDCl$_3$) δ 7.59 (app q, J=8.0 Hz, 1H), 7.09 (app d, J=8.3 Hz, 2H), 6.95 (app t, J=7.2 Hz, 1H), 6.87 (app t, J=7.4 Hz, 1H), 6.62 (dd, J=17.5, 10.9 Hz, 1H), 6.12 (s, 1H), 5.81 (d, J=17.4 Hz, 1H), 5.43 (d, J=10.9 Hz, 1H), 5.25 (br s, 2H), 2.07 (s, 3H); LC/MS C-18 column, t$_r$=3.17 minutes (5 to 95% acetonitrile/water over 5 minutes at 1 ml/min with detection 254 nm, at 50° C.). ES-MS m/z 468 (M+H). ES-HRMS m/z 468.0249 (M+H calcd for C$_{21}$H$_{15}$BrF$_4$NO$_2$ requires 468.0217).

Example 668

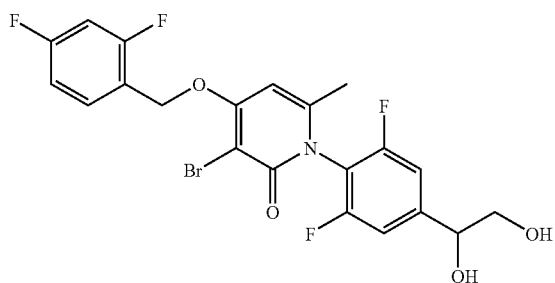

3-bromo-4-[(2,4-difluorobenzyl)oxy]-1-[4-(1,2-dihydroxyethyl)-2,6-difluorophenyl]-6-methylpyridin-2(1H)-one Step 1: Preparation of the title compound. To a room temperature solution of 3-bromo-4-[(2,4-difluorobenzyl)oxy]-1-(2,6-difluoro-4-vinylphenyl)-6-methylpyridin-2(1H)-one (408.0 mg, 0.871 mmol) in water/acetone 1:3 (8.0 mL) was added, sequentially, N-methyl morpholine oxide (268.0 mg, 2.29 mmol) and osmium tetroxide (4% water solution, 0.25 mL or approximately 10 mg, 0.039 mmol). The resulting solution was stirred for 8 hours until complete consumption of starting material by LCMS analysis, and the reaction was concentrated in vacuo to one-fourth original volume. The resulting solution was diluted with ethyl acetate (300 mL) and washed with water (2×100 mL). The organic extract was separated, Na$_2$SO$_4$ dried, and concentrated in vacuo and the resulting dark residue was subjected to SiO$_2$ chromatography with ethyl acetate/hexanes/methanol (6:3.5:0.5) to furnish a solid (389 mg, 88%). $^1$H NMR (400 MHz, d$_4$-MeOH) δ 7.62 (app q, J=8.0 Hz, 1H), 7.26 (dd, J=9.6, 4.5 Hz, 2H), 7.04 (app t, J=8.6 Hz, 2H), 6.67 (s, 1H), 5.36 (s, 2H), 4.75 (app t, J=5.6 Hz, 1H), 3.68–3.61 (m, 2H), 2.11 (s, 3H); LC/MS C-18 column, t$_r$=2.26 minutes (5 to 95% acetonitrile/water over 5 minutes at 1 ml/min with detection 254 nm, at 50° C.). ES-MS m/z 502 (M+H). ES-HRMS m/z 502.0247 (M+H calcd for C$_{21}$H$_{17}$BrF$_4$NO$_4$ requires 502.0272).

Example 669

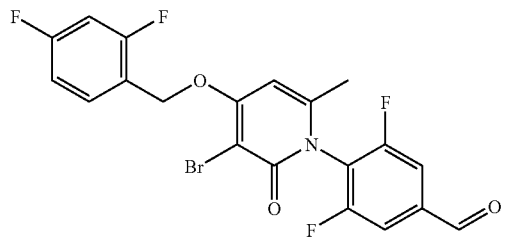

4-[3-bromo-4-[(2,4-difluorobenzyl)oxy]-6-methyl-2-oxopyridin-1(2H)-yl]-3,5-difluorobenzaldehyde Step 1: Preparation of the title compound. To a room temperature solution of 3-bromo-4-[(2,4-difluorobenzyl)oxy]-1-[4-(1,2-dihydroxyethyl)-2,6-difluorophenyl]-6-methylpyridin-2(1H)-one (310 mg, 0.615 mmol) in toluene (3.0 mL) was added lead(IV) acetate (443 mg, 1.63 mmol). The resulting dark brown solution was stirred for one hour until complete consumption of starting material by LCMS analysis. The reaction mixture was then diluted with ethyl acetate (100 mL), water washed (3×100 mL), and brine washed (3×30 mL). The resulting organic extract was separated, Na$_2$SO$_4$ dried, and concentrated. The resulting dark residue was subjected to SiO$_2$ chromatography with ethyl acetate/hexanes (1:1) to furnish a light yellow solid (269 mg, 93%). Caution, product is easily air oxidized. $^1$H NMR (300 MHz, d$_4$-MeOH) δ 10.05 (s, 1H), 7.68 (app q, J=7.2 Hz, 1H), 7.38 (d, J=8.0 Hz, 2H), 7.05 (app t, J=8.2 Hz, 2H), 6.73 (s, 1H), 5.40 (s, 2H), 2.15 (s, 3H); LC/MS C-18 column, t$_r$=2.72 minutes (5 to 95% acetonitrile/water over 5 minutes at 1 ml/min with detection 254 nm, at 50° C.) ES-MS m/z 470 (M+H). ES-HRMS m/z 470.0049 (M+H calcd for C$_{20}$H$_{13}$BrF$_4$NO$_3$ requires 470.0009).

Example 670

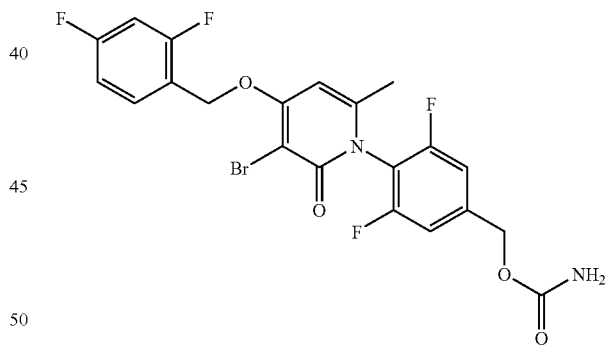

4-[3-bromo-4-[(2,4-difluorobenzyl)oxy]-6-methyl-2-oxopyridin-1(2H)-yl]-3,5-difluorobenzyl carbamate Step 1: To a room temperature solution of 4-[3-bromo-4-[(2,4-difluorobenzyl)oxy]-6-methyl-2-oxopyridin-1(2H)-yl]-3,5-difluorobenzaldehyde (220 mg, 0.468 mmol) in methanol (10 mL) was added solid sodium borohydride (60.0 mg, 1.58 mmol). The resulting solution evolved gas for approximately 0.5 minute and was stirred for 10 additional minutes until complete consumption of starting material by LCMS analysis. The reaction was then diluted with saturated aqueous solution of ammonium chloride (10 mL) and extracted with ethyl acetate (4×50 mL). The organic extract was separated, Na$_2$SO$_4$ dried, and concentrated to a residue. This resulting residue was then diluted with methylene chloride (5.0 mL) and a solution of trichloroacetyl isocyanate (toluene, 0.53 M, 1.0 mL, 0.53 mmol) was added. The resulting solution was stirred for one hour until complete consumption of starting material by LCMS analysis. The reaction mixture was then directly applied to $Al_2O_3$ (0.5 g of activity type I) and the slurry was matured for three hours. At this time, the $Al_2O_3$ plug was flushed with ethyl acetate/methanol (95:5) and the resulting mother liquor was concentrated to a residue that was subjected to $SiO_2$ chromatography using ethyl acetate/hexanes/methanol (6:3.8:0.2) to furnish a white solid (181 mg, 75%). $^1$H NMR (400 MHz, $d_4$-MeOH) δ 7.63 (app q, J=8.0 Hz, 1H), 7.43 (d, J=8.2 Hz, 2H), 7.04 (app t, J=8.1 Hz, 2H), 6.68 (s, 1H), 5.37 (s, 2H), 5.12 (m, 2H), 2.11 (s, 3H); LC/MS C-18 column, $t_r$=2.54 minutes (5 to 95% acetonitrile/water over 5 minutes at 1 ml/min with detection 254 nm, at 50° C.). ES-MS m/z 515 (M+H). ES-HRMS m/z 515.0232 (M+H calcd for $C_{21}H_{16}BrF_4N_2O_4$ requires 515.0234).

Example 671–687

The following compounds are prepared essentially according to the procedures outlined in the schemes and the above examples

| Example No. |
| --- |
| Example 671 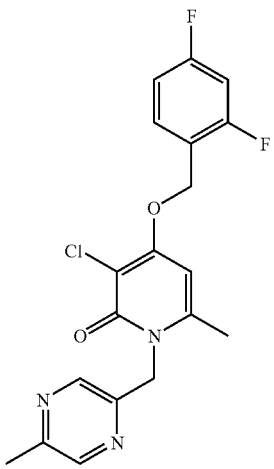 |
| Example 672 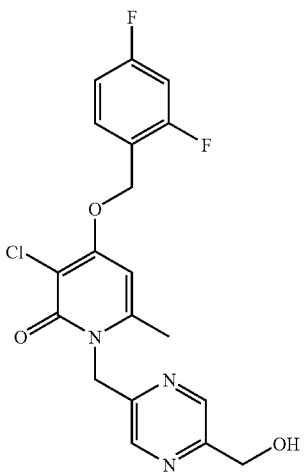 |
| Example 673 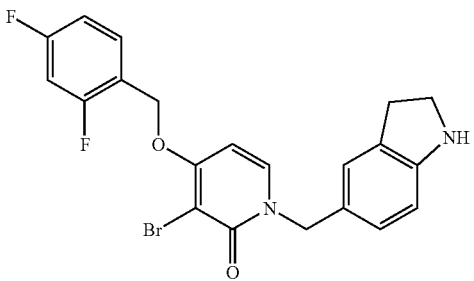 |

-continued
| Example No. | |
|---|---|
| Example 674 | 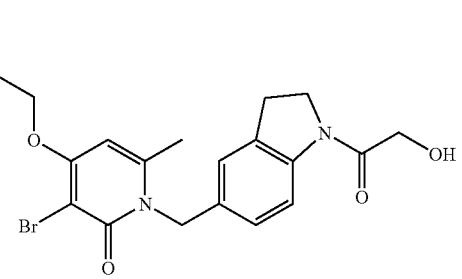 |
| Example 675 | 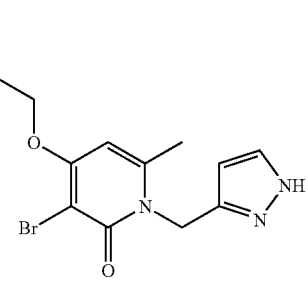 |
| Example 676 | 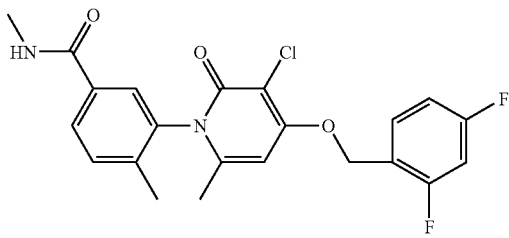 |
| Example 677 | 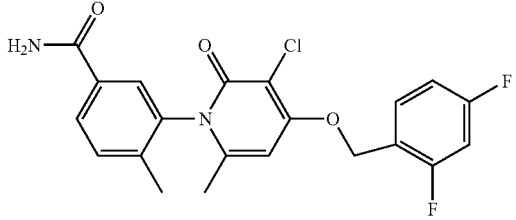 |
| Example 678 | 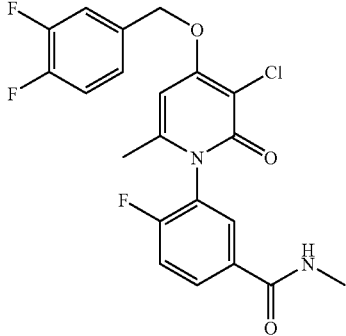 |

| Example No. | |
|---|---|
| Example 679 | 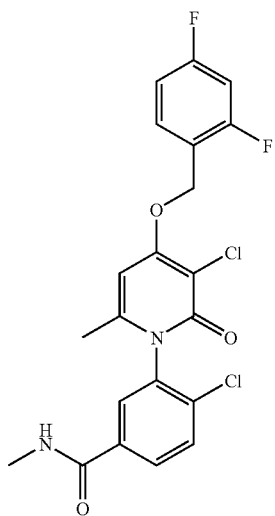 |
| Example 680 | 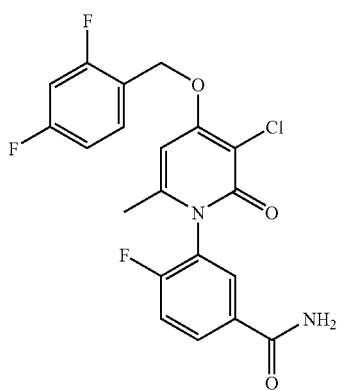 |
| Example 681 | 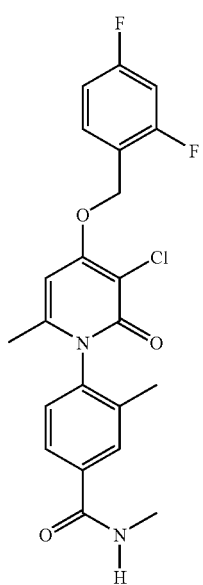 |

-continued
| Example No. |
| --- |
| Example 682 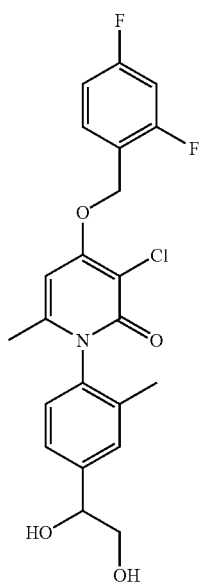 |
| Example 683 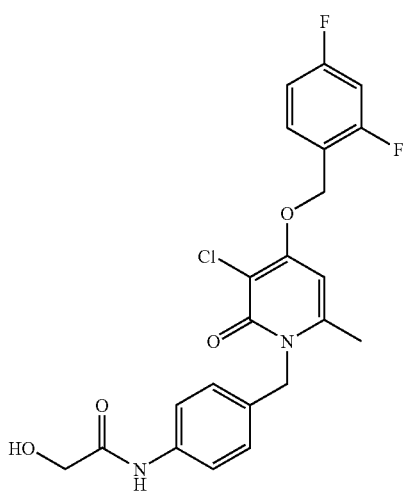 |
| Example 684 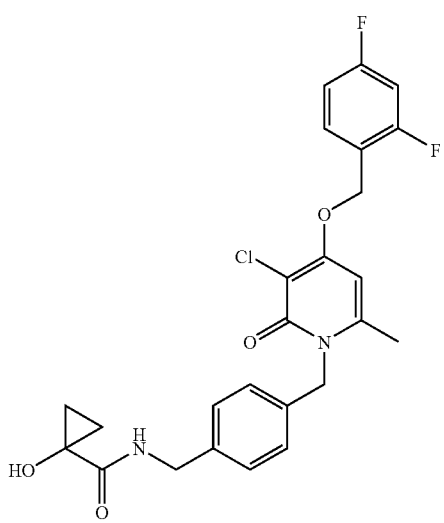 |

-continued
| Example No. |
|---|
| Example 685 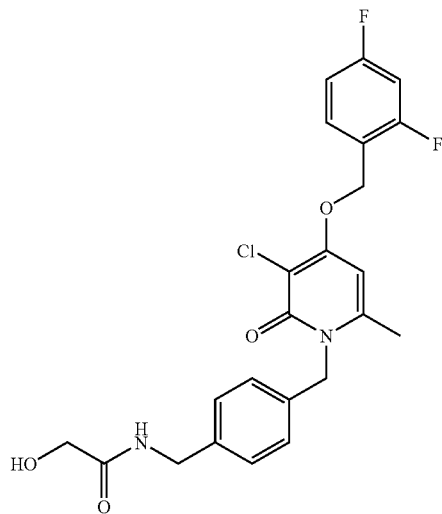 |
| Example 686 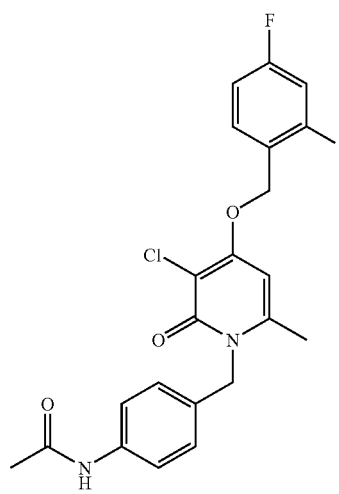 |
| Example 687 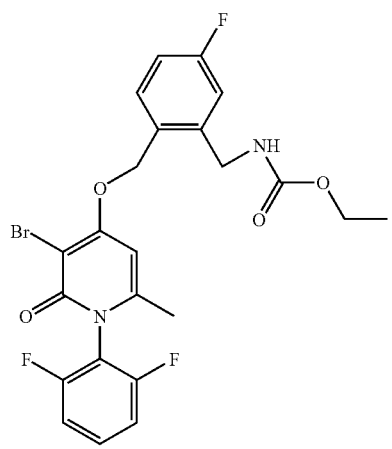 |

| Example No. | |
|---|---|
| Example 688 | 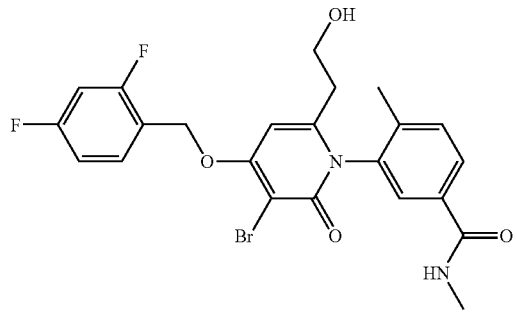 |
| Example 689 | 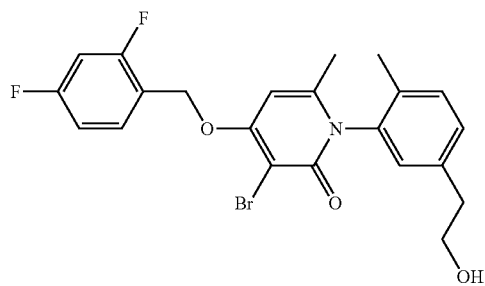 |
| Example 690 | 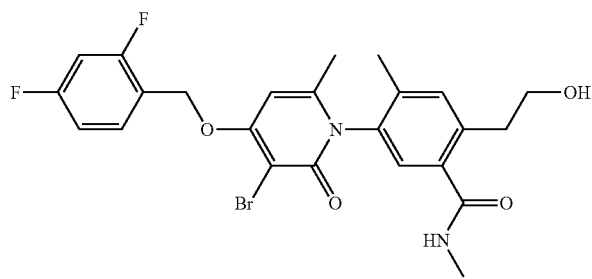 |
| Example 691 | 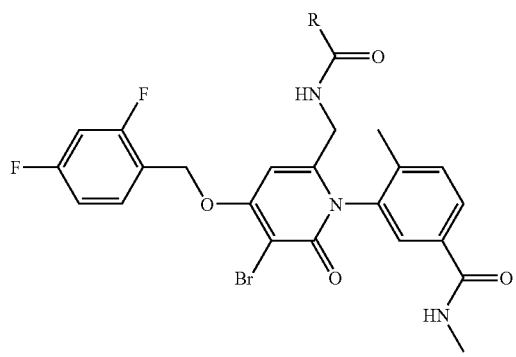 |
| Example 692 | 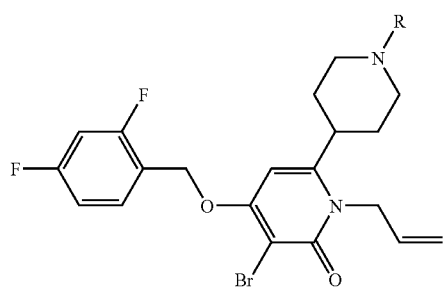 |

| Example No. | |
|---|---|
| Example 693 | 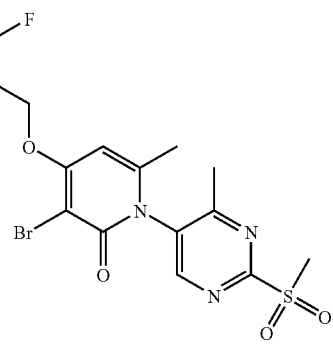 |
| Example 694 | 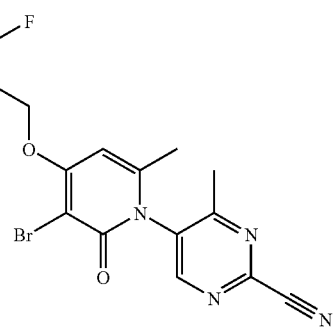 |
| Example 695 | 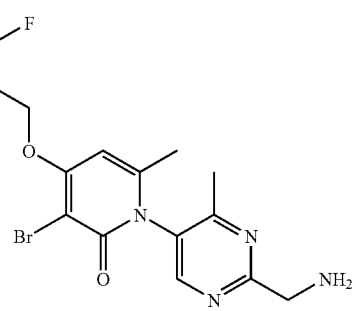 |
| Example 696 | 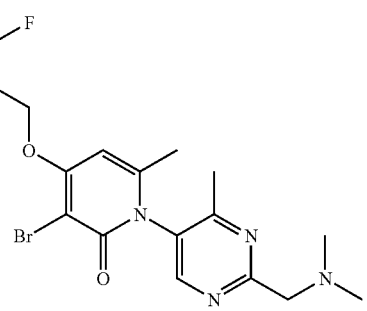 |

-continued
| Example No. | |
|---|---|
| Example 697 | 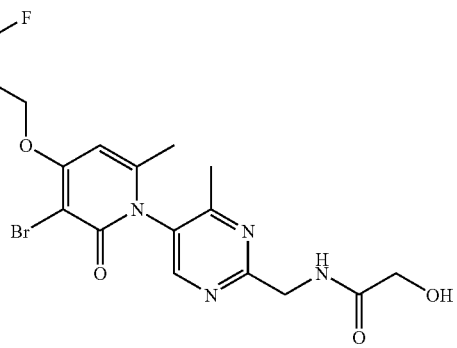 |
| Example 698 | 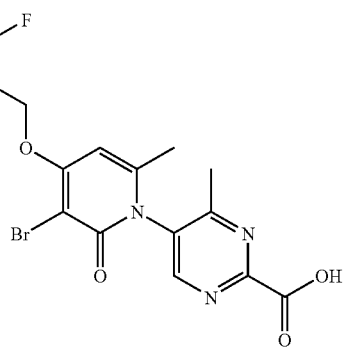 |
| Example 699 | 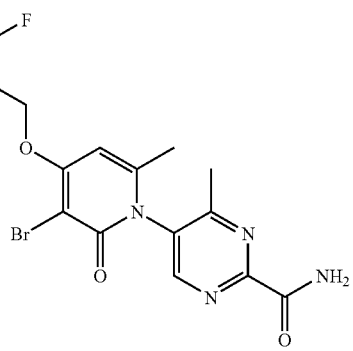 |
| Example 700 | 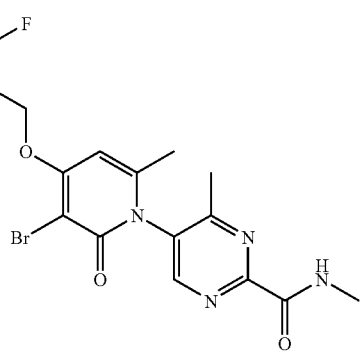 |

Example 701

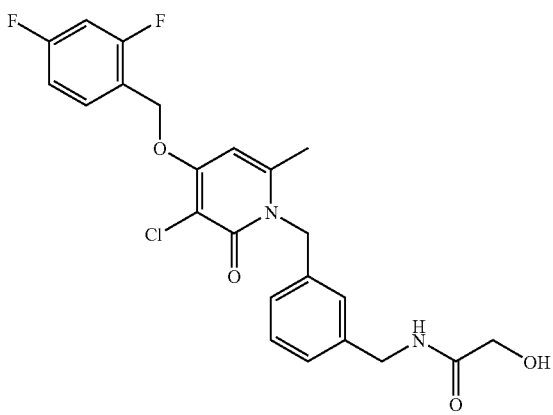

N-(4-{[3-chloro-4-[(2,4-difluorobenzyl)oxy]-6-methyl-2-oxopyridin-1(2H)-yl]methyl}benzyl)-2-hydroxyacetamide Step 1. Preparation of 1-[4-(aminomethyl)benzyl]-3-chloro-4-[(2,4-difluorobenzyl)oxy]-6-methylpyridin-2(1H)-one.

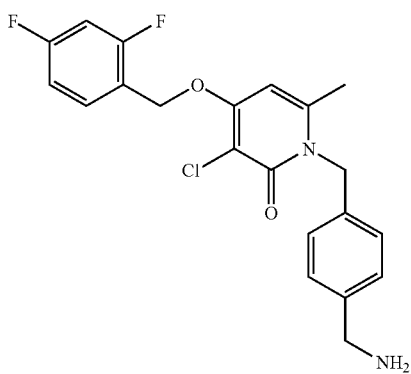

The compound of Example 606 (10.0 g, 23.38 mmol) was suspended in tetrahydrofuran (100 mL) and cooled in an ice-bath. Borane dimethyl sulfide (29.9 mL, 2.0 M in tetrahydrofuran, 59.7 mmol) was added. The resulting mixture was heated to reflux overnight and then cooled in an ice-bath. Additional borane dimethyl sulfide (5.85 mL, 2.0 M in tetrahydrofuran, 11.7 mmol) was added. The resulting mixture was heated to reflux overnight and the cooled to room temperature. The flask was fitted with a distillation head and the reaction was partially concentrated. Additional borane dimethyl sulfide (5.85 mL, 2.0 M in tetrahydrofuran, 11.7 mmol) was added. The mixture was heated to reflux overnight and the cooled in an ice-bath. The reaction was quenched by the addition of 1.0 N HCl (75.0 mL) then partially concentrated. The aqueous layer was made alkaline with 2.5 N NaOH and a precipitate developed. The solid was collected by filtration washing with diethyl ether to give a pale purple solid (3.00 g, 32%). $^1$H NMR (400 MHz, DMSO-$d_6$) δ 7.64 (app q, J=7.9 Hz, 1H), 7.44 (d, J=7.9 Hz, 2H), 7.32 (app dt, J=2.4, 9.9 Hz, 1H), 7.14 (app dt, J=1.9, 8.5 Hz, 1H), 7.13 (d, J=7.9 Hz, 2H), 6.61 (s, 1H), 5.27 (s, 4H), 3.90 (s, 2H), 2.29 (s, 3H).

Step 2. Preparation of N-(4-{[3-chloro-4-[(2,4-difluorobenzyl)oxy]-6-methyl-2-oxopyridin-1(2H)-yl]methyl}benzyl)-2-hydroxyacetamide.

Acetoxyacetic acid (1.46 g, 12.35 mmol) was dissolved in N,N-dimethylformamide (30 mL) and 1-Hydroxybenzotriazole (1.84 g, 13.59 mmol) was added followed by 4-methylmorpholine (2.04 mL, 18.53 mmol), 1-[4-(aminomethyl)benzyl]-3-chloro-4-[(2,4-difluorobenzyl)oxy]-6-methylpyridin-2(1H)-one (compound of step 1) (2.50 g, 6.18 mmol) and then 1-[3-(dimethylamino)propyl]-3-ethylcarbodiimide hydrochloride (2.84 g, 14.83 mmol). The resulting mixture was stirred at room temperature for 1 hour at which time the reaction was diluted with H$_2$O (100 mL). The reaction mixture was then extracted with ethyl acetate. The combined organic extracts were washed with saturated NaHCO$_3$, brine, dried over Na$_2$SO$_4$, filtered and concentrated. Chromatography (silica gel, hexanes/ethyl acetate with 10% methanol) provided a white foam. The resulting foam was dissolved in 10% aqueous methanol (20 mL). K$_2$CO$_3$ (0.653 g, 4.73 mmol) was added and the mixture was stirred at room temperature for 2 hours. The reaction mixture was concentrated and H$_2$O (50 mL) was added. The resulting precipitate was collected by filtration washing with diethyl ether to give an off-white solid (1.34 g, 47%). $^1$H NMR (400 MHz, CDCl$_3$) δ 7.50 (app q, J=7.7 Hz, 1H), 7.27 (app t, J=5.8 Hz, 1H), 7.12 (d, J=8.1 Hz, 2H), 6.97 (d, J=8.1 Hz, 2H), 6.94–6.89 (m, 1H), 6.86–6.81 (m, 1H), 6.09 (s, 2H), 5.23 (s, 2H), 5.18 (s, 2H), 4.53 (t, J=5.8 Hz, 1H), 4.33 (d, J=5.9 Hz, 2H), 3.85 (d, J=5.6 Hz, 2H), 2.30 (s, 3H). ES-HRMS m/z 463.1256 (M+H calcd for C$_{23}$H$_{22}$ClF$_2$N$_2$O$_4$ requires 463.1231).

Example 702

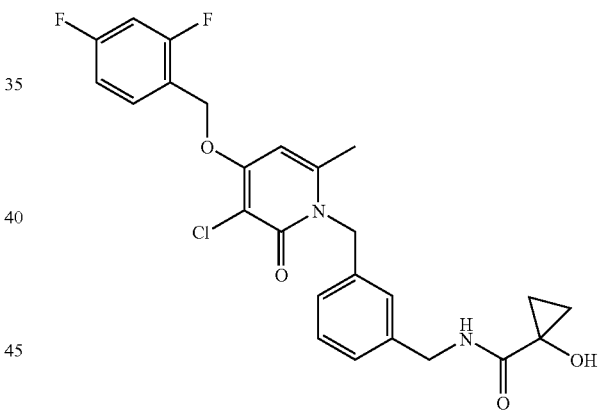

N-(4-{[3-chloro-4-[(2,4-difluorobenzyl)oxy]-6-methyl-2-oxopyridin-1(2H)-yl]methyl}benzyl)-1-hydroxycyclopropanecarboxamide Preparation of N-(4-{[3-chloro-4-[(2,4-difluorobenzyl)oxy]-6-methyl-2-oxopyridin-1(2H)-yl]methyl}benzyl)-1-hydroxycyclopropanecarboxamide. 1-Hydroxy-1-cyclopropane-carboxylic acid (1.26 g, 12.35 mmol) was dissolved in N,N-dimethylformamide (30 mL). 1-Hydroxybenzotriazole (1.84 g, 13.59 mmol) was added followed by 4-methylmorpholine (2.04 mL, 18.53 mmol), 1-[4-(aminomethyl)benzyl]-3-chloro-4-[(2,4-difluorobenzyl)oxy]-6-methylpyridin-2(1H)-one (Example 701, step 1) (2.50 g, 6.18 mmol) and then 1-[3-(dimethylamino)propyl]-3-ethylcarbodiimide hydrochloride (2.84 g, 14.83 mmol). The resulting mixture was stirred at room temperature for 24 hours at which time the reaction was diluted with H₂O (100 mL). The reaction mixture was then extracted with ethyl acetate. The combined organic extracts were washed with saturated NaHCO₃, brine, dried over Na₂SO₄, filtered and concentrated. Chromatography (silica gel, hexanes/ethyl acetate with 10% methanol) provided a white foam. The resulting foam was dissolved in 10% aqueous methanol (20 mL) to provide an white foam (1.45 g, 48%). ¹H NMR (400 MHz, CDCl₃) δ 7.52–7.46 (m, 1H), 7.34 (t, J=5.9 Hz, 1H), 7.08 (d, J=8.2 Hz, 2H), 6.92 (app d, J=8.2 Hz, 2H), 6.92–6.89 (m, 1H), 6.86–6.81 (m, 1H), 6.11 (s, 1H), 5.22 (s, 2H), 5.18 (s, 2H), 4.30 (d, J=5.9 Hz, 2H), 2.28 (s, 3H), 1.11 (app q, J=4.1 Hz, 2H), 0.90 (app q, J=4.1 Hz, 2H). ES-HRMS m/z 489.1420 (M+H calcd for C₂₅H₂₄ClF₂N₂O₄ requires 489.1387).

Example 703

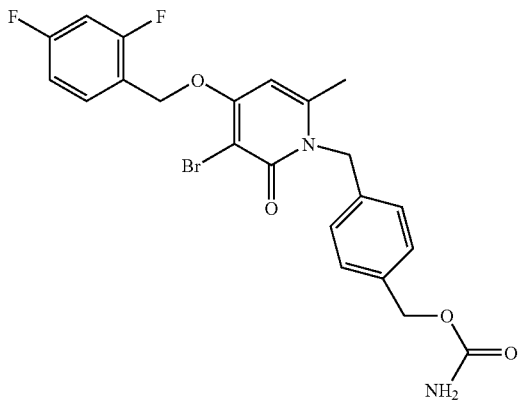

4-{[3-bromo-4-[(2,4-difluorobenzyl)oxy]-6-methyl-2-oxopyridin-1(2H)-yl]methyl}benzyl carbamate Preparation of 4-{[3-bromo-4-[(2,4-difluorobenzyl)oxy]-6-methyl-2-oxopyridin-1(2H)-yl]methyl}benzyl carbamate Compound of Example 206 (0.868 g, 1.93 mmol) was suspended in dichloromethane (7.0 mL). Trichloroacetyl isocyanate (4.00 mL, 0.53 M in toluene, 2.12 mmol) was added. The resulting mixture was stirred at room temperature for 3 hours then diluted with tetrahydrofuran (50 mL) and Al2O3 (5.0 g) was added and the mixture was stirred at room temperature overnight. The reaction mixture was filtered through a pad of Celite® washing with methonal. The filtrate was then concentrated and the residue was redissolved in tetrahydrofuran (30 mL). Al₂O₃ (5.0 g) was added and the mixture was heated to 40° C. for 3 hours. After cooling to room temperature, the reaction was filtered through a pad of Celite ® washing with methanol. The filtrate was concentrated and the resulting solid was washed with diethyl ether to give an off-white solid (0.831 g, 87%). ¹H NMR (400 MHz, CDCl₃) δ 7.54 (app q, J=7.7 Hz, 1H), 7.25 (d, J=8.2 Hz, 2H), 7.13 (d, J=8.2 Hz, 2H), 6.25 (app dt, J=2.0, 8.3 Hz, 1H), 6.86–6.30 (m, 1H), 5.97 (s, 1H), 5.32 (s, 2H), 5.18 (s, 2H), 5.02 (s, 2H), 4.81 (br s, 2H), 2.25 (s, 3H). ES-HRMS m/z 493.0580 (M+H calcd for C₂₂H₂₀BrF₂N₂O₄ requires 493.0569).

Example 704

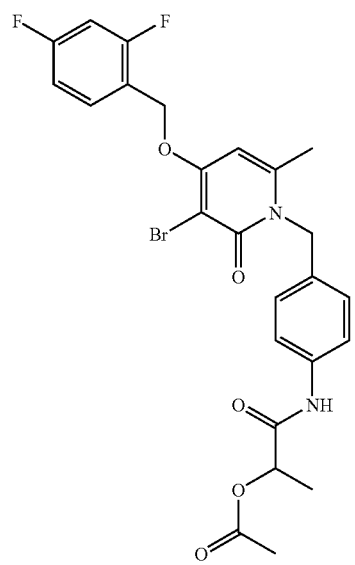

2-[(4-{[3-bromo-4-[(2,4-difluorobenzyl)oxy]-6-methyl-2-oxopyridin-1(2H)-yl]methyl}phenyl)amino]-1-methyl-2-oxoethyl acetate To a reaction vessel (borosilicate culture tube) was added compound of Example 611 (0.300 g, 0.69 mmol) and dichloromethane (3.0 mL). A stock solution of N-methylmorpholine (0.30 M, 3.0 mL) was added and the parallel reaction apparatus was then orbitally shaken (Labline Benchtop Orbital Shaker) at approximately 200 RPM at room temperature for 10 minutes. (S)-(−)-2-Acetoxypropionyl chloride (0.131 mL, 1.04 mmol) was then added to the reaction vessel and the reaction apparatus was orbitally shaken at room temperature for 1.5 hours. At this time the reaction was diluted with dichloromethane (20 mL) and treated with approximately 2.1 g of polyamine resin (2.63 mmol/g) and approximately 3.8 g of methylisocyanate fucntionalized polystyrene (1.10 mmol/g) and the orbital shaking was continued at 200 RPM at room temperature overnight. The reaction vessel was then opened and the solution Phase products were separated from the insoluble quenched byproducts by filtration and collection into a vial. After partial evaporation the insoluble byproducts were rinsed with dichloromethane (2×10 mL). The filtrate was evaporated by blowing N₂ over the vial to afford an off-white solid (0.375 g, 99%). ¹H NMR (400 MHz, DMF-d₆) δ 10.14 (s, 1H), 7.75 (app dt, J=6.98, 8.59 Hz, 1H), 7.67–7.64 (m, 2H), 7.30 (ddd, J=2.55, 9.26, 11.81 Hz, 1H), 7.21–7.17 (m, 3H), 6.61 (s, 1H), 5.37 (s, 4H), 5.11 (q, J=6.85 Hz, 1H), 2.40 (s, 3H), 2.10 (s, 3H), 1.46 (d, J=6.85 Hz, 3H). ES-HRMS m/z 549.0790 (M+H calcd for C₂₅H₂₃BrF₂N₂O₅ requires 549.0831).

Example 705

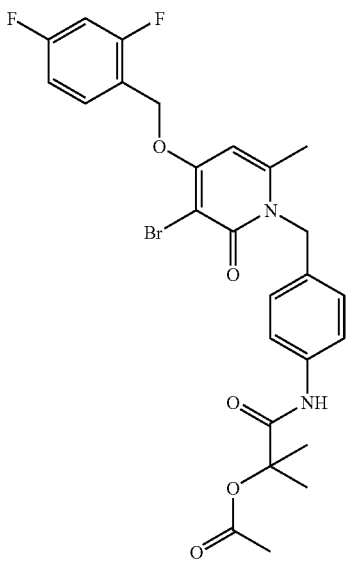

2-[(4-{[3-bromo-4-[(2,4-difluorobenzyl)oxy]-6-methyl-2-oxopyridin-1(2H)-yl]methyl}phenyl)amino]-1,1-dimethyl-2-oxoethyl acetate By the method for Example 704 and substituting (S)-(-)-2-acetoxypropionyl chloride with 2-acetoxy-2-methylpropionyl chloride, the title compound was prepared (0.380 g, 98%). $^1$H NMR (400 MHz, DMF-$d_6$) δ 9.68 (s, 1H), 7.75 (app dt, J=6.72, 8.60 Hz, 1H), 7.71–7.68 (m, 2H), 7.30 (ddd, J=2.55, 9.40, 11.95 Hz, 1H), 7.21–7.15 (m, 3H), 6.61 (s, 1H), 5.37 (s, 4H), 2.41 (s, 3H), 2.04 (s, 3H), 1.59 (s, 6H). ES-HRMS m/z 563.1027 (M+H calcd for $C_{26}H_{25}BrF_2N_2O_5$ requires 563.0988).

Example 706

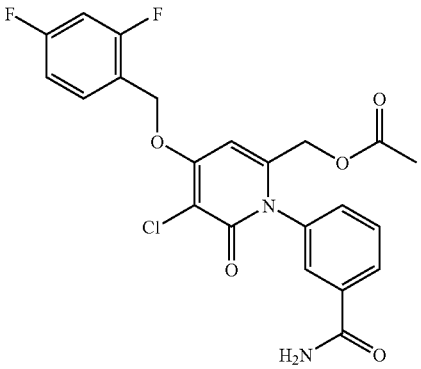

{1-[3-(aminocarbonyl)phenyl]-5-chloro-4-[(2,4-difluorobenzyl)oxy]-6-oxo-1,6-dihydropyridin-2-yl}methyl acetate Step 1: Preparation of {1-[3-(aminocarbonyl)phenyl]-4-hydroxy-6-oxo-1,6-dihydropyridin-2-yl}methyl acetate.

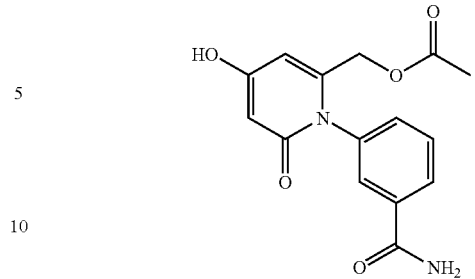

3-(2,2-dimethyl-4-oxo-4H-1,3-dioxin-6-yl)-2-oxopropyl acetate (4.00 g, 16.52 mmol) was dissolved in 1,4-dioxane (160 mL) and 3-aminobenzamide (1.73 g, 12.71 mmol) was added. The reaction was heated to reflux for 1 hour then cooled to 70° C. Methanesulfonic acid (1.22 g, 12.71 mmol) was added and the reaction brought back to reflux for 1 hour. The reaction was cooled to room temperature, concentrated and used as crude product for the next step.

Step 2: Preparation of {1-[3-(aminocarbonyl)phenyl]-4-[(2,4-difluorobenzyl)oxy]-6-oxo-1,6-dihydropyridin-2-yl}methyl acetate.

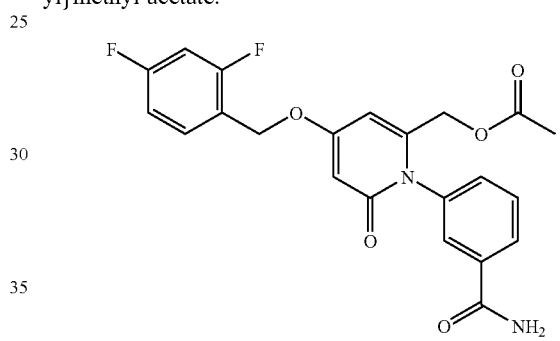

{1-[3-(aminocarbonyl)phenyl]-4-hydroxy-6-oxo-1,6-dihydropyridin-2-yl}methyl acetate (crude from step 1) (3.61 g, 11.94 mmol) was dissolved in N,N-dimethylformamide (40 mL). $K_2CO_3$ (3.80 g, 27.46 mmol) was added followed by 2,4-difluorobenzyl bromide (5.44 g, 26.27 mmol). The reaction mixture was stirred for 48 hours at room temperature. The reaction mixture was then partially concentrated and the residue taken up in dichloromethane/tetrahydrofuran 1:1 and filtered. The filtrate was collected, concentrated and the residue tritrated with dichloromethane to afford a tan solid (1.64 g, 32%). $^1$H NMR (400 MHz, DMF-$d_6$) δ 8.19 (br s, 1H), 8.07 (app dt, J=1.35, 7.66 Hz, 1H), 7.91 (app t, J=1.81 Hz, 1H), 7.76 (app dt, J=6.58, 8.59 Hz, 1H), 7.62 (t, J=7.79 Hz, 1H), 7.55 (ddd, J=1.21, 2.01, 7.79 Hz, 1H), 7.46 (br s, 1H), 7.34 (ddd, J=2.55, 9.40, 10.47 Hz, 1H), 7.23–7.18 (m, 1H), 6.26 (d, J=2.55 Hz, 1H), 6.11 (d, J=2.69 Hz, 1H), 5.23 (s, 2H), 4.62 (AB q, $J_{AB}$=14.97 Hz, 2H), 1.96 (s, 3H). ES-HRMS m/z 429.1280 (M+H calcd for $C_{22}H_{18}F_2N_2O_5$ requires 429.1257).

Step 3: Preparation of the Title Compound.

{1-[3-(aminocarbonyl)phenyl]-4-[(2,4-difluorobenzyl)oxy]-6-oxo-1,6-dihydropyridin-2-yl}methyl acetate (from step 2) (1.02 g, 2.39 mmol) was suspended in dichloromethane (15 mL) and N-chlorosuccinimide (0.37 g, 2.75 mmol) was added. Dichloroacetic acid (0.10 ml, 1.22 mmol) was added and the reaction mixture was stirred at 40° C. for 1.5 hours. The reaction was cooled to room temperature and a precipitate formed. The reaction mixture was diluted with diethyl ether and the precipitate was collected by filtration and washed with diethyl ether (3×15 mL) to afford a tan solid (0.940 g, 85%). ¹H NMR (400 MHz, DMF-d₆) δ 8.21 (br s, 1H), 8.11 (app dt, J=1.48, 7.52 Hz, 1H), 7.95 (app t, J=1.61 Hz, 1H), 7.80 (app dt, J=6.72, 8.59 Hz, 1H), 7.69–7.60 (m, 2H), 7.48 (br s, 1H), 7.35 (ddd, J=2.55, 9.53, 10.61 Hz, 1H), 7.24–7.19 (m, 1H), 6.97 (s, 1H), 5.49 (s, 2H), 4.71 (AB q, J$_{AB}$=15.04 Hz, 2H), 1.98 (s, 3H). ES-HRMS m/z 463.0883 (M+H calcd for $C_{22}H_{17}ClF_2N_2O_5$ requires 463.0867).

Example 707

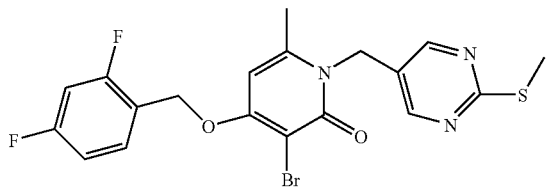

3-bromo-4-[(2,4-difluorobenzyl)oxy]-6-methyl-1-{ [2-(methylthio)pyrimidin-5-yl]methyl}pyridin-2 (1H)-one Step 1. Preparation of methyl 2-(methylthio)pyrimidine-5-carboxylate

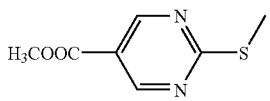

A solution of the sodium salt of 3,3-dimethoxy-2-methoxycarbonylpropen-1-ol (5.0 g, 25 mmol), 2-methyl-2-thiopseudourea sulfate (3.5 g, 25 mmol) in anhydrous methanol (25 mL) was refluxed for 3 hours under anhydrous conditions. The reaction mixture was cooled and diluted with ethyl acetate. The reaction mixture was filtered and the residue was washed with ethyl acetate. The filtrate was concentrated and the residue was purified by flash chromatography (silica gel) using 25% ethyl acetate in hexane to afford the desired product (3.5 g, 75%) as a white powder. ¹H-NMR (d₆-DMSO, 400 MHz) δ 9.0 (s, 2H), 3.92 (s, 3H), 2.58 (s, 3H); ES-HRMS m/z 185.041 (M+H $C_7H_8N_2O_2S$ requires 185.0379).

Step 2. Preparation of [2-(methylthio)pyrimidin-5-yl]methanol

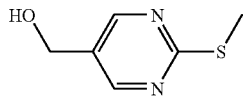

To a cold suspension of methyl 2-(methylthio)pyrimidine-5-carboxylate (1.74 g, 9.4 mmol) in dichloromethane (20 mL, −70° C.) was added DIBAL (20.8 mL, 20 mmol) dropwise via an addition funnel. The mixture was stirred under nitrogen at −70° C. for 1 hour and then at −50° C. for 3 hours. The reaction was diluted with dichloromethane (50 mL) and quenched with a suspension of sodium sulfate decahydrate (10 g) in water (50 mL). The slurry was filtered through celite and the filtrate was concentrated. The residue was purified by flash chromatography (silica gel) using 100% ethyl acetate to afford the desired compound (0.7813 g, 39%) as a yellow solid. ¹H-NMR ((CD₃OD, 400 MHz) δ 8.53 (s, 2H), 4.56 (s, 2H), 2.54 (s, 3H); ES-HRMS m/z 157.0409 (M+H $C_6H_8N_2OS$ requires 157.0430).

Step 3. Preparation of 5-(chloromethyl)-2-(methylthio) pyrimidine

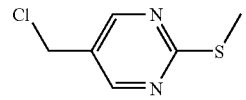

To a cold solution of [2-(methylthio)pyrimidin-5-yl] methanol (0.7813 g, 5.0 mmol) in anhydrous dichloromethane (10 mL, 0° C.) was added triethylamine (0.836 mL, 8.2 mmol) followed by the addition of methanesulfonyl chloride (0.465 mL, 6.0 mmol). The reaction mixture stirred at 0° C. under a nitrogen atmosphere for 30 minutes then at room temperature for 3.5 hours. The reaction was quenched with sodium bicarbonate (5%, 100 mL)) and extracted with dichloromethane (50 mL). The organic extracts were concentrated and the residue was purified by flash chromatography (silica gel) using 15% ethyl acetate in hexane to afford the desired compound (0.720 g, 82%) as a white solid. ¹H-NMR ((CD₃OD, 400 MHz) δ 8.60 (s, 2H), 4.64 (s, 2H), 2.54 (s, 3H); ES-HRMS m/z 175.0106 (M+H $C_6H_7N_2ClS$ requires 175.0091).

Step 4. Preparation of 3-bromo-4-[(2,4-difluorobenzyl) oxy]-6-methyl-1-{[2-(methylthio)pyrimidin-5-yl] methyl}pyridin-2(1H)-one To a solution of 5-(chloromethyl)-2-(methylthio) pyrimidine (0.62 g, 3.56 mmol) in anhydrous DMF (10 mL) was added KBr (0.424, 3.56 mmol). After the suspension stirred at room temperature for 30 minutes, 3-bromo-4-[(2, 4-difluorobenzyl)oxy]-6-methylpyridin-2(1H)-one (1.05 g, 3.19 mmol) was added followed by NaH (0.102 g, 4.25 mmol). The reaction mixture stirred at 70° C. under a nitrogen atmosphere for 3.5 hours. The solvent was distilled and the residue was washed with water and extracted with ethyl acetate. The organic extracts were concentrated and the residue was purified by reverse phase HPLC using a 10–90% acetonitrile/water (30 minute gradient) at a 70 mL/min flow rate to afford the desired TFA salt (0.32 g, 15%) as a white powder. The TFA compound was washed with sodium bicarbonate (5%) and extracted with dichloromethane (50 mL). The organic extract was concentrated to afford the desired compound (0.295 g, 18%) as a yellow solid. ¹H-NMR (CD₃OD, 400 MHz) δ 8.47 (s, 2H), 7.62 (q, 1H, J=8 Hz), 7.03 (m, 2H), 6.51 (s, 1H), 5.31 (s, 2H), 5.29 (s, 2H), 2.52 (s, 3H), 2.47 (s, 2H); ES-HRMS m/z 468.0174/ 470.0156 (M+H $C_{19}H_{16}N_3O_2F_2BrS$ requires 468.0187/ 470.0168).

Example 708

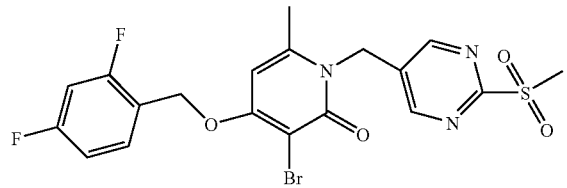

3-bromo-4-[(2,4-difluorobenzyl)oxy]-6-methyl-1-{ [2-(methylsulfonyl)pyrimidin-5-yl]methyl}pyridin-2 (1H)-one To a solution of 3-bromo-4-[(2,4-difluorobenzyl)oxy]-6-methyl-1-{[2-(methylthio)pyrimidin-5-yl]methyl}pyridin-2 (1H)-one (example 707) (0.26 g, 0.55 mmol) in acetonitrile:

water (4:1 v/v, 10 mL) was added MMPP (0.549 g, 1.1 mmol). The reaction stirred at room temperature for 30 hours. The reaction mixture was diluted with ethyl acetate and filtered. The filtrate was concentrated and the residue was purified by reverse phase HPLC using a 10–90% acetonitrile/water (30 minute gradient) at a 70 mL/min flow rate to afford the desired TFA salt of the title compound (0.13 g, 38%) as a white powder. $^1$H-NMR ((CD$_3$OD, 400 MHz) δ 8.86 (s, 2H), 7.62 (q, 1H, J=8 Hz), 7.02 (m, 2H), 6.56 (s, 1H), 5.48 (s, 2H), 5.31 (s, 2H), 3.34 (s, 3H), 2.49 (s, 2H); ES-HRMS m/z 500.0109/502.0066 (M+H C$_{19}$H$_{16}$N$_3$O$_4$F$_2$BrS requires 500.0086/502.0067).

Example 709

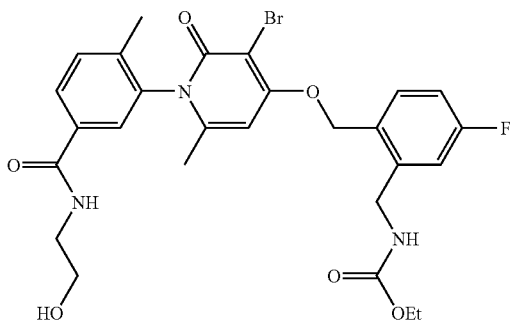

Ethyl 2-({[3-bromo-1-(5-{[(2-hydroxyethyl)amino]carbonyl}-2-methylphenyl)-6-methyl-2-oxo-1,2-dihydropyridin-4-yl]oxy}methyl)-5-fluorobenzylcarbamate To a cooled (–10° C.) solution of 3-[3-bromo-4-[(2-{[(ethoxycarbonyl)amino]methyl}-4-fluorobenzyl)oxy]-6-methyl-2-oxopyridin-1(2H)-yl]-4-methylbenzoic acid (0.25 g, 0.46 mmol) and 4-methylmorpholine (0.06 mL, 0.55 mmol) in DMF was added isobutyl chloroformate (0.07 mL, 0.55 mmol). The colorless solution gradually turned dark brown. After 30 min, ethaolamine (0.04 mL, 0.69 mmol) was added and the solution warmed to RT. After 1 h, solvent was removed and the crude product was purified by preparatory HPLC. Acetonitrile was evaporated and the solution washed with 5% NaHCO$_3$ (20 mL) and extracted in DCM (3×15 mL). The organic extracts were dried over Na$_2$SO$_4$, filtered, and concentrated to a white solid, dried in vacuo (0.09 g, 33%). $^1$H NMR (CD$_3$OD/400 MHz) δ 7.88 (m, 1H), 7.61 (s, 1H), 7.53 (m, 2H), 7.13 (m, 1H), 7.05 (m, 1H), 6.68 (s, 1H), 5.40 (s, 2H), 4.43 (s, 2H), 4.07 (q, 2H, J=7.2 Hz), 3.68 (t, 2H, J=5.6 Hz), 3.48 (t, 2H, J=5.6 Hz), 2.09 (s, 3H), 2.00 (s, 3H), 1.22 (t, 3H, J=7.2 Hz). ES HRMS m/z 590.1266 and 592.1254 (M+H calculated for C$_{27}$H$_{30}$BrFN$_3$O$_6$ requires 590.1297 and 592.1281).

Example 710

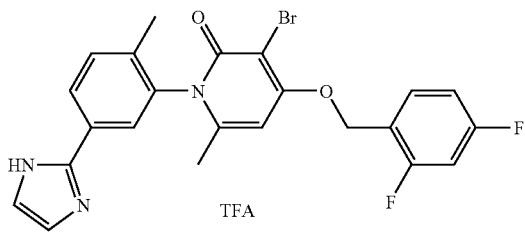

3-bromo-4-[(2,4-difluorobenzyl)oxy]-1-[5-(1H-imidazol-2-yl)-2-methylphenyl]-6-methylpyridin-2(1H)-one trifluoroacetate An oven-dried flask was alternately evacuated and flushed with argon. Toluene (2.18 mL) and trimethyl aluminum (1.25 mL, 2.51 mmol) were added sequentially and the solution cooled to –5° C. Ethylene diamine (0.17 mL, 2.51 mmol) was added dropwise. Methyl 3-[3-bromo-4-[(2,4-difluorobenzyl)oxy]-6-methyl-2-oxopyridin-1(2H)-yl]-4-methylbenzoate (0.75 g, 1.57 mmol) was added portionwise to the cooled solution. The reaction mixture was then refluxed at 110° C. for 4 h. The solution was cooled and water (0.7 mL), DCM (2.2 mL), and MeOH (2.2 mL) were added. The solution was refluxed for 15 min following this addition and then dried over Na$_2$SO$_4$, filtered, and concentrated. The residue was dissolved in EtOAc (20 mL), refluxed 15 min, dried over Na$_2$SO$_4$, filtered, and concentrated. The crude product was purified by preparatory HPLC. The product was isolated by freeze-drying and evaporation of the solvent to give a white solid, dried in vacuo (0.30 g, 31%).

$^1$H NMR (CD$_3$OD/400 MHz) δ 7.88 (m, 1H), 7.71 (d, 1H, J=8.0 Hz), 7.64 (m, 2H), 7.05 (m, 2H), 6.70 (s, 1H), 5.37 (s, 2H), 4.09 (s, 4H), 2.16 (s, 3H), 2.01 (s, 3H). ES HRMS m/z 488.0750 and 490.0774 (M+H calculated for C$_{23}$H$_{21}$BrF$_2$N$_3$O$_2$ requires 488.0780 and 490.0762).

Example 711

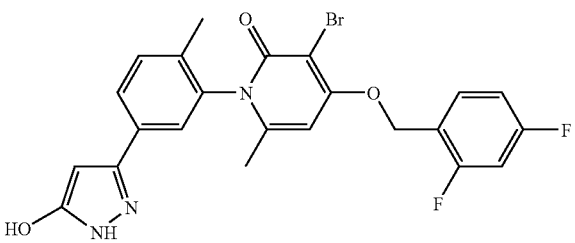

3-bromo-4-[(2,4-difluorobenzyl)oxy]-1-[5-(5-hydroxy-1H-pyrazol-3-yl)-2-methylphenyl]-6-methylpyridin-2(1H)-one Step 1: Preparation of ethyl 3-{3-[3-bromo-4-[(2,4-difluorobenzyl)oxy]-6-methyl-2-oxopyridin-1(2H)-yl]-4-methylphenyl}-3-oxopropanoate.

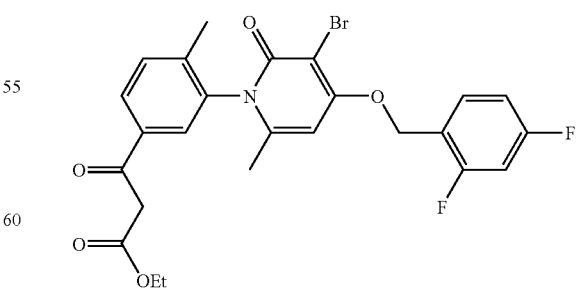

In an oven-dried round bottom flask, 3-[3-bromo-4-[(2,4-difluorobenzyl)oxy]-6-methyl-2-oxopyridin-1(2H)-yl]-4- methylbenzoic acid (see Example 487) (0.75 g, 1.62 mmol), DCM (2.00 mL), and oxalyl chloride (0.97 mL, 1.94 mmol) were combined under argon. DMF (3–5 drops) was added to aid in dissolution. Stirred at RT overnight. Solvent was removed and the crude acid chloride was coevaporated with DCM (3–5 mL×3) and dried in vacuo to give an orange solid. In a separate oven-dried flask, in an argon atmosphere, a solution of monoethyl malonate (0.38 mL, 3.23 mmol) in THF (3.00 mL) was cooled to −78° C. Isopropyl magnesium chloride (3.23 mL, 6.46 mmol) was added dropwise. The solution was stirred for 30 min at −78° C. The acid chloride prepared as described above was added dropwise as a solution in THF. The reaction was warmed to RT. After 30 min, the reaction was cooled (0° C.) and 10% citric acid (5.0 mL) added. The crude product was extracted in EtOAc, washed with 5% NaHCO$_3$, dried over Na$_2$SO$_4$, filtered, and concentrated to a crude brown oil. Recrystallization from DCM and hexane. Filtered a beige solid, dried in vacuo (0.41 g, 47%). $^1$H NMR (CD$_3$OD/400 MHz) δ 8.02 (m, 1H), 7.79 (s, 1H), 7.65 (m, 2H), 7.05 (t, 2H, J=9.2 Hz), 6.66 (s, 1H), 5.36 (s, 2H), 4.16 (q, 2H, J=7.2 Hz), 2.11 (s, 3H), 2.07 (s, 2H), 1.99 (s, 3H), 1.23 (t, 3H, J=7.2 Hz). ES HRMS m/z 534.0744 and 536.0746 (M+H calculated for C$_{25}$H$_{23}$BrF$_2$NO$_5$ requires 534.0722 and 536.0706).

Step 2: Preparation of the Title Compound.

To a mixture of ethyl 3-{3-[3-bromo-4-[(2,4-difluorobenzyl)oxy]-6-methyl-2-oxopyridin-1(2H)-yl]-4-methylphenyl}-3-oxopropanoate (from Step 1) (0.20 g, 0.37 mmol) in EtOH (5.00 mL) was added hydrazine hydrate (0.01 mL, 0.41 mmol). The reaction mixture was heated at 60° C. with a condensere. After 1 h, additional hydrazine hydrate (0.01 mL) was added. After 2 h, acetic acid (2 drops) was added. At 4 h, additional hydrazine was added (0.1 mL). At 5 h, the reaction appeared to be complete. Left in fridge overnight. Precipitate filtered, washed with hexane, found to be product, a white solid (0.10 g, 54%). $^1$H NMR (CD$_3$OD/400 MHz) δ 7.66 (m, 2H), 7.45 (m, 2H), 7.05 (t, 2H, J=9.6 Hz), 6.65 (s, 1H), 5.36 (s, 2H), 2.04 (s, 3H), 2.02 (s, 3H). ES HRMS m/z 502.0552 and 504.0569 (M+H calculated for C$_{23}$H$_{19}$BrF$_2$N$_3$O$_3$ requires 502.0572 and 504.0555).

Example 712

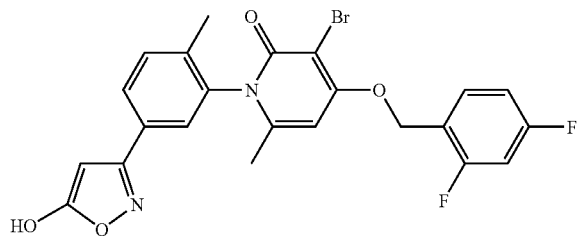

3-bromo-4-[(2,4-difluorobenzyl)oxy]-1-[5-(5-hydroxyisoxazol-3-yl)-2-methylphenyl]-6-methylpyridin-2(1H)-one A solution of ethyl 3-{3-[3-bromo-4-[(2,4-difluorobenzyl)oxy]-6-methyl-2-oxopyridin-1(2H)-yl]-4-methylphenyl}-3-oxopropanoate (0.20 g, 0.37 mmol), triethylamine (0.06 mL, 0.41 mmol), and hydroxylamine hydrochloride (0.03 g, 0.41 mmol) in EtOH (3.00 mL) was heated overnight at 60° C. with a condenser. Additional triethylamine (0.06 mL) and hydroxylamine hydrochloride (0.03 g) were added. After 2.5 h, the additions of triethylamine and hydroxylamine hydrochloride were repeated. After 1 h, the reaction was concentrated and purified by preparatory HPLC. The product was isolated by freeze-drying and evaporation of the solvent to give a white solid. Dissolved solid in DCM. Upon addition of 5% NaHCO$_3$, solution became a milky emulsion. Added additional DCM and some brine. Organic extracts were dried over Na$_2$SO$_4$, filtered, and concentrated to a pink solid, dried in vacuo (120 mg, 64%). $^1$H NMR (CD$_3$OD/400 MHz) δ 7.66 (m, 2H), 7.44 (m, 2H), 7.04 (t, 2H, J=8.8 Hz), 6.64 (s, 1H), 5.36 (s, 2H), 2.04 (s, 3H), 2.01 (s, 3H). ES HRMS m/z 503.0415 and 505.0402 (M+H calculated for C$_{23}$H$_{18}$BrF$_2$N$_2$O$_4$ requires 503.0413 and 505.0395).

Example 713

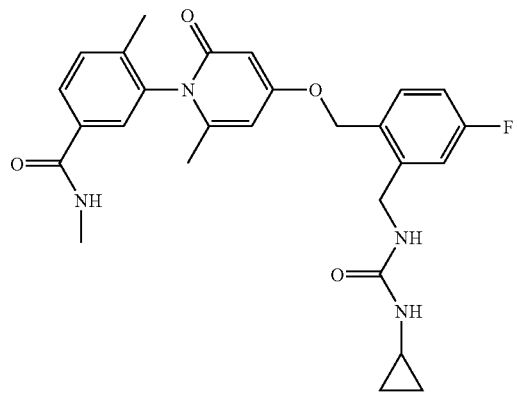

3-[4-{[2-({[(cyclopropylamino)carbonyl]amino}methyl)-4-fluorobenzyl]oxy}-6-methyl-2-oxopyridin-1(2H)-yl]-N,4-dimethylbenzamide To a cooled (−15° C.) solution of 3-[4-{[2-({[(cyclopropylamino)carbonyl]amino}methyl)-4-fluorobenzyl]oxy}-6-methyl-2-oxopyridin-1(2H)-yl]-4-methylbenzoic acid (see Example 651) (0.30 g, 0.63 mmol) and isobutyl chloroformate (0.10 mL, 0.75 mmol) in DMF (3.00 mL) was added 4-methylmorpholine (0.08 mL, 0.75 mmol). The solution instantly turned yellow and was dark brown within minutes. After 20 min, methylamine (0.47 mL of 2.0M solution in THF, 0.94 mmol) was added. The reaction was carried out at RT. After 2.5 h, a catalytic amount of DMAP and additional methylamine (0.47 mL, 0.94 mmol) were added. After an additional 2.5 h, the reaction was concentrated to a dark red oil. The crude product was purified by preparatory HPLC. Acetonitrile was evaporated and the solution washed with 5% NaHCO$_3$ (20 mL) and extracted in DCM (3×15 mL). The organic extracts were dried over Na$_2$SO$_4$, filtered, and concentrated to an off-white solid, dried in vacuo (0.06 g, 19%). $^1$H NMR (CD$_3$OD/400 MHz) δ 7.85 (m, 1H), 7.58 (s, 1H), 7.48 (m, 2H), 7.14 (m, 1H), 7.02 (m, 1H), 6.23 (s, 1H), 6.09 (s, 1H), 5.20 (s, 2H), 4.45 (s, 2H), 2.90 (s, 3H), 2.49 (m, 1H), 2.11 (s, 3H), 1.91 (s, 3H), 0.71 (m, 2H), 0.48 (m, 2H). ES HRMS m/z 493.2260 (M+H calculated for C$_{27}$H$_{30}$N$_4$O$_4$F requires 493.2246).

Example 714

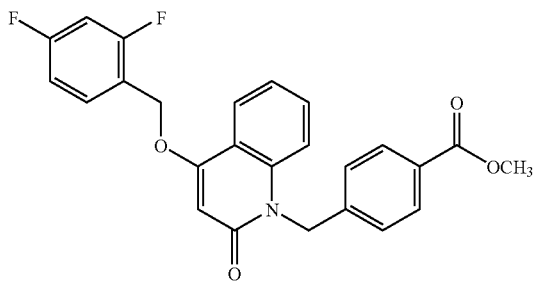

Methyl 4-{[4-[(2,4-difluorobenzyl)oxy]-2-oxoquinolin-1(2H)-yl]methyl}benzoate

Step 1: Preparation of 3-bromo-4-[(2,4-difluorobenzyl)oxy]quinolin-2(1H)-one.

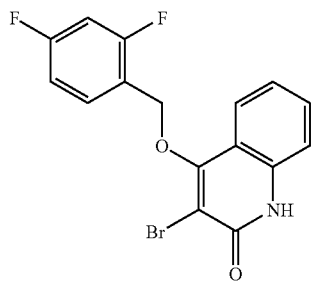

To a room temperature solution of 4-hydroxy-1,2-dihydroquinolin-2-one (500 mg, 3.10 mmol) in $CH_2Cl_2$ (10.0 mL) was added portion-wise solid N-bromosuccinimide (551.5 mg, 3.10 mmol). The reaction was stirred vigorously for 1.0 h, followed by the sequential addition of $K_2CO_3$ (540 mg, 3.90 mmol), DMF (4.0 mL), and 2,4 difluorobenzyl bromide (0.430 mL, 3.30 mmol). The resulting suspension was stirred for 4.5 hours until complete formation of desired product was seen by LCMS analysis. The reaction was then diluted with ethyl acetate (400 mL) and brine washed (3×200 mL). The resulting organic extract was $Na_2SO_4$ dried, filtered, and concentrated in vacuo to a residue that was subjected to $SiO_2$ chromatography with ethyl acetate/hexanes/methanol (60:35:5) to furnish a solid (529 mg, 47%). $^1H$ NMR (300 MHz, $d_6$-DMSO) δ 12.23 (s, 1H), 7.68 (app q, J=7.5 Hz, 1H), 7.64 (app q, J=8.5 Hz, 1H), 7.54 (app q, J=8.3 Hz, 1H), 7.38–7.27 (m, 2H), 7.20 (app t, J=7.4 Hz, 1H), 7.13 (app dt, J=8.4, 2.6 Hz, 1H), 5.25 (s, 2H); LC/MS C-18 column, $t_r$=2.64 minutes (5 to 95% acetonitrile/water over 5 minutes at 1 ml/min with detection 254 nm, at 50° C.). ES-MS m/z 366 (M+H). ES-HRMS m/z 365.9967 (M+H calcd for $C_{16}H^{11}BrF_2NO_2$ requires 365.9936).

Step 2: Preparation of methyl 4-{[3-bromo-4-[(2,4-difluorobenzyl)oxy]-2-oxoquinolin-1(2H)-yl]methyl}benzoate.

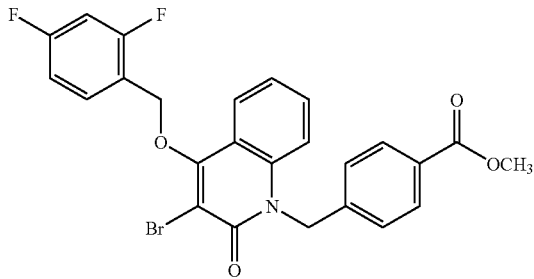

To a room temperature solution of 3-bromo-4-[(2,4-difluorobenzyl)oxy]quinolin-2(1H)-one (400 mg, 1.09 mmol) in THF (4.5 mL) was added portion-wise solid sodium hydride (95% oil-free, 60.0 mg, 2.49 mmol). The reaction was vigorously stirred for 30 minutes followed by addition of methyl-4-(bromomethyl)-benzoate (400 mg, 1.75 mmol). This resulting suspension was then heated to 60° C. for 12.0 hours. The resulting solution was then treated with saturated aqueous ammonium chloride (400 mL) and extracted with ethyl acetate (3×300 mL). The resulting organic extracts were $Na_2SO_4$ dried, filtered, and concentrated in vacuo to a residue that was subjected to $SiO_2$ chromatography with ethyl acetate/hexanes (60:40) to furnish a solid (396 mg, 71%). $^1H$ NMR (400 MHz, $CDCl_3$) δ 7.97 (app d, J=8.0 Hz, 2H), 7.87 (d, J=7.5 Hz, 1H), 7.60 (app q, J=8.4 Hz, 1H), 7.49–7.42 (m, 1H), 7.30–7.15 (m, 4H), 6.94 (app t, J=6.3 Hz, 1H), 6.88 (app t, J=9.4 Hz, 1H), 5.64 (s, 2H), 5.33 (s, 2H), 3.88 (s, 3H); LC/MS C-18 column, $t_r$=3.46 minutes (5 to 95% acetonitrile/water over 5 minutes at 1 ml/min with detection 254 nm, at 50° C.). ES-MS m/z 514 (M+H). ES-HRMS m/z 514.0451 (M+H calcd for $C_{25}H_{19}BrF_2NO_4$ requires 514.0460).

Step 3: Preparation of the title compound. In a 25 mL round bottom flask was added, at room temperature, a solution of methyl 4-{[3-bromo-4-[(2,4-difluorobenzyl)oxy]-2-oxoquinolin-1(2H)-yl]methyl}benzoate (step 2) (120 mg, 0.233 mmol) in MeOH (3.0 mL). Next, a combination of Pd on carbon (10% Pd, weight by weight 50% water, 100 mg, 0.047 mmol) and $Pd(OAc)_2$ (15 mg, 0.067 mmol) was added to the reaction vessel that purged with argon and then fitted with a septum. The vessel was then equipped with a 2.0 L hydrogen balloon (c.a. 20 psi). The resulting suspension was allowed to stir of 12.0 hours and was then directly applied to $SiO_2$ chromatography using ethyl acetate/hexanes (3:7) to furnish the desired title compound as a solid (52 mg, 51%). $^1H$ NMR (300 MHz, $CDCl_3$) δ 8.05–7.98 (m, 3H), 7.55 (app q, J=8.3 Hz, 1H), 7.48 (app t, J=7.5 Hz, 1H), 7.30 (d, J=8.0 Hz, 2H), 7.19 (app q, J=8.5, 2H), 7.05–6.90 (m, 2H), 6.28 (s, 1H), 5.60 (s, 2H), 5.26 (s, 2H), 3.91 (s, 3H); LC/MS C-18 column, $t_r$=3.71 minutes (5 to 95% acetonitrile/water over 5 minutes at 1 ml/min with detection 254 nm, at 50° C.). ES-MS m/z 436 (M+H). ES-HRMS m/z 436.1371 (M+H calcd for $C_{25}H_{20}BrF_2NO_4$ requires 436.1355).

Example 715

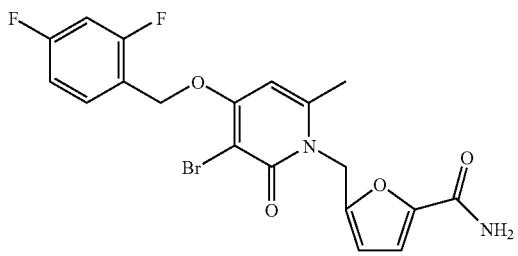

5-{[3-bromo-4-[(2,4-difluorobenzyl)oxy]-6-methyl-2-oxopyridin-1(2H)-yl]methyl}-2-furamide Step 1: Preparation of 5-{[3-bromo-4-[(2,4-difluorobenzyl)oxy]-6-methyl-2-oxopyridin-1(2H)-yl]methyl}-2-furoic acid.

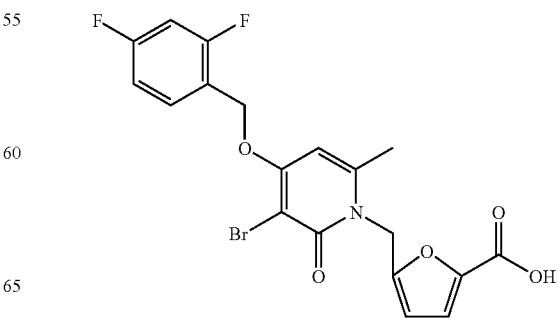

To a room temperature solution of methyl 5-{[3-bromo-4-[(2,4-difluorobenzyl)oxy]-6-methyl-2-oxopyridin-1(2H)-yl]methyl}-2-furoate (Example 660) (608 g, 1.30 mmol) in THF (8.0 mL) was added dropwise an aqueous solution of sodium hydroxide (3.0 M, 0.50 mL, 1.50 mmol). The reaction was then heated to 60° C. for 12.0 hours. The resulting suspension was then diluted with 500 mL of ethyl acetate and neutralized with an aqueous solution of hydrochloric acid (1.0 N, 1.5 mL, 10 mmol). The resulting biphasic solution was then concentrated in vacuo to a volume of 50 mL. At this time a white solid began to form and the resulting solid suspension was allowed to sit until precipitation appeared to stop (approximately 1.0 hour). The precipitate was collected and dried in vacuo (1.0 mm Hg) to furnish the solid acid as an intermediate (500 mg, 85%). $^1$H NMR (300 MHz, d$_4$-MeOH) δ 7.64 (app q, J=8.3 Hz, 1H), 7.18 (d, J=3.4 Hz, 1H), 7.10–7.02 (m, 2H), 6.54 (s, 1H), 6.50 (d, J=3.5 Hz, 1H), 5.42 (s, 2H), 5.37 (s, 2H), 2.64 (s, 3H); LC/MS C-18 column, t$_r$=2.38 minutes (5 to 95% acetonitrile/water over 5 minutes at 1 ml/min with detection 254 nm, at 50° C.). ES-MS m/z 454 (M+H). ES-HRMS m/z 454.0070 (M+H calcd for C$_{19}$H$_{15}$BrF$_2$NO$_5$ requires 454.0096).

Step 2: Preparation of the title compound. To a room temperature suspension of 5-{[3-bromo-4-[(2,4-difluorobenzyl)oxy]-6-methyl-2-oxopyridin-1(2H)-yl]methyl}-2-furoic acid (500 mg, 1.10 mmol) in THF (6.0 mL) was added 2-chloro-4,6 dimethoxy-1,3,5 triazine (307 mg, 1.75 mmol) and N-methyl morpholine (NMM, 184 mg, 1.82 mmol) sequentially. The resulting solution was matured for 2 hours and then a saturated aqueous solution of ammonium hydroxide (0.70 mL) was added. The resulting suspension was allowed to continue for 1 additional hour. The reaction mixture was diluted with 400 mL of brine and extracted with ethyl acetate (3×400 mL). The organic extracts were separated, Na$_2$SO$_4$ dried, and concentrated in vacuo and the resulting residue was subjected to SiO$_2$ chromatography with ethyl acetate/hexanes/methanol (57:38:5) to provide the title compound (370 g, 74%). $^1$H NMR (300 MHz, d$_4$-MeOH) δ 7.64 (app q, J=8.1 Hz, 1H), 7.10–7.00 (m, 3H), 6.53 (s, 1H), 6.52 (d, J=3.4 Hz, 1H), 5.43 (s, 2H), 5.32 (s, 2H), 2.61 (s, 3H); LC/MS C-18 column, t$_r$=2.15 minutes (5 to 95% acetonitrile/water over 5 minutes at 1 ml/min with detection 254 nm, at 50° C.). ES-MS m/z 453 (M+H). ES-HRMS m/z 453.0249 (M+H calcd for C$_{19}$H$_{16}$BrF$_2$N$_2$O$_4$ requires 453.0256).

Example 716

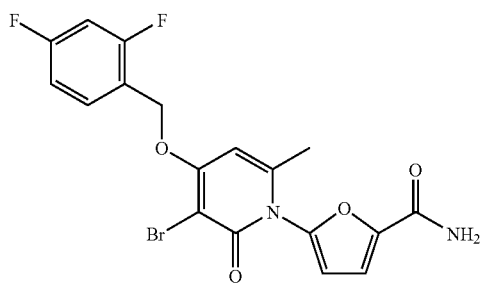

5-[3-bromo-4-[(2,4-difluorobenzyl)oxy]-6-methyl-2-oxopyridin-1(2H)-yl]-2-furamide Step 1: Preparation of methyl 5-(4-hydroxy-6-methyl-2-oxopyridin-1(2H)-yl)-2-furoate.

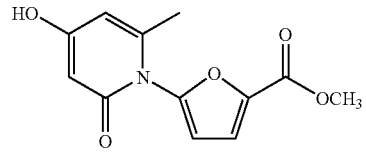

To a room temperature solution of methyl-2-amino-5-furoate (4.85 g, 34.4 mmol) in 1,4 dioxane (28.0 mL) was added 5-(1-hydroxy-3-oxobutylidene)-2,2-dimethyl-1,3-dioxane-4,6-dione (8.16 g, 44.3 mmol). The reaction was stirred vigorously and heated quickly (within 8 minutes) to an internal temperature of 98° C. Upon reaching temperature, the reaction was maintained for 1.0 hour. At this time, the reaction was cooled to room temperature rapidly using an ice-bath and methane sulfonic acid (3.30 g, 34.4 mmol) was added. The reaction mixture was once again brought to an internal temperature of approximately 100° C. After 1.0 hour the reaction was diluted with 10 mL of toluene and allowed to cool to room temperature on its own accord. A solid formed after 3.0 hours that was collected and subsequently recrystallized from methanol/ethyl acetate (1:1). The developing crystals were allowed to form and stand for 12.0 hours prior to collection to furnish the desired product as a solid (3.78 g, 44%). $^1$H NMR (400 MHz, d$_7$-DMF) δ 11.34 (s, 1H), 7.43 (app d, J=3.6 Hz, 1H), 6.79 (app d, J=3.6 Hz, 1H), 6.01 (s, 1H), 5.63 (d, J=2.0 Hz, 1H), 3.87 (s, 3H), 2.02 (s, 3H); LC/MS C-18 column, t$_r$=1.47 minutes (5 to 95% acetonitrile/water over 5 minutes at 1 ml/min with detection 254 nm, at 50° C.). ES-MS m/z 250 (M+H). ES-HRMS m/z 250.0696 (M+H calcd for C$_{12}$H$_{12}$NO$_5$ requires 250.0710).

Step 2: Preparation of methyl 5-[3-bromo-4-[(2,4-difluorobenzyl)oxy]-6-methyl-2-oxopyridin-1(2H)-yl]-2-furoate.

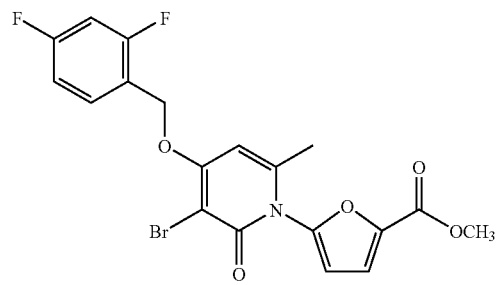

To a room temperature solution of methyl 5-(4-hydroxy-6-methyl-2-oxopyridin-1(2H)-yl)-2-furoate (step 1) (3.19 g, 12.8 mmol) in DMF (14 mL) was added portion-wise solid N-bromosuccinimide (2.29 g, 12.9 mmol). The reaction was stirred vigorously for 1.0 h, followed by the sequential addition of K$_2$CO$_3$ (1.88 g, 13.6 mmol), DMF (4.0 mL), and 2,4 difluorobenzyl bromide (2.00 mL, 15.55 mmol). The resulting suspension was stirred for 9.0 hours until complete formation of desired product was seen by LCMS analysis. The reaction was then diluted with saturated brine (300 mL) and extracted with ethyl acetate (3×300 mL). The resulting organic extracts were Na$_2$SO$_4$ dried, filtered, and concentrated in vacuo to a residue that was subjected to SiO$_2$ chromatography with a gradient elution using ethyl acetate/ hexanes (40:60 to 60:40) to furnish a solid (3.20 mg, 55%). $^1$H NMR (400 MHz, d$_7$-DMF) δ 7.78 (app q, J=8.6 Hz, 1H), 7.48 (app d, J=3.6 Hz, 1H), 7.33 (app dt, J=10.0, 2.4 Hz, 1H), 7.21 (app dt, J=8.5, 1.8 Hz, 1H), 6.92 (d, J=3.6 Hz, 1H), 6.81 (s, 1H), 5.47 (s, 2H), 3.88 (s, 3H), 2.15 (s, 3H); LC/MS C-18 column, t$_r$=3.11 minutes (5 to 95% acetonitrile/water over 5 minutes at 1 ml/min with detection 254 nm, at 50° C.). ES-MS m/z 454 (M+H). ES-HRMS m/z 454.0117 (M+H calcd for C$_{19}$H$_{15}$BrF$_2$N$_2$O$_5$ requires 454.0096).

Step 3: 5-[3-bromo-4-[(2,4-difluorobenzyl)oxy]-6-methyl-2-oxopyridin-1(2H)-yl]-2-furoic acid.

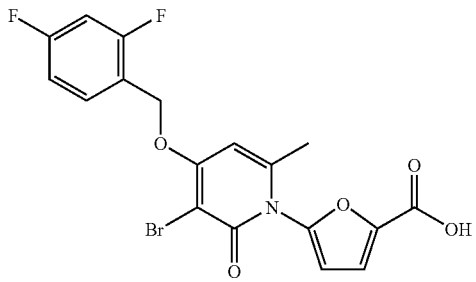

To a room temperature solution of methyl 5-[3-bromo-4-[(2,4-difluorobenzyl)oxy]-6-methyl-2-oxopyridin-1(2H)-yl]-2-furoate (step 2) (3.00 g, 6.61 mmol) in THF (20 mL) was added dropwise an aqueous solution of sodium hydroxide (3.0 M, 4.00 mL, 12.0 mmol). The reaction was then heated to 60° C. for 12.0 hours. The resulting suspension was then diluted with 800 mL of ethyl acetate and neutralized with an aqueous solution of hydrochloric acid (3.0 N, 4.0 mL, 12 mmol). The resulting biphasic solution was then concentrated in vacuo to a volume of 90 mL. At this time a white solid began to form and the resulting solid suspension was allowed to sit until precipitation appeared to stop (approximately 1.0 hour). The precipitate was collected and dried in vacuo (1.0 mm Hg) to furnish the solid acid as an intermediate (2.27 g, 78%). $^1$H NMR (400 MHz, d$_7$-DMF) δ 7.79 (app q, J=8.0 Hz, 1H), 7.32 (t, J=9.2 Hz, 1H), 7.20 (app t, J=7.4 Hz, 1H), 6.88 (app d, J=2.5 Hz, 1H), 6.74 (s, 1H), 6.51 (d, J=2.5 Hz, 1H), 5.44 (s, 2H), 2.10 (s, 3H); LC/MS C-18 column, t$_r$=2.77 minutes (5 to 95% acetonitrile/water over 5 minutes at 1 ml/min with detection 254 nm, at 50° C.). ES-MS m/z 440 (M+H). ES-HRMS m/z 439.9959 (M+H calcd for C$_{18}$H$_{13}$BrF$_2$NO$_5$ requires 439.9940).

Step 4: Preparation of the Title Compound.

To a room temperature suspension of 5-[3-bromo-4-[(2,4-difluorobenzyl)oxy]-6-methyl-2-oxopyridin-1(2H)-yl]-2-furoic acid (1.00 g, 2.27 mmol) in THF (8.0 mL) was added 2-chloro-4,6 dimethoxy-1,3,5 triazine (610 mg, 3.47 mmol) and N-methyl morpholine (NMM, 368 mg, 3.62 mmol) sequentially. The resulting solution was matured for 2 hours and then a saturated aqueous solution of ammonium hydroxide (1.5 mL) was added. The resulting suspension was allowed to continue for 1 additional hour. The reaction mixture was diluted with 800 mL of brine and extracted with ethyl acetate (3×600 mL). The organic extracts were separated, Na$_2$SO$_4$ dried, and concentrated in vacuo and the resulting residue was subjected to SiO$_2$ chromatography with ethyl acetate/hexanes/methanol (57:38:5) to provide the title compound (710 mg, 71%). $^1$H NMR (400 MHz, d$_7$-DMF) δ 8.07 (s, 1H), 7.79 (app q, J=8.6 Hz, 1H), 7.50 (br s, 1H), 7.32 (app dt, J=10.1, 2.2 Hz, 1H), 7.30 (app dd, J=8.0, 3.3 Hz, 1H), 7.20 (app dt, J=8.6, 2.0 Hz, 1H), 6.81 (s, 1H), 6.79 (d, J=3.4 Hz, 1H), 5.47 (s, 2H), 2.14 (s, 3H); LC/MS C-18 column, t$_r$=2.60 minutes (5 to 95% acetonitrile/water over 5 minutes at 1 ml/min with detection 254 nm, at 50° C.). ES-MS m/z 439 (M+H). ES-HRMS m/z 439.0088 (M+H calcd for C$_{18}$H$_{14}$BrF$_2$N$_2$O$_4$ requires 439.0010).

Example 717

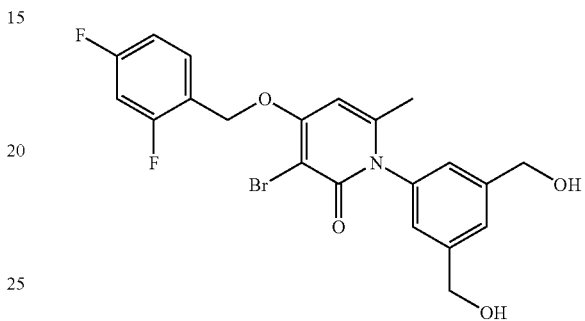

1-[3,5-bis(hydroxymethyl)phenyl]-3-bromo-4-[(2,4-difluorobenzyl)oxy]-6-methylpyridin-2(1H)-one Step 1: Preparation of dimethyl 5-(4-hydroxy-6-methyl-2-oxopyridin-1(2H)-yl)isophthalate

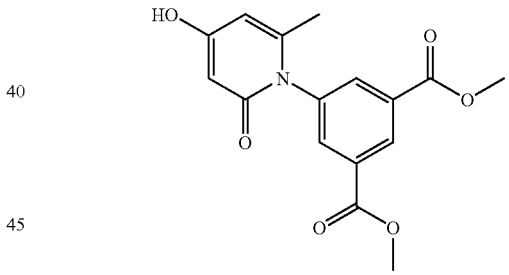

Dimethyl 5-aminoisophthalate (24.45 g, 117 mmol) was dissolved in 500 ml toluene and heated to reflux. 5-(1-hydroxy-3-oxobutylidene)-2,2-dimethyl-1,3-dioxane-4,6-dione (40.0 g, 175.3 mmol) was added and refluxed for 15 minutes. The reaction was evaporated. 500 ml of acetonitrile and p-toluenesulphonic acid (22.25 g, 117 mmol) was added and refluxed for 1 hour. The reaction was allowed to cool to room temperature and stand over night. The resulting precipitate was filtered, washed three times with 250 ml water and 250 ml acetonitrile and dried in vacuo to give a tan solid (18.85 g, 51% yield). $^1$H NMR (300 MHz, DMSO-d$_6$) δ 10.70 (br s, 1H), 8.47 (t, J=1.54 Hz, 1H), 7.99 (d, J=1.47 Hz, 2H), 5.90 (d, J=1.61 Hz, 1H), 5.55 (d, J=2.42 Hz, 1H), 3.87 (s, 6H), 1.82 (s, 3H); LC/MS, t$_r$=1.79 minutes (5 to 95% acetonitrile/water over 5 minutes at 1 ml/min, at 254 nm, at 50° C.), ES-MS m/z 318 (M+H). ES-HRMS m/z 318.0994 (M+H calcd for C$_{16}$H$_{16}$NO$_6$ requires 318.0972).

Step 2: Preparation of dimethyl 5-(3-bromo-4-hydroxy-6-methyl-2-oxopyridin-1(2H)-yl)isophthalate

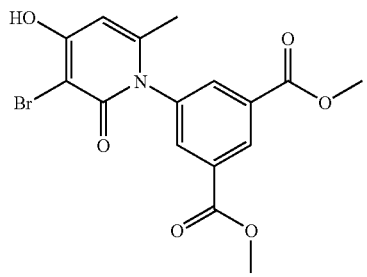

Dimethyl 5-(4-hydroxy-6-methyl-2-oxopyridin-1(2H)-yl)isophthalate (from Step 1) (18.0 g, 56.7 mmol) was stirred at room temperature with N-Bromosuccinimide (10.6 g, 59.6 mmol) in 35 ml of N,N-dimethylformamide and 180 ml of methylene chloride. After stirring for 1 hour, a white precipitate had formed. The precipitate was filtered, washed with acetonitrile and dried in vacuo to give a white solid (11.55 g, 51%). $^1$H NMR (400 MHz, DMSO-$d_6$) δ 11.49 (br s, 1H), 8.49 (t, J=1.24 Hz, 1H), 8.06 (d, J=1.47 Hz, 2H), 6.07 (s, 1H), 3.88 (s, 6H), 1.82 (s, 3H); LC/MS, $t_r$=1.81 minutes (5 to 95% acetonitrile/water over 5 minutes at 1 ml/min, at 254 nm, at 50° C.), ES-MS m/z 396 (M+H). ES-HRMS m/z 396.0102 (M+H calcd for $C_{16}H_{15}BrNO_6$ requires 396.0077).

Step 3: Preparation of dimethyl 5-[3-bromo-4-[(2,4-difluorobenzyl)oxy]-6-methyl-2-oxopyridin-1(2H)-yl]isophthalate.

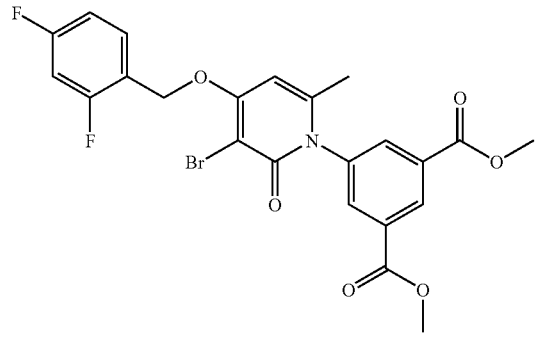

Dimethyl 5-(3-bromo-4-hydroxy-6-methyl-2-oxopyridin-1(2H)-yl)isophthalate (from Step 2) (11.3 g, 28.5 mmol) was stirred briskly with 2,4-difluorobenzylbromide (3.66 ml, 28.5 mmol) and $K_2CO_3$ (5.91 g, 42.8 mmol) in 50 ml of N,N-dimethylformamide at room temperature for 3 hours. The reaction was then poured into 1L of cold water and the resulting precipitate was filtered, washed with water and diethyl ether, and dried in vacuo to yield a white solid (13.8 g, 93%). $^1$H NMR (400 MHz, DMSO-$d_6$) δ 8.51 (t, J=1.60 Hz, 1H), 8.12, (d, J=1.60 Hz, 2H), 7.67 (app q, J=7.92 Hz, 1H), 7.34 (app dt, J=9.94, 2.19 Hz, 1H), 7.17 (dt, J=8.53, 2.11 Hz, 1H), 6.68 (s, 1H), 5.33 (s, 2H), 3.88 (s, 6H), 1.93 (s, 3H); LC/MS, $t_r$=2.77 minutes (5 to 95% acetonitrile/water over 5 minutes at 1 ml/min, at 254 nm, at 50° C.), ES-MS m/z 522 (M+H). ES-HR/MS m/z 522.0335 (M+H calcd for $C_{23}H_{19}BrF_2NO_6$ requires 522.0358).

Step 4: Preparation of 5-[3-bromo-4-[(2,4-difluorobenzyl)oxy]-6-methyl-2-oxopyridin-1(2H)-yl]isophthalic acid.

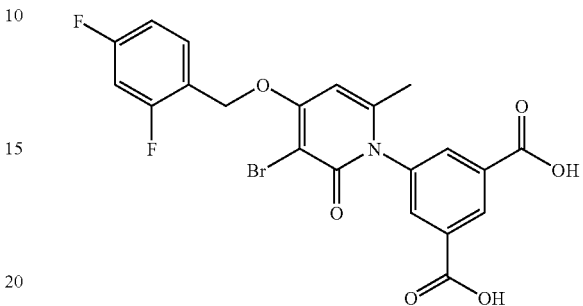

Dimethyl 5-[3-bromo-4-[(2,4-difluorobenzyl)oxy]-6-methyl-2-oxopyridin-1(2H)-yl]isophthalate (from Step 3) (5.0 g, 9.57 mmol) was stirred at room temperature with 2.5 N NaOH (15.3 ml, 38.3 mmol) in 30 ml of 5:1 THF/water for 1 hour. The reaction was then acidified with 1 N HCl and the resulting precipitate was filtered, washed with water, and dried in vacuo to yield a white solid (4.48 g, 95%). $^1$H NMR (400 MHz, DMSO-$d_6$) δ 13.50 (br s, 2H), 8.51 (t, J=1.41 Hz, 1H), 8.02, (d, J=1.48 Hz, 2H), 7.67 (app q, J=7.88 Hz, 1H), 7.32 (dt, J=9.94, 2.19 Hz, 1H), 7.16 (dt, J=8.52, 1.99 Hz, 1H), 6.68 (s, 1H), 5.32 (s, 2H), 1.94 (s, 3H); LC/MS, $t_r$=2.27 minutes (5 to 95% acetonitrile/water over 5 minutes at 1 ml/min, at 254 nm, at 50° C.), ES-MS m/z 494 (M+H). ES-HRMS m/z 494.0054 (M+H calcd for $C_{21}H_{15}BrF_2NO_6$ requires 494.0045).

Step 5: Preparation of the title compound. 5-[3-bromo-4-[(2,4-difluorobenzyl)oxy]-6-methyl-2-oxopyridin-1(2H)-yl]isophthalic acid (from Step 4 above) (500 mg, 1.01 mmol) was added to a solution of 1M borane-dimethylsulfide complex in tetrahydrofuran (9.0 ml, 9.00 mmol) in 2.5 ml tetrahydrofuran at 0° C. The reaction was allowed to warm to room temperature while stirring. After stirring overnight, more 1M borane-dimethylsulfide complex in tetrahydrofuran (0.60 ml, 0.60 mmol) was added and stirring at room temperature. After 4 hours, ice chips were added to quench the reaction. The reaction was extracted 2 times with ethyl acetate and the combined organic layers were washed with brine, dried over $MgSO_4$ and evaporated. The resulting solid was washed with acetonitrile and diethyl ether and dried in vacuo to give a white solid (281 mg, 60%). $^1$H NMR (400 MHz, DMSO-$d_6$) δ 7.66 (app q, J=7.92 Hz, 1H), 7.35 (s, 1H), 7.33 (dt, J=9.40, 2.24 Hz, 1H), 7.16 (dt, J=8.52, 1.88 Hz, 1H), 6.99 (s, 2H), 6.62 (s, 1H), 5.31 (s, 2H), 5.27 (br s, 2H), 4.51 (s, 4H), 1.93 (s, 3H); LC/MS, $t_r$=2.19 minutes (5 to 95% acetonitrile/water over 5 minutes at 1 ml/min, at 254 nm, at 50° C.), ES-MS m/z 466 (M+H). ES-HRMS m/z 466.0454 (M+H calcd for $C_{21}H_{19}BrF_2NO_4$ requires 466.0460).

Example 718

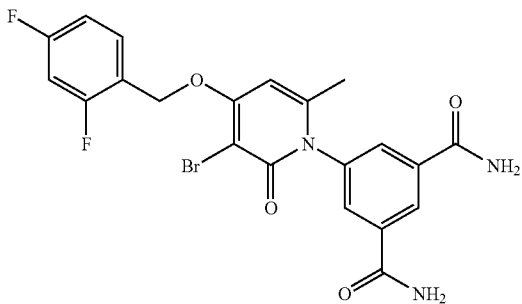

5-[3-bromo-4-[(2,4-difluorobenzyl)oxy]-6-methyl-2-oxopyridin-1(2H)-yl]isophthalamide 5-[3-bromo-4-[(2,4-difluorobenzyl)oxy]-6-methyl-2-oxopyridin-1(2H)-yl]isophthalic acid (Example 717, step 4) (500 mg, 1.01 mmol) was dissolved in 4 ml of tetrahydrofuran. 0.5M ammonia in 1,4-dioxane (12.12 ml, 6.06 mmol) was added, followed, in order, by EDCI (494 mg, 2.53 mmol), 1-hydroxybenzotriazole (342 mg, 2.53 mmol) and triethylamine (563 µl, 4.04 mmol). The reaction was stirred at room temperature overnight. The reaction evaporated and water was used to triturate the product. The resulting solid was filtered and washed with water, acetonitrile, ethyl acetate and diethyl ether, and dried in vacuo to give a white solid (202 mg, 41%). $^1$H NMR (400 MHz, DMSO-$d_6$) δ 8.45 (s, 1H), 8.08 (br s, 2H), 7.86, (d, J=1.34 Hz, 2H), 7.67 (app q, J=7.92 Hz, 1H), 7.55 (br s, 2H), 7.33 (dt, J=9.94, 2.18 Hz, 1H), 7.17 (dt, J=8.59, 1.92 Hz, 1H), 6.70 (s, 1H), 5.34 (s, 2H), 1.96 (s, 3H); LC/MS, $t_r$=2.10 minutes (5 to 95% acetonitrile/water over 5 minutes at 1 ml/min, at 254 nm, at 50° C.), ES-MS m/z 492 (M+H). ES-HRMS m/z 492.0381 (M+H calcd for $C_{21}H_{17}BrF_2N_3O_4$ requires 492.0365).

Example 719

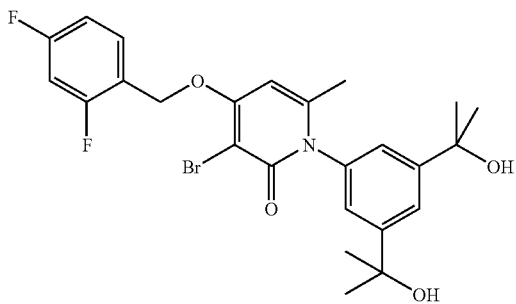

1-[3,5-bis(1-hydroxy-1-methylethyl)phenyl]-3-bromo-4-[(2,4-difluorobenzyl)oxy]-6-methylpyridin-2(1H)-one Dimethyl 5-[3-bromo-4-[(2,4-difluorobenzyl)oxy]-6-methyl-2-oxopyridin-1(2H)-yl]isophthalate (Example 717, step 3) (500 mg, 0.96 mmol) was added dropwise to a solution of 3M MeMgBr in diethyl ether (1.6 ml, 4.79 mmol) in 15 ml of tetrahydrofuran at −5° C. and stirred at −5° C. The reaction turned red. After 2.5 hours, the reaction was quenched with a saturated NH$_4$Cl solution and extracted 2 times with ethyl acetate. The combined organic layers were washed with NaHCO$_3$ solution and brine, dried over MgSO$_4$ and evaporated. The resulting solid was washed with diethyl ether and dried in vacuo to give a white solid (329 mg, 66%). $^1$H NMR (400 MHz, DMSO-$d_6$) δ 7.69–7.63 (m, 2H), 7.33 (dt, J=9.87, 2.41 Hz, 1H), 7.16 (dt, J=8.46, 1.75 Hz, 1H), 7.07 (d, J=1.48 Hz, 2H), 6.61 (s, 1H), 5.32 (s, 2H), 5.06 (s, 2H), 1.89 (s, 3H), 1.41 (s, 12H); LC/MS, $t_r$=2.45 minutes (5 to 95% acetonitrile/water over 5 minutes at 1 ml/min, at 254 nm, at 50° C.), ES-MS m/z 522 (M+H). ES-HRMS m/z 522.1098 (M+H calcd for $C_{25}H_{27}BrF_2NO_4$ requires 522.1086).

Example 720

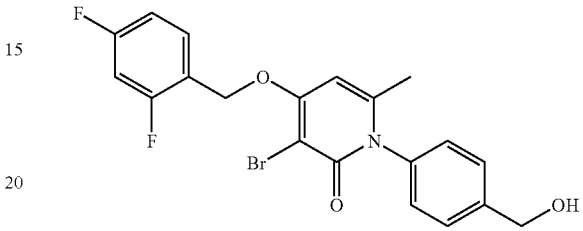

3-bromo-4-[(2,4-difluorobenzyl)oxy]-1-[4-(hydroxymethyl)phenyl]-6-methylpyridin-2(1H)-one 4-[3-bromo-4-[(2,4-difluorobenzyl)oxy]-6-methyl-2-oxopyridin-1(2H)-yl]benzoic acid (Example 203) (500 mg, 1.11 mmol) was added to a solution of 2M borane-dimethylsulfide complex in tetrahydrofuran (3.33 ml, 6.66 mmol) in 2.5 ml tetrahydrofuran at 0° C. The reaction was allowed to warm to room temperature while stirring. After 2.5 hours, ice chips were added to quench the reaction. The resulting precipitate was filtered, washed with diethyl ether and dried in vacuo to give a white solid (160 mg, 33%). $^1$H NMR (400 MHz, DMSO-$d_6$) δ 7.66 (app q, J=7.88 Hz, 1H), 7.42 (d, J=8.19 Hz, 2H), 7.33 (dt, J=9.87, 2.06 Hz, 1H), 7.19–7.14 (m, 3H), 6.62 (s, 1H), 5.31 (s, 2H), 5.30 (s, 1H), 4.54 (d, J=5.24 Hz, 2H), 1.92 (s, 3H); LC/MS, $t_r$=2.36 minutes (5 to 95% acetonitrile/water over 5 minutes at 1 ml/min, at 254 nm, at 50° C.), ES-MS m/z 436 (M+H). ES-HRMS m/z 436.0374 (M+H calcd for $C_{20}H_{17}BrF_2NO_3$ requires 436.0354).

Example 721

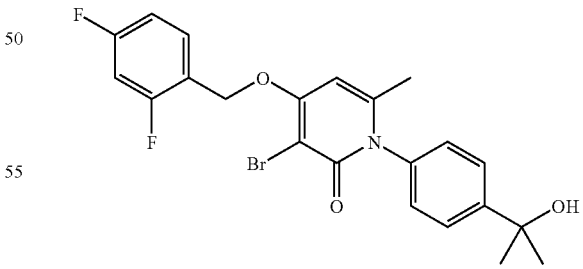

3-bromo-4-[(2,4-difluorobenzyl)oxy]-1-[4-(1-hydroxy-1-methylethyl)phenyl]-6-methylpyridin-2(1H)-one Methyl-4-[3-bromo-4-[(2,4-difluorobenzyl)oxy]-6-methyl-2-oxopyridin-1(2H)-yl]benzoate (Example 202)

(500 mg, 1.08 mmol) was added dropwise to a solution of 3M MeMgBr in diethyl ether (0.90 ml, 2.69 mmol) in 15 ml of tetrahydrofuran at −5° C. and stirred at −5° C. After 2.75 hours, more 3M MeMgBr in diethyl ether (0.45 ml, 1.35 mmol) was added and stirred at −5° C. After 4 hours, the reaction was quenched with a saturated NH$_4$Cl solution and extracted 2 times with ethyl acetate. The combined organic layers were washed with NaHCO$_3$ solution and brine, dried over MgSO$_4$ and evaporated. The resulting solid was washed with diethyl ether and dried in vacuo to give a white solid (268 mg, 53%). $^1$H NMR (400 MHz, DMSO-d$_6$) δ 7.66 (app q, J=7.92 Hz, 1H), 7.57 (d, J=8.46 Hz, 2H), 7.33 (dt, J=9.87, 2.11 Hz, 1H), 7.16 (dt, J=8.59, 2.24 Hz, 1H), 7.14 (d, J=8.63 Hz, 2H), 6.62 (s, 1H), 5.31 (s, 2H), 5.12 (s, 1H), 1.91 (s, 3H), 1.44 (s, 6H); LC/MS, t$_r$=2.54 minutes (5 to 95% acetonitrile/water over 5 minutes at 1 ml/min, at 254 nm, at 50° C.), ES-MS m/z 464 (M+H). ES-HRMS m/z 464.0604 (M+H calcd for C$_{22}$H$_{21}$BrF$_2$NO$_3$ requires 464.0667).

Example 722

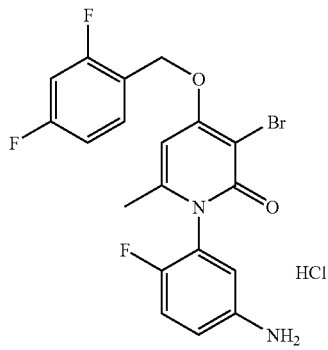

1-(5-amino-2-fluorophenyl)-3-bromo-4-[(2,4-difluorobenzyl)oxy]-6-methylpyridin-2(1H)-one hydrochloride Step 1 Preparation of tert-butyl 3-[3-bromo-4-[(2,4-difluorobenzyl)oxy]-6-methyl-2-oxopyridin-1(2H)-yl]-4-fluorophenylcarbamate

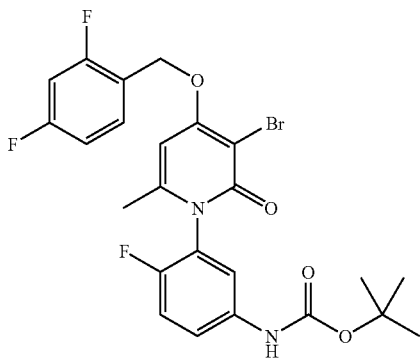

A solution of the compound of Example 519 (4.3 g, 9.2 mmol) in tert-butanol (50 mL) was flushed with nitrogen. Diphenyl phosphoryl azide (2 mL, 9.2 mmol) and triethyl amine (1.3 mL, 9.2 mmol) were added. After heating at 90 C for 20 h, the reaction mixture was concentrated in vacuo. The residue was diluted with methylene chloride and was washed sequentially with aqueous ammonium chloride and aqueous NaHCO$_3$. The organic layer was concentrated in vacuo; the resulting solids were suspended in acetonitrile and filtered to give the title compound (2.9 g, 58%). $^1$H NMR (400 MHz, CD$_3$OD) δ 7.64 (q, J=7.2 and 14.4 Hz, 1H), 7.49 (m, 1H), 7.43 (m, 1H), 7.24 (t, J=9.6 Hz, 1H), 7.04 (t, J=8.4 Hz, 2H), 6.62 (s, 1H), 5.35 (s, 2H), 2.09 (s, 3H), 1.49 (s, 9H) ppm. $^{19}$F NMR (300 MHz, CD$_3$OD) δ−111.53 (1F), −115.93 (1F), −132.58 ppm. ES-HRMS m/z 540.0822 (M+H calcd for C$_{24}$H$_{23}$BrF$_3$N$_2$O$_4$ requires 540.0820).

Step 2 Preparation of 1-(5-amino-2-fluorophenyl)-3-bromo-4-[(2,4-difluorobenzyl)oxy]-6-methylpyridin-2(1H)-one hydrochloride

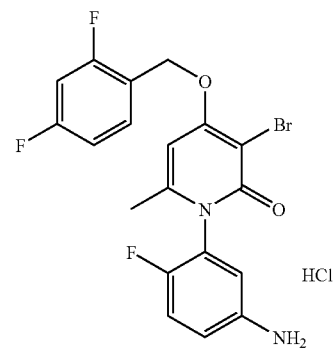

The product of Step 1, (2.9 g, 5.3 mmol) was dissolved in tetrahydrofuran (75 mL) and 6N HCl (10 mL). The reaction mixture was heated at 60 C for 18 h and was concentrated in vacuo to give the final product (1.89 g, 75%). $^1$H NMR (400 MHz, CD$_3$OD) δ 7.64 (q, J=8.4 and 15.2 Hz, 1H), 7.56 (m, 2H), 7.46 (m, 1H), 7.05 (m, 2H), 6.69 (s, 1H), 5.37 (s, 2H), 2.10 (s, 3H) ppm. $^{19}$F NMR (400 MHz, CD$_3$OD) δ−111.37 (1F), −115.86 (1F), −123.16 ppm. ES-HRMS m/z 440.0334 (M+H calcd for C$_{19}$H$_{15}$BrF$_3$N$_2$O$_2$ requires 440.0295).

Example 723

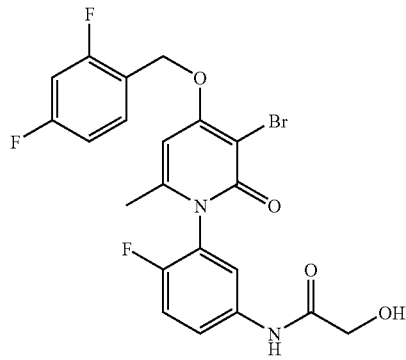

N-{3-[3-bromo-4-[(2,4-difluorobenzyl)oxy]-6-methyl-2-oxopyridin-1(2H)-yl]-4-fluorophenyl}-2-hydroxyacetamide Step 1 Preparation of 2-({3-[3-bromo-4-[(2,4-difluorobenzyl)oxy]-6-methyl-2-oxopyridin-1(2H)-yl]-4-fluorophenyl}amino)-2-oxoethyl acetate

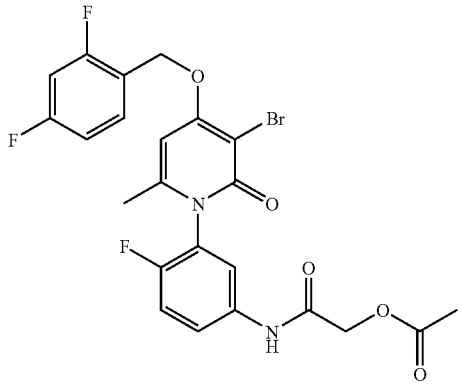

A solution of the compound of Example 722 (0.5 g, 1.05 mmol) in tetrahydrofuran (20 mL) was treated with triethyl amine (0.3 mL, 2.1 mmol) and acetoxy acetylchloride (0.12 mL, 1.15 mmol). After stirring at room temperature for 2 h, the reaction was complete. The reaction mixture was poured into saturated aqueous ammonium chloride. The solids were filtered off and were washed with water and diethyl ether. Title product was isolated as a white solid (0.32 g, 58%). $^1$H NMR (400 MHz, CD$_3$OD) δ 7.65 (m, 3H), 7.32 (t, J=8.4 Hz, 1H), 7.04 (t, J=8.4 Hz, 2H), 6.64 (s, 1H), 5.35 (s, 2H), 4.68 (s, 2H), 2.15 (s, 3H), 2.10 (s, 3H) ppm. $^{19}$F NMR (400 MHz, CD$_3$OD) δ –111.56 (1F), –115.99 (1F), –129.48 (1F) ppm. LC/MS, t$_r$=5.35 minutes (5 to 95% acetonitrile/water over 8 minutes at 1 ml/min with detection 254 nm, at 50° C.). ES-MS m/z 540 (M+H).

Step 2 Preparation of N-{3-[3-bromo-4-[(2,4-difluorobenzyl)oxy]-6-methyl-2-oxopyridin-1(2H)-yl]-4-fluorophenyl}-2-hydroxyacetamide

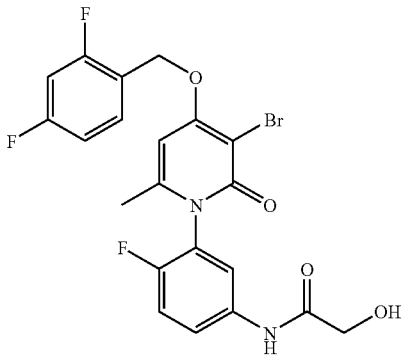

The product of Step 1, (0.1 g, 0.18 mmol) was suspended in tetrahydrofuran (10 mL), methanol (2 mL), and 2.5 N NaOH (1 mL). After stirring at room temperature for 1 hour, the reaction was complete and the organics were removed in vacuo. The aqueous layer was acidified to pH 1 with 6N HCl, the solids were suspended in water, filtered, and washed with diethyl ether. The title compound was obtained as a white powder (56.2 mg, 61%). $^1$H NMR (400 MHz, CD$_3$OD) δ 7.75 (dq, J=2.9, 4.8 and 9.2 Hz, 1H), 7.71 (dd, J=2.4 and 6.8 Hz, 1H), 7.64 (q, J=8 and 14.8 Hz, 1H), 7.32 (t, J=9.6 Hz, 1H), 7.04 (t, J=8.8 Hz, 2H), 6.64 (s, 1H), 5.36 (s, 2H), 4.10 (s, 2H), 2.10 (s, 3H) ppm. $^{19}$F NMR (400 MHz, CD$_3$OD) δ–111.54 (1F), –115.99 (1F), –129.71 (1F) ppm. LC/MS, t$_r$=5.04 minutes (5 to 95% acetonitrile/water over 8 minutes at 1 ml/min with detection 254 nm, at 50° C.). ES-MS m/z 498 (M+H).

Example 724

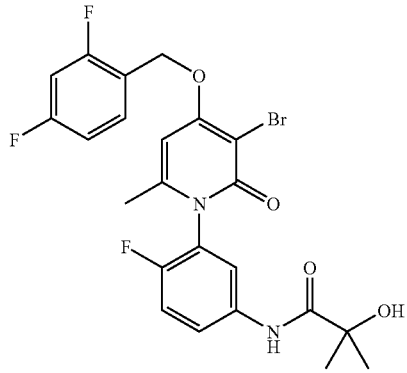

N-{3-[3-bromo-4-[(2,4-difluorobenzyl)oxy]-6-methyl-2-oxopyridin-1(2H)-yl]-4-fluorophenyl}-2-hydroxy-2-methylpropanamide Step 1 Preparation of 2-({3-[3-bromo-4-[(2,4-difluorobenzyl)oxy]-6-methyl-2-oxopyridin-1(2H)-yl]-4-fluorophenyl}amino)-1,1-dimethyl-2-oxoethyl acetate

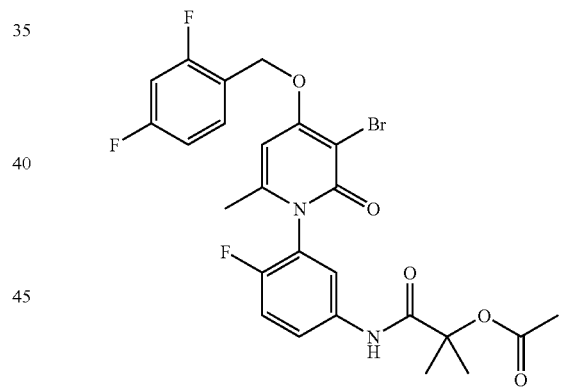

A solution of the compound of Example 722 (0.5 g, 1.05 mmol) in tetrahydrofuran (20 mL) was treated with triethyl amine (0.3 mL, 2.1 mmol) and 1-chlorocarbonyl-1-methylethyl acetate (0.16 mL, 1.15 mmol). After stirring at room temperature for 2 h, the reaction was complete. The reaction mixture was poured into saturated aqueous ammonium chloride. The solids were filtered off and were washed with water and diethyl ether. The compound of Step 1 was isolated as a white solid (0.23 g, 39%). $^1$H NMR (400 MHz, CD$_3$OD) δ 7.64 (m, 2H), 7.54 (dd, J=2.8 and 6.8 Hz, 1H), 7.30 (t, J=9.2 Hz, 1H), 7.04 (t, J=9.2 Hz, 2H), 6.64 (s, 1H), 5.35 (s, 2H), 2.11 (s, 3H), 2.08 (s, 3H), 1.61 (s, 6H) ppm. $^{19}$F NMR (400 MHz, CD$_3$OD) δ –111.57 (1F), –116.00 (1F), –129.56 (1F) ppm. LC/MS, t$_r$=5.65 minutes (5 to 95% acetonitrile/water over 8 minutes at 1 ml/min with detection 254 nm, at 50° C.). ES-MS m/z 568 (M+H).

Step 2 Preparation of N-{3-[3-bromo-4-[(2,4-difluorobenzyl)oxy]-6-methyl-2-oxopyridin-1(2H)-yl]-4-fluorophenyl}-2-hydroxy-2-methylpropanamide

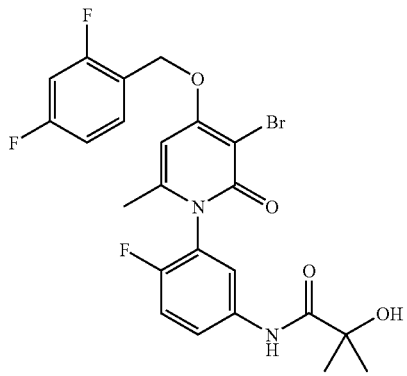

The product of Step 1 (0.1 g, 0.17 mmol) was suspended in tetrahydrofuran (10 mL), methanol (2 mL), and 2.5 N NaOH (1 mL). After stirring at room temperature for 1 hour, the reaction was complete and the organics were removed in vacuo. The aqueous layer was acidified to pH 1 with 6N HCl, the solids were suspended in water, filtered, and washed with diethyl ether. The title compound was obtained as a white powder (56 mg, 61%). $^1$H NMR (400 MHz, CD$_3$OD) δ 7.75 (dq, J=2.8, 4.4 and 9.2 Hz, 1H), 7.69 (dd, J=2.8 and 6.8 Hz, 1H), 7.64 (q, J=8 and 14.8 Hz, 1H), 7.31 (t, J=9.2 Hz, 1H), 7.04 (t, J=8.4 Hz, 2H), 6.64 (s, 1H), 5.35 (s, 2H), 2.10 (s, 3H), 1.43 (s, 6H) ppm. $^{19}$F NMR (400 MHz, CD$_3$OD) δ–111.55 (1F), –115.95 (1F), –129.80 (1F) ppm. LC/MS, t$_r$=5.34 minutes (5 to 95% acetonitrile/water over 8 minutes at 1 ml/min with detection 254 nm, at 50° C.). ES-MS m/z 526 (M+H).

Example 725

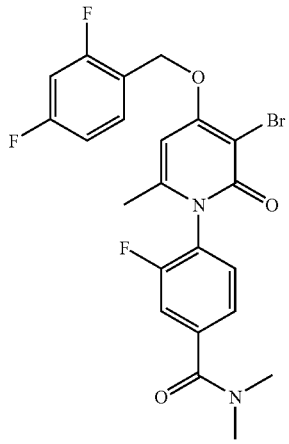

4-[3-bromo-4-[(2,4-difluorobenzyl)oxy]-6-methyl-2-oxopyridin-1(2H)-yl]-3-fluoro-N,N-dimethylbenzamide Step 1 Preparation of 4-[3-bromo-4-[(2,4-difluorobenzyl)oxy]-6-methyl-2-oxopyridin-1(2H)-yl]-3-fluorobenzoic acid

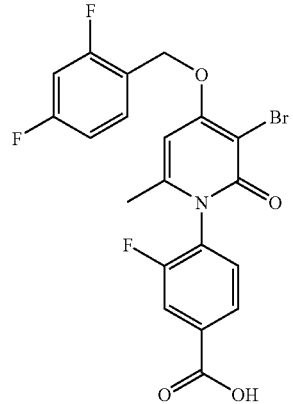

Compound of Example 604 (4.1 g, 8.5 mmol) was suspended in tetrahydrofuran (30 mL), methanol (15 mL), water (15 mL) and 2.5 N NaOH (6.8 mL, 17 mmol)). After stirring at room temperature for 2 hour, the reaction was complete and the organics were removed. The aqueous layer was acidified to pH 1 with 3N HCl, the solids were suspended in water, filtered, and washed with diethyl ether. The title compound was obtained as a white powder and used without further purification (4.4 g). $^1$H NMR (400 MHz, CD$_3$OD) δ 8.00 (dd, J=1.8 and 8.8 Hz, 1H), 7.93 (dd, J=1.48 and 10 Hz, 1H), 7.64 (q, J=8 and 14.8 Hz, 1H), 7.49 (t, J=7.6 Hz, 1H), 7.05 (t, J=10 Hz, 2H), 6.66 (s, 1H), 5.36 (s, 2H), 2.08 (s, 3H) ppm. $^{19}$F NMR (400 MHz, CD$_3$OD) δ–111.48 (1F), –115.96 (1F), –123.35 (1F) ppm. ES-HRMS m/z 468.9987 (M+H calcd for C$_{20}$H$_{14}$BrF$_3$NO$_4$ requires 469.0086).

Step 2 Preparation of 4-[3-bromo-4-[(2,4-difluorobenzyl)oxy]-6-methyl-2-oxopyridin-1(2H)-yl]-3-fluoro -N,N-dimethylbenzamide

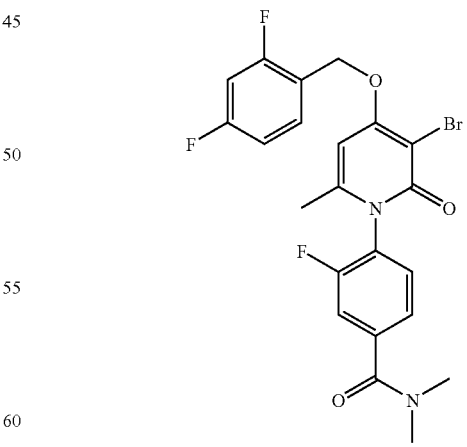

A solution of the product of Step 1 (0.5 g, 1.07 mmol) in N,N-dimethyl formamide was cooled to 0 C. Iso-butyl chloroformate (0.14 mL, 1.07 mmol) and N-methyl morpholine (0.12 mL, 1.07 mmol) were added. After 20 minutes, N,N-dimethylamine (2.0 M, 1.1 mL, 2.14 mmol) was added and the reaction mixture was warmed to room temperature over 18 h. The reaction mixture was partitioned between ethyl acetate and saturated aqueous NaHCO$_3$. The organics were washed with brine and concentrated in vacuo. The resulting semi-solid was treated with ethyl acetate and acetone to precipitate the title compound (90 mg, 17%). $^1$H NMR (400 MHz, dmso-d$_6$) δ 7.67 (q, J=8 and 14.8 Hz, 1H), 7.52 (m, 2H), 7.35 (m, 2H), 7.18 (td, J=2.8 and 8.8 Hz, 1H), 6.73 (s, 1H), 5.34 (s, 2H), 2.98 (s, 3H), 2.91 (s, 3H), 2.00 (s, 3H) ppm. $^{19}$F NMR (400 MHz, dmso-d$_6$) δ−109.50 (1F) −113.63 (1F), −122.09 (1F) ppm. ES-HRMS m/z 496.0570 (M+H calcd for C$_{22}$H$_{19}$BrF$_3$N$_2$O$_3$ requires 496.0558).

Example 726

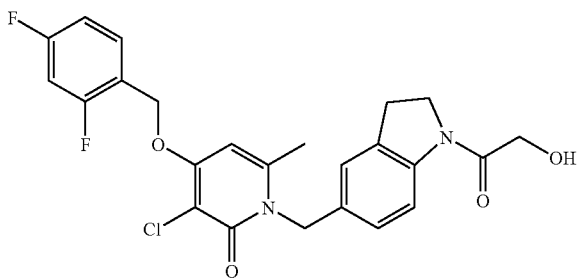

3-chloro-4-[(2,4-difluorobenzyl)oxy]-1-[(1-glycoloyl-2,3-dihydro-1H-indol-5-yl)methyl]-6-methylpyridin-2(1H)-one A 10 mL round bottomed flask equipped with stirbar and nitrogen inlet was charged with compound of Example 633 (180 mg, 0.43 mmol), acetoxyacetyl chloride (51 μL, 0.47 mmol), triethylamine (119 μL, 0.86 mmol) and tetrahydrofuran (3.0 mL). After stirring at 25° C. for 20 min the reaction was completed by LC-MS. NaOH (2.5M, 2.24 mmol, 1.0 mL) and MeOH (2.0 mL) was added and stirred for 20 min to give the title compound. The compound precipitated out of solution. The precipitated was filtered and washed with water and diethyl ether to obtain the title compound (130 mg, 64%) as a white solid. $^1$H NMR (400 MHz, (DMSO) δ 7.9 (d, J=8.2, 1H), 7.6 (q, J=8.5 and 6.9 Hz, 1H), 7.3 (t, J=8.7 Hz, 1H), 7.1 (t, J=7.9 Hz, 1H), 6.9 (s, 2H), 6.5 (s, 1H), 5.25 (s, 2H), 4.1 (d, J=5.5 Hz, 2H), 3.9 (t, J=8.6 Hz, 2H), 3.42 (t, J=5.4 Hz, 1H), 3.35 (t, J=4.8 Hz, 1H), 3.2 (t, J=8.5 Hz, 2H), 2.3 (s, 3H) ppm. ES-HRMS m/z 475.1220 (M+H calcd for C$_{24}$H$_{22}$ClF$_2$N$_2$O$_4$ requires 475.1231).

Example 727

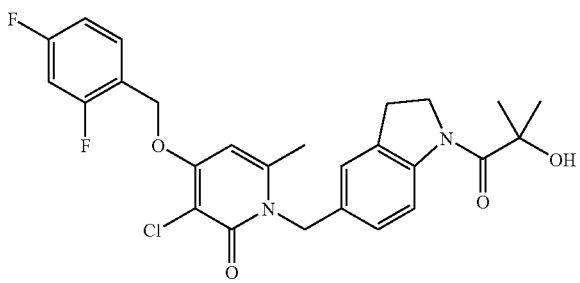

3-chloro-4-[(2,4-diflurobenzyl)oxy]-1-{[1-(2-hydroxy-2-methylpropanoyl)-2,3-dihydro-1H-indol-5-yl]methyl}-6-methylpyridin-2(1H)-one A 10 mL round bottomed flask equipped with stirbar and nitrogen inlet was charged with compound of Example 633 (200 mg, 0.48 mmol), 1-chlorocarbonyl-1-methylethyl acetate (104.3 μL, 0.72 mmol), triethylamine (133 μL, 0.96 mmol) and tetrahydrofuran (4.0 mL). After stirring at 25° C. for 20 min the reaction was completed by LC-MS. NaOH (2.5M, 2.24 mmol, 1.5 mL) and MeOH (2.0 mL) was added and stirred for 20 min to give the title compound. The compound precipitated out of solution. The precipitate was filtered and washed with water and diethyl ether to obtain a white solid (240 mg, 99%). $^1$H NMR (400 MHz, (DMSO) δ 8.0 (d, J=8.3, 1H), 7.6 (q, J=8.6 and 6.9 Hz, 1H), 7.3 (td, J=2.5 and 7.8 Hz, 1H), 7.1 (td, J=1.75 and 6.7 Hz, 1H), 6.95 (s, 1H), 6.89 (d, J=8.5 Hz, 1H), 6.58 (s, 1H), 5.25 (s, 2H), 4.3 (t, J=8.3 Hz, 2H), 3.42 (t, J=5.4 Hz, 1H), 3.35 (t, J=5.2 Hz, 1H), 3.0 (t, J=8.2 Hz, 2H), 2.3 (s, 3H), 1.3 (s, 6H) ppm. ES-HRMS m/z 503.1561 (M+H calcd for C$_{26}$H$_{26}$ClF$_2$N$_2$O$_4$ requires 503.1544).

Example 728

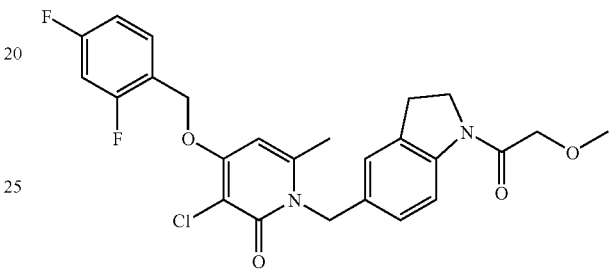

3-chloro-4-[(2,4-difluorobenzyl)oxy]-1-{[1-(methoxyacetyl)-2,3-dihydro-1H-indol-5-yl]methyl}-6-methylpyridin-2(1H)-one A 10 mL round bottomed flask equipped with stirbar and nitrogen inlet was charged with compound of Example 633 (200 mg, 0.48 mmol), methoxyacetyl chloride (66 μL, 0.72 mmol), triethylamine (134 μL, 0.96 mmol) and tetrahydrofuran (4.0 mL). After stirring at 25° C. for 20 min the reaction was completed by LC-MS. The compound precipitated out of solution. The precipitate was filtered and washed with water and diethyl ether to obtain a white solid (195 mg, 83%). $^1$H NMR (400 MHz, (DMSO) δ 8.0 (d, J=8.0, 1H), 7.6 (q, J=8.6-and 6.7 Hz, 1H), 7.3 (td, J=2.4 and 6.7 Hz, 1H), 7.1 (td, J=1.88 and 6.6 Hz, 1H), 6.9 (s, 2H), 6.58 (s, 1H), 5.25 (s, 2H), 4.15 (s, 2H), 3.9 (t, J=8.3 Hz, 2H), 3.45 (m, 1H), 3.4 (m, 1H), 3.32 (s, 3H), 3.0 (t, J=8.5 Hz, 2H), 2.3 (s, 3H) ppm. ES-HRMS m/z 489.1387 (M+H calcd for C$_{25}$H$_{24}$ClF$_2$N$_2$O$_4$ requires 489.1387).

Example 729

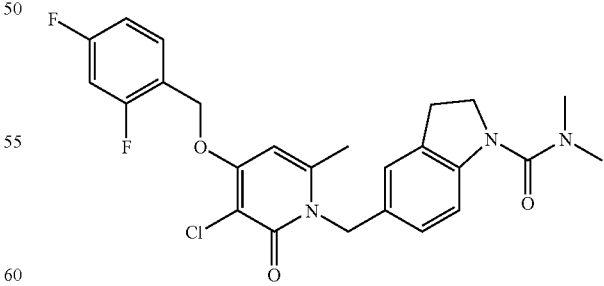

5-{[3-chloro-4-[(2,4-difluorobenzyl)oxy]-6-methyl-2-oxopyridin-1(2H)-yl]methyl}-N,N-dimethylindoline-1-carboxamide A 10 mL round bottomed flask equipped with stirbar and nitrogen inlet was charged with compound of Example 633

(200 mg, 0.48 mmol), dimethylcarbamyl chloride (66 µL, 0.72 mmol), triethylamine (133 µL, 0.96 mmol) and tetrahydrofuran (4.0 mL). After stirring at 25° C. for 5 min the reaction was completed by LC-MS. The compound precipitated out of solution. The precipitate was filtered and washed with water and diethyl ether to obtain a white solid (198 mg, 85%). $^1$H NMR (400 MHz, (DMSO) δ 7.6 (q, J=7.4 Hz, 1H), 7.3 (t, J=8.9 Hz, 1H), 7.1 (t, J=8.5 Hz, 2H), 6.93 (s, 1H), 6.86 (s, 1H), 6.58 (s, 1H), 5.25 (s, 2H), 3.9 (t, J=8.2 Hz, 2H), 3.45 (m, 1H), 3.4 (m, 1H), 2.9 (t, J=8.3 Hz, 2H), 2.8 (s, 6H), 2.3 (s, 3H) ppm. ES-HRMS m/z 488.1548 (M+H calcd for $C_{25}H_{24}ClF_2N_2O_4$ requires 488.1547).

Example 730

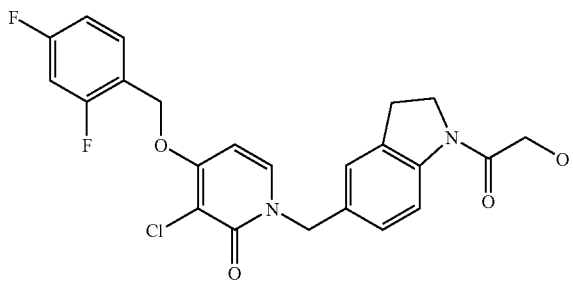

3-chloro-4-[(2,4-difluorobenzyl)oxy]-1-[(1-glycotoyl-2,3-dihydro-1H-indol-5-yl)methyl]pyridin-2(1H)-one A 10 mL round bottomed flask equipped with stirbar and nitrogen inlet was charged with compound of Example 88 (200 mg, 0.5 mmol), acetoxyacetyl chloride (59 µL, 0.55 mmol), triethylamine (140 mL, 1.0 mmol) and tetrahydrofuran (3.0 mL). After stirring at 25° C. for 20 min the reaction was completed by LC-MS. NaOH (2.5M, 2.24 mmol, 1.0 mL) and MeOH (2.0 mL) was added and stirred for 20 min to give the title compound. The compound precipitated out of solution. The precipitated was filtered and washed with water and diethyl ether to obtain the title compound (200 mg, 83%) as a white solid. $^1$H NMR (400 MHz, (DMSO) δ 7.98 (d, J=8.1, 1H), 7.9 (d, J=7.8 Hz, 1H), 7.6 (q, J=8.6 and 6.6 Hz, 1H), 7.3 (dt, J=2.4 and 7.2 Hz, 1H), 7.1 (m, 2H), 6.56 (d, J=7.8 Hz, 1H), 5.25 (s, 2H), 5.1 (s, 2H), 4.8 (t, J=5.8 Hz, 1H), 4.1 (d, J=5.6 Hz, 2H), 3.9 (t, J=7.9 Hz, 2H), 3.1 (t, J=7.9 Hz, 2H) ppm. ES-HRMS m/z 461.1088 (M+H calcd for $C_{23}H_{20}ClF_2N_2O_4$ requires 461.1074).

Example 731

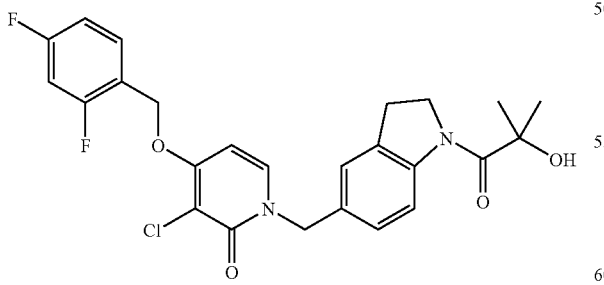

Preparation of 3-chloro-4-[(2,4-difluorobenzyl)oxy]-1-[(1-glycoloyl-2,3-dihydro-1H-indol-5-yl)methyl]pyridin-2(1H)-one A 10 mL round bottomed flask equipped with stirbar and nitrogen inlet was charged with compound of Example 88 (200 mg, 0.50 mmol), 1-chlorocarbonyl-1-methylethyl acetate (80 µL, 0.55 mmol), triethylamine (140 µL, 1.0 mmol) and tetrahydrofuran (4.0 mL). After stirring at 25° C. for 20 min the reaction was completed by LC-MS. NaOH (2.5M, 2.24 mmol, 1.5 mL) and MeOH (2.0 mL) was added and stirred for 20 min to give the title compound. The compound precipitated out of solution. The precipitated was filtered and washed with water and diethyl ether to obtain the title compound (136 mg, 55%) a white solid. $^1$H NMR (400 MHz, (DMSO) δ 7.98 (d, J=8.1, 1H), 7.9 (d, J=7.8 Hz, 1H), 7.6 (q, J=8.6 and 6.6 Hz, 1H), 7.3 (m, 1H), 7.1 (m, 2H), 6.56 (d, J=7.8 Hz, 1H), 5.25 (s, 2H), 5.0 (s, 2H), 4.3 (t, J=7.8 Hz, 2H), 3.0 (t, J=7.9 Hz, 2H), 1.3 (s, 6H) ppm. ES-HRMS m/z 489.1376 (M+H calcd for $C_{25}H_{24}ClF_2N_2O_4$ requires 489.1387).

Example 732

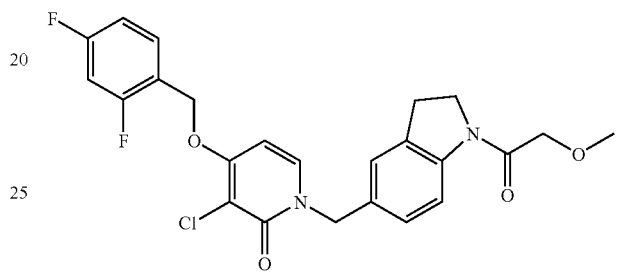

3-chloro-4-[(2,4-difluorobenzyl)oxy]-1-{[1-(methoxyacetyl)-2,3-dihydro-1H-indol-5-yl]methyl}pyridin-2(1H)-one A 10 mL round bottomed flask equipped with stirbar and nitrogen inlet was charged with the compound of Example 88 (200 mg, 0.5 mmol), methoxyacetyl chloride (69 µL, 0.75 mmol), triethylamine (139 µL, 1.0 mmol) and tetrahydrofuran (4.0 mL). After stirring at 25° C. for 20 min the reaction was completed by LC-MS. The compound precipitated out of solution. The precipitate was filtered and washed with water and diethyl ether to obtain a white solid (195 mg, 83%). $^1$H NMR (400 MHz, (DMSO) δ 7.98 (d, J=8.2, 1H), 7.9 (d, J=7.7 Hz, 1H), 7.6 (d, J=8.5 Hz, 1H), 7.3 (t, J=9.6 Hz, 1H), 7.1 (m, 3H), 6.56 (d, J=7.8 Hz, 1H), 5.25 (s, 2H), 5.1 (s, 2H), 4.1 (s, 2H), 3.98 (t, J=7.9 Hz, 2H), 3.33 (s, 3H), 3.0 (t, J=7.9 Hz, 2H) ppm. ES-HRMS m/z 461.1088 (M+H calcd for $C_{23}H_{20}ClF_2N_2O_4$ requires 461.1074).

Example 733

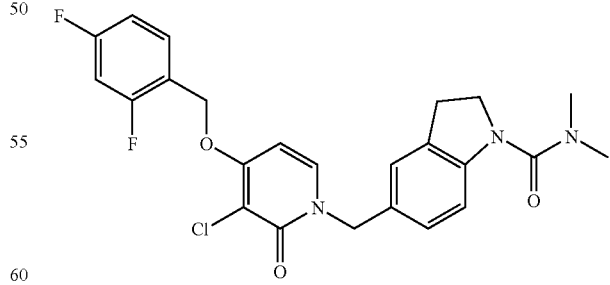

5-{[3-chloro-4-[(2,4-difluorobenzyl)oxy]-2-oxopyridin-1(2H)-yl]methyl}-N,N-dimethylindoline-1-carboxamide A 10 mL round bottomed flask equipped with stirbar and nitrogen inlet was charged with the compound of Example 88 (200 mg, 0.5 mmol), dimethylcarbamyl chloride (69 μL, 0.75 mmol), triethylamine (139 μL, 1.0 mmol) and tetrahydrofuran (4.0 mL). After stirring at 25° C. for 5 min the reaction was completed by LC-MS. The compound precipitated out of solution. The precipitate was filtered and washed with water and diethyl ether to obtain a white solid (188 mg, 58%). $^1$H NMR (400 MHz, (DMSO) δ 7.9 (d, J=8.1, 1H), 7.6 (q, J=8.6 and 6.6 Hz, 1H), 7.3 (t, J=9.3 Hz, 1H), 7.1 (m, 3H), 6.8 (d, J=8.0 Hz, 1H), 6.5 (d, J=7.8 Hz, H), 5.25 (s, 2H), 5.0 (s, 2H), 3.7 (t, J=8.6 Hz, 2H), 2.9 (t, J=7.9 Hz, 2H), 2.8 (s, 6H) ppm. ES-HRMS m/z 474.1387 (M+H calcd for $C_{24}H_{23}ClF_2N_3O_3$ requires 474.1391).

Biological Evaluation p38 Kinase Assay

Cloning of Human p38a:

The coding region of the human p38a cDNA was obtained by PCR-amplification from RNA isolated from the human monocyte cell line THP.1. First strand cDNA was synthesized from total RNA as follows: 2 μg of RNA was annealed to 100 ng of random hexamer primers in a 10 μl reaction by heating to 70° C. for 10 minutes followed by 2 minutes on ice. cDNA was then synthesized by adding 1 μl of RNAsin (Promega, Madison Wis.), 2 μl of 50 mM dNTP's, 4 μl of 5× buffer, 2 μl of 100 mM DTT and 1 μl (200 U) of Superscript II™ AMV reverse transcriptase. Random primer, dNTP's and Superscript II™ reagents were all purchased from Life-Technologies, Gaithersburg, Mass. The reaction was incubated at 42° C. for 1 hour. Amplification of p38 cDNA was performed by aliquoting 5 μl of the reverse transcriptase reaction into a 100 μl PCR reaction containing the following: 80 μl dH.sub.2O, 2.0 μl 50 mM dNTP's, 1 μl each of forward and reverse primers (50 μmol/μl), 10 μl of 10×buffer and 1 μl Expand™ polymerase (Boehringer Mannheim). The PCR primers incorporated BamHI sites onto the 5' and 3' end of the amplified fragment, and were purchased from Genosys. The sequences of the forward and reverse primers were
5'-GATCGAGGATTCATGTCTCAGGAGAGGCCCA-3' and 5' GATCGAGGATTCTCAGGACTCCATCTCTTC-3' respectively. The PCR amplification was carried out in a DNA Thermal Cycler (Perkin Elmer) by repeating 30 cycles of 940 C. for 1 minute, 60° C. for 1 minute and 68° C. for 2 minutes. After amplification, excess primers and unincorporated dNTP's were removed from the amplified fragment with a Wizard™ PCR prep (Promega) and digested with BamHI (New England Biolabs). The BamHI digested fragment was ligated into BamHI digested pGEX 2T plasmid DNA (PharmaciaBiotech) using T-4 DNA ligase (New England Biolabs) as described by T. Maniatis, Molecular Cloning: A Laboratory Manual, 2nd ed. (1989). The ligation reaction was transformed into chemically competent E. coli DH10B cells purchased from Life-Technologies following the manufacturer's instructions. Plasmid DNA was isolated from the resulting bacterial colonies using a Promega Wizard™ miniprep kit. Plasmids containing the appropriate BamHI fragment were sequenced in a DNA Thermal Cycler (Perkin Elmer) with Prism™ (Applied Biosystems Inc.). cDNA clones were identified that coded for both human p38a isoforms (Lee et al. Nature 372, 739). One of the clones that contained the cDNA for p38a-2 (CSB-2) inserted in the cloning site of PGEX 2T, 3' of the GST coding region was designated pMON 35802. The sequence obtained for this clone is an exact match of the cDNA clone reported by Lee et al. This expression plasmid allows for the production of a GST-p38a fusion protein.

Expression of Human p38a

GST/p38a fusion protein w as expressed from the plasmid pMON 35802 in E. coli, stain DH10B (Life Technologies, Gibco-BRL). Overnight cultures were grown in Luria Broth (LB) containing 100 mg/ml ampicillin. The next day, 500 ml of fresh LB was inoculated with 10 ml of overnight culture, and grown in a 2 liter flask at 37° C. with constant shaking until the culture reached an absorbance of 0.8 at 600 nm. Expression of the fusion protein was induced by addition of isopropyl b-D-thiogalactosidase (IPTG) to a final concentration of 0.05 mM. The cultures were shaken for three hours at room temperature, and the cells were harvested by centrifugation. The cell pellets were stored frozen until protein purification.

Purification of P38 Kinase-alpha

All chemicals were from Sigma Chemical Co. unless noted. Twenty grams of E. coli cell pellet collected from five 1 L shake flask fermentations was resuspended in a volume of PBS (140 mM NaCl, 2.7 mM KCl, 10 mM Na.sub.2HPO.sub.4, 1.8 mM KH.sub.2PO.sub.4, pH 7.3) up to 200 ml. The cell suspension was adjusted to 5 mM DTT with 2 M DTT and then split equally into five 50 ml Falcon conical tubes. The cells were sonnicated (Ultrasonics model W375) with a 1 cm probe for 3.times.1 minutes (pulsed) on ice. Lysed cell material was removed by centrifugation (12,000×g, 15 minutes) and the clarified supernatant applied to glutathione-sepharose resin (Pharmacia).

Glutathione-Sepharose Affinity Chromatography

Twelve ml of a 50% glutathione sepharose-PBS suspension was added to 200 ml clarified supernatant and incubated batchwise for 30 minutes at room temperature. The resin was collected by centrifugation (600.times.g, 5 min) and washed with 2.times.150 ml PBS/1% Triton X-100, followed by 4.times.40 ml PBS. To cleave the p38 kinase from the GST-p38 fusion protein, the glutathione-sepharose resin was resuspended in 6 ml PBS containing 250 units thrombin protease (Pharmacia, specific activity >7500 units/mg) and mixed gently for 4 hours at room temperature. The glutathione-sepharose resin was removed by centrifugation (600.times.g, 5 min) and washed 2.times.6 ml with PBS. The PBS wash fractions and digest supernatant containing p38 kinase protein were pooled and adjusted to 0.3 mM PMSF.

Mono Q Anion Exchange Chromatography

The thrombin-cleaved p38 kinase was further purified by FPLC-anion exchange chromatography. Thrombin-cleaved sample was diluted 2-fold with Buffer A (25 mM HEPES, pH 7.5, 25 mM beta-glycerophosphate, 2 mM DTT, 5% glycerol) and injected onto a Mono Q HR 10/10 (Pharmacia) anion exchange column equilibrated with Buffer A. The column was eluted with a 160 ml 0.1 M–0.6 M NaCl/Buffer A gradient (2 ml/minute flowrate). The p38 kinase peak eluting at 200 mM NaCl was collected and concentrated to 3–4 ml with a Filtron 10 concentrator (Filtron Corp.).

Sephacryl S100 Gel Filtration Chromatography

The concentrated Mono Q-p38 kinase purified sample was purified by gel filtration chromatography (Pharmacia HiPrep 26/60 Sephacryl S100 column equilibrated with Buffer B (50 mM HEPES, pH 7.5, 50 mM NaCl, 2 mM DTT, 5% glycerol)). Protein was eluted from the column with Buffer B at a 0.5 ml/minute flowrate and protein was detected by absorbance at 280 nm. Fractions containing p38 kinase (detected by SDS-polyacrylamide gel electrophoresis) were pooled and frozen at −80° C. Typical purified protein yields from 5 L E. coli shake flasks fermentations were 35 mg p38 kinase.

In Vitro Assay

The ability of compounds to inhibit human p38 kinase alpha was evaluated using two in vitro assay methods. In the first method, activated human p38 kinase alpha phosphorylates a biotinylated substrate, PHAS-I (phosphorylated heat and acid stable protein-insulin inducible), in the presence of gamma $^{32}$P-ATP ($^{32}$P-ATP). PHAS-I was biotinylated prior to the assay and provides a means of capturing the substrate, which is phosphorylated during the assay. p38 Kinase was activated by MKK6. Compounds were tested in 10 fold serial dilutions over the range of 100 µM to 0.001 µM using 1% DMSO. Each concentration of inhibitor was tested in triplicate.

All reactions were carried out in 96 well polypropylene plates. Each reaction well contained 25 mM HEPES pH 7.5, 10 mM magnesium acetate and 50 µM unlabeled ATP. Activation of p38 was required to achieve sufficient signal in the assay. Biotinylated PHAS-I was used at 1–2 µg per 50 µl reaction volume, with a final concentration of 1.5 µM. Activated human p38 kinase alpha was used at 1 µg per 50 µl reaction volume representing a final concentration of 0.3 µM. Gamma $^{32}$P-ATP was used to follow the phosphorylation of PHAS-I. $^{32}$P-ATP has a specific activity of 3000 Ci/mmol and was used at 1.2 µCi per 50 µl reaction volume. The reaction proceeded either for one hour or overnight at 30° C.

Following incubation, 20 µl of reaction mixture was transferred to a high capacity streptavidin coated filter plate (SAM-streptavidin-matrix, Promega) prewetted with phosphate buffered saline. The transferred reaction mix was allowed to contact the streptavidin membrane of the Promega plate for 1–2 minutes. Following capture of biotinylated PHAS-I with $^{32}$P incorporated, each well was washed to remove unincorporated $^{32}$P-ATP three times with 2M NaCl, three washes of 2M NaCl with 1% phosphoric, three washes of distilled water and finally a single wash of 95% ethanol. Filter plates were air-dried and 20 µl of scintillant was added. The plates were sealed and counted.

A second assay format was also employed that is based on p38 kinase alpha induced phosphorylation of EGFRP (epidermal growth factor receptor peptide, a 21 mer) in the presence $^{33}$P-ATP. Compounds were tested in 10 fold serial dilutions over the range of 100 µM to 0.001 µM in 1% DMSO. Each concentration of inhibitor was tested in triplicate. Compounds were evaluated in 50 µl reaction volumes in the presence of 25 mM Hepes pH 7.5, 10 mM magnesium acetate, 4% glycerol, 0.4% bovine serum albumin, 0.4 mM DTT, 50 µM unlabeled ATP, 25 µg EGFRP (200 µM), and 0.05 µCi $^{33}$P-ATP. Reactions were initiated by addition of 0.09 µg of activated, purified human GST-p38 kinase alpha. Activation was carried out using GST-MKK6 (5:1, p38:MKK6) for one hour at 30° C. in the presence of 50 µM ATP. Following incubation for 60 minutes at room temperature, the reaction was stopped by addition of 150 µl of AG 1.times.8 resin in 900 mM sodium formate buffer, pH 3.0 (1 volume resin to 2 volumes buffer). The mixture was mixed three times with pipetting and the resin was allowed to settle. A total of 50 µl of clarified solution head volume was transferred from the reaction wells to Microlite-2 plates. 150 µl of Microscint 40 was then added to each well of the Microlite plate, and the plate was sealed, mixed, and counted.

Representative compounds that exibit IC$_{50}$ values between 1 and 25 µM (p38 alpha kinase assay) are: Example Nos. 20, 22, 23, 39, 43, 44, 48, 50, 52, 53, 55, 57, 58, 62, 92, 115, 118, 136, 139, 141, 142, 149, 156, 157, 169, 174, 219, 220, 244, 245, 387, 288, 289, 291, 292, 293, 294, 295, 296, 298, 297, 300, 301, 302 304, 305, 309, 310, 311, 323, 360, 394, 403, 414, 415, 416, 418, 420, 444, 447, 449, 451, 452, 471, 485, 486, 496, 498, 499, 503, 506, 561, 569, 574, 575 and 576.

Representatve compounds that exibit IC$_{50}$ values between 25 and 100 µM (p38 alpha kinase assay) are: Example Nos. 1, 25, 33, 35, 37, 42, 45, 47, 49, 119, 204, 308, 558, 560, 564, 565, 566, 568 and 577.

Representatve compounds that exibit IC$_{50}$ values less than 1 µM (p38 alpha kinase assay) are: Example Nos. 6, 14, 8, 17, 10, 15, 4, 117, 161, 162, 165, 170, 171, 172, 173, 176, 179, 217, 218, 219, 220, 221, 223, 225, 230, 231, 234, 235, 272, 273, 275, 276, 278, 280, 282, 286, 285, 290, 312, 313, 314, 315, 316, 317, 318, 320, 321, 322, 364, 366, 400, 402, 405, 421, 422, 423, 446, 448, 450, 458, 466, 467, 468, 469, 470, 481, 482, 483, 484, 487, 489, 492, 493, 494, 495, 504, 521, 522, 523, 557, 587, 589, 590, 591, 597, 609, 610, 613, 629, 642, and 643.

Representatve compounds that exibit IC$_{50}$ values greater than 100 µM (p38 alpha kinase assay) are: Example Nos. 3, 11, 38, 56, 116, 121, 237, 236, 413, 497 and 578.

TNF Cell Assays

Method of Isolation of Human Peripheral Blood Mononuclear Cells:

Human whole blood was collected in Vacutainer tubes containing EDTA as an anticoagulant. A blood sample (7 ml) was carefully layered over 5 ml PMN Cell Isolation Medium (Robbins Scientific) in a 15 ml round bottom centrifuge tube. The sample was centrifuged at 450–500.times.g for 30–35 minutes in a swing out rotor at room temperature. After centrifugation, the top band of cells were removed and washed 3 times with PBS w/o calcium or magnesium. The cells were centrifuged at 400.times.g for 10 minutes at room temperature. The cells were resuspended in Macrophage Serum Free Medium (Gibco BRL) at a concentration of 2 million cells/mi.

LPS Stimulation of Human PBMs

PBM cells (0.1 ml, 2 million/ml) were co-incubated with 0.1 ml compound (10–0.41 µM, final concentration) for 1 hour in flat bottom 96 well microtiter plates. Compounds were dissolved in DMSO initially and diluted in TCM for a final concentration of 0.1% DMSO. LPS (Calbiochem, 20 ng/ml, final concentration) was then added at a volume of 0.010 ml. Cultures were incubated overnight at 370 C. Supernatants were then removed and tested by ELISA for TNF-a and IL1-b. Viability was analyzed using MTS. After 0.1 ml supernatant was collected, 0.020 ml MTS was added to remaining 0.1 ml cells. The cells were incubated at 37° C. for 2–4 hours, then the O.D. was measured at 490–650 nM.

Maintenance and Differentiation of the U937 Human Histiocytic Lymphoma Cell Line U937 cells (ATCC) were propagated in RPMI 1640 containing 10% fetal bovine serum, 100 IU/ml penicillin, 100 µg/ml streptomycin, and 2 mM glutamine (Gibco). Fifty million cells in 100 ml media were induced to terminal monocytic differentiation by 24 hour incubation with 20 ng/ml phorbol 12-myristate 13-acetate (Sigma). The cells were washed by centrifugation (200.times.g for 5 min) and resuspended in 100 ml fresh medium. After 24–48 hours, the cells were harvested, centrifuged, and resuspended in culture medium at 2 million cells/ml.

LPS Stimulation of TNF Production by U937 Cells

U937 cells (0.1 ml, 2 million/ml) were incubated with 0.1 ml compound (0.004–50 µM, final concentration) for 1 hour in 96 well microtiter plates. Compounds were prepared as 10 mM stock solutions in DMSO and diluted in culture medium to yield a final DMSO concentration of 0.1% in the cell assay. LPS (*E coli,* 100 ng/ml final concentration) was then added at a volume of 0.02 ml. After 4 hour incubation at 370 C., the amount of TNF-.alpha. released in the culture medium was quantitated by ELISA. Inhibitory potency is expressed as IC50 (µM).

Rat Assay

The efficacy of the novel compounds in blocking the production of TNF also was evaluated using a model based on rats challenged with LPS. Male Harlen Lewis rats [Sprague Dawley Co.] were used in this model. Each rat weighed approximately 300 g and was fasted overnight prior to testing. Compound administration was typically by oral gavage (although intraperitoneal, subcutaneous and intravenous administration were also used in a few instances) 1 to 24 hours prior to the LPS challenge. Rats were administered 30 μg/kg LPS [*salmonella typhosa*, Sigma Co.] intravenously via the tail vein. Blood was collected via heart puncture 1 hour after the LPS challenge. Serum samples were stored at −20° C. until quantitative analysis of TNF-.alpha. by Enzyme Linked-Immuno-Sorbent Assay ("ELISA") [Biosource]. Additional details of the assay are set forth in Perretti, M., et al., Br. J. Pharmacol. (1993), 110, 868–874, which is incorporated by reference in this application.

Mouse Assay

Mouse Model of LPS-Induced TNF Alpha Production

TNF alpha was induced in 10–12 week old BALB/c female mice by tail vein injection with 100 ng lipopolysaccharide (from *S. Typhosa*) in 0.2 ml saline. One hour later mice were bled from the retroorbital sinus and TNF concentrations in serum from clotted blood were quantified by ELISA. Typically, peak levels of serum TNF ranged from 2–6 ng/ml one hour after LPS injection.

The compounds tested were administered to fasted mice by oral gavage as a suspension in 0.2 ml of 0.5% methylcellulose and 0.025% Tween 20 in water at 1 hour or 6 hours prior to LPS injection. The 1 hour protocol allowed evaluation of compound potency at Cmax plasma levels whereas the 6 hour protocol allowed estimation of compound duration of action. Efficacy was determined at each time point as percent inhibition of serum TNF levels relative to LPS injected mice that received vehicle only.

Induction and Assessment of Collagen-Induced Arthritis in Mice

Arthritis was induced in mice according to the procedure set forth in J. M. Stuart, Collagen Autoimmune Arthritis, Annual Rev. Immunol. 2:199 (1984), which is incorporated herein by reference. Specifically, arthritis was induced in 8–12 week old DBA/1 male mice by injection of 50 μg of chick type II collagen (CII) (provided by Dr. Marie Griffiths, Univ. of Utah, Salt Lake City, Utah) in complete Freund's adjuvant (Sigma) on day 0 at the base of the tail. Injection volume was 100 μl. Animals were boosted on day 21 with 50 μg of CII in incomplete Freund's adjuvant (100 μl volume). Animals were evaluated several times each week for signs of arthritis. Any animal with paw redness or swelling was counted as arthritic. Scoring of arthritic paws was conducted in accordance with the procedure set forth in Wooley et al., Genetic Control of Type II Collagen Induced Arthritis in Mice: Factors Influencing Disease Susceptibility and Evidence for Multiple MHC Associated Gene Control., Trans. Proc., 15:180 (1983). Scoring of severity was carried out using a score of 1–3 for each paw (maximal score of 12/mouse). Animals displaying any redness or swelling of digits or the paw were scored as 1. Gross swelling of the whole paw or deformity was scored as 2. Ankylosis of joints was scored as 3. Animals were evaluated for 8 weeks. 8–10 animals per group were used.

The invention and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the spirit or scope of the present invention as set forth in the claims. To particularly point out and distinctly claim the subject matter regarded as invention, the following claims conclude this specification.

What is claimed is:

1. A compound of the formula:

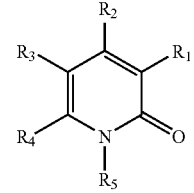

or a pharmaceutically acceptable salt thereof, wherein
$R_1$ is halogen substituted with 1, 2, 3, 4, or 5 groups that are independently halogen, —($C_1$–$C_6$)alkyl-N(R)—$CO_2R_{30}$, haloalkyl, heteroaryl, heteroarylalkyl, —$NR_6R_7$, $R_6R_7$N—($C_1$–$C_6$ alkyl)-, —C(O)$NR_6R_7$, —($C_1$–$C_4$)alkyl-C(O)$NR_6R_7$, —($C_1$–$C_4$ alkyl)-NRC(O)$NR_{16}R_{17}$, haloalkoxy, alkyl, CN, hydroxyalkyl, dihydroxyalkyl, alkoxy, alkoxycarbonyl, phenyl, —$SO_2$-phenyl wherein the phenyl and —$SO_2$-phenyl groups are optionally substituted with 1, 2, or 3 groups that are independently halogen or $NO_2$, or —OC(O)$NR_6R_7$, wherein
$R_{16}$ and $R_{17}$ are independently H or $C_1$–$C_6$ alkyl; or
$R_{16}$, $R_{17}$ and the nitrogen to which they are attached form a morpholinyl ring;
$R_6$ and $R_7$ are independently at each occurrence H, alkyl, hydroxyalkyl, dihydroxyalkyl, alkoxy, alkanoyl, arylalkyl, arylalkoxy, alkoxycarbonyl, —$SO_2$-alkyl, OH, alkoxy, alkoxyalkyl, arylalkoxycarbonyl, —($C_1$–$C_4$)alkyl-$CO_2$-alkyl, heteroarylalkyl, or arylalkanoyl, wherein each is unsubstituted or substituted with 1, 2, or 3 groups that are independently, halogen, OH, SH, heterocycloalkyl, heterocycloalkylalkyl, $C_3$–$C_7$ cycloalkyl, alkoxy, $NH_2$, NH(alkyl), N(alkyl)(alkyl), —O-alkanoyl, alkyl, haloalkyl, carboxaldehyde, or haloalkoxy; or
$R_6$, $R_7$, and the nitrogen to which they are attached form a morpholinyl, pyrrolidinyl, thiomorpholinyl, thiomorpholinyl S-oxide, thiomorpholinyl S,S-dioxide, piperidinyl, pyrrolidinyl, or piperazinyl ring which is optionally substituted with 1 or 2 groups that are independently $C_1$–$C_4$ alkyl, alkoxycarbonyl, $C_1$–$C_4$ alkoxy, hydroxyl, hydroxyalkyl, dihydroxyalkyl, or halogen;
$R_{30}$ is $C_1$–$C_6$ alkyl optionally substituted with 1 or 2 groups that are independently OH, SH, halogen, amino, monoalkylamino, dialkylamino or $C_3$–$C_6$ cycloalkyl;
$R_3$ is H, halogen, alkoxycarbonyl, arylalkoxycarbonyl, aryloxycarbonyl, arylalkyl, —OC(O)NH($CH_2$)$_n$aryl, arylalkoxy, —OC(O)N(alkyl)($CH_2$)$_n$aryl, aryloxy, arylthio, thioalkoxy, arylthioalkoxy, alkenyl, —$NR_6R_7$, $NR_6R_7$—($C_1$–$C_6$)alkyl, or alkyl, wherein
the aryl portion of arylalkoxycarbonyl, aryloxycarbonyl, arylalkyl, —OC(O)NH($CH_2$)$_n$aryl, arylalkoxy, —OC(O)N(alkyl)($CH_2$)$_n$aryl, and arylthioalkoxy, is unsubstituted or substituted with 1, 2, 3, 4, or 5 groups that are independently, halogen, alkoxy, alkyl, haloalkyl, or haloalkoxy, wherein n is 0, 1, 2, 3, 4, 5, or 6; or $R_4$ is alkyl unsubstituted or substituted with one or two groups that are independently $CO_2R$, $-CO_2-(C_1-C_6)$ alkyl, $-C(O)NR_6R_7$, $-C(O)R_6$, $-N(R_{30})C(O)NR_{16}R_{17}$, $-N(R_{30})C(O)-(C_1-C_6)$alkoxy, or $-NR_6R_7$, arylalkoxy, arylalkyl, heteroaryl, heteroarylalkyl, hydroxyalkyl, dihydroxyalkyl, haloalkyl, $R_6R_7N-(C_1-C_6$ alkyl)-, $-NR_6R_7$, alkoxy, carboxaldehyde, $-C(O)NR_6R_7$, $CO_2R$, alkoxyalkyl, or alkoxyalkoxy, wherein the heteroaryl or aryl portions of is the above are unsubstituted or substituted with 1, 2, 3, 4, or 5 groups that are independently halogen, hydroxy, alkoxy, alkyl, $-CO_2-(C_1-C_6)$ alkyl, $-CONR_6R_7$, $-NR_6R_7$, $R_6R_7N-(C_1-C_6)$ alkyl-, nitro, haloalkyl, or haloalkoxy; and $R_5$ is H, aryl, arylalkyl, arylthioalkyl, alkyl optionally substituted with 1, 2, or 3 groups that are independently arylalkoxycarbonyl, $-NR_8R_9$, halogen, $-C(O)NR_8R_9$, alkoxycarbonyl, $C_3-C_7$ cycloalkyl, or alkanoyl, alkoxy, alkoxyalkyl optionally substituted with one trimethylsilyl group, amino, alkoxycarbonyl, hydroxyalkyl, dihydroxyalkyl, alkynyl, $-SO_2$-alkyl, alkoxy optionally substituted with one trimethylsilyl group, heterocycloalkylalkyl, cycloalkyl, cycloalkylalkyl, -alkyl-S-aryl, -alkyl-$SO_2$-aryl, heteroarylalkyl, heterocycloalkyl, heteroaryl, or alkenyl optionally substituted with alkoxycarbonyl, wherein each of the above is unsubstituted or substituted with 1, 2, 3, 4, or 5 groups that are independently alkyl, halogen, alkoxy, hydroxyalkyl, dihydroxyalkyl, arylalkoxy, thioalkoxy, alkoxycarbonyl, arylalkoxycarbonyl, $CO_2R$, CN, OH, hydroxyalkyl, dihydroxyalkyl, amidinooxime, $-NR_6R_7$, $-NR_8R_9$, $R_6R_7N-(C_1-C_6$ alkyl)-, carboxaldehyde, $SO_2$ alkyl, $-SO_2H$, $-SO_2NR_6R_7$, alkanoyl wherein the alkyl portion is optionally substituted with OH, halogen or alkoxy, $-C(O)NR_6R_7$, $-(C_1-C_4$ alkyl)-$C(O)NR_6R_7$, amidino, haloalkyl, $-(C_1-C_4$ alkyl)-$NR_{15}C(O)NR_{16}R_{17}$, $-(C_1-C_4$ alkyl)-$NR_{15}C(O)R_{18}$, $-O-CH_2-O$, $-O-CH_2CH_2-O-$, or haloalkoxy; wherein $R_{15}$ is H or $C_1-C_6$ alkyl; and $R_{18}$ is $C_1-C_6$ alkyl optionally substituted with $-O-$ ($C_2-C_6$ alkanoyl, $C_1-C_6$ hydroxyalkyl, $C_1-C_6$ dihydroxyalkyl, $C_1-C_6$ alkoxy, $C_1-C_6$ alkoxy $C_1-C_6$ alkyl; amino $C_1-C_6$ alkyl, mono or dialkylamino $C_1-C_6$ alkyl.

2. A compound according to claim 1, of the formula:

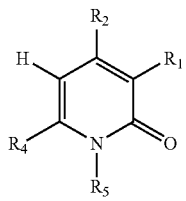

or a pharmaceutically acceptable salt thereof, wherein
$R_1$ halogen,
$R_2$ is alkoxy substituted with 1, 2, 3, 4, or 5 groups that are independently halogen, $-NR_6R_7$, haloalkyl, haloalkoxy, alkyl, heteroaryl, heteroarylalkyl, $-(C_1-C_4)$alkyl-$C(O)NR_6R_7$, $R_6R_7N-(C_1-C_6$ alkyl)-, $-C(O)NR_6R_7$, $-(C_1-C_4$ alkyl)-$NRC(O)NR_{16}R_{17}$, CN, hydroxyalkyl, dihydroxyalkyl, $-OC(O)NR_6R_7$, or $-(C_1-C_6)$alkyl-N(R)$-CO_2R_{30}$, wherein $R_{16}$ and $R_{17}$ are independently H or $C_1-C_6$ alkyl; or
$R_{16}$, $R_{17}$ and the nitrogen to which they are attached form a morpholinyl ring;

$R_6$ and $R_7$ are independently at each occurrence H, alkyl, hydroxyalkyl, dihydroxyalkyl, alkoxy, alkoxyalkyl, alkanoyl, arylalkyl, arylalkoxy, arylalkoxycarbonyl, or arylalkanoyl, wherein each of the above is unsubstituted or substituted with 1, 2, or 3 groups that are independently, halogen, alkoxy, alkyl, OH, SH, carboxaldehyde, haloalkyl, or haloalkoxy; or $R_6$, $R_7$, and the nitrogen to which they are attached form a morpholinyl, thiomorpholinyl, thiomorpholinyl S-oxide, thiomorpholinyl S,S-dioxide, piperidinyl, pyrrolidinyl, or piperazinyl ring which is optionally substituted with 1 or 2 groups that are independently $C_1-C_4$ alkyl, alkoxycarbonyl, hydroxyl, hydroxyalkyl, dihydroxyalkyl, or halogen;

$R_{30}$ is $C_1-C_6$ alkyl optionally substituted with 1 or 2 groups that are independently OH, SH, halogen, amino, monoalkylamino, dialkylamino or $C_3-C_6$ cycloalkyl;

$R_4$ is alkyl substituted with one or two groups that are independently $CO_2R$, $-CO_2$ alkyl, $-C(O)NR_6R_7$, $-C(O)R_6$, $-N(R_{30})C(O)NR_{16}R_{17}$, $-N(R_{30})C(O)-$ ($C_1-C_6$)alkoxy, or $-NR_6R_7$, arylalkoxy, heteroaryl, arylalkyl, hydroxyalkyl, dihydroxyalkyl, haloalkyl, $-NR_6R_7$, $-C(O)NR_6R_7$, alkoxy, alkoxyalkyl, or alkoxyalkoxy, wherein the heteroaryl or aryl portions of the above are unsubstituted or substituted with 1, 2, 3, 4, or 5 groups that are independently halogen, hydroxy, alkoxy, alkyl, $-CO_2-(C_1-C_6)$alkyl, $-CONR_6R_7$, $-NR_6R_7$, $R_6R_7N-(C_1-C_6)$alkyl-, nitro, haloalkyl, or haloalkoxy; and $R_5$ is H, arylalkyl, alkyl optionally substituted with 1, 2, or 3 groups that are independently arylalkoxycarbonyl, $-NR_8R_9$, halogen, $-C(O)NR_8R_9$, alkoxycarbonyl, or alkanoyl, alkoxyalkyl optionally substituted with one trimethylsilyl group, alkoxycarbonyl, amino, hydroxyalkyl, dihydroxyalkyl, alkenyl optionally substituted with alkoxycarbonyl, alkynyl, $-SO_2$-alkyl, aryl, alkoxy optionally substituted with one trimethylsilyl group, heterocycloalkylalkyl, heteroarylalkyl, heterocycloalkyl, or heteroaryl, wherein each of the above is unsubstituted or substituted with 1, 2, 3, 4, or 5 groups that are independently alkyl, halogen, alkoxy, arylalkoxy, hydroxyalkyl, dihydroxyalkyl, thioalkoxy, $-SO_2$ alkyl, alkoxycarbonyl, arylalkoxycarbonyl, $CO_2R$, CN, OH, amidinooxime, $NR_8R_9$, $R_6R_7N-(C_1-C_6$ alkyl)-, $-C(O)NR_6R_7$, amidino, hydroxyalkyl, dihydroxyalkyl, carboxaldehyde, $-NR_6R_7$, haloalkyl, $-(C_1-C_4$ alkyl)-$C(O)NR_6R_7$, $-(C_1-C_4$ alkyl)-$CO_2R$, $-(C_1-C_4$ alkyl)-$C_1-C_6$ alkoxycarbonyl, $-(C_1-C_4$ alkyl)-CN, $-(C_1-C_4$ alkyl)-$NR_{15}C(O)R_{18}$, $-O-CH_2-O-$, $-O-CH_2CH_2-O-$, phenyl or haloalkoxy;

$R_8$ is hydrogen, alkyl, alkanoyl, arylalkyl and arylalkanoyl;

$R_9$ is alkyl, alkanoyl, arylalkyl, heteroaryl, aminoalkyl, monoalkylaminoalkyl, dialkylaminoalkyl, and arylalkanoyl.

3. A compound according to claim 2 wherein
$R_1$ is halogen;
$R_2$ is $C_1-C_8$ alkoxy substituted with 1, 2, 3, 4, or 5 groups that are independently halogen, $NR_6R_7$, haloalkyl, haloalkoxy, hydroxyalkyl, dihydroxyalkyl, alkyl, phenyl, pyridyl, piperidinyl, piperazinyl, —($C_1$–$C_6$) alkyl-N(R)—$CO_2R_{30}$, $R_6R_7N$—($C_1$–$C_6$ alkyl)-, —C(O)$NR_6R_7$, —($C_1$–$C_4$)alkyl-C(O)$NR_6R_7$, —($C_1$–$C_4$ alkyl)-NRC(O)$NR_{16}R_{17}$, or —OC(O) $NR_6R_7$, wherein $R_6$ and $R_7$ are independently at each occurrence H, alkyl, ($C_1$–$C_4$)hydroxyalkyl, ($C_1$–$C_4$) dihydroxyalkyl, ($C_1$–$C_4$)alkoxy, ($C_1$–$C_4$)alkoxy ($C_1$–$C_4$)alkyl, ($C_1$–$C_4$)alkanoyl, phenyl($C_1$–$C_4$) alkyl, phenyl($C_1$–$C_4$)alkoxy, phenyl($C_1$–$C_4$) alkoxycarbonyl, or phenyl($C_1$–$C_4$)alkanoyl, wherein each of the above is unsubstituted or substituted with 1, 2, or 3 groups that are independently, halogen, OH, SH, $C_3$–$C_6$ cycloalkyl, ($C_1$–$C_4$)alkoxy, ($C_1$–$C_4$) alkyl, $CF_3$, carboxaldehyde, $NH_2$, NH($C_1$–$C_6$)alkyl, N($C_1$–$C_6$)alkyl($C_1$–$C_6$)alkyl, $OCF_3$; or $R_6$, $R_7$, and the nitrogen to which they are attached form a morpholinyl, thiomorpholinyl, piperidinyl, pyrrolidinyl, or piperazinyl ring which is optionally substituted with 1 or 2 groups that are independently $C_1$–$C_4$ alkyl, hydroxy, hydroxy $C_1$–$C_4$ alkyl, $C_1$–$C_4$ dihydroxyalkyl, $C_1$–$C_4$ alkoxycarbonyl, or halogen; and $R_4$ is H, alkyl optionally substituted with one or two groups that are independently $CO_2R$, —$CO_2$ alkyl, —C(O)$NR_6R_7$, —C(O)$R_6$, —N($R_{30}$)C(O)$NR_{16}R_{17}$, —N($R_{30}$)C(O)—($C_1$–$C_6$)alkoxy, or —$NR_6R_7$, —C(O) $NR_6R_7$, phenyl($C_1$–$C_6$)alkoxy, phenyl($C_1$–$C_6$)alkyl, hydroxyalkyl, dihydroxyalkyl, haloalkyl, alkoxy, alkoxyalkyl, or alkoxyalkoxy, wherein the phenyl groups are unsubstituted or substituted with 1, 2, 3, 4, or 5 groups that are independently halogen, hydroxy, alkoxy, alkyl, nitro, $CF_3$, $OCF_3$;

$R^5$ is phenyl benzyl, phenylethyl optionally substituted with 1, 2, 3, 4, or 5 groups that are independently phenyl $C_1$–$C_4$ alkoxycarbonyl, —$NR_8R_9$, halogen, —C(O)$NR_8R_9$, alkoxycarbonyl, or alkanoyl, phenyl, alkoxy, $C_2$–$C_6$ alkynyl, $C_2$–$C_6$ alkenyl optionally substituted with alkoxycarbonyl, indolyl, quinolinyl, isoquinolinyl, isoindolyl, dihydroindolyl, pyrazolyl, imidazolyl, dihydroisoindolyl, indolon-2-yl, indazolyl, benzimidazolyl, pyridyl, imidazolidine dione, pyrazolyl($C_1$–$C_6$ alkyl), imidazolyl($C_1$–$C_6$ alkyl), piperidinyl($C_1$–$C_6$)alkyl, pyrrolidinyl($C_1$–$C_6$)alkyl, imidazolidinyl($C_1$–$C_6$)alkyl, tetrahydroisoquinolinyl ($C_1$–$C_6$)alkyl, 1H-indazolyl($C_1$–$C_6$)alkyl, dihydroindolon-2-yl($C_1$–$C_6$ alkyl), indolinyl($C_1$–$C_6$ alkyl), dihydrobenzimidazolyl($C_1$–$C_6$ alkyl), or dihydrobenzoimidazolonyl($C_1$–$C_6$ alkyl), pyridyl ($C_1$–$C_6$)alkyl, pyridazinyl($C_1$–$C_6$)alkyl, pyrimidinyl ($C_1$–$C_6$)alkyl, pyrazinyl($C_1$–$C_6$)alkyl, tetrahydrofuryl ($C_1$–$C_6$)alkyl, naphthyl($C_1$–$C_6$)alkyl, morpholinyl ($C_1$–$C_6$)alkyl, tetrahydrofuryl($C_1$–$C_6$)alkyl, thienyl ($C_1$–$C_6$)alkyl, piperazinyl($C_1$–$C_6$)alkyl, indolyl ($C_1$–$C_6$)alkyl, quinolinyl($C_1$–$C_6$)alkyl, isoquinolinyl ($C_1$–$C_6$)alkyl, isoindolyl($C_1$–$C_6$)alkyl, dihydroindolyl ($C_1$–$C_6$)alkyl, pyrazolyl($C_1$–$C_4$)alkyl, imidazolyl ($C_1$–$C_4$)alkyl, dihydroisoindolyl($C_1$–$C_6$)alkyl, indoon-2-yl($C_1$–$C_6$)alkyl, indolon-2-yl($C_1$–$C_6$)alkyl, or morpholinyl $C_1$–$C_6$ alkyl, wherein each of the above is unsubstituted or substituted with 1, 2, 3, 4, or 5 groups that are independently $C_1$–$C_6$ alkyl, halogen, $C_1$–$C_6$ alkoxy, phenyl $C_1$–$C_6$ alkoxy, $C_1$–$C_6$ thioalkoxy, $C_1$–$C_6$ alkoxycarbonyl, $CO_2R$, CN, —$SO_2$($C_1$–$C_6$)alkyl, amidinooxime, $NR_8R_9$, —$NR_6R_7$, $NR_6R_7C_1$–$C_6$ alkyl, —C(O)$NR_6R_7$, —($C_1$–$C_4$)alkyl-C(O)$NR_6R_7$, amidino, $C_1$–$C_4$ haloalkyl, hydroxy $C_1$–$C_6$ alkyl, $C_1$–$C_6$ dihydroxyalkyl, or $C_1$–$C_4$ haloalkoxy; wherein $R_8$ is hydrogen, $C_1$–$C_6$ alkyl, $C_1$–$C_6$ alkanoyl, phenyl $C_1$–$C_6$ alkyl and phenyl $C_1$–$C_6$ alkanoyl; and $R_9$ is aminoalkyl, mono $C_1$–$C_6$ alkylamino $C_1$–$C_6$ alkyl, di $C_1$–$C_6$ alkylamino $C_1$–$C_6$ alkyl, $C_1$–$C_6$ alkyl, $C_1$–$C_6$ alkanoyl, phenyl $C_1$–$C_6$ alkyl, indazolyl, and phenyl $C_1$–$C_6$ alkanoyl.

4. A compound according to claim 3, wherein $R_1$ is halogen;

$R_2$ is $C_1$–$C_8$ alkoxy substituted with 1, 2, 3, 4, or 5 groups that are independently halogen, —($C_1$–$C_6$)alkyl-N (R)—$CO_2R_{30}$, $NR_6R_7$, —($C_1$–$C_4$)alkyl-C(O)$NR_6R_7$, ($C_1$–$C_4$)haloalkyl, —C(O)$NR_6R_7$, —($C_1$–$C_4$ alkyl)-NRC(O)$NR_{16}R_{17}$, ($C_1$–$C_4$)haloalkoxy, hydroxyalkyl, $C_1$–$C_6$ dihydroxyalkyl, ($C_1$–$C_6$)alkyl, pyridyl, or $R_6R_7N$—($C_1$–$C_6$ alkyl)-.

5. A compound according to claim 4, wherein $R_5$ is phenyl, benzyl, or phenylethyl, wherein each of the above is unsubstituted or substituted with 1, 2, 3, 4, or 5 groups that are independently alkyl, halogen, alkoxy, benzyloxy, hydroxyalkyl, dihydroxyalkyl, thioalkoxy, —$CO_2$($C_1$–$C_5$ alkyl), $CO_2R$, CN, amidinooxime, —$NR_8R_9$, —$NR_6R_7$, $R_6R_7N$—($C_1$–$C_6$ alkyl)-, —C(O)$NR_6R_7$, —($C_1$–$C_4$) alkyl-C(O)$NR_6R_7$, amidino, $CF_3$, or $OCF_3$;

$R_8$ is hydrogen, $C_1$–$C_6$ alkyl, $C_1$–$C_6$ alkanoyl, phenyl $C_1$–$C_6$ alkyl and phenyl $C_1$–$C_6$ alkanoyl; and $R_9$ is aminoalkyl, mono $C_1$–$C_6$ alkylamino $C_1$–$C_6$ alkyl, di $C_1$–$C_6$ alkylamino $C_1$–$C_6$ alkyl, $C_1$–$C_6$ alkyl, $C_1$–$C_6$ alkanoyl, phenyl $C_1$–$C_4$ alkyl, indazolyl, and phenyl $C_1$–$C_4$ alkanoyl.

6. A compound according to claim 4, wherein $R_5$ is phenyl, benzyl, or phenylethyl, which is unsubstituted or substituted with 1, 2, 3, 4, or 5 groups that are independently alkyl, halogen, alkoxy, benzyloxy, thioalkoxy, —$CO_2$($C_1$–$C_5$ alkyl), $CO_2R$, CN, amidinooxime, —$NR_8R_9$, —$NR_6R_7$, $R_6R_7N$—($C_1$–$C_6$ alkyl)-, —C(O)$NR_6R_7$, —($C_1$–$C_4$)—C(O)$NR_6R_7$, amidino, $CF_3$, or $OCF_3$; wherein $R_6$ and $R_7$ are independently at each occurrence H, $C_1$–$C_4$ alkyl, $C_1$–$C_4$ hydroxyalkyl, $C_1$–$C_4$ dihydroxyalkyl, $C_1$–$C_4$ alkoxy, $C_1$–$C_4$ alkoxy $C_1$–$C_4$ alkyl, $C_1$–$C_4$ alkanoyl, phenyl $C_1$–$C_4$ alkyl, phenyl $C_1$–$C_4$ alkoxy, or phenyl $C_1$–$C_4$ alkanoyl, wherein each is unsubstituted or substituted with 1, 2, or 3 groups that are independently, halogen, OH, SH, $C_3$–$C_6$ cycloalkyl, $C_1$–$C_4$ alkoxy, $C_1$–$C_4$ alkyl, $CF_3$, or $OCF_3$; or $R_6$, $R_7$, and the nitrogen to which they are attached form a morpholinyl, thiomorpholinyl, or piperazinyl ring which is optionally substituted with 1 or 2 groups that are independently $C_1$–$C_4$ alkyl, hydroxy, hydroxy $C_1$–$C_4$ alkyl, $C_1$–$C_4$ dihydroxyalkyl, or halogen;

$R_8$ is hydrogen, $C_1$–$C_6$ alkyl, $C_1$–$C_6$ alkanoyl, phenyl $C_1$–$C_6$ alkyl and phenyl $C_1$–$C_6$ alkanoyl; and $R_9$ is aminoalkyl, mono $C_1$–$C_6$ alkylamino $C_1$–$C_6$ alkyl, di $C_1$–$C_6$ alkylamino $C_1$–$C_6$ alkyl, $C_1$–$C_6$ alkyl, $C_1$–$C_6$ alkanoyl, phenyl $C_1$–$C_4$ alkyl, indazolyl, and phenyl $C_1$–$C_4$ alkanoyl.

7. A compound according to claim 6, wherein $R_5$ is phenyl, benzyl or phenethyl, wherein each is optionally substituted with 1, 2, 3, 4, or 5 groups that are independently $C_1$–$C_6$ alkyl, —$NR_6R_7$, —C(O)$NR_6R_7$, —($C_1$–$C_4$ alkyl)-C(O)$NR_6R_7$, —$NR_8R_9$, halogen, $C_1$–$C_6$ alkoxy, $CO_2R$, —($C_1$–$C_4$ alkyl)-$CO_2R$, $C_1$–$C_6$ thioalkoxy, amidinooxime, $C_1$–$C_6$ alkoxycarbonyl, —($C_1$–$C_4$ alkyl)-$C_1$–$C_6$ alkoxycarbonyl, $C_1$–$C_6$ hydroxyalkyl, $C_1$–$C_6$ dihydroxyalkyl, —($C_1$–$C_4$ alkyl)-CN, CN, phenyl $C_1$–$C_6$ alkoxy, OH, $C_1$–$C_4$ haloalkyl, $C_1$–$C_4$ haloalkoxy, $R_6R_7$N—($C_1$–$C_6$ alkyl)-, —($C_1$–$C_4$ alkyl)-$NR_{15}$C(O)$R_{18}$, amidinooxime, —$SO_2$($C_1$–$C_6$ alkyl), —O—$CH_2$—O—, —O—$CH_2CH_2$—O—, phenyl $C_1$–$C_4$ alkoxy, or phenyl; wherein $R_6$ and $R_7$ are independently at each occurrence H, $C_1$–$C_4$ alkyl, $C_1$–$C_4$ hydroxyalkyl, $C_1$–$C_4$ dihydroxyalkyl, $C_1$–$C_4$ alkanoyl, or $C_1$–$C_4$ alkoxy, each of which is optionally substituted with 1, 2, or 3 groups that are independently halogen, OH, SH, $C_3$–$C_6$ cycloalkyl, $C_1$–$C_4$ alkoxy, $C_1$–$C_4$ alkyl, OH, $CF_3$, or $OCF_3$.

8. A compound according to claim 7, wherein $R_5$ is phenyl, benzyl or phenethyl, each of which is unsubstituted or substituted with 1, 2, 3, 4, or 5 groups that are independently CN, halogen, $C_1$–$C_4$ alkoxy, $CF_3$, $OCF_3$, $C_1$–$C_4$ alkyl, —$NR_8R_9$, —$NR_6R_7$, $R_6R_7$N—($C_1$–$C_6$ alkyl)-, or —C(O)$NR_6R_7$, wherein $R_6$ and $R_7$ are independently at each occurrence H, $C_1$–$C_4$ alkyl, $C_1$–$C_4$ hydroxyalkyl, $C_1$–$C_4$ dihydroxyalkyl, $C_1$–$C_4$ alkanoyl, or $C_1$–$C_4$ alkoxy, each of which is optionally substituted with 1, 2, or 3 groups that are independently halogen, OH, SH, $C_3$–$C_6$ cycloalkyl, $C_1$–$C_4$ alkoxy, $C_1$–$C_4$ alkyl, OH, $CF_3$, or $OCF_3$.

9. A compound according to claim 4, wherein the $R_5$ group is of the formula:

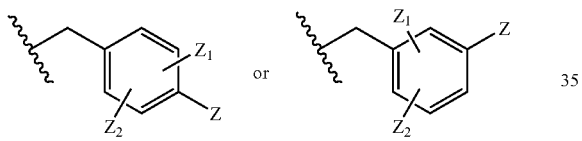

wherein $Z_1$ and $Z_2$ are independently H, halogen, $C_1$–$C_4$ alkyl, or $CO_2R$; and Z is —C(O)$NR_6R_7$, —($C_1$–$C_4$)alkyl-C(O)$NR_6R_7$, —($C_1$–$C_4$ alkyl)-$NR_{15}$C(O)$R_{18}$, —$NR_6R_7$, $R_6R_7$N—($C_1$–$C_6$ alkyl)-, —$NR_8R_9$, $C_1$–$C_6$ hydroxyalkyl, $C_1$–$C_6$ dihydroxyalkyl, $C_1$–$C_6$ alkyl, $CO_2R$, or halogen; wherein $R_6$ and $R_7$ at each occurrence are independently H, OH, $C_1$–$C_6$ alkyl, amino $C_1$–$C_4$ alkyl, NH($C_1$–$C_6$ alkyl) alkyl, N($C_1$–$C_6$ alkyl)($C_1$–$C_6$ alkyl)$C_1$–$C_6$ alkyl, $C_1$–$C_6$ hydroxyalkyl, $C_1$–$C_6$ dihydroxyalkyl, $C_1$–$C_6$ alkoxy $C_1$–$C_6$ alkyl, or —$SO_2$($C_1$–$C_6$ alkyl) each of which is optionally substituted with 1, 2, or 3 groups that are independently halogen, OH, SH, $C_3$–$C_6$ cycloalkyl, $C_1$–$C_4$ alkoxy, $C_1$–$C_4$ alkyl, OH, $CF_3$, or $OCF_3$;

or $R_6$, $R_7$, and the nitrogen to which they are attached form a piperidinyl, pyrrolidinyl, piperazinyl, or a morpholinyl, thiomorpholinyl, ring optionally substituted with 1 or 2 groups that are independently alkyl, hydroxy, hydroxy $C_1$–$C_4$ alkyl, $C_1$–$C_4$ dihydroxyalkyl, or halogen; and $R_{18}$ is $C_1$–$C_6$ alkyl optionally substituted with —O—($C_2$–$C_6$ alkanoyl, $C_1$–$C_6$ hydroxyalkyl, $C_1$–$C_4$ dihydroxyalkyl, $C_1$–$C_6$ alkoxy, $C_1$–$C_6$ alkoxy $C_1$–$C_6$ alkyl; amino $C_1$–$C_6$ alkyl, mono or dialkylamino $C_1$–$C_6$ alkyl.

10. A compound according to claim 4, wherein $R_5$ is phenyl, which is optionally substituted with 1, 2, 3, 4, or 5 groups that are independently $C_1$–$C_4$ alkyl, —C(O)$NR_6R_7$, —($C_1$–$C_4$ alkyl)-C(O)$NR_6R_7$, —$NR_6R_7$, $NR_6R_7$($C_1$–$C_6$ alkyl), $C_1$–$C_6$ hydroxyalkyl, dihydroxyalkyl, halogen, $C_1$–$C_4$ alkoxy, $CO_2R$, OH, $C_1$–$C_6$ alkoxycarbonyl, $CF_3$, —($C_1$–$C_4$ alkyl)-$NR_{15}$C(O)$NR_{16}R_{17}$, —($C_1$–$C_4$ alkyl)-$NR_{15}$C(O)$R_{18}$; wherein $R_{15}$ is H or $C_1$–$C_6$ alkyl;

$R_{16}$ and $R_{17}$ are independently H or $C_1$–$C_6$ alkyl; or $R_{16}$, $R_{17}$, and the nitrogen to which they are attached form a morpholinyl ring; and $R_{18}$ is $C_1$–$C_6$ alkyl optionally substituted with —O—($C_2$–$C_6$ alkanoyl, $C_1$–$C_6$ hydroxyalkyl, $C_1$–$C_6$ dihydroxyalkyl, $C_1$–$C_6$ alkoxy, $C_1$–$C_6$ alkoxy $C_1$–$C_6$ alkyl; amino $C_1$–$C_6$ alkyl, mono or dialkylamino $C_1$–$C_6$ alkyl.

11. A compound according to claim 10, wherein $R_5$ is of the formula:

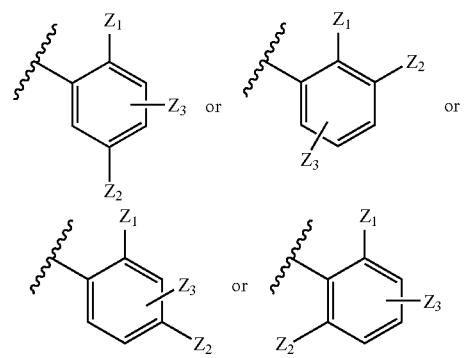

$Z_1$ is H, halogen, $C_1$–$C_4$ alkyl, $C_1$–$C_4$ haloalkyl, $C_1$–$C_4$ hydroxyalkyl, $C_1$–$C_4$ dihydroxyalkyl, or $C_1$–$C_4$ alkoxy; and $Z_2$ is $C_1$–$C_4$ alkyl, —C(O)$NR_6R_7$, —($C_1$–$C_4$ alkyl)-C(O)$NR_6R_7$, —$NR_6R_7$, $NR_6R_7$($C_1$–$C_6$ alkyl), $C_1$–$C_6$ hydroxyalkyl, $C_1$–$C_6$ dihydroxyalkyl, halogen, $C_1$–$C_4$ alkoxy, $CO_2R$, OH, $C_1$–$C_6$ alkoxycarbonyl, or $C_1$–$C_4$ haloalkyl;

$Z_3$ is H, $C_1$–$C_4$ alkyl, —C(O)$NR_6R_7$, —($C_1$–$C_4$ alkyl)-C(O)$NR_6R_7$, —$NR_6R_7$, $NR_6R_7$($C_1$–$C_6$ alkyl), $C_1$–$C_6$ hydroxyalkyl, $C_1$–$C_6$ dihydroxyalkyl, halogen, $C_1$–$C_4$ alkoxy, $CO_2R$, OH, $C_1$–$C_6$ alkoxycarbonyl, or $C_1$–$C_4$ haloalkyl;

wherein $R_6$ and $R_7$ at each occurrence are independently H, OH, $C_1$–$C_6$ alkyl, amino $C_1$–$C_4$ alkyl, NH($C_1$–$C_6$ alkyl) alkyl, N($C_1$–$C_6$ alkyl)($C_1$–$C_6$ alkyl)$C_1$–$C_6$ alkyl, $C_1$–$C_6$ hydroxyalkyl, $C_1$–$C_6$ dihydroxyalkyl, $C_1$–$C_6$ alkoxy $C_1$–$C_6$ alkyl, —$SO_2$($C_1$–$C_6$ alkyl), —$SO_2NH_2$, —$SO_2$NH($C_1$–$C_6$ alkyl), —$SO_2$N($C_1$–$C_6$ alkyl)($C_1$–$C_6$ alkyl), or $C_1$–$C_6$ alkanoyl, each of which is optionally substituted with 1, 2, or 3 groups that are independently halogen, OH, SH, $C_3$–$C_6$ cycloalkyl, $C_1$–$C_4$ alkoxy, $C_1$–$C_4$ alkyl, OH, $CF_3$, or $OCF_3$.

12. A compound according to claim 11, wherein R$_5$ is of the formula:

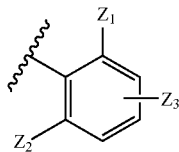

wherein

Z$_1$ is H, halogen, C$_1$–C$_4$ alkyl, C$_1$–C$_4$ haloalkyl, C$_1$–C$_4$ hydroxyalkyl, C$_1$–C$_4$ dihydroxyalkyl, or C$_1$–C$_4$ alkoxy; and Z$_2$ is C$_1$–C$_4$ alkyl, —C(O)NR$_6$R$_7$, —(C$_1$–C$_4$ alkyl)-C(O)NR$_6$R$_7$, —NR$_6$R$_7$, NR$_6$R$_7$(C$_1$–C$_6$ alkyl), C$_1$–C$_6$ hydroxyalkyl, C$_1$–C$_6$ dihydroxyalkyl, halogen, C$_1$–C$_4$ alkoxy, CO$_2$R, OH, C$_1$–C$_6$ alkoxycarbonyl, or C$_1$–C$_4$ haloalkyl;

Z$_3$ is H, C$_1$–C$_4$ alkyl, —C(O)NR$_6$R$_7$, —(C$_1$–C$_4$ alkyl)-C(O)NR$_6$R$_7$, —NR$_6$R$_7$, NR$_6$R$_7$(C$_1$–C$_6$ alkyl), C$_1$–C$_6$ hydroxyalkyl, C$_1$–C$_6$ dihydroxyalkyl, halogen, C$_1$–C$_4$ alkoxy, CO$_2$R, OH, C$_1$–C$_6$ alkoxycarbonyl, or C$_1$–C$_4$ haloalkyl, wherein R$_6$ and R$_7$ at each occurrence are independently H, OH, C$_1$–C$_6$ alkyl, amino C$_1$–C$_4$ alkyl, NH(C$_1$–C$_6$ alkyl) alkyl, N(C$_1$–C$_6$ alkyl)(C$_1$–C$_6$ alkyl)C$_1$–C$_6$ alkyl, C$_1$–C$_6$ hydroxyalkyl, C$_1$–C$_6$ dihydroxyalkyl, C$_1$–C$_6$ alkoxy C$_1$–C$_6$ alkyl, —SO$_2$(C$_1$–C$_6$ alkyl), —SO$_2$NH$_2$, —SO$_2$NH(C$_1$–C$_6$ alkyl), —SO$_2$N(C$_1$–C$_6$ alkyl)(C$_1$–C$_6$ alkyl), or C$_1$–C$_6$ alkanoyl, each of which is optionally substituted with 1, 2, or 3 groups that are independently halogen, OH, SH, C$_3$–C$_6$ cycloalkyl, C$_1$–C$_4$ alkoxy, C$_1$–C$_4$ alkyl, OH, CF$_3$, or OCF$_3$.

13. A compound according to claim 11, wherein R$_5$ is of the formula:

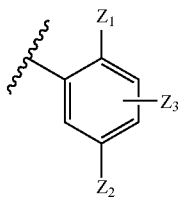

wherein

Z$_1$ is H, halogen, C$_1$–C$_4$ alkyl, C$_1$–C$_4$ haloalkyl, C$_1$–C$_4$ hydroxyalkyl, C$_1$–C$_4$ dihydroxyalkyl, or C$_1$–C$_4$ alkoxy; and Z$_2$ is C$_1$–C$_4$ alkyl, —C(O)NR$_6$R$_7$, —(C$_1$–C$_4$ alkyl)-C(O)NR$_6$R$_7$, —NR$_6$R$_7$, NR$_6$R$_7$(C$_1$–C$_6$ alkyl), C$_1$–C$_6$ hydroxyalkyl, C$_1$–C$_6$ dihydroxyalkyl, halogen, C$_1$–C$_4$ alkoxy, CO$_2$R, OH, C$_1$–C$_6$ alkoxycarbonyl, or C$_1$–C$_4$ haloalkyl;

Z$_3$ is H, C$_1$–C$_4$ alkyl, —C(O)NR$_6$R$_7$, —(C$_1$–C$_4$ alkyl)-C(O)NR$_6$R$_7$, —NR$_6$R$_7$, NR$_6$R$_7$(C$_1$–C$_6$ alkyl), C$_1$–C$_6$ hydroxyalkyl, C$_1$–C$_6$ dihydroxyalkyl, halogen, C$_1$–C$_4$ alkoxy, CO$_2$R, OH, C$_1$–C$_6$ alkoxycarbonyl, or C$_1$–C$_4$ haloalkyl, wherein R$_6$ and R$_7$ at each occurrence are independently H, OH, C$_1$–C$_6$ alkyl, amino C$_1$–C$_4$ alkyl, NH(C$_1$–C$_6$ alkyl) alkyl, N(C$_1$–C$_6$ alkyl)(C$_1$–C$_6$ alkyl)C$_1$–C$_6$ alkyl, C$_1$–C$_6$ hydroxyalkyl, C$_1$–C$_6$ dihydroxyalkyl, C$_1$–C$_6$ alkoxy C$_1$–C$_6$ alkyl, —SO$_2$(C$_1$–C$_6$ alkyl), —SO$_2$NH$_2$, —SO$_2$NH(C$_1$–C$_6$ alkyl), —SO$_2$N(C$_1$–C$_6$ alkyl)(C$_1$–C$_6$ alkyl), or C$_1$–C$_6$ alkanoyl, each of which is optionally substituted with 1, 2, or 3 groups that are independently halogen, OH, SH, C$_3$–C$_6$ cycloalkyl, C$_1$–C$_4$ alkoxy, C$_1$–C$_4$ alkyl, OH, CF$_3$, or OCF$_3$.

14. A compound according to claim 10, wherein R$_5$ is either

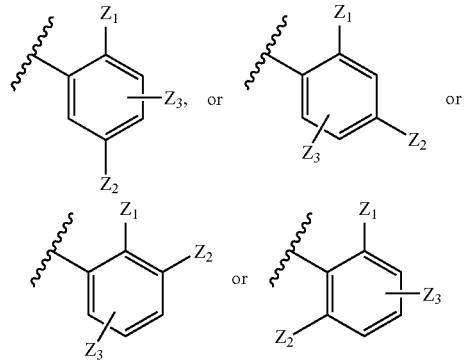

wherein

Z$_1$ is H, halogen, C$_1$–C$_4$ alkyl, C$_1$–C$_4$ haloalkyl, C$_1$–C$_4$ hydroxyalkyl, C$_1$–C$_4$ dihydroxyalkyl, or C$_1$–C$_4$ alkoxy; and Z$_2$ is C$_1$–C$_4$ alkyl, —C(O)NR$_6$R$_7$, —(C$_1$–C$_4$ alkyl)-C(O)NR$_6$R$_7$, —NR$_6$R$_7$, NR$_6$R$_7$(C$_1$–C$_6$ alkyl), C$_1$–C$_6$ hydroxyalkyl, C$_1$–C$_6$ dihydroxyalkyl, halogen, C$_1$–C$_4$ alkoxy, CO$_2$R, C$_1$–C$_6$ alkoxycarbonyl, —(C$_1$–C$_4$ alkyl)-NR$_{15}$C(O)NR$_{16}$R$_{17}$, or —(C$_1$–C$_4$ alkyl)-NR$_{15}$C(O)R$_{18}$;

Z$_3$ is H, C$_1$–C$_4$ alkyl, —C(O)NR$_6$R$_7$, —(C$_1$–C$_4$ alkyl)-C(O)NR$_6$R$_7$, —NR$_6$R$_7$, NR$_6$R$_7$(C$_1$–C$_6$ alkyl), C$_1$–C$_6$ hydroxyalkyl, C$_1$–C$_6$ dihydroxyalkyl, halogen, C$_1$–C$_4$ alkoxy, CO$_2$R, C$_1$–C$_6$ alkoxycarbonyl, —(C$_1$–C$_4$ alkyl)-NR$_{15}$C(O)NR$_{16}$R$_{17}$, or —(C$_1$–C$_4$ alkyl)-NR$_{15}$C(O)R$_{18}$;

R$_6$, R$_7$, and the nitrogen to which they are attached form a piperidinyl, pyrrolidinyl, piperazinyl, or a morpholinyl ring optionally substituted with 1 or 2 groups that are independently alkyl, hydroxy, hydroxy C$_1$–C$_4$ alkyl, C$_1$–C$_4$ dihydroxyalkyl, or halogen;

R$_1$ is H or C$_1$–C$_6$ alkyl;

R$_{16}$ and R$_{17}$ are independently H or C$_1$–C$_6$ alkyl; or

R$_{16}$, R$_{17}$, and the nitrogen to which they are attached form a morpholinyl ring;

R$_{18}$ is C$_1$–C$_6$ alkyl optionally substituted with —O—(C$_2$–C$_6$ alkanoyl, C$_1$–C$_6$ hydroxyalkyl, C$_1$–C$_6$ dihydroxyalkyl, C$_1$–C$_6$ alkoxy, C$_1$–C$_6$ alkoxy C$_1$–C$_6$ alkyl; amino C$_1$–C$_6$ alkyl, mono or dialkylamino C$_1$–C$_6$ alkyl.

15. A compound according to claim 14, wherein R$_5$ is of the formula:

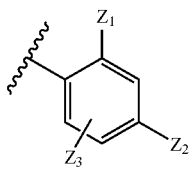

$Z_1$ is H, halogen, $C_1$–$C_4$ alkyl, $C_1$–$C_4$ haloalkyl, $C_1$–$C_4$ hydroxyalkyl, $C_1$–$C_4$ dihydroxyalkyl, or $C_1$–$C_4$ alkoxy; and $Z_2$ is $C_1$–$C_4$ alkyl, —C(O)NR$_6$R$_7$, —($C_1$–$C_4$ alkyl)-C(O)NR$_6$R$_7$, —NR$_6$R$_7$, NR$_6$R$_7$($C_1$–$C_6$ alkyl), $C_1$–$C_6$ hydroxyalkyl, $C_1$–$C_6$ dihydroxyalkyl, halogen, $C_1$–$C_4$ alkoxy, CO$_2$R, $C_1$–$C_6$ alkoxycarbonyl, —($C_1$–$C_4$ alkyl)-NR$_{15}$C(O)NR$_{16}$R$_{17}$, or —($C_1$–$C_4$ alkyl)-NR$_{15}$C(O)R$_{18}$;

$Z_3$ is H, $C_1$–$C_4$ alkyl, —C(O)NR$_6$R$_7$, —($C_1$–$C_4$ alkyl)-C(O)NR$_6$R$_7$, —NR$_6$R$_7$, NR$_6$R$_7$($C_1$–$C_6$ alkyl), $C_1$–$C_6$ hydroxyalkyl, $C_1$–$C_6$ dihydroxyalkyl, halogen, $C_1$–$C_4$ alkoxy, CO$_2$R, $C_1$–$C_6$ alkoxycarbonyl, —($C_1$–$C_4$ alkyl)-NR$_{15}$C(O)NR$_{16}$R$_{17}$, or —($C_1$–$C_4$ alkyl)-NR$_{15}$C(O)R$_{18}$;

$R_6$, $R_7$, and the nitrogen to which they are attached form a piperidinyl, pyrrolidinyl, piperazinyl, or a morpholinyl ring optionally substituted with 1 or 2 groups that are independently alkyl, hydroxy, hydroxy $C_1$–$C_4$ alkyl, $C_1$–$C_4$ dihydroxyalkyl, or halogen;

$R_{15}$ is H or $C_1$–$C_6$ alkyl;

$R_{16}$ and $R_{17}$ are independently H or $C_1$–$C_6$ alkyl; or $R_{16}$, $R_{17}$, and the nitrogen to which they are attached form a morpholinyl ring;

$R_{18}$ is $C_1$–$C_6$ alkyl optionally substituted with —O—($C_2$–$C_6$ alkanoyl, $C_1$–$C_6$ hydroxyalkyl, $C_1$–$C_6$ dihydroxyalkyl, $C_1$–$C_6$ alkoxy, $C_1$–$C_6$ alkoxy $C_1$–$C_6$ alkyl; amino $C_1$–$C_6$ alkyl, mono or dialkylamino $C_1$–$C_6$ alkyl.

16. A compound according to claim 14, wherein $R_5$ is of the formula:

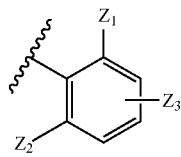

wherein $Z_1$ is H, halogen, $C_1$–$C_4$ alkyl $C_1$–$C_4$ haloalkyl, $C_1$–$C_4$ hydroxyalkyl, $C_1$–$C_4$ dihydroxyalkyl, or $C_1$–$C_4$ alkoxy; and $Z_2$ is $C_1$–$C_4$ alkyl, —C(O)NR$_6$R$_7$, —($C_1$–$C_4$ alkyl)-C(O)NR$_6$R$_7$, —NR$_6$R$_7$, NR$_6$R$_7$($C_1$–$C_6$ alkyl), $C_1$–$C_6$ hydroxyalkyl, $C_1$–$C_6$ dihydroxyalkyl, halogen, $C_1$–$C_4$ alkoxy, CO$_2$R, $C_1$–$C_6$ alkoxycarbonyl, —($C_1$–$C_4$ alkyl)-NR$_{15}$C(O)NR$_{16}$R$_{17}$, or —($C_1$–$C_4$ alkyl)-NR$_{15}$C(O)R$_{18}$;

$Z_3$ is H, $C_1$–$C_4$ alkyl, —C(O)NR$_6$R$_7$, —($C_1$–$C_4$ alkyl)-C(O)NR$_6$R$_7$, —NR$_6$R$_7$, NR$_6$R$_7$($C_1$–$C_6$ alkyl), $C_1$–$C_6$ hydroxyalkyl, $C_1$–$C_6$ dihydroxyalkyl, halogen, $C_1$–$C_4$ alkoxy, CO$_2$R, $C_1$–$C_6$ alkoxycarbonyl, —($C_1$–$C_4$ alkyl)-NR$_{15}$C(O)NR$_{16}$R$_{17}$, or —($C_1$–$C_4$ alkyl)-NR$_{15}$C(O)R$_{18}$;

$R_6$, $R_7$, and the nitrogen to which they are attached form a piperidinyl, pyrrolidinyl, piperazinyl, or a morpholinyl ring, each of which is optionally substituted with 1 or 2 groups that are independently alkyl, hydroxy, hydroxy $C_1$–$C_4$ alkyl, $C_1$–$C_4$ dihydroxyalkyl, or halogen;

$R_{15}$ is H or $C_1$–$C_6$ alkyl;

$R_{16}$ and $R_{17}$ are independently H or $C_1$–$C_6$ alkyl; or $R_{16}$, $R_{17}$, and the nitrogen to which they are attached form a morpholinyl ring;

$R_{18}$ is $C_1$–$C_6$ alkyl optionally substituted with —O—($C_2$–$C_6$ alkanoyl, $C_1$–$C_6$ hydroxyalkyl, $C_1$–$C_6$ dihydroxyalkyl, $C_1$–$C_6$ alkoxy, $C_1$–$C_6$ alkoxy $C_1$–$C_6$ alkyl; amino $C_1$–$C_6$ alkyl, mono or dialkylamino $C_1$–$C_6$ alkyl.

17. A compound according to claim 12, wherein $Y_2$, $Y_4$, and Y are independently halogen; and $Y_1$ and $Y_3$ are both hydrogen.

18. A compound according to claim 17, wherein

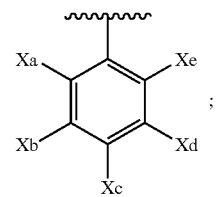

$R_5$ is $X_1$ and $X_2$ are independently H, methyl, NR$_6$R$_7$, —($C_1$–$C_4$ alkyl)-C(O)NR$_6$R$_7$, R$_6$R$_7$N—($C_1$–$C_6$ alkyl)-, —C(O)NR$_6$R$_7$, $C_1$–$C_6$ hydroxyalkyl, $C_1$–$C_6$ dihydroxyalkyl, or —($C_1$–$C_4$ alkyl)-morpholinyl; and $X_a$ and $X_e$ are independently halogen, NH$_2$, NH($C_1$–$C_6$ alkyl), N($C_1$–$C_6$ alkyl)($C_1$–$C_6$ alkyl), methyl, or hydrogen.

19. A compound according to claim 18, wherein one of $X_b$ and $X_c$ is hydrogen and the other is —NR$_6$R$_7$, R$_6$R$_7$N—($C_1$–$C_6$ alkyl)-, —C(O)NR$_6$R$_7$, —SO$_2$NR$_6$R$_7$, or halogen; where $R_6$ and $R_7$ are independently at each occurrence H, $C_1$–$C_6$ alkyl, $C_1$–$C_6$ alkoxy, $C_1$–$C_6$ alkoxy $C_1$–$C_6$ alkyl, $C_1$–$C_6$ alkoxycarbonyl, OH, $C_1$–$C_6$ hydroxyalkyl, $C_1$–$C_6$ dihydroxyalkyl, —($C_1$–$C_4$)alkyl-CO$_2$-alkyl, pyridyl $C_1$–$C_6$ alkyl, $C_1$–$C_6$ alkanoyl, benzyl, phenyl $C_1$–$C_6$ alkoxy, or phenyl $C_1$–$C_6$ alkanoyl, wherein each of the above is unsubstituted or substituted with 1, 2, or 3 groups that are independently, halogen, $C_3$–$C_6$ cycloalkyl, $C_1$–$C_6$ alkoxy, piperidinyl $C_1$–$C_6$ alkyl, morpholinyl $C_1$–$C_6$ alkyl, piperazinyl $C_1$–$C_6$ alkyl, OH, SH, NH$_2$, NH(alkyl), N(alkyl)(alkyl), —O—$C_1$–$C_4$ alkanoyl, $C_1$–$C_4$ alkyl, CF$_3$, or OCF$_3$; or $R_6$, $R_7$, and the nitrogen to which they are attached form a morpholinyl, thiomorpholinyl, piperidinyl, pyrrolidinyl, or piperazinyl ring which is optionally substituted with 1 or 2 groups that are independently $C_1$–$C_4$ alkyl, $C_1$–$C_4$ alkoxy, hydroxy, hydroxy $C_1$–$C_4$ alkyl, $C_1$–$C_4$ dihydroxyalkyl, or halogen.

20. A compound according to claim 19, wherein $R_6$ and $R_7$ are independently at each occurrence H, $C_1$–$C_6$ alkyl, $C_1$–$C_6$ alkoxy, $C_1$–$C_6$ alkoxy $C_1$–$C_6$ alkyl, $C_1$–$C_6$ alkoxycarbonyl, OH, $C_1$–$C_6$ hydroxyalkyl, $C_1$–$C_6$ dihydroxyalkyl, —($C_1$–$C_4$)alkyl-CO$_2$-alkyl, pyridyl $C_1$–$C_6$ alkyl, $C_1$–$C_6$ alkanoyl, benzyl, phenyl $C_1$–$C_6$ alkoxy, or phenyl $C_1$–$C_6$ alkanoyl, wherein each of the above is unsubstituted or substituted with 1, 2, or 3 groups that are independently, halogen, $C_3$–$C_6$ cycloalkyl, $C_1$–$C_6$ alkoxy, piperidinyl $C_1$–$C_6$ alkyl, morpholinyl $C_1$–$C_6$ alkyl, piperazinyl $C_1$–$C_6$ alkyl, OH, NH$_2$, NH(alkyl), N(alkyl)(alkyl), —O—$C_1$–$C_4$ alkanoyl, $C_1$–$C_4$ alkyl, CF$_3$, or OCF$_3$.

21. A compound according to claim 20, wherein $X_a$ is hydrogen, methyl, fluorine, or chlorine; $X_c$ and $X_d$ are both hydrogen;

$X_b$ is —NR$_6$R$_7$, —(C$_1$–C$_4$ alkyl)-C(O)NR$_6$R$_7$, R$_6$R$_7$N—(C$_1$–C$_6$ alkyl)-, —C(O)NR$_6$R$_7$; wherein
R$_6$ and R$_7$ are independently at each occurrence H, C$_1$–C$_6$ alkyl, C$_1$–C$_6$ hydroxyalkyl, C$_1$–C$_4$ dihydroxyalkyl, C$_1$–C$_6$ alkoxy, C$_1$–C$_6$ alkoxy C$_1$–C$_6$ alkyl, or C$_1$–C$_6$ alkanoyl, wherein each of the above is optionally substituted with 1, 2, or 3 groups that are independently OH, SH, halogen, or C$_3$–C$_6$ cycloalkyl.

22. A compound according to claim 17, wherein

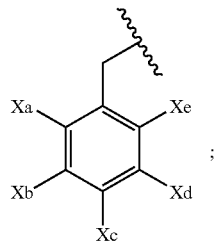

R$_5$ is
X$_a$ is H, fluoro, chloro, or methyl;
X$_e$ is hydrogen, halogen, or methyl; and
X$_b$ is H;
X$_d$ is H or halogen.

23. A compound according to claim 22, wherein
X$_c$ is —SO$_2$NR$_6$R$_7$, or halogen; wherein
R$_6$ and R$_7$ are independently at each occurrence H, C$_1$–C$_6$ alkyl, C$_1$–C$_6$ alkoxy, C$_1$–C$_6$ alkoxy C$_1$–C$_6$ alkyl, C$_1$–C$_6$ alkoxycarbonyl, OH, C$_1$–C$_6$ hydroxyalkyl, C$_1$–C$_6$ dihydroxyalkyl, —(C$_1$–C$_4$)alkyl-CO$_2$-alkyl, pyridyl C$_1$–C$_6$ alkyl, C$_1$–C$_6$ alkanoyl, benzyl, phenyl C$_1$–C$_6$ alkoxy, or phenyl C$_1$–C$_6$ alkanoyl, wherein each of the above is unsubstituted or substituted with 1, 2, or 3 groups that are independently, halogen, C$_3$–C$_6$ cycloalkyl, C$_1$–C$_6$ alkoxy, piperidinyl C$_1$–C$_6$ alkyl, morpholinyl C$_1$–C$_6$ alkyl, piperazinyl C$_1$–C$_6$ alkyl, OH, SH, NH$_2$, NH(alkyl), N(alkyl)(alkyl), —O—C$_1$–C$_4$ alkanoyl, C$_1$–C$_4$ alkyl, CF$_3$, or OCF$_3$; or
R$_6$, R$_7$, and the nitrogen to which they are attached form a morpholinyl, thiomorpholinyl, piperidinyl, pyrrolidinyl, or piperazinyl ring which is optionally substituted with 1 or 2 groups that are independently C$_1$–C$_4$ alkyl, C$_1$–C$_4$ alkoxy, hydroxy, hydroxy C$_1$–C$_4$ alkyl, C$_1$–C$_4$ dihydroxyalkyl, or halogen; or
X$_c$ is fluoro, chloro, —NH$_2$, —NH(C$_1$–C$_6$ alkyl), —N(C$_1$–C$_6$ alkyl)(C$_1$–C$_6$ alkyl), —SO$_2$NH$_2$, —SO$_2$NH(C$_1$–C$_6$ alkyl), —SO$_2$N(C$_1$–C$_6$ alkyl)(C$_1$–C$_6$ alkyl), or piperazinyl, wherein the piperazinyl group is optionally substituted with 1 or 2 groups that are independently C$_1$–C$_4$ alkyl, C$_1$–C$_4$ alkoxy, hydroxy, hydroxy C$_1$–C$_4$ alkyl, C$_1$–C$_4$ dihydroxyalkyl, or halogen.

24. A compound according to claim 22, wherein
X$_c$ is —C(O)NR$_6$R$_7$, —(C$_1$–C$_6$ alkyl)-C(O)NR$_6$R$_7$, —NR$_6$R$_7$, or R$_6$R$_7$N—(C$_1$–C$_6$ alkyl)-; wherein
R$_6$ and R$_7$ are independently at each occurrence H, C$_1$–C$_6$ alkyl, C$_1$–C$_6$ alkoxy, C$_1$–C$_6$ alkoxy C$_1$–C$_6$ alkyl, C$_1$–C$_6$ alkoxycarbonyl, OH, C$_1$–C$_6$ hydroxyalkyl, C$_1$–C$_6$ dihydroxyalkyl, —(C$_1$–C$_4$)alkyl-CO$_2$-alkyl, pyridyl C$_1$–C$_6$ alkyl, C$_1$–C$_6$ alkanoyl, benzyl, phenyl C$_1$–C$_6$ alkoxy, or phenyl C$_1$–C$_6$ alkanoyl, wherein each of the above is unsubstituted or substituted with 1, 2, or 3 groups that are independently, halogen, C$_3$–C$_6$ cycloalkyl, C$_1$–C$_6$ alkoxy, piperidinyl C$_1$–C$_6$ alkyl, morpholinyl C$_1$–C$_6$ alkyl, piperazinyl C$_1$–C$_6$ alkyl, OH, —NH$_2$, —NH(alkyl), —N(alkyl)(alkyl), —O—C$_1$–C$_4$ alkanoyl, C$_1$–C$_4$ alkyl, CF$_3$, or OCF$_3$; or
R$_6$, R$_7$, and the nitrogen to which they are attached form a morpholinyl, thiomorpholinyl, piperidinyl, pyrrolidinyl, or piperazinyl ring which is optionally substituted with 1 or 2 groups that are independently C$_1$–C$_4$ alkyl, C$_1$–C$_4$ alkoxy, hydroxy, hydroxy C$_1$–C$_4$ alkyl, C$_1$–C$_4$ dihydroxyalkyl, or halogen.

25. A compound according to claim 24, wherein R$_6$ is hydrogen; and R$_7$ is C$_1$–C$_6$ alkyl or C$_1$–C$_6$ alkanoyl, each of which is optionally substituted with 1, 2, or 3 groups that are independently NH$_2$, NH(C$_1$–C$_6$ alkyl), N(C$_1$–C$_6$ alkyl)(C$_1$–C$_6$ alkyl), OH, SH, cyclopropyl, or C$_1$–C$_4$ alkoxy.

26. A compound according to claim 25, wherein X$_c$ is —C(O)NR$_6$R$_7$.

27. A compound according to claim 25, wherein X$_c$ is NR$_6$R$_7$, or R$_6$R$_7$N—(C$_1$–C$_6$ alkyl)-.

28. A compound according to claim 1, wherein
X$_a$ is hydrogen;
two of X$_b$, X$_c$, and X$_d$ are hydrogen and the other is —C(O)NR$_6$R$_7$, —(C$_1$–C$_6$ alkyl)-C(O)NR$_6$R$_7$, —NR$_6$R$_7$, R$_6$R$_7$N—(C$_1$–C$_6$ alkyl)- or —CO$_2$—(C$_1$–C$_6$)alkyl; wherein
R$_6$ and R$_7$ are independently at each occurrence H, C$_1$–C$_6$ alkyl, C$_1$–C$_6$ alkoxy, C$_1$–C$_6$ alkoxy C$_1$–C$_6$ alkyl, C$_1$–C$_6$ alkoxycarbonyl, OH, C$_1$–C$_6$ hydroxyalkyl, C$_1$–C$_6$ dihydroxyalkyl, —(C$_1$–C$_4$)alkyl-CO$_2$-alkyl, pyridyl C$_1$–C$_6$ alkyl, C$_1$–C$_6$ alkanoyl, benzyl, phenyl C$_1$–C$_6$ alkoxy, or phenyl C$_1$–C$_6$ alkanoyl, wherein each of the above is unsubstituted or substituted with 1, 2, or 3 groups that are independently, halogen, C$_3$–C$_6$ cycloalkyl, C$_1$–C$_6$ alkoxy, piperidinyl C$_1$–C$_6$ alkyl, morpholinyl C$_1$–C$_6$ alkyl, piperazinyl C$_1$–C$_6$ alkyl, OH, NH$_2$, NH(alkyl), N(alkyl)(alkyl), —O—C$_1$–C$_4$ alkanoyl, C$_1$–C$_4$ alkyl, CF$_3$, or OCF$_3$; or
R$_6$, R$_7$, and the nitrogen to which they are attached form a morpholinyl, piperidinyl, pyrrolidinyl, or piperazinyl ring which is optionally substituted with 1 or 2 groups that are independently C$_1$–C$_4$ alkyl, C$_1$–C$_4$ alkoxy, hydroxy, hydroxy C$_1$–C$_4$ alkyl, C$_1$–C$_4$ dihydroxyalkyl, or halogen; and
X$_e$ is hydrogen, methyl, C$_1$–C$_2$ alkoxy, or halogen.

29. A compound according to claim 28, wherein
X$_b$ is —C(O)NR$_6$R$_7$, —(C$_1$–C$_6$ alkyl)-C(O)NR$_6$R$_7$, —NR$_6$R$_7$, or R$_6$R$_7$N—(C$_1$–C$_6$ alkyl)- wherein
R$_6$ is hydrogen or C$_1$–C$_4$ alkyl;
R$_7$ is OH, C$_1$–C$_6$ alkyl or C$_1$–C$_6$ alkanoyl, wherein the alkyl and alkanoyl groups substituted with 1, 2, or 3 groups that are independently NH$_2$, NH(C$_1$–C$_6$ alkyl), N(C$_1$–C$_6$ alkyl)(C$_1$–C$_6$ alkyl), C$_3$–C$_6$ cycloalkyl, OH, or C$_1$–C$_4$ alkoxy.

30. A compound according to claim 1, wherein
X$_a$ is halogen or methyl;
X$_b$ is H, —NR$_6$R$_7$, R$_6$R$_7$N—(C$_1$–C$_6$ alkyl)-, —C(O)NR$_6$R$_7$, or —CO$_2$—(C$_1$–C$_6$)alkyl;
X$_c$ is —NR$_6$R$_7$, R$_6$R$_7$N—(C$_1$–C$_6$ alkyl)-, —C(O)NR$_6$R$_7$, halogen, —CO$_2$—(C$_1$–C$_6$)alkyl, NH$_2$, NH(C$_1$–C$_6$ alkyl), N(C$_1$–C$_6$ alkyl)(C$_1$–C$_6$ alkyl), —SO$_2$NH$_2$, —SO$_2$NH(C$_1$–C$_6$ alkyl), —SO$_2$N(C$_1$–C$_6$ alkyl)(C$_1$–C$_6$ alkyl), or piperazinyl, wherein the piperazinyl group is optionally substituted with 1 or 2 groups that are independently $C_1$–$C_4$ alkyl, $C_1$–$C_4$ alkoxy, hydroxy, hydroxy $C_1$–$C_4$ alkyl, $C_1$–$C_4$ dihydroxyalkyl, or halogen;

$X_d$ is hydrogen;

$X_e$ is H, methyl, $NH_2$, $NH(C_1$–$C_6$ alkyl) or $N(C_1$–$C_6$ alkyl)($C_1$–$C_6$ alkyl).

31. A compound according to claim 38, wherein $X_1$, $X_2$, $X_a$, $X_b$, $X_c$, $X_d$, and $X_e$ are independently selected from H, OH, halogen, $CF_3$, alkyl, $OCF_3$, pyridyl, pyridazinyl, pyrimidyl, pyrazinyl, thienyl, furyl, pyrrolyl, piperidinyl, piperazinyl, or $C_3$–$C_7$ cycloalkyl, wherein each of the above is optionally substituted with —$NR_6R_7$, —$C(O)NR_6R_7$, —($C_1$–$C_4$ alkyl)-$C(O)NR_6R_7$, $R_6R_7N$—($C_1$–$C_6$ alkyl)-, $C_1$–$C_6$ alkyl, $C_1$–$C_6$ alkoxy, or halogen.

32. A compound which is (−)-3-[3-bromo-4[(2,4-difluorobenzyl)oxy]-6-methyl-2-oxopyridin-1(2H)-yl]-N,4-dimethylbenzamide or a pharmaceutically acceptable salt thereof.

33. A compound which is (+)-3-[3-bromo-4[(2,4-difluorobenzyl)oxy]-6-methyl-2-oxopyridin-1(2H)-yl]-N,4-dimethylbenzamide or a pharmaceutically acceptable salt thereof.

34. A compound of claim 1 which is

3-Chloro-4-(2,4-difluorobenzyloxy)-6-methyl-1-(1H-pyrazol-4-ylmethyl-1H-pyridin-2-one;

2-{[3-bromo-4-[(2,4-difluorobenzyl)oxy]-6-methyl-2-oxopyridin-1(2H)-yl]-methyl}benzonitrile;

3-{[3-bromo-4-[(2,4-difluorobenzyl)oxy]-6-methyl-2-oxopyridin-1(2H)-yl]-methyl}benzonitrile;

4-{[3-bromo-4-[(2,4-difluorobenzyl)oxy]-6-methyl-2-oxopyridin-1(2H)-yl]-methyl}benzonitrile;

4-{[3-bromo-4-[(2,4-difluorobenzyl)oxy]-6-methyl-2-oxopyridin-1(2H)-yl]-methyl}benzamide;

Methyl 4-{[3-bromo-4-[(2,4-difluorobenzyl)oxy]-6-methyl-2-oxopyridin-1(2H)-yl]-methyl}benzate;

Methyl 3-{[3-bromo-4-[(2,4-difluorobenzyl)oxy]-6-methyl-2-oxopyridin-1(2H)-yl]-methyl}benzate;

3-{[3-bromo-4-[(2,4-difluorobenzyl)oxy]-6-methyl-2-oxopyridin-1(2H)-yl]-methyl}benzamide;

2-{[3-bromo-4-[(2,4-difluorobenzyl)oxy]-6-methyl-2-oxopyridin-1(2H)-yl]-methyl}benzamide;

1-[2-(aminomethyl)benzyl]-3-bromo-4-[(2,4-difluorobenzyl)oxy]-6-methylpyridin-1(2H)-yl-one;

3-bromo-1-[3-(bromomethyl)benzyl]-4[(2,4-difluorobenzyl)oxy]-6-methylpyridin-2(1H)-one;

3-bromo-1-[4-(bromomethyl)benzyl]-4-[(2,4-difluorobenzyl)oxy]-6-methylpyridin-2(1H)-one;

1-[4-(aminomethyl)benzyl]-3-bromo-4-[(2,4-difluorobenzyl)oxy]-6-methylpyridin-2(1H)-one;

1-[3-(aminomethyl)benzyl]-3-bromo-4-[(2,4-difluorobenzyl)oxy]-6-methylpyridin-2(1H)-one;

1-[3-((morpholin-4-yl)methyl)benzyl]-3-bromo-4-[(2,4-difluorobenzyl)oxy]-6-methylpyridin-2(1H)-one;

1-[3-((dimethylamino)methyl)benzyl]-3-bromo-4-[(2,4-difluorobenzyl)oxy]-6-methylpyridin-2(1H)-one;

1-[3-((isopropylamino)methyl)benzyl]-3-bromo-4-[(2,4-difluorobenzyl)oxy]-6-methylpyridin-2(1H)-one;

1-[3-((piperidin-1-yl)methyl)benzyl]-3-bromo-4-[(2,4-difluorobenzyl)oxy]-6-methylpyridin-2(1H)-one;

1-[3-((2-hydroxyethyl)amino)methyl)benzyl]-3-bromo-4-[(2,4-difluorobenzyl)oxy]-6-methylpyridin-2(1H)-one;

1-[3-((bis(2-hydroxyethyl)amino)methyl)benzyl]-3-bromo-4-[(2,4-difluorobenzyl)oxy]-6-methylpyridin-2(1H)-one;

1-[3-((piperazin-1-yl)methyl)benzyl]-3-bromo-4-[(2,4-difluorobenzyl)oxy]-6-methylpyridin-2(1H)-one;

3-{[3-bromo-4-[(2,4-difluorobenzyl)oxy]-6-methyl-2-oxopyridin-1(2H)-yl]methyl}benzoic acid;

1-[3-((1-oxoethyl)aminomethyl)benzyl]-3-bromo-4-[(2,4-difluorobenzyl)oxy]-6-methylpyridin-2(1H)-one;

1-[3-(carbomethoxyaminomethyl)benzyl]-3-bromo-4-[(2,4-difluorobenzyl)oxy]-6-methylpyridin-2(1H)-one;

1-[3-(methylsulfonylaminomethyl)benzyl]-3-bromo-4-[(2,4-difluorobenzyl)oxy]-6-methylpyridin-2(1H)-one;

1-[3-(glycolylaminomethyl)benzyl]-3-bromo-4-[(2,4-difluorobenzyl)oxy]-6-methylpyridin-2(1H)-one;

1-[3-(aminocarbonylaminomethyl)benzyl]-3-bromo-4-[(2,4-difluorobenzyl)oxy]-6-methylpyridin-2(1H)-one;

1-[4-(isopropylaminomethyl)benzyl]-3-bromo-4-[(2,4-difluorobenzyl)oxy]-6-methylpyridin-2(1H)-one;

1-[4-(morpholin-4-ylmethyl)benzyl]-3-bromo-4-[(2,4-difluorobenzyl)oxy]-6-methylpyridin-2(1H)-one;

1-[4-(dimethylaminomethyl)benzyl]-3-bromo-4-[(2,4-difluorobenzyl)oxy]-6-methylpyridin-2(1H)-one;

1-[4-(piperidin-1-ylmethyl)benzyl]-3-bromo-4-[(2,4-difluorobenzyl)oxy]-6-methylpyridin-2(1H)-one;

1-[4([bis(2-hydroxyethyl)amino]methyl)benzyl]-3-bromo-4-[(2,4-difluorobenzyl)oxy]-6-methylpyridin-2(1H)-one;

1-[4-((2-etholyl)aminomethyl)benzyl]-3-bromo-4-[(2,4-difluorobenzyl)oxy]-6-methylpyridin-2(1H)-one;

1-[4-piperazin-1-ylmethyl)benzyl]-3-bromo-4-[(2,4-difluorobenzyl)oxy]-6-methylpyridin-2(1H)-one;

1-[4-(methoxycarbonylaminomethyl)benzyl]-3-bromo-4-[(2,4-difluorobenzyl)oxy]-6-methylpyridin-2(1H)-one;

1-[4-(acetylaminomethylbenzyl]-3-bromo-4-[(2,4-difluorobenzyl)oxy]-6-methylpyridin-2(1H)-one;

1-[4-(methylsulfonylaminomethyl)benzyl]-3-bromo-4-[(2,4-difluorobenzyl)oxy]-6-methylpyridin-2(1H)-one;

1-[4-(carbamylaminomethyl)benzyl]-3-bromo-4-[(2,4-diflorobenzyl)oxy]-6-methylpyridin-2(1H)-one;

4-(4-{[3-bromo-4-[(2,4-difluorobenzyl)oxy]-6-methyl-2-oxopyridin-1(2H)-yl]methyl}benzoyl)piperazine-1-carboxamide;

N-(4-{[3-bromo-4-[(2,4-difluorobenzyl)oxy]-6-methyl-2-oxopyridin-1(2H)-yl]methyl}benzyl)-2-methoxyacetamide;

methyl 2-(4-((4-(2,4-difluorobenzyloxy)-3-bromo-6-methyl-2-oxopyridin-1(2H)-yl)methyl)benzylcarbamoyl)acetate;

N-(4-((4-(2,4-difluorobenzyloxy)-3-bromo-6-methyl-2-oxopyridin-1(2H)-yl)methyl)benzyl)-2-hydroxy-2-methylpropanamide;

N-(4-((4-(2,4-difluorobenzyloxy)-3-bromo-6-methyl-2-oxopyridin-1(2H)-yl)methyl)benzyl)-1-hydroxycyclopropanecarboxamide;

N-(4-((4-(2,4-difluorobenzyloxy)-3-bromo-6-methyl-2-oxopyridin-1(2H)-yl)methyl)benzyl)-2-aminoacetamide;

N-(4-((4-(2,4-difluorobenzyloxy)-3-bromo-6-methyl-2-oxopyridin-1(2H)-yl)methyl)benzyl)-2-hydroxyacetamide;

N-(4-((4-(2,4-difluorobenzyloxy)-3-bromo-6-methyl-2-oxopyridin-1(2H)-yl)methyl)benzyl)-2-(1-oxoethylamino)acetamide;

1-{4-[(4-acetylpiperazin-1-yl)carbonyl]benzyl}-3-bromo-4-[(2,4-difluorobenzyl)oxy]-6-methylpyridin-2(1H)-one;

3-bromo-4-[(2,4-difluorobenzyl)oxy]-6-methyl-1-(4-{[4-(methylsulfonyl)piperazin-1-yl]carbonyl}benzyl)pyridin-2(1H)-one;

3-Bromo-4-[(2,4-diflurorbenzyl)oxy]-1-[3-(hydroxymethyl)phenyl]-6-methylpyridin-2(1H)-one;

Methyl-4-[3-bromo-4-[(difluorobenzyl)oxy]-6-methyl-2-oxopyridin-1-(2H)-yl]benzoate;

or pharmaceutically acceptable salts thereof.

35. A comyound of claim 1 which is

4-[3-bromo-4-[(difluorobenzyl)oxy]-6-methyl-2-oxopyridin-1(2H)-yl]benzoic acid;

4-(Benzyloxy)-1-(3-fluorobenzyl)-3-(trifluoromethyl)pyridin-2(1H)-one;

4-{[3-bromo-4-[(2,4-difluorobenzyloxy-6-methyl-2-oxopyridin-1(2H)-yl]methyl}benzoic acid;

3-Bromo-4-[(2,4-difluorobenzyl)oxy]-1-[4-(hydroxymethyl)benzyl]-6-methylpyridin-2(1H)-one;

3-Bromo-4-[(2,4-diflurobenzyl)oxy]-1-[4-(1-hydroxy-1-methylethyl)benzyl]-6-methylpyridin-2(1H)-one;

3-bromo-4-[(2,4-difluorobenzyl)oxy]-6-methyl-1-{4-[(methylamino)methyl]benzyl}pyridin-2(1H)-one;

4-[(2,4-diflurobenzyl)oxy]-1-(4-methoxybenzyl)-6-methylpyridin-2(1H)-one;

3-bromo-4-[(2,4-difluorobenzyl)oxy]-1-(4-methoxybenzyl)-6-methylpyridin-2(1H)-one;

3-bromo-4-[(2,4-difluorobenzyl)oxy]-1-(4-hydroxybenzyl)-6-methylpyridin-2(1H)-one;

3-bromo-4-[(2,4-difluorobenzyl)oxy]-1{4-[(4-hydroxy-4-methylpiperidin-1-yl)carbonyl]benzyl}-6-methylpyridin-2(1H)-one;

4-{[3-bromo-4-[(2,4-difluorobenzyloxy-6-methyl-2-oxypyridin-1(2H)-yl]methyl}-N-(2-hydroxy-2-methylpropyl)benzamide;

3-bromo-4-[(2,4-difluorobenzyl)oxy]-1{4-[(4-hydroxypiperidin-1-yl)carbonyl]benzyl}-6-methylpyridin-2(1H)-one;

4-{[3-bromo-4-[(2,4-difluorobenzyl)oxy]-6-methyl-2-oxopyridin-1(2H)-yl]methyl}-N-(2-hydroxyethyl)benzamide;

3-bromo-4-(2,4-difluorophenoxy)-6-methyl-1-[4-((aminoethyl)aminocarbonyl)benzyl]pyridin-2(1H)-one;

3-bromo-4-(2,4-difluorophenoxy)-6-methyl-1-[4-((aminopropyl)aminocarbonyl)benzyl]pyridin-2(1H)-one;

3-bromo-4-(2,4-difluorophenoxy)-6-methyl-1-[4-(hydroxyaminocarbonyl)benzyl]pyridin-2(1H)-one;

3-bromo-4-(2,4-difluorophenoxy)-6-methyl-1-[4-((aminomethyl)aminocarbonyl)benzyl]pyridin-2(1H)-one;

3-bromo-4-(2,4-difluorophenoxy)-6-methyl-1-[4-(dimethylaminocarbonyl)benzyl]pyridin-2(1H)-one;

3-bromo-4-(2,4-difluorophenoxy)-6-methyl-1-[4-(diethanol-2-ylaminocarbonyl)benzyl]pyridin-2(1H)-one;

3-bromo-4-(2,4-difluorophenoxy)-6-methyl-1-[4-(isoyropylaminocarbonyl)benzyl]pyridin-2(1H)-one;

3-bromo-4-(2,4-difluorophenoxy)-6-methyl-1-[4-((dimethylaminoethyl)aminocarbonyl)benzyl]pyridin-2(1H)-one;

3-bromo-4-(2,4-difluorophenoxy)-6-methyl-1-[4-((methoxyethyl)aminocarbonyl)benzyl]pyridin-2(1H)-one;

3-bromo-4-(2,4-difluorophenoxy)-6-methyl-1-[4-((ethanol-2-yl)methylaminocarbonyl)benzyl]pyridin-2(1H)-one;

3-bromo-4-(2,4-difluorophenoxy)-6-methyl-1-[4-((methoxyethyl)methylaminocarbonyl)benzyl]pyridin-2(1H)-one;

4-{[3-bromo-4-[(2,4-difluorobenzyl)oxy]-6-methyl-2-oxopyridin-1(2H)-yl]-N-(2-hydroxyethyl)benzamide;

4-(4-(2,4-difluorobenzyloxy)-3-bromo-6-methyl-2-oxopyridin-1(2H)-yl)-N-(2-aminoethyl)benzamide;

4-(4-(2,4-difluorobenzyloxy)-3-bromo-6-methyl-2-oxopyridin-1(2H)-yl)-N-(3-aminopropyl)benzamide;

4-(4-(2,4-difluorobenzyloxy)-3-bromo-6-methyl-2-oxopyridin-1(2H)-yl)-N-hydroxybenzamide;

4-(4-(2,4-difluorobenzyloxy)-3-bromo-6-methyl-2-oxopyridin-1(2H)-yl)-N-methylbenzamide;

4-(4-(2,4-difluorobenzyloxy)-3-bromo-6-methyl-2-oxopyridin-1(2H)-yl)-N,N-dimethylbenzamide;

4-(4-(2,4-difluorobenzyloxy)-3-bromo-6-methyl-2-oxopyridin-1(2H)-yl)-N,N-bis(2-hydroxyethyl)benzamide;

4-(4-(2,4-difluorobenzyloxy)-3-bromo-6-methyl-2-oxopyridin-1(2H)-yl)-N-isopropylbenzamide;

4-[3-bromo-4-[(2,4-difluorobenzyl)oxy]-6-methyl-2-oxopyridin-1(2H)-yl]benzamide;

Methyl-4-{[3-chloro-4-[(2,4-difluorobenzyl)oxy]-6-methyl-2-oxopyridin-1(2H)-yl]methyl}benzoate;

3-{[3-bromo-4-[(2,4-difluorobenzyl)oxy]-6-methyl-2-oxopyridin-1(2H)-yl]methyl}-N-methylbenzamide;

3-((4-(2,4-difluorobenzyloxy)-3-bromo-6-methyl-2-oxopyridin-1(2H)-yl)methyl)-N-(2-aminoethyl)benzamide;

3-((4-(2,4-difluorobenzyloxy)-3-bromo-6-methyl-2-oxopyridin-1(2H)-yl)methyl)-N-(3-aminopropyl)benzamide;

3-((4-(2,4-difluorobenzyloxy)-3-bromo-6-methyl-2-oxopyridin-1(2H)-yl)methyl)-N-hydroxybenzamide;

3-((4-(2,4-difluorobenzyloxy)-3-bromo-6-methyl-2-oxopyridin-1(2H)-yl)methyl)-N,N-dimethylbenzamide;

3-((4-(2,4-difluorobenzyloxy)-3-bromo-6-methyl-2-oxopyridin-1(2H)-yl)methyl)-N-(2-hydroxyethyl)benzamide;

3-((4-(2,4-difluorobenzyloxy)-3-bromo-6-methyl-2-oxopyridin-1(2H)-yl)methyl)-N,N-bis(2-hydroxyethyl)benzamide;

3-((4-(2,4-difluorobenzyloxy)-3-bromo-6-methyl-2-oxopyridin-1(2H)-yl)methyl)-N-isopropylbenzamide;

N-(3-{[3-bromo-4-[(2,4-difluorobenzyl)oxy]-6-methyl-2-oxopyridin-1(2H)-yl]methyl}benzyl]-2-methoxyacetamide;

N-(3-((4-(2,4-difluorobenzyloxy)-3-bromo-6-methyl-2-oxopyridin-1(2H)-yl)methyl)benzyl)-2-aminoacetamide;

N-(3-((4-(2,4-difluorobenzyloxy)-3-bromo-6-methyl-2-oxopyridin-1(2H)-yl)methyl)benzyl)-2-(1-oxoethylamino)acetamide;

N-(3-((4-(2,4-difluorobenzyloxy)-3-bromo-6-methyl-2-oxopyridin-1(2H)-yl)methyl)benzyl)-3-oxobutanamide;

N-(3-{[3-bromo-4-[(2,4-difluorobenzyl)oxy]-6-methyl-2-oxopyridin-1(2H)-yl]methyl}benzyl)-2-hydroxy-2-methylpropanamide;

N-(3-{[3-bromo-4-[(2,4-difluorobenzyl)oxy]-6-methyl-2-oxopyridin-1(2H)-yl]methyl}benzyl)-1-hydroxycyclopropanecarboxamide;

N'-(3-{[3-bromo-4-[(2,4-difluorobenzyl)oxy]-6-methyl-2-oxopyridin-1(2H)-yl]methyl}benzyl)-N,N-dimethylurea;

1-(3-((4-(2,4-difluorobenzyloxy)-3-bromo-6-methyl-2-oxopyridin-1(2H)-yl)methyl)benzyl)-3-methylurea;

3-[3-bromo-4-[(2,4-difluorobenzyl)oxy]-6-methyl-2-oxopyridin-1(2H)-yl]benzoic acid;

Ethyl 3-[3-bromo-4-[(2,4-difluorobenzyl)oxy]-6-methyl-2-oxopyridin-1(2H)-yl]benzoate;

3-[3-bromo-4-[(2,4-difluorobenzyl)oxy]-6-methyl-2-oxopyridin-1(2H)-yl]-N-methylbenzamide;

or pharmaceutically acceptable salts thereof.

36. A compound of claim 1 which is 3-(4-(2,4-difluorobenzyloxy)-3-bromo-6-methyl-2-oxopyridin-1(2H)-yl)-N-(2-aminoethyl)benzamide;

3-(4-(2,4-difluorobenzyloxy)-3-bromo-6-methyl-2-oxopyridin-1(2H)-yl)-N-(3-aminopropyl)benzamide;

3-(4-(2,4-difluorobenzyloxy)-3-bromo-6-methyl-2-oxopyridin-1(2H)-yl)-N-hydroxybenzamide;

3-(4-(2,4-difluorobenzyloxy)-3-bromo-6-methyl-2-oxopyridin-1(2H)-yl)-N,N-dimethylbenzamide;

3-(4-(2,4-difluorobenzyloxy)-3-bromo-6-methyl-2-oxopyridin-1(2H)-yl)-N-(2-hydroxyethyl)benzamide;

3-(4-(2,4-difluorobenzyloxy)-3-bromo-6-methyl-2-oxopyridin-1(2H)-yl)-N-isopropylbenzamide;

3-(4-(2,4-difluorobenzyloxy)-3-bromo-6-methyl-2-oxopyridin-1(2H)-yl)-N-(2-(dimethylamino)ethyl)benzamide;

3-(4-(2,4-difluorobenzyloxy)-3-bromo-6-methyl-2-oxopyridin-1(2H)-yl)-N-(2-methoxyethyl)benzamide;

3-(4-(2,4-difluorobenzyloxy)-3-bromo-6-methyl-2-oxopyridin-1(2H)-yl)-N-(2-(dimethylamino)ethyl)-N-methylbenzamide;

3-(4-(2,4-difluorobenzyloxy)-3-bromo-6-methyl-2-oxopyridin-1(2H)-yl)-N-(2-hydroxyethyl)-N-methylbenzamide;

3-(4-(2,4-difluorobenzyloxy)-3-bromo-6-methyl-2-oxopyridin-1(2H)-yl)-N-(2-methoxyethyl)-N-methylbenzamide; 3-[3-bromo-4-[(2,4-difluorobenzyl)oxy]-6-methyl-2-oxopyridin-1(2H)-yl]benzamide;

3-[3-chloro-4-[(2,4-difluorobenzy)oxy]-6-methyl-2-oxopyridin-1(2H)-yl]benzoic acid;

3-chloro-4-[(2,4-difluorobenzyl)oxy]-1-[3-(hydroxymethyl)phenyl]-6-methylpyridin-2(1H)-one;

1-[3-(aminomethyl)phenyl]-3-bromo-4-[(2,4-difluorobenzyl)oxy]-6-methylpyridin-2(1H)-one;

N-{3-[3-bromo-4-[(2,4-difluorobenzyl)oxy]-6-methyl-2-oxopyridin-1(2H)-yl]benzyl}methanesulfonamide;

N-(3-(4-(2,4-difluorobenzyloxy)-3-bromo-6-methyl-2-oxopyridin-1(2H)-yl)benzyl)acetamide;

methyl 3-(4-(2,4-difluorobenzyloxy)-3-bromo-6-methyl-2-oxopyridin-1(2H)-yl)benzylcarbamate;

N-{3-[3-bromo-4-[(2,4-difluorobenzyl)oxy]-6-methyl-2-oxopyridin-1(2H)-yl]benzyl}-2-methoxyacetamide;

N-(3-(4-(2,4-difluorobenzyloxy)-3-bromo-6-methyl-2-oxopyridin-1(2H)-yl)benzyl)-2-aminoacetamide;

N-(3-(4-(2,4-difluorobenzyloxy)-3-bromo-6-methyl-2-oxopyridin-1(2H)-yl)benzyl)-2-hydroxyacetamide;

N'-{3-[3-bromo-4-[(2,4-difluorobenzyl)oxy]-6-methyl-2-oxopyridin-1(2H)-yl]benzyl}-N,N-dimethylurea;

1-(3-(4-(2,4-difluorobenzyloxy)-3-bromo-6-methyl-2-oxopyridin-1(2H)-yl)benzyl)-3-methylurea;

N-{3-[3-bromo-4-[(2,4-difluorobenzyl)oxy]-6-methyl-2-oxopyridin-1(2H)-yl]benzyl}urea;

3-bromo-4-[(2,4-difluorobenzyl)oxy]-1-{3-[(dimethylamino)methyl]phenyl}-6-methylpyridin-2(1H)-one;

3-bromo-4-[(2,4-difluorobenzyloxy]-6-methyl-1-(2-morpholin-4-ylethyl)pyridin-2(1H)-one;

3-bromo-1-(4-bromo-2,6-difluorophenyl)-4-[(2,4-difluorobenzyl)oxy]-6-methylpyridin-2(1H)-one;

3-bromo-4-[(2,4-difluorobenzyl)oxy]-6-methyl-1-(2,4,6-trifluorophenyl)pyridin-2(1H)-one;

3-chloro-4-[(2,4-difluorobenzyl)oxy]-6-methyl-1-(2,4,6-trifluorophenyl)pyridin-2(1H)-one;

3-bromo-4-[(2,4-difluorobenzyl)oxy]-6-(hydroxymethyl)-1-(2,4,6-trifluorophenyl)pyridin-2(1H)-one;

3-chloro-4-[(2,4-difluorobenzyl)oxy]-6-(hydroxymethyl)-1-(2,4,6-trifluorophenyl)pyridin-2(1H)-one;

3-bromo-4-[(2,4-difluorobenzyl)oxy]-1-(2,6-difluoro-4-morpholin-4-ylphenyl)-6-methylpyridin-2(1H)-one;

3-bromo-4-[(2,4-difluorobenzyl)oxy]-1-[2,6-difluoro-4-(4-methylpiperazin-1-yl)phenyl]-6-methylpyridin-2(1H)-one;

3-chloro-4-[(2,4-difluorobenzyl)oxy]-1-[2,6-difluoro-4-(4-methylpiperazin-1-yl)phenyl]-6-methylpyridin-2(1H)-one;

3-bromo-4-[(2,4-difluorobenzyl)oxy]-1-[4-(dimethylamino)-2,6-difluorophenyl]-6-methylpyridin-2(1H)-one;

3-bromo-4-[(2,4-difluorobenzyl)oxy]-1-{2,6-difluoro-4-[(2-hydroxyethyl)(methyl)amino]phenyl}-6-methylpyridin-2(1H)-one;

3-bromo-1-(3,5-dibromo-2,6-difluoro-4-hydroxyobenyl)-4-[(2,4-difluorobenzyl)oxy]-6-methylpyridin-2(1H)-one;

2-{4-[3-bromo-4-[(2,4-difluorobenzyl)oxy]-6-methyl-2-oxopyridin-1(2H)-yl]-3,5-difluorophenoxyl}acetamide;

3-bromo-4-[(2,4-difluorobenzyl)oxy]-1-[2,6-difluoro-4-(2-hydroxyethoxy)phenyl]-6-methypyridin-2(1H)-one;

3-bromo-1-(2,6-difluorophenyl)-4-{[4-fluoro-2-(hydroxymethyl)benzyl]oxy}-6-methylpyridin-2(1H)-one;

3-chloro-1-(2,6-difluorophenyl)-4-{[4-fluoro-2-(hydroxymethyl)benzyl]oxy}-6-methylpyridin-2(1H)-one;

3-[3-bromo-4-[(2,4-difluorobenzyl)oxy]-6-methyl-2-oxopyridin-1(2H)-yl]-2-methyl)-N-(2-morpholin-4-ylethyl)benzamide;

3-(4-(2,4-difluorobenzyloxy)-3-bromo-6-methyl-2-oxopyridin-1(2H)-yl)-N-(2-methoxyethyl)-2-methylbenzamide;

3-(4-(2,4-difluorobenzyloxy)-3-bromo-6-methyl-2-oxopyridin-1(2H)-yl)-N,N,2-trimethylbenzamide;

3-(4-(2,4-difluorobenzyloxy)-3-bromo-6-methyl-2-oxopyridin-1(2H)-yl)-N-(2-hydroxyethyl)-2-methylbenzamide;

3-(4-(2,4-difluorobenzyloxy)-3-bromo-6-methyl-2-oxopyridin-1(2H)-yl)-N,2-dimethylbenzamide;

3-(4-(2,4-difluorobenzyloxy)-3-bromo-6-methyl-2-oxopyridin-1(2H)-yl)-N-(2-hydroxyethyl)-N,2-dimethylbenzamide;

4-(2,4-difluorobenzyloxy)-1-(3-(4-methylpiperazin-1-yl)carbonyl-2-methylphenyl)-3-bromo-6-methylpyridin-2(1H)-one;

4-(2,4-difluorobenzyloxy)-1-(3-(morpholin-4-yl)carbonyl-2-methylphenyl)-3-bromo-6-methylpyridin-2(1H)-one;

3-(4-(2,4-difluorobenzyloxy)-3-bromo-6-methyl-2-oxopyridin-1(2H)-yl)-N-(2-methoxyethyl)-N,2-dimethylbenzamide;

or pharmaceutically acceptable salts thereof.

37. A compound of claim 1 which is 3-(4-(2,4-difluorobenzyloxy)-3-bromo-6-methyl-2-oxopyridin-1(2H)-yl)-2-methylbenzamide;

3-bromo-4-[(2,4-difluorobenzyl)oxy]-1-[3-(hydroxymethyl)-2-methylphenyl]-6-methylpyridin-2(1H)-one;

3-[3-chloro-4-[(2,4-difluorobenzyhoxy)-6-methyl-2-oxopyridin-1(2H)-yl]-N-(2-methoxyethyl)-2-methylbenzamide;

3-[3-chloro-4-[(2,4-difluorobenzyl)oxy)-6-methyl-2-oxopyridin-1(2H)-yl]-N,2-dimethylbenzamide;

3-[3-chloro-4-[(2,4-difluorobenzyl)oxy)-6-methyl-2-oxopyridin-1(2H)-yl]-N-(2-hydroxyethyl)-2-methylbenzamide;

3-[3-chloro-4-[(2,4-difluorobenzyl)oxy)-6-methyl-2-oxopyridin-1(2H)-yl]-2-methylbenzamide;

3-Bromo-4-[(2,4-difluorobenzyl)oxy]-1-(2,6-dimethylphenyl)-6-methylpyridin-2(1H)-one;

3-Bromo-1-(2,6-dimethylphenyl)-4-[(4-fluorobenzyl)oxy]-6-methylpyridin-2(1H)-one;

3-Bromo-1-(2,6-dimethylphenyl)-6-methyl-4-[(2,4,6-trifluorobenzyl)oxy]pyridin-2(1H)-one;

3-Bromo-4-[(2,6-difluorobenzyl)oxy]-1-(2,6-dimethylphenyl)-6-methylpyridin-2(1H)-one;

3-Bromo-1-(2,6-dichlorophenyl)-4-[(4-fluorobenzyl)oxy]-6-methylpyridin-2(1H)-one;

3-Bromo-1-(2,6-dichlorophenyl)-4-[(2,4-difluorobenzyl)oxy]-6-methylpyridin-2(1H)-one;

3-Bromo-1-(2,6-dichloroyhenyl)-4-[(2,6-difluorobenzyl)oxy]-6-methylpyridin-2(1H)-one;

3-Bromo-4-[(2,4-difluorobenzyl)oxy]-1-(2-methoxy-6-methylphenyl)-6-methylpyridin-2(1H)-one;

4-[3-bromo-4-[(2,4-difluorobenzyl)oxy]-6-methyl-2-oxopyridin-1(2H)-yl]-3,5-dichlorobenzenesulfonamide;

3-Bromo-4-[(2,4-difluorobenzyl)oxy]-1-(2,6-difluorophenyl)-6-methylpyridin-2(1H)-one;

3-Bromo-4-[(2,4-difluorobenzyl)oxy]-1-(2,6-difluorophenyl)-5-iodo-6-methylpyridin-2(1H)-one;

3-Bromo-4-[(2,4-difluorobenzyl)oxy]-1-[2-(dimethylamino)-4,6-difluorophenyl]-6-methylpyridin-2(1H)-one;

3-Bromo-4-[(2,4-difluorobenzyl)oxy]-1-{2,4-difluoro-6-[(2-hydroxyethyl)(methyl)amino]phenyl}-6-methylpyridin-2(1H)-one;

2-({[3-Bromo-1-(2,6-difluorophenyl)-6-methyl-2-oxo-1,2-dihydropyridin-4-yl]oxy}methyl)-5-fluorobenzonitrile;

4-{[2-(Aminomethyl)-4-fluorobenzyl]oxy}-3-bromo-1-(2,6-difluorophenyl)-6-methylpyridin-2(1H)-one trifluoroacetate;

N-[2-({[3-bromo-1-(2,6-difluorophenyl)-6-methyl-2-oxo-1,2-dihydropyridin-4-yl]oxy}methyl)-5-fluorobenzyl]urea;

Methyl 2-({[3-bromo-1-(2,6-difluorophenyl)-6-methyl-2-oxo-1,2-dihydropyridin-4-yl]oxy}methyl)-5-fluorobenzylcarbamate;

N-[2-({[3-bromo-1-(2,6-difluorophenyl)-6-methyl-2-oxo-1,2-dihydropyridin-4-yl]oxy}methyl)-5-fluorobenzyl]-2-hydroxyacetamide;

Ethyl 2-({[3-chloro-1-(2,6-difluorophenyl)-6-methyl-2-oxo-1,2-dihydropyridin-4-yl]oxy}methyl)-5-fluorobenzylcarbamate;

Isobutyl 2-({[3-chloro-1-(2,6-difluorophenyl)-6-methyl-2-oxo-1,2-dihydropyridin-4-yl]oxy}methyl)-5-fluorobenzylcarbamate;

Cycloyronylmethyl 2-({[3-chloro-1-(2,6-difluorophenyl)-6-methyl-2-oxo-1,2-dihydropyridin-4-yl]oxy}methyl)-5-fluorobenzylcarbamate;

1-[(4-amino-2-methylpyrimidin-5-yl)methyl]-3-bromo-4-[(2,4-difluorobenzyl)oxy]-6-methylpyridin-2(1H)-one trifluoroacetate;

1-[(4-amino-2-methylpyrimidin-5-yl)methyl]-3-bromo-4-[(2,4-difluorobenzyl)oxy]-6-methylpyridin-2(1H)-one hydrochloride;

1-[(4-amino-2-methylpyrimidin-5-yl)methyl]-3-chloro-4-[(2,4-difluorobenzyl)oxy]-6-methylpyridin-2(1H)-one trifluoroacetate;

1-[(4-amino-2-methylpyrimidin-5-yl)methyl]-3-chloro-4-[(2,4-difluorobenzyl)oxy]-6-methylpyridin-2(1H)-one hydrochloride;

3-Bromo-4-[(2,4-difluorobenzyl)oxy]-1-(1H-indazol-5-ylmethyl)-6-methylpyridin-2(1H)-one trifluoroacetate;

3-bromo-4-[(2,4-difluorobenzyl)oxy]-6-methyl-1-{[2-(methylthio)pyrimidin-4-yl]methyl}pyridin-2(1H)-one;

3-Bromo-4-[(2,4-difluorobenzyl)oxy]-6-methyl-1-{[2-(methylsulfonyl)pyrimidin-4-yl]methyl}pyridin-2(1H)-one;

4-{[3-Bromo-4-[(2,4-difluorobenzyl)oxy]-6-methyl-2-oxopyridin-1(2H)-yl]methyl}pyrimidine-2-carbonitrile trifluoroacetate;

4-{[2-(Aminomethyl)-4-fluorobenzyl]oxy}-3-bromo-1-(2,6-difluorophenyl)-6-methylpyridin-2(1H)-one trifluoroacetate;

3-Bromo-4-[(2,4-difluorobenzyl)oxy]-1-[(2-methoxypyrimidin-4-yl)methyl]-6-methylpyridin-2(1H)-one trifluoroacetate;

Methyl 4-{[3-bromo-4-[(2,4-difluorobenzyl)oxy]-6-methyl-2-oxopyridin-1(2H)-yl]methyl}pyrimidine-2-carboxylate trifluoroacetate;

3-Bromo-4-[(2,4-difluorobenzyl)oxy]-1-[(2-hydroxypyrimidin-4-yl)methyl]-6-methylpyridin-2(1H)-one trifluoroacetate;

4-{[3-bromo-4-[(2,4-difluorobenzyl)oxy]-6-methyl-2-oxopyridin-1(2H)-yl]methyl}pyrimidine-2-carboxamide trifluoroacetate;

Methyl (4-{[3-bromo-4-[(2,4-difluorobenzyl)oxy]-6-methyl-2-oxopyridin-1(2H)-yl]methyl}pyrimidin-2-yl)methylcarbamate;

3-Bromo-4-[(2,4-difluorobenzyl)oxy]-6-methyl-1-[(5-methylpyrazin-2-yl)methyl]pyridin-2(1H)-one;

3-bromo-4-[(2,4-difluorobenzyl)oxy]-6-methyl-1-(pyrazin-2-ylmethyl)pyridin-2(1H)-one;

3-Bromo-4-[(2,4-difluorobenzyl)oxy]-1-{[5-(hydroxymethyl)pyrazin-2-yl]methyl}-6-methylpyridin-2(1H)-one;

3-Bromo-4-[(2,4-difluorobenzyl)oxy]-1-{5-[(dimethylamino)methyl]pyrazin-2-yl}methyl)-6-methylpyridin-2(1H)-one trifluoroacetate;

3-Bromo-4-[(2,4-difluorobenzyl)oxy]-1-[(5-{[(2-hydroxyethyl)-(methyl)amino]methyl}pyrazin-2-yl)methyl]-6-methylpyridin-2(1H)-one trifluoroacetate;

3-Bromo-4-[(2,4-difluorobenzyl)oxy]-6-methyl-1-({5-[(4-methylpiperazin-1-yl)carbonyl]pyrazin-2-yl}methyl)pyridin-2(1H)-one trifluoroacetate;

3-Bromo-4-[(2,4-difluorobenzyl)oxy]-6-methyl-1-({5-[(4-methylpiperazin-1-yl)carbonyl]pyrazin-2-yl}methyl)pyridin-2(1H)-one;

5-{[3-Bromo-4-[(2,4-difluorobenzyl)oxy]-6-methyl-2-oxopyridin-1(2H)-yl]methyl}-N-(2-hydroxyethyl)-N-methylpyrazine-2-carboxamide;

5-{[3-Bromo-4-[(2,4-difluorobenzyl)oxy]-6-methyl-2-oxopyridin-1(2H)-yl]methyl}-N-(2,3-dihydroxypropyl)pyrazine-2-carboxamide;

5-{[3-Bromo-4-[(2,4-difluorobenzyl)oxy]-6-methyl-2-oxopyridin-1(2H)-yl]methyl}-N-(2-hydroxyethyl)pyrazine-2-carboxamide;

or pharmaceutically acceptable salts thereof.

38. A compound of claim 1 which is

3-Bromo-4-[(2,4-difluorobenzyl)oxy]-1-{[5-(methoxymethyl)pyrazin-2-yl]methyl}-6-methylpyridin-2(1H)-one;

3-Bromo-4-[(2,4-difluorobenzyl)oxy]-1-({5-[(2-methoxyethoxy)methyl]pyrazin-2-yl}methyl)-6-methylpyridin-2(1H)-one;

(5-{[3-Bromo-4-[(2,4-difluorobenzyl)oxy]-6-methyl-2-oxopyridin-1(2H)-yl]methyl}pyrazin-2-yl)methyl carbamate;

1-benzyl-3-bromo-4-[(2,4-difluorobenzyl)oxy]-6-methylpyridin-2(1H)-one;

3-chloro-4-[(2,4-difluorobenzyl)oxy]-1-(2,6-difluorophenyl)-6-methylpyridin-2(1H)-one;

3-bromo-1-(4-fluorobenzyl)-4-[(4-fluorobenzyl)amino]-6-methylpyridin-2(1H)-one;

3-bromo-1-(cyclpyropylmethyl)-4-[(2,4-difluorobenzyl)oxy]-6-methylpyridin-2(1H)-one;

3-bromo-4-[(2,4-difluorobenzyl)oxy]-6-methyl-1-(pyridin-4-ylmethyl)pyridin-2(1H)-one;

4-(4-fluorobenzyloxy)-3-bromo-6-methyl-1-((pyridin-4-yl)methyl)pyridin-2(1H)-one;

4-(2,4,6-trifluorobenzyloxy)-3-bromo-6-methyl-1-((pyridin-4-yl)methyl)pyridin-2(1H)-one;

4-(2,6-difluorobenzyloxy)-3-bromo-6-methyl-1-((pyridin-4-yl)methyl)pyridin-2(1H)-one;

3-bromo-4-[(2,4-difluorobenzyl)oxy]-6-methyl-1-(pyridin-3-ylmethyl)pyridin-2(1H)-one;

4-(4-fluorobenzyloxy)-3-bromo-6-methyl-1-((pyridin-3-yl)methyl)pyridin-2(1H)-one;

4-(2,4,6-trifluorobenzyloxy)-3-bromo-6-methyl-1-(pyridin-3-yl)methyl)pyridin-2(1H)-one;

4-(2-fluorobenzyloxy)-3-bromo-6-methyl-1-((pyridin-3-yl)methyl)pyridin-2(1H)-one;

4-(2,4,5-trifluorobenzyloxy)-3-bromo-6-methyl-1-((pyridin-3-yl)methyl)pyridin-2(1H)-one;

4-(4-chloro-2-fluorobenzyloxy)-3-bromo-6-methyl-1-((pyridin-3-yl)methyl)pyridin-2(1H)-one;

4-(2-chloro-4-fluorobenzyloxy)-3-bromo-6-methyl-1-((pyridin-3-yl)methyl)pyridin-2(1H)-one;

3-bromo-4-[(2,4-difluorobenzyl)oxy]-6-methyl-1-(pyridin-2-ylmethyl)pyridin-2(1H)-one;

4-(2,6-difluorobenzyloxy)-3-bromo-6-methyl-1-((pyridin-3-yl)methyl)pyridin-2(1H)-one;

4-(4-fluorobenzyloxy)-3-bromo-6-methyl-1-((pyridin-2-yl)methyl)pyridin-2(1H)-one;

4-(2,4,6-trifluorobenzyloxy)-3-bromo-6-methyl-1-((pyridin-2-yl)methyl)pyridin-2(1H)-one;

4-(2,4,5-trifluorobenzyloxy)-3-bromo-6-methyl-1-((pyridin-2-yl)methyl)pyridin-2(1H)-one;

3-bromo-4-[2-(4-fluorophenyl)ethyl]-6-methyl-1-(pyridin-3-ylmethyl)pyridin-2(1H)-one;

3-bromo-4-[2-(4-fluorophenyl)ethyl]-6-methyl-1-(pyridin-4-ylmethyl)pyridin-2(1H)-one;

3-chloro-4-[(2,4-difluorobenzyl)oxy]-6-methyl-1-(pyridin-3-ylmethyl)pyridin-2(1H)-one;

1-[(4-amino-2-methylpyrimidin-5-ylmethyl]-3-bromo-6-methyl-4-[(2,4,6-trifluorobenzyl)oxy]pyridin-2(1H)-one trifluoroacetate;

3-bromo-4-[(2,4-difluorobenzyl)oxy]-6-methyl-1-{[2-methyl-4-(methylamino)pyrimidin-5-yl]methyl}pyridin-2(1H)-one trifluoroacetate;

ethyl N-(5-{[3-bromo-4-[(2,4-difluorobenzyl)oxy]-6-methyl-2-oxopyridin-1(2H)-yl]methyl}-2-methylpyrimidin-4-yl)glycinate trifluoroacetate;

N-(5-{[3-chloro-4-[(2,4-difluorobenzyl)oxy]-6-methyl-2-oxopyridin-1(2H)-yl]methyl}-2-methylpyrimidin-4-yl)-2-hydroxyacetamide trifluoroacetate;

3-chloro-4-[(2,4-difluorobenzyl)oxy]-1-({5-[(4-hydroxypiperidin-1-yl)carbonyl]pyrazin-2-yl}methyl)-6-methylpyridin-2(1H)-one;

5-{[3-chloro-4-[(2,4-difluorobenzyl)oxy]-6-methyl-2-oxopyridin-1(2H)-yl]methyl}-N-(3-hydroxy-2,2-dimethylpropyl)pyrazine-2-carboxamide;

5-{[3-chloro-4-[(2,4-difluorobenzyl)oxy]-6-methyl-2-oxopyridin-1(2H)-yl]methyl}-N-(2,2,2-trifluoroethyl-pyrazine-2-carboxamide;

1-allyl-3-bromo-4-[(2,4-difluorobenzyl)oxy]-6-methylpyridin-2(1H)-one;

1-allyl-3-chloro-4-[(2,4-difluorobenzyl)oxy]-6-methylpyridin-2(1H)-one;

Methyl (2E)-4-[3-bromo-4-[(2,4-difluorobenzyl)oxy]-6-methyl-2-oxopyridin-1(2H)-yl]but-2-enoate;

3-bromo-4-[(2,4-difluorobenzyl)oxy]-6-methyl-1-prop-2-ynylpyridin-2(1H)-one;

3-Bromo-4-[(2,4-difluorobenzyl)oxy]-6-(hydroxymethyl)-1-(pyridin-3-ylmethyl)pyridin-2(1H)-one;

3-bromo-4-[(2,4-difluorobenzyl)oxy]-6-[(dimethylamino)methyl-1-(pyridin-3-ylmethyl)pyridin-2(1H)-one;

3-bromo-4-[(2,4-difluorobenzyl)oxy]-1-(2,6-difluorophenyl)-6-(hydroxymethyl)pyridin-2(1H)-one;

3-chloro-4-[(2,4-difluorobenzyl)oxy]-1-(2,6-difluorophenyl)-6-(hydroxymethyl)pyridin-2(1H)-one;

5-bromo-4-[(2,4-difluorobenzyl)oxy]-1-(2,6-difluorophenyl)-6-oxo-1,6-dihydropyridine-2-carbaldehyde;

3-bromo-4-[(2,4-difluorobenzyl)oxy]-1-(2,6-difluorophenyl)-6-[(dimethylamino)methyl]pyridin-2(1H)-one;
3-bromo-4-[(2,4-difluorobenzyl)oxy]-1-(2,6-difluorophenyl)-6-(morpholin-4-ylmethyl)pyridin-2(1H)-one;
3-bromo-4-[(2,4-difluorobenzyl)oxy]-1-(2,6-difluorophenyl)-6-{[(2-methoxyethyl)amino]methyl}pyridin-2(1H)-one;
5-bromo-4-[(2,4-difluorobenzyl)oxy]-1-(2,6-difluorophenyl)-6-oxo-1,6-dihydropyridine-2-carboxylic acid;
Methyl 4-[3-bromo-4-[(2,4-difluorobenzyl)oxy]-6-methyl-2-oxopyridin-1(2H)-yl]-3-methylbenzoate;
4-(4-(2,4-difluorobenzyloxy)-3-bromo-6-methyl-2-oxopyridin-1(2H)-yl)-3-methylbenzoic acid;
4-(2,4-difluorobenzyloxy)-3-bromo-1-(4-(hydroxymethyl)-2-methylphenyl)-6-methylpyridin-2(1H)-one;
4-(4-(2,4-difluorobenzyloxy)-3-bromo-6-methyl-2-oxopyridin-1(2H)-yl)-N-(2-methoxyethyl)-3-methylbenzamide;
4-(4-(2,4-difluorobenzyloxy)-3-bromo-6-methyl-2-oxopyridin-1(2H)-yl)-N,3-dimethylbenzamide;
or pharmaceutically acceptable salts thereof.

39. A compound of claim 1 which is
3-bromo-4-[(2,4-difluorobenzyl)oxy]-6-methyl-1-(2-methyl-4-vinylphenyl)pyridin-2(1H)-one;
3-bromo-4-[(2,4-difluorobenzyl)oxy]-1-[4-(1,2-dihydroxyethyl)-2-methylphenyl]-6-methylpyridin-2(1H)-one;
methyl 3-[3-bromo-4-[(2,4-difluorobenzyl)oxy]-6-methyl-2-oxopyridin-1(2H)-yl]-4-chlorobenzoate;
3-[3-bromo-4-[(2,4-difluorobenzyl)oxy]-6-methyl-2-oxopyridin-1(2H)-yl]-4-chlorobenzoic acid;
3-bromo-4-[(2,4-difluorobenzyl)oxy]-1-[5-(hydroxymethyl)-2-methylphenyl]-6-methylpyridin-2(1H)-one;
3-chloro-4-[(2,4-difluorobenzyl)oxy]-1-[5-(hydroxymethyl)-2-methylphenyl]-6-methypyridin-2(1H)-one;
3-bromo-4-[(2,4-difluorobenzyl)oxy]-1-{5-[(dimethylamino)methyl]-2-methylphenyl}-6-methylpyridin-2(1H)-one hydrochloride;
3-bromo-4-[(2,4-difluorobenzyl)oxy]-1-{5-[(ispropylamino)methyl]-2-methylphenyl}-6-methylpyridin-2(1H)-one hydrochloride;
3-[3-bromo-4-[(2,4-difluorobenzyl)oxy]-6-methyl-2-oxopyridin-1(2H)-yl]-N-(2-hydroxyethyl)-4-methylbenzamide;
3-(4-(2,4-difluorobenzyloxy)-3-bromo-6-methyl-2-oxopyridin-1(2H)-yl)-N-(2-methoxyethyl)-4-methylbenzamide;
3-(4-(2,4-difluorobenzyloxy)-3-bromo-6-methyl-2-oxopyridin-1(2H)-yl)-N,4-dimethylbenzamide;
3-(4-(2,4-difluorobenzyloxy)-3-bromo-6-methyl-2-oxopyridin-1(2H)-yl)-N,N,4-trimethylbenzamide;
3-bromo-4-[(2,4-difluorobenzyl)oxy]-1-[5-(1-hydroxy-1-methylethyl)-2-methylphenyl]-6-methylpyridin-2(1H)-one;
methyl 3-[3-chloro-4-[(2,4-difluorobenzyl)oxy]-6-methyl-2-oxopyridin-1(2H)-yl]-4-methylbenzoate;
methyl 4-[3-bromo-4-[(2,4-difluorobenzyl)oxy]-6-methyl-2-oxopyridin-1(2H)-yl]-3-chlorobenzoate;
3-bromo-4-[(2,4-difluorobenzyl)amino]-6-methyl-1-(pyridin-4-ylmethyl)pyridin-2(1H)-one;
3-bromo-4-[(2,4-difluorobenzyl)amino]-6-methyl-1-(pyridin-3-ylmethyl)pyridin-2(1H)-one;
3-bromo-4-[(2,4-difluorobenzyl)amino]-1-(2,6-difluorophenyl)-6-methylpyridin-2(1H)-one;
3-chloro-4-[(2,4-difluorobenzyl)amino]-1-(2,6-difluorophenyl)-6-methylpyridin-2(1H)-one;
3-{[3-chloro-4-[(2,4-difluorobenzyl)amino]-6-methyl-2-oxopyridin-1(2H)-yl]methyl}benzonitrile;
4-{[3-chloro-4-[(2,4-difluorobenzyl)amino]-6-methyl-2-oxopyridin-1(2H)-yl]methyl}benzonitrile;
3-bromo-4-[(2,4-difluorobenzyl)oxy]-1-[2-fluoro-5-(hydroxymethyl)phenyl]-6-methylpyridin-2(1H)-one;
3-[3-chloro-4-[(2,4-difluorobenzyl)oxy]-6-methyl-2-oxopyridin-1(2H)-yl]-4-fluorobenzoic acid;
3-[3-chloro-4-[(2,4-difluorobenzyl)oxy]-6-methyl-2-oxopyridin-1(2H)-yl]-4-fluoro-N-methylbenzamide;
3-(4-(2,4-difluorobenzyloxy)-3-chloro-6-methyl-2-oxopyridin-1(2H)-yl)-4-fluoro-N,N-dimethylbenzamide;
3-(4-(2,4-difluorobenzyloxy)-3-chloro-6-methyl-2-oxopyridin-1(2H)-yl)-4-fluoro-N-(2-hydroxyethyl)benzamide;
3-(4-(2,4-difluorobenzyloxy)-3-chloro-6-methyl-2-oxopyridin-1(2H)-yl)-4-fluoro-N-(2-methoxyethyl)benzamide;
3-(4-(2,4-difluorobenzyloxy)-3-chloro-6-methyl-2-oxopyridin-1(2H)-yl)-4-fluoro-N-(2-hydroxyethyl)-N-methylbenzamide;
3-(4-(2,4-difluorobenzyloxy)-3-chloro-6-methyl-2-oxopyridin-1(2H)-yl)-4-fluoro-N-(3-hydroxyoropyl)benzamide;
3-(4-(2,4-difluorobenzyloxy)-3-chloro-6-methyl-2-oxopyridin-1(2H)-yl)-4-fluoro-N-(2,3-dihydroxypropyl)benzamide;
3-[3-bromo-4-[(2,4-difluorobenzyl)oxy]-6-methyl-2-oxopyridin-1(2H)-yl]-4-fluorobenzoic acid;
3-[3-bromo-4-[(2,4-difluorobenzyl)oxy]-6-methyl-2-oxopyridin-1(2H)-yl]-4-methoxybenzoic acid;
3-[3-bromo-4-[(2,4-difluorobenzyl)oxy]-6-methyl-2-oxopyridin-1(2H)-yl]-4-methoxy-N-methylbenzamide;
3-[3-bromo-4-[(2,4-difluorobenzyl)oxy]-6-methyl-2-oxopyridin-1(2H)-yl]-4-methoxy-N,N-dimethylbenzamide;
1-[(5-aminomethyl)-2-fluorophenyl]-3-chloro-4-[(2,4-difluorobenzyl)oxy]-6-methylpyridin-2(1H)-one hydrochloride;
3-[3-chloro-4-[(2,4-difluorobenzyl)oxy]-6-methyl-2-oxopyridin-1(2H)-yl]-4-fluoro-N-[2-hydroxy-1-(hydroxymethyl)ethyl]benzamide;
N-(3-(4-(2,4-difluorobenzyloxy)-3-chloro-6-methyl-2-oxopyridin-1(2H)-yl)-4-fluorobenzyl)acetamide;
N-(3-(4-(2,4-difluorobenzyloxy)-3-chloro-6-methyl-2-oxopyridin-1(2H)-yl)-4-fluorobenzyl)-2-methoxyacetamide;
N-(3-(4-(2,4-difluorobenzyloxy)-3-chloro-6-methyl-2-oxopyridin-1(2H)-yl)-4-fluorobenzyl)-methylsulfonamine;
1-(3-(4-(2,4-difluorobenzyloxy)-3-chloro-6-methyl-2-oxopyridin-1(2H)-yl)-4-fluorobenzyl)urea;
2-({[3-chloro-1-(2,6-difluorophenyl)-6-methyl-2-oxo-1,2-dihydropyridin-4-yl]oxy}methyl)-5-fluorobenzonitrile;

4-{[2-(aminomethyl)-4-fluorobenzyl]oxy}-3-chloro-1-(2,6-difluorophenyl)-6-methylpyridin-2(1H)-one trifluoroacetate;

methyl 2-((3-chloro-1-(2,6-difluorophenyl)-1,2-dihydro-6-methyl-2-oxopyridin-4-yloxy)methyl)-5-fluorobenzylcarbamate;

N-(2-((3-chloro-1-(2,6-difluorophenyl)-1,2-dihydro-6-methyl-2-oxopyridin-4-yloxy)methyl)-5-fluorobenzyl)-2,2,2-trifluoroacetamide;

isopropyl 2-((3-chloro-1-(2,6-difluorophenyl)-1,2-dihydro-6-methyl-2-oxopyridin-4-yloxy)methyl)-5-fluorobenzylcarbamate;

1-(2-((3-chloro-1-(2,6-difluorophenyl)-1,2-dihydro-6-methyl-2-oxopyridin-4-yloxy)methyl)-5-fluorobenzyl)-3-ethylurea;

tetrahydrofuran-3-yl 2-((3-chloro-1-(2,6-difluorophenyl)-1,2-dihydro-6-methyl-2-oxopyridin-4-yloxy)methyl)-5-fluorobenzylcarbamate;

propyl 2-((3-chloro-1-(2,6-difluorophenyl)-1,2-dihydro-6-methyl-2-oxopyridin-4-yloxy)methyl)-5-fluorobenzylcarbamate;

allyl 2-((3-chloro-1-(2,6-difluorophenyl)-1,2-dihydro-6-methyl-2-oxopyridin-4-yloxy)methyl)-5-fluorobenzylcarbamate;

prop-2-ynyl 2-((3-chloro-1-(2,6-difluorophenyl)-1,2-dihydro-6-methyl-2-oxopyridin-4-yloxy)methyl)-5-fluorobenzylcarbamate;

or pharmaceutically acceptable salts thereof.

40. A compound of claim 1 which is t-butyl 2-((3-chloro-1-(2,6-difluorophenyl)-1,2-dihydro-6-methyl-2-oxopyridin-4-yloxy)methyl)-5-fluorobenzylcarbamate;

1-(2-((3-chloro-1-(2,6-difluorophenyl)-1,2-dihydro-6-methyl-2-oxopyridin-4-yloxy)methyl)-5-fluorobenzyl)-3-tert-butylurea;

N-(2-((3-chloro-1-(2,6-difluoroyhenyl)-1,2-dihydro-6-methyl-2-oxopyridin-4-yloxy)methyl)-5-fluorobenzyl)-2-(propylsulfonyl)acetamide;

N-(2-((3-chloro-1-(2,6-difluorophenyl)-1,2-dihydro-6-methyl-2-oxopyridin-4-yloxy)methyl)-5-fluorobenzyl)-2-(ethylsulfonyl)acetamide;

1-(2-((3-chloro-1-(2,6-difluorophenyl)-1,2-dihydro-6-methyl-2-oxopyridin-4-yloxy)methyl)-5-fluorobenzyl)-3-isopropylurea 1-(2-((3-chloro-1-(2,6-difluorophenyl)-1,2-dihydro-6-methyl-2-oxopyridin-4-yloxy)methyl)-5-fluorobenzyl)-3-methylurea;

3-(2-((3-chloro-1-(2,6-difluorophenyl)-1,2-dihydro-6-methyl-2-oxopyridin-4-yloxy)methyl)-5-fluorobenzyl)-1-tert-butyl-1-methylurea;

1-(2-((3-chloro-1-(2,6-difluorophenyl)-1,2-dihydro-6-methyl-2-oxopyridin-4-yloxy)methyl)-5-fluorobenzyl)-3-cyclpyropylurea;

1-(2-((3-chloro-1-(2,6-difluorophenyl)-1,2-dihydro-6-methyl-2-oxopyridin-4-yloxy)methyl)-5-fluorobenzyl)-3-(2,2,2-trifluoroethyl)urea;

1-(2-((3-chloro-1-(2,6-difluorophenyl)-1,2-dihydro-6-methyl-2-oxopyridin-4-yloxy)methyl)-5-fluorobenzyl)-3-(cyclopropylmethyl)urea;

1-(2-((3-chloro-1-(2,6-difluorophenyl)-1,2-dihydro-6-methyl-2-oxopyridin-4-yloxy)methyl)-5-fluorobenzyl)-3-neopentylurea;

3-(2-((3-chloro-1-(2,6-difluorophenyl)-1,2-dihydro-6-methyl-2-oxopyridin-4-yloxy)methyl)-5-fluorobenzyl)-1,1-dimethylurea;

3-bromo-4-[(2,4-difluorobenzyl)oxy]-1-{[5-(1-hydroxy-1-methylethyl)pyridin-2-yl]methyl}-6-methylpyridin-2(1H)-one;

3-bromo-4-[(2,4-difluorobenzyl)oxy]-1-{[5-(hydroxymethyl)pyridin-2-yl]methyl}-6-methylpyridin-2(1H)-one;

6-{[3-bromo-4-[(2,4-difluorobenzyl)oxy]-6-methyl-2-oxopyridin-1(2H)-yl]methyl}-N-(2-hydroxyethyl)-N-methylnicotinamide;

6-{[3-bromo-4-[(2,4-difluorobenzyl)oxy]-6-methyl-2-oxopyridin-1(2H)-yl]methyl}-N-(2-hydroxyethyl)nicotinamide;

6-{[3-bromo-4-[(2,4-difluorobenzyl)oxy]-6-methyl-2-oxopyridin-1(2H)-yl]methyl}-N,N-dimethylnicotinamide;

3-bromo-4-[(2,4-difluorobenzyl)oxy]-6-methyl-1-[2-(trifluoromethyl)phenyl]pyridin-2(1H)-one;

3-bromo-4-[(2,4-difluorobenzyl)oxy]-1-(2,6-difluorophenyl)-6-methyl-5-vinylpyridin-2(1H)-one;

3-bromo-4-[(2,4-difluorobenzyl)oxy]-1-(2,6-difluorophenyl)-5-(1,2-dihydroxyethyl)-6-methylpyridin-2(1H)-one;

3-bromo-4-[(2,4-difluorobenzyl)oxy]-1-(2,6-difluorophenyl)-5-(hydroxymethyl)-6-methylpyridin-2(1H)-one;

4-(benzyloxy)-3-bromo-1-(2,6-difluorophenyl)-6-methylpyridin-2(1H)-one;

5-bromo-4-[(2,4-difluorobenzyl)oxy]-1-(2,6-difluorophenyl)-2-methyl-6-oxo-1,6-dihydropyridin-3-yl]methyl carbamate;

5-bromo-4-[(2,4-difluorobenzyl)oxy]-1-(2,6-difluorophenyl)-2-methyl-6-oxo-1,6-dihydropyridine-3-carbaldehyde;

5-bromo-4-[(2,4-difluorobenzyl)oxy]-1-(2,6-difluoropbenyl)-2-methyl-6-oxo-1,6-dihydropyridine-3-carbaldehyde oxime;

5-bromo-4-[(2,4-difluorobenzyl)oxy]-1-(2,6-difluorophenyl)-2-methyl-6-oxo-1,6-dihydropyridine-3-carbonitrile;

4-(benzyloxy)-3-bromo-1-(2,6-difluorophenyl)-5-iodo-6-methylpyridin-2(1H)-one;

3-bromo-4-[(2,4-difluorobenzyloxy]-1-(2,6-difluorophenyl)-6-methyl-5-oxiran-2-ylpyridin-2(1H)-one;

4-(benzylamino)-3-bromo-1-(2,6-difluorophenyl)-5-iodo-6-methylpyridin-2(1H)-one;

3-bromo-4-[(2,4-difluorobenzyl)oxy]-1-(2,6-difluorophenyl)-6-methyl-5-[(E)-2-phenylethenyl]pyridin-2(1H)-one;

ethyl 3-bromo-4-[(2,4-difluorobenzyl)oxy]-6-methyl-2-oxo-2H-1,2'-bipyridine-5'-carboxylate;

3-bromo-4-[(2,4-difluorobenzyl)oxy]-5'-(1-hydroxy-1-methylethyl)-6-methyl-2H-1,2-bipyridin-2-one;

3-bromo-4-[(2,4-difluorobenzyl)oxy]-1-(2-furylmethyl)-6-methylpyridin-2(1H)-one;

3-bromo-4-[(2,4-difluorobenzyl)oxy]-6-methyl-1-(thien-2-ylmethy)pyridin-2(1H)-one;

3-bromo-1-(2,6-difluorophenyl)-4-(2-furylmethoxy)-6-methylpyridin-2(1H)-one;

3-bromo-1-[2-fluoro-6-(3-furylmethoxy)phenyl]-4-(3-furylmethoxy)-6-methylpyridin-2(1H)-one;

3-bromo-1-[2-fluoro-6-(thien-3-ylmethoxy)phenyl]-6-methyl-4-(thien-3-ylmethoxy)pyridin-2(1H)-one;

methyl 2-[3-bromo-4-[(2,4-difluorobenzyl)oxy]-6-methyl-2-oxopyridin-1(2H)-yl]-4-[(methylamino)carbonyl]benzoate;
3-[3-bromo-4-[(2,4-difluorobenzyl)oxy]-6-methyl-2-oxopyridin-1(2H)-yl]-4-(1-hydroxy-1-methylethyl)-N-methylbenzamide;
4-[3-bromo-4-[(2,4-difluorobenzyl)oxy]-6-methyl-2-oxopyridin-1(2H)-yl]-3-chlorobenzamide;
3-[3-chloro-4-[(2,4-difluorobenzyl)oxy]-6-methyl-2-oxopyridin-1(2H)-yl]-4-methylbenzamide;
3-[3-chloro-4-[(2,4-difluorobenzyloxy)-6-methyl-2-oxopyridin-1(2H)-yl]-N,4-dimethylbenzamide;
N-{3-[3-chloro-4-[(2,4-difluorobenzyl)oxy]-6-methyl-2-oxopyridin-1(2H)-yl]-4-fluorobenzyl}propanamide;
N-{3-[3-chloro-4-[(2,4-difluorobenzyl)oxy]-6-methyl-2-oxopyridin-1(2H)-yl]-4-fluorobenzyl}dimethylurea;
N-{3-[3-chloro-4-[(2,4-difluorobenzyl)oxy]-6-methyl-2-oxopyridin-1(2H)-yl]-4-fluorobenzyl}-2-hydroxyacetamide;
N-{3-[3-chloro-4-[(2,4-difluorobenzyl)oxy]-6-methyl-2-oxopyridin-1(2H)-yl]-4-fluorobenzyl}-2-hydroxy-2-methylpropanamide;
N-{3-[3-chloro-4-[(2,4-difluorobenzy)oxy]-6-methyl-2-oxopyridin-1(2H)-yl]-4-fluorobenzyl}glycinamide hydrochloride;
3-[3-bromo-4-[(2,4-difluorobenzyl)oxy]-6-methyl-2-oxopyridin-1(2H)-yl]-4-fluorobenzamide;
3-[3-bromo-4-[(2,4-difluorobenzyl)oxy]-6-methyl-2-oxopyridin-1(2H)-yl]-4-fluoro-N-methylbenzamide;
3-[3-bromo-4-[(2,4-difluorobenzyl)oxy]-6-methyl-2-oxopyridin-1(2H)-yl]-4-fluoro-N,N-dimethylbenzamide;
3-bromo-4-[(2,4-difluorobenzyl)oxy]-1-{2-fluoro-5-[(4-methylpiperazin-1-yl)carbonyl]phenyl}-6-methylpyridin-2(1H)-one;

or pharmaceutically acceptable salts thereof.

41. A compound of claim 1 which is
3-(4-(2,4-difluorobenzyloxy)-3-bromo-6-methyl-2-oxopyridin-1(2H)-yl)-4-fluoro-N-(2-hydroxyethyl)-N-methylbenzamide;
3-(4-(2,4-difluorobenzyloxy)-3-bromo-6-methyl-2-oxopyridin-1(2H)-yl)-4-fluoro-N-(2-hydroxy-2-methylpropyl)benzamide;
methyl 4-[3-bromo-4-[(2,4-difluorobenzyl)oxy]-6-methyl-2-oxopyridin-1(2H)-yl]-3-fluorobenzoate;
4-{[3-chloro-4-[(2,4-difluorobenzyl)oxy]-6-methyl-2-oxopyridin-1(2H)-yl]methyl}benzoic acid;
4-{[3-chloro-4-[(2,4-difluorobenzyl)oxy]-6-methyl-2-oxopyridin-1(2H)-yl]methyl}benzamide;
4-{[3-chloro-4-[(2,4-difluorobenzyl)oxy]-6-methyl-2-oxopyridin-1(2H)-yl]methyl}-N,N-dimethylbenzamide;
4-{[3-chloro-4-[(2,4-difluorobenzyl)oxy]-6-methyl-2-oxopyridin-1(2H)-yl]methyl}-N-(2-hydroxy-2-methylpropyl)benzamide;
N-{4-[3-bromo-4-[(2,4-difluorobenzyl)oxy]-6-methyl-2-oxopyridin-1(2H)-yl]benzyl}-2-hydroxyacetamide;
3-[3-chloro-4-[(2,4-difluorobenzyl)oxy]-6-methyl-2-oxopyridin-1(2H)-yl]benzamide;
1-(4-aminobenzyl)-3-bromo-4-[(2,4-difluorobenzyl)oxy]-6-methylpyridin-2(1H)-one;
1-(3-aminobenzyl)-3-bromo-4-[(2,4-difluorobenzyl)oxy]-6-methylpyridin-2(1H)-one;
N-(4-{[3-bromo-4-[(2,4-difluorobenzyl)oxy]-6-methyl-2-oxopyridin-1(2H)-yl]methyl}phenyl)acetamide;
N-(4-((4-(2,4-difluorobenzyloxy)-3-bromo-6-methyl-2-oxopyridin-1(2H)-yl)methyl)phenyl)-2-hydroxyacetamide;
N-(4-((4-(2,4-difluorobenzyloxy)-3-bromo-6-methyl-2-oxopyridin-1(2H)-yl)methyl)phenyl)-(dimethylaminosulfonylcarbonyl)amine;
N-(3-{[3-bromo-4-[(2,4-difluorobenzyl)oxy]-6-methyl-2-oxopyridin-1(2H)-yl]methyl}phenyl)acetamide;
N-(3-((4-(2,4-difluorobenzyloxy)-3-bromo-6-methyl-2-oxopyridin-1(2H)-yl)methyl)phenyl)-(dimethylaminosulfonylcarbonyl)amine;
N-(3-((4-(2,4-difluorobenzyloxy)-3-bromo-6-methyl-2-oxopyridin-1(2H)-yl)methyl)phenyl)-2-hydroxyacetamide;
N-(4-{[3-bromo-4-[(2,4-difluorobenzyl)oxy]-6-methyl-2-oxopyridin-1(2H)-yl]methyl}benzyl)-N'-methylurea;
N-(4-{[3-bromo-4-[(2,4-difluorobenzyl)oxy]-6-methyl-2-oxopyridin-1(2H)-yl]methyl}benzyl)-N'-(2-hydroxy-2-methylpropyl)urea;
N-(4-{[3-bromo-4-[(2,4-difluorobenzyl)oxy]-6-methyl-2-oxopyridin-1(2H)-yl]methyl}benzyl)piperidine-1-carboxamide;
N-(4-{[3-bromo-4-[(2,4-difluorobenzyl)oxy]-6-methyl-2-oxopyridin-1(2H)-yl]methyl}benzyl)morpholine-4-carboxamide;
N-(4-{[3-bromo-4-[(2,4-difluorobenzyl)oxy]-6-methyl-2-oxopyridin-1(2H)-yl]methyl}benzyl)piperazine-1-carboxamide hydrochloride;
N-(4-{[3-bromo-4-[(2,4-difluorobenzyl)oxy]-6-methyl-2-oxopyridin-1(2H)-yl]methyl}benzyl)-N'-(2-hydroxyethyl)urea;
N'-(4-{[3-bromo-4-[(2,4-difluorobenzyl)oxy]-6-methyl-2-oxopyridin-1(2H)-yl]methyl}benzyl)-N,N-dimethylurea;
N-(4-{[3-bromo-4-[(2,4-difluorobenzyl)oxy]-6-methyl-2-oxopyridin-1(2H)-yl]methyl}benzyl)-4-hydroxypiperidine-1-carboxamide;
4-{[3-bromo-4-[(2,4-difluorobenzyl)oxy]-6-methyl-2-oxopyridin-1(2H)-yl]methyl}-N,N-dimethylbenzenesulfonamide;
4-{[3-bromo-4-[(2,4-difluorobenzyl)oxy]-6-methyl-2-oxopyridin-1(2H)-yl]methyl}-N-(2-hydroxyethyl)benzenesulfonamide;
4-{[3-bromo-4-[(2,4-difluorobenzyl)oxy]-6-methyl-2-oxopyridin-1(2H)-yl]methyl}-N-(2-hydroxy-2-methyloropyl)benzenesulfonamide;
3-Chloro-4-(2,4-difluorobenzyloxy)-6-methyl-1-(1H-pyrazol-3-ylmethyl)-1H-pyridin-2-one;
3-Chloro-4-(2,4-difluorobenzyloxy)-6-methyl-1-(2,3-dihydro-1H-indol-5-ylmethyl)-1H-pyridin-2-one;
5-[3-Chloro-4-(2,4-difluorobenzyloxy)-6-methyl-2-oxo-2H-pyridin-1-ylmethyl]-1,3-dihydro-indol-2-one;
N-[(5-{[3-Bromo-4-[(2,4-difluorobenzyl)oxy]-6-methyl-2-oxopyridin-1(2H)-yl]methyl}pyrazin-2-yl)methyl]-N-methylmethanesulfonamide;
Methyl (5-{[3-Bromo-4-[(2,4-difluorobenzyl)oxy]-6-methyl-2-oxopyridin-1(2H)-yl]methyl}pyrazin-2-yl)methyl(methyl)carbamate;
N-[(5-{[3-Bromo-4-[(2,4-difluorobenzyl)oxy]-6-methyl-2-oxopyridin-1(2H)-yl]methyl}pyrazin-2-yl)methyl]-2-hydroxy-N,2-dimethylpropanamide;

5-{[3-Bromo-4-[(2,4-difluorobenzyhoxy]-6-methyl-2-oxopyridin-1(2H)-yl]methyl}-N-(2-hydroxy-2-methylpropyl)pyrazine-2-carboxamide;

1-[(5-Aminopyrazin-2-yl)methyl]-3-bromo-4-[(2,4-difluorobenzyl)oxy]-6-methylpyridin-2(1H)-one trifluoroacetate;

3-Bromo-4-[(2,4-difluorobenzyl)oxy]-6-methyl-1-[(3-methyl-1,2,4-triazin-6-yl)methyl]pyridin-2(1H)-one trifluoroacetate;

3-Bromo-4-[(2,4-difluorobenzyl)oxy]-1-(1H-indazol-5-yl)-6-methylpyridin-2(1H)-one;

3-bromo-4-[(2,4-difluorobenzyl)oxy]-1-(1H-indazol-6-yl)-6-methylpyridin-2(1H)-one;

methyl 2-{[(3-bromo-6-methyl-1-{2-methyl-5-[(methylamino)carbonyl]phenyl}-2-oxo-1,2-dihydropyridin-4-yl)oxy]methyl}-5-fluorobenzylcarbamate;

methyl 2-({[3-bromo-1-(5-{[(2-hydroxyethyl)amino]carbonyl}-2-methylphenyl)-6-methyl-2-oxo-1,2-dihydropyridin-4-yl]oxy}methyl)-5-fluorobenzylcarbamate;

methyl 2-({[3-bromo-1-(5-{[(2-hydroxy-2-methylpropyl)amino]carbonyl}-2-methylphenyl)-6-methyl-2-oxo-1,2-dihydropyridin-4-yl]oxy}methyl)-5-fluorobenzylcarbamate;

methyl 2-({[3-bromo-1-(5-{[(2-methoxyethyl)amino]carbonyl}-2-methylphenyl)-6-methyl-2-oxo-1,2-dihydropyridin-4-yl]oxy}methyl)-5-fluorobenzylcarbamate;

methyl 2-[({1-[5-(aminocarbonyl)-2-methylphenyl]-3-bromo-6-methyl-2-oxo-1,2-dihydropyridin-4-yl}oxy)methyl]-5-fluorobenzylcarbamate;

N-[2-({[3-chloro-1-(2,6-difluorophenyl)-6-methyl-2-oxo-1,2-dihydropyridin-4-yl]oxy}methyl)-5-fluorobenzyl]-N'-phenylurea;

thien-3-ylmethyl 2-({[3-chloro-1-(2,6-difluorophenyl)-6-methyl-2-oxo-1,2-dihydropyridin-4-yl]oxy}methyl)-5-fluorobenzylcarbamate;

ethyl 2-{[(3-bromo-6-methyl-1-{2-methyl-5-[(methylamino)carbonyl]phenyl}-2-oxo-1,2-dihydropyridin-4-yl)oxy]methyl}-5-fluorobenzylcarbamate;

3-[3-bromo-4-{[2-({[(cyclopropylamino)carbonyl]amino}methyl)-4-fluorobenzyl]oxy}-6-methyl-2-oxopyridin-1(2H)-yl]-N,4-dimethylbenzamide;

3-[3-bromo-4-{[2-({[(cyclopropylamino)carbonyl]amino}methyl)-4-fluorobenzyl]oxy}-6-methyl-2-oxopyridin-1(2H)-yl]-4-methylbenzoic acid;

methyl 3-[6-[(acetyloxy)methyl]-3-bromo-4-[(2,4-difluorobenzyl)oxy]-2-oxopyridin-1(2H)-yl]-4-methylbenzoate;

3-[3-bromo-4-[(2,4-difluorobenzyl)oxy]-6-(hydroxymethyl)-2-oxopyridin-1(2H)-yl]-4-methylbenzoic acid;

or pharmaceutically acceptable salts thereof.

42. A compound of claim 1 which is

3-[3-bromo-4-[(2,4-difluorobenzyl)oxy]-6-(hydroxymethyl)-2-oxopyridin-1(2H)-yl]-4-methylbenzoic acid;

3-[3-bromo-4-[(2,4-difluorobenzyl)oxy]-6-(hydroxymethyl)-2-oxopyridin-1(2H)-yl]-N-(2-hydroxyethyl)-4-methylbenzamide;

3-[3-bromo-4-[(2,4-difluorobenzyl)oxy]-6-(hydroxymethyl)-2-oxopyridin-1(2H)-yl]-N,4-dimethylbenzamide;

3-[3-bromo-4-[(2,4-difluorobenzyl)oxy]-6-(hydroxymethyl)-2-oxopyridin-1(2H)-yl]-4-methylbenzamide;

(5-bromo-4-[(2,4-difluorobenzyl)oxy]-1-{2-methyl-5-[(methylamino)carbonyl]phenyl}-6-oxo-1,6-dihydropyridin-2-yl)methyl acetate;

(2E)-4-[3-bromo-4-[(2,4-difluorobenzyl)oxy]-6-methyl-2-oxopyridin-1(2H)-yl]-N-methylbut-2-enamide;

methyl 5-{[3-bromo-4-[(2,4-difluorobenzyl)oxy]-6-methyl-2-oxopyridin-1(2H)-yl]methyl}-2-furoate;

3-[3-bromo-4-[(2,4-difluorobenzyl)oxy]-6-methyl-2-oxopyridin-1(2H)-yl]-4-(hydroxymethyl)-N-methylbenzamide;

2-[3-bromo-4-[(2,4-difluorobenzyl)oxy]-6-methyl-2-oxopyridin-1(2H)-yl]-N,N'-dimethylterephthalamide;

2-[3-bromo-4-[(2,4-difluorobenzyl)oxy]-6-methyl-2-oxopyridin-1(2H)-yl]-N-(4-methylterephthalamide;

methyl 4-(aminocarbonyl)-2-[3-bromo-4-[(2,4-difluorobenzyl)oxy]-6-methyl-2-oxopyridin-1(2H)-yl] benzoate;

2-[3-bromo-4-[(2,4-difluorobenzyl)oxy]-6-methyl-2-oxopyridin-1(2H)-yl]-$N^1,N^1,N^4$-trimethylterephthalamide;

2-[3-bromo-4-[(2,4-difluorobenzyl)oxy]-6-methyl-2-oxopyridin-1(2H)-yl]-4-[(methylamino)carbonyl] benzyl carbamate;

3-bromo-4-[(2,4-difluorobenzyl)oxy]-1-(2,6-difluoro-4-vinylphenyl)-6-methylpyridin-2(1H)-one;

3-bromo-4-[(2,4-difluorobenzyl)oxy]-1-[4-(1,2-dihydroxyethyl)-2,6-difluorophenyl]-6-methylpyridin-2(1H)-one;

4-[3-bromo-4-[(2,4-difluorobenzyl)oxy]-6-methyl-2-oxopyridin-1(2H)-yl]-3,5-difluorobenzaldehyde;

4-[3-bromo-4-[(2,4-difluorobenzyl)oxy]-6-methyl-2-oxopyridin-1(2H)-yl]-3,5-difluorobenzyl carbamate;

4-(2,4-difluorobenzyloxy)-3-chloro-6-methyl-1-((5-methylpyrazin-2-yl)methyl)pyridin-2(1H)-one;

4-(2,4-difluorobenzyloxy)-3-chloro-1-((5-(hydroxymethyl)pyrazin-2-yl)methyl)-6-methylpyridin-2(1H)-one;

4-(2,4-difluorobenzyloxy)-3-bromo-1-((1-(2-hydroxyacetyl)indolin-5-yl)methyl)-6-methylpyridin-2(1H)-one;

1-((1H-pyrazol-3-yl)methyl)-4-(2,4-difluorobenzyloxy)-3-bromo-6-methylpyridin-2(1H)-one;

3-(4-(2,4-difluorobenzyloxy)-3-chloro-6-methyl-2-oxopyridin-1(2H)-yl)-N,4-dimethylbenzamide;

3-(4-(2,4-difluorobenzyloxy)-3-chloro-6-methyl-2-oxopyridin-1(2H)-yl)-4-methylbenzamide;

3-(4-(2,4-difluorobenzyloxy)-3-chloro-6-methyl-2-oxopyridin-1(2H)-yl)-4-fluoro-N-methylbenzamide;

3-(4-(2,4-difluorobenzyloxy)-3-chloro-6-methyl-2-oxopyridin-1(2H)-yl)-4-chloro-N-methylbenzamide;

3-(4-(2,4-difluorobenzyloxy)-3-chloro-6-methyl-2-oxopyridin-1(2H)-yl)-4-fluorobenzamide;

4-(4-(2,4-difluorobenzyloxy)-3-chloro-6-methyl-2-oxopyridin-1(2H)-yl)-N,3-dimethylbenzamide;

4-(2,4-difluorobenzyloxy)-3-chloro-1-(4-(1,2-dihydroxyethyl)-2-methylphenyl)-6-methylpyridin-2(1H)-one;

N-(4-((4-(2,4-difluorobenzyloxy)-3-chloro-6-methyl-2-oxopyridin-1(2H)-yl)methyl)phenyl)-2-hydroxyacetamide;

N-(4-((4-(2,4-difluorobenzyloxy)-3-chloro-6-methyl-2-oxopyridin-1(2H)-yl)methyl)benzyl)-1-hydroxycyclopropanecarboxamide;

N-(4-((4-(2,4-difluorobenzyloxy)-3-chloro-6-methyl-2-oxopyridin-1(2H)-yl)methyl)benzyl)-2-hydroxyacetamide;

N-(4-((4-(2,4-difluorobenzyloxy)-3-chloro-6-methyl-2-oxopyridin-1(2H))-ylmethyl)phenyl)acetamide;

ethyl 2-((3-bromo-1-(2,6-difluorophenyl-1,2-dihydro-6-methyl-2-oxopyridin-4-yloxy)methyl)-5-fluorobenzylcarbamate;

3-(4-(2,4-difluorobenzyloxy)-3-bromo-6-(2-hydroxyethyl)-2-oxopyridin-1(2H)-yl)-N,4-dimethylbenzamide;

4-(2,4-difluorobenzyloxy)-3-bromo-1-(5-(2-hydroxyethyl)-2-methylphenyl)-6-methylpyridin-2(1H)-one;

5-(4-(2,4-difluorobenzyloxy)-3-bromo-6-methyl-2-oxopyridin-1(2H)-yl)-2-(2-hydroxyethyl)-N,4-dimethylbenzamide;

4-(2,4-difluorobenzyloxy)-3-bromo-6-methyl-1-(4-methyl-2-(methylsulfonyl)pyrimidin-5-yl)-pyridin-2(1H)-one;

5-(4-(2,4-difluorobenzyloxy)-3-bromo-6-methyl-2-oxopyridin-1(2H)-yl)-4-methylpyrimidine-2-carbonitrile;

4-(2,4-difluorobenzyloxy)-1-(2-(aminomethyl)-4-methylpyrimidin-5-yl)-3-bromo-6-methylpyridin-2(1H)-one;

4-(2,4-difluorobenzyloxy)-3-bromo-1-(2-((dimethylamino)methyl)-4-methylpyrimidin-5-yl)-6-methylpyridin-2(1H)-one;

N-((5-(4-(2,4-difluorobenzyloxy)-3-bromo-6-methyl-2-oxopyridin-1(2H)-yl)-4-methylpyrimidin-2-yl)methyl)-2-hydroxyacetamide;

5-(4-(2,4-difluorobenzyloxy)-3-bromo-6-methyl-2-oxopyridin-1(2H)-yl)-4-methylpyrimidine-2-carboxylic acid;

5-(4-(2,4-difluorobenzyloxy)-3-bromo-6-methyl-2-oxopyridin-1(2H)-yl)-4-methylpyrimidine-2-carboxamide;

5-(4-(2,4-difluorobenzyloxy)-3-bromo-6-methyl-2-oxopyridin-1(2H)-yl)-N,4-dimethylpyrimidine-2-carboxamide;

N-(4-{[3-chloro-4-[(2,4-difluorobenzyl)oxy]-6-methyl-2-oxopyridin-1(2H)-yl]methyl}benzyl)-2-hydroxyacetamide;

N-(4-{[3-chloro-4-[(2,4-difluorobenzyl)oxy]-6-methyl-2-oxopyridin-1(2H)-yl]methyl}benzyl)-1-hydroxycyclopropanecarboxamide;

4-{[3-bromo-4-[(2,4-difluorobenzyl)oxy]-6-methyl-2-oxopyridin-1(2H)-yl]methyl}benzyl carbamate;

2-[4-{[3-bromo-4-[(2,4-difluorobenzyl)oxy]-6-methyl-2-oxopyridin-1(2H)-yl]methyl}phenyl)amino]-1-methyl-2-oxoethyl acetate;

2-[4-{[3-bromo-4-[(2,4-difluorobenzyl)oxy]-6-methyl-2-oxopyridin-1(2H)-yl]methyl}phenyl)amino]-1,1-dimethyl-2-oxoethyl acetate;

{1-[3-(aminocarbonyl)phenyl]-5-chloro-4-[(2,4-difluorobenzyl)oxy]-6-oxo-1,6-dihydropyridin-2-yl}methyl acetate;

or pharmaceutically acceptable salts thereof.

43. A compound of claim 1 which is 3-bromo-4-[(2,4-difluorobenzyl)oxy]-6-methyl-1-{[2-(methylthio)pyrimidin-5-yl]methyl}pyridin-2(1H)-one;

3-bromo-4-[(2,4-difluorobenzyl)oxy]-6-methyl-1-{[2-(methylsulfonyl)pyrimidin-5-yl]methyl}pyridin-2(1H)-one;

Ethyl 2-({[3-bromo-1-(5-{[(2-hydroxyethyl)amino]carbonyl}-2-methylphenyl)-6-methyl-2-oxo-1,2-dihydropyridin-4-yl]oxy}methyl)-5-fluorobenzylcarbamate;

3-bromo-4-[(2,4-difluorobenzyl)oxy]-1-[5-(1H-imidazol-2-yl)-2-methylphenyl]-6-methylpyridin-2(1H)-one trifluoroacetate;

3-bromo-4-[(2,4-difluorobenzyl)oxy]-1-[5-(5-hydroxy-1H-pyrazol-3-yl)-2-methylphenyl]-6-methylpyridin-2(1H)-one;

3-bromo-4-[(2,4-difluorobenzyl)oxy]-1-[5-(5-hydroxyisoxazol-3-yl)-2-methylphenyl]-6-methylpyridin-2(1H)-one;

5-{[3-bromo-4-[(2,4-difluorobenzyl)oxy]-6-methyl-2-oxopyridin-1(2H)-yl]methyl}-2-furamide;

5-[3-bromo-4-[(2,4-difluorobenzyl)oxy]-6-methyl-2-oxopyridin-1(2H)-yl]-2-furamide;

1-[3,5-bis(hydroxymethyl)phenyl]-3-bromo-4-[(2,4-difluorobenzyloxy]-6-methylpyridin-2(1H)-one;

5-[3-bromo-4-[(2,4-difluorobenzyl)oxy]-6-methyl-2-oxopyridin-1(2H)-yl]isophthalamide;

1-[3,5-bis(1-hydroxy-1-methylethyl)phenyl]-3-bromo-4-[(2,4-difluorobenzyl)oxy]-6-methylpyridin-2(1H)-one;

3-bromo-4-[(2,4-difluorobenzyl)oxy]-1-[4-(hydroxymethyl)phenyl]-6-methylpyridin-2(1H)-one;

3-bromo-4-[(2,4-difluorobenzyl)oxy]-1-[4-(1-hydroxy-1-methylethyl)phenyl]-6-methylpyridin-2(1H)-one;

1-(5-amino-2-fluorophenyl)-3-bromo-4-[(2,4-difluorobenzyl)oxy]-6-methylpyridin-2(1H)-one hydrochloride;

N-{3-[3-bromo-4-[(2,4-difluorobenzyl)oxy]-6-methyl-2-oxopyridin-1(2H)-yl]-4-fluorophenyl}-2-hydroxyacetamide;

N-{3-[3-bromo-4-[(2,4-difluorobenzyl)oxy]-6-methyl-2-oxopyridin-1(2H)-yl]-4-fluorophenyl}-2-hydroxy-2-methylpropanamide;

4-[3-bromo-4-[(2,4-difluorobenzyl)oxy]-6-methyl-2-oxopyridin-1(2H)-yl]-3-fluoro-N,N-dimethylbenzamide;

3-chloro-4-[(2,4-difluorobenzyl)oxy]-1-[(1-glycoloyl-2,3-dihydro-1H-indol-5-yl)methyl]-6-methylpyridin-2(1H)-one;

3-chloro-4-[(2,4-difluorobenzyl)oxy]-1-{[1-(2-hydroxy-2-methylpropanoyl)-2,3-dihydro-1H-indol-5-yl]methyl}-6-methylpyridin-2(1H)-one;

3-chloro-4-[(2,4-difluorobenzyl)oxy]-1-{[1-(methoxyacetyl)-2,3-dihydro-1H-indol-5-yl]methyl}-6-methylpyridin-2(1H)-one;

5-{[3-chloro-4-[(2,4-difluorobenzyl)oxy]-6-methyl-2-oxopyridin-1(2H)-yl]methyl}-N,N-dimethylindoline-1-carboxamide;

or pharmaceutically acceptable salts thereof.

44. A pharmaceutical composition comprising a therapeutically effective amount of a compound of claim 1, or a pharmaceutically acceptable salt thereof, and a pharmaceutically acceptable carrier.

45. A pharmaceutical composition comprising a therapeutically effective amount of (−)-3-[3-bromo-4-[(2,4-difluorobenzyl)oxy]-6-methyl-2-oxopyridin-1(2H)-yl]-N,4-dimethylbenzamide, or a pharmaceutically acceptable salt thereof, and a pharmaceutically acceptable carrier.

* * * * *

UNITED STATES PATENT AND TRADEMARK OFFICE
CERTIFICATE OF CORRECTION

PATENT NO. : 7,067,540 B2
APPLICATION NO. : 10/367987
DATED : June 27, 2006
INVENTOR(S) : Balekudru Devadas et al.

It is certified that error appears in the above-identified patent and that said Letters Patent is hereby corrected as shown below:

COLUMN 586

Lines 19-29, should read as follows:

$R_1$ is halogen;
$R_2$ is alkoxy substituted with 1, 2, 3, 4, or 5 groups that are independently halogen, -(C1-C6)alkyl-N(R)- CO2R30, haloalkyl, heteroaryl, heteroarylalkyl, -NR6R7, R6R7N-(C1-C6 alkyl)-, -C(O)NR6R7, -(C1-C4)alkyl-C (O)NR6R7, -(C1-C4 alkyl)-NRC(O)NR16R17, haloalkoxy, alkyl, CN, hydroxyalkyl, dihydroxyalkyl, alkoxy, alkoxycarbonyl, phenyl, -SO2-phenyl wherein the phenyl and –SO2-phenyl groups are optionally substituted with 1, 2, or 3 groups that are independently halogen or NO2, or –OC(O)NR6R7, wherein COLUMN 587
Line 16, should read as follows:

$R_5$ is phenyl, benzyl, phenylethyl optionally

COLUMN 588
Line 36, should read as follows:

$R_5$ is phenyl, benzyl, phenylethyl optionally substituted with 1, 2

Signed and Sealed this

Twenty-eighth Day of November, 2006

JON W. DUDAS
*Director of the United States Patent and Trademark Office*